US012741976B2

(12) United States Patent
Lucas et al.

(10) Patent No.: US 12,741,976 B2
(45) Date of Patent: Sep. 22, 2026

(54) QUINOXALINE DERIVATIVES AND USES THEREOF

(71) Applicant: Black Diamond Therapeutics, Inc., Cambridge, MA (US)

(72) Inventors: Matthew C. Lucas, Lexington, MA (US); Fernando Padilla, Arlington, MA (US)

(73) Assignee: Black Diamond Therapeutics, Inc., Cambridge, MA (US)

( * ) Notice: Subject to any disclaimer, the term of this patent is extended or adjusted under 35 U.S.C. 154(b) by 315 days.

(21) Appl. No.: 18/275,232

(22) PCT Filed: Feb. 4, 2022

(86) PCT No.: PCT/US2022/015353
§ 371 (c)(1),
(2) Date: Aug. 1, 2023

(87) PCT Pub. No.: WO2022/170122
PCT Pub. Date: Aug. 11, 2022

(65) Prior Publication Data

US 2024/0368181 A1 Nov. 7, 2024

Related U.S. Application Data

(60) Provisional application No. 63/242,260, filed on Sep. 9, 2021, provisional application No. 63/223,255, filed on Jul. 19, 2021, provisional application No. 63/146,312, filed on Feb. 5, 2021.

(51) Int. Cl.

| | |
|---|---|
| ***C07D 498/04*** | (2006.01) |
| ***A61K 31/498*** | (2006.01) |
| ***A61K 31/5377*** | (2006.01) |
| ***A61K 31/5383*** | (2006.01) |
| ***A61K 31/5386*** | (2006.01) |
| ***A61K 31/541*** | (2006.01) |
| ***A61P 35/00*** | (2006.01) |
| ***C07D 401/14*** | (2006.01) |
| ***C07D 403/14*** | (2006.01) |
| ***C07D 405/14*** | (2006.01) |
| ***C07D 407/14*** | (2006.01) |
| ***C07D 409/14*** | (2006.01) |
| ***C07D 413/14*** | (2006.01) |
| ***C07D 417/14*** | (2006.01) |
| ***C07D 451/02*** | (2006.01) |
| ***C07D 471/04*** | (2006.01) |
| ***C07D 498/08*** | (2006.01) |

(52) U.S. Cl.
CPC .......... *C07D 498/04* (2013.01); *A61K 31/498* (2013.01); *A61K 31/5377* (2013.01); *A61K 31/5383* (2013.01); *A61K 31/5386* (2013.01); *A61K 31/541* (2013.01); *A61P 35/00* (2018.01); *C07D 401/14* (2013.01); *C07D 403/14* (2013.01); *C07D 405/14* (2013.01); *C07D 407/14* (2013.01); *C07D 409/14* (2013.01); *C07D 413/14* (2013.01); *C07D 417/14* (2013.01); *C07D 451/02* (2013.01); *C07D 471/04* (2013.01); *C07D 498/08* (2013.01)

(58) Field of Classification Search
CPC .. C07D 498/04; C07D 401/14; C07D 403/14; C07D 405/14; C07D 407/14; C07D 409/14; C07D 413/14; C07D 417/14; C07D 451/02; C07D 471/04; C07D 498/08; A61P 35/00; A61K 31/498; A61K 31/5377; A61K 31/5383; A61K 31/5386; A61K 31/541
See application file for complete search history.

(56) References Cited

U.S. PATENT DOCUMENTS

2017/0179402 A1 6/2017 Kim et al.

FOREIGN PATENT DOCUMENTS

| | | | | |
|---|---|---|---|---|
| WO | WO-2011088196 A2 | 7/2011 | | |
| WO | WO-2011135376 A1 | 11/2011 | | |
| WO | WO-2013061081 A1 | 5/2013 | | |
| WO | WO-2013112950 A2 * | 8/2013 | | A61P 35/00 |
| WO | WO-2015126907 A1 | 8/2015 | | |
| WO | WO-2015144803 A1 | 10/2015 | | |
| WO | WO-2021119108 A1 | 6/2021 | | |
| WO | WO-2021250198 A1 | 12/2021 | | |

OTHER PUBLICATIONS

U.S. Appl. No. 63/604,977, inventor Kumar; Santosh, filed Dec. 1, 2023.

* cited by examiner

*Primary Examiner* — James H Alstrum-Acevedo
*Assistant Examiner* — Justin Christopher Sanchez
(74) *Attorney, Agent, or Firm* — Fenwick & West LLP; Heidi A. Erlacher; Christine McCain

(57) ABSTRACT

The present disclosure relates compounds of Formula (I'):

(I')

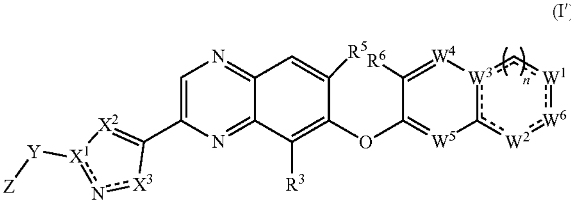

and pharmaceutically acceptable salts and stereoisomers thereof. The present disclosure also relates to methods of preparing the compounds, compositions comprising the compounds, and methods of using the compounds, e.g., in the treatment of cancer.

23 Claims, No Drawings

QUINOXALINE DERIVATIVES AND USES THEREOF

RELATED APPLICATIONS

The application is a U.S. National Phase application, filed under U.S.C. § 371, of International Application No. PCT/US2022/015353, filed Feb. 4, 2022, which claims priority to, and the benefit of, U.S. Provisional Application No. 63/146,312, filed on Feb. 5, 2021, 63/223,255, filed on Jul. 19, 2021, and 63/242,260, filed Sep. 9, 2021, the contents of each of which are incorporated herein by reference in their entirety.

BACKGROUND

Specific mutations in the human genes FGFR2 and FGFR3, which encode for the proteins FGFR2 and FGFR3 respectively, have been associated with several different types of cancers. A variety of different inhibitors for FGFR2 and/or FGFR3 have been developed for the treatment of cancer, including FDA-approved drugs such as erdafitinib and pemigatinib. However, existing inhibitors exhibit a variety of flaws that limit their effectiveness in the clinical. First, some of the existing inhibitors target only FGFR2 and fail to inhibit FGFR3, limiting their ability to treat certain types of cancers. Additionally, several of the existing inhibitors also target FGFR1, leading to dose-limiting toxicities such as hyperphosphatemia. Finally, following administration of some existing inhibitors, many patients develop additional mutations in FGFR2 and/or FGFR3, referred to as gatekeeper mutations, that results in resistance to the existing inhibitors. Thus, there is a long-felt need in the art for new therapies that specifically target FGFR2 and FGFR3. The present disclosure provides compositions and methods for preventing or treating cancer in patients with overexpression of and/or oncogenic mutations in FGFR2 and/or FGFR3, and the FGFR2 and/or FGFR3.

SUMMARY

In some aspects, the present disclosure provides a compound of Formula (I'):

(I')

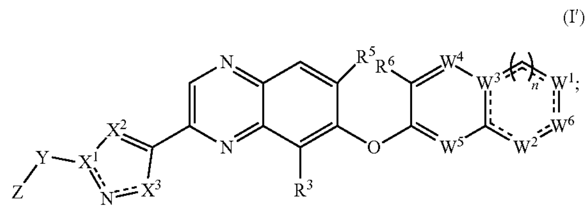

or a pharmaceutically acceptable salt or stereoisomer thereof, wherein:

each ---- independently represents a single bond or a double bond;

n is 0 or 1;

$W^1$ is $C(R^{W1})$ when connected to one double bond and one single bond, $N(R^{W1})$ when connected to two single bonds, or N when connected to one double bond and one single bond;

$R^{W1}$ is H, $C_1$-$C_6$ alkyl, or —S(=O)$_2$—($C_1$-$C_6$ alkyl);

$W^2$ is $C(R^{W2})$ when connected to one double bond and one single bond, $N(R^{W2})$ or O when connected to two single bonds, or N when connected to one double bond and one single bond;

$R^{W2}$ is H, $C_1$-$C_6$ alkyl, or —S(=O)$_2$—($C_1$-$C_6$ alkyl);

$W^3$ is C or N;

$W^4$ is $C(R^{W4})$ or N;

$R^{W4}$ is H, halogen, cyano, $C_1$-$C_6$ alkyl, or —S(=O)$_2$—($C_1$-$C_6$ alkyl);

$W^5$ is $C(R^{W5})$ or N;

$R^{W5}$ is H, halogen, cyano, $C_1$-$C_6$ alkyl, or —S(=O)$_2$—($C_1$-$C_6$ alkyl);

$W^6$ is $C(R^{W6})$ when connected to one double bond and one single bond, $N(R^{W6})$ when connected to two single bonds, or N when connected to one double bond and one single bond;

$R^{W6}$ is H, halogen, cyano, $C_1$-$C_6$ alkyl, $C_1$-$C_6$ alkoxyl, $C_1$-$C_6$ haloalkyl, or —S(=O)$_2$—($C_1$-$C_6$ alkyl);

$X^1$ is C or N;

$X^2$ is N, O, or $C(R^{X2})$;

$R^{X2}$ is H or $C_1$-$C_6$ alkyl;

$X^3$ is N, O, or $C(R^{X3})$;

$R^{X3}$ is H or $C_1$-$C_6$ alkyl;

$R^3$ is H, halogen, cyano, $NH_2$, —NH($C_1$-$C_6$ alkyl), —NHC(=O)($C_1$-$C_6$ haloalkyl), —NHC(=O)O($C_1$-$C_6$ alkyl), N($C_1$-$C_6$ alkyl)$_2$, —S(=O)$_2$—($C_1$-$C_6$ alkyl), —C(=O)H, —C(=O)($C_1$-$C_6$ alkyl), —C(=O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the —NH($C_1$-$C_6$ alkyl), —NHC(=O)($C_1$-$C_6$ haloalkyl), —NHC(=O)O($C_1$-$C_6$ alkyl), N($C_1$-$C_6$ alkyl)$_2$, —S(=O)$_2$—($C_1$-$C_6$ alkyl), —C(=O)H, —C(=O)($C_1$-$C_6$ alkyl), —C(=O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, is optionally substituted with one or more $R^{3a}$, each $R^{3a}$ independently is halogen, cyano, oxo, —OH, $NH_2$, —NH($C_1$-$C_6$ alkyl), —NHC(=O)O($C_1$-$C_6$ alkyl), N($C_1$-$C_6$ alkyl)$_2$, —S(=O)$_2$—($C_1$-$C_6$ alkyl), —C(=O)($C_1$-$C_6$ alkyl), —C(=O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, 3- to 12-membered heterocycloalkyl, $C_6$-$C_{10}$ aryl, or 5- to 10-membered heteroaryl, wherein the NHC(=O)O($C_1$-$C_6$ alkyl) is optionally substituted with one or more halogen;

$R^5$ is H, halogen, cyano, or $C_1$-$C_6$ alkyl;

$R^6$ is H, halogen, cyano, or $C_1$-$C_6$ alkyl;

Y is absent, $C_1$-$C_6$ alkyl, $C_2$-$C_6$ alkenyl, or $C_1$-$C_6$ alkoxyl, wherein the $C_1$-$C_6$ alkyl, $C_2$-$C_6$ alkenyl, or $C_1$-$C_6$ alkoxyl is optionally substituted with one or more halogen, oxo, cyano, —OH, $NH_2$, —NH($C_1$-$C_6$ alkyl)-OH, $C_1$-$C_6$ alkyl, $C_2$-$C_6$ alkenyl, $C_1$-$C_6$ alkoxyl optionally substituted with —($C_1$-$C_6$ alkyl) ($C_6$-$C_{10}$ aryl), or $C_3$-$C_{12}$ cycloalkyl;

Z is absent, H, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl or 5- to 10-membered heteroaryl, is optionally substituted with one or more $R^Z$;

each $R^Z$ independently is oxo, halogen, cyano, —OH, $=NR^{Za}$, $NH_2$, $NHR^{Za}$, $NH(C_1-C_6$ alkyl), $N(C_1-C_6$ alkyl$)_2$, $—S(C_1-C_6$ alkyl), $—S(=O)(=NR^{Za})—(C_1-C_6$ alkyl), $—S(=O)_2—(C_1-C_6$ alkyl), $—S(=O)_2—(C_2-C_6$ alkenyl), —C(=O)(3- to 12-membered heterocycloalkyl), $—C(=O)NH(C_1-C_6$ alkyl), $—C(=O)NR^{Za}$, $—C(=O)—(C_1-C_6$ alkyl), $—C(=O)—(C_2-C_6$ alkenyl), $—C(=O)—(C_1-C_6$ alkoxyl), $C_1-C_6$ alkyl, $C_2-C_6$ alkenyl, $C_2-C_6$ alkynyl, $C_1-C_6$ alkoxyl, $C_3-C_{12}$ cycloalkyl, 3- to 12-membered heterocycloalkyl, or 5- to 10-membered heteroaryl, wherein the $NH(C_1-C_6$ alkyl), $N(C_1-C_6$ alkyl$)_2$, $—S(=O)_2—(C_1-C_6$ alkyl), $—C(=O)—(C_1-C_6$ alkyl), $—C(=O)—(C_2-C_6$ alkenyl), $C_1-C_6$ alkyl, $C_2-C_6$ alkenyl, $C_2-C_6$ alkynyl, $C_1-C_6$ alkoxyl, $C_3-C_{12}$ cycloalkyl, 3- to 12-membered heterocycloalkyl, or 5- to 10-membered heteroaryl is optionally substituted with one or more $R^{Za}$, each $R^{Za}$ independently is H, oxo, halogen, cyano, —OH, $NH_2$, $NH(C_1-C_6$ alkyl), $N(C_1-C_6$ alkyl$)_2$, $—S(=O)_2—(C_1-C_6$ alkyl), $—C(=O)—(C_1-C_6$ alkyl), $—C(=O)—(C_2-C_6$ alkenyl), $C_1-C_6$ alkyl, $C_2-C_6$alkenyl, $C_2-C_6$ alkynyl, $C_1-C_6$ alkoxyl, $C_3-C_{12}$ cycloalkyl, or 3- to 12-membered heterocycloalkyl, wherein the $NH(C_1-C_6$ alkyl), $N(C_1-C_6$ alkyl$)_2$, $—S(=O)_2—(C_1-C_6$ alkyl), $—C(=O)—(C_1-C_6$ alkyl), $—C(=O)—(C_2-C_6$ alkenyl), $C_1-C_6$ alkyl, $C_2-C_6$ alkenyl, $C_2-C_6$ alkynyl, $C_1-C_6$ alkoxyl, $C_3-C_{12}$ cycloalkyl, or 3- to 12-membered heterocycloalkyl is optionally substituted with one or more $R^{Zb}$ and each $R^{Zb}$ independently is oxo, halogen, cyano, —OH, $NH_2$, $NH(C_1-C_6$ alkyl), $N(C_1-C_6$ alkyl$)_2$, $—S(=O)_2—(C_1-C_6$ alkyl), $—C(=O)—(C_1-C_6$ alkyl), $—C(=O)—(C_2-C_6$ alkenyl), $C_1-C_6$ alkyl, $C_2-C_6$ alkenyl, $C_2-C_6$ alkynyl, or $C_1-C_6$ alkoxyl.

In some aspects, the present disclosure provides compound of Formula (I):

(I)

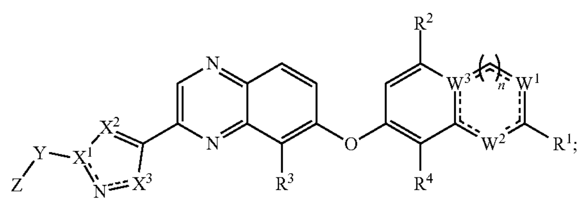

or a pharmaceutically acceptable salt or stereoisomer thereof, wherein:

each ⎓ independently represents a single bond or a double bond;

n is 0 or 1;

$W^1$ is $C(R^{W1})$ when connected to one double bond and one single bond, $N(R^{W1})$ when connected to two single bonds, or N when connected to one double bond and one single bond;

$R^{W1}$ is H, $C_1-C_6$ alkyl, or $—S(=O)_2—(C_1-C_6$ alkyl);

$W^2$ is $C(R^{W2})$ when connected to one double bond and one single bond, $N(R^{W2})$ when connected to two single bonds, or N when connected to one double bond and one single bond;

$R^{W2}$ is H, $C_1-C_6$ alkyl, or $—S(=O)_2—(C_1-C_6$ alkyl);

$W^3$ is C or N;

$X^1$ is C or N;

$X^2$ is N, O, or $C(R^{X2})$;

$R^{X2}$ is H or $C_1-C_6$ alkyl;

$X^3$ is N, O, or $C(R^{X3})$;

$R^{X3}$ is H or $C_1-C_6$ alkyl;

$R^1$ is H, halogen, cyano, or $C_1-C_6$ alkyl;

$R^2$ is H, halogen, cyano, or $C_1-C_6$ alkyl;

$R^3$ is H, halogen, cyano, or $C_1-C_6$ alkyl;

$R^4$ is H, halogen, cyano, or $C_1-C_6$ alkyl;

Y is absent or $C_1-C_6$ alkyl optionally substituted with one or more oxo or —OH;

Z is H, $C_3-C_8$ cycloalkyl, or 3- to 8-membered heterocycloalkyl, wherein the $C_3-C_8$ cycloalkyl or 3- to 8-membered heterocycloalkyl is optionally substituted with one or more $R^Z$, each $R^Z$ independently is oxo, halogen, cyano, —OH, $NH_2$, $NH(C_1-C_6$ alkyl), $N(C_1-C_6$ alkyl$)_2$, $—S(=O)_2—(C_1-C_6$ alkyl), $—C(=O)—(C_1-C_6$ alkyl), $—C(=O)—(C_2-C_6$ alkenyl), $C_1-C_6$ alkyl, $C_2-C_6$ alkenyl, $C_2-C_6$ alkynyl, $C_1-C_6$ alkoxyl, $C_3-C_8$ cycloalkyl, or 3- to 8-membered heterocycloalkyl, wherein the $NH(C_1-C_6$ alkyl), $N(C_1-C_6$ alkyl$)_2$, $—S(=O)_2—(C_1-C_6$ alkyl), $—C(=O)—(C_1-C_6$ alkyl), $—C(=O)—(C_2-C_6$ alkenyl), $C_1-C_6$ alkyl, $C_2-C_6$ alkenyl, $C_2-C_6$ alkynyl, $C_1-C_6$ alkoxyl, $C_3-C_8$ cycloalkyl, or 3- to 8-membered heterocycloalkyl is optionally substituted with one or more $R^{Za}$;

each $R^{Za}$ independently is oxo, halogen, cyano, —OH, $NH_2$, $NH(C_1-C_6$ alkyl), $N(C_1-C_6$ alkyl$)_2$, $—S(=O)_2—(C_1-C_6$ alkyl), $—C(=O)—(C_1-C_6$ alkyl), $—C(=O)—(C_2-C_6$ alkenyl), $C_1-C_6$ alkyl, $C_2-C_6$ alkenyl, $C_2-C_6$ alkynyl, $C_1-C_6$ alkoxyl, $C_3-C_8$ cycloalkyl, or 3- to 8-membered heterocycloalkyl, wherein the $NH(C_1-C_6$ alkyl), $N(C_1-C_6$ alkyl$)_2$, $—S(=O)_2—(C_1-C_6$ alkyl), $—C(=O)—(C_1-C_6$ alkyl), $—C(=O)—(C_2-C_6$ alkenyl), $C_1-C_6$ alkyl, $C_2-C_6$ alkenyl, $C_2-C_6$ alkynyl, $C_1-C_6$ alkoxyl, $C_3-C_8$ cycloalkyl, or 3- to 8-membered heterocycloalkyl is optionally substituted with one or more $R^{2b}$; and each $R^{Zb}$ independently is oxo, halogen, cyano, —OH, $NH_2$, $NH(C_1-C_6$ alkyl), $N(C_1-C_6$ alkyl$)_2$, $—S(=O)_2—(C_1-C_6$ alkyl), $—C(=O)—(C_1-C_6$ alkyl), $—C(=O)—(C_2-C_6$ alkenyl), $C_1-C_6$ alkyl, $C_2-C_6$ alkenyl, $C_2-C_6$ alkynyl, or $C_1-C_6$ alkoxyl.

In some aspects, the present disclosure provides an isotopic derivative of a compound described herein.

In some aspects, the present disclosure provides a method of preparing a compound described herein.

In some aspects, the present disclosure provides a pharmaceutical composition comprising a compound described herein and one or more pharmaceutically acceptable carriers or excipients.

In some aspects, the present disclosure provides a method of treating or preventing cancer in a subject, the method comprising administering to the subject a therapeutically effective amount of a compound described herein.

In some aspects, the present disclosure provides a compound described herein for treating or preventing cancer in a subject.

In some aspects, the present disclosure provides a use of a compound described herein in the manufacture of a medicament for treating or preventing cancer in a subject.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

Compounds of the Present Disclosure

In some aspects, the present disclosure provides a compound of Formula (I'):

(I')

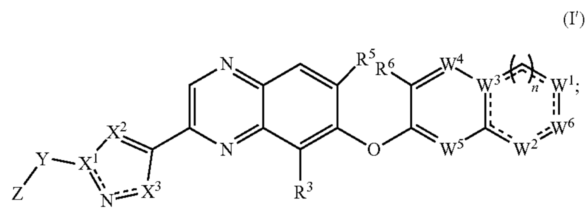

or a pharmaceutically acceptable salt or stereoisomer thereof, wherein:

each ---- independently represents a single bond or a double bond;

n is 0 or 1;

$W^1$ is $C(R^{W1})$ when connected to one double bond and one single bond, $N(R^{W1})$ when connected to two single bonds, or N when connected to one double bond and one single bond;

$R^{W1}$ is H, $C_1$-$C_6$ alkyl, or —S(═O)$_2$—($C_1$-$C_6$ alkyl);

$W^2$ is $C(R^{W2})$ when connected to one double bond and one single bond, $N(R^{W2})$ or O when connected to two single bonds, or N when connected to one double bond and one single bond;

$R^{W2}$ is H, $C_1$-$C_6$ alkyl, or —S(═O)$_2$—($C_1$-$C_6$ alkyl);

$W^3$ is C or N;

$W^4$ is $C(R^{W4})$ or N;

$R^{W4}$ is H, halogen, cyano, $C_1$-$C_6$ alkyl, or —S(═O)$_2$—($C_1$-$C_6$ alkyl);

$W^5$ is $C(R^{W5})$ or N;

$R^{W5}$ is H, halogen, cyano, $C_1$-$C_6$ alkyl, or —S(═O)$_2$—($C_1$-$C_6$ alkyl);

$W^6$ is $C(R^{W6})$ when connected to one double bond and one single bond, $N(R^{W6})$ when connected to two single bonds, or N when connected to one double bond and one single bond;

$R^{W6}$ is H, halogen, cyano, $C_1$-$C_6$ alkyl, $C_1$-$C_6$ alkoxyl, $C_1$-$C_6$ haloalkyl, or —S(═O)$_2$—($C_1$-$C_6$ alkyl);

$X^1$ is C or N;

$X^2$ is N, O, or $C(R^{X2})$;

$R^{X2}$ is H or $C_1$-$C_6$ alkyl;

$X^3$ is N, O, or $C(R^{X3})$;

$R^{X3}$ is H or $C_1$-$C_6$ alkyl;

$R^3$ is H, halogen, cyano, $NH_2$, —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, is optionally substituted with one or more $R^{3a}$;

each $R^{3a}$ independently is halogen, cyano, oxo, —OH, $NH_2$, —NH($C_1$-$C_6$ alkyl), —NHC(═O)O($C_1$-$C_6$ alkyl), N($C_1$-$C_6$ alkyl)$_2$, —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, 3- to 12-membered heterocycloalkyl, $C_6$-$C_{10}$ aryl, or 5- to 10-membered heteroaryl, wherein the NHC(═O)O($C_1$-$C_6$ alkyl) is optionally substituted with one or more halogen;

$R^5$ is H, halogen, cyano, or $C_1$-$C_6$ alkyl;

$R^6$ is H, halogen, cyano, or $C_1$-$C_6$ alkyl;

Y is absent, $C_1$-$C_6$ alkyl, $C_2$-$C_6$ alkenyl, or $C_1$-$C_6$ alkoxyl, wherein the $C_1$-$C_6$ alkyl, $C_2$-$C_6$ alkenyl, or $C_1$-$C_6$ alkoxyl is optionally substituted with one or more halogen, oxo, cyano, —OH, $NH_2$, —NH($C_1$-$C_6$ alkyl)-OH, $C_1$-$C_6$ alkyl, $C_2$-$C_6$ alkenyl, $C_1$-$C_6$ alkoxyl optionally substituted with —($C_1$-$C_6$ alkyl)($C_6$-$C_{10}$ aryl), or $C_3$-$C_{12}$ cycloalkyl;

Z is absent, H, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl or 5- to 10-membered heteroaryl, is optionally substituted with one or more RZ;

each $R^Z$ independently is oxo, halogen, cyano, —OH, =$NR^{Za}$, $NH_2$, $NHR^{Za}$, NH($C_1$-$C_6$ alkyl), N($C_1$-$C_6$ alkyl)$_2$, —S($C_1$-$C_6$ alkyl), —S(═O)(═$NR^{Za}$)—($C_1$-$C_6$ alkyl), —S(═O)$_2$—($C_1$-$C_6$ alkyl), —S(═O)$_2$—($C_2$-$C_6$ alkenyl), —C(═O)(3- to 12-membered heterocycloalkyl), —C(═O)NH($C_1$-$C_6$ alkyl), —C(═O)$NR^{Za}$, —C(═O)—($C_1$-$C_6$ alkyl), —C(═O)—($C_2$-$C_6$ alkenyl), —C(═O)—($C_1$-$C_6$ alkoxyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, 3- to 12-membered heterocycloalkyl, or 5- to 10-membered heteroaryl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, 3- to 12-membered heterocycloalkyl, or 5- to 10-membered heteroaryl is optionally substituted with one or more $R^{Za}$, each $R^{Za}$ independently is H, oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, or 3- to 12-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, or 3- to 12-membered heterocycloalkyl is optionally substituted with one or more $R^{20}$; and each $R^{Zb}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, or $C_1$-$C_6$ alkoxyl.

In some aspects, the present disclosure provides a compound of Formula (I):

(I)

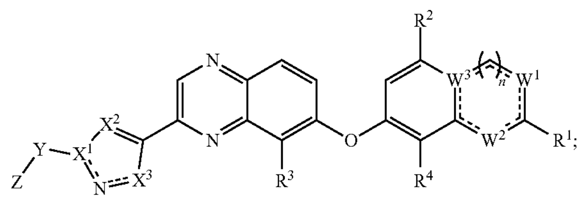

or a pharmaceutically acceptable salt or stereoisomer thereof, wherein:

each ⎓ independently represents a single bond or a double bond;

n is 0 or 1;

$W^1$ is C($R^{W1}$) when connected to one double bond and one single bond, N($R^{W1}$) when connected to two single bonds, or N when connected to one double bond and one single bond;

$R^{W1}$ is H, $C_1$-$C_6$ alkyl, or —S(═O)$_2$—($C_1$-$C_6$ alkyl);

$W^2$ is C($R^{W2}$) when connected to one double bond and one single bond, N($R^{W2}$) when connected to two single bonds, or N when connected to one double bond and one single bond;

$R^{W2}$ is H, $C_1$-$C_6$ alkyl, or —S(═O)$_2$—($C_1$-$C_6$ alkyl);

$W^3$ is C or N;

$X^1$ is C or N;

$X^2$ is N, O, or C($R^{X2}$);

$R^{X2}$ is H or $C_1$-$C_6$ alkyl;

$X^3$ is N, O, or C($R^{X3}$);

$R^{X3}$ is H or $C_1$-$C_6$ alkyl;

$R^1$ is H, halogen, cyano, or $C_1$-$C_6$ alkyl;

$R^2$ is H, halogen, cyano, or $C_1$-$C_6$ alkyl;

$R^3$ is H, halogen, cyano, or $C_1$-$C_6$ alkyl;

$R^4$ is H, halogen, cyano, or $C_1$-$C_6$ alkyl;

Y is absent or $C_1$-$C_6$ alkyl optionally substituted with one or more oxo or —OH;

Z is H, $C_3$-$C_8$ cycloalkyl, or 3- to 8-membered heterocycloalkyl, wherein the $C_3$-$C_8$ cycloalkyl or 3- to 8-membered heterocycloalkyl is optionally substituted with one or more $R^Z$;

each $R^Z$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Za}$;

each $R^{Za}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Zb}$, and each $R^{Zb}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, or $C_1$-$C_6$ alkoxyl.

In some aspects, the present disclosure provides a compound of Formula (I'), or a pharmaceutically acceptable salt or stereoisomer thereof, wherein:

each ⎓ independently represents a single bond or a double bond;

n is 0;

$W^1$ is C($R^{W1}$) when connected to one double bond and one single bond, N($R^{W1}$) when connected to two single bonds, or N when connected to one double bond and one single bond;

$R^{W1}$ is H;

$W^2$ is C($R^{W2}$) when connected to one double bond and one single bond, N($R^{W2}$) or O when connected to two single bonds, or N when connected to one double bond and one single bond;

$R^{W2}$ is H;

$W^3$ is N;

$W^4$ is C($R^{W4}$);

$R^{W4}$ is H or halogen;

$W^5$ is C($R^{W5}$);

$R^{W5}$ is H or halogen;

$W^6$ is C($R^{W6}$) when connected to one double bond and one single bond, N($R^{W6}$) when connected to two single bonds, or N when connected to one double bond and one single bond;

$R^{W6}$ is H or $C_1$-$C_6$ alkyl;

$X^1$ is N;

$X^2$ is C($R^{X2}$);

$R^{X2}$ is H or $C_1$-$C_6$ alkyl;

$X^3$ is C($R^{X3}$);

$R^{X3}$ is H or $C_1$-$C_6$ alkyl;

$R^3$ is H, halogen, cyano, $NH_2$, NHC(═O)O($C_1$-$C_6$ alkyl), —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, $C_2$-$C_6$ alkenyl, $C_3$-$C_{12}$ cycloalkyl, 3- to 12-membered heterocycloalkyl, 3- to 12-membered heterocycloalkenyl, or 5- to 10-membered heteroaryl, wherein the NHC(═O)O($C_1$-$C_6$ alkyl), —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, 3- to 12-membered heterocycloalkyl, 3- to 12-membered heterocycloalkenyl, or 5- to 10-membered heteroaryl, is optionally substituted with one or more $R^{3a}$, each $R^{3a}$ independently is halogen, oxo, NHC(═O)O($C_1$-$C_6$ alkyl), —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, or $C_2$-$C_6$ alkenyl, wherein the —NHC(═O)O($C_1$-$C_6$ alkyl), —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, or $C_2$-$C_6$ alkenyl is optionally substituted with one or more halogen;

$R^5$ is H or $C_1$-$C_6$ alkyl;

$R^6$ is H or halogen;

Y is absent, $C_1$-$C_6$ alkyl, $C_2$-$C_6$ alkenyl, or $C_1$-$C_6$ alkoxyl, wherein the $C_1$-$C_6$ alkyl, $C_2$-$C_6$ alkenyl, or $C_1$-$C_6$ alkoxyl is optionally substituted with one or more halogen, oxo, cyano, —OH, $NH_2$, $C_1$-$C_6$ alkyl, $C_2$-$C_6$ alkenyl, $C_1$-$C_6$ alkoxyl optionally substituted with —($C_1$-$C_6$ alkyl) ($C_6$-$C_{10}$aryl), or $C_3$-$C_{12}$ cycloalkyl;

Z is absent, $C_3$-$C_{12}$ cycloalkyl, 3- to 12-membered heterocycloalkyl, 3- to 12-membered heterocycloalkenyl, $C_6$-$C_{10}$ aryl, or 5- to 10-membered heteroaryl, wherein the $C_3$-$C_{12}$ cycloalkyl, 3- to 12-membered heterocycloalkyl, 3- to 12-membered heterocycloalkenyl, $C_6$-$C_{10}$ aryl or 5- to 10-membered heteroaryl is optionally substituted with one or more $R^Z$;

each $R^Z$ independently is oxo, halogen, —OH, $=NR^{Za}$, $NH_2$, $NHR^{Za}$, NH($C_1$-$C_6$ alkyl), N($C_1$-$C_6$ alkyl)$_2$, —S($C_1$-$C_6$ alkyl), —S(=O)(=$NR^{Za}$)—($C_1$-$C_6$ alkyl), —S(=O)$_2$—($C_1$-$C_6$ alkyl), —S(=O)$_2$—($C_2$-$C_6$ alkenyl), —C(=O)NH($C_1$-$C_6$ alkyl), —C(=O)$NR^{Za}$, —C(=O)—($C_1$-$C_6$ alkyl), —C(=O)—($C_2$-$C_6$ alkenyl), —C(=O)—($C_1$-$C_6$ alkoxyl), $C_1$-$C_6$ alkyl, $C_2$-$C_6$ alkenyl, $C_1$-$C_6$ alkoxyl, $C_3$-$C_{12}$ cycloalkyl, 3- to 12-membered heterocycloalkyl, or 5- to 10-membered heteroaryl, wherein the NH($C_1$-$C_6$ alkyl), N($C_1$-$C_6$ alkyl)$_2$, —S($C_1$-$C_6$ alkyl), —S(=O)(=$NR^{Za}$)—($C_1$-$C_6$ alkyl), —S(=O)$_2$—($C_1$-$C_6$ alkyl), —S(=O)$_2$—($C_2$-$C_6$ alkenyl), —C(=O)NH($C_1$-$C_6$ alkyl), —C(=O)$NR^{Za}$, —C(=O)—($C_1$-$C_6$ alkyl), —C(=O)—($C_2$-$C_6$ alkenyl), —C(=O)—($C_1$-$C_6$ alkoxyl), $C_1$-$C_6$ alkyl, $C_2$-$C_6$ alkenyl, $C_1$-$C_6$ alkoxyl, $C_3$-$C_{12}$ cycloalkyl, 3- to 12-membered heterocycloalkyl, or 5- to 10-membered heteroaryl is optionally substituted with one or more $R^{Za}$, each $R^{Za}$ independently is H, oxo, halogen, cyano, —OH, $NH_2$, NH($C_1$-$C_6$ alkyl), N($C_1$-$C_6$ alkyl)$_2$, —S(=O)$_2$—($C_1$-$C_6$ alkyl), —C(=O)—($C_1$-$C_6$ alkyl), $C_1$-$C_6$ alkyl, $C_2$-$C_6$ alkenyl, $C_1$-$C_6$ alkoxyl, $C_3$-$C_{12}$ cycloalkyl, or 3- to 12-membered heterocycloalkyl, wherein the NH($C_1$-$C_6$ alkyl), N($C_1$-$C_6$ alkyl)$_2$, —S(=O)$_2$—($C_1$-$C_6$ alkyl), —C(=O)—($C_1$-$C_6$ alkyl), $C_1$-$C_6$ alkyl, $C_2$-$C_6$ alkenyl, $C_1$-$C_6$ alkoxyl, $C_3$-$C_{12}$ cycloalkyl, or 3- to 12-membered heterocycloalkyl is optionally substituted with one or more $R^{Zb}$; and each $R^{Zb}$ independently is oxo, halogen, —OH.

In some aspects, the present disclosure provides a compound of Formula (I) or a pharmaceutically acceptable salt or stereoisomer thereof, wherein:

each ═ independently represents a single bond or a double bond;

n is 0 or 1;

$W^1$ is C($R^{W1}$) or N($R^{W1}$) when connected to two single bonds, or C or N when connected to one double bond and one single bond;

$R^{W1}$ is H, $C_1$-$C_6$ alkyl, or —S(=O)$_2$—($C_1$-$C_6$ alkyl);

$W^2$ is C($R^{W2}$) or N($R^{W2}$) when connected to two single bonds, or C or N when connected to one double bond and one single bond;

$R^{W2}$ is H, $C_1$-$C_6$ alkyl, or —S(=O)$_2$—($C_1$-$C_6$ alkyl);

$W^3$ is C or N;

$X^1$ is C or N;

$X^2$ is N, O, or C($R^{X2}$);

$R^{X2}$ is H or $C_1$-$C_6$ alkyl;

$X^3$ is N, O, or C($R^{X3}$);

$R^{X3}$ is H or $C_1$-$C_6$ alkyl;

$R^1$ is H, halogen, cyano, or $C_1$-$C_6$ alkyl;

$R^2$ is H, halogen, cyano, or $C_1$-$C_6$ alkyl;

$R^3$ is H, halogen, cyano, or $C_1$-$C_6$ alkyl;

$R^4$ is H, halogen, cyano, or $C_1$-$C_6$ alkyl;

Y is absent or $C_1$-$C_6$ alkyl optionally substituted with one or more oxo or —OH;

Z is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^Z$;

each $R^Z$ independently is oxo, halogen, cyano, —OH, $NH_2$, NH($C_1$-$C_6$ alkyl), N($C_1$-$C_6$ alkyl)$_2$, —S(=O)$_2$—($C_1$-$C_6$ alkyl), —C(=O)—($C_1$-$C_6$ alkyl), —C(=O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(=O)$_2$—($C_1$-$C_6$ alkyl), —C(=O)—($C_1$-$C_6$ alkyl), —C(=O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Za}$;

each $R^{Za}$ independently is oxo, halogen, cyano, —OH, $NH_2$, NH($C_1$-$C_6$ alkyl), N($C_1$-$C_6$ alkyl)$_2$, —S(=O)$_2$—($C_1$-$C_6$ alkyl), —C(=O)—($C_1$-$C_6$ alkyl), —C(=O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(=O)$_2$—($C_1$-$C_6$ alkyl), —C(=O)—($C_1$-$C_6$ alkyl), —C(=O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Zb}$; and each $R^{Zb}$ independently is oxo, halogen, cyano, —OH, $NH_2$, NH($C_1$-$C_6$ alkyl), N($C_1$-$C_6$ alkyl)$_2$, —S(=O)$_2$—($C_1$-$C_6$ alkyl), —C(=O)—($C_1$-$C_6$ alkyl), —C(=O)—($C_2$-$C_6$ alkenyl), $C_1$-$C_6$ alkyl, $C_2$-$C_6$ alkenyl, $C_2$-$C_6$ alkynyl, or $C_1$-$C_6$ alkoxyl.

In some aspects, the present disclosure provides a compound of Formula (I) or a pharmaceutically acceptable salt or stereoisomer thereof, wherein:

each ═ independently represents a single bond or a double bond;

n is 0 or 1;

$W^1$ is C($R^{W1}$) or N($R^{W1}$) when connected to two single bonds, or C or N when connected to one double bond and one single bond;

$R^{W1}$ is H, $C_1$-$C_6$ alkyl, or —S(=O)$_2$—($C_1$-$C_6$ alkyl);

$W^2$ is C($R^{W2}$) or N($R^{W2}$) when connected to two single bonds, or C or N when connected to one double bond and one single bond;

$R^{W2}$ is H, $C_1$-$C_6$ alkyl, or —S(=O)$_2$—($C_1$-$C_6$ alkyl);

$W^3$ is C or N;

$X^1$ is C or N;

$X^2$ is N, O, or C($R^{X2}$);

$R^{X2}$ is H or $C_1$-$C_6$ alkyl;

$X^3$ is N, O, or C($R^{X3}$);

$R^{X3}$ is H or $C_1$-$C_6$ alkyl;

$R^1$ is H, halogen, cyano, or $C_1$-$C_6$ alkyl;

$R^2$ is H, halogen, cyano, or $C_1$-$C_6$. alkyl;

$R^3$ is H, halogen, cyano, or $C_1$-$C_6$ alkyl;

$R^4$ is H, halogen, cyano, or $C_1$-$C_6$ alkyl;

Y is $C_1$-$C_6$ alkyl optionally substituted with one or more oxo or —OH;

Z is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^Z$;

each $R^Z$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Za}$, each $R^{Za}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Zb}$, and each $R^{Zb}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, or $C_1$-$C_6$ alkoxyl.

Variables n, $W^1$, $R^{W1}$, $W^2$, $R^{W2}$, $W^3$, $W^4$, $R^{W4}$, $W^5$, $R^{W5}$, $W^6$, and $R^{W6}$ In some embodiments, each ⎓ independently represents a single bond or a double bond.

In some embodiments, each ⎓ independently represents a single bond. In some embodiments, each ⎓ independently represents a double bond.

In some embodiments, n is 0. In some embodiments, n is 1.

In some embodiments, $W^1$ is C($R^{W1}$) when connected to one double bond and one single bond, N($R^{W1}$) when connected to two single bonds, or N when connected to one double bond and one single bond.

In some embodiments, $W^1$ is C($R^{W1}$) when connected to one double bond and one single bond.

In some embodiments, $W^1$ is N($R^{W1}$) when connected to two single bonds.

In some embodiments, $W^1$ is N when connected to one double bond and one single bond.

In some embodiments, $W^1$ is C($R^{W1}$) or N($R^{W1}$).

In some embodiments, $W^1$ is C($R^{W1}$). In some embodiments, $W^1$ is CH.

In some embodiments, $W^1$ is N($R^{W1}$). In some embodiments, $W^1$ is NH.

In some embodiments, $W^1$ is N(—S(═O)$_2$—($C_1$-$C_6$ alkyl)). In some embodiments, $W^1$ is N(—S(═O)$_2$—$CH_3$).

In some embodiments, $W^1$ is N.

In some embodiments, $R^{W1}$ is H.

In some embodiments, $R^{W1}$ is $C_1$-$C_6$ alkyl or —S(═O)$_2$—($C_1$-$C_6$ alkyl).

In some embodiments, $R^{W1}$ is $C_1$-$C_6$ alkyl.

In some embodiments, $R^{W1}$ is —S(═O)$_2$—($C_1$-$C_6$ alkyl). In some embodiments, $R^{W1}$ is —S(═O)$_2$—$CH_3$.

In some embodiments, $W^2$ is C($R^{W2}$) when connected to one double bond and one single bond, N($R^{W2}$) when connected to two single bonds, or N when connected to one double bond and one single bond.

In some embodiments, $W^2$ is C($R^{W2}$) when connected to one double bond and one single bond.

In some embodiments, $W^2$ is N($R^{W2}$) when connected to two single bonds.

In some embodiments, $W^2$ is N when connected to one double bond and one single bond.

In some embodiments, $W^2$ is C($R^{W2}$) or N($R^{W2}$).

In some embodiments, $W^2$ is C($R^{W2}$). In some embodiments, $W^2$ is CH.

In some embodiments, $W^2$ is N($R^{W2}$). In some embodiments, $W^2$ is NH.

In some embodiments, $W^2$ is N(—S(═O)$_2$—($C_1$-$C_6$ alkyl)). In some embodiments, $W^2$ is N(—S(═O)$_2$—$CH_3$).

In some embodiments, $W^2$ is N.

In some embodiments, $R^{W2}$ is H.

In some embodiments, $R^{W2}$ is $C_1$-$C_6$ alkyl or —S(═O)$_2$—($C_1$-$C_6$ alkyl).

In some embodiments, $R^{W2}$ is $C_1$-$C_6$ alkyl.

In some embodiments, $R^{W2}$ is —S(═O)$_2$—($C_1$-$C_6$ alkyl). In some embodiments, $R^{W2}$ is —S(═O)$_2$—$CH_3$.

In some embodiments, $W^3$ is C. In some embodiments, $W^3$ is N.

In some embodiments, $W^4$ is C($R^{W4}$). In some embodiments, $W^4$ is CH. In some embodiments, $W^4$ is C (halogen).

In some embodiments, $W^4$ is N.

In some embodiments, $R^{W4}$ is H.

In some embodiments, $R^{W4}$ is halogen, cyano, $C_1$-$C_6$ alkyl or —S(═O)$_2$—($C_1$-$C_6$ alkyl).

In some embodiments, $R^{W4}$ is halogen or cyano.

In some embodiments, $R^{W4}$ is halogen. In some embodiments, $R^{W4}$ is F, Cl, Br, or I. In some embodiments, $R^{W4}$ is F. In some embodiments, $R^{W4}$ is Cl. In some embodiments, $R^{W4}$ is Br. In some embodiments, $R^{W4}$ is I.

In some embodiments, $R^{W4}$ is cyano.

In some embodiments, $R^{W4}$ is $C_1$-$C_6$ alkyl.

In some embodiments, $R^{W4}$ is —S(═O)$_2$—($C_1$-$C_6$ alkyl). In some embodiments, $R^{W4}$ is —S(═O)$_2$—$CH_3$.

In some embodiments, $W^5$ is C($R^{W5}$). In some embodiments, $W^5$ is CH. In some embodiments, $W^5$ is C (halogen).

In some embodiments, $W^5$ is N.

In some embodiments, $R^{W5}$ is H.

In some embodiments, $R^{W5}$ is halogen, cyano, $C_1$-$C_6$ alkyl or —S(═O)$_2$—($C_1$-$C_6$ alkyl).

In some embodiments, $R^{W5}$ is halogen or cyano.

In some embodiments, $R^{W5}$ is halogen. In some embodiments, $R^{W5}$ is F, Cl, Br, or I. In some embodiments, $R^{W5}$ is F. In some embodiments, $R^{W5}$ is Cl. In some embodiments, $R^{W5}$ is Br. In some embodiments, $R^{W5}$ is I.

In some embodiments, $R^{W5}$ is cyano.

In some embodiments, $R^{W5}$ is $C_1$-$C_6$ alkyl.

In some embodiments, $R^{W5}$ is —S(═O)$_2$—($C_1$-$C_6$ alkyl). In some embodiments, $R^{W5}$ is —S(═O)$_2$—$CH_3$.

In some embodiments, $W^6$ is C($R^{W6}$) when connected to one double bond and one single bond, N($R^{W6}$) when connected to two single bonds, or N when connected to one double bond and one single bond.

In some embodiments, $W^6$ is C($R^{W6}$) when connected to one double bond and one single bond.

In some embodiments, $W^6$ is N($R^{W6}$) when connected to two single bonds.

In some embodiments, $W^6$ is N when connected to one double bond and one single bond.

In some embodiments, $W^6$ is C($R^{W6}$) or N($R^{W6}$).

In some embodiments, $W^6$ is C($R^{W6}$). In some embodiments, $W^6$ is CH.

In some embodiments, $W^6$ is N($R^{W6}$). In some embodiments, $W^6$ is NH.

In some embodiments, $W^6$ is N(—S(═O)$_2$—($C_1$-$C_6$ alkyl)). In some embodiments, $W^6$ is N(—S(═O)$_2$—$CH_3$).

In some embodiments, $W^6$ is N.

In some embodiments, $R^{W6}$ is H.

In some embodiments, $R^{W6}$ is halogen, cyano, $C_1$-$C_6$ alkyl, $C_1$-$C_6$ alkoxyl, $C_1$-$C_6$ haloalkyl, or —S(═O)$_2$—($C_1$-$C_6$ alkyl).

In some embodiments, $R^{W6}$ is halogen or cyano.

In some embodiments, $R^{W6}$ is halogen. In some embodiments, $R^{W6}$ is F, Cl, Br, or I. In some embodiments, $R^{W6}$ is F. In some embodiments, $R^{W6}$ is Cl. In some embodiments, $R^{W6}$ is Br. In some embodiments, $R^{W6}$ is I.

In some embodiments, $R^{W6}$ is cyano.

In some embodiments, $R^{W6}$ is $C_1$-$C_6$ alkyl.

In some embodiments, $R^{W6}$ is $C_1$-$C_6$ alkoxy.

In some embodiments, $R^{W6}$ is $C_1$-$C_6$ haloalkyl.

In some embodiments, $R^{W6}$ is —S(═O)$_2$—($C_1$-$C_6$ alkyl). In some embodiments, $R^{W1}$ is —S(═O)$_2$—$CH_3$.

In some embodiments,

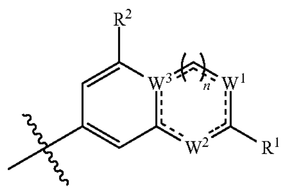

is

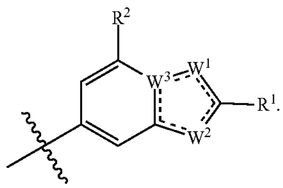

In some embodiments,

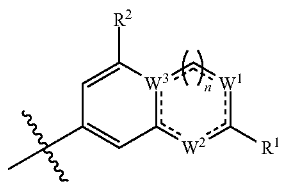

is

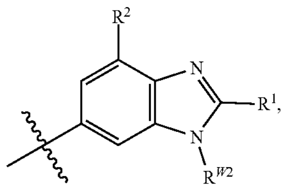

In some embodiments,

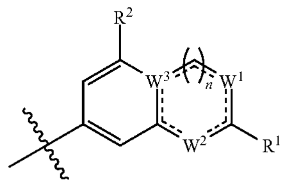

is

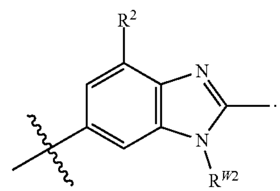

In some embodiments,

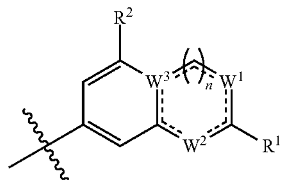

is

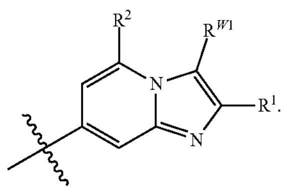

In some embodiments,

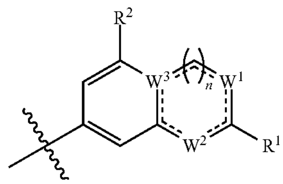

is

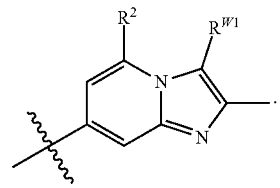

In some embodiments,

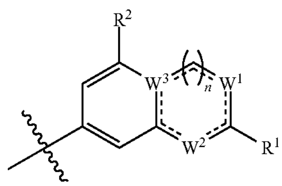

is

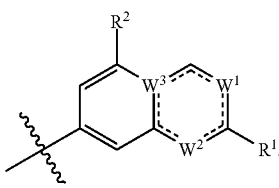

In some embodiments,

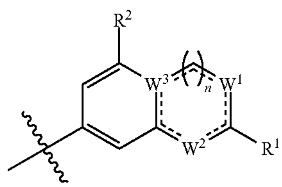

is

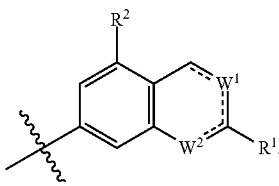

In some embodiments,

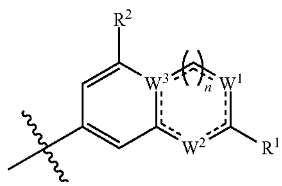

is

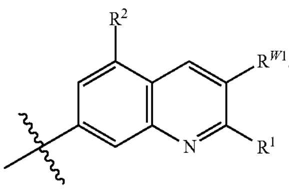

In some embodiments,

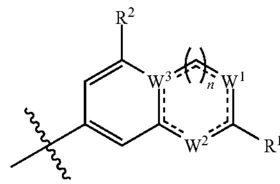

is

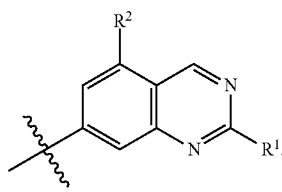

Variables $X^1$, $X^2$, $R^{X2}$, $X^3$, and $R^{X3}$

In some embodiments, $X^1$ is C. In some embodiments, $X^1$ is N.

In some embodiments, $X^2$ is N. In some embodiments, $X^2$ is O.

In some embodiments, $X^2$ is $C(R^{X2})$. In some embodiments, $X^2$ is CH. In some embodiments, $X^2$ is $C(C_1\text{-}C_6$ alkyl). In some embodiments, $X^2$ is $C(CH_3)$.

In some embodiments, $R^{X2}$ is H.

In some embodiments, $R^{X2}$ is $C_1\text{-}C_6$ alkyl. In some embodiments, $R^{X2}$ is $CH_3$.

In some embodiments, $X^3$ is N. In some embodiments, $X^3$ is O.

In some embodiments, $X^3$ is $C(R^{X3})$. In some embodiments, $X^3$ is CH. In some embodiments, $X^3$ is $C(C_1\text{-}C_6$ alkyl). In some embodiments, $X^3$ is $C(CH_3)$.

In some embodiments, $R^{X3}$ is H.

In some embodiments, $R^{X3}$ is $C_1\text{-}C_6$ alkyl. In some embodiments, $R^{X3}$ is $CH_3$.

In some embodiments, $X^1$ is N, $X^2$ is $C(R^{X2})$, and $X_3$ is $C(R^{X3})$.

In some embodiments, $X^1$ is C, $X^2$ is $C(R^{X2})$, and $X_3$ is O.

In some embodiments,

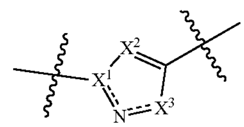

is

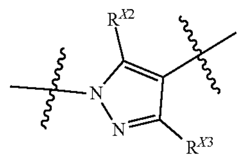

In some embodiments,

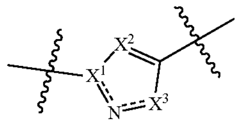

is

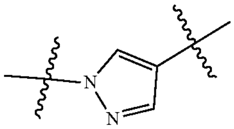

In some embodiments,

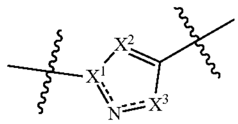

is

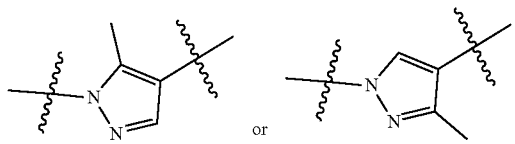

In some embodiments,

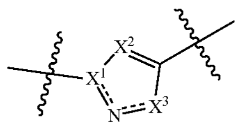

is

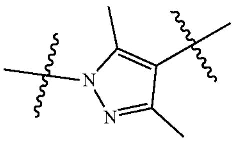

In some embodiments,

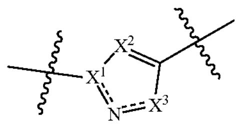

is

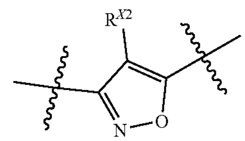

In some embodiments,

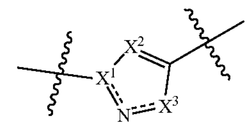

is

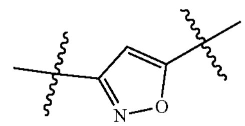

Variables $R^1$, $R^2$, $R^3$, $R^{3a}$, $R^4$, $R^5$, and $R^6$

In some embodiments, $R^1$ is H.

In some embodiments, $R^1$ is halogen, cyano, or $C_1$-$C_6$ alkyl.

In some embodiments, $R^1$ is halogen. In some embodiments, $R^1$ is F or Cl.

In some embodiments, $R^1$ is F. In some embodiments, $R^1$ is Cl.

In some embodiments, $R^1$ is cyano.

In some embodiments, $R^1$ is $C_1$-$C_6$ alkyl. In some embodiments, $R^1$ is $CH_3$.

In some embodiments, $R^2$ is H.

In some embodiments, $R^2$ is halogen, cyano, or $C_1$-$C_6$ alkyl.

In some embodiments, $R^2$ is halogen. In some embodiments, $R^2$ is F or Cl.

In some embodiments, $R^2$ is F. In some embodiments, $R^2$ is Cl.

In some embodiments, $R^2$ is cyano.

In some embodiments, $R^2$ is $C_1$-$C_6$ alkyl. In some embodiments, $R^2$ is $CH_3$.

In some embodiments, $R^3$ is H, halogen, cyano, $NH_2$, —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, is optionally substituted with one or more $R^{3a}$.

In some embodiments, $R^3$ is H, halogen, cyano, $NH_2$, —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl.

In some embodiments, $R^3$ is H.

In some embodiments, $R^3$ is halogen, cyano, $NH_2$, —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, is optionally substituted with one or more $R^{3a}$.

In some embodiments, $R^3$ is halogen, cyano, $NH_2$, —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl.

In some embodiments, $R^3$ is halogen, cyano, $NH_2$, —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), or —C(═O)O($C_1$-$C_6$ alkyl), wherein the —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), or —C(═O)O($C_1$-$C_6$ alkyl) is optionally substituted with one or more $R^{3a}$.

In some embodiments, $R^3$ is halogen, cyano, $NH_2$, —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), or —C(═O)O($C_1$-$C_6$ alkyl).

In some embodiments, $R^3$ is $NH_2$, —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), or —C(═O)O($C_1$-$C_6$ alkyl), wherein the —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), or —C(═O)O($C_1$-$C_6$ alkyl) is optionally substituted with one or more $R^{3a}$.

In some embodiments, $R^3$ is $NH_2$, —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)H, —C(═O)($C_1$-$C_6$ alkyl), or —C(═O)O($C_1$-$C_6$ alkyl).

In some embodiments, $R^3$ is $NH_2$, —NH($C_1$-$C_6$ alkyl), —NHC(═O)($C_1$-$C_6$ haloalkyl), —NHC(═O)O($C_1$-$C_6$ alkyl), or N($C_1$-$C_6$ alkyl)$_2$, wherein the —NH($C_1$-$C_6$ alkyl), —NHC(═O)($C_1$-$C_6$ haloalkyl), —NHC(═O)O($C_1$-$C_6$ alkyl), or N($C_1$-$C_6$ alkyl)$_2$ is optionally substituted with one or more $R^{3a}$.

In some embodiments, $R^3$ is $NH_2$, —NH($C_1$-$C_6$ alkyl), —NHC(═O)($C_1$-$C_6$ haloalkyl), —NHC(═O)O($C_1$-$C_6$ alkyl), or N($C_1$-$C_6$ alkyl)$_2$.

In some embodiments, $R^3$ is $NH_2$.

In some embodiments, $R^3$ is —NH($C_1$-$C_6$ alkyl) optionally substituted with one or more $R^{3a}$.

In some embodiments, $R^3$ is —NH($C_1$-$C_6$ alkyl).

In some embodiments, $R^3$ is —NHC(═O)($C_1$-$C_6$ haloalkyl) optionally substituted with one or more $R^{3a}$.

In some embodiments, $R^3$ is —NHC(═O)($C_1$-$C_6$ haloalkyl).

In some embodiments, $R^3$ is —NHC(═O)O($C_1$-$C_6$ alkyl) optionally substituted with one or more $R^{3a}$.

In some embodiments, $R^3$ is —NHC(═O)O($C_1$-$C_6$ alkyl).

In some embodiments, $R^3$ is N($C_1$-$C_6$ alkyl)$_2$ optionally substituted with one or more $R^{3a}$.

In some embodiments, $R^3$ is N($C_1$-$C_6$ alkyl)$_2$.

In some embodiments, $R^3$ is —S(═O)$_2$—($C_1$-$C_6$ alkyl), —C(═O)H, —C(═O)($C_1$-$C_6$ alkyl), or —C(═O)O($C_1$-$C_6$ alkyl), wherein the —S(═O)$_2$—($C_1$-$C_6$ alkyl), —C(═O)H, —C(═O)($C_1$-$C_6$ alkyl), or —C(═O)O($C_1$-$C_6$ alkyl) is optionally substituted with one or more $R^{3a}$.

In some embodiments, $R^3$ is —S(═O)$_2$—($C_1$-$C_6$ alkyl), —C(═O)H, —C(═O)($C_1$-$C_6$ alkyl), or —C(═O)O($C_1$-$C_6$ alkyl).

In some embodiments, $R^3$ is —S(═O)$_2$—($C_1$-$C_6$ alkyl) optionally substituted with one or more $R^{3a}$.

In some embodiments, $R^3$ is —S(═O)$_2$—($C_1$-$C_6$ alkyl).

In some embodiments, $R^3$ is —C(═O)H.

In some embodiments, $R^3$ is —C(═O)($C_1$-$C_6$ alkyl) optionally substituted with one or more $R^{3a}$.

In some embodiments, $R^3$ is —C(═O)($C_1$-$C_6$ alkyl).

In some embodiments, $R^3$ is —C(═O)O($C_1$-$C_6$ alkyl) optionally substituted with one or more $R^{3a}$.

In some embodiments, $R^3$ is —C(═O)O($C_1$-$C_6$ alkyl).

In some embodiments, $R^3$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, is optionally substituted with one or more $R^{3a}$.

In some embodiments, $R^3$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl.

In some embodiments, $R^3$ is $C_1$-$C_6$ alkyl, $C_2$-$C_6$ alkenyl, $C_2$-$C_6$ alkynyl, or $C_1$-$C_6$ alkoxy, wherein the $C_1$-$C_6$ alkyl, $C_2$-$C_6$ alkenyl, $C_2$-$C_6$ alkynyl, or $C_1$-$C_6$ alkoxy is optionally substituted with one or more $R^{3a}$.

In some embodiments, $R^3$ is $C_1$-$C_6$ alkyl, $C_2$-$C_6$ alkenyl, $C_2$-$C_6$ alkynyl, or $C_1$-$C_6$ alkoxy.

In some embodiments, $R^3$ is $C_1$-$C_6$ alkyl optionally substituted with one or more $R^{3a}$.

In some embodiments, $R^3$ is $C_2$-$C_6$ alkenyl optionally substituted with one or more $R^{3a}$.

In some embodiments, $R^3$ is $C_2$-$C_6$ alkenyl.

In some embodiments, $R^3$ is $C_2$-$C_6$ alkynyl optionally substituted with one or more $R^{3a}$.

In some embodiments, $R^3$ is $C_2$-$C_6$ alkynyl.

In some embodiments, $R^3$ is $C_1$-$C_6$ alkoxy optionally substituted with one or more $R^{3a}$.

In some embodiments, $R^3$ is $C_1$-$C_6$ alkoxy.

In some embodiments, $R^3$ is $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, is optionally substituted with one or more $R^{3a}$.

In some embodiments, $R^3$ is $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl.

In some embodiments, $R^3$ is $C_3$-$C_{12}$ cycloalkyl optionally substituted with one or more $R^{3a}$.

In some embodiments, $R^3$ is $C_3$-$C_{12}$ cycloalkyl.

In some embodiments, $R^3$ is $C_3$-$C_{12}$ cycloalkenyl optionally substituted with one or more $R^{3a}$.

In some embodiments, $R^3$ is $C_3$-$C_{12}$ cycloalkenyl.

In some embodiments, $R^3$ is 3- to 12-membered heterocycloalkyl optionally substituted with one or more $R^{3a}$.

In some embodiments, $R^3$ is 3- to 12-membered heterocycloalkyl.

In some embodiments, $R^3$ is 3- to 12-membered heterocycloalkenyl optionally substituted with one or more $R^{3a}$.

In some embodiments, $R^3$ is 3- to 12-membered heterocycloalkenyl.

In some embodiments, $R^3$ is $C_6$-$C_{10}$ aryl optionally substituted with one or more $R^{3a}$.

In some embodiments, $R^3$ is $C_6$-$C_{10}$ aryl.

In some embodiments, $R^3$ is 5- to 10-membered heteroaryl optionally substituted with one or more $R^{3a}$.

In some embodiments, $R^3$ is 5- to 10-membered heteroaryl.

In some embodiments, $R^3$ is halogen, cyano, or $C_1$-$C_6$ alkyl.

In some embodiments, $R^3$ is halogen. In some embodiments, $R^3$ is F or Cl.

In some embodiments, $R^3$ is F. In some embodiments, $R^3$ is Cl.

In some embodiments, $R^3$ is cyano.

In some embodiments, $R^3$ is $C_1$-$C_6$ alkyl. In some embodiments, $R^3$ is $CH_3$.

In some embodiments, each $R^{3a}$ independently is halogen, cyano, oxo, —OH, $NH_2$, —NH($C_1$-$C_6$ alkyl), —NHC(═O)O($C_1$-$C_6$ alkyl), N($C_1$-$C_6$ alkyl)$_2$, —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, 3- to 12-membered heterocycloalkyl, $C_6$-$C_{10}$ aryl, or 5- to 10-membered heteroaryl, wherein the —NH($C_1$-$C_6$ alkyl), —NHC(═O)O($C_1$-$C_6$ alkyl), N($C_1$-$C_6$ alkyl)$_2$, —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, 3- to 12-membered heterocycloalkyl, $C_6$-$C_{10}$ aryl, or 5- to 10-membered heteroaryl is optionally substituted with one or more halogen.

In some embodiments, each $R^{3a}$ independently is halogen, cyano, oxo, —OH, $NH_2$, —NH($C_1$-$C_6$ alkyl), —NHC(═O)O($C_1$-$C_6$ alkyl), N($C_1$-$C_6$ alkyl)$_2$, —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, 3- to 12-membered heterocycloalkyl, $C_6$-$C_{10}$ aryl, or 5- to 10-membered heteroaryl, wherein the NHC(═O)O($C_1$-$C_6$ alkyl) is optionally substituted with one or more halogen.

In some embodiments, each $R^{3a}$ independently is halogen, cyano, oxo, —OH, $NH_2$, —NH($C_1$-$C_6$ alkyl), —NHC(═O)O($C_1$-$C_6$ alkyl), N($C_1$-$C_6$ alkyl)$_2$, —S(═O)$_2$—($C_1$-$C_6$ alkyl), —C(═O)($C_1$-$C_6$ alkyl), or —C(═O)O($C_1$-$C_6$ alkyl), wherein the NHC(═O)O($C_1$-$C_6$ alkyl) is optionally substituted with one or more halogen.

In some embodiments, each $R^{3a}$ independently is halogen, cyano, oxo, or —OH.

In some embodiments, each $R^{3a}$ independently is halogen. In some embodiments, each $R^{3a}$ independently is cyano. In some embodiments, each $R^{3a}$ independently is oxo. In some embodiments, each $R^{3a}$ independently is —OH.

In some embodiments, each $R^{3a}$ independently is $NH_2$, —NH($C_1$-$C_6$ alkyl), —NHC(═O)O($C_1$-$C_6$ alkyl), N($C_1$-$C_6$ alkyl)$_2$, —S(═O)$_2$—($C_1$-$C_6$ alkyl), —C(═O)($C_1$-$C_6$ alkyl), or —C(═O)O($C_1$-$C_6$ alkyl), wherein the NHC(═O)O($C_1$-$C_6$ alkyl) is optionally substituted with one or more halogen.

In some embodiments, each $R^{3a}$ independently is $NH_2$.

In some embodiments, each $R^{3a}$ independently is —NH($C_1$-$C_6$ alkyl).

In some embodiments, each $R^{3a}$ independently is —NHC(═O)O($C_1$-$C_6$ alkyl) optionally substituted with one or more halogen.

In some embodiments, each $R^{3a}$ independently is —NHC(═O)O($C_1$-$C_6$ alkyl).

In some embodiments, each $R^{3a}$ independently is N($C_1$-$C_6$ alkyl)$_2$.

In some embodiments, each $R^{3a}$ independently is —S(═O)$_2$—($C_1$-$C_6$ alkyl).

In some embodiments, each $R^{3a}$ independently is —C(═O)($C_1$-$C_6$ alkyl).

In some embodiments, each $R^{3a}$ independently is —C(═O)O($C_1$-$C_6$ alkyl).

In some embodiments, each $R^{3a}$ independently is $C_1$-$C_6$ alkyl, $C_2$-$C_6$ alkenyl, $C_2$-$C_6$ alkynyl, or $C_1$-$C_6$ alkoxy.

In some embodiments, each $R^{3a}$ independently is $C_1$-$C_6$ alkyl.

In some embodiments, each $R^{3a}$ independently is $C_2$-$C_6$ alkenyl.

In some embodiments, each $R^{3a}$ independently is $C_2$-$C_6$ alkynyl.

In some embodiments, each $R^{3a}$ independently is $C_1$-$C_6$ alkoxy.

In some embodiments, each $R^{3a}$ independently is $C_3$-$C_{12}$ cycloalkyl, 3- to 12-membered heterocycloalkyl, $C_6$-$C_{10}$ aryl, or 5- to 10-membered heteroaryl.

In some embodiments, each $R^{3a}$ independently is $C_3$-$C_{12}$ cycloalkyl.

In some embodiments, each $R^{3a}$ independently is 3- to 12-membered heterocycloalkyl.

In some embodiments, each $R^{3a}$ independently is $C_6$-$C_{10}$ aryl.

In some embodiments, each $R^{3a}$ independently is 5- to 10-membered heteroaryl.

In some embodiments, $R^4$ is H.

In some embodiments, $R^4$ is halogen, cyano, or $C_1$-$C_6$ alkyl.

In some embodiments, $R^4$ is halogen. In some embodiments, $R^4$ is F or Cl.

In some embodiments, $R^4$ is F. In some embodiments, $R^4$ is Cl.

In some embodiments, $R^4$ is cyano.

In some embodiments, $R^4$ is $C_1$-$C_6$ alkyl. In some embodiments, $R^4$ is $CH_3$.

In some embodiments, $R^5$ is H.

In some embodiments, $R^5$ is halogen, cyano, or $C_1$-$C_6$ alkyl.

In some embodiments, $R^5$ is halogen. In some embodiments, $R^5$ is F or Cl.

In some embodiments, $R^5$ is F. In some embodiments, $R^5$ is Cl.

In some embodiments, $R^5$ is cyano.

In some embodiments, $R^5$ is $C_1$-$C_6$ alkyl. In some embodiments, $R^5$ is $CH_3$.

In some embodiments, $R^6$ is H.

In some embodiments, $R^6$ is halogen, cyano, or $C_1$-$C_6$ alkyl.

In some embodiments, $R^6$ is halogen. In some embodiments, $R^6$ is F or Cl.

In some embodiments, $R^6$ is F. In some embodiments, $R^6$ is Cl.

In some embodiments, $R^6$ is cyano.

In some embodiments, $R^6$ is $C_1$-$C_6$ alkyl. In some embodiments, $R^6$ is $CH_3$.

Variables Y, Z, $R^Z$, $R^{Za}$, and $R^{Zb}$

In some embodiments, Y is absent, $C_1$-$C_6$ alkyl, $C_2$-$C_6$ alkenyl, or $C_1$-$C_6$ alkoxyl, wherein the $C_1$-$C_6$ alkyl, $C_2$-$C_6$ alkenyl, or $C_1$-$C_6$ alkoxyl is optionally substituted with one or more halogen, oxo, cyano, —OH, $NH_2$, —NH($C_1$-$C_6$ alkyl)-OH, $C_1$-$C_6$ alkyl, $C_2$-$C_6$ alkenyl, $C_1$-$C_6$ alkoxyl optionally substituted with —($C_1$-$C_6$ alkyl) ($C_6$-$C_{10}$ aryl), or $C_3$-$C_{12}$ cycloalkyl.

In some embodiments, Y is absent.

In some embodiments, Y is $C_1$-$C_6$ alkyl, $C_2$-$C_6$ alkenyl, or $C_1$-$C_6$ alkoxyl, wherein the $C_1$-$C_6$ alkyl, $C_2$-$C_6$ alkenyl, or $C_1$-$C_6$ alkoxyl is optionally substituted with one or more halogen, oxo, cyano, —OH, $NH_2$, —NH($C_1$-$C_6$ alkyl)-OH, $C_1$-$C_6$ alkyl, $C_2$-$C_6$ alkenyl, $C_1$-$C_6$ alkoxyl optionally substituted with —($C_1$-$C_6$ alkyl) ($C_6$-$C_{10}$ aryl), or $C_3$-$C_{12}$ cycloalkyl.

In some embodiments, Y is $C_1$-$C_6$ alkyl, $C_2$-$C_6$ alkenyl, or $C_1$-$C_6$ alkoxyl.

In some embodiments, Y is $C_1$-$C_6$ alkyl optionally substituted with one or more halogen, oxo, cyano, —OH, $NH_2$, —NH($C_1$-$C_6$ alkyl)-OH, $C_1$-$C_6$ alkyl, $C_2$-$C_6$ alkenyl, $C_1$-$C_6$ alkoxyl.

In some embodiments, Y is $C_1$-$C_6$ alkyl. In some embodiments, Y is —$CH_2$—.

In some embodiments, Y is $C_1$-$C_6$ alkyl optionally substituted with one or more oxo, cyano, or —OH.

In some embodiments, Y is $C_1$-$C_6$ alkyl optionally substituted with one or more oxo.

In some embodiments, Y is $C_1$-$C_6$ alkyl substituted with one or more oxo.

In some embodiments, Y is methyl optionally substituted with one or more oxo.

In some embodiments, Y is methyl substituted oxo, i.e., Y is —C(═O)—.

In some embodiments, Y is $C_1$-$C_6$ alkyl optionally substituted with one or more cyano.

In some embodiments, Y is $C_1$-$C_6$ alkyl substituted with one or more cyano.

In some embodiments, Y is methyl optionally substituted with one or more cyano.

In some embodiments, Y is $C_1$-$C_6$ alkyl optionally substituted with one or more —OH.

In some embodiments, Y is $C_1$-$C_6$ alkyl substituted with one or more —OH.

In some embodiments, Z is H.

In some embodiments, Z is $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl or 5- to 10-membered heteroaryl, is optionally substituted with one or more $R^Z$.

In some embodiments, Z is $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl.

In some embodiments, Z is $C_3$-$C_{12}$ cycloalkyl optionally substituted with one or more $R^Z$.

In some embodiments, Z is $C_3$-$C_{12}$ cycloalkyl.

In some embodiments, Z is $C_3$-$C_{12}$ cycloalkenyl optionally substituted with one or more $R^Z$.

In some embodiments, Z is $C_3$-$C_{12}$ cycloalkenyl.

In some embodiments, Z is 3- to 12-membered heterocycloalkyl optionally substituted with one or more $R^Z$.

In some embodiments, Z is 3- to 12-membered heterocycloalkyl.

In some embodiments, Z is 3- to 12-membered heterocycloalkenyl optionally substituted with one or more $R^Z$.

In some embodiments, Z is 3- to 12-membered heterocycloalkenyl.

In some embodiments, Z is $C_6$-$C_{10}$ aryl optionally substituted with one or more $R^Z$.

In some embodiments, Z is $C_6$-$C_{10}$ aryl.

In some embodiments, Z is 5- to 10-membered heteroaryl optionally substituted with one or more $R^Z$.

In some embodiments, Z is 5- to 10-membered heteroaryl.

In some embodiments, Z is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^Z$.

In some embodiments, Z is $C_3$-$C_8$ cycloalkyl or 3- to 8-membered heterocycloalkyl.

In some embodiments, Z is $C_3$-$C_8$ cycloalkyl or 3- to 8-membered heterocycloalkyl, wherein the $C_3$-$C_8$ cycloalkyl or 3- to 8-membered heterocycloalkyl is substituted with one or more $R^Z$.

In some embodiments, Z is $C_3$-$C_8$ cycloalkyl optionally substituted with one or more $R^Z$.

In some embodiments, Z is $C_3$-$C_8$ cycloalkyl.

In some embodiments, Z is $C_3$-$C_8$ cycloalkyl substituted with one or more $R^Z$.

In some embodiments, Z is cyclopropyl optionally substituted with one or more $R^Z$.

In some embodiments, Z is cyclobutyl optionally substituted with one or more $R^Z$.

In some embodiments, Z is cyclohexyl optionally substituted with one or more $R^Z$.

In some embodiments, Z is 3- to 8-membered heterocycloalkyl optionally substituted with one or more $R^2$.

In some embodiments, Z is 3- to 8-membered heterocycloalkyl.

In some embodiments, Z is 3- to 8-membered heterocycloalkyl substituted with one or more $R^Z$.

In some embodiments, Z is azetidinyl or oxetanyl, wherein the azetidinyl or oxetanyl is optionally substituted with one or more Rz.

In some embodiments, Z is azetidinyl or oxetanyl.

In some embodiments, Z is azetidinyl or oxetanyl, wherein the azetidinyl or oxetanyl is substituted with one or more $R^Z$.

In some embodiments, Z is pyrrolidinyl or tetrahydrofuranyl, wherein the pyrrolidinyl or tetrahydrofuranyl is optionally substituted with one or more $R^Z$.

In some embodiments, Z is pyrrolidinyl or tetrahydrofuranyl.

In some embodiments, Z is pyrrolidinyl or tetrahydrofuranyl, wherein the pyrrolidinyl or tetrahydrofuranyl is substituted with one or more $R^Z$.

In some embodiments, Z is piperidinyl or tetrahydropyranyl, wherein the piperidinyl or tetrahydropyranyl is optionally substituted with one or more $R^Z$.

In some embodiments, Z is piperidinyl or tetrahydropyranyl.

In some embodiments, Z is piperidinyl or tetrahydropyranyl, wherein the piperidinyl or tetrahydropyranyl is substituted with one or more Rz.

In some embodiments, each $R^Z$ independently is oxo, halogen, cyano, —OH, =$NR^{Za}$, $NH_2$, $NHR^{Za}$, $NH(C_1-C_6$ alkyl), $N(C_1-C_6$ alkyl$)_2$, —$S(C_1-C_6$ alkyl), —S(═O)(═$NR^{Za}$)—($C_1-C_6$ alkyl), —S(═O)$_2$—($C_1-C_6$ alkyl), —S(═O)$_2$—($C_2-C_6$ alkenyl), —C(═O)(3- to 12-membered heterocycloalkyl), —C(═O)NH($C_1-C_6$ alkyl), —C(═O)$NR^{Za}$, —C(═O)—($C_1-C_6$ alkyl), —C(═O)—($C_2-C_6$ alkenyl), —C(═O)—($C_1-C_6$ alkoxyl), $C_1-C_6$ alkyl, $C_2-C_6$ alkenyl, $C_2-C_6$ alkynyl, $C_1-C_6$ alkoxyl, $C_3-C_{12}$ cycloalkyl, 3- to 12-membered heterocycloalkyl, or 5- to 10-membered heteroaryl, wherein the $NH(C_1-C_6$ alkyl), $N(C_1-C_6$ alkyl$)_2$, —S(═O)$_2$—($C_1-C_6$ alkyl), —C(═O)—($C_1-C_6$ alkyl), —C(═O)—($C_2-C_6$ alkenyl), $C_1$- $C_6$ alkyl, $C_2-C_6$ alkenyl, $C_2-C_6$ alkynyl, $C_1-C_6$ alkoxyl, $C_3-C_{12}$ cycloalkyl, 3- to 12-membered heterocycloalkyl, or 5- to 10-membered heteroaryl is optionally substituted with one or more $R^{Za}$.

In some embodiments, each $R^Z$ independently is oxo, halogen, cyano, —OH, =$NR^{Za}$, $NH_2$, $NHR^{Za}$, $NH(C_1-C_6$ alkyl), $N(C_1-C_6$ alkyl$)_2$, —$S(C_1-C_6$ alkyl), —S(═O)(═$NR^{Za}$)—($C_1-C_6$ alkyl), —S(═O)$_2$—($C_1-C_6$ alkyl), —S(═O)$_2$—($C_2-C_6$ alkenyl), —C(═O) (3- to 12-membered heterocycloalkyl), —C(═O)NH($C_1-C_6$ alkyl), —C(═O)$NR^{Za}$, —C(═O)—($C_1-C_6$ alkyl), —C(═O)—($C_2-C_6$ alkenyl), —C(═O)—($C_1-C_6$ alkoxyl), $C_1-C_6$ alkyl, $C_2-C_6$ alkenyl, $C_2-C_6$ alkynyl, $C_1-C_6$ alkoxyl, $C_3-C_{12}$ cycloalkyl, 3- to 12-membered heterocycloalkyl, or 5- to 10-membered heteroaryl.

In some embodiments, each $R^Z$ independently is oxo, halogen, cyano, —OH.

In some embodiments, each $R^Z$ independently is $R^Z$ is oxo.

In some embodiments, each $R^Z$ independently is $R^Z$ is halogen. In some embodiments, each $R^Z$ independently is F or Cl.

In some embodiments, each $R^2$ independently is F. In some embodiments, each $R^Z$ independently is Cl.

In some embodiments, each $R^Z$ independently is cyano. In some embodiments, each $R^Z$ independently is —OH.

In some embodiments, each $R^Z$ independently is =$NR^{Za}$. In some embodiments, each $R^Z$ independently is $NHR^{Za}$.

In some embodiments, each $R^Z$ independently is $NH_2$, $NH(C_1-C_6$ alkyl), or $N(C_1-C_6$ alkyl$)_2$, wherein the $NH(C_1-C_6$ alkyl) or $N(C_1-C_6$ alkyl$)_2$ is optionally substituted with one or more $R^{Za}$.

In some embodiments, each $R^Z$ independently is $NH_2$.

In some embodiments, each $R^Z$ independently is $NH(C_1-C_6$ alkyl), or $N(C_1-C_6$ alkyl$)_2$, wherein the $NH(C_1-C_6$ alkyl) or $N(C_1-C_6$ alkyl$)_2$ is optionally substituted with one or more $R^{Za}$.

In some embodiments, each $R^Z$ independently is $NH(C_1-C_6$ alkyl), or $N(C_1-C_6$ alkyl$)_2$.

In some embodiments, each $R^Z$ independently is $NH(C_1-C_6$ alkyl), or $N(C_1-C_6$ alkyl$)_2$, wherein the $NH(C_1-C_6$ alkyl) or $N(C_1-C_6$ alkyl$)_2$ is substituted with one or more $R^{Za}$.

In some embodiments, each $R^Z$ independently is —S(═O)$_2$—($C_1-C_6$ alkyl) optionally substituted with one or more $R^{Za}$.

In some embodiments, each $R^Z$ independently is —S(═O)$_2$—($C_1-C_6$ alkyl).

In some embodiments, each $R^Z$ independently is —S(═O)$_2$—$CH_3$.

In some embodiments, each $R^Z$ independently is —$S(C_1-C_6$ alkyl) optionally substituted with one or more $R^{Za}$.

In some embodiments, each $R^Z$ independently is —$S(C_1-C_6$ alkyl) substituted with one or more $R^{Za}$.

In some embodiments, each $R^Z$ independently is —$S(C_1-C_6$ alkyl)!

In some embodiments, each $R^Z$ independently is —S(═$NR^{Za}$)—($C_1-C_6$ alkyl) optionally substituted with one or more $R^{Za}$.

In some embodiments, each $R^Z$ independently is —S(═$NR^{Za}$)—($C_1-C_6$ alkyl) substituted with one or more $R^{Za}$.

In some embodiments, each $R^Z$ independently is —S(═$NR^{Za}$)—($C_1-C_6$ alkyl).

In some embodiments, each $R^Z$ independently is —$S(C_2-C_6$ alkenyl) optionally substituted with one or more $R^{Za}$.

In some embodiments, each $R^Z$ independently is —$S(C_2-C_6$ alkenyl) substituted with one or more $R^{Za}$.

In some embodiments, each $R^Z$ independently is —$S(C_2-C_6$ alkenyl).

In some embodiments, at least one $R^Z$ is —C(═O)—($C_1-C_6$ alkyl) or —C(═O)—($C_2-C_6$ alkenyl), wherein the —C(═O)—($C_1-C_6$ alkyl) or —C(═O)—($C_2-C_6$ alkenyl) is optionally substituted with one or more $R^{Za}$.

In some embodiments, each $R^Z$ independently is —C(═O)—($C_1-C_6$ alkyl) or —C(═O)—($C_2-C_6$ alkenyl).

In some embodiments, each $R^Z$ independently is —C(═O)—($C_1-C_6$ alkyl).

In some embodiments, each $R^Z$ independently is —C(═O)—($C_1-C_6$ alkyl).

In some embodiments, each $R^Z$ independently is —C(═O)—CH═$CH_2$.

In some embodiments, each $R^Z$ independently is —C(═O)—($C_1-C_6$ alkyl) or —C(═O)—($C_2-C_6$ alkenyl), wherein the —C(═O)—($C_1-C_6$ alkyl) or —C(═O)—($C_2-C_6$ alkenyl) is substituted with one or more $R^{Za}$.

In some embodiments, each $R^Z$ independently is —S(═O)$_2$—($C_2-C_6$ alkenyl), —C(═O)(3- to 12-membered heterocycloalkyl), —C(═O)NH($C_1-C_6$ alkyl), —C(═O)$NR^{Za}$, —C(═O)—($C_1-C_6$ alkyl), —C(═O)—($C_2-C_6$ alkenyl), or —C(═O)—($C_1-C_6$ alkoxyl), wherein the —S(═O)$_2$—($C_2-C_6$ alkenyl), —C(═O) (3- to 12-membered heterocycloalkyl), —C(═O)NH($C_1-C_6$ alkyl), —C(═O)$NR^{Za}$, —C(═O)—($C_1-C_6$ alkyl), —C(═O)—($C_2-C_6$ alkenyl), or —C(═O)—($C_1-C_6$ alkoxyl) is optionally substituted with one or more $R^{Za}$.

In some embodiments, each $R^Z$ independently is —S(═O)$_2$—($C_2-C_6$ alkenyl), —C(═O)(3- to 12-membered heterocycloalkyl), —C(═O)NH($C_1-C_6$ alkyl), —C(═O)$NR^{Za}$, —C(═O)—($C_1-C_6$ alkyl), —C(═O)—($C_2-C_6$ alkenyl), or —C(═O)—($C_1-C_6$ alkoxyl).

In some embodiments, each $R^Z$ independently is —S(═O)$_2$—($C_2-C_6$ alkenyl) optionally substituted with one or more $R^{Za}$.

In some embodiments, each $R^Z$ independently is —S(═O)$_2$—($C_2-C_6$ alkenyl).

In some embodiments, each $R^Z$ independently is —C(═O) (3- to 12-membered heterocycloalkyl) optionally substituted with one or more $R^{Za}$.

In some embodiments, each $R^Z$ independently is —C(═O)(3- to 12-membered heterocycloalkyl).

In some embodiments, each $R^Z$ independently is —C(═O)NH($C_1$-$C_6$ alkyl) optionally substituted with one or more $R^{Za}$.

In some embodiments, each $R^Z$ independently is —C(═O)NH($C_1$-$C_6$ alkyl).

In some embodiments, each $R^Z$ independently is —C(═O)$NR^{Za}$.

In some embodiments, each $R^Z$ independently is —C(═O)—($C_1$-$C_6$ alkyl) optionally substituted with one or more $R^{Za}$.

In some embodiments, each $R^Z$ independently is C(═O)—($C_1$-$C_6$ alkyl).

In some embodiments, each $R^Z$ independently is —C(═O)—($C_2$-$C_6$ alkenyl) optionally substituted with one or more $R^{Za}$.

In some embodiments, each $R^Z$ independently is —C(═O)—($C_2$-$C_6$ alkenyl).

In some embodiments, each $R^Z$ independently is —C(═O)—($C_1$-$C_6$ alkoxyl) optionally substituted with one or more $R^{Za}$.

In some embodiments, each $R^Z$ independently is —C(═O)—($C_1$-$C_6$ alkoxyl).

In some embodiments, each $R^Z$ independently is 5- to 10-membered heteroaryl optionally substituted with one or more $R^{Za}$.

In some embodiments, each $R^Z$ independently is 5- to 10-membered heteroaryl.

In some embodiments, each $R^Z$ independently is $C_1$-$C_6$ alkyl, $C_2$-$C_6$ alkenyl, $C_2$-$C_6$ alkynyl, or $C_1$-$C_6$ alkoxyl, wherein the $C_1$-$C_6$ alkyl, $C_2$-$C_6$ alkenyl, $C_2$-$C_6$ alkynyl, or $C_1$-$C_6$ alkoxyl is optionally substituted with one or more $R^{Za}$.

In some embodiments, each $R^Z$ independently is $C_1$-$C_6$ alkyl optionally substituted with one or more $R^{Za}$.

In some embodiments, each $R^Z$ independently is $C_1$-$C_6$ alkyl.

In some embodiments, each $R^Z$ independently is $C_1$-$C_6$ alkyl substituted with one or more $R^{Za}$.

In some embodiments, each $R^Z$ independently is $C_2$-$C_6$ alkenyl optionally substituted with one or more $R^{Za}$.

In some embodiments, each $R^Z$ independently is $C_2$-$C_6$ alkenyl.

In some embodiments, each $R^Z$ independently is $C_2$-$C_6$ alkenyl substituted with one or more $R^{Za}$.

In some embodiments, each $R^Z$ independently is $C_2$-$C_6$ alkynyl optionally substituted with one or more $R^{Za}$.

In some embodiments, each $R^Z$ independently is $C_2$-$C_6$ alkynyl.

In some embodiments, each $R^Z$ independently is $C_2$-$C_6$ alkynyl substituted with one or more $R^{Za}$.

In some embodiments, each $R^Z$ independently is $C_1$-$C_6$ alkoxyl is optionally substituted with one or more $R^{Za}$.

In some embodiments, each $R^Z$ independently is $C_1$-$C_6$ alkoxyl.

In some embodiments, each $R^Z$ independently is $C_1$-$C_6$ alkoxyl is substituted with one or more $R^{Za}$.

In some embodiments, each $R^Z$ independently is $C_3$-$C_{12}$ cycloalkyl or 3- to 12-membered heterocycloalkyl, wherein the $C_3$-$C_{12}$ cycloalkyl or 3- to 12-membered heterocycloalkyl is optionally substituted with one or more $R^{Za}$.

In some embodiments, each $R^Z$ independently is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^{Za}$.

In some embodiments, each $R^Z$ independently is $C_3$-$C_{12}$ cycloalkyl optionally substituted with one or more $R^{Za}$.

In some embodiments, each $R^Z$ independently is $C_3$-$C_{12}$ cycloalkyl.

In some embodiments, each $R^Z$ independently is $C_3$-$C_{12}$ cycloalkyl substituted with one or more $R^{Za}$.

In some embodiments, each $R^Z$ independently is $C_3$-$C_8$ cycloalkyl optionally substituted with one or more $R^{Za}$.

In some embodiments, each $R^Z$ independently is $C_3$-$C_8$ cycloalkyl.

In some embodiments, each $R^Z$ independently is $C_3$-$C_8$ cycloalkyl substituted with one or more $R^{Za}$.

In some embodiments, each $R^Z$ independently is 3- to 12-membered heterocycloalkyl optionally substituted with one or more $R^{Za}$.

In some embodiments, each $R^Z$ independently is 3- to 12-membered heterocycloalkyl.

In some embodiments, each $R^Z$ independently is 3- to 12-membered heterocycloalkyl substituted with one or more $R^{Za}$.

In some embodiments, each $R^Z$ independently is 3- to 8-membered heterocycloalkyl optionally substituted with one or more $R^{Za}$.

In some embodiments, each $R^Z$ independently is 3- to 8-membered heterocycloalkyl.

In some embodiments, each $R^Z$ independently is 3- to 8-membered heterocycloalkyl substituted with one or more $R^{Za}$.

In some embodiments, each $R^{Za}$ independently is H, oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$- $C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, or 3- to 12-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, or 3- to 12-membered heterocycloalkyl is optionally substituted with one or more $R^{Zb}$.

In some embodiments, each $R^{Za}$ independently is H, oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$- $C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, or 3- to 12-membered heterocycloalkyl.

In some embodiments, each $R^{Za}$ independently is H.

In some embodiments, each $R^{Za}$ independently is oxo, halogen, cyano, —OH.

In some embodiments, each $R^{Za}$ independently is oxo.

In some embodiments, each $R^{Za}$ independently is halogen. In some embodiments, each $R^{Za}$ independently is F or Cl.

In some embodiments, each $R^{Za}$ independently is F. In some embodiments, each $R^{Za}$ independently is Cl.

In some embodiments, each $R^{Za}$ independently is cyano.

In some embodiments, each $R^{Za}$ independently is —OH.

In some embodiments, each $R^{Za}$ independently is $NH_2$, NH($C_1$-$C_6$ alkyl), or N($C_1$-$C_6$ alkyl)$_2$, wherein the NH($C_1$-$C_6$ alkyl) or N($C_1$-$C_6$ alkyl)$_2$ is optionally substituted with one or more $R^{Zb}$.

In some embodiments, each $R^{Za}$ independently is $NH_2$.

In some embodiments, each $R^{Za}$ independently is NH($C_1$-$C_6$ alkyl), or N($C_1$-$C_6$ alkyl)$_2$, wherein the NH($C_1$-$C_6$ alkyl) or N($C_1$-$C_6$ alkyl)$_2$ is optionally substituted with one or more $R^{Zb}$.

In some embodiments, each $R^{Za}$ independently is NH($C_1$-$C_6$ alkyl), or N($C_1$-$C_6$ alkyl)$_2$.

In some embodiments, each $R^{Za}$ independently is $NH(C_1-C_6$ alkyl), or $N(C_1-C_6$ alkyl$)_2$, wherein the $NH(C_1-C_6$ alkyl) or $N(C_1-C_6$ alkyl$)_2$ is substituted with one or more $R^{Zb}$.

In some embodiments, each $R^{Za}$ independently is $—S(=O)_2—(C_1-C_6$ alkyl) optionally substituted with one or more $R^{Zb}$.

In some embodiments, each $R^{Za}$ independently is $—S(=O)_2—(C_1-C_6$ alkyl).

In some embodiments, each $R^{Za}$ independently is $—S(=O)_2—CH_3$.

In some embodiments, each $R^{Za}$ independently is $—S(=O)_2—(C_1-C_6$ alkyl) substituted with one or more $R^{Zb}$.

In some embodiments, each $R^{Za}$ independently is $—C(=O)—(C_1-C_6$ alkyl) or $—C(=O)—(C_2-C_6$ alkenyl), wherein the $—C(=O)—(C_1-C_6$ alkyl) or $—C(=O)—(C_2-C_6$ alkenyl) is optionally substituted with one or more $R^{Zb}$.

In some embodiments, each $R^{Za}$ independently is $—C(=O)—(C_1-C_6$ alkyl) or $—C(=O)—(C_2-C_6$ alkenyl).

In some embodiments, each $R^{Za}$ independently is $—C(=O)—(C_1-C_6$ alkyl).

In some embodiments, each $R^{Za}$ independently is $—C(=O)—(C_1-C_6$ alkyl).

In some embodiments, each $R^{Za}$ independently is $—C(=O)—CH=CH_2$.

In some embodiments, each $R^{Za}$ independently is $—C(=O)—(C_1-C_6$ alkyl) or $—C(=O)—(C_2-C_6$ alkenyl), wherein the $—C(=O)—(C_1-C_6$ alkyl) or $—C(=O)—(C_2-C_6$ alkenyl) is substituted with one or more $R^{Zb}$.

In some embodiments, each $R^{Za}$ independently is $C_1-C_6$ alkyl, $C_2-C_6$ alkenyl, $C_2-C_6$ alkynyl, or $C_1-C_6$ alkoxyl, wherein the $C_1-C_6$ alkyl, $C_2-C_6$ alkenyl, $C_2-C_6$ alkynyl, or $C_1-C_6$ alkoxyl is optionally substituted with one or more $R^{Zb}$.

In some embodiments, each $R^{Za}$ independently is $C_1-C_6$ alkyl optionally substituted with one or more $R^{Zb}$.

In some embodiments, each $R^{Za}$ independently is $C_1-C_6$ alkyl.

In some embodiments, each $R^{Za}$ independently is $C_1-C_6$ alkyl substituted with one or more $R^{Zb}$.

In some embodiments, each $R^{Za}$ independently is $C_2-C_6$ alkenyl optionally substituted with one or more $R^{Zb}$.

In some embodiments, each $R^{Za}$ independently is $C_2-C_6$ alkenyl.

In some embodiments, each $R^{Za}$ independently is $C_2-C_6$ alkenyl substituted with one or more $R^{Zb}$.

In some embodiments, each $R^{Za}$ independently is $C_2-C_6$ alkynyl optionally substituted with one or more $R^{Zb}$.

In some embodiments, each $R^{Za}$ independently is $C_2-C_6$ alkynyl.

In some embodiments, each $R^{Za}$ independently is $C_2-C_6$ alkynyl substituted with one or more $R^{Zb}$.

In some embodiments, each $R^{Za}$ independently is $C_1-C_6$ alkoxyl is optionally substituted with one or more $R^{Zb}$.

In some embodiments, each $R^{Za}$ independently is $C_1-C_6$ alkoxyl.

In some embodiments, each $R^{Za}$ independently is $C_1-C_6$ alkoxyl is substituted with one or more $R^{Zb}$.

In some embodiments, each $R^{Za}$ independently is $C_3-C_{12}$ cycloalkyl or 3- to 12-membered heterocycloalkyl, wherein the $C_3-C_{12}$ cycloalkyl or 3- to 12-membered heterocycloalkyl is optionally substituted with one or more $R^{Zb}$.

In some embodiments, each $R^{Za}$ independently is $C_3-C_{12}$ cycloalkyl optionally substituted with one or more $R^{Zb}$.

In some embodiments, each $R^{Za}$ independently is $C_3-C_{12}$ cycloalkyl.

In some embodiments, each $R^{Za}$ independently is $C_3-C_{12}$ cycloalkyl substituted with one or more $R^{Zb}$.

In some embodiments, each $R^{Za}$ independently is 3- to 12-membered heterocycloalkyl optionally substituted with one or more $R^{Zb}$.

In some embodiments, each $R^{Za}$ independently is 3- to 12-membered heterocycloalkyl.

In some embodiments, each $R^{Za}$ independently is 3- to 12-membered heterocycloalkyl substituted with one or more $R^{Zb}$.

In some embodiments, each $R^{Za}$ independently is $C_3-C_8$ cycloalkyl or 3- to 8-membered heterocycloalkyl, wherein the $C_3-C_8$ cycloalkyl or 3- to 8-membered heterocycloalkyl is optionally substituted with one or more $R^{Zb}$.

In some embodiments, each $R^{Za}$ independently is $C_3-C_8$ cycloalkyl optionally substituted with one or more $R^{Zb}$.

In some embodiments, each $R^{Za}$ independently is $C_3-C_8$ cycloalkyl.

In some embodiments, each $R^{Za}$ independently is $C_3-C_8$ cycloalkyl substituted with one or more $R^{Zb}$.

In some embodiments, each $R^{Za}$ independently is 3- to 8-membered heterocycloalkyl optionally substituted with one or more $R^{Zb}$.

In some embodiments, each $R^{Za}$ independently is 3- to 8-membered heterocycloalkyl.

In some embodiments, each $R^{Za}$ independently is 3- to 8-membered heterocycloalkyl substituted with one or more $R^{Zb}$.

In some embodiments, each $R^{Zb}$ independently is oxo, halogen, cyano, —OH, $NH_2$, $NH(C_1-C_6$ alkyl), $N(C_1-C_6$ alkyl$)_2$, $—S(=O)_2—(C_1-C_6$ alkyl), $—C(=O)—(C_1-C_6$ alkyl), $—C(=O)—(C_2-C_6$ alkenyl), $C_1-C_6$ alkyl, $C_2-C_6$ alkenyl, $C_2-C_6$ alkynyl, or $C_1-C_6$ alkoxyl.

In some embodiments, each $R^{Zb}$ independently is oxo, halogen, cyano, or —OH.

In some embodiments, each $R^{Zb}$ independently is oxo.

In some embodiments, each $R^{Zb}$ independently is halogen. In some embodiments, each $R^{Zb}$ independently is F or Cl.

In some embodiments, each $R^{Zb}$ independently is F. In some embodiments, each $R^{Zb}$ independently is Cl.

In some embodiments, each $R^{Zb}$ independently is cyano. In some embodiments, each $R^{Zb}$ independently is —OH.

In some embodiments, each $R^{2b}$ independently is $NH_2$, $NH(C_1-C_6$ alkyl), or $N(C_1-C_6$ alkyl$)_2$.

In some embodiments, each $R^{Zb}$ independently is $NH_2$.

In some embodiments, each $R^{Zb}$ independently is $NH(C_1-C_6$ alkyl).

In some embodiments, each $R^{Zb}$ independently is $N(C_1-C_6$ alkyl$)_2$.

In some embodiments, each $R^{Zb}$ independently is $—S(=O)_2—(C_1-C_6$ alkyl).

In some embodiments, each $R^{Zb}$ independently is $—C(=O)—(C_1-C_6$ alkyl) or $—C(=O)—(C_2-C_6$ alkenyl).

In some embodiments, each $R^{Zb}$ independently is $—C(=O)—(C_1-C_6$ alkyl).

In some embodiments, each $R^{Zb}$ independently is $—C(=O)—(C_2-C_6$ alkenyl).

In some embodiments, each $R^{Zb}$ independently is $—C(=O)—CH=CH_2$.

In some embodiments, each $R^{Zb}$ independently is $C_1-C_6$ alkyl, $C_2-C_6$ alkenyl, $C_2-C_6$ alkynyl, or $C_1-C_6$ alkoxyl.

In some embodiments, each $R^{Zb}$ independently is $C_1-C_6$ alkyl.

In some embodiments, each $R^{Zb}$ independently is $C_2-C_6$ alkenyl.

In some embodiments, each $R^{Zb}$ independently is $C_2-C_6$ alkynyl.

In some embodiments, each $R^{Z}6$ independently is $C_1-C_6$ alkoxyl.

EXEMPLARY EMBODIMENTS OF THE COMPOUNDS

In some embodiments, the compound is of Formula (I'):

(I')

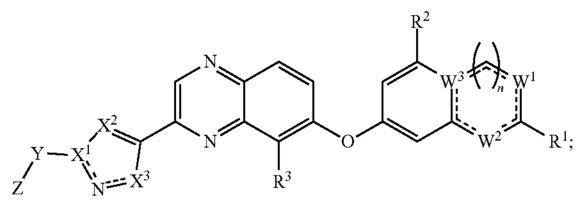

or a pharmaceutically acceptable salt or stereoisomer thereof.

In some embodiments, the compound is of Formula (I-a), (I-b), (I-c), or (I-d):

(I-a)

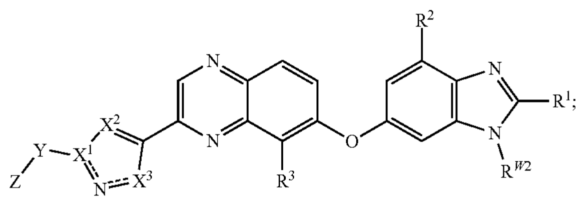

(I-b)

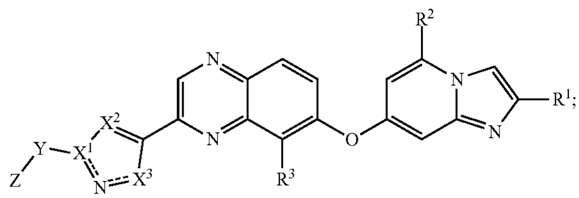

(I-c)

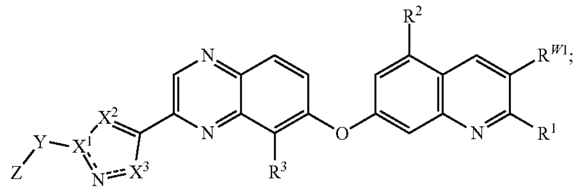

(I-d)

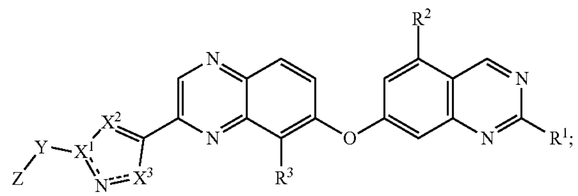

or a pharmaceutically acceptable salt or stereoisomer thereof.

In some embodiments, the compound is of Formula (II):

(II)

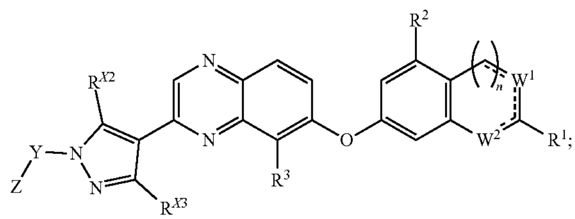

or a pharmaceutically acceptable salt or stereoisomer thereof.

In some embodiments, the compound is of Formula (II-a), (II-b), (II-c), or (II-d):

(II-a)

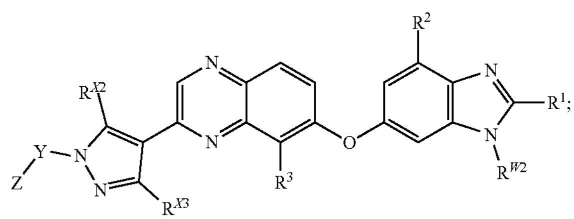

(II-b)

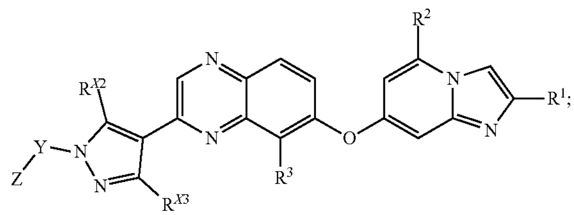

(II-c)

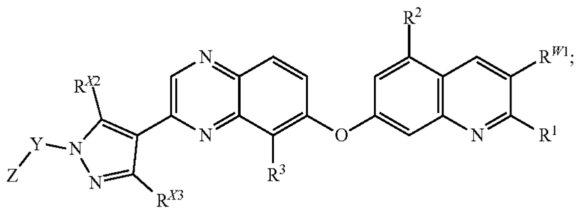

(II-d)

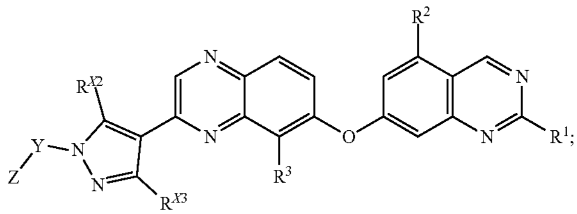

or a pharmaceutically acceptable salt or stereoisomer thereof.

In some embodiments, the compound is a compounds described in Table I and II, or a pharmaceutically acceptable salt or stereoisomer thereof.

In some embodiments, the compound is a compounds described in Table I and II, or a pharmaceutically acceptable salt thereof.

In some embodiments, the compound is a compounds described in Table I and II.

In some embodiments, the compound is a compounds described in Table II, or a pharmaceutically acceptable salt or stereoisomer thereof.

In some embodiments, the compound is a compounds described in Table II, or a pharmaceutically acceptable salt thereof.

In some embodiments, the compound is a compounds described in Table II.

In some embodiments, the compound is a compounds described in Table I, or a pharmaceutically acceptable salt or stereoisomer thereof.

In some embodiments, the compound is a compounds described in Table I, or a pharmaceutically acceptable salt thereof.

In some embodiments, the compound is a compounds described in Table I.

TABLE I

| Compound No. | Structure |
|---|---|
| 1 | 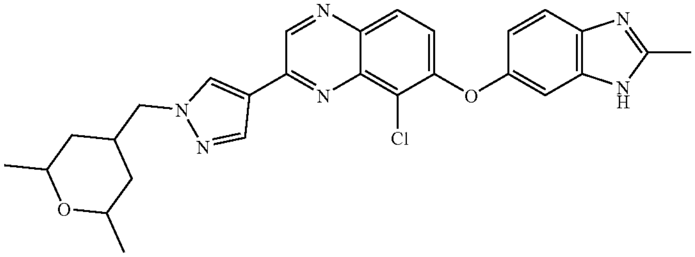 |
| 2 | 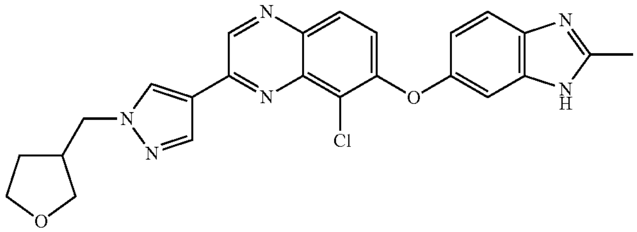 [SMILES: Cc1nc2ccc(Oc3ccc4ncc(-c5cnn(CC6CCOC6)c5)nc4c3Cl)cc2[nH]1] |
| 3 | 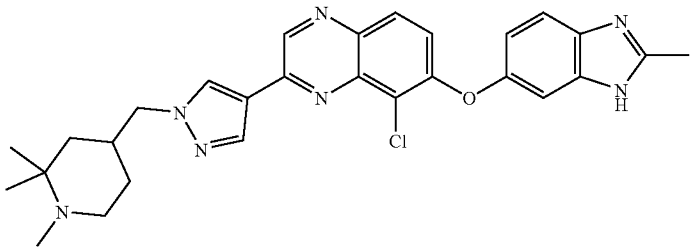 |
| 4 | 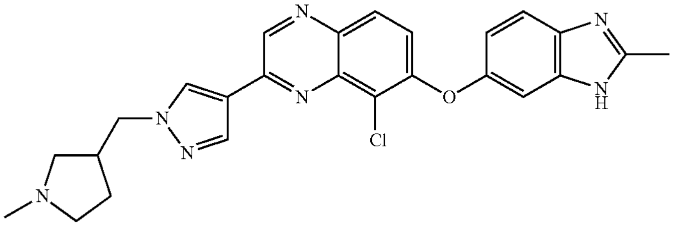 |
| 5 | 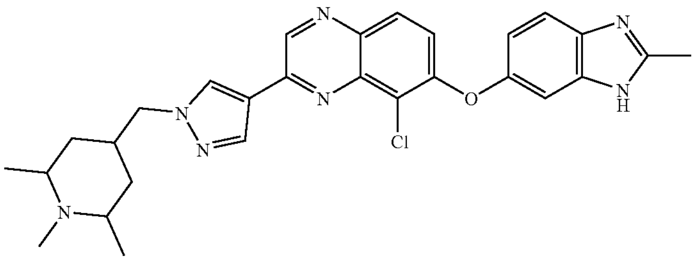 |

TABLE I-continued
| Compound No. | Structure |
|---|---|
| 6 | 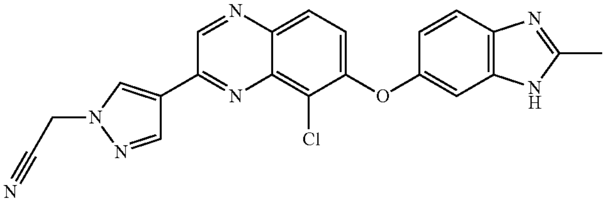 [SMILES: Cc1nc2ccc(Oc3ccc4ncc(-c5cnn(CC#N)c5)nc4c3Cl)cc2[nH]1] |
| 7 | 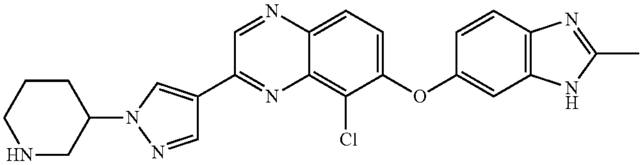 [SMILES: Cc1nc2ccc(Oc3ccc4ncc(-c5cnn(C6CCCNC6)c5)nc4c3Cl)cc2[nH]1] |
| 8 | 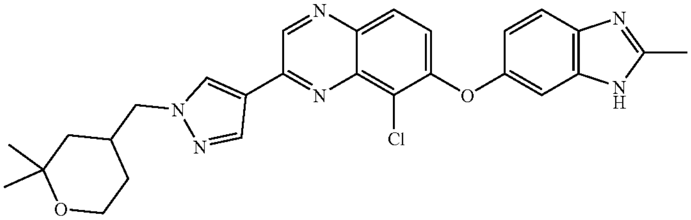 |
| 9 | 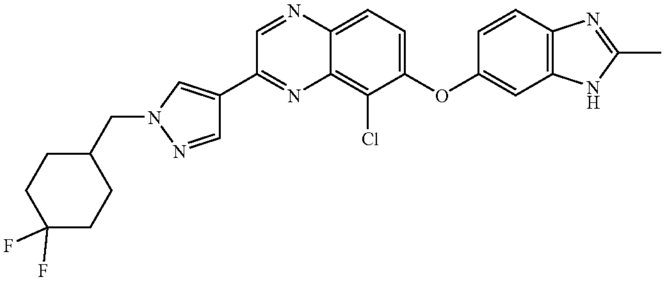 |
| 10 | 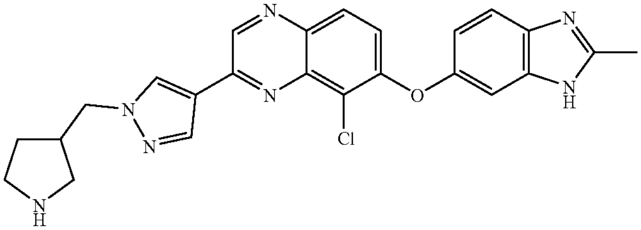 |
| 11 | 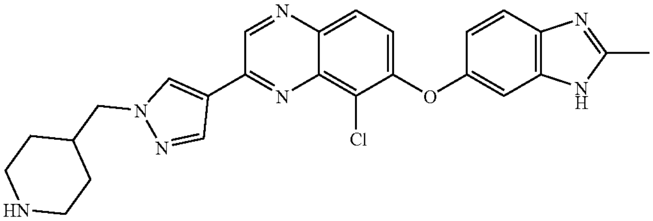 |

TABLE I-continued
| Compound No. | Structure |
|---|---|
| 12 | 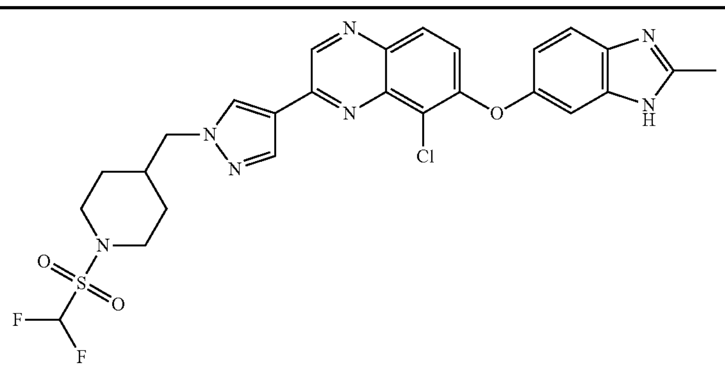 |
| 13 | 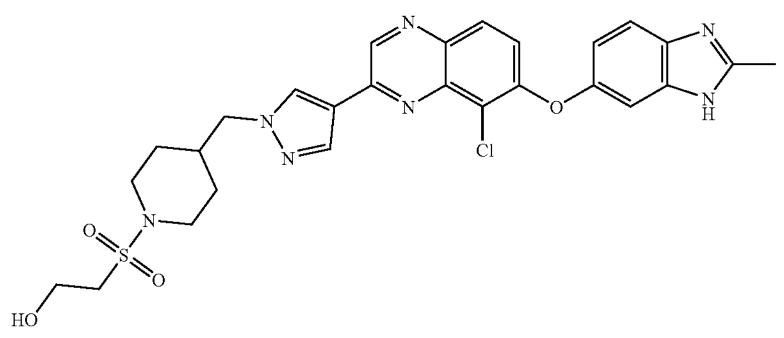 |
| 14 | 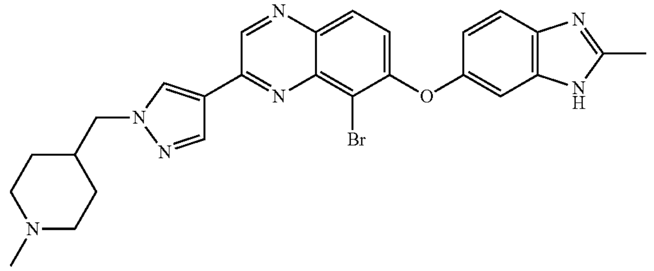 [SMILES: Cc1nc2ccc(Oc3ccc4ncc(-c5cnn(CC6CCN(C)CC6)c5)nc4c3Br)cc2[nH]1] |
| 15 | 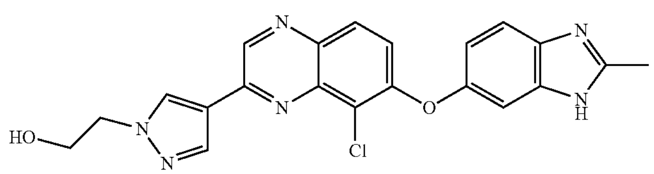 [SMILES: Cc1nc2ccc(Oc3ccc4ncc(-c5cnn(CCO)c5)nc4c3Cl)cc2[nH]1] |
| 16 | 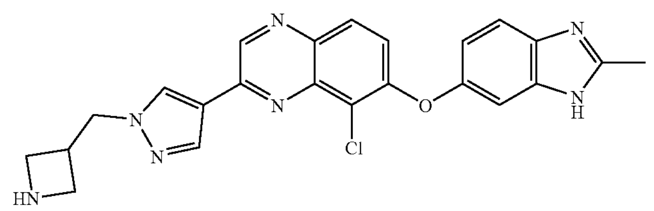 |
| 17 | 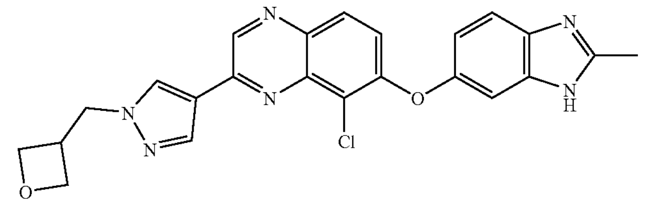 |

TABLE I-continued
| Compound No. | Structure |
|---|---|
| 18 | 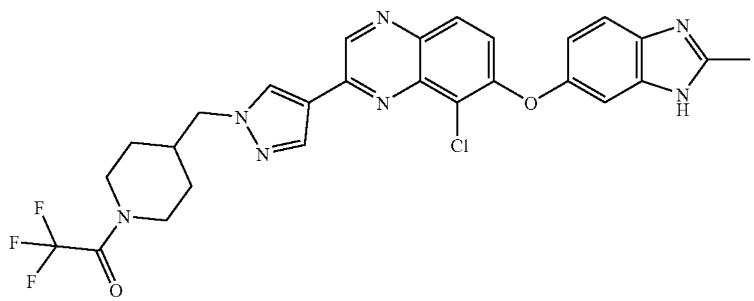 |
| 19 | 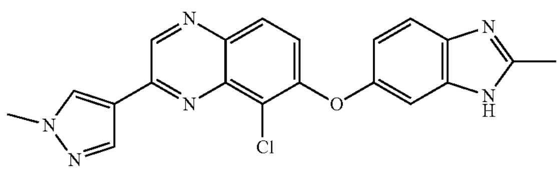 |
| 20 | 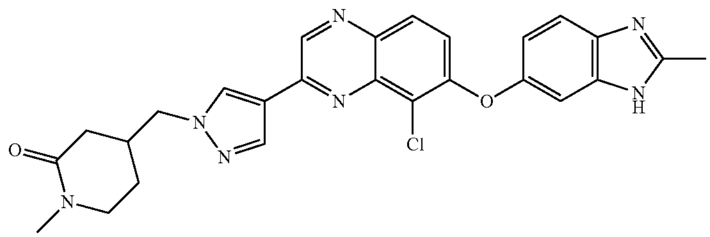 [SMILES: Cc1nc2ccc(Oc3ccc4ncc(-c5cnn(CC6CCN(C)C(=O)C6)c5)nc4c3Cl)cc2[nH]1] |
| 21 | 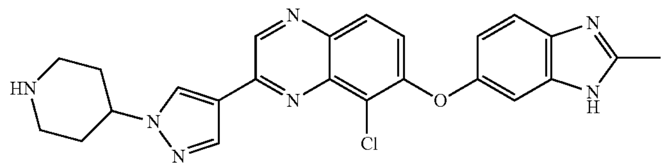 [SMILES: Cc1nc2ccc(Oc3ccc4ncc(-c5cnn(C6CCNCC6)c5)nc4c3Cl)cc2[nH]1] |
| 22 | 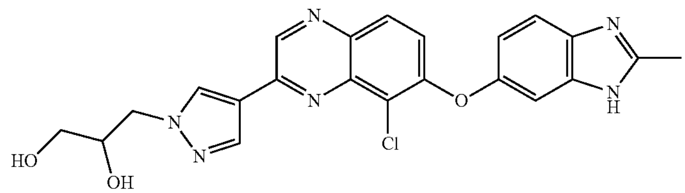 [SMILES: Cc1nc2ccc(Oc3ccc4ncc(-c5cnn(CC(O)CO)c5)nc4c3Cl)cc2[nH]1] |
| 23 | 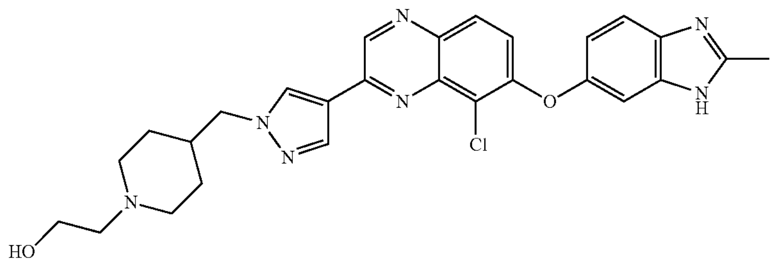 [SMILES: Cc1nc2ccc(Oc3ccc4ncc(-c5cnn(CC6CCN(CCO)CC6)c5)nc4c3Cl)cc2[nH]1] |

TABLE I-continued
| Compound No. | Structure |
|---|---|
| 24 | 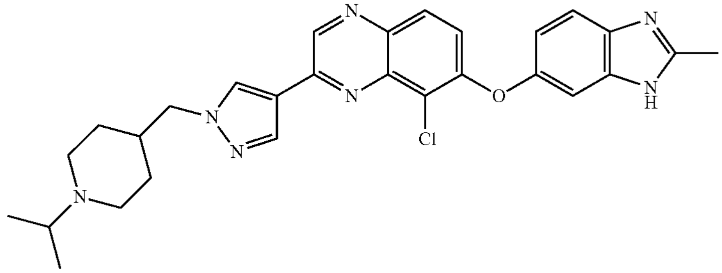 [SMILES: Cc1nc2ccc(Oc3ccc4ncc(-c5cnn(CC6CCN(C(C)C)CC6)c5)nc4c3Cl)cc2[nH]1] |
| 25 | 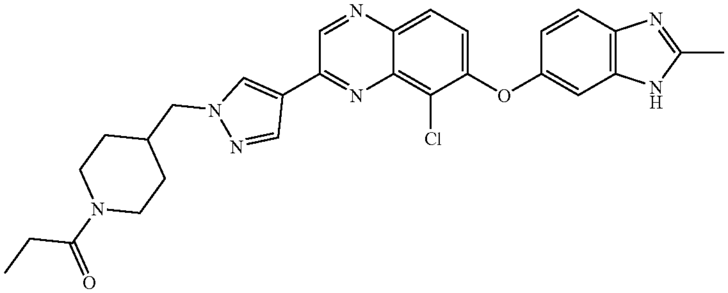 |
| 26 | 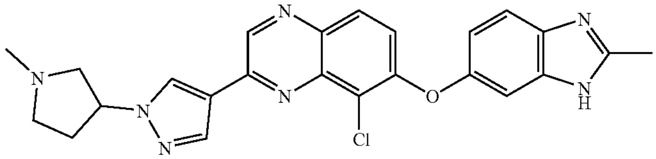 |
| 27 | 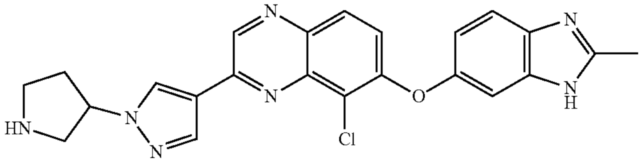 [SMILES: Cc1nc2ccc(Oc3ccc4ncc(-c5cnn(C6CCNC6)c5)nc4c3Cl)cc2[nH]1] |
| 28 | 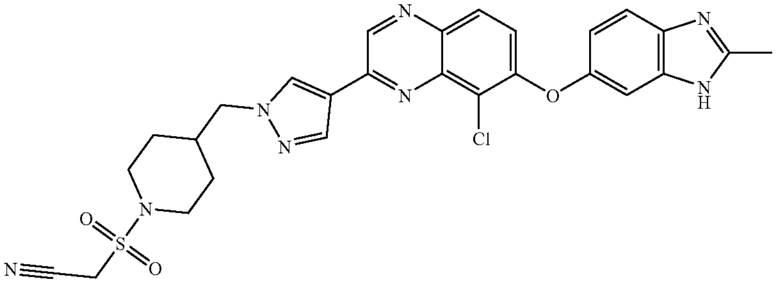 |
| 29 | 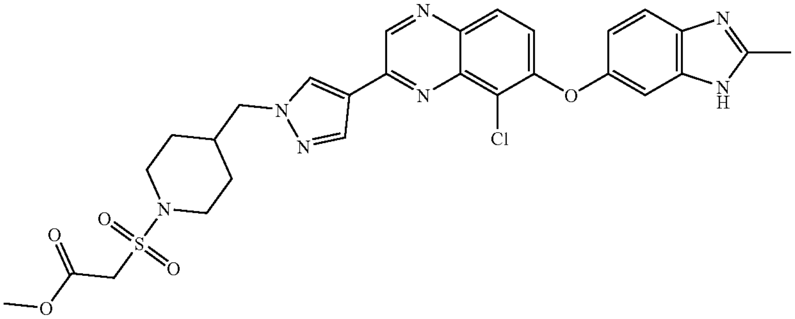 |

TABLE I-continued
| Compound No. | Structure |
|---|---|
| 30 | 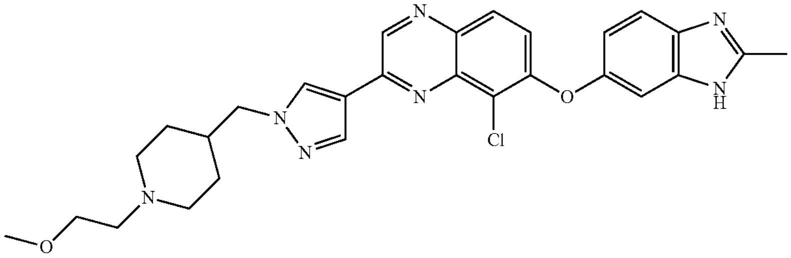 |
| 31 | 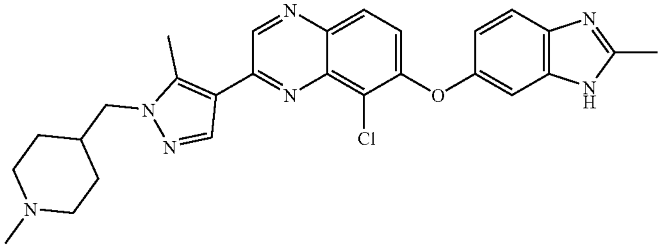 |
| 32 | 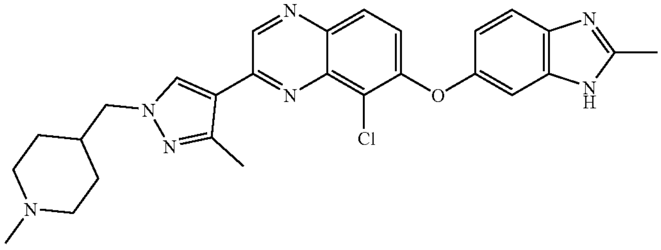 |
| 33 | 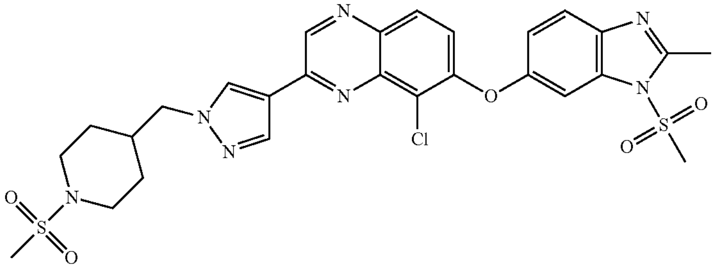 |
| 34 | 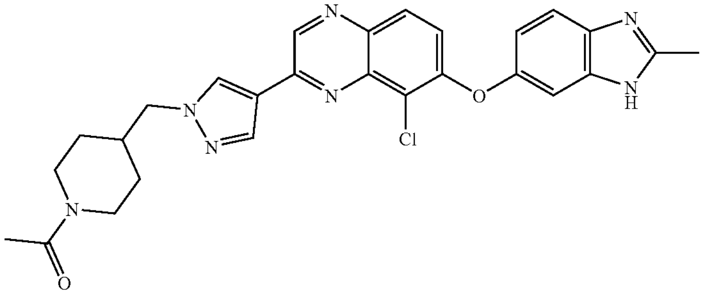 |

TABLE I-continued
| Compound No. | Structure |
| --- | --- |
| 35 | 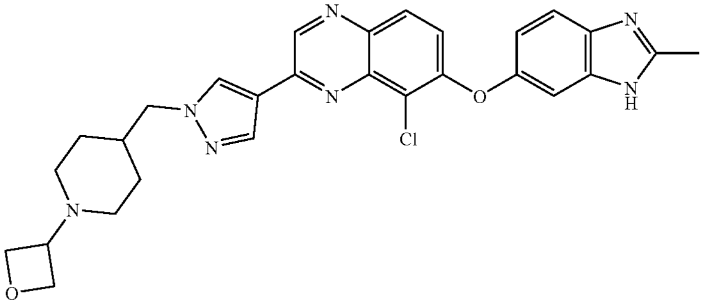 |
| 36 | 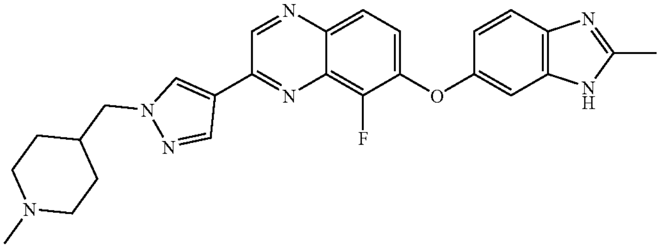 |
| 37 | 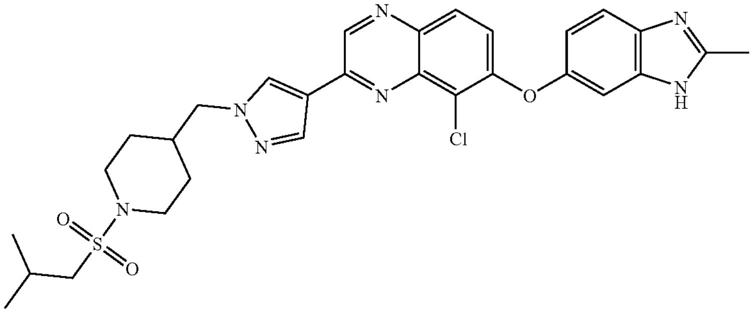 |
| 38 | 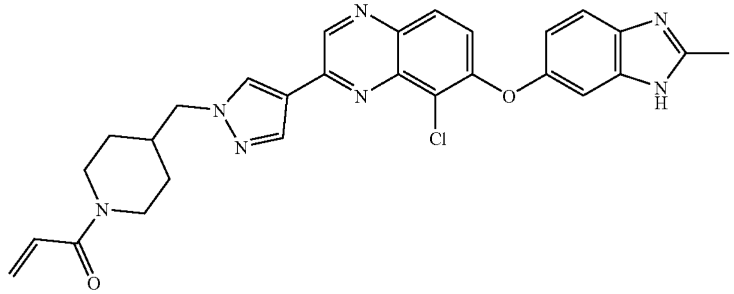 |
| 39 | 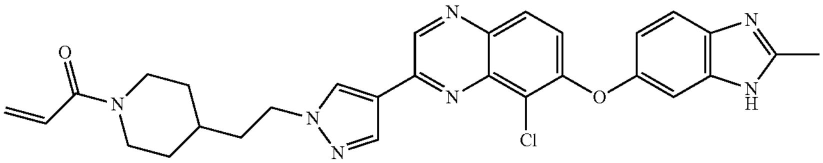 [SMILES: C=CC(=O)N1CCC(CCn2cc(-c3cnc4ccc(Oc5ccc6nc(C)[nH]c6c5)c(Cl)c4n3)cn2)CC1] |

TABLE I-continued
| Compound No. | Structure |
| --- | --- |
| 40 | 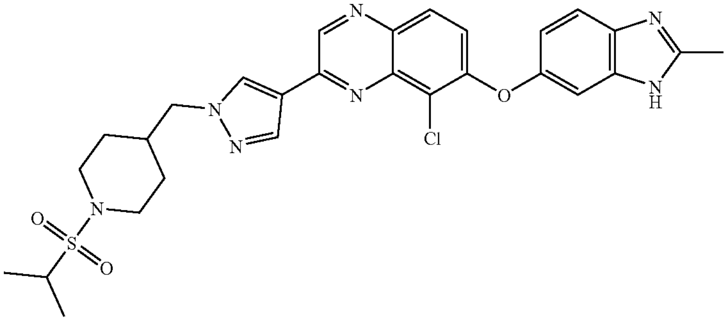 |
| 41 | 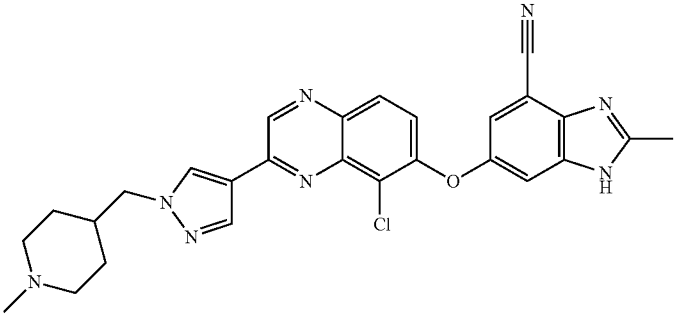 |
| 42 | 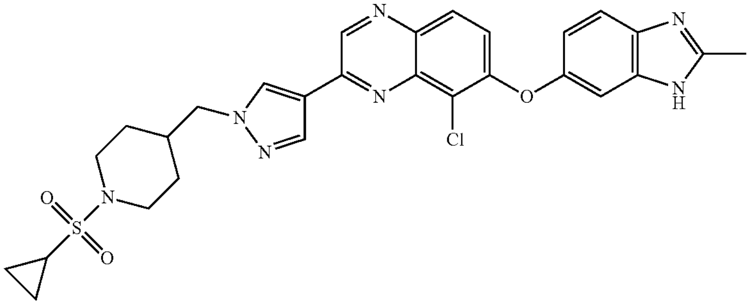 [SMILES: Cc1nc2ccc(Oc3ccc4ncc(-c5cnn(CC6CCN(S(=O)(=O)C7CC7)CC6)c5)nc4c3Cl)cc2[nH]1] |
| 43 | 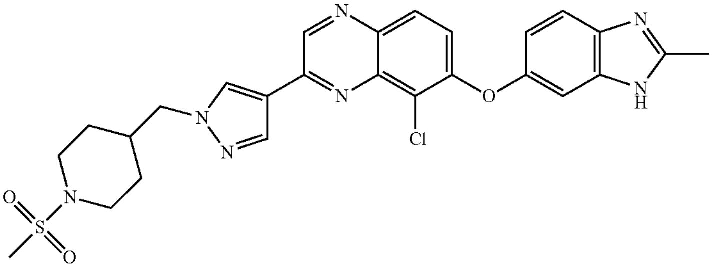 |
| 44 | 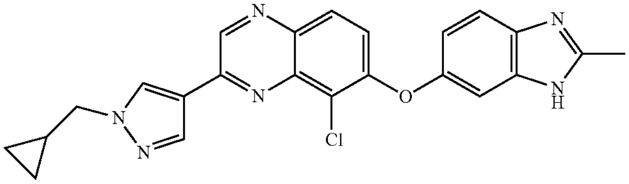 [SMILES: Cc1nc2ccc(Oc3ccc4ncc(-c5cnn(CC6CC6)c5)nc4c3Cl)cc2[nH]1] |

TABLE I-continued
| Compound No. | Structure |
|---|---|
| 45 | 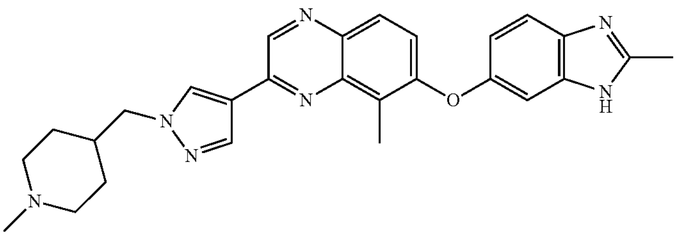 |
| 46 | 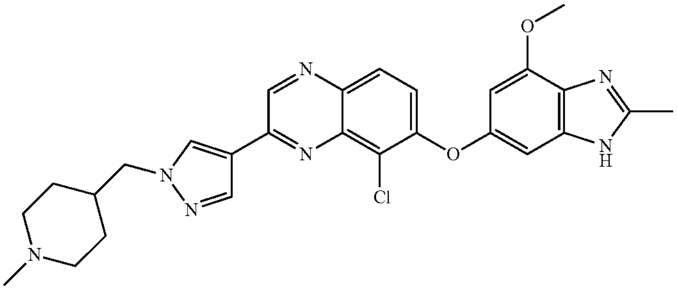 |
| 47 | 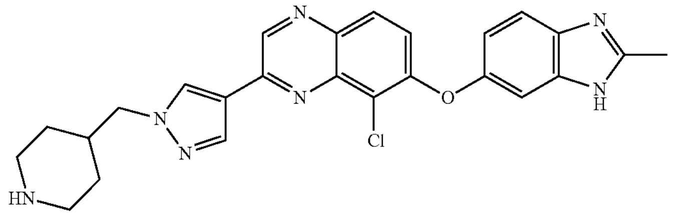 [SMILES: Cc1nc2ccc(Oc3ccc4ncc(-c5cnn(CC6CCNCC6)c5)nc4c3Cl)cc2[nH]1] |
| 48 | 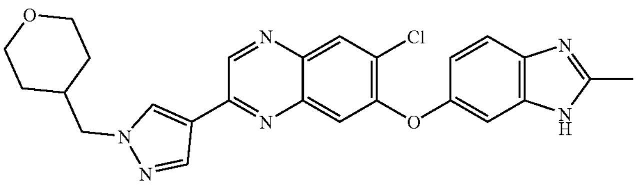 |
| 49 | 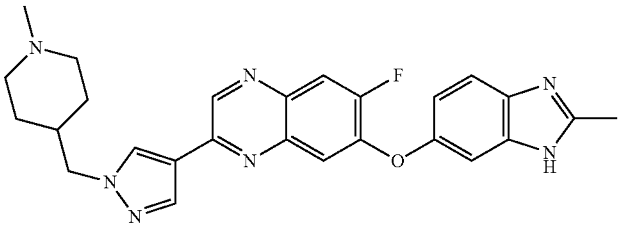 |
| 50 | 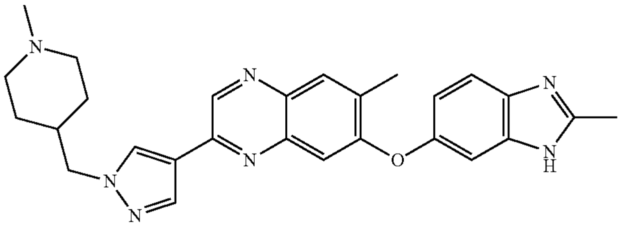 [SMILES: Cc1nc2ccc(Oc3cc4nc(-c5cnn(CC6CCN(C)CC6)c5)cnc4cc3C)cc2[nH]1] |

TABLE I-continued
| Compound No. | Structure |
|---|---|
| 51 | 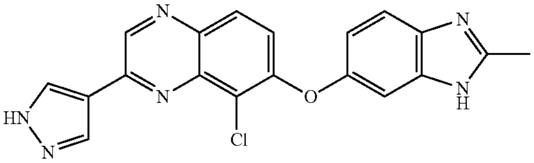 [SMILES: Cc1nc2ccc(Oc3ccc4ncc(-c5cn[nH]c5)nc4c3Cl)cc2[nH]1] |
| 52 | 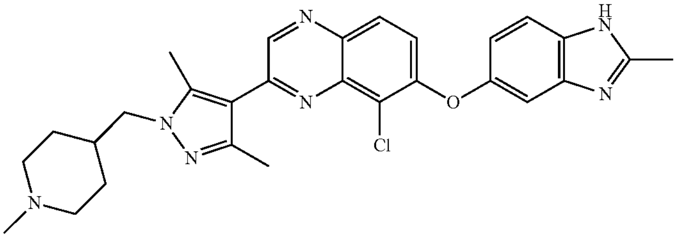 |
| 53 | 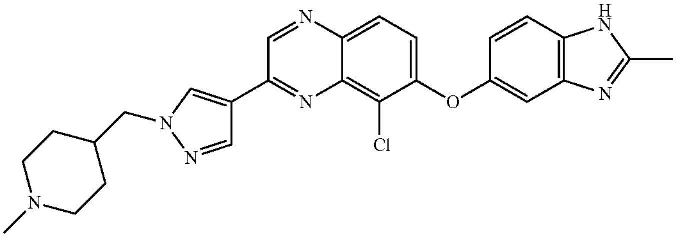 |
| 54 | 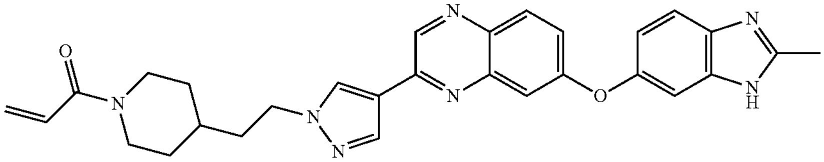 [SMILES: C=CC(=O)N1CCC(CCn2cc(-c3cnc4ccc(Oc5ccc6nc(C)[nH]c6c5)cc4n3)cn2)CC1] |
| 55 | 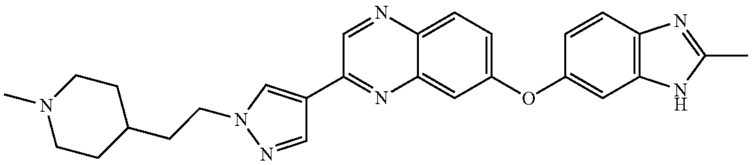 |
| 56 | 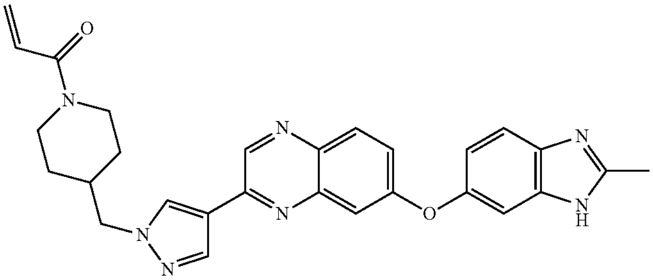 [SMILES: C=CC(=O)N1CCC(Cn2cc(-c3cnc4ccc(Oc5ccc6nc(C)[nH]c6c5)cc4n3)cn2)CC1] |
| 57 | 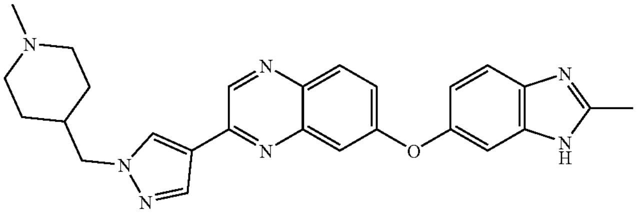 |

TABLE I-continued
| Compound No. | Structure |
|---|---|
| 58 | 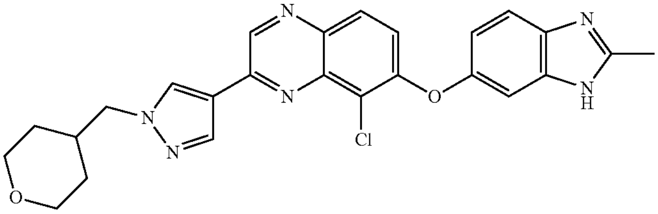 [SMILES: Cc1nc2ccc(Oc3ccc4ncc(-c5cnn(CC6CCOCC6)c5)nc4c3Cl)cc2[nH]1] |
| 59 | 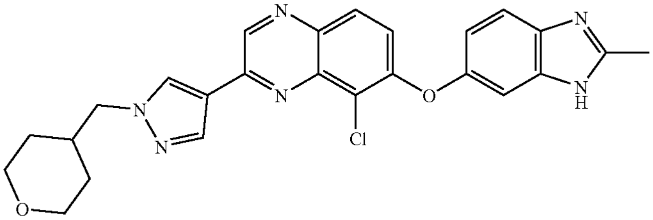 |
| 60 | 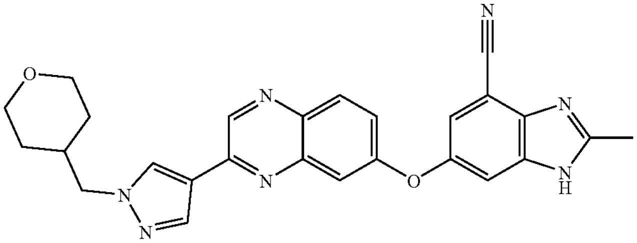 |
| 61 | 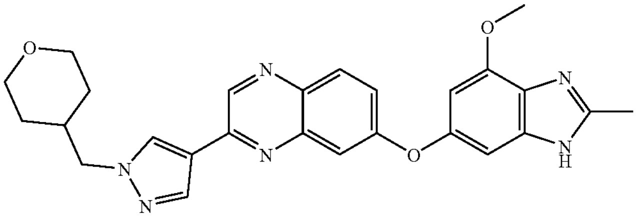 |
| 62 | 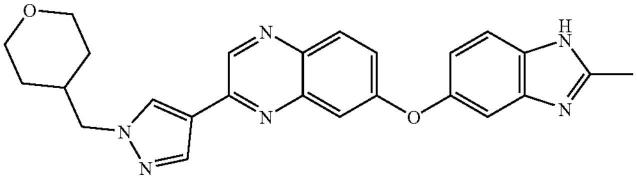 |
| 63 | 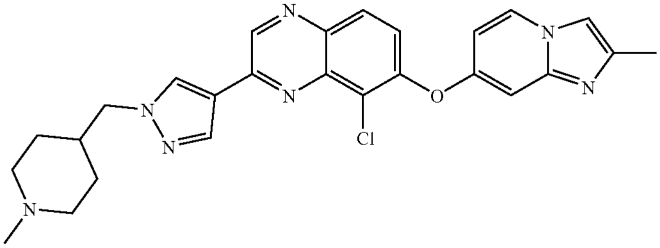 |

TABLE I-continued
| Compound No. | Structure |
|---|---|
| 64 | 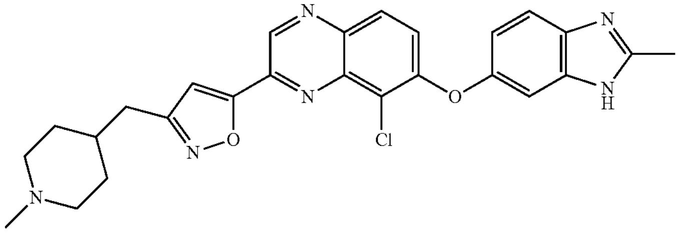 |
| 65 | 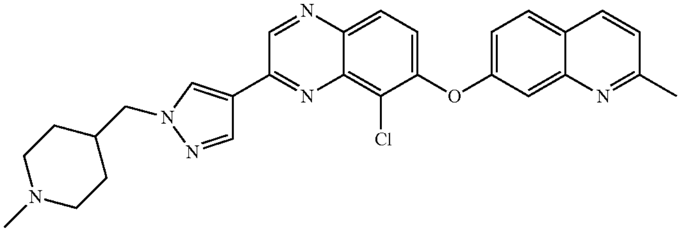 |
| 66 | 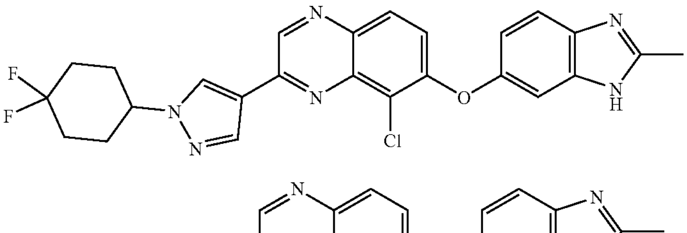 |
| 67 | 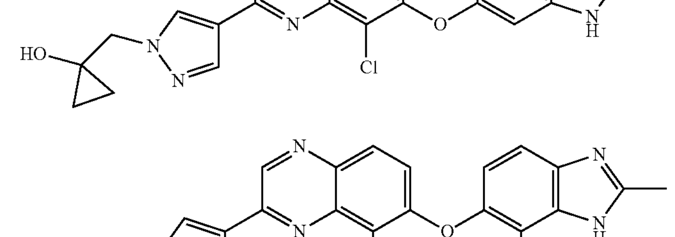 |
| 68 | 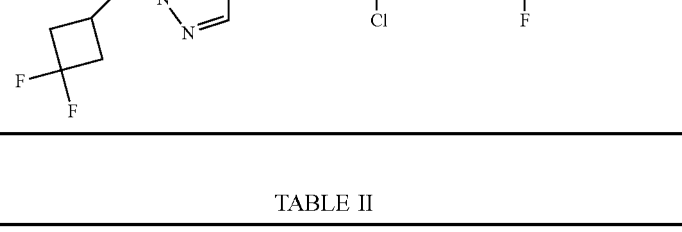 |
TABLE II
| Compound No. | Structure |
|---|---|
| 69 | 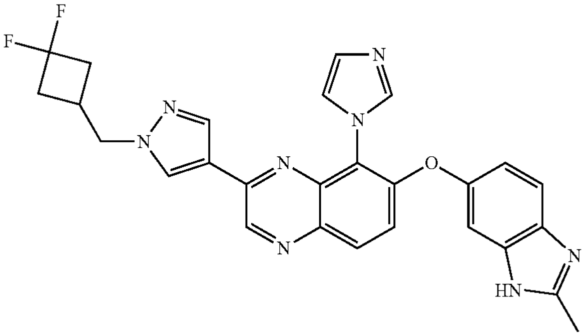 [SMILES: Cc1nc2ccc(Oc3ccc4ncc(-c5cnn(CC6CC(F)(F)C6)c5)nc4c3-n3ccnc3)cc2[nH]1] |

TABLE II-continued
| Compound No. | Structure |
| --- | --- |
| 70 | 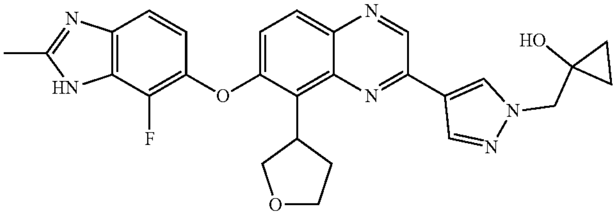 [SMILES: Cc1nc2ccc(Oc3ccc4ncc(-c5cnn(CC6(O)CC6)c5)nc4c3C3CCOC3)c(F)c2[nH]1] |
| 71 | 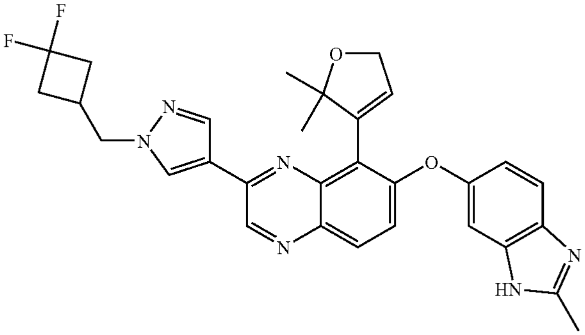 [SMILES: Cc1nc2ccc(Oc3ccc4ncc(-c5cnn(CC6CC(F)(F)C6)c5)nc4c3C3=CCOC3(C)C)cc2[nH]1] |
| 72 | 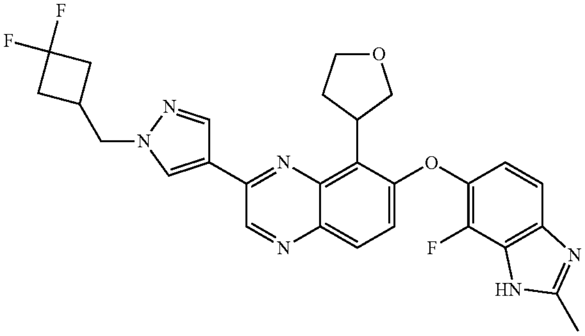 [SMILES: Cc1nc2ccc(Oc3ccc4ncc(-c5cnn(CC6CC(F)(F)C6)c5)nc4c3C3CCOC3)c(F)c2[nH]1] |
| 73 | 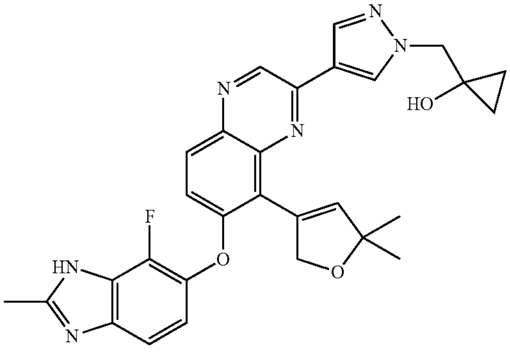 [SMILES: Cc1nc2ccc(Oc3ccc4ncc(-c5cnn(CC6(O)CC6)c5)nc4c3C3=CC(C)(C)OC3)c(F)c2[nH]1] |
| 74 | 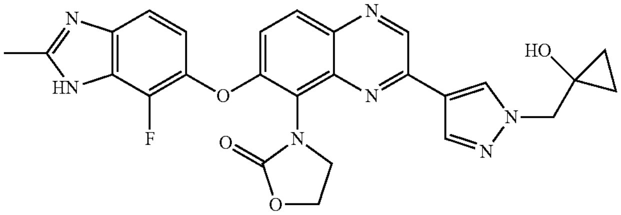 [SMILES: Cc1nc2ccc(Oc3ccc4ncc(-c5cnn(CC6(O)CC6)c5)nc4c3N3CCOC3=O)c(F)c2[nH]1] |

TABLE II-continued
| Compound No. | Structure |
|---|---|
| 75 | 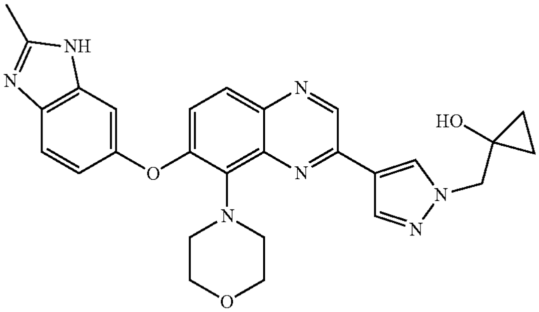 [SMILES: Cc1nc2ccc(Oc3ccc4ncc(-c5cnn(CC6(O)CC6)c5)nc4c3N3CCOCC3)cc2[nH]1] |
| 76 | 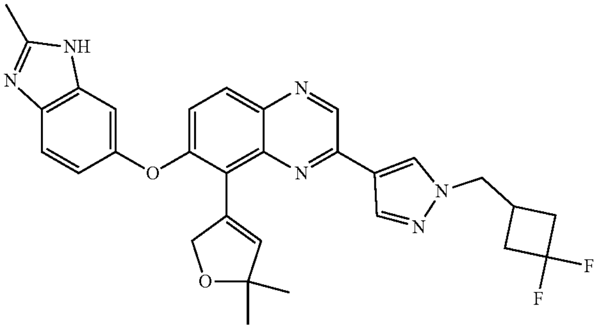 [SMILES: Cc1nc2ccc(Oc3ccc4ncc(-c5cnn(CC6CC(F)(F)C6)c5)nc4c3C3=CC(C)(C)OC3)cc2[nH]1] |
| 77 | 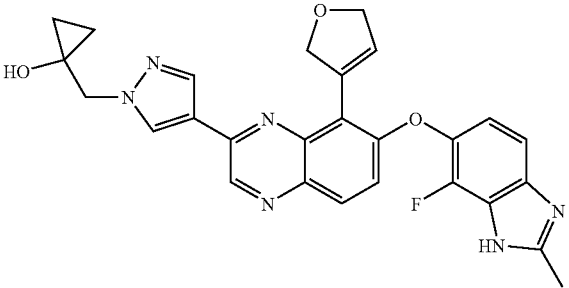 [SMILES: Cc1nc2ccc(Oc3ccc4ncc(-c5cnn(CC6(O)CC6)c5)nc4c3C3=CCOC3)c(F)c2[nH]1] |
| 78 | 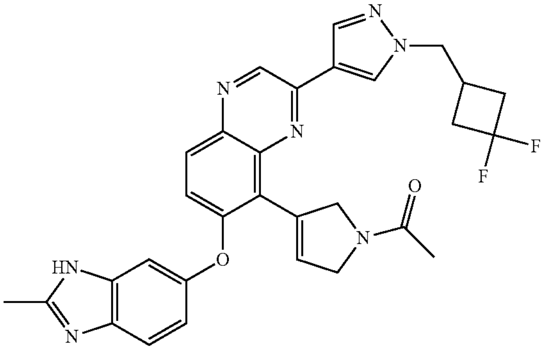 [SMILES: CC(=O)N1CC=C(c2c(Oc3ccc4nc(C)[nH]c4c3)ccc3ncc(-c4cnn(CC5CC(F)(F)C5)c4)nc23)C1] |

TABLE II-continued
| Compound No. | Structure |
| --- | --- |
| 79 | 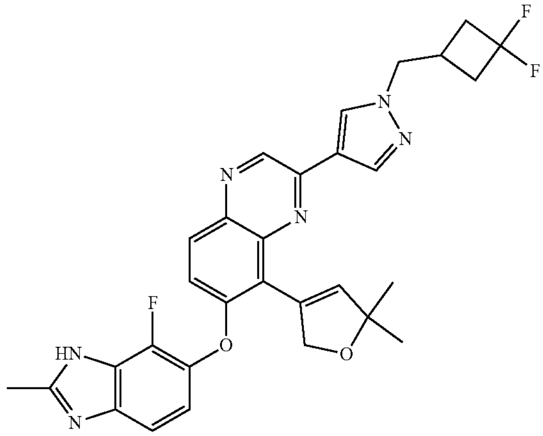 [SMILES: Cc1nc2ccc(Oc3ccc4ncc(-c5cnn(CC6CC(F)(F)C6)c5)nc4c3C3=CC(C)(C)OC3)c(F)c2[nH]1] |
| 80 | 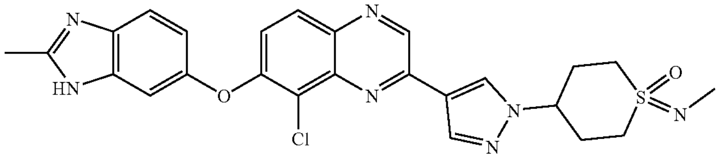 |
| 81 | 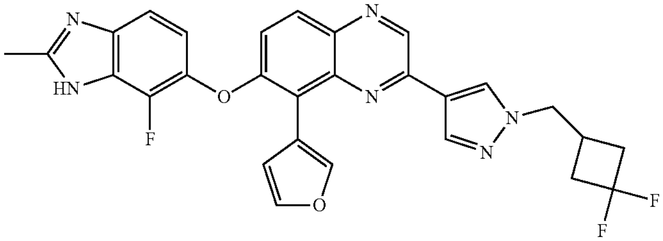 [SMILES: Cc1nc2ccc(Oc3ccc4ncc(-c5cnn(CC6CC(F)(F)C6)c5)nc4c3-c3ccoc3)c(F)c2[nH]1] |
| 82 | 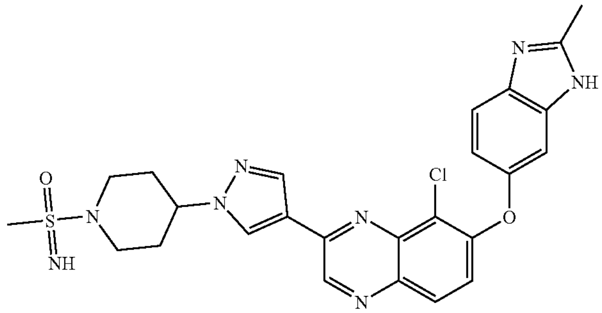 |
| 83 | 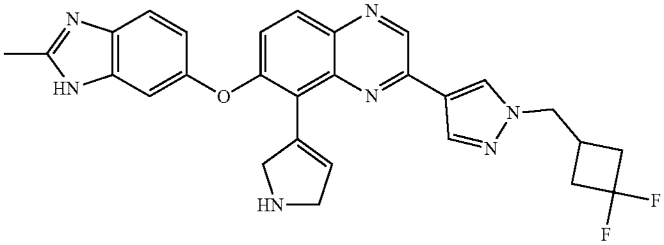 [SMILES: Cc1nc2ccc(Oc3ccc4ncc(-c5cnn(CC6CC(F)(F)C6)c5)nc4c3C3=CCNC3)cc2[nH]1] |

TABLE II-continued
| Compound No. | Structure |
|---|---|
| 84 | 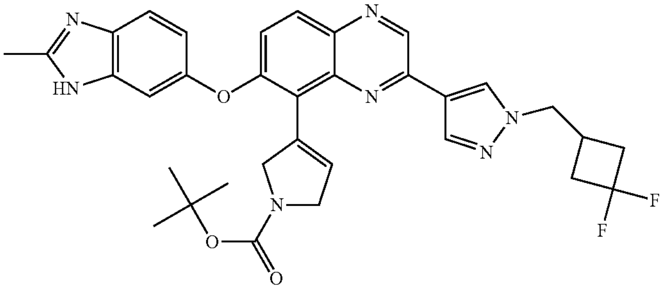 [SMILES: Cc1nc2ccc(Oc3ccc4ncc(-c5cnn(CC6CC(F)(F)C6)c5)nc4c3C3=CCN(C(=O)OC(C)(C)C)C3)cc2[nH]1] |
| 85 | 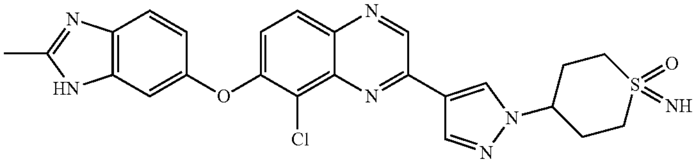 [SMILES: Cc1nc2ccc(Oc3ccc4ncc(-c5cnn(C6CCS(=N)(=O)CC6)c5)nc4c3Cl)cc2[nH]1] |
| 86 | 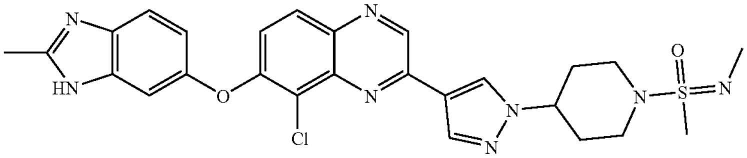 |
| 87 | 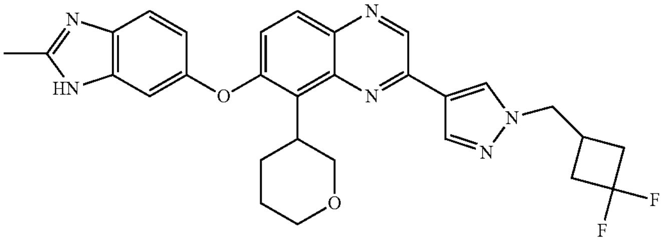 [SMILES: Cc1nc2ccc(Oc3ccc4ncc(-c5cnn(CC6CC(F)(F)C6)c5)nc4c3C3CCCOC3)cc2[nH]1] |
| 88 | 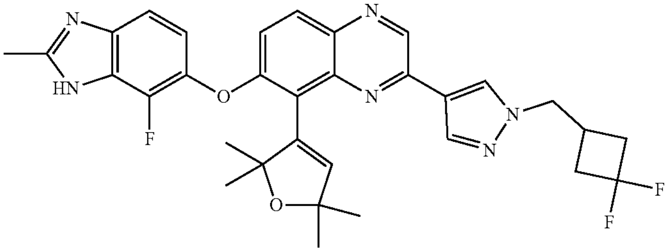 [SMILES: Cc1nc2ccc(Oc3ccc4ncc(-c5cnn(CC6CC(F)(F)C6)c5)nc4c3C3=CC(C)(C)OC3(C)C)c(F)c2[nH]1] |
| 89 | 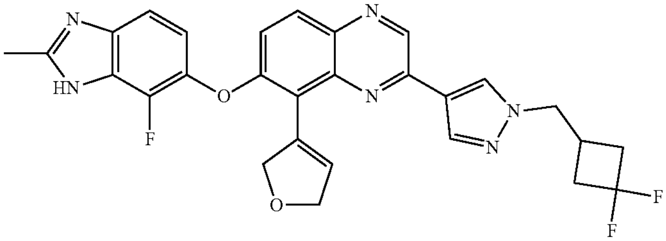 [SMILES: Cc1nc2ccc(Oc3ccc4ncc(-c5cnn(CC6CC(F)(F)C6)c5)nc4c3C3=CCOC3)c(F)c2[nH]1] |

TABLE II-continued
| Compound No. | Structure |
|---|---|
| 90 | 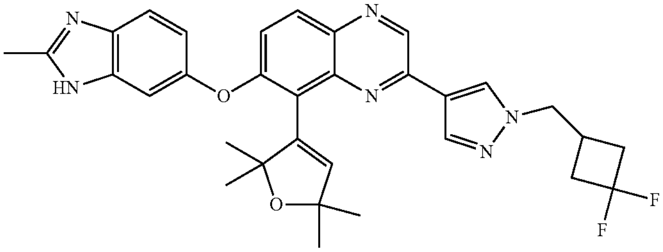 [SMILES: Cc1nc2ccc(Oc3ccc4ncc(-c5cnn(CC6CC(F)(F)C6)c5)nc4c3C3=CC(C)(C)OC3(C)C)cc2[nH]1] |
| 91 | 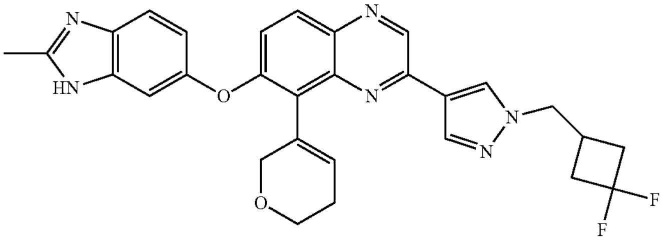 [SMILES: Cc1nc2ccc(Oc3ccc4ncc(-c5cnn(CC6CC(F)(F)C6)c5)nc4c3C3=CCCOC3)cc2[nH]1] |
| 92 | 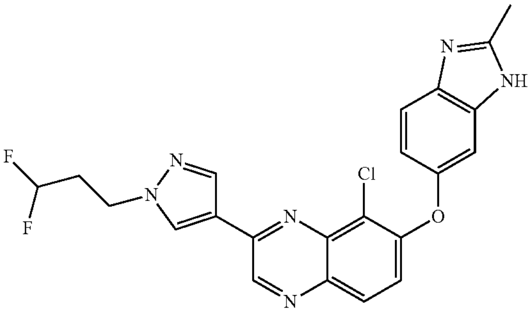 [SMILES: Cc1nc2ccc(Oc3ccc4ncc(-c5cnn(CCC(F)F)c5)nc4c3Cl)cc2[nH]1] |
| 93 | 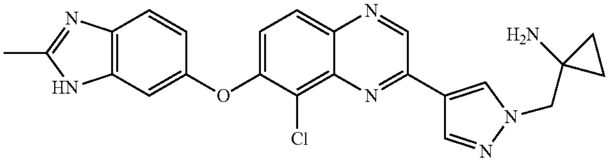 [SMILES: Cc1nc2ccc(Oc3ccc4ncc(-c5cnn(CC6(N)CC6)c5)nc4c3Cl)cc2[nH]1] |
| 94 | 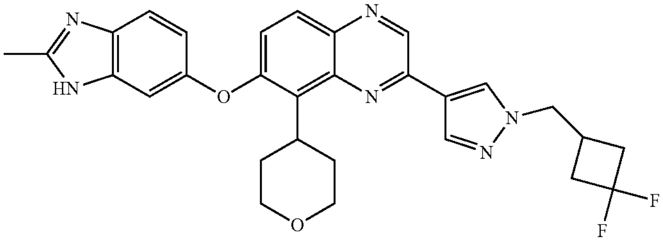 [SMILES: Cc1nc2ccc(Oc3ccc4ncc(-c5cnn(CC6CC(F)(F)C6)c5)nc4c3C3CCOCC3)cc2[nH]1] |
| 95 | 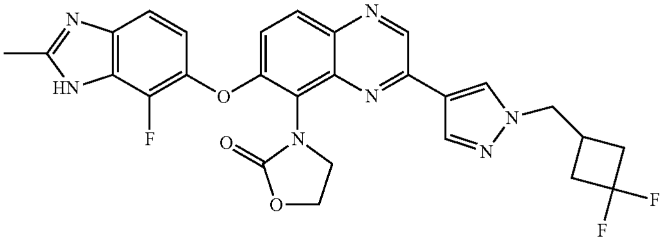 [SMILES: Cc1nc2ccc(Oc3ccc4ncc(-c5cnn(CC6CC(F)(F)C6)c5)nc4c3N3CCOC3=O)c(F)c2[nH]1] |

TABLE II-continued
| Compound No. | Structure |
|---|---|
| 96 | 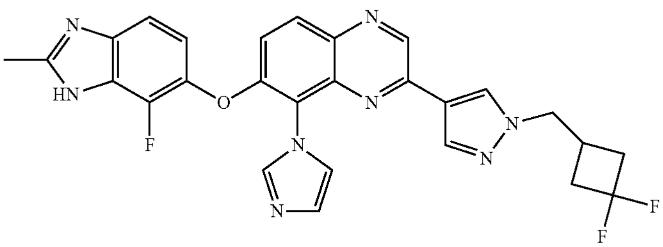 [SMILES: Cc1nc2ccc(Oc3ccc4ncc(-c5cnn(CC6CC(F)(F)C6)c5)nc4c3-n3ccnc3)c(F)c2[nH]1] |
| 97 | 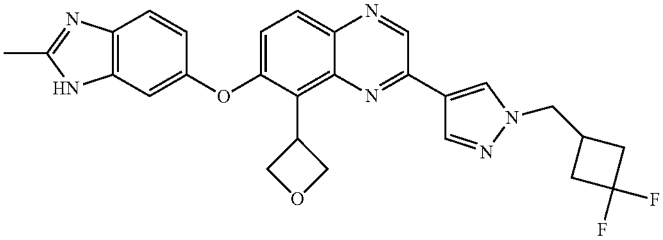 [SMILES: Cc1nc2ccc(Oc3ccc4ncc(-c5cnn(CC6CC(F)(F)C6)c5)nc4c3C3COC3)cc2[nH]1] |
| 98 | 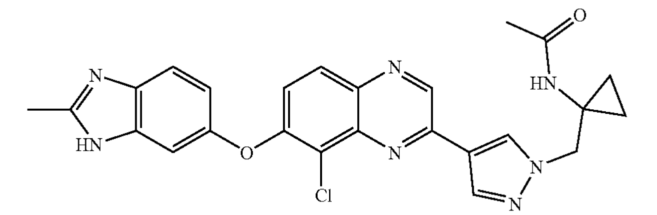 [SMILES: CC(=O)NC1(Cn2cc(-c3cnc4ccc(Oc5ccc6nc(C)[nH]c6c5)c(Cl)c4n3)cn2)CC1] |
| 99 | 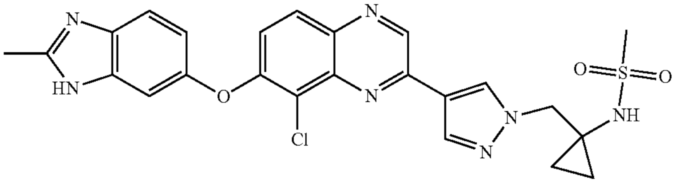 [SMILES: Cc1nc2ccc(Oc3ccc4ncc(-c5cnn(CC6(NS(C)(=O)=O)CC6)c5)nc4c3Cl)cc2[nH]1] |
| 100 | 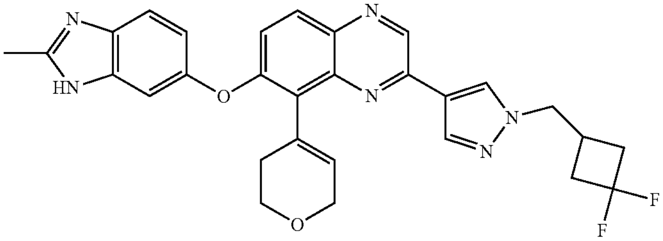 [SMILES: Cc1nc2ccc(Oc3ccc4ncc(-c5cnn(CC6CC(F)(F)C6)c5)nc4c3C3=CCOCC3)cc2[nH]1] |
| 101 | 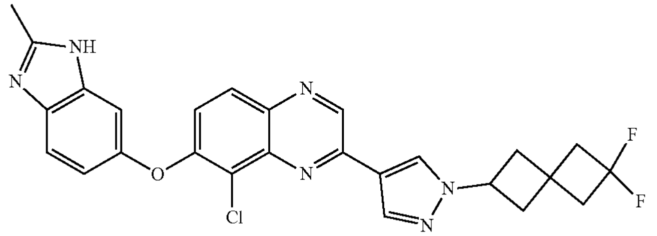 [SMILES: Cc1nc2ccc(Oc3ccc4ncc(-c5cnn(C6CC7(C6)CC(F)(F)C7)c5)nc4c3Cl)cc2[nH]1] |

TABLE II-continued
| Compound No. | Structure |
|---|---|
| 102 | 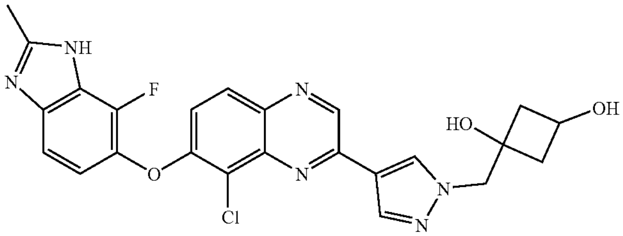 [SMILES: Cc1nc2ccc(Oc3ccc4ncc(-c5cnn(CC6(O)CC(O)C6)c5)nc4c3Cl)c(F)c2[nH]1] |
| 103 | 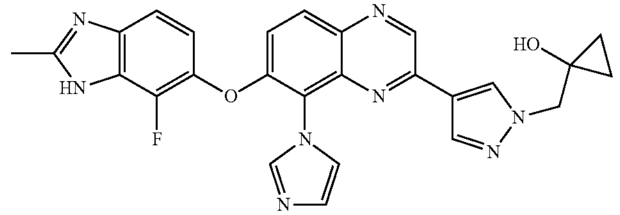 [SMILES: Cc1nc2ccc(Oc3ccc4ncc(-c5cnn(CC6(O)CC6)c5)nc4c3-n3ccnc3)c(F)c2[nH]1] |
| 104 | 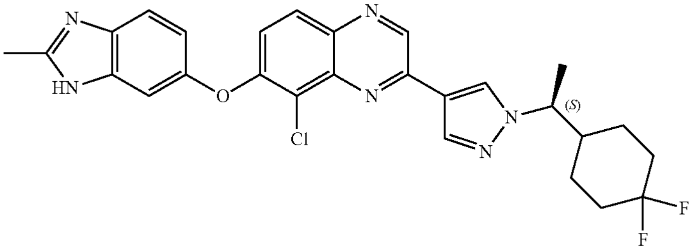 |
| 105 | 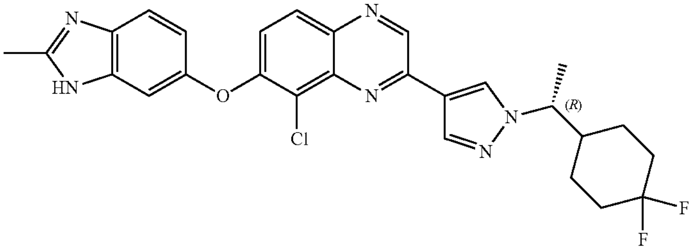 |
| 106 | 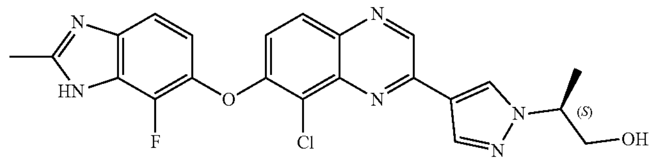 |
| 107 | 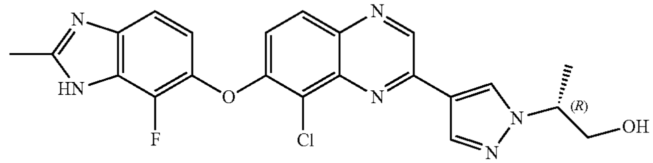 |
| 108 | 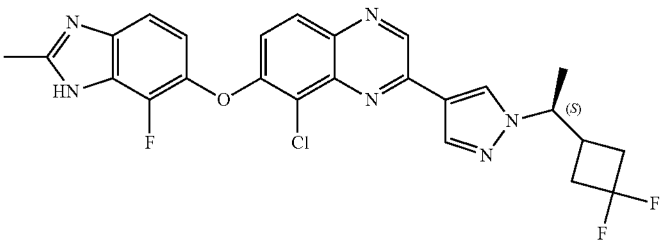 |

TABLE II-continued
| Compound No. | Structure |
|---|---|
| 109 | 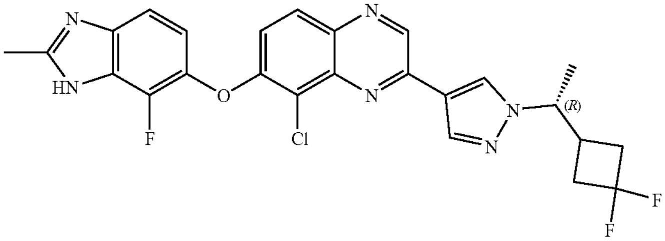 |
| 110 | 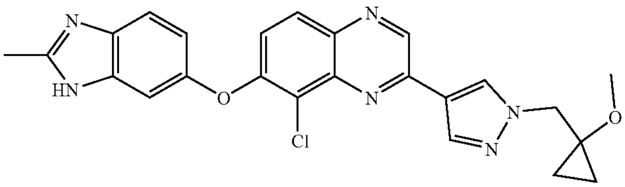 [SMILES: COC1(Cn2cc(-c3cnc4ccc(Oc5ccc6nc(C)[nH]c6c5)c(Cl)c4n3)cn2)CC1] |
| 111 | 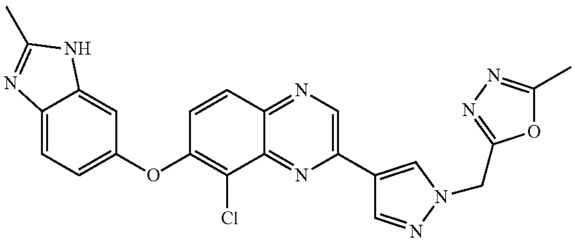 |
| 112 | 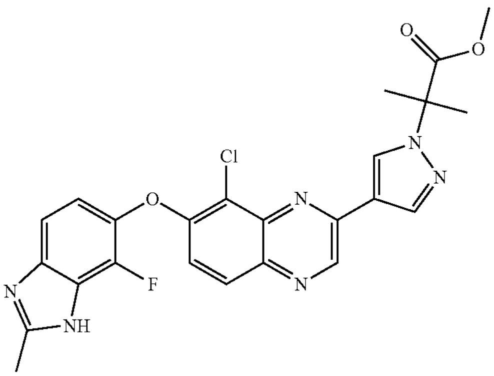 [SMILES: COC(=O)C(C)(C)n1cc(-c2cnc3ccc(Oc4ccc5nc(C)[nH]c5c4F)c(Cl)c3n2)cn1] |
| 113 | 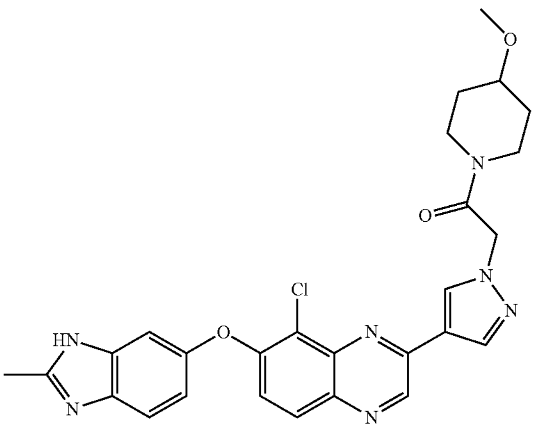 [SMILES: COC1CCN(C(=O)Cn2cc(-c3cnc4ccc(Oc5ccc6nc(C)[nH]c6c5)c(Cl)c4n3)cn2)CC1] |

TABLE II-continued
| Compound No. | Structure |
| --- | --- |
| 114 | 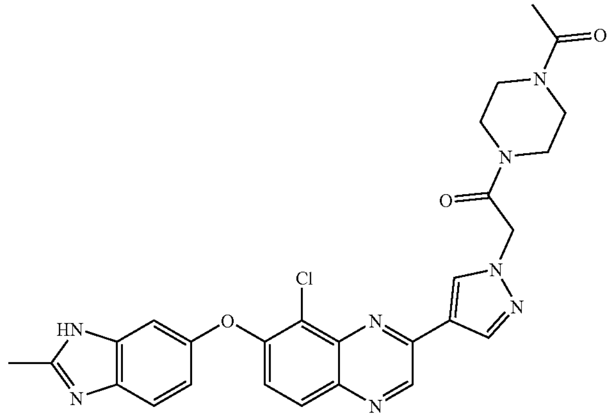 [SMILES: CC(=O)N1CCN(C(=O)Cn2cc(-c3cnc4ccc(Oc5ccc6nc(C)[nH]c6c5)c(Cl)c4n3)cn2)CC1] |
| 115 | 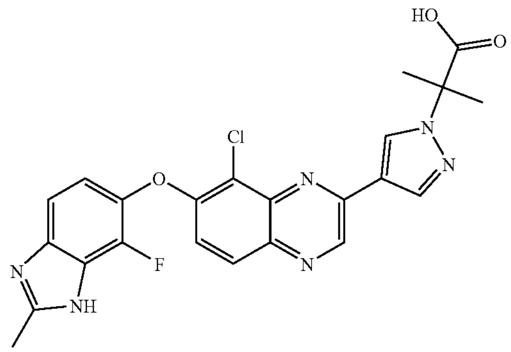 [SMILES: Cc1nc2ccc(Oc3ccc4ncc(-c5cnn(C(C)(C)C(=O)O)c5)nc4c3Cl)c(F)c2[nH]1] |
| 116 | 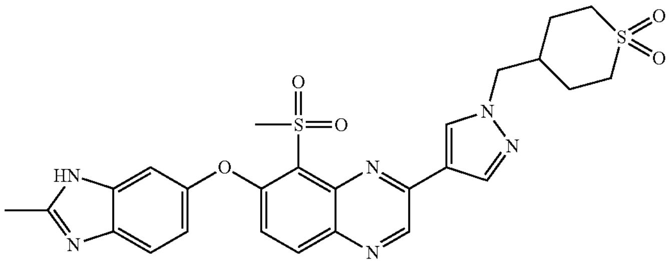 [SMILES: Cc1nc2ccc(Oc3ccc4ncc(-c5cnn(CC6CCS(=O)(=O)CC6)c5)nc4c3S(C)(=O)=O)cc2[nH]1] |
| 117 | 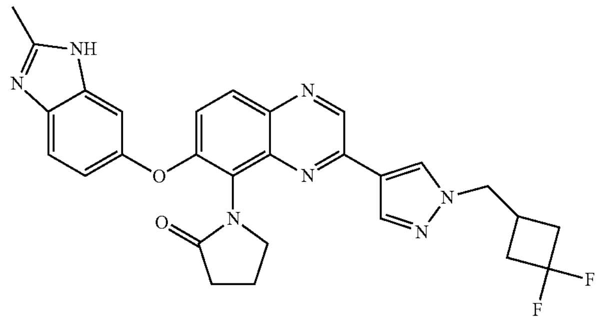 [SMILES: Cc1nc2ccc(Oc3ccc4ncc(-c5cnn(CC6CC(F)(F)C6)c5)nc4c3N3CCCC3=O)cc2[nH]1] |
| 118 | 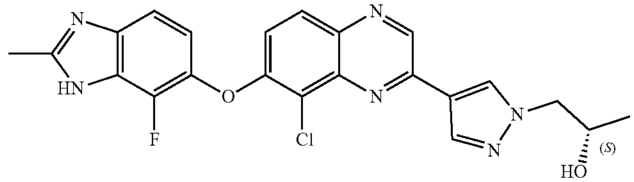 |

TABLE II-continued
| Compound No. | Structure |
| --- | --- |
| 119 | 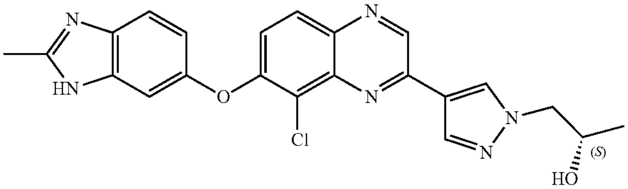 |
| 120 | 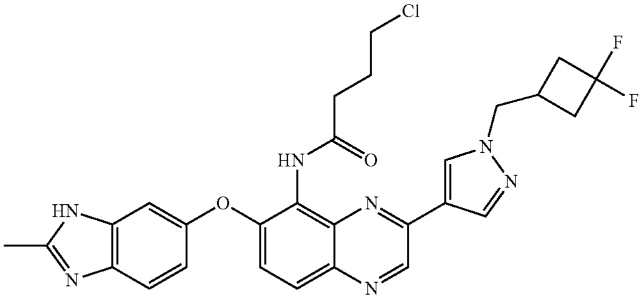 [SMILES: Cc1nc2ccc(Oc3ccc4ncc(-c5cnn(CC6CC(F)(F)C6)c5)nc4c3NC(=O)CCCCl)cc2[nH]1] |
| 121 | 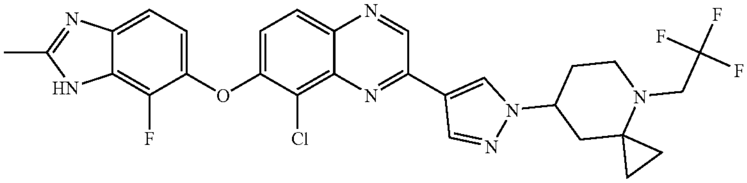 [SMILES: Cc1nc2ccc(Oc3ccc4ncc(-c5cnn(C6CCN(CC(F)(F)F)C7(CC7)C6)c5)nc4c3Cl)c(F)c2[nH]1] |
| 122 | 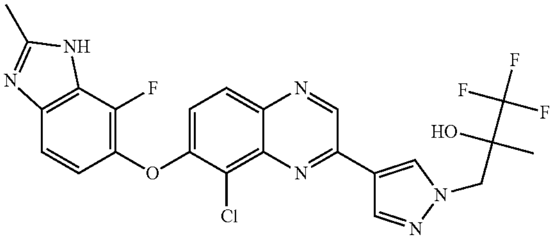 [SMILES: Cc1nc2ccc(Oc3ccc4ncc(-c5cnn(CC(C)(O)C(F)(F)F)c5)nc4c3Cl)c(F)c2[nH]1] |
| 123 | 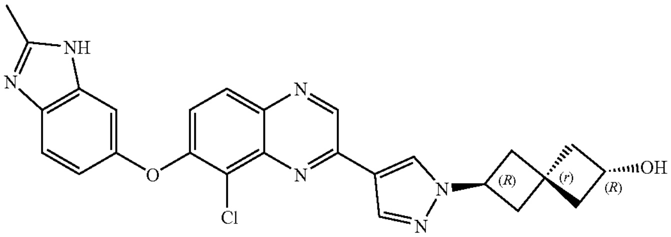 |
| 124 | 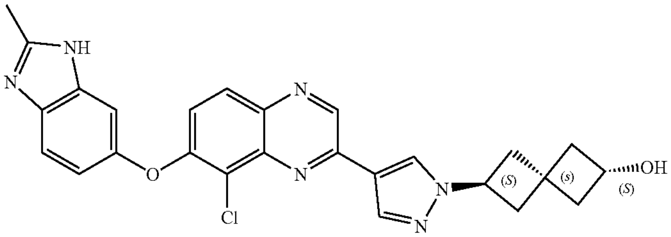 |

TABLE II-continued
| Compound No. | Structure |
| --- | --- |
| 125 | 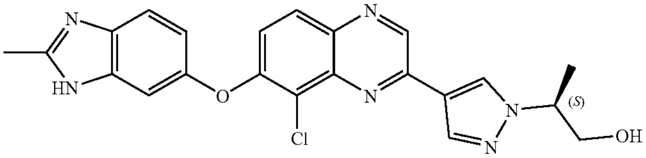 |
| 126 | 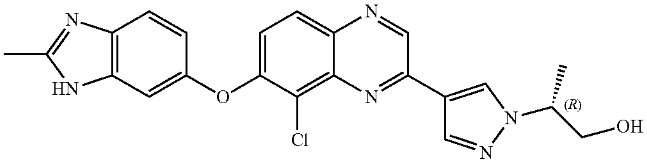 |
| 127 | 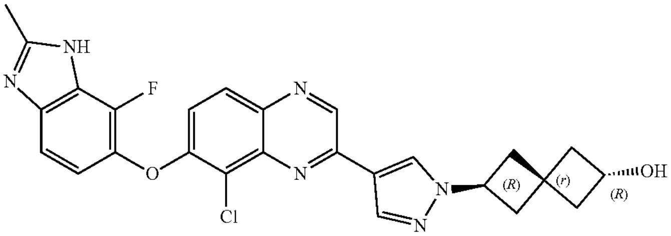 |
| 128 | 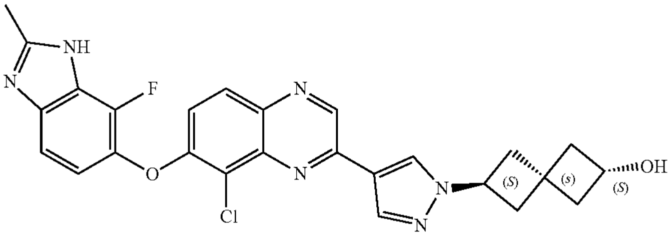 |
| 129 | 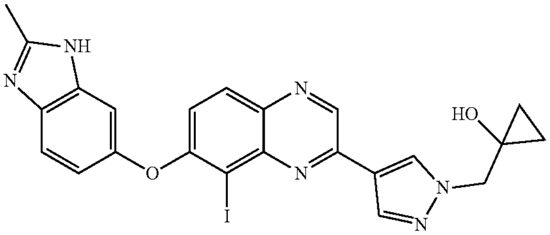 [SMILES: Cc1nc2ccc(Oc3ccc4ncc(-c5cnn(CC6(O)CC6)c5)nc4c3I)cc2[nH]1] |
| 130 | 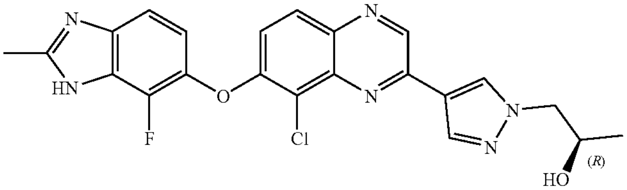 |
| 131 | 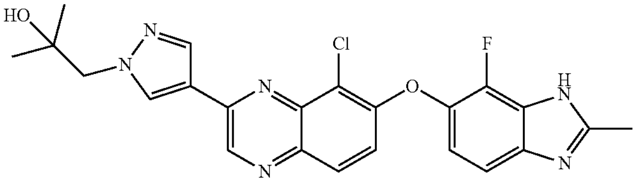 [SMILES: Cc1nc2ccc(Oc3ccc4ncc(-c5cnn(CC(C)(C)O)c5)nc4c3Cl)c(F)c2[nH]1] |

TABLE II-continued
| Compound No. | Structure |
| --- | --- |
| 132 | 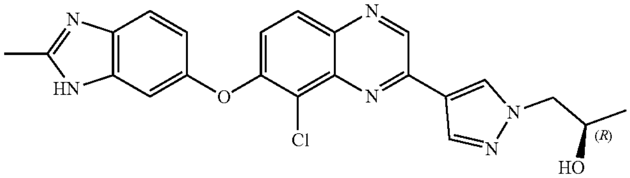 |
| 133 | 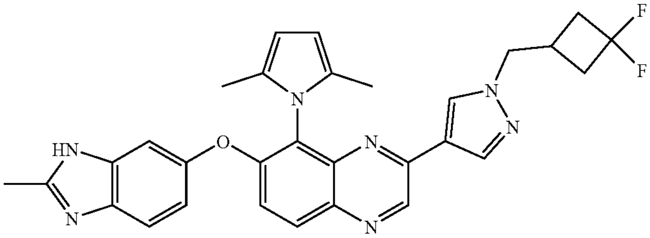 [SMILES: Cc1nc2ccc(Oc3ccc4ncc(-c5cnn(CC6CC(F)(F)C6)c5)nc4c3-n3c(C)ccc3C)cc2[nH]1] |
| 134 | 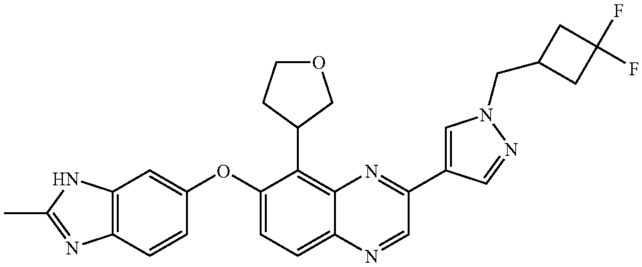 [SMILES: Cc1nc2ccc(Oc3ccc4ncc(-c5cnn(CC6CC(F)(F)C6)c5)nc4c3C3CCOC3)cc2[nH]1] |
| 135 | 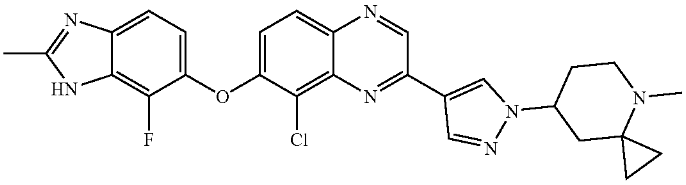 |
| 136 | 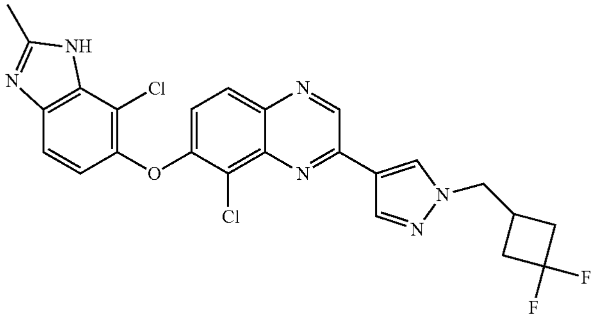 [SMILES: Cc1nc2ccc(Oc3ccc4ncc(-c5cnn(CC6CC(F)(F)C6)c5)nc4c3Cl)c(Cl)c2[nH]1] |
| 137 | 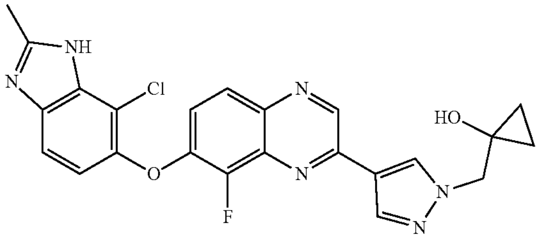 [SMILES: Cc1nc2ccc(Oc3ccc4ncc(-c5cnn(CC6(O)CC6)c5)nc4c3F)c(Cl)c2[nH]1] |

TABLE II-continued
| Compound No. | Structure |
| --- | --- |
| 138 | 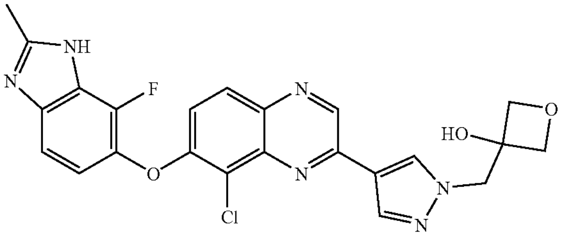 [SMILES: Cc1nc2ccc(Oc3ccc4ncc(-c5cnn(CC6(O)COC6)c5)nc4c3Cl)c(F)c2[nH]1] |
| 139 | 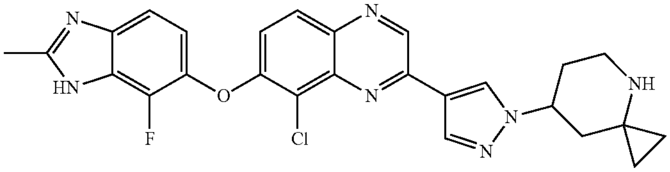 [SMILES: Cc1nc2ccc(Oc3ccc4ncc(-c5cnn(C6CCNC7(CC7)C6)c5)nc4c3Cl)c(F)c2[nH]1] |
| 140 | 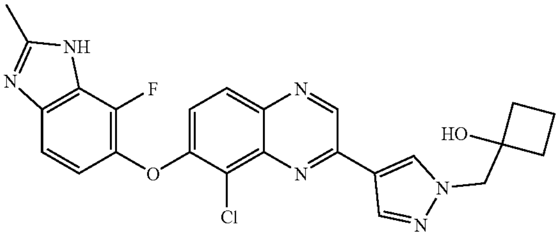 [SMILES: Cc1nc2ccc(Oc3ccc4ncc(-c5cnn(CC6(O)CCC6)c5)nc4c3Cl)c(F)c2[nH]1] |
| 141 | 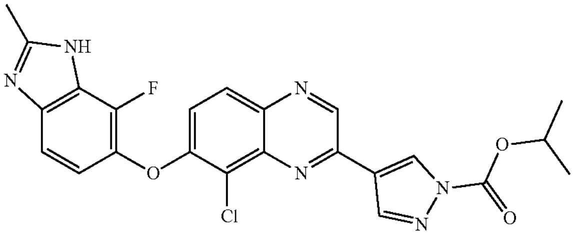 [SMILES: Cc1nc2ccc(Oc3ccc4ncc(-c5cnn(C(=O)OC(C)C)c5)nc4c3Cl)c(F)c2[nH]1] |
| 142 | 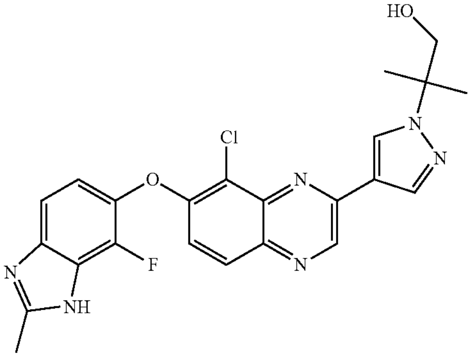 [SMILES: Cc1nc2ccc(Oc3ccc4ncc(-c5cnn(C(C)(C)CO)c5)nc4c3Cl)c(F)c2[nH]1] |
| 143 | 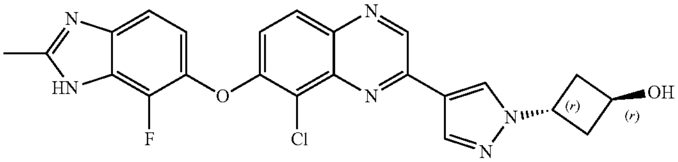 [SMILES: Cc1nc2ccc(Oc3ccc4ncc(-c5cnn([C@H]6C[C@H](O)C6)c5)nc4c3Cl)c(F)c2[nH]1] |

TABLE II-continued
| Compound No. | Structure |
|---|---|
| 144 | 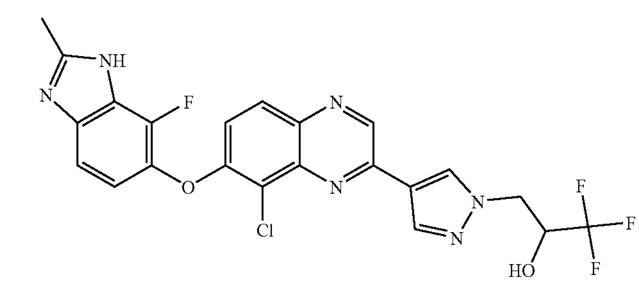 [SMILES: Cc1nc2ccc(Oc3ccc4ncc(-c5cnn(CC(O)C(F)(F)F)c5)nc4c3Cl)c(F)c2[nH]1] |
| 145 | 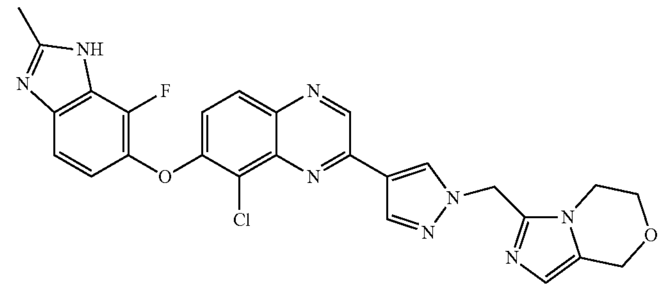 [SMILES: Cc1nc2ccc(Oc3ccc4ncc(-c5cnn(Cc6ncc7n6CCOC7)c5)nc4c3Cl)c(F)c2[nH]1] |
| 146 | 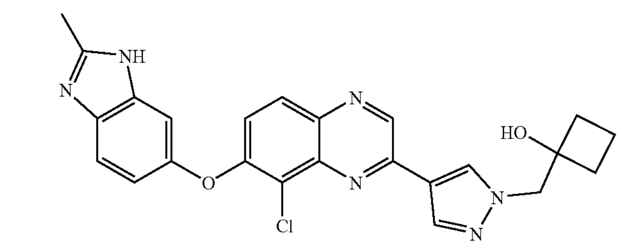 [SMILES: Cc1nc2ccc(Oc3ccc4ncc(-c5cnn(CC6(O)CCC6)c5)nc4c3Cl)cc2[nH]1] |
| 147 | 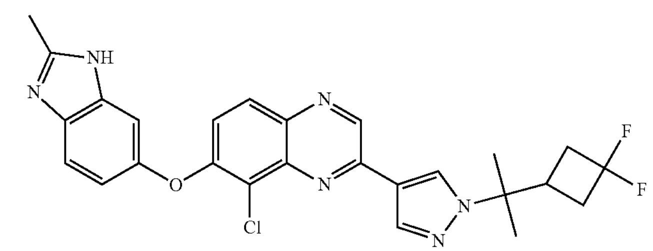 [SMILES: Cc1nc2ccc(Oc3ccc4ncc(-c5cnn(C(C)(C)C6CC(F)(F)C6)c5)nc4c3Cl)cc2[nH]1] |
| 148 | 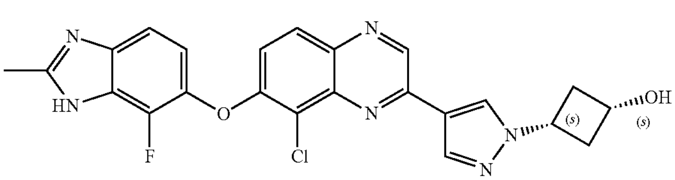 [SMILES: Cc1nc2ccc(Oc3ccc4ncc(-c5cnn([C@H]6C[C@@H](O)C6)c5)nc4c3Cl)c(F)c2[nH]1] |
| 149 | 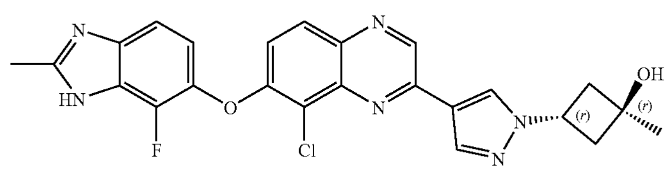 |

TABLE II-continued
| Compound No. | Structure |
|---|---|
| 150 | 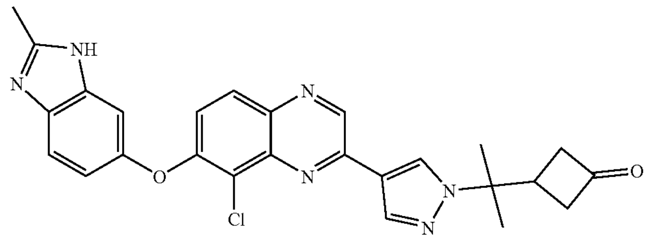 [SMILES: Cc1nc2ccc(Oc3ccc4ncc(-c5cnn(C(C)(C)C6CC(=O)C6)c5)nc4c3Cl)cc2[nH]1] |
| 151 | 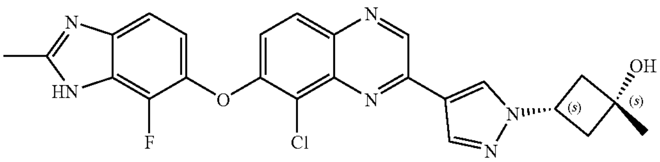 |
| 152 | 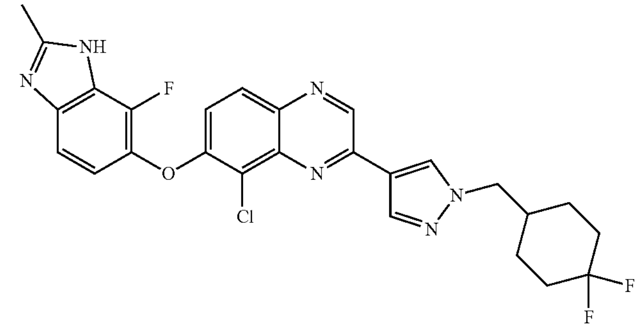 [SMILES: Cc1nc2ccc(Oc3ccc4ncc(-c5cnn(CC6CCC(F)(F)CC6)c5)nc4c3Cl)c(F)c2[nH]1] |
| 153 | 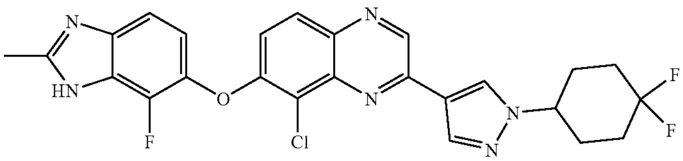 [SMILES: Cc1nc2ccc(Oc3ccc4ncc(-c5cnn(C6CCC(F)(F)CC6)c5)nc4c3Cl)c(F)c2[nH]1] |
| 154 | 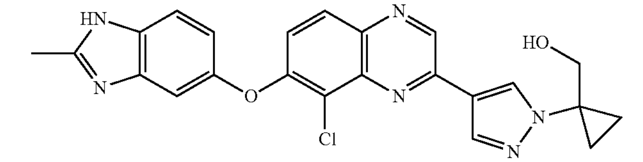 [SMILES: Cc1nc2cc(Oc3ccc4ncc(-c5cnn(C6(CO)CC6)c5)nc4c3Cl)ccc2[nH]1] |
| 155 | 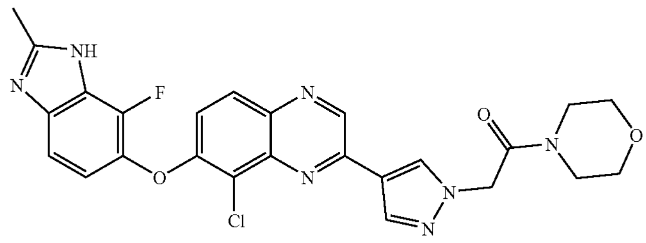 [SMILES: Cc1nc2ccc(Oc3ccc4ncc(-c5cnn(CC(=O)N6CCOCC6)c5)nc4c3Cl)c(F)c2[nH]1] |
| 156 | 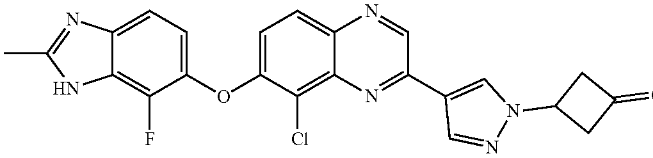 |

TABLE II-continued
| Compound No. | Structure |
|---|---|
| 157 | 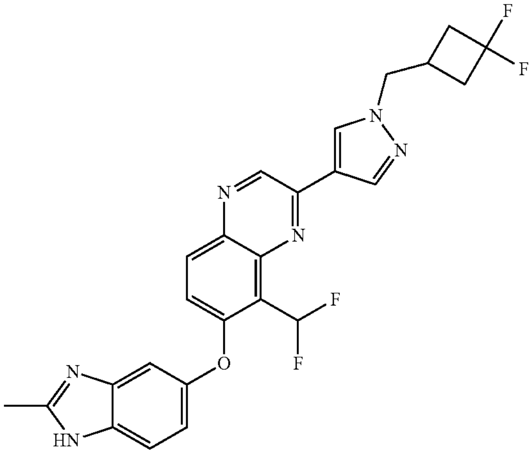 [SMILES: Cc1nc2cc(Oc3ccc4ncc(-c5cnn(CC6CC(F)(F)C6)c5)nc4c3C(F)F)ccc2[nH]1] |
| 158 | 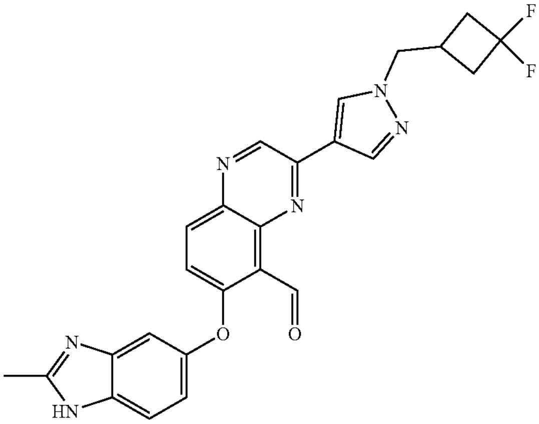 [SMILES: Cc1nc2cc(Oc3ccc4ncc(-c5cnn(CC6CC(F)(F)C6)c5)nc4c3C=O)ccc2[nH]1] |
| 159 | 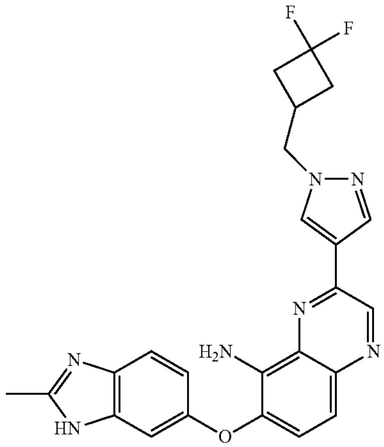 [SMILES: Cc1nc2ccc(Oc3ccc4ncc(-c5cnn(CC6CC(F)(F)C6)c5)nc4c3N)cc2[nH]1] |
| 160 | 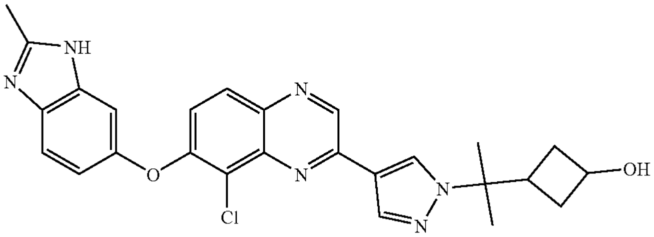 [SMILES: Cc1nc2ccc(Oc3ccc4ncc(-c5cnn(C(C)(C)C6CC(O)C6)c5)nc4c3Cl)cc2[nH]1] |

TABLE II-continued
| Compound No. | Structure |
| --- | --- |
| 161 | 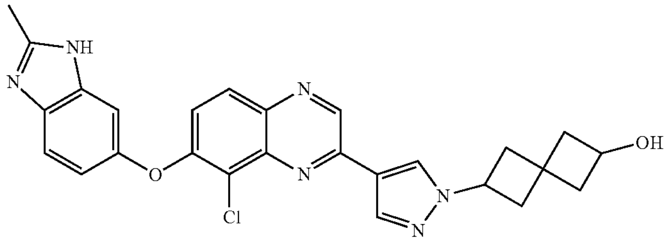 [SMILES: Cc1nc2ccc(Oc3ccc4ncc(-c5cnn(C6CC7(CC(O)C7)C6)c5)nc4c3Cl)cc2[nH]1] |
| 162 | 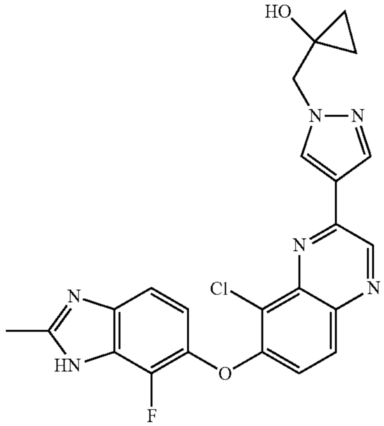 [SMILES: Cc1nc2ccc(Oc3ccc4ncc(-c5cnn(CC6(O)CC6)c5)nc4c3Cl)c(F)c2[nH]1] |
| 163 | 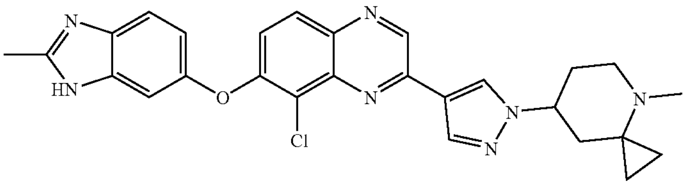 |
| 164 | 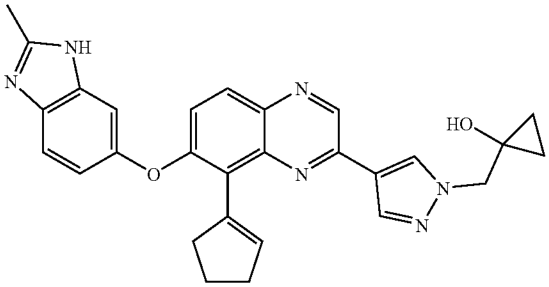 [SMILES: Cc1nc2ccc(Oc3ccc4ncc(-c5cnn(CC6(O)CC6)c5)nc4c3C3=CCCC3)cc2[nH]1] |
| 165 | 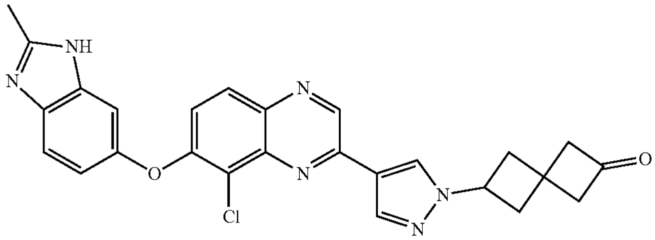 [SMILES: Cc1nc2ccc(Oc3ccc4ncc(-c5cnn(C6CC7(CC(=O)C7)C6)c5)nc4c3Cl)cc2[nH]1] |

TABLE II-continued
| Compound No. | Structure |
|---|---|
| 166 | 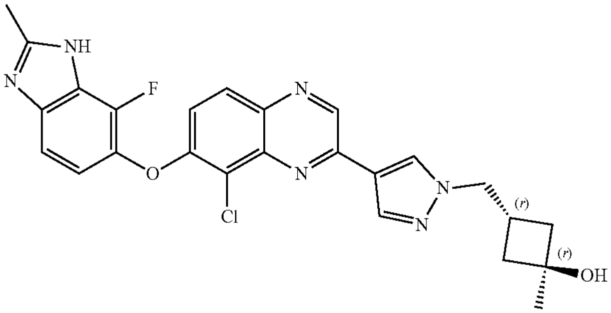 [SMILES: Cc1nc2ccc(Oc3ccc4ncc(-c5cnn(C[C@H]6C[C@](C)(O)C6)c5)nc4c3Cl)c(F)c2[nH]1] |
| 167 | 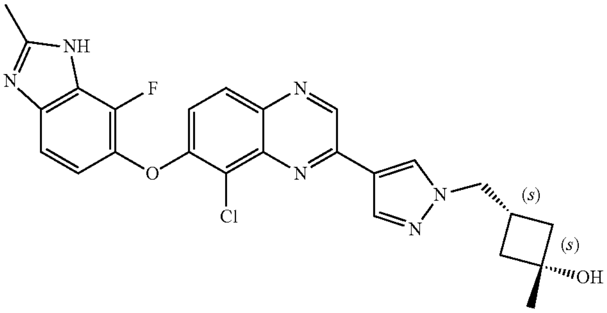 [SMILES: Cc1nc2ccc(Oc3ccc4ncc(-c5cnn(C[C@H]6C[C@@](C)(O)C6)c5)nc4c3Cl)c(F)c2[nH]1] |
| 168 | 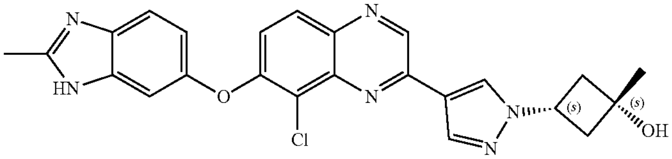 |
| 169 | 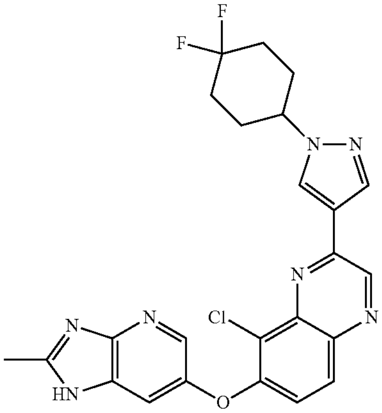 |
| 170 | 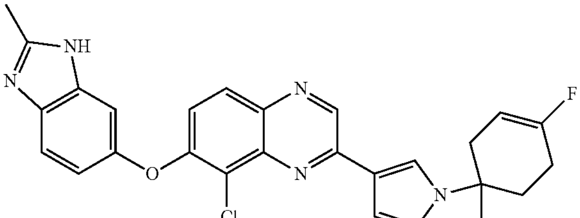 |

TABLE II-continued
| Compound No. | Structure |
| --- | --- |
| 171 | 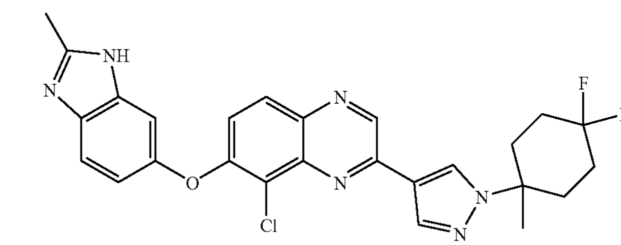 |
| 172 | 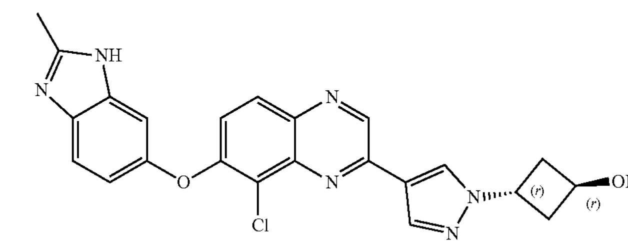 |
| 173 | 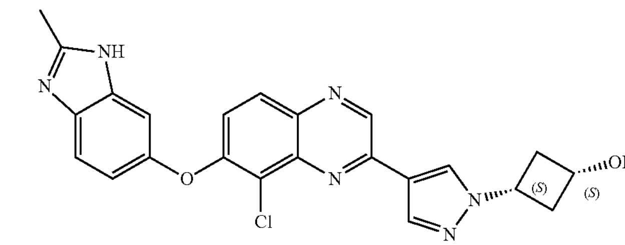 |
| 174 | 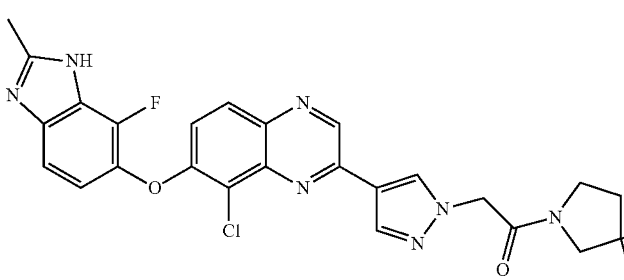 |
| 175 | 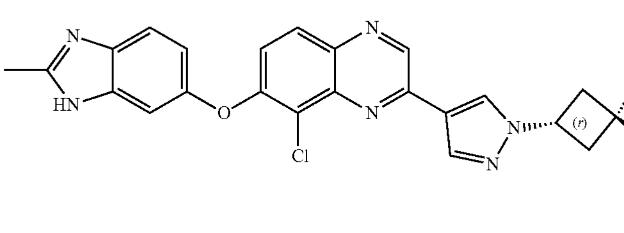 |
| 176 | 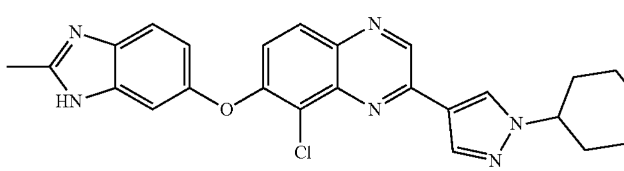 |

TABLE II-continued
| Compound No. | Structure |
|---|---|
| 177 | 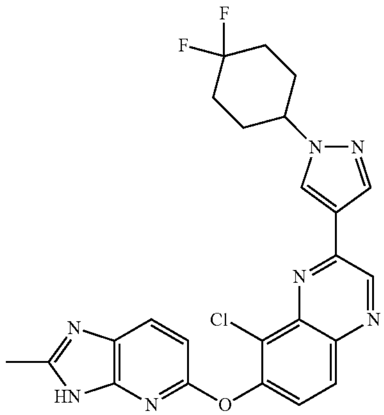 |
| 178 | 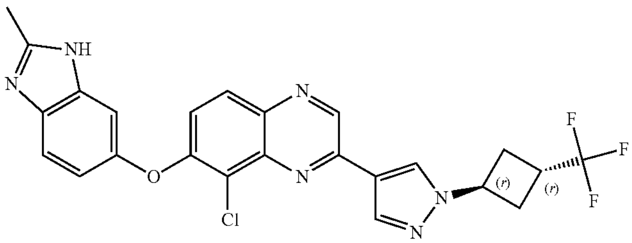 [SMILES: Cc1nc2ccc(Oc3ccc4ncc(-c5cnn([C@H]6C[C@H](C(F)(F)F)C6)c5)nc4c3Cl)cc2[nH]1] |
| 179 | 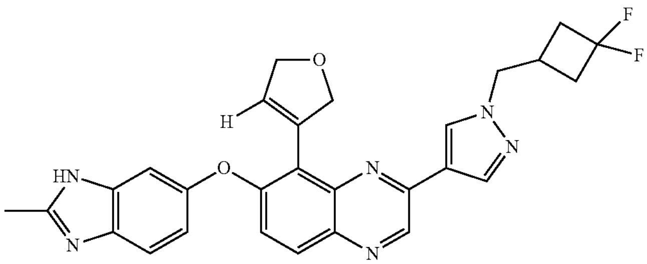 [SMILES: Cc1nc2ccc(Oc3ccc4ncc(-c5cnn(CC6CC(F)(F)C6)c5)nc4c3C3=CCOC3)cc2[nH]1] |
| 180 | 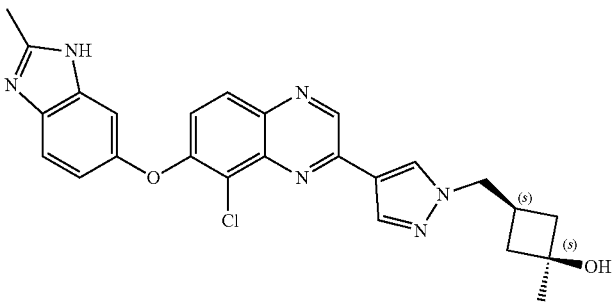 [SMILES: Cc1nc2ccc(Oc3ccc4ncc(-c5cnn(C[C@H]6C[C@@](C)(O)C6)c5)nc4c3Cl)cc2[nH]1] |
| 181 | 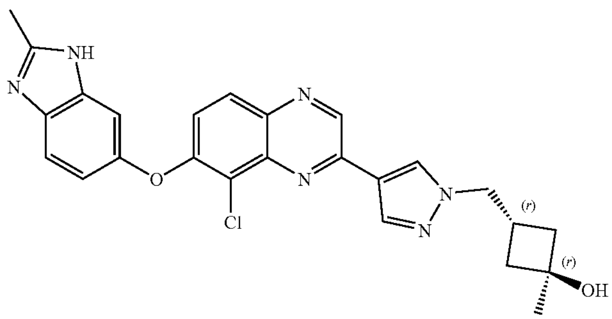 |

TABLE II-continued
| Compound No. | Structure |
|---|---|
| 182 | 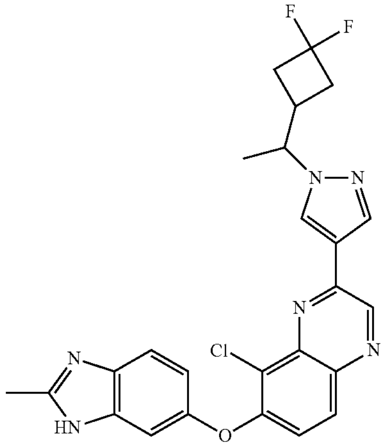 [SMILES: Cc1nc2ccc(Oc3ccc4ncc(-c5cnn(C(C)C6CC(F)(F)C6)c5)nc4c3Cl)cc2[nH]1] |
| 183 | 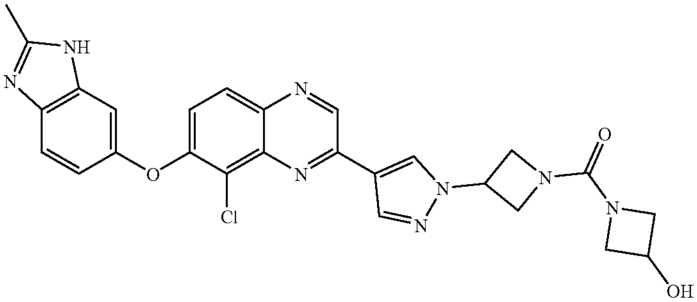 [SMILES: Cc1nc2ccc(Oc3ccc4ncc(-c5cnn(C6CN(C(=O)N7CC(O)C7)C6)c5)nc4c3Cl)cc2[nH]1] |
| 184 | 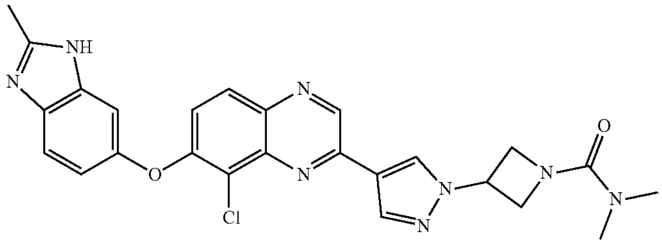 |
| 185 | 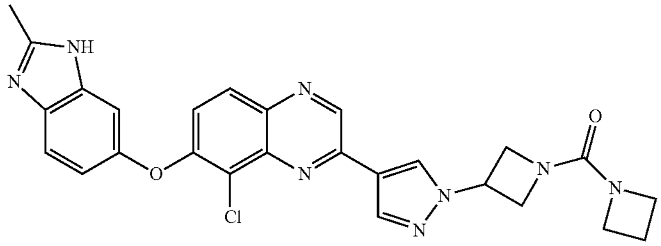 [SMILES: Cc1nc2ccc(Oc3ccc4ncc(-c5cnn(C6CN(C(=O)N7CCC7)C6)c5)nc4c3Cl)cc2[nH]1] |

TABLE II-continued
| Compound No. | Structure |
| --- | --- |
| 186 | 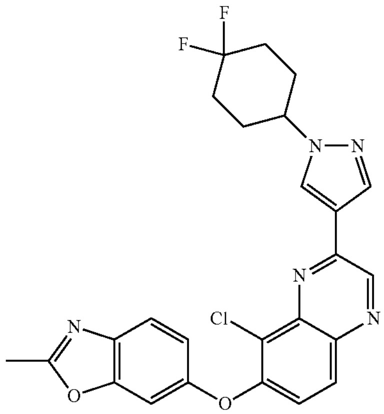 [SMILES: Cc1nc2ccc(Oc3ccc4ncc(-c5cnn(C6CCC(F)(F)CC6)c5)nc4c3Cl)cc2o1] |
| 187 | 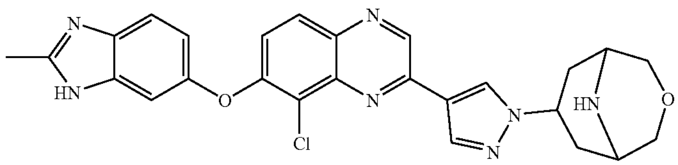 [SMILES: Cc1nc2ccc(Oc3ccc4ncc(-c5cnn(C6CC7COCC(C6)N7)c5)nc4c3Cl)cc2[nH]1] |
| 188 | 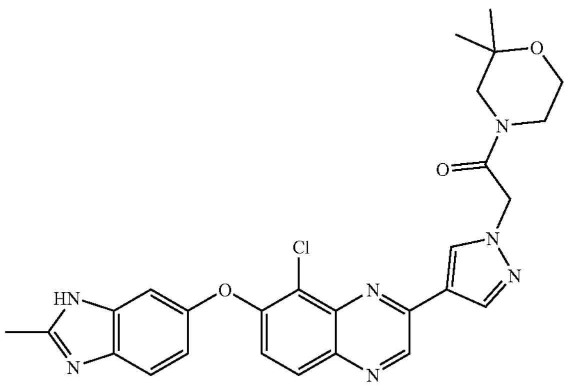 [SMILES: Cc1nc2ccc(Oc3ccc4ncc(-c5cnn(CC(=O)N6CCOC(C)(C)C6)c5)nc4c3Cl)cc2[nH]1] |
| 189 | 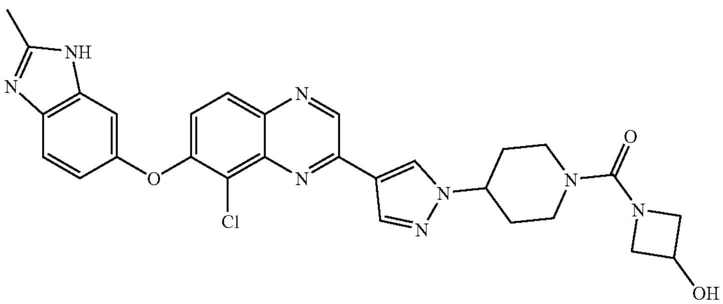 [SMILES: Cc1nc2ccc(Oc3ccc4ncc(-c5cnn(C6CCN(C(=O)N7CC(O)C7)CC6)c5)nc4c3Cl)cc2[nH]1] |
| 190 | 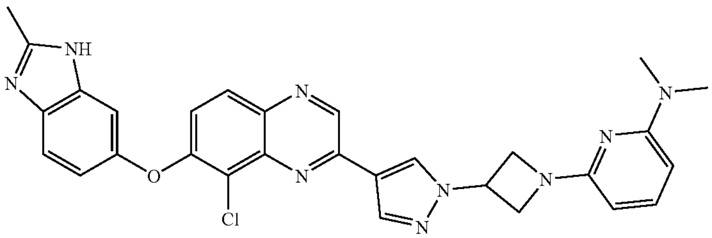 |

TABLE II-continued
| Compound No. | Structure |
| --- | --- |
| 191 | 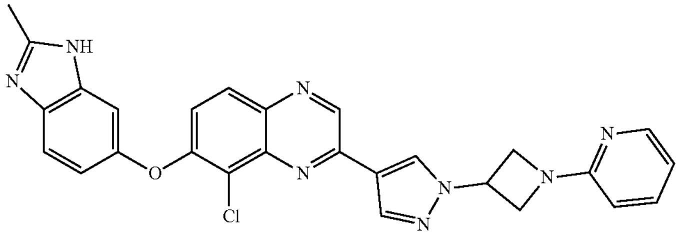 [SMILES: Cc1nc2ccc(Oc3ccc4ncc(-c5cnn(C6CN(c7ccccn7)C6)c5)nc4c3Cl)cc2[nH]1] |
| 192 | 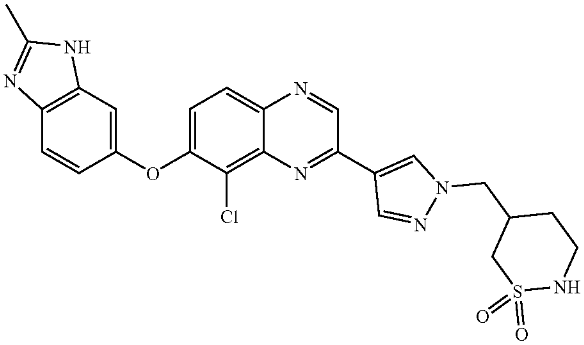 [SMILES: Cc1nc2ccc(Oc3ccc4ncc(-c5cnn(CC6CCNS(=O)(=O)C6)c5)nc4c3Cl)cc2[nH]1] |
| 193 | 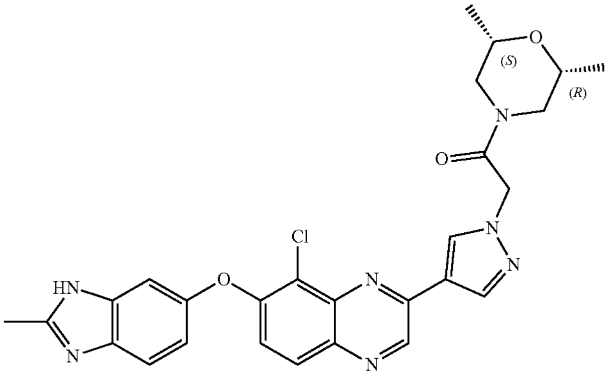 |
| 194 | 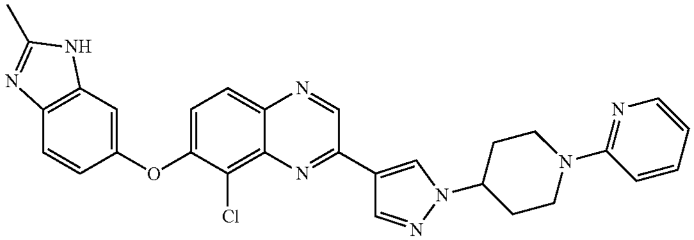 [SMILES: Cc1nc2ccc(Oc3ccc4ncc(-c5cnn(C6CCN(c7ccccn7)CC6)c5)nc4c3Cl)cc2[nH]1] |
| 195 | 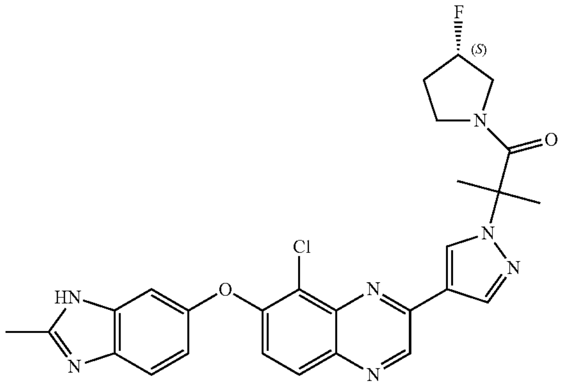 |

TABLE II-continued
| Compound No. | Structure |
|---|---|
| 196 | 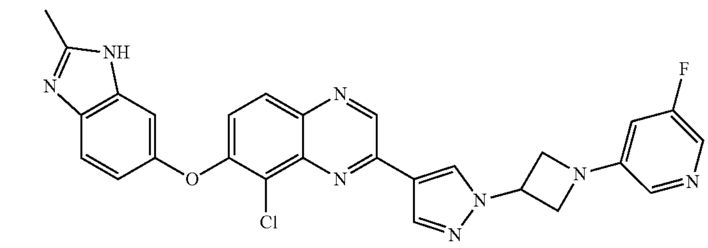 [SMILES: Cc1nc2ccc(Oc3ccc4ncc(-c5cnn(C6CN(c7cncc(F)c7)C6)c5)nc4c3Cl)cc2[nH]1] |
| 197 | 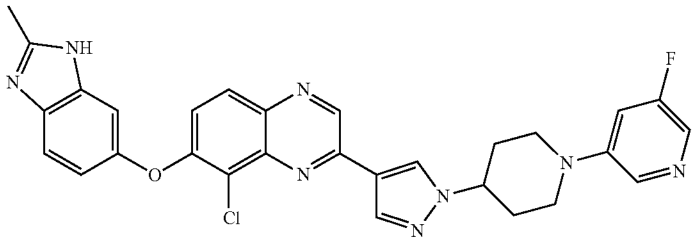 [SMILES: Cc1nc2ccc(Oc3ccc4ncc(-c5cnn(C6CCN(c7cncc(F)c7)CC6)c5)nc4c3Cl)cc2[nH]1] |
| 198 | 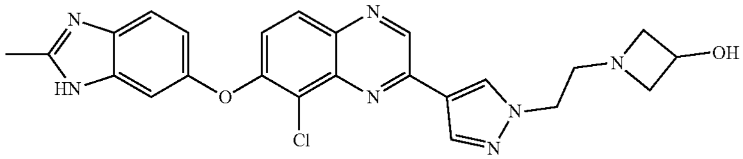 [SMILES: Cc1nc2ccc(Oc3ccc4ncc(-c5cnn(CCN6CC(O)C6)c5)nc4c3Cl)cc2[nH]1] |
| 199 | 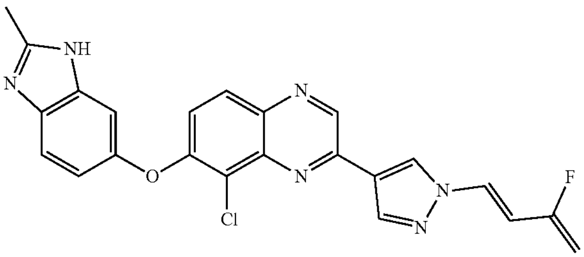 [SMILES: C=C(F)/C=C/n1cc(-c2cnc3ccc(Oc4ccc5nc(C)[nH]c5c4)c(Cl)c3n2)cn1] |
| 200 | 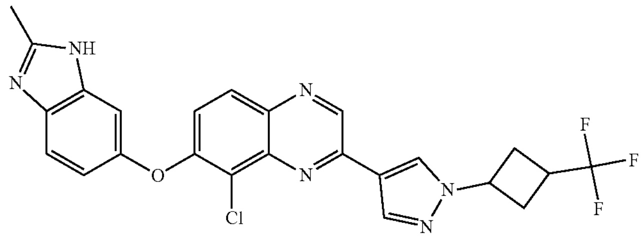 [SMILES: Cc1nc2ccc(Oc3ccc4ncc(-c5cnn(C6CC(C(F)(F)F)C6)c5)nc4c3Cl)cc2[nH]1] |
| 201 | 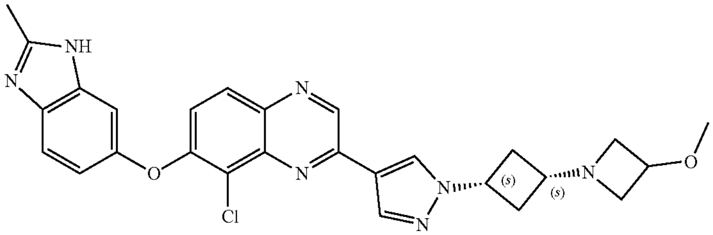 |

TABLE II-continued
| Compound No. | Structure |
| --- | --- |
| 202 | 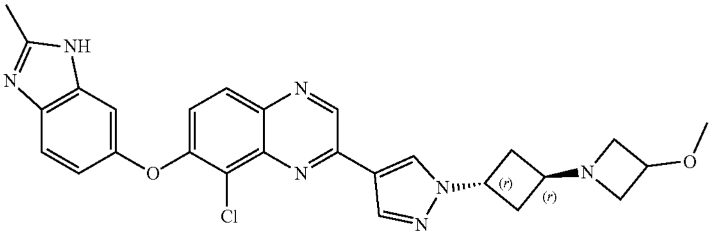 |
| 203 | 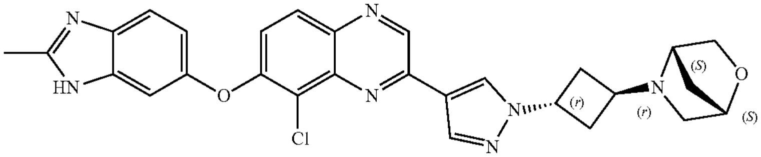 |
| 204 | 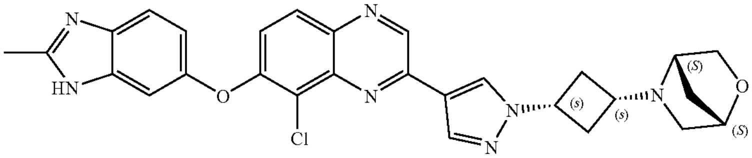 |
| 205 | 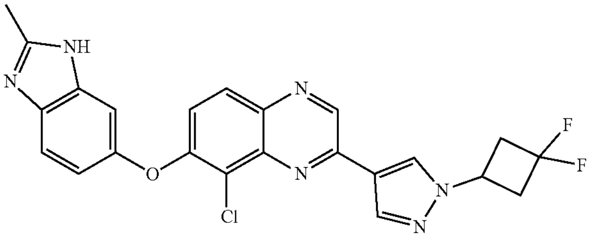 [SMILES: Cc1nc2ccc(Oc3ccc4ncc(-c5cnn(C6CC(F)(F)C6)c5)nc4c3Cl)cc2[nH]1] |
| 206 | 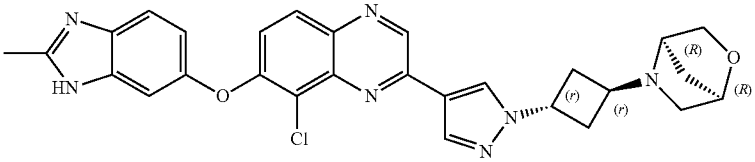 |
| 207 | 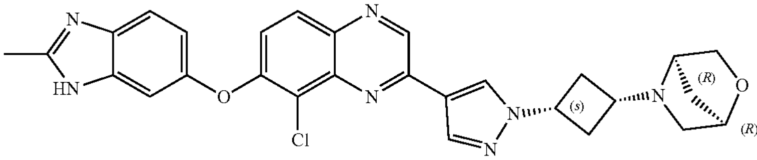 |
| 208 | 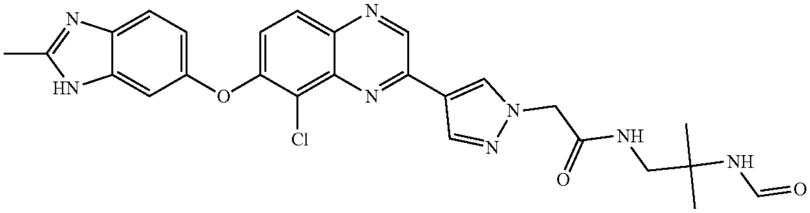 [SMILES: Cc1nc2ccc(Oc3ccc4ncc(-c5cnn(CC(=O)NCC(C)(C)NC=O)c5)nc4c3Cl)cc2[nH]1] |

TABLE II-continued
| Compound No. | Structure |
| --- | --- |
| 209 | 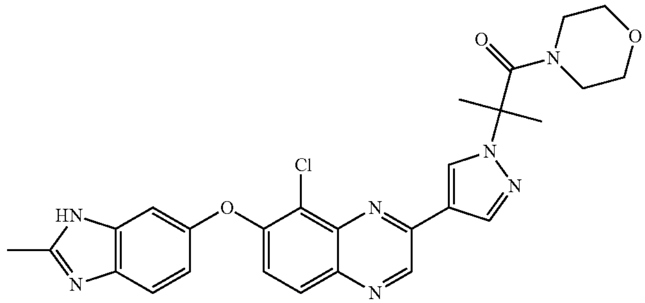 [SMILES: Cc1nc2ccc(Oc3ccc4ncc(-c5cnn(C(C)(C)C(=O)N6CCOCC6)c5)nc4c3Cl)cc2[nH]1] |
| 210 | 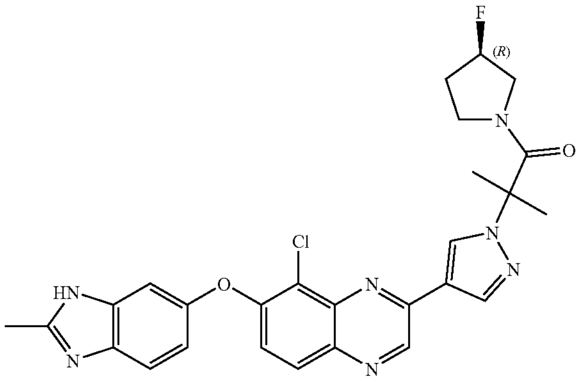 |
| 211 | 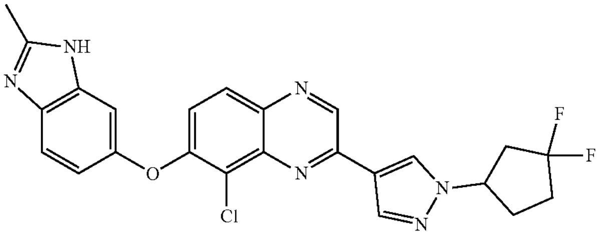 [SMILES: Cc1nc2ccc(Oc3ccc4ncc(-c5cnn(C6CCC(F)(F)C6)c5)nc4c3Cl)cc2[nH]1] |
| 212 | 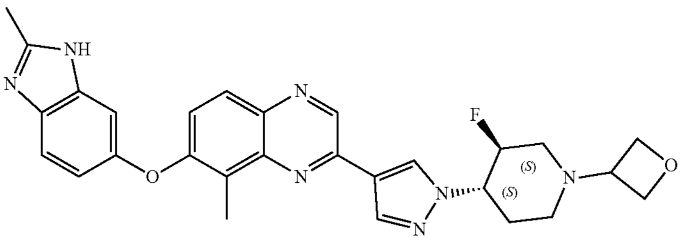 |
| 213 | 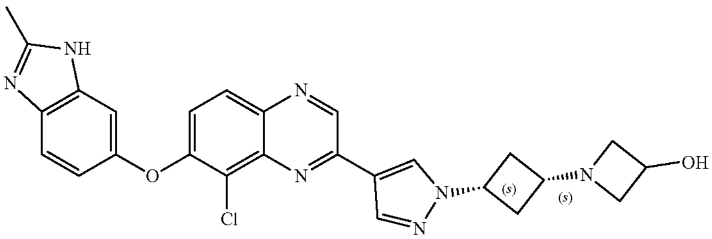 [SMILES: Cc1nc2ccc(Oc3ccc4ncc(-c5cnn([C@H]6C[C@@H](N7CC(O)C7)C6)c5)nc4c3Cl)cc2[nH]1] |

TABLE II-continued
| Compound No. | Structure |
|---|---|
| 214 | 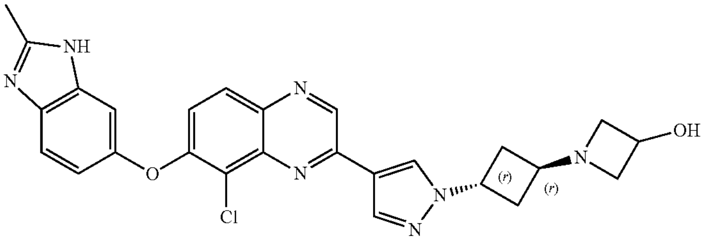 [SMILES: Cc1nc2ccc(Oc3ccc4ncc(-c5cnn([C@H]6C[C@H](N7CC(O)C7)C6)c5)nc4c3Cl)cc2[nH]1] |
| 215 | 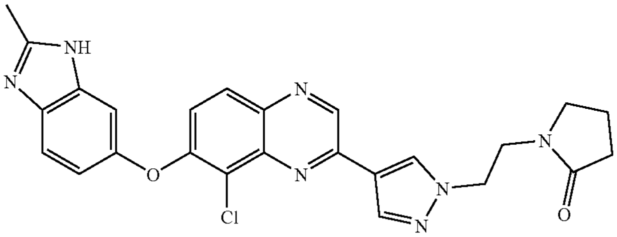 [SMILES: Cc1nc2ccc(Oc3ccc4ncc(-c5cnn(CCN6CCCC6=O)c5)nc4c3Cl)cc2[nH]1] |
| 216 | 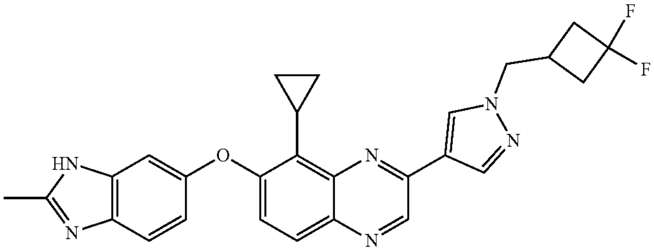 [SMILES: Cc1nc2ccc(Oc3ccc4ncc(-c5cnn(CC6CC(F)(F)C6)c5)nc4c3C3CC3)cc2[nH]1] |
| 217 | 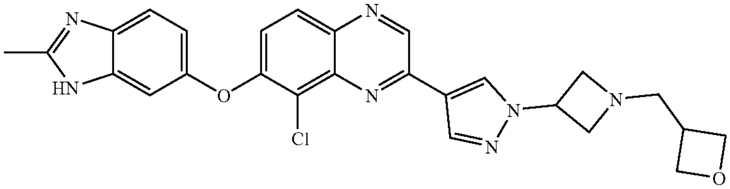 [SMILES: Cc1nc2ccc(Oc3ccc4ncc(-c5cnn(C6CN(CC7COC7)C6)c5)nc4c3Cl)cc2[nH]1] |
| 218 | 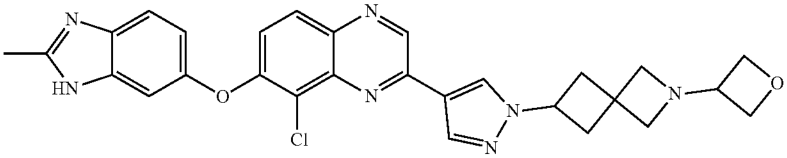 [SMILES: Cc1nc2ccc(Oc3ccc4ncc(-c5cnn(C6CC7(C6)CN(C6COC6)C7)c5)nc4c3Cl)cc2[nH]1] |
| 219 | 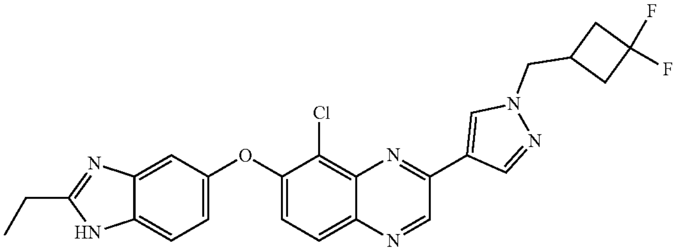 [SMILES: CCc1nc2cc(Oc3ccc4ncc(-c5cnn(CC6CC(F)(F)C6)c5)nc4c3Cl)ccc2[nH]1] |
| 220 | 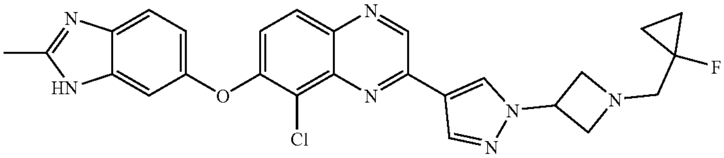 [SMILES: Cc1nc2ccc(Oc3ccc4ncc(-c5cnn(C6CN(CC7(F)CC7)C6)c5)nc4c3Cl)cc2[nH]1] |

TABLE II-continued
| Compound No. | Structure |
|---|---|
| 221 | 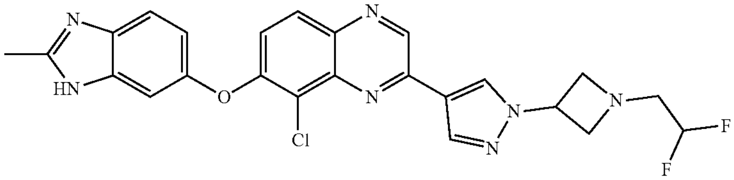 [SMILES: Cc1nc2ccc(Oc3ccc4ncc(-c5cnn(C6CN(CC(F)F)C6)c5)nc4c3Cl)cc2[nH]1] |
| 222 | 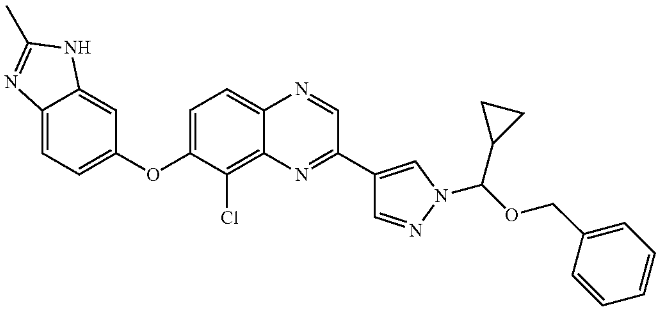 [SMILES: Cc1nc2ccc(Oc3ccc4ncc(-c5cnn(C(OCc6ccccc6)C6CC6)c5)nc4c3Cl)cc2[nH]1] |
| 223 | 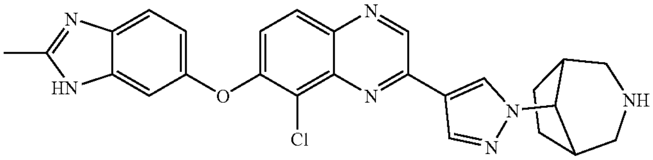 [SMILES: Cc1nc2ccc(Oc3ccc4ncc(-c5cnn(C6C7CCC6CNC7)c5)nc4c3Cl)cc2[nH]1] |
| 224 | 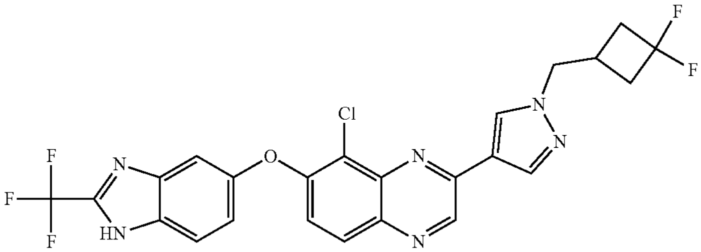 [SMILES: FC1(F)CC(Cn2cc(-c3cnc4ccc(Oc5ccc6[nH]c(C(F)(F)F)nc6c5)c(Cl)c4n3)cn2)C1] |
| 225 | 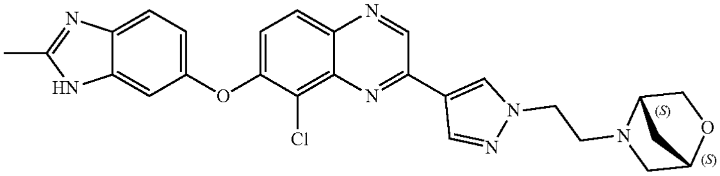 |
| 226 | 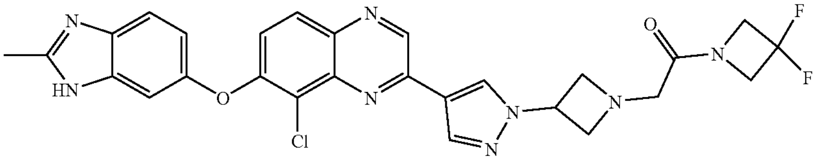 [SMILES: Cc1nc2ccc(Oc3ccc4ncc(-c5cnn(C6CN(CC(=O)N7CC(F)(F)C7)C6)c5)nc4c3Cl)cc2[nH]1] |
| 227 | 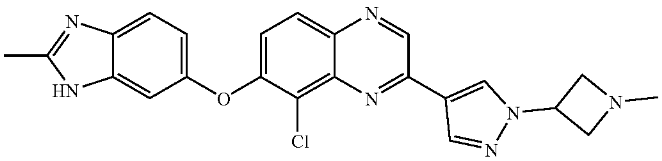 |

TABLE II-continued
| Compound No. | Structure |
|---|---|
| 228 | 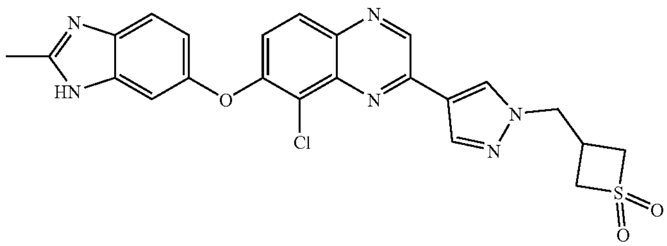 [SMILES: Cc1nc2ccc(Oc3ccc4ncc(-c5cnn(CC6CS(=O)(=O)C6)c5)nc4c3Cl)cc2[nH]1] |
| 229 | 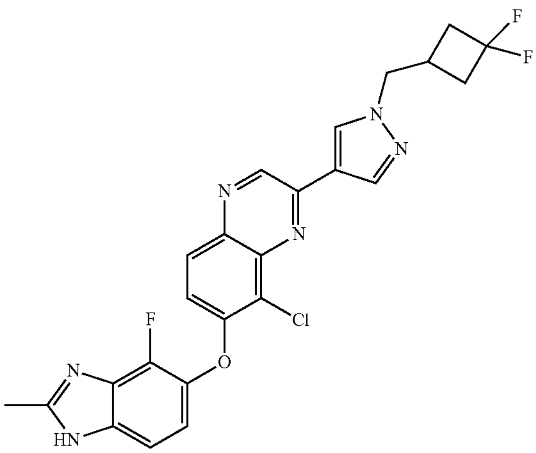 [SMILES: Cc1nc2c(F)c(Oc3ccc4ncc(-c5cnn(CC6CC(F)(F)C6)c5)nc4c3Cl)ccc2[nH]1] |
| 230 | 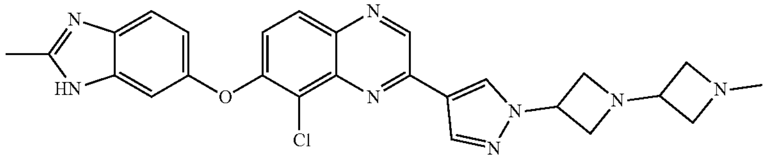 |
| 231 | 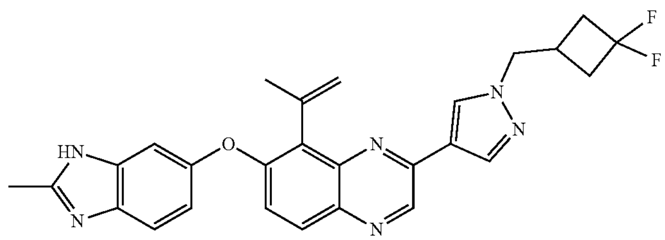 [SMILES: C=C(C)c1c(Oc2ccc3nc(C)[nH]c3c2)ccc2ncc(-c3cnn(CC4CC(F)(F)C4)c3)nc12] |
| 232 | 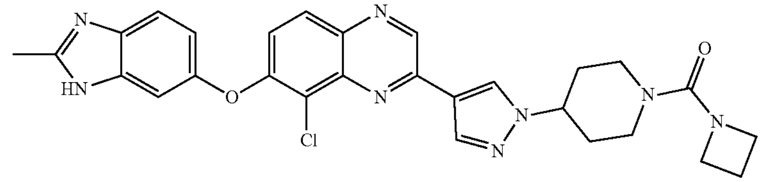 [SMILES: Cc1nc2ccc(Oc3ccc4ncc(-c5cnn(C6CCN(C(=O)N7CCC7)CC6)c5)nc4c3Cl)cc2[nH]1] |
| 233 | 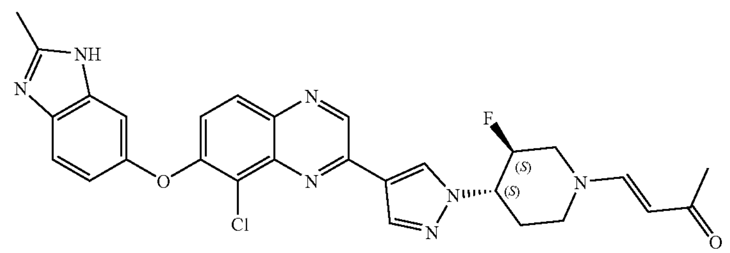 |

TABLE II-continued
| Compound No. | Structure |
| --- | --- |
| 234 | 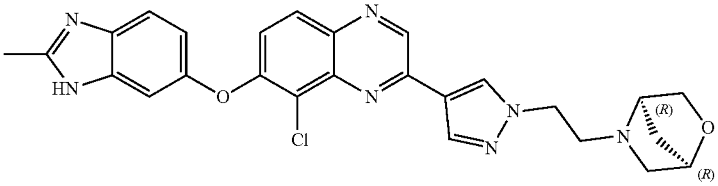 |
| 235 | 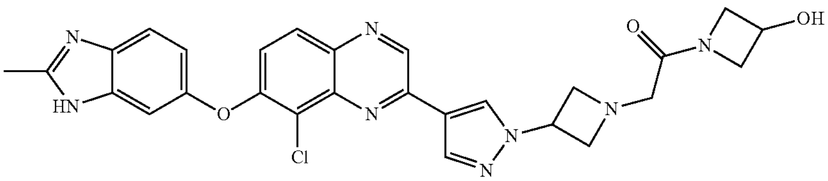 [SMILES: Cc1nc2ccc(Oc3ccc4ncc(-c5cnn(C6CN(CC(=O)N7CC(O)C7)C6)c5)nc4c3Cl)cc2[nH]1] |
| 236 | 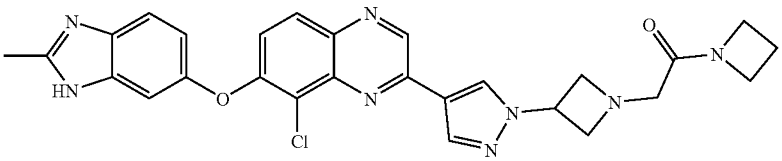 [SMILES: Cc1nc2ccc(Oc3ccc4ncc(-c5cnn(C6CN(CC(=O)N7CCC7)C6)c5)nc4c3Cl)cc2[nH]1] |
| 237 | 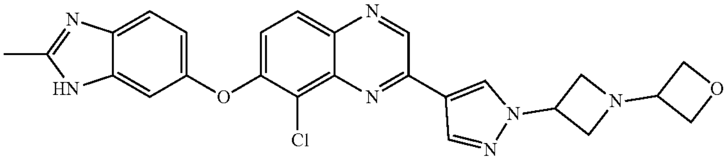 [SMILES: Cc1nc2ccc(Oc3ccc4ncc(-c5cnn(C6CN(C7COC7)C6)c5)nc4c3Cl)cc2[nH]1] |
| 238 | 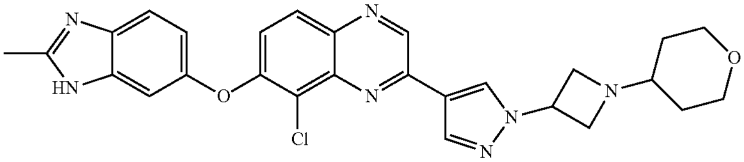 [SMILES: Cc1nc2ccc(Oc3ccc4ncc(-c5cnn(C6CN(C7CCOCC7)C6)c5)nc4c3Cl)cc2[nH]1] |
| 239 | 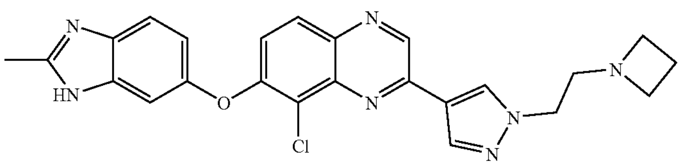 [SMILES: Cc1nc2ccc(Oc3ccc4ncc(-c5cnn(CCN6CCC6)c5)nc4c3Cl)cc2[nH]1] |
| 240 | 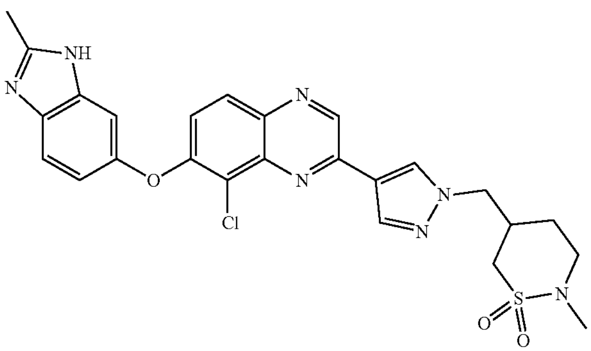 |

TABLE II-continued
| Compound No. | Structure |
|---|---|
| 241 | 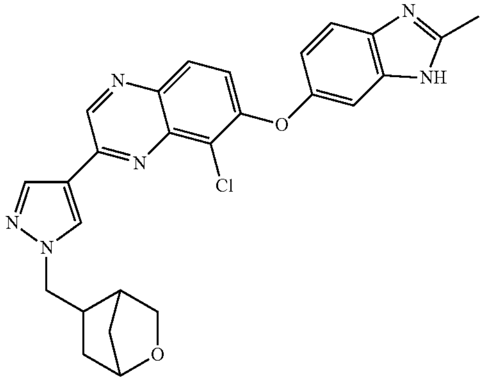 [SMILES: Cc1nc2ccc(Oc3ccc4ncc(-c5cnn(CC6CC7CC6CO7)c5)nc4c3Cl)cc2[nH]1] |
| 242 | 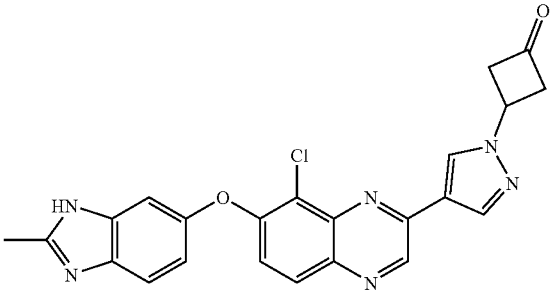 [SMILES: Cc1nc2ccc(Oc3ccc4ncc(-c5cnn(C6CC(=O)C6)c5)nc4c3Cl)cc2[nH]1] |
| 243 | 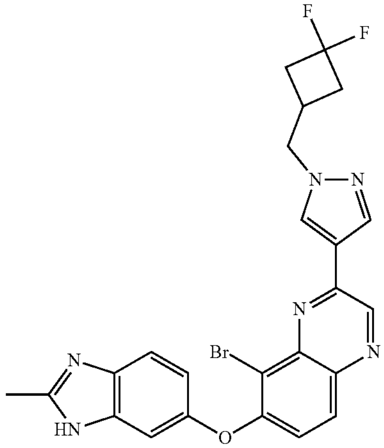 [SMILES: Cc1nc2ccc(Oc3ccc4ncc(-c5cnn(CC6CC(F)(F)C6)c5)nc4c3Br)cc2[nH]1] |
| 244 | 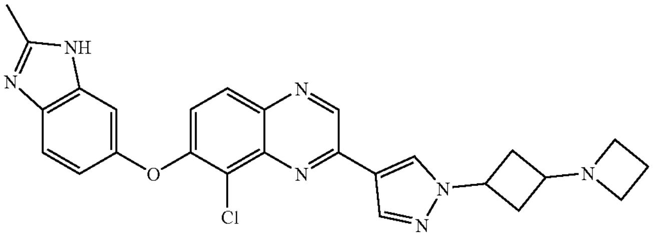 [SMILES: Cc1nc2ccc(Oc3ccc4ncc(-c5cnn(C6CC(N7CCC7)C6)c5)nc4c3Cl)cc2[nH]1] |

TABLE II-continued
| Compound No. | Structure |
|---|---|
| 245 | 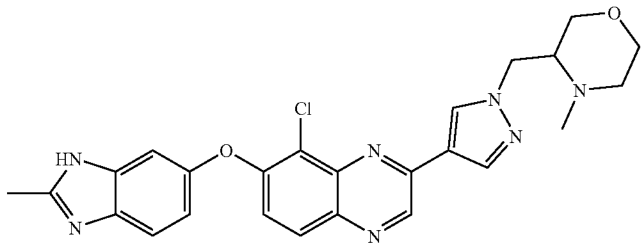 [SMILES: Cc1nc2ccc(Oc3ccc4ncc(-c5cnn(CC6COCCN6C)c5)nc4c3Cl)cc2[nH]1] |
| 246 | 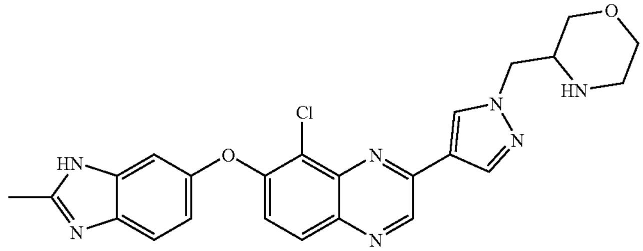 [SMILES: Cc1nc2ccc(Oc3ccc4ncc(-c5cnn(CC6COCCN6)c5)nc4c3Cl)cc2[nH]1] |
| 247 | 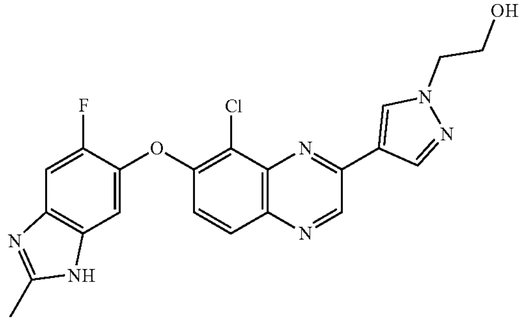 [SMILES: Cc1nc2cc(F)c(Oc3ccc4ncc(-c5cnn(CCO)c5)nc4c3Cl)cc2[nH]1] |
| 248 | 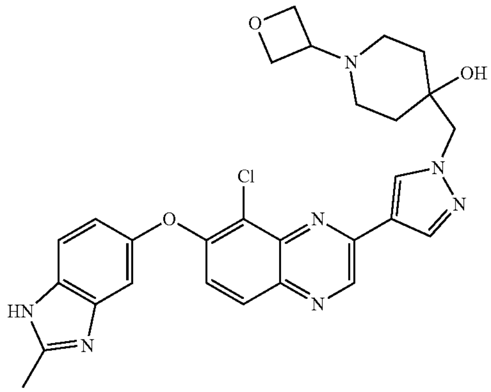 [SMILES: Cc1nc2cc(Oc3ccc4ncc(-c5cnn(CC6(O)CCN(C7COC7)CC6)c5)nc4c3Cl)ccc2[nH]1] |
| 249 | 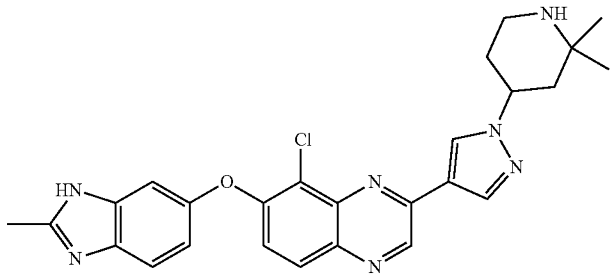 |

TABLE II-continued
| Compound No. | Structure |
|---|---|
| 250 | 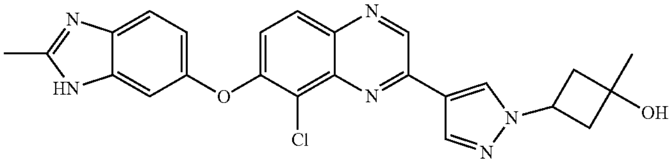 [SMILES: Cc1nc2ccc(Oc3ccc4ncc(-c5cnn(C6CC(C)(O)C6)c5)nc4c3Cl)cc2[nH]1] |
| 251 | 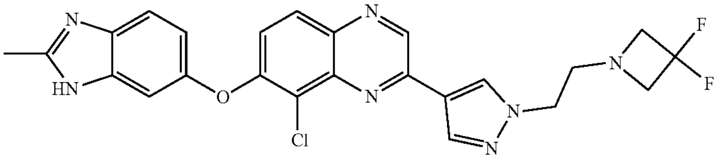 [SMILES: Cc1nc2ccc(Oc3ccc4ncc(-c5cnn(CCN6CC(F)(F)C6)c5)nc4c3Cl)cc2[nH]1] |
| 252 | 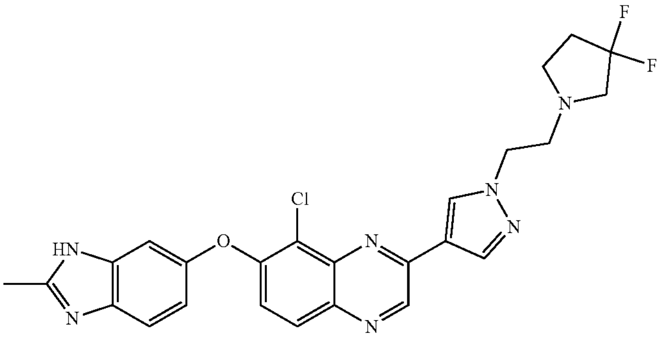 [SMILES: Cc1nc2ccc(Oc3ccc4ncc(-c5cnn(CCN6CCC(F)(F)C6)c5)nc4c3Cl)cc2[nH]1] |
| 253 | 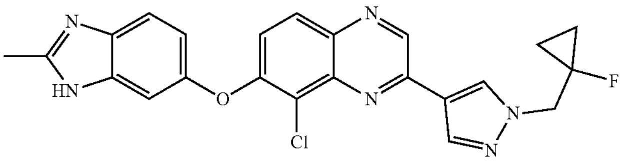 [SMILES: Cc1nc2ccc(Oc3ccc4ncc(-c5cnn(CC6(F)CC6)c5)nc4c3Cl)cc2[nH]1] |
| 254 | 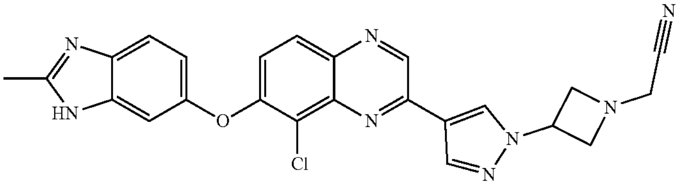 [SMILES: Cc1nc2ccc(Oc3ccc4ncc(-c5cnn(C6CN(CC#N)C6)c5)nc4c3Cl)cc2[nH]1] |
| 255 | 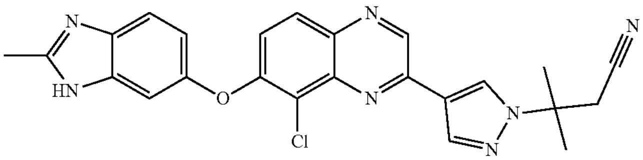 [SMILES: Cc1nc2ccc(Oc3ccc4ncc(-c5cnn(C(C)(C)CC#N)c5)nc4c3Cl)cc2[nH]1] |
| 256 | 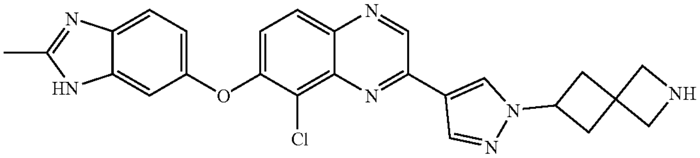 [SMILES: Cc1nc2ccc(Oc3ccc4ncc(-c5cnn(C6CC7(CNC7)C6)c5)nc4c3Cl)cc2[nH]1] |

TABLE II-continued
| Compound No. | Structure |
| --- | --- |
| 257 | 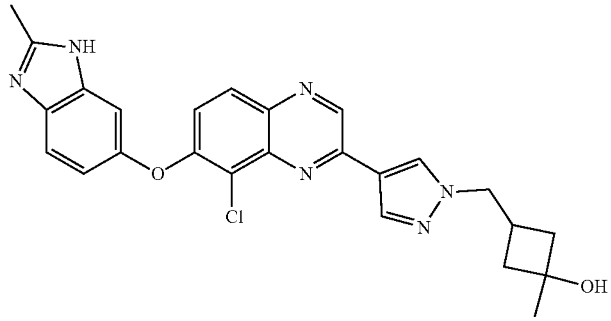 [SMILES: Cc1nc2ccc(Oc3ccc4ncc(-c5cnn(CC6CC(C)(O)C6)c5)nc4c3Cl)cc2[nH]1] |
| 258 | 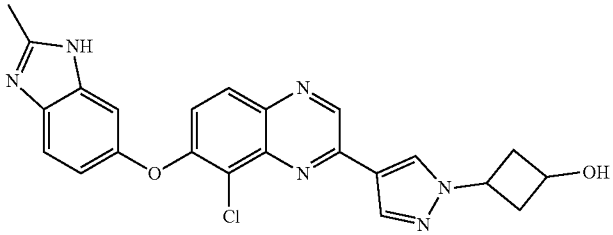 [SMILES: Cc1nc2ccc(Oc3ccc4ncc(-c5cnn(C6CC(O)C6)c5)nc4c3Cl)cc2[nH]1] |
| 259 | 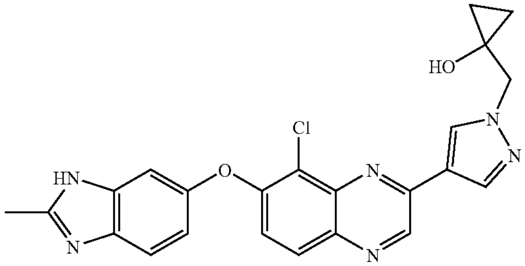 [SMILES: Cc1nc2ccc(Oc3ccc4ncc(-c5cnn(CC6(O)CC6)c5)nc4c3Cl)cc2[nH]1] |
| 260 | 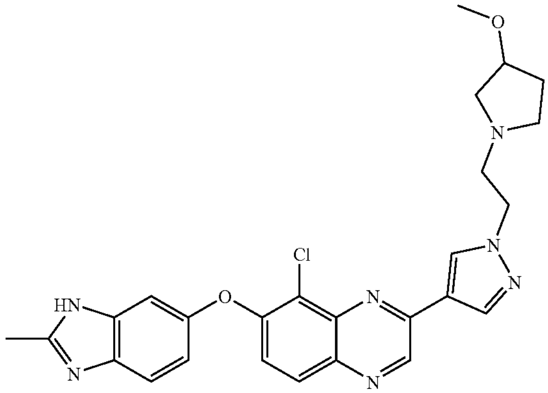 [SMILES: COC1CCN(CCn2cc(-c3cnc4ccc(Oc5ccc6nc(C)[nH]c6c5)c(Cl)c4n3)cn2)C1] |
| 261 | 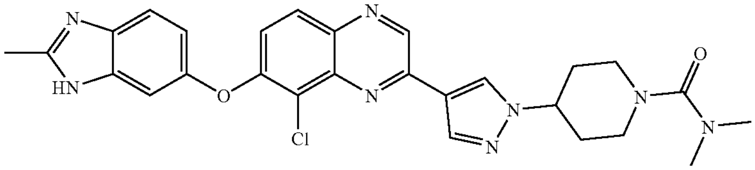 |

TABLE II-continued
| Compound No. | Structure |
|---|---|
| 262 | 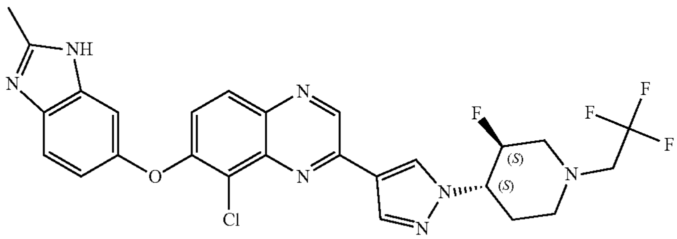 |
| 263 | 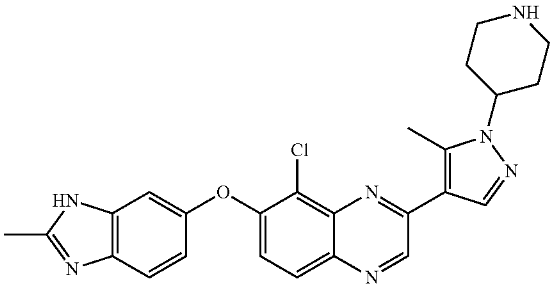 [SMILES: Cc1nc2ccc(Oc3ccc4ncc(-c5cnn(C6CCNCC6)c5C)nc4c3Cl)cc2[nH]1] |
| 264 | 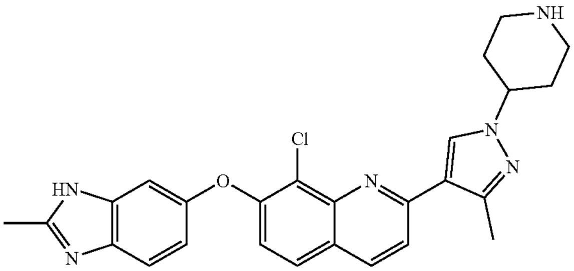 [SMILES: Cc1nc2ccc(Oc3ccc4ccc(-c5cn(C6CCNCC6)nc5C)nc4c3Cl)cc2[nH]1] |
| 265 | 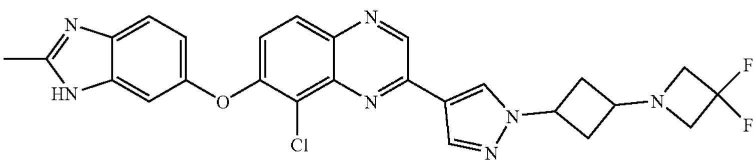 [SMILES: Cc1nc2ccc(Oc3ccc4ncc(-c5cnn(C6CC(N7CC(F)(F)C7)C6)c5)nc4c3Cl)cc2[nH]1] |
| 266 | 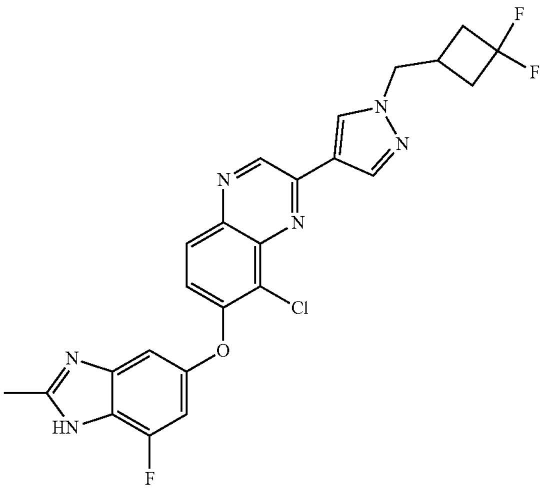 [SMILES: Cc1nc2cc(Oc3ccc4ncc(-c5cnn(CC6CC(F)(F)C6)c5)nc4c3Cl)cc(F)c2[nH]1] |

TABLE II-continued
| Compound No. | Structure |
|---|---|
| 267 | 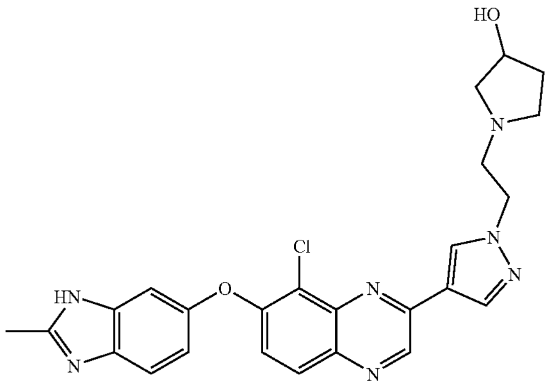 [SMILES: Cc1nc2ccc(Oc3ccc4ncc(-c5cnn(CCN6CCC(O)C6)c5)nc4c3Cl)cc2[nH]1] |
| 268 | 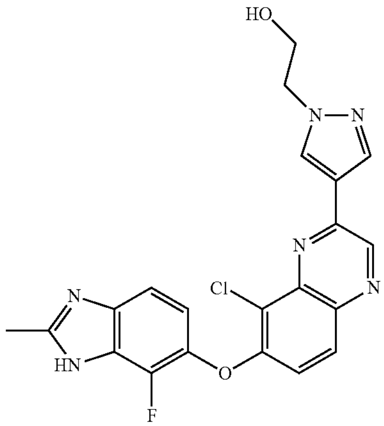 [SMILES: Cc1nc2ccc(Oc3ccc4ncc(-c5cnn(CCO)c5)nc4c3Cl)c(F)c2[nH]1] |
| 269 | 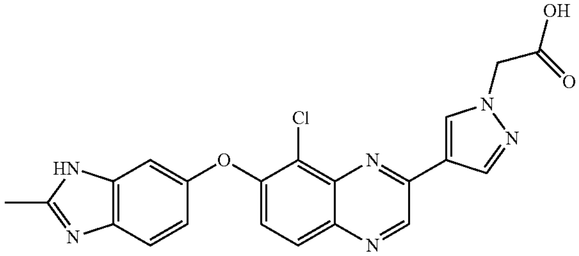 [SMILES: Cc1nc2ccc(Oc3ccc4ncc(-c5cnn(CC(=O)O)c5)nc4c3Cl)cc2[nH]1] |
| 270 | 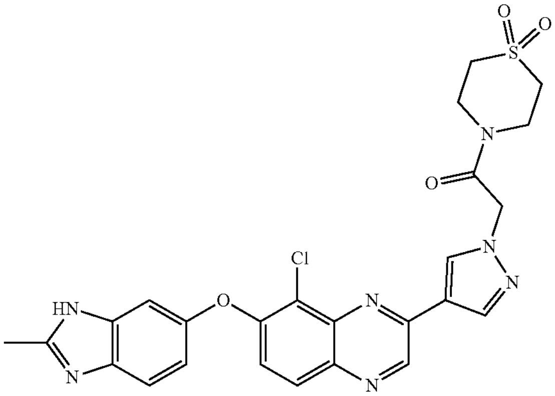 [SMILES: Cc1nc2ccc(Oc3ccc4ncc(-c5cnn(CC(=O)N6CCS(=O)(=O)CC6)c5)nc4c3Cl)cc2[nH]1] |

TABLE II-continued
| Compound No. | Structure |
|---|---|
| 271 | 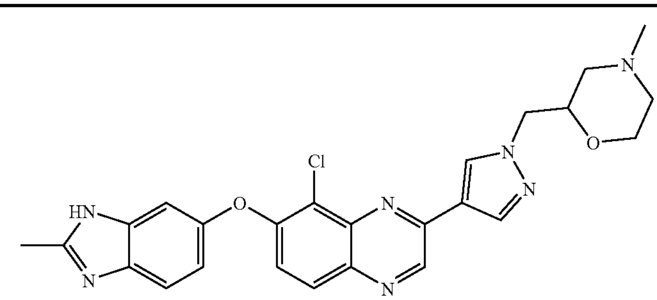 |
| 272 | 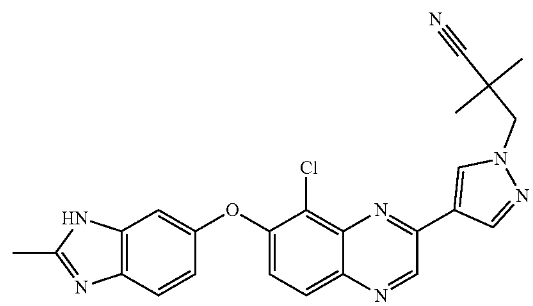 [SMILES: Cc1nc2ccc(Oc3ccc4ncc(-c5cnn(CC(C)(C)C#N)c5)nc4c3Cl)cc2[nH]1] |
| 273 | 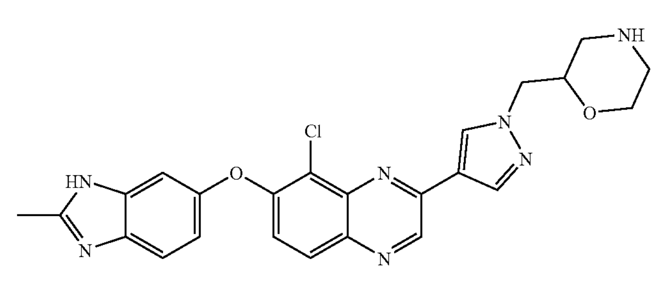 [SMILES: Cc1nc2ccc(Oc3ccc4ncc(-c5cnn(CC6CNCCO6)c5)nc4c3Cl)cc2[nH]1] |
| 274 | 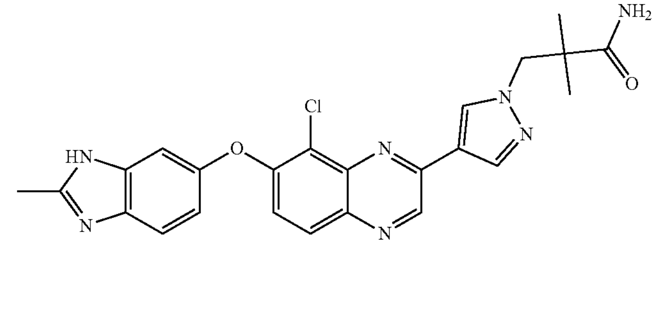 [SMILES: Cc1nc2ccc(Oc3ccc4ncc(-c5cnn(CC(C)(C)C(N)=O)c5)nc4c3Cl)cc2[nH]1] |
| 275 | 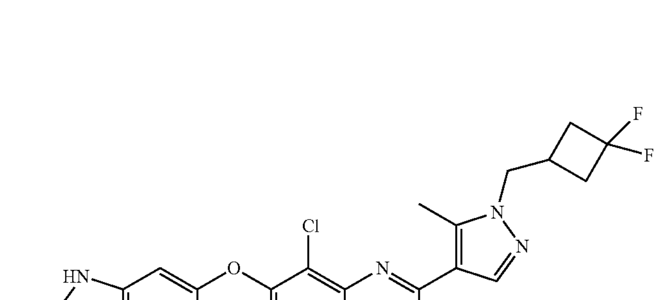 |

TABLE II-continued
| Compound No. | Structure |
| --- | --- |
| 276 | 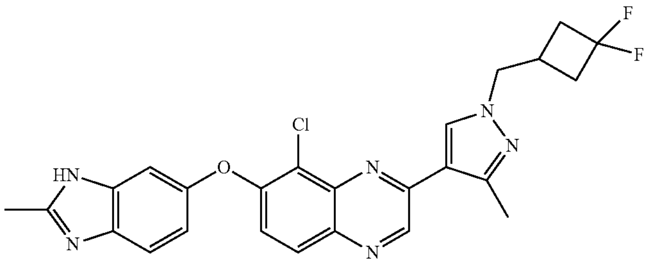 [SMILES: Cc1nc2ccc(Oc3ccc4ncc(-c5cn(CC6CC(F)(F)C6)nc5C)nc4c3Cl)cc2[nH]1] |
| 277 | 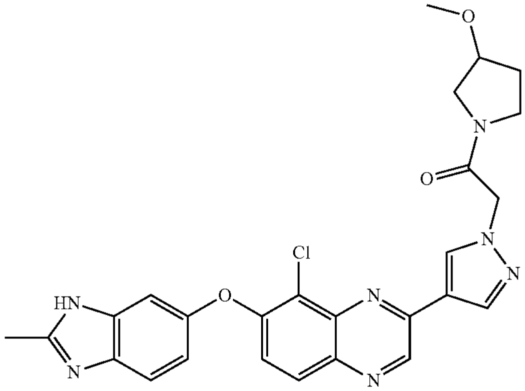 [SMILES: COC1CCN(C(=O)Cn2cc(-c3cnc4ccc(Oc5ccc6nc(C)[nH]c6c5)c(Cl)c4n3)cn2)C1] |
| 278 | 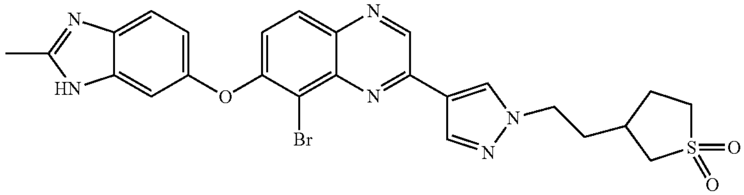 [SMILES: Cc1nc2ccc(Oc3ccc4ncc(-c5cnn(CCC6CCS(=O)(=O)C6)c5)nc4c3Br)cc2[nH]1] |
| 279 | 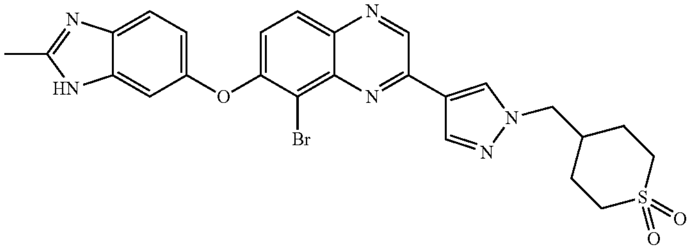 [SMILES: Cc1nc2ccc(Oc3ccc4ncc(-c5cnn(CC6CCS(=O)(=O)CC6)c5)nc4c3Br)cc2[nH]1] |
| 280 | 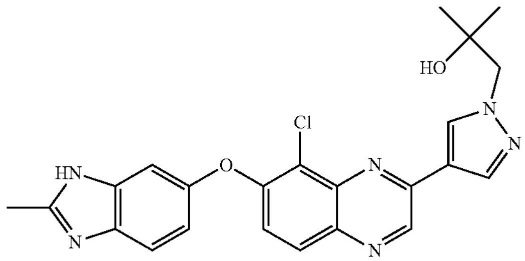 [SMILES: Cc1nc2ccc(Oc3ccc4ncc(-c5cnn(CC(C)(C)O)c5)nc4c3Cl)cc2[nH]1] |

TABLE II-continued
| Compound No. | Structure |
|---|---|
| 281 | 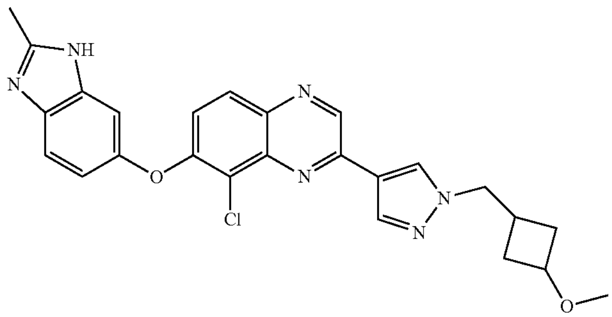 |
| 282 | 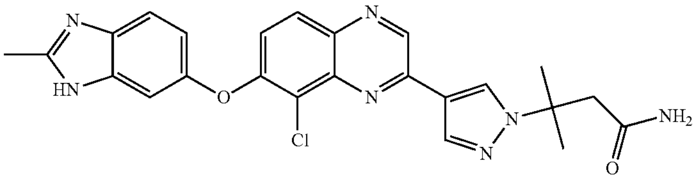 [SMILES: Cc1nc2ccc(Oc3ccc4ncc(-c5cnn(C(C)(C)CC(N)=O)c5)nc4c3Cl)cc2[nH]1] |
| 283 | 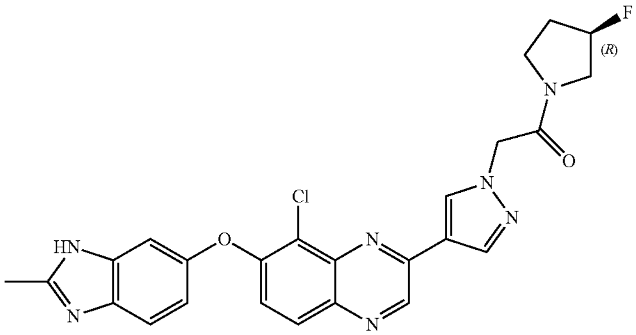 |
| 284 | 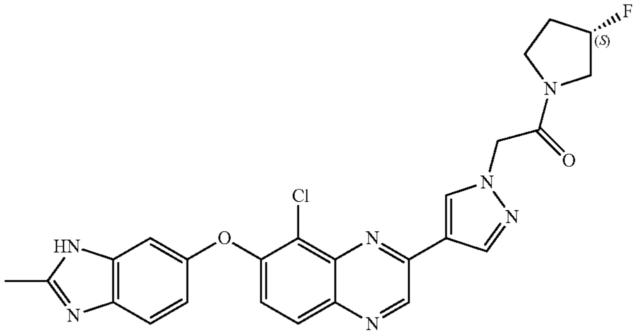 |
| 285 | 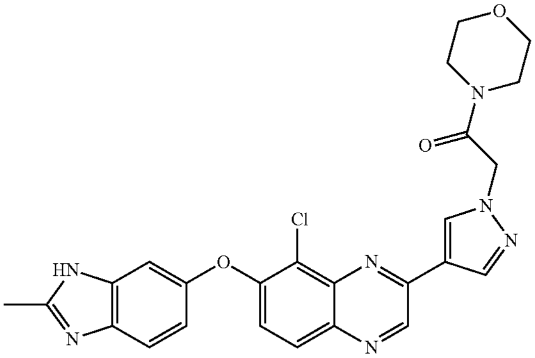 [SMILES: Cc1nc2ccc(Oc3ccc4ncc(-c5cnn(CC(=O)N6CCOCC6)c5)nc4c3Cl)cc2[nH]1] |

TABLE II-continued
| Compound No. | Structure |
|---|---|
| 286 | 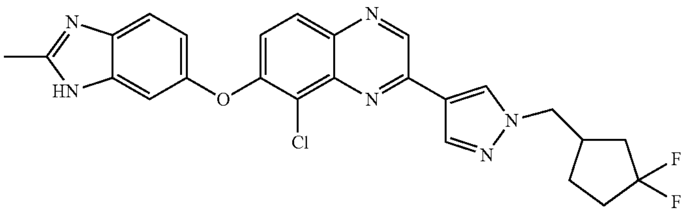 [SMILES: Cc1nc2ccc(Oc3ccc4ncc(-c5cnn(CC6CCC(F)(F)C6)c5)nc4c3Cl)cc2[nH]1] |
| 287 | 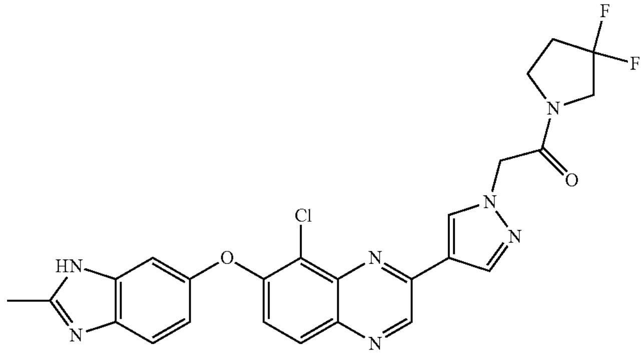 [SMILES: Cc1nc2ccc(Oc3ccc4ncc(-c5cnn(CC(=O)N6CCC(F)(F)C6)c5)nc4c3Cl)cc2[nH]1] |
| 288 | 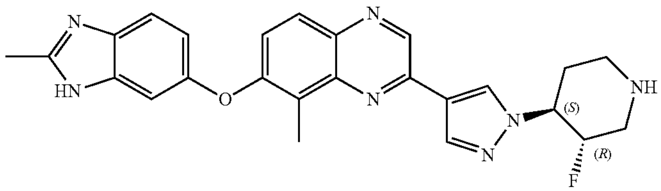 |
| 289 | 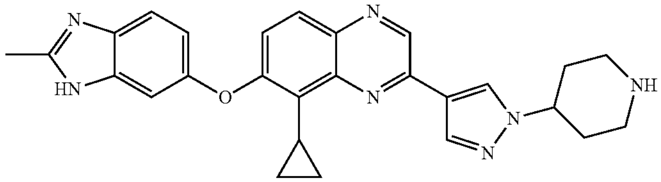 [SMILES: Cc1nc2ccc(Oc3ccc4ncc(-c5cnn(C6CCNCC6)c5)nc4c3C3CC3)cc2[nH]1] |
| 290 | 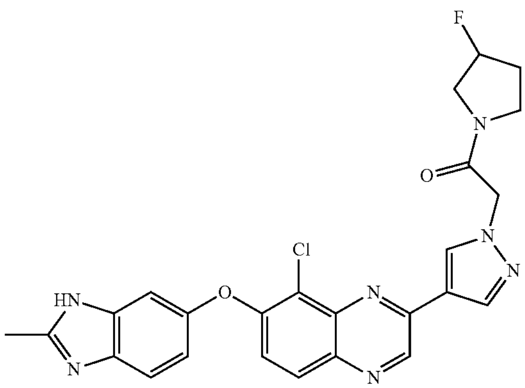 [SMILES: Cc1nc2ccc(Oc3ccc4ncc(-c5cnn(CC(=O)N6CCC(F)C6)c5)nc4c3Cl)cc2[nH]1] |

TABLE II-continued
| Compound No. | Structure |
|---|---|
| 291 | 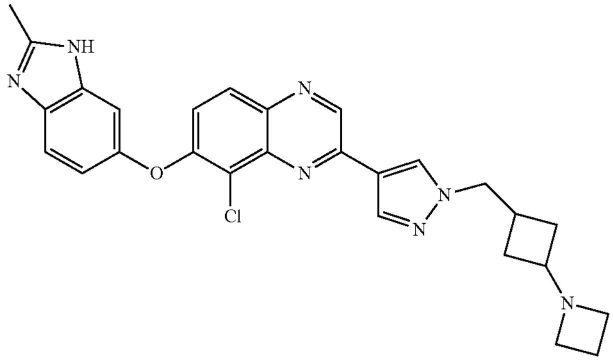 [SMILES: Cc1nc2ccc(Oc3ccc4ncc(-c5cnn(CC6CC(N7CCC7)C6)c5)nc4c3Cl)cc2[nH]1] |
| 292 | 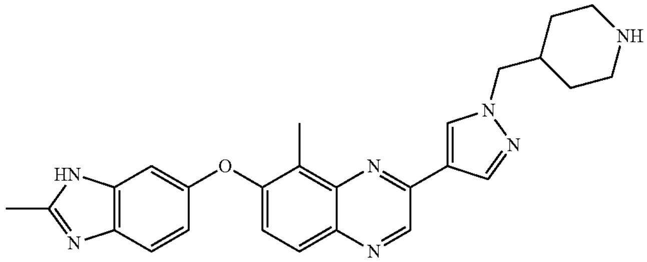 [SMILES: Cc1nc2ccc(Oc3ccc4ncc(-c5cnn(CC6CCNCC6)c5)nc4c3C)cc2[nH]1] |
| 293 | 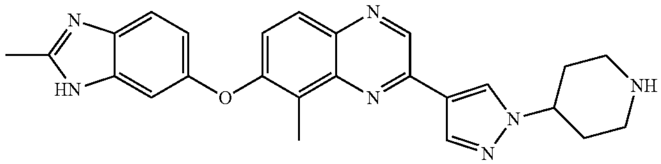 [SMILES: Cc1nc2ccc(Oc3ccc4ncc(-c5cnn(C6CCNCC6)c5)nc4c3C)cc2[nH]1] |
| 294 | 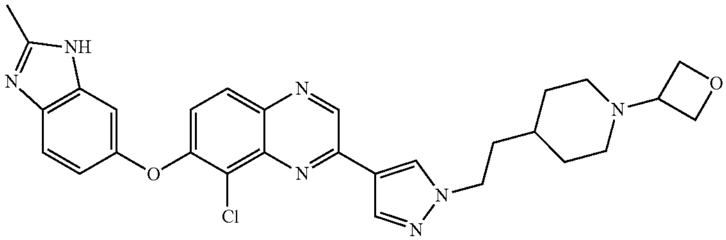 [SMILES: Cc1nc2ccc(Oc3ccc4ncc(-c5cnn(CCC6CCN(C7COC7)CC6)c5)nc4c3Cl)cc2[nH]1] |

TABLE II-continued
| Compound No. | Structure |
| --- | --- |
| 295 | 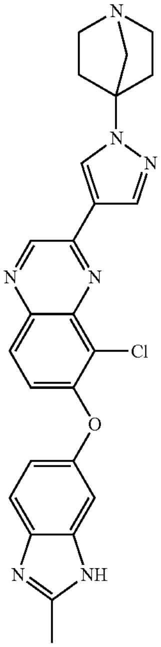 [SMILES: Cc1nc2ccc(Oc3ccc4ncc(-c5cnn(C67CCN(CC6)C7)c5)nc4c3Cl)cc2[nH]1] |
| 296 | 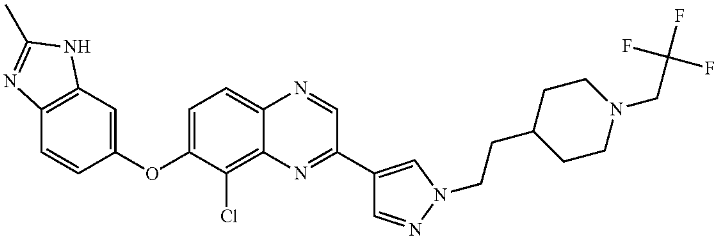 [SMILES: Cc1nc2ccc(Oc3ccc4ncc(-c5cnn(CCC6CCN(CC(F)(F)F)CC6)c5)nc4c3Cl)cc2[nH]1] |
| 297 | 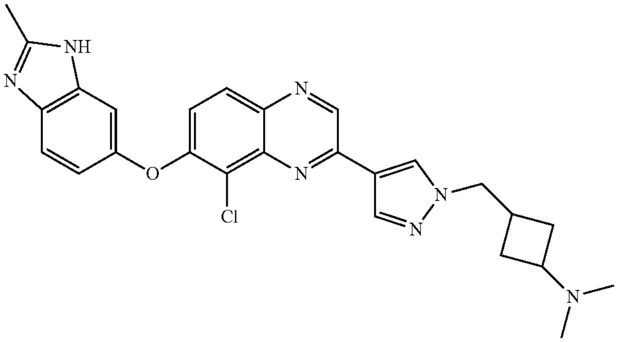 |
| 298 | 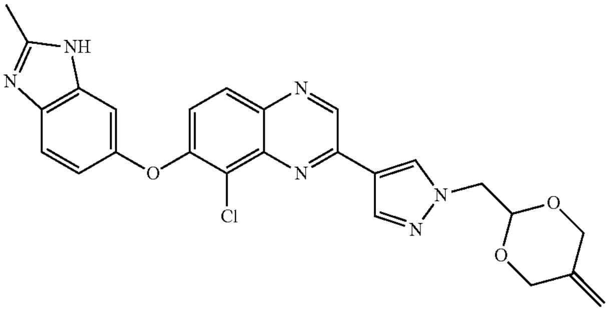 |

TABLE II-continued
| Compound No. | Structure |
| --- | --- |
| 299 | 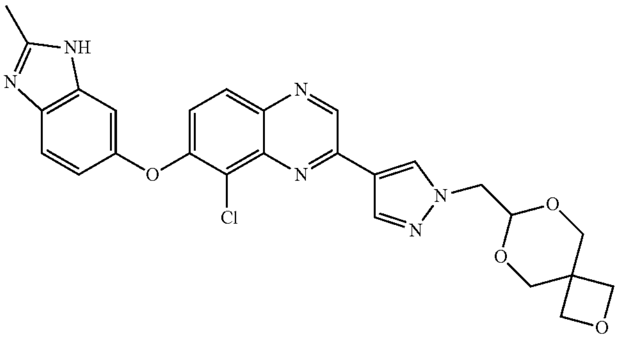 [SMILES: Cc1nc2ccc(Oc3ccc4ncc(-c5cnn(CC6OCC7(COC7)CO6)c5)nc4c3Cl)cc2[nH]1] |
| 300 | 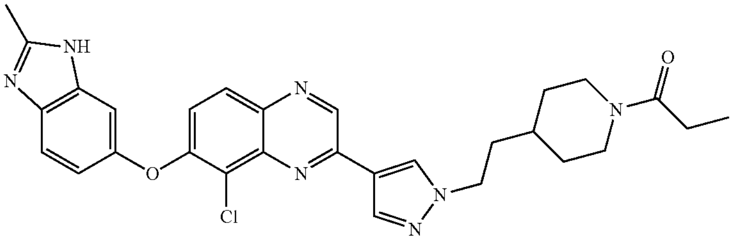 [SMILES: CCC(=O)N1CCC(CCn2cc(-c3cnc4ccc(Oc5ccc6nc(C)[nH]c6c5)c(Cl)c4n3)cn2)CC1] |
| 301 | 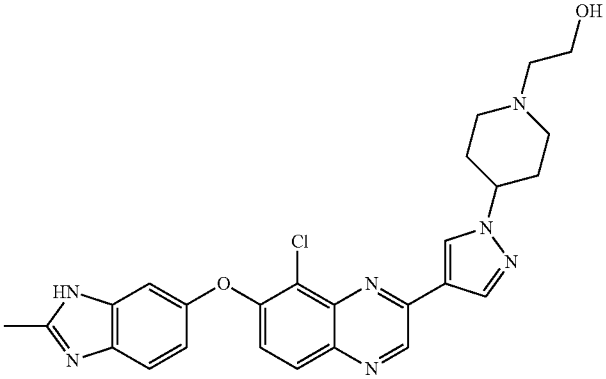 [SMILES: Cc1nc2ccc(Oc3ccc4ncc(-c5cnn(C6CCN(CCO)CC6)c5)nc4c3Cl)cc2[nH]1] |
| 302 | 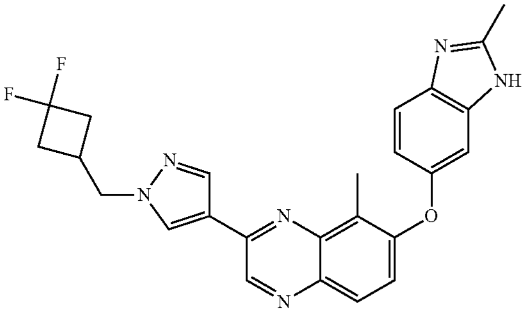 [SMILES: Cc1nc2ccc(Oc3ccc4ncc(-c5cnn(CC6CC(F)(F)C6)c5)nc4c3C)cc2[nH]1] |
| 303 | 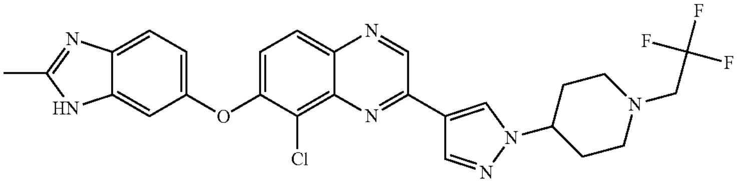 [SMILES: Cc1nc2ccc(Oc3ccc4ncc(-c5cnn(C6CCN(CC(F)(F)F)CC6)c5)nc4c3Cl)cc2[nH]1] |

TABLE II-continued
| Compound No. | Structure |
| --- | --- |
| 304 | 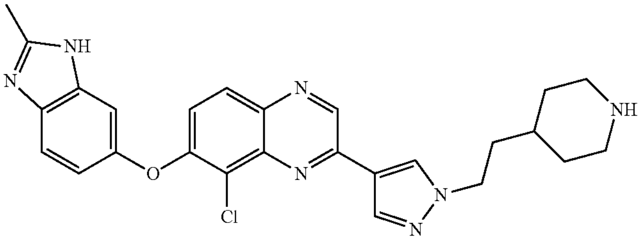 [SMILES: Cc1nc2ccc(Oc3ccc4ncc(-c5cnn(CCC6CCNCC6)c5)nc4c3Cl)cc2[nH]1] |
| 305 | 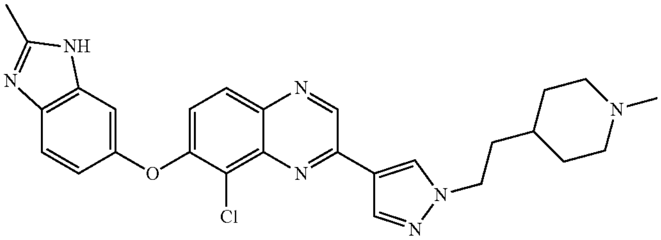 |
| 306 | 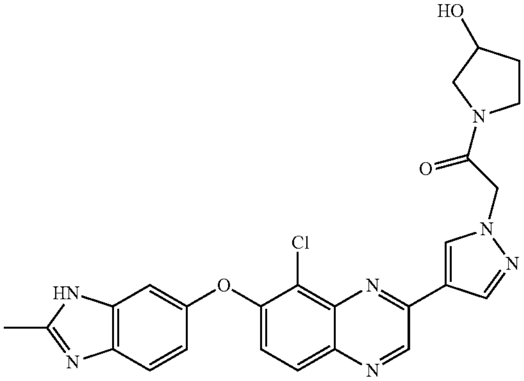 [SMILES: Cc1nc2ccc(Oc3ccc4ncc(-c5cnn(CC(=O)N6CCC(O)C6)c5)nc4c3Cl)cc2[nH]1] |
| 307 | 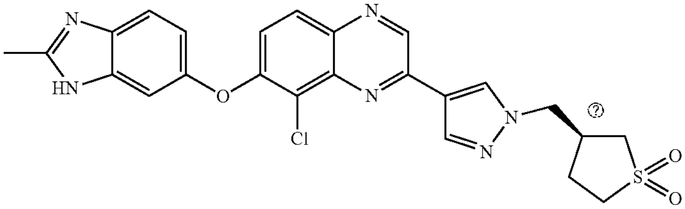 [SMILES: Cc1nc2ccc(Oc3ccc4ncc(-c5cnn(C[C@@H]6CCS(=O)(=O)C6)c5)nc4c3Cl)cc2[nH]1] |
| 308 | 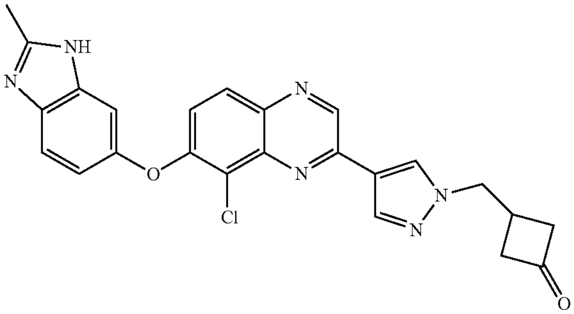 [SMILES: Cc1nc2ccc(Oc3ccc4ncc(-c5cnn(CC6CC(=O)C6)c5)nc4c3Cl)cc2[nH]1] |

TABLE II-continued
| Compound No. | Structure |
| --- | --- |
| 309 | 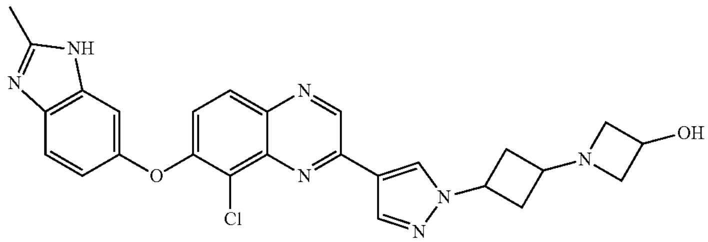 [SMILES: Cc1nc2ccc(Oc3ccc4ncc(-c5cnn(C6CC(N7CC(O)C7)C6)c5)nc4c3Cl)cc2[nH]1] |
| 310 | 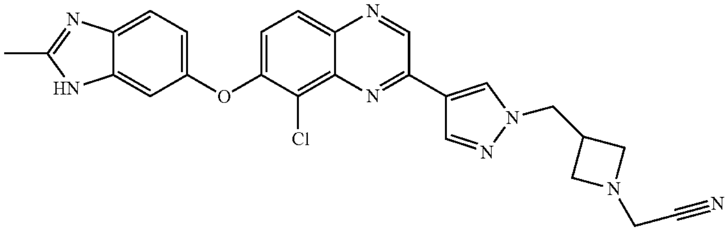 [SMILES: Cc1nc2ccc(Oc3ccc4ncc(-c5cnn(CC6CN(CC#N)C6)c5)nc4c3Cl)cc2[nH]1] |
| 311 | 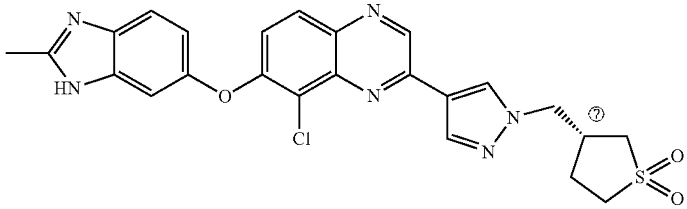 [SMILES: Cc1nc2ccc(Oc3ccc4ncc(-c5cnn(C[C@H]6CCS(=O)(=O)C6)c5)nc4c3Cl)cc2[nH]1] |
| 312 | 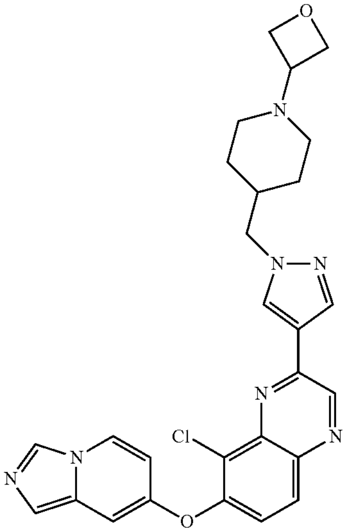 [SMILES: Clc1c(Oc2ccn3cncc3c2)ccc2ncc(-c3cnn(CC4CCN(C5COC5)CC4)c3)nc12] |
| 313 | 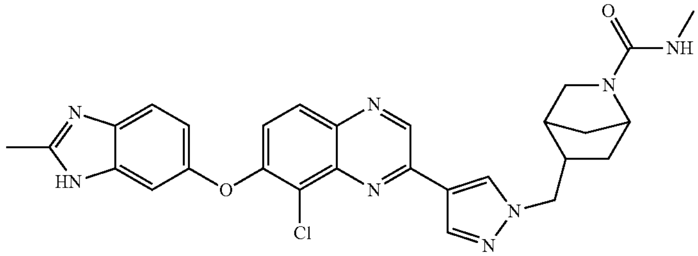 |

TABLE II-continued
| Compound No. | Structure |
| --- | --- |
| 314 | 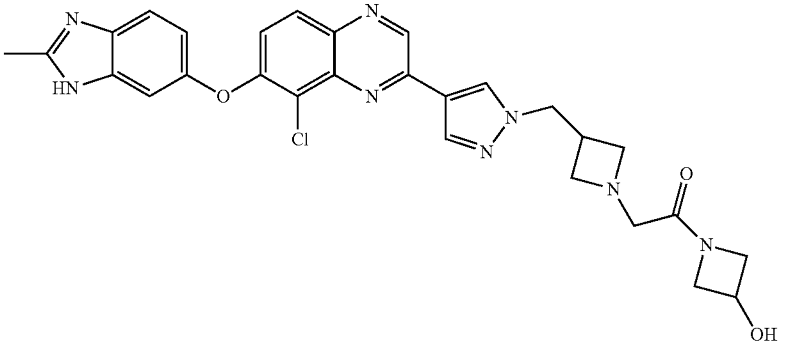 [SMILES: Cc1nc2ccc(Oc3ccc4ncc(-c5cnn(CC6CN(CC(=O)N7CC(O)C7)C6)c5)nc4c3Cl)cc2[nH]1] |
| 315 | 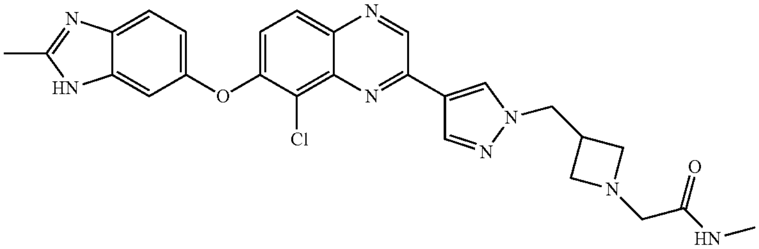 |
| 316 | 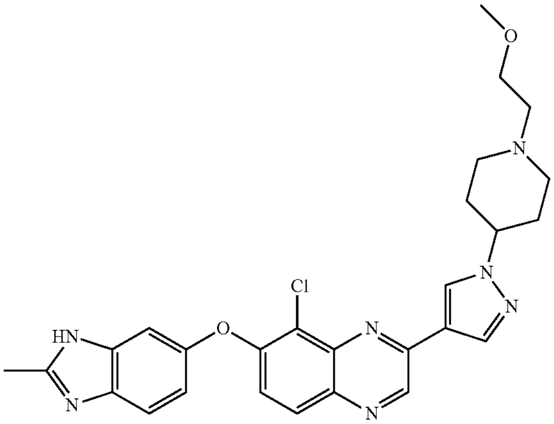 [SMILES: COCCN1CCC(n2cc(-c3cnc4ccc(Oc5ccc6nc(C)[nH]c6c5)c(Cl)c4n3)cn2)CC1] |
| 317 | 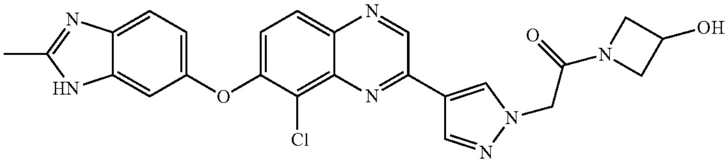 [SMILES: Cc1nc2ccc(Oc3ccc4ncc(-c5cnn(CC(=O)N6CC(O)C6)c5)nc4c3Cl)cc2[nH]1] |
| 318 | 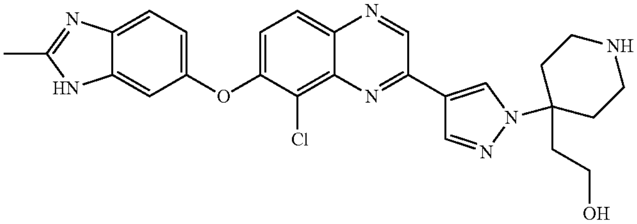 [SMILES: Cc1nc2ccc(Oc3ccc4ncc(-c5cnn(C6(CCO)CCNCC6)c5)nc4c3Cl)cc2[nH]1] |

TABLE II-continued
| Compound No. | Structure |
| --- | --- |
| 319 | 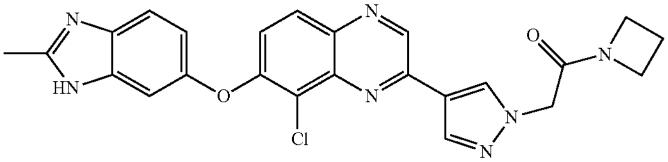 [SMILES: Cc1nc2ccc(Oc3ccc4ncc(-c5cnn(CC(=O)N6CCC6)c5)nc4c3Cl)cc2[nH]1] |
| 320 | 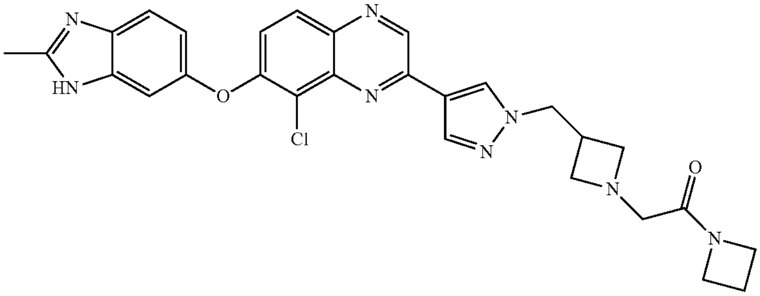 [SMILES: Cc1nc2ccc(Oc3ccc4ncc(-c5cnn(CC6CN(CC(=O)N7CCC7)C6)c5)nc4c3Cl)cc2[nH]1] |
| 321 | 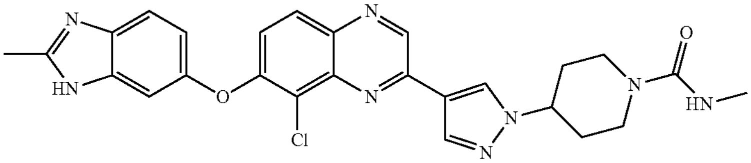 |
| 322 | 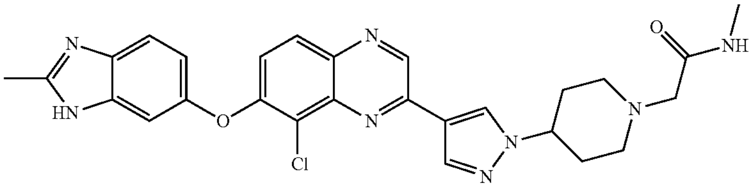 |
| 323 | 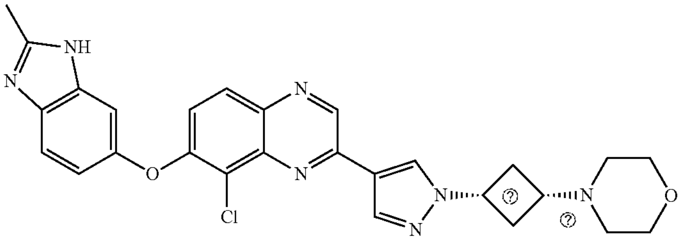 [SMILES: Cc1nc2ccc(Oc3ccc4ncc(-c5cnn([C@H]6C[C@@H](N7CCOCC7)C6)c5)nc4c3Cl)cc2[nH]1] |
| 324 | 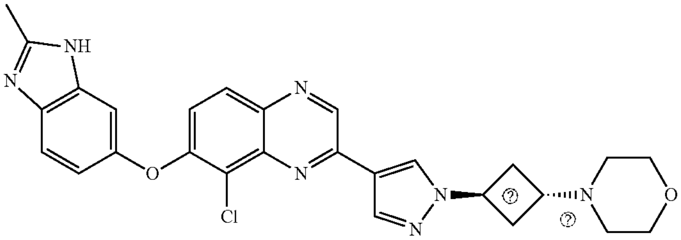 [SMILES: Cc1nc2ccc(Oc3ccc4ncc(-c5cnn([C@H]6C[C@H](N7CCOCC7)C6)c5)nc4c3Cl)cc2[nH]1] |

TABLE II-continued
| Compound No. | Structure |
|---|---|
| 325 | 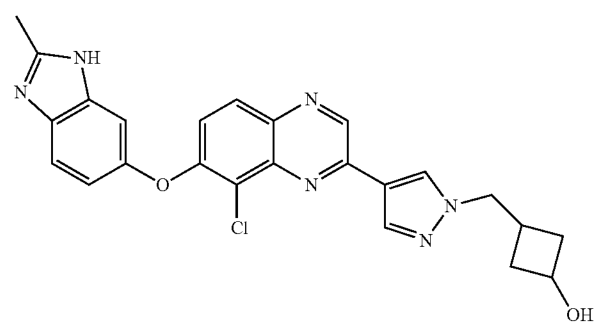 [SMILES: Cc1nc2ccc(Oc3ccc4ncc(-c5cnn(CC6CC(O)C6)c5)nc4c3Cl)cc2[nH]1] |
| 326 | 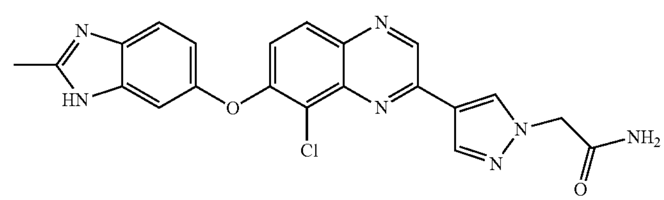 [SMILES: Cc1nc2ccc(Oc3ccc4ncc(-c5cnn(CC(N)=O)c5)nc4c3Cl)cc2[nH]1] |
| 327 | 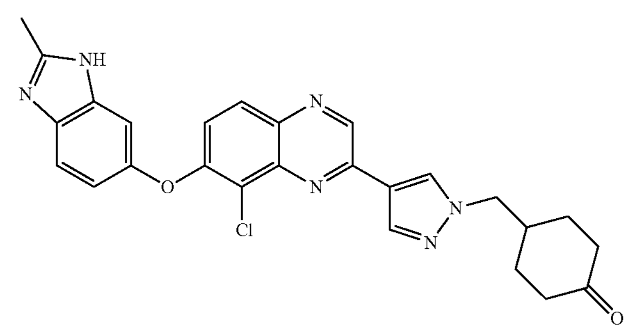 [SMILES: Cc1nc2ccc(Oc3ccc4ncc(-c5cnn(CC6CCC(=O)CC6)c5)nc4c3Cl)cc2[nH]1] |
| 328 | 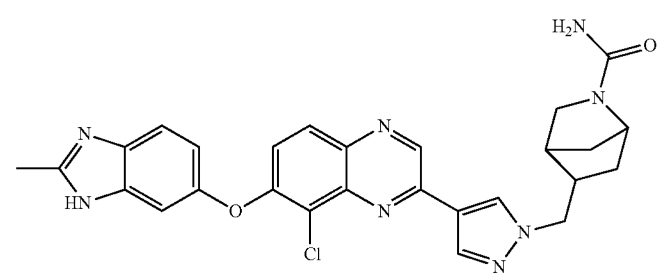 [SMILES: Cc1nc2ccc(Oc3ccc4ncc(-c5cnn(CC6CC7CC6CN7C(N)=O)c5)nc4c3Cl)cc2[nH]1] |
| 329 | 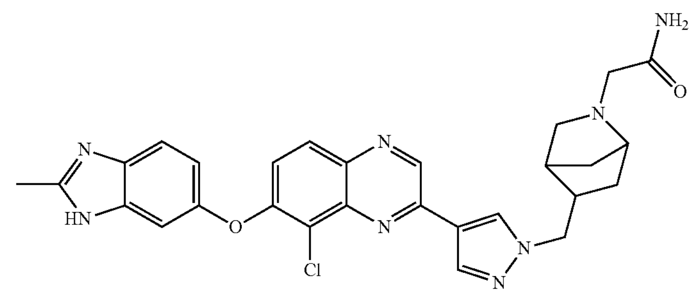 [SMILES: Cc1nc2ccc(Oc3ccc4ncc(-c5cnn(CC6CC7CC6CN7CC(N)=O)c5)nc4c3Cl)cc2[nH]1] |

TABLE II-continued
| Compound No. | Structure |
| --- | --- |
| 330 | 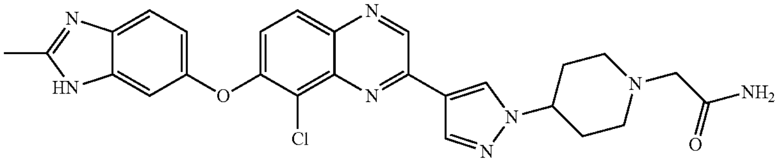 [SMILES: Cc1nc2ccc(Oc3ccc4ncc(-c5cnn(C6CCN(CC(N)=O)CC6)c5)nc4c3Cl)cc2[nH]1] |
| 331 | 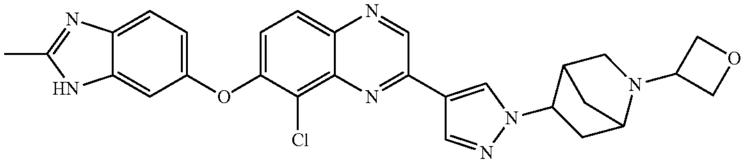 [SMILES: Cc1nc2ccc(Oc3ccc4ncc(-c5cnn(C6CC7CC6CN7C6COC6)c5)nc4c3Cl)cc2[nH]1] |
| 332 | 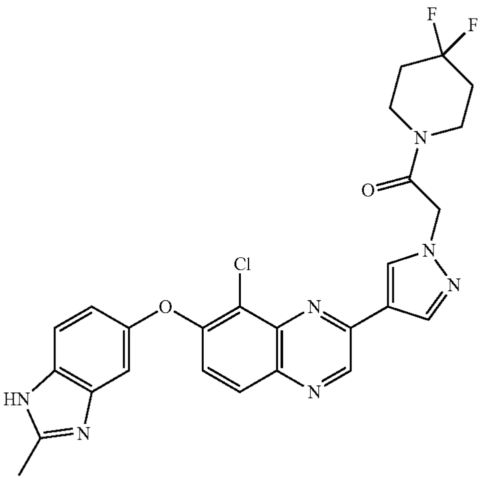 [SMILES: Cc1nc2cc(Oc3ccc4ncc(-c5cnn(CC(=O)N6CCC(F)(F)CC6)c5)nc4c3Cl)ccc2[nH]1] |
| 333 | 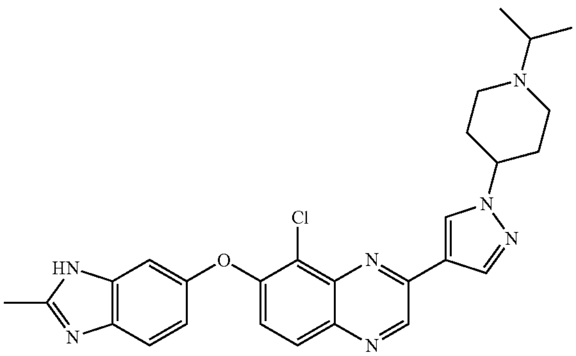 [SMILES: Cc1nc2ccc(Oc3ccc4ncc(-c5cnn(C6CCN(C(C)C)CC6)c5)nc4c3Cl)cc2[nH]1] |
| 334 | 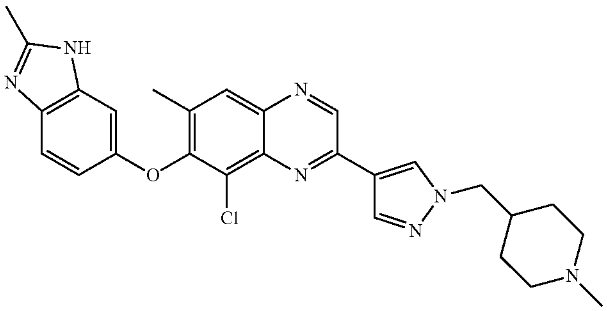 |

TABLE II-continued
| Compound No. | Structure |
| --- | --- |
| 335 | 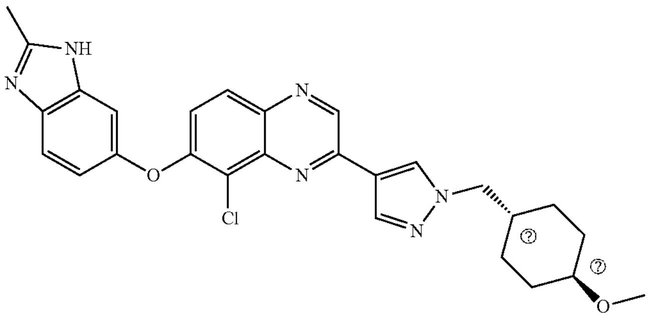 |
| 336 | 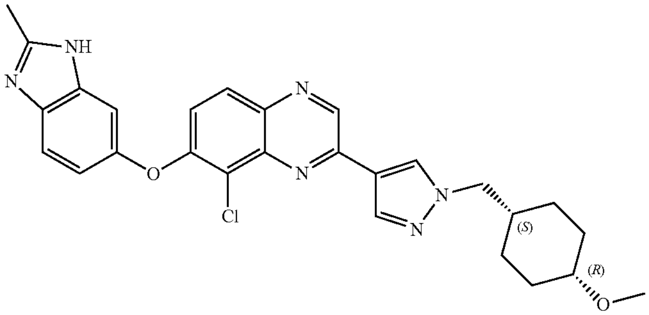 |
| 337 | 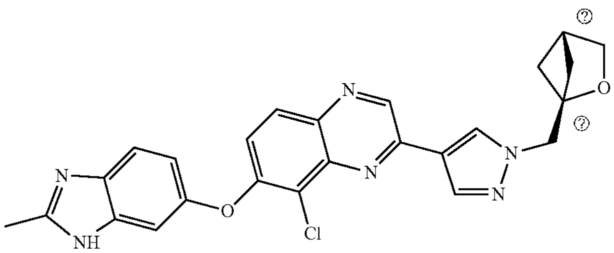 [SMILES: Cc1nc2ccc(Oc3ccc4ncc(-c5cnn(C[C@]67C[C@H](CO6)C7)c5)nc4c3Cl)cc2[nH]1] |
| 338 | 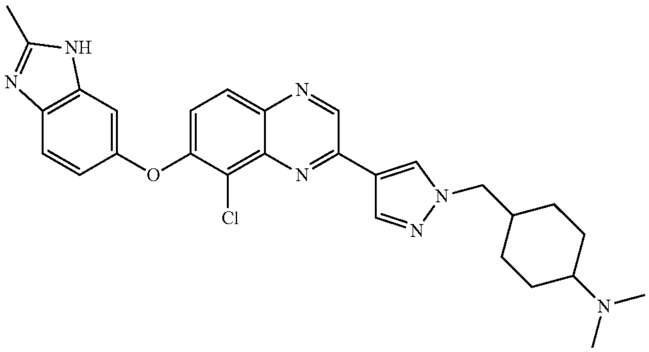 |

TABLE II-continued
| Compound No. | Structure |
|---|---|
| 339 | 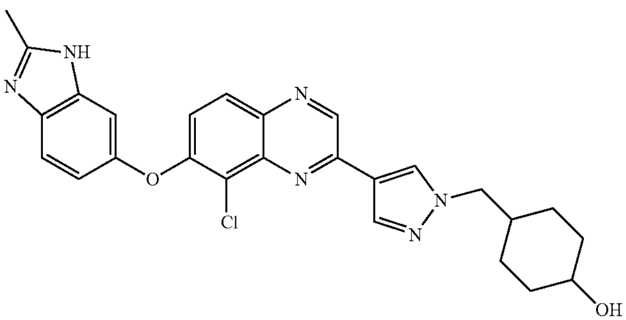 [SMILES: Cc1nc2ccc(Oc3ccc4ncc(-c5cnn(CC6CCC(O)CC6)c5)nc4c3Cl)cc2[nH]1] |
| 340 | 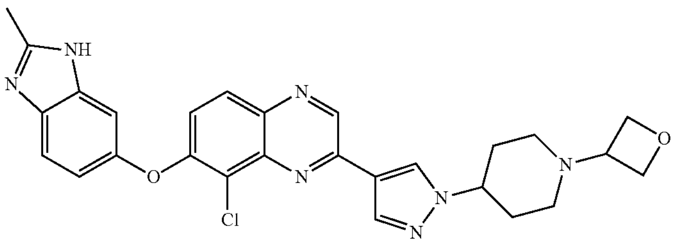 [SMILES: Cc1nc2ccc(Oc3ccc4ncc(-c5cnn(C6CCN(C7COC7)CC6)c5)nc4c3Cl)cc2[nH]1] |
| 341 | 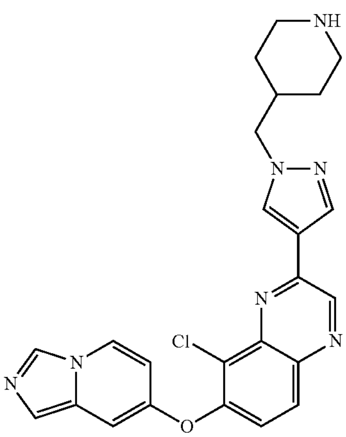 [SMILES: Clc1c(Oc2ccn3cncc3c2)ccc2ncc(-c3cnn(CC4CCNCC4)c3)nc12] |
| 342 | 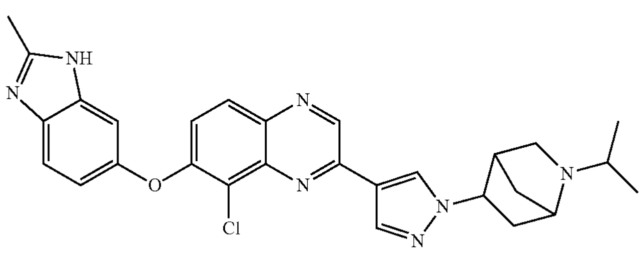 [SMILES: Cc1nc2ccc(Oc3ccc4ncc(-c5cnn(C6CC7CC6CN7C(C)C)c5)nc4c3Cl)cc2[nH]1] |
| 343 | 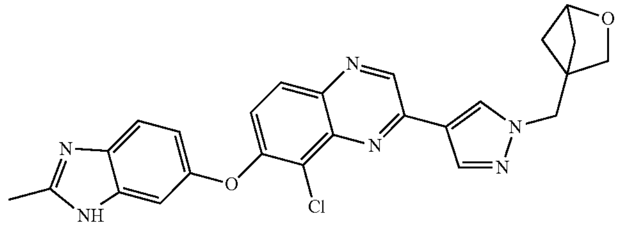 [SMILES: Cc1nc2ccc(Oc3ccc4ncc(-c5cnn(CC67COC(C6)C7)c5)nc4c3Cl)cc2[nH]1] |

TABLE II-continued
| Compound No. | Structure |
|---|---|
| 344 | 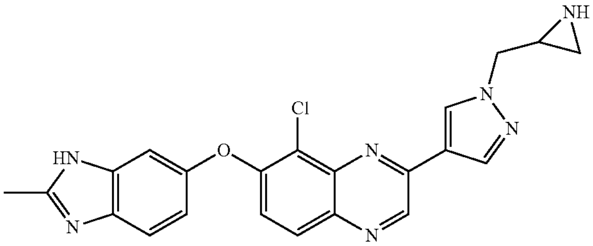 [SMILES: Cc1nc2ccc(Oc3ccc4ncc(-c5cnn(CC6CN6)c5)nc4c3Cl)cc2[nH]1] |
| 345 | 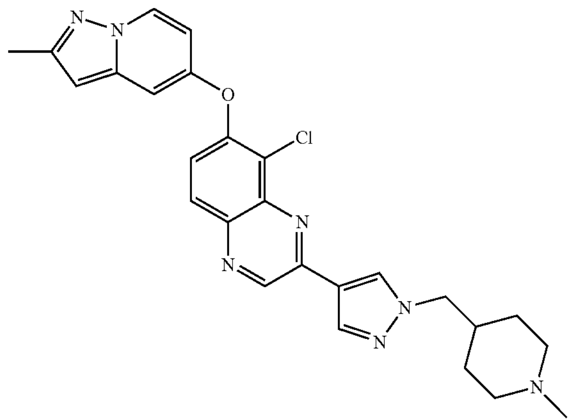 |
| 346 | 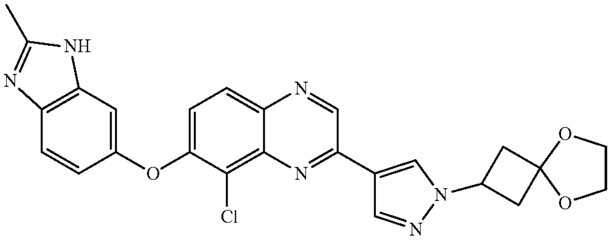 [SMILES: Cc1nc2ccc(Oc3ccc4ncc(-c5cnn(C6CC7(C6)OCCO7)c5)nc4c3Cl)cc2[nH]1] |
| 347 | 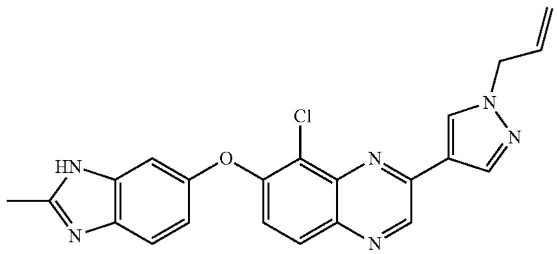 [SMILES: C=CCn1cc(-c2cnc3ccc(Oc4ccc5nc(C)[nH]c5c4)c(Cl)c3n2)cn1] |
| 348 | 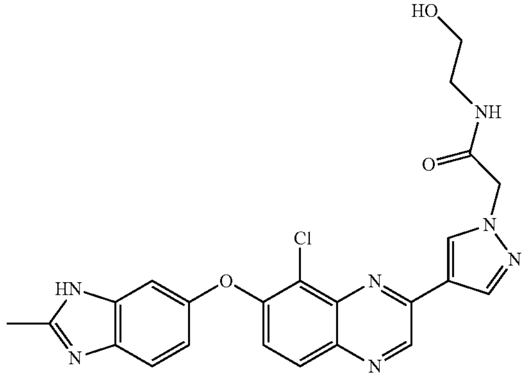 [SMILES: Cc1nc2ccc(Oc3ccc4ncc(-c5cnn(CC(=O)NCCO)c5)nc4c3Cl)cc2[nH]1] |

TABLE II-continued
| Compound No. | Structure |
| --- | --- |
| 349 | 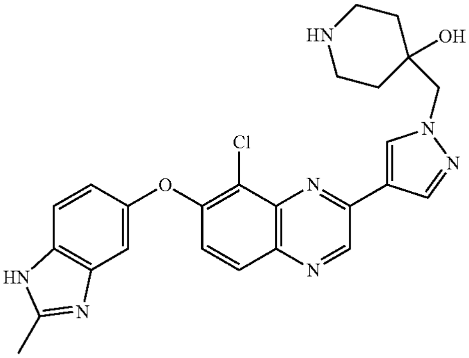 [SMILES: Cc1nc2cc(Oc3ccc4ncc(-c5cnn(CC6(O)CCNCC6)c5)nc4c3Cl)ccc2[nH]1] |
| 350 | 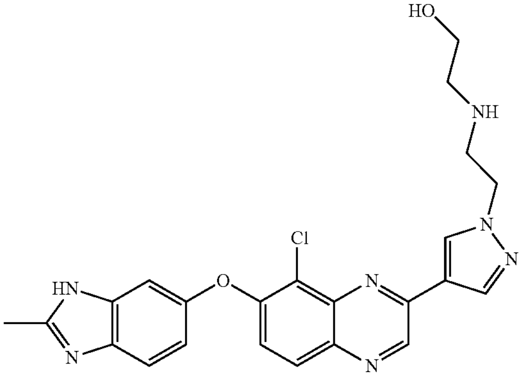 [SMILES: Cc1nc2ccc(Oc3ccc4ncc(-c5cnn(CCNCCO)c5)nc4c3Cl)cc2[nH]1] |
| 351 | 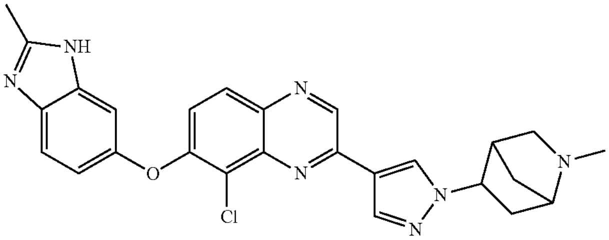 |
| 352 | 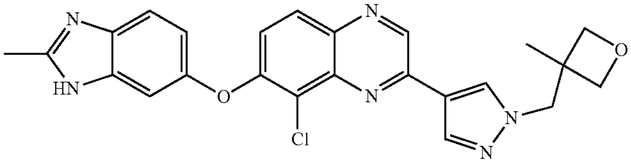 [SMILES: Cc1nc2ccc(Oc3ccc4ncc(-c5cnn(CC6(C)COC6)c5)nc4c3Cl)cc2[nH]1] |
| 353 | 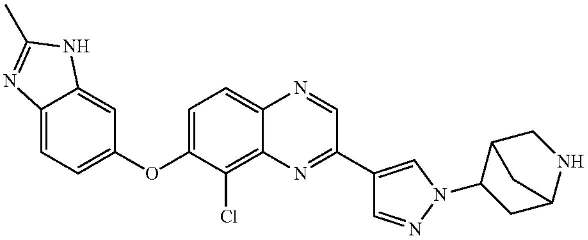 [SMILES: Cc1nc2ccc(Oc3ccc4ncc(-c5cnn(C6CC7CC6CN7)c5)nc4c3Cl)cc2[nH]1] |

TABLE II-continued
| Compound No. | Structure |
| --- | --- |
| 354 | 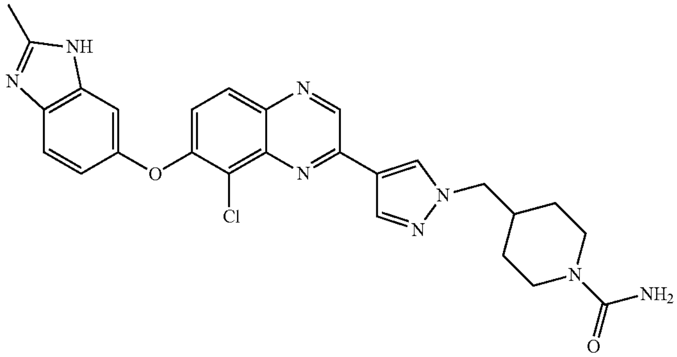 [SMILES: Cc1nc2ccc(Oc3ccc4ncc(-c5cnn(CC6CCN(C(N)=O)CC6)c5)nc4c3Cl)cc2[nH]1] |
| 355 | 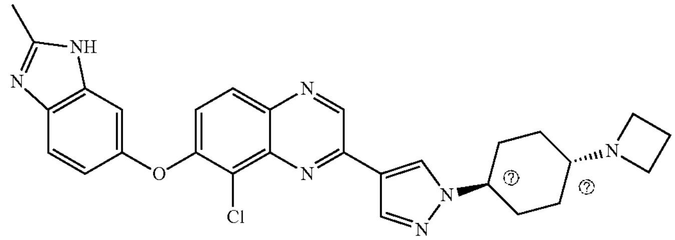 [SMILES: Cc1nc2ccc(Oc3ccc4ncc(-c5cnn([C@H]6CC[C@H](N7CCC7)CC6)c5)nc4c3Cl)cc2[nH]1] |
| 356 | 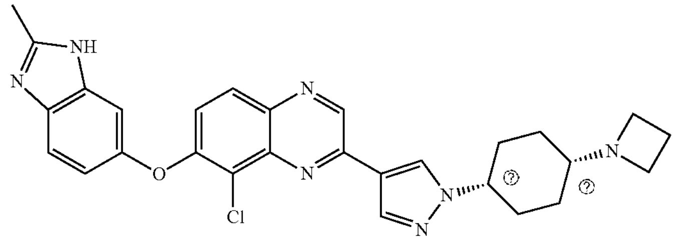 [SMILES: Cc1nc2ccc(Oc3ccc4ncc(-c5cnn([C@H]6CC[C@@H](N7CCC7)CC6)c5)nc4c3Cl)cc2[nH]1] |
| 357 | 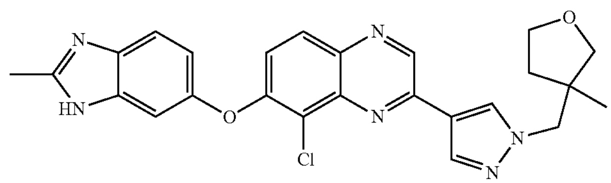 |
| 358 | 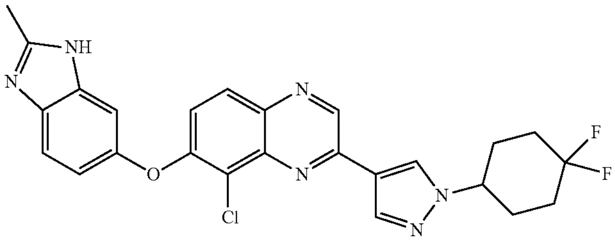 [SMILES: Cc1nc2ccc(Oc3ccc4ncc(-c5cnn(C6CCC(F)(F)CC6)c5)nc4c3Cl)cc2[nH]1] |
| 359 | 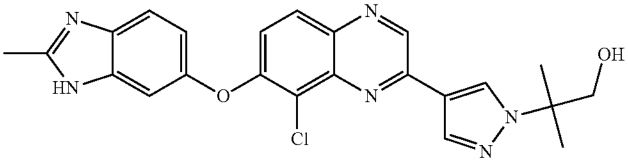 [SMILES: Cc1nc2ccc(Oc3ccc4ncc(-c5cnn(C(C)(C)CO)c5)nc4c3Cl)cc2[nH]1] |

TABLE II-continued
| Compound No. | Structure |
| --- | --- |
| 360 | 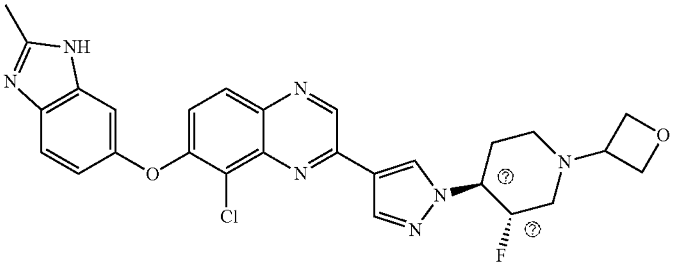 [SMILES: Cc1nc2ccc(Oc3ccc4ncc(-c5cnn([C@H]6CCN(C7COC7)C[C@@H]6F)c5)nc4c3Cl)cc2[nH]1] |
| 361 | 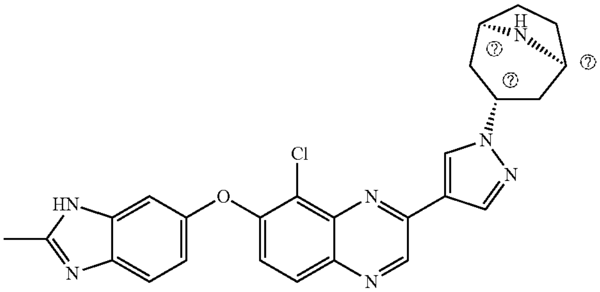 [SMILES: Cc1nc2ccc(Oc3ccc4ncc(-c5cnn([C@@H]6C[C@H]7CC[C@@H](C6)N7)c5)nc4c3Cl)cc2[nH]1] |
| 362 | 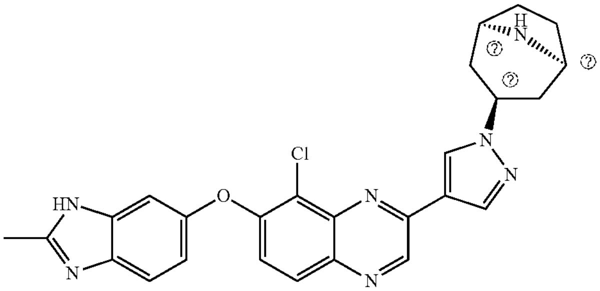 [SMILES: Cc1nc2ccc(Oc3ccc4ncc(-c5cnn([C@H]6C[C@H]7CC[C@@H](C6)N7)c5)nc4c3Cl)cc2[nH]1] |
| 363 | 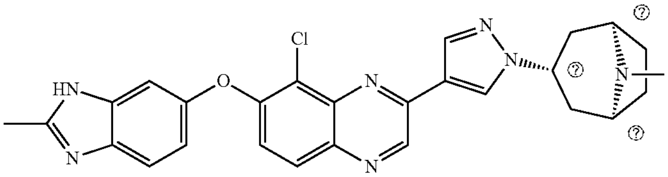 |
| 364 | 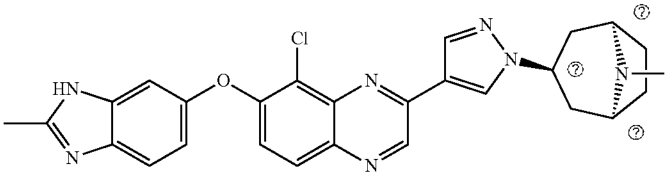 |
| 365 | 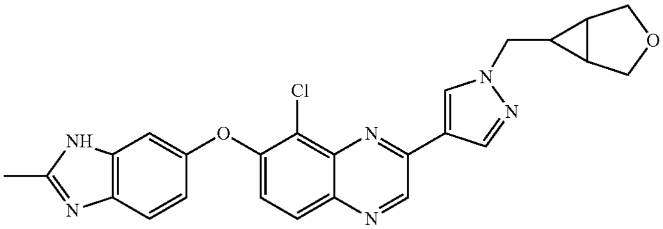 [SMILES: Cc1nc2ccc(Oc3ccc4ncc(-c5cnn(CC6C7COCC76)c5)nc4c3Cl)cc2[nH]1] |

TABLE II-continued
| Compound No. | Structure |
|---|---|
| 366 | 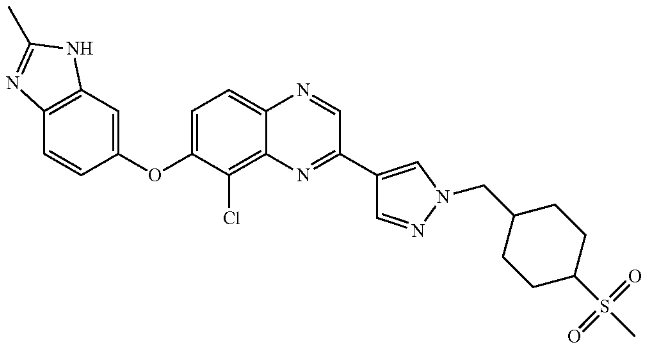 [SMILES: Cc1nc2ccc(Oc3ccc4ncc(-c5cnn(CC6CCC(S(C)(=O)=O)CC6)c5)nc4c3Cl)cc2[nH]1] |
| 367 | 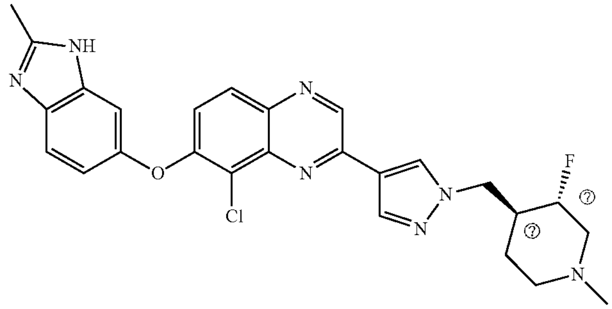 |
| 368 | 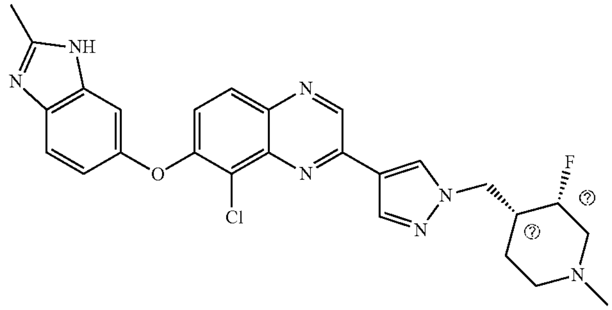 |
| 369 | 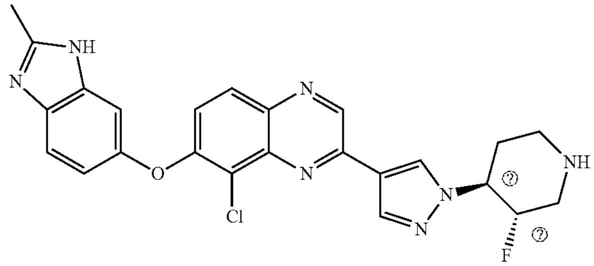 [SMILES: Cc1nc2ccc(Oc3ccc4ncc(-c5cnn([C@H]6CCNC[C@@H]6F)c5)nc4c3Cl)cc2[nH]1] |
| 370 | 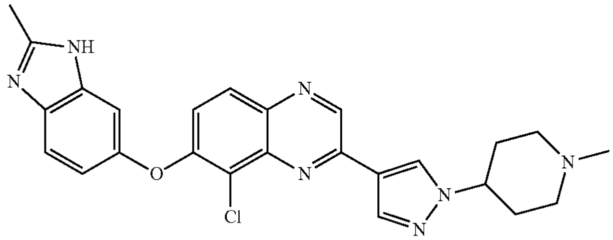 |

TABLE II-continued
| Compound No. | Structure |
|---|---|
| 371 | 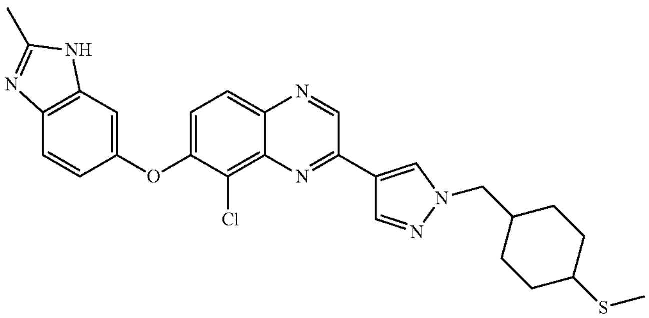 |
| 372 | 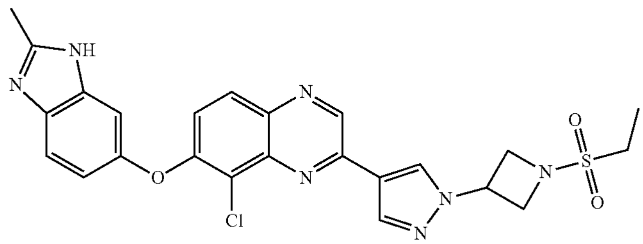 [SMILES: CCS(=O)(=O)N1CC(n2cc(-c3cnc4ccc(Oc5ccc6nc(C)[nH]c6c5)c(Cl)c4n3)cn2)C1] |
| 373 | 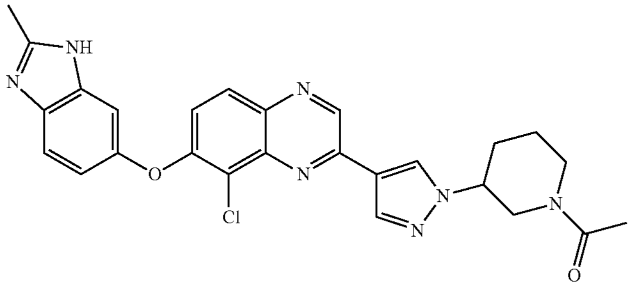 [SMILES: CC(=O)N1CCCC(n2cc(-c3cnc4ccc(Oc5ccc6nc(C)[nH]c6c5)c(Cl)c4n3)cn2)C1] |
| 374 | 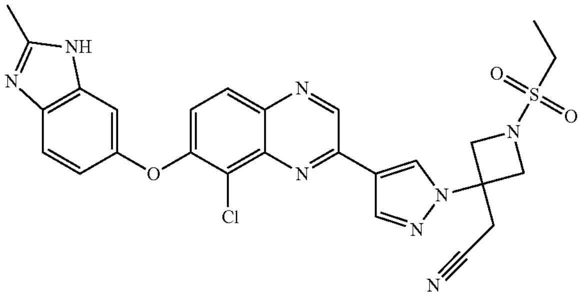 [SMILES: CCS(=O)(=O)N1CC(CC#N)(n2cc(-c3cnc4ccc(Oc5ccc6nc(C)[nH]c6c5)c(Cl)c4n3)cn2)C1] |
| 375 | 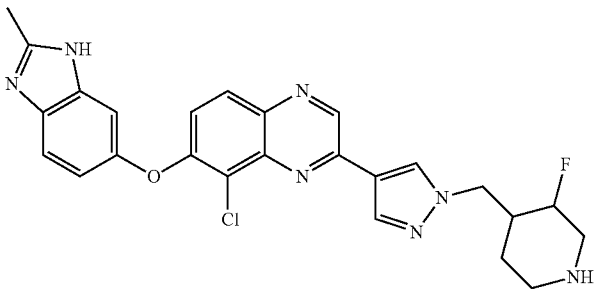 [SMILES: Cc1nc2ccc(Oc3ccc4ncc(-c5cnn(CC6CCNCC6F)c5)nc4c3Cl)cc2[nH]1] |

TABLE II-continued
| Compound No. | Structure |
| --- | --- |
| 376 | 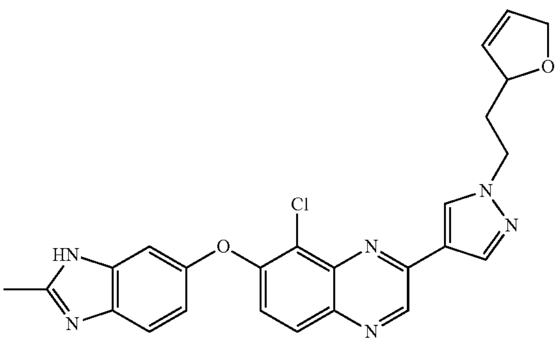 [SMILES: Cc1nc2ccc(Oc3ccc4ncc(-c5cnn(CCC6C=CCO6)c5)nc4c3Cl)cc2[nH]1] |
| 377 | 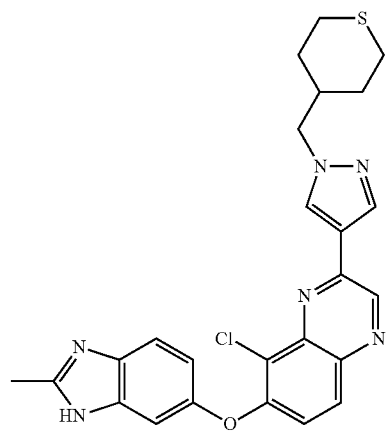 [SMILES: Cc1nc2ccc(Oc3ccc4ncc(-c5cnn(CC6CCSCC6)c5)nc4c3Cl)cc2[nH]1] |
| 378 | 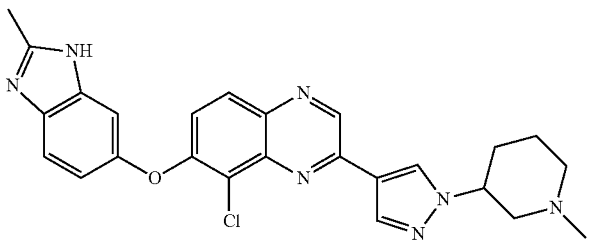 |
| 379 | 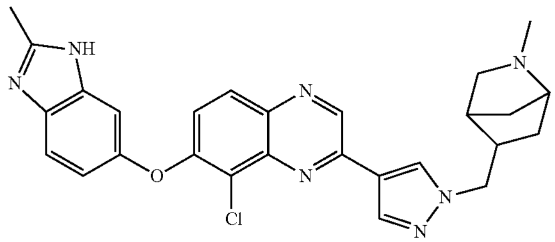 [SMILES: Cc1nc2ccc(Oc3ccc4ncc(-c5cnn(CC6CC7CC6CN7C)c5)nc4c3Cl)cc2[nH]1] |

TABLE II-continued
| Compound No. | Structure |
|---|---|
| 380 | 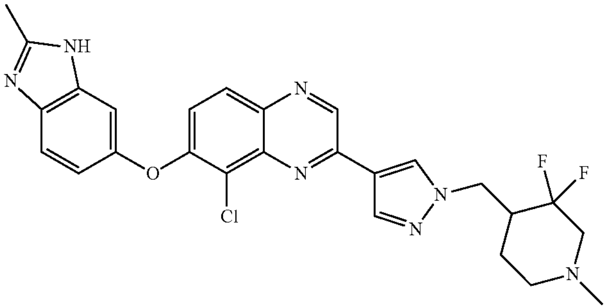 |
| 381 | 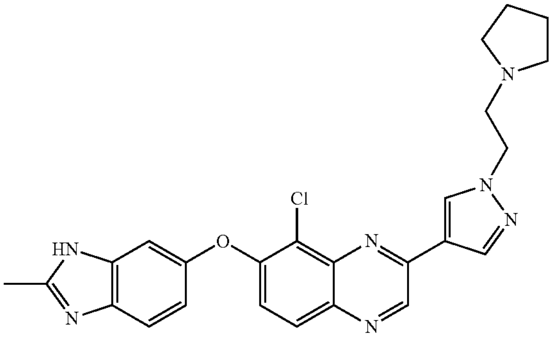 [SMILES: Cc1nc2ccc(Oc3ccc4ncc(-c5cnn(CCN6CCCC6)c5)nc4c3Cl)cc2[nH]1] |
| 382 | 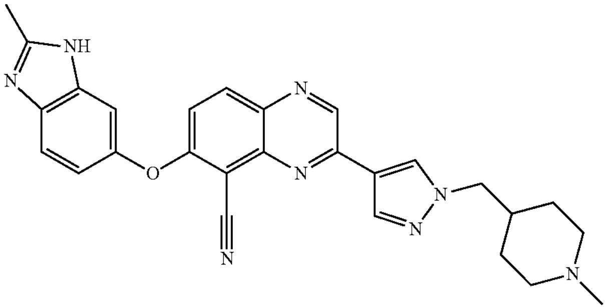 |
| 383 | 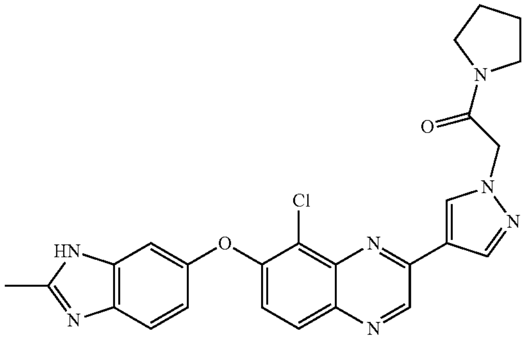 [SMILES: Cc1nc2ccc(Oc3ccc4ncc(-c5cnn(CC(=O)N6CCCC6)c5)nc4c3Cl)cc2[nH]1] |

TABLE II-continued
| Compound No. | Structure |
|---|---|
| 384 | 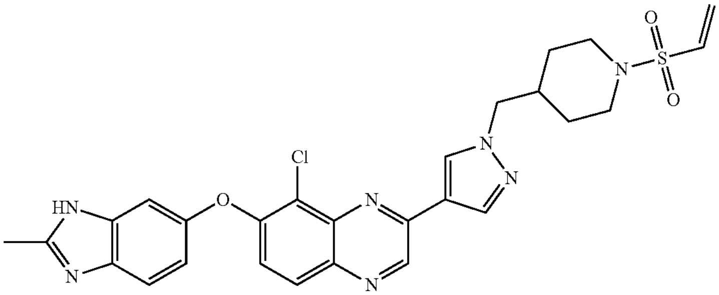 [SMILES: C=CS(=O)(=O)N1CCC(Cn2cc(-c3cnc4ccc(Oc5ccc6nc(C)[nH]c6c5)c(Cl)c4n3)cn2)CC1] |
| 385 | 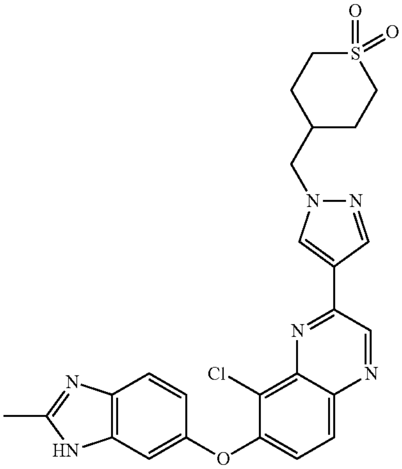 [SMILES: Cc1nc2ccc(Oc3ccc4ncc(-c5cnn(CC6CCS(=O)(=O)CC6)c5)nc4c3Cl)cc2[nH]1] |
| 386 | 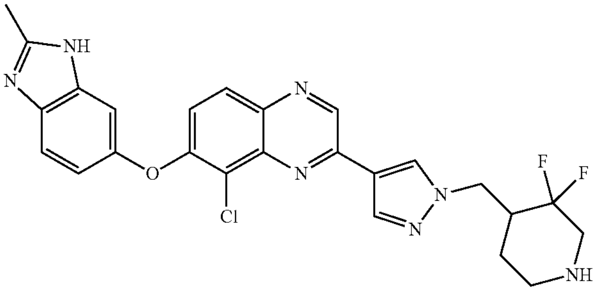 [SMILES: Cc1nc2ccc(Oc3ccc4ncc(-c5cnn(CC6CCNCC6(F)F)c5)nc4c3Cl)cc2[nH]1] |
| 387 | 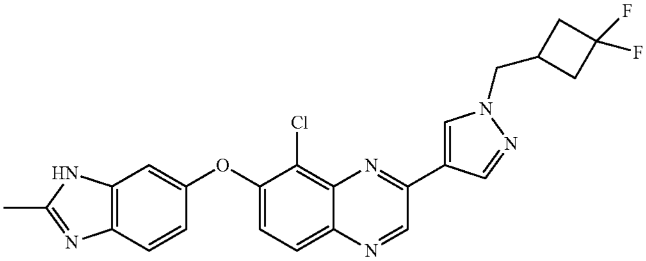 [SMILES: Cc1nc2ccc(Oc3ccc4ncc(-c5cnn(CC6CC(F)(F)C6)c5)nc4c3Cl)cc2[nH]1] |

TABLE II-continued

| Compound No. | Structure |
| --- | --- |
| 388 | 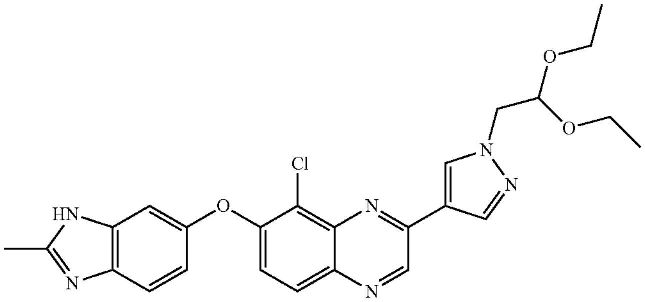 [SMILES: CCOC(Cn1cc(-c2cnc3ccc(Oc4ccc5nc(C)[nH]c5c4)c(Cl)c3n2)cn1)OCC] |
| 389 | 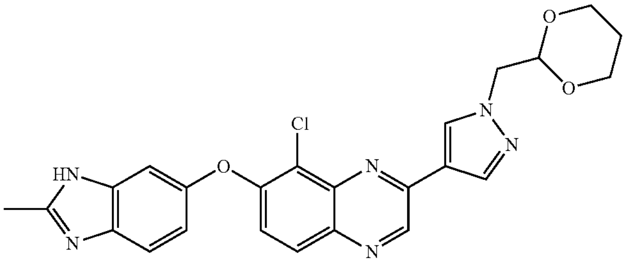 [SMILES: Cc1nc2ccc(Oc3ccc4ncc(-c5cnn(CC6OCCCO6)c5)nc4c3Cl)cc2[nH]1] |

In some aspects, the present disclosure provides a compound being an isotopic derivative (e.g., isotopically labeled compound) of any one of the compounds disclosed herein.

In some embodiments, the compound is an isotopic derivative of any one of the compounds described in Table I and Table II, or a pharmaceutically acceptable salt thereof.

In some embodiments, the compound is an isotopic derivative of any one of the compounds described in Table I and II.

In some embodiments, the compound is an isotopic derivative of any one of the compounds described in Table I, or a pharmaceutically acceptable salt thereof.

In some embodiments, the compound is an isotopic derivative of any one of the compounds described in Table I.

In some embodiments, the compound is an isotopic derivative of any one of the compounds described in Table II, or a pharmaceutically acceptable salt thereof.

In some embodiments, the compound is an isotopic derivative of any one of the compounds described in Table II.

It is understood that the isotopic derivative can be prepared using any of a variety of art-recognized techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

In some embodiments, the compound is a deuterium labeled compound of any one of the compounds described in Table I and Table II, or a pharmaceutically acceptable salt thereof.

In some embodiments, the compound is a deuterium labeled compound of any one of the compounds described in Table I and Table II.

In some embodiments, the compound is a deuterium labeled compound of any one of the compounds described in Table I, or a pharmaceutically acceptable salt thereof.

In some embodiments, the compound is a deuterium labeled compound of any one of the compounds described in Table I.

In some embodiments, the compound is a deuterium labeled compound of any one of the compounds described in Table II, or a pharmaceutically acceptable salt thereof.

In some embodiments, the compound is a deuterium labeled compound of any one of the compounds described in Table II.

It is understood that the deuterium labeled compound comprises a deuterium atom having an abundance of deuterium that is substantially greater than the natural abundance of deuterium, which is 0.015%.

In some embodiments, the deuterium labeled compound has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). As used herein, the term "deuterium enrichment factor" means the ratio between the deuterium abundance and the natural abundance of a deuterium.

It is understood that the deuterium labeled compound can be prepared using any of a variety of art-recognized techniques. For example, the deuterium labeled compound can generally be prepared by carrying out the procedures disclosed in the Schemes and/or in the Examples described herein, by substituting a deuterium labeled reagent for a non-deuterium labeled reagent.

A compound of the invention or a pharmaceutically acceptable salt or solvate thereof that contains the aforementioned deuterium atom(s) is within the scope of the invention. Further, substitution with deuterium (i.e., $^2H$) may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

A suitable pharmaceutically acceptable salt of a compound of the disclosure is, for example, an acid-addition salt of a compound of the disclosure which is sufficiently basic, for example, an acid-addition salt with, for example, an inorganic or organic acid, for example hydrochloric, hydrobromic, sulphuric, phosphoric, trifluoroacetic, formic, citric methane sulphonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

It will be understood that the compounds of the present disclosure and any pharmaceutically acceptable salts thereof, comprise stereoisomers, mixtures of stereoisomers, polymorphs of all isomeric forms of said compounds.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew, Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centers; such compounds can therefore be produced as individual (R)- or(S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centers (E- and Z-isomers). It is to be understood that the present disclosure encompasses all optical, diastereoisomers and geometric isomers and mixtures thereof that possess inflammasome inhibitory activity.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulphate, bisulphate, sulphamate, nitrate, phosphate, citrate, methanesulphonate, trifluoroacetate, glutamate, glucuronate, glutarate, malate, maleate, succinate, fumarate, tartrate, tosylate, salicylate, lactate, naphthalenesulphonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulphonamides, tetrazoles, sulphonates and phosphonates. See, e.g., Patani and LaVoie, *Chem. Rev.* 96, 3147-3176, 1996.

It is also to be understood that certain compounds of the present disclosure may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of the present disclosure may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of the present disclosure may exist in a number of different tautomeric forms and references to compounds of the present disclosure include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro,

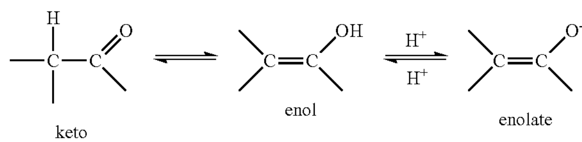

Compounds of the present disclosure containing an amine function may also form N-oxides. A reference herein to a compound disclosed herein that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidising agent such as hydrogen peroxide or a peracid (e.g. a peroxycarboxylic acid), see for example Advanced Organic Chemistry, by Jerry March 4th Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of the present disclosure may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached.

Examples of prodrugs include derivatives containing in vivo cleavable alkyl or acyl substituents at the sulphonylurea group in a compound of the any one of the Formulae disclosed herein. Accordingly, the present disclosure includes those compounds of the present disclosure as defined hereinbefore when made available by organic synthesis and when made available within the human or animal body by way of cleavage of a prodrug thereof. Accordingly, the present disclosure includes those compounds of the present disclosure that are produced by organic synthetic means and also such compounds that are produced in the human or animal body by way of metabolism of a precursor compound, that is a compound of the present disclosure may be a synthetically-produced compound or a metabolically-produced compound.

A suitable pharmaceutically acceptable prodrug of a compound of the present disclosure is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of the present disclosure that possesses a hydroxy group is, for example, an in vivo cleavable ester or ether thereof. An in vivo cleavable ester or ether of a compound of the present disclosure containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl) piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of the present disclosure that possesses a carboxy group is, for example, an in vivo cleavable amide thereof, for example an amide formed with an amine such as ammonia, a $C_{1-4}$alkylamine such as methylamine, a ($C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of the present disclosure that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl, and 4-($C_1$-$C_4$ alkyl) piperazin-1-ylmethyl.

The in vivo effects of a compound of the present disclosure may be exerted in part by one or more metabolites that are formed within the human or animal body after administration of a compound of the present disclosure. As stated hereinbefore, the in vivo effects of a compound of the present disclosure may also be exerted by way of metabolism of a precursor compound (a prodrug).

Methods of Synthesis

In some aspects, the present disclosure provides a method of preparing a compound disclosed herein.

In some aspects, the present disclosure provides a method of preparing a compound, comprising one or more steps as described herein.

In some aspects, the present disclosure provides a compound obtainable by, or obtained by, or directly obtained by a method for preparing a compound described herein.

In some aspects, the present disclosure provides an intermediate being suitable for use in a method for preparing a compound described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of the present disclosure has been synthesized by any one of the processes defined herein, the processes may then further comprise the additional steps of: (i) removing any protecting groups present; (ii) converting the compound of the present disclosure into another compound of the present disclosure; (iii) forming a pharmaceutically acceptable salt, hydrate or solvate thereof; and/or (iv) forming a prodrug thereof.

The resultant compounds of the present disclosure can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulphoxides, such as dimethyl sulphoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilizing the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognize which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesized by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply-whenever necessary or useful-synthetic protecting (or protective) groups; suitable protecting groups as well as methods for introducing and removing them are well-known to the person skilled in the art of chemical synthesis and are described, in more detail, in, e.g., P.G.M. Wuts, T.W. Greene, "Greene's Protective Groups in Organic Synthesis", 4th edition (2006) (John Wiley & Sons).
General routes for the preparation of a compound of the application are described in Scheme 1 and Scheme 2.
Scheme 1
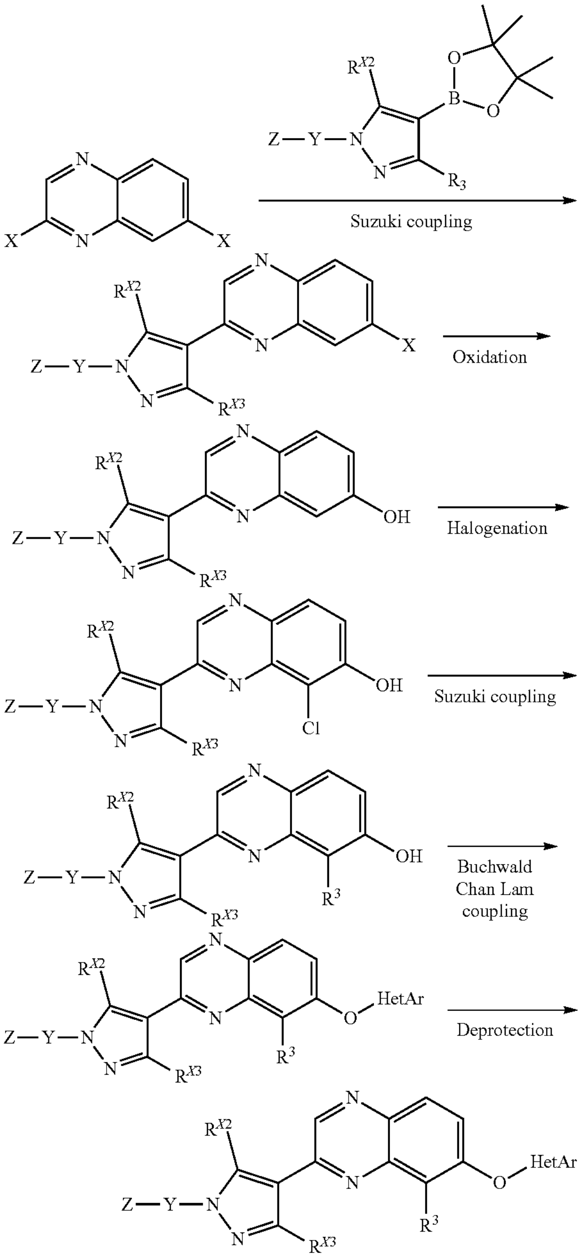
Scheme 2
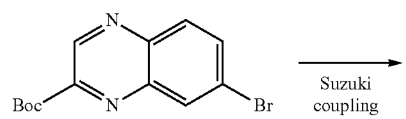
-continued
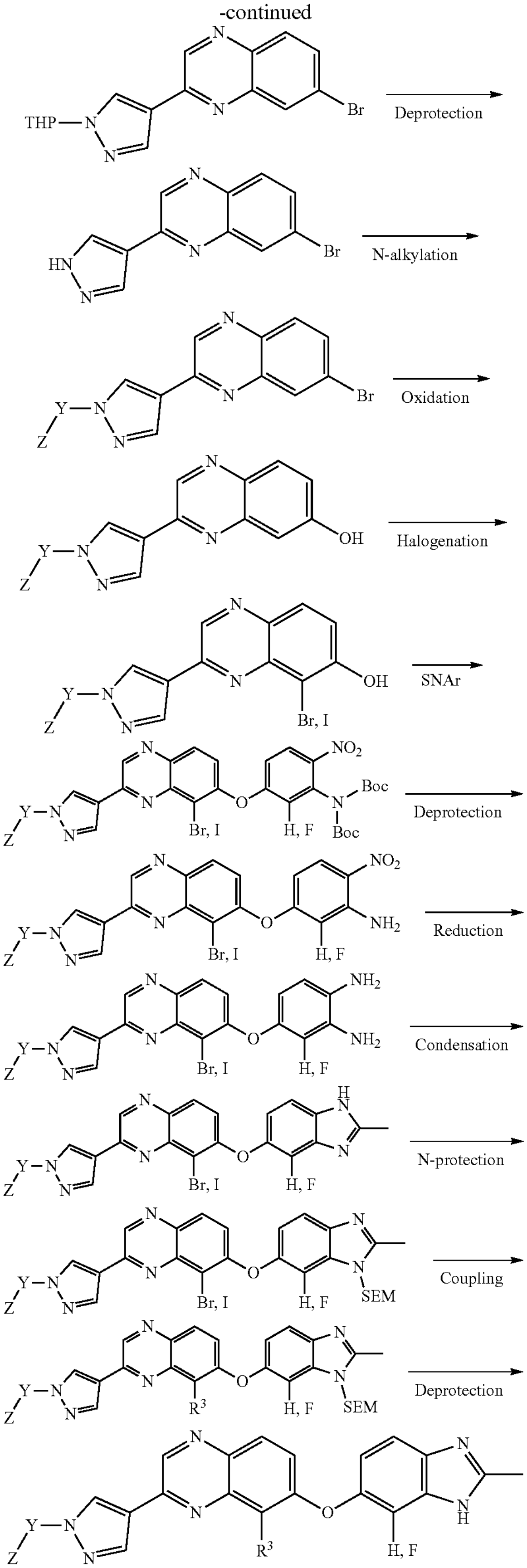

Biological Assays

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

In some embodiments, the biological assay assess the ability of the compounds to inhibit cell proliferation.

In some embodiments, cells (e.g., SNU-16 (FGFR2-amplification) cells) may be suspended and dispensed in plates. In some embodiments, cells (e.g., UM-UC-14 (FGFR3-S249C) cells) may be suspended and dispensed in plates. In some embodiments, cells (e.g., DMS-114 (FGFR1 overexpression) cells) may by suspended and dispensed in plates. In some embodiments, cells (e.g., RT-112 (FGFR3-Tacc3 fusion) cells) may be suspended and dispensed in plates. In some embodiments, to determine the effect of the compounds of the present disclosure on cell proliferation, cells (e.g., SNU-16, UM-UC-14, DMS-114 and RT112 cells) may be incubated in the presence of vehicle control (e.g., DMSO) or a compound of the present disclosure at varying concentrations and the inhibition of cell growth may be determined by luminescent quantification (e.g., of intracellular ATP content using CellTiterGlo), according to the manufacturers protocol. In some embodiments, to determine the IC50 values, the vehicle-treated cells were normalized as viable cells and the growth was analyzed using a software (e.g., the CDD Vault software (Collaborative Drug Discovery, Burlingame, CA)).

Pharmaceutical Compositions

In some aspects, the present disclosure provides a pharmaceutical composition comprising a compound of the present disclosure as an active ingredient.

In some embodiments, the present disclosure provides a pharmaceutical composition comprising a compound described herein and one or more pharmaceutically acceptable carriers or excipients. In some embodiments, the present disclosure provides a pharmaceutical composition comprising at least one compound selected from Table I. In some embodiments, the present disclosure provides a pharmaceutical composition comprising at least one compound selected from Table II.

As used herein, the term “composition” is intended to encompass a product comprising the specified ingredients in the specified amounts, as well as any product which results, directly or indirectly, from combination of the specified ingredients in the specified amounts.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio) propyl-β-cyclodextrin, glucosyl-β-cyclodextrin, sulphated B-cyclodextrin (S-β-CD), maltosyl-β-cyclodextrin, β-cyclodextrin sulphobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols-such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base-depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more coloring, sweetening, flavoring and/or preservative agents.

An effective amount of a compound of the present disclosure for use in therapy is an amount sufficient to treat or prevent an inflammasome related condition referred to herein, slow its progression and/or reduce the symptoms associated with the condition.

The size of the dose for therapeutic or prophylactic purposes of a compound of the present disclosure will naturally vary according to the nature and severity of the conditions, the age and sex of the animal or patient and the route of administration, according to well-known principles of medicine.

Methods of Use

In some aspects, the present disclosure provides methods of treating or preventing cancer in a subject, the method comprising administering to the subject a therapeutically effective amount of at least one compound of the present disclosure, or a pharmaceutically acceptable salt thereof.

In some aspects, the present disclosure provides methods of treating or preventing cancer in a subject, the method comprising administering to the subject a therapeutically effective amount of a compound of the present disclosure, or a pharmaceutically acceptable salt thereof.

In some aspects, the present disclosure provides methods of treating or preventing cancer in a subject, the method comprising administering to the subject a compound of the present disclosure, or a pharmaceutically acceptable salt thereof.

In some aspects, the present disclosure provides methods of treating cancer in a subject, the method comprising administering to the subject a therapeutically effective amount of at least one compound of the present disclosure, or a pharmaceutically acceptable salt thereof.

In some aspects, the present disclosure provides methods of treating cancer in a subject, the method comprising administering to the subject a therapeutically effective amount of a compound of the present disclosure, or a pharmaceutically acceptable salt thereof.

In some aspects, the present disclosure provides methods of treating cancer in a subject, the method comprising administering to the subject a compound of the present disclosure, or a pharmaceutically acceptable salt thereof.

In some aspects, the present disclosure provides at least one compound of the present disclosure, or a pharmaceutically acceptable salt thereof, for treating or preventing cancer in a subject.

In some aspects, the present disclosure provides a compound of the present disclosure, or a pharmaceutically acceptable salt thereof, for treating or preventing cancer in a subject.

In some aspects, the present disclosure provides at least one compound of the present disclosure, or a pharmaceutically acceptable salt thereof, for treating cancer in a subject.

In some aspects, the present disclosure provides a compound of the present disclosure, or a pharmaceutically acceptable salt thereof, for treating cancer in a subject.

In some aspects, the present disclosure provides a use of at least one compound of the present disclosure, or a pharmaceutically acceptable salt thereof, in the manufacture of a medicament for treating or preventing cancer in a subject.

In some aspects, the present disclosure provides a use of a compound of the present disclosure, or a pharmaceutically acceptable salt thereof, in the manufacture of a medicament for treating or preventing cancer in a subject.

In some aspects, the present disclosure provides a use of at least one compound of the present disclosure, or a pharmaceutically acceptable salt thereof, in the manufacture of a medicament for treating cancer in a subject.

In some aspects, the present disclosure provides a use of a compound of the present disclosure, or a pharmaceutically acceptable salt thereof, in the manufacture of a medicament for treating cancer in a subject.

In some aspects, the present disclosure provides a use of at least one compound of the present disclosure, or a pharmaceutically acceptable salt thereof, for treating or preventing cancer in a subject.

In some aspects, the present disclosure provides a use of a compound of the present disclosure, or a pharmaceutically acceptable salt thereof, for treating or preventing cancer in a subject.

In some aspects, the present disclosure provides a use of at least one compound of the present disclosure, or a pharmaceutically acceptable salt thereof, for treating cancer in a subject.

In some aspects, the present disclosure provides a use of a compound of the present disclosure, or a pharmaceutically acceptable salt thereof, for treating cancer in a subject.

In some aspects, the present disclosure provides methods of treating or preventing cancer in a subject, the method comprising administering to the subject a therapeutically effective amount of a pharmaceutical composition comprising at least one compound of the present disclosure, or a pharmaceutically acceptable salt thereof.

In some aspects, the present disclosure provides methods of treating or preventing cancer in a subject, the method comprising administering to the subject a therapeutically effective amount of a pharmaceutical composition comprising a compound of the present disclosure, or a pharmaceutically acceptable salt thereof.

In some aspects, the present disclosure provides methods of treating or preventing cancer in a subject, the method comprising administering to the subject a pharmaceutical composition comprising a compound of the present disclosure, or a pharmaceutically acceptable salt thereof.

In some aspects, the present disclosure provides methods of treating cancer in a subject, the method comprising administering to the subject a therapeutically effective amount of a pharmaceutical composition comprising at least one compound of the present disclosure, or a pharmaceutically acceptable salt thereof.

In some aspects, the present disclosure provides methods of treating cancer in a subject, the method comprising administering to the subject a therapeutically effective amount of a pharmaceutical composition comprising a compound of the present disclosure, or a pharmaceutically acceptable salt thereof.

In some aspects, the present disclosure provides methods of treating cancer in a subject, the method comprising administering to the subject a pharmaceutical composition comprising a compound of the present disclosure, or a pharmaceutically acceptable salt thereof.

In some aspects, the present disclosure provides a pharmaceutical composition comprising at least one compound of the present disclosure, or a pharmaceutically acceptable salt thereof, for treating or preventing cancer in a subject.

In some aspects, the present disclosure provides a pharmaceutical composition comprising a compound of the present disclosure, or a pharmaceutically acceptable salt thereof, for treating or preventing cancer in a subject.

In some aspects, the present disclosure provides a pharmaceutical composition comprising at least one compound of the present disclosure, or a pharmaceutically acceptable salt thereof, for treating cancer in a subject.

In some aspects, the present disclosure provides a pharmaceutical composition comprising a compound of the present disclosure, or a pharmaceutically acceptable salt thereof, for treating cancer in a subject.

In some aspects, the present disclosure provides a use of a pharmaceutical composition comprising at least one compound of the present disclosure, or a pharmaceutically acceptable salt thereof, in the manufacture of a medicament for treating or preventing cancer in a subject.

In some aspects, the present disclosure provides a use of a pharmaceutical composition comprising a compound of the present disclosure, or a pharmaceutically acceptable salt thereof, in the manufacture of a medicament for treating or preventing cancer in a subject.

In some aspects, the present disclosure provides a use of a pharmaceutical composition comprising at least one compound of the present disclosure, or a pharmaceutically acceptable salt thereof, in the manufacture of a medicament for treating cancer in a subject.

In some aspects, the present disclosure provides a use of a pharmaceutical composition comprising a compound of the present disclosure, or a pharmaceutically acceptable salt thereof, in the manufacture of a medicament for treating cancer in a subject.

In some aspects, the present disclosure provides a use of a pharmaceutical composition comprising at least one compound of the present disclosure, or a pharmaceutically acceptable salt thereof, for treating or preventing cancer in a subject.

In some aspects, the present disclosure provides a use of a pharmaceutical composition comprising a compound of the present disclosure, or a pharmaceutically acceptable salt thereof, for treating or preventing cancer in a subject.

In some aspects, the present disclosure provides a use of a pharmaceutical composition comprising at least one compound of the present disclosure, or a pharmaceutically acceptable salt thereof, for treating cancer in a subject.

In some aspects, the present disclosure provides a use of a pharmaceutical composition comprising a compound of the present disclosure, or a pharmaceutically acceptable salt thereof, for treating cancer in a subject.

In some aspects, the present disclosure provides methods of treating or preventing cancer in a subject, the method comprising administering to the subject a therapeutically effective amount of a pharmaceutical kit comprising at least one compound of the present disclosure, or a pharmaceutically acceptable salt thereof.

In some aspects, the present disclosure provides methods of treating or preventing cancer in a subject, the method comprising administering to the subject a therapeutically effective amount of a pharmaceutical kit comprising a compound of the present disclosure, or a pharmaceutically acceptable salt thereof.

In some aspects, the present disclosure provides methods of treating or preventing cancer in a subject, the method comprising administering to the subject a pharmaceutical kit comprising a compound of the present disclosure, or a pharmaceutically acceptable salt thereof.

In some aspects, the present disclosure provides methods of treating cancer in a subject, the method comprising administering to the subject a therapeutically effective amount of a pharmaceutical kit comprising at least one compound of the present disclosure, or a pharmaceutically acceptable salt thereof.

In some aspects, the present disclosure provides methods of treating cancer in a subject, the method comprising administering to the subject a therapeutically effective amount of a pharmaceutical kit comprising a compound of the present disclosure, or a pharmaceutically acceptable salt thereof.

In some aspects, the present disclosure provides methods of treating cancer in a subject, the method comprising administering to the subject a pharmaceutical kit comprising a compound of the present disclosure, or a pharmaceutically acceptable salt thereof.

In some aspects, the present disclosure provides a pharmaceutical kit comprising at least one compound of the present disclosure, or a pharmaceutically acceptable salt thereof, for treating or preventing cancer in a subject.

In some aspects, the present disclosure provides a pharmaceutical kit comprising a compound of the present disclosure, or a pharmaceutically acceptable salt thereof, for treating or preventing cancer in a subject.

In some aspects, the present disclosure provides a pharmaceutical kit comprising at least one compound of the present disclosure, or a pharmaceutically acceptable salt thereof, for treating cancer in a subject.

In some aspects, the present disclosure provides a pharmaceutical kit comprising a compound of the present disclosure, or a pharmaceutically acceptable salt thereof, for treating cancer in a subject.

In some aspects, the present disclosure provides a use of a pharmaceutical kit comprising at least one compound of the present disclosure, or a pharmaceutically acceptable salt thereof, in the manufacture of a medicament for treating or preventing cancer in a subject.

In some aspects, the present disclosure provides a use of a pharmaceutical kit comprising a compound of the present disclosure, or a pharmaceutically acceptable salt thereof, in the manufacture of a medicament for treating or preventing cancer in a subject.

In some aspects, the present disclosure provides a use of a pharmaceutical kit comprising at least one compound of the present disclosure, or a pharmaceutically acceptable salt thereof, in the manufacture of a medicament for treating cancer in a subject.

In some aspects, the present disclosure provides a use of a pharmaceutical kit comprising a compound of the present disclosure, or a pharmaceutically acceptable salt thereof, in the manufacture of a medicament for treating cancer in a subject.

In some aspects, the present disclosure provides a use of a pharmaceutical kit comprising at least one compound of the present disclosure, or a pharmaceutically acceptable salt thereof, for treating or preventing cancer in a subject.

In some aspects, the present disclosure provides a use of a pharmaceutical kit comprising a compound of the present disclosure, or a pharmaceutically acceptable salt thereof, for treating or preventing cancer in a subject.

In some aspects, the present disclosure provides a use of a pharmaceutical kit comprising at least one compound of the present disclosure, or a pharmaceutically acceptable salt thereof, for treating cancer in a subject.

In some aspects, the present disclosure provides a use of a pharmaceutical kit comprising a compound of the present disclosure, or a pharmaceutically acceptable salt thereof, for treating cancer in a subject.

FGFR2 is a human gene located on chromosome 10 that encodes for a protein known as FGFR2. FGFR3 is a human gene located on chromosome 4 that encodes for a protein known as FGFR3. Both FGFR2 and FGFR3 are produced in a variety of different isoforms through alternative splicing. The "b isoforms" are primarily expressed in epithelial tissues while the "c isoforms" are primarily expressed mesenchymal tissues.

FGFR2 and FGFR3 are members of the fibroblast growth factor receptor family. Members of the fibroblast growth factor receptor family are proteins that are located on the cellular surface and bind to various members of the fibroblast growth factor (FGF) family of proteins. FGFR2 and FGFR3 have an extracellular ligand domain, composed of three immunoglobulin-like domains, a single transmembrane helix domain, and an intracellular tyrosine kinase domain. Upon binding of an FGF ligand to extracellular ligand domains, the receptors dimerize, and the intracellular tyrosine kinase domains within the dimer cross-phosphorylate each other, thereby activating the kinases domains, allowing them to subsequently bind to adaptor proteins and phosphorylate other intracellular signaling molecules. Members of the fibroblast growth factor receptor family are known to regulate various cellular process including, but not limited to, proliferation and differentiation, particularly within the context of development and tissue repair.

Overexpression of FGFR2 has been implicated in a variety of different cancers, including, but not limited to, gastric cancer and triple negative breast cancer.

Overexpression of FGFR3 has been implicated in a variety of different cancers, including, but not limited to, lung cancer and bladder cancer.

Mutations in the FGFR2 gene, which produce mutant FGFR2 proteins, have been implicated in a variety of different cancers, including, but not limited to, endometrial carcinoma and lung cancer.

Mutations in the FGFR3 gene, which produce mutant FGFR3 proteins, have been implicated in a variety of different cancers, including, but not limited to, bladder cancer.

Fusions of the FGFR2 gene, which produce fusions of FGFR2 proteins, have been implicated in a variety of different cancers, including, but not limited to, bladder cancer and intrahepatic cholangiocarcinoma.

Fusions of the FGFR3 gene, which produce fusions of FGFR3 proteins, have been implicated in a variety of different cancers, including, but not limited to, bladder cancer and glioblastoma.

In some embodiments, the subject is a mammal.

In some embodiments, the subject is a human.

In some embodiments, the subject has previously undergone at least one round of anti-cancer therapy. In some embodiments, the subject has previously undergone at least one round of anti-cancer therapy and has acquired resistance to treatment with the anti-cancer therapy. In some embodiments, the anti-cancer therapy can comprise the administration of at least one of futibatinib, pemigatinib, erdafitinib, infigratinib, Debio-1347.

In some embodiments, the cancer is characterized by at least one oncogenic mutation in the FGFR2 gene.

In some embodiments, the cancer is characterized by at least one oncogenic mutation in the FGFR3 gene.

It is understood that a cancer that is characterized by at least one oncogenic mutation in the FGFR2 gene and/or FGFR3 gene is a cancer that is typically associated with at least one oncogenic mutation in the FGFR2 gene and/or FGFR3 gene, including, but not limited to, cancers whose primary oncogenic activity is thought to be driven by the at least one oncogenic mutation in the FGFR2 gene and/or FGFR3 gene.

In some embodiments, the cancer is characterized by overexpression of the FGFR2 gene.

In some embodiments, the cancer is characterized by overexpression of the FGFR3 gene.

It is understood that a cancer that is characterized by overexpression of the FGFR2 gene and/or FGFR3 gene is a cancer that is typically associated with the overexpression of the FGFR2 gene and/or FGFR3 gene, including, but not limited to, cancers whose primary oncogenic activity is thought to be driven by the overexpression of the FGFR2 gene and/or FGFR3 gene.

In some embodiments, the cancer is characterized by at least one oncogenic variant of FGFR2.

In some embodiments, the cancer is characterized by at least one oncogenic variant of FGFR3.

It is understood that a cancer that is characterized by least one oncogenic variant of FGFR2 and/or FGFR3 is a cancer that is typically associated with at least one oncogenic variant of FGFR2 and/or FGFR3, including, but not limited to, cancers whose primary oncogenic activity is thought to be driven by the at least one oncogenic variant of FGFR2 and/or FGFR3.

In some embodiments, the cancer is characterized by overexpression of FGFR2.

In some embodiments, the cancer is characterized by overexpression of FGFR3.

It is understood that a cancer that is characterized by overexpression of FGFR2 and/or FGFR3 is a cancer that is typically associated with overexpression of FGFR2 and/or FGFR3, including, but not limited to, cancers whose primary oncogenic activity is thought to be driven by overexpression of FGFR2 and/or FGFR3.

It is understood that an oncogenic variant of FGFR2 is an FGFR2 protein that comprises at least one oncogenic mutation and that is produced as the result of the expression of a FGFR2 gene that comprises at least one oncogenic mutation.

It is understood that an oncogenic variant of FGFR3 is an FGFR3 protein that comprises at least one oncogenic mutation and that is produced as the result of the expression of a FGFR3 gene that comprises at least one oncogenic mutation.

In some embodiments, the subject has at least one oncogenic mutation in the FGFR2 gene.

In some embodiments, the subject has at least one oncogenic mutation in the FGFR3 gene.

In some embodiments, the subject has at least one tumor and/or cancerous cell that expresses an oncogenic variant of FGFR2.

In some embodiments, the subject has at least one tumor and/or cancerous cell that expresses an oncogenic variant of FGFR3.

In some embodiments, the subject has at least one tumor and/or cancerous cell that overexpresses FGFR2.

In some embodiments, the subject has at least one tumor and/or cancerous cell that overexpresses FGFR3.

As would be appreciated by the skilled artisan, in the context of a gene (e.g. FGFR2 and/or FGFR3), an oncogenic mutation can include, but is not limited to a mutation that results in the substitution of one amino acid for another at a specific position within FGFR2 and/or FGFR3, a mutation that results in the substitution of one or more amino acids for one or more amino acids between two specific positions within FGFR2 and/or FGFR3, a mutation that results in an insertion of one or more amino acids between two positions within FGFR2 and/or FGFR3, a mutation that results in the deletion of one more amino acids between two positions within FGFR2 and/or FGFR3, and mutation that results in a fusion of FGFR2 and/or FGFR3, or portion thereof, with another protein, or portion thereof, or any combination thereof. As would be appreciated by the skilled artisan, in the context of a gene, an oncogenic mutation can include, but is not limited to, a missense mutation, a nonsynonymous mutation, an insertion of one or more nucleotides, a deletion of one or more nucleotides, an inversion and a deletion-insertion. As would be appreciated by the skilled artisan, in the context of a gene (e.g. FGRF2 and/or FGFR3), the gene can have one or more of the aforementioned types of oncogenic mutations, including combinations of different types of oncogenic mutations.

As would be appreciated by the skilled artisan, in the context of a protein (e.g. FGFR2 and/or FGFR3), an oncogenic mutation, but is not limited to, the substitution of one amino acid for another at a specific position within FGFR2 and/or FGFR3, the substitution of one or more amino acids for one or more amino acids between two specific positions within FGFR2 and/or FGFR3, an insertion of one or more amino acids between two positions within FGFR2 and/or FGFR3, a deletion of one more amino acids between two positions within FGFR2 and/or FGFR3, and a fusion of FGFR2 and/or FGFR3, or portion thereof, with another protein, or portion thereof, or any combination thereof. As would be appreciated by the skilled artisan, in the context of a protein (e.g. FGFR2 and/or FGFR3), the protein can have one or more of the aforementioned types of oncogenic mutations, including combinations of different types of oncogenic mutations.

In some embodiments, an oncogenic mutation of FGFR2 can be any of the FGFR2 mutations put forth in Table 1a. In some embodiments, an oncogenic mutation of FGFR2 can be a gatekeeper mutation that results in resistance to the existing inhibitors, wherein the gatekeeper mutation is V5651 or V565F.

TABLE 1a

| FGFR2 mutations | | |
|---|---|---|
| S252W | V565F | V565I |
| V565I | N550K | |

In some embodiments, an oncogenic mutation of FGFR3 can be any of the FGFR3 mutations put forth in Table 1b. In some embodiments, an oncogenic mutation of FGFR3 can be a gatekeeper mutation that results in resistance to the existing inhibitors, wherein the gatekeeper mutation is V555M, V555L, or V555F.

TABLE 1b

| FGFR3 mutations | | |
|---|---|---|
| S249C | Tacc3 fusion | V55SL |
| V555F | V555M | |

In some embodiments, an oncogenic variant of FGFR2 can be any of the FGFR2 variants put forth in Table 1c.

TABLE 1c

| FGFR2 oncogenic variants | | |
|---|---|---|
| FGFR2-S252W | FGFR2-V565F | FGFR2-S252W + V565F |
| FGFR2-V565I | FGFR2-N550K | FGFR2-S252W + V565I |
| FGRF2-V565I | | |

In some embodiments, an oncogenic variant of FGFR3 can be any of the FGFR3 variants put forth in Table 1d.

TABLE 1d

| FGFR3 oncogenic variants | | |
|---|---|---|
| FGFR3-S249C | FGFR3-Tacc3 fusion | FGFR3-S249C + V555M |
| FGFR3-V555F | FGFR3-S249C + V555F | FGFR3-S249C + V555L |
| FGFR3-V555L | FGFR3-V555M | |

in some embodiments, an oncogenic variant of FGFR2 can comprise a gatekeeper mutation that results in resistance to the existing inhibitors, wherein the gatekeeper mutation is V565I or V565F.

In some embodiments, an oncogenic variant of FGFR3 can comprise a gatekeeper mutation that results in resistance to the existing inhibitors, wherein the gatekeeper mutation is V555M, V555L or V555F.

As used herein, the term "activating mutation" refers to any oncogenic mutation that results in at least one of: a) increased ligand binding of FGFR2 and/or FGFR3; b) ligand-independent dimerization and activation of FGFR2 and/or FGFR3; and c) increased kinase activity of FGFR2 and/or FGFR3.

In some embodiments, the cancer is a carcinoma, a lymphoma, a blastoma, a sarcoma, a leukemia, a brain cancer, a breast cancer, a blood cancer, a bone cancer, a lung cancer, a skin cancer, a liver cancer, an ovarian cancer, a bladder cancer, a renal cancer, a kidney cancer, a gastric cancer, a thyroid cancer, a pancreatic cancer, an esophageal cancer, a prostate cancer, a cervical cancer, a uterine cancer, a stomach cancer, a soft tissue cancer, a laryngeal cancer, a small intestine cancer, a testicular cancer, an anal cancer, a vulvar cancer, a joint cancer, an oral cancer, a pharynx cancer or a colorectal cancer.

In some embodiments, the cancer is adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer, cervical cancer, Acute lymphoblastic leukemia (ALL), Acute myeloid leukemia (AML), Adrenal gland tumors, Anal cancer, Bile duct cancer, Bladder cancer, Bone cancer, Bowel cancer, Brain tumors, Breast cancer, Cancer of unknown primary (CUP), Cancer spread to bone, Cancer spread to brain, Cancer spread to liver, Cancer spread to lung, Carcinoid, Cervical cancer, Children's cancers, Chronic lymphocytic leukemia (CLL), Chrome myeloid leukemia (CML), Colorectal cancer, Ear cancer, Endometrial cancer, Eye cancer, Follicular dendritic cell sarcoma, Gallbladder cancer, Gastric cancer, Gastro esophageal junction cancers, Germ cell tumors, Gestational trophoblastic disease (GIT)), Hairy cell leukemia, Head and neck cancer, Hodgkin lymphoma, Kaposi's sarcoma, Kidney cancer, Laryngeal cancer, Leukemia, Gastric linitis plastica, Liver cancer, Lung cancer, Lymphoma, Malignant schwannoma, Mediastinal germ cell tumors, Melanoma skin cancer, Men's cancer, Merkel cell skin cancer, Mesothelioma, Molar pregnancy, Mouth and oropharyngeal cancer, Myeloma, Nasal and paranasal sinus cancer, Nasopharyngeal cancer, Neuroblastoma, Neuroendocrine tumors, Non-Hodgkin lymphoma (NHL), Esophageal cancer, Ovarian cancer, Pancreatic cancer, Penile cancer, Persistent trophoblastic disease and choriocarcinoma, Pheochromocytoma, Prostate cancer, Pseudomyxoma peritonei, Rectal cancer. Retinoblastoma, Salivary gland cancer, Secondary' cancer, Signet cell cancer, Skin cancer, Small bowel cancer, Soft tissue sarcoma, Stomach cancer, T cell childhood non Hodgkin lymphoma (NHL), Testicular cancer, Thymus gland cancer, Thyroid cancer, Tongue cancer, Tonsil cancer, Tumors of the adrenal gland, Uterine cancer. Vaginal cancer, Vulval cancer, Wilms' tumor, Womb cancer and Gynaecological cancer. Examples of cancer also include, but are not limited to, Hematologic malignancies, Lymphoma, Cutaneous T-cell lymphoma, Peripheral T-cell lymphoma, Hodgkin's lymphoma, Non-Hodgkin's lymphoma, Multiple myeloma, Chrome lymphocytic leukemia, chronic myeloid leukemia, acute myeloid leukemia, Myelodysplastic syndromes, Myelofibrosis, Biliary tract cancer, Hepatocellular cancer, Colorectal cancer, Breast cancer, Lung cancer, Non-small cell lung cancer, Ovarian cancer, Thyroid Carcinoma, Renal Cell Carcinoma, Pancreatic cancer, Bladder cancer, skin cancer, malignant melanoma, merkel cell carcinoma, Uveal Melanoma or Glioblastoma multiforme.

In some embodiments, the cancer is gastric cancer, triple negative breast cancer, melanoma, hepatobiliary cancer, cancer of unknown primary, esophagogastric cancer, cervical cancer, head and neck cancer, CNS cancer, brain cancer, NSCLC, ovarian cancer, breast cancer, soft tissue sarcoma, pancreatic cancer, prostate cancer, renal cell carcinoma, thyroid cancer, lung cancer, bladder cancer, endometrial carcinoma, intrahepatic cholangiocarcinoma or glioblastoma.

Definitions

Unless otherwise stated, the following terms used in the specification and claims have the following meanings set out below.

Without wishing to be limited by this statement, it is understood that, while various options for variables are described herein, the disclosure intends to encompass operable embodiments having combinations of the options. The disclosure may be interpreted as excluding the non-operable embodiments caused by certain combinations of the options.

It is to be understood that a compound of the present disclosure may be depicted in a neutral form, a cationic form (e.g., carrying one or more positive charges), or an anionic form (e.g., carrying one or more negative charges), all of which are intended to be included in the scope of the present disclosure. For example, when a compound of the present disclosure is depicted in an anionic form, it should be understood that such depiction also refers to the various neutral forms, cationic forms, and anionic forms of the compound. For another example, when a compound the present disclosure is depicted in an anionic form, it should be understood that such depiction also refers to various salts (e.g., sodium salt) of the anionic form of the compound.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched)divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, alkylsulphinyl, sulphonato, sulphamoyl, sulphonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated Jor partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo [3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c] pyrazolyl, 3,4,5,6,7,8-hexahydropyrido[4,3-d]pyrimidinyl, 4,5,6,7-tetrahydro-1H-pyrazolo[3,4-c] pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic heterocycloalkyl, only one of the rings in the heterocycloalkyl needs to be non-aromatic (e.g., 4,5,6,7-tetrahydrobenzo[c] isoxazolyl).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur. The nitrogen atom may be substituted or unsubstituted (i.e., N or NR wherein R is H or other substituents, as defined). The nitrogen and sulphur heteroatoms may optionally be oxidised (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c] isoxazolyl).

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthyridine, indole, benzofuran, purine, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or $—O^-$.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5th edition, John Wiley & Sons: New York, 2001; Greene, T.W., Wuts, P.G. M., *Protective Groups in Organic Synthesis,* 3rd edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T.W., Wuts, P.G. M., *Protective Groups in Organic Synthesis,* 3rd edition, John Wiley & Sons: New York, 1999.

It is to be understood that, unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

As used herein, the term "subject" includes human and non-human animals, as well as cell lines, cell cultures, tissues, and organs. In some embodiments, the subject is a mammal. The mammal can be e.g., a human or appropriate non-human mammal, such as primate, mouse, rat, dog, cat, cow, horse, goat, camel, sheep or a pig. The subject can also be a bird or fowl. In some embodiments, the subject is a human.

As used herein, the term "subject in need thereof" refers to a subject having a disease or having an increased risk of developing the disease. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

It is to be understood that a compound of the present disclosure, or a pharmaceutically acceptable salt, polymorph or solvate thereof, can or may also be used to prevent a relevant disease, condition, or disorder, or used to identify suitable candidates for such purposes.

As used herein, the term "preventing," "prevent," or "protecting against" describes reducing or eliminating the onset of the symptoms or complications of such disease, condition or disorder.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, New York (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, $18^{th}$ edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulphite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebuliser.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulphonic, acetic, ascorbic, benzene sulphonic, benzoic, bicarbonic, carbonic, citric, edetic, ethane disulphonic, 1,2-ethane sulphonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulphonic, maleic, malic, mandelic, methane sulphonic, napsylic, nitric, oxalic, pamoic, pantothenic, phenylacetic, phosphoric, polygalacturonic, propionic, salicylic, stearic, subacetic, succinic, sulphamic, sulphanilic, sulphuric, tannic, tartaric, toluene sulphonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulphonic acid, 2-naphthalenesulphonic acid, 4-toluenesulphonic acid, camphorsulphonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilising the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy*, $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

As would be appreciated by the skilled artisan, the FGFR2 gene is commonly referred to as one of FGFR2, fibroblast growth factor receptor 2, BEK, JWS, BBDS, CEK3, CFD1, ECT1, KGFR, TK14, TK25, BFR-1, CD332, cluster of differentiation 332 and K-SAM. Thus, these terms are used herein interchangeably to refer to the FGFR2 gene.

As would be appreciated by the skilled artisan, the FGFR2 protein, encoded by the FGFR2 gene, is commonly referred to as one of FGFR2, fibroblast growth factor receptor 2, BEK, JWS, BBDS, CEK3, CFD1, ECT1, KGFR, TK14, TK25, BFR-1, CD332, cluster of differentiation 332 and K-SAM. Thus, these terms are used herein interchangeably to refer to the FGFR2 protein.

As used herein, the term FGFR2 can refer to any isoform of the FGFR2 protein, including, but not limited to, FGFR2-IIIB and FGFR2-IIIC.

As would be appreciated by the skilled artisan, the FGFR3 gene is commonly referred to as one of FGFR3, fibroblast growth factor receptor 3, ACH, CD333, cluster of differentiation 333, CEK2, HSFGFR3EX and JTK4. Thus, these terms are used herein interchangeably to refer to the BRAF gene.

As would be appreciated by the skilled artisan, the FGFR3 protein, encoded by the FGFR3 gene, is commonly referred to as one of FGFR3, fibroblast growth factor receptor 3, ACH, CD333, cluster of differentiation 333, CEK2, HSFGFR3EX and JTK4. Thus, these terms are used herein interchangeably to refer to the FGFR3 protein.

As used herein, the term FGFR2 can refer to any isoform of the FGFR2 protein, including, but not limited to, FGFR2-IIIB and FGFR2-IIIC.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXEMPLARY EMBODIMENTS

Embodiment 1. A compound of Formula (I'):

(I')

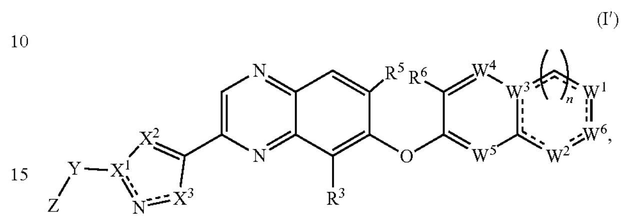

or a pharmaceutically acceptable salt or stereoisomer thereof, wherein:

each ---- independently represents a single bond or a double bond;

n is 0 or 1;

$W^1$ is $C(R^{W1})$ when connected to one double bond and one single bond, $N(R^{W1})$ when connected to two single bonds, or N when connected to one double bond and one single bond;

$R^{W1}$ is H, $C_1$-$C_6$ alkyl, or —S(=O)$_2$—($C_1$-$C_6$ alkyl);

$W^2$ is $C(R^{W2})$ when connected to one double bond and one single bond, $N(R^{W2})$ or O when connected to two single bonds, or N when connected to one double bond and one single bond;

$R^{W2}$ is H, $C_1$-$C_6$ alkyl, or —S(=O)$_2$—($C_1$-$C_6$ alkyl);

$W^3$ is C or N;

$W^4$ is $C(R^{W4})$ or N;

$R^{W4}$ is H, halogen, cyano, $C_1$-$C_6$ alkyl, or —S(=O)$_2$—($C_1$-$C_6$ alkyl);

$W^5$ is $C(R^{W5})$ or N;

$R^{W5}$ is H, halogen, cyano, $C_1$-$C_6$ alkyl, or —S(=O)$_2$—($C_1$-$C_6$ alkyl);

$W^6$ is $C(R^{W6})$ when connected to one double bond and one single bond, $N(R^{W6})$ when connected to two single bonds, or N when connected to one double bond and one single bond;

$R^{W6}$ is H, halogen, cyano, $C_1$-$C_6$ alkyl, $C_1$-$C_6$ alkoxyl, $C_1$-$C_6$ haloalkyl, or —S(=O)$_2$—($C_1$-$C_6$ alkyl);

$X^1$ is C or N;

$X^2$ is N, O, or $C(R^{X2})$;

$R^{X2}$ is H or $C_1$-$C_6$ alkyl;

$X^3$ is N, O, or $C(R^{X3})$;

$R^{X3}$ is H or $C_1$-$C_6$ alkyl;

$R^3$ is H, halogen, cyano, $NH_2$, —NH($C_1$-$C_6$ alkyl), —NHC(=O)($C_1$-$C_6$ haloalkyl), —NHC(=O)O($C_1$-$C_6$ alkyl), N($C_1$-$C_6$ alkyl)$_2$, —S(=O)$_2$—($C_1$-$C_6$ alkyl), —C(=O)H, —C(=O)($C_1$-$C_6$ alkyl), —C(=O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the —NH($C_1$-$C_6$ alkyl), —NHC(=O)($C_1$-$C_6$ haloalkyl), —NHC(=O)O($C_1$-$C_6$ alkyl), N($C_1$-$C_6$ alkyl)$_2$, —S(=O)$_2$—($C_1$-$C_6$ alkyl), —C(=O)H, —C(=O)($C_1$-$C_6$ alkyl), —C(=O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, is optionally substituted with one or more $R^{3a}$, each $R^{3a}$ independently is halogen, cyano, oxo, —OH, $NH_2$, —NH($C_1$-$C_6$ alkyl), —NHC(═O)O($C_1$-$C_6$ alkyl), N($C_1$-$C_6$ alkyl)$_2$, —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, 3- to 12-membered heterocycloalkyl, $C_6$-$C_{10}$ aryl, or 5- to 10-membered heteroaryl, wherein the NHC(═O)O($C_1$-$C_6$ alkyl) is optionally substituted with one or more halogen;

$R^5$ is H, halogen, cyano, or $C_1$-$C_6$ alkyl;

$R^6$ is H, halogen, cyano, or $C_1$-$C_6$ alkyl;

Y is absent, $C_1$-$C_6$ alkyl, $C_2$-$C_6$ alkenyl, or $C_1$-$C_6$ alkoxyl, wherein the $C_1$-$C_6$ alkyl, $C_2$-$C_6$ alkenyl, or $C_1$-$C_6$ alkoxyl is optionally substituted with one or more halogen, oxo, cyano, —OH, $NH_2$, —NH($C_1$-$C_6$ alkyl)-OH, $C_1$-$C_6$ alkyl, $C_2$-$C_6$ alkenyl, $C_1$-$C_6$ alkoxyl optionally substituted with —($C_1$-$C_6$ alkyl)($C_6$-$C_{10}$ aryl), or $C_3$-$C_{12}$ cycloalkyl;

Z is absent, H, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl or 5- to 10-membered heteroaryl, is optionally substituted with one or more $R^Z$;

each $R^Z$ independently is oxo, halogen, cyano, —OH, =$NR^{Za}$, $NH_2$, $NHR^{Za}$, NH($C_1$-$C_6$ alkyl), N($C_1$-$C_6$ alkyl)$_2$, —S($C_1$-$C_6$ alkyl), —S(═O)(═$NR^{Za}$)—($C_1$-$C_6$ alkyl), —S(═O)$_2$—($C_1$-$C_6$ alkyl), —S(═O)$_2$—($C_2$-$C_6$ alkenyl), —C(═O) (3- to 12-membered heterocycloalkyl), —C(═O)NH($C_1$-$C_6$ alkyl), —C(═O)$NR^{Za}$, —C(═O)—($C_1$-$C_6$ alkyl), —C(═O)—($C_2$-$C_6$ alkenyl), —C(═O)—($C_1$-$C_6$ alkoxyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, 3- to 12-membered heterocycloalkyl, or 5- to 10-membered heteroaryl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, 3- to 12-membered heterocycloalkyl, or 5- to 10-membered heteroaryl is optionally substituted with one or more $R^{Za}$, each $R^{Za}$ independently is H, oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, or 3- to 12-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, or 3- to 12-membered heterocycloalkyl is optionally substituted with one or more $R^{Zb}$; and each $R^{Zb}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, or $C_1$-$C_6$ alkoxyl.

Embodiment 2. a Compound of Formula (I)

(I)

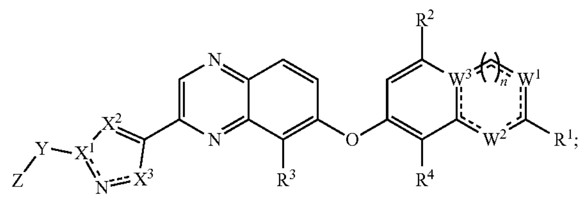

or a pharmaceutically acceptable salt or stereoisomer thereof, wherein:

each ⎓ independently represents a single bond or a double bond;

n is 0 or 1;

$W^1$ is C($R^{W1}$) or N($R^{W1}$) when connected to two single bonds, or C or N when connected to one double bond and one single bond;

$R^{W1}$ is H, $C_1$-$C_6$ alkyl, or —S(═O)$_2$—($C_1$-$C_6$ alkyl);

$W^2$ is C($R^{W2}$) or N($R^{W2}$) when connected to two single bonds, or C or N when connected to one double bond and one single bond;

$R^{W2}$ is H, $C_1$-$C_6$ alkyl, or —S(═O)$_2$—($C_1$-$C_6$ alkyl);

$W^3$ is C or N;

$X^1$ is C or N;

$X^2$ is N, O, or C($R^{X2}$);

$R^{X2}$ is H or $C_1$-$C_6$ alkyl;

$X^3$ is N, O, or C($R^{X3}$);

$R^{X3}$ is H or $C_1$-$C_6$ alkyl;

$R^1$ is H, halogen, cyano, or $C_1$-$C_6$ alkyl;

$R^2$ is H, halogen, cyano, or $C_1$-$C_6$ alkyl;

$R^3$ is H, halogen, cyano, or $C_1$-$C_6$ alkyl;

$R^4$ is H, halogen, cyano, or $C_1$-$C_6$ alkyl;

Y is absent or $C_1$-$C_6$ alkyl optionally substituted with one or more oxo or —OH;

Z is H, $C_3$-$C_8$ cycloalkyl, or 3- to 8-membered heterocycloalkyl, wherein the $C_3$-$C_8$ cycloalkyl or 3- to 8-membered heterocycloalkyl is optionally substituted with one or more $R^Z$;

each $R^Z$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Za}$;

each $R^{Za}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Zb}$; and each $R^{Zb}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, or $C_1$-$C_6$ alkoxyl.

Embodiment 3. The compound of any one of the preceding embodiments, wherein:

each ⎓ independently represents a single bond or a double bond;

n is 0 or 1;

$W^1$ is C($R^{W1}$) or N($R^{W1}$) when connected to two single bonds, or C or N when connected to one double bond and one single bond;

$R^{W1}$ is H, $C_1$-$C_6$ alkyl, or —S(═O)$_2$—($C_1$-$C_6$ alkyl);

$W^2$ is C($R^{W2}$) or N($R^{W2}$) when connected to two single bonds, or C or N when connected to one double bond and one single bond;

$R^{W2}$ is H, $C_1$-$C_6$ alkyl, or —S(═O)$_2$—($C_1$-$C_6$ alkyl);

$W^3$ is C or N;

$X^1$ is C or N;

$X^2$ is N, O, or C($R^{X2}$);

$R^{X2}$ is H or $C_1$-$C_6$ alkyl;

$X^3$ is N, O, or C($R^{X3}$);

$R^{X3}$ is H or $C_1$-$C_6$ alkyl;

$R^1$ is H, halogen, cyano, or $C_1$-$C_6$ alkyl;

$R^2$ is H, halogen, cyano, or $C_1$-$C_6$ alkyl;

$R^3$ is H, halogen, cyano, or $C_1$-$C_6$ alkyl;

$R^4$ is H, halogen, cyano, or $C_1$-$C_6$ alkyl;

Y is absent or $C_1$-$C_6$ alkyl optionally substituted with one or more oxo or —OH;

Z is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^Z$;

each $R^Z$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Za}$, each $R^{Za}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Zb}$, and each $R^{Zb}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, or $C_1$-$C_6$ alkoxyl.

Embodiment 4. The compound of any one of the preceding embodiments, wherein:

each ⎓ independently represents a single bond or a double bond;

n is 0 or 1;

$W^1$ is C($R^{W1}$) or N($R^{W1}$) when connected to two single bonds, or C or N when connected to one double bond and one single bond;

$R^{W1}$ is H, $C_1$-$C_6$ alkyl, or —S(═O)$_2$—($C_1$-$C_6$ alkyl);

$W^2$ is C($R^{W2}$) or N($R^{W2}$) when connected to two single bonds, or C or N when connected to one double bond and one single bond;

$R^{W2}$ is H, $C_1$-$C_6$ alkyl, or —S(═O)$_2$—($C_1$-$C_6$ alkyl);

$W^3$ is C or N;

$X^1$ is C or N;

$X^2$ is N, O, or C($R^{X2}$);

$R^{X2}$ is H or $C_1$-$C_6$ alkyl;

$X^3$ is N, O, or C($R^{X3}$);

$R^{X3}$ is H or $C_1$-$C_6$ alkyl;

$R^1$ is H, halogen, cyano, or $C_1$-$C_6$ alkyl;

$R^2$ is H, halogen, cyano, or $C_1$-$C_6$ alkyl;

$R^3$ is H, halogen, cyano, or $C_1$-$C_6$ alkyl;

$R^4$ is H, halogen, cyano, or $C_1$-$C_6$ alkyl;

Y is $C_1$-$C_6$ alkyl optionally substituted with one or more oxo or —OH;

Z is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^Z$;

each $R^Z$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Za}$;

each $R^{Za}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Zb}$; and each $R^{Zb}$ independently is oxo, halogen, cyano, —OH, $NH_2$, NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, or $C_1$-$C_6$ alkoxyl.

Embodiment 5. The compound of any one of the preceding embodiments, wherein

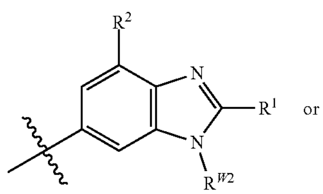

or

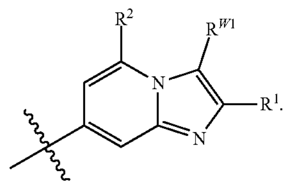

is

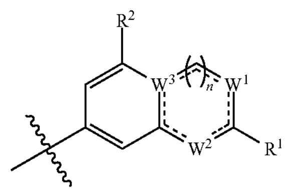

Embodiment 6. The compound of any one of the preceding embodiments, wherein

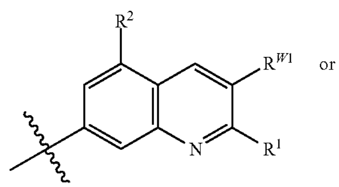

or

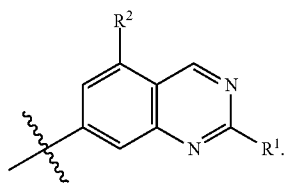

is

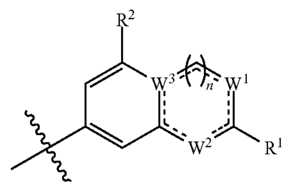

Embodiment 7. The compound of any one of the preceding embodiments, wherein

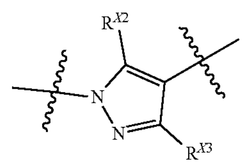

is

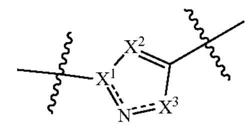

Embodiment 8. The compound of any one of the preceding embodiments, wherein

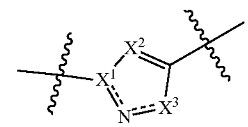

is

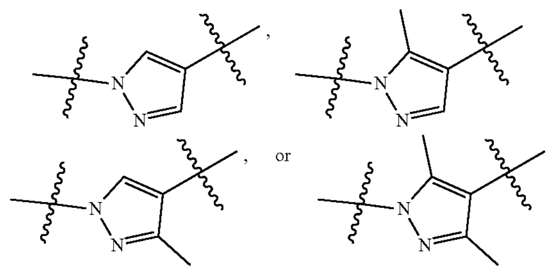

Embodiment 9. The compound of any one of the preceding embodiments, wherein

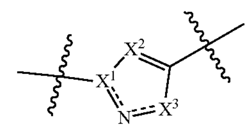

is

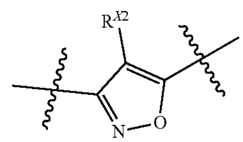

Embodiment 10. The compound of any one of the preceding embodiments, wherein

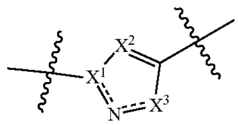

is

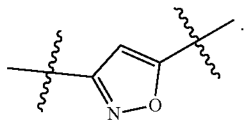 [SMILES: *c1cc(*)on1]

Embodiment 11. The compound of any one of the preceding embodiments, wherein $R^1$ is H.

Embodiment 12. The compound of any one of the preceding embodiments, wherein $R^1$ is halogen, cyano, or $C_1$-$C_6$ alkyl.

Embodiment 13. The compound of any one of the preceding embodiments, wherein $R^1$ is $C_1$-$C_6$ alkyl.

Embodiment 14. The compound of any one of the preceding embodiments, wherein $R^1$ is $CH_3$.

Embodiment 15. The compound of any one of the preceding embodiments, wherein $R^2$ is H.

Embodiment 16. The compound of any one of the preceding embodiments, wherein $R^2$ is halogen, cyano, or $C_1$-$C_6$ alkyl.

Embodiment 17. The compound of any one of the preceding embodiments, wherein $R^3$ is H.

Embodiment 18. The compound of any one of the preceding embodiments, wherein $R^3$ is halogen, cyano, or $C_1$-$C_6$ alkyl.

Embodiment 19. The compound of any one of the preceding embodiments, wherein $R^3$ is halogen.

Embodiment 20. The compound of any one of the preceding embodiments, wherein $R^3$ is Cl.

Embodiment 21. The compound of any one of the preceding embodiments, wherein $R^3$ is $C_1$-$C_6$ alkyl.

Embodiment 22. The compound of any one of the preceding embodiments, wherein $R^3$ is $CH_3$.

Embodiment 23. The compound of any one of the preceding embodiments, wherein $R^4$ is H.

Embodiment 24. The compound of any one of the preceding embodiments, wherein $R^4$ is halogen, cyano, or $C_1$-$C_6$ alkyl.

Embodiment 25. The compound of any one of the preceding embodiments, wherein $R^4$ is halogen.

Embodiment 26. The compound of any one of the preceding embodiments, wherein $R^4$ is Cl.

Embodiment 27. The compound of any one of the preceding embodiments, wherein $R^4$ is $C_1$-$C_6$ alkyl.

Embodiment 28. The compound of any one of the preceding embodiments, wherein $R^4$ is $CH_3$.

Embodiment 29. The compound of any one of the preceding embodiments, wherein Y is absent.

Embodiment 30. The compound of any one of the preceding embodiments, wherein Y is $C_1$-$C_6$ alkyl optionally substituted with one or more oxo or —OH.

Embodiment 31. The compound of any one of the preceding embodiments, wherein Y is $C_1$-$C_6$ alkyl.

Embodiment 32. The compound of any one of the preceding embodiments, wherein Y is —$CH_2$—.

Embodiment 33. The compound of any one of the preceding embodiments, wherein Y is $C_1$-$C_6$ alkyl substituted with one or more —OH.

Embodiment 34. The compound of any one of the preceding embodiments, wherein Z is H.

Embodiment 35. The compound of any one of the preceding embodiments, wherein Z is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^Z$.

Embodiment 36. The compound of any one of the preceding embodiments, wherein Z is azetidinyl or oxetanyl, wherein the azetidinyl or oxetanyl is optionally substituted with one or more $R^Z$.

Embodiment 37. The compound of any one of the preceding embodiments, wherein Z is azetidinyl or oxetanyl.

Embodiment 38. The compound of any one of the preceding embodiments, wherein Z is pyrrolidinyl or tetrahydrofuranyl, wherein the pyrrolidinyl or tetrahydrofuranyl is optionally substituted with one or more $R^Z$.

Embodiment 39. The compound of any one of the preceding embodiments, wherein Z is pyrrolidinyl or tetrahydrofuranyl.

Embodiment 40. The compound of any one of the preceding embodiments, wherein Z is piperidinyl or tetrahydropyranyl, wherein the piperidinyl or tetrahydropyranyl is optionally substituted with one or more $R^Z$.

Embodiment 41. The compound of any one of the preceding embodiments, wherein Z is piperidinyl or tetrahydropyranyl.

Embodiment 42. The compound of any one of the preceding embodiments, wherein at least one $R^Z$ is oxo, halogen, cyano, —OH.

Embodiment 43. The compound of any one of the preceding embodiments, wherein at least one $R^Z$ is $NH_2$, $NH(C_1$-$C_6$ alkyl), or $N(C_1$-$C_6$ alkyl$)_2$, wherein the $NH(C_1$-$C_6$ alkyl) or $N(C_1$-$C_6$ alkyl$)_2$ is optionally substituted with one or more $R^{Za}$.

Embodiment 44. The compound of any one of the preceding embodiments, wherein at least one $R^Z$ is —S(═O)$_2$—($C_1$-$C_6$ alkyl) optionally substituted with one or more $R^{Za}$.

Embodiment 45. The compound of any one of the preceding embodiments, wherein at least one $R^Z$ is —C(═O)—($C_1$-$C_6$ alkyl) or —C(═O)—($C_2$-$C_6$ alkenyl), wherein the —C(═O)—($C_1$-$C_6$ alkyl) or —C(═O)—($C_2$-$C_6$ alkenyl) is optionally substituted with one or more $R^{Za}$.

Embodiment 46. The compound of any one of the preceding embodiments, wherein at least one $R^Z$ is —C(═O)—CH═$CH_2$.

Embodiment 47. The compound of any one of the preceding embodiments, wherein at least one $R^Z$ is $C_1$-$C_6$ alkyl, $C_2$-$C_6$ alkenyl, $C_2$-$C_6$ alkynyl, or $C_1$-$C_6$ alkoxyl, wherein the $C_1$-$C_6$ alkyl, $C_2$-$C_6$ alkenyl, $C_2$-$C_6$ alkynyl, or $C_1$-$C_6$ alkoxyl is optionally substituted with one or more $R^{Za}$.

Embodiment 48. The compound of any one of the preceding embodiments, wherein at least one $R^Z$ is $C_1$-$C_6$ alkyl optionally substituted with one or more $R^{Za}$.

Embodiment 49. The compound of any one of the preceding embodiments, wherein at least one $R^Z$ is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^{Za}$.

Embodiment 50. The compound of any one of the preceding embodiments, wherein at least one $R^{Za}$ is oxo, halogen, cyano, or —OH.

Embodiment 51. The compound of any one of the preceding embodiments, wherein at least one $R^{Za}$ is $NH_2$, $NH(C_1-C_6\ alkyl)$, or $N(C_1-C_6\ alkyl)_2$, wherein the $NH(C_1-C_6\ alkyl)$ or $N(C_1-C_6\ alkyl)_2$ is optionally substituted with one or more $R^{Zb}$.

Embodiment 52. The compound of any one of the preceding embodiments, wherein at least one $R^{Za}$ is —S(═O)$_2$—($C_1$-$C_6$ alkyl) optionally substituted with one or more $R^{Zb}$.

Embodiment 53. The compound of any one of the preceding embodiments, wherein at least one $R^{Za}$ is —C(═O)—($C_1$-$C_6$ alkyl) or —C(═O)—($C_2$-$C_6$ alkenyl), wherein the —C(═O)—($C_1$-$C_6$ alkyl) or —C(═O)—($C_2$-$C_6$ alkenyl) is optionally substituted with one or more $R^{Zb}$.

Embodiment 54. The compound of any one of the preceding embodiments, wherein at least one $R^{Za}$ is —C(═O)—CH—$CH_2$.

Embodiment 55. The compound of any one of the preceding embodiments, wherein at least one $R^{Za}$ is $C_1$-$C_6$ alkyl, $C_2$-$C_6$ alkenyl, $C_2$-$C_6$ alkynyl, or $C_1$-$C_6$ alkoxyl, wherein the $C_1$-$C_6$ alkyl, $C_2$-$C_6$ alkenyl, $C_2$-$C_6$ alkynyl, or $C_1$-$C_6$ alkoxyl is optionally substituted with one or more $R^{Zb}$.

Embodiment 56. The compound of any one of the preceding embodiments, wherein at least one $R^{Za}$ is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^{Zb}$.

Embodiment 57. The compound of any one of the preceding embodiments, wherein at least one $R^{Zb}$ is oxo, halogen, cyano, or —OH.

Embodiment 58. The compound of any one of the preceding embodiments, wherein at least one $R^{Zb}$ is $NH_2$, $NH(C_1-C_6\ alkyl)$, or $N(C_1-C_6\ alkyl)_2$.

Embodiment 59. The compound of any one of the preceding embodiments, wherein at least one $R^{Zb}$ is —S(═O)$_2$—($C_1$-$C_6$ alkyl).

Embodiment 60. The compound of any one of the preceding embodiments, wherein at least one $R^{Zb}$ is —C(═O)—($C_1$-$C_6$ alkyl) or —C(═O)—($C_2$-$C_6$ alkenyl).

Embodiment 61. The compound of any one of the preceding embodiments, wherein at least one $R^{Zb}$ is —C(═O)—CH═$CH_2$.

Embodiment 62. The compound of any one of the preceding embodiments, wherein at least one $R^{Zb}$ is $C_1$-$C_6$ alkyl, $C_2$-$C_6$ alkenyl, $C_2$-$C_6$ alkynyl, or $C_1$-$C_6$ alkoxyl.

Embodiment 63. The compound of any one of the preceding embodiments, being of Formula (I-a), (I-b), (I-c), or (I-d):

(I-a)

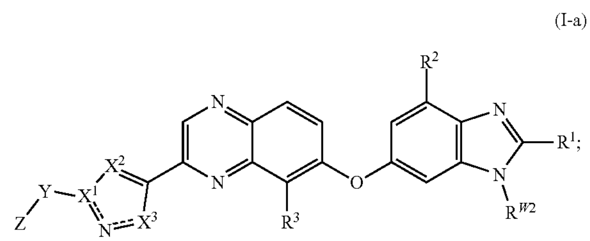

-continued (I-b)

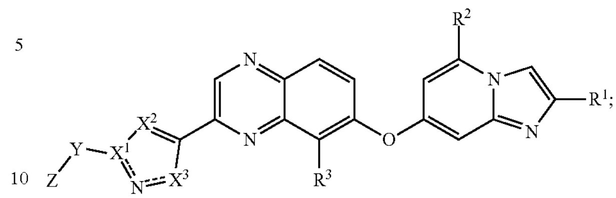

(I-c)

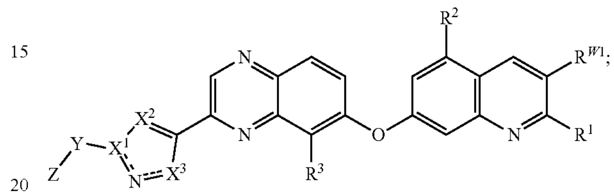

(I-d)

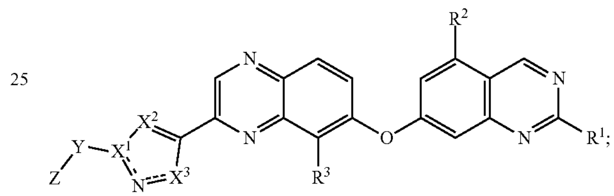

or a pharmaceutically acceptable salt or stereoisomer thereof.

Embodiment 64. The compound of any one of the preceding embodiments, being of Formula (II):

(II)

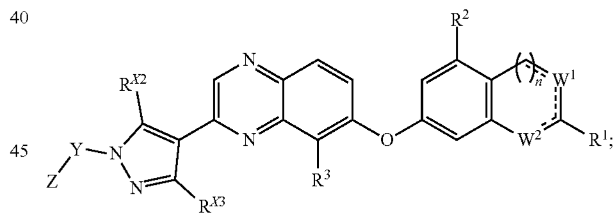

or a pharmaceutically acceptable salt or stereoisomer thereof.

Embodiment 65. The compound of any one of the preceding embodiments, being of Formula (II-a), (II-b), (II-c), or (II-d):

(II-a)

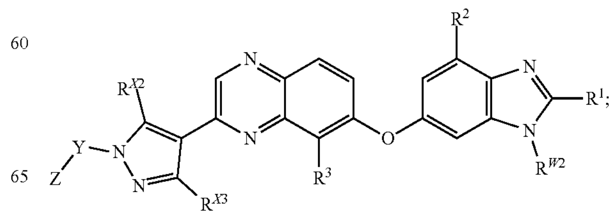

-continued (II-b)

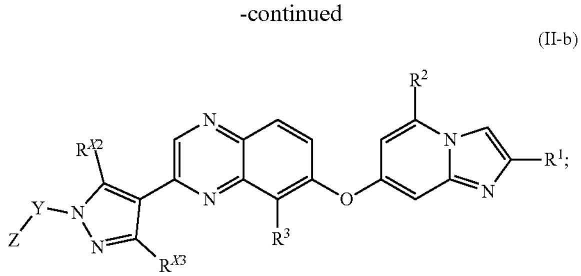

(II-c)

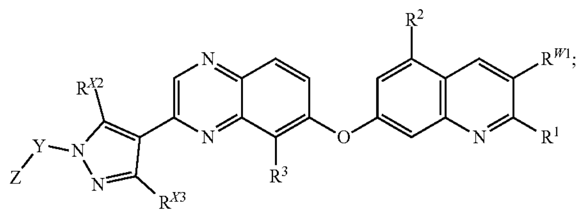

(II-d)

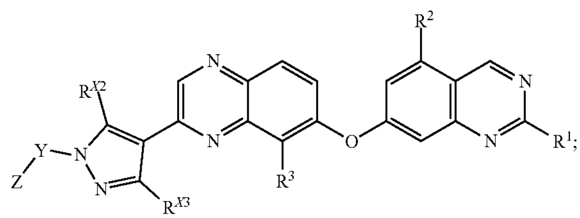

or a pharmaceutically acceptable salt or stereoisomer thereof.

Embodiment 66. The compound of any one of the preceding embodiments, being selected from the compounds described in Table I and Table II, or a pharmaceutically acceptable salt or stereoisomer thereof.

Embodiment 67. An isotopic derivative of the compound of any one of the preceding embodiments.

Embodiment 68. A method of preparing the compound of any one of the preceding embodiments.

Embodiment 69. A pharmaceutical composition comprising the compound of any one of the preceding embodiments and one or more pharmaceutically acceptable carriers or excipients.

Embodiment 70. A method of treating or preventing cancer in a subject, the method comprising administering to the subject a compound of any one of the preceding embodiments.

Embodiment 71. A compound of any one of the preceding embodiments for treating or preventing cancer in a subject.

Embodiment 72. Use of the compound of any one of the preceding embodiments in the manufacture of a medicament for treating or preventing cancer in a subject.

Embodiment 73. Use of the compound of any one of the preceding embodiments for treating or preventing cancer in a subject.

Embodiment 74. The method, compound, or use of any one of embodiments 70-73, wherein the subject is a human.

Embodiment 75. The method, compound, or use of any one of embodiments 70-74, wherein the subject has previously undergone at least one round of anti-cancer therapy.

Embodiment 76. The method, compound, or use of any one of embodiments 70-75, wherein the cancer is characterized by at least one oncogenic mutation in the FGFR2 gene.

Embodiment 77. The method, compound, or use of any one of embodiments 70-75, wherein the cancer is characterized by at least one oncogenic mutation in the FGFR3 gene.

Embodiment 78. The method, compound, or use of any one of embodiments 70-75, wherein the cancer is characterized by overexpression of the FGFR2 gene.

Embodiment 79. The method, compound, or use of any one of embodiments 70-75, wherein the cancer is characterized by overexpression of the FGFR3 gene.

Embodiment 80. The method, compound, or use of any one of embodiments 70-75, wherein the cancer is characterized by at least one oncogenic variant of FGFR2.

Embodiment 81. The method, compound, or use of any one of embodiments 70-75, wherein the cancer is characterized by at least one oncogenic variant of FGFR3.

Embodiment 82. The method, compound, or use of any one of embodiments 70-75, wherein the cancer is characterized by overexpression of FGFR2.

Embodiment 83. The method, compound, or use of any one of embodiments 70-75, wherein the cancer is characterized by overexpression of FGFR3.

Embodiment 84. The method, compound, or use of any one of embodiments 70-83, wherein the cancer is a carcinoma, a lymphoma, a blastoma, a sarcoma, a leukemia, a brain cancer, a breast cancer, a blood cancer, a bone cancer, a lung cancer, a skin cancer, a liver cancer, an ovarian cancer, a bladder cancer, a renal cancer, a kidney cancer, a gastric cancer, a thyroid cancer, a pancreatic cancer, an esophageal cancer, a prostate cancer, a cervical cancer, a uterine cancer, a stomach cancer, a soft tissue cancer, a laryngeal cancer, a small intestine cancer, a testicular cancer, an anal cancer, a vulvar cancer, a joint cancer, an oral cancer, a pharynx cancer or a colorectal cancer.

Embodiment 85. The method, compound, or use of any one of embodiments 70-83, wherein the cancer is adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer, cervical cancer, Acute lymphoblastic leukemia (ALL), Acute myeloid leukemia (AML), Adrenal gland tumors, Anal cancer, Bile duct cancer, Bladder cancer, Bone cancer, Bowel cancer, Brain tumors, Breast cancer, Cancer of unknown primary (CUP), Cancer spread to bone, Cancer spread to brain, Cancer spread to liver, Cancer spread to lung, Carcinoid, Cervical cancer, Children's cancers, Chronic lymphocytic leukemia (CLL), Chrome myeloid leukemia (CML), Colorectal cancer, Ear cancer, Endometrial cancer, Eye cancer, Follicular dendritic cell sarcoma, Gallbladder cancer, Gastric cancer, Gastro esophageal junction cancers, Germ cell tumors, Gestational trophoblastic disease (GIT)), Hairy cell leukemia, Head and neck cancer, Hodgkin lymphoma, Kaposi's sarcoma, Kidney cancer, Laryngeal cancer, Leukemia, Gastric linitis plastica, Liver cancer, Lung cancer, Lymphoma, Malignant schwannoma, Mediastinal germ cell tumors, Melanoma skin cancer, Men's cancer, Merkel cell skin cancer, Mesothelioma, Molar pregnancy, Mouth and oropharyngeal cancer, Myeloma, Nasal and paranasal sinus cancer, Nasopharyngeal cancer, Neuroblastoma, Neuroendocrine tumors, Non-Hodgkin lymphoma (NHL), Esophageal cancer, Ovarian cancer, Pancreatic cancer, Penile cancer, Persistent trophoblastic disease and choriocarcinoma, Pheochromocytoma, Prostate cancer, Pseudomyxoma peritonei, Rectal cancer. Retinoblastoma, Salivary gland cancer, Secondary' cancer, Signet cell cancer, Skin cancer, Small bowel cancer, Soft tissue sarcoma, Stomach cancer, T cell childhood non Hodgkin lymphoma (NHL), Testicular cancer, Thymus gland cancer, Thyroid cancer, Tongue cancer, Tonsil cancer, Tumors of the adrenal gland, Uterine cancer. Vaginal cancer, Vulval cancer, Wilms' tumor, Womb cancer and Gynaecological cancer. Examples of cancer also include, but are not limited to, Hematologic malignancies, Lymphoma, Cutaneous T-cell lymphoma, Peripheral T-cell lymphoma, Hodgkin's lymphoma, Non-Hodgkin's lymphoma, Multiple myeloma, Chrome lymphocytic leukemia, chronic myeloid leukemia, acute myeloid leukemia, Myelodysplastic syndromes, Myelofibrosis, Biliary tract cancer, Hepatocellular cancer, Colorectal cancer, Breast cancer, Lung cancer, Non-small cell lung cancer, Ovarian cancer, Thyroid Carcinoma, Renal Cell Carcinoma, Pancreatic cancer, Bladder cancer, skin cancer, malignant melanoma, merkel cell carcinoma, Uveal Melanoma or Glioblastoma multiforme.

Embodiment 86. The method, compound, or use of any one of embodiments 70-83, wherein the cancer is gastric cancer, triple negative breast cancer, melanoma, hepatobiliary cancer, cancer of unknown primary, esophagogastric cancer, cervical cancer, head and neck cancer, CNS cancer, brain cancer, NSCLC, ovarian cancer, breast cancer, soft tissue sarcoma, pancreatic cancer, prostate cancer, renal cell carcinoma, thyroid cancer, lung cancer, bladder cancer, endometrial carcinoma, intrahepatic cholangiocarcinoma or glioblastoma.

EXAMPLES

For exemplary purpose, salts of the compounds of Formula (I') and (I) are synthesized and tested in the examples. It is understood that neutral compounds of Formula (I') and (I) may be similarly synthesized and tested using the exemplary procedures described in the examples. Further, it is understood that the salts (e.g., sodium salt) of the compounds of Formula (I') and (I) may be converted to the corresponding neutral compounds using routine techniques in the art (e.g., pH adjustment and, optionally, extraction (e.g., into an aqueous phase)).

Compounds of Formula (I') and (I) can be prepared using the methods detailed herein. Those skilled in the art may be able to envisage alternative synthetic routes, using a variety of starting materials and reagents to prepare the disclosed compounds of Formula (I') and (I) and to make further modifications. For exemplary purpose, salts of some of the compounds of Formula (I') and (I) are synthesized and tested in the examples. It is understood that neutral compounds of Formula (I') and (I) may be similarly synthesized and tested using the exemplary procedures described in the examples. Further, it is understood that the salts (e.g., hydrochloride salt) of the compounds of Formula (I') and (I) may be converted to the corresponding neutral compounds using routine techniques in the art (e.g., pH adjustment and, optionally, extraction (e.g., into an aqueous phase)).

Abbreviations aq. Aqueous
ACN Acetonitrile
$^1H$ NMR Proton nuclear magnetic resonance spectroscopy
$CDCl_3$ Deuterated chloroform
DCM Dichloromethane
DMF Dimethylformamide
DMSO-$d_6$ Hexadeuterodimethylsulfoxide
EtOAc Ethyl acetate
eq. Equivalents
h Hour(s)
HPLC high performance liquid chromatography
LC-MS Liquid chromatography-mass spectrometry
min Minute(s)
prep-HPLC preparative high performance liquid chromatography
$Et_3N$ Triethylamine
TFA Trifluoroacetic acid
THF Tetrahydrofuran
TLC Thin layer chromatography
Y Yield

SYNTHESIS OF INTERMEDIATES

Intermediate 1 and 34:8-chloro-7-((2-methyl-1-((2-(trimethylsilyl)ethoxy)methyl)-1H-benzo[d]imidazol-6-yl)oxy)-2-(1-(piperidin-4-yl)-1H-pyrazol-4-yl) quinoxaline and tert-butyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)piperidine-1-carboxylate

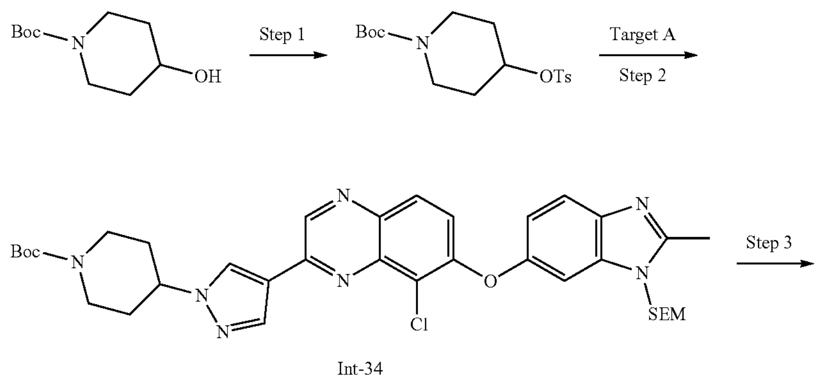

Int-34

-continued

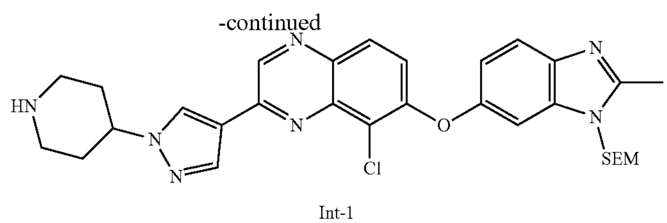

Int-1

Step 1. tert-Butyl 4-(tosyloxy)piperidine-1-carboxylate

To a solution of tert-butyl 4-hydroxypiperidine-1-carboxylate (500 mg, 2.48 mmol) in dichloromethane (10 mL) was added triethylamine (754 mg, 7.45 mmol) and p-toluenesulfonyl chloride (947 mg, 4.97 mmol). The mixture was stirred at 25° C. for 16 h. On completion, the mixture was poured into water (50 mL) and extracted with ethyl acetate (30 mL×3). The organic layers were washed with 1 M hydrochloric acid (10 mL) and concentrated under reduced pressure. The residue was purified by column chromatography (silica gel, petroleum ether/ethyl acetate=10/1 to 3/1) to give tert-butyl 4-(tosyloxy) piperidine-1-carboxylate (600 mg, 1.69 mmol, 67%) as a white solid.

Step 2. tert-Butyl 4-[4-[8-chloro-7-[2-methyl-3-(2-trimethylsilylethoxymethyl)benzimidazol-5-yl]oxy-quinoxalin-2-yl]pyrazol-1-yl]piperidine-1-carboxylate)

To a solution of 2-[[6-[5-chloro-3-(1H-pyrazol-4-yl)quinoxalin-6-yl]oxy-2-methyl-benzimidazol-1-yl]methoxy]ethyl-trimethyl-silane (1 g, 1.97 mmol) in N,N-dimethyl formamide (10 mL) was added cesium carbonate (1.29 g, 3.94 mmol) and tert-butyl 4-(p-tolylsulfonyloxy) piperidine-1-carboxylate (841 mg, 2.37 mmol). The mixture was stirred at 80° C. for 3 h. The reaction mixture was diluted with water (10 mL) and extracted with ethyl acetate (20 mL×3). The combined organic layers were washed with saturated brine (20 mL×3), dried over anhydrous sodium sulfate, filtered and concentrated in vacuo to give tert-butyl 4-[4-[8-chloro-7-[2-methyl-3-(2-trimethylsilylethoxymethyl) benzimidazol-5-yl]oxy-quinoxalin-2-yl]pyrazol-1-yl]piperidine-1-carboxylate (2 g, crude) as a yellow oil. $^1$H NMR (400 MHz, $CD_3OD$) δ 9.29 (d, J=2.8 Hz, 1H), 8.76 (s, 1H), 8.48 (s, 1H), 7.74 (dd, J=7.2, 8.8 Hz, 1H), 7.56 (d, J=8.0 Hz, 1H), 7.48 (dd, J=9.2, 11.2 Hz, 1H), 7.38 (dd, J=2.0, 13.8 Hz, 1H), 7.23-7.16 (m, 1H), 5.79-5.64 (m, 2H), 4.38 (d, J=13.2 Hz, 2H), 3.80-3.56 (m, 4H), 2.29-2.08 (m, 4H), 1.62-1.54 (m, 9H), 1.08-0.81 (m, 2H), 0.13-0.08 (m, 9H); m/z ES+ $[M+H]^+$ 690.4.

Step 3. 2-[[6-[5-chloro-3-[1-(4-piperidyl)pyrazol-4-yl]quinoxalin-6-yl]oxy-2-methyl-benzimidazol-1-yl] methoxy]ethyl-trimethyl-silane To a solution of tert-butyl 4-[4-[8-chloro-7-[2-methyl-3-(2-trimethylsilylethoxymethyl)benzimidazol-5-yl]oxy-quinoxalin-2-yl]pyrazol-1-yl]piperidine-1-carboxylate (2 g, 2.90 mmol) in dichloromethane (20 mL) was added trifluoroacetic acid (4 mL). The mixture was stirred at 25° C. for 2 h. The reaction mixture was concentrated in vacuo. The residue was purified by reversed-phase HPLC (mobile phase: [water (0.225% formic acid)-acetonitrile]; (B %: 50%-55%, 10 min) to give 2-[[6-[5-chloro-3-[ ]-(4-piperidyl)pyrazol-4-yl]quinoxalin-6-yl]oxy-2-methyl-benzimidazol-1-yl]methoxy]ethyl-trimethyl-silane (700 mg, 1.19 mmol, 41%) as a yellow solid. $^1$H NMR (400 MHz, $CD_3OD$): δ=9.28 (s, 1H), 8.73 (s, 1H), 8.46 (s, 1H), 8.08-7.93 (m, 1H), 7.77-7.70 (m, 1H), 7.54-7.43 (m, 1H), 7.40-7.38 (m, 1H), 7.32-7.08 (m, 1H), 5.82-5.59 (m, 2H), 4.62-4.45 (m, 1H), 3.83-3.60 (m, 2H), 3.40-3.17 (m, 2H), 2.99-2.86 (m, 2H), 2.77 (d, J=6.4 Hz, 3H), 2.37-2.26 (m, 2H), 1.09-0.83 (m, 2H), 0.08 (s, 9H); m/z ES+ $[M+H]^+$ 590.1.

Intermediate 2:2-(1-(Azetidin-3-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline

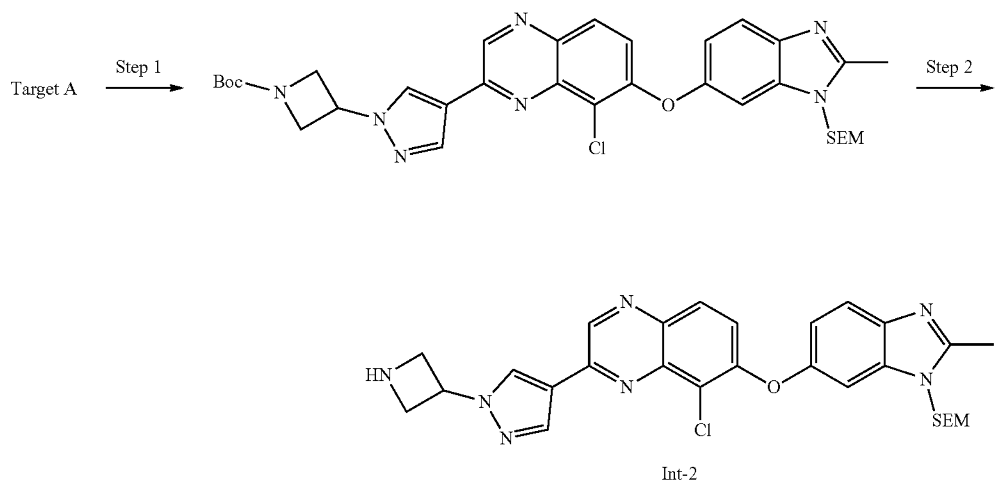

Int-2

Step 1. tert-Butyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)azetidine-1-carboxylate To a solution of 2-[[6-[5-chloro-3-(1H-pyrazol-4-yl)quinoxalin-6-yl]oxy-2-methyl-benzimidazol-1-yl]methoxy] ethyl-trimethyl-silane (2 g, 3.94 mmol), tert-butyl 3-iodoazetidine-1-carboxylate (1.67 g, 5.92 mmol) in N,N-dimethyl formamide (20 mL) was added potassium carbonate (1.09 g, 7.89 mmol). The mixture was stirred at 60° C. for 32 h. The reaction mixture was quenched by addition water (200 mL) at 20° C., and then diluted with ethyl acetate (200 mL) and extracted with ethyl acetate (200 mL×3). The combined organic layers were washed with water (100 mL×2), dried over anhydrous sodium sulfate, filtered and concentrated under reduced pressure. The residue was purified by column chromatography (petroleum ether/ethyl acetate=10/1 to give tert-butyl 3-[4-[8-chloro-7-[2-methyl-3-(2-1/1) to trimethylsilylethoxymethyl)benzimidazol-5-yl]oxy-quinoxalin-2-yl]pyrazol-1-yl]azetidine-1-carboxylate (2.70 g, 3.67 mmol, 93%) as a yellow solid. m/z ES+ $[M+H]^+$ 662.4.

Step 2. 2-(1-(azetidin-3-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline A solution of tert-butyl 3-[4-[8-chloro-7-[2-methyl-3-(2-trimethylsilylethoxymethyl)benzimidazol-5-yl]oxy-quinoxalin-2-yl]pyrazol-1-yl]azetidine-1-carboxylate (2.5 g, 3.77 mmol) in trifluoroacetic acid (2 mL) and dichloromethane (20 mL) was stirred at 25° C. for 16 h. The reaction mixture was quenched with saturated sodium bicarbonate (50 mL) at 25° C., and then diluted with dichloromethane (50 mL) and extracted with dichloromethane (50 mL×3). The combined organic layers were washed with water (20 mL×2), dried over anhydrous sodium sulfate, filtered and concentrated under reduced pressure to give 2-(1-(azetidin-3-yl)-1H-pyrazol-4-yl)-8-chloro-7-((2-methyl-1-((2-(trimethylsilyl)ethoxy)methyl)-1H-benzo[d]imidazol-6-yl)oxy) quinoxaline (2.0 g, 2.49 mmol, 66%) as a yellow solid. $^1H$ NMR (400 MHz, DMSO-$d_6$) δ=9.48-9.37 (m, 1H), 9.27-9.01 (m, 1H), 8.86 (s, 1H), 8.60 (s, 1H), 8.07 (d, J=9.2 Hz, 1H), 7.84 (d, J=9.2 Hz, 1H), 7.56-7.48 (m, 2H), 7.31 (dd, J=2.4, 8.8 Hz, 1H), 5.66-5.49 (m, 1H), 4.70 (s, 1H), 4.60-4.39 (m, 4H), 4.02 (q, J=7.2 Hz, 2H), 1.98 (s, 2H); m/z ES+ $[M+H]^+$ 562.4.

Intermediate 3:5-(((tert-Butyldiphenylsilyl)oxy) methyl)-1,2-thiazinane 1,1-dioxide

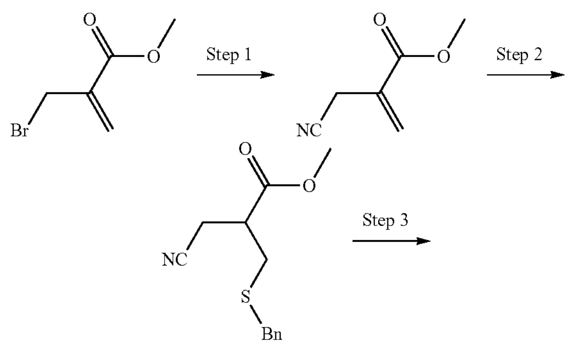

-continued

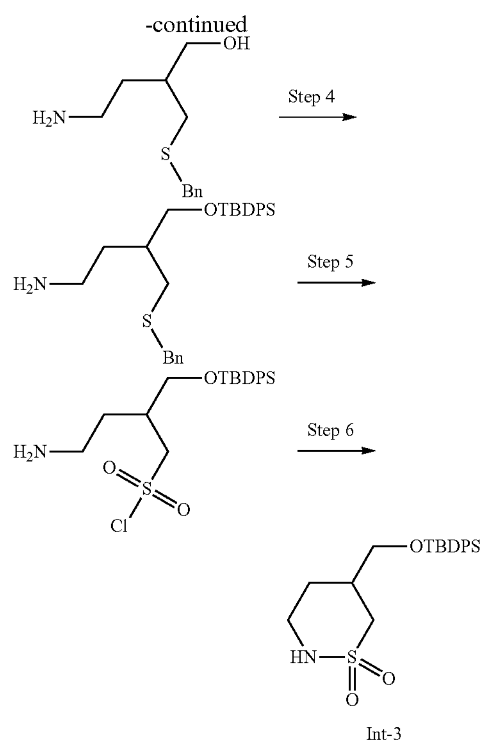

Int-3

Step 1. Methyl 2-(cyanomethyl)acrylate

To a solution of methyl methyl 2-(bromomethyl)acrylate (23.0 g, 128 mmol), trimethylsilylformonitrile (12.7 g, 128 mmol) in acetonitrile (500 mL) was added tetrabutylammonium fluoride (1 M in THF, 128.48 mL) dropwise at 25° C., the mixture was stirred at 25° C. for 1 h. The mixture was concentrated under reduced pressure. The residue was purified by column chromatography (silica gel, petroleum ether/ethyl acetate=3/1) to give methyl 2-(cyanomethyl)acrylate (13.0 g, 103 mmol, 80%) as a colourless oil. $^1H$ NMR (400 MHz, $CDCl_3$) δ 6.40 (d, J=0.8 Hz, 1H), 6.01 (s, 1H), 3.75 (d, J=0.8 Hz, 3H), 3.35 (s, 2H).

Step 2. Methyl 3-(benzylthio)-2-(cyanomethyl)propanoate

To a solution of methyl 2-(cyanomethyl)acrylate (6.50 g, 51.9 mmol) in tetrahydrofuran (80 mL) was added triethylamine (15.7 g, 155 mmol) and phenylmethanethiol (7.74 g, 62.3 mmol), the mixture was stirred at 20° C. for 1 h. The reaction mixture was diluted with water (250 mL) and extracted with ethyl acetate (3× 150 mL). The combined organic layers were dried over anhydrous sodium sulfate, filtered and concentrated under reduced pressure. The residue was purified by column chromatography (silica gel, petroleum ether:ethyl acetate=30:1 to 15:1) to give methyl 3-(benzylthio)-2-(cyanomethyl) propanoate (22.0 g, 88.2 mmol, 85%) as a colorless oil.

Step 3. 4-Amino-2-((benzylthio)methyl)butan-1-ol

To a solution of methyl 3-(benzylthio)-2-(cyanomethyl) propanoate (10.0 g, 40.1 mmol) in tetrahydrofuran (200 mL) was carefully added lithium aluminum hydride (4.57 g, 120 mmol) portion-wise at 0° C. The mixture was stirred at 25° C. for 1 h. The mixture was carefully quenched with sodium sulfate decahydride (10 g) and water (5 mL). The resulting precipitate was filtered.

The filtrate was dried over sodium sulfate, filtered and concentrated in vacuo to give 4-amino-2-((benzylthio) methyl)butan-1-ol (9 g, crude) as a yellow oil.

Step 4. 4-(Benzylthio)-3-(((tert-butyldiphenylsilyl) oxy)methyl)butan-1-amine

A solution of 4-amino-2-((benzylthio)methyl)butan-1-ol (7 g, 31.0 mmol), tert-butylchlorodimethylsilane (8.54 g, 31.0 mmol), imidazole (3.17 g, 46.5 mmol) in dichloromethane (50 mL) was stirred at 25° C. for 16 h. The mixture was poured into water (20 mL) and extracted with ethyl acetate (3×30 mL). The organic layers were dried with sodium sulfate, filtered and concentrated under reduced pressure. The residue was purified by reversed-phase HPLC (0.1% formic acid condition) to give 4-(benzylthio)-3-(((tert-butyldiphenylsilyl)oxy)methyl)butan-1-amine (6.60 g, 14.2 mmol, 45%) as a yellow oil. m/z ES+ $[M+H]^+$ 464.2.

Step 5. 4-Amino-2-(((tert-butyldiphenylsilyl)oxy) methyl)butane-1-sulfonyl chloride To a solution of 4-(benzylthio)-3-(((tert-butyldiphenylsilyl)oxy)methyl)butan-1-amine (3 g, 6.47 mmol) in acetic acid (30 mL) and water (9 mL) was added N-chlorosuccinimide (2.59 g, 19.4 mmol). The reaction was stirred at 25° C. for 0.5 h. The mixture was concentrated under reduced pressure to give 4-amino-2-(((tert-butyldiphenylsilyl)oxy) methyl)butane-1-sulfonyl chloride (2.80 g, crude) as a yellow oil.

Step 6. Methyl 3-(benzylthio)-2-(cyanomethyl)propanoate

A solution of 4-amino-2-[[tert-butyl(diphenyl)silyl] oxymethyl]butane-1-sulfonyl chloride (2.8 g, 6.36 mmol) and triethylamine (1.93 g, 19.0 mmol) in dichloromethane (30 mL) was stirred at 25° C. for 16 h. The mixture was concentrated under reduced pressure. The residue was purified by column chromatography (silica gel, petroleum ether/ethyl acetate=1/0 to 3/1) to give 5-(((tert-butyldiphenylsilyl) oxy)methyl)-1,2-thiazinane 1,1-dioxide (1 g, 2.48 mmol, 38%) as a white solid. $^1$H NMR (400 MHz, $CDCl_3$) δ 7.64 (d, J=7.2 Hz, 4H), 7.56-7.36 (m, 7H), 3.73-3.26 (m, 4H), 2.82 (t, J=12.8 Hz, 1H), 2.52 (s, 1H), 1.55-1.38 (m, 2H), 1.13-1.04 (m, 9H).

Intermediate 4 and 5:3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl) cyclobutan-1-one and 3-(4-(8-chloro-7-((2-methyl-1H-benzo[d]imidazol-6-yl)oxy)quinoxalin-2-yl)-1H-pyrazol-1-yl)cyclobutan-1-one

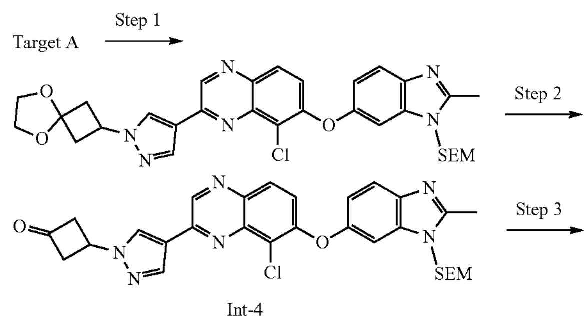

Int-4

-continued

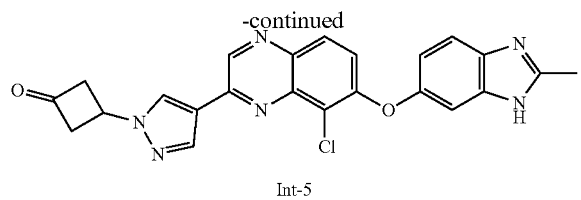

Int-5

Step 1. 2-(1-(5,8-Dioxaspiro[3.4]octan-2-yl)-1H-pyrazol-4-yl)-8-chloro-7-((2-methyl-1-((2-(trimethylsilyl)ethoxy)methyl)-1H-benzo[d]imidazol-6-yl) oxy)quinoxaline To a solution of 2-[[6-[5-chloro-3-(1H-pyrazol-4-yl)quinoxalin-6-yl]oxy-2-methyl-benzimidazol-1-yl]methoxy] ethyl-trimethyl-silane (830 mg, 1.65 mmol) and 2-bromo-5,8-dioxaspiro[3.4]octane (350 mg, 1.80 mmol) in N,N-dimethyl formamide (9 mL) was added potassium carbonate (680 mg, 4.90 mmol) and potassium iodide (27.0 mg, 165 μmol). The mixture was stirred at 100° C. for 12 h. The reaction mixture was diluted with water (30 mL) and extracted with ethyl acetate (100 mL×3). The combined organic layers were washed with brine (25 mL×2), dried over anhydrous sodium sulfate, filtered and concentrated under reduced pressure. The residue was purified by column chromatography (dichloromethane:methanol=100:1 to 10:1) to give 2-(1-(5,8-dioxaspiro[3.4]octan-2-yl)-1H-pyrazol-4-yl)-8-chloro-7-((2-methyl-1-((2-(trimethylsilyl)ethoxy) methyl)-1H-benzo[d]imidazol-6-yl)oxy)quinoxaline (680 mg, 1.05 mmol, 64%) as a yellow solid. m/z ES+ $[M+H]^+$ 619.1.

Step 2. 3-[4-[8-Chloro-7-[2-methyl-3-(2-trimethylsilylethoxymethyl)benzimidazol-5-yl]oxy-quinoxalin-2-yl]pyrazol-1-yl]cyclobutanone To a solution of 2-[[6-[5-chloro-3-[1-(5,8-dioxaspiro[3.4] octan-2-yl)pyrazol-4-yl]quinoxalin-6-yl]oxy-2-methyl-benzimidazol-1-yl]methoxy]ethyl-trimethyl-silane (680 mg, 1.10 mmol) in dichloromethane (6.8 mL) and water (0.5 mL) was added formic acid (8.30 g, 180 mmol). The mixture was stirred at 40° C. for 12 h. The reaction mixture was concentrated under reduced pressure and then diluted with water (20 mL). The mixture was adjusted to pH=8~9 with saturated sodium bicarbonate (30 mL), and then extracted with ethyl acetate (100 mL×3). The combined organic layers were washed with brine (25 mL×2), dried over anhydrous sodium sulfate, filtered and concentrated under reduced pressure to give 3-[4-[8-chloro-7-[2-methyl-3-(2-trimethylsilylethoxymethyl)benzimidazol-5-yl]oxy-quinoxalin-2-yl] pyrazol-1-yl]cyclobutanone (550 mg, crude) as a white solid. m/z ES+ $[M+H]^+$ 575.3.

Step 3. 3-[4-[8-Chloro-7-[(2-methyl-3H-benzimidazol-5-yl)oxy]quinoxalin-2-yl]pyrazol-1-yl]cyclobutanone A solution of 3-[4-[8-chloro-7-[2-methyl-3-(2-trimethylsilylethoxymethyl)benzimidazol-5-yl]oxy-quinoxalin-2-yl] pyrazol-1-yl]cyclobutanone (350 mg, 0.61 mmol) in trifluoroacetic acid (3.5 mL) was stirred at 25° C. for 0.5 h. The reaction mixture was concentrated under reduced pressure and then diluted with water (30 mL). The mixture was adjusted to pH-9 with sat. sodium carbonate solution and then extracted with ethyl acetate (100 mL×2). The combined organic layers were washed with brine (50 mL), dried over sodium sulfate, filtered and concentrated under reduced pressure to give 3-[4-[8-chloro-7-[(2-methyl-3H-benzimidazol-5-yl)oxy]quinoxalin-2-yl]pyrazol-1-yl]cyclobutanone (300 mg, crude) as a white solid. $^1$H NMR (400 MHz, DMSO-$d_6$) δ=9.33 (s, 1H), 8.95 (s, 1H), 8.45 (s, 1H), 7.96 (d, J=9.2 Hz, 1H), 7.52 (d, J=8.8 Hz, 1H), 7.33 (d, J=9.2 Hz, 1H), 7.23 (d, J=2.0 Hz, 1H), 6.96 (dd, J=2.4, 8.8 Hz, 1H), 5.41-5.31 (m, 1H), 3.70-3.64 (m, 4H), 2.50 (s, 3H); m/z ES+ $[M+H]^+$ 445.0.

Intermediate 6:2-(1-(Azetidin-3-yl)-1H-pyrazol-4-yl)-8-chloro-7-((2-methyl-1H-benzo[d]imidazol-6-yl)oxy)quinoxaline

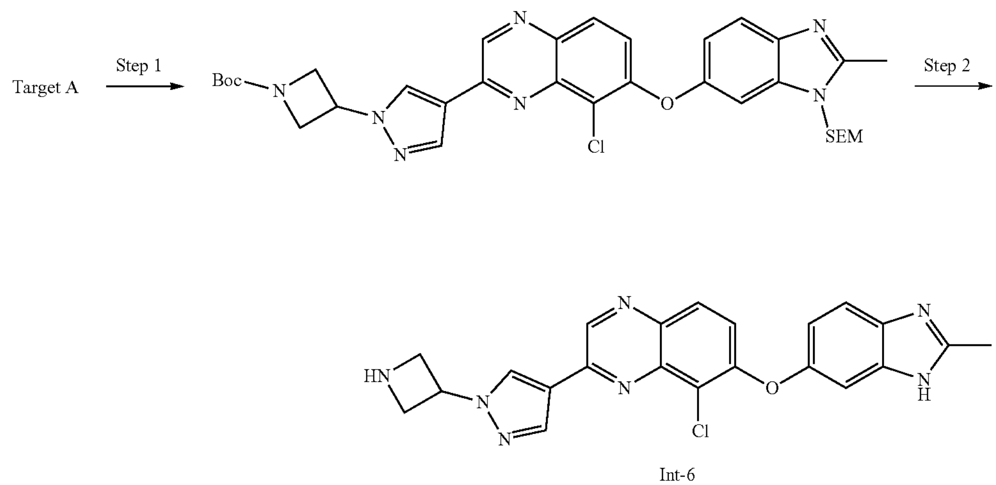

Int-6

Step 1. tert-Butyl 3-[4-[8-chloro-7-[2-methyl-3-(2-trimethylsilylethoxymethyl)benzimidazol-5-yl]oxy-quinoxalin-2-yl]pyrazol-1-yl]azetidine-1-carboxylate To a solution of 2-[[6-[5-chloro-3-(1H-pyrazol-4-yl)quinoxalin-6-yl]oxy-2-methyl-benzimidazol-1-yl]methoxy] ethyl-trimethyl-silane (1 g, 1.97 mmol) in N,N-dimethylformamide (15 mL) was added cesium carbonate (1.29 g, 3.94 mmol) and tert-butyl 3-iodoazetidine-1-carboxylate (614 mg, 2.17 mmol). The mixture was stirred at 50° C. for 12 h. The reaction mixture was diluted with water (50 mL) and extracted with ethyl acetate (40 mL×3). The combined organic layers were dried over anhydrous sodium sulfate, concentrated under reduced pressure. The residue was purified by prep-HPLC (column: Phenomenex Luna C18 150*40 mm*15 μm; mobile phase: [water (0.1% TFA)-acetonitrile]; (B %: 35%-65%, 11 min) to give tert-butyl 3-[4-[8-chloro-7-[2-methyl-3-(2-trimethylsilylethoxymethyl)benzimidazol-5-yl]oxy-quinoxalin-2-yl]pyrazol-1-yl] azetidine-1-carboxylate (800 mg, 1.21 mmol, 61%) as a white solid. m/z ES+ $[M+1]^+$662.4.

Step 2. 2-[1-(Azetidin-3-yl)pyrazol-4-yl]-8-chloro-7-[(2-methyl-3H-benzimidazol-5-yl)oxy]quinoxaline A mixture of tert-butyl 3-[4-[8-chloro-7-[2-methyl-3-(2-trimethylsilylethoxymethyl)benzimidazol-5-yl]oxy-quinoxalin-2-yl]pyrazol-1-yl]azetidine-1-carboxylate (790 mg, 1.19 mmol) in trifluoroacetic acid (3 mL) was stirred at 25° C. for 6 h. The reaction mixture was concentrated under reduced pressure to give 2-[1-(azetidin-3-yl)pyrazol-4-yl]-8-chloro-7-[(2-methyl-3H-benzimidazol-5-yl)oxy]quinoxaline (500 mg, crude, TFA salt) as a yellow solid. $^1$H NMR (400 MHz, DMSO-$d_6$) δ=9.37 (s, 1H), 9.26 (d, J=6.4 Hz, 1H), 8.86 (s, 1H), 8.59 (s, 1H), 8.02 (d, J=9.2 Hz, 1H), 7.72-7.63 (m, 1H), 7.42 (d, J=9.2 Hz, 1H), 7.37 (d, J=2.4 Hz, 1H), 7.15-7.09 (m, 1H), 5.64-5.54 (m, 1H), 4.54-4.39 (m, 4H), 2.64 (s, 3H); m/z ES+ $[M+1]^+$ 432.2.

Intermediate 7: tert-Butyl N-tert-butoxycarbonyl-N-(3,5-difluoro-2-nitro-phenyl) carbamate

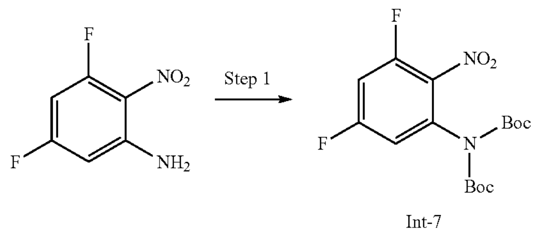 [SMILES: Nc1cc(F)cc(F)c1[N+](=O)[O-] ; CC(C)(C)OC(=O)N(C(=O)OC(C)(C)C)c1cc(F)cc(F)c1[N+](=O)[O-]]

Int-7

Step 1. tert-Butyl N-tert-butoxycarbonyl-N-(3,5-difluoro-2-nitro-phenyl) carbamate To a solution of 3, 5-difluoro-2-nitro-aniline (500 mg, 2.87 mmol) in dichloromethane (8 mL) was added 4-dimethylaminopyridine (35.1 mg, 287 μmol), di-tert-butyl dicarbonate (1.25 g, 5.74 mmol) and triethylamine (872 mg, 8.62 mmol), the mixture was stirred at 25° C. for 2 h. The reaction mixture was concentrated under reduced pressure. The residue was purified by column chromatography (petroleum ether/ethyl acetate=10/1 to 4/1) to give tert-butyl N-tert-butoxycarbonyl-N-(3,5-difluoro-2-nitro-phenyl) carbamate (800 mg, 1.34 mmol, 74%) as a yellow solid. $^1$H NMR (400 MHz, $CDCl_3$) δ 7.35-6.98 (m, 1H), 6.94-6.82 (m, 1H), 1.44 (s, 18H).

Intermediate 8: (3,3-Difluorocyclobutyl)methylmethanesulfonate

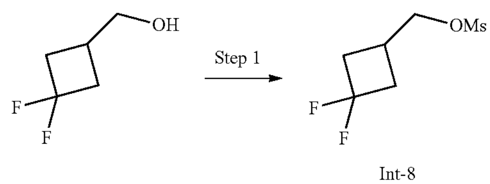 [SMILES: OCC1CC(F)(F)C1 ; CS(=O)(=O)OCC1CC(F)(F)C1]

Step 1. (3,3-Difluorocyclobutyl)methylmethanesulfonate

To a solution of (3,3-difluorocyclobutyl) methanol (5 g, 41.0 mmol) and triethylamine (10.4 g, 102 mmol) in dichloromethane (60 mL) was added methanesulfonyl chloride (7.04 g, 61.4 mmol, 4.75 mL) at 0° C., the mixture was stirred at 20° C. for 1 h. The reaction mixture was quenched with water (15 mL), and then extracted with ethyl acetate (3× 50 mL). The combined organic layers were washed with brine, dried over sodium sulfate, filtered and concentrated under reduced pressure to give (3,3-difluorocyclobutyl) methylmethanesulfonate (9 g, crude) as a yellow oil. $^{1}H$ NMR (400 MHz, $CDCl_3$) δ 4.25 (d, J=6.4 Hz, 2H), 3.03 (d, J=1.2 Hz, 3H), 2.79-2.65 (m, 2H), 2.63-2.50 (m, 1H), 2.49-2.32 (m, 2H).

Intermediate 9, 10 and 11:7-bromo-2-(1-(tetrahydro-2H-pyran-2-yl)-1H-pyrazol-4-yl)quinoxaline and 3-(1-((3,3-difluorocyclobutyl)methyl)-1H-pyrazol-4-yl)quinoxalin-6-ol and 5-chloro-3-(1-((3,3-difluorocyclobutyl)methyl)-1H-pyrazol-4-yl)quinoxalin-6-ol

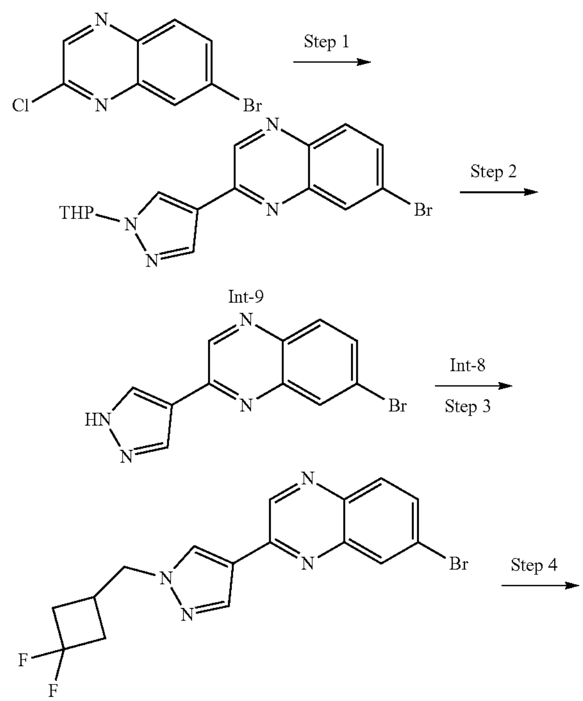

-continued

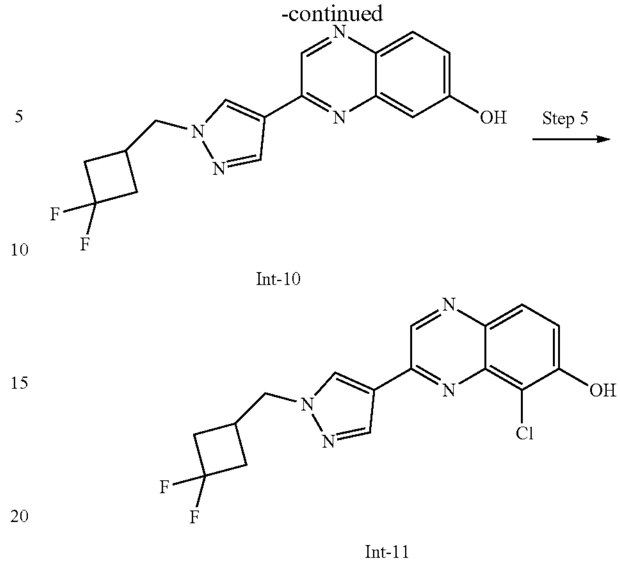

Step 1. 7-Bromo-2-(1-(tetrahydro-2H-pyran-2-yl)-1H-pyrazol-4-yl)quinoxaline

To a mixture of 7-bromo-2-chloro-quinoxaline (3 g, 12.3 μmol) and 1-tetrahydropyran-2-yl-4-(4,4,5,5-tetramethyl-1,3,2-dioxaborolan-2-yl)pyrazole (3.61 g, 13.0 μmol) in dioxane (30 mL) and water (6 mL) was added potassium acetate (3.63 g, 37.0 μmol) and cyclopenta-2,4-dien-1-yl (diphenyl)phosphane; dichloropalladium;iron(II) (902 mg, 1.23 μmol). The mixture was stirred at 60° C. for 12 hours under nitrogen. On completion, the mixture was quenched with water (100 mL) and extracted with ethyl acetate (125 mL×3). The combined organic phases were dried over anhydrous sodium sulfate, filtered and concentrated and the residue was purified by column chromatography (petroleum ether:ethyl acetate=30:1 to 0:1) to give 7-bromo-2-(1-(tetrahydro-2H-pyran-2-yl)-1H-pyrazol-4-yl)quinoxaline (2.80 g, crude) as a yellow solid. $^{1}H$ NMR (400 MHz, $CDCl_3$) δ 9.06 (s, 1H), 8.41 (s, 1H), 8.29-8.20 (m, 2H), 7.92 (d, J=8.8 Hz, 1H), 7.76 (dd, J=2.0, 8.8 Hz, 1H), 5.54-5.45 (m, 1H), 4.21-4.08 (m, 1H), 3.83-3.72 (m, 1H), 2.23-2.15 (m, 2H), 2.12-2.06 (m, 1H), 1.76-1.66 (m, 3H).

Step 2. 7-Bromo-2-(1H-pyrazol-4-yl)quinoxaline

To a solution of 7-bromo-2-(1-tetrahydropyran-2-ylpyrazol-4-yl)quinoxaline (5.20 g, 14.5 mmol) in dichloromethane (60 mL) was added trifluoroacetic acid (20 mL), the mixture was stirred at 20° C. for 1 h. The reaction mixture was concentrated under reduced pressure. The residue was diluted with saturated sodium bicarbonate solution (100 mL) and extracted with ethyl acetate (3×60 mL). The combined organic layers were dried over sodium sulfate, filtered and concentrated under reduced pressure to give 7-bromo-2-(1H-pyrazol-4-yl)quinoxaline (5 g, crude) as a black solid. m/z ES+ $[M+H]^+$ 274.7.

Step 3. 7-Bromo-2-(1-((3,3-difluorocyclobutyl)methyl)-1H-pyrazol-4-yl)quinoxaline To a solution of 7-bromo-2-(1H-pyrazol-4-yl)quinoxaline (2.30 g, 8.36 mmol) in N,N-dimethylformamide (40 mL) was added potassium carbonate (2.31 g, 16.7 mmol) and (3,3-difluorocyclobutyl)methyl methanesulfonate (1.67 g, 8.36 mmol), the mixture was stirred at 80° C. for 12 h. The reaction mixture was diluted with water (200 mL) and extracted with ethyl acetate (3× 200 mL). The combined organic layers were dried over sodium sulfate, filtered and concentrated under reduced pressure. The residue was purified by column chromatography (petroleum ether/ethyl acetate=5/1 to 1/1) to give a residue. The residue was triturated with petroleum ether/ethyl acetate (20:1, 40 mL) at 20° C. for 30 min to give 7-bromo-2-(1-((3,3-difluorocyclobutyl)methyl)-1H-pyrazol-4-yl)quinoxaline (800 mg, 2.11 mmol, 12%) as a yellow solid. $^1$H NMR (400 MHz, DMSO-$d_6$) δ 9.43-9.31 (m, 1H), 8.73 (s, 1H), 8.34 (s, 1H), 8.20 (d, J=2.0 Hz, 1H), 7.99 (d, J=8.8 Hz, 1H), 7.88 (dd, J=2.0, 8.8 Hz, 1H), 4.37 (d, J=6.0 Hz, 2H), 3.30 (s, 1H), 2.77-2.57 (m, 4H); m/z ES+ $[M+H]^+$ 378.8.

Step 4. 3-(1-((3,3-Difluorocyclobutyl)methyl)-1H-pyrazol-4-yl)quinoxalin-6-ol

A mixture of 7-bromo-2-[1-[(3,3-difluorocyclobutyl) methyl]pyrazol-4-yl]quinoxaline (600 mg, 1.58 mmol), tris (dibenzylideneacetone) dipalladium (145 mg, 158 μmol), ditert-butyl-[2-(2,4,6-triisopropylphenyl)phenyl] phosphane (67.2 mg, 158 μmol) and potassium hydroxide (888 mg, 15.8 mmol) in dioxane (10 mL) and water (2 mL) was degassed and purged with nitrogen for 3 times, and then the mixture was stirred at 100° C. for 1 h under nitrogen atmosphere. The mixture was concentrated under reduced pressure. The residue was purified by column chromatography (petroleum ether/ethyl acetate=5/1 to 1/1) to give 3-(1-((3,3-difluorocyclobutyl)methyl)-1H-pyrazol-4-yl)quinoxalin-6-ol (400 mg, 1.26 mmol, 68%) as a yellow solid. $^1$H NMR (400 MHz, DMSO-$d_6$) δ=10.69-10.25 (m, 1H), 9.05 (s, 1H), 8.66 (s, 1H), 8.28 (s, 1H), 7.86 (d, J=9.2 Hz, 1H), 7.28 (dd, J=2.4, 9.2 Hz, 1H), 7.18 (d, J=2.4 Hz, 1H), 4.34 (d, J-5.6 Hz, 2H), 2.75-2.56 (m, 4H), 2.47 (s, 1H); m/z ES+ $[M+H]^+$ 317.1.

Step 5. 5-Chloro-3-(1-((3,3-difluorocyclobutyl) methyl)-1H-pyrazol-4-yl)quinoxalin-6-ol To a solution of 3-[1-[(3,3-difluorocyclobutyl)methyl] pyrazol-4-yl]quinoxalin-6-ol (400 mg, 1.26 mmol) in chloroform (5 mL) was added N-chlorosuccinimide (338 mg, 2.53 mmol), nickel chloride (164 mg, 1.26 mmol) and triethylamine (128 mg, 1.26 mmol). The mixture was stirred at 60° C. for 2 h. The reaction mixture was concentrated under reduced pressure. The residue was purified by column chromatography (petroleum ether/ethyl acetate=5/1 to 1/1) to give 5-chloro-3-(1-((3,3-difluorocyclobutyl)methyl)-1H-pyrazol-4-yl)quinoxalin-6-ol (500 mg, 1.43 mmol, 95%) as a yellow solid. $^1$H NMR (400 MHz, DMSO-$d_6$) δ=9.14 (s, 1H), 8.69 (s, 1H), 8.32 (s, 1H), 7.86 (d, J=9.2 Hz, 1H), 7.48 (d, J=9.2 Hz, 1H), 4.37 (d, J=6.0 Hz, 2H), 3.16 (s, 1H), 2.77-2.59 (m, 4H); m/z ES+ $[M+H]^+$ 351.0.

Intermediate 12: tert-Butyl N-tert-butoxycarbonyl-N-(5-fluoro-2-nitro-phenyl) carbamate

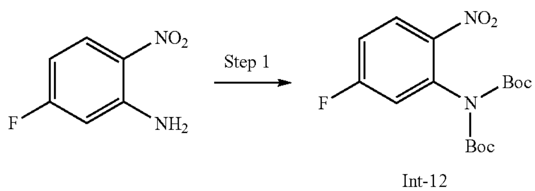 [SMILES: Nc1cc(F)ccc1[N+](=O)[O-] ; CC(C)(C)OC(=O)N(C(=O)OC(C)(C)C)c1cc(F)ccc1[N+](=O)[O-]]

Int-12

Step 1. tert-Butyl N-tert-butoxycarbonyl-N-(5-fluoro-2-nitro-phenyl) carbamate

To a solution of 5-fluoro-2-nitro-aniline (10 g, 64.1 μmol) in dichloromethane (100 mL) was added di-tert-butyl dicarbonate (28.0 g, 128 μmol), triethylamine (19.5 g, 192 μmol) and N,N-dimethylpyridin-4-amine (783 mg, 6.41 μmol). The mixture was stirred at 20° C. for 1 h. On completion, the reaction mixture was concentrated under reduced pressure. The residue was purified by column chromatography (petroleum ether/ethyl acetate=10/1 to 8/1) to give tert-butyl N-tert-butoxycarbonyl-N-(5-fluoro-2-nitro-phenyl) carbamate (20 g, 56.1 μmol, 88%) as a yellow solid. $^1$H NMR (400 MHz, $CDCl_3$) δ=8.14 (dd, J=5.6, 9.2 Hz, 1H), 7.23-7.14 (m, 1H), 7.05 (dd, J=2.8, 8.4 Hz, 1H), 1.40 (s, 18H).

Intermediate 13:2-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)ethyl methanesulfonate

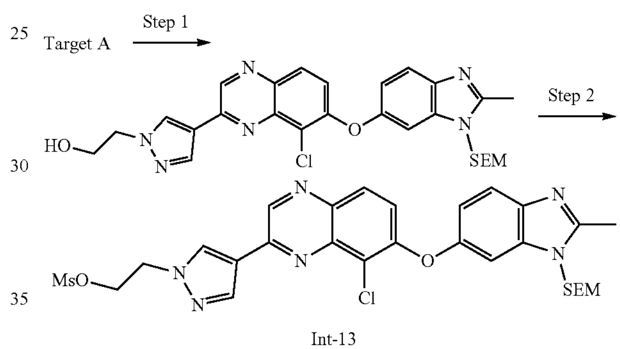

Int-13

Step 1. 2-[4-[8-Chloro-7-[2-methyl-3-(2-trimethylsilylethoxymethyl)benzimidazol-5-yl]oxy-quinoxalin-2-yl]pyrazol-1-yl]ethanol To a mixture of 2-[[6-[5-chloro-3-(1H-pyrazol-4-yl)quinoxalin-6-yl]oxy-2-methyl-benzimidazol-1-yl]methoxy] ethyl-trimethyl-silane (2 g, 3.94 mmol) and 2-bromoethanol (1.48 g, 11.83 mmol, 840 μL) in N,N-dimethylformamide (15 mL) was added potassium carbonate (1.64 g, 11.83 mmol). The mixture was then heated to 80° C. and stirred for 16 h. On completion, the reaction mixture was quenched with water (150 mL) at 20° C., and then extracted with ethyl acetate (100 mL×3). The combined organic layers were washed with water (50 mL×2), dried over anhydrous sodium sulfate, filtered and concentrated under reduced pressure. The residue was purified by column chromatography (dichloromethane:methanol=100:1 to 20:1) to give 2-[4-[8-chloro-7-[2-methyl-3-(2-trimethylsilylethoxymethyl)benzimidazol-5-yl]oxy-quinoxalin-2-yl]pyrazol-1-yl]ethanol (2.5 g, 3.86 mmol, 98%) as a yellow oil. m/z ES+ $[M+H]^+$ 551.4.

Step 2. 2-[4-[8-Chloro-7-[2-methyl-3-(2-trimethylsilylethoxymethyl)benzimidazol-5-yl]oxy-quinoxalin-2-yl]pyrazol-1-yl]ethyl methanesulfonate To a mixture of 2-[4-[8-chloro-7-[2-methyl-3-(2-trimethylsilylethoxymethyl)benzimidazol-5-yl]oxy-quinoxalin-2- yl]pyrazol-1-yl]ethanol (2.5 g, 4.54 mmol) in dichloromethane (30 mL) was added triethylamine (1.38 g, 13.61 mmol) and methanesulfonyl chloride (1.04 g, 9.07 mmol) at 0° C. The mixture was stirred at 0° C. for 2 h. On completion, the reaction mixture was quenched with water (30 mL) at 0° C., and then extracted with dichloromethane (30 mL×3). The combined organic layers were washed with brine (30 mL×2), dried over anhydrous sodium sulfate, filtered and concentrated under reduced pressure to give 2-[4-[8-chloro-7-[2-methyl-3-(2-trimethylsilylethoxymethyl)benzimidazol-5-yl]oxy-quinoxalin-2-yl]pyrazol-1-yl]ethyl methanesulfonate (2.6 g, 3.64 mmol, 80%) as a yellow oil. m/z ES+ $[M+H]^+$ 629.4.

Intermediate 14, 23 and 15: tert-Butyl (3S,4S)-4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-fluoropiperidine-1-carboxylate, 8-chloro-2-(1-((3S,4S)-3-fluoropiperidin-4-yl)-1H-pyrazol-4-yl)-7-((2-methyl-1-((2-(trimethylsilyl)ethoxy)methyl)-1H-benzo[d]imidazol-6-yl)oxy)quinoxaline and 8-chloro-2-(1-((3S,4S)-3-fluoropiperidin-4-yl)-1H-pyrazol-4-yl)-7-((2-methyl-1H-benzo[d]imidazol-6-yl)oxy)quinoxaline

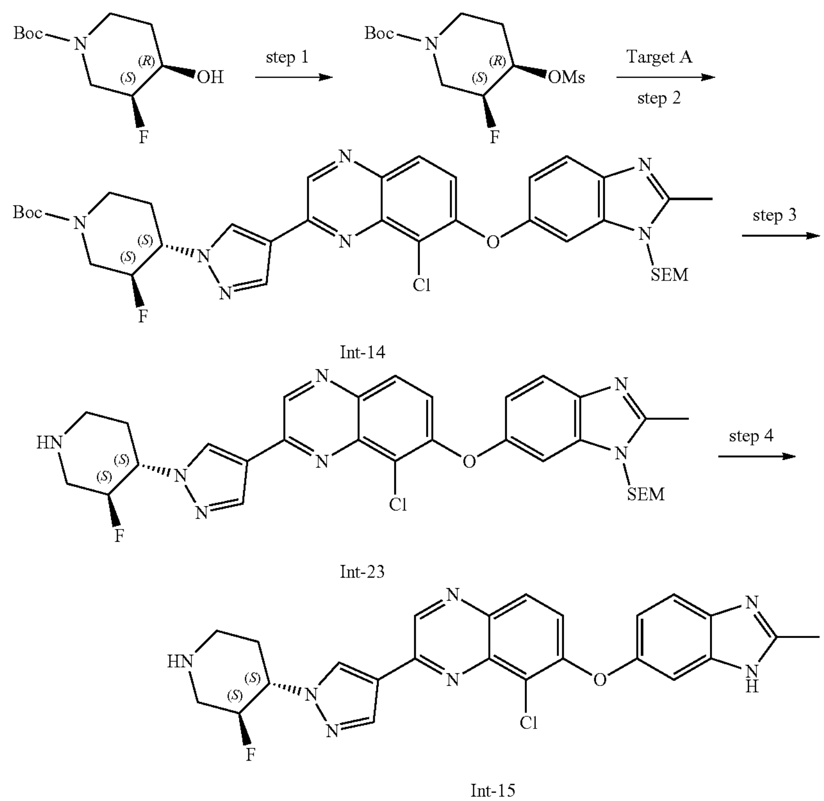

Int-14

Int-23

Int-15

Step 1. (3S,4R)-tert-Butyl 3-fluoro-4-((methylsulfonyl)oxy) piperidine-1-carboxylate To a solution of (3S,4R)-tert-butyl 3-fluoro-4-hydroxypiperidine-1-carboxylate (500 mg, 2.28 mmol) in dichloromethane (5 mL) was added methanesulfonyl chloride (392 mg, 3.42 mmol) and triethylamine (692 mg, 6.84 mmol), the mixture was stirred at 0° C. for 0.5 h. The reaction mixture was quenched with water (10 mL) and extracted with dichloromethane (3×20 mL). The combined organic layers were washed with brine (3×10 mL), dried over anhydrous sodium sulfate, filtered and concentrated under reduced pressure to give (3S,4R)-tert-butyl 3-fluoro-4-((methylsulfonyl)oxy) piperidine-1-carboxylate (720 mg, crude) as an orange solid. $^1H$ NMR (400 MHz, DMSO-$d_6$) δ 4.99-4.92 (m, 1H), 4.91-4.83 (m, 1H), 4.13-4.02 (m, 1H), 3.88 (s, 1H), 3.26 (s, 3H), 3.24-3.07 (m, 1H), 3.06-2.86 (m, 1H), 1.91-1.77 (m, 2H), 1.39 (s, 9H).

Step 2. (3S,4S)-tert-Butyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-fluoropiperidine-1-carboxylate To a solution of 8-Chloro-7-((2-methyl-1-((2-(trimethylsilyl)ethoxy)methyl)-1H-benzo[d]imidazol-6-yl)oxy)-2-(1H-pyrazol-4-yl)quinoxaline (600 mg, 1.18 mmol) in N,N-dimethylformamide (4 mL) was added potassium carbonate (491 mg, 3.55 mmol) and (3S,4R)-tert-butyl 3-fluoro-4-((methylsulfonyl)oxy) piperidine-1-carboxylate (704 mg, 2.37 mmol), the mixture was stirred at 100° C. for 12 h. The reaction mixture was quenched with water (0.5 mL) and concentrated under reduced pressure and the residue was purified by reversed-phase HPLC (0.1% formic acid condition, 85-90% acetonitrile, 5 min) to give (3S,4S)-tert-butyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-fluoropiperidine-1-carboxylate (600 mg, 849 μmol, 72%) as an off-white solid. $^1H$ NMR (400 MHz, DMSO-$d_6$) δ 9.33 (d, J=3.6 Hz, 1H), 8.87 (s, 1H), 8.44 (s, 1H), 8-7.95 (m, 1H), 7.70-7.57 (m, 1H), 7.47-7.29 (m, 2H), 7.10-6.99 (m, 1H), 5.65-5.52 (m, 2H), 5.01-4.80 (m, 1H), 4.78-4.70 (m, 1H), 4.41-4.27 (m, 1H), 4.10-3.96 (m, 1H), 3.57-3.46 (m, 2H), 3.10-2.93 (m, 2H), 2.57 (d, J=6.8 Hz, 3H), 2.17-2 (m, 2H), 1.45 (s, 9H), 0.87-0.77 (m, 2H), −0.06-−0.15 (m, 9H); m/z ES+ $[M+H]^+$ 708.3.

Step 3. 8-Chloro-2-(1-((3S,4S)-3-fluoropiperidin-4-yl)-1H-pyrazol-4-yl)-7-((2-methyl-1-((2-(trimethylsilyl)ethoxy)methyl)-1H-benzo[d]imidazol-6-yl)oxy)quinoxaline A solution of (3S,4S)-tert-butyl 4-(4-(8-chloro-7-((2-methyl-1-((2-(trimethylsilyl) ethoxy)methyl)-1H-benzo[d]imidazol-6-yl)oxy)quinoxalin-2-yl)-1H-pyrazol-1-yl)-3-fluoropiperidine-1-carboxylate (300 mg, 424 μmol) in dichloromethane (1 mL) and trifluoroacetic acid (0.1 mL) was stirred at 25° C. for 1.5 h. The reaction mixture was concentrated under reduced pressure to give 8-chloro-2-(1-((3S,4S)-3-fluoropiperidin-4-yl)-1H-pyrazol-4-yl)-7-((2-methyl-1-((2-(trimethylsilyl)ethoxy)methyl)-1H-benzo[d]imidazol-6-yl)oxy)quinoxaline (250 mg, crude) as a yellow oil. $^1$H NMR (400 MHz, DMSO-$d_6$) δ=9.52-9.45 (m, 1H), 8.89 (s, 1H), 8.53 (s, 1H), 8.43 (s, 2H), 8.10 (d, J=9.2 Hz, 1H), 7.83-7.72 (m, 1H), 7.60-7.42 (m, 2H), 7.25-7.12 (m, 1H), 5.81-5.61 (m, 2H), 4.77-4.66 (m, 1H), 4.17 (q, J=7.2 Hz, 1H), 3.63 (d, J=7.6 Hz, 3H), 3.52-3.43 (m, 3H), 3.17-3.05 (m, 2H), 2.71 (d, J=6.4 Hz, 3H), 2.37-2.25 (m, 3H), 1.02-0.90 (m, 2H), 0.09-0.01 (m, 9H); m/z ES+ $[M+H]^+$ 608.3.

Step 4. 8-Chloro-2-(1-((3S,4S)-3-fluoropiperidin-4-yl)-1H-pyrazol-4-yl)-7-((2-methyl-1H-benzo[d]imidazol-6-yl)oxy)quinoxaline To a solution of 8-chloro-2-(1-((3S,4S)-3-fluoropiperidin-4-yl)-1H-pyrazol-4-yl)-7-((2-methyl-1-((2-(trimethylsilyl) ethoxy)methyl)-1H-benzo[d]imidazol-6-yl)oxy)quinoxaline (250 mg, 411 μmol) in tetrahydrofuran (2 mL) was added pyridine hydrofluoride (407 mg, 4.11 mmol), the mixture was stirred at 80° C. for 1 h. The reaction mixture was concentrated under reduced pressure and the residue was purified by reversed-phase HPLC (0.1% formic acid condition, 30%-40% acetonitrile, 5 min) to give 8-chloro-2-(1-((3S,4S)-3-fluoropiperidin-4-yl)-1H-pyrazol-4-yl)-7-((2-methyl-1H-benzo[d]imidazol-6-yl)oxy)quinoxaline (120 mg, 251 μmol, 55%) as an off-white solid. m/z ES+ $[M+H]^+$ 478.2.

Intermediate 16: (2-Methyl-1-((2-(trimethylsilyl) ethoxy)methyl)-1H-benzo[d]imidazol-6-yl)boronic acid

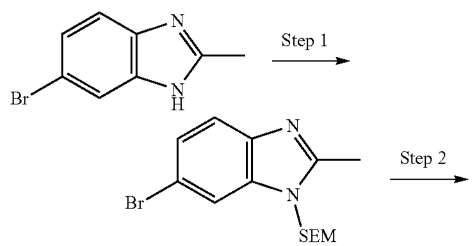

-continued

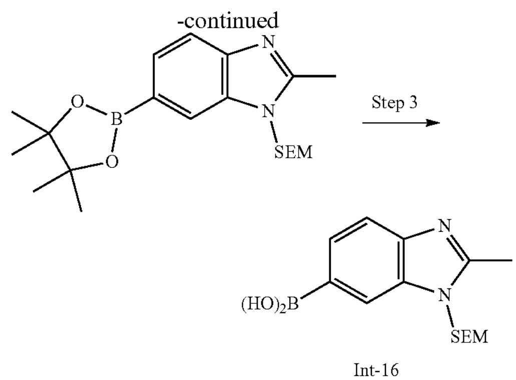

Int-16

Step 1. 6-Bromo-2-methyl-1-((2-(trimethylsilyl) ethoxy)methyl)-1H-benzo[d]imidazole To a solution of 5-bromo-2-methyl-1H-benzimidazole (20 g, 94.8 mmol) in THF (400 mL) was added NaH (7.58 g, 189 mmol, 60% in mineral oil) portion-wise at 0° C. The reaction was stirred at 0° C. for 0.5 h. Then (2-(chloromethoxy)ethyl) trimethylsilane (23.7 g, 142 mmol, 25 mL) was added dropwise at 0° C. The mixture was stirred at 25° C. for 1.5 h. On completion, The reaction mixture was slowly poured into ice water (700 mL), and then extracted with ethyl acetate (300 mL×4). The combined organic layers were washed with brine (100 mL×2), dried over sodium sulfate, filtered and concentrated under reduced pressure to give 6-bromo-2-methyl-1-((2-(trimethylsilyl)ethoxy)methyl)-1H-benzo[d]imidazole (39 g, crude, mixture of regio-isomers) as a white solid. $^1$H NMR (400 MHz, DMSO-$d_6$) δ=7.87 (s, 0.5H), 7.73 (s, 0.5H), 7.58 (d, J=8.4 Hz, 0.5H), 7.48 (d, J=8.4 Hz, 0.5H), 7.36 (dd, J=8.4, 1.2 Hz, 0.5H), 7.34 (dd, J=8.4, 1.2 Hz, 0.5H), 5.58 (s, 2H), 3.60-3.50 (m, 4H), 2.65-2.47 (m, 6H), 0.90-0.70 (m, 4H), 0.10-−0.80 (m, 18H); m/z ES+ $[M+H]^+$ 341.1.

Step 2. 2-Methyl-6-(4,4,5,5-tetramethyl-1,3,2-dioxaborolan-2-yl)-1-((2-(trimethylsilyl)ethoxy)methyl)-1H-benzo[d]imidazole To a solution of 2-[(5-bromo-2-methyl-benzimidazol-1-yl) methoxy]ethyl-trimethyl-silane (39.29 g, 115 mmol, mixture of regio-isomers) and 4,4,5,5-tetramethyl-2-(4,4,5,5-tetramethyl-1,3,2-dioxaborolan-2-yl)-1,3,2-dioxaborolane (87.69 g, 345 mmol) in dioxane (600 mL) was added potassium acetate (33.89 g, 345 mmol) and cyclopenta-2,4-dien-1-yl(diphenyl)phosphane;dichloropalladium;iron(II) (8.42 g, 11.51 mmol). The mixture was stirred at 60° C. for 12 h under nitrogen. On completion, the reaction mixture was concentrated under vacuum and the residue was purified by column chromatography (silica gel, petroleum ether/ethyl acetate=10/1 to 0/1) to give 2-methyl-6-(4,4,5,5-tetramethyl-1,3,2-dioxaborolan-2-yl)-1-((2-(trimethylsilyl)ethoxy) methyl)-1H-benzo[d]imidazole (44.2 g, 114 mmol, 99%, mixture of regio-isomers) as a yellow solid. m/z ES+ $[M+H]^+$ 389.3.

Step 3. (2-Methyl-1-((2-(trimethylsilyl)ethoxy) methyl)-1H-benzo[d]imidazol-6-yl)boronic acid To a solution of trimethyl-[2-[[2-methyl-5-(4,4,5,5-tetramethyl-1,3,2-dioxaborolan-2-yl)benzimidazol-1-yl] methoxy]ethyl] silane (25 g, 64.37 mmol) in tetrahydrofuran (250 mL) and water (250 mL) was added sodium periodate (41.30 g, 193 mmol) and ammonium acetate (14.89 g, 193 mmol). The mixture was stirred at 30° C. for 12 h. On completion, the reaction mixture was filtered and the filtrate was extracted with ethyl acetate (300 mL×4). The combined organic layers were washed with sat. sodium sulfite (250 mL×2), dried over sodium sulfate, filtered and concentrated under reduced pressure. The residue was purified by reversed-phase HPLC (column: I.D.100 mm*H400 mm, mobile phase: [water (10 mM ammonium bicarbonate)-acetonitrile]; (B %: 20-75%, 40 min; 75%, 35 min) to give (2-methyl-1-((2-(trimethylsilyl)ethoxy)methyl)-1H-benzo[d]imidazol-6-yl)boronic acid (8.2 g, 26.78 mmol, 42%) as a white solid. $^1$H NMR (400 MHz, DMSO-$d_6$) δ=8.01 (d, J=7.2 Hz, 1H), 7.94 (s, 1H), 7.92 (s, 1H), 7.67-7.60 (m, 1H), 7.52 (d, J=8.4 Hz, 0.5H), 7.48 (d, J=8.4 Hz, 0.5H), 5.56 (d, J=4.0 Hz, 2H), 3.52 (q, J=7.6 Hz, 2H), 2.56 (d, J=4.4 Hz, 3H), 0.84 (dd, J=14.0, 8.0 Hz, 2H), −0.09 (d, J=2.0 Hz, 9H); m/z ES+ $[M+H]^+$307.2.

Intermediate 17, 20 and 30:8-Bromo-2-(1-((3,3-difluorocyclobutyl)methyl)-1H-pyrazol-4-yl)-7-((2-methyl-1-((2-(trimethylsilyl)ethoxy)methyl)-1H-benzo[d]imidazol-6-yl)oxy)quinoxaline, 3-(1-(tetrahydro-2H-pyran-2-yl)-1H-pyrazol-4-yl)quinoxalin-6-ol and 8-bromo-7-((2-methyl-1-((2-(trimethylsilyl)ethoxy)methyl)-1H-benzo[d]imidazol-6-yl)oxy)-2-(1H-pyrazol-4-yl)quinoxaline

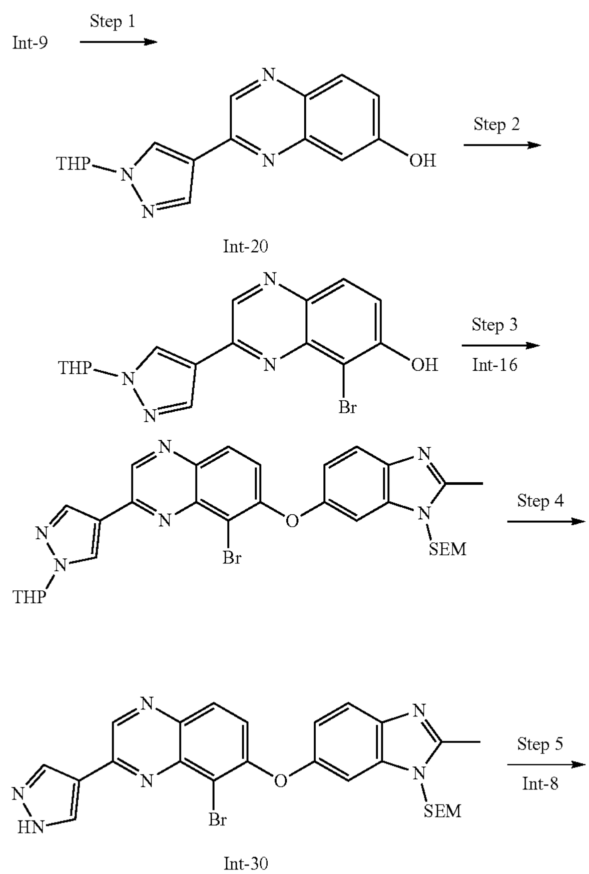

-continued

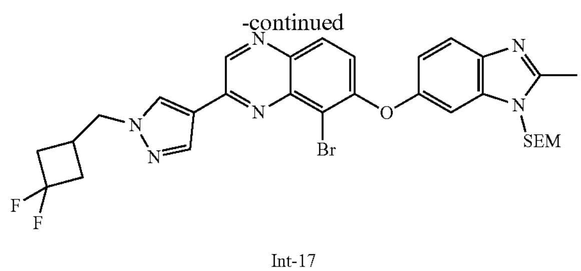

Int-17

Step 1. 3-(1-(Tetrahydro-2H-pyran-2-yl)-1H-pyrazol-4-yl)quinoxalin-6-ol

To a solution of 7-bromo-2-(1-tetrahydropyran-2-ylpyrazol-4-yl)quinoxaline (4.90 g, 13.6 mmol) in dioxane (50 mL) and water (25 mL) was added tris(dibenzylideneacetone) dipalladium (1.25 g, 1.36 mmol), ditert-butyl-[2-(2,4,6-triisopropylphenyl)phenyl] phosphane (579 mg, 1.36 mmol) and potassium hydroxide (7.65 g, 136 mmol). The mixture was degassed and purged with nitrogen for 3 times, and then stirred at 100° C. for 3 h under nitrogen. The reaction mixture was concentrated under reduced pressure. The residue was purified by column chromatography (silica gel, petroleum ether/ethyl acetate=10/1 to 1/1) to give 3-(1-(tetrahydro-2H-pyran-2-yl)-1H-pyrazol-4-yl)quinoxalin-6-ol (1.70 g, 5.39 mmol, 39%) as a yellow solid. $^1$H NMR (400 MHz, DMSO-$d_6$) δ=10.44 (s, 1H), 9.10 (s, 1H), 8.78 (s, 1H), 8.28 (s, 1H), 7.87 (d, J=8.8 Hz, 1H), 7.29 (dd, J=2.4, 9.2 Hz, 1H), 7.20 (d, J=2.4 Hz, 1H), 5.50 (dd, J=2.0, 9.6 Hz, 1H), 3.97 (d, J=11.6 Hz, 1H), 3.72-3.62 (m, 1H), 2.22-2.10 (m, 1H), 2.03-1.92 (m, 2H), 1.77-1.64 (m, 1H), 1.58 (d, J=3.6 Hz, 2H); m/z ES+ $[M+H]^+$ 297.1.

Step 2. 5-Bromo-3-(1-(tetrahydro-2H-pyran-2-yl)-1H-pyrazol-4-yl)quinoxalin-6-ol

To a solution of 3-(1-tetrahydropyran-2-ylpyrazol-4-yl)quinoxalin-6-ol (1.70 g, 5.74 mmol) in chloroform (34 mL) was added N-bromosuccinimide (1.53 g, 8.61 mmol), dichloronickel (744 mg, 5.74 mmol) and triethylamine (581 mg, 5.74 mmol). The mixture was stirred at 60° C. for 2 h. The reaction mixture was cooled to 25° C. and filtered. The filtrate was washed with saturated sodium bicarbonate solution (2×50 mL), dried over sodium sulfate, filtered and concentrated to give 5-bromo-3-(1-(tetrahydro-2H-pyran-2-yl)-1H-pyrazol-4-yl)quinoxalin-6-ol (2.80 g, crude) as a yellow solid. $^1$H NMR (400 MHz, DMSO-$d_6$) δ=9.13 (s, 1H), 8.79 (s, 1H), 8.31 (s, 1H), 7.87 (d, J=9.2 Hz, 1H), 7.46 (d, J=9.2 Hz, 1H), 5.54 (dd, J=2.0, 9.6 Hz, 1H), 4.02-3.96 (m, 1H), 3.74-3.61 (m, 1H), 2.19-2.09 (m, 1H), 2.04-1.93 (m, 2H), 1.77-1.66 (m, 1H), 1.61-1.54 (m, 2H).

Step 3. 8-Bromo-7-((2-methyl-1-((2-(trimethylsilyl)ethoxy)methyl)-1H-benzo[d]imidazol-6-yl)oxy)-2-(1-(tetrahydro-2H-pyran-2-yl)-1H-pyrazol-4-yl)quinoxaline To a solution of 5-bromo-3-(1-tetrahydropyran-2-ylpyrazol-4-yl)quinoxalin-6-ol (1.40 g, 3.73 mmol) and [2-methyl-1-(2-trimethylsilylethoxymethyl)benzimidazol-5-yl]boronic acid (1.22 g, 3.99 mmol) in 1,2-dimethoxyethane (30 mL) was added cesium carbonate (2.67 g, 8.21 mmol), 4 Å MS (1.50 g) and copper(II) acetate (813 mg, 4.48 mmol). The mixture was stirred at 60° C. for 6 h under oxygen atmosphere. The reaction mixture was filtered and concentrated under reduced pressure. The residue was purified by column chromatography (silica gel, petroleum ether/ethyl acetate=1/1 to 1/5) to give 8-bromo-7-((2-methyl-1-((2-(trimethylsilyl)ethoxy)methyl)-1H-benzo[d]imidazol-6-yl)oxy)-2-(1-(tetrahydro-2H-pyran-2-yl)-1H-pyrazol-4-yl)quinoxaline (670 mg, 980 μmol, 26%) as a yellow solid. m/z ES+ $[M+H]^+$ 637.2.

Step 4. 8-Bromo-7-((2-methyl-1-((2-(trimethylsilyl)ethoxy)methyl)-1H-benzo[d]imidazol-6-yl)oxy)-2-(1H-pyrazol-4-yl)quinoxaline To a solution of 2-[[6-[5-bromo-3-(1-tetrahydropyran-2-ylpyrazol-4-yl)quinoxalin-6-yl]oxy-2-methyl-benzimidazol-1-yl]methoxy]ethyl-trimethyl-silane (670 mg, 1.05 mmol) in methanol (7 mL) was added hydrochloric acid (1 M, 7 mL), the mixture was stirred at 25° C. for 12 h. The reaction mixture was diluted with saturated sodium bicarbonate solution (20 mL) and extracted with ethyl acetate (3×15 mL). The combined organic layers were dried over sodium sulfate, filtered and concentrated under reduced pressure. The residue was purified by column chromatography (silica gel, petroleum ether/ethyl acetate=1/3 to 0/1) to give 8-bromo-7-((2-methyl-1-((2-(trimethylsilyl)ethoxy)methyl)-1H-benzo[d]imidazol-6-yl)oxy)-2-(1H-pyrazol-4-yl)quinoxaline (360 mg, 587 μmol, 55%) as a yellow oil. m/z ES+ $[M+H]^+$ 553.1.

Step 5. 8-Bromo-2-(1-((3,3-difluorocyclobutyl)methyl)-1H-pyrazol-4-yl)-7-((2-methyl-1-((2-(trimethylsilyl)ethoxy)methyl)-1H-benzo[d]imidazol-6-yl)oxy)quinoxaline To a solution of 2-[[6-[5-bromo-3-(1H-pyrazol-4-yl)quinoxalin-6-yl]oxy-2-methyl-benzimidazol-1-yl]methoxy]ethyl-trimethyl-silane (290 mg, 526 μmol) and (3,3-difluorocyclobutyl)methyl methanesulfonate (158 mg, 789 μmol) in N,N-dimethylformamide (6 mL) was added potassium carbonate (218 mg, 1.58 mmol). The mixture was stirred at 80° C. for 3 h. The reaction mixture was poured into water (20 mL) and extracted with ethyl acetate (15 mL×3). The combined organic layers were washed with brine (20 mL×2), dried over anhydrous sodium sulfate, filtered and concentrated under reduced pressure to give 8-bromo-2-(1-((3,3-difluorocyclobutyl)methyl)-1H-pyrazol-4-yl)-7-((2-methyl-1-((2-(trimethylsilyl)ethoxy)methyl)-1H-benzo[d]imidazol-6-yl)oxy)quinoxaline (430 mg, crude) as a yellow solid. m/z ES+ $[M+H]^+$ 657.2.

Intermediate 18:8-Chloro-7-((7-fluoro-2-methyl-1-((2-(trimethylsilyl)ethoxy)methyl)-1H-benzo[d]imidazol-6-yl)oxy)-2-(1H-pyrazol-4-yl)quinoxaline

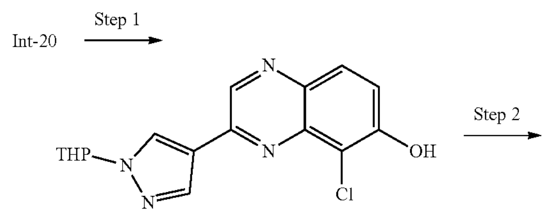

-continued

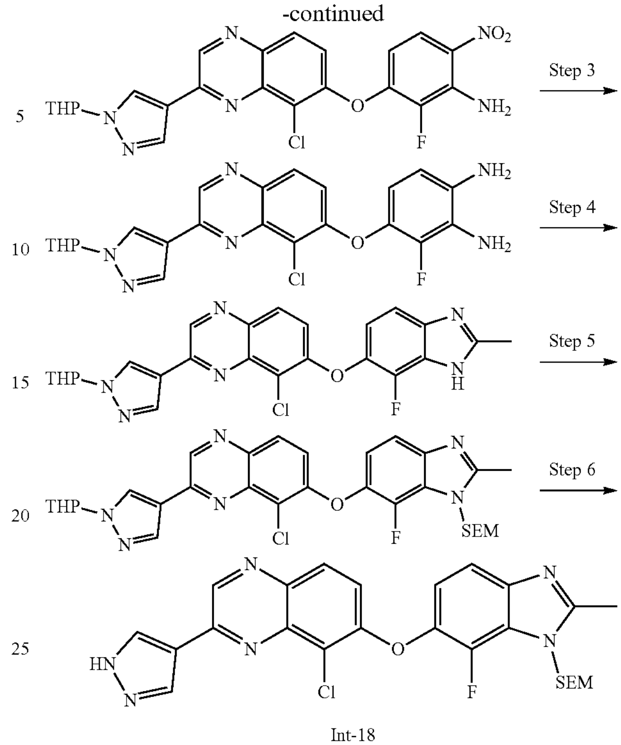

Int-18

Step 1. 5-Chloro-3-(1-(tetrahydro-2H-pyran-2-yl)-1H-pyrazol-4-yl)quinoxalin-6-ol To a solution of 3-(1-tetrahydropyran-2-ylpyrazol-4-yl)quinoxalin-6-ol (4.50 g, 15.2 mmol) in chloroform (90 mL) was added 1-chloropyrrolidine-2,5-dione (4.06 g, 30.4 mmol), dichloronickel (1.97 g, 15.2 mmol) and diisopropylethylamine (2.94 g, 22.8 mmol). The mixture was stirred at 60° C. for 2 h. On completion, the reaction mixture was filtered and concentrated under reduced pressure. The residue was purified by column chromatography (petroleum ether/ethyl acetate=1/1 to 0/1) to give 2-chloro-3-(2-fluoro-5-methoxyphenoxy)-6-nitroaniline (7 g, 21.2 mmol, 70% yield) as a yellow solid. $^1H$ NMR (400 MHz, DMSO-$d_6$) δ=11.05 (s, 1H), 9.19 (s, 1H), 8.80 (s, 1H), 8.32 (s, 1H), 7.87 (d, J=9.2 Hz, 1H), 7.50 (d, J=9.2 Hz, 1H), 5.53 (dd, J=2.0, 9.6 Hz, 1H), 3.98 (d, J=12.8 Hz, 1H), 3.72-3.64 (m, 1H), 2.21-2.09 (m, 1H), 2.04-1.98 (m, 2H), 1.77-1.66 (m, 1H), 1.61-1.54 (m, 2H); m/z ES+ $[M+H]^+$ 331.0.

Step 2. 3-((5-Chloro-3-(1-(tetrahydro-2H-pyran-2-yl)-1H-pyrazol-4-yl)quinoxalin-6-yl)oxy)-2-fluoro-6-nitroaniline To a solution of 5-chloro-3-(1-tetrahydropyran-2-ylpyrazol-4-yl)quinoxalin-6-ol (5.90 g, 17.8 mmol) and 2,3-difluoro-6-nitro-aniline (3.11 g, 17.8 mmol) in N,N-dimethylformamide (160 mL) was added potassium carbonate (4.93 g, 35.7 mmol). The mixture was stirred at 130° C. for 4 h. On completion, the reaction mixture was poured into water (400 mL) and extracted with ethyl acetate (200 mL×3). The combined organic layers were washed with brine (200 mL×2), dried over anhydrous sodium sulfate, filtered and concentrated under reduced pressure. The residue was purified by column chromatography (petroleum ether/ethyl acetate=10/1 to 0/1). The resulting solid was triturated with petroleum ether/ethyl acetate (1/2, 30 mL) to give 3-chloro-4-(2-fluoro-5-methoxyphenoxy)benzene-1,2-diamine (6.59 g, 12.2 mmol, 69%) as a yellow solid. $^1$H NMR (400 MHz, DMSO-$d_6$) δ=9.44 (s, 1H), 8.90 (s, 1H), 8.38 (s, 1H), 8.09 (d, J=9.2 Hz, 1H), 7.86 (dd, J=1.6, 9.6 Hz, 1H), 7.69 (d, J=9.2 Hz, 1H), 7.48 (s, 2H), 6.27 (dd, J=7.6, 9.6 Hz, 1H), 5.56 (dd, J=2.0, 9.6 Hz, 1H), 3.99 (d, J=11.6 Hz, 1H), 3.74-3.66 (m, 1H), 2.21-2.10 (m, 1H), 2.04-1.93 (m, 2H), 1.78-1.67 (m, 1H), 1.62-1.55 (m, 2H); m/z ES+ $[M+H]^+$ 485.1.

Step 3. 4-((5-Chloro-3-(1-(tetrahydro-2H-pyran-2-yl)-1H-pyrazol-4-yl)quinoxalin-6-yl)oxy)-3-fluorobenzene-1,2-diamine To a solution of 3-[5-chloro-3-(1-tetrahydropyran-2-ylpyrazol-4-yl)quinoxalin-6-yl]oxy-2-fluoro-6-nitro-aniline (6.59 g, 13.6 mmol) in ethanol (80 mL) and water (40 mL) was added ammonium chloride (7.27 g, 136 mmol) and iron powder (3.80 g, 68.0 mmol). The mixture was stirred at 60° C. for 12 h. On completion, the reaction mixture was filtered and concentrated under reduced pressure. The residue was diluted in water (100 mL) and extracted with dichloromethane (150 mL×3). The combined organic layers were dried over anhydrous sodium sulfate, filtered and concentrated under reduced pressure. The residue was purified by column chromatography (petroleum ether/ethyl acetate=3/1 to 1/2) to give 4-((5-chloro-3-(1-(tetrahydro-2H-pyran-2-yl)-1H-pyrazol-4-yl)quinoxalin-6-yl)oxy)-3-fluorobenzene-1,2-diamine (4.40 g, 9.38 mmol, 69%) as a yellow solid. $^1$H NMR (400 MHz, DMSO-$d_6$) δ=9.32 (s, 1H), 8.86 (s, 1H), 8.37 (s, 1H), 7.94 (d, J=9.2 Hz, 1H), 7.23 (d, J=9.2 Hz, 1H), 6.42-6.31 (m, 2H), 5.55 (dd, J=2.4, 9.6 Hz, 1H), 4.84 (s, 2H), 4.72 (s, 2H), 4.02-3.95 (m, 1H), 3.74-3.66 (m, 1H), 2.21-2.11 (m, 1H), 2.06-1.97 (m, 2H), 1.78-1.67 (m, 1H), 1.62-1.55 (m, 2H); m/z ES+ $[M+H]^+$ 455.1.

Step 4. 8-Chloro-7-((7-fluoro-2-methyl-1H-benzo[d]imidazol-6-yl)oxy)-2-(1-(tetrahydro-2H-pyran-2-yl)-1H-pyrazol-4-yl)quinoxaline To a solution of 4-[5-chloro-3-(1-tetrahydropyran-2-ylpyrazol-4-yl)quinoxalin-6-yl]oxy-3-fluoro-benzene-1,2-diamine (4.40 g, 9.67 mmol) and 1,1,1-trimethoxyethane (5.81 g, 48.4 mmol) in methanol (100 mL) was added sulfamic acid (1.88 g, 19.4 mmol). The mixture was stirred at 25° C. for 1 h. On completion, the reaction mixture was quenched with saturated aqueous sodium bicarbonate (20 mL), then diluted with water (200 mL) and extracted with ethyl acetate (200 mL×3). The combined organic layers were dried over anhydrous sodium sulfate, filtered and concentrated under reduced pressure to give 8-chloro-7-((7-fluoro-2-methyl-1H-benzo[d]imidazol-6-yl)oxy)-2-(1-(tetrahydro-2H-pyran-2-yl)-1H-pyrazol-4-yl)quinoxaline (4.80 g, crude) as a yellow solid. m/z ES+ $[M+H]^+$ 479.0.

Step 5. 8-Chloro-7-((7-fluoro-2-methyl-1-((2-(trimethylsilyl)ethoxy)methyl)-1H-benzo[d]imidazol-6-yl)oxy)-2-(1-(tetrahydro-2H-pyran-2-yl)-1H-pyrazol-4-yl)quinoxaline To a solution of 8-chloro-7-[(4-fluoro-2-methyl-3H-benzimidazol-5-yl)oxy]-2-(1-tetrahydropyran-2-ylpyrazol-4-yl)quinoxaline (2.60 g, 5.43 mmol) in tetrahydrofuran (60 mL) was added sodium hydride (543 mg, 13.6 mmol, 60% in mineral oil) portion-wise at 0° C. The mixture was then stirred at 0° C. for 0.5 h. Then a solution of (2-(chloromethoxy)ethyl)trimethylsilane (1.36 g, 8.14 mmol) in anhydrous tetrahydrofuran (5 mL) was added dropwise at 0° C. The mixture was stirred at 25° C. for 1 h. On completion, the reaction mixture was poured into 50 ml of water and extracted with ethyl acetate (30 mL×3). The combined organic layers were dried over anhydrous sodium sulfate, filtered and concentrated under reduced pressure. The residue was purified by column chromatography (petroleum ether/ethyl acetate=1/1 to 0/1) to give 8-chloro-7-((7-fluoro-2-methyl-1-((2-(trimethylsilyl)ethoxy)methyl)-1H-benzo[d]imidazol-6-yl)oxy)-2-(1-(tetrahydro-2H-pyran-2-yl)-1H-pyrazol-4-yl)quinoxaline (2.90 g, 4.76 mmol, 88%) as a yellow solid. m/z ES+ $[M+H]^+$ 609.2.

Step 6. 8-Chloro-7-((7-fluoro-2-methyl-1-((2-(trimethylsilyl)ethoxy)methyl)-1H-benzo[d]imidazol-6-yl)oxy)-2-(1H-pyrazol-4-yl)quinoxaline To a solution of 2-[[6-[5-chloro-3-(1-tetrahydropyran-2-ylpyrazol-4-yl)quinoxalin-6-yl]oxy-7-fluoro-2-methyl-benzimidazol-1-yl]methoxy]ethyl-trimethyl-silane (2.90 g, 4.76 mmol) in methanol (29 mL) was added aqueous hydrochloric acid (1 N, 29 mL). The mixture was stirred at 25° C. for 12 h. The reaction mixture was basified with saturated aqueous sodium bicarbonate until pH=8 and extracted with ethyl acetate (50 mL×3). The combined organic layers were dried over anhydrous sodium sulfate, filtered and concentrated under reduced pressure to give 8-chloro-7-((7-fluoro-2-methyl-1-((2-(trimethylsilyl)ethoxy)methyl)-1H-benzo[d]imidazol-6-yl)oxy)-2-(1H-pyrazol-4-yl)quinoxaline (2.60 g, crude) as a white solid. m/z ES+ $[M+H]^+$ 525.2.

Intermediate 19:3-(4-(8-Chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)cyclobutan-1-one Int-18

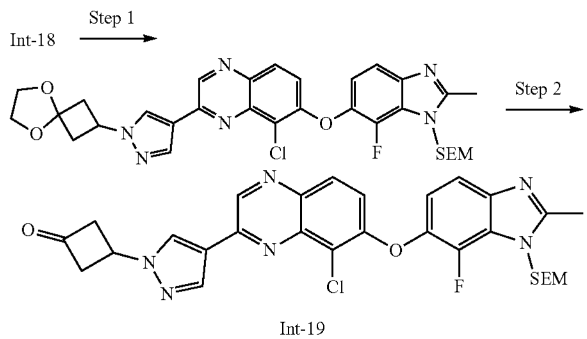

Int-19

Step 1. 2-(1-(5,8-Dioxaspiro[3.4]octan-2-yl)-1H-pyrazol-4-yl)-8-chloro-7-((7-fluoro-2-methyl-1-((2-(trimethylsilyl)ethoxy)methyl)-1H-benzo[d]imidazol-6-yl)oxy)quinoxaline To a solution of 2-[[6-[5-chloro-3-(1H-pyrazol-4-yl)quinoxalin-6-yl]oxy-7-fluoro-2-methyl-benzimidazol-1-yl]methoxy]ethyl-trimethyl-silane (500 mg, 952 μmol) and 2-bromo-5,8-dioxaspiro[3.4]octane (276 mg, 1.43 mmol) in N,N-dimethylformamide (8 mL) was added potassium carbonate (395 mg, 2.86 mmol) and potassium iodide (15.8 mg, 95.2 μmol). The mixture was stirred at 100° C. for 24 h. On completion, the reaction mixture was poured into water (30 mL) and extracted with ethyl acetate (20 mL×3). The combined organic layers were washed with brine (20 mL), dried over anhydrous sodium sulfate, filtered and concentrated under reduced pressure. The residue was purified by column chromatography (silica gel, petroleum ether/ethyl acetate=5/1 to 1/3) to give 2-(1-(5,8-dioxaspiro[3.4]octan-2-yl)-1H-pyrazol-4-yl)-8-chloro-7-((7-fluoro-2-methyl-1-((2-(trimethylsilyl)ethoxy)methyl)-1H-benzo[d]imidazol-6-yl)oxy)quinoxaline (460 mg, 686 μmol, 72%) as a yellow solid. $^1$H NMR (400 MHz, DMSO-$d_6$) δ 9.32 (d, J=2.8 Hz, 1H), 8.82 (s, 1H), 8.42 (s, 1H), 7.95 (dd, J=2.4, 9.2 Hz, 1H), 7.56-7.44 (m, 1H), 7.28-7.12 (m, 2H), 5.63 (d, J=10.4 Hz, 2H), 4.89 (t, J=8.0 Hz, 1H), 3.96-3.84 (m, 4H), 3.59-3.54 (m, 2H), 2.95-2.79 (m, 4H), 2.61 (d, J-7.2 Hz, 3H), 0.87-0.80 (m, 2H), 0.07 (s, 4H), 0.13 (s, 5H); m/z ES+ [M+H]$^+$ 637.2.

Step 2. 3-(4-(8-Chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)cyclobutanone To a solution of 2-[[6-[5-chloro-3-[1-(5,8-dioxaspiro[3.4]octan-2-yl)pyrazol-4-yl]quinoxalin-6-yl]oxy-7-fluoro-2-methyl-benzimidazol-1-yl]methoxy]ethyl-trimethyl-silane (360 mg, 565 μmol) in dichloromethane (1.8 mL) and water (0.5 mL) was added formic acid (4.39 g, 95.4 mmol, 3.6 mL). The mixture was stirred at 40° C. for 12 h. The reaction mixture was concentrated under reduced pressure. The residue was diluted with water (10 mL) and then adjusted to pH 8~9 with saturated aqueous sodium bicarbonate. Then the mixture was extracted with ethyl acetate (20 mL×2). The combined organic layers were dried over anhydrous sodium sulfate, filtered and concentrated under reduced pressure. The residue was purified by column chromatography (silica gel, petroleum ether/ethyl acetate=3/1 to 1/3) to give 3-(4-(8-chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)cyclobutanone (280 mg, 467 μmol, 83%) as a yellow oil. m/z ES+ [M+H]$^+$ 593.2.

Intermediate 21:7-((5,7-Difluoro-2-methyl-1-((2-(trimethylsilyl)ethoxy)methyl)-1H-benzo[d]imidazol-6-yl)oxy)-2-(1H-pyrazol-4-yl)quinoxaline

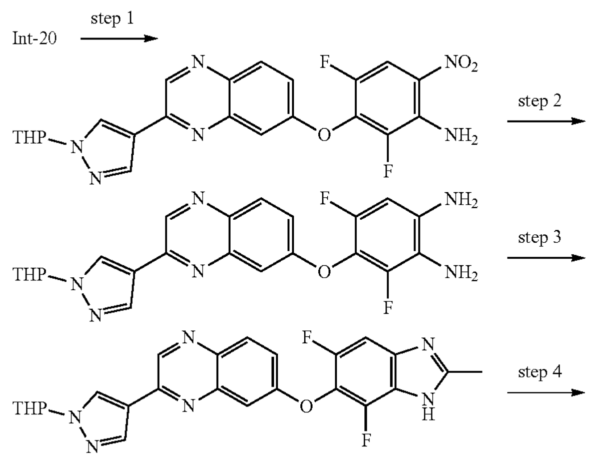

-continued

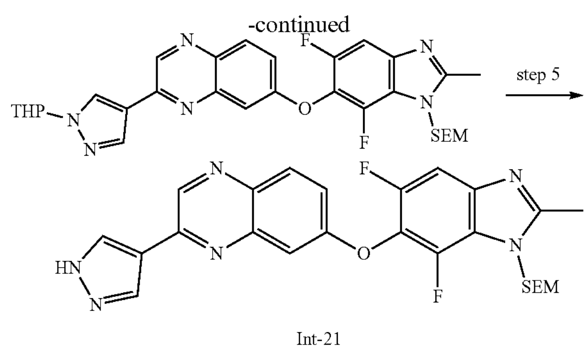

Int-21

Step 1. 2,4-Difluoro-6-nitro-3-((3-(1-(tetrahydro-2H-pyran-2-yl)-1H-pyrazol-4-yl)quinoxalin-6-yl)oxy) aniline To a solution of 3-(1-tetrahydropyran-2-ylpyrazol-4-yl)quinoxalin-6-ol (3 g, 10.1 mmol) in 1-methylpiperidin-2-one (30 mL) was added cesium carbonate (6.60 g, 20.3 mmol) and 2,3,4-trifluoro-6-nitro-aniline (1.94 g, 10.1 mmol). The mixture was stirred at 110° C. for 2 h. On completion, the reaction mixture was diluted with water (100 mL). The resulting precipitate was collected by filtration to give 2,4-difluoro-6-nitro-3-((3-(1-(tetrahydro-2H-pyran-2-yl)-1H-pyrazol-4-yl)quinoxalin-6-yl)oxy) aniline (3.9 g, crude) as a brown solid. $^1$H NMR (400 MHz, DMSO-$d_6$) δ 9.30 (s, 1H), 8.83 (s, 1H), 8.28 (s, 1H), 8.14-7.95 (m, 2H), 7.69 (dd, J=2.8, 9.2 Hz, 1H), 7.49 (s, 2H), 7.39 (d, J=2.8 Hz, 1H), 5.49 (dd, J=2.4, 10.0 Hz, 1H), 3.95 (d, J=11.6 Hz, 1H), 3.75-3.63 (m, 1H), 2.14-2.08 (m, 1H), 2.02-1.95 (m, 2H), 1.78-1.64 (m, 1H), 1.61-1.51 (m, 2H); m/z ES+ [M+H]$^+$ 469.2.

Step 2. 3,5-Difluoro-4-((3-(1-(tetrahydro-2H-pyran-2-yl)-1H-pyrazol-4-yl)quinoxalin-6-yl)oxy)benzene-1,2-diamine To a solution of 2,4-difluoro-6-nitro-3-((3-(1-(tetrahydro-2H-pyran-2-yl)-1H-pyrazol-4-yl)quinoxalin-6-yl)oxy) aniline (3.9 g, 8.33 mmol) in ethanol (60 mL) and water (6 mL) was added iron powder (2.32 g, 41.6 mmol) and ammonium chloride (4.45 g, 83.3 mmol). The mixture was stirred at 60° C. for 2 h. On completion, the reaction mixture was filtered. The filtrate was concentrated under reduced pressure to give 3,5-difluoro-4-((3-(1-(tetrahydro-2H-pyran-2-yl)-1H-pyrazol-4-yl)quinoxalin-6-yl)oxy)benzene-1,2-diamine (5 g, crude) as a yellow solid. m/z ES+ [M+H]$^+$ 439.0.

Step 3. 7-((5,7-Difluoro-2-methyl-1H-benzo[d]imidazol-6-yl)oxy)-2-(1-(tetrahydro-2H-pyran-2-yl)-1H-pyrazol-4-yl)quinoxaline To a solution of 3,5-difluoro-4-((3-(1-(tetrahydro-2H-pyran-2-yl)-1H-pyrazol-4-yl)quinoxalin-6-yl)oxy)benzene-1,2-diamine (5 g, 11.4 mmol) in methanol (80 mL) was added 1,1,1-trimethoxyethane (6.85 g, 57.0 mmol) and sulfamic acid (2.21 g, 22.8 mmol). The mixture was stirred at 20° C. for 2 h. On completion, the reaction mixture was concentrated under reduced pressure. The residue was purified by column chromatography (ethyl acetate/methanol=1/0 to 10/1) to give 7-((5,7-difluoro-2-methyl-1H-benzo[d]imidazol-6-yl)oxy)-2-(1-(tetrahydro-2H-pyran-2-yl)-1H-pyrazol-4-yl)quinoxaline (3.9 g, 6.75 mmol, 59%) as a yellow solid. $^1H$ NMR (400 MHz, $CDCl_3$) δ 8.96 (s, 1H), 8.43-7.93 (m, 3H), 7.71-7.40 (m, 2H), 7.11 (s, 1H), 5.43 (s, 1H), 4.06 (d, J=10.4 Hz, 1H), 3.86 (s, 3H), 3.81-3.64 (m, 1H), 2.17-1.97 (m, 3H), 1.77-1.56 (m, 3H); m/z ES+ $[M+H]^+$ 463.3.

Step 4. 7-((5,7-Difluoro-2-methyl-1-((2-(trimethylsilyl)ethoxy)methyl)-1H-benzo[d]imidazol-6-yl)oxy)-2-(1-(tetrahydro-2H-pyran-2-yl)-1H-pyrazol-4-yl) quinoxaline To a solution of 7-((5,7-difluoro-2-methyl-1H-benzo[d]imidazol-6-yl)oxy)-2-(1-(tetrahydro-2H-pyran-2-yl)-1H-pyrazol-4-yl)quinoxaline (2.0 g, 4.32 mmol) in anhydrous tetrahydrofuran (60 mL) was added sodium hydride (1.04 g, 26.0 mmol, 60% in mineral oil) at 0° C. The mixture was stirred at 0° C. for 2 h. Then (2-(chloromethoxy)ethyl) trimethylsilane (865 mg, 5.19 mmol) was added. The mixture was stirred at 20° C. for 14 h. On completion, the reaction mixture was quenched with water (50 mL) and extracted with ethyl acetate (50 mL×3). The combined organic layers were dried over anhydrous sodium sulfate, filtered and concentrated under reduced pressure. The residue was purified by column chromatography (petroleum ether/ethyl acetate=1/1 to 0/1) to give 7-((5,7-difluoro-2-methyl-1-((2-(trimethylsilyl)ethoxy)methyl)-1H-benzo[d]imidazol-6-yl)oxy)-2-(1-(tetrahydro-2H-pyran-2-yl)-1H-pyrazol-4-yl)quinoxaline (600 mg, 810 μmol, 19%) as a yellow solid. m/z ES+ $[M+H]^+$ 593.4.

Step 5. 7-((5,7-Difluoro-2-methyl-1-((2-(trimethylsilyl)ethoxy)methyl)-1H-benzo[d]imidazol-6-yl)oxy)-2-(1H-pyrazol-4-yl)quinoxaline To a solution of 7-((5,7-difluoro-2-methyl-1-((2-(trimethylsilyl)ethoxy)methyl)-1H-benzo[d]imidazol-6-yl)oxy)-2-(1-(tetrahydro-2H-pyran-2-yl)-1H-pyrazol-4-yl)quinoxaline (450 mg, 759 μmol) in methanol (5 mL) was added hydrochloric acid (1 M, 4.5 mL). The mixture was stirred at 20° C. for 2 h. On completion, the reaction mixture was concentrated under reduced pressure to give 7-((5,7-difluoro-2-methyl-1-((2-(trimethylsilyl)ethoxy)methyl)-1H-benzo[d]imidazol-6-yl)oxy)-2-(1H-pyrazol-4-yl)quinoxaline (600 mg, crude) as a yellow solid. $^1H$ NMR (400 MHz, $CDCl_3$) δ 9.45-8.96 (m, 1H), 8.61-8.51 (m, 1H), 8.30 (s, 1H), 8.18-7.99 (m, 1H), 7.75-7.54 (m, 1H), 7.27 (s, 1H), 7.26-7.13 (m, 1H), 5.90-5.37 (m, 2H), 3.76-3.49 (m, 2H), 3.10-2.70 (m, 3H), 1.06-0.78 (m, 2H), 0.06--0.08 (m, 9H); m/z ES+ $[M+H]^+$ 509.3.

Intermediate 22:4,4-Difluorocyclohexyl methanesulfonate

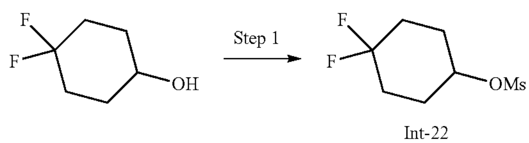 [SMILES: OC1CCC(F)(F)CC1 ; CS(=O)(=O)OC1CCC(F)(F)CC1]

Int-22

Step 1. 4,4-Difluorocyclohexyl methanesulfonate

To a solution of 4,4-difluorocyclohexanol (500 mg, 3.67 mmol) and triethylamine (743 mg, 7.35 mmol) in dichloromethane (1 mL) was added methanesulfonyl chloride (631 mg, 5.51 mmol). The mixture was stirred at 0° C. for 1 h. The mixture was poured into water (50 mL) and extracted with ethyl acetate (30 mL×3). The organic layers were dried over sodium sulfate, filtered and concentrated under reduced pressure. The residue was purified by column chromatography (silica gel, petroleum ether/ethyl acetate=1/0 to 3:1) to give 4,4-difluorocyclohexyl methanesulfonate (750 mg, 3.50 mmol, 95%) as a colourless oil. $^1H$ NMR (400 MHz, $CDCl_3$) δ 4.95-4.92 (m, 1H), 3.07 (s, 3H), 2.13-1.87 (m, 8H).

Intermediate 23:4-((4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl) methyl)cyclohexan-1-one

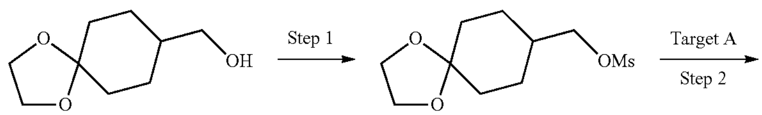

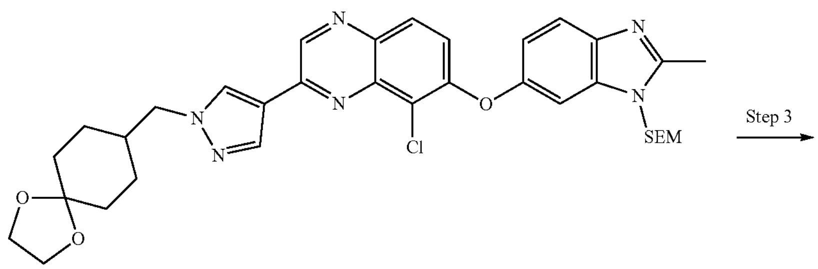

-continued

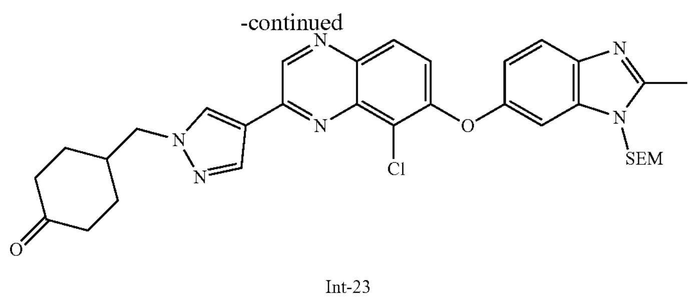

Int-23

Step 1. 1,4-Dioxaspiro[4.5]decan-8-ylmethyl methanesulfonate

To a solution of 1,4-dioxaspiro[4.5]decan-8-ylmethanol (500 mg, 2.90 mmol) and triethylamine (582 mg, 5.75 mmol) in dichloromethane (5 mL) was added methanesulfonyl chloride (444 mg, 3.88 mmol). The mixture was stirred at 0° C. for 1 h. The mixture was quenched with water (10 mL) and extracted with ethyl acetate (12 mL×3). The combined organic phases were dried over anhydrous sodium sulfate, filtered and concentrated to give 1,4-dioxaspiro[4.5]decan-8-ylmethyl methanesulfonate (850 mg, crude) as a yellow oil. $^1$H NMR (400 MHz, $CDCl_3$) δ 4.05-3.95 (m, 2H), 3.94-3.88 (s, 4H), 2.99 (s, 3H), 1.85-1.72 (m, 5H), 1.54-1.51 (m, 1H), 136-1.31 (m, 1H).

Step 2. 2-[[6-[5-Chloro-3-[1-(1,4-dioxaspiro[4.5]decan-8-ylmethyl)pyrazol-4-yl]quinoxalin-6-yl]oxy-2-methyl-benzimidazol-1-yl]methoxy]ethyl-trimethyl-silane To a solution of 1,4-dioxaspiro[4.5]decan-8-ylmethyl methanesulfonate (370 mg, 1.48 mmol) and 2-[[6-[5-chloro-3-(1H-pyrazol-4-yl)quinoxalin-6-yl]oxy-2-methyl-benzimidazol-1-yl]methoxy]ethyl-trimethyl-silane (500 mg, 986 μmol) in N,N-dimethylformamide (8 mL) was added potassium carbonate (300 mg, 2.17 mmol). The mixture was stirred at 80° C. for 12 h. The mixture was quenched with water (5 mL) and extracted with ethyl acetate (8 mL×3). The combined organic phase was dried over anhydrous sodium sulfate, filtered and concentrated to give 2-[[6-[5-chloro-3-[1-(1,4-dioxaspiro[4.5]decan-8-ylmethyl)pyrazol-4-yl]quinoxalin-6-yl]oxy-2-methyl-benzimidazol-1-yl]methoxy]ethyl-trimethyl-silane (900 mg, crude) as a yellow oil. m/z ES+ $[M+H]^+$ 661.3.

Step 3. 4-[[4-[8-Chloro-7-[2-methyl-3-(2-trimethylsilylethoxymethyl)benzimidazol-5-yl]oxy-quinoxalin-2-yl]pyrazol-1-yl]methyl]cyclohexanone To a solution of 2-[[6-[5-chloro-3-[1-(1,4-dioxaspiro[4.5]decan-8-ylmethyl)pyrazol-4-yl]quinoxalin-6-yl]oxy-2-methyl-benzimidazol-1-yl]methoxy]ethyl-trimethyl-silane (900 mg, 1.36 mmol) in dichloromethane (4 mL) was added formic acid (4 mL). The mixture was stirred at 25° C. for 8 h. The mixture was concentrated under reduced pressure. The residue was dissolved in water (2 mL) and adjusted to pH=7 with sat. sodium bicarbonate solution. Then the mixture was extracted with ethyl acetate (10 mL×3). The combined organic phase was dried over anhydrous sodium sulfate, filtered and concentrated to give 4-[[4-[8-chloro-7-[2-methyl-3-(2-trimethylsilylethoxymethyl)benzimidazol-5-yl]oxy-quinoxalin-2-yl]pyrazol-1-yl]methyl]cyclohexanone (780 mg, crude) as a yellow oil. m/z ES+ $[M+H]^+$ 617.3.

Intermediate 24:3-((4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)cyclobutan-1-one

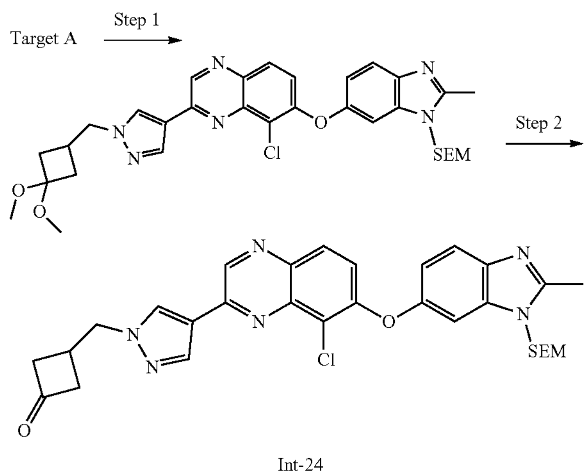

Int-24

Step 1. 2-[[6-[5-Chloro-3-[1-[(3,3-dimethoxycyclobutyl)methyl]pyrazol-4-yl]quinoxalin-6-yl]oxy-2-methyl-benzimidazol-1-yl]methoxy]ethyl-trimethyl-silane To a solution of 2-[[6-[5-chloro-3-(1H-pyrazol-4-yl)quinoxalin-6-yl]oxy-2-methyl-benzimidazol-1-yl]methoxy]ethyl-trimethyl-silane (150 mg, 296 μmol) and (3,3-dimethoxycyclobutyl)methyl methanesulfonate (79.6 mg, 355 μmol) in N,N-dimethylformamide (1.5 mL) was added potassium carbonate (123 mg, 887 μmol) and potassium iodide (49.1 mg, 296 umol), the mixture was stirred at 80° C. for 16 h. The reaction mixture was diluted with water (3 mL) and extracted with ethyl acetate (3×3 mL). The combined organic layers were washed with brine (3×3 mL), dried over sodium sulfate, filtered and concentrated in vacuo to give 2-[6-[5-chloro-3-[1-[(3,3-dimethoxycyclobutyl)methyl]pyrazol-4-yl]quinoxalin-6-yl]oxy-2-methyl-benzimidazol-1-yl]methoxy]ethyl-trimethyl-silane (180 mg, crude) as a yellow oil. m/z ES+ $[M+H]^+$ 635.3.

Step 2. 3-[[4-[8-Chloro-7-[2-methyl-3-(2-trimethylsilylethoxymethyl)benzimidazol-5-yl]oxy-quinoxalin-2-yl]pyrazol-1-yl]methyl]cyclobutanone To a solution of 2-[[6-[5-chloro-3-[1-[(3,3-dimethoxycyclobutyl)methyl]pyrazol-4-yl]quinoxalin-6-yl]oxy-2-methyl-benzimidazol-1-yl]methoxy]ethyl-trimethyl-silane (180 mg, 283 μmol) in dichloromethane (1 mL) was added formic acid (13.6 mg, 283 μmol), the mixture was stirred at 25° C. for 2 h. The reaction mixture was concentrated in vacuo. The residue was washed with saturated sodium bicarbonate solution (3 mL) and then extracted with ethyl acetate (3×5 mL). The combined organic layers were washed with brine (3×5 mL), dried over sodium sulfate, filtered and concentrated in vacuo to give 3-[[4-[8-chloro-7-[2-methyl-3-(2-trimethylsilylethoxymethyl)benzimidazol-5-yl]oxy-quinoxalin-2-yl]pyrazol-1-yl]methyl]cyclobutanone (110 mg, crude) as a yellow gum. $^1$H NMR (400 MHz, DMSO-$d_6$) δ 9.31 (d, J=4.4 Hz, 1H), 8.77 (s, 1H), 8.38 (s, 1H), 7.98-7.93 (m, 2H), 7.70-7.56 (m, 1H), 7.48-7.26 (m, 2H), 7.11-6.96 (m, 1H), 5.75-5.30 (m, 2H), 4.49 (br d, J=6.4 Hz, 2H), 3.58-3.45 (m, 2H), 3.14 (dt, J=6.4, 11.8 Hz, 2H), 3.01 (br t, J=4.8 Hz, 2H), 2.57 (br d, J=6.4 Hz, 3H), 0.93-0.71 (m, 2H), −0.05-−0.17 (m, 9H); m/z ES+ $[M+H]^+$ 589.3.

Intermediate 25: tert-Butyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-4-(2-hydroxyethyl) piperidine-1-carboxylate

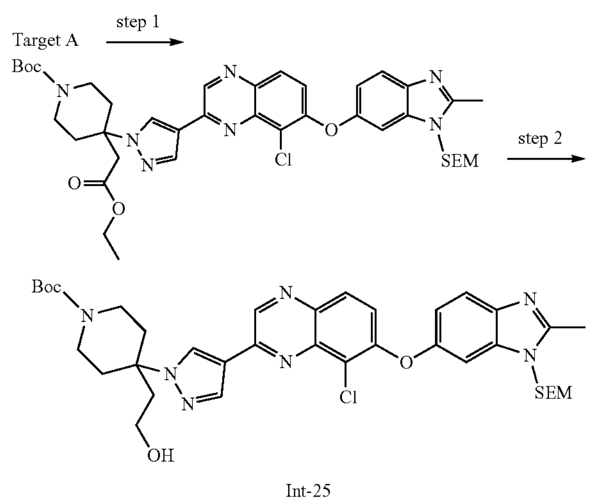

Int-25

Step 1. tert-Butyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-4-(2-ethoxy-2-oxoethyl) piperidine-1-carboxylate To a solution of 2-[[6-[5-chloro-3-(1H-pyrazol-4-yl)quinoxalin-6-yl]oxy-2-methyl-benzimidazol-1-yl]methoxy]ethyl-trimethyl-silane (1 g, 1.97 mmol) in acetonitrile (10 mL) was added tert-butyl 4-(2-ethoxy-2-oxo-ethylidene)piperidine-1-carboxylate (595 mg, 2.21 mmol) and 1,8-diazabicyclo[5.4.0]undec-7-ene (330 mg, 2.17 mmol). The mixture was stirred at 60° C. for 24 h. The reaction mixture was concentrated under reduced pressure. The residue was purified by column chromatography (silica gel, dichloromethane/methanol=1/0 to 80/1) to give tert-butyl 4-(4-(8-chloro-7-((2-methyl-1-((2-(trimethylsilyl)ethoxy)methyl)-1H-benzo[d]=imidazol-6-yl)oxy)quinoxalin-2-yl)-1H-pyrazol-1-yl)-4-(2-ethoxy-2-oxoethyl) piperidine-1-carboxylate (900 mg, 1.04 mmol, 53%) as a yellow solid. m/z ES+ $[M+H]^+$ 776.5.

Step 2. tert-Butyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-4-(2-hydroxyethyl) piperidine-1-carboxylate To a solution of tert-butyl 4-[4-[8-chloro-7-[2-methyl-3-(2-trimethylsilylethoxymethyl)benzimidazol-5-yl]oxy-quinoxalin-2-yl]pyrazol-1-yl]-4-(2-ethoxy-2-oxo-ethyl) piperidine-1-carboxylate (700 mg, 902 μmol) in tetrahydrofuran (14 mL) was added diisobutyl aluminium hydride (1 M in toluene, 2.7 mL) at 0° C. The mixture was stirred at 0° C. for 1.5 h. The reaction mixture was carefully quenched with water (30 mL) and extracted with ethyl acetate (20 mL×3). The combined organic layers were dried over sodium sulfate, filtered and concentrated under reduced pressure. The residue was purified by column chromatography (silica gel, dichloromethane/methanol=1/0 to 80/1) to give tert-butyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-4-(2-hydroxyethyl) piperidine-1-carboxylate (350 mg, 451 μmol, 50%) as a yellow solid. m/z ES+ $[M+H]^+$ 734.1.

Intermediate 26:2-(1-((2-Azabicyclo[2.2.1]heptan-5-yl)methyl)-1H-pyrazol-4-yl)-8-chloro-7-((2-methyl-1-((2-(trimethylsilyl)ethoxy)methyl)-1H-benzo[d]imidazol-6-yl)oxy)quinoxaline

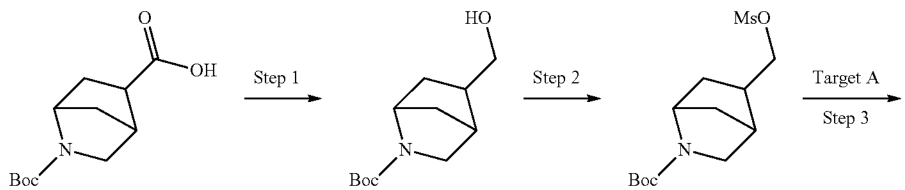

-continued

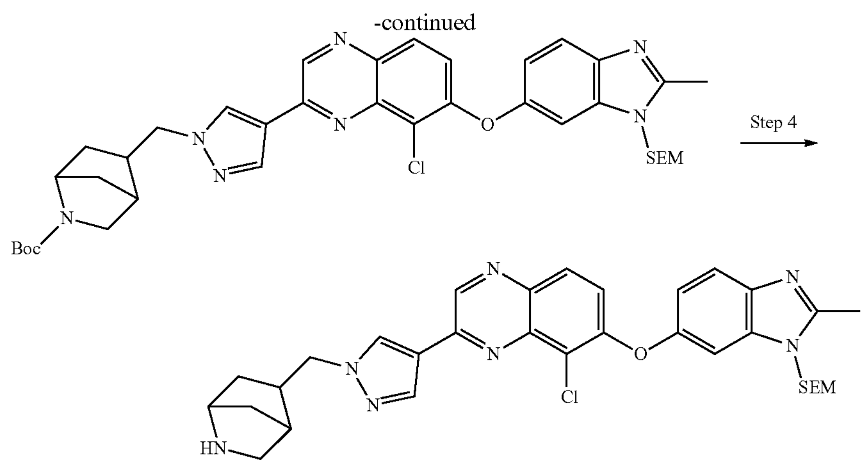

Int-26

Step 1. tert-Butyl 5-(hydroxymethyl)-2-azabicyclo[2.2.1]heptane-2-carboxylate

To a solution of 2-(tert-butoxycarbonyl)-2-azabicyclo[2.2.1]heptane-5-carboxylic acid (500 mg, 2.07 mmol) in tetrahydrofuran (6 mL) was added borane-tetrahydrofuran complex (1 M, 12.4 mL) dropwise at 0° C. The mixture was stirred at 25° C. for 12 h. On completion, the reaction mixture was carefully quenched with methanol (60 mL) at 25° C., and then stirred at 60° C. for 30 min. The reaction was concentrated under reduced pressure. The residue was purified by prep-TLC (silica gel, petroleum ether/ethyl acetate=1/1) to give tert-butyl 5-(hydroxymethyl)-2-azabicyclo[2.2.1]heptane-2-carboxylate (460 mg, 2.03 mmol, 78%) as a yellow oil. $^1$H NMR (400 MHz, DMSO-$d_6$) δ 4.55 (t, J=4.8 Hz, 1H), 3.95 (d, J=8.8 Hz, 1H), 3.50-3.37 (m, 1H), 3.28-3.18 (m, 2H), 3.05-2.94 (m, 1H), 2.48 (s, 1H), 2.11 (dt, J=5.6, 9.6 Hz, 1H), 1.76-1.59 (m, 2H), 1.52-1.42 (m, 1H), 1.39 (s, 9H), 1.01-0.89 (m, 1H).

Step 2. tert-Butyl 5-(((methylsulfonyl)oxy)methyl)-2-azabicyclo[2.2.1]heptane-2-carboxylate To a solution of tert-butyl 5-(hydroxymethyl)-2-azabicyclo[2.2.1]heptane-2-carboxylate (460 mg, 2.02 mmol) in dichloromethane (6 mL) was added triethylamine (614 mg, 6.07 mmol, 0.845 mL) and methanesulfonyl chloride (348 mg, 3.04 mmol, 0.235 mL). The mixture was stirred at 0° C. for 1 h. On completion, the reaction mixture was quenched with water (10 mL) and extracted with dichloromethane (20 mL×3). The combined organic layers were washed with brine (10 mL×3), dried over anhydrous sodium sulfate, filtered and concentrated under reduced pressure to give tert-butyl 5-(((methylsulfonyl)oxy)methyl)-2-azabicyclo[2.2.1]heptane-2-carboxylate (760 mg, crude) as an orange solid. $^1$H NMR (400 MHz, DMSO-$d_6$) δ 4.37-4.27 (m, 1H), 4.15-4.05 (m, 2H), 3.25 (s, 3H), 3.24 (d, J=2.0 Hz, 1H), 3.18-3.07 (m, 1H), 2.50-2.38 (m, 1H), 1.93-1.81 (m, 1H), 1.72 (t, J=10.8 Hz, 1H), 1.64-1.58 (m, 1H), 1.45 (s, 9H), 1.24 (t, J=7.2 Hz, 1H), 1.15 (t, J=7.2 Hz, 1H).

Step 3. tert-Butyl 5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-2-azabicyclo[2.2.1]heptane-2-carboxylate To a solution of 8-chloro-7-((2-methyl-1-((2-(trimethylsilyl)ethoxy)methyl)-1H-benzo[d]imidazol-6-yl)oxy)-2-(1H-pyrazol-4-yl)quinoxaline (360 mg, 710 μmol) in N,N-dimethylformamide (4 mL) was added potassium carbonate (294 mg, 2.13 mmol) and tert-butyl 5-(((methylsulfonyl)oxy)methyl)-2-azabicyclo[2.2.1]heptane-2-carboxylate (434 mg, 1.42 mmol). The mixture was stirred at 80° C. for 12 h. On completion, the reaction mixture was concentrated under reduced pressure and the residue was purified by reversed-phase HPLC (0.1% formic acid condition, 95%-100% acetonitrile, 8 min) to give tert-butyl 5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-2-azabicyclo[2.2.1]heptane-2-carboxylate (430 mg, 0.60 mmol, 85%) as an orange solid. $^1$H NMR (400 MHz, DMSO-$d_6$): δ=9.33 (d, J=4.0 Hz, 1H), 8.80-8.75 (m, 1H), 8.39-8.36 (m, 1H), 7.97 (dd, J=1.2, 9.2 Hz, 1H), 7.70-7.58 (m, 1H), 7.44 (d, J=2.0 Hz, 1H), 7.37-7.29 (m, 2H), 7.10-6.99 (m, 1H), 5.62 (s, 1H), 5.55 (s, 1H), 4.36-4.18 (m, 2H), 4.06 (d, J=12.0 Hz, 1H), 3.56 (t, J=8.0 Hz, 1H), 3.51-3.45 (m, 2H), 3.19-3.07 (m, 1H), 2.68 (d, J=2.0 Hz, 1H), 2.58 (d, J=7.2 Hz, 3H), 2.34 (d, J=2.0 Hz, 1H), 1.92-1.81 (m, 1H), 1.70-1.61 (m, 1H), 1.59-1.53 (m, 1H), 1.44 (d, J=3.6 Hz, 9H), 1.38 (s, 1H), 1.24 (s, 1H), 0.89-0.78 (m, 2H), −0.06-−0.14 (m, 9H); m/z ES+ $[M+H]^+$ 716.2.

Step 4. 2-(1-((2-Azabicyclo[2.2.1]heptan-5-yl)methyl)-1H-pyrazol-4-yl)-8-chloro-7-((2-methyl-1-((2-(trimethylsilyl)ethoxy)methyl)-1H-benzo[d]imidazol-6-yl)oxy)quinoxaline A solution of tert-butyl 5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-2-azabicyclo[2.2.1]heptane-2-carboxylate (400 mg, 558 μmol) in trifluoroacetic acid (0.1 mL) and dichloromethane (1 mL) was stirred at 25° C. for 1 h. On completion, the reaction mixture was concentrated under reduced pressure to give 2-(1-(2-azabicyclo[2.2.1]heptan-5-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (340 mg, crude) as a yellow oil. m/z ES+ $[M+H]^+$ 616.1.

Intermediate 27:2-(1-(Azetidin-3-ylmethyl)-1H-pyrazol-4-yl)-8-chloro-7-((2-methyl-1H-benzo[d]imidazol-6-yl)oxy)quinoxaline

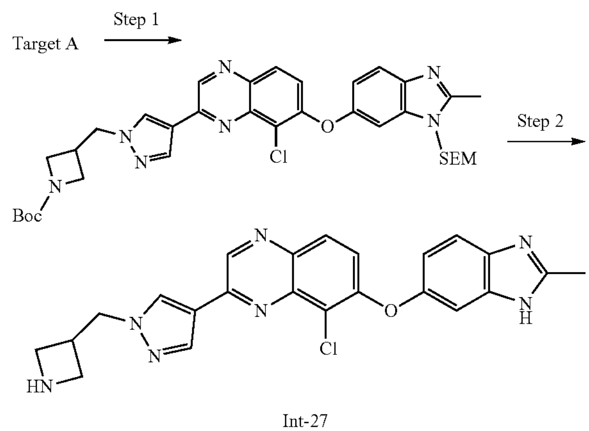

Int-27

Step 1. tert-Butyl 3-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)azetidine-1-carboxylate To a solution of 2-[[6-[5-chloro-3-(1H-pyrazol-4-yl)quinoxalin-6-yl]oxy-2-methyl-benzimidazol-1-yl]methoxy]ethyl-trimethyl-silane (500 mg, 986 μmol) and tert-butyl 3-(iodomethyl)azetidine-1-carboxylate (290 mg, 976 μmol) in N,N-dimethylformamide (10 mL) was added cesium carbonate (1 g, 3.07 mmol). The mixture was stirred at 100° C. for 14 h. On completion, the mixture was quenched with water (10 mL) and extracted with ethyl acetate (15 mL×3). The combined organic layers were dried over anhydrous sodium sulfate, filtered and concentrated and the residue was purified by column chromatography (silica gel, dichloromethane/methanol=30/1 to 10/1) to give tert-butyl 3-[[4-[8-chloro-7-[2-methyl-3-(2-trimethylsilylethoxymethyl)benzimidazol-5-yl]oxy-quinoxalin-2-yl]pyrazol-1-yl]methyl]azetidine-1-carboxylate (800 mg, crude) as a yellow oil. m/z ES+ $[M+H]^+$ 676.1.

Step 2. 2-(1-(Azetidin-3-ylmethyl)-1H-pyrazol-4-yl)-8-chloro-7-((2-methyl-1H-benzo[d]imidazol-6-yl)oxy)quinoxaline A solution of tert-butyl 3-[[4-[8-chloro-7-[2-methyl-3-(2-trimethylsilylethoxymethyl)benzimidazol-5-yl]oxy-quinoxalin-2-yl]pyrazol-1-yl]methyl]azetidine-1-carboxylate (400 mg, 591 μmol) in trifluoroacetic acid (4 mL) was stirred at 25° C. for 1.5 h. On completion, the mixture was concentrated under reduced pressure. The residue was purified by reversed-phase HPLC (mobile phase: [water (0.1% formic acid)-acetonitrile]; (B %: 10%-40%, 8 min) to give 2-[1-(azetidin-3-ylmethyl)pyrazol-4-yl]-8-chloro-7-[(2-methyl-3H-benzimidazol-5-yl)oxy]quinoxaline (240 mg, 538 μmol, 91%, formic acid salt) as a yellow solid. $^1$H NMR (400 MHz, DMSO-$d_6$) δ 9.32 (s, 1H), 8.73 (s, 1H), 8.43-8.37 (m, 2H), 7.96 (d, J=9.2 Hz, 1H), 7.51 (d, J=8.4 Hz, 1H), 7.32 (d, J=9.2 Hz, 1H), 7.21 (d, J=2.0 Hz, 1H), 6.97-6.90 (m, 1H), 4.51 (d, J=7.2 Hz, 2H), 3.87 (d, J=8.8 Hz, 2H), 3.75 (t, J=8.0 Hz, 2H), 3.33-3.22 (m, 1H), 2.49 (s, 3H); m/z ES+ $[M+H]^+$ 446.0.

Intermediate 28:8-Chloro-7-((2-methyl-1-((2-(trimethylsilyl)ethoxy)methyl)-1H-benzo[d]imidazol-6-yl)oxy)-2-(5-methyl-1H-pyrazol-4-yl)quinoxaline

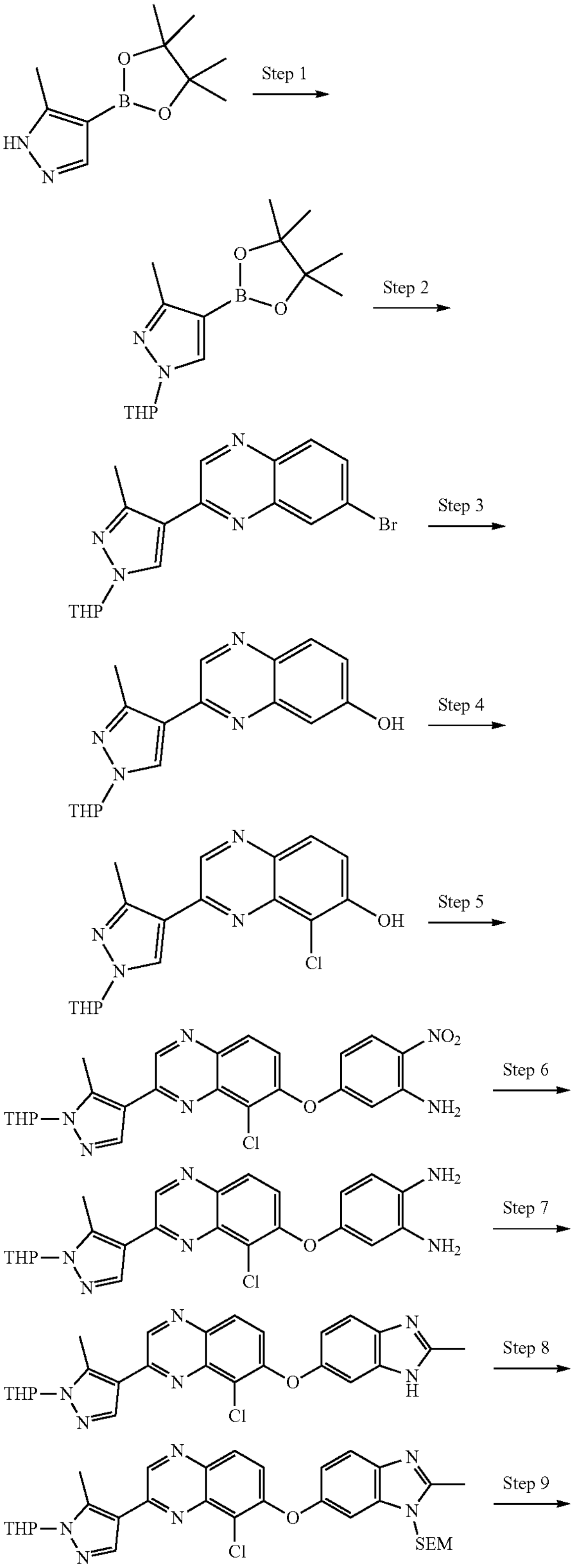

-continued

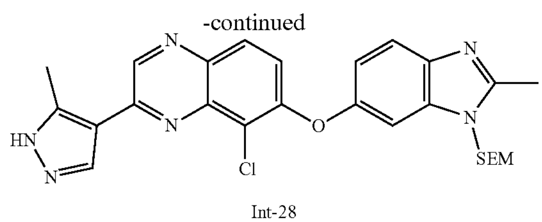

Int-28

Step 1. 3-Methyl-1-(tetrahydro-2H-pyran-2-yl)-4-(4,4,5,5-tetramethyl-1,3,2-dioxaborolan-2-yl)-1H-pyrazole To a solution of 5-methyl-4-(4,4,5,5-tetramethyl-1,3,2-dioxaborolan-2-yl)-1H-pyrazole (18.0 g, 86.5 mmol) in toluene (200 mL) was added p-toluenesulfonic acid (1.49 g, 8.65 mmol) and 3,4-dihydro-2H-pyran (8.73 g, 103 mmol). The mixture was stirred at 60° C. for 12 h. On completion, the reaction mixture was diluted with water (100 mL) and extracted with ethyl acetate (100 mL×3). The combined organic layers were dried over anhydrous sodium sulfate, filtered and concentrated under reduced pressure. The residue was purified by column chromatography (silica gel, petroleum ether/ethyl acetate=5/1) to give 5-methyl-1-tetrahydropyran-2-yl-4-(4,4,5,5-tetramethyl-1,3,2-dioxaborolan-2-yl)pyrazole (20 g, 68.4 mmol, 64%) as a yellow oil. $^1$H NMR (400 MHz, $CDCl_3$) δ 7.83 (s, 1H), 5.33-5.29 (m, 1H), 4.09-4.03 (m, 1H), 3.69-3.64 (m, 1H), 2.41 (s, 3H), 2.04-1.97 (m, 2H), 1.71-1.55 (m, 4H), 1.30 (s, 12H).

Step 2. 7-Bromo-2-(5-methyl-1-tetrahydropyran-2-yl-pyrazol-4-yl)quinoxaline

A mixture of 7-bromo-2-chloro-quinoxaline (16.0 g, 65.7 mmol), 5-methyl-1-tetrahydropyran-2-yl-4-(4,4,5,5-tetramethyl-1,3,2-dioxaborolan-2-yl)pyrazole (20.0 g, 68.4 mmol), tetrakis(triphenylphosphine) palladium (3.95 g, 3.42 mmol), potassium phosphate (29.1 g, 136 mmol) in dioxane (200 mL) and water (40 mL) was degassed and purged with nitrogen for 3 times, and then the mixture was stirred at 80° C. for 12 h under nitrogen atmosphere. On completion, the reaction mixture was concentrated under reduced pressure. The residue was purified by column chromatography (silica gel, petroleum ether/ethyl acetate=5/1 to 3/1) to give 7-bromo-2-(5-methyl-1-tetrahydropyran-2-yl-pyrazol-4-yl) quinoxaline (26.0 g, 69.6 mmol, 93%) as a yellow solid. $^1$H NMR (400 MHz, $CDCl_3$) δ 8.99 (s, 1H), 8.22 (s, 1H), 8.19 (d, J=2.0 Hz, 1H), 7.88 (d, J=8.8 Hz, 1H), 7.73-7.69 (m, 1H), 5.41-5.32 (m, 1H), 3.77-3.67 (m, 1H), 2.68 (s, 3H), 2.31-2.25 (m, 3H), 2.15-2.10 (m, 2H), 1.76-1.59 (m, 4H).

Step 3. 3-(5-Methyl-1-tetrahydropyran-2-yl-pyrazol-4-yl)quinoxalin-6-ol

A mixture of 7-bromo-2-(5-methyl-1-tetrahydropyran-2-yl-pyrazol-4-yl)quinoxaline (26.0 g, 69.6 mmol), potassium hydroxide (39.0 g, 696 mmol), tris(dibenzylideneacetone) dipalladium (6.38 g, 6.97 mmol) and t-Bu XPhos (5.92 g, 13.9 mmol) in dioxane (300 mL) and water (50 mL) was degassed and purged with nitrogen for 3 times, and then the mixture was stirred at 100° C. for 3 h under nitrogen atmosphere. On completion, the reaction mixture was diluted with water (500 mL) and extracted with ethyl acetate (500 mL×3). The combined organic layers were dried over anhydrous sodium sulfate, filtered and concentrated under reduced pressure. The residue was purified by column chromatography (silica gel, petroleum ether/ethyl acetate=10/1 to 0/1) to give 3-(5-methyl-1-tetrahydropyran-2-yl-pyrazol-4-yl)quinoxalin-6-ol (17.0 g, 54.8 mmol, 60%) as a white solid. m/z ES+ $[M+H]^+$ 311.1.

Step 4. 5-Chloro-3-(5-methyl-1-tetrahydropyran-2-yl-pyrazol-4-yl)quinoxalin-6-ol To a solution of 3-(5-methyl-1-tetrahydropyran-2-yl-pyrazol-4-yl)quinoxalin-6-ol (16.0 g, 51.5 mmol) in trichloromethane (300 mL) was added chlorosuccinimide (13.7 g, 103 mmol), nickel chloride (6.68 g, 51.5 mmol) and triethylamine (5.22 g, 51.5 mmol). The mixture was stirred at 60° C. for 2 h. On completion, the reaction mixture was concentrated under reduced pressure. The residue was purified by column chromatography (silica gel, petroleum ether/ethyl acetate=10/1 to 1/1) to give 5-chloro-3-(5-methyl-1-tetrahydropyran-2-yl-pyrazol-4-yl) quinoxalin-6-ol (7 g, 20 mmol, 39%) as a yellow solid. $^1$H NMR (400 MHz, $CDCl_3$) δ 8.93 (s, 1H), 8.26 (s, 1H), 7.91 (d, J=9.2 Hz, 1H), 7.45 (d, J=9.2 Hz, 1H), 5.53-5.28 (m, 1H), 4.20-4.12 (m, 1H), 3.81-3.70 (m, 1H), 2.79 (s, 3H), 2.19-2.12 (m, 2H), 1.80-1.67 (m, 4H).

Step 5. 5-[5-Chloro-3-(5-methyl-1-tetrahydropyran-2-yl-pyrazol-4-yl)quinoxalin-6-yl]oxy-2-nitro-aniline To a solution of 5-chloro-3-(5-methyl-1-tetrahydropyran-2-yl-pyrazol-4-yl)quinoxalin-6-ol (1.30 g, 3.77 mmol) in N,N-dimethyl formamide (20 mL) was added potassium carbonate (1.56 g, 11.31 mmol) and 5-fluoro-2-nitro-aniline (765 mg, 4.90 mmol). The mixture was stirred at 120° C. for 12 h. On completion, the reaction mixture was diluted with water (25 mL) and extracted with ethyl acetate (25 mL×3). The combined organic layers were dried over anhydrous sodium sulfate, filtered and concentrated under reduced pressure. The residue was purified by column chromatography (silica gel, dichloromethane:methanol=1/0 to 100/5) to give 5-[5-chloro-3-(5-methyl-1-tetrahydropyran-2-yl-pyrazol-4-yl)quinoxalin-6-yl]oxy-2-nitro-aniline (500 mg, 1.04 mmol, 22%) as a yellow solid. m/z ES+ $[M+H]^+$ 481.1

Step 6. 4-[5-Chloro-3-(5-methyl-1-tetrahydropyran-2-yl-pyrazol-4-yl)quinoxalin-6-yl]oxybenzene-1,2-diamine To a solution of 5-[5-chloro-3-(5-methyl-1-tetrahydropyran-2-yl-pyrazol-4-yl)quinoxalin-6-yl]oxy-2-nitro-aniline (500 mg, 1.04 mmol) in ethanol (10 mL) and water (5 mL) was added iron powder (464 mg, 8.32 mmol) and ammonium chloride (444 mg, 8.32 mmol). The mixture was stirred at 60° C. for 12 h. On completion, the reaction mixture was filtered. The filtrate was diluted with water (25 mL) and extracted with ethyl acetate (25 mL×3). The combined organic layers were dried over anhydrous sodium sulfate, filtered and concentrated under reduced pressure to give 4-[5-chloro-3-(5-methyl-1-tetrahydropyran-2-yl-pyrazol-4-yl)quinoxalin-6-yl]oxybenzene-1,2-diamine (350 mg, crude) as a yellow solid. m/z ES+ $[M+H]^+$ 451.1

Step 7. 8-Chloro-7-[(2-methyl-3H-benzimidazol-5-yl)oxy]-2-(5-methyl-1-tetrahydropyran-2-yl-pyrazol-4-yl)quinoxaline To a solution of 4-[5-chloro-3-(5-methyl-1-tetrahydropyran-2-yl-pyrazol-4-yl)quinoxalin-6-yl]oxybenzene-1,2-diamine (800 mg, 1.77 mmol) in methanol (10 mL) was added sulfamic acid (344 mg, 3.55 mmol) and 1,1,1-trimethoxyethane (1.07 g, 8.87 mmol). The mixture was stirred at 25° C. for 2 h. On completion, the reaction pH was adjusted to pH ~ 8 with sat. ammonium hydroxide and then concentrated under reduced pressure. The residue was purified by column chromatography (silica gel, dichloromethane: methanol=1/0 to 10/1) to give 8-chloro-7-[(2-methyl-3H-benzimidazol-5-yl)oxy]-2-(5-methyl-1-tetrahydropyran-2-yl-pyrazol-4-yl)quinoxaline (1 g, 2.11 mmol, 89%) as a yellow solid. $^1$H NMR (400 MHz, $CDCl_3$) δ 8.99 (s, 1H), 8.29 (s, 1H), 7.86 (d, J=9.2 Hz, 1H), 7.56 (d, J=8.8 Hz, 1H), 7.29 (s, 1H), 7.25 (d, J=2.0 Hz, 1H), 7.07-7.02 (m, 1H), 5.44-5.38 (m, 1H), 3.79-3.70 (m, 2H), 2.81 (s, 3H), 2.67 (s, 3H), 2.13-2.04 (m, 2H), 1.76-1.63 (m, 4H).

Step 8. 2-[[6-[5-Chloro-3-(5-methyl-1-tetrahydropyran-2-yl-pyrazol-4-yl)quinoxalin-6-yl]oxy-2-methyl-benzimidazol-1-yl]methoxy]ethyl-trimethyl-silane To a solution of 8-chloro-7-[(2-methyl-3H-benzimidazol-5-yl)oxy]-2-(5-methyl-1-tetrahydropyran-2-yl-pyrazol-4-yl) quinoxaline (800 mg, 1.68 mmol) in tetrahydrofuran (10 mL) was added sodium hydroxide (134 mg, 3.37 mmol, 60% in mineral oil) at 0° C. The mixture was stirred at 0° C. for 0.5 h. Then (2-(chloromethoxy)ethyl)trimethylsilane (421 mg, 2.53 mmol) was added dropwise and the mixture was stirred at 25° C. for 1.5 h. On completion, the reaction mixture was quenched with water (20 mL) at 25° C. and then extracted with ethyl acetate (25 mL×3). The combined organic layers were dried over anhydrous sodium sulfate, filtered and concentrated under reduced pressure. The residue was purified by column chromatography (silica gel, dichloromethane:methanol=1/0 to 20/1) to give 2-[[6-[5-chloro-3-(5-methyl-1-tetrahydropyran-2-yl-pyrazol-4-yl) quinoxalin-6-yl]oxy-2-methyl-benzimidazol-1-yl]methoxy] ethyl-trimethyl-silane (900 mg, 3.14 mmol, 85%) as a yellow solid. m/z ES+ $[M+H]^+$ 605.2

Step 9. 2-[[6-[5-Chloro-3-(5-methyl-1H-pyrazol-4-yl)quinoxalin-6-yl]oxy-2-methyl-benzimidazol-1-yl] methoxy]ethyl-trimethyl-silane To a solution of 2-[[6-[5-chloro-3-(5-methyl-1-tetrahydropyran-2-yl-pyrazol-4-yl)quinoxalin-6-yl]oxy-2-methyl-benzimidazol-1-yl]methoxy]ethyl-trimethyl-silane (0.90 g, 1.49 mmol) in methanol (9 mL) was added aqueous hydrochloride (1 M, 9 mL). The mixture was stirred at 25° C. for 1 h. On completion, the reaction mixture was diluted with water (25 mL) and extracted with ethyl acetate (25 mL×3). The combined organic layers were dried over anhydrous sodium sulfate, filtered and concentrated under reduced pressure and the residue was purified by reversed-phase HPLC (0.1% formic acid condition) to give 2-[[6-[5-chloro-3-(5-methyl-1H-pyrazol-4-yl)quinoxalin-6-yl]oxy-2-methyl-benzimidazol-1-yl]methoxy]ethyl-trimethyl-silane (1.1 g, crude) as a yellow solid. $^1$H NMR (400 MHz, DMSO-$d_6$) δ 9.32 (d, J=4.0 Hz, 1H), 7.93 (d, J=9.2 Hz, 1H), 7.66 (d, J-8.8 Hz, 1H), 7.59 (d, J=8.8 Hz, 1H), 7.42 (d, J=2.4 Hz, 1H), 7.29 (d, J=1.6 Hz, 1H), 6.99 (d, J=2.4 Hz, 1H), 5.65-5.50 (m, 2H), 3.59-3.41 (m, 2H), 2.56 (d, J=7.2 Hz, 3H), 2.50 (s, 3H), 0.88-0.75 (m, 2H), −0.07-−0.16 (m, 9H).

Intermediate 29:2-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl) acetic acid

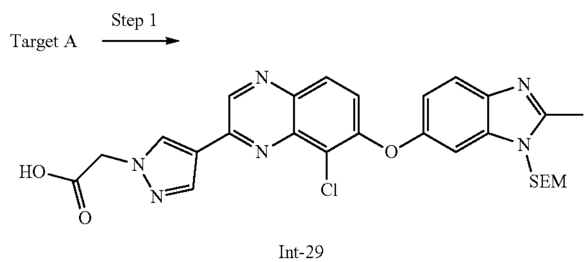

Int-29

Step 1. 2-[4-[8-Chloro-7-[2-methyl-3-(2-trimethylsilylethoxymethyl)benzimidazol-5-yl] oxy-quinoxalin-2-yl]pyrazol-1-yl]acetic acid To a solution of 2-[[6-[5-chloro-3-(1H-pyrazol-4-yl)quinoxalin-6-yl]oxy-2-methyl-benzimidazol-1-yl]methoxy] ethyl-trimethylsilane (500 mg, 986 μmol) in tetrahydrofuran (7 mL) was added sodium hydride (118 mg, 2.96 mmol, 60% in mineral oil), the mixture was stirred at 25° C. for 30 min. And then 2-bromoacetic acid (206 mg, 1.48 mmol) was added, and the mixture was stirred at 60° C. for 12 h. The reaction mixture was quenched with saturated citric acid (7 mL) and then filtered. The filtered cake was dried in vacuo to give 2-[4-[8-chloro-7-[2-methyl-3-(2-trimethylsilylethoxymethyl)benzimidazol-5-yl]oxy-quinoxalin-2-yl] pyrazol-1-yl]acetic acid (556 mg, 984 μmol, 99%) as a yellow solid. $^1$H NMR (400 MHz, DMSO-$d_6$) δ=9.35 (s, 1H), 8.72 (s, 1H), 8.40 (s, 1H), 7.97 (d, J=9.2 Hz, 1H), 7.60 (d, J=8.8 Hz, 1H), 7.45 (d, J=2.0 Hz, 1H), 7.33 (d, J=9.2 Hz, 1H), 7.02 (dd, J=2.4, 8.8 Hz, 1H), 5.54 (s, 2H), 5.13 (s, 2H), 3.48 (t, J=8.0 Hz, 2H), 2.56 (s, 3H), 0.79 (t, J=8.0 Hz, 2H), −0.11-−0.20 (m, 9H); m/z ES+ $[M+H]^+$ 565.2.

Intermediates 31 and 32: (Tetrahydro-2H-thiopyran-4-yl)methyl methanesulfonate and 8-chloro-7-((2-methyl-1-((2-(trimethylsilyl)ethoxy)methyl)-1H-benzo[d]imidazol-6-yl)oxy)-2-(1-((tetrahydro-2H-thiopyran-4-yl)methyl)-1H-pyrazol-4-yl)quinoxaline

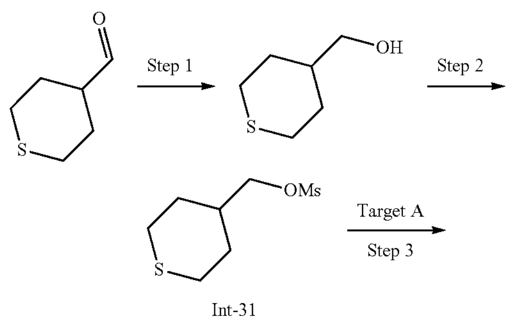

Int-31

-continued

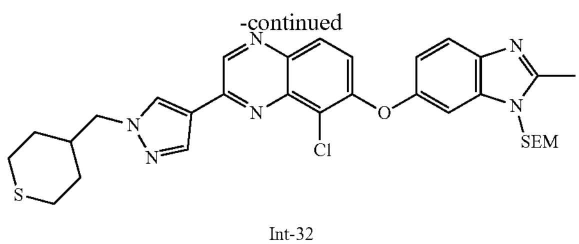

Int-32

Step 1. (Tetrahydro-2H-thiopyran-4-yl) methanol

To a solution of tetrahydrothiopyran-4-carbaldehyde (0.20 g, 1.54 mmol) in ethanol (5 mL) was added sodium borohydride (581 mg, 15.7 mmol), then the mixture was stirred at 25° C. for 2 h. On completion, the reaction mixture was poured into water (80 mL) and methanol (10 mL), and then extracted with ethyl acetate (30 mL×3). The combined organic layers were dried over sodium sulfate, filtered and concentrated under reduced pressure to afford tetrahydrothiopyran-4-ylmethanol (0.20 g, crude) as a colorless oil. $^1$H NMR (400 MHz, $CDCl_3$) δ 3.47 (d, J=6.0 Hz, 2H), 2.75-2.60 (m, 4H), 2.08 (dd, J=13.2, 2.8 Hz, 2H), 1.60-1.50 (m, 1H), 1.45-1.35 (m, 2H).

Step 2. (Tetrahydro-2H-thiopyran-4-yl)methyl methanesulfonate

To a solution of tetrahydrothiopyran-4-ylmethanol (180 mg, 1.36 mmol) in dichloromethane (2 mL) was added methanesulfonyl chloride (312 mg, 2.72 mmol) and triethylamine (413 mg, 4.08 mmol) at 0° C., then the mixture was stirred at 25° C. for 1 h. On completion, the reaction mixture was poured into aqueous ammonium chloride solution (30 mL) and extracted with ethyl acetate (20 mL×3). The combined organic layers were dried over anhydrous sodium sulfate, filtered and concentrated under reduced pressure to give tetrahydrothiopyran-4-ylmethyl methanesulfonate (344 mg, crude) as a white solid. $^1$H NMR (400 MHz, $CDCl_3$) δ 4.04 (d, J=6.4 Hz, 2H), 3.02 (s, 3H), 2.71-2.63 (m, 4H), 1.81-1.80 (m, 1H), 1.50-1.40 (m, 4H).

Step 3. 8-Chloro-7-((2-methyl-1-((2-(trimethylsilyl)ethoxy)methyl)-1H-benzo[d]imidazol-6-yl)oxy)-2-(1-((tetrahydro-2H-thiopyran-4-yl)methyl)-1H-pyrazol-4-yl)quinoxaline To a mixture of tetrahydrothiopyran-4-ylmethyl methanesulfonate (0.30 g, 1.43 mmol) and 2-[[6-[5-chloro-3-(1H-pyrazol-4-yl)quinoxalin-6-yl]oxy-2-methyl-benzimidazol-1-yl]methoxy]ethyl-trimethyl-silane (723 mg, 1.43 mmol) in N,N-dimethylformamide (5 mL) was added potassium carbonate (394 mg, 2.85 mmol), then the mixture was stirred at 80° C. for 12 hours. On completion, the mixture was concentrated under reduced pressure. The crude product was triturated with water (30 mL) at 15° C. for 40 min to give 8-chloro-7-((2-methyl-1-((2-(trimethylsilyl)ethoxy)methyl)-1H-benzo[d]imidazol-6-yl)oxy)-2-(1-((tetrahydro-2H-thiopyran-4-yl)methyl)-1H-pyrazol-4-yl)quinoxaline (0.20 g, 0.32 mmol, 23%) as a yellow solid. m/z ES+ $[M+H]^+$ 621.3.

Intermediate 33:2-(1-((3S,4S)-3-Fluoropiperidin-4-yl)-1H-pyrazol-4-yl)-8-methyl-7-((2-methyl-1-((2-(trimethylsilyl)ethoxy)methyl)-1H-benzo[d]imidazol-6-yl)oxy)quinoxaline Int-14

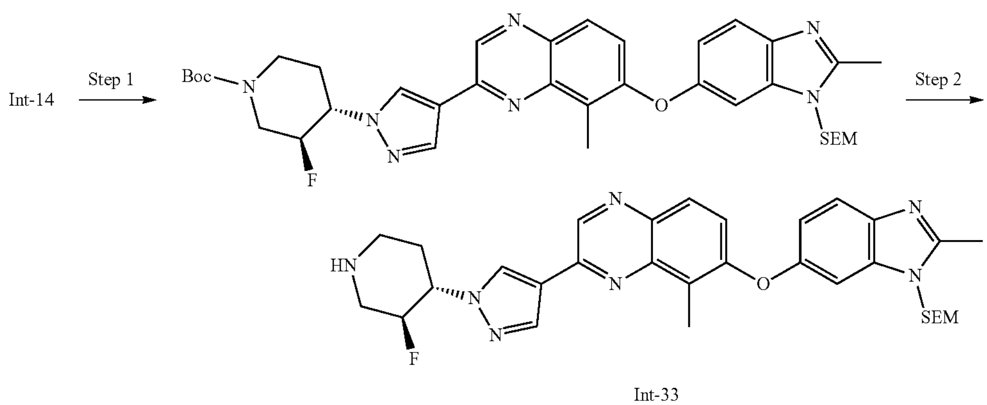

Int-33

Step 1. (3S,4S)-tert-Butyl 3-fluoro-4-(4-(8-methyl-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate To a solution of tert-butyl (3S,4S)-4-[4-[8-chloro-7-[2-methyl-3-(2-trimethylsilylethoxymethyl)benzimidazol-5-yl]oxy-quinoxalin-2-yl]pyrazol-1-yl]-3-fluoro-piperidine-1-carboxylate (220 mg, 311 μmol) and methylboronic acid (186 mg, 3.11 mmol) in dioxane (5 mL) and water (0.5 mL) was added sodium carbonate (98.8 mg, 932 μmol) and methanesulfonato (2-dicyclohexylphosphino-2,4,6-tri-i-propyl-1,1'-biphenyl) (2-amino-1,1'-biphenyl-2-yl) palladium (II) (36.7 mg, 46.6 μmol). The mixture was stirred at 110° C. for 12 h under nitrogen. The reaction mixture was poured into water (30 mL) and extracted with ethyl acetate (20 mL×3). The combined organic layers were dried over anhydrous sodium sulfate, filtered and concentrated under reduced pressure. The residue was purified by column chromatography (petroleum ether/ethyl acetate=10/1 to 1/8) to give (3S,4S)-tert-butyl 3-fluoro-4-(4-(8-methyl-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (140 mg, 203 μmol, 66%) as a yellow solid; m/z ES+ $[M+H]^+$ 688.4.

Step 2. 2-(1-((3S,4S)-3-Fluoropiperidin-4-yl)-1H-pyrazol-4-yl)-8-methyl-7-((2-methyl-1-((2-(trimethylsilyl)ethoxy)methyl)-1H-benzo[d]imidazol-6-yl)oxy)quinoxaline To a solution of tert-butyl (3S,4S)-3-fluoro-4-[4-[8-methyl-7-[2-methyl-3-(2-trimethylsilylethoxymethyl)benzimidazol-5-yl]oxy-quinoxalin-2-yl]pyrazol-1-yl]piperidine-1-carboxylate (130 mg, 189 μmol) in dichloromethane (3 mL) was added trifluoroacetic acid (462 mg, 4.05 mmol). The mixture was stirred at 25° C. for 1 h. The reaction mixture was diluted with sat. sodium bicarbonate (30 mL) and extracted with dichloromethane (20 mL×3). The combined organic layers were dried over anhydrous sodium sulfate, filtered and concentrated under reduced pressure to give 2-(1-((3S,4S)-3-fluoropiperidin-4-yl)-1H-pyrazol-4-yl)-8-methyl-7-((2-methyl-1-((2-(trimethylsilyl)ethoxy)methyl)-1H-benzo[d]imidazol-6-yl)oxy)quinoxaline (100 mg, crude) as a yellow solid. m/z ES+ $[M+H]^+$ 588.2.

Intermediate 35 and 36: tert-Butyl 4-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl) piperidine-1-carboxylate and 8-chloro-7-((2-methyl-1-((2-(trimethylsilyl)ethoxy)methyl)-1H-benzo[d]imidazol-6-yl)oxy)-2-(1-(piperidin-4-ylmethyl)-1H-pyrazol-4-yl)quinoxaline Step 1. tert-Butyl 4-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl) piperidine-1-carboxylate To a solution of 2-[[6-[5-chloro-3-(1H-pyrazol-4-yl)quinoxalin-6-yl]oxy-2-methyl-benzimidazol-1-yl]methoxy]ethyl-trimethyl-silane (500 mg, 0.99 mmol) and tert-butyl 4-(bromomethyl) piperidine-1-carboxylate (302 mg, 1.08 mmol) in N,N-dimethylformamide (10 mL) was added potassium carbonate (409 mg, 2.96 mmol). The mixture was stirred at 80° C. for 12 hours. The reaction mixture was diluted with $H_2O$ (30 mL) and extracted with ethyl acetate (20 mL×3). The combined organic layers were dried over sodium sulfate, filtered and concentrated under reduced pressure. The residue was purified by column chromatography (silica gel, dichloromethane:methanol=100/1 to 10/1) to give tert-butyl 4-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl) piperidine-1-carboxylate (700 mg, 974 μmol, 99%) as a yellow oil. m/z ES+ $[M+H]^+$ 704.3.

Step 2. 8-Chloro-7-((2-methyl-1-((2-(trimethylsilyl)ethoxy)methyl)-1H-benzo[d]imidazol-6-yl)oxy)-2-(1-(piperidin-4-ylmethyl)-1H-pyrazol-4-yl)quinoxaline To a solution of tert-butyl 4-[[4-[8-chloro-7-[2-methyl-3-(2-trimethylsilylethoxymethyl)benzimidazol-5-yl]oxy-quinoxalin-2-yl]pyrazol-1-yl]methyl]piperidine-1-carboxylate (700 mg, 0.99 mmol) in dichloromethane (10 mL) was added trifluoroacetic acid (1.54 g, 13.51 mmol, 1 mL). The mixture was stirred at 25° C. for 3 hours. The reaction mixture was diluted with sat. sodium bicarbonate (50 mL) and extracted with dichloromethane (20 mL×3). The com-

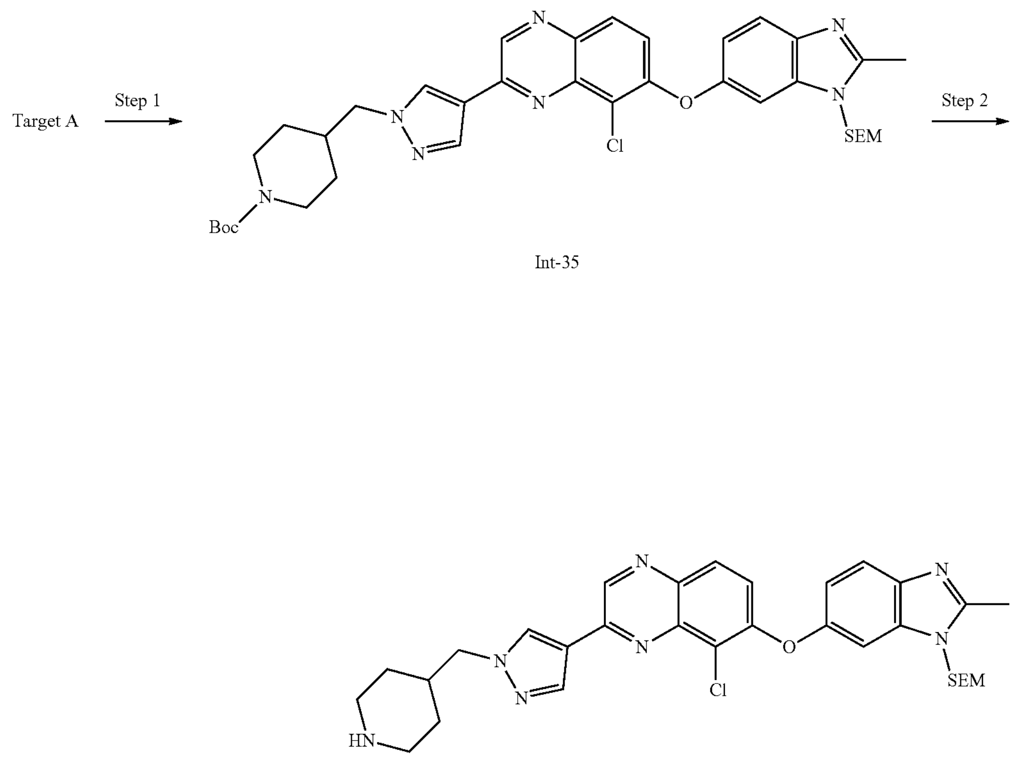

Int-35

Int-36 bined organic layers were dried over sodium sulfate, filtered and concentrated under reduced pressure to give 8-chloro-7-((2-methoxypyridin-4-yl)oxy)-2-(1-(piperidin-4-ylmethyl)-1H-pyrazol-4-yl)quinoxaline (680 mg, crude) as a yellow solid. m/z ES+ $[M+H]^+$ 604.1.

Intermediate 37:8-Chloro-7-((2-methyl-1H-benzo[d]imidazol-6-yl)oxy)-2-(1-(2-(piperidin-4-yl)ethyl)-1H-pyrazol-4-yl)quinoxaline

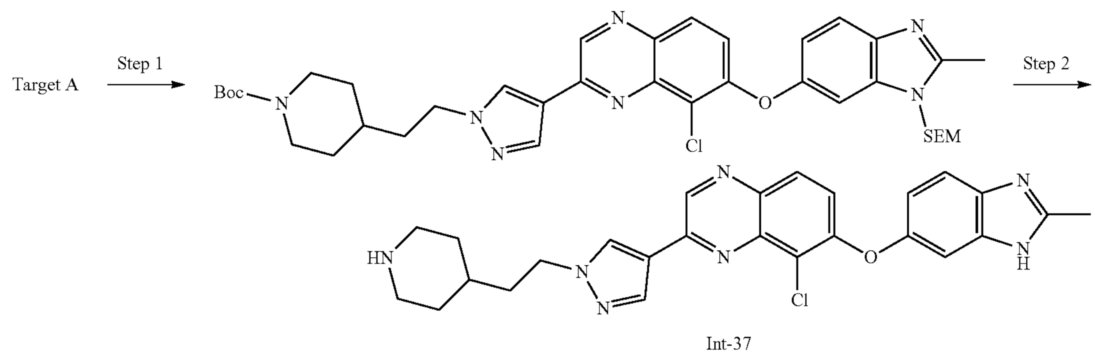

Int-37

Step 1. tert-Butyl 4-[2-[4-[8-chloro-7-[2-methyl-3-(2-trimethylsilylethoxymethyl)benzimidazol-5-yl]oxy-quinoxalin-2-yl]pyrazol-1-yl]ethyl]piperidine-1-carboxylate To a solution of 2-[[6-[5-chloro-3-(1H-pyrazol-4-yl)quinoxalin-6-yl]oxy-2-methyl-benzimidazol-1-yl]methoxy]ethyl-trimethyl-silane (832 mg, 1.64 mmol) in N,N-dimethyl formamide (10 mL) was added potassium carbonate (681 mg, 4.93 mmol) and tert-butyl 4-(2-bromoethyl) piperidine-1-carboxylate (480 mg, 1.64 mmol). The mixture was stirred at 80° C. for 2 h. On completion, the reaction mixture was diluted with water (25 mL) and extracted with ethyl acetate (25 mL×3). The combined organic layers were dried over anhydrous sodium sulfate, filtered and concentrated under reduced pressure to give tert-butyl 4-[2-[4-[8-chloro-7-[2-methyl-3-(2-trimethylsilylethoxymethyl)benzimidazol-5-yl]oxy-quinoxalin-2-yl]pyrazol-1-yl]ethyl]piperidine-1-carboxylate (1.20 g, crude) as a yellow oil. m/z ES+ $[M+H]^+$ 718.2.

Step 2. 8-Chloro-7-[(2-methyl-3H-benzimidazol-5-yl)oxy]-2-[1-[2-(4-piperidyl)ethyl]pyrazol-4-yl]quinoxaline A solution of tert-butyl 4-[2-[4-[8-chloro-7-[2-methyl-3-(2-trimethylsilylethoxymethyl)benzimidazol-5-yl]oxy-quinoxalin-2-yl]pyrazol-1-yl]ethyl]piperidine-1-carboxylate (500 mg, 696 μmol) in trifluoroacetic acid (6 mL) was stirred at 25° C. for 0.5 h. On completion, the reaction mixture was concentrated under reduced pressure to give 8-chloro-7-[(2-methyl-3H-benzimidazol-5-yl)oxy]-2-[1-[2-(4-piperidyl)ethyl]pyrazol-4-yl]quinoxaline (500 mg, crude) as a yellow oil. m/z ES+ $[M+H]^+$ 488.1.

Intermediate 38:8-Chloro-7-((2-methyl-1-((2-(trimethylsilyl)ethoxy)methyl)-1H-benzo[d]imidazol-6-yl)oxy)-2-(1-((4-(methylthio)cyclohexyl)methyl)-1H-pyrazol-4-yl)quinoxaline

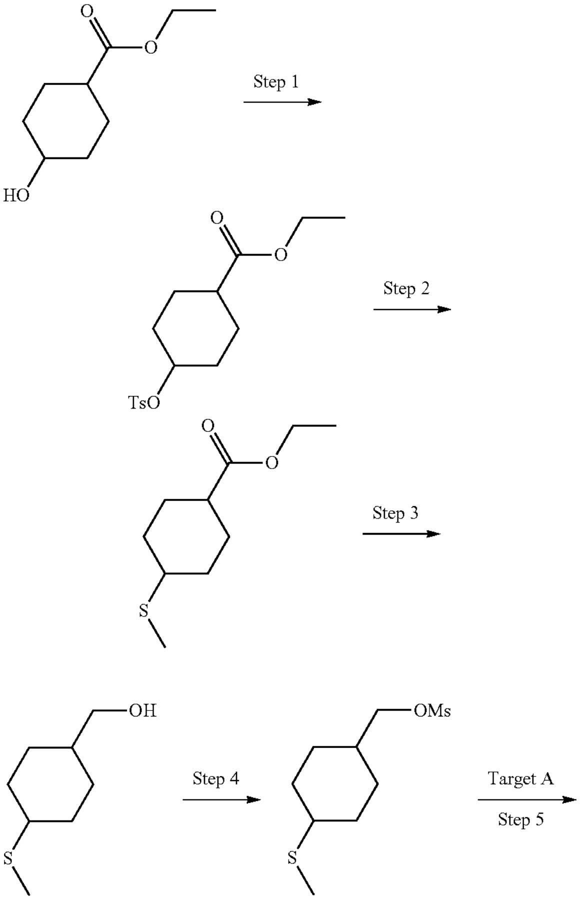

-continued

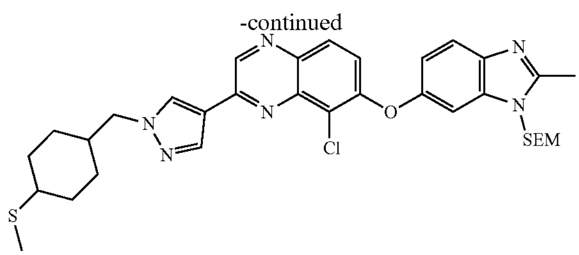

Int-38

Step 1. Ethyl 4-(p-tolylsulfonyloxy)cyclohexanecarboxylate

To a solution of ethyl 4-hydroxycyclohexanecarboxylate (1 g, 5.81 mmol) in dichloromethane (20 mL) was added 4-methylbenzenesulfonyl chloride (1.22 g, 6.39 mmol), triethylamine (646 mg, 6.39 mmol) and 4-dimethylaminopyridine (70.9 mg, 581 μmol), the mixture was stirred at 20° C. for 24 h. On completion, the mixture was quenched with water (10 mL) and extracted with dichloromethane (3×20 mL). The combined organic layers were dried over anhydrous sodium sulfate, filtered and concentrated. The residue was purified by column chromatography (petroleum ether/ethyl acetate from 50/1 to 10/1) to give ethyl 4-(p-tolylsulfonyloxy)cyclohexanecarboxylate (1.7 g, 5.21 mmol, 87%) as a colorless oil. $^1$H NMR (400 MHz, $CDCl_3$) δ 7.82 (d, J=8.4 Hz, 2H), 7.36 (d, J=8.0 Hz, 2H), 4.17-4.08 (m, 2H), 3.25 (q, J=7.2 Hz, 1H), 2.47 (s, 3H), 2.35-2.20 (m, 1H), 2.04-1.94 (m, 3H), 1.92-1.85 (m, 1H), 1.77-1.67 (m, 1H), 1.55-1.43 (m, 3H), 1.26 (q, J=7.2 Hz, 3H).

Step 2. Ethyl 4-methylsulfanylcyclohexanecarboxylate

To a solution of ethyl 4-(p-tolylsulfonyloxy)cyclohexanecarboxylate (1.2 g, 3.68 mmol) in ethanol (20 mL) was added sodium methanethiolate (1.29 g, 18.38 mmol), the mixture was stirred at 80° C. for 2 h. On completion, the mixture was quenched with water (20 mL) and extracted with ethyl acetate (3×20 mL). The combined organic layers were dried over sodium sulfate, filtered and concentrated in vacuo. The residue was purified by column chromatography (petroleum ether/ethyl acetate from 20/1 to 5/1) to give ethyl 4-methylsulfanylcyclohexanecarboxylate (550 mg, 2.72 mmol, 74%) as a colorless oil. $^1$H NMR (400 MHz, $CDCl_3$) δ 4.15 (s, 2H), 2.86-2.77 (m, 1H), 2.50-2.42 (m, 1H), 2.09 (s, 3H), 2.08-2.01 (m, 2H), 1.88-1.64 (m, 5H), 1.54-1.31 (m, 1H), 1.30-1.26 (m, 3H).

Step 3. (4-Methylsulfanylcyclohexyl)methanol

To a solution of ethyl 4-methylsulfanylcyclohexanecarboxylate (150 mg, 741 μmol) in tetrahydrofuran (10 mL) was added lithium borohydride (48.5 mg, 2.22 mmol) at 0° C., then the mixture was stirred at 20° C. for 2 h. On completion, the mixture was quenched with water (10 mL) and extracted with ethyl acetate (3×10 mL). The organic layers were dried over anhydrous sodium sulfate, filtered and concentrated. The residue was purified by column chromatography (petroleum ether/ethyl acetate from 10/1 to 3/1) to give (4-methylsulfanylcyclohexyl) methanol (60 mg, 370 umol, 50%) as a colorless oil. $^1$H NMR (400 MHz, $CDCl_3$) δ 3.54 (d, J=6.0 Hz, 2H), 3.01-2.95 (J=4.0 Hz, 1H), 2.09 (s, 3H), 1.90-1.72 (m, 4H), 1.64-1.47 (m, 5H).

Step 4. (4-methylsulfanylcyclohexyl)methyl methanesulfonate

To a solution of (4-methylsulfanylcyclohexyl) methanol (60.0 mg, 374 μmol) and diisopropylethylamine (145 mg, 1.12 mmol) in tetrahydrofuran (5 mL) was added methanesulfonyl chloride (98.6 mg, 861 μmol), the mixture was stirred at 20° C. for 1 h. On completion, the mixture was quenched with water (10 mL) and extracted with ethyl acetate (3×10 mL). The combined organic layers were dried over anhydrous sodium sulfate, filtered and concentrated in vacuo to give (4-methylsulfanylcyclohexyl)methyl methanesulfonate (70 mg, crude) as a colorless oil. 1H NMR (400 MHz, $CDCl_3$) δ 4.13-4.03 (m, 2H), 3.70 (s, 3H), 3.09-2.95 (m, 4H), 2.14-2.08 (m, 3H), 1.89-1.75 (m, 4H), 1.65-1.53 (m, 4H).

Step 5. 2-[[6-[5-Chloro-3-[1-[(4-methylsulfanylcyclohexyl)methyl]pyrazol-4-yl]quinoxalin-6-yl]oxy-2-methyl-benzimidazol-1-yl]methoxy]ethyl-trimethyl-silane A mixture of 2-[[6-[5-chloro-3-(1H-pyrazol-4-yl)quinoxalin-6-yl]oxy-2-methyl-benzimidazol-1-yl]methoxy]ethyl-trimethyl-silane (100 mg, 197 μmol), (4-methylsulfanylcyclohexyl)methyl methanesulfonate (68.2 mg, 286 μmol) and potassium carbonate (81.8 mg, 592 μmol) in N,N-dimethylformamide (2 mL) was stirred at 80° C. for 1 h. On completion, the mixture was quenched with water (5 mL) and extracted with ethyl acetate (10 mL×3). The combined organic layers were dried over anhydrous sodium sulfate, filtered and concentrated. The residue was purified by column chromatography (dichloromethane/methanol=100/1 to 20/1) to give 2-[[6-[5-chloro-3-[1-[(4-methylsulfanylcyclohexyl)methyl]pyrazol-4-yl]quinoxalin-6-yl]oxy-2-methyl-benzimidazol-1-yl]methoxy]ethyl-trimethyl-silane (35 mg, 54.0 umol, 22%) as a yellow solid. m/z ES+ $[M+H]^+$ 649.2.

Intermediate 39:8-Chloro-7-((2-methyl-1-((2-(trimethylsilyl)ethoxy)methyl)-1H-benzo[d]imidazol-6-yl)oxy)-2-(1-((1-((tetrahydro-2H-pyran-2-yl)oxy)cyclopropyl)methyl)-1H-pyrazol-4-yl)quinoxaline

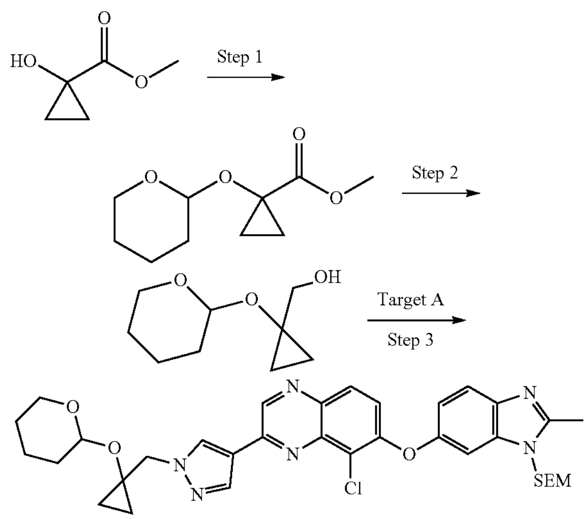

Int-39

Step 1. Methyl 1-tetrahydropyran-2-yloxycyclopropanecarboxylate

To a solution of methyl 1-hydroxycyclopropanecarboxylate (1 g, 8.61 mmol) in dichloromethane (15 mL) was added pyridinium p-toluenesulfonate (216 mg, 861 μmol) and 3,4-dihydro-2H-pyran (761 mg, 9.04 mmol). The mixture was stirred at 25° C. for 3 h. The reaction mixture was diluted with water (20 mL) and extracted with dichloromethane (20 mL×3). The combined organic layers were washed with brine (30 mL), dried over anhydrous sodium sulfate, filtered and concentrated under reduced pressure. The residue was purified by column chromatography (petroleum ether/ethyl acetate=10/1 to 6/1) to give methyl 1-tetrahydropyran-2-yloxycyclopropanecarboxylate (1.15 g, 5.74 mmol, 67%) as a white oil. $^1$H NMR (400 MHz, DMSO-d$_6$) δ 4.86-4.81 (m, 1H), 3.76-3.72 (m, 1H), 3.64 (s, 1H), 3.45-3.40 (m, 1H), 1.71-1.65 (m, 2H), 1.71-1.65 (m, 2H), 1.58-1.34 (m, 6H), 1.20-1.10 (m, 2H).

Step 2. (1-Tetrahydropyran-2-yloxycyclopropyl)methanol

To a mixture of methyl 1-tetrahydropyran-2-yloxycyclopropanecarboxylate (100 mg, 499 umol) in tetrahydrofuran (1 mL) at 0° C. was added lithium aluminum hydride (37.9 mg, 998 μmol) portion-wise under nitrogen atmosphere, the reaction mixture was stirred at 0° C. for 0.5 h. The reaction mixture was quenched with water (3 mL), sodium hydroxide solution (4 N, 3 mL) and then filtered. The filtrate was concentrated under reduced pressure to give (1-tetrahydropyran-2-yloxycyclopropyl) methanol (80.0 mg, 464 μmol, 93%) as a white oil without further purification. $^1$H NMR (400 MHz, CDCl$_3$) δ 4.73-4.63 (m, 1H), 4.11-3.98 (m, 2H), 3.68-3.58 (m, 1H), 3.11 (d, J=12.8 Hz, 1H), 1.87-1.79 (m, 1H), 1.71-1.64 (m, 1H), 1.61-1.54 (m, 3H), 1.53-1.50 (m, 1H), 0.96-0.89 (m, 1H), 0.85-0.78 (m, 1H), 0.76-0.69 (m, 1H), 0.66-0.56 (m, 1H).

Step 3. 2-[[6-[5-Chloro-3-[1-[(1-tetrahydropyran-2-yloxycyclopropyl)methyl]pyrazol-4-yl]quinoxalin-6-yl]oxy-2-methyl-benzimidazol-1-yl]methoxy]ethyl-trimethyl-silane To a solution of (1-tetrahydropyran-2-yloxycyclopropyl) methanol (100 mg, 580 μmol), 2-[[6-[[5-chloro-3-(1H-pyrazol-4-yl)quinoxalin-6-yl]oxy-2-methyl-benzimidazol-1-yl] methoxy]ethyl-trimethyl-silane (245 mg, 483 μmol) in toluene (2 mL) was added triphenylphosphine (190 mg, 725 μmol), the reaction was degassed and purged with nitrogen for 3 times. Then diisopropyl azodicarboxylate (146 mg, 725 μmol) was added dropwise, and the mixture was stirred at 60° C. for 1.5 h. The reaction mixture was washed with water (20 mL) and extracted with ethyl acetate (2×30 mL). The combined organic layers were washed with brine (2× 30 mL), dried over anhydrous sodium sulfate, filtered and concentrated under reduced pressure. The residue was purified by prep-TLC (silica gel, petroleum ether:ethyl acetate=1:1) to give 2-[[6-[5-chloro-3-[1-[(1-tetrahydropyran-2-yloxycyclopropyl)methyl]pyrazol-4-yl]quinoxalin-6-yl]oxy-2-methyl-benzimidazol-1-yl]methoxy]ethyl-trimethyl-silane (200 mg, 32.0 μmol, 62%) as a yellow oil. m/z ES+ [M+H]$^+$ 661.1.

Intermediate 40: tert-Butyl 4-((4-(4,4,5,5-tetramethyl-1,3,2-dioxaborolan-2-yl)-1H-pyrazol-1-yl) methyl) piperidine-1-carboxylate

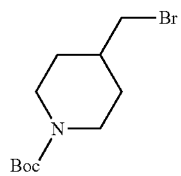

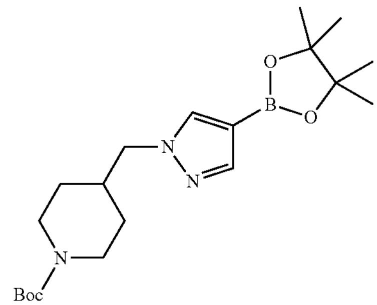

Int-40

Step 1. tert-Butyl 4-[[4-(4,4,5,5-tetramethyl-1,3,2-dioxaborolan-2-yl)pyrazol-1-yl]methyl]piperidine-1-carboxylate To a mixture of tert-butyl 4-(bromomethyl) piperidine-1-carboxylate (500 mg, 1.80 mmol) and 4-(4,4,5,5-tetramethyl-1,3,2-dioxaborolan-2-yl)-1H-pyrazole (366 mg, 1.89 mmol) in N,N-dimethyl formamide (8 mL) was added potassium carbonate (500 mg, 3.62 mmol). Then the mixture was stirred at 80° C. for 12 h. The mixture was quenched with water (20 mL) and extracted with ethyl acetate (25 mL×3). The combined organic phases were dried over anhydrous sodium sulfate, filtered and concentrated and the residue was purified by column chromatography (petroleum ether:ethyl acetate-10:1 to 2:1) to give tert-butyl 4-[[4-(4,4,5,5-tetramethyl-1,3,2-dioxaborolan-2-yl)pyrazol-1-yl] methyl]piperidine-1-carboxylate (450 mg, 1.15 mmol, 57%) as a colorless oil. $^1$H NMR (400 MHz, CDCl$_3$) δ 7.92 (s, 1H), 7.71 (s, 1H), 4.19 (d, J=6.4 Hz, 2H), 4.14-4.07 (m, 2H), 2.72-2.63 (m, 2H), 2.26-2.13 (m, 1H), 1.57 (d, J=12.4 Hz, 2H), 1.45 (s, 9H), 1.24 (s, 12H), 1.21-1.11 (m, 2H); m/z ES+ [M+H]$^+$ 392.0.

Example 1. Synthesis of 1-[4-[2-[4-[8-chloro-7-[(2-methyl-3H-benzimidazol-5-yl)oxy]-quinoxalin-2-yl] pyrazol-1-yl]ethyl]-1-piperidyl]prop-2-en-1-one

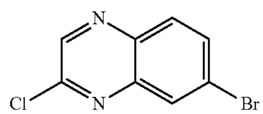

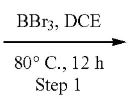

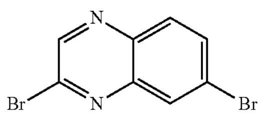

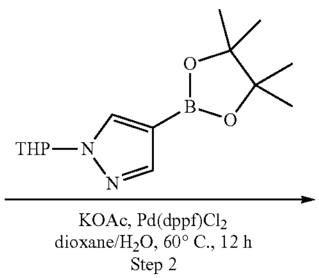

-continued
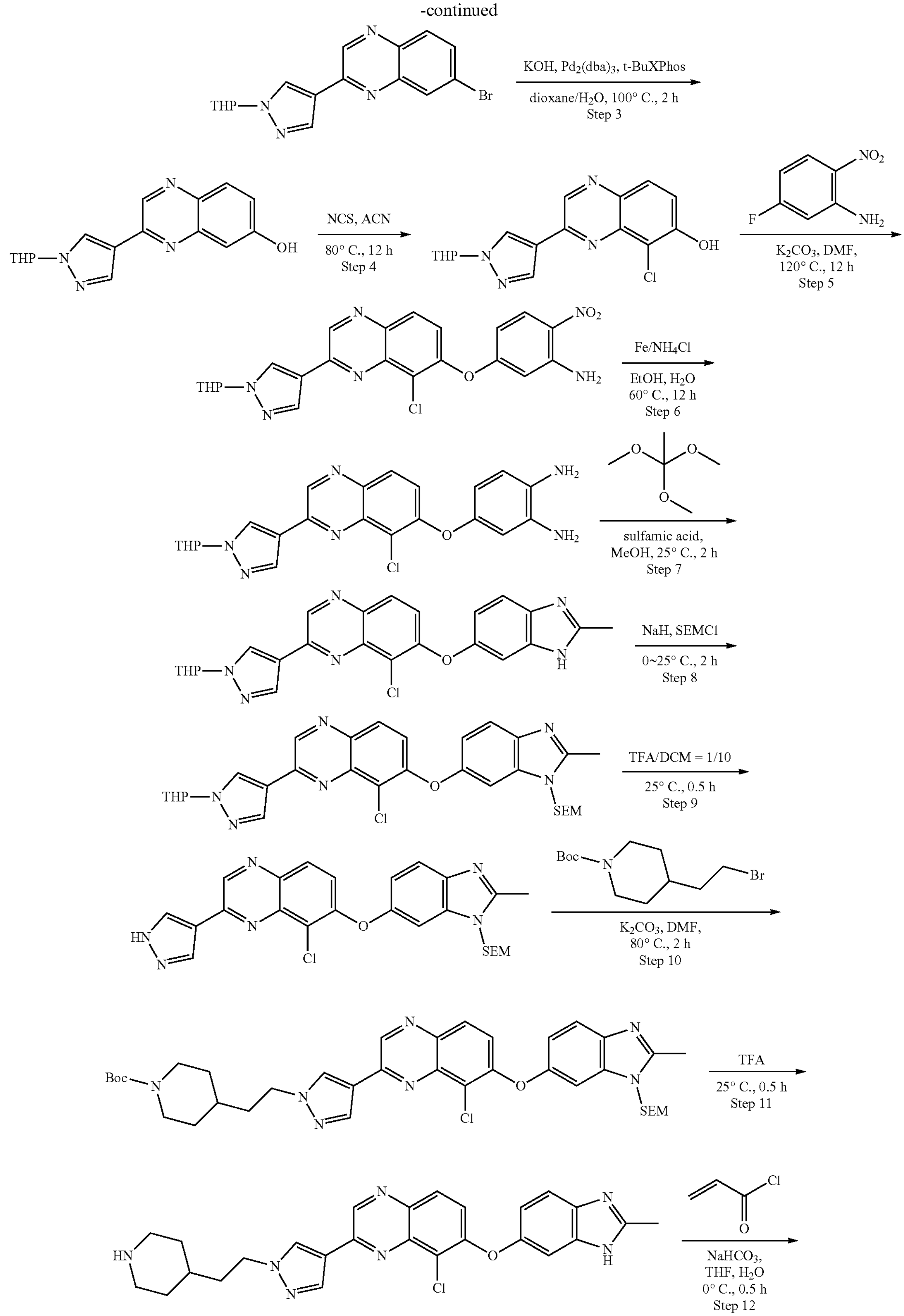

-continued

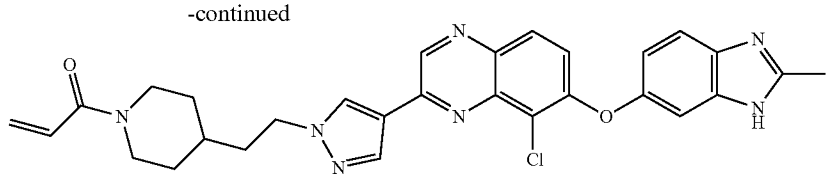

Step 1. To a solution of 7-bromo-2-chloro-quinoxaline (5 g, 20.5 mmol) in dichloroethane (50 mL) was added $BBr_3$ (25.7 g, 102 mmol). The mixture was stirred at 80° C. for 12 h. On completion, the reaction mixture was diluted with water (50 mL) and extracted with ethyl acetate (50 mL×3). The combined organic layers were dried over anhydrous sodium sulfate, filtered and concentrated under reduced pressure to give 2,7-dibromoquinoxaline (5.8 g, crude) as a red solid. $^1$H NMR (400 MHz, $CDCl_3$) δ 8.86 (s, 1H), 8.21 (d, J=2.0 Hz, 1H), 8.01-7.95 (m, 1H), 7.90-7.84 (m, 1H).

Step 2. A mixture of 2,7-dibromoquinoxaline (5.8 g, 20.1 mmol), 1-tetrahydropyran-2-yl-4-(4,4,5,5-tetramethyl-1,3,2-dioxaborolan-2-yl)pyrazole (5.32 g, 19.1 mmol), KOAc (5.93 g, 60.4 mmol), Pd(dppf)$Cl_2$ (1.47 g, 2.01 mmol) in dioxane (100 mL) and $H_2O$ (10 mL) was degassed and purged with $N_2$ for 3 times, and then the mixture was stirred at 60° C. for 12 h under $N_2$ atmosphere. On completion, the reaction mixture was diluted with water (25 mL) and extracted with ethyl acetate (25 mL×3). The combined organic layers were dried over anhydrous sodium sulfate, filtered and concentrated under reduced pressure. The residue was purified by column chromatography (silica gel, petroleum ether/ethyl acetate=10/1 to 2/1) to give 7-bromo-2-(1-tetrahydropyran-2-ylpyrazol-4-yl)quinoxaline (3.5 g, 34%) as a red solid. m/z ES+ $[M+H]^+$ 359.1.

Step 3. A mixture of 7-bromo-2-(1-tetrahydropyran-2-ylpyrazol-4-yl)quinoxaline (3.5 g, 9.74 mmol), $Pd_2(dba)_3$ (892 mg, 974 μmol), t-BuXPhos (413 mg, 974 μmol) and KOH (5.47 g, 97.4 mmol) in dioxane (30 mL) and $H_2O$ (10 mL) was degassed and purged with $N_2$ for 3 times, and then the mixture was stirred at 100° C. for 2 h under $N_2$ atmosphere. On completion, the reaction mixture was concentrated under reduced pressure. The residue was purified by column chromatography (silica gel, petroleum ether/ethyl acetate=10/1 to 1/1) to give 3-(1-tetrahydropyran-2-ylpyrazol-4-yl)quinoxalin-6-ol (1.10 g, 38%) as a red solid. m/z ES+ $[M+H]^+$ 297.2.

Step 4. To a solution of 3-(1-tetrahydropyran-2-ylpyrazol-4-yl)quinoxalin-6-ol (3.4 g, 11.4 mmol) in acetonitrile (50 mL) was added N-chlorosuccinimide (1.53 g, 11.4 mmol) portion-wise. The mixture was stirred at 80° C. for 12 h. On completion, the reaction mixture was concentrated under reduced pressure. The residue was purified by column chromatography (silica gel, petroleum ether/ethyl acetate=10/1 to 1/1) to give 5-chloro-3-(1-tetrahydropyran-2-ylpyrazol-4-yl)quinoxalin-6-ol (2.5 g, 62%) as a yellow solid. m/z ES+ $[M+H]^+$ 330.9.

Step 5. To a solution of 5-chloro-3-(1-tetrahydropyran-2-ylpyrazol-4-yl)quinoxalin-6-ol (1 g, 3.02 mmol) in DMF (20 mL) was added $K_2CO_3$ (835 mg, 6.05 mmol) and 5-fluoro-2-nitro-aniline (707 mg, 4.53 mmol). The mixture was stirred at 120° C. for 12 h. On completion, the reaction mixture was diluted with water (25 mL) and extracted with ethyl acetate (25 mL×3). The combined organic layers were dried over anhydrous sodium sulfate, filtered and concentrated under reduced pressure. The residue was purified by column chromatography (silica gel, petroleum ether/ethyl acetate=10/1 to 1/1) to give 5-[5-chloro-3-(1-tetrahydropyran-2-ylpyrazol-4-yl)quinoxalin-6-yl]oxy-2-nitro-aniline (800 mg, 36%) as a yellow solid. m/z ES+ $[M+H]^+$ 467.1.

Step 6. To a solution of 5-[5-chloro-3-(1-tetrahydropyran-2-ylpyrazol-4-yl)quinoxalin-6-yl]oxy-2-nitro-aniline (800 mg, 1.71 mmol) in ethanol (10 mL) and $H_2O$ (2 mL) was added iron powder (765 mg, 13.7 mmol) and $NH_4Cl$ (733 mg, 13.7 mmol). The mixture was stirred at 60° C. for 12 h. On completion, the reaction mixture was concentrated under reduced pressure then the residue was diluted with water (25 mL) and extracted with ethyl acetate (25 mL×3). The combined organic layers were dried over anhydrous sodium sulfate, filtered and concentrated under reduced pressure. The residue was purified by column chromatography (silica gel, petroleum ether/ethyl acetate=10/1 to 0/1) to give 4-[5-chloro-3-(1-tetrahydropyran-2-ylpyrazol-4-yl)quinoxalin-6-yl]oxybenzene-1,2-diamine (300 mg, 36%) as a yellow solid. m/z ES+ $[M+H]^+$ 504.4.

Step 7. To a solution of 4-[5-chloro-3-(1-tetrahydropyran-2-ylpyrazol-4-yl)quinoxalin-6-yl]oxybenzene-1,2-diamine (250 mg, 572 μmol) in methanol (3 mL) was added sulfamic acid (111 mg, 1.14 mmol) and 1,1,1-trimethoxyethane (343 mg, 2.86 mmol). The mixture was stirred at 25° C. for 2 h. On completion, the reaction mixture was concentrated under reduced pressure to give 8-chloro-7-[(2-methyl-3H-benzimidazol-5-yl)oxy]-2-(1-tetrahydropyran-2-ylpyrazol-4-yl)quinoxaline (400 mg, crude) as a red solid. m/z ES+ $[M+H]^+$ 461.4.

Step 8. To a solution of 8-chloro-7-[(2-methyl-3H-benzimidazol-5-yl)oxy]-2-(1-tetrahydropyran-2-ylpyrazol-4-yl)quinoxaline (380 mg, 824 μmol) in THF (5 mL) was added NaH (65.9 mg, 1.65 mmol, 60% purity) at 0° C. and the mixture was stirred at 0° C. for 0.5 h. Then SEM-Cl (206 mg, 1.24 mmol) was added and the mixture was stirred at 25° C. for 1.5 h. On completion, the reaction mixture was diluted with water (5 mL) and extracted with ethyl acetate (5 mL×3). The combined organic layers were dried over anhydrous sodium sulfate, filtered and concentrated under reduced pressure. The residue was purified by column chromatography (silica gel, petroleum ether/ethyl acetate=10/1 to 0/1) to give 2-[[6-[5-chloro-3-(1-tetrahydropyran-2-ylpyrazol-4-yl)quinoxalin-6-yl]oxy-2-methyl-benzimidazol-1-yl]methoxy]ethyl-trimethyl-silane (220 mg, 35%) as a yellow solid. m/z ES+ $[M+H]^+$ 591.3.

Step 9. To a solution of 2-[[6-[5-chloro-3-(1-tetrahydropyran-2-y] pyrazol-4-yl)quinoxalin-6-yl]oxy-2-methyl-benzimidazol-1-yl]methoxy]ethyl-trimethyl-silane (170 mg, 287 μmol) in dichloromethane (3 mL) was added TFA (462 mg, 4.05 mmol, 0.3 mL). The mixture was stirred at 25° C. for 0.5 h. On completion, the reaction mixture was concentrated under reduced pressure. The crude product was purified by reversed-phase HPLC (0.1% ammonium hydroxide) to give 2-[[6-[5-chloro-3-(1H-pyrazol-4-yl)quinoxalin-6-yl]oxy-2-methyl-benzimidazol-1-yl]methoxy]ethyl-trimethyl-silane (50 mg, crude) as a red oil. m/z ES+ $[M+H]^+$ 507.2.

Step 10. To a solution of 2-[6-[5-chloro-3-(1H-pyrazol-4-yl)quinoxalin-6-ylJoxy-2-methyl-benzimidazol-1-yl]methoxy]ethyl-trimethyl-silane (45 mg, 88.7 μmol) in DMF (1 mL) was added $K_2CO_3$ (36.8 mg, 266 μmol) and tert-butyl 4-(2-bromoethyl) piperidine-1-carboxylate (25.9 mg, 88.7 μmol). The mixture was stirred at 80° C. for 2 h. On completion, the reaction mixture was diluted with water (5 mL) and extracted with ethyl acetate (5 mL×3). The combined organic layers were dried over $Na_2SO_4$, filtered and concentrated under reduced pressure to give tert-butyl 4-[2-[4-[8-chloro-7-[2-methyl-3-(2-trimethylsilylethoxymethyl) benzimidazol-5-yl]oxy-quinoxalin-2-yl]pyrazol-1-yl]ethyl] piperidine-1-carboxylate (50 mg, crude) as a yellow oil. m/z ES+ $[M+H]^+$ 718.3.

Step 11. A solution of tert-butyl 4-[2-[4-[8-chloro-7-[2-methyl-3-(2-trimethylsilylethoxymethyl)benzimidazol-5-yl] oxy-quinoxalin-2-yl]pyrazol-1-yl]ethyl]piperidine-1-carboxylate (45 mg, 62.6 μmol) in TFA (1 mL) was stirred at 25° C. for 0.5 h. On completion, the reaction mixture was concentrated under reduced pressure to give 8-chloro-7-[(2-methyl-3H-benzimidazol-5-yl)oxy]-2-[1-[2-(4-piperidyl) ethyl]pyrazol-4-yl]quinoxaline (50 mg, crude) as a red oil. m/z ES+ $[M+H]^+$ 488.0.

Step 12. To a solution of 8-chloro-7-[(2-methyl-3H-benzimidazol-5-yl)oxy]-2-[1-[2-(4-piperidyl)ethyl]pyrazol-4-yl]quinoxaline (35 mg, 71.7 μmol) in THF (0.5 mL) and $H_2O$ (0.5 mL) was added $NaHCO_3$ (18.1 mg, 215 μmol) and prop-2-enoyl chloride (9.74 mg, 108 μmol). The mixture was stirred at 0° C. for 0.5 h. On completion, the reaction mixture was concentrated under reduced pressure. The residue was purified by preparative-HPLC (column: Phenomenex Gemini-NX C18 75*30 mm*3 μm; mobile phase: [water (0.225% formic acid)-acetonitrile]; B %: 15%-45%, 7 min) to give 1-[4-[2-[4-[8-chloro-7-[(2-methyl-3H-benzimidazol-5-yl)oxy]quinoxalin-2-yl]pyrazol-1-yl]ethyl]-1-piperidyl]prop-2-en-1-one (18.4 mg, 46%) as a yellow solid. m/z ES+ $[M+H]^+$ 542.5; $^1H$ NMR (400 MHz, DMSO-$d_6$) δ 12.33 (br s, 1H), 9.31 (s, 1H), 8.75 (s, 1H), 8.36 (s, 1H), 7.95 (d, J=9.2 Hz, 1H), 7.51 (d, J=8.0 Hz, 1H), 7.38-7.16 (m, 2H), 6.98-6.91 (m, 1H), 6.85-6.75 (m, 1H), 6.11-6.03 (m, 1H), 5.68-5.61 (m, 1H), 4.40 (d, J=11.6 Hz, 1H), 4.33-4.26 (m, 2H), 4.03 (d, J=13.2 Hz, 1H), 3.05-2.94 (m, 1H), 2.64-2.54 (m, 1H), 2.49 (s, 3H), 1.87-1.73 (m, 4H), 1.59-1.46 (m, 1H), 1.16-0.99 (m, 2H).

Example 2. Synthesis of 8-chloro-7-[(2-methyl-3H-benzimidazol-5-yl)oxy]-2-[1-[(1,2,2-trimethyl-4-piperidyl)methyl]pyrazol-4-yl]quinoxaline

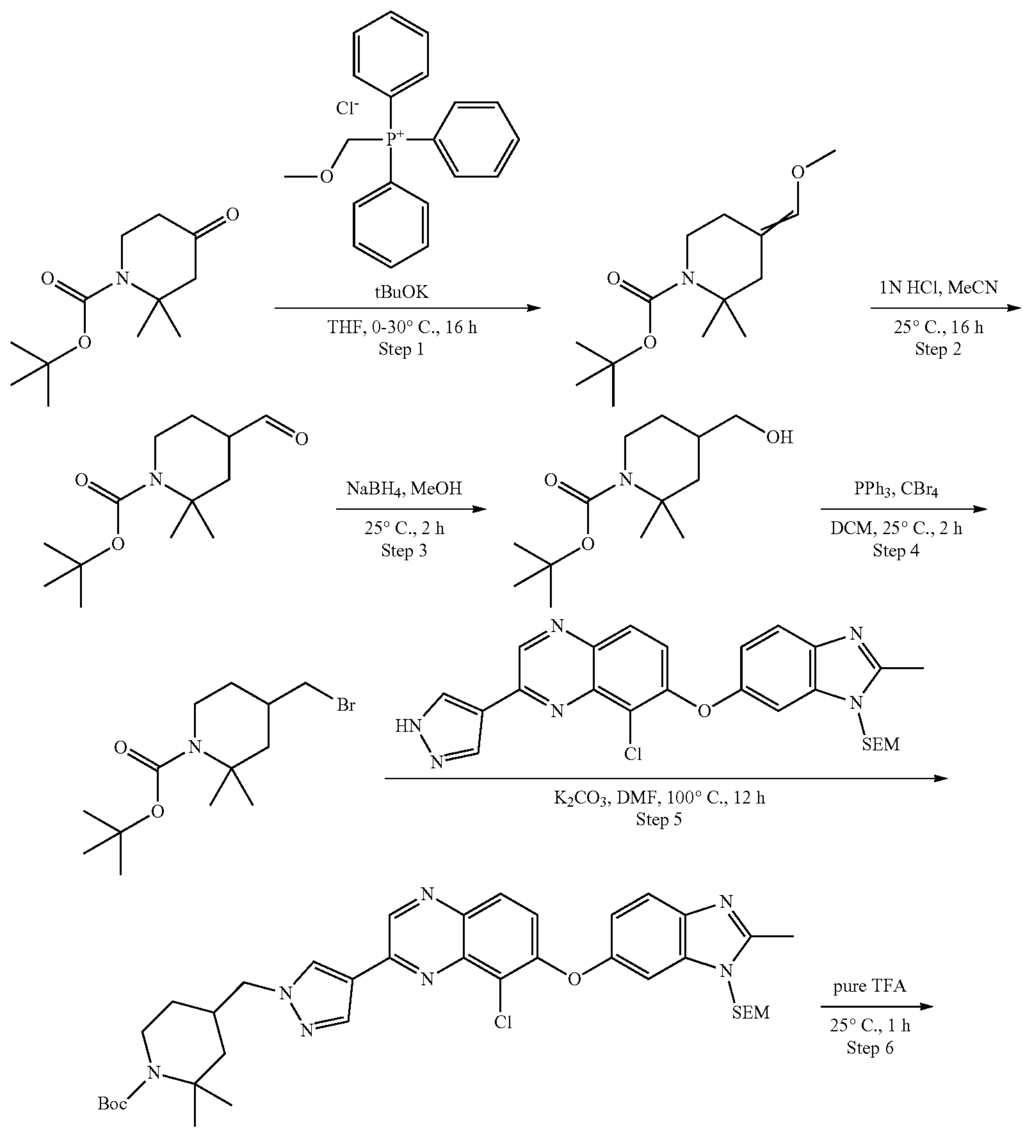

-continued

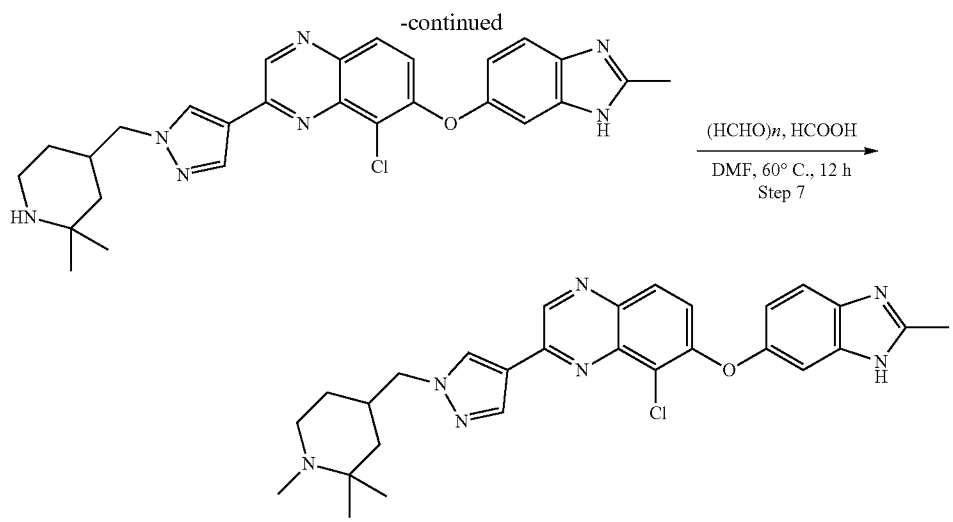

Step 1. To a solution of (methoxymethyl)triphenylphosphonium chloride (4.52 g, 13.2 mmol) in THF (15 mL) was added tBuOK (1.48 g, 13.2 mmol) portion-wise at 0° C. The mixture was stirred at 0° C. for 1 h, then tert-butyl 2,2-dimethyl-4-oxo-piperidine-1-carboxylate (2 g, 8.8 mmol) in THF (15 mL) was added. The mixture was stirred at 30° C. for 15 h. The reaction mixture was concentrated under reduced pressure, then diluted with water (30 mL) and extracted with ethyl acetate (30 mL×3). The combined organic layers were washed with brine (30 mL×3), dried over $Na_2SO_4$, filtered and concentrated in vacuo. The residue was purified by column chromatography (silica gel, petroleum ether/ethyl acetate=50/1 to 20/1) to give tert-butyl 4-(methoxymethylene)-2,2-dimethyl-piperidine-1-carboxylate (1.7 g, 76%) as a colorless oil. $^1H$ NMR (400 MHz, $CDCl_3$) δ 5.93 (s, 1H), 5.84 (s, 1H), 3.58 (s, 4H), 2.36-2.33 (m, 2H), 2.22 (t, J=6.0 Hz, 3H), 2.11 (s, 2H), 1.39 (s, 9H), 1.37 (s, 6H).

Step 2. To a solution of tert-butyl 4-(methoxymethylene)-2,2-dimethyl-piperidine-1-carboxylate (1.7 g, 6.66 mmol) in acetonitrile (170 mL) at 0° C. was added HCl (1 M, 7.99 mL). The mixture was stirred at 25° C. for 16 h. The reaction mixture was quenched by sat. $NaHCO_3$ solution (20 mL) and concentrated under reduced pressure. The residue was then diluted with water (50 mL) and extracted with ethyl acetate (50 mL×3). The combined organic layers were washed with brine (50 mL×3), dried over $Na_2SO_4$, filtered and concentrated in vacuo to give tert-butyl 4-formyl-2,2-dimethyl-piperidine-1-carboxylate (1.6 g, 99%) as a white solid. $^1H$ NMR (400 MHz, $CDCl_3$) δ 9.68 (d, J=0.8 Hz, 1H), 3.57 (ddd, J=4.4, 8.0, 13.6 Hz, 1H), 3.48-3.37 (m, 1H), 2.69-2.56 (m, 1H), 1.99-1.87 (m, 1H), 1.84-1.69 (m, 3H), 1.50 (s, 3H), 1.47 (s, 9H), 1.39 (s, 3H).

Step 3. To a solution of tert-butyl 4-formyl-2,2-dimethyl-piperidine-1-carboxylate (1.6 g, 6.63 mmol) in ethanol (15 mL) was added $NaBH_4$ (276 mg, 7.29 mmol). The mixture was stirred at 25° C. for 2 h. The reaction mixture was quenched with water (30 mL) at 0° C. and extracted with dichloromethane (20 mL×3). The combined organic layers were washed with brine (30 mL×3), dried over $Na_2SO_4$, filtered and concentrated in vacuo to give tert-butyl 4-(hydroxymethyl)-2,2-dimethyl-piperidine-1-carboxylate (1.45 g, 90%) as a colorless oil. $^1H$ NMR (400 MHz, $CDCl_3$) δ 5.39-5.22 (m, 1H), 3.66 (ddd, J=4.4, 6.4, 13.6 Hz, 1H), 3.55-3.42 (m, 2H), 3.32-3.16 (m, 1H), 1.84 (br s, 2H), 1.56-1.54 (m, 1H), 1.50 (s, 3H), 1.46 (s, 9H), 1.38 (br d, J=12.8 Hz, 1H), 1.32 (s, 3H), 1.27-1.13 (m, 1H).

Step 4. Tert-butyl 4-(hydroxymethyl)-2,2-dimethyl-piperidine-1-carboxylate (500 mg, 2.05 mmol) and $CBr_4$ (886 mg, 2.67 mmol) were dissolved in dichloromethane (5 mL) and cooled to 0° C., then $PPh_3$ (647 mg, 2.47 mmol) was added. The mixture was stirred at 25° C. for 2 h. The reaction mixture was diluted with water (10 mL) and extracted with dichloromethane (10 mL×3). The combined organic layers were washed with brine (10 mL×3), dried over $Na_2SO_4$, filtered and concentrated in vacuo. The residue was purified by column chromatography (silica gel, petroleum ether/ethyl acetate=50/1 to 30/1) to give tert-butyl 4-(bromomethyl)-2,2-dimethyl-piperidine-1-carboxylate (550 mg, 87%) as a colorless oil. $^1H$ NMR (400 MHz, $CDCl_3$) δ 3.72 (ddd, J=4.4, 6.0, 13.6 Hz, 1H), 3.29 (d, J=6.4 Hz, 2H), 3.21 (ddd, J=4.0, 9.2, 13.6 Hz, 1H), 2.08-1.86 (m, 2H), 1.62-1.56 (m, 1H), 1.52 (s, 3H), 1.46 (s, 9H), 1.41 (br d, J=12.8 Hz, 1H), 1.30 (s, 3H), 1.28-1.20 (m, 1H).

Step 5. To a solution of 2-[[6-[5-chloro-3-(1H-pyrazol-4-yl)quinoxalin-6-yl]oxy-2-methyl-benzimidazol-1-yl]methoxy]ethyl-trimethyl-silane (80 mg, 158 μmol) in DMF (1 mL) was added $K_2CO_3$ (65.4 mg, 473 μmol), tert-butyl 4-(bromomethyl)-2,2-dimethyl-piperidine-1-carboxylate (72.47 mg, 237 μmol). The mixture was stirred at 100° C. for 2 h. The reaction mixture was diluted with water (3 mL) and extracted with ethyl acetate (3 mL×3). The combined organic layers were washed with brine (3 mL×3), dried over $Na_2SO_4$, filtered and concentrated in vacuo to give tert-butyl 4-[[4-[8-chloro-7-[2-methyl-3-(2-trimethylsilylethoxymethyl)benzimidazol-5-yl]oxy-quinoxalin-2-yl]pyrazol-1-yl]methyl]-2,2-dimethyl-piperidine-1-carboxylate (120 mg, crude) as a yellow solid. m/z ES+ $[M+H]^+$ 732.3.

Step 6. A solution of tert-butyl 4-[[4-[8-chloro-7-[2-methyl-3-(2-trimethylsilylethoxymethyl)benzimidazol-5-yl]oxy-quinoxalin-2-yl]pyrazol-1-yl]methyl]-2,2-dimethyl-piperidine-1-carboxylate (120 mg, 164 μmol) in TFA (1 mL) was stirred at 25° C. for 1 h. The reaction mixture was concentrated in vacuo to give 8-chloro-2-[1-[(2,2-dimethyl-4-piperidyl)methyl]pyrazol-4-yl]-7-[(2-methyl-3H-benzimidazol-5-yl)oxy]quinoxaline (100 mg, crude) as a yellow oil. m/z ES+ $[M+H]^+$ 502.0.

Step 7. To a solution of 8-chloro-2-[1-[(2,2-dimethyl-4-piperidyl)methyl]pyrazol-4-yl]-7-[(2-methyl-3H-benzimidazol-5-yl)oxy]quinoxaline (90 mg, 146 μmol, TFA) in DMF (1 mL) was added formic acid (140 mg, 2.92 mmol) and paraformaldehyde (87.7 mg, 2.92 mmol). The mixture was stirred at 60° C. for 12 h. The reaction mixture was filtered and concentrated in vacuo, which was purified by preparative-HPLC (column: Unisil 3-100 C18 Ultra 150*50 mm*3 μm; mobile phase: [water (0.225% formic acid)-acetonitrile]; B %: 5%-35%, 10 min) to give 8-chloro-7-[(2-methyl-3H-benzimidazol-5-yl)oxy]-2-[1-[(1,2,2-trimethyl-4-piperidyl)methyl]pyrazol-4-yl]quinoxaline (40.7 mg, 54%) as an off-white solid. m/z ES+ $[M+H]^+$ 516.3; $^1H$ NMR (400 MHz, DMSO-$d_6$) δ 12.29 (br s, 1H), 9.31 (s, 1H), 8.71 (s, 1H), 8.40 (s, 1H), 8.15 (s, 1H), 7.96 (d, J=9.2 Hz, 1H), 7.49 (br s, 1H), 7.32 (d, J=9.2 Hz, 1H), 7.21 (s, 1H), 6.97-6.88 (m, 1H), 4.22-4.08 (m, 2H), 3.10-3.00 (m, 1H), 2.98-2.89 (m, 1H), 2.50 (s, 6H), 2.35-2.26 (m, 1H), 1.65-1.55 (m, 2H), 1.47-1.31 (m, 2H), 1.28-1.21 (m, 3H), 1.15 (s, 3H).

Example 3. Synthesis of 4-((4-(8-chloro-7-((2-methyl-1H-benzo[d]imidazol-6-yl)oxy)-quinoxalin-2-yl)-1H-pyrazol-1-yl)methyl)-1-methylpiperidin-2-one

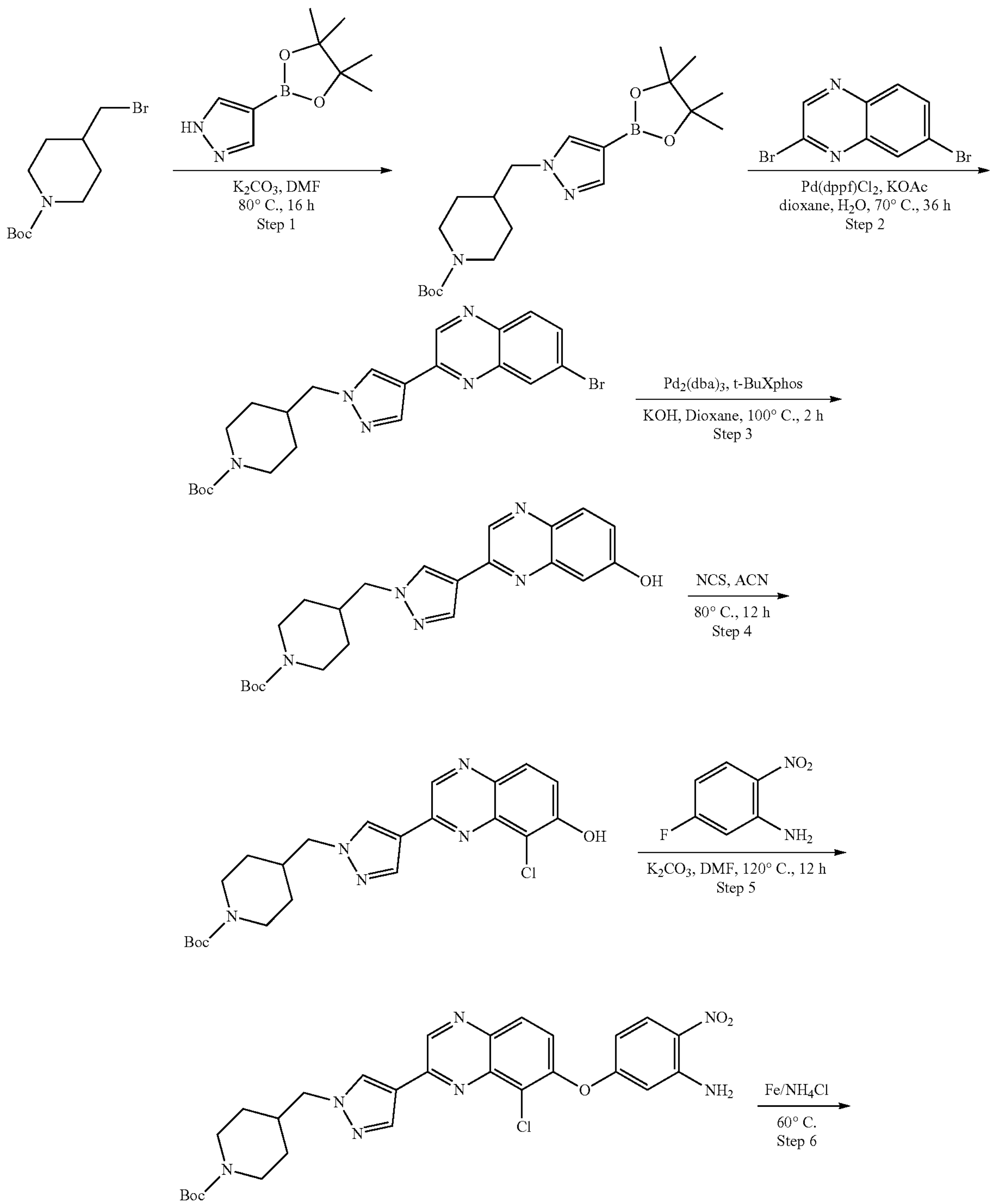

-continued
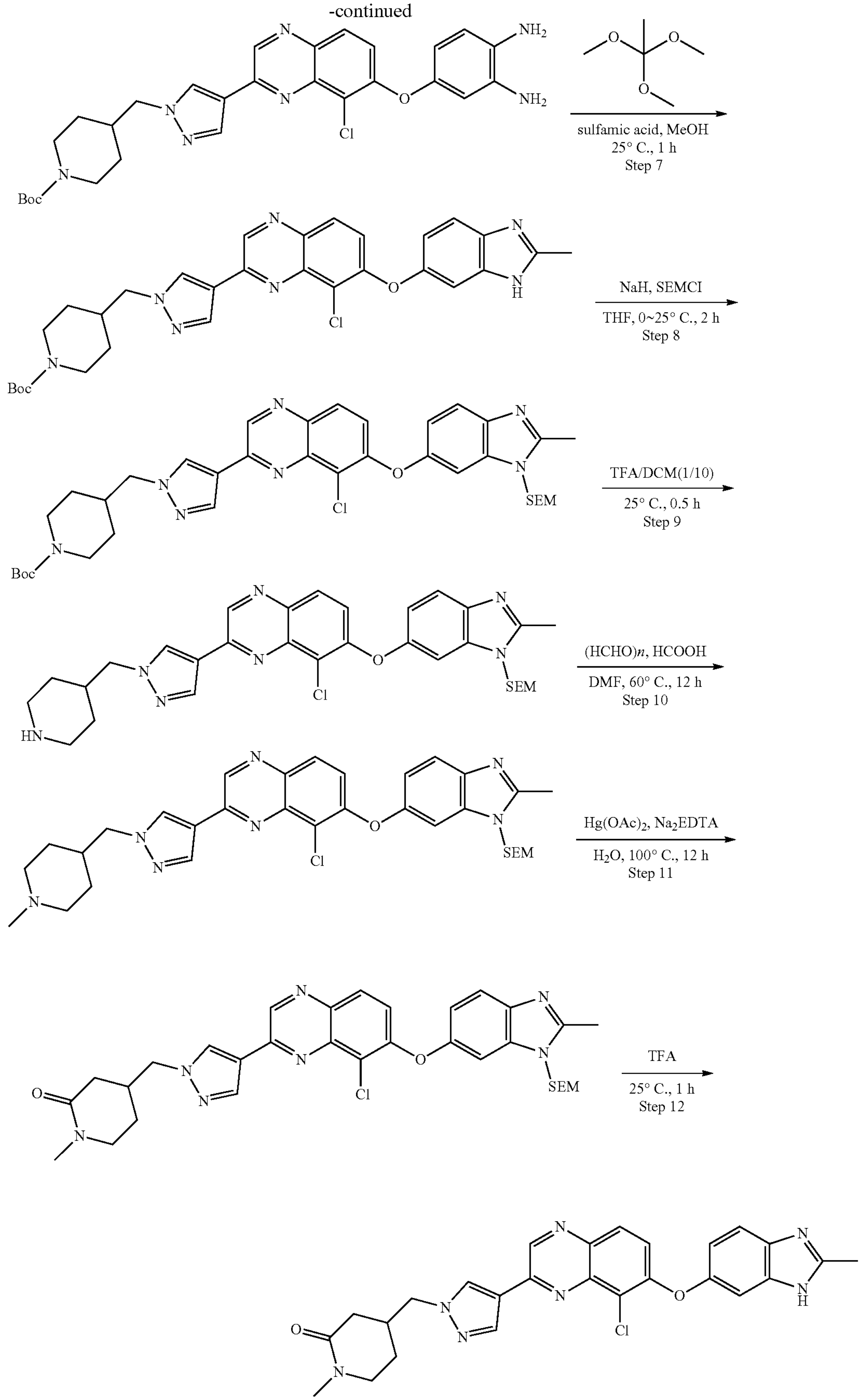

Step 1. To a solution of tert-butyl 4-(bromomethyl) piperidine-1-carboxylate (9.5 g, 34 mmol) in DMF (90 mL) was added $K_2CO_3$ (9.4 g, 68 mmol) and 4-(4,4,5,5-tetramethyl-1,3,2-dioxaborolan-2-yl)-1H-pyrazole (6.9 g, 36 mmol). The mixture was stirred at 80° C. for 12 h. The reaction mixture was diluted with $H_2O$ (150 mL) and extracted with ethyl acetate (80 mL×3). The combined organic layers were dried over $Na_2SO_4$, filtered and concentrated under reduced pressure. The residue was purified by column chromatography (silica gel, petroleum ether/ethyl acetate=20/1 to 3/1) to give 1-(4-((4-(8-chloro-7-((2-methyl-1H-benzo[d]imidazol-6-yl) oxy)quinoxalin-2-yl)-1H-pyrazol-1-yl)methyl) piperidin-1-yl)ethanone (7.2 g, 51%) as a white solid. $^1$H NMR (400 MHz, $CDCl_3$) δ ppm 7.80 (s, 1H) 7.65 (s, 1H) 4.13 (d, J=7.2 Hz, 2H) 4.01 (d, J=7.2 Hz, 2H) 2.66 (t, J=12.4 Hz, 2H) 2.15-2.05 (m, 1H) 1.54 (d, J=12.8 Hz, 2H) 1.45 (s, 9H) 1.32 (s, 12H) 1.20-1.12 (m, 2H).

Step 2. To a solution of tert-butyl 4-[[4-(4,4,5,5-tetramethyl-1,3,2-dioxaborolan-2-yl)pyrazol-1-yl]methyl]piperidine-1-carboxylate (20 g, 51 mmol) and 2,7-dibromoquinoxaline (18 g, 61 mmol) in dioxane (200 mL) and $H_2O$ (40 mL) was added KOAc (15 g, 0.15 mol) and Pd(dppf)$Cl_2$ (3.7 g, 5.1 mmol). The mixture was stirred at 70° C. for 36 h under $N_2$. The reaction mixture was diluted with $H_2O$ (500 mL) and extracted with dichloromethane (300 mL×3). The combined organic layers were dried over $Na_2SO_4$, filtered and concentrated under reduced pressure. The residue was purified by column chromatography (silica gel, petroleum ether/ethyl acetate=5/1 to 1/2) to give tert-butyl 4-((4-(7-bromoquinoxalin-2-yl)-1H-pyrazol-1-yl)methyl) piperidine-1-carboxylate (27 g, 54%) as a yellow solid. $^1$H NMR (400 MHz, $CDCl_3$) δ ppm 9.05 (s, 1H) 8.21 (s, 2H) 8.14 (s, 1H) 7.92 (d, J=8.8 Hz, 1H) 7.75 (dd, J=8.8, 2.0 Hz, 1H) 4.10 (d, J=7.2 Hz, 4H) 2.71 (t, J=12.0 Hz, 2H) 2.24-2.11 (m, 1H) 1.63 (d, J=12.4 Hz, 2H) 1.46 (s, 9H) 1.31-1.18 (m, 2H).

Step 3. To a solution of tert-butyl 4-[[4-(7-bromoquinoxalin-2-yl)pyrazol-1-yl]methyl]piperidine-1-carboxylate (27 g, 58 mmol) in dioxane (280 mL) and $H_2O$ (140 mL) was added $Pd_2(dba)_3$ (5.30 g, 5.8 mmol), t-BuXPhos (2.5 g, 5.8 mmol) and KOH (32 g, 0.58 mol). The mixture was degassed and purged with $N_2$ for 3 times, and then stirred at 100° C. for 3 h under $N_2$. The reaction mixture was diluted with $H_2O$ (500 mL) and extracted with dichloromethane (300 mL×3). The combined organic layers were dried over $Na_2SO_4$, filtered and concentrated under reduced pressure. The residue was purified by column chromatography (silica gel, petroleum ether/ethyl acetate=3/1 to dichloromethane/methanol=20/1) to give tert-butyl 4-((4-(7-hydroxyquinoxalin-2-yl)-1H-pyrazol-1-yl)methyl) piperidine-1-carboxylate (20 g, 84%) as a yellow solid. m/z ES+ $[M+H]^+$ 410.0.

Step 4. To a solution of tert-butyl 4-[[4-(7-hydroxyquinoxalin-2-yl)pyrazol-1-yl]methyl]piperidine-1-carboxylate (10 g, 12 mmol) in acetonitrile (100 mL) was added N-chlorosuccinimide (1.5 g, 11 mmol) portion-wise. The mixture was stirred at 80° C. for 12 h. The solids were removed by filtration and the filtrate concentrated under reduced pressure. The residue was purified by column chromatography (silica gel, petroleum ether/ethyl acetate=3/1 to dichloromethane/methanol=20/1) to give tert-butyl 4-((4-(8-chloro-7-hydroxyquinoxalin-2-yl)-1H-pyrazol-1-yl)methyl) piperidine-1-carboxylate (7.9 g, 68%) as a yellow solid. m/z ES+ $[M+H]^+$ 444.1.

Step 5. To a solution of tert-butyl 4-[[4-(8-chloro-7-hydroxy-quinoxalin-2-yl)pyrazol-1-yl]methyl]piperidine-1-carboxylate (4.7 g, 11 mmol) and 5-fluoro-2-nitro-aniline (2 g, 13 mmol) in DMF (50 mL) was added $K_2CO_3$ (4.4 g, 32 mmol) and KI (0.17 g, 1.1 mmol). The mixture was stirred at 120° C. for 12 h. The reaction mixture was diluted with $H_2O$ (100 mL) and extracted with ethyl acetate (50 mL×3). The combined organic layers were dried over $Na_2SO_4$, filtered and concentrated under reduced pressure. The residue was purified by column chromatography (silica gel, petroleum ether/ethyl acetate=10/1 to 1/4) to give tert-butyl 4-((4-(7-(3-amino-4-nitrophenoxy)-8-chloroquinoxalin-2-yl)-1H-pyrazol-1-yl)methyl) piperidine-1-carboxylate (3 g, 39%) as a yellow solid. m/z ES+ $[M+H]^+$ 580.2.

Step 6. To a solution of tert-butyl 4-[[4-[7-(3-amino-4-nitro-phenoxy)-8-chloro-quinoxalin-2-yl]pyrazol-1-yl] methyl]piperidine-1-carboxylate (3 g, 4.1 mmol, 80% purity) in ethanol (40 mL) and $H_2O$ (20 mL) was added iron powder (1.2 g, 21 mmol) and $NH_4Cl$ (2.2 g, 41 mmol). The mixture was stirred at 60° C. for 12 h. The reaction mixture was filtered and concentrated under reduced pressure to remove ethanol. The reaction mixture was extracted with dichloromethane (30 mL×3). The combined organic layers were dried over $Na_2SO_4$, filtered and concentrated under reduced pressure. The residue was purified by column chromatography (silica gel, petroleum ether/ethyl acetate=1/1 to 0/1) to give tert-butyl 4-((4-(8-chloro-7-(3,4-diaminophenoxy)quinoxalin-2-yl)-1H-pyrazol-1-yl)methyl) piperidine-1-carboxylate (1.6 g, 68%) as a yellow solid. m/z ES+ $[M+H]^+$ 550.1.

Step 7. To a solution of tert-butyl 4-[[4-[8-chloro-7-(3,4-diaminophenoxy)quinoxalin-2-yl]pyrazol-1-yl]methyl]piperidine-1-carboxylate (1.6 g, 2.9 mmol) and 1,1,1-trimethoxyethane (1.7 g, 14 mmol, 1.8 mL) in methanol (30 mL) was added sulfamic acid (0.56 g, 5.7 mmol). The mixture was stirred at 25° C. for 1 h. The reaction mixture was concentrated under reduced pressure to give tert-butyl 4-((4-(8-chloro-7-((2-methyl-1H-benzo[d]imidazol-6-yl) oxy)quinoxalin-2-yl)-1H-pyrazol-1-yl)methyl) piperidine-1-carboxylate (2.5 g, crude) as a yellow solid. m/z ES+ $[M+H]^+$ 574.2.

Step 8. To a solution of tert-butyl 4-[[4-[8-chloro-7-[(2-methyl-3H-benzimidazol-5-yl)oxy]quinoxalin-2-yl]pyrazol-1-yl]methyl]piperidine-1-carboxylate (1.1 g, 1.9 mmol) in THF (15 mL) was added NaH (0.15 g, 3.8 mmol, 60% purity) at 0° C. and the mixture was stirred at 0° C. for 30 min. Then SEM-$C_1$ (0.48 g, 2.9 mmol, 0.51 mL) was added at 0° C. The mixture was stirred at 25° C. for 1.5 h. The reaction mixture was diluted with $H_2O$ (100 mL) and extracted with ethyl acetate (50 mL×3). The combined organic layers were dried over $Na_2SO_4$, filtered and concentrated under reduced pressure. The residue was purified by column chromatography (silica gel, dichloromethane/methanol=100/1 to 20/1) to give tert-butyl 4-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl) piperidine-1-carboxylate (1 g, 1.3 mmol, 67%) as a yellow solid. m/z ES+ $[M+H]^+$ 704.3.

Step 9. To a solution of tert-butyl 4-[[4-[8-chloro-7-[2-methyl-3-(2-trimethylsilylethoxymethyl)benzimidazol-5-yl] oxy-quinoxalin-2-yl]pyrazol-1-yl]methyl]piperidine-1-carboxylate (1.2 g, 1.7 mmol) in dichloromethane (15 mL) was added TFA (2.30 g, 20 mmol, 1.5 mL). The mixture was stirred at 25° C. for 5 h. The reaction mixture was diluted with $NaHCO_3$ solution (50 mL) and extracted with dichloromethane (20 mL×3). The combined organic layers were dried over $Na_2SO_4$, filtered and concentrated under reduced pressure to give 8-chloro-7-((2-methyl-1-((2-(trimethylsilyl) ethoxy)methyl)-1H-benzo[d]imidazol-6-yl)oxy)-2-(1-(piperidin-4-ylmethyl)-1H-pyrazol-4-yl)quinoxaline (1.30 g, crude) as a brown solid. m/z ES+ $[M+H]^+$ 604.2.

Step 10. To a solution of 2-[[6-[5-chloro-3-[1-(4-piperidylmethyl)pyrazol-4-yl]quinoxalin-6-yl]oxy-2-methyl-benzimidazol-1-yl]methoxy]ethyl-trimethyl-silane (0.1 mg, 0.17 mmol) in DMF (2 mL) was added paraformaldehyde (99 mg, 3.3 mmol) and formic acid (0.16 g, 3.3 mmol). The mixture was stirred at 60° C. for 12 h. The reaction mixture was diluted with $NaHCO_3$ solution (20 mL) and extracted with dichloromethane (10 mL×3). The combined organic layers were dried over $Na_2SO_4$, filtered and concentrated under reduced pressure to give 8-chloro-7-((2-methyl-1-((2-(trimethylsilyl)ethoxy)methyl)-1H-benzo[d]imidazol-6-yl)oxy)-2-(1-((1-methylpiperidin-4-yl)methyl)-1H-pyrazol-4-yl)quinoxaline (90 mg, crude) as a yellow oil. m/z ES+ $[M+H]^+$ 618.3.

Step 11. To a solution of 2-[[6-[5-chloro-3-[1-[(1-methyl-4-piperidyl)methyl]pyrazol-4-yl]quinoxalin-6-yl]oxy-2-methyl-benzimidazol-1-yl]methoxy]ethyl-trimethyl-silane (80 mg, 0.13 mmol) in $H_2O$ (4 mL) was added $Hg(OAc)_2$ (0.1 g, 0.32 mmol) and 2-[2-[bis(carboxymethyl)amino]ethyl-(carboxymethyl)amino]acetic acid (91 mg, 0.31 mmol). The mixture was stirred at 100° C. for 16 h. The reaction mixture was diluted with $NaHCO_3$ solution (20 mL) and extracted with dichloromethane (10 mL×3). The combined organic layers were dried over $Na_2SO_4$, filtered and concentrated under reduced pressure. The residue was purified by column chromatography (silica gel, dichloromethane/methanol=100 to 20/1) to give 4-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-1-methylpiperidin-2-one (12 mg, 19 μmol, 14%) as a yellow oil. m/z ES+ $[M+H]^+$ 632.3.

Step 12. A solution of 4-[[4-[8-chloro-7-[2-methyl-3-(2-trimethylsilylethoxymethyl)-benzimidazol-5-yl]oxy-quinoxalin-2-yl]pyrazol-1-yl]methyl]-1-methyl-piperidin-2-one (12 mg, 19 μmol) in TFA (0.3 mL) was stirred at 25° C. for 1 h. The reaction mixture was concentrated under reduced pressure. The residue was purified by preparative-HPLC (neutral condition column: Waters Xbridge 150*25 mm*5 μm; mobile phase: [water (10 mM $NH_4HCO_3$)-acetonitrile]; B %: 8%-38%, 10 min) to give 4-((4-(8-chloro-7-((2-methyl-1H-benzo[d]imidazol-6-yl)oxy)-quinoxalin-2-yl)-1H-pyrazol-1-yl)methyl)-1-methylpiperidin-2-one (6 mg, 12 μmol, 62%) as an off-white solid. m/z ES+ $[M+H]^+$ 502.1; $^1H$ NMR (400 MHz, DMSO) ϵ ppm 9.33 (s, 1H), 8.72 (s, 1H), 8.40 (s, 1H), 7.98 (d, J=9.2 Hz, 1H), 7.59 (d, J=8.8 Hz, 1H), 7.36 (d, J=9.2 Hz, 1 H), 7.28 (d, J=2.0 Hz, 1H), 7.04 (dd, $J_1$=8.8, 2.4 Hz, 1H), 4.21 (d, J=6.8 Hz, 2H), 3.22-3.29 (m, 2H), 2.80 (s, 3H), 2.56 (s, 3H), 2.46-2.37 (m, 1H), 2.25-2.16 (m, 1H), 2.11-2.02 (m, 1 H), 1.80 (d, J=12.4 Hz, 1H), 1.58-1.46 (m, 1H).

Example 4. Synthesis of 8-chloro-7-[(2-methyl-3H-benzimidazol-5-yl)oxy]-2-[1-(4-piperidyl)pyrazol-4-yl]quinoxaline

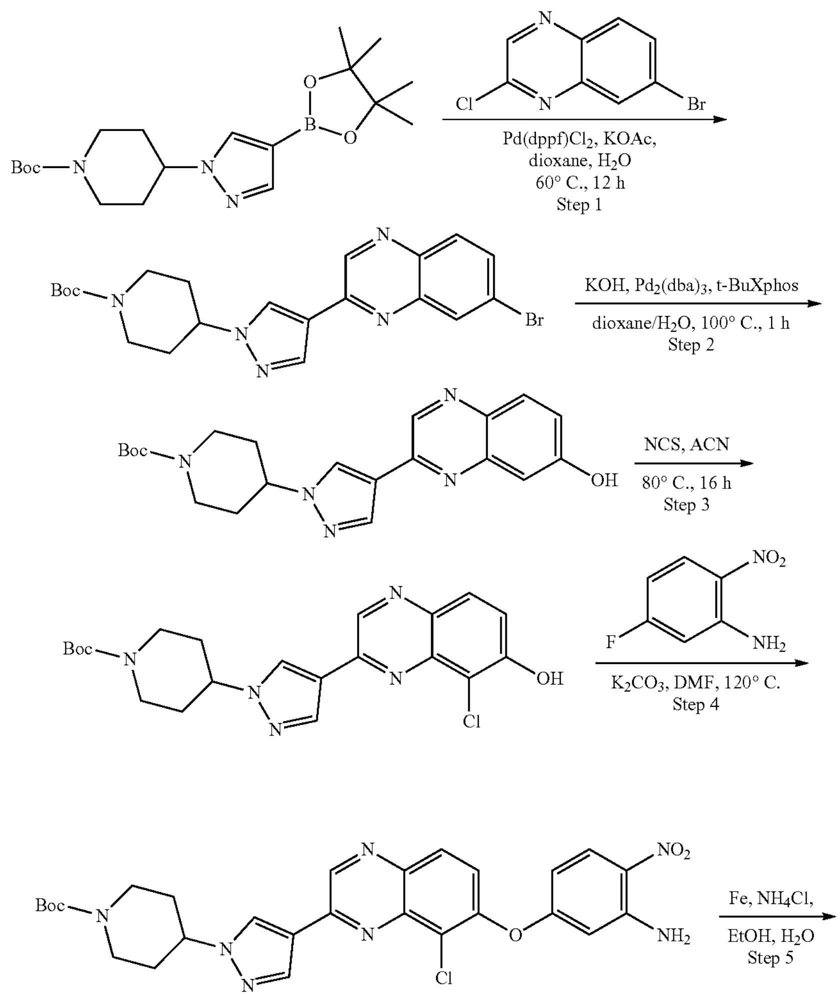

-continued

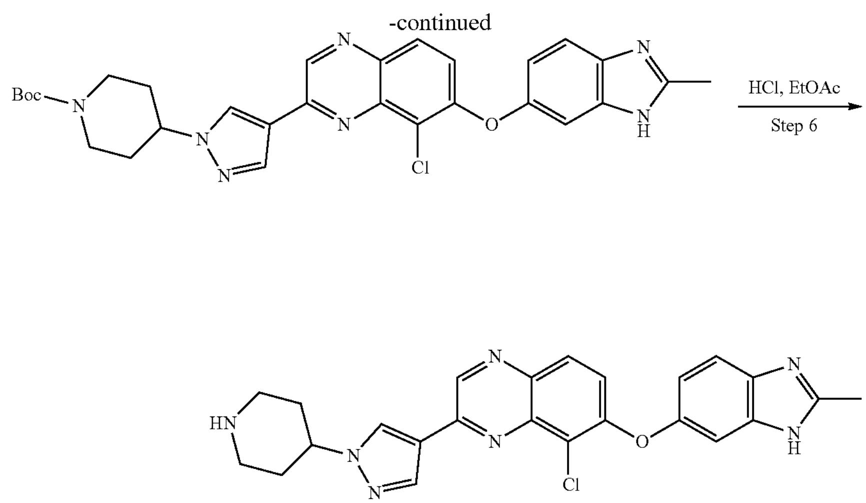

Step 1. A mixture of 7-bromo-2-chloro-quinoxaline (750 mg, 3.08 mmol), tert-butyl 4-[4-(4,4,5,5-tetramethyl-1,3,2-dioxaborolan-2-yl)pyrazol-1-yl]piperidine-1-carboxylate (1.1 g, 2.93 mmol), KOAc (907 mg, 9.24 mmol), Pd(dppf)$Cl_2$ (225 mg, 308 μmol) in dioxane (10 mL) and $H_2O$ (2 mL) was degassed and purged with $N_2$ for 3 times, and then the mixture was stirred at 60° C. for 12 h under $N_2$ atmosphere. On completion, the mixture was poured into the water (10 mL) and extracted with ethyl acetate (30 mL×3). The organic layers were dried by sodium sulfate, filtered and concentrated under reduced pressure. The residue was purified by column chromatography (silica gel, petroleum ether/ethyl acetate=5/1 to 3/1) to give tert-butyl 4-[4-(7-bromo-quinoxalin-2-yl)pyrazol-1-yl]piperidine-1-carboxylate (630 mg, 45%) as a white solid. m/z ES+ $[M+H]^+$ 458.1.

Step 2. a solution of tert-butyl 4-[4-(7-bromoquinoxalin-2-yl)pyrazol-1-yl]piperidine-1-carboxylate (600 mg, 1.31 mmol) in dioxane (6 mL) and $H_2O$ (2 mL) was added KOH (734 mg, 13.1 mmol), $Pd_2(dba)_3$ (119 mg, 131 μmol) and t-BuXPhos (55.6 mg, 131 μmol). The mixture was stirred at 100° C. for 1 h under nitrogen. On completion, the mixture was poured into the water (10 mL) and extracted with ethyl acetate (30 mL×3). The combined organic layers were dried by sodium sulfate, filtered and concentrated under reduced pressure. The residue was purified by column chromatography (silica gel, petroleum ether/ethyl acetate=3/1 to 1/1) to give tert-butyl 4-[4-(7-hydroxyquinoxalin-2-yl)pyrazol-1-yl]piperidine-1-carboxylate (400 mg, 77%) as a white solid. $^1$H NMR (400 MHz, $CD_3OD$) δ 8.98 (s, 1H), 8.56 (s, 1H), 8.29 (s, 1H), 7.88 (d, J=8.8 Hz, 1H), 7.33 (dd, J=2.8, 9.0 Hz, 1H), 7.29 (d, J=2.4 Hz, 1H), 4.55-4.45 (m, 1H), 4.27 (d, J=13.8 Hz, 2H), 3.02 (s, 2H), 2.18 (d, J=11.7 Hz, 2H), 2.09-1.92 (m, 2H), 1.51 (s, 9H).

Step 3. To a solution of tert-butyl 4-[[4-(7-hydroxyquinoxalin-2-y]) pyrazol-1-yl]piperidine-1-carboxylate (350 mg, 885 μmol) in acetonitrile (35 mL) was added N-chlorosuccinimide (118 mg, 885 μmol). The mixture was stirred at 80° C. for 16 h. On completion, the mixture was concentrated under reduced pressure. The residue was purified by column chromatography (silica gel, petroleum ether/ethyl acetate=2/1 to 1/1) to give tert-butyl 4-[4-(8-chloro-7-hydroxy-quinoxalin-2-yl)pyrazol-1-yl]piperidine-1-carboxylate (350 mg, 92%) as a yellow solid. m/z ES+ $[M+H]^+$ 430.3.

Step 4. To a solution of tert-butyl 4-[4-(8-chloro-7-hydroxy-quinoxalin-2-yl)pyrazol-1-yl]piperidine-1-carboxylate (100 mg, 233 μmol), 5-fluoro-2-nitro-aniline (72.6 mg, 465 μmol) in DMF (1 mL) was added $K_2CO_3$ (96.5 mg, 697 μmol). The mixture was stirred at 120° C. for 3 h. On completion, the solids were removed by filtration and the filtrate concentrated under reduced pressure. The residue was purified by reversed-phase HPLC (mobile phase: [water/formic acid-acetonitrile]) to give tert-butyl 4-[4-[7-(3-amino-4-nitro-phenoxy)-8-chloro-quinoxalin-2-yl]pyrazol-1-yl]piperidine-1-carboxylate (50 mg, 38%) as a yellow solid. m/z ES+ $[M+H]^+$ 566.5.

Step 5. To a solution of tert-butyl 4-[4-[7-(3-amino-4-nitro-phenoxy)-8-chloro-quinoxalin-2-yl]pyrazol-1-yl]piperidine-1-carboxylate (30 mg, 53 μmol) in ethanol (5 mL) and $H_2O$ (5 mL) was added iron powder (14.8 mg, 265 μmol) and $NH_4Cl$ (14.2 mg, 265 μmol). The mixture was stirred at 60° C. for 16 h. On completion, the solids were removed by filtration and the filtrate concentrated under reduced pressure. The residue was purified by reversed-phase HPLC (mobile phase: [water/formic acid-acetonitrile]) to give tert-butyl 4-[4-[8-chloro-7-[(2-methyl-3H-benzimidazol-5-yl)oxy]quinoxalin-2-yl]pyrazol-1-yl] piperidine-1-carboxylate (25 mg, 84%) as a yellow solid. m/z ES+ $[M+H]^+$ 560.3.

Step 6. To a solution of tert-butyl 4-[4-[8-chloro-7-[(2-methyl-3H-benzimidazol-5-yl)oxy]quinoxalin-2-yl]pyrazol-1-yl]piperidine-1-carboxylate (25 mg, 44.6 μmol) in HCl/ethyl acetate (4 M, 1.25 mL) was stirred at 25° C. for 10 min. On completion, the mixture was concentrated under reduced pressure. The residue was purified by preparative-HPLC (column: Phenomenex Gemini-NX C18 75*30 mm*3 μm; mobile phase: [water (0.225% formic acid)-acetonitrile]; B %: 2%-32%, 7 min) to give 8-chloro-7-[(2-methyl-3H-benzimidazol-5-yl)oxy]-2-[1-(4-piperidyl)pyrazol-4-yl]quinoxaline (7.95 mg, 39%) as an off-white solid. m/z ES+ $[M+H]^+$460.2; $^1$H NMR (400 MHz, $CD_3OD$) δ 9.16 (s, 1H), 8.65 (s, 1H), 8.39 (s, 1H), 8.37 (s, 2H), 7.90 (d, J=9.2 Hz, 1H), 7.55 (d, J=8.8 Hz, 1H), 7.36 (d, J=9.2 Hz, 1H), 7.20 (d, J=2.2 Hz, 1H), 7.03 (dd, J=2.4, 8.8 Hz, 1H), 4.70-4.60 (m, 1H), 3.73-3.58 (m, 2H), 3.31-3.18 (m, 2H), 2.60 (s, 3H), 2.49-2.32 (m, 4H).

Example 5. Synthesis of 2-(4-((4-(8-chloro-7-((2-methyl-1H-benzo[d]imidazol-6-yl)oxy)-quinoxalin-2-yl)-1H-pyrazol-1-yl)methyl) piperidin-1-yl)ethanol

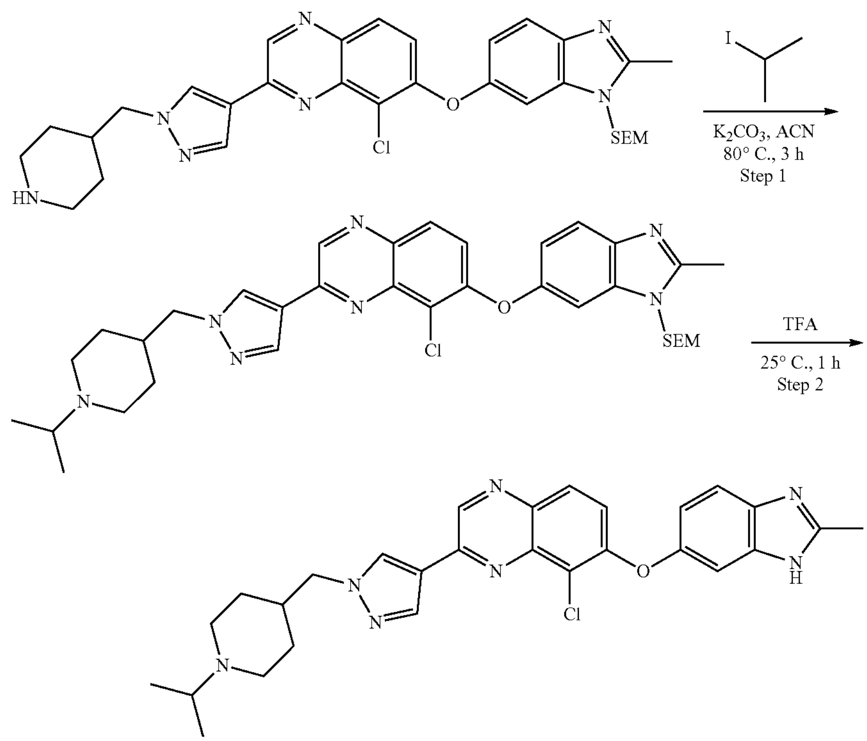

Step 1. To a solution of 2-[[6-[5-chloro-3-[1-(4-piperidylmethyl)pyrazol-4-y]]quinoxalin-6-yl]oxy-2-methyl-benzimidazol-1-yl]methoxy]ethyl-trimethyl-silane (50 mg, 82.75 μmol) and 2-iodopropane (17 mg, 99 μmol) in acetonitrile (1 mL) was added $K_2CO_3$ (23 mg, 0.17 mmol). The mixture was stirred at 80° C. for 3 h. The reaction mixture was concentrated under reduced pressure to give 8-chloro-2-(1-((1-isopropylpiperidin-4-yl)methyl)-1H-pyrazol-4-yl)-7-((2-methyl-1-((2-(trimethylsilyl)ethoxy)methyl)-1H-benzo[d]imidazol-6-yl)oxy)quinoxaline (53 mg, crude) as a yellow solid. m/z ES+ $[M+H]^+$ 646.4.

Step 2. To a solution of 2-[[6-[5-chloro-3-[1-[(1-isopropyl-4-piperidyl)methyl]pyrazol-4-yl]quinoxalin-6-yl]oxy-2-methyl-benzimidazol-1-yl]methoxy]ethyl-trimethyl-silane (53 mg, 82 umol) in TFA (1 mL) was stirred at 25° C. for 1 h. The reaction mixture was concentrated under reduced pressure to give a residue. The residue was purified by preparative-HPLC (neutral condition; column: Waters Xbridge 150*25 mm*5 μm; mobile phase: [water (10 mM $NH_4HCO_3$)-acetonitrile]; B %: 22%-52%, 10 min) to give 8-chloro-2-(1-((1-isopropylpiperidin-4-yl)methyl)-1H-pyrazol-4-yl)-7-((2-methyl-1H-benzo[d]imidazol-6-yl)oxy)quinoxaline (15 mg, 32%, as formic acid salt) as a yellow solid. m/z ES+ $[M+H]^+$ 516.2; $^1H$ NMR (400 MHz, DMSO-$d_6$) δ ppm 9.34 (s, 1H), 9.15 (s, 1H), 8.74 (s, 1H), 8.42 (s, 1H), 8.14 (s, 1H), 7.99 (d, J=9.2 Hz, 1H), 7.60 (d, J=8.8 Hz, 1H), 7.37 (d, J=9.2 Hz, 1H), 7.30 (d, J=2.4 Hz, 1H), 7.04 (dd, J=8.8, 2.4 Hz, 1H), 4.22 (d, J=6.4 Hz, 2H), 3.46-3.33 (m, 3H), 3.02-2.90 (m, 2H), 2.58 (s, 3H), 2.28-2.18 (m, 1H), 1.85-1.75 (m, 2H), 1.54 (q, J=12.4 Hz, 2H), 1.22 (d, J=6.8 Hz, 6H).

Examples 6 and 7. Synthesis of 2-[[6-[5-chloro-3-(1-tetrahydropyran-2-ylpyrazol-4-yl)quinoxalin-6-yl]oxy-2-methyl-benzimidazol-1-yl]methoxy]ethyl-trimethyl-silane and 8-chloro-7-[(2-methyl-3H-benzimidazol-5-yl)oxy]-2-[5-methyl-1-[(1-methyl-4-piperidyl)methyl]pyrazol-4-yl]quinoxaline

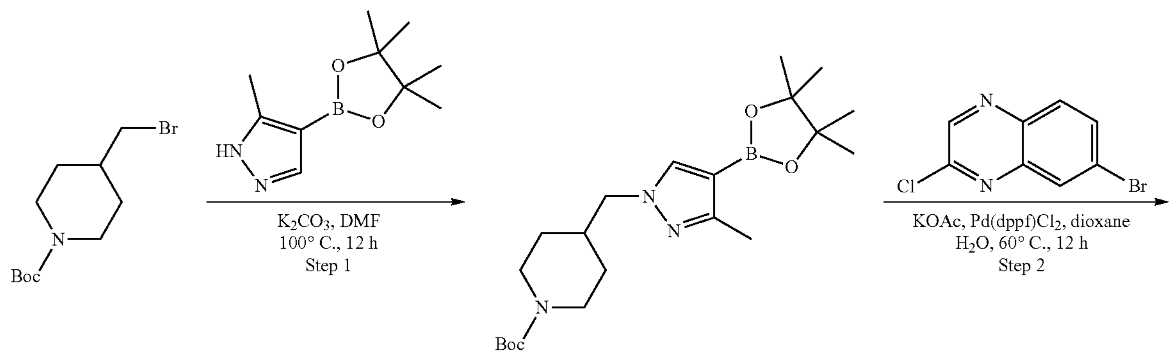

-continued
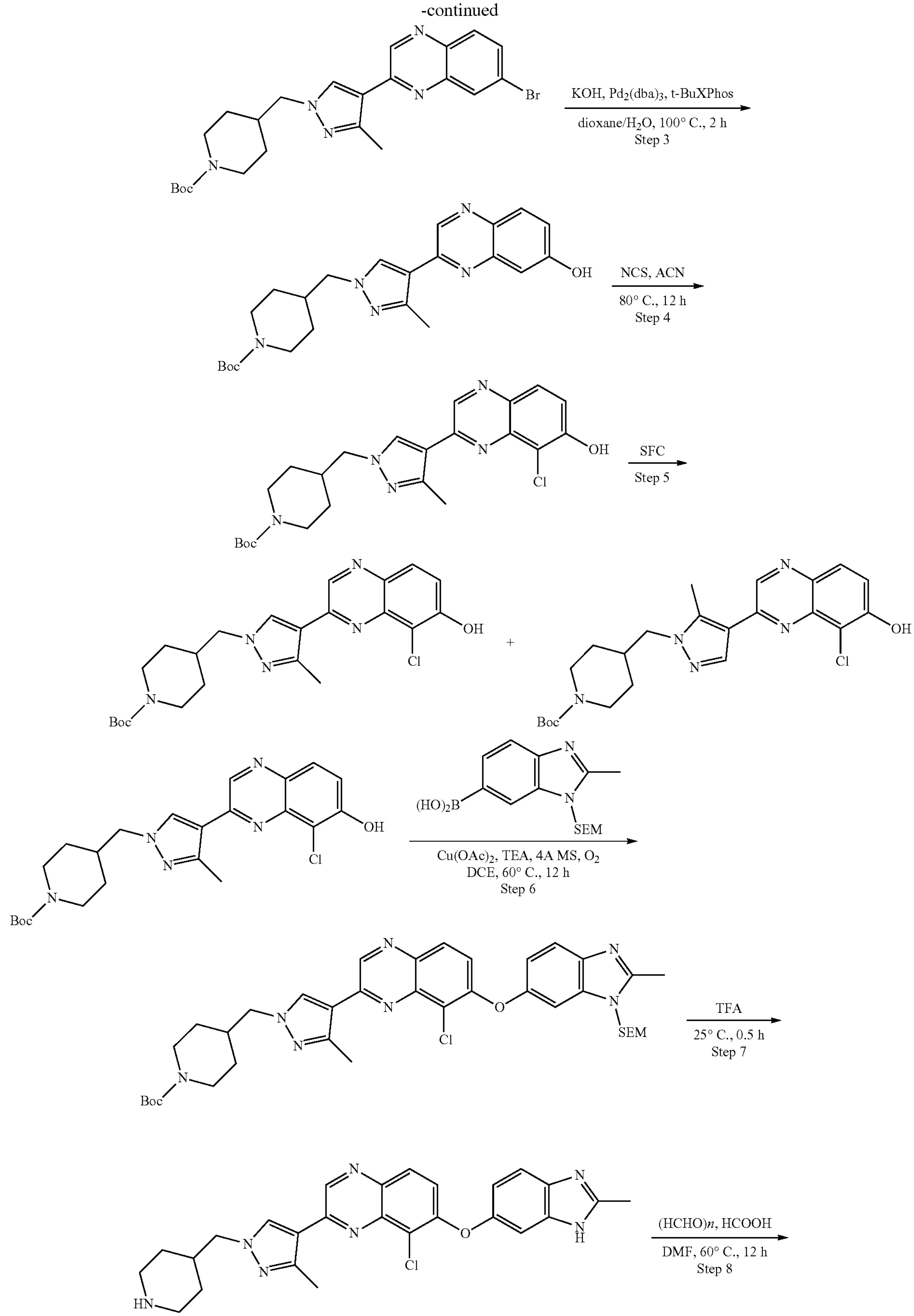

-continued

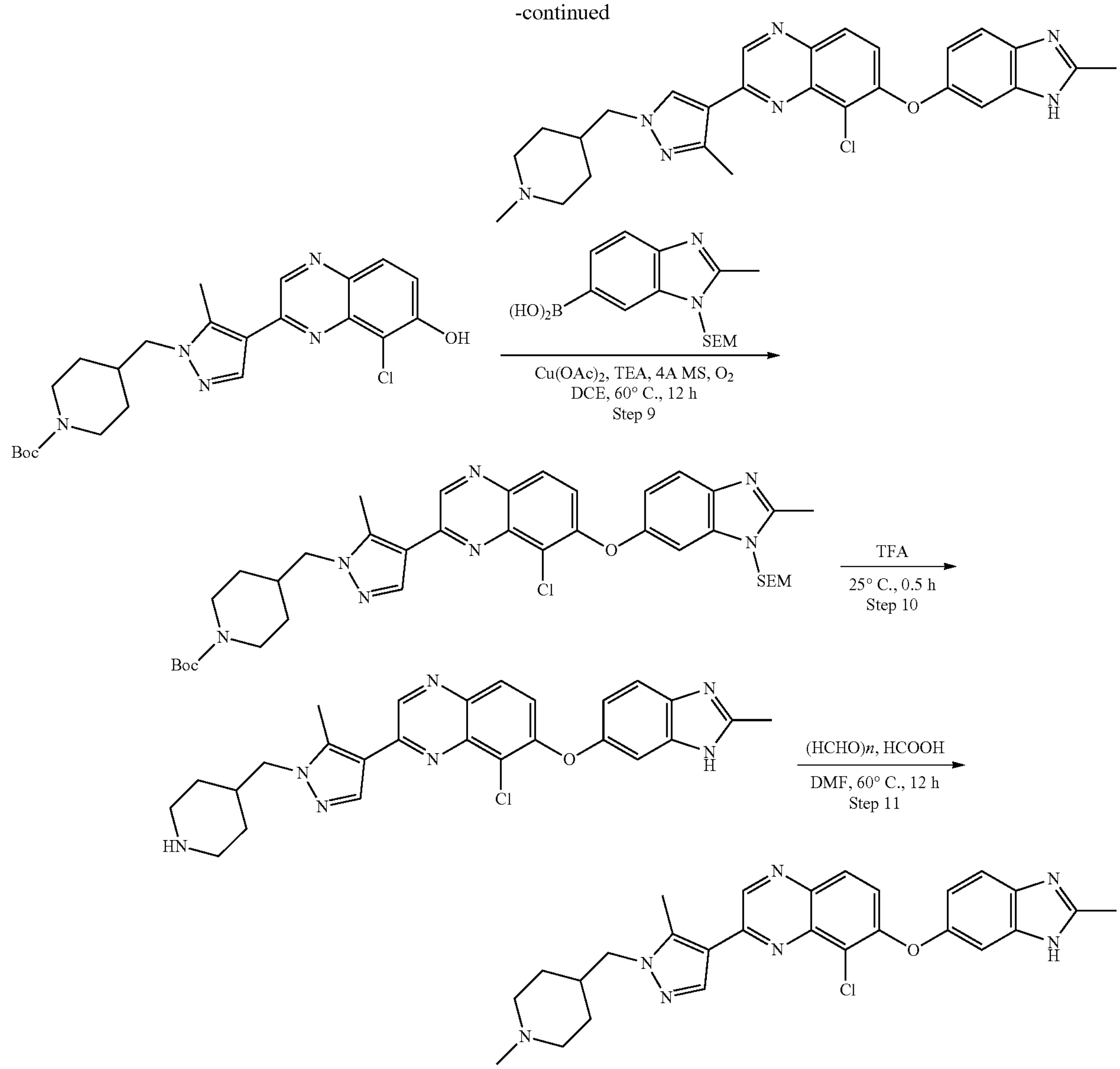

Step 1. To a solution of 5-methyl-4-(4,4,5,5-tetramethyl-1,3,2-dioxaborolan-2-yl)-1H-pyrazole (5 g, 24 mmol) in DMF (50 mL) was added $K_2CO_3$ (9.96 g, 72.1 mmol) and tert-butyl 4-(bromomethyl) piperidine-1-carboxylate (6.69 g, 24 mmol). The mixture was stirred at 100° C. for 12 h. On completion, the reaction mixture was diluted with water (50 mL) and extracted with ethyl acetate (50 mL×3). The combined organic layers were dried over anhydrous sodium sulfate, filtered and concentrated under reduced pressure. The residue was purified by column chromatography (silica gel, petroleum ether/ethyl acetate=10/1 to 3/1) to give tert-butyl 4-[[3-methyl-4-(4,4,5,5-tetramethyl-1,3,2-dioxaborolan-2-yl)pyrazol-1-yl]methyl]piperidine-1-carboxylate (5 g, 40%) as a colorless oil. m/z ES+ $[M+H]^+$ 406.5.

Step 2. A mixture of tert-butyl 4-[[3-methyl-4-(4,4,5,5-tetramethyl-1,3,2-dioxaborolan-2-yl)pyrazol-1-yl]methyl] piperidine-1-carboxylate (5 g, 12.3 mmol), 7-bromo-2-chloro-quinoxaline (3.30 g, 13.5 mmol), KOAc (3.63 g, 37 mmol), Pd(dppf)$Cl_2$ (902 mg, 1.23 mmol) in dioxane (50 mL) and $H_2O$ (10 mL) was degassed and purged with $N_2$ for 3 times, and then the mixture was stirred at 60° C. for 3 h under $N_2$ atmosphere. On completion, the reaction mixture was diluted with water (25 mL) and extracted with ethyl acetate (25 mL×3). The combined organic layers were dried over anhydrous sodium sulfate, filtered and concentrated under reduced pressure. The residue was purified by column chromatography (silica gel, petroleum ether/ethyl acetate=10/1 to 2/1) to give tert-butyl 4-[[4-(7-bromoquinoxalin-2-yl)-3-methyl-pyrazol-1-yl]methyl]piperidine-1-carboxylate (3.1 g, 50%) as a yellow solid. $^1$H NMR (400 MHz, $CDCl_3$) δ 9.03 (d, J=18.4 Hz, 1H), 8.24-8.18 (m, 1H), 8.10-7.95 (m, 1H), 7.93-7.88 (m, 1H), 7.78-7.70 (m, 1H), 4.25-4.08 (m, 2H), 4.06-3.98 (m, 2H), 2.80-2.62 (m, 5H), 2.23-2.07 (m, 1H), 1.63 (d, J=12.0 Hz, 2H), 1.46 (d, J=1.2 Hz, 9H), 1.29-1.19 (m, 2H).

Step 3. A mixture of tert-butyl 4-[[4-(7-bromoquinoxalin-2-yl)-3-methyl-pyrazol-1-yl]methyl]piperidine-1-carboxylate (2.8 g, 5.76 mmol), KOH (3.23 g, 57.5 mmol), t-BuXPhos (244 mg, 575 μmol) and $Pd_2(dba)_3$ (527 mg, 575 μmol) in dioxane (30 mL) and $H_2O$ (10 mL) was degassed and purged with $N_2$ for 3 times, and then the mixture was stirred at 100° C. for 2 h under $N_2$ atmosphere. On completion, the reaction mixture was concentrated under reduced pressure. The residue was purified by column chromatography (silica gel, petroleum ether/ethyl acetate=10/1 to 1/1) to give tert-butyl 4-[[4-(7-hydroxyquinoxalin-2-yl)-3-methyl-pyrazol- 1-yl]methyl]piperidine-1-carboxylate (1.9 g, 72.3%) as a yellow solid. m/z ES+ $[M+H]^+$ 424.1.

Step 4. To a solution of tert-butyl 4-[[4-(7-hydroxyquinoxalin-2-yl)-3-methyl-pyrazol-1-yl]methyl]piperidine-1-carboxylate (1.7 g, 4.01 mmol) in acetonitrile (20 mL) was added N-chlorosuccinimide (536 mg, 4.01 mmol). The mixture was stirred at 80° C. for 12 h. On completion, the reaction mixture was concentrated under reduced pressure. The residue was purified by column chromatography (silica gel, petroleum ether/ethyl acetate=10/1 to 1/1) to give tert-butyl 4-[[4-(8-chloro-7-hydroxy-quinoxalin-2-yl)-3-methyl-pyrazol-1-yl]methyl]piperidine-1-carboxylate (1.1 g, 56%) as a yellow solid. m/z ES+ $[M+H]^+$ 458.0.

Step 5. tert-butyl 4-[[4-(8-chloro-7-hydroxy-quinoxalin-2-yl)-3-methyl-pyrazol-1-yl]methyl]piperidine-1-carboxylate (1.1 g, 2.4 mmol) was separated by SFC (column: Daicel ChiralPak IG (250*30 mm, 10 μm); mobile phase: [0.1% aqueous ammonium hydroxide in methanol]; B %: 60%-60%, 5.9 min; 60 min) to give tert-butyl 4-[[4-(8-chloro-7-hydroxy-quinoxalin-2-yl)-3-methyl-pyrazol-1-yl]methyl]piperidine-1-carboxylate (450 mg, 38%) as a yellow solid and tert-butyl 4-[[4-(8-chloro-7-hydroxy-quinoxalin-2-yl)-5-methyl-pyrazol-1-yl]methyl]piperidine-1-carboxylate (350 mg, 29%) as a yellow solid.

Step 6. A mixture of tert-butyl 4-[[4-(8-chloro-7-hydroxy-quinoxalin-2-yl)-3-methyl-pyrazol-1-yl]methyl]piperidine-1-carboxylate (200 mg, 436 μmol), [2-methyl-1-(2-trimethylsilylethoxymethyl)benzimidazol-5-yl]boronic acid (200 mg, 655 μmol), $Cu(OAc)_2$ (39.6 mg, 218 μmol), triethylamine (132 mg, 1.31 mmol) in dichloroethane (5 mL) was degassed and purged with $O_2$ for 3 times, and then the mixture was stirred at 60° C. for 12 h under $O_2$ atmosphere. On completion, the reaction mixture was concentrated under reduced pressure to give a residue. The residue was purified by preparative-TLC (silica gel, dichloromethane/methanol=10/1) twice to give tert-butyl 4-[[4-[8-chloro-7-[2-methyl-1-(2-trimethylsilylethoxymethyl)-benzimidazol-5-yl]oxy-quinoxalin-2-yl]-3-methyl-pyrazol-1-yl]methyl]piperidine-1-carboxylate (60 mg, 16%) as a yellow oil. m/z ES+ $[M+H]^+$ 539.3.

Step 7. A solution of tert-butyl 4-[[4-[8-chloro-7-[2-methyl-1-(2-trimethylsilylethoxymethyl)benzimidazol-5-yl]oxy-quinoxalin-2-yl]-3-methyl-pyrazol-1-yl]-methyl]piperidine-1-carboxylate (50 mg, 69.6 μmol) in TFA (1 mL) was stirred at 25° C. for 0.5 h. On completion, the reaction mixture was concentrated under reduced pressure to give 8-chloro-7-[(2-methyl-3H-benzimidazol-5-yl)oxy]-2-[3-methyl-1-(4-piperidylmethyl)pyrazol-4-yl]quinoxaline (50 mg, crude) as a red oil. m/z ES+ $[M+H]^+$ 488.1.

Step 8. To a solution of 8-chloro-7-[(2-methyl-3H-benzimidazol-5-yl)oxy]-2-[3-methyl-1-(4-piperidylmethyl)pyrazol-4-yl]quinoxaline (50 mg, 102.46 μmol) in DMF (1 mL) was added paraformaldehyde (61.5 mg, 2.05 mmol) and formic acid (98.4 mg, 2.05 mmol). The mixture was stirred at 60° C. for 12 h. On completion, the solids were removed by filtration and the filtrate concentrated. The residue was purified twice by preparative-HPLC (column: Phenomenex Gemini-NX C18 75*30 mm*3 μm; mobile phase: [water (0.225% formic acid)-acetonitrile]; B %: 5%-35%, 7 min) to give 8-chloro-7-[(2-methyl-3H-benzimidazol-5-yl)oxy]-2-[3-methyl-1-[(1-methyl-4-piperidyl)methyl]pyrazol-4-yl]quinoxaline (7.86 mg, 15%) as a brown solid. m/z ES+ $[M+H]^+$ 502.5; $^1H$ NMR (400 MHz, DMSO-$d_6$) δ 12.50 (br s, 1H), 9.23 (s, 1H), 8.77 (s, 1H), 7.95 (d, J=9.2 Hz, 1H), 7.52 (d, J=8.8 Hz, 1H), 7.31 (d, J=9.2 Hz, 1H), 7.22 (d, J=2.4 Hz, 1H), 6.99-6.93 (m, 1H), 4.21-4.03 (m, 2H), 3.43 (d, J=12 Hz, 2H), 2.99-2.87 (m, 2H), 2.74 (s, 3H), 2.71 (s, 3H), 2.49 (s, 3H), 2.20-2.07 (m, 1H), 1.79 (d, J=12.4 Hz, 2H), 1.55-1.38 (m, 2H).

Step 9. A mixture of tert-butyl 4-[[4-(8-chloro-7-hydroxy-quinoxalin-2-yl)-5-methyl-pyrazol-1-yl]methyl]piperidine-1-carboxylate (200 mg, 436 μmol), [2-methyl-1-(2-trimethylsilylethoxymethyl)benzimidazol-5-yl]boronic acid (200 mg, 655 μmol), $Cu(OAc)_2$ (39.6 mg, 218 μmol), triethylamine (132 mg, 1.31 mmol) in dichloroethane (5 mL) was degassed and purged with $O_2$ 3 times, and the mixture was stirred at 60° C. for 12 h under $O_2$ atmosphere. On completion, the reaction mixture was concentrated under reduced pressure. The residue was purified by preparative-TLC (silica gel, dichloromethane/methanol=10/1) twice to give tert-butyl 4-[[4-[8-chloro-7-[2-methyl-1-(2-trimethylsilylethoxymethyl)benzimidazol-5-yl]oxy-quinoxalin-2-yl]-5-methyl-pyrazol-1-yl]methyl]piperidine-1-carboxylate (50 mg, 13%) as a yellow oil. m/z ES+ $[M+H]^+$ 507.2.

Step 10. A solution of tert-butyl 4-[[4-[8-chloro-7-[2-methyl-1-(2-trimethylsilyl-ethoxymethyl)benzimidazol-5-yl]oxy-quinoxalin-2-yl]-5-methyl-pyrazol-1-yl]methyl]piperidine-1-carboxylate (50 mg, 69.6 μmol) in TFA (1 mL) was stirred at 25° C. for 0.5 h. On completion, the reaction mixture was concentrated under reduced pressure to give 8-chloro-7-[(2-methyl-3H-benzimidazol-5-yl)oxy]-2-[5-methyl-1-(4-piperidylmethyl)pyrazol-4-yl]quinoxaline (50 mg, crude) as a red oil. m/z ES+ $[M+H]^+$ 488.1.

Step 11. To a solution of 8-chloro-7-[(2-methyl-3H-benzimidazol-5-yl)oxy]-2-[5-methyl-1-(4-piperidylmethyl)pyrazol-4-yl]quinoxaline (50 mg, 102.46 μmol) in DMF (1 mL) was added paraformaldehyde (61.5 mg, 2.05 mmol) and formic acid (98.4 mg, 2.05 mmol). The mixture was stirred at 60° C. for 12 h. On completion, the solids were removed by filtration and the filtrate concentrated. The residue was purified by preparative-HPLC (column: Phenomenex Gemini-NX C18 75*30 mm*3 μm; mobile phase: [water (0.225% formic acid)-acetonitrile]; B %: 5%-35%, 7 min) to give 8-chloro-7-[(2-methyl-3H-benzimidazol-5-yl)oxy]-2-[5-methyl-1-[(1-methyl-4-piperidyl)methyl]pyrazol-4-yl]quinoxaline (18.2 mg, 35%) as a brown solid. m/z ES+ $[M+H]^+$ 502.4; $^1H$ NMR (400 MHz, DMSO-$d_6$) δ 12.29 (br s, 1H), 9.34 (s, 1H), 8.46 (s, 1H), 7.95 (d, J=9.2 Hz, 1H), 7.51 (d, J=8.0 Hz, 1H), 7.31 (d, J=9.2 Hz, 1H), 7.21 (s, 1H), 6.94 (d, J=8.4 Hz, 1H), 4.16 (d, J=6.4 Hz, 2H), 3.40-3.34 (m, 2H), 2.96-2.85 (m, 5H), 2.71 (s, 3H), 2.49 (s, 3H), 2.23-2.09 (m, 1H), 1.77 (d, J=12.0 Hz, 2H), 1.60-1.40 (m, 2H).

Example 8. Synthesis of 8-fluoro-7-[(2-methyl-3H-benzimidazol-5-yl)oxy]-2-[1-[(1-methyl-4-piperidyl)methyl]pyrazol-4-yl]quinoxaline

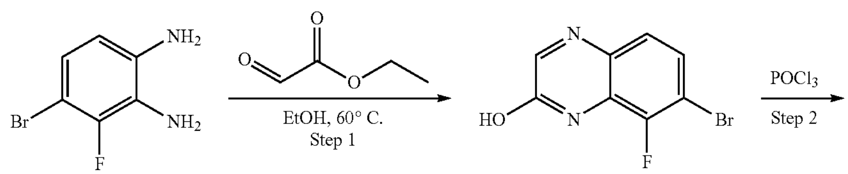

-continued
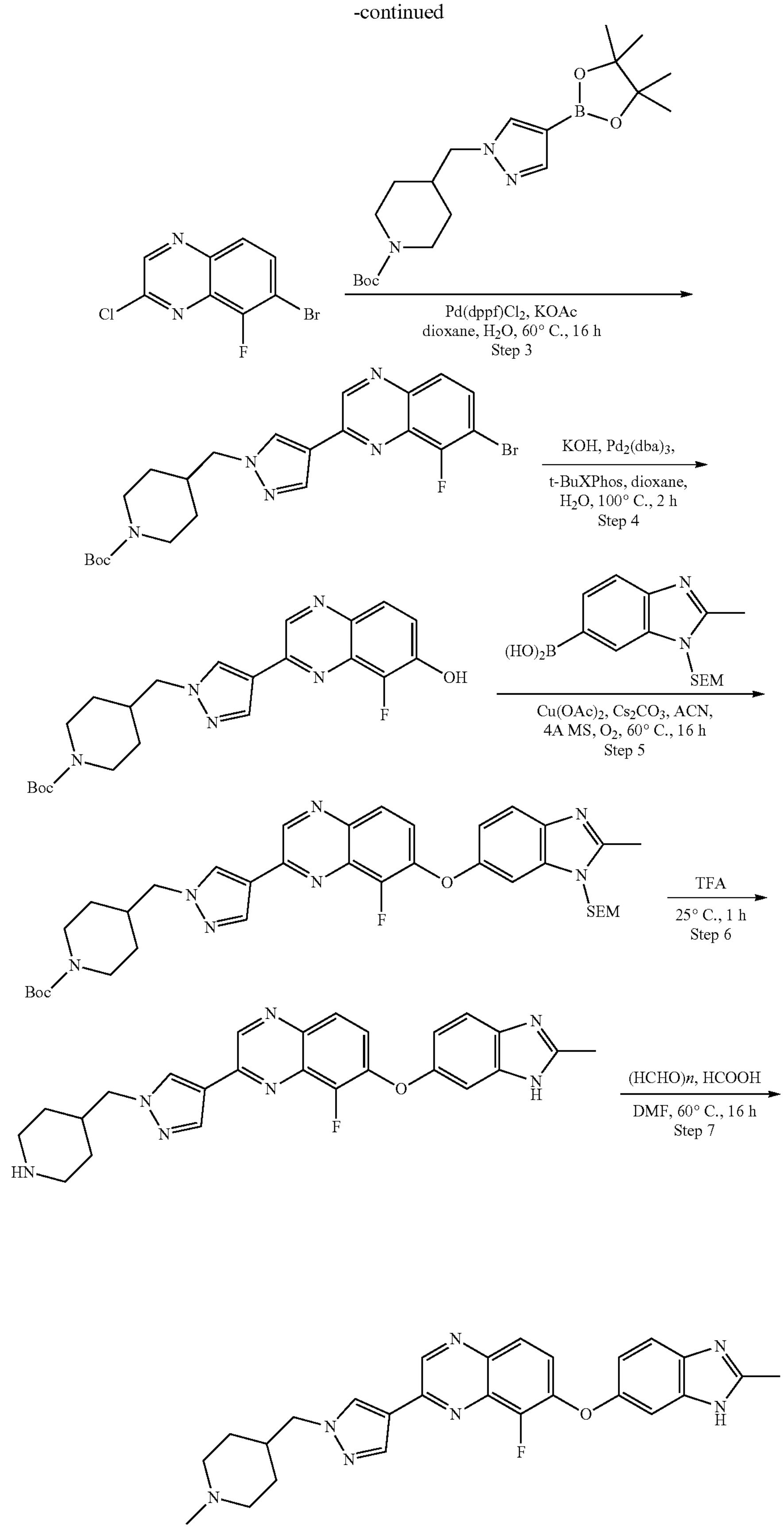

Step 1. To a solution of 4-bromo-3-fluoro-benzene-1,2-diamine (4.5 g, 21.95 mmol) in ethanol (50 mL) was added ethyl 2-oxoacetate (4.48 g, 22 mmol). The mixture was stirred at 60° C. for 16 h. After cooling to room temperature, the solid formed was separated by filtration and the filter cake was washed with petroleum ether (50 mL) to give 7-bromo-8-fluoro-quinoxalin-2-ol (5 g, 94%) as a dark brown solid.

Step 2. A solution of 7-bromo-8-fluoro-quinoxalin-2-01 (5 g, 20.6 mmol) in $POCl_3$ (15 mL) was stirred at 100° C. for 1 h. On completion, the mixture was concentrated under reduced pressure to give a residue. Then aq. $NaHCO_3$ solution (50 mL) was added and the mixture was extracted with ethyl acetate (30 mL×3). The organic layers were dried by sodium sulfate, filtered and concentrated under reduced pressure. The residue was purified by column chromatography (silica gel, petroleum ether/ethyl acetate=1/0 to 50/1) to give 7-bromo-2-chloro-8-fluoro-quinoxaline (4 g, 74%) as a yellow solid. $^1H$ NMR (400 MHz, $CDCl_3$) δ 8.85 (s, 1H), 7.95-7.76 (m, 2H).

Step 3. A mixture of 7-bromo-2-chloro-8-fluoro-quinoxaline (4 g, 15.3 mmol), tert-butyl 4-[[4-(4,4,5,5-tetramethyl-1,3,2-dioxaborolan-2-yl)pyrazol-1-yl]methyl]piperidine-1-carboxylate (6.58 g, 16.8 mmol), $Pd(dppf)Cl_2$ (560 mg, 764 μmol), KOAc (4.5 g, 45.89 mmol) in dioxane (40 mL) and $H_2O$ (20 mL) was degassed and purged with $N_2$ for 3 times, and then the mixture was stirred at 60° C. for 16 h under $N_2$ atmosphere. On completion, the mixture was poured into water (10 mL) and extracted with ethyl acetate (50 mL×3). The organic layers were dried with sodium sulfate, filtered and concentrated under reduced pressure. The residue was purified by column chromatography (silica gel, petroleum ether/ethyl acetate=10/1 to 3/1) to give tert-butyl 4-[[4-(7-bromo-8-fluoro-quinoxalin-2-yl)pyrazol-1-yl]methyl]piperidine-1-carboxylate (5 g, 66%) as a dark brown solid. m/z ES+ $[M+H]^+$ 436.3.

Step 4. To a solution of tert-butyl 4-[[4-(7-bromo-8-fluoro-quinoxalin-2-yl)pyrazol-1-yl]methyl]piperidine-1-carboxylate (3 g, 6.12 mmol) in dioxane (50 mL), $H_2O$ (25 mL) was added $Pd_2(dba)_3$ (280 mg, 305 μmol), KOH (3.43 g, 61.18 mmol) and t-BuXPhos (130 mg, 305.89 μmol). The mixture was stirred at 100° C. for 1 h under nitrogen. On completion, the mixture was poured into water (10 mL) and extracted with ethyl acetate (50 mL×3). The organic layers were dried by sodium sulfate, filtered and concentrated under reduced pressure. The residue was purified by column chromatography (silica gel, petroleum ether/ethyl acetate-3/1 to 1/1) to give tert-butyl 4-[[4-(8-fluoro-7-hydroxy-quinoxalin-2-yl)pyrazol-1-yl]methyl]piperidine-1-carboxylate (1.5 g, 57%) as a yellow solid. tert-butyl 4-[[4-(8-fluoro-7-hydroxy-quinoxalin-2-yl)pyrazol-1-yl]methyl]piperidine-1-carboxylate (1.4 g) was then separated by SFC (column: DAICEL CHIRALCEL OJ(250 mm*30 mm, 10 μm); mobile phase: [0.1% aqueous ammonium hydroxide in methanol]; B %: 55%-55%, 5 min; 40 min) to give tert-butyl 4-[[4-(8-fluoro-7-hydroxy-quinoxalin-2-yl)pyrazol-1-yl]methyl]piperidine-1-carboxylate (1.1 g, 78%) as a yellow solid and tert-butyl 4-[[4-(5-fluoro-6-hydroxy-quinoxalin-2-yl)pyrazol-1-yl]methyl]piperidine-1-carboxylate (300 mg, 21%) as a yellow solid. $^1H$ NMR (400 MHz, $CD_3OD$) δ 9.03 (s, 1H), 8.53 (s, 1H), 8.33 (s, 1H), 7.72 (d, J=8.8 Hz, 1H), 7.43 (t, J=8.4 Hz, 1H), 4.18-4.09 (m, 4H), 2.85-2.75 (m, 2H), 2.21-2.15 (m, 1H), 1.68-1.58 (m, 2H), 1.46 (s, 9H), 1.30-1.11 (m, 2H).

Step 5. A mixture of tert-butyl 4-[[4-(8-fluoro-7-hydroxy-quinoxalin-2-yl)pyrazol-1-yl]methyl]piperidine-1-carboxylate (300 mg, 701 μmol), [2-methyl-3-(2-trimethylsilylethoxymethyl)benzimidazol-5-yl]boronic acid (429 mg, 1.4 mmol), $Cu(OAc)_2$ (63.7 mg, 351 μmol), 4 Å MS (10 mg) and $Cs_2CO_3$ (457 mg, 1.4 mmol) in acetonitrile (10 mL) was stirred at 60° C. for 16 h under $O_2$ (15 psi) atmosphere. On completion, the solids were removed by filtration and the filtrate concentrated under reduced pressure. The residue was purified by preparative-TLC (silica gel, dichloromethane/methanol=50/1) to give tert-butyl 4-[[4-[8-fluoro-7-[2-methyl-3-(2-trimethylsilylethoxymethyl)benzimidazol-5-yl]oxy-quinoxalin-2-yl]pyrazol-1-yl]methyl]piperidine-1-carboxylate (140 mg, 29%) as a yellow solid. m/z ES+ $[M+H]^+$ 688.6.

Step 6. To a solution of tert-butyl 4-[[4-[8-fluoro-7-[2-methyl-3-(2-trimethylsilylethoxymethyl)benzimidazol-5-yl]oxy-quinoxalin-2-yl]pyrazol-1-yl]methyl]-piperidine-1-carboxylate (70 mg, 102 μmol) in TFA (1 mL) was stirred at 25° C. for 1 h. On completion, the mixture was concentrated under reduced pressure to give 8-fluoro-7-[(2-methyl-3H-benzimidazol-5-yl)oxy]-2-[1-(4-piperidylmethyl)pyrazol-4-yl]quinoxaline (45 mg, crude) as a yellow oil. m/z ES+ $[M+H]^+$ 458.4.

Step 7. To a solution of 8-fluoro-7-[(2-methyl-3H-benzimidazol-5-yl)oxy]-2-[1-(4-piperidylmethyl)pyrazol-4-yl]quinoxaline (45 mg, 98.3 μmol) in DMF (1 mL) was added paraformaldehyde (29.5 mg, 983 μmol) and formic acid (47.2 mg, 983 μmol). The mixture was stirred at 60° C. for 16 h. On completion, the solids were removed by filtration and the filtrate concentrated. The residue was purified by preparative-HPLC (column: Phenomenex Gemini-NX C18 75*30 mm*3 μm; mobile phase: [water (0.225% formic acid)-acetonitrile]; B %: 2%-32%, 7 min) to give 8-fluoro-7-[(2-methyl-3H-benzimidazol-5-yl)oxy]-2-[1-[(1-methyl-4-piperidyl)-methyl]pyrazol-4-yl]quinoxaline (22.1 mg, 47%) as a brown solid. m/z ES+ $[M+H]^+$ 472.5; 1H NMR (400 MHz, DMSO-$d_6$) δ 9.32 (s, 1H), 8.73 (s, 1H), 8.39 (s, 1H), 8.17 (s, 1H), 7.85 (d, J=9.2 Hz, 2H), 7.51-7.39 (m, 2H), 7.22 (s, 1H), 6.96 (d, J=8.4 Hz, 1H), 4.17 (d, J=6.8 Hz, 2H), 3.10 (d, J=11.6 Hz, 2H), 2.49 (s, 3H), 2.43 (s, 3H), 2.42-2.35 (m, 2H), 2.02 (s, 1H), 1.64-1.56 (m, 2H), 1.43-1.34 (m, 2H).

Example 9. Synthesis of 8-methyl-7-((2-methyl-1H-benzo[d]imidazol-6-yl)oxy)-2-(1-((1-methylpiperidin-4-yl)methyl)-1H-pyrazol-4-yl)quinoxaline

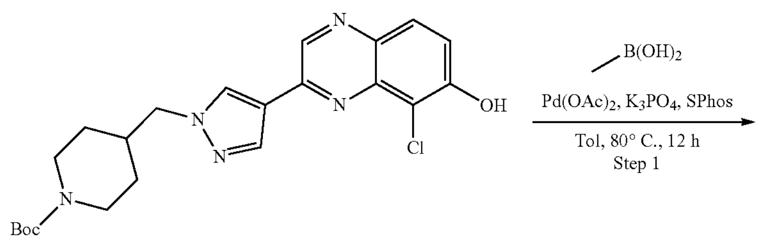

-continued

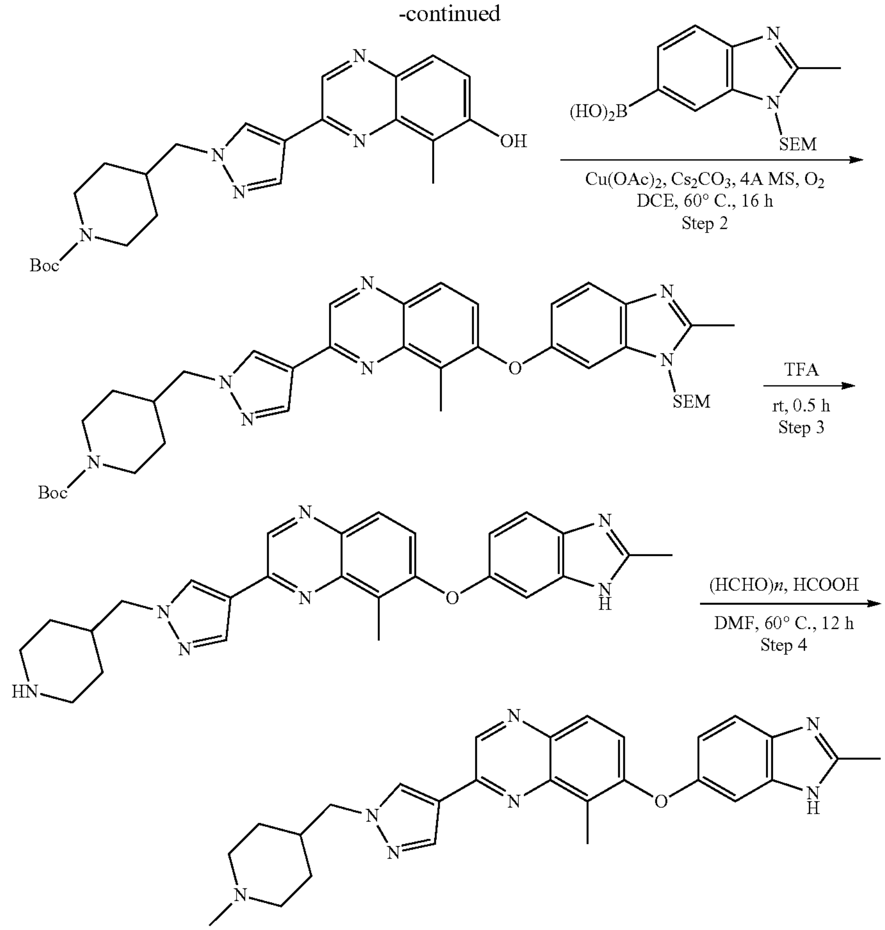

Step 1. A solution of tert-butyl 4-[[4-(8-chloro-7-hydroxy-quinoxalin-2-yl)pyrazol-1-yl]methyl]piperidine-1-carboxylate (600 mg, 1.4 mmol), methylboronic acid (809 mg, 14 mmol), $K_3PO_4$ (860 mg, 4.1 mmol), SPhos (55 mg, 0.14 mmol) and $Pd(OAc)_2$ (61 mg, 0.27 mmol) in toluene (10 mL) was stirred at 80° C. for 12 h under $N_2$. The reaction mixture was concentrated under reduced pressure. The residue was purified by column chromatography (silica gel, petroleum ether/ethyl acetate=5/1 to 1/1) to give tert-butyl 4-[[4-(7-hydroxy-8-methyl-quinoxalin-2-yl)pyrazol-1-yl]methyl]piperidine-1-carboxylate (250 mg, 37%) as a yellow solid. m/z ES+ $[M+H]^+$ 424.4; $^1$H NMR (400 MHz, $CDCl_3$) δ ppm 8.89 (s, 1H), 8.23 (s, 1H), 8.13 (s, 1H), 7.82 (d, J=9.2 Hz, 1H), 7.31 (d, J=9.2 Hz, 1H), 4.11 (d, J=7.2 Hz, 2H), 2.79-2.70 (m, 2H), 2.69 (s, 3H), 2.15-2.10 (m; 1H), 1.70-1.63 (m, 2H), 1.46 (s, 9H), 1.32-1.16 (m, 4H).

Step 2. To a solution of tert-butyl 4-[[4-(7-hydroxy-8-methyl-quinoxalin-2-yl)pyrazol-1-yl]methyl]piperidine-1-carboxylate (240 mg, 0.28 mmol), [2-methyl-3-(2-trimethylsilylethoxymethyl)benzimidazol-5-yl]boronic acid (350 mg, 0.57 mmol) in dichloroethane (2 mL) was added $Cu(OAc)_2$ (102 mg, 0.28 mmol), 4 Å MS (400 mg) and $Cs_2CO_3$ (370 mg, 0.57 mmol). The mixture was stirred at 60° C. for 12 h under $O_2$ (15 psi). The reaction mixture was filtered and concentrated under reduced pressure. The residue was purified by preparative-TLC (silica gel, dichloromethane/methanol=20/1) to give tert-butyl 4-[[4-[8-methyl-7-[2-methyl-3-(2-trimethylsilylethoxymethyl)benzimidazol-5-yl]oxy-quinoxalin-2-yl]pyrazol-1-yl]methyl]piperidine-1-carboxylate (44 mg, 11%) as a yellow solid. m/z ES+ $[M+H]^+$ 684.3.

Step 3. A solution of 4-[[4-[8-methyl-7-[2-methyl-3-(2-trimethylsilylethoxymethyl)-benzimidazol-5-yl]oxy-quinoxalin-2-yl]pyrazol-1-yl]methyl]piperidine-1-carboxylate (44 mg, 64 μmol) in TFA (0.5 mL) was stirred at 25° C. for 0.5 h. The reaction mixture was concentrated under reduced pressure to give 8-methyl-7-[(2-methyl-3H-benzimidazol-5-yl)oxy]-2-[1-(4-piperidylmethyl)pyrazol-4-yl]quinoxaline (35 mg, crude) as a yellow oil. m/z ES+ $[M+H]^+$ 454.3.

Step 4. To a solution of 8-methyl-7-[(2-methyl-3H-benzimidazol-5-yl)oxy]-2-[1-(4-piperidylmethyl)pyrazol-4-yl]quinoxaline (35 mg, 77 μmol) in DMF (0.5 mL) was added paraformaldehyde (46 mg, 1.5 mmol) and formic acid (74 mg, 1.5 mmol). The mixture was stirred at 60° C. for 12 h. The reaction mixture was filtered and concentrated under vacuum. The residue was purified by preparative-HPLC (neutral condition; Waters Xbridge 150×25 mm×5 μm; mobile phase: [water (10 mM $NH_4HCO_3$)-acetonitrile]; B %: 24%-54%, 10 min) to give 8-methyl-7-[(2-methyl-3H-benzimidazol-5-yl)oxy]-2-[1-[(1-methyl-4-piperidyl)methyl]pyrazol-4-yl]quinoxaline (8.54 mg, 19%) as a white solid. m/z ES+ $[M+H]^+$ 468.5; $^1$H NMR (400 MHz, DMSO-$d_6$) δ ppm 9.23 (s, 1H), 8.68 (s, 1H), 8.36 (s, 1H), 8.24 (s, 1H), 7.84 (d, J=9.2 Hz, 1H), 7.46 (d, J=8.4 Hz, 1H), 7.24 (d, J=9.2 Hz, 1H), 7.06 (d, J=2.0 Hz, 1H), 6.87 (dd, J=8.8, 2.2 Hz, 1H), 4.14 (d, J=7.2 Hz, 2H), 2.95 (d, J=11.6 Hz, 2H), 2.69 (s, 3H), 2.47 (s, 3H), 2.31 (s, 3H), 2.16 (t, J=10.8 Hz, 2H), 1.94 (s, 1H), 1.57 (d, J=11.6 Hz, 2H), 1.42-1.25 (m, 2H).

Example 10. Synthesis of 8-chloro-7-((2-methylimidazo[1,2-a]pyridin-7-yl)oxy)-2-(1-((1-methylpiperidin-4-yl)methyl)-1H-pyrazol-4-yl)quinoxaline

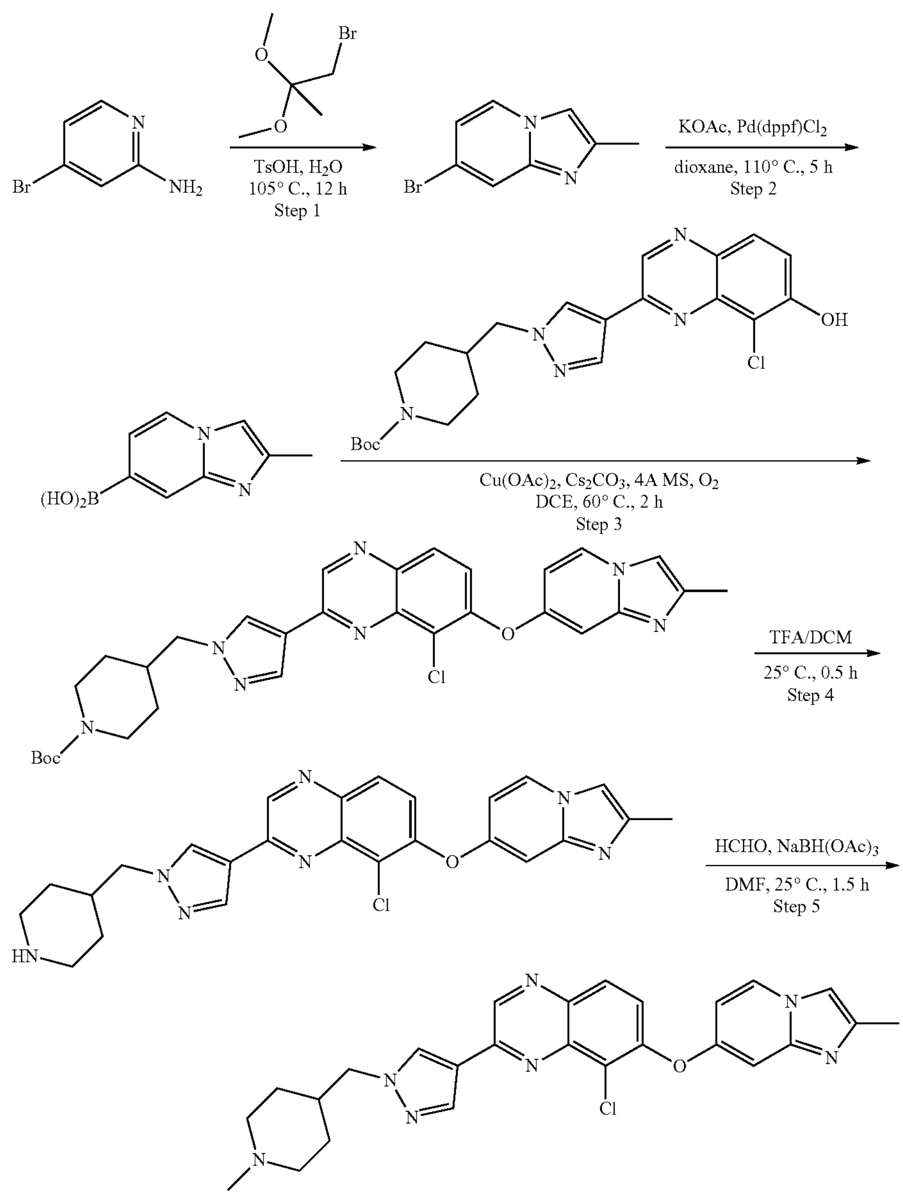

Step 1. To a solution of 4-bromopyridin-2-amine (7 g, 40 mmol) and 1-bromo-2,2-dimethoxy-propane (36 g, 198.25 mmol, 26.68 mL) in $H_2O$ (0.14 L) was added p-toluenesulfonic acid (1.32 g, 7.69 mmol). The mixture was stirred at 105° C. for 18 h. The reaction mixture was adjusted to pH=9 with saturated $NaHCO_3$ aqueous solution and extracted with ethyl acetate (100 mL×2). The combined organic layers were dried over $Na_2SO_4$, filtered and concentrated under reduced pressure to give a residue. The residue was purified by column chromatography (silica gel, petroleum ether/ethyl acetate=10/1 to 2/1) to give 7-bromo-2-methylimidazo[1,2-a]pyridine (2.9 g, 13.7 mmol, 34%) as a yellow solid. m/z ES+ $[M+H]^+$ 213.0.

Step 2. To a solution of 7-bromo-2-methyl-imidazo[1,2-a]pyridine (1 g, 4.74 mmol) in dioxane (40 mL) was added 4,4,5,5-tetramethyl-2-(4,4,5,5-tetramethyl-1,3,2-dioxaborolan-2-yl)-1,3,2-dioxaborolane (6.02 g, 23.69 mmol), KOAc (1.86 g, 18.95 mmol) and Pd(dppf)$Cl_2$·$CH_2Cl_2$ (387 mg, 0.47 mmol). The mixture was stirred at 110° C. for 5 h under $N_2$. The reaction mixture was diluted with $H_2O$ (150 mL) and extracted with dichloromethane (100 mL×3). The combined organic layers were dried over $Na_2SO_4$, filtered and concentrated under reduced pressure to give a residue. The crude product was purified by reversed-phase HPLC (mobile phase: [water/formic acid-acetonitrile]) to give (2-methylimidazo[1,2-a]pyridin-7-yl)boronic acid (480 mg, 2.73 mmol, 58%) as a white solid. m/z ES+ $[M+H]^+$ 177.0.

Step 3. To a solution of tert-butyl 4-[[4-(8-chloro-7-hydroxy-quinoxalin-2-yl)pyrazol-1-yl]methyl]piperidine-1-carboxylate (50 mg, 0.11 mmol) and (2-methylimidazo[1, 2-a]pyridin-7-yl)boronic acid (39.64 mg, 0.23 mmol) in dichloroethane (1 mL) was added $Cu(OAc)_2$ (24.6 mg, 0.14 mmol), 4 Å MS (100 mg) and $Cs_2CO_3$ (73.4 mg, 0.23 mmol). The mixture was stirred at 60° C. for 2 h under $O_2$ at 15 psi. The reaction mixture was filtered and concentrated under reduced pressure to give a residue. The residue was purified by column chromatography (silica gel, petroleum ether/ethyl acetate-3/1 to dichloromethane/methanol=30/1) to give tert-butyl 4-((4-(8-chloro-7-((2-methylimidazo[1,2-a]pyridin-7-yl)oxy)quinoxalin-2-yl)-1H-pyrazol-1-yl) methyl) piperidine-1-carboxylate (12 mg, 17.4 μmol, 15%) as a yellow oil. m/z ES+ $[M+H]^+$ 574.2.

Step 4. To a solution of tert-butyl 4-[[4-[8-chloro-7-(2-methylimidazo[1,2-a]pyridin-7-yl)oxy-quinoxalin-2-yl] pyrazol-1-yl]methyl]piperidine-1-carboxylate (10 mg, 14.5 μmol) in dichloromethane (0.3 mL) was added TFA (154 mg, 1.35 mmol, 0.1 mL). The mixture was stirred at 25° C. for 0.5 h. The reaction mixture was concentrated under reduced pressure to give desired 8-chloro-7-((2-methylimidazo[1,2-a]pyridin-7-yl)oxy)-2-(1-(piperidin-4-ylmethyl)-1H-pyrazol-4-yl)quinoxaline (10 mg, crude, as TFA salt) as a yellow oil. m/z ES+ $[M+H]^+$ 474.2.

Step 5. To a solution of 8-chloro-7-(2-methylimidazo[1,2-a]pyridin-7-yl)oxy-2-[1-(4-piperidylmethyl)pyrazol-4-yl] quinoxaline (10 mg, 17 μmol, TFA salt) in DMF (0.5 mL) was added aq. paraformaldehyde solution (13.8 mg, 170 μmol, 37% purity). The mixture was stirred at 25° C. for 0.5 h. Then NaBH(OAc) 3 (18 mg, 85 μmol) was added. The mixture was stirred at 25° C. for 1 h. The reaction mixture was diluted with $H_2O$ (5 mL) and extracted with ethyl acetate (5 mL×3). The combined organic layers were dried over $Na_2SO_4$, filtered and concentrated under reduced pressure to give a residue. The residue was purified by preparative-HPLC (neutral condition; column: Waters Xbridge 150*25 mm*5 μm; mobile phase: [water (10 mM $NH_4HCO_3$)-acetonitrile]; B %: 18%-48%, 10 min) to give 8-chloro-7-((2-methylimidazo[1,2-a]pyridin-7-yl)oxy)-2-(1-((1-methylpiperidin-4-yl)methyl)-1H-pyrazol-4-yl)quinoxaline (1.41 mg, 2.68 μmol, 16%) as a yellow solid. m/z ES+ $[M+H]^+$ 488.1; $^1H$ NMR (400 MHz, DMSO-$d_6$) δ ppm 9.37 (s, 1 H), 8.70 (s, 1H), 8.51 (d, J=7.2 Hz, 1H), 8.37 (s, 1H), 8.07 (d, J=9.2 Hz, 1H), 7.64 (d, J=7.2 Hz, 2H), 6.85-6.77 (m, 2H), 4.13 (d, J=7.2 Hz, 2H), 2.74 (d, J=11.2 Hz, 2H), 2.28 (s, 3H), 2.12 (s, 3H), 1.87-1.73 (m, 3H), 1.49 (d, J=11.2 Hz, 2H), 1.29-1.23 (m, 2H).

Example 11. Synthesis of 5-[8-chloro-7-[(2-methyl-3H-benzimidazol-5-yl)oxy]quinoxalin-2-yl]-3-[(1-methyl-4-piperidyl)methyl] isoxazole

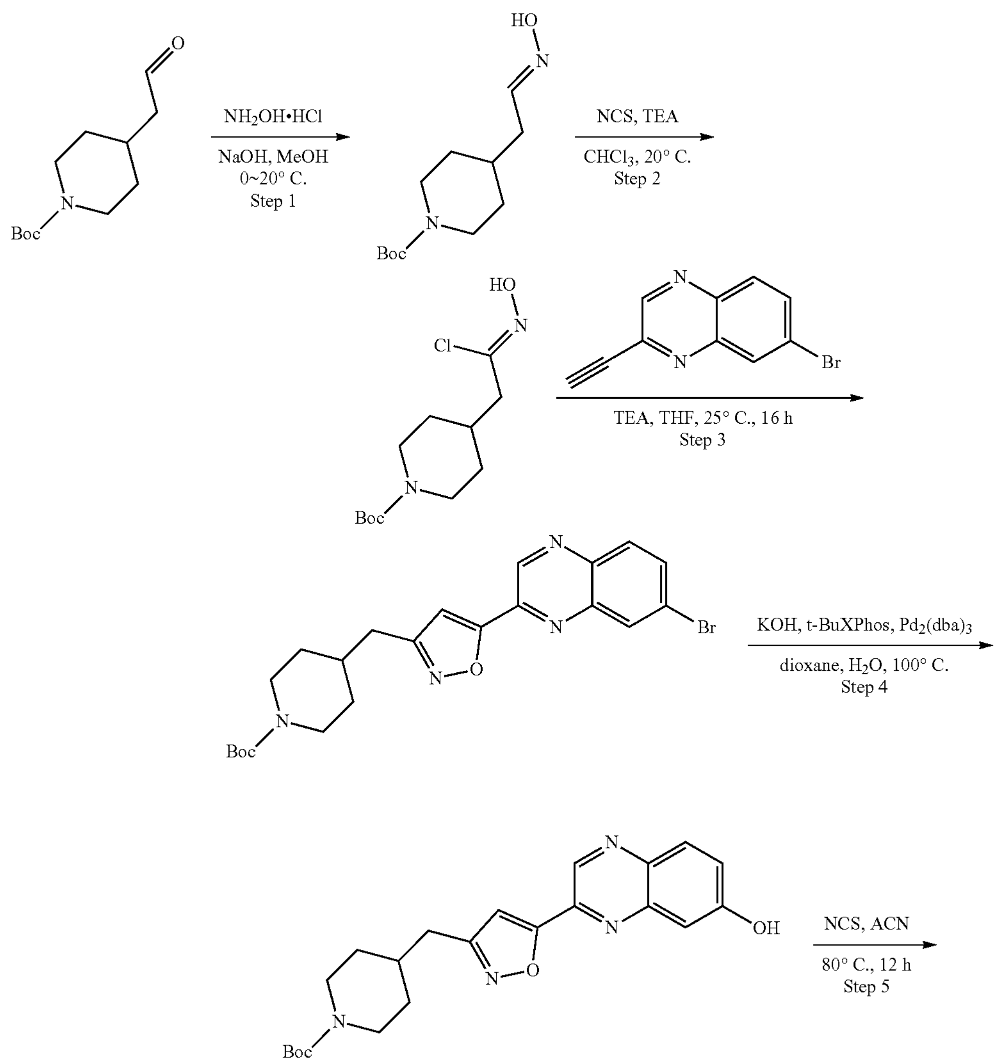

-continued

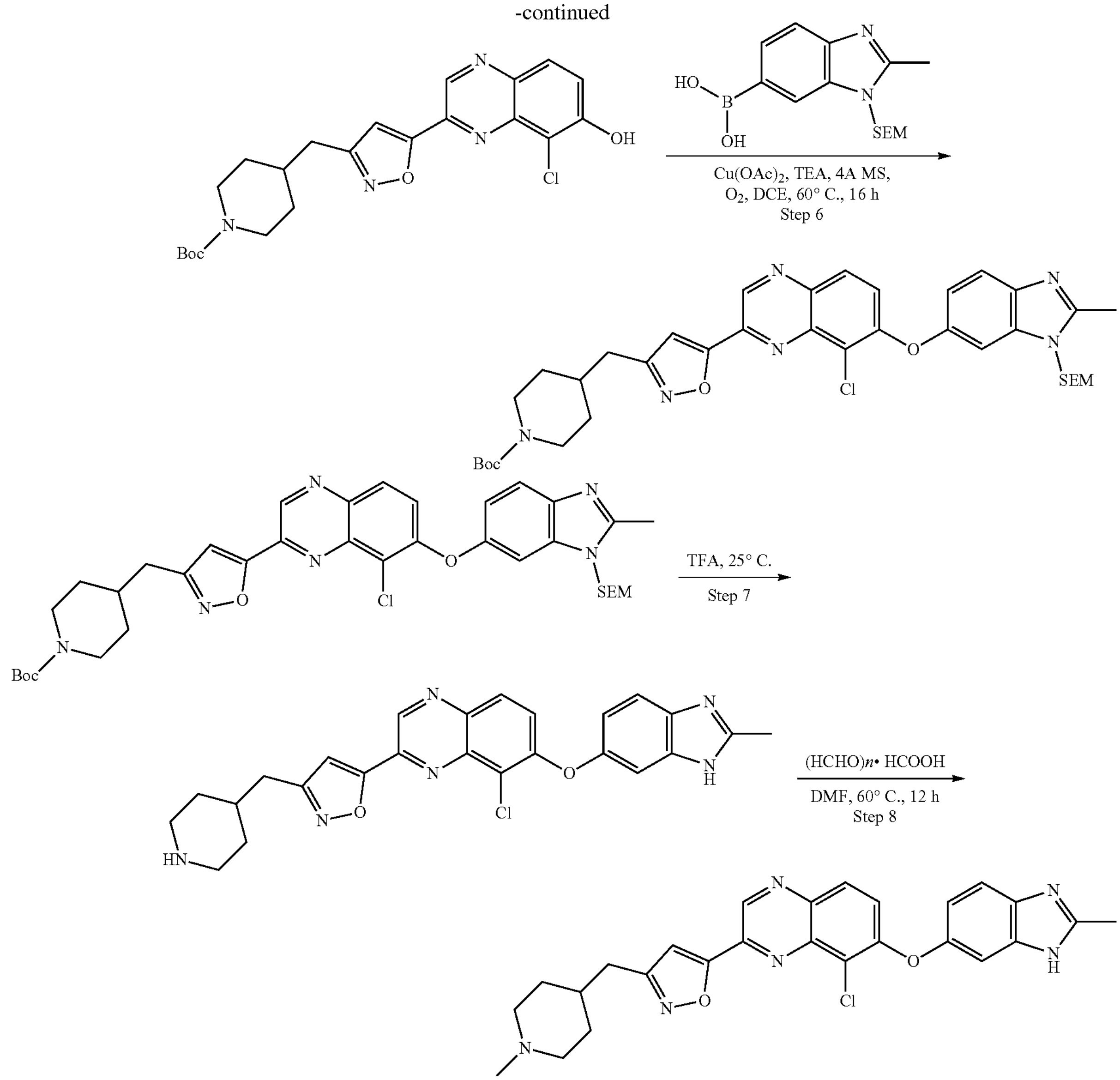

Step 1. To a solution of tert-butyl 4-(2-oxoethyl) piperidine-1-carboxylate (1 g, 4.4 mmol) hydroxylamine (367 mg, 5.28 mmol) in methanol (10 mL) was added NaOH (3 M, 1.76 mL) at 0° C. dropwise, and the mixture was stirred at 25° C. for 16 h. On completion, the mixture was concentrated under reduced pressure, then poured into water (50 mL) and extracted with ethyl acetate (30 mL×3). The organic layers were dried by sodium sulfate, filtered and concentrated under reduced pressure to give tert-butyl 4-[(2E)-2-hydroxyiminoethyl]piperidine-1-carboxylate (1 g, 94%) as a colourless oil. $^1$H NMR (400 MHz, $CDCl_3$) δ 9.79 (s, 1H), 7.45 (t, J=6.4 Hz, 1H), 6.95 (s, 1H), 4.16-4.05 (m, 2H), 2.80-2.60 (m, 2H), 2.46-2.35 (m, 1H), 2.18 (t, J=6.4 Hz, 1H), 1.79-1.59 (m, 3H), 1.46 (s, 9H), 1.25-1.10 (m, 2H).

Step 2. To a solution of tert-butyl 4-[(2E)-2-hydroxyiminoethyl]piperidine-1-carboxylate (1 g, 4.13 mmol) in dichloromethane (10 mL) was added N-chlorosuccinimide (551 mg, 4.13 mmol) and pyridine (32.6 mg, 412 μmol). The mixture was stirred at 25° C. for 16 h. On completion, the mixture was poured into water (50 mL) and extracted with ethyl acetate (30 mL×3). The organic layers was dried by sodium sulfate, filtered and concentrated under reduced pressure to remove the solvent and give tert-butyl 4-[(2Z)-2-chloro-2-hydroxyimino-ethyl]piperidine-1-carboxylate (1.4 g, crude) as a white solid. $^1$H NMR (400 MHz, $CDCl_3$) δ 9.19 (s, 1H), 8.58-8.20 (m, 1H), 7.97-7.83 (m, 1H), 4.04 (d, J=13.4 Hz, 2H), 2.69-2.56 (m, 2H), 2.35 (d, J=7.2 Hz, 2H), 1.90-1.82 (m, 1H), 1.68-1.54 (m, 2H), 1.38 (s, 9H), 1.13-1.02 (m, 2H).

Step 3. To a solution of tert-butyl 4-[(2Z)-2-chloro-2-hydroxyimino-ethyl]piperidine-1-carboxylate (1 g, 3.61 mmol) 7-bromo-2-ethynyl-quinoxaline (400 mg, 1.72 mmol) in THF (3 mL) was added triethylamine (174 mg, 1.72 mmol). The mixture was stirred at 25° C. for 16 h. One completion, the mixture was concentrated under reduced pressure to remove the solvent and give a residue. The residue was triturated with methanol (20 mL) to give tert-butyl 4-[[5-(7-bromoquinoxalin-2-yl) isoxazol-3-yl]methyl] piperidine-1-carboxylate (600 mg, 73%) as a white solid.

Step 4. To a solution of tert-butyl 4-[[5-(7-bromoquinoxalin-2-yl) isoxazol-3-yl]methyl]piperidine-1-carboxylate (650 mg, 1.37 mmol) in dioxane (10 mL) and $H_2O$ (2 mL) was added KOH (770 mg, 13.7 mmol), t-BuXPhos (58.3 mg, 137 μmol) and $Pd_2(dba)_3$ (125 mg, 137 μmol). The mixture was stirred at 100° C. for 1 h under nitrogen. On completion, the mixture was filtered and concentrated under reduced pressure. The residue was purified by column chromatography (silica gel, petroleum ether/ethyl acetate-3/1 to 1/1) to give tert-butyl 4-[[5-(7-hydroxyquinoxalin-2-yl) isoxazol-3-yl]methyl]piperidine-1-carboxylate (270 mg, 47%) as a yellow solid. $^1$H NMR (400 MHz, $CD_3OD$) δ 9.23 (s, 1H), 7.95 (d, J=9.2 Hz, 1H), 7.60 (d, J=9.2 Hz, 1H), 7.27 (s, 1H), 4.11 (d, J=13.4 Hz, 2H), 2.78 (d, J=7.2 Hz, 4H), 2.11-1.89 (m, 1H), 1.78 (d, J=12.4 Hz, 2H), 1.47 (s, 9H), 1.33-1.15 (m, 2H).

Step 5. A solution of tert-butyl 4-[[5-(7-hydroxyquinoxalin-2-yl) isoxazol-3-yl]methyl]piperidine-1-carboxylate (220 mg, 535 μmol), N-chlorosuccinimide (85.8 mg, 643 μmol) in acetonitrile (1 mL) was stirred at 80° C. for 16 h. On completion, the reaction mixture was concentrated. The residue was purified by column chromatography (silica gel, petroleum ether/ethyl acetate=5/1 to 3/1) to give tert-butyl 4-[[5-(8-chloro-7-hydroxy-quinoxalin-2-yl) isoxazol-3-yl] methyl]piperidine-1-carboxylate (200 mg, 84%) as a yellow solid. $^1$H NMR (400 MHz, $CD_3OD$) δ 9.23 (s, 1H), 7.95 (d, J=9.2 Hz, 1H), 7.60 (d, J=9.2 Hz, 1H), 7.27 (s, 1H), 4.11 (d, J=13.2 Hz, 2H), 2.78 (d, J=7.2 Hz, 4H), 2.11-1.89 (m, 1H), 1.78 (d, J=12.4 Hz, 2H), 1.47 (s, 9H), 1.33-1.15 (m, 2H).

Step 6. A mixture of tert-butyl 4-[[5-(8-chloro-7-hydroxy-quinoxalin-2-yl) isoxazol-3-yl]methyl]piperidine-1-carboxylate (180 mg, 404 μmol), [2-methyl-3-(2-trimethylsilylethoxymethyl)benzimidazol-5-yl]boronic acid (247 mg, 809 μmol), $Cu(OAc)_2$ (36.7 mg, 202 μmol), 4 Å MS (5 mg, 405 μmol) and triethylamine (81.8 mg, 809 μmol) in dichloroethane (10 mL) was stirred at 60° C. for 16 h under $O_2$ atmosphere (15 psi). On completion, the mixture was concentrated under reduced. The residue was purified by column chromatography (silica gel, petroleum ether/ethyl acetate 5:1 to 3:1 and dichloromethane/methanol=1/0 to 100/1) and reversed-phase HPLC (mobile phase: [water/formic acid-acetonitrile]) to give tert-butyl 4-[[5-[8-chloro-7-[2-methyl-3-(2-trimethylsilylethoxymethyl)benzimidazol-5-yl]oxy-quinoxalin-2-yl] isoxazol-3-yl]methyl] piperidine-1-carboxylate (30 mg, 42.5 μmol, 11%) as a yellow oil. m/z ES+ $[M+H]^+$ 705.2.

Step 7. A solution of tert-butyl 4-[[5-[8-chloro-7-[2-methyl-3-(2-trimethylsilylethoxymethyl)benzimidazol-5-yl] oxy-quinoxalin-2-yl] isoxazol-3-yl]methyl]-piperidine-1-carboxylate (25 mg, 35.4 μmol) in TFA (1 mL) was stirred at 25° C. for 10 min. On completion, the mixture was concentrated under reduced pressure to remove the solvent and give 5-[8-chloro-7-[(2-methyl-3H-benzimidazol-5-yl) oxy]quinoxalin-2-yl]-3-(4-piperidylmethyl) isoxazole (16 mg, crude) as a yellow oil. m/z ES+ $[M+H]^+$ 475.1.

Step 8. To a solution of 5-[8-chloro-7-[(2-methyl-3H-benzimidazol-5-yl)oxy]quinoxalin-2-yl]-3-(4-piperidylmethyl) isoxazole (16 mg, 33.7 μmol) in DMF (1 mL) was added formic acid (16.2 mg, 336 μmol), paraformaldehyde (10.1 mg, 336 μmol). The mixture was stirred at 60° C. for 16 h. On completion, the solids were removed by filtration and the filtrate concentrated under reduced pressure. The residue was purified by preparative-HPLC (column: Phenomenex Gemini-NX C18 75*30 mm*3 μm; mobile phase: [water (0.225% formic acid)-acetonitrile]; B %: 5%-35%, 7 min) to give 5-[8-chloro-7-[(2-methyl-3H-benzimidazol-5-yl)oxy]quinoxalin-2-yl]-3-[(1-methyl-4-piperidyl)methyl] isoxazole (8.73 mg, 53%) as a yellow solid. m/z ES+ $[M+H]^+$ 489.1; $^1$H NMR (400 MHz, DMSO-$d_6$) δ 9.47 (s, 1H), 8.21 (s, 1H), 8.07 (d, J=9.2 Hz, 1H), 7.56-7.47 (m, 3H), 7.26 (s, 1H), 6.97 (d, J=8.4 Hz, 1H), 2.87 (d, J-11.2 Hz, 2H), 2.72 (d, J=6.8 Hz, 2H), 2.49 (s, 3H), 2.25 (s, 3H), 2.04 (t, J=11.6 Hz, 2H), 1.80-1.64 (m, 3H), 1.43-1.25 (m, 2H).

Example 12. Synthesis of 8-chloro-7-[(2-methyl-3H-benzimidazol-5-yl)oxy]-2-[1-(tetrahydrofuran-3-ylmethyl)pyrazol-4-yl]quinoxaline

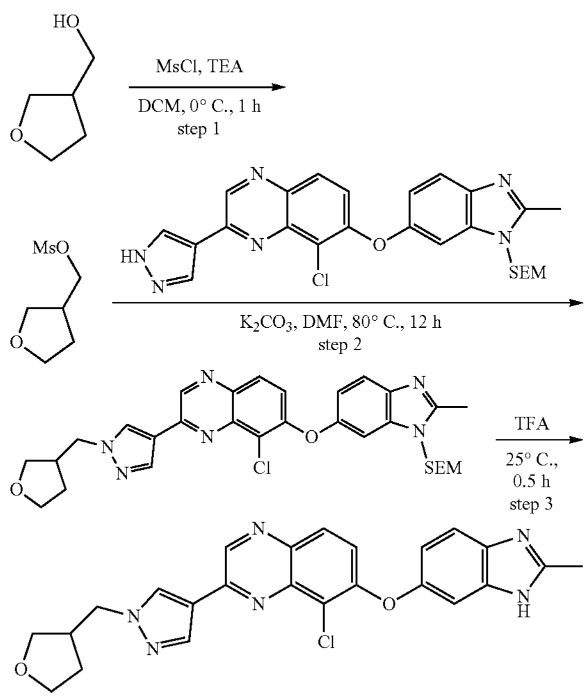

Step 1. To a solution of tetrahydrofuran-3-ylmethanol (200 mg, 1.96 mmol) in dichloromethane (3 mL) was added methanesulfonyl chloride (336 mg, 2.94 mmol) and triethylamine (594 mg, 5.87 mmol). The mixture was stirred at 0° C. for 1 h. On completion, the reaction mixture was diluted with $NaHCO_3$ solution (5 mL) and extracted with ethyl acetate (5 mL× 3). The combined organic layers were dried over anhydrous sodium sulfate, filtered and concentrated under reduced pressure to give tetrahydrofuran-3-ylmethyl methanesulfonate (400 mg, crude) as a white oil. $^1$H NMR (400 MHz, $CDCl_3$) δ 4.25-4.07 (m, 2H), 3.94-3.70 (m, 3H), 3.67-3.61 (m, 1H), 3.03 (s, 3H), 2.75-2.62 (m, 1H), 2.16-2.06 (m, 1H), 1.74-1.58 (m, 1H).

Step 2. To a solution of 2-[[6-[5-chloro-3-(1H-pyrazol-4-yl)quinoxalin-6-yl]oxy-2-methyl-benzimidazol-1-yl] methoxy]ethyl-trimethyl-silane (50 mg, 98.6 μmol) in DMF (1 mL) was added $K_2CO_3$ (40.8 mg, 295 μmol) and tetrahydrofuran-3-ylmethyl methanesulfonate (30 mg, 166 μmol). The mixture was stirred at 80° C. for 12 h. On completion, the reaction mixture was diluted with water (5 mL) and extracted with ethyl acetate (5 mL×3). The combined organic layers were dried over anhydrous sodium sulfate, filtered and concentrated under reduced pressure to give 2-[[6-[5-chloro-3-[1-(tetrahydrofuran-3-ylmethyl) pyrazol-4-yl]quinoxalin-6-yl]oxy-2-methyl-benzimidazol-1-yl]methoxy]ethyl-trimethyl-silane (50 mg, crude) as a white solid. m/z ES+ $[M+H]^+$ 591.1.

Step 3. To a solution of 2-[[6-[5-chloro-3-[1-(tetrahydrofuran-3-ylmethyl)pyrazol-4-yl]quinoxalin-6-yl]oxy-2- methyl-benzimidazol-1-yl]methoxy]ethyl-trimethyl-silane (50 mg, 84.5 µmol) in TFA (0.5 mL) was added TFA (770 mg, 6.75 mmol). The mixture was stirred at 25° C. for 0.5 h. On completion, the reaction mixture was concentrated under reduced pressure. The residue was purified by preparative-HPLC (column: Phenomenex Gemini-NX C18 75*30 mm*3 µm; mobile phase: [water (0.225% formic acid)-acetonitrile]; B %: 15%-45%, 7 min) to give 8-chloro-7-[(2-methyl-3H-benzimidazol-5-yl)oxy]-2-[1-(tetrahydrofuran-3-ylmethyl)pyrazol-4-yl]quinoxaline (15.2 mg, 39%) as a yellow solid. m/z ES+ $[M+H]^+$ 461.1; $^1$H NMR (400 MHz, $CDCl_3$) δ 8.99 (s, 1H), 8.27 (s, 1H), 8.25 (br s, 1H), 8.23 (s, 1H), 7.86 (d, J=9.2 Hz, 1H), 7.58 (d, J=8.8 Hz, 1H), 7.29 (d, J=4.0 Hz, 1H), 7.11-7.04 (m, 1H), 4.22 (d, J-7.6 Hz, 2H), 3.99-3.91 (m, 1H), 3.87-3.75 (m, 2H), 3.70-3.63 (m, 1H), 3.02-2.88 (m, 1H), 2.74 (s, 3H), 2.17-2.04 (m, 1H), 1.79-1.68 (m, 1H).

Example 13. Synthesis of Azetidin-1-yl(3-(4-(8-chloro-7-((2-methyl-1H-benzo[d]imidazol-6-yl)oxy) quinoxalin-2-yl)-1H-pyrazol-1-yl)azetidin-1-yl) methanone

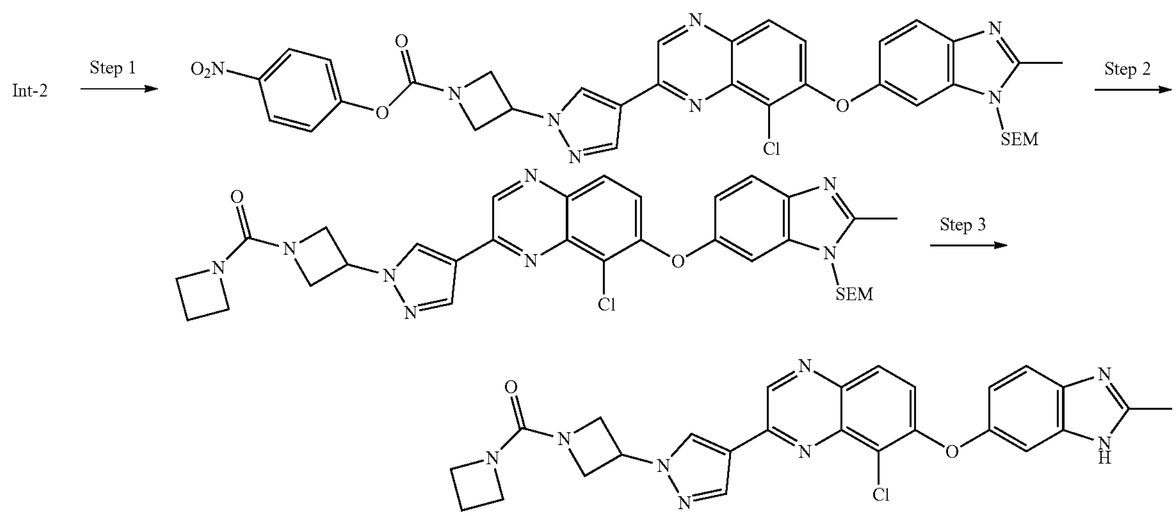

Step 1. 4-Nitrophenyl 3-(4-(8-chloro-7-((2-methyl-1-((2-(trimethylsilyl)ethoxy)methyl)-1H-benzo[d] imidazol-6-yl)oxy)quinoxalin-2-yl)-1H-pyrazol-1-yl) azetidine-1-carboxylate To a mixture of 2-[[6-[3-[1-(azetidin-3-yl)pyrazol-4-yl]-5-chloro-quinoxalin-6-yl]oxy-2-methyl-benzimidazol-1-yl] methoxy]ethyl-trimethyl-silane (500 mg, |889 µmol) and (4-nitrophenyl) carbonochloridate (179 mg, 889 µmol) in dichloromethane (10 mL) was added triethylamine (180 mg, 1.78 mmol) in one portion under nitrogen. The mixture was stirred at 20° C. stirred for 2 hours. The reaction mixture was concentrated under reduced pressure to give 4-nitrophenyl 3-(4-(8-chloro-7-((2-methyl-1-((2-(trimethylsilyl)ethoxy) methyl)-1H-benzo[d]imidazol-6-yl)oxy)quinoxalin-2-yl)-1H-pyrazol-1-yl)azetidine-1-carboxylate (0.6 g, 578 µmol, 65%) as a yellow solid. m/z ES+ $[M+H]^+$ 727.4

Step 2. Azetidin-1-yl(3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) azetidin-1-yl) methanone A mixture of azetidine (118 mg, 2.06 mmol) and (4-nitrophenyl) 3-[4-[8-chloro-7-[2-methyl-3-(2-trimethylsilylethoxymethyl)benzimidazol-5-yl]oxy-quinoxalin-2-yl] pyrazol-1-yl]azetidine-1-carboxylate (300 mg, 413 µmol) in dichloromethane (5 mL) was stirred at 25° C. for 16 hours. The reaction mixture was concentrated under reduced pressure. The residue was purified by reversed-phase HPLC (0.1% formic acid condition) to give azetidin-1-yl-[3-[4-[8-chloro-7-[2-methyl-3-(2-trimethylsilylethoxymethyl)benzimidazol-5-yl]oxy-quinoxalin-2-yl]pyrazol-1-yl]azetidin-1-yl]methanone (70 mg, 86.8 µmol, 21%) as a yellow solid. m/z ES+ $[M+H]^+$ 645.4

Step 3. Azetidin-1-yl(3-(4-(8-chloro-7-((2-methyl-1H-benzo[d]imidazol-6-yl)oxy)quinoxalin-2-yl)-1H-pyrazol-1-yl)azetidin-1-yl) methanone A solution of azetidin-1-yl-[3-[4-[8-chloro-7-[2-methyl-3-(2-trimethylsilylethoxymethyl)benzimidazol-5-yl]oxy-quinoxalin-2-yl]pyrazol-1-yl]azetidin-1-yl]methanone (70.0 mg, 108 µmol) in trifluoroacetic acid (0.5 mL) was stirred at 25° C. for 1 h. The reaction mixture was concentrated under reduced pressure. The residue was purified by prep-HPLC (column: Phenomenex Luna C18 150*25 mm*10 µm; mobile phase: [water (formic acid)-acetonitrile]; (B %: 11%-41%, 10 min) to give azetidin-1-yl-[3-[4-[8-chloro-7-[(2-methyl-3H-benzimidazol-5-yl)oxy]quinoxalin-2-yl] pyrazol-1-yl]azetidin-1-yl]methanone (16.8 mg, 32.7 µmol, 30%) as an off-white solid. $^1$H NMR (400 MHz, $CD_3OD$) δ 9.18 (s, 1H), 8.65 (s, 1H), 8.41 (s, 1H), 7.98 (d, J=9.2 Hz, 1H), 7.74 (d, J=8.8 Hz, 1H), 7.47 (d, J=9.2 Hz, 1H), 7.34-7.26 (m, 2H), 5.40-5.29 (m, 1H), 4.52-4.44 (m, 2H), 4.43-4.36 (m, 2H), 4.05 (t, J=7.6 Hz, 4H), 2.81 (s, 3H), 2.39-2.25 (m, 2H). m/z ES+ $[M+H]^+$ 514.1

Example 14. Synthesis of 7-[4-[8-chloro-7-[(2-methyl-3H-benzimidazol-5-yl)oxy]quinoxalin-2-yl]pyrazol-1-yl]-3-oxa-9-azabicyclo[3.3.1]nonane

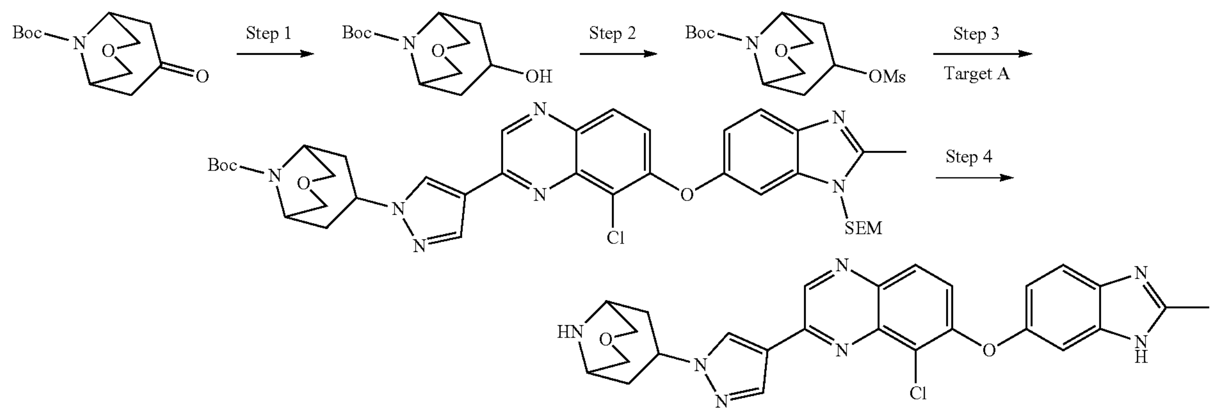

Step 1. tert-Butyl 7-hydroxy-3-oxa-9-azabicyclo[3.3.1]nonane-9-carboxylate

To a solution of tert-butyl 7-oxo-3-oxa-9-azabicyclo[3.3.1]nonane-9-carboxylate (450 mg, 1.87 mmol) in methanol (5 mL) was added sodium borohydride (141 mg, 3.73 mmol) portion-wise. The mixture was stirred at 0° C. for 2 h. The reaction mixture was quenched with saturated ammonium chloride (10 mL) at 0° C., then diluted with water (20 mL) and extracted with ethyl acetate (20 mL×3). The combined organic layers were washed with brine (50 mL), dried over anhydrous sodium sulfate, filtered and concentrated under reduced pressure to give tert-butyl 7-hydroxy-3-oxa-9-azabicyclo[3.3.1]nonane-9-carboxylate (400 mg, 1.65 mmol, 88%) as a white solid. $^1H$ NMR (400 MHz, $CDCl_3$) δ=5.59-5.43 (m, 1H), 4.15 (d, J=2.4 Hz, 1H), 4.06-3.93 (m, 2H), 3.90-3.81 (m, 2H), 3.79-3.70 (m, 2H), 2.23-2.08 (m, 2H), 1.82 (dd, J=3.2, 14.8 Hz, 2H), 1.47 (s, 9H).

Step 2. tert-Butyl 7-methylsulfonyloxy-3-oxa-9-azabicyclo[3.3.1]nonane-9-carboxylate To a solution of tert-butyl 7-hydroxy-3-oxa-9-azabicyclo[3.3.1]nonane-9-carboxylate (100 mg, 411 μmol) in dichloromethane (2 mL) was added triethylamine (83.1 mg, 822 μmol) at 0° C. Then methanesulfonyl chloride (70.6 mg, 616 μmol) was added. The mixture was stirred at 0° C. for 2 h. The reaction mixture was quenched with addition water (10 mL) at 0° C., and then extracted with dichloromethane (20 mL×3). The combined organic layers were washed with brine (20 mL), dried over anhydrous sodium sulfate, filtered and concentrated under reduced pressure. The residue was purified by column chromatography (petroleum ether:ethyl acetate 1:1) to give tert-butyl 7-methylsulfonyloxy-3-oxa-9-azabicyclo[3.3.1]nonane-9-carboxylate (60.0 mg, 187 μmol, 45%) as a white solid. $^1H$ NMR (400 MHz, $CDCl_3$) δ=4.91-4.86 (m, 1H), 4.20 (d, J=6.4 Hz, 1H), 4.06 (d, J=7.2 Hz, 1H), 3.78-3.70 (m, 2H), 3.68-3.61 (m, 2H), 3.03 (s, 3H), 2.44-2.30 (m, 2H), 2.05-1.99 (m, 2H), 1.48 (s, 9H).

Step 3. tert-Butyl 7-[4-[8-chloro-7-[2-methyl-3-(2-trimethylsilylethoxymethyl)benzimidazol-5-yl]oxy-quinoxalin-2-yl]pyrazol-1-yl]-3-oxa-9-azabicyclo[3.3.1]nonane-9-carboxylate To a solution of 2-[[6-[5-chloro-3-(1H-pyrazol-4-yl)quinoxalin-6-yl]oxy-2-methyl-benzimidazol-1-yl]methoxy]ethyl-trimethyl-silane (47.3 mg, 93.3 μmol) and tert-butyl 7-methylsulfonyloxy-3-oxa-9-azabicyclo[3.3.1]nonane-9-carboxylate (36.0 mg, 112 μmol) in N,N-dimethylformamide (2 mL) was added cesium carbonate (60.8 mg, 186 μmol) and 4-pyrrolidin-1-ylpyridine (13.8 mg, 93.3 μmol). The mixture was stirred at 80° C. for 12 h. The mixture was filtered and concentrated in vacuo and the residue was purified by prep-HPLC (column: Phenomenex Synergi C18 150*25 mm*10 μm; mobile phase: [water (0.225% formic acid)-acetonitrile]; (B %: 46%-79%, 11 min) to give tert-butyl 7-[4-[8-chloro-7-[2-methyl-3-(2-trimethylsilylethoxymethyl)benzimidazol-5-yl]oxy-quinoxalin-2-yl]pyrazol-1-yl]-3-oxa-9-azabicyclo[3.3.1]nonane-9-carboxylate (28.0 mg, 32.8 μmol, 40%) as a yellow solid. m/z ES+ $[M+1]^+$ 732.0.

Step 4. 7-[4-[8-chloro-7-[(2-methyl-3H-benzimidazol-5-yl)oxy]quinoxalin-2-yl]pyrazol-1-yl]-3-oxa-9-azabicyclo[3.3.1]nonane A solution of tert-butyl 7-[4-[8-chloro-7-[2-methyl-3-(2-trimethylsilylethoxymethyl)benzimidazol-5-yl]oxy-quinoxalin-2-yl]pyrazol-1-yl]-3-oxa-9-azabicyclo[3.3.1]nonane-9-carboxylate (20.0 mg, 27.3 μmol) in trifluoroacetic acid (1 mL) was stirred at 25° C. for 0.5 h. The mixture was concentrated in vacuo and the residue was purified by prep-HPLC (column: Phenomenex Synergi C18 150*25 mm*10 μm; mobile phase: [water (formic acid)-acetonitrile]; (B %: 0%-26%, 10 min) to give 7-[4-[8-chloro-7-[(2-methyl-3H-benzimidazol-5-yl)oxy]quinoxalin-2-yl]pyrazol-1-yl]-3-oxa-9-azabicyclo[3.3.1]nonane (13.4 mg, 26.7 μmol, 85%, formic acid salt) as an off-white solid. $^1H$ NMR (400 MHz, $CD_3OD$) δ=9.13 (s, 1H), 8.65 (s, 1H), 8.39-8.35 (m, 2H), 7.88 (d, J=9.6 Hz, 1H), 7.53 (d, J=8.6 Hz, 1H), 7.34 (d, J=9.6 Hz, 1H), 7.19 (d, J=2.0 Hz, 1H), 7.01 (dd, J=2.4, 8.8 Hz, 1H), 5.77-5.68 (m, 1H), 4.20-4.14 (m, 2H), 4.11-4.04 (m, 2H), 3.71 (s, 2H), 2.77-2.64 (m, 2H), 2.60-2.53 (m, 5H). m/z ES+ $[M+1]^+$ 502.0.

Example 15. Synthesis of (4-(4-(8-chloro-7-((2-methyl-1H-benzo[d]imidazol-6-yl)oxy)quinoxalin-2-yl)-1H-pyrazol-1-yl) piperidin-1-yl) (3-hydroxyazetidin-1-yl) methanone

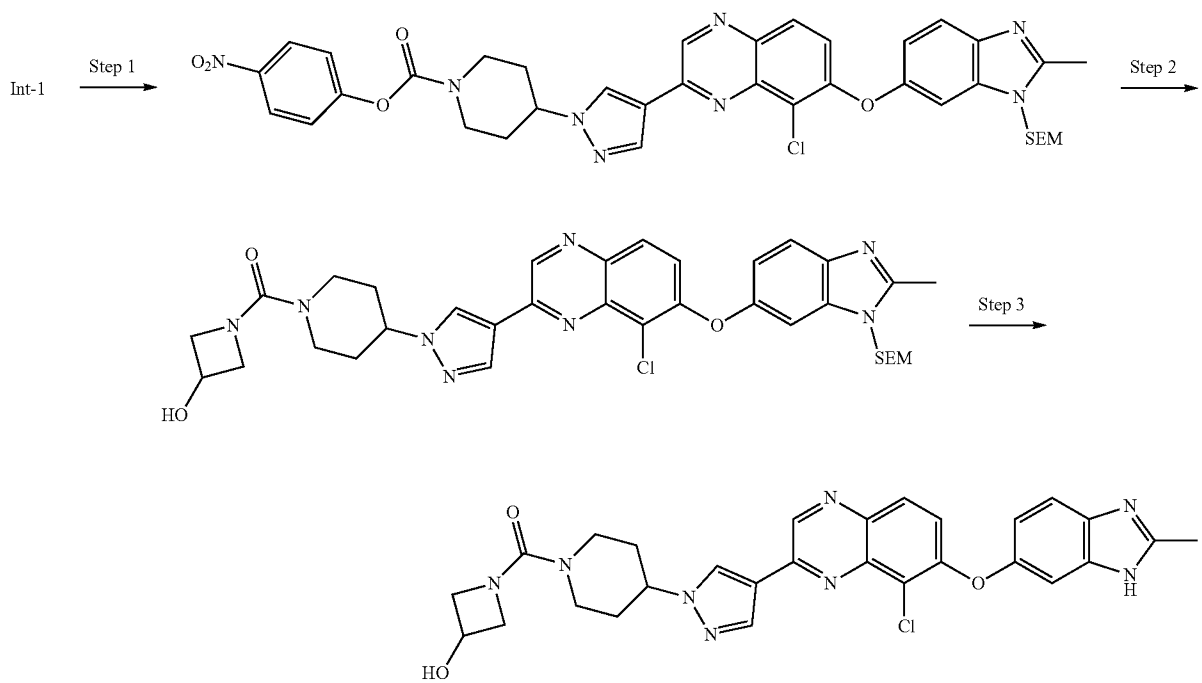

Step 1. 4-Nitrophenyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate To a solution of 2-[[6-[5-chloro-3-[1-(4-piperidyl)pyrazol-4-yl]quinoxalin-6-yl]oxy-2-methyl-benzimidazol-1-yl] methoxy]ethyl-trimethyl-silane (170 mg, 288 μmol) in dichloromethane (1.5 mL) was added (4-nitrophenyl) carbonochloridate (116 mg, 576 μmol) and triethylamine (87.4 mg, 864 μmol). The mixture was stirred at 25° C. for 1 h. The reaction mixture was concentrated in vacuo. The residue was purified by column chromatography (petroleum ether/ethyl acetate=1/1 to 0/1) to give 4-nitrophenyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (190 mg, 242 μmol, 84%) as a white solid. m/z ES+ $[M+H]^+$ 755.2.

Step 2. (4-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidin-1-yl) (3-hydroxyazetidin-1-yl) methanone To a solution of 4-nitrophenyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (170 mg, 225 μmol) in tetrahydrofuran (1.5 mL) was added triethylamine (68.3 mg, 675 μmol) and azetidin-3-ol (74.0 mg, 675 μmol, HCl). The mixture was stirred at 60° C. for 16 h. The reaction mixture was diluted with water (10 mL) and extracted with ethyl acetate (15 mL×3). The combined organic layers were washed with brine (3 mL×3), dried over anhydrous sodium sulfate, filtered and concentrated in vacuo to give (4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidin-1-yl) (3-hydroxyazetidin-1-yl) methanone (140 mg, 203 μmol, 90%) as a yellow solid. m/z ES+ $[M+H]^+$ 689.1.

Step 3. (4-(4-(8-Chloro-7-((2-methyl-1H-benzo[d]imidazol-6-yl)oxy)quinoxalin-2-yl)-1H-pyrazol-1-yl) piperidin-1-yl) (3-hydroxyazetidin-1-yl) methanone A solution of (4-(4-(8-chloro-7-((2-methyl-1-((2-(trimethylsilyl)ethoxy)methyl)-1H-benzo[d]imidazol-6-yl)oxy) quinoxalin-2-yl)-1H-pyrazol-1-yl) piperidin-1-yl) (3-hydroxyazetidin-1-yl) methanone (70.0 mg, 102 μmol) in trifluoroacetic acid (0.5 mL) was stirred at 25° C. for 1 h. The reaction mixture was filtered and concentrated in vacuo. The residue was purified by prep-HPLC (column: Phenomenex Luna C18 150*25 mm*10 μm; mobile phase: [water (formic acid)-acetonitrile]; (B %: 9%-39%, 10 min) to give (4-(4-(8-chloro-7-((2-methyl-1H-benzo[d]imidazol-6-yl) oxy)quinoxalin-2-yl)-1H-pyrazol-1-yl) piperidin-1-yl) (3-hydroxyazetidin-1-yl) methanone (24.8 mg, 44.2 μmol, 44%) as a white solid. $^1H$ NMR (400 MHz, $CD_3OD$) δ 9.18 (s, 1H), 8.64 (s, 1H), 8.36 (s, 1H), 8.12 (s, 1H), 7.92 (d, J=9.2 Hz, 1H), 7.58 (d, J=8.8 Hz, 1H), 7.38 (d, J=9.2 Hz, 1H), 7.20 (d, J=2.0 Hz, 1H), 7.07 (dd, J=2.4, 8.8 Hz, 1H), 4.59-4.47 (m, 2H), 4.31-4.22 (m, 2H), 4.04 (d, J=13.6 Hz, 2H), 3.86 (dd, J=4.8, 9.2 Hz, 2H), 3.04 (t, J=12.0 Hz, 2H), 2.63 (s, 3H), 2.25-2.14 (m, 2H), 2.10-2.01 (m, 2H); m/z ES+ $[M+H]^+$ 559.0.

Example 16. Synthesis of 6-[3-[4-[8-chloro-7-[(2-methyl-3H-benzimidazol-5-yl)oxy]quinoxalin-2-yl]pyrazol-1-yl]azetidin-1-yl]-N,N-dimethyl-pyridin-2-amine

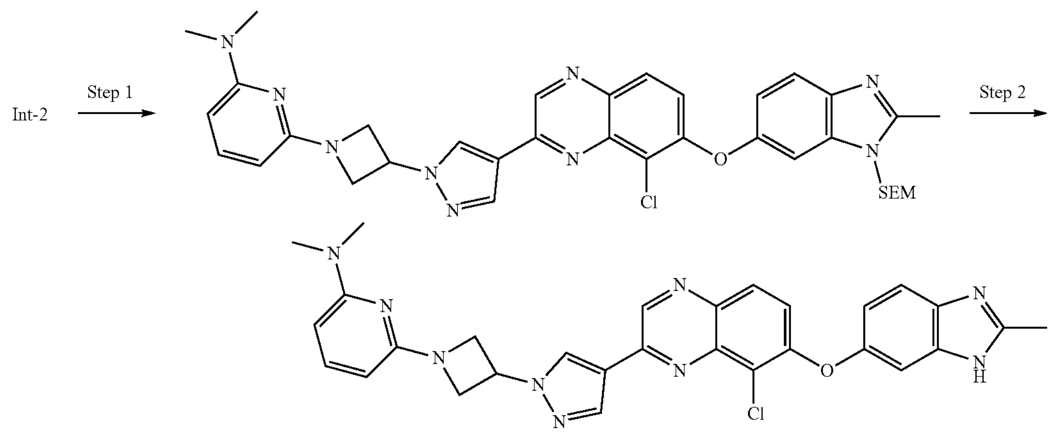

Step 1. 6-[3-[4-[8-Chloro-7-[2-methyl-3-(2-trimethylsilylethoxymethyl)benzimidazol-5-yl]oxy-quinoxalin-2-yl]pyrazol-1-yl]azetidin-1-yl]-N,N-dimethyl-pyridin-2-amine To a solution of 2-[[6-[3-[1-(azetidin-3-yl)pyrazol-4-yl]-5-chloro-quinoxalin-6-yl]oxy-2-methyl-benzimidazol-1-yl]methoxy]ethyl-trimethyl-silane (130 mg, 230 μmol) and 6-bromo-N,N-dimethyl-pyridin-2-amine (51.0 mg, 250 μmol) in dioxane (3 mL) was added tris(dibenzylideneacetone) dipalladium (21.0 mg, 23.0 μmol), (5-diphenylphosphanyl-9,9-dimethylxanthen-4-yl)-diphenylphosphane (13.0 mg, 23.0 μmol) and cesium carbonate (151 mg, 460 μmol). The mixture was stirred at 80° C. for 12 h under nitrogen. The reaction mixture was diluted with water (15 mL) and extracted with ethyl acetate (20 mL×3). The combined organic layers were then washed with brine (25 ml× 2), dried over anhydrous sodium sulfate, and then concentrated under reduced pressure. The residue was purified by column chromatography (petroleum ether:ethyl acetate=10:1 to 0:1) to give 6-[3-[4-[8-chloro-7-[2-methyl-3-(2-trimethylsilylethoxymethyl)benzimidazol-5-yl]oxy-quinoxalin-2-yl]pyrazol-1-yl]azetidin-1-yl]-N,N-dimethyl-pyridin-2-amine (50.0 mg, 73.4 μmol, 28%) as a white solid. m/z ES+ $[M+H]^+$ 682.2.

Step 2. 6-[3-[4-[8-Chloro-7-[(2-methyl-3H-benzimidazol-5-yl)oxy]quinoxalin-2-yl]pyrazol-1-yl]azetidin-1-yl]-N,N-dimethyl-pyridin-2-amine A solution of 6-[3-[4-[8-chloro-7-[2-methyl-3-(2-trimethylsilylethoxymethyl)benzimidazol-5-yl]oxy-quinoxalin-2-yl]pyrazol-1-yl]azetidin-1-yl]-N,N-dimethyl-pyridin-2-amine (40.0 mg, 58.0 μmol) in trifluoroacetic acid (0.5 mL) was stirred at 25° C. for 0.5 h. The reaction mixture was concentrated under reduced pressure. The residue was purified by prep-HPLC (neutral condition; column: Waters Xbridge 150×25 mm× 5 μm; mobile phase: [water (10 mM ammonium bicarbonate)-acetonitrile]; (B %: 44%-74%, 10 min) to give 6-[3-[4-[8-chloro-7-[(2-methyl-3H-benzimidazol-5-yl)oxy]quinoxalin-2-yl]pyrazol-1-yl]azetidin-1-yl]-N,N-dimethyl-pyridin-2-amine (2.68 mg, 4.86 μmol, 7.9%) as a white solid. $^1H$ NMR (400 MHz, DMSO-$d_6$) δ=12.34-12.24 (m, 1H), 9.35 (s, 1H), 8.92 (s, 1H), 8.45 (s, 1H), 7.98-7.92 (m, 1H), 7.60-7.42 (m, 1H), 7.38-7.28 (m, 1H), 7.25-7.16 (m, 1H), 6.98-6.90 (m, 1H), 5.84 (d, J=8.0 Hz, 1H), 5.72 (d, J=8.0 Hz, 1H), 5.53-5.49 (m, 1H), 4.40 (t, J=8.0 Hz, 1H), 4.28-4.23 (m, 2H), 2.98 (s, 6H), 2.50 (s, 3H); m/z ES+ $[M+H]^+$ 552.1.

Example 17. Synthesis of 8-chloro-7-[(2-methyl-3H-benzimidazol-5-yl)oxy]-2-[1-[1-(2-pyridyl)azetidin-3-yl]pyrazol-4-yl]quinoxaline

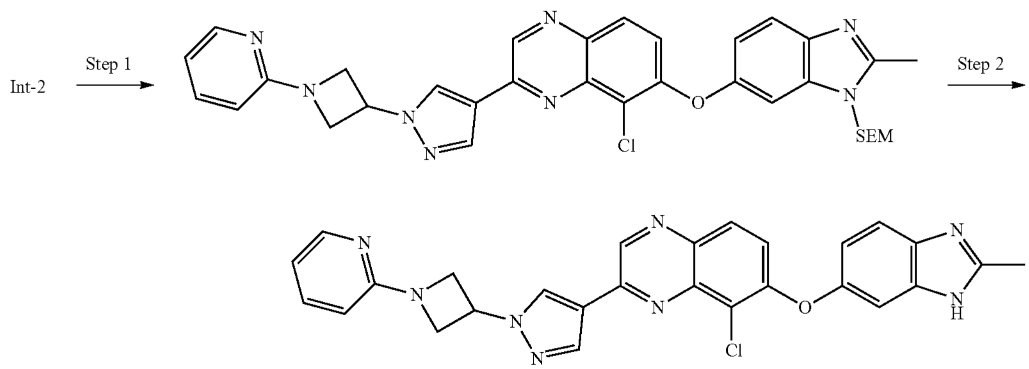

Step 1. 2-[[6-[5-Chloro-3-[1-[1-(2-pyridyl)azetidin-3-yl]pyrazol-4-yl]quinoxalin-6-yl]oxy-2-methyl-benzimidazol-1-yl]methoxy]ethyl-trimethyl-silane To a solution of 2-bromopyridine (40.0 mg, 250 μmol) and 2-[[6-[3-[1-(azetidin-3-yl)pyrazol-4-yl]-5-chloro-quinoxalin-6-yl]oxy-2-methyl-benzimidazol-1-yl]methoxy]ethyl-trimethyl-silane (130 mg, 230 μmol) in dioxane (3 mL) was added tris(dibenzylideneacetone) dipalladium (21.0 mg, 23.0 μmol), (5-diphenylphosphanyl-9,9-dimethylxanthen-4-yl)-diphenylphosphane (13.0 mg, 23.0 μmol) and cesium carbonate (150 mg, 460 μmol). The mixture was stirred at 80° C. for 12 h under nitrogen. The reaction mixture was quenched with water (20 mL) and extracted with ethyl acetate (20 ml× 3). The combined organic layers were washed with brine (25 ml× 2), dried with anhydrous sodium sulfate, and then concentrated under reduced pressure. The residue was purified by column chromatography (petroleum ether:ethyl acetate=10:1 to 0:1) to give 2-[[6-[5-chloro-3-[1-[1-(2-pyridyl)azetidin-3-yl]pyrazol-4-yl]quinoxalin-6-yl]oxy-2-methyl-benzimidazol-1-yl]methoxy]ethyl-trimethyl-silane (70.0 mg, 110 μmol, 34%) as a white solid. m/z ES+ $[M+H]^+$ 639.3.

Step 2. 8-Chloro-7-[(2-methyl-3H-benzimidazol-5-yl)oxy]-2-[1-[1-(2-pyridyl)azetidin-3-yl]pyrazol-4-yl]quinoxaline A solution of 2-[[6-[5-chloro-3-[1-[1-(2-pyridyl)azetidin-3-yl]pyrazol-4-yl]quinoxalin-6-yl]oxy-2-methyl-benzimidazol-1-yl]methoxy]ethyl-trimethyl-silane (60.0 mg, 94.0 μmol) in trifluoroacetic acid (0.6 mL) was stirred at 25° C. for 0.5 h. The residue directly was purified by prep-HPLC (formic acid condition; column: Phenomenex Luna C18 150×25 mm× 10 μm; mobile phase: [water (0.225% formic acid)-acetonitrile]; (B %: 2%-32%, 10 min) to give 8-chloro-7-[(2-methyl-3H-benzimidazol-5-yl)oxy]-2-[1-[1-(2-pyridyl)azetidin-3-yl]pyrazol-4-yl]quinoxaline (24.3 mg, 47.8 μmol, 50%) as a white solid. $^1$H NMR (400 MHz, DMSO-$d_6$) δ=9.36 (s, 1H), 8.93 (s, 1H), 8.46 (s, 1H), 8.15-8.11 (m, 1H), 7.99 (d, J=9.2 Hz, 1H), 7.64-7.57 (m, 2H), 7.37 (d, J=9.2 Hz, 1H), 7.30 (d, J=2.4 Hz, 1H), 7.05 (dd, J=2.4, 8.8 Hz, 1H), 6.73 (dd, J=5.6, 6.8 Hz, 1H), 6.55 (d, J=8.4 Hz, 1H), 5.61-5.51 (m, 1H), 4.50 (t, J=8.4 Hz, 2H), 4.34 (dd, J=5.6, 8.8 Hz, 2H), 2.57 (s, 3H); m/z ES+ $[M+H]^+$ 509.0.

Example 18. Synthesis of 5-((4-(8-chloro-7-((2-methyl-1H-benzo[d]imidazol-6-yl)oxy)quinoxalin-2-yl)-1H-pyrazol-1-yl)methyl)-1,2-thiazinane 1,1-dioxide

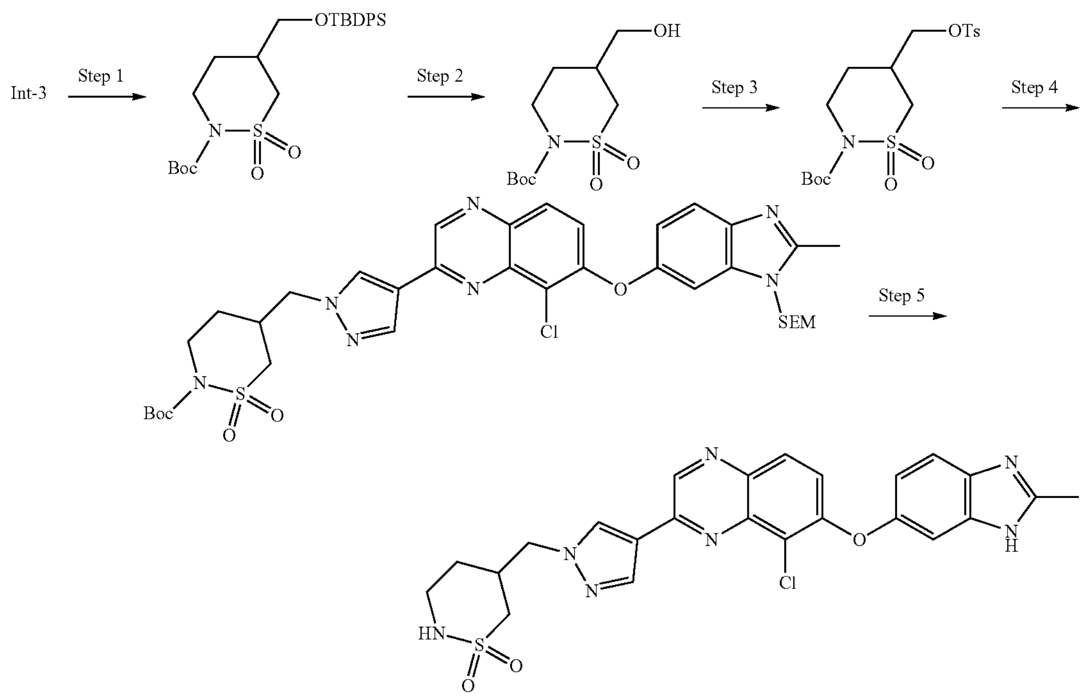

Step 1. tert-Butyl 5-(((tert-butyldiphenylsilyl)oxy)methyl)-1,2-thiazinane-2-carboxylate 1,1-dioxide To a solution of 5-(((tert-butyldiphenylsilyl)oxy)methyl)-1,2-thiazinane 1,1-dioxide (300 mg, 743 μmol) and 4-dimethylaminopyridine (181 mg, 1.49 mmol) in dichloromethane (10 mL) was added di-tert-butyl dicarbonate (324 mg, 1.49 mmol) dropwise at 25° C. The mixture was stirred at 25° C. for 16 h. The mixture was concentrated under reduced pressure. The residue was purified by column chromatography (petroleum ether/ethyl acetate=5/1) to give tert-butyl 5-(((tert-butyldiphenylsilyl)oxy)methyl)-1,2-thiazinane-2-carboxylate 1,1-dioxide (330 mg, 655 μmol, 88%) as a white oil. $^1$H NMR (400 MHz, $CDCl_3$) δ 7.54 (d, J=7.6 Hz, 3H), 7.43-7.27 (m, 6H), 4.23 (td, J=3.6, 14.0 Hz, 1H), 3.63-3.40

(m, 3H), 3.25 (dd, J=3.2, 13.6 Hz, 1H), 2.94 (t, J=12.8 Hz, 1H), 2.47 (s, 1H), 1.64 (d, J=11.6 Hz, 1H), 1.45 (s, 9H), 0.98 (s, 9H).

Step 2. tert-Butyl 5-(hydroxymethyl)-1,2-thiazinane-2-carboxylate 1,1-dioxide

A solution of tert-butyl 5-(((tert-butyldiphenylsilyl)oxy) methyl)-1,2-thiazinane-2-carboxylate 1,1-dioxide (270 mg, 536 μmol), tetrabutylammonium fluoride (1 M in THF, 0.8 mL) in tetrahydrofuran (10 mL) was stirred at 25° C. for 5 h. The mixture was poured into water (20 mL) and then extracted with ethyl acetate (30 mL×3). The organic layers were dried by sodium sulfate, filtered and concentrated under reduced pressure to give tert-butyl 5-(hydroxymethyl)-1,2-thiazinane-2-carboxylate 1,1-dioxide (150 mg, crude) as a colorless oil.

Step 3. tert-Butyl 5-((tosyloxy)methyl)-1,2-thiazinane-2-carboxylate 1,1-dioxide To a solution of tert-butyl 5-(hydroxymethyl)-1,2-thiazinane-2-carboxylate 1,1-dioxide (150 mg, 565 μmol) in dichloromethane (5 mL) was added 4-methylbenzenesulfonyl chloride (161 mg, 848 μmol) and triethylamine (171 mg, 1.70 mmol). The mixture was stirred at 25° C. for 16 h. The mixture was concentrated under reduced pressure. The residue was purified by reversed-phase HPLC (0.1% formic acid condition) to give tert-butyl 5-((tosyloxy)methyl)-1,2-thiazinane-2-carboxylate 1,1-dioxide (140 mg, 333 μmol, 59%) as a colorless oil. $^1$H NMR (400 MHz, $CDCl_3$) δ 7.79 (d, J=8.4 Hz, 2H), 7.39 (d, J=8.0 Hz, 2H), 4.30 (td, J=4.0, 14.0 Hz, 1H), 4.09-3.90 (m, 2H), 3.73-3.51 (m, 1H), 3.30-3.15 (m, 1H), 3.01-2.84 (m, 1H), 2.69 (s, 1H), 2.48 (s, 3H), 1.78 (d, J=14.0 Hz, 1H), 1.52 (s, 9H).

Step 4. tert-Butyl 5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) methyl)-1,2-thiazinane-2-carboxylate 1,1-dioxide A solution of 8-chloro-7-((2-methyl-1-((2-(trimethylsilyl) ethoxy)methyl)-1H-benzo[d]imidazol-6-yl)oxy)-2-(1H-pyrazol-4-yl)quinoxaline (70.0 mg, 138 μmol), tert-butyl 5-((tosyloxy)methyl)-1,2-thiazinane-2-carboxylate 1,1-dioxide (70.0 mg, 166 μmol), cesium carbonate (134 mg, 414 μmol) in N,N-dimethyl formamide (1 mL) was stirred at 80° C. for 3 h. The mixture was poured into water (50 mL) and extracted with ethyl acetate (30 mL×3). The organic layers was washed by brine (50 mL×3), dried by sodium sulfate, filtered and concentrated under reduced pressure to give tert-butyl 5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-1,2-thiazinane-2-carboxylate 1,1-dioxide (70.0 mg, 92.0 μmol, 67%) as a yellow oil.

Step 5. 5-((4-(8-Chloro-7-((2-methyl-1H-benzo[d] imidazol-6-yl)oxy)quinoxalin-2-yl)-1H-pyrazol-1-yl) methyl)-1,2-thiazinane 1,1-dioxide A solution of tert-butyl 5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-1,2-thiazinane-2-carboxylate 1,1-dioxide (70 mg, 92.9 μmol) in trifluoroacetic acid (1 mL) was stirred at 25° C. for 10 min. The mixture was concentrated under reduced pressure. The residue was purified by prep-HPLC (column: Waters Xbridge 150*25 mm*5 μm; mobile phase: [water (10 mM ammonium bicarbonate)-acetonitrile]; (B %: 22%-52%, 8 min) to give 5-((4-(8-chloro-7-((2-methyl-1H-benzo[d]imidazol-6-yl)oxy)quinoxalin-2-yl)-1H-pyrazol-1-yl)methyl)-1,2-thiazinane 1,1-dioxide (7.5 mg, 14.2 μmol, 15%) as a white solid. $^1$H NMR (400 MHz, $CD_3OD$) δ 9.12 (s, 1H), 8.57 (s, 1H), 8.36 (s, 1H), 7.87 (d, J=9.2 Hz, 1H), 7.52 (d, J=8.6 Hz, 1H), 7.33 (d, J=9.2 Hz, 1H), 7.18 (d, J=2.2 Hz, 1H), 7 (dd, J=2.4, 8.4 Hz, 1H), 4.39-4.20 (m, 2H), 3.39-3.32 (m, 2H), 3.17 (d, J=10.1 Hz, 1H), 2.96-2.78 (m, 2H), 2.57 (s, 3H), 1.78-1.65 (m, 1H), 1.48-1.25 (m, 1H); m/z ES+ $[M+H]^+$ 524.0.

Example 19. Synthesis of 8-chloro-7-[(2-methyl-3H-benzimidazol-5-yl)oxy]-2-[1-[1-(2-pyridyl)-4-piperidyl]pyrazol-4-yl]quinoxaline

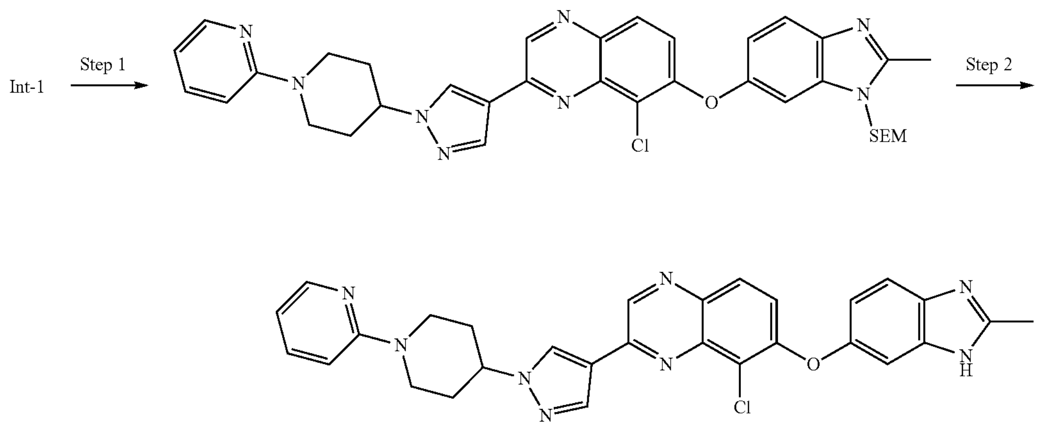

Step 1. 2-[[6-[5-Chloro-3-[1-[1-(2-pyridyl)-4-piperidyl]pyrazol-4-yl]quinoxalin-6-yl]oxy-2-methyl-benzimidazol-1-yl]methoxy]ethyl-trimethyl-silane To a solution of 2-[[6-[5-chloro-3-[1-(4-piperidyl)pyrazol-4-yl]quinoxalin-6-yl]oxy-2-methyl-benzimidazol-1-yl]methoxy]ethyl-trimethyl-silane (150 mg, 254 μmol) and 2-bromopyridine (40.2 mg, 254 μmol) in dioxane (1.5 mL) was added methanesulfonato (2-dicyclohexylphosphino-2,6-di-i-propoxy-1,1-biphenyl) (2-amino-1,1-biphenyl-2-yl) palladium(II) (21.3 mg, 25.4 μmol) and cesium carbonate (166 mg, 508 μmol). The mixture was degassed and purged with nitrogen for 3 times, and then stirred at 80° C. for 12 h. The reaction mixture was filtered and concentrated in vacuo. The residue was purified by column chromatography (petroleum ether/ethyl acetate=2/1 to 0/1) to give 2-[[6-[5-chloro-3-[1-[1-(2-pyridyl)-4-piperidyl]pyrazol-4-yl]quinoxalin-6-yl]oxy-2-methyl-benzimidazol-1-yl]methoxy]ethyl-trimethyl-silane (100 mg, 150 μmol, 59%) as a yellow oil. m/z ES+ $[M+H]^+$ 667.3.

Step 2. 8-Chloro-7-[(2-methyl-3H-benzimidazol-5-yl)oxy]-2-[1-[1-(2-pyridyl)-4-piperidyl]pyrazol-4-yl]quinoxaline A solution of 2-[[6-[5-chloro-3-[1-[1-(2-pyridyl)-4-piperidyl]pyrazol-4-yl]quinoxalin-6-yl]oxy-2-methyl-benzimidazol-1-yl]methoxy]ethyl-trimethyl-silane (65.0 mg, 97.4 μmol) in trifluoroacetic acid (0.5 mL) was stirred at 25° C. for 1 h. The reaction mixture was concentrated in vacuo. The residue was purified by prep-HPLC (column: Phenomenex Luna C18 150*25 mm*10 μm; mobile phase: [water (0.225% formic acid)-acetonitrile]; (B %: 5%-35%, 10 min) to give 8-chloro-7-[(2-methyl-3H-benzimidazol-5-yl)oxy]-2-[1-[1-(2-pyridyl)-4-piperidyl]pyrazol-4-yl]quinoxaline (27.0 mg, 50.3 μmol, 52%) as an off-white solid. $^1$H NMR (400 MHz, $CD_3OD$) δ 9.14 (s, 1H), 8.62 (s, 1H), 8.33 (s, 1H), 8.07 (dd, J=1.2, 5.2 Hz, 1H), 7.90 (d, J=9.2 Hz, 1H), 7.72-7.65 (m, 1H), 7.62 (d, J=8.8 Hz, 1H), 7.38 (d, J=9.2 Hz, 1H), 7.23 (d, J=2.0 Hz, 1H), 7.14 (dd, J=2.4, 8.8 Hz, 1H), 7.04 (d, J=8.8 Hz, 1H), 6.75 (t, J=6.0 Hz, 1H), 4.66-4.54 (m, 1H), 4.42 (br d, J=13.6 Hz, 2H), 3.23-3.11 (m, 2H), 2.68 (s, 3H), 2.33-2.24 (m, 2H), 2.23-2.10 (m, 2H); m/z ES+ $[M+H]^+$ 537.0.

Example 20. Synthesis of 8-chloro-2-(1-(1-(5-fluoropyridin-3-yl)azetidin-3-yl)-1H-pyrazol-4-yl)-7-((2-methyl-1H-benzo[d]imidazol-6-yl)oxy)quinoxaline

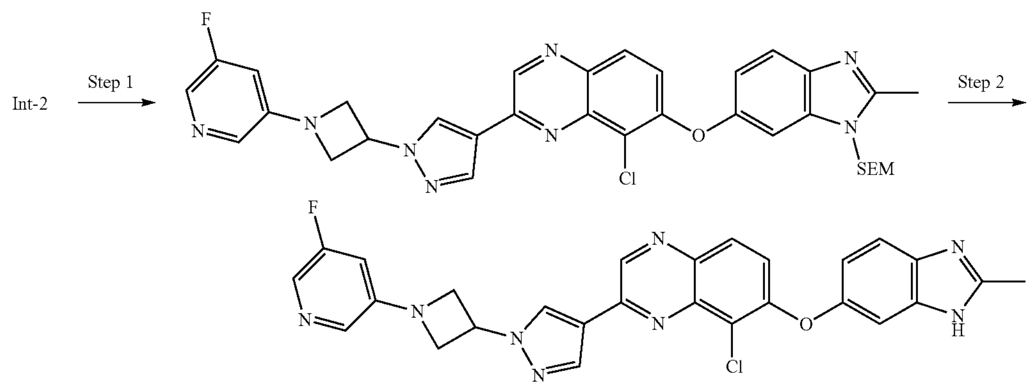

Step 1. 8-Chloro-2-(1-(1-(5-fluoropyridin-3-yl)azetidin-3-yl)-1H-pyrazol-4-yl)-7-((2-methyl-1-((2-(trimethylsilyl)ethoxy)methyl)-1H-benzo[d]imidazol-6-yl)oxy)quinoxaline To a solution of 2-[[6-[3-[1-(azetidin-3-yl)pyrazol-4-yl]-5-chloro-quinoxalin-6-yl]oxy-2-methyl-benzimidazol-1-yl]methoxy]ethyl-trimethyl-silane (130 mg, 231 μmol) and 3-bromo-5-fluoro-pyridine (44.8 mg, 254 μmol) in dioxane (2) mL) was added tris(dibenzylideneacetone) dipalladium (21.2 mg, 23.1 μmol), (5-diphenylphosphanyl-9,9-dimethylxanthen-4-yl)-diphenylphosphane (13.4 mg, 23.1 μmol) and cesium carbonate (151 mg, 463 μmol). The mixture was degassed and purged with nitrogen atmosphere for 3 times, and then stirred at 80° C. for 12 h under nitrogen atmosphere. The reaction mixture was poured into water (30 mL) and extracted with ethyl acetate (20 mL×3). The combined organic layers were dried over anhydrous sodium sulfate, filtered and concentrated under reduced pressure. The residue was purified by column chromatography (ethyl acetate/methanol=1/0 to 20/1) to give 8-chloro-2-(1-(1-(5-fluoropyridin-3-yl)azetidin-3-yl)-1H-pyrazol-4-yl)-7-((2-methyl-1-((2-(trimethylsilyl)ethoxy)methyl)-1H-benzo[d]imidazol-6-yl)oxy)quinoxaline (30.0 mg, 42.5 μmol, 18%) as a yellow oil. m/z ES+ $[M+H]^+$ 657.2.

Step 2. 8-Chloro-2-(1-(1-(5-fluoropyridin-3-yl)azetidin-3-yl)-1H-pyrazol-4-yl)-7-((2-methyl-1H-benzo[d]imidazol-6-yl)oxy)quinoxaline A solution of 2-[[6-[5-chloro-3-[1-[1-(5-fluoro-3-pyridy])azetidin-3-yl]pyrazol-4-yl]quinoxalin-6-yl]oxy-2-methyl-benzimidazol-1-yl]methoxy]ethyl-trimethyl-silane (30.0 mg, 38.0 μmol) in trifluoroacetic acid (0.5 mL) was stirred at 25° C. for 0.5 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 11%-41%, 10 min) to give 8-chloro-2-(1-(1-(5-fluoropyridin-3-yl)azetidin-3-yl)-1H-pyrazol-4-yl)-7-((2-methyl-1H-benzo[d]imidazol-6-yl)oxy)quinoxaline (24.5 mg, 46.2 μmol, 99%) as an off-white solid. $^1$H NMR (400 MHz, DMSO-$d_6$) δ=9.35 (s, 1H), 8.93 (s, 1H), 8.48 (s, 1H), 8.19 (s, 1H), 7.99-7.91 (m, 2H), 7.82 (s, 1H), 7.51 (d, J=8.3 Hz, 1H), 7.32 (d, J=9.2 Hz, 1H), 7.22 (s, 1H), 6.97-6.89 (m, 2H), 5.64-5.56 (m, 1H), 4.49 (t, J=8.0 Hz, 2H), 4.31 (dd, J=5.5, 8.2 Hz, 2H), 2.48 (s, 3H); m/z ES+ $[M+H]^+$ 527.0.

Example 21. Synthesis of 8-chloro-2-[1-[1-(5-fluoro-3-pyridyl)-4-piperidyl]pyrazol-4-yl]-7-[(2-methyl-3H-benzimidazol-5-yl)oxy]quinoxaline

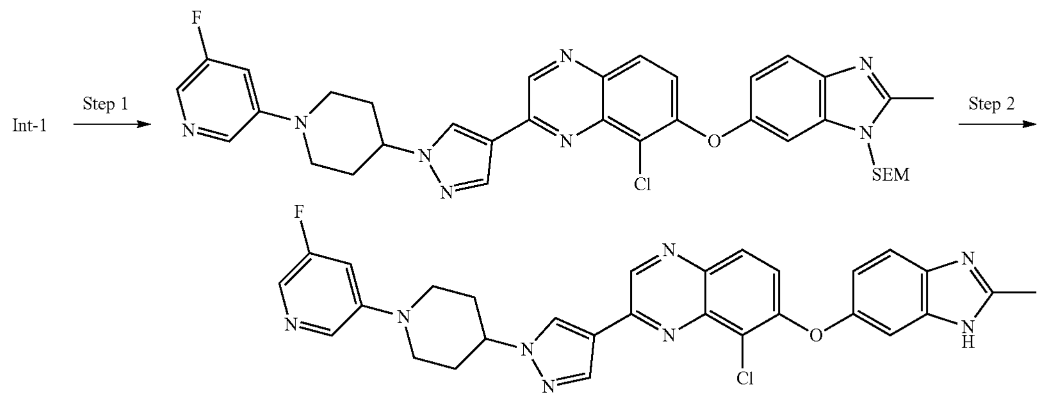

Step 1. 2-[[6-[5-Chloro-3-[1-[1-(5-fluoro-3-pyridyl)-4-piperidyl]pyrazol-4-yl]quinoxalin-6-yl]oxy-2-methyl-benzimidazol-1-yl]methoxy]ethyl-trimethyl-silane To a solution of 2-[[6-[5-chloro-3-[1-(4-piperidyl)pyrazol-4-yl]quinoxalin-6-yl]oxy-2-methyl-benzimidazol-1-yl]methoxy]ethyl-trimethyl-silane (200 mg, 339 μmol) and 3-bromo-5-fluoro-pyridine (59.6 mg, 339 μmol) in dioxane (2 mL) was added cesium carbonate (221 mg, 678 μmol), tris(dibenzylideneacetone) dipalladium (31.0 mg, 33.9 μmol) and (5-diphenylphosphanyl-9,9-dimethylxanthen-4-yl)-diphenylphosphane (19.6 mg, 33.9 μmol). The mixture was degassed and purged with nitrogen for 3 times, and then stirred at 80° C. for 16 h. The reaction mixture was diluted with water (10 mL) and extracted with ethyl acetate (20 mL×3). The combined organic layers were washed with brine (15 mL×3), dried over anhydrous sodium sulfate, filtered and concentrated in vacuo. The residue was purified by column chromatography (petroleum ether/ethyl acetate=1/1 to ethyl acetate/methanol=20/1) to give 2-[[6-[5-chloro-3-[1-[1-(5-fluoro-3-pyridyl)-4-piperidyl]pyrazol-4-yl]quinoxalin-6-yl]oxy-2-methyl-benzimidazol-1-yl]methoxy]ethyl-trimethyl-silane (120 mg, 175 μmol, 48%) as a yellow solid. m/z ES+ $[M+H]^+$ 685.2.

Step 2. 8-Chloro-2-[1-[1-(5-fluoro-3-pyridyl)-4-piperidyl]pyrazol-4-yl]-7-[(2-methyl-3H-benzimidazol-5-yl)oxy]quinoxaline A solution of 2-[[6-[5-chloro-3-[1-[1-(5-fluoro-3-pyridyl)-4-piperidyl]pyrazol-4-yl]quinoxalin-6-yl]oxy-2-methyl-benzimidazol-1-yl]methoxy]ethyl-trimethyl-silane (60.0 mg, 87.6 μmol) in trifluoroacetic acid (0.5 mL) was stirred at 25° C. for 1 h. The reaction mixture was concentrated in vacuo. The residue was purified by prep-HPLC (column: Phenomenex Gemini-NX C18 75*30 mm*3 μm; mobile phase: [water (0.225% formic acid)-acetonitrile]; (B %: 15%-45%, 7 min) to give 8-chloro-2-[1-[1-(5-fluoro-3-pyridyl)-4-piperidyl]pyrazol-4-yl]-7-[(2-methyl-3H-benzimidazol-5-yl)oxy]quinoxaline (24.2 mg, 40.1 μmol, 39%) as an off-white solid. $^1$H NMR (400 MHz, $CD_3OD$) δ 9.20 (s, 1H), 8.67 (s, 1H), 8.38 (s, 1H), 8.18 (s, 1H), 7.95 (d, J=9.2 Hz, 1H), 7.86 (d, J=2.0 Hz, 1H), 7.63 (d, J=8.8 Hz, 1H), 7.42 (d, J=9.2 Hz, 1H), 7.29 (td, J=2.4, 12.0 Hz, 1H), 7.24 (d, J=2.0 Hz, 1H), 7.18-7.13 (m, 1H), 4.62-4.51 (m, 1H), 4.03 (d, J=13.2 Hz, 2H), 3.15-3.07 (m, 2H), 2.69 (s, 3H), 2.33-2.22 (m, 4H); m/z ES+ $[M+H]^+$ 555.0.

Example 22. Synthesis of 1-(2-(4-(8-chloro-7-((2-methyl-1H-benzo[d]imidazol-6-yl)oxy)quinoxalin-2-yl)-1H-pyrazol-1-yl)ethyl)azetidin-3-ol

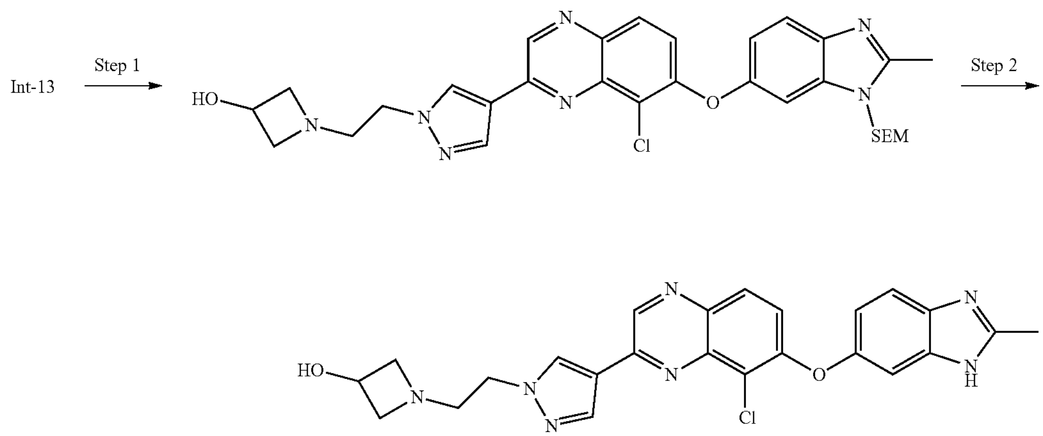 [SMILES: Cc1nc2ccc(Oc3ccc4ncc(-c5cnn(CCN6CC(O)C6)c5)nc4c3Cl)cc2n1COCC[Si](C)(C)C ; Cc1nc2ccc(Oc3ccc4ncc(-c5cnn(CCN6CC(O)C6)c5)nc4c3Cl)cc2[nH]1]

Step 1. 1-(2-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)ethyl)azetidin-3-ol To a solution of 2-[[4-[8-chloro-7-[2-methyl-3-(2-trimethylsilylethoxymethyl)benzimidazol-5-yl]oxy-quinoxalin-2-yl]pyrazol-1-ylethylmethanesulfonate (200 mg, 318 μmol) in methanol (1 mL) and tetrahydrofuran (1 mL) was added triethylamine (96.5 mg, 954 μmol) and azetidin-3-ol (69.7 mg, 636 μmol, HCl). The mixture was stirred at 80° C. for 12 h. The reaction mixture was concentrated under reduced pressure. The residue was purified by column chromatography (ethyl acetate/methanol=10/1 to 1/1) to give 1-(2-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)ethyl)azetidin-3-ol (100 mg, 124 μmol, 39%) as a yellow solid. m/z ES+ $[M+H]^+$ 606.1.

Step 2. 1-(2-(4-(8-Chloro-7-((2-methyl-1H-benzo[d]imidazol-6-yl)oxy)quinoxalin-2-yl)-1H-pyrazol-1-yl)ethyl)azetidin-3-ol A solution of 1-[2-[4-[8-chloro-7-[2-methyl-3-(2-trimethylsilylethoxymethyl)benzimidazol-5-yl]oxy-quinoxalin-2-yl]pyrazol-1-yl]ethyl]azetidin-3-ol (80.0 mg, 132 μmol) in trifluoroacetic acid (0.5 mL) was stirred at 20° C. for 0.5 h. The reaction mixture was concentrated under reduced pressure. The residue was purified by SFC (column: Daicel Chiralcel OD (250 mm*30 mm*10 μm); mobile phase: [0.1% ammonium hydroxide/methanol]; (B %: 45%-45%, 4.5 min, total run 50 min) and prep-HPLC (column: Waters Xbridge 150*25 mm*5 μm; mobile phase: [water (ammonium bicarbonate)-acetonitrile]; (B %: 21%-51%, 10 min) to give 1-(2-(4-(8-chloro-7-((2-methyl-1H-benzo[d]imidazol-6-yl)oxy)quinoxalin-2-yl)-1H-pyrazol-1-yl)ethyl)azetidin-3-ol (6.6 mg, 13.4 μmol, 10%) as a yellow solid. $^1$H NMR (400 MHz, $CD_3OD$) δ 9.14 (s, 1H), 8.56 (s, 1H), 8.35 (s, 1H), 7.89 (d, J=9.2 Hz, 1H), 7.52 (d, J=8.8 Hz, 1H), 7.34 (d, J=9.2 Hz, 1H), 7.17 (d, J=2.0 Hz, 1H), 7 (dd, J=2.0, 8.8 Hz, 1H), 4.36-4.23 (m, 3H), 3.68-3.55 (m, 2H), 3.03 (t, J=6.0 Hz, 2H), 2.92 (d, J=2.0 Hz, 2H), 2.57 (s, 3H); m/z ES+ $[M+H]^+$ 476.0.

Example 23. Synthesis of 8-chloro-2-[1-[(1E)-3-fluorobuta-1,3-dienyl]pyrazol-4-yl]-7-[(2-methyl-3H-benzimidazol-5-yl)oxy]quinoxaline

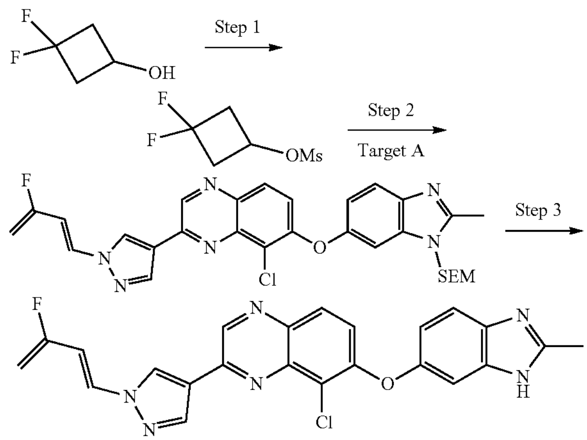

Step 1. (3,3-Difluorocyclobutyl) methanesulfonate

To a solution of 3,3-difluorocyclobutanol (100 mg, 925 μmol) in dichloromethane (2 mL) was added triethylamine (102 mg, 1.02 mmol) and methanesulfonyl chloride (116 mg, 1.02 mmol) at 0° C. The mixture was stirred at 0° C. for 0.5 h. The reaction mixture was quenched by addition water (10 mL) at 0° C. and extracted with ethyl acetate (20 mL×3). The combined organic layers were washed with brine (10 mL), dried over anhydrous sodium sulfate, filtered and concentrated under reduced pressure to give (3,3-difluorocyclobutyl) methanesulfonate (172 mg, crude) as a brown oil.

Step 2. 2-[[6-[5-Chloro-3-[1-[(1E)-3-fluorobuta-1,3-dienyl]pyrazol-4-yl]quinoxalin-6-yl]oxy-2-methyl-benzimidazol-1-yl]methoxy]ethyl-trimethyl-silane To a solution of 2-[6-[5-chloro-3-(1H-pyrazol-4-yl)quinoxalin-6-yl]oxy-2-methyl-benzimidazol-1-yl]methoxy]ethyl-trimethyl-silane (150 mg, 295 μmol) in N,N-dimethylformamide (1.5 mL) was added cesium carbonate (192 mg, 591 μmol), potassium iodide (9.82 mg, 59.1 μmol) and (3,3-difluorocyclobutyl) methanesulfonate (82.6 mg, 443 μmol). The mixture was stirred at 80° C. for 12 hours. The reaction mixture was concentrated under reduced pressure and the residue was purified by prep-HPLC (column: Phenomenex Synergi C18 150*25 mm*10 μm; mobile phase: [water (0.225% formic acid)-acetonitrile]; (B %: 46%-76%, 10 min) to give 2-[6-[5-chloro-3-[1-[(1E)-3-fluorobuta-1,3-dienyl]pyrazol-4-yl]quinoxalin-6-yl]oxy-2-methyl-benzimidazol-1-yl]methoxy]ethyl-trimethyl-silane (120 mg, 208 μmol, 70%) as a white solid. $^1$H NMR (400 MHz, $CDCl_3$) δ ppm 9.09 (s, 1H), 8.43 (d, J=4.8 Hz, 2H), 7.97 (d, J=8.8 Hz, 1H), 7.88-7.79 (m, 1H), 7.42-7.34 (m, 2H), 7.19 (s, 1H), 7.17-7.10 (m, 1H), 6.87-6.72 (m, 1H), 5.49 (s, 2H), 4.87 (dd, J=3.2, 16.4 Hz, 1H), 4.77-4.57 (m, 1H), 3.55 (t, J=8.0 Hz, 2H), 2.86 (s, 3H), 0.90 (t, J=7.6 Hz, 2H), −0.05 (s, 9H); m/z ES+ $[M+H]^+$ 577.3.

Step 3. 8-Chloro-2-[1-[(1E)-3-fluorobuta-1,3-dienyl]pyrazol-4-yl]-7-[(2-methyl-3H-benzimidazol-5-yl)oxy]quinoxaline To a solution of 2-[[6-[5-chloro-3-[1-[(1E)-3-fluorobuta-1,3-dienyl]pyrazol-4-yl]quinoxalin-6-yl]oxy-2-methyl-benzimidazol-1-yl]methoxy]ethyl-trimethyl-silane (90.0 mg, 155 μmol) in tetrahydrofuran (0.5 mL) was added tetrabutylammonium fluoride (1 M in THF, 1.56 mL). The mixture was stirred at 80° C. for 0.5 h. The reaction mixture was concentrated under reduced pressure and the residue was purified by prep-HPLC (column: Welch Ultimate XB-CN 250*70*10 μm; mobile phase: [heptane-ethanol (0.1% ammonium hydroxide)]; (B %: 30%-70%, 15 min) and further purified by prep-HPLC (column: Shim-pack C18 150*25*10 μm; mobile phase: [water (0.225% formic acid)-acetonitrile]; (B %: 15%-45%, 10 min) to give 8-chloro-2-[1-[(1E)-3-fluorobuta-1,3-dienyl]pyrazol-4-yl]-7-[(2-methyl-3H-benzimidazol-5-yl)oxy]quinoxaline (26.1 mg, 58.5 μmol, 36%) as an off-white solid. $^1$H NMR (400 MHz, $CDCl_3$): δ ppm 9.04 (s, 1H), 8.43 (s, 1H), 8.40 (s, 1H), 7.90 (d, J=9.2 Hz, 1H), 7.56 (d, J=8.8 Hz, 1H), 7.38 (d, J=14.0 Hz, 1H), 7.32 (d, J=9.2 Hz, 1H), 7.26 (d, J-2.0 Hz, 1H), 7.04 (dd, J=2.0, 8.8 Hz, 1H), 6.84-6.70 (m, 1H), 4.86 (dd, J=3.2, 16.4 Hz, 1H), 4.76-4.57 (m, 1H), 2.66 (s, 3H); m/z ES+ $[M+H]^+$ 447.0.

Example 24. Synthesis of 8-chloro-7-((2-methyl-1H-benzo[d]imidazol-6-yl)oxy)-2-(1-(3-(trifluoromethyl)cyclobutyl)-1H-pyrazol-4-yl)quinoxaline

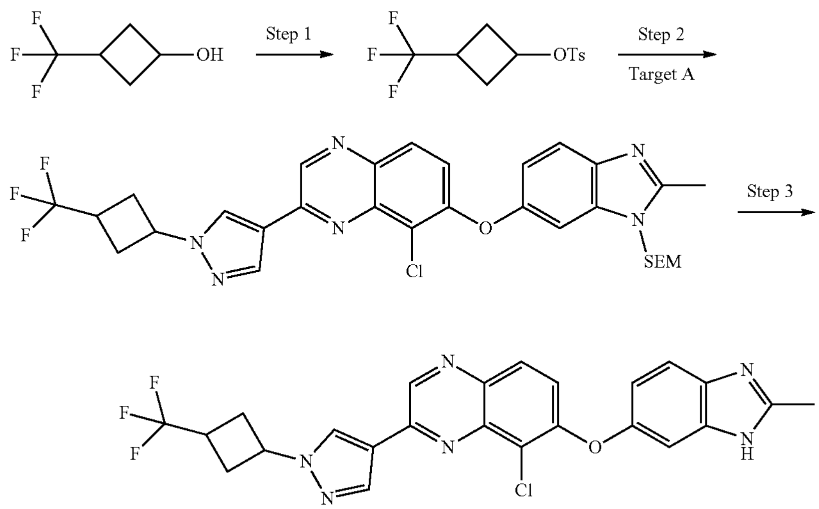

Step 1. 3-(Trifluoromethyl)cyclobutyl 4-methylbenzenesulfonate

To a solution of 3-(trifluoromethyl)cyclobutanol (50 mg, 357 μmol) in dichloromethane (3 mL) was added 4-methylbenzenesulfonyl chloride (102 mg, 535 μmol), triethylamine (72.2 mg, 714 μmol) and 4-dimethylaminopyridine (4.36 mg, 35.7 μmol). The mixture was stirred at 20° C. for 12 h. The reaction mixture was concentrated under reduced pressure. The residue was purified by prep-TLC (petroleum ether:ethyl acetate=4:1) to give 3-(trifluoromethyl)cyclobutyl 4-methylbenzenesulfonate (50.0 mg, 170 μmol, 48%) as a yellow oil. $^1$H NMR (400 MHz, $CDCl_3$) δ=7.79 (d, J=8.4 Hz, 2H), 7.36 (d, J-8.0 Hz, 2H), 4.75 (t, J=7.2 Hz, 1H), 2.47 (s, 3H), 2.54-2.46 (m, 2H), 2.36-2.26 (m, 2H).

Step 2. 8-Chloro-7-((2-methyl-1-((2-(trimethylsilyl)ethoxy)methyl)-1H-benzo[d]imidazol-6-yl)oxy)-2-(1-(3-(trifluoromethyl)cyclobutyl)-1H-pyrazol-4-yl)quinoxaline To a solution of 2-[[6-[5-chloro-3-(1H-pyrazol-4-yl)quinoxalin-6-yl]oxy-2-methyl-benzimidazol-1-yl]methoxy]ethyl-trimethyl-silane (70.0 mg, 138 μmol) in N,N-dimethylformamide (1 mL) was added cesium carbonate (135 mg, 414 μmol) and [3-(trifluoromethyl)cyclobutyl] 4-methylbenzenesulfonate (40.6 mg, 138 μmol). The mixture was stirred at 80° C. for 2 h. The reaction mixture was diluted with water (30 mL) and extracted with ethyl acetate (30 mL×3). The combined organic layers were dried over anhydrous sodium sulfate, filtered and concentrated under reduced pressure to give 8-chloro-7-((2-methyl-1-((2-(trimethylsilyl)ethoxy)methyl)-1H-benzo[d]imidazol-6-yl)oxy)-2-(1-(3-(trifluoromethyl)cyclobutyl)-1H-pyrazol-4-yl)quinoxaline (80.0 mg, crude) as a yellow oil. m/z ES+ $[M+H]^+$ 629.4.

Step 3. 8-Chloro-7-((2-methyl-1H-benzo[d]imidazol-6-yl)oxy)-2-(1-(3-(trifluoromethyl)cyclobutyl)-1H-pyrazol-4-yl)quinoxaline A solution of 2-[[6-[5-chloro-3-[1-[3-(trifluoromethyl)cyclobutyl]pyrazol-4-yl]quinoxalin-6-yl]oxy-2-methyl-benzimidazol-1-yl]methoxy]ethyl-trimethyl-silane (80 mg, 127 μmol) in trifluoroacetic acid (0.3 mL) was stirred at 20° C. for 0.5 h. The reaction mixture was concentrated under reduced pressure. The residue was purified by prep-HPLC (column: Phenomenex Luna C18 250*50 mm*15 μm; mobile phase: [water (0.2% formic acid)-acetonitrile]; (B %: 22%-52%, 10 min) to give 8-chloro-7-((2-methyl-1H-benzo[d]imidazol-6-yl)oxy)-2-(1-(3-(trifluoromethyl)cyclobutyl)-1H-pyrazol-4-yl)quinoxaline (51.8 mg, 104 μmol, 82%) as a white solid. $^1$H NMR (400 MHz, DMSO-$d_6$) δ ppm 9.35 (s, 1H), 8.84 (s, 1H), 8.45 (s, 1H), 8.02 (d, J=9.2 Hz, 1H), 7.69 (d, J=8.8 Hz, 1H), 7.47-7.35 (m, 2H), 7.15 (dd, J-2.0, 8.8 Hz, 1H), 5.30-5.13 (m, 1H), 3.35 (d, J=4.8 Hz, 1H), 2.96-2.87 (m, 2H), 2.73-2.67 (m, 2H), 2.65 (s, 3H); m/z ES+ $[M+H]^+$ 499.0.

Example 25. Synthesis of 8-chloro-2-(1-((1s,3s)-3-(3-methoxyazetidin-1-yl)cyclobutyl)-1H-pyrazol-4-yl)-7-((2-methyl-1H-benzo[d]imidazol-6-yl)oxy)quinoxaline and 8-chloro-2-(1-((1r,3r)-3-(3-methoxyazetidin-1-yl)cyclobutyl)-1H-pyrazol-4-yl)-7-((2-methyl-1H-benzo[d]imidazol-6-yl)oxy)quinoxaline

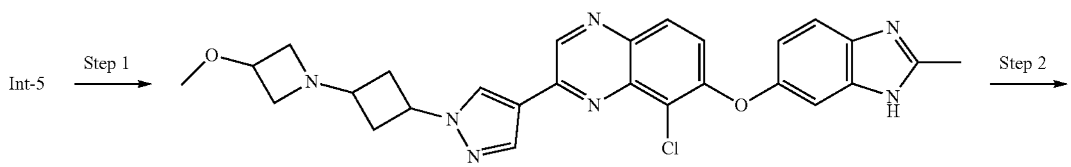

-continued

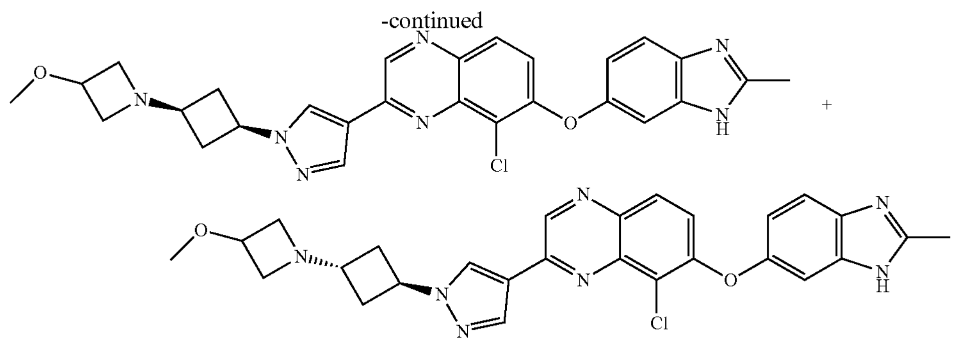

Step 1. 8-Chloro-2-(1-(3-(3-methoxyazetidin-1-yl) cyclobutyl)-1H-pyrazol-4-yl)-7-((2-methyl-1H-benzo[d]imidazol-6-yl)oxy)quinoxaline To a solution of 3-[4-[8-chloro-7-[(2-methyl-3H-benzimidazol-5-yl)oxy]quinoxalin-2-yl]pyrazol-1-yl]cyclobutanone (150 mg, 337 μmol) and 3-methoxyazetidine hydrochloride (125 mg, 1.01 mmol) in methanol (2 mL) was added diisopropylethylamine (131 mg, 1.01 mmol) and titanium (IV) propan-2-olate (192 mg, 674 μmol). The mixture was stirred at 60° C. for 2 h. Then sodium cyanoborohydride (21 mg, 337 μmol) was added and the reaction mixture was stirred at 25° C. for 12 h. The reaction mixture was diluted with sat. sodium bicarbonate solution (20 mL) and extracted with ethyl acetate (50 mL×3). The combined organic layers were washed with brine (25 mL×2), dried over anhydrous sodium sulfate, filtered and concentrated under reduced pressure. The residue was purified by prep-HPLC (formic acid condition; column: Phenomenex Luna C18 150×25 mm× 10 μm; mobile phase: [water (0.225% formic acid)-acetonitrile]; (B %: 1%-30%, 10 min) to give 8-chloro-2-(1-(3-(3-methoxyazetidin-1-yl)cyclobutyl)-1H-pyrazol-4-yl)-7-((2-methyl-1H-benzo[d]imidazol-6-yl)oxy) quinoxaline (60.0 mg, 112 μmol, 33%) as a white solid. m/z ES+ $[M+H]^+$ 516.1.

Step 2. 8-Chloro-2-(1-((1s,3s)-3-(3-methoxyazetidin-1-yl)cyclobutyl)-1H-pyrazol-4-yl)-7-((2-methyl-1H-benzo[d]imidazol-6-yl)oxy)quinoxaline and 8-chloro-2-(1-((1r,3r)-3-(3-methoxyazetidin-1-yl) cyclobutyl)-1H-pyrazol-4-yl)-7-((2-methyl-1H-benzo[d]imidazol-6-yl)oxy)quinoxaline 8-Chloro-2-[1-[3-(3-methoxyazetidin-1-yl)cyclobutyl] pyrazol-4-yl]-7-[(2-methyl-3H-benzimidazol-5-yl)oxy]quinoxaline (60.0 mg, 116 μmol) was purified by SFC (basic condition, column: Daicel Chiralpak IE (50×250 mm, 10 μm); mobile phase: [hexane-ethyl alcohol (0.1% ammonium hydroxide]; (B %: 80%-80%, 30, 120 min) to give 8-chloro-2-(1-((1s,3s)-3-(3-methoxyazetidin-1-yl)cyclobutyl)-1H-pyrazol-4-yl)-7-((2-methyl-1H-benzo[d]imidazol-6-yl)oxy) quinoxaline (11.3 mg, 18.4 μmol, 16%) as an off-white solid and 8-chloro-2-(1-((1r,3r)-3-(3-methoxyazetidin-1-yl)cyclobutyl)-1H-pyrazol-4-yl)-7-((2-methyl-1H-benzo[d]imidazol-6-yl)oxy)quinoxaline (6.0 mg, 11.3 μmol, 9.8%) as a white solid.

$^1$H NMR (400 MHz, DMSO-$d_6$) δ=9.16 (s, 1H), 8.63 (s, 1H), 8.41 (s, 2H), 7.90 (d, J=9.2 Hz, 1H), 7.53 (d, J=8.8 Hz, 1H), 7.35 (d, J=9.2 Hz, 1H), 7.18 (d, J=2.4 Hz, 1H), 7.01 (dd, J=2.4, 8.8 Hz, 1H), 4.79 (s, 1H), 4.25-4.17 (m, 1H), 4.07-4 (m, 2H), 3.65 (dd, J=4.8, 10.4 Hz, 2H), 3.62-3.55 (m, 1H), 3.34 (s, 3H), 2.90-2.81 (m, 2H), 2.70-2.65 (m, 2H), 2.58 (s, 3H); m/z ES+ $[M+H]^+$ 516.0.1H NMR (400 MHz, DMSO-$d_6$) δ=9.16-9.14 (m, 1H), 8.61 (s, 1H), 8.39 (s, 1H), 7.89 (d, J=9.2 Hz, 1H), 7.53 (d, J=8.8 Hz, 1H), 7.34 (d, J=9.2 Hz, 1H), 7.18 (d, J=2.4 Hz, 1H), 7.01 (dd, J=2.4, 8.8 Hz, 1H), 5.18-5.05 (m, 1H), 4.21-4.13 (m, 1H), 3.94-3.84 (m, 2H), 3.76-3.65 (m, 1H), 3.40 (dd, J=5.2, 10.0 Hz, 2H), 3.32 (s, 3H), 2.85-2.75 (m, 2H), 2.57 (s, 3H), 2.56-2.49 (m, 2H); m/z ES+ $[M+H]^+$ 516.0.

Example 26. Synthesis of (1S,4S)-5-((1r,3S)-3-(4-(8-chloro-7-((2-methyl-1H-benzo[d]imidazol-6-yl) oxy)quinoxalin-2-yl)-1H-pyrazol-1-yl)cyclobutyl)-2-oxa-5-azabicyclo[2.2.1]heptane and (1S,4S)-5-((1s, 3R)-3-(4-(8-chloro-7-((2-methyl-1H-benzo[d] imidazol-6-yl)oxy)quinoxalin-2-yl)-1H-pyrazol-1-yl) cyclobutyl)-2-oxa-5-azabicyclo[2.2.1]heptane

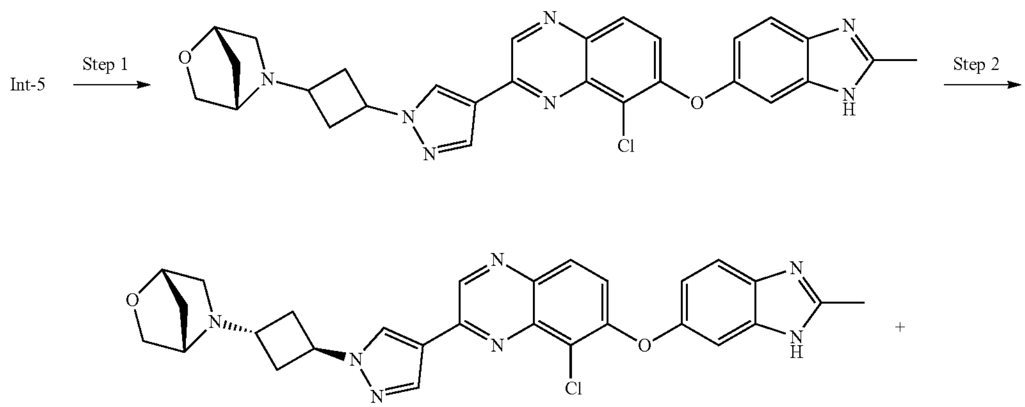

-continued

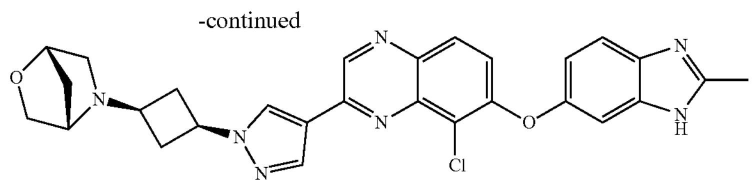

Step 1. (1S,4S)-5-[3-[4-[8-Chloro-7-[(2-methyl-3H-benzimidazol-5-yl)oxy]quinoxalin-2-yl]pyrazol-1-yl]cyclobutyl]-2-oxa-5-azabicyclo[2.2.1]heptane To a solution of 3-[4-[8-chloro-7-[(2-methyl-3H-benzimidazol-5-yl)oxy]quinoxalin-2-yl]pyrazol-1-yl]cyclobutanone (200 mg, 450 μmol) and (1S,4S)-2-oxa-5-azabicyclo[2.2.1]heptane hydrochloride (180 mg, 1.35 mmol) in methanol (4 mL) was added diisopropylethylamine (174 mg, 1.35 mmol, 235 μL) and titanium (IV) propan-2-olate (256 mg, 900 μmol). The mixture was stirred at 60° C. for 2 h. Then sodium cyanoborohydride (28 mg, 450 μmol) was added, and the reaction mixture was stirred at 25° C. for 2 h. The reaction mixture was diluted with sat. sodium bicarbonate solution (20 mL), and then extracted with ethyl acetate (50 mL×3). The combined organic layers were washed with brine (25 mL×2), dried over anhydrous sodium sulfate, filtered and concentrated under reduced pressure. The residue was purified by prep-HPLC (formic acid condition; column: Phenomenex Luna C18 150×25 mm× 10 μm; mobile phase: [water (0.225% formic acid)-acetonitrile]; (B %: 1%-30%, 10 min) to give (1S,4S)-5-[3-[4-[8-chloro-7-[(2-methyl-3H-benzimidazol-5-yl)oxy]quinoxalin-2-yl]pyrazol-1-yl]cyclobutyl]-2-oxa-5-azabicyclo[2.2.1]heptane (38.0 mg, 71.3 μmol, 16%) as a colorless oil. m/z ES+ $[M+H]^+$ 528.1.

Step 2. (1S,4S)-5-((1r,3S)-3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptane and (1S,4S)-5-((1s,3R)-3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptane (1S,4S)-5-[3-[4-[8-Chloro-7-[(2-methyl-3H-benzimidazol-5-yl)oxy]quinoxalin-2-yl]pyrazol-1-yl]cyclobutyl]-2-oxa-5-azabicyclo[2.2.1]heptane (54.0 mg, 102 μmol) was separated by SFC (basic condition, column: Daicel Chiralpak IG (250 mm×50 mm, 10 μm); mobile phase: [hexane-ethyl alcohol (0.1% ammonium hydroxide)]; (B %: 80%-80%, 12 min) to give (1S,4S)-5-((1r,3S)-3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptane (36.4 mg, 66.9 μmol, 65%) as a white solid and (1S,4S)-5-((1s,3R)-3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptane (8.4 mg, 14.6 μmol, 14%) as a white solid.

$^1H$ NMR (400 MHz, DMSO-$d_6$) δ=12.42-12.20 (m, 1H), 9.33 (s, 1H), 8.80 (s, 1H), 8.37 (s, 1H), 7.95 (d, J=9.2 Hz, 1H), 7.59-7.42 (m, 1H), 7.38-7.27 (m, 1H), 7.26-7.11 (m, 1H), 6.99-6.89 (m, 1H), 4.78-4.68 (m, 1H), 4.38 (s, 1H), 3.79 (d, J=7.2 Hz, 1H), 3.54-3.49 (m, 2H), 3.18-3.08 (m, 1H), 2.77 (d, J=8.8 Hz, 1H), 2.71-2.56 (m, 3H), 2.49-2.47 (m, 3H), 2.44-2.36 (m, 2H), 1.72 (d, J=8.4 Hz, 1H), 1.58 (d, J=10.0 Hz, 1H); m/z ES+ $[M+H]^+$ 528.0.

$^1H$ NMR (400 MHz, DMSO-$d_6$) δ=12.48-12.17 (m, 1H), 9.31 (s, 1H), 8.80 (s, 1H), 8.39 (s, 1H), 7.95 (dd, J=3.6, 8.8 Hz, 1H), 7.58-7.44 (m, 1H), 7.31 (d, J=10.4 Hz, 1H), 7.26-7.13 (m, 1H), 6.94 (dd, J=8.8, 10.4 Hz, 1H), 5.16-5.07 (m, 1H), 4.38 (s, 1H), 3.80 (d, J=7.6 Hz, 1H), 3.56 (s, 1H), 3.53 (dd, J=1.6, 7.2 Hz, 1H), 3.47-3.40 (m, 2H), 2.76-2.71 (m, 1H), 2.69-2.54 (m, 2H), 2.49-2.47 (m, 3H), 2.43-2.34 (m, 2H), 1.76 (d, J=9.2 Hz, 1H), 1.58 (d, J=9.2 Hz, 1H); m/z ES+ $[M+H]^+$ 528.0.

Example 27. Synthesis of 8-chloro-2-[1-(3,3-difluorocyclobutyl)pyrazol-4-yl]-7-[(2-methyl-3H-benzimidazol-5-yl)oxy]quinoxaline

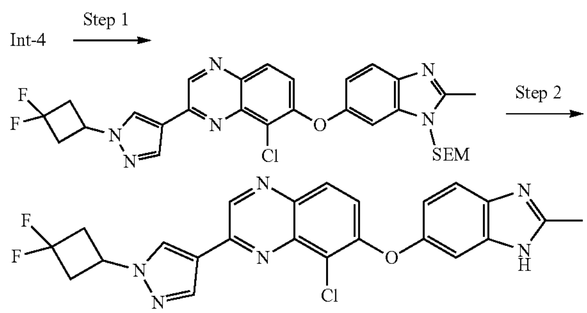

Step 1. 2-[[6-[5-Chloro-3-[1-(3,3-difluorocyclobutyl)pyrazol-4-yl]quinoxalin-6-yl]oxy-2-methyl-benzimidazol-1-yl]methoxy]ethyl-trimethyl-silane To a solution of 3-[4-[8-chloro-7-[2-methyl-3-(2-trimethylsilylethoxymethyl)benzimidazol-5-yl]oxy-quinoxalin-2-yl]pyrazol-1-yl]cyclobutanone (20.0 mg, 34.7 μmol) in dichloromethane (0.5 mL) was added bis(2-methoxyethyl)aminosulfur trifluoride (76.9 mg, 347 μmol) at 0° C. The mixture was stirred at 25° C. for 1.5 hours under nitrogen atmosphere. The reaction mixture was quenched with aqueous saturated sodium bicarbonate (20 mL) at 0° C. and extracted with ethyl acetate (20 mL×3). The combined organic layers were washed with brine (20 mL), dried over anhydrous sodium sulfate, filtered and concentrated under reduced pressure and the residue was purified by prep-HPLC (column: Welch Ultimate XB-SiOH 250*50*10 μm; mobile phase: [heptane-ethanol (0.1% ammonium hydroxide)]; (B %: 1%-35%, 15 min) to give 2-[[6-[5-chloro-3-[1-(3,3-difluorocyclobutyl)pyrazol-4-yl]quinoxalin-6-yl]oxy-2-methyl-benzimidazol-1-yl]methoxy]ethyl-trimethyl-silane (20.0 mg, 33.6 μmol, 91%) as a yellow solid. m/z ES+ $[M+H]^+$ 597.3.

Step 2. 8-Chloro-2-[1-(3,3-difluorocyclobutyl)pyrazol-4-yl]-7-[(2-methyl-3H-benzimidazol-5-yl)oxy]quinoxaline A solution of 2-[[6-[5-chloro-3-[1-(3, 3-difluorocyclobutyl)pyrazol-4-yl]quinoxalin-6-yl]oxy-2-methyl-benzimidazol-1-yl]methoxy]ethyl-trimethyl-silane (17.0 mg, 28.4 μmol) in trifluoroacetic acid (0.5 mL) was stirred at 25° C. for 0.5 h. The reaction mixture was concentrated under reduced pressure and the residue was purified by prep-HPLC (column: Phenomenex Synergi C18 150*25 mm*10 μm; mobile phase: [water (0.225% formic acid)-acetonitrile]; (B %: 12%-42%, 10 min) to give 8-chloro-2-[1-(3,3-difluorocyclobutyl)pyrazol-4-yl]-7-[(2-methyl-3H-benzimidazol-5-yl)oxy]quinoxaline (11.4 mg, 24.5 μmol, 85%) as a yellow solid. $^1$H NMR (400 MHz, $CDCl_3$) δ ppm 9.02 (s, 1H), 8.35 (s, 1H), 8.30 (s, 1H), 7.89 (d, J=9.2 Hz, 1H), 7.55 (d, J=8.8 Hz, 1H), 7.31 (d, J=9.2 Hz, 1H), 7.27-7.25 (m, 1H), 7.03 (dd, J=2.4, 8.8 Hz, 1H), 4.90-4.78 (m, 1H), 3.43-3.28 (m, 2H), 3.27-3.13 (m, 2H), 2.66 (s, 3H); m/z ES+ $[M+H]^+$ 467.0.

Example 28. Synthesis of (1R,4R)-5-((1r,3R)-3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptanes and (1R,4R)-5-((1s,3S)-3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptanes

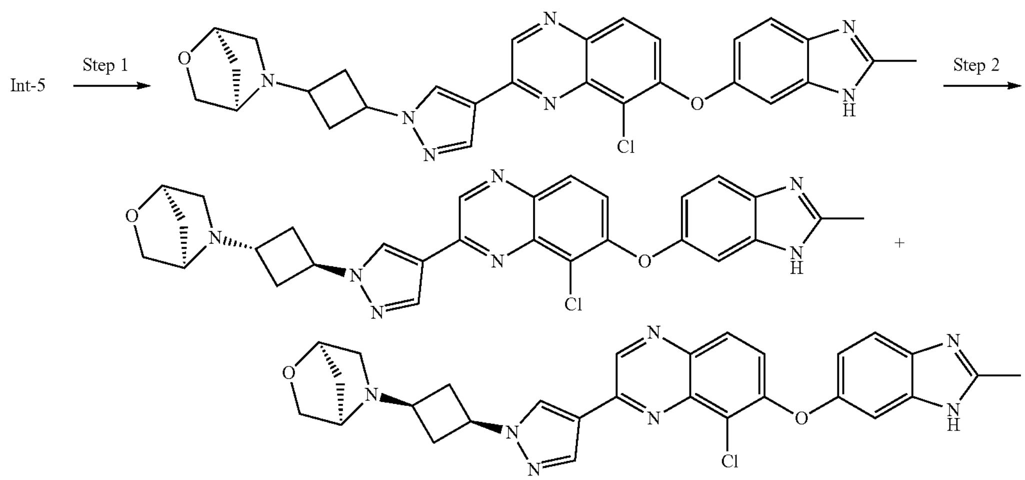

Step 1. (1R,4R)-5-(3-(4-(8-Chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptane To a solution of 3-[4-[8-chloro-7-[(2-methyl-3H-benzimidazol-5-yl)oxy]quinoxalin-2-yl]pyrazol-1-yl]cyclobutanone (50.0 mg, 112 μmol) and (1R,4R)-2-oxa-5-azabicyclo[2.2.1]heptane;hydrochloride (45.7 mg, 337 μmol) in methanol (2 mL) was added diisopropylethylamine (43.6 mg, 337 μmol) and titanium (IV) propan-2-olate (63.9 mg, 225 μmol). The mixture was stirred at 60° C. for 2 hours. Then sodium cyanoborohydride (7.06 mg, 112 μmol) was added and the reaction mixture was stirred at 25° C. for 2 hours. The reaction mixture was poured into saturated sodium bicarbonate (30 mL) and extracted with ethyl acetate (20 mL×3). The combined organic layers were dried over anhydrous sodium sulfate, filtered and concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 1%-30%, 10 min) to give (1R,4R)-5-(3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptane (38.0 mg, 72.0 μmol, 21%) as a white solid. m/z ES+ $[M+H]^+$ 528.3.

Step 2. (1R,4R)-5-((1r,3R)-3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptanes and (1R,4R)-5-((1s,3S)-3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptanes Compound (1R,4R)-5-(3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptane (38.0 mg, 72.0 μmol) was separated by SFC (column: Daicel Chiralpak IG (250 mm*50 mm, 10 μm); mobile phase: [hexane-EtOH (0.1% ammonium hydroxide)]; (B %: 90%-90%, 30 min) to give (1R,4R)-5-((1r,3R)-3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptanes (32.4 mg, 55.9 μmol, 78%) as an off-white solid and (1R,4R)-5-((1s,3S)-3-(4-(8-chloro-7-((2-methyl-1H-benzo[d]imidazol-6-yl)oxy)quinoxalin-2-yl)-1H-pyrazol-1-yl)cyclobutyl)-2-oxa-5-azabicyclo[2.2.1]heptanes (6.91 mg, 12.3 μmol, 17%) as an off-white solid.

$^1$H NMR (400 MHz, DMSO-$d_6$) δ=12.53-12.14 (m, 1H), 9.33 (s, 1H), 8.81 (s, 1H), 8.38 (s, 1H), 7.96 (d, J=8.8 Hz, 1H), 7.52 (d, J=6.8 Hz, 1H), 7.32 (d, J=8.8 Hz, 1H), 7.22 (s, 1H), 6.95 (d, J=8.0 Hz, 1H), 4.82-4.68 (m, 1H), 4.40 (s, 1H), 3.81 (d, J=6.8 Hz, 1H), 3.54 (d, J=4.0 Hz, 2H), 3.17 (s, 1H), 2.79 (d, J=10.0 Hz, 1H), 2.67-2.56 (m, 3H), 2.54-2.51 (m, 3H), 2.46-2.35 (m, 2H), 1.79-1.56 (m, 2H); m/z ES+ $[M+H]^+$ 528.0.

$^1$H NMR (400 MHz, $CD_3OD$) δ=9.12 (s, 1H), 8.61 (s, 1H), 8.39 (s, 1H), 7.87 (d, J=9.2 Hz, 1H), 7.53 (d, J=8.4 Hz, 1H), 7.33 (d, J=9.6 Hz, 1H), 7.18 (s, 1H), 7.01 (d, J=8.4 Hz, 1H), 5.24-5.14 (m, 1H), 4.59 (s, 1H), 4.14-3.87 (m, 4H), 3.76 (d, J=8.8 Hz, 1H), 3.11-2.98 (m, 2H), 2.92-2.72 (m, 4H), 2.57 (s, 3H), 2.11 (d, J=10.8 Hz, 1H), 1.97 (d, J=10.6 Hz, 1H); m/z ES+ $[M+H]^+$ 528.0.

Example 29. Synthesis of 2-[4-[8-chloro-7-[(2-methyl-3H-benzimidazol-5-yl)oxy]quinoxalin-2-yl]pyrazol-1-yl]-N-(2-formamido-2-methylpropyl) acetamide

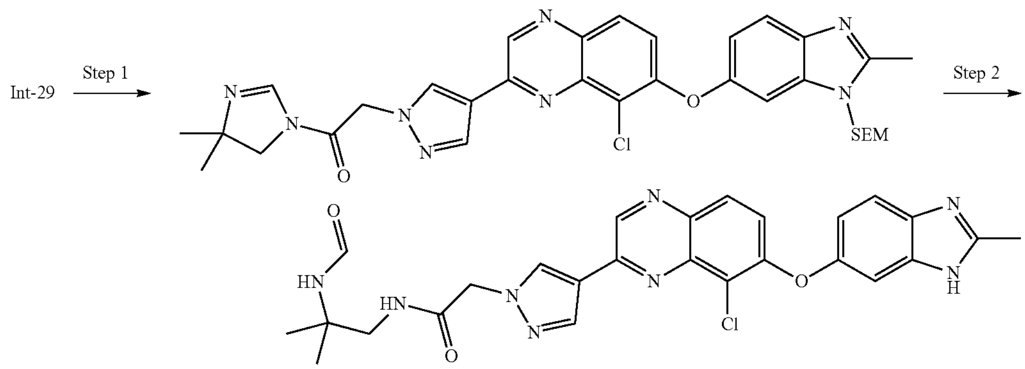

Step 1. 2-[4-[8-Chloro-7-[2-methyl-3-(2-trimethylsilylethoxymethyl)benzimidazol-5-yl]oxy-quinoxalin-2-yl]pyrazol-1-yl]-1-(5,5-dimethyl-4H-imidazol-3-yl)ethanone To a solution of 2-[4-[8-chloro-7-[2-methyl-3-(2-trimethylsilylethoxymethyl)benzimidazol-5-yl]oxy-quinoxalin-2-yl]pyrazol-1-yl]acetic acid (70.0 mg, 124 μmol), 4,4-dimethyl-1,5-dihydroimidazole (15.8 mg, 161 μmol) and diisopropylethylamine (64.0 mg, 495 μmol) in N,N-dimethyl formamide (2 mL) was added [dimethylamino (triazolo[4,5-b]pyridin-3-yloxy)methylidene]-dimethylazanium;hexafluorophosphate (236 mg, 619 μmol). The mixture was stirred at 25° C. for 5 h. The reaction mixture was diluted with water (30 mL) and extracted with ethyl acetate (30 mL×2). The combined organic layers were washed with brine (50 mL×2), dried over anhydrous sodium sulfate, filtered and concentrated in vacuo to give 2-[4-[8-chloro-7-[2-methyl-3-(2-trimethylsilylethoxymethyl)benzimidazol-5-yl]oxy-quinoxalin-2-yl]pyrazol-1-yl]-1-(5,5-dimethyl-4H-imidazol-3-yl)ethanone (105 mg, crude) as a yellow solid. m/z ES+ $[M+H]^+$ 645.2.

Step 2. 2-[4-[8-Chloro-7-[(2-methyl-3H-benzimidazol-5-yl)oxy]quinoxalin-2-yl]pyrazol-1-yl]-N-(2-formamido-2-methylpropyl) acetamide A solution of 2-[4-[8-chloro-7-[2-methyl-3-(2-trimethylsilylethoxymethyl)benzimidazol-5-yl]oxy-quinoxalin-2-yl]pyrazol-1-yl]-1-(5,5-dimethyl-4H-imidazol-3-yl)ethanone (105 mg, 163 μmol) in trifluoroacetic acid (2 mL) was stirred at 25° C. for 1 h. The reaction mixture was concentrated in vacuo to give a residue. The crude product was purified by prep-HPLC (column: Waters Xbridge 150*25 mm*5 μm; mobile phase: [water (10 mM ammonium bicarbonate)-acetonitrile]; (B %: 22%-52%, 10 min) and re-purified by prep-HPLC (column: Phenomenex Synergi C18 150*25 mm*10 μm; mobile phase: [water (0.225% formic acid)-acetonitrile]; (B %: 10%-30%, 10 min) to give 2-[4-[8-chloro-7-[(2-methyl-3H-benzimidazol-5-yl)oxy]quinoxalin-2-yl]pyrazol-1-yl]-N-(2-formamido-2-methylpropyl) acetamide (6.58 mg, 12.6 μmol, 7.6%) as an off-white solid. $^1$H NMR (400 MHz, DMSO-$d_6$) δ 12.85-11.67 (m, 1H), 9.33 (s, 1H), 8.74-8.62 (m, 1H), 8.42-8.31 (m, 1H), 8.29-8.20 (m, 1H), 7.96 (d, J=9.2 Hz, 1H), 7.92-7.86 (m, 1H), 7.71 (s, 1H), 7.56-7.45 (m, 1H), 7.32 (d, J=9.2 Hz, 1H), 7.22 (s, 1H), 6.95 (dd, J=2.4, 8.8 Hz, 1H), 5.06-4.87 (m, 2H), 3.41 (d, J=6.0 Hz, 2H), 2.49 (s, 3H), 1.25-1.17 (m, 6H); m/z ES+ $[M+H]^+$ 533.0.

Example 30. Synthesis of 8-chloro-2-(1-(3,3-difluorocyclopentyl)-1H-pyrazol-4-yl)-7-((2-methyl-1H-benzo[d]imidazol-6-yl)oxy)quinoxaline

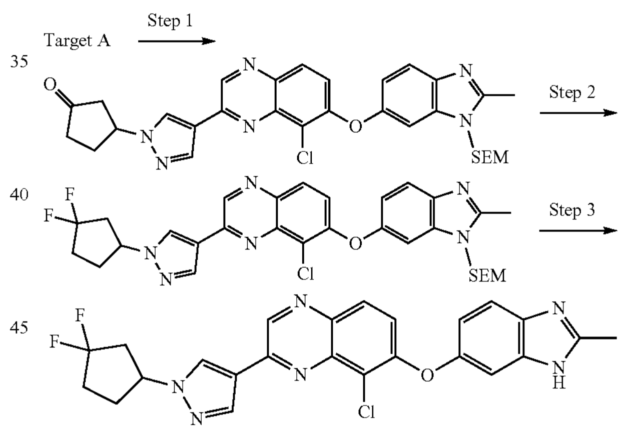

Step 1. 3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)cyclopentanone To solution of 8-chloro-7-((2-methyl-1-((2-(trimethylsilyl)ethoxy)methyl)-1H-benzo[d]imidazol-6-yl)oxy)-2-(1H-pyrazol-4-yl)quinoxaline (300 mg, 592 μmol) in acetonitrile (4 mL) was added scandium (III) trifluoromethanesulfonate (29.1 mg, 59.2 μmol) and cyclopent-2-en-1-one (194 mg, 2.37 mmol). The mixture was stirred at 25° C. for 13 h. The reaction mixture was quenched with water (40 mL) and extracted with ethyl acetate (50 mL×3). The combined organic layers were washed with brine (30 mL×3), dried over anhydrous sodium sulfate, filtered and concentrated under reduced pressure and the residue was purified by reversed-phase HPLC (0.1% formic acid condition, 50%-80% acetonitrile, 10 min) to give 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)cyclopentanone (300 mg, 510 μmol, 82%) as a yellow solid. $^1$H NMR (400 MHz, DMSO-$d_6$) δ 9.33 (d, J=3.6 Hz, 1H), 8.83 (s, 1H), 8.39 (s, 1H), 7.96 (dd, J=0.8, 9.2 Hz, 1H), 7.69-7.57 (m, 1H), 7.46-7.28 (m, 2H), 7.09-6.99 (m, 1H), 5.65-5.52 (m, 2H), 5.29-5.21 (m, 1H), 3.56-3.45 (m, 2H), 2.90-2.66 (m, 2H), 2.57 (d, J=6.4 Hz, 3H), 2.55-2.52 (m, 1H), 2.47-2.41 (m, 1H), 2.39-2.28 (m, 2H), 0.90-0.75 (m, 2H), −0.07-−0.14 (m, 9H); m/z ES+ $[M+H]^+$ 589.3.

Step 2. 8-Chloro-2-(1-(3,3-difluorocyclopentyl)-1H-pyrazol-4-yl)-7-((2-methyl-1-((2-(trimethylsilyl)ethoxy)methyl)-1H-benzo[d]imidazol-6-yl)oxy)quinoxaline To a solution of 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)cyclopentanone (280 mg, 475 μmol) in dichloromethane (3 mL) was slowly added bis(2-methoxyethyl)aminosulfur trifluoride (210 mg, 951 μmol) at 0° C. The mixture was stirred at 25° C. for 12 h. The reaction mixture was quenched with aqueous sodium bicarbonate (40 mL) and extracted with dichloromethane (50 mL×3). The combined organic layers were washed with brine (30 mL×3), dried over anhydrous sodium sulfate, filtered and concentrated under reduced pressure and the residue was purified by reversed-phase HPLC (0.1% formic acid condition, 75%-80% acetonitrile, 5 min) to give 8-chloro-2-(1-(3,3-difluorocyclopentyl)-1H-pyrazol-4-yl)-7-((2-methyl-1-((2-(trimethylsilyl)ethoxy)methyl)-1H-benzo[d]imidazol-6-yl)oxy)quinoxaline (140 mg, 230 μmol, 48%) as an orange oil. m/z ES+ $[M+H]^+$ 611.1.

Step 3. 8-Chloro-2-(1-(3,3-difluorocyclopentyl)-1H-pyrazol-4-yl)-7-((2-methyl-1H-benzo[d]imidazol-6-yl)oxy)quinoxaline A solution of 8-chloro-2-(1-(3,3-difluorocyclopentyl)-1H-pyrazol-4-yl)-7-((2-methyl-1-((2-(trimethylsilyl)ethoxy)methyl)-1H-benzo[d]imidazol-6-yl)oxy)quinoxaline (60.0 mg, 98.2 μmol) in trifluoroacetic acid (1 mL) was stirred at 25° C. for 1 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 15%-45%, 10 min) to give 8-chloro-2-(1-(3,3-difluorocyclopentyl)-1H-pyrazol-4-yl)-7-((2-methyl-1H-benzo[d]imidazol-6-yl)oxy)quinoxaline (27.7 mg, 57.5 μmol, 59%) as an off-white solid. $^1$H NMR (400 MHz, DMSO-$d_6$) δ 9.34 (s, 1H), 8.81 (s, 1H), 8.42 (s, 1H), 7.99 (d, J=9.2 Hz, 1H), 7.60 (d, J=8.8 Hz, 1H), 7.40-7.29 (m, 2H), 7.05 (dd, J=2.4, 8.8 Hz, 1H), 5.12 (q, J=7.6 Hz, 1H), 2.86-2.75 (m, 1H), 2.67 (dd, J=7.6, 16.0 Hz, 1H), 2.57 (s, 3H), 2.45-2.36 (m, 2H), 2.31-2.19 (m, 2H); m/z ES+ $[M+H]^+$ 481.0.

Example 31. Synthesis of 2-(1-((3S,4S)-3-fluoro-1-(oxetan-3-yl) piperidin-4-yl)-1H-pyrazol-4-yl)-8-methyl-7-((2-methyl-1H-benzo[d]imidazol-6-yl)oxy)quinoxaline

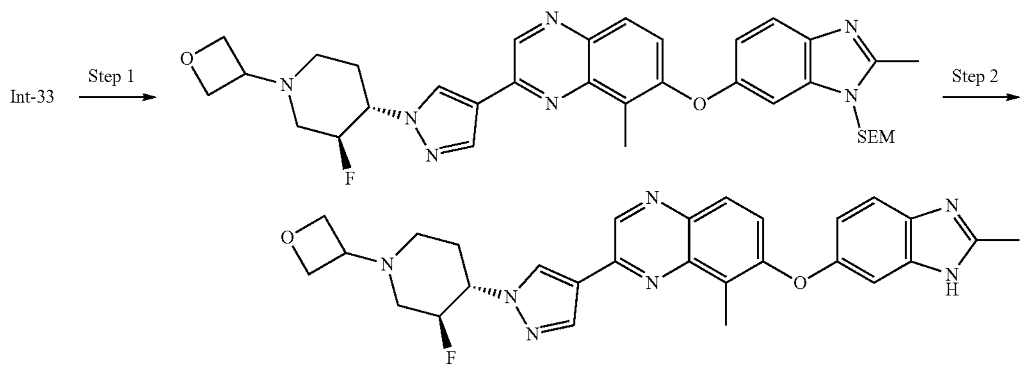

Step 1. 2-(1-((3S,4S)-3-Fluoro-1-(oxetan-3-yl) piperidin-4-yl)-1H-pyrazol-4-yl)-8-methyl-7-((2-methyl-1-((2-(trimethylsilyl)ethoxy)methyl)-1H-benzo[d]imidazol-6-yl)oxy)quinoxaline To a solution of 2-(1-((3S,4S)-3-fluoropiperidin-4-yl)-1H-pyrazol-4-yl)-8-methyl-7-((2-methyl-1-((2-(trimethylsilyl)ethoxy)methyl)-1H-benzo[d]imidazol-6-yl)oxy)quinoxaline (90.0 mg, 153 μmol) in tetrahydrofuran (2 mL) was added oxetan-3-one (22.1 mg, 306 μmol), the mixture was stirred at 25° C. for 0.5 h. Then sodium triacetoxyborohydride (97.4 mg, 459 μmol) was added into the mixture. The mixture was stirred at 25° C. for 12 h. The reaction mixture was diluted with water (30 mL) and extracted with ethyl acetate (20 mL×3). The combined organic layers were dried over anhydrous sodium sulfate, filtered and concentrated under reduced pressure. The residue was purified by prep-TLC (dichloromethane:methanol=10:1) to give 2-(1-((3S,4S)-3-fluoro-1-(oxetan-3-yl) piperidin-4-yl)-1H-pyrazol-4-yl)-8-methyl-7-((2-methyl-1-((2-(trimethylsilyl)ethoxy)methyl)-1H-benzo[d]imidazol-6-yl)oxy)quinoxaline (40.0 mg, 61.5 μmol, 40%) as a yellow oil. m/z ES+ $[M+H]^+$ 644.4.

Step 2. 2-(1-((3S,4S)-3-Fluoro-1-(oxetan-3-yl) piperidin-4-yl)-1H-pyrazol-4-yl)-8-methyl-7-((2-methyl-1H-benzo[d]imidazol-6-yl)oxy)quinoxaline To a solution of 2-(1-((3S,4S)-3-fluoro-1-(oxetan-3-yl) piperidin-4-yl)-1H-pyrazol-4-yl)-8-methyl-7-((2-methyl-1-

((2-(trimethylsilyl)ethoxy)methyl)-1H-benzo[d]imidazol-6-yl)oxy)quinoxaline (35.0 mg, 54.4 μmol) in tetrahydrofuran (1 mL) was added pyridine hydrofluoride (220 mg, 2.22 mmol). The mixture was stirred at 80° C. for 0.5 h. The reaction mixture was concentrated under reduced pressure. The residue was purified by prep-HPLC (formic acid condition; column: Unisil 3-100 C18 Ultra 150*50 mm*3 μm; mobile phase: [water (0.225% formic acid)-acetonitrile]; (B %: 10%-40%, 10 min) to give 2-(1-((3S,4S)-3-fluoro-1-(oxetan-3-yl) piperidin-4-yl)-1H-pyrazol-4-yl)-8-methyl-7-((2-methyl-1H-benzo[d]imidazol-6-yl)oxy)quinoxaline (23.5 mg, 44.8 μmol, 82%) as a white solid. $^1$H NMR (400 MHz, DMSO-$d_6$) δ=9.24 (s, 1H), 8.83 (s, 1H), 8.42 (s, 1H), 7.85 (d, J=9.2 Hz, 1H), 7.50 (d, J=8.8 Hz, 1H), 7.26 (d, J=9.2 Hz, 1H), 7.10 (d, J=2.4 Hz, 1H), 6.92 (dd, J=2.4, 8.8 Hz, 1H), 5.11-4.90 (m, 1H), 4.60-4.55 (m, 2H), 4.50-4.45 (m, 2H), 3.62 (s, 1H), 3.21 (s, 1H), 2.81 (d, J=10.0 Hz, 1H), 2.69 (s, 3H), 2.51-2.50 (m, 1H), 2.49-2.48 (m, 3H), 2.17-2.04 (m, 4H); m/z ES+ [M+H]$^+$ 514.1.

Example 32. Synthesis of 1-((1s,3s)-3-(4-(8-chloro-7-((2-methyl-1H-benzo[d]imidazol-6-yl)oxy)quinoxalin-2-yl)-1H-pyrazol-1-yl)cyclobutyl)azetidin-3-ol and 1-((1r,3r)-3-(4-(8-chloro-7-((2-methyl-1H-benzo[d]imidazol-6-yl)oxy)quinoxalin-2-yl)-1H-pyrazol-1-yl)cyclobutyl)azetidin-3-ol

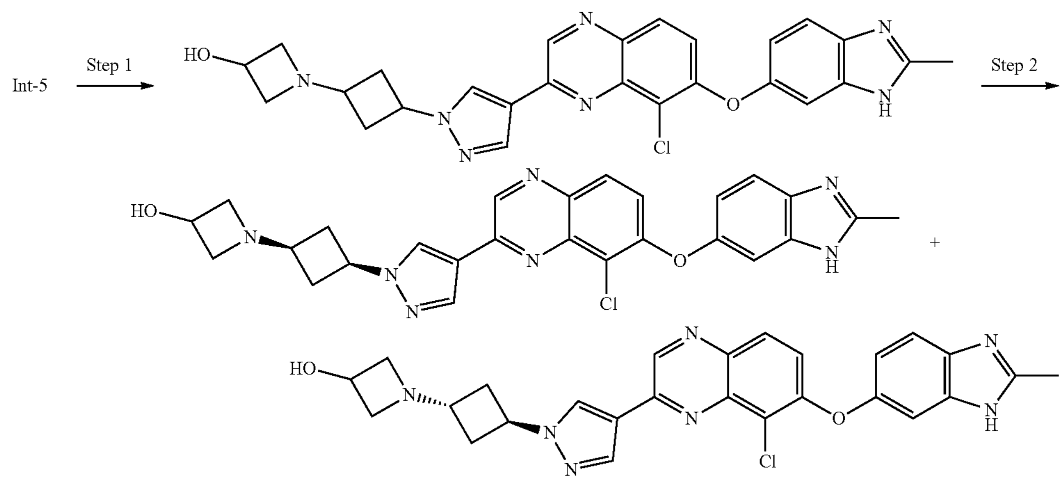

Step 1. 1-(3-(4-(8-Chloro-7-((2-methyl-1H-benzo[d]imidazol-6-yl)oxy)quinoxalin-2-yl)-1H-pyrazol-1-yl)cyclobutyl)azetidin-3-ol To a solution of 3-[4-[8-chloro-7-[(2-methyl-3H-benzimidazol-5-yl)oxy]quinoxalin-2-yl]pyrazol-1-yl]cyclobutanone (150 mg, 340 μmol) and azetidin-3-ol hydrochloride (111 mg, 1.01 mmol) in methanol (2 mL) was added titanium (IV) propan-2-olate (192 mg, 674 μmol) and diisopropylethylamine (131 mg, 1.01 mmol). The mixture was stirred at 60° C. for 2 h. Then sodium cyanoborohydride (21.0 mg, 337 μmol) was added and the mixture was stirred at 25° C. for 2 h. The reaction mixture was diluted with sat. sodium bicarbonate (20 mL), and then extracted with ethyl acetate (50 mL×3). The combined organic layers were washed with brine (25 mL×2), dried over anhydrous sodium sulfate, filtered and concentrated under reduced pressure to give 1-(3-(4-(8-chloro-7-((2-methyl-1H-benzo[d]imidazol-6-yl)oxy)quinoxalin-2-yl)-1H-pyrazol-1-yl)cyclobutyl)azetidin-3-ol (30.0 mg, 60.0 μmol, 18%) as a white solid. m/z ES+ [M+H]$^+$ 502.3.

Step 2. 1-((1s,3s)-3-(4-(8-Chloro-7-((2-methyl-1H-benzo[d]imidazol-6-yl)oxy)quinoxalin-2-yl)-1H-pyrazol-1-yl)cyclobutyl)azetidin-3-ol and 1-((1r,3r)-3-(4-(8-chloro-7-((2-methyl-1H-benzo[d]imidazol-6-yl)oxy)quinoxalin-2-yl)-1H-pyrazol-1-yl)cyclobutyl) azetidin-3-ol 1-[3-[4-[8-Chloro-7-[(2-methyl-3H-benzimidazol-5-yl) oxy]quinoxalin-2-yl]pyrazol-1-yl]cyclobutyl]azetidin-3-ol (80.0 mg, 160 μmol) was separated by SFC (basic condition; column: Daicel Chiralpak IG (250 mm×50 mm, 10 μm); mobile phase: [hexane-ethyl alcohol (0.1% ammonium hydroxide)]; (B %: 40%-40%, 22, 66 min) to give 1-((1s, 3s)-3-(4-(8-chloro-7-((2-methyl-1H-benzo[d]imidazol-6-yl) oxy)quinoxalin-2-yl)-1H-pyrazol-1-yl)cyclobutyl)azetidin-3-ol (39.5 mg, 77.1 μmol, 48%) as a yellow solid and 1-((1r,3r)-3-(4-(8-chloro-7-((2-methyl-1H-benzo[d]imidazol-6-yl)oxy)quinoxalin-2-yl)-1H-pyrazol-1-yl)cyclobutyl) azetidin-3-ol (18.6 mg, 36.4 μmol, 23%) as a white solid.

$^1$H NMR (400 MHz, DMSO-$d_6$) δ=12.40-12.10 (m, 1H), 9.33 (s, 1H), 8.77 (s, 1H), 8.38 (s, 1H), 7.95 (d, J=9.2 Hz, 1H), 7.62-7.43 (m, 1H), 7.39-7.28 (m, 1H), 7.27-7.12 (m, 1H), 6.94 (d, J=7.2 Hz, 1H), 5.32 (d, J=6.8 Hz, 1H), 4.75-4.64 (m, 1H), 4.25-4.16 (m, 1H), 3.44 (t, J=6.8 Hz, 2H), 3.11-3 (m, 1H), 2.90 (t, J=6.8 Hz, 2H), 2.57-2.52 (m, 2H), 2.49-2.47 (m, 3H), 2.42-2.32 (m, 2H); m/z ES+ [M+H]$^+$ 502.0.

$^1$H NMR (400 MHz, DMSO-$d_6$) δ=12.53-12.09 (m, 1H), 9.30 (s, 1H), 8.77 (s, 1H), 8.37 (s, 1H), 7.95 (d, J=9.2 Hz, 1H), 7.58-7.44 (m, 1H), 7.31 (d, J=8.0 Hz, 1H), 7.21 (s, 1H), 6.94 (d, J=7.2 Hz, 1H), 5.34 (s, 1H), 5.14-5 (m, 1H), 4.21 (s, 1H), 3.55 (s, 2H), 3.21-3.14 (m, 1H), 2.75 (s, 2H), 2.59-2.53 (m, 2H), 2.49-2.45 (m, 3H), 2.31-2.21 (m, 2H); m/z ES+ [M+H]$^+$ 502.0.

Example 33. Synthesis of 1-(2-(4-(8-chloro-7-((2-methyl-1H-benzo[d]imidazol-6-yl)oxy)quinoxalin-2-yl)-1H-pyrazol-1-yl)ethyl)pyrrolidin-2-one

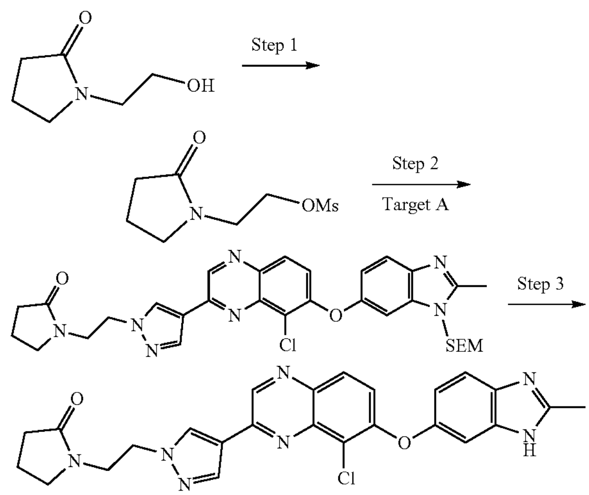

Step 1. 2-(2-Oxopyrrolidin-1-yl)ethyl methanesulfonate

To a solution of 1-(2-hydroxyethyl)pyrrolidin-2-one (500 mg, 3.87 mmol) in dichloromethane (5 mL) was added triethylamine (1.18 g, 11.6 mmol) and methanesulfonyl chloride (665 mg, 5.81 mmol). The mixture was stirred at 0° C. for 1 h. The reaction mixture was quenched with water (10 mL) and extracted with dichloromethane (20 mL×3). The combined organic layers were washed with brine (10 mL×3), dried over anhydrous sodium sulfate, filtered and concentrated under reduced pressure to give 2-(2-oxopyrrolidin-1-yl)ethyl methanesulfonate (700 mg, crude) as a yellow oil. $^1$H NMR (400 MHz, DMSO-$d_6$) δ 4.28 (t, J=5.2 Hz, 2H), 3.49 (t, J=5.2 Hz, 2H), 3.40 (t, J=7.2 Hz, 2H), 3.18 (s, 3H), 2.26-2.19 (m, 2H), 1.97-1.89 (m, 2H).

Step 2. 1-(2-(4-(8-Chloro-7-((2-methyl-1-((2-(trimethylsilyl) thoxy)methyl)-1H-benzo[d]imidazol-6-yl)oxy)quinoxalin-2-yl)-1H-pyrazol-1-yl)ethyl)pyrrolidin-2-one To a solution of 8-chloro-7-((2-methyl-1-((2-(trimethylsilyl)ethoxy)methyl)-1H-benzo[d]imidazol-6-yl)oxy)-2-(1H-pyrazol-4-yl)quinoxaline (200 mg, 394 μmol) in N,N-dimethyl formamide (2 mL) was added potassium acetate (164 mg, 1.18 mmol) and 2-(2-oxopyrrolidin-1-yl)ethyl methanesulfonate (163 mg, 789 μmol). The mixture was stirred at 80° C. for 12 h. Then the reaction was stirred at 100° C. for 2 h. The reaction mixture was diluted with water (30 mL) and extracted with ethyl acetate (50 mL×3). The combined organic layers were washed with brine (10 mL×3), dried over anhydrous sodium sulfate, filtered and concentrated under reduced pressure and the residue was purified by reversed-phase HPLC (0.1% formic acid condition, 80%-90% acetonitrile, 5 min) to give 1-(2-(4-(8-chloro-7-((2-methyl-1-((2-(trimethylsilyl)thoxy)methyl)-1H-benzo[d]imidazol-6-yl)oxy)quinoxalin-2-yl)-1H-pyrazol-1-yl)ethyl)pyrrolidin-2-one (150 mg, 243 μmol, 62%) as an orange solid. m/z ES+ $[M+H]^+$ 618.1.

Step 3. 1-(2-(4-(8-Chloro-7-((2-methyl-1H-benzo[d]imidazol-6-yl)oxy)quinoxalin-2-yl)-1H-pyrazol-1-yl)ethyl)pyrrolidin-2-one A solution of 1-(2-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)ethyl)pyrrolidin-2-one (50.0 mg, 80.9 μmol) in trifluoroacetic acid (1 mL) was stirred at 25° C. for 0.5 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 9%-39%, 10 min) to give 1-(2-(4-(8-chloro-7-((2-methyl-1H-benzo[d]imidazol-6-yl)oxy)quinoxalin-2-yl)-1H-pyrazol-1-yl)ethyl)pyrrolidin-2-one (13.1 mg, 26.9 μmol, 33%) as a yellow solid. $^1$H NMR (400 MHz, DMSO-$d_6$) δ 9.30 (s, 1H), 8.72 (s, 1H), 8.36 (s, 1H), 7.95 (d, J=9.2 Hz, 1H), 7.51 (d, J=8.8 Hz, 1H), 7.32 (d, J=9.2 Hz, 1H), 7.21 (d, J=1.6 Hz, 1H), 6.94 (dd, J=2.4, 8.8 Hz, 1H), 4.38 (t, J=6.0 Hz, 2H), 3.65 (t, J=6.0 Hz, 2H), 3.22 (t, J=7.2 Hz, 2H), 2.48 (s, 3H), 2.19-2.13 (m, 2H), 1.87 (q, J=7.6 Hz, 2H); m/z ES+ $[M+H]^+$ 488.1.

Example 34. Synthesis of 8-cyclopropyl-2-(1-((3,3-difluorocyclobutyl)methyl)-1H-pyrazol-4-yl)-7-((2-methyl-1H-benzo[d]imidazol-6-yl)oxy)quinoxaline

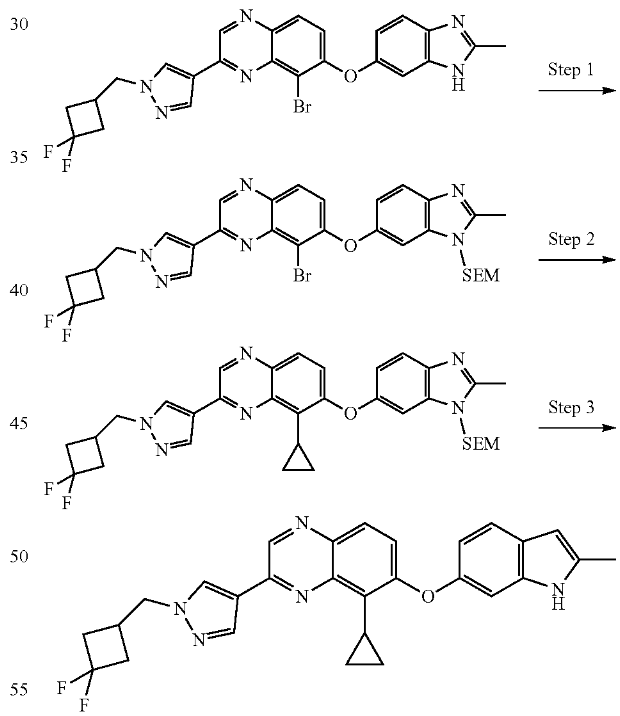

Step 1. 8-Bromo-2-(1-((3,3-difluorocyclobutyl)methyl)-1H-pyrazol-4-yl)-7-((2-methyl-1-((2-(trimethylsilyl)ethoxy)methyl)-1H-benzo[d]imidazol-6-yl)oxy)quinoxaline To a solution of 8-bromo-2-[1-[(3,3-difluorocyclobutyl)methyl]pyrazol-4-yl]-7-[(2-methyl-3H-benzimidazol-5-yl)oxy]quinoxaline (100 mg, 190 μmol) in tetrahydrofuran (2 mL) was added sodium hydride (15.2 mg, 381 μmol, 60% in mineral oil) at 0° C. The mixture was stirred at 0° C. for 30 min. Then 2-(chloromethoxy)ethyl-trimethyl-silane (47.6 mg, 286 μmol) was added at 0° C. The mixture was stirred at 25° C. for 1.5 h. The reaction mixture was poured into water (30 mL) and extracted with ethyl acetate (20 mL×3). The combined organic layers were dried over anhydrous sodium sulfate, filtered and concentrated under reduced pressure. The residue was purified by column chromatography (petroleum ether/ethyl acetate=10/1 to 1/4) to give 8-bromo-2-(1-((3,3-difluorocyclobutyl)methyl)-1H-pyrazol-4-yl)-7-((2-methyl-1-((2-(trimethylsilyl)ethoxy)methyl)-1H-benzo[d]imidazol-6-yl)oxy)quinoxaline (30.0 mg, 45.8 μmol, 24%) as a yellow solid. m/z ES+ $[M+H]^+$ 657.2.

Step 2. 8-Cyclopropyl-2-(1-((3,3-difluorocyclobutyl)methyl)-1H-pyrazol-4-yl)-7-((2-methyl-1-((2-(trimethylsilyl)ethoxy)methyl)-1H-benzo[d]imidazol-6-yl)oxy)quinoxaline To a solution of 2-[[6-[5-bromo-3-[1-[(3,3-difluorocyclobutyl)methyl]pyrazol-4-yl]quinoxalin-6-yl]oxy-2-methyl-benzimidazol-1-yl]methoxy]ethyl-trimethyl-silane (25.0 mg, 38.1 μmol) and cyclopropylboronic acid (32.8 mg, 381 μmol) in dioxane (0.5 mL) and water (0.05 mL) was added sodium carbonate (12.1 mg, 114 μmol) and methanesulfonato (2-dicyclohexylphosphino-2,4,6-tri-i-propyl-1,1'-biphenyl) (2-amino-1,1'-biphenyl-2-yl) palladium(II) (4.50 mg, 5.72 μmol). The mixture was stirred at 110° C. for 8 h under nitrogen. The reaction mixture was poured into water (10 mL) and extracted with ethyl acetate (10 mL×3). The combined organic layers were dried over anhydrous sodium sulfate, filtered and concentrated under reduced pressure. The residue was purified by column chromatography (petroleum ether/ethyl acetate=1/1 to 1/9) to give 8-cyclopropyl-2-(1-((3,3-difluorocyclobutyl)methyl)-1H-pyrazol-4-yl)-7-((2-methyl-1-((2-(trimethylsilyl)ethoxy)methyl)-1H-benzo[d]imidazol-6-yl)oxy)quinoxaline (15.0 mg, 19.9 μmol, 52%) as a yellow oil. m/z ES+ $[M+H]^+$ 617.4.

Step 3. 8-Cyclopropyl-2-(1-((3,3-difluorocyclobutyl)methyl)-1H-pyrazol-4-yl)-7-((2-methyl-1H-benzo[d]imidazol-6-yl)oxy)quinoxaline A solution of 2-[[6-[5-cyclopropyl-3-[1-[(3,3-difluorocyclobutyl)methyl]pyrazol-4-yl]quinoxalin-6-yl]oxy-2-methyl-benzimidazol-1-yl]methoxy]ethyl-trimethyl-silane (13.0 mg, 17.3 μmol) in trifluoroacetic acid (0.5 mL) was stirred at 25° C. for 0.5 h. The reaction mixture was concentrated under reduced pressure. The residue was purified by prep-HPLC (formic acid condition; column: Phenomenex Synergi C18 150*25 mm*10 μm; mobile phase: [water (0.225% formic acid)-acetonitrile]; (B %: 20%-50%, 10 min) to give 8-cyclopropyl-2-(1-((3,3-difluorocyclobutyl)methyl)-1H-pyrazol-4-yl)-7-((2-methyl-1H-benzo[d]imidazol-6-yl)oxy)quinoxaline (3.7 mg, 7.43 μmol, 43%) as a yellow solid. $^1H$ NMR (400 MHz, $CD_3OD$) δ ppm 9.06 (s, 1H), 8.50 (s, 1H), 8.27 (s, 1H), 7.74 (d, J=9.2 Hz, 1H), 7.48 (d, J=8.8 Hz, 1H), 7.25 (d, J=9.2 Hz, 1H), 7.03 (d, J=2.0 Hz, 1H), 6.93 (dd, J=2.4, 8.8 Hz, 1H), 4.39 (d, J=6.8 Hz, 2H), 2.92-2.81 (m, 1H), 2.77-2.63 (m, 3H), 2.55 (s, 3H), 2.52-2.39 (m, 2H), 1.65-1.58 (m, 2H), 1.07-1.02 (m, 2H); m/z ES+ $[M+H]^+$ 487.1.

Example 35. Synthesis of 8-chloro-7-[(2-methyl-3H-benzimidazol-5-yl)oxy]-2-[1-[1-(oxetan-3-ylmethyl)azetidin-3-yl]pyrazol-4-yl]quinoxaline

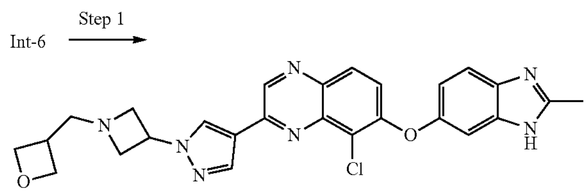

Step 1. 8-Chloro-7-[(2-methyl-3H-benzimidazol-5-yl])oxy]-2-[1-[1-(oxetan-3-ylmethyl)azetidin-3-yl]pyrazol-4-yl]quinoxaline To a mixture of 2-[1-(azetidin-3-yl)pyrazol-4-yl]-8-chloro-7-[(2-methyl-3H-benzimidazol-5-yl)oxy]quinoxaline (100 mg, 231 μmol) in tetrahydrofuran (0.8 mL) and methanol (0.8 mL) was added triethylamine (46.8 mg, 463 μmol), and then oxetan-3-ylmethyl methanesulfonate (38.4 mg, 231 μmol) was added. The reaction mixture was stirred at 80° C. for 12 h. The reaction mixture was quenched with water (3 mL) and extracted with ethyl acetate (20 mL×2). The combined organic layers were washed with brine (20 mL×2), dried over anhydrous sodium sulfate, filtered and concentrated under reduced pressure and the residue was purified by prep-HPLC (column: Phenomenex Synergi C18 150*25 mm*10 μm; mobile phase: [water (0.225% formic acid)-acetonitrile]; (B %: 0%-24%, 10 min) to give 8-chloro-7-[(2-methyl-3H-benzimidazol-5-yl)oxy]-2-[1-[1-(oxetan-3-ylmethyl)azetidin-3-yl]pyrazol-4-yl]quinoxaline (26.2 mg, 51.2 μmol, 22%) as a white solid. $^1H$ NMR (400 MHz, DMSO-$d_6$) δ=9.33 (s, 1H), 8.84 (s, 1H), 8.41 (s, 1H), 8.19 (s, 1H), 7.95 (d, J=9.2 Hz, 1H), 7.51 (d, J=8.4 Hz, 1H), 7.32 (d, J=9.2 Hz, 1H), 7.21 (d, J=2.4 Hz, 1H), 6.94 (dd, J=2.4, 8.8 Hz, 1H), 5.20-5.05 (m, 1H), 4.70-4.55 (m, 2H), 4.29 (t, J=6.0 Hz, 2H), 3.74 (t, J=7.6 Hz, 2H), 3.49 (t, J=7.2 Hz, 2H), 3.04-2.96 (m, 1H), 2.83 (d, J=7.6 Hz, 2H), 2.48 (s, 3H); m/z ES+ $[M+H]^+$ 502.0.

Example 36. Synthesis of 2-[1-(2-azaspiro[3.3]heptan-6-yl)pyrazol-4-yl]-8-chloro-7-[(2-methyl-3H-benzimidazol-5-yl)oxy]quinoxaline and 8-chloro-7-[(2-methyl-3H-benzimidazol-5-yl)oxy]-2-[1-[2-(oxetan-3-yl)-2-azaspiro[3.3]heptan-6-yl]pyrazol-4-yl]quinoxaline

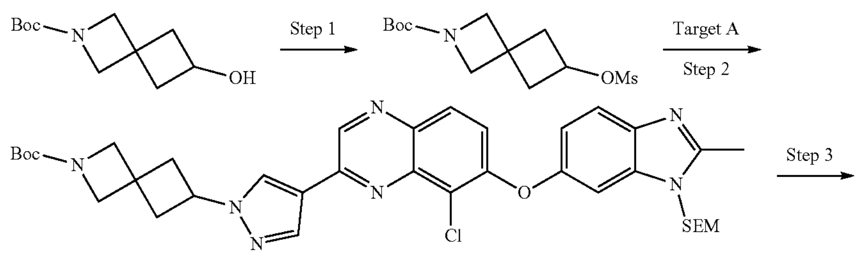

-continued

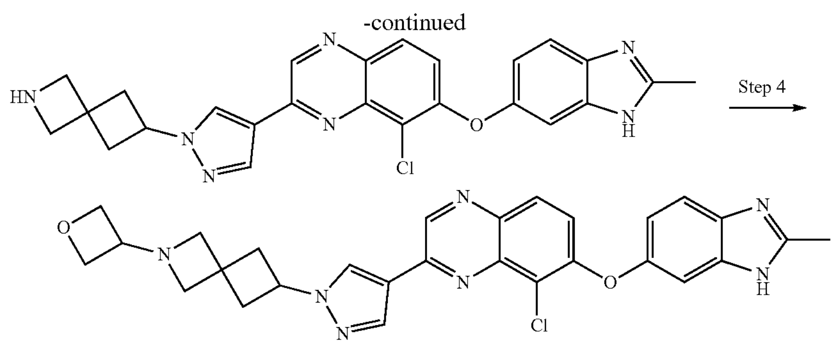

Step 1. tert-Butyl 6-methylsulfonyloxy-2-azaspiro[3.3]heptane-2-carboxylate

To a solution of tert-butyl 6-hydroxy-2-azaspiro[3.3]heptane-2-carboxylate (150 mg, 703 μmol) in dichloromethane (3 mL) was added triethylamine (214 mg, 2.11 mmol) and methanesulfonyl chloride (161 mg, 1.41 mmol), the mixture was stirred at 0° C. for 4 h. The reaction mixture was quenched with water (5 mL) at 0° C. and extracted with ethyl acetate (3×5 mL). The combined organic layers were washed with water (3×5 mL), dried over sodium sulfate, filtered and concentrated under reduced pressure to give tert-butyl 6-methylsulfonyloxy-2-azaspiro[3.3]heptane-2-carboxylate (220 mg, 755 μmol, 96%) as a yellow oil. m/z ES+ $[M-55]^+$ 236.1.

Step 2. tert-Butyl 6-[4-[8-chloro-7-[2-methyl-3-(2-trimethylsilylethoxymethyl)benzimidazol-5-yl]oxy-quinoxalin-2-yl]pyrazol-1-yl]-2-azaspiro[3.3]heptane-2-carboxylate To a solution of 2-[[6-[5-chloro-3-(1H-pyrazol-4-yl)quinoxalin-6-yl]oxy-2-methyl-benzimidazol-1-yl]methoxy]ethyl-trimethyl-silane (50.0 mg, 98.6 μmol), tert-butyl 6-methylsulfonyloxy-2-azaspiro[3.3]heptane-2-carboxylate (43.1 mg, 148 μmol) in N,N-dimethylformamide (5 mL) was added potassium carbonate (54.5 mg, 394 μmol). The mixture was stirred at 100° C. for 16 h. The reaction mixture was quenched with water (50 mL) at 20° C. and extracted with ethyl acetate (3×20 mL). The combined organic layers were washed with water (2× 50 mL), dried over sodium sulfate, filtered and concentrated under reduced pressure. The residue was purified by prep-TLC (petroleum ether:ethyl acetate=1:1) to give tert-butyl 6-[4-[8-chloro-7-[2-methyl-3-(2-trimethylsilylethoxymethyl)benzimidazol-5-yl]oxy-quinoxalin-2-yl]pyrazol-1-yl]-2-azaspiro[3.3]heptane-2-carboxylate (80.0 mg, 114 μmol, 90%) as a yellow oil. m/z ES+ $[M+H]^+$ 702.5.

Step 3. 2-[1-(2-Azaspiro[3.3]heptan-6-yl)pyrazol-4-yl]-8-chloro-7-[(2-methyl-3H-benzimidazol-5-yl)oxy]quinoxaline A solution of tert-butyl 6-[4-[8-chloro-7-[2-methyl-3-(2-trimethylsilylethoxymethyl)benzimidazol-5-yl]oxy-quinoxalin-2-yl]pyrazol-1-yl]-2-azaspiro[3.3]heptane-2-carboxylate (80.0 mg, 114 μmol) in trifluoroacetic acid (0.5 mL) was stirred at 20° C. for 2 h. The reaction mixture was concentrated under reduced pressure. The residue was purified by prep-HPLC (column: Phenomenex Luna C18 150*25 mm*10 μm; mobile phase: [water (0.225% formic acid)-acetonitrile]; (B %: 3%-33%, 10 min) to give 2-[1-(2-azaspiro[3.3]heptan-6-yl)pyrazol-4-yl]-8-chloro-7-[(2-methyl-3H-benzimidazol-5-yl)oxy]quinoxaline (15.4 mg, 32.6 μmol, 36%) as a yellow solid. $^1H$ NMR (400 MHz, DMSO-$d_6$) δ 9.22 (s, 1H), 8.60 (s, 1H), 8.40 (s, 1H), 8.01 (d, J=9.2 Hz, 1H), 7.78-7.74 (m, 1H), 7.50 (d, J=9.2 Hz, 1H), 7.35-7.28 (m, 2H), 4.98-4.92 (m, 1H), 4.24 (d, J=18.0 Hz, 4H), 3.02-2.87 (m, 4H), 2.84 (s, 3H); m/z ES+ $[M+H]^+$ 472.1.

Step 4. 8-Chloro-7-[(2-methyl-3H-benzimidazol-5-yl)oxy]-2-[1-[2-(oxetan-3-yl)-2-azaspiro[3.3]heptan-6-yl]pyrazol-4-yl]quinoxaline To a mixture of 2-[1-(2-azaspiro[3.3]heptan-6-yl)pyrazol-4-yl]-8-chloro-7-[(2-methyl-3H-benzimidazol-5-yl)oxy]quinoxaline (100.0 mg, 212 μmol) and oxetan-3-one (30.6 mg, 424 μmol) in methanol (1 mL) was added sodium cyanoborohydride (40.0 mg, 636 μmol) and sodium acetate (87.9 mg, 1.06 mmol). The mixture was stirred at 20° C. for 2 hours. The reaction mixture was filtered and concentrated under reduced pressure. The residue was purified by prep-HPLC (column: Waters Xbridge 150*25 mm*5 μm; mobile phase: [water (10 mM ammonium bicarbonate)-acetonitrile]; (B %: 27%-57%, 8 min) to give 8-chloro-7-[(2-methyl-3H-benzimidazol-5-yl)oxy]-2-[1-[2-(oxetan-3-yl)-2-azaspiro[3.3]heptan-6-yl]pyrazol-4-yl]quinoxaline (17.7 mg, 32.0 μmol, 15%) as a yellow solid. $^1H$ NMR (400 MHz, $CD_3OD$) δ 9.11 (d, J=1.6 Hz, 1H), 8.56 (s, 1H), 8.34 (s, 1H), 7.86 (dd, J=1.6, 9.2 Hz, 1H), 7.52 (br d, J=8.4 Hz, 1H), 7.37-7.26 (m, 1H), 7.17 (s, 1H), 7 (dd, J=2.0, 8.8 Hz, 1H), 4.99-4.90 (m, 1H), 4.73 (t, J=6.8 Hz, 2H), 4.48 (dd, J=5.2, 6.8 Hz, 2H), 3.86-3.73 (m, 1H), 3.48 (s, 2H), 3.40 (s, 2H), 2.79 (d, J=8.4 Hz, 4H), 2.57 (s, 3H); m/z ES+ $[M+H]^+$ 528.1.

Example 37. Synthesis of 8-chloro-2-[1-[1-[(1-fluorocyclopropyl)methyl]azetidin-3-yl]pyrazol-4-yl]-7-[(2-methyl-3H-benzimidazol-5-yl)oxy]quinoxaline

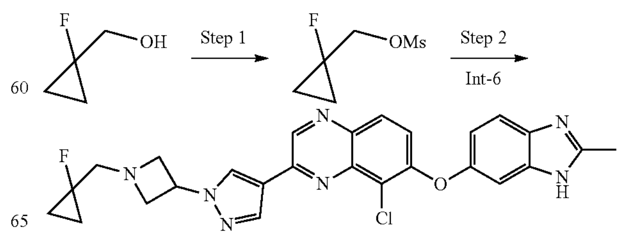

Step 1. (1-Fluorocyclopropyl)methyl methanesulfonate

To a mixture of (1-fluorocyclopropyl) methanol (500 mg, 5.55 mmol) in dichloromethane (6 mL) was added triethylamine (1.12 g, 11.1 mmol), and then methanesulfonyl chloride (953 mg, 8.32 mmol) was added at 0° C. The reaction mixture was stirred at 25° C. for 2 hours. The reaction mixture was quenched with water (10 mL) and extracted with dichloromethane (20 mL×2). The combined organic layers were washed with brine (20 mL×2), dried over anhydrous sodium sulfate, filtered and concentrated under reduced pressure. The residue was purified by column chromatography (petroleum ether/ethyl acetate=20/1 to 1/1) to give (1-fluorocyclopropyl)methyl methanesulfonate (400 mg, 2.38 mmol, 42%) as a white solid. $^1$H NMR (400 MHz, $CDCl_3$) δ=4.55-4.41 (m, 2H), 3.11 (s, 3H), 1.31-1.15 (m, 2H), 0.87 (d, J=7.6 Hz, 2H).

Step 2. 8-Chloro-2-[1-[1-[(1-fluorocyclopropyl) methyl] azetidin-3-yl]pyrazol-4-yl]-7-[(2-methyl-3H-benzimidazol-5-yl)oxy]quinoxaline To a mixture of 2-[1-(azetidin-3-yl)pyrazol-4-yl]-8-chloro-7-[(2-methyl-3H-benzimidazol-5-yl)oxy]quinoxaline (100 mg, 231 μmol) and (1-fluorocyclopropyl)methyl methanesulfonate (38.9 mg, 231 μmol) in tetrahydrofuran (1 mL) and methanol (1 mL) was added triethylamine (46.8 mg, 463 μmol), the reaction mixture was stirred at 80° C. for 12 h. The reaction mixture was quenched with water (15 mL) and extracted with ethyl acetate (20 mL×2). The combined organic layers were washed with brine (20 mL×2), dried over anhydrous sodium sulfate, filtered and concentrated under reduced pressure. The residue was purified by prep-HPLC (column: Phenomenex Synergi C18 150*25 mm*10 μm; mobile phase: [water (0.225% formic acid)-acetonitrile]; (B %: 0%-28%, 10 min) to give 8-chloro-2-[1-[1-[(1-fluorocyclopropyl)methyl] azetidin-3-yl]pyrazol-4-yl]-7-[(2-methyl-3H-benzimidazol-5-yl)oxy]quinoxaline (14.3 mg, 28.2 μmol, 12%) as a white solid. $^1$H NMR (400 MHz, DMSO-$d_6$) δ=12.89-11.79 (m, 1H), 9.33 (s, 1H), 8.87 (s, 1H), 8.42 (s, 1H), 8.14 (s, 1H), 7.96 (d, J=8.8 Hz, 1H), 7.51 (d, J=8.4 Hz, 1H), 7.32 (d, J=9.2 Hz, 1H), 7.21 (s, 1H), 7-6.91 (m, 1H), 5.24-5.14 (m, 1H), 3.86 (t, J=7.6 Hz, 2H), 3.61 (s, 2H), 2.94-2.88 (m, 2H), 2.49 (s, 3H), 1.05-0.90 (m, 2H), 0.75-0.63 (m, 2H); m/z ES+ [M+H]$^+$ 504.0.

Example 38. Synthesis of 8-chloro-2-[1-[1-(2,2-difluoroethyl)azetidin-3-yl]pyrazol-4-yl]-7-[(2-methyl-3H-benzimidazol-5-yl)oxy]quinoxaline

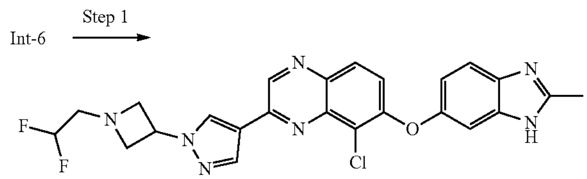

Step 1. 8-Chloro-2-[1-[1-(2,2-difluoroethyl)azetidin-3-yl]pyrazol-4-yl]-7-[(2-methyl-3H-benzimidazol-5-yl)oxy]quinoxaline To a mixture of 2-[1-(azetidin-3-yl)pyrazol-4-yl]-8-chloro-7-[(2-methyl-3H-benzimidazol-5-yl)oxy]quinoxaline (100 mg, 231 μmol) and 2,2-difluoroethyl trifluoromethanesulfonate (49.5 mg, 231 μmol) in acetonitrile (1.5 mL) was added potassium carbonate (96.0 mg, 694 μmol) and potassium iodide (3.84 mg, 23.1 μmol), the reaction mixture was stirred at 70° C. for 2 h. The reaction mixture was extracted with ethyl acetate (20 mL×2). The combined organic layers were washed with brine (20 mL×2), dried over anhydrous sodium sulfate, filtered and concentrated under reduced pressure and the residue was purified by reversed-phase HPLC (column: Phenomenex Synergi C18 150*25 mm*10 μm; mobile phase: [water (0.225% formic acid)-acetonitrile]; (B %: 0%-31%, 11 min) to give 8-chloro-2-[1-[1-(2,2-difluoroethyl)azetidin-3-yl]pyrazol-4-yl]-7-[(2-methyl-3H-benzimidazol-5-yl)oxy]quinoxaline (25.2 mg, 50.4 μmol, 22%) as a white solid. $^1$H NMR (400 MHz, DMSO-$d_6$) δ=12.55-12.11 (m, 1H), 9.34 (s, 1H), 8.94-8.81 (m, 1H), 8.43 (s, 1H), 7.96 (d, J=9.2 Hz, 1H), 7.51 (d, J=8.4 Hz, 1H), 7.32 (d, J=9.6 Hz, 1H), 7.22 (s, 1H), 7.05-6.85 (m, 1H), 6.21-5.87 (m, 1H), 5.26-5.13 (m, 1H), 3.86 (t, J=7.6 Hz, 2H), 3.67 (t, J=7.2 Hz, 2H), 3.05-2.92 (m, 2H), 2.49 (s, 3H); m/z ES+ [M+H]$^+$ 496.0.

Example 39. Synthesis of 2-[1-[benzyloxy (cyclopropyl)methyl]pyrazol-4-yl]-8-chloro-7-[(2-methyl-3H-benzimidazol-5-yl)oxy]quinoxaline

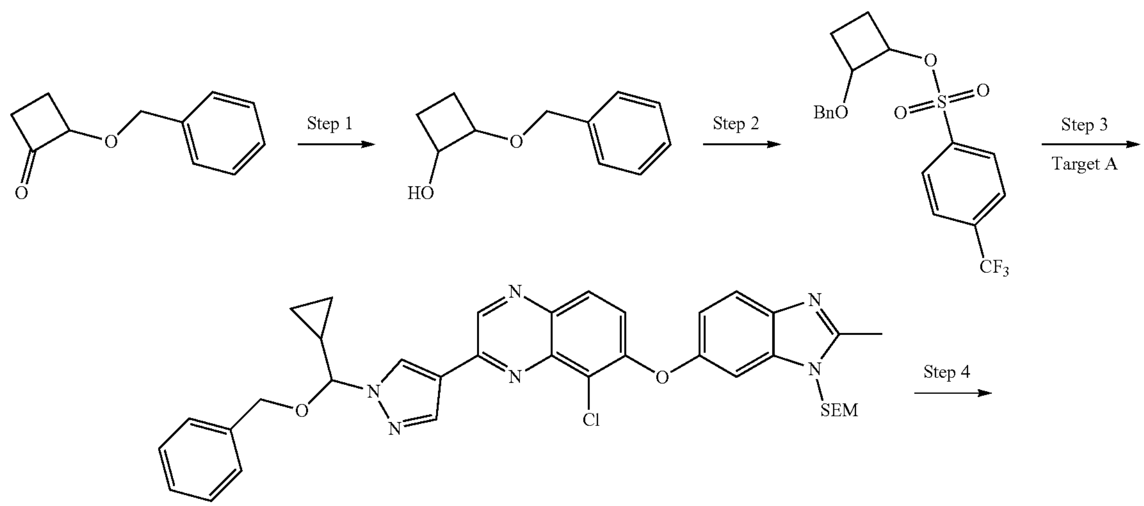

-continued

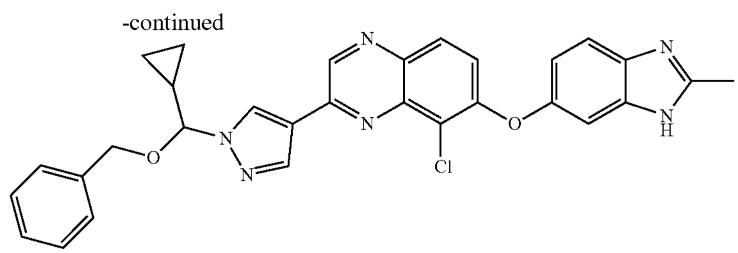

Step 1. 2-Benzyloxycyclobutanol

To a solution of 2-benzyloxycyclobutanone (800 mg, 4.54 mmol) in methanol (8 mL) was added sodium borohydride (258 mg, 6.81 mmol). The mixture was stirred at 0° C. for 2 h. The reaction mixture was quenched by addition water (10 mL) at 0° C., then diluted with water (30 mL) and extracted with ethyl acetate (80 mL×3). The combined organic layers were washed with brine (30 mL×3), dried over anhydrous sodium sulfate, filtered and concentrated in vacuo. The residue was purified by column chromatography (petroleum ether/ethyl acetate=5/1 to 3/1) to give 2-benzyloxycyclobutanol (350 mg, 1.96 mmol, 43%) as a colorless oil. $^1$H NMR (400 MHz, DMSO-$d_6$) δ 7.38-7.26 (m, 5H), 5.29 (d, J=6.8 Hz, 1H), 4.51-4.41 (m, 2H), 3.86 (m, 1H), 3.69 (q, J=7.6 Hz, 1H), 1.93-1.83 (m, 2H), 1.26-1.15 (m, 2H).

Step 2. (2-Benzyloxycyclobutyl) 4-(trifluoromethyl)benzenesulfonate

To a solution of 2-benzyloxycyclobutanol (410 mg, 2.30 mmol) and 4-(trifluoromethyl)benzenesulfonyl chloride (1.13 g, 4.60 mmol) in dichloromethane (4 mL) was added diisopropylethylamine (1.19 g, 9.20 mmol, 1.6 mL) and 4-dimethylaminopyridine (56.2 mg, 460 μmol). The mixture was stirred at 25° C. for 16 h. The reaction mixture was diluted with water (20 mL) and extracted with dichloromethane (20 mL×3). The combined organic layers were washed with brine (20 mL×3), dried over anhydrous sodium sulfate, filtered and concentrated in vacuo. The residue was purified by column chromatography (petroleum ether/ethyl acetate=20/1 to 10/1) to give (2-benzyloxycyclobutyl) 4-(trifluoromethyl)benzenesulfonate (400 mg, crude) as a white solid. $^1$H NMR (400 MHz, $CD_3OD$) δ=8.13 (d, J=8.4 Hz, 2H), 7.92 (d, J=8.0 Hz, 2H), 7.37-7.21 (m, 5H), 4.79-4.65 (m, 1H), 4.44-4.25 (m, 2H), 4.07-3.95 (m, 1H), 2.11-1.97 (m, 2H), 1.67-1.50 (m, 1H), 1.48-1.39 (m, 1H).

Step 3. 2-[[6-[3-[1-(2-Benzyloxycyclobutyl)pyrazol-4-yl]-5-chloro-quinoxalin-6-yl]oxy-2-methyl-benzimidazol-1-yl]methoxy]ethyl-trimethyl-silane To a solution of 2-[[6-[5-chloro-3-(1H-pyrazol-4-yl)quinoxalin-6-yl]oxy-2-methyl-benzimidazol-1-yl]methoxy]ethyl-trimethyl-silane (100 mg, 197 μmol), (2-benzyloxycyclobutyl) 4-(trifluoromethyl)benzenesulfonate (229 mg, 592 μmol) in N,N-dimethylformamide (1.5 mL) was added potassium carbonate (81.8 mg, 592 μmol). The mixture was stirred at 80° C. for 16 h. The reaction mixture was diluted with water (20 mL) and extracted with ethyl acetate (20 mL×3). The combined organic layers were washed with brine (20 mL×3), dried over anhydrous sodium sulfate, filtered and concentrated in vacuo. The residue was purified by column chromatography (petroleum ether/ethyl acetate=2/1 to 0/1) to give 2-[[6-[3-[1-(2-benzyloxycyclobutyl)pyrazol-4-yl]-5-chloro-quinoxalin-6-yl]oxy-2-methyl-benzimidazol-1-yl]methoxy]ethyl-trimethyl-silane (90.0 mg, 135 μmol, 68%) as a yellow solid. m/z ES+ $[M+H]^+$ 667.1.

Step 4. 2-[1-[Benzyloxy (cyclopropyl)methyl]pyrazol-4-yl]-8-chloro-7-[(2-methyl-3H-benzimidazol-5-yl)oxy]quinoxaline To a solution of 2-[[6-[3-[1-(2-benzyloxycyclobutyl)pyrazol-4-yl]-5-chloro-quinoxalin-6-yl]oxy-2-methyl-benzimidazol-1-yl]methoxy]ethyl-trimethyl-silane (35.0 mg, 52.4 μmol) in tetrahydrofuran (1 mL) was added tetrabutylammonium fluoride (1 M in THF, 105 μL). The mixture was stirred at 40° C. for 16 h. The reaction mixture was diluted with water (10 mL) and extracted with ethyl acetate (10 mL×3). The combined organic layers were washed with brine (10 mL×3), dried over anhydrous sodium sulfate, filtered and concentrated in vacuo. The residue was purified by prep-TLC (ethyl acetate/methanol=20:1) and then purified by prep-HPLC (column: Waters Xbridge 150*25 mm*5 μm; mobile phase: [water (10 mM ammonium bicarbonate)-acetonitrile]; (B %: 40%-70%, 9 min) to give 2-[1-[benzyloxy (cyclopropyl)methyl]pyrazol-4-yl]-8-chloro-7-[(2-methyl-3H-benzimidazol-5-yl)oxy]quinoxaline (6.0 mg, 11.2 μmol, 21%) as a white solid. $^1$H NMR (400 MHz, DMSO-$d_6$) δ 9.40 (s, 1H), 8.97 (s, 1H), 8.45 (s, 1H), 7.98 (d, J=8.8 Hz, 1H), 7.51 (d, J=8.8 Hz, 1H), 7.45-7.28 (m, 6H), 7.22 (s, 1H), 6.95 (d, J=7.6 Hz, 1H), 5.17-5.07 (m, 1H), 4.53-4.40 (m, 2H), 2.49-2.47 (m, 3H), 1.70 (d, J-3.6 Hz, 1H), 0.77-0.61 (m, 2H), 0.58-0.39 (m, 2H); m/z ES+ $[M+H]^+$ 537.2.

Example 40. Synthesis of 2-[1-(3-azabicyclo[3.2.1]octan-8-yl)pyrazol-4-yl]-8-chloro-7-[(2-methyl-3H-benzimidazol-5-yl)oxy]quinoxaline

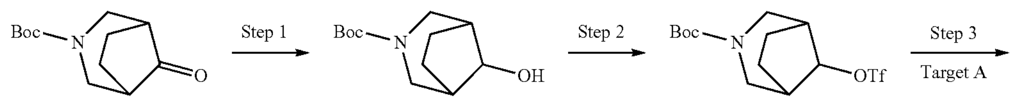

-continued

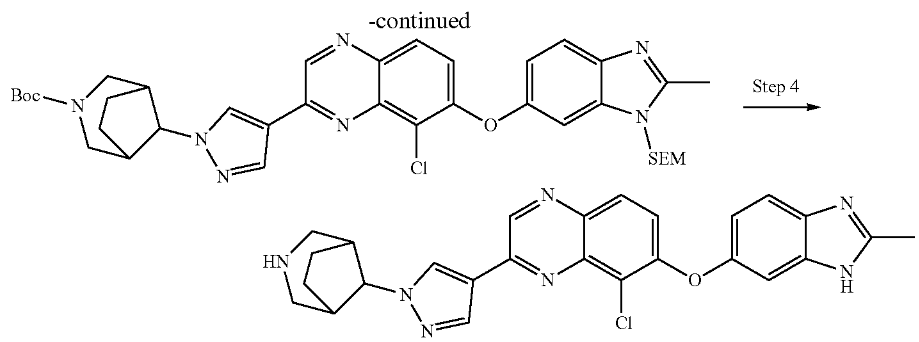

Step 1. tert-Butyl 8-hydroxy-3-azabicyclo[3.2.1]octane-3-carboxylate

To a solution of tert-butyl 8-oxo-3-azabicyclo[3.2.1]octane-3-carboxylate (500 mg, 2.22 mmol) in methanol (5 mL) was added sodium borohydride (126 mg, 3.33 mmol). The mixture was stirred at 0° C. for 2 h. The reaction mixture was quenched by addition water 2 mL at 0° C., then diluted with water (3 mL) and extracted with ethyl acetate (3 mL×3). The combined organic layers were washed with brine (3 mL×3), dried over anhydrous sodium sulfate, filtered and concentrated in vacuo to give tert-butyl 8-hydroxy-3-azabicyclo[3.2.1]octane-3-carboxylate (440 mg, 1.94 mmol, 87%) as a white solid. $^1$H NMR (400 MHz, $CD_3OD$) δ 3.97 (t, J=5.2 Hz, 1H), 3.58 (d, J=12.4 Hz, 2H), 3.40 (d, J=12.4 Hz, 1H), 3.33 (dd, J=1.6, 3.2 Hz, 1H), 2.03-1.91 (m, 2H), 1.81-1.70 (m, 2H), 1.57-1.51 (m, 2H), 1.48 (s, 9H).

Step 2. tert-Butyl 8-(trifluoromethylsulfonyloxy)-3-azabicyclo[3.2.1]octane-3-carboxylate To a mixture of tert-butyl 8-hydroxy-3-azabicyclo[3.2.1]octane-3-carboxylate (200 mg, 880 μmol), pyridine (696 mg, 8.80 mmol) in dichloromethane (2 mL) at −78° C. was added trifluoromethylsulfonyl trifluoromethanesulfonate (497 mg, 1.76 mmol) dropwise. The mixture was slowly warmed to 0° C. and stirred at 0° C. for 1 h. The reaction mixture was diluted with saturated sodium bicarbonate (5 mL) and extracted with dichloromethane (3 mL×3). The combined organic layers were washed with brine (3 mL×3), dried over anhydrous sodium sulfate, filtered and concentrated in vacuo. The residue was purified by column chromatography (petroleum ether/ethyl acetate=1/0 to 20/1) to give tert-butyl 8-(trifluoromethylsulfonyloxy)-3-azabicyclo[3.2.1]octane-3-carboxylate (230 mg, 640 μmol, 73%) as a colorless oil. $^1$H NMR (400 MHz, $CDCl_3$) δ 5.04 (t, J=5.2 Hz, 1H), 3.85 (d, J=12.8 Hz, 1H), 3.70 (d, J=12.8 Hz, 1H), 3.31 (d, J=13.2 Hz, 1H), 3.21 (d, J=13.2 Hz, 1H), 2.43-2.26 (m, 2H), 1.81-1.66 (m, 4H), 1.47 (s, 9H).

Step 3. tert-Butyl 8-[4-[8-chloro-7-[2-methyl-3-(2-trimethylsilylethoxymethyl)benzimidazol-5-yl]oxy-quinoxalin-2-yl]pyrazol-1-yl]-3-azabicyclo[3.2.1]octane-3-carboxylate To a solution of 2-[[6-[5-chloro-3-(1H-pyrazol-4-yl)quinoxalin-6-yl]oxy-2-methyl-benzimidazol-1-yl]methoxy]ethyl-trimethyl-silane (150 mg, 296 μmol) and tert-butyl 8-(trifluoromethylsulfonyloxy)-3-azabicyclo[3.2.1]octane-3-carboxylate (128 mg, 355 μmol) in N,N-dimethylformamide (2 mL) was added cesium carbonate (193 mg, 592 μmol). The mixture was stirred at 80° C. for 16 h. The reaction mixture was diluted with water (3 mL) and extracted with ethyl acetate (3 mL×3). The combined organic layers were washed with brine (3 mL×3), dried over anhydrous sodium sulfate, filtered and concentrated in vacuo. The residue was purified by column chromatography (petroleum ether/ethyl acetate=1/1 to 0/1) to give tert-butyl 8-[4-[8-chloro-7-[2-methyl-3-(2-trimethylsilylethoxymethyl)benzimidazol-5-yl]oxy-quinoxalin-2-yl]pyrazol-1-yl]-3-azabicyclo[3.2.1]octane-3-carboxylate (90.0 mg, 126 μmol, 43%) as a colorless oil. m/z ES+ $[M+H]^+$ 716.3.

Step 4. 2-[1-(3-Azabicyclo[3.2.1]octan-8-yl)pyrazol-4-yl]-8-chloro-7-[(2-methyl-3H-benzimidazol-5-yl)oxy]quinoxaline A mixture of tert-butyl 8-[4-[8-chloro-7-[2-methyl-3-(2-trimethylsilylethoxymethyl)benzimidazol-5-yl]oxy-quinoxalin-2-yl]pyrazol-1-yl]-3-azabicyclo[3.2.1]octane-3-carboxylate (90.0 mg, 126 μmol) in trifluoroacetic acid (1 mL) was stirred at 25° C. for 1 h. The reaction mixture was concentrated in vacuo. The residue was purified by prep-HPLC (column: Phenomenex Gemini-NX C18 75*30 mm*3 μm; mobile phase: [water (0.225% formic acid)-acetonitrile]; (B %: 2%-32%, 7 min) to give 2-[1-(3-azabicyclo[3.2.1]octan-8-yl)pyrazol-4-yl]-8-chloro-7-[(2-methyl-3H-benzimidazol-5-yl)oxy]quinoxaline (34.6 mg, 71.0 μmol, 57%) as a white solid. $^1$H.NMR (400 MHz, $CD_3OD$) δ 9.23 (s, 1H), 8.69 (s, 1H), 8.39 (s, 1H), 7.98 (d, J=9.2 Hz, 1H), 7.68 (d, J=8.8 Hz, 1H), 7.45 (d, J=9.2 Hz, 1H), 7.28 (d, J=1.2 Hz, 1H), 7.21 (d, J=8.4 Hz, 1H), 3.46 (d, J=3.6 Hz, 4H), 3.33-3.32 (m, 1H), 3.27 (s, 2H), 2.74 (s, 3H), 2.07 (s, 2H), 1.98-1.85 (m, 2H); m/z ES+ $[M+H]^+$ 486.1.

Example 41. Synthesis of 8-chloro-2-(1-((3,3-difluorocyclobutyl)methyl)-1H-pyrazol-4-yl)-7-((2-(trifluoromethyl)-1H-benzo[d]imidazol-5-yl)oxy)quinoxaline

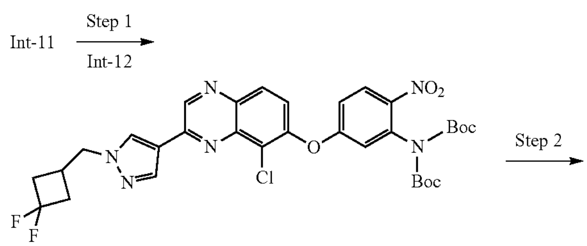

-continued

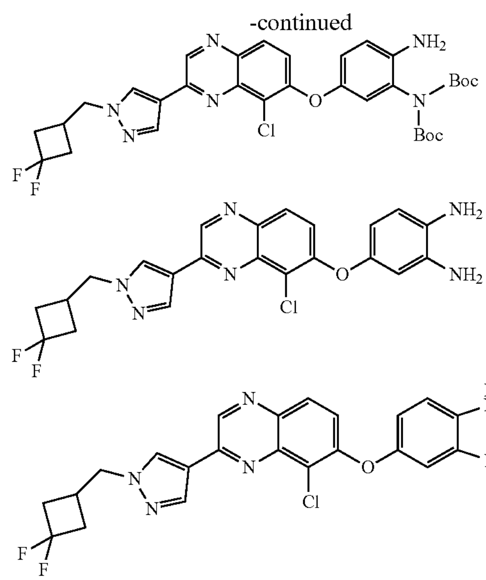

Step 1. tert-Butyl N-tert-butoxycarbonyl-N-[5-[5-chloro-3-[1-[(3,3-difluorocyclobutyl)methyl]pyrazol-4-yl]quinoxalin-6-yl]oxy-2-nitro-phenyl]carbamate To a solution of 5-chloro-3-[1-[(3,3-difluorocyclobutyl) methyl]pyrazol-4-yl]quinoxalin-6-ol (250 mg, 713 μmol) in N,N-dimethylformamide (3 mL) was added potassium carbonate (197 mg, 1.43 mmol) and tert-butyl N-tert-butoxycarbonyl-N-(5-fluoro-2-nitro-phenyl) carbamate (508 mg, 1.43 mmol). The mixture was stirred at 80° C. for 2 h. The reaction mixture was diluted with water (10 mL) and extracted with ethyl acetate (10 mL×3). The combined organic layers were dried over anhydrous sodium sulfate, filtered and concentrated under reduced pressure. The residue was purified by column chromatography (petroleum ether/ethyl acetate=5/1 to 1/1) to give tert-butyl N-tert-butoxycarbonyl-N-[5-[5-chloro-3-[1-[(3,3-difluorocyclobutyl)methyl]pyrazol-4-yl]quinoxalin-6-yl]oxy-2-nitro-phenyl]carbamate (380 mg, 542 μmol, 76%) as a yellow oil. m/z ES+ $[M+H]^+$ 687.5.

Step 2. tert-Butyl N-[2-amino-5-[5-chloro-3-[1-[(3,3-difluorocyclobutyl)methyl]pyrazol-4-yl]quinoxalin-6-yl]oxy-phenyl]-N-tert-butoxycarbonyl-carbamate To a solution of tert-butyl N-tert-butoxycarbonyl-N-[5-[5-chloro-3-[1-[(3,3-difluorocyclobutyl)methyl]pyrazol-4-yl]quinoxalin-6-yl]oxy-2-nitro-phenyl]carbamate (330 mg, 480 μmol) in ethanol (5 mL) and water (1 mL) was added iron powder (134 mg, 2.40 mmol) and ammonium chloride (257 mg, 4.80 mmol). The mixture was stirred at 60° C. for 2 h. The reaction mixture was filtered and concentrated under reduced pressure to give tert-butyl N-[2-amino-5-[5-chloro-3-[1-[(3,3-difluorocyclobutyl)methyl]pyrazol-4-yl] quinoxalin-6-yl]oxy-phenyl]-N-tert-butoxycarbonyl-carbamate (200 mg, crude) as a yellow oil. m/z ES+ $[M+H]^+$ 657.1.

Step 3. 4-((5-Chloro-3-(1-((3,3-difluorocyclobutyl) methyl)-1H-pyrazol-4-yl)quinoxalin-6-yl)oxy)benzene-1,2-diamine To a solution of tert-butyl N-[2-amino-5-[5-chloro-3-[1-[(3,3-difluorocyclobutyl)methyl]pyrazol-4-yl]quinoxalin-6-yl]oxy-phenyl]-N-tert-butoxycarbonyl-carbamate (200 mg, 304 μmol) in dichloromethane (1.5 mL) was added trifluoroacetic acid (0.5 mL). The mixture was stirred at 20° C. for 20 min. The reaction mixture was concentrated under reduced pressure and the residue was purified by reversed-phase HPLC (0.1% formic acid condition) to give 4-((5-chloro-3-(1-((3,3-difluorocyclobutyl)methyl)-1H-pyrazol-4-yl)quinoxalin-6-yl)oxy)benzene-1,2-diamine (100 mg, 212 μmol, 70%) as a yellow solid. m/z ES+ $[M+H]^+$ 457.0.

Step 4. 8-Chloro-2-(1-((3,3-difluorocyclobutyl) methyl)-1H-pyrazol-4-yl)-7-((2-(trifluoromethyl)-1H-benzo[d]imidazol-5-yl)oxy)quinoxaline A solution of 4-((5-chloro-3-(1-((3,3-difluorocyclobutyl) methyl)-1H-pyrazol-4-yl)quinoxalin-6-yl)oxy)benzene-1,2-diamine (50 mg, 109 μmol) in trifluoroacetic acid (1 mL) was stirred at 60° C. for 6 h. The reaction mixture was concentrated under reduced pressure to give a residue. The residue was purified by prep-HPLC (column: Phenomenex Luna C18 250*50 mm*15 um; mobile phase: [water (0.2% formic acid)-acetonitrile]; (B %: 50%-80%, 10 min) to give 8-chloro-2-(1-((3,3-difluorocyclobutyl)methyl)-1H-pyrazol-4-yl)-7-((2-(trifluoromethyl)-1H-benzo[d]imidazol-5-yl)oxy)quinoxaline (38.5 mg, 71.9 μmol, 66%) as a yellow solid. $^1$H NMR (400 MHz, $CD_3OD$) δ=9.19 (s, 1H), 8.61 (s, 1H), 8.37 (s, 1H), 7.97 (d, J=8.8 Hz, 1H), 7.78 (d, J=8.8 Hz, 1H), 7.45 (d, J=9.6 Hz, 1H), 7.32-7.21 (m, 2H), 4.40 (d, J=6.8 Hz, 2H), 2.79-2.64 (m, 3H), 2.57-2.43 (m, 2H); m/z ES+ $[M+H]^+$ 535.0.

Example 42. Synthesis of (1S,4S)-5-[2-[4-[8-chloro-7-[(2-methyl-3H-benzimidazol-5-yl)oxy] quinoxalin-2-yl]pyrazol-1-ylethyl]-2-oxa-5-azabicyclo[2.2.1]heptane

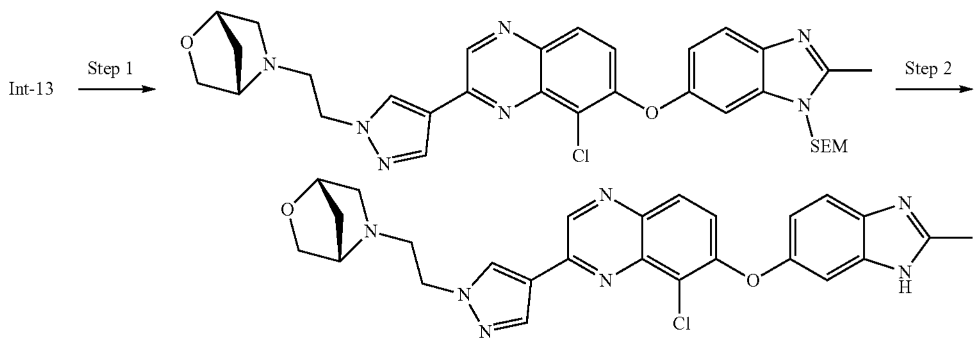

Step 1. 2-[[6-[5-Chloro-3-[1-[2-[(1S,4S)-2-oxa-5-azabicyclo[2.2.1]heptan-5-yl]ethyl]pyrazol-4-yl]quinoxalin-6-yl]oxy-2-methyl-benzimidazol-1-yl]methoxy]ethyl-trimethyl-silane To a solution of 2-[4-[8-chloro-7-[2-methyl-3-(2-trimethylsilylethoxymethyl)benzimidazol-5-yl]oxy-quinoxalin-2-yl]pyrazol-1-yl]ethyl methanesulfonate (300 mg, 476 μmol) and (1S,4S)-2-oxa-5-azabicyclo[2.2.1]heptane hydrochloride (193 mg, 1.43 mmol) in acetonitrile (5 mL) was added sodium bicarbonate (200 mg, 2.38 mmol). The mixture was stirred at 80° C. for 12 h. The mixture was concentrated in vacuo and the residue was purified by flash silica gel chromatography (petroleum ether:ethyl acetate=0:1) to give 2-[[6-[5-chloro-3-[1-[2-[(1S,4S)-2-oxa-5-azabicyclo[2.2.1]heptan-5-yl]ethyl]pyrazol- 4-yl]quinoxalin-6-yl]oxy-2-methyl-benzimidazol-1-yl]methoxy]ethyl-trimethyl-silane (100 mg, 158 μmol, 30%) as a yellow solid. m/z ES+ $[M+H]^+$ 632.3.

Step 2. (1S,4S)-5-[2-[4-[8-Chloro-7-[(2-methyl-3H-benzimidazol-5-yl)oxy]quinoxalin-2-yl]pyrazol-1-yl]ethyl]-2-oxa-5-azabicyclo[2.2.1]heptane A solution of 2-[[6-[5-chloro-3-[1-[2-[(1S,4S)-2-oxa-5-azabicyclo[2.2.1]heptan-5-yl]ethyl]pyrazol-4-yl]quinoxalin-6-yl]oxy-2-methyl-benzimidazol-1-yl]methoxy]ethyl-trimethyl-silane (90.0 mg, 142 μmol) in trifluoroacetic acid (1 mL) was stirred at 25° C. for 6 h. The mixture was concentrated in vacuo and the residue was purified by prep-HPLC (column: Phenomenex Synergi C18 150*25 mm*10 μm; mobile phase: [water (0.225% formic acid)-acetonitrile]; (B %: 0%-29%, 11 min) and repurified by prep-TLC (dichloromethane:methanol=10:1) to give (1S,4S)-5-[2-[4-[8-chloro-7-[(2-methyl-3H-benzimidazol-5-yl)oxy]quinoxalin-2-yl]pyrazol-1-yl]ethyl]-2-oxa-5-azabicyclo[2.2.1]heptane (8.2 mg, 16.4 μmol, 10%) as a yellow solid. $^1$H NMR (400 MHz, $CD_3OD$) δ ppm 9.16 (s, 1H), 8.61 (s, 1H), 8.37 (s, 1H), 7.90 (d, J=9.2 Hz, 1H), 7.53 (d, J=8.4 Hz, 1H), 7.35 (d, J=9.6 Hz, 1H), 7.17 (s, 1H), 7.01 (dd, J=2.0, 8.8 Hz, 1H), 4.59 (s, 1H), 4.44-4.32 (m, 3H), 4 (d, J=8.0 Hz, 1H), 3.62 (dd, J=2.0, 8.0 Hz, 1H), 3.52 (s, 1H), 3.23-3.08 (m, 2H), 2.89 (dd, J=1.6, 10.0 Hz, 1H), 2.60 (s, 1H), 2.57 (s, 3H), 1.87 (d, J=10.0 Hz, 1H), 1.73 (d, J=10.0 Hz, 1H); m/z ES+ $[M+H]^+$ 502.0.

Example 43. Synthesis of 2-[3-[4-[8-chloro-7-[(2-methyl-3H-benzimidazol-5-yl)oxy]quinoxalin-2-yl]pyrazol-1-yl]azetidin-1-yl]-1-(3,3-difluoroazetidin-1-yl)ethanone

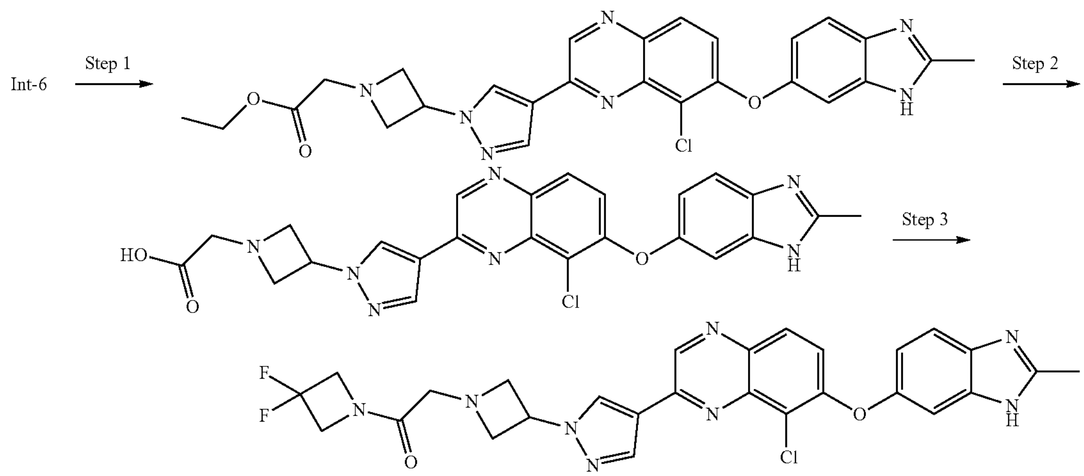

Step 1. Ethyl 2-[3-[4-[8-chloro-7-[(2-methyl-3H-benzimidazol-5-yl)oxy]quinoxalin-2-yl]pyrazol-1-yl]azetidin-1-yl]acetate To a mixture of 2-[1-(azetidin-3-yl)pyrazol-4-yl]-8-chloro-7-[(2-methyl-3H-benzimidazol-5-yl)oxy]quinoxaline (100 mg, 231 μmol) in dichloromethane (1.5 mL) was added diisopropylethylamine (74.8 mg, 578 μmol) and ethyl 2-bromoacetate (31.7 mg, 189 μmol), the reaction mixture was stirred at 40° C. for 1 h. The reaction mixture was concentrated in vacuo to give ethyl 2-[3-[4-[8-chloro-7-[(2-methyl-3H-benzimidazol-5-yl)oxy]quinoxalin-2-yl]pyrazol-1-yl]azetidin-1-yl]acetate (100 mg, 193 μmol, 83%) as a white solid. m/z BS+ $[M+H]^+$ 518.4.

Step 2. 2-[3-[4-[8-Chloro-7-[(2-methyl-3H-benzimidazol-5-yl)oxy]quinoxalin-2-yl] p yrazol-1-yl]azetidin-1-yl]acetic acid To a mixture of ethyl 2-[3-[4-[8-chloro-7-[(2-methyl-3H-benzimidazol-5-yl)oxy]quinoxalin-2-yl]p yrazol-1-yl]azetidin-1-yl]acetate (100 mg, 193 μmol) in tetrahydrofuran (1 mL) and water (1 mL) was added lithium hydroxide monohydrate (40.5 mg, 965 μmol), the reaction mixture was stirred at 25° C. for 1 h. The reaction mixture was quenched with 1 N HCl solution to PH ~3. The mixture was directly purified by prep-HPLC (column: Phenomenex Synergi C18 150*25 mm*10 um; mobile phase: [water (0.225% formic acid)-acetonitrile]; (B %: 0%-28%, 10 min) to give 2-[3-[4-[8-chloro-7-[(2-methyl-3H-benzimidazol-5-yl)oxy]quinoxalin-2-yl]pyrazol-1-yl]azetidin-1-yl]acetic acid (50.0 mg, 102 μmol, 52%) as a white solid. m/z ES+ $[M+H]^+$ 490.3.

Step 3. 2-[3-[4-[8-Chloro-7-[(2-methyl-3H-benzimidazol-5-yl)oxy]quinoxalin-2-yl]pyrazol-1-yl]azetidin-1-yl]-1-(3,3-difluoroazetidin-1-yl)ethanone To a mixture of 3,3-difluoroazetidine hydrochloride (10.5 mg, 81.6 μmol) and 2-[3-[4-[8-chloro-7-[(2-methyl-3H-benzimidazol-5-yl)oxy]quinoxalin-2-yl]pyrazol-1-yl]azetidin-1-yl]acetic acid (40.0 mg, 81.6 μmol) in dichloromethane (1 mL) was added diisopropylethylamine (31.6 mg, 244 μmol), the reaction mixture was stirred at 25° C. for 10 min. Then 3-(ethyliminomethylideneamino)propyl-dimethylazanium; chloride (23.4 mg, 122 μmol) and 1-hydroxybenzotriazole (16.5 mg, 122 μmol) was added, and the reaction mixture was stirred at 40° C. for 2 h. The reaction mixture was diluted with water (10 mL) and extracted with ethyl acetate (20 mL×2). The combined organic layers were washed with brine (20 mL×2), dried over anhydrous sodium sulfate, filtered and concentrated under reduced pressure and the residue was purified by prep-HPLC (column: Phenomenex Synergi C18 150*25 mm*10 μm; mobile phase: [water (0.225% formic acid)-acetonitrile]; (B %: 0%-29%, 11 min) to give 2-[3-[4-[8-chloro-7-[(2-methyl-3H-benzimidazol-5-yl)oxy]quinoxalin-2-yl]pyrazol-1-yl]azetidin-1-yl]-1-(3,3-difluoroazetidin-1-yl)ethanone (17.5 mg, 30.7 μmol, 37%) as a white solid. $^1$H NMR (400 MHz, DMSO-$d_6$) δ=12.57-12.09 (m, 1H), 9.34 (s, 1H), 8.87 (s, 1H), 8.43 (s, 1H), 8.28 (s, 1H), 7.96 (d, J=9.2 Hz, 1H), 7.59-7.42 (m, 1H), 7.39-7.09 (m, 2H), 6.98-6.75 (m, 1H), 5.18 (t, J=6.4 Hz, 1H), 4.70-4.61 (m, 2H), 4.34-4.24 (m, 2H), 3.85 (t, J=7.6 Hz, 2H), 3.59 (t, J=8.0 Hz, 2H), 3.42-3.38 (m, 2H), 2.55-2.46 (m, 3H); m/z ES+ $[M+H]^+$ 565.1.

Example 44. Synthesis of 8-chloro-2-[1-(1-methylazetidin-3-yl)pyrazol-4-yl]-7-[(2-methyl-3H-benzimidazol-5-yl)oxy]quinoxaline Int-6

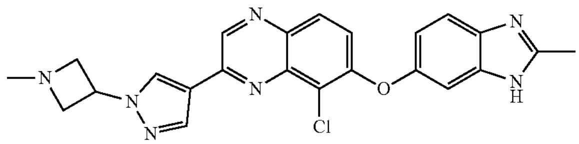

Step 1. 8-Chloro-2-[1-(1-methylazetidin-3-yl)pyrazol-4-yl]-7-[(2-methyl-3H-benzimidazol-5-yl)oxy]quinoxaline To a solution of 2-[1-(azetidin-3-yl)pyrazol-4-yl]-8-chloro-7-[(2-methyl-3H-benzimidazol-5-yl)oxy]quinoxaline (50.0 mg, 116 μmol), formaldehyde (69.5 mg, 2.32 mmol, 37% aqueous solution) and diisopropylethylamine (74.8 mg, 579 μmol) in tetrahydrofuran (1.5 mL) was added sodium triacetoxyborohydride (49.1 mg, 232 μmol). The mixture was stirred at 25° C. for 3 h. The reaction mixture was diluted with water (30 mL) and extracted with ethyl acetate (30 mL×2). The combined organic layers were washed with brine (50 mL×2), dried over sodium sulfate, filtered and concentrated in vacuo to give a residue. The crude product was purified by prep-HPLC (column: Phenomenex Synergi C18 150*25 mm*10 μm; mobile phase: [water (0.225% formic acid)-acetonitrile]; (B %: 1%-29%, 10 min) to give 8-chloro-2-[1-(1-methylazetidin-3-yl)pyrazol-4-yl]-7-[(2-methyl-3H-benzimidazol-5-yl)oxy]quinoxaline (26.9 mg, 60.3 μmol, 52%) as a yellow gum. $^1$H NMR (400 MHz, $CD_3OD$) § =9.16 (s, 1H), 8.64 (s, 1H), 8.53 (s, 1H), 8.33 (s, 1H), 7.91 (d, J=9.2 Hz, 1H), 7.54 (d, J=8.8 Hz, 1H), 7.37 (d, J=9.2 Hz, 1H), 7.19 (d, J=2.0 Hz, 1H), 7.02 (dd, J=2.0, 8.8 Hz, 1H), 5.52-5.40 (m, 1H), 4.69-4.61 (m, 2H), 4.54-4.48 (m, 2H), 3.05 (s, 3H), 2.58 (s, 3H); m/z ES+ $[M+H]^+$ 446.0.

Example 45. Synthesis of 3-((4-(8-chloro-7-((2-methyl-1H-benzo[d]imidazol-6-yl)oxy)quinoxalin-2-yl)-1H-pyrazol-1-yl)methyl) thietane 1,1-dioxide

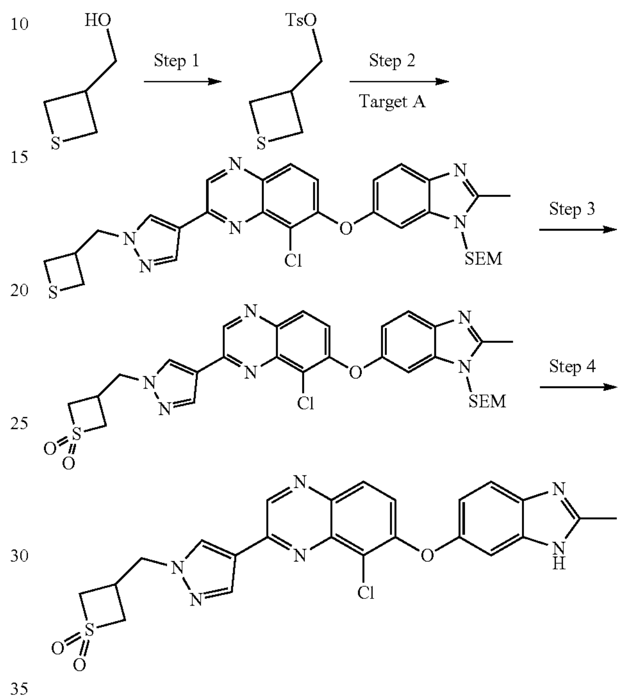

Step 1. Thietan-3-ylmethyl 4-methylbenzenesulfonate

To a solution of thietan-3-ylmethanol (30.0 mg, 287 μmol), triethylamine (87.4 mg, 863 μmol) in dichloromethane (1 mL) was added 4-methylbenzenesulfonyl chloride (82.3 mg, 431 μmol) at 0° C. The mixture was stirred at 25° C. for 16 h. The mixture was concentrated under reduced pressure. The residue was purified by prep-TLC (petroleum ether:ethyl acetate=3:1) to give thietan-3-ylmethyl 4-methylbenzenesulfonate (60.0 mg, 232 μmol, 80%) as a yellow oil. $^1$H NMR (400 MHz, $CDCl_3$) δ=7.73 (d, J=8.0 Hz, 2H), 7.30 (d, J=8.4 Hz, 2H), 4.03 (d, J=6.8 Hz, 2H), 3.55-3.32 (m, 1H), 3.11 (t, J=8.8 Hz, 2H), 2.86 (dd, J=6.4, 9.6 Hz, 2H), 2.39 (s, 3H).

Step 2. 8-Chloro-7-((2-methyl-1-((2-(trimethylsilyl)ethoxy)methyl)-1H-benzo[d]imidazol-6-yl)oxy)-2-(1-(thietan-3-ylmethyl)-1H-pyrazol-4-yl)quinoxaline A solution of 8-chloro-7-((2-methyl-1-((2-(trimethylsilyl)ethoxy)methyl)-1H-benzo[d]imidazol-6-yl)oxy)-2-(1H-pyrazol-4-yl)quinoxaline (100 mg, 197 μmol), thietan-3-ylmethyl 4-methylbenzenesulfonate (50.9 mg, 197 μmol) and cesium carbonate (128 mg, 394 μmol) in N,N-dimethyl formamide (1 mL) was stirred at 80° C. for 3 h. The mixture was poured into water (10 mL) and extracted with ethyl acetate (30 mL×3). The organic layers were washed with brine (50 mL×3), dried with anhydrous sodium sulfate, filtered and concentrated under reduced pressure. The residue was purified by column chromatography (petroleum ether/ethyl acetate=2/1 to 0/1) to give 8-chloro-7-((2-methyl-1-((2-(trimethylsilyl)ethoxy)methyl)-1H-benzo[d]

imidazol-6-yl)oxy)-2-(1-(thietan-3-ylmethyl)-1H-pyrazol-4-yl)quinoxaline (100 mg, 168 μmol, 85%) as a yellow oil. m/z ES+ $[M+H]^+$ 593.2.

Step 3. 3-((4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl) thietane 1,1-dioxide To a solution of 2-[[6-[5-chloro-3-[1-(thietan-3-ylmethyl)pyrazol-4-yl]quinoxalin-6-yl]oxy-2-methyl-benzimidazol-1-yl]methoxy]ethyl-trimethyl-silane (100 mg, 168 μmol) in dichloromethane (1 mL) was added 3-chloroperoxybenzoic acid (116 mg, 505 μmol). The mixture was stirred at 25° C. for 16 h. The mixture was poured into sat. sodium sulfite solution (50 mL) and extracted with ethyl acetate (30 mL×3). The organic layers were dried by sodium sulfate, filtered and concentrated under reduced pressure. The residue was purified by column chromatography (petroleum ether/ethyl acetate=1/1 to 0/1) to give 3-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl) thietane 1,1-dioxide (80.0 mg, 127 μmol, 75%) as a yellow solid. m/z ES+ $[M+H]^+$ 625.2.

Step 4. 3-((4-(8-Chloro-7-((2-methyl-1H-benzo[d]imidazol-6-yl)oxy)quinoxalin-2-yl)-1H-pyrazol-1-yl)methyl) thietane 1,1-dioxide A solution of 3-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl) thietane 1,1-dioxide (80 mg, 127 μmol) in trifluoroacetic acid (1 mL) was stirred at 25° C. for 10 min. The mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 10%-40%, 7 min) and repurified by prep-HPLC (column: Waters Xbridge 150*25 mm*5 μm; mobile phase: [water (10 mM ammonium bicarbonate)-acetonitrile]; (B %: 25%-55%, 7 min) to give 3-((4-(8-chloro-7-((2-methyl-1H-benzo[d]imidazol-6-yl)oxy)quinoxalin-2-yl)-1H-pyrazol-1-yl)methyl) thietane 1,1-dioxide (8.9 mg, 17.0 μmol, 14%) as an off-white solid. $^1H$ NMR (400 MHz, DMSO-$d_6$) δ 9.16-9.12 (m, 1H), 8.65-8.62 (m, 1H), 8.38-8.35 (m, 1H), 7.92-7.86 (m, 1H), 7.53 (d, J=8.8 Hz, 1H), 7.37-7.33 (m, 1H), 7.19 (s, 1H), 7.02 (d, J=8.8 Hz, 1H), 4.57 (d, J=7.6 Hz, 2H), 4.30-4.24 (m, 2H), 4.11-4.06 (m, 2H), 3.20 (m, 1H), 2.58 (s, 3H); m/z ES+ $[M+H]^+$ 495.0.

Example 46. Synthesis of 8-chloro-2-[1-[(3,3-difluorocyclobutyl)methyl]pyrazol-4-yl]-7-[(4-fluoro-2-methyl-1H-benzimidazol-5-yl)oxy]quinoxaline

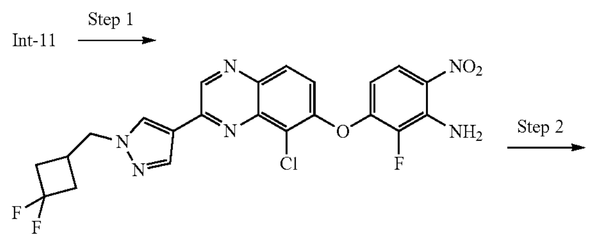

-continued

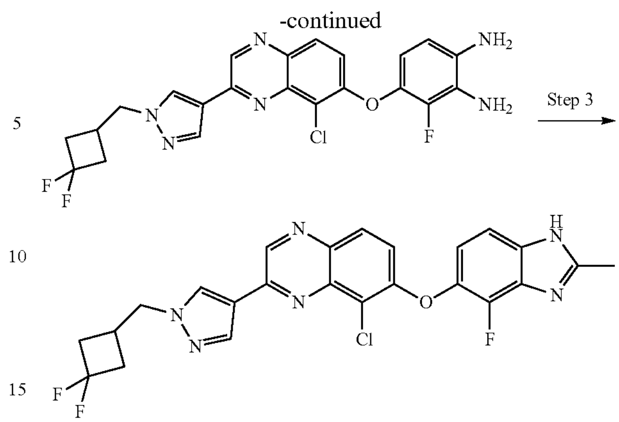

Step 1. 3-[5-Chloro-3-[1-[(3,3-difluorocyclobutyl)methyl]pyrazol-4-yl]quinoxalin-6-yl]oxy-2-fluoro-6-nitro-aniline To a solution of 5-chloro-3-[1-[(3,3-difluorocyclobutyl)methyl]pyrazol-4-yl]quinoxalin-6-ol (150 mg, 427 μmol) in N,N-dimethylformamide (3 mL) was added potassium carbonate (177 mg, 1.28 mmol) and 2,3-difluoro-6-nitro-aniline (105 mg, 603 μmol). The mixture was stirred at 80° C. for 12 hs. The reaction mixture was diluted with water (15 mL) and extracted with ethyl acetate (15 mL×3). The combined organic layers were dried over anhydrous sodium sulfate, filtered and concentrated under reduced pressure and the residue was purified by reversed-phase HPLC (0.1% formic acid condition) to give 3-[5-chloro-3-[1-[(3,3-difluorocyclobutyl)methyl]pyrazol-4-yl]quinoxalin-6-yl]oxy-2-fluoro-6-nitro-aniline (180 mg, 357 μmol, 66%) as a yellow solid. m/z ES+ $[M+H]^+$ 505.0.

Step 2. 4-[5-Chloro-3-[1-[(3,3-difluorocyclobutyl)methyl]pyrazol-4-yl]quinoxalin-6-yl]oxy-3-fluoro-benzene-1,2-diamine To a solution of 3-[5-chloro-3-[1-[(3,3-difluorocyclobutyl)methyl]pyrazol-4-yl]quinoxalin-6-yl]oxy-2-fluoro-6-nitro-aniline (150 mg, 297 μmol) in ethanol (2 mL) and water (0.4 mL) was added iron powder (82.9 mg, 1.49 mmol) and ammonium chloride (79.4 mg, 1.49 mmol). The mixture was stirred at 60° C. for 12 hs. The reaction mixture was filtered and the filtrate was concentrated under reduced pressure to give 4-[5-chloro-3-[1-[(3,3-difluorocyclobutyl)methyl]pyrazol-4-yl]quinoxalin-6-yl]oxy-3-fluoro-benzene-1,2-diamine (180 mg, crude) as a yellow solid. m/z ES+ $[M+H]^+$ 475.2.

Step 3. 8-Chloro-2-[1-[(3,3-difluorocyclobutyl)methyl]pyrazol-4-yl]-7-[(4-fluoro-2-methyl-1H-benzimidazol-5-yl)oxy]quinoxaline To a solution of 1,1,1-trimethoxyethane (189 mg, 1.58 mmol) in MeOH (3 mL) was added sulfamic acid (61.3 mg, 631 μmol) and 4-[5-chloro-3-[1-[(3,3-difluorocyclobutyl)methyl]pyrazol-4-yl]quinoxalin-6-yl]oxy-3-fluoro-benzene-1,2-diamine (150 mg, 315. μmol). The mixture was stirred at 25° C. for 2 hs. The reaction mixture was concentrated under reduced pressure. The residue was purified by prep-HPLC (column: Phenomenex Synergi C18 150*25 mm*10 μm; mobile phase: [water (0.225% formic acid)-acetonitrile]; (B %: 29%-59%, 10 min) to give 8-chloro-2-[1-[(3,3-difluorocyclobutyl)methyl]pyrazol-4-yl]-7-[(4-fluoro-2-methyl-1H-benzimidazol-5-yl)oxy]quinoxaline (101 mg, 203 μmol, 62%) as a yellow solid. $^1$H NMR (400 MHz, DMSO-$d_6$) δ 12.81-12.56 (m, 1H), 9.31 (s, 1H), 8.77 (s, 1H), 8.39 (s, 1H), 7.94 (d, J=9.2 Hz, 1H), 7.49-6.99 (m, 3H), 4.39 (d, J=6.0 Hz, 2H), 2.76-2.63 (m, 3H), 2.56 (s, 1H), 2.53 (s, 3H), 2.49-2.44 (m, 1H); m/z ES+ [M+H]$^+$ 499.0.

Example 47. Synthesis of 8-chloro-2-[1-[1-(1-methylazetidin-3-yl)azetidin-3-yl]pyrazol-4-yI]-7-[(2-methyl-3H-benzimidazol-5-yl)oxy]quinoxaline

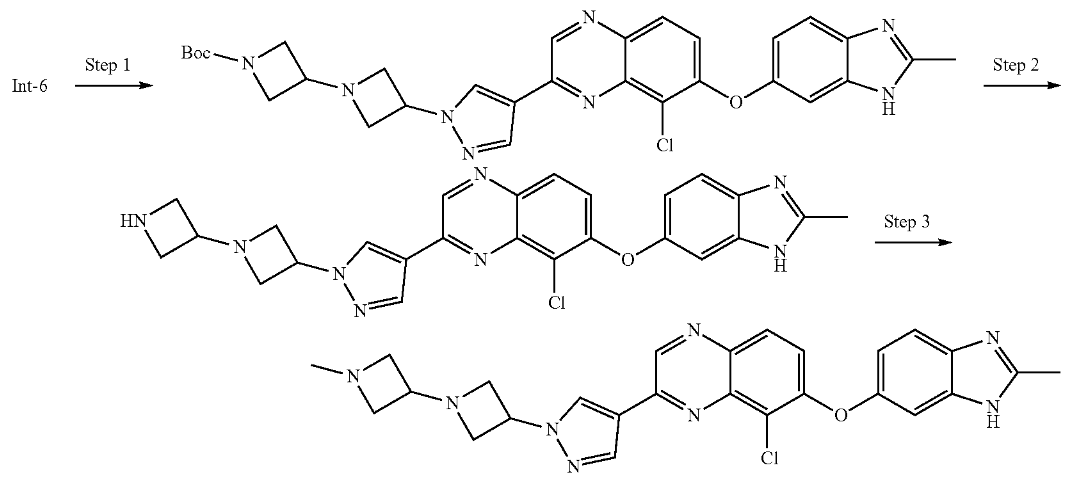

Step 1. tert-Butyl 3-[3-[4-[8-chloro-7-[(2-methyl-3H-benzimidazol-5-yl)oxy]quinoxalin-2-yl]pyrazol-1-yl]azetidin-1-yl]azetidine-1-carboxylate A mixture of 2-[1-(azetidin-3-yl)pyrazol-4-yl]-8-chloro-7-[(2-methyl-3H-benzimidazol-5-yl)oxy]quinoxaline (100 mg, 231 μmol), tert-butyl 3-oxoazetidine-1-carboxylate (51.5 mg, 301 μmol), sodium triacetoxyborohydride (147 mg, 694 μmol) in tetrahydrofuran (1 mL) was stirred at 25° C. for 12 h. The reaction mixture was diluted with water (10 mL) and extracted with ethyl acetate (30 mL×3). The combined organic layers were dried over anhydrous sodium sulfate, concentrated under reduced pressure. The residue was purified by prep-HPLC (column: Waters Xbridge 150*25 mm*5 μm; mobile phase: [water (10 mM ammonium bicarbonate)-acetonitrile]; (B %: 35%-65%, 9 min) to give tert-butyl 3-[3-[4-[8-chloro-7-[(2-methyl-3H-benzimidazol-5-yl)oxy]quinoxalin-2-yl]pyrazol-1-yl]azetidin-1-yl]azetidine-1-carboxylate (50.0 mg, 85.3 μmol, 37%) as a white solid. m/z ES+ [M+1]$^+$ 587.4.

Step 2. 2-[1-[1-(Azetidin-3-yl)azetidin-3-yl]pyrazol-4-yl]-8-chloro-7-[(2-methyl-3H-benzimidazol-5-yl)oxy]quinoxaline To a solution of tert-butyl 3-[3-[4-[8-chloro-7-[(2-methyl-3H-benzimidazol-5-yl)oxy]quinoxalin-2-yl]pyrazol-1-yl]azetidin-1-yl]azetidine-1-carboxylate (50 mg, 85.1 μmol) in dichloromethane (5 mL) was added trifluoroacetic acid (1 mL). The mixture was stirred at 25° C. for 1 h. The reaction mixture was concentrated under reduced pressure to give 2-[1-[1-(azetidin-3-yl)azetidin-3-yl]pyrazol-4-yl]-8-chloro-7-[(2-methyl-3H-benzimidazol-5-yl)oxy]quinoxaline (40.0 mg, crude) as a yellow solid. m/z ES+ [M+1]$^+$ 487.2.

Step 3. 8-Chloro-2-[1-[1-(1-methylazetidin-3-yl)azetidin-3-yl]pyrazol-4-yl]-7-[(2-methyl-3H-benzimidazol-5-yl)oxy]quinoxaline To a solution of 2-[1-[1-(azetidin-3-yl)azetidin-3-yl]pyrazol-4-yl]-8-chloro-7-[(2-methyl-3H-benzimidazol-5-yl)oxy]quinoxaline (35.0 mg, 71.8 μmol) in methanol (2 mL) was added formaldehyde (43.1 mg, 1.44 mmol, 37% aqueous solution) and sodium triacetoxyborohydride (76.1 mg, 359 μmol). The mixture was stirred at 25° C. for 12 h. The reaction mixture was diluted with water (10 mL) and extracted with ethyl acetate (30 mL×3). The combined organic layers were dried over anhydrous sodium sulfate, concentrated under reduced pressure. The residue was purified by prep-HPLC (column: Waters Xbridge 150*25 mm*5 μm; mobile phase: [water (10 mM ammonium bicarbonate)-acetonitrile]; (B %: 24%-54%, 10 min) to give 8-chloro-2-[1-[1-(1-methylazetidin-3-yl)azetidin-3-yl]pyrazol-4-yl]-7-[(2-methyl-3H-benzimidazol-5-yl)oxy]quinoxaline (24.3 mg, 48.6 μmol, 67%) as a white solid. $^1$H NMR (400 MHz, DMSO-$d_6$) δ=9.34 (s, 1H), 8.85 (s, 1H), 8.42 (s, 1H), 7.96 (d, J=9.2 Hz, 1H), 7.51 (d, J=8.8 Hz, 1H), 7.32 (d, J=9.2 Hz, 1H), 7.21 (d, J=1.6 Hz, 1H), 6.95-+6.82 (m, 1H), 5.20-5.10 (m, 1H), 3.70 (t, J=7.6 Hz, 2H), 3.58 (t, J=7.2 Hz, 2H), 3.39-3.38 (m, 1H), 3.27-3.24 (m, 2H), 2.95 (t, J=6.4 Hz, 2H), 2.48 (s, 3H), 2.21 (s, 3H); m/z ES+ [M+1]$^+$ 501.1.

Example 48. Synthesis of 2-(1-((3,3-difluorocyclobutyl)methyl)-1H-pyrazol-4-yl)-7-((2-methyl-1H-benzo[d]imidazol-6-yl)oxy)-8-(prop-1-en-2-yl)quinoxaline

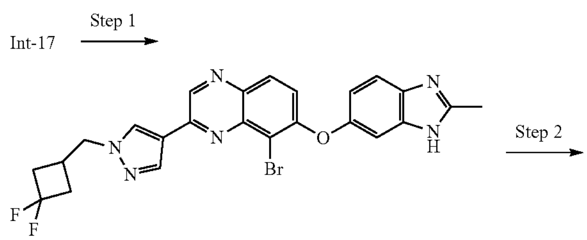

-continued

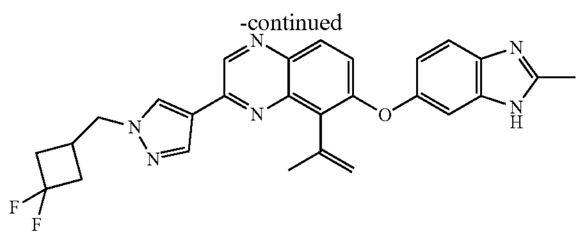

Step 1. 8-Bromo-2-(1-((3,3-difluorocyclobutyl) methyl)-1H-pyrazol-4-yl)-7-((2-methyl-1H-benzo[d] imidazol-6-yl)oxy)quinoxaline A solution of 8-bromo-2-(1-((3,3-difluorocyclobutyl) methyl)-1H-pyrazol-4-yl)-7-((2-methyl-1-((2-(trimethylsilyl)ethoxy)methyl)-1H-benzo[d]imidazol-6-yl)oxy)quinoxaline (430 mg, 656 μmol) in trifluoroacetic acid (5 mL) was stirred at 25° C. for 0.5 h. The reaction mixture was concentrated under reduced pressure. The residue was diluted with sat. sodium bicarbonate (30 mL) and extracted with ethyl acetate (20 mL×3). The combined organic layers were dried over anhydrous sodium sulfate, filtered and concentrated under reduced pressure to give 8-bromo-2-(1-((3,3-difluorocyclobutyl)methyl)-1H-pyrazol-4-yl)-7-((2-methyl-1H-benzo[d]imidazol-6-yl)oxy)quinoxaline (300 mg, crude) as a yellow solid. m/z ES+ $[M+H]^+$ 527.1.

Step 2. 2-(1-((3,3-Difluorocyclobutyl)methyl)-1H-pyrazol-4-yl)-7-((2-methyl-1H-benzo[d]imidazol-6-yl)oxy)-8-(prop-1-en-2-yl)quinoxaline To a solution of 8-bromo-2-[1-[(3,3-difluorocyclobutyl) methyl]pyrazol-4-yl]-7-[(2-methyl-3H-benzimidazol-5-yl) oxy]quinoxaline (100 mg, 190 μmol) and potassium trifluoro (prop-1-en-2-yl)borate (282 mg, 1.90 mmol) in dioxane (2 mL) and water (0.2 mL) was added sodium carbonate (60.5 mg, 571 μmol) and methanesulfonato (2-dicyclohexylphosphino-2,4,6-tri-i-propyl-1,1'-biphenyl) (2-amino-1,1'-biphenyl-2-yl) palladium(II) (22.5 mg, 28.6 μmol). The mixture was stirred at 110° C. for 2 h under nitrogen. The reaction mixture was poured into water (20 mL) and extracted with ethyl acetate (15 mL×3). The combined organic layers were dried over anhydrous sodium sulfate, filtered and concentrated under reduced pressure. The residue was purified by prep-HPLC (formic acid condition; column: Phenomenex Luna C18 150*25 mm*10 um; mobile phase: [water (0.225% formic acid)-acetonitrile]; (B %: 19%-49%, 10 min) to give 2-(1-((3,3-difluorocyclobutyl)methyl)-1H-pyrazol-4-yl)-7-((2-methyl-1H-benzo[d]imidazol-6-yl) oxy)-8-(prop-1-en-2-yl)quinoxaline (17.8 mg, 35.8 μmol, 18.8%) as a yellow solid. $^1$H NMR (400 MHz, $CD_3OD$) δ=9.08 (s, 1H), 8.49 (s, 1H), 8.26 (s, 1H), 7.88 (d, J=9.2 Hz, 1H), 7.48 (d, J=8.8 Hz, 1H), 7.33 (d, J=9.2 Hz, 1H), 7.07 (d, J-2.0 Hz, 1H), 6.95 (dd, J=2.4, 8.8 Hz, 1H), 5.47 (s, 1H), 5.05 (s, 1H), 4.38 (d, J=6.8 Hz, 2H), 2.82-2.62 (m, 3H), 2.57 (s, 3H), 2.54-2.40 (m, 2H), 2.24 (s, 3H); m/z ES+ $[M+H]^+$ 487.1.

Example 49. Synthesis of 3-[[4-[8-Chloro-7-[(2-methyl-3H-benzimidazol-5-yl)oxy]quinoxalin-2-yl] pyrazol-1-yl]methyl]-1-methyl-cyclobutanol

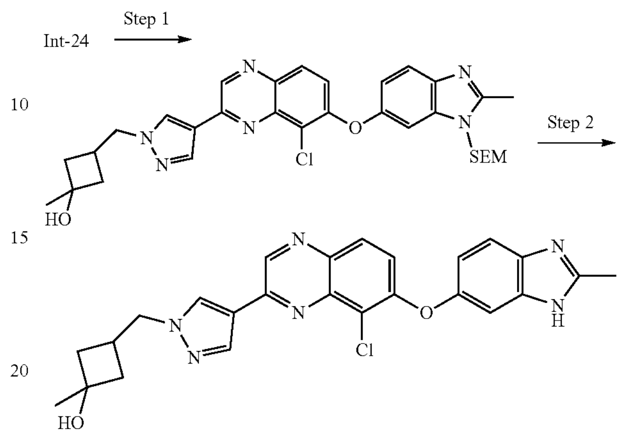

Step 1. 3-[[4-[8-Chloro-7-[2-methyl-3-(2-trimethylsilylethoxymethyl)benzimidazol-5-yl]oxy-quinoxalin-2-yl]pyrazol-1-yl]methyl]-1-methyl-cyclobutanol A solution of 3-[[4-[8-chloro-7-[2-methyl-3-(2-trimethylsilylethoxymethyl)benzimidazol-5-yl]oxy-quinoxalin-2-yl] pyrazol-1-yl]methyl]cyclobutanone (100 mg, 170 μmol) in tetrahydrofuran (1 mL) was degassed and purged with nitrogen for 3 times. Then methyl magnesium bromide (3 M in THF, 170 μL) was added dropwise at 0° C. The mixture was stirred at 0° C. for 2 h. The reaction mixture was diluted with water (3 mL) and extracted with ethyl acetate (3×3 mL). The combined organic layers were washed with brine (3×3 mL), dried over sodium sulfate, filtered and concentrated in vacuo. The residue was purified by prep-TLC (silica gel, ethyl acetate:methanol 10:1) give to 3-[[4-[8-chloro-7-[2-methyl-3-(2-trimethylsilylethoxymethyl)benzimidazol-5-yl]oxy-quinoxalin-2-yl]pyrazol-1-yl]methyl]-1-methyl-cyclobutanol (35.0 mg, 57.2 μmol, 33%) as a white solid. m/z ES+ $[M+H]^+$ 605.2.

Step 2. 3-[[4-[8-Chloro-7-[(2-methyl-3H-benzimidazol-5-yl)oxy]quinoxalin-2-yl]pyrazol-1-yl]methyl]-1-methyl-cyclobutanol A solution of 3-[[4-[8-chloro-7-[2-methyl-3-(2-trimethylsilylethoxymethyl)benzimidazol-5-yl]oxy-quinoxalin-2-yl] pyrazol-1-yl]methyl]-1-methyl-cyclobutanol (35.0 mg, 57.8 μmol) in trifluoroacetic acid (2.16 g, 18.9 mmol) was stirred at 25° C. for 1 h. The reaction mixture was concentrated in vacuo and the residue was purified by prep-HPLC (column: Phenomenex Gemini-NX C18 75*30 mm*3 μm; mobile phase: [water (0.225% formic acid)-acetonitrile]; (B %: 12%-42%, 7 min) to give 3-[[4-[8-chloro-7-[(2-methyl-3H-benzimidazol-5-yl)oxy]quinoxalin-2-yl]pyrazol-1-yl] methyl]-1-methyl-cyclobutanol (18.0 mg, 37.5 μmol, 64%) as a white solid. $^1$H NMR (400 MHz, $CD_3OD$) δ ppm 9.16 (s, 1H), 8.57-8.54 (m, 1H), 8.35 (s, 1H), 7.91 (d, J=9.2 Hz, 1H), 7.56 (d, J=8.8 Hz, 1H), 7.36 (d, J=9.2 Hz, 1H), 7.20 (d, J=2.4 Hz, 1H), 7.04 (dd, J=2.4, 8.8 Hz, 1H), 4.31 (d, J-7.2 Hz, 2H), 2.61 (s, 3H), 2.47 (t, J=7.6 Hz, 1H), 2.24-2.10 (m, 2H), 2.02-1.90 (m, 2H), 1.36 (s, 2H), 1.35 (s, 1H); m/z ES+ $[M+H]^+$ 475.1.

Example 50. Synthesis of 5-((4-(8-Chloro-7-((2-methyl-1H-benzo[d]imidazol-6-yl)oxy)quinoxalin-2-yl)-1H-pyrazol-1-yl)methyl)-2-methyl-1,2-thiazinane 1,1-dioxide

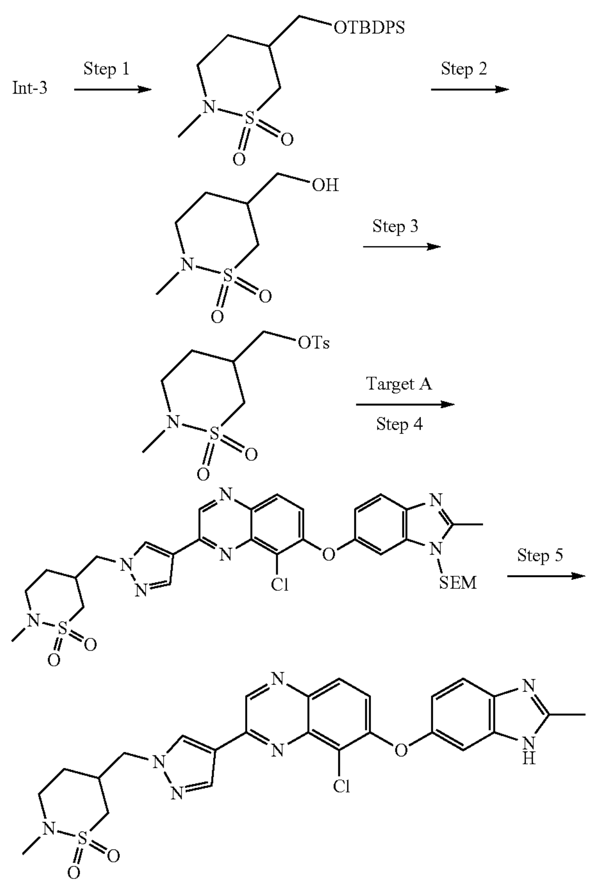

Step 1. 5-(((tert-Butyldiphenylsilyl)oxy)methyl)-2-methyl-1,2-thiazinane 1,1-dioxide To a solution of tert-butyl-[(1,1-dioxothiazinan-5-yl) methoxy]-diphenyl-silane (1 g, 2.48 mmol) in tetrahydrofuran (20 mL) was added potassium carbonate (1.03 g, 7.43 mmol) and methyl iodide (1.76 g, 12.4 mmol), the mixture was stirred at 60° C. for 30 h. The mixture was poured into water (50 mL) and extracted with ethyl acetate (3×30 mL). The organic layers were dried over sodium sulfate, filtered and concentrated under reduced pressure to give 5-(((tert-butyldiphenylsilyl)oxy)methyl)-2-methyl-1,2-thiazinane 1,1-dioxide (1.30 g, crude) as a yellow oil. m/z ES+ $[M+H]^+$ 418.2.

Step 2. 5-(Hydroxymethyl)-2-methyl-1,2-thiazinane 1,1-dioxide

A solution of tert-butyl-[(2-methyl-1,1-dioxo-thiazinan-5-yl) methoxy]-diphenyl-silane (500 mg, 1.20 mmol) in aqueous sodium hydroxide (5 M, 10 mL) was stirred at 40° C. for 16 h. The mixture was poured into water (50 mL) and extracted with ethyl acetate (3×30 mL). The aqueous layer was acidified with concentrated hydrochloric acid (12 M) to pH<5 and then extracted with ethyl acetate (50 mL×3). The combined organic layers were dried over sodium sulphate, filtered and concentrated under reduced pressure to give 5-(hydroxymethyl)-2-methyl-1,2-thiazinane1,1-dioxide (500 mg, crude) as a yellow oil. m/z ES+ $[M+H]^+$ 179.9.

Step 3. (2-Methyl-1,1-dioxido-1,2-thiazinan-5-yl)methyl 4-methylbenzenesulfonate To a solution of 5-(hydroxymethyl)-2-methyl-1,2-thiazinane 1,1-dioxide (500 mg, crude) in dichloromethane (5 mL) was added 4-methylbenzenesulfonyl chloride (239 mg, 1.26 mmol) and triethylamine (254 mg, 2.51 mmol), the mixture was stirred at 25° C. for 16 h. The mixture was concentrated under reduced pressure. The residue was purified by reversed-phase HPLC (0.1% formic acid condition) to give (2-methyl-1,1-dioxido-1,2-thiazinan-5-yl)methyl 4-methylbenzenesulfonate (100 mg, 299 μmol, 35%) as a yellow solid. $^1H$ NMR (400 MHz, $CDCl_3$) δ 7.71 (d, J=8.4 Hz, 2H), 7.31 (d, J=8.0 Hz, 2H), 3.90 (d, J=5.2 Hz, 2H), 3.51-3.36 (m, 1H), 3.12-3.03 (m, 1H), 2.95 (dd, J-3.2, 13.2 Hz, 1H), 2.72 (s, 3H), 2.67 (d, J=13.2 Hz, 1H), 2.62-2.49 (m, 1H), 2.40 (s, 3H), 1.63-1.54 (m, 3H).

Step 4. 5-((4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-2-methyl-1,2-thiazinane 1,1-dioxide A solution of 8-chloro-7-((2-methyl-1-((2-(trimethylsilyl)ethoxy)methyl)-1H-benzo[d]imidazol-6-yl)oxy)-2-(1H-pyrazol-4-yl)quinoxaline (100 mg, 197 μmol), (2-methyl-1,1-dioxido-1,2-thiazinan-5-yl)methyl 4-methylbenzenesulfonate (80.0 mg, 240 μmol), cesium carbonate (192 mg, 591 μmol) in N,N-dimethylformamide (1 mL) was stirred at 80° C. for 3 h. The mixture was poured into water (50 mL) and extracted with ethyl acetate (3×30 mL). The organic layers were washed by brine (3×50 mL), dried over sodium sulfate, filtered and concentrated under reduced pressure to give 5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-2-methyl-1,2-thiazinane 1,1-dioxide (130 mg, crude) as a yellow oil. m/z ES+ $[M+H]^+$ 668.2.

Step 5. 5-((4-(8-Chloro-7-((2-methyl-1H-benzo[d]imidazol-6-yl)oxy)quinoxalin-2-yl)-1H-pyrazol-1-yl)methyl)-2-methyl-1,2-thiazinane 1,1-dioxide A solution of 5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-2-methyl-1,2-thiazinane 1,1-dioxide (130 mg, crude) in trifluoroacetic acid (2 mL) was stirred at 25° C. for 0.5 h. The mixture was concentrated under reduced pressure. The residue was purified by prep-HPLC (column: Phenomenex Gemini-NX C18 75*30 mm*3 μm; mobile phase: [water (0.225% formic acid)-acetonitrile]; (12%-42%, 7 min) to give 5-((4-(8-chloro-7-((2-methyl-1H-benzo[d]imidazol-6-yl)oxy)quinoxalin-2-yl)-1H-pyrazol-1-yl)methyl)-2-methyl-1,2-thiazinane 1,1-dioxide (74.9 mg, 139 μmol, 71%) as an off-white solid. $^1H$ NMR (400 MHz, $CD_3OD$) δ 9.15 (s, 1H), 8.56 (s, 1H), 8.34 (s, 1H), 8.02-7.87 (m, 1H), 7.75 (d, J=8.0 Hz, 1H), 7.46 (d, J=6.0 Hz, 1H), 7.33 (s, 2H), 4.40-4.23 (m, 2H), 3.59-3.38 (m, 1H), 3.25 (s, 1H), 3.11-2.85 (m, 3H), 2.84 (s, 3H), 2.79 (s, 3H), 1.80-1.46 (m, 2H); m/z ES+ $[M+H]^+$ 538.0.

Example 51. Synthesis of 3-(4-(8-Chloro-7-((2-methyl-1H-benzo[d]imidazol-6-yl)oxy)quinoxalin-2-yl)-1H-pyrazol-1-yl)-3-methylbutanenitrile

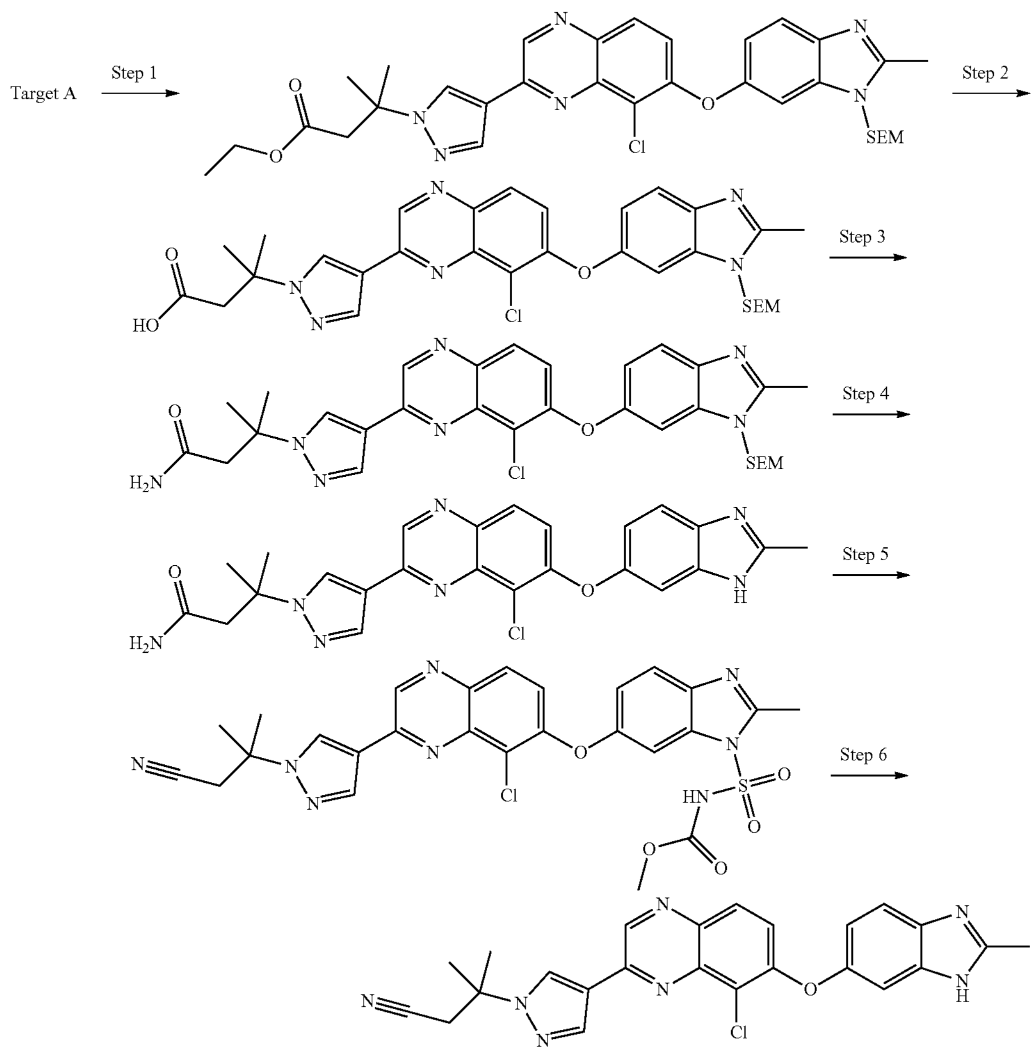

Step 1. Ethyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanoate To a solution of 2-[[6-[5-chloro-3-(1H-pyrazol-4-yl)quinoxalin-6-yl]oxy-2-methyl-benzimidazol-1-yl]methoxy]ethyl-trimethyl-silane (700 mg, 1.38 mmol) and ethyl 3-methylbut-2-enoate (265 mg, 2.07 mmol, 288 μL) in N,N-dimethylformamide (14 mL) was added cesium carbonate (900 mg, 2.76 mmol), the mixture was stirred at 25° C. for 48 h. The reaction mixture was diluted with water (50 mL) and extracted with ethyl acetate (3× 20 mL). The combined organic layers were dried over sodium sulfate, filtered and concentrated under reduced pressure. The residue was purified by column chromatography (silica gel, petroleum ether/ethyl acetate=1/0 to 1/9) to give ethyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanoate (340 mg, 455 μmol, 32%) as a yellow solid. $^1$H NMR (400 MHz, DMSO-$d_6$) δ=9.38-9.36 (m, 1H), 8.79 (s, 1H), 8.34 (s, 1H), 7.96 (d, J=9.2 Hz, 1H), 7.60 (d, J=8.8 Hz, 1H), 7.44 (d, J=2.4 Hz, 1H), 7.34-7.30 (m, 1H), 7.01 (dd, J=2.4, 8.8 Hz, 1H), 5.56-5.52 (m, 2H), 3.96 (q, J=7.2 Hz, 2H), 3.51-3.46 (m, 2H), 3 (s, 2H), 2.57-2.54 (m, 3H), 1.73 (s, 6H), 1.07 (t, J=7.2 Hz, 3H), 0.81-0.75 (m, 2H), −0.12-−0.16 (m, 9H).

Step 2. 3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanoic acid To a solution of ethyl 3-[4-[8-chloro-7-[2-methyl-3-(2-trimethylsilylethoxymethyl)benzimidazol-5-yl]oxy-quinoxalin-2-yl]pyrazol-1-yl]-3-methyl-butanoate (270 mg, 361 μmol) in methanol (2.5 mL), tetrahydrofuran (2.5 mL) and water (2.5 mL) was added lithium hydroxide monohydrate (45.5 mg, 1.08 mmol). The mixture was stirred at 25° C. for 1 h. The reaction mixture was concentrated in vacuo. The residue was adjusted to pH=5 with citric acid aqueous solution, then filtered and concentrated in vacuo to give 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanoic acid (150 mg, crude) as a yellow solid. m/z ES+ $[M+H]^+$ 607.3.

Step 3. 3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanamide To a solution of 3-[4-[8-chloro-7-[2-methyl-3-(2-trimethylsilylethoxymethyl)benzimidazol-5-yl]oxy-quinoxalin-2-yl]pyrazol-1-yl]-3-methyl-butanoic acid (150 mg, 247 μmol) and ammonium chloride (132 mg, 2.47 mmol) in N,N-dimethylformamide (5 mL) was added diisopropylethylamine (95.8 mg, 741 μmol, 129 μL) and [dimethylamino(triazolo[4,5-b]pyridin-3-yloxy)methylene]-dimethyl-ammonium;hexafluorophosphate (141 mg, 371 μmol), the mixture was stirred at 25° C. for 12 h. The reaction mixture was diluted with water (20 mL) and extracted with ethyl acetate (3×15 mL). The combined organic layers were dried over sodium sulfate, filtered and concentrated under reduced pressure to give 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanamide (180 mg, crude) as a yellow oil. m/z ES+ $[M+H]^+$ 606.3.

Step 4. 3-(4-(8-Chloro-7-((2-methyl-1H-benzo[d]imidazol-6-yl)oxy)quinoxalin-2-yl)-1H-pyrazol-1-yl)-3-methylbutanamide A solution of 3-[4-[8-chloro-7-[2-methyl-3-(2-trimethylsilylethoxymethyl)benzimidazol-5-yl]oxy-quinoxalin-2-yl]pyrazol-1-yl]-3-methyl-butanamide (50.0 mg, 82.5 μmol) in trifluoroacetic acid (1 mL) was stirred at 25° C. for 0.5 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 10%-40%, 10 min) to give 3-(4-(8-chloro-7-((2-methyl-1H-benzo[d]imidazol-6-yl)oxy)quinoxalin-2-yl)-1H-pyrazol-1-yl)-3-methylbutanamide (17.8 mg, 37.4 μmol, 45%) as an off-white solid. $^1H$ NMR (400 MHz, DMSO-$d_6$) δ=9.36 (s, 1H), 8.75 (s, 1H), 8.35 (s, 1H), 7.96 (d, J=9.2 Hz, 1H), 7.53 (d, J=8.8 Hz, 1H), 7.33-7.27 (m, 2H), 7.23 (s, 1H), 6.97 (d, J=8.8 Hz, 1H), 6.82 (s, 1H), 2.74 (s, 2H), 2.49-2.48 (m, 3H), 1.73 (s, 6H); m/z ES+ $[M+H]^+$ 476.1.

Step 5. 4-(4-(8-Chloro-7-((2-methyl-1H-benzo[d]imidazol-6-yl)oxy)quinoxalin-2-yl)-1H-pyrazol-1-yl)quinuclidine To a solution of 3-[4-[8-chloro-7-[(2-methyl-3H-benzimidazol-5-yl)oxy]quinoxalin-2-yl]pyrazol-1-yl]-3-methyl-butanamide (8 mg, 16.8 μmol) in acetonitrile (0.5 mL) was added methoxycarbonyl-(triethylammonio) sulfonyl-azanide (8.01 mg, 33.6 μmol), the mixture was stirred at 25° C. for 1 h. The reaction mixture was filtered and concentrated in vacuo to give a mixture. The residue was purified by prep-HPLC (neutral condition; column: Waters Xbridge 150*25 mm*5 μm; mobile phase: [water (10 mM ammonium bicarbonate)-acetonitrile]; (B %: 10%-40%, 10 min) to give 4-(4-(8-chloro-7-((2-methyl-1H-benzo[d]imidazol-6-yl)oxy)quinoxalin-2-yl)-1H-pyrazol-1-yl)quinuclidine (10.0 mg, 16.6 μmol, 98%) as a yellow solid. m/z ES+ $[M+H]^+$ 595.0.

Step 6. 3-(4-(8-Chloro-7-((2-methyl-1H-benzo[d]imidazol-6-yl)oxy)quinoxalin-2-yl)-1H-pyrazol-1-yl)-3-methylbutanenitrile To a solution of methyl N-[6-[5-chloro-3-[1-(2-cyano-1,1-dimethyl-ethyl)pyrazol-4-yl]quinoxalin-6-yl]oxy-2-methyl-benzimidazol-1-yl]sulfonylcarbamate (8 mg, 13.4 μmol) in dimethylsulfoxide (0.5 mL) was added potassium carbonate (3.72 mg, 26.9 μmol), the mixture was stirred at 25° C. for 2 h. The reaction mixture was filtered and concentrated in vacuo and the residue was purified by prep-HPLC (neutral condition; column: Waters Xbridge 150*25 mm*5 μm; mobile phase: [water (10 mM ammonium bicarbonate)-acetonitrile]; (B %: 12%-42%, 10 min) to give 3-(4-(8-chloro-7-((2-methyl-1H-benzo[d]imidazol-6-yl)oxy)quinoxalin-2-yl)-1H-pyrazol-1-yl)-3-methylbutanenitrile (3.3 mg, 6.80 μmol, 50%) as a yellow solid. $^1H$ NMR (400 MHz, DMSO-$d_6$) δ=9.38 (s, 1H), 8.89 (s, 1H), 8.44 (s, 1H), 7.97 (d, J=9.2 Hz, 1H), 7.51 (d, J=8.4 Hz, 1H), 7.32 (d, J=9.2 Hz, 1H), 7.21 (s, 1H), 6.95 (dd, J=2.4, 8.8 Hz, 1H), 3.32-3.31 (m, 2H), 2.49-2.48 (m, 3H), 1.75 (s, 6H); m/z ES+ $[M+H]^+$ 458.0.

Example 52. Synthesis of 2-(1-(2-Oxabicyclo[2.2.1]heptan-5-ylmethyl)-1H-pyrazol-4-yl)-8-chloro-7-((2-methyl-1H-benzo[d]imidazol-6-yl)oxy)quinoxaline

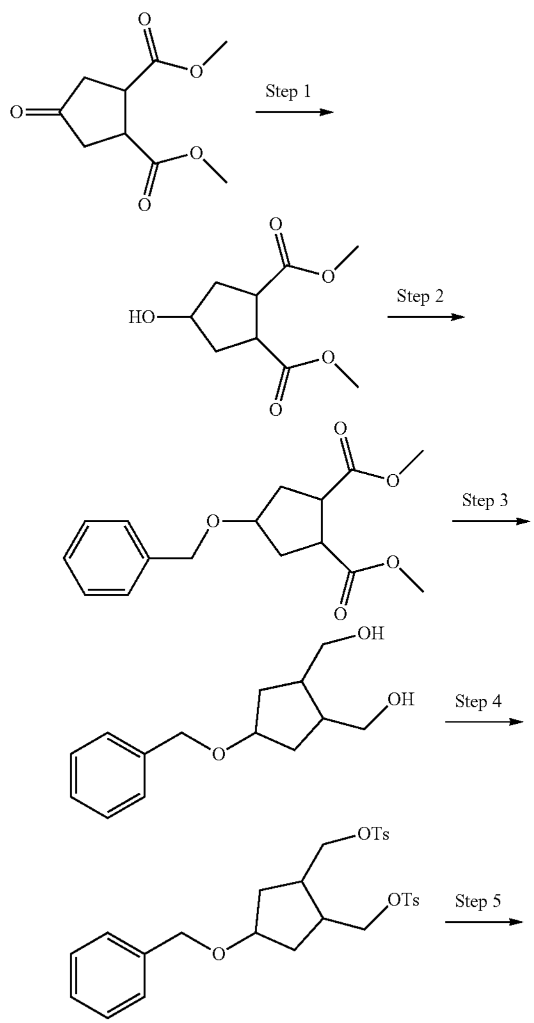

-continued

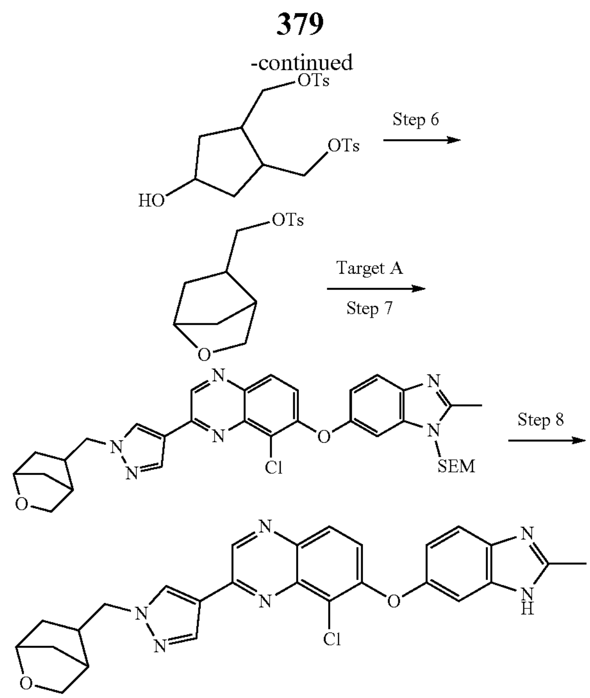

Step 1. Dimethyl 4-hydroxycyclopentane-1,2-dicarboxylate

To a solution of dimethyl 4-oxocyclopentane-1,2-dicarboxylate (17.5 g, 87.4 mmol) in methanol (200 mL) was added sodium borohydride (3.64 g, 96.2 mmol) portion-wise at 0° C. The mixture was stirred at 0° C. for 1 h. The reaction mixture was quenched with brine (100 mL) at 0° C., and then extracted with ethyl acetate (3×100 mL). The combined organic layers were washed with brine (50 mL), dried over anhydrous sodium sulfate, filtered and concentrated under reduced pressure. The residue was purified by column chromatography (petroleum ether/ethyl acetate=5/1 to 1/1) to give dimethyl 4-hydroxycyclopentane-1,2-dicarboxylate (10.0 g, 49.5 mmol, 56%) as a colorless oil. $^1$H NMR (400 MHz, $CDC_3$) δ 4.50-4.32 (m, 1H), 3.72 (d, J=4.8 Hz, 6H), 3.47-3.36 (m, 1H), 3.28-3.19 (m, 1H), 2.32-2.08 (m, 3H), 2.06-1.88 (m, 2H).

Step 2. Dimethyl 4-(benzyloxy)cyclopentane-1,2-dicarboxylate

To a solution of dimethyl 4-hydroxycyclopentane-1,2-dicarboxylate (2 g, 9.89 mmol) in N, N-dimethylformamide (20 mL) was added sodium hydride (396 mg, 9.89 mmol, 60% in mineral oil) in portions at 0° C., the mixture was stirred at 20° C. for 0.5 h. Then benzyl bromide (1.69 g, 9.89 mmol, 1.17 mL) was added slowly and the resulting mixture was stirred at 20° C. for 0.5 h. The reaction mixture was quenched with water (100 mL) at 0° C., and then extracted with ethyl acetate (3×100 mL). The combined organic layers were washed with brine (100 mL), dried over anhydrous sodium sulfate, filtered and concentrated under reduced pressure. The residue was purified by column chromatography (petroleum ether/ethyl acetate=10/1 to 3/1) to give dimethyl 4-(benzyloxy)cyclopentane-1,2-dicarboxylate (1 g, 3.42 mmol, 35%) as a colorless oil. $^1$H NMR (400 MHz, $CDCl_3$) δ 7.33-7.19 (m, 5H), 4.47-4.37 (m, 2H), 4.07-3.99 (m, 1H), 3.69-3.59 (m, 6H), 3.47-3.36 (m, 1H), 3.17-3.06 (m, 1H), 2.29-2.11 (m, 3H), 1.96-1.84 (m, 1H); m/z ES+ $[M+H]^+$ 293.1.

Step 3. (4-(Benzyloxy)cyclopentane-1,2-diyl)dimethanol

To a solution of dimethyl 4-benzyloxycyclopentane-1,2-dicarboxylate (1 g, 3.42 mmol) in tetrahydrofuran (10 mL) was added lithium aluminum hydride (493 mg, 13.0 mmol) in portions at 0° C., the mixture was stirred at 20° C. for 12 h under nitrogen atmosphere. The reaction mixture was sequentially quenched with water (0.5 mL), 10% aqueous sodium hydroxide solution (0.5 mL) and water (1.5 mL) at 0° C., and then dried over anhydrous sodium sulfate, filtered and concentrated under reduced pressure to give (4-(benzyloxy)cyclopentane-1,2-diyl)dimethanol (800 mg, crude) as a yellow oil. $^1$H NMR (400 MHz, $CDCl_3$) δ 7.38-7.27 (m, 5H), 4.45 (d, J=1.2 Hz, 2H), 4.07-3.95 (m, 1H), 3.79-3.68 (m, 2H), 3.49 (t, J=9.6 Hz, 1H), 3.37 (t, J=9.6 Hz, 1H), 3.12 (s, 2H), 2.23-2.15 (m, 1H), 2.12-2.03 (m, 1H), 2.03-1.95 (m, 1H), 1.94-1.83 (m, 1H), 1.53-1.45 (m, 1H), 1.44-1.35 (m, 1H); m/z ES+ $[M+H]^+$ 237.2.

Step 4. (4-(Benzyloxy)cyclopentane-1,2-diyl)bis(methylene)bis(4-methylbenzenesulfonate)

To a solution of [4-benzyloxy-2-(hydroxymethyl)cyclopentyl]methanol (100 mg, 423 μmol) in pyridine (2 mL) was added 4-methylbenzenesulfonyl chloride (242 mg, 1.27 mmol), the mixture was stirred at 25° C. for 2 h. The reaction mixture was concentrated under reduced pressure. The residue was purified by column chromatography (petroleum ether/ethyl acetate=10 to 5/1) to give (4-(benzyloxy)cyclopentane-1,2-diyl)bis(methylene)bis(4-methylbenzenesulfonate) (150 mg, 262 μmol, 62%) as a colorless oil. $^1$H NMR (400 MHz, $CDCl_3$) δ 7.68 (dd, J=8.4, 13.2 Hz, 4H), 7.31-7.14 (m, 9H), 4.33-4.19 (m, 2H), 3.94-3.84 (m, 5H), 2.37 (d, J=12.4 Hz, 6H), 2.16-2.02 (m, 1H), 1.99-1.84 (m, 3H), 1.57-1.38 (m, 3H); m/z ES+ $[M+18]^+$ 562.4.

Step 5. (4-Hydroxycyclopentane-1,2-diyl)bis(methylene)bis(4-methylbenzenesulfonate)

To a solution of [4-benzyloxy-2-(p-tolylsulfonyloxymethyl)cyclopentyl]methyl4-methylbenzenesulfonate (140 mg, 257 μmol) in dichloromethane (1 mL) was added boron trichloride (1 mL). The mixture was stirred at 20° C. for 0.5 h. The reaction mixture was quenched with saturated sodium bicarbonate solution (5 mL) and extracted with ethyl acetate (3×5 mL). The combined organic layers were dried over anhydrous sodium sulfate, filtered and concentrated under reduced pressure. The residue was purified by column chromatography (petroleum ether/ethyl acetate-5/1 to 1/1) to give (4-hydroxycyclopentane-1,2-diyl)bis(methylene)bis(4-methylbenzenesulfonate) (80.0 mg, 176 μmol, 68%) as a yellow oil. $^1$H NMR (400 MHz, $CDCl_3$) δ 7.77 (dd, J=2.0, 8.4 Hz, 4H), 7.36 (dd, J=4.0, 8.0 Hz, 4H), 4.39-4.20 (m, 1H), 4.04-3.88 (m, 4H), 2.47 (d, J=2.0 Hz, 6H), 2.31-2.16 (m, 1H), 2.13-1.95 (m, 3H), 1.84-1.75 (m, 1H), 1.58 (dd, J=4.8, 9.6 Hz, 1H), 1.43 (d, J=2.0 Hz, 1H); m/z ES+ $[M+18]^+$ 471.9.

Step 6. 2-Oxabicyclo[2.2.1]heptan-5-ylmethyl 4-methylbenzenesulfonate

To a solution of [4-hydroxy-2-(p-tolylsulfonyloxymethyl)cyclopentyl]methyl4-methylbenzenesulfonate (80.0 mg, 176 μmol) in anhydrous tetrahydrofuran (1 mL) was added sodium hydride (14.1 mg, 352 μmol, 60% in mineral oil), the mixture was stirred at 0° C. for 2 h. The reaction mixture was quenched with sat. ammonium chloride (5 mL) at 0° C. and extracted with ethyl acetate (3×5 mL). The combined organic layers were dried over anhydrous sodium sulfate, filtered and concentrated under reduced pressure. The residue was purified by column chromatography (petroleum ether/ethyl acetate=5/1 to 1/1) to give 2-oxabicyclo[2.2.1]heptan-5-ylmethyl 4-methylbenzenesulfonate (45.0 mg, 159 μmol, 91%) as a yellow oil. $^1$H NMR (400 MHz, $CDCl_3$) δ 7.80 (d, J=8.4 Hz, 2H), 7.37 (d, J=8.4 Hz, 2H), 4.30 (s, 1H), 3.88-3.79 (m, 2H), 3.67 (dd, J=2.8, 7.2 Hz, 1H), 3.47 (d, J=7.2 Hz, 1H), 2.47 (s, 3H), 2.15-2.08 (m, 1H), 1.86-1.77 (m, 1H), 1.64-1.55 (m, 2H), 1.43 (d, J=10.8 Hz, 1H), 1.06 (dd, J=4.4, 13.2 Hz, 1H).

Step 7. 2-(1-(2-Oxabicyclo[2.2.1]heptan-5-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline To a solution of 2-[[6-[5-chloro-3-(1H-pyrazol-4-yl)quinoxalin-6-yl]oxy-2-methyl-benzimidazol-1-yl]methoxy]ethyl-trimethyl-silane (100 mg, 197 μmol) in N,N-dimethylformamide (1 mL) was added potassium carbonate (54.5 mg, 394 μmol) and 2-oxabicyclo[2.2.1]heptan-5-ylmethyl 4-methylbenzenesulfonate (44.6 mg, 158 μmol), the mixture was stirred at 80° C. for 12 h. The reaction mixture was diluted with water (5 mL) and extracted with ethyl acetate (3×5 mL). The combined organic layers were dried over anhydrous sodium sulfate, filtered and concentrated under reduced pressure to give 2-(1-(2-oxabicyclo[2.2.1]heptan-5-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (120 mg, crude) as a black solid, m/z ES+ $[M+H]^+$ 617.2.

Step 8. 2-(1-(2-Oxabicyclo[2.2.1]heptan-5-ylmethyl)-1H-pyrazol-4-yl)-8-chloro-7-((2-methyl-1H-benzo[d]imidazol-6-yl)oxy)quinoxaline A solution of 2-[[6-[5-chloro-3-[1-(2-oxabicyclo[2.2.1]heptan-5-ylmethyl)pyrazol-4-yl]quinoxalin-6-yl]oxy-2-methyl-benzimidazol-1-yl]methoxy]ethyl-trimethyl-silane (70.0 mg, 113 μmol) in trifluoroacetic acid (0.5 mL) was stirred at 20° C. for 0.5 h. The reaction mixture was filtered and concentrated under reduced pressure. The residue was purified by prep-HPLC (column: Phenomenex Luna C18 150*25 mm*10 μm; mobile phase: [water (0.2% formic acid)-acetonitrile]; (B %: 14%-44%, 10 min) to give 2-(1-(2-oxabicyclo[2.2.1]heptan-5-ylmethyl)-1H-pyrazol-4-yl)-8-chloro-7-((2-methyl-1H-benzo[d]imidazol-6-yl)oxy)quinoxaline (22.9 mg, 45.7 μmol, 40%) as an off-white solid. $^1$H NMR (400 MHz, DMSO-$d_6$) δ=9.29 (d, J=3.6 Hz, 1H), 8.75 (s, 1H), 8.37 (s, 1H), 7.93 (s, 1H), 7.53 (s, 1H), 7.40-7.12 (m, 2H), 6.96 (s, 1H), 4.33-4.06 (m, 3H), 3.55-3.32 (m, 2H), 2.55-2.51 (m, 3H), 2.31 (s, 2H), 1.67 (s, 2H), 1.55-1.42 (m, 1H), 1.27 (d, J=0.8 Hz, 1H); m/z ES+ $[M+H]^+$ 487.1.

Example 53. Synthesis of 2-[1-[3-(Azetidin-1-yl)cyclobutyl]pyrazol-4-yl]-8-chloro-7-[(2-methyl-3H-benzimidazol-5-yl)oxy]quinoxaline

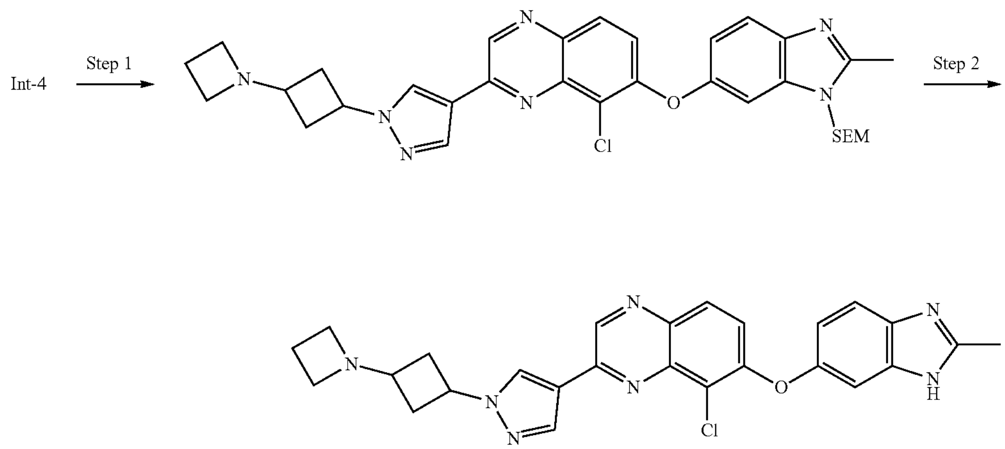

Step 1. 2-(1-(3-(Azetidin-1-yl)cyclobutyl)-1H-pyrazol-4-yl)-8-chloro-7-((1-((2-(trimethylsilyl)ethoxy)methyl)-1H-benzo[d]imidazol-6-yl)oxy)quinoxaline To a solution of 3-[4-[8-chloro-7-[2-methyl-3-(2-trimethylsilylethoxymethyl)benzimidazol-5-yl]oxy-quinoxalin-2-yl]pyrazol-1-yl]cyclobutanone (100 mg, 174 μmol) and azetidine (48.8 mg, 522 μmol) in methanol (2 mL) was added tetraisopropoxytitanium (98.8 mg, 348 μmol) and diisopropylethylamine (67.4 mg, 522 μmol), the mixture was stirred at 60° C. for 2 h. Then sodium cyanoborohydride (10.9 mg, 174 μmol) was added, and the mixture was stirred at 25° C. for 2 h. The reaction mixture was quenched with saturated sodium bicarbonate solution (20 mL) and then filtered. The filtrate was extracted with ethyl acetate (3×50 mL). The combined organic layers were washed with brine (3×25 mL), dried over anhydrous sodium sulfate, filtered and concentrated under reduced pressure. The crude produce was purified by prep-TLC (silica gel, dichloromethane: methanol=10:1) to give 2-(1-(3-(azetidin-1-yl)cyclobutyl)-1H-pyrazol-4-yl)-8-chloro-7-((1-((2-(trimethylsilyl)ethoxy)

methyl)-1H-benzo[d]imidazol-6-yl)oxy)quinoxaline (30.0 mg, 48.7 μmol, 28%) as a white solid. m/z ES+ $[M+H]^+$ 616.3.

Step 2. 2-[1-[3-(Azetidin-1-yl)cyclobutyl]pyrazol-4-yl]-8-chloro-7-[(2-methyl-3H-benzimidazol-5-yl)oxy]quinoxaline A solution of 2-[[6-[3-[1-[3-(azetidin-1-yl)cyclobutyl]pyrazol-4-yl]-5-chloro-quinoxalin-6-yl]oxy-2-methyl-benzimidazol-1-yl]methoxy]ethyl-trimethyl-silane (25.0 mg, 40.6 μmol) in trifluoroacetic acid (0.5 mL) was stirred at 25° C. for 0.5 h. The reaction mixture was filtered and concentrated under reduced pressure. The residue was purified by prep-HPLC (formic acid condition; column: Unisil 3-100 C18 Ultra 150*50 mm*3 μm; mobile phase: [water (0.225% formic acid)-acetonitrile]; (B %: 3%-33%, 10 min) to give 2-[1-[3-(azetidin-1-yl)cyclobutyl]pyrazol-4-yl]-8-chloro-7-[(2-methyl-3H-benzimidazol-5-yl)oxy]quinoxaline (12.4 mg, 23.9 μmol, 60%) as a white solid. $^1$HNMR (400 MHz, DMSO-$d_6$) δ=9.35-9.30 (m, 1H), 8.87-8.79 (m, 1H), 8.42 (d, J=2.4 Hz, 1H), 8.15 (s, 1H), 7.96 (d, J=9.2 Hz, 1H), 7.51 (d, J=8.8 Hz, 1H), 7.32 (d, J=9.2 Hz, 1H), 7.21 (s, 1H), 6.94 (dd, J=1.2, 8.4 Hz, 1H), 5.22-4.78 (m, 1H), 3.82 (t, J=8.0 Hz, 3H), 3.69 (t, J=7.6 Hz, 2H), 2.81-2.58 (m, 4H), 2.49-2.48 (m, 3H), 2.30-2.13 (m, 2H); m/z ES+ $[M+H]^+$ 486.1.

Example 54. Synthesis of 8-Chloro-2-[1-[3-(3,3-difluoroazetidin-1-yl)cyclobutyl]pyrazol-4-yl]-7-[(2-methyl-3H-benzimidazol-5-yl)oxy]quinoxaline

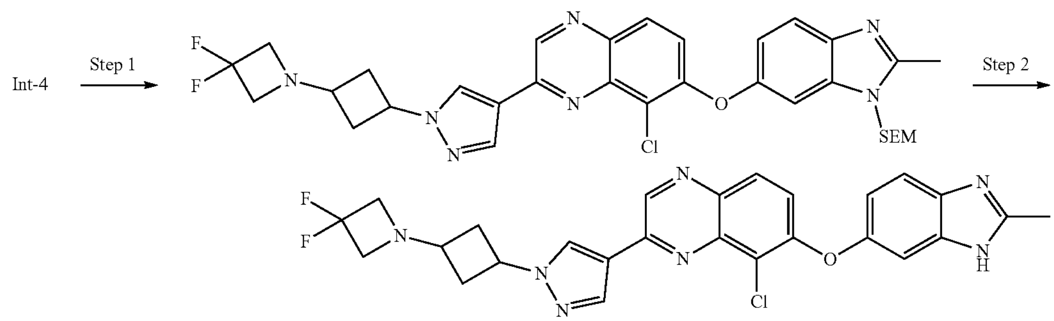

Step 1. 2-[[6-[5-Chloro-3-[1-[3-(3,3-difluoroazetidin-1-yl)cyclobutyl]pyrazol-4-yl]quinoxalin-6-yl]oxy-2-methyl-benzimidazol-1-yl]methoxy]ethyl-trimethyl-silane To a solution of 3-[4-[8-chloro-7-[2-methyl-3-(2-trimethylsilylethoxymethyl)benzimidazol-5-yl]oxy-quinoxalin-2-yl]pyrazol-1-yl]cyclobutanone (100 mg, 170 μmol) and 3,3-difluoroazetidine (68.0 mg, 520 μmol) in methanol (1.5 mL) was added diisopropylethylamine (67.0 mg, 520 μmol) and tetraisopropoxytitanium (99.0 mg, 350 μmol), the mixture was stirred at 60° C. for 2 h. Then sodium cyanoborohydride (11.0 mg, 170 μmol) was added. The mixture was stirred at 40° C. for 12 h. The reaction mixture was then filtered. The filtrate was washed with water (20 mL) and extracted with ethyl acetate (2×10 mL). The combined organic layers were washed with sat. sodium bicarbonate (2×10 mL), dried over sodium sulfate, filtered and concentrated under reduced pressure. The residue was purified by prep-TLC (silica gel, dichloromethane:methanol=10:1) to give 2-[[6-[5-chloro-3-[1-[3-(3,3-difluoroazetidin-1-yl)cyclobutyl]pyrazol-4-yl]quinoxalin-6-yl]oxy-2-methyl-benzimidazol-1-yl]methoxy]ethyl-trimethyl-silane (40.0 mg, 61.3 μmol, 36%) as a white solid. m/z ES+ $[M+H]^+$ 652.2.

Step 2. 8-Chloro-2-[1-[3-(3,3-difluoroazetidin-1-yl)cyclobutyl]pyrazol-4-yl]-7-[(2-methyl-3H-benzimidazol-5-yl)oxy]quinoxaline A solution of 2-[[6-[5-chloro-3-[1-[3-(3,3-difluoroazetidin-1-yl)cyclobutyl]pyrazol-4-yl]quinoxalin-6-yl]oxy-2-methyl-benzimidazol-1-yl]methoxy]ethyl-trimethyl-silane (30.0 mg, 46.0 μmol) in trifluoroacetic acid (0.2 mL) was stirred at 25° C. for 0.5 h. The reaction mixture was concentrated under reduced pressure. The residue was purified by prep-HPLC (neutral condition; column: Waters Xbridge 150*25 mm*5 μm; mobile phase: [water (10 mM ammonium bicarbonate)-acetonitrile]; (B %: 35%-65%, 10 min) to give 8-chloro-2-[1-[3-(3,3-difluoroazetidin-1-yl)cyclobutyl]pyrazol-4-yl]-7-[(2-methyl-3H-benzimidazol-5-yl)oxy]quinoxaline (13.7 mg, 26.2 μmol, 56%) as a white solid. $^1$HNMR (400 MHz, DMSO-$d_6$) δ=12.62-11.89 (m, 1H), 9.34-9.29 (m, 1H), 8.81-8.76 (m, 1H), 8.39 (s, 1H), 7.95 (d, J=9.2 Hz, 1H), 7.50. (d, J=9.6 Hz, 1H), 7.31 (d, J=9.2 Hz, 1H), 7.21 (d, J=1.6 Hz, 1H), 6.94 (dd, J=2.4, 8.8 Hz, 1H), 5.15-4.67 (m, 1H), 3.69-3.60 (m, 4H), 3.25-3.17 (m, 1H), 2.63-2.57 (m, 2H), 2.49 (s, 3H), 2.43-2.32 (m, 2H); m/z ES+ $[M+H]^+$ 522.1.

Example 55. Synthesis of 1-[[4-[8-Chloro-7-[(2-methyl-3H-benzimidazol-5-yl)oxy]quinoxalin-2-yl]pyrazol-1-yl]methyl]cyclopropanol

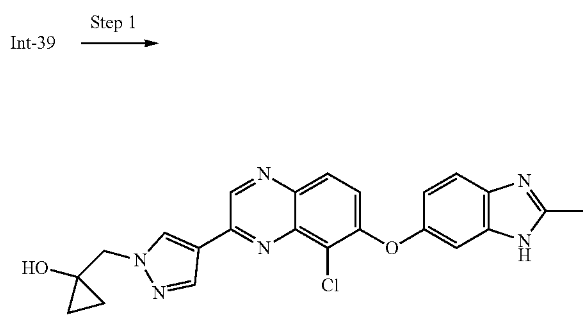

Step 1. 1-[[4-[8-Chloro-7-[(2-methyl-3H-benzimidazol-5-yl)oxy]quinoxalin-2-yl]pyrazol-1-yl]methyl]cyclopropanol A solution of 2-[[6-[5-chloro-3-[1-[(1-tetrahydropyran-2-yloxycyclopropyl)methyl]pyrazol-4-yl]quinoxalin-6-yl]oxy-2-methyl-benzimidazol-1-yl]methoxy]ethyl-trimethyl-silane (190 mg, 287 μmol) in trifluoroacetic acid (2 mL) was stirred at 25° C. for 0.5 h. The reaction mixture was concentrated in vacuo and the residue was purified by prep-HPLC (column: Phenomenex Synergi C18 150*25 mm*10 μm; mobile phase: [water (0.225% formic acid)-acetonitrile]; (B %: 8%-38%, 10 min) to give 1-[[4-[8-chloro-7-[(2-methyl-3H-benzimidazol-5-yl)oxy]quinoxalin-2-yl]pyrazol-1-yl]methyl]cyclopropanol (74.6 mg, 167 μmol, 58%) as a white solid. $^1$H NMR (400 MHz, DMSO-$d_6$) δ=9.40 (s, 1H), 8.69 (s, 1H), 8.37 (s, 1H), 8.03 (d, J=9.2 Hz, 1H), 7.75 (d, J=8.8 Hz, 1H), 7.46-7.42 (m, 2H), 7.23 (dd, J=2.0, 8.8 Hz, 1H), 5.90-5.42 (m, 1H), 4.30 (s, 2H), 2.71 (s, 3H), 0.79-0.68 (m, 4H); m/z ES+ [M+H]$^+$ 447.0.

Example 56. Synthesis of 8-Chloro-7-[(2-methyl-3H-benzimidazol-5-yl)oxy]-2-[3-methyl-1-(4-piperidyl)pyrazol-4-yl]quinoxaline and 8-Chloro-7-[(2-methyl-3H-benzimidazol-5-yl)oxy]-2-[5-methyl-1-(4-piperidyl)pyrazol-4-yl]quinoxaline

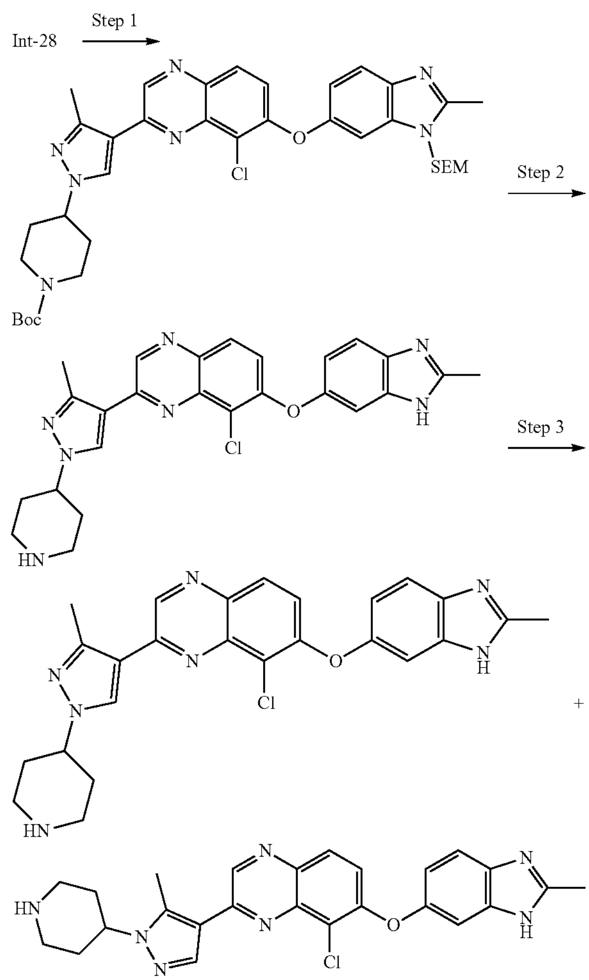

Step 1. tert-Butyl 4-[4-[8-chloro-7-[2-methyl-3-(2-trimethylsilylethoxymethyl)benzimidazol-5-yl]oxy-quinoxalin-2-yl]-3-methyl-pyrazol-1-yl]piperidine-1-carboxylate To a solution of 2-[[6-[5-chloro-3-(5-methyl-1H-pyrazol-4-yl)quinoxalin-6-yl]oxy-2-methyl-benzimidazol-1-yl]methoxy]ethyl-trimethyl-silane (200 mg, 383 μmol) in N,N-dimethylformamide (3 mL) was added cesium carbonate (625 mg, 1.92 mmol) and tert-butyl 4-(p-tolylsulfonyloxy)piperidine-1-carboxylate (409 mg, 1.15 mmol). The mixture was stirred at 100° C. for 12 hs. The reaction mixture was concentrated under reduced pressure to give a residue, the residue was purified by reversed-phase HPLC (0.1% formic acid condition) to give tert-butyl 4-[4-[8-chloro-7-[2-methyl-3-(2-trimethylsilylethoxymethyl)benzimidazol-5-yl]oxy-quinoxalin-2-yl]-3-methyl-pyrazol-1-yl]piperidine-1-carboxylate (100 mg, 142 μmol, 36%) as a yellow solid. m/z ES+ [M+H]$^+$ 704.2.

Step 2. 8-Chloro-7-[(2-methyl-3H-benzimidazol-5-yl)oxy]-2-[3-methyl-1-(4-piperidyl)pyrazol-4-yl]quinoxaline A solution of tert-butyl 4-[4-[8-chloro-7-[2-methyl-3-(2-trimethylsilylethoxymethyl)benzimidazol-5-yl]oxy-quinoxalin-2-yl]-3-methyl-pyrazol-1-yl]piperidine-1-carboxylate (90.0 mg, 127 μmol) in trifluoroacetic acid (1 mL) was stirred at 25° C. for 0.5 h. The reaction mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 5%-35%, 7 min) to give 8-chloro-7-[(2-methyl-3H-benzimidazol-5-yl)oxy]-2-[3-methyl-1-(4-piperidyl)pyrazol-4-yl]quinoxaline (60.0 mg, 126 μmol, 99%) as a white solid. m/z ES+ [M+H]$^+$ 474.2.

Step 3. 8-Chloro-7-[(2-methyl-3H-benzimidazol-5-yl)oxy]-2-[3-methyl-1-(4-piperidyl)pyrazol-4-yl]quinoxaline and 8-Chloro-7-[(2-methyl-3H-benzimidazol-5-yl)oxy]-2-[5-methyl-1-(4-piperidyl)pyrazol-4-yl]quinoxaline 8-Chloro-7-[(2-methyl-3H-benzimidazol-5-yl)oxy]-2-[3-methyl-1-(4-piperidyl)pyrazol-4-yl]quinoxaline (50.0 mg, 105 μmol) was separated by SFC (column: Daicel ChiralPak IG (250*30 mm, 10 μm); mobile phase: [0.1% ammonium hydroxide/ethanol]; (B %: 70%-70%, 5.4 min, total run 60 min) and then repurified by prep-HPLC (column: Phenomenex Gemini-NX C18 75*30 mm*3 μm; mobile phase: [water (0.225% formic acid)-acetonitrile]; (B %: 5%-35%, 7 min) to give 8-chloro-7-[(2-methyl-3H-benzimidazol-5-yl)oxy]-2-[3-methyl-1-(4-piperidyl)pyrazol-4-yl]quinoxaline (11.3 mg, 23.8 μmol, 22%) as a white solid and 8-chloro-7-[(2-methyl-3H-benzimidazol-5-yl)oxy]-2-[5-methyl-1-(4-piperidyl)pyrazol-4-yl]quinoxaline (8.3 mg, 17.4 μmol, 16%) as a white solid.

$^1$H NMR (400 MHz, $CD_3OD$) δ 9.12 (s, 1H), 8.59 (s, 1H), 8.48 (s, 1H), 7.89 (d, J=9.2 Hz, 1H), 7.53 (d, J=8.8 Hz, 1H), 7.34 (d, J=9.2 Hz, 1H), 7.18 (d, J=2.4 Hz, 1H), 7.03-6.98 (m, 1H), 4.64-4.51 (m, 1H), 3.60 (d, J=13.2 Hz, 2H), 3.29-3.19 (m, 2H), 2.79 (s, 3H), 2.57 (s, 3H), 2.46-2.25 (m, 4H); m/z ES+ [M+H]$^+$ 474.1.

$^1$H NMR (400 MHz, $CD_3OD$) δ 9.15 (s, 1H), 8.33 (s, 2H), 7.89 (d, J=9.2 Hz, 1H), 7.54 (d, J=8.8 Hz, 1H), 7.34 (d, J=9.2 Hz, 1H), 7.19 (d, J=2.4 Hz, 1H), 7.02-7 (m, 1H), 4.82-4.72 (m, 1H), 3.63 (d, J=13.2 Hz, 2H), 3.36-3.32 (m, 1H), 3.30-3.25 (m, 1H), 3.01 (s, 3H), 2.59 (s, 3H), 2.50-2.35 (m, 2H), 2.25 (d, J-11.6 Hz, 2H); m/z ES+ [M+H]$^+$ 474.1.

Example 57. Synthesis of 8-Chloro-2-(1-((3,3-difluorocyclobutyl)methyl)-1H-pyrazol-4-yl)-7-((7-fluoro-2-methyl-1H-benzo[d]imidazol-5-yl)oxy)quinoxaline

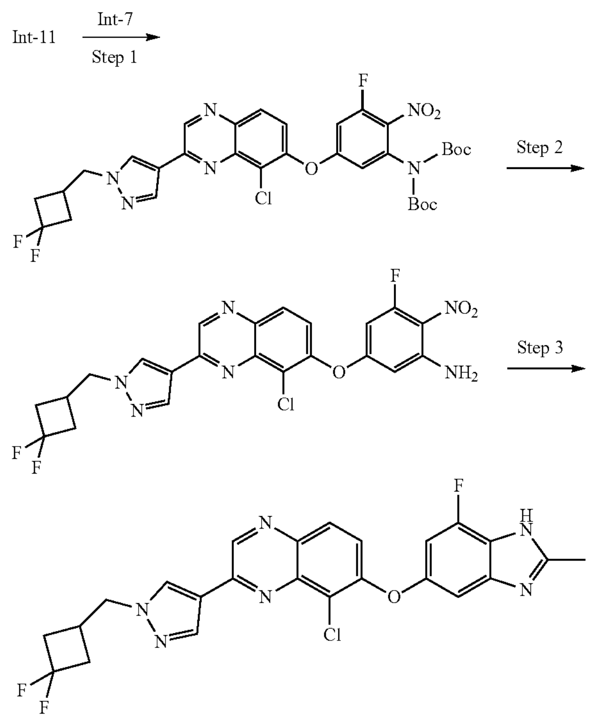

Step 1. tert-Butyl N-tert-butoxycarbonyl-N-[5-[5-chloro-3-[1-[(3,3-difluorocyclobutyl)methyl]pyrazol-4-yl]quinoxalin-6-yl]oxy-3-fluoro-2-nitro-phenyl]carbamate To a solution of 5-chloro-3-[1-[(3,3-difluorocyclobutyl)methyl]pyrazol-4-yl]quinoxalin-6-ol (200 mg, 570 μmol) in N,N-dimethylformamide (3 mL) was added potassium carbonate (236 mg, 1.71 mmol) and tert-butyl N-tert-butoxycarbonyl-N-(3,5-difluoro-2-nitro-phenyl) carbamate (320 mg, 855 μmol). The mixture was stirred at 80° C. for 1 h. The reaction mixture was concentrated under reduced pressure. The residue was purified by column chromatography (petroleum ether/ethyl acetate=10/1 to 5/1) to give tert-butyl N-tert-butoxycarbonyl-N-[5-[5-chloro-3-[1-[(3,3-difluorocyclobutyl)methyl]pyrazol-4-yl]quinoxalin-6-yl]oxy-3-fluoro-2-nitro-phenyl]carbamate (120 mg, 170 μmol, 30%) as a yellow oil. m/z ES+ $[M+H]^+$ 705.2.

Step 2. 5-((5-Chloro-3-(1-((3,3-difluorocyclobutyl)methyl)-1H-pyrazol-4-yl)quinoxalin-6-yl)oxy)-3-fluoro-2-nitroaniline To a solution of tert-butyl N-tert-butoxycarbonyl-N-[5-[5-chloro-3-[1-[(3,3-difluorocyclobutyl)methyl]pyrazol-4-yl]quinoxalin-6-yl]oxy-3-fluoro-2-nitro-phenyl]carbamate (100 mg, 142 μmol) in dichloromethane (0.9 mL) was added trifluoroacetic acid (0.3 mL). The mixture was stirred at 20° C. for 0.5 h. The reaction mixture was concentrated under reduced pressure to give 5-((5-chloro-3-(1-((3,3-difluorocyclobutyl)methyl)-1H-pyrazol-4-yl)quinoxalin-6-yl)oxy)-3-fluoro-2-nitroaniline (90 mg, crude, trifluoroacetic acid salt) as a yellow oil. m/z ES+ $[M+H]^+$ 505.0.

Step 3. 8-Chloro-2-(1-((3,3-difluorocyclobutyl)methyl)-1H-pyrazol-4-yl)-7-((7-fluoro-2-methyl-1H-benzo[d]imidazol-5-yl)oxy)quinoxaline To a solution of 5-[5-chloro-3-[1-[(3,3-difluorocyclobutyl)methyl]pyrazol-4-yl]quinoxalin-6-yl]oxy-3-fluoro-2-nitro-aniline (80 mg, 129 μmol, trifluoroacetic acid salt) in ethanol (5 mL) and water (1 mL) was added iron powder (36.1 mg, 646 μmol) and ammonium chloride (69.2 mg, 1.29 mmol). The mixture was stirred at 60° C. for 12 h. The reaction mixture was filtered and concentrated under reduced pressure. The residue was purified by prep-HPLC (column: Phenomenex Luna C18 150*25 mm*10 μm; mobile phase: [water (0.2% formic acid)-acetonitrile]; (B %: 28%-58%, 10 min) to give 8-chloro-2-(1-((3,3-difluorocyclobutyl)methyl)-1H-pyrazol-4-yl)-7-((7-fluoro-2-methyl-1H-benzo[d]imidazol-5-yl)oxy)quinoxaline (29.0 mg, 58.1 μmol, 45%) as an off-white solid. $^1$H NMR (400 MHz, $CD_3OD$) δ 9.19 (s, 1H), 8.61 (s, 1H), 8.37 (s, 1H), 7.96 (d, J=8.8 Hz, 1H), 7.44 (d, J=9.2 Hz, 1H), 6.96 (s, 1H), 6.82 (d, J=10.8 Hz, 1H), 4.41 (d, J=6.8 Hz, 2H), 2.89-2.66 (m, 3H), 2.62-2.43 (m, 5H); m/z ES+ $[M+H]^+$ 499.0.

Example 58. Synthesis of 2-[[6-[3-[1-[2-(Azetidin-1-yl)ethyl]pyrazol-4-yl]-5-chloro-quinoxalin-6-yl]oxy-2-methyl-benzimidazol-1-yl]methoxy]ethyl-trimethyl-silane

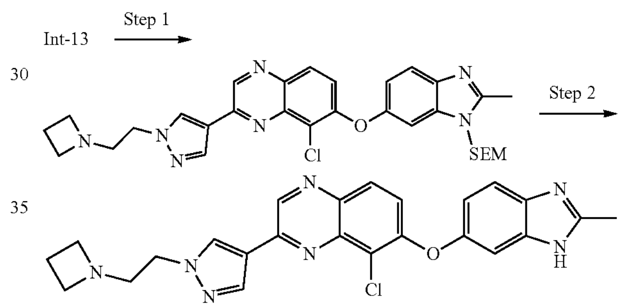

Step 1. tert-Butyl 4-(3-(methoxycarbonyl)-4-nitrophenyl) hexahydropyrrolo[3,2-b]pyrrole-1 (2H)-carboxylate To a solution of 2-[4-[8-chloro-7-[2-methyl-3-(2-trimethylsilylethoxymethyl)benzimidazol-5-yl]oxy-quinoxalin-2-yl]pyrazol-1-yl]ethyl methanesulfonate (200 mg, 318 μmol) in isopropanol (8 mL) was added azetidine (60.0 mg, 1.05 mmol), the mixture was stirred at 80° C. for 2.5 h. The mixture was concentrated under reduced pressure. The residue was purified by prep-TLC (silica gel, dichloromethane:methanol=10:1) to give 2-[[6-[3-[1-[2-(azetidin-1-yl)ethyl]pyrazol-4-yl]-5-chloro-quinoxalin-6-yl]oxy-2-methyl-benzimidazol-1-yl]methoxy]ethyl-trimethyl-silane (35.0 mg, 59.3 μmol, 19%) as a yellow solid. m/z ES+ $[M+H]^+$ 590.2.

Step 2. 2-[1-[2-(Azetidin-1-yl)ethyl]pyrazol-4-yl]-8-chloro-7-[(2-methyl-3H-benzimidazol-5-yl)oxy]quinoxaline A solution of 2-[[6-[3-[1-[2-(azetidin-1-yl)ethyl]pyrazol-4-y]]-5-chloro-quinoxalin-6-yl]oxy-2-methyl-benzimidazol-1-yl]methoxy]ethyl-trimethyl-silane (30.0 mg, 50.8 μmol) in trifluoroacetic acid (2 mL) was stirred at 25° C. for 2 h. The mixture was concentrated under reduced pressure. The residue was purified by prep-TLC (silica gel, dichloromethane:methanol=10:1) to give 2-[1-[2-(azetidin-1-yl)ethyl]pyrazol-4-yl]-8-chloro-7-[(2-methyl-3H-benzimidazol-5-yl)oxy]quinoxaline (11.8 mg, 24.4 μmol, 48%) as a yellow gum. $^1$H NMR (400 MHz, $CD_3OD$) δ 9.13 (s, 1H), 8.56 (s, 1H), 8.36 (s, 1H), 7.88 (d, J=9.2 Hz, 1H), 7.52 (d, J=8.8 Hz, 1H), 7.33 (d, J=9.2 Hz, 1H), 7.18 (d, J=2.0 Hz, 1H), 7.03-6.97 (m, 1H), 4.30 (t, J=6.0 Hz, 2H), 3.39 (t, J=7.2 Hz, 4H), 3.11 (t, J=6.0 Hz, 2H), 2.57 (s, 3H), 2.15 (t, J=7.2 Hz, 2H); m/z ES+ $[M+H]^+$ 460.1.

Example 59. Synthesis of 1-(2-(4-(8-Chloro-7-((2-methyl-1H-benzo[d]imidazol-6-yl)oxy)quinoxalin-2-yl)-1H-pyrazol-1-yl)ethyl)pyrrolidin-3-ol

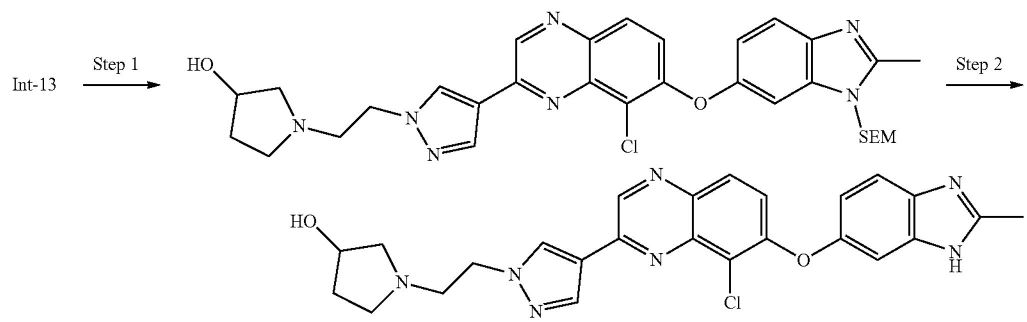

Step 1. 1-(2-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)ethyl)pyrrolidin-3-01

A solution of 2-[4-[8-chloro-7-[2-methyl-3-(2-trimethylsilylethoxymethyl)benzimidazol-5-yl]oxy-quinoxalin-2-yl]pyrazol-1-yl]ethyl methanesulfonate (0.2 g, 317 μmol). pyrrolidin-3-ol (83.0 mg, 953 μmol), sodium bicarbonate (186 mg, 2.23 mmol) in acetonitrile (3 mL) was stirred at 80° C. for 16 h. The reaction mixture was poured into water (20 mL) and extracted with ethyl acetate (3×100 mL). The combined organic layers were washed with brine (3×10 mL), dried by sodium sulphate, filtered and concentrated in vacuo and the residue was purified by reversed-phase HPLC (0.1% formic acid condition) to give 1-(2-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)ethyl)pyrrolidin-3-ol (50 mg, 80.6 μmol, 25%) as a yellow solid. m/z ES+ $[M+H]^+$ 620.2.

Step 2. 1-(2-(4-(8-Chloro-7-((2-methyl-1H-benzo[d]imidazol-6-yl)oxy)quinoxalin-2-yl)-1H-pyrazol-1-yl)ethyl)pyrrolidin-3-ol A solution of 1-(2-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)ethyl)pyrrolidin-3-ol (50 mg, 80.6 μmol) in trifluoroacetic acid (45.9 mg, 403 μmol) was stirred at 25° C. for 4 h. The mixture was concentrated in vacuo and the residue was purified by prep-HPLC (column: Waters Xbridge 150*25 mm*5 μm; mobile phase: [water (ammonium bicarbonate)-acetonitrile]; (B %: 19%-49%, 8 min) to give 1-(2-(4-(8-chloro-7-((2-methyl-1H-benzo[d]imidazol-6-yl)oxy)quinoxalin-2-yl)-1H-pyrazol-1-yl)ethyl)pyrrolidin-3-ol (8.0 mg, 16.3 μmol, 20%) as a yellow solid. $^1$H NMR (400 MHz, DMSO-$d_6$) δ 12.41-12.12 (m, 1H), 9.30 (s, 1H), 8.72 (s, 1H), 8.35 (s, 1H), 7.95 (d, J=8.0 Hz, 1H), 7.60-7.43 (m, 1H), 7.39-7.11 (m, 2H), 6.94 (t, J=9.6 Hz, 1H), 4.69 (d, J=4.4 Hz, 1H), 4.33 (t, J=6.4 Hz, 2H), 4.20-4.14 (m, 1H), 2.90 (t, J=6.4 Hz, 2H), 2.81-2.73 (m, 1H), 2.68-2.52 (m, 2H), 2.50 (s, 3H), 2.38-2.33 (m, 1H), 1.99-1.90 (m, 1H), 1.58-1.48 (m, 1H); m/z ES+ $[M+H]^+$ 490.1.

Example 60. Synthesis of 8-Chloro-2-[1-[2-(3-methoxypyrrolidin-1-yl)ethyl]pyrazol-4-yl]-7-[(2-methyl-3H-benzimidazol-5-yl)oxy]quinoxaline

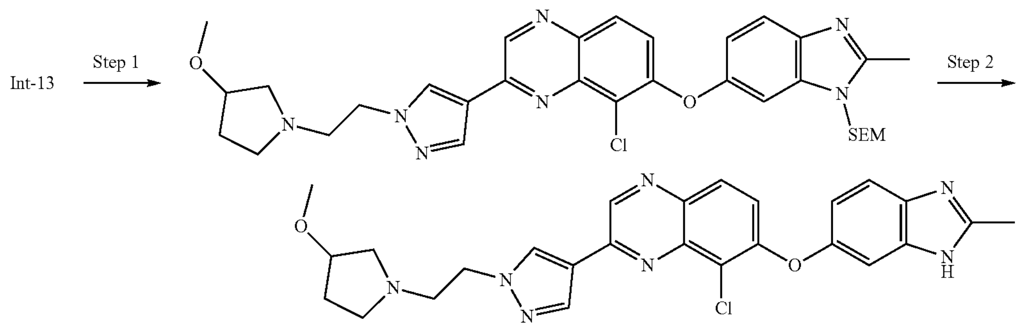

Step 1. 2-[[6-[5-Chloro-3-[1-[2-(3-methoxypyrrolidin-1-yl)ethyl]pyrazol-4-yl]quinoxalin-6-yl]oxy-2-methyl-benzimidazol-1-yl]methoxy]ethyl-trimethyl-silane To a solution of 2-[4-[8-chloro-7-[2-methyl-3-(2-trimethylsilylethoxymethyl)benzimidazol-5-yl]oxy-quinoxalin-2-yl]pyrazol-1-yl]ethyl methanesulfonate (200 mg, 318 μmol) and 3-methoxypyrrolidine (131 mg, 954 μmol) in acetonitrile (3 mL) was added sodium bicarbonate (134 mg, 1.59 mmol), the mixture was stirred at 80° C. for 12 h. The reaction mixture was filtered and concentrated in vacuo and the residue was purified by prep-TLC (silica gel, dichloromethane:methanol=10:1) to give 2-[[6-[5-chloro-3-[1-[2-(3-methoxypyrrolidin-1-yl)ethyl]pyrazol-4-yl]quinoxalin-6-yl]oxy-2-methyl-benzimidazol-1-yl]methoxy]ethyl-trimethyl-silane (45.0 mg, 70.9 μmol, 22%) as a yellow solid. m/z ES+ $[M+H]^+$ 634.3.

Step 2. 8-Chloro-2-[1-[2-(3-methoxypyrrolidin-1-yl)ethyl]pyrazol-4-yl]-7-[(2-methyl-3H-benzimidazol-5-yl)oxy]quinoxaline A solution of 2-[[6-[5-chloro-3-[1-[2-(3-methoxypyrrolidin-1-yl)ethyl]pyrazol-4-yl]quinoxalin-6-yl]oxy-2-methyl-benzimidazol-1-yl]methoxy]ethyl-trimethyl-silane (39.0 mg, 61.5 μmol) in trifluoroacetic acid (1.6 mL) was stirred at 25° C. for 1 h. The reaction mixture was concentrated in vacuo and the residue was purified by prep-HPLC (column: Waters Xbridge 150*25 mm*5 μm; mobile phase: [water (10 mM ammonium bicarbonate)-acetonitrile]; (B %: 28%-58%, 10 min) and re-purified by prep-HPLC (column: Waters Xbridge 150*25 mm*5 μm; mobile phase: [water (0.05% ammonium hydroxide v/v)-acetonitrile]; (B %: 21%-51%, 9 min) to give 8-chloro-2-[1-[2-(3-methoxypyrrolidin-1-yl)ethyl]pyrazol-4-yl]-7-[(2-methyl-3H-benzimidazol-5-yl)oxy]quinoxaline (1.5 mg, 3.02 μmol, 4%) as an off-white solid. $^1$H NMR (400 MHz, DMSO-$d_6$) δ=9.35 (s, 1H), 8.79 (s, 1H), 8.47 (s, 1H), 7.98 (d, J=9.2 Hz, 1H), 7.52 (d, J=8.8 Hz, 1H), 7.34 (d, J=9.2 Hz, 1H), 7.22 (s, 1H), 7-6.92 (m, 1H), 4.62 (d, J=4.4 Hz, 2H), 4.15-3.99 (m, 1H), 3.72-3.44 (m, 2H), 3.30-3.29 (m, 2H), 3.23 (s, 3H), 3.18-2.95 (m, 2H), 2.49-2.49 (m, 3H), 2.24-1.79 (m, 2H); m/z ES+ $[M+H]^+$ 504.1.

Example 61. Synthesis of 8-Chloro-2-[1-[2-(3,3-difluoropyrrolidin-1-yl)ethyl]pyrazol-4-yl]-7-[(2-methyl-3H-benzimidazol-5-yl)oxy]quinoxaline Step 1. 2-[[6-[5-Chloro-3-[1-[2-(3,3-difluoropyrrolidin-1-yl)ethyl]pyrazol-4-yl]quinoxalin-6-yl]oxy-2-methyl-benzimidazol-1-yl]methoxy]ethyl-trimethyl-silane To a solution of 2-[4-[8-chloro-7-[2-methyl-3-(2-trimethylsilylethoxymethyl)benzimidazol-5-yl]oxy-quinoxalin-2-yl]pyrazol-1-yl]ethylmethanesulfonate (200 mg, 318 μmol) and 3,3-difluoropyrrolidine hydrochloride (137 mg, 954 μmol) in acetonitrile (3 mL) was added sodium bicarbonate (134 mg, 1.59 mmol), the mixture was stirred at 80° C. for 12 h. The reaction mixture was filtered and concentrated in vacuo and the residue was purified by prep-TLC (silica gel, dichloromethane:methanol=10:1) to give 2-[[6-[5-chloro-3-[1-[2-(3,3-difluoropyrrolidin-1-yl)ethyl]pyrazol-4-yl]quinoxalin-6-yl]oxy-2-methyl-benzimidazol-1-yl]methoxy]ethyl-trimethyl-silane (41.0 mg, 64.0 μmol, 20%) as a yellow solid. m/z ES+ $[M+H]^+$ 640.2.

Step 2. 8-Chloro-2-[1-[2-(3,3-difluoropyrrolidin-1-yl)ethyl]pyrazol-4-yl]-7-[(2-methyl-3H-benzimidazol-5-yl)oxy]quinoxaline A solution of 2-[[6-[5-chloro-3-[1-[2-(3,3-difluoropyrrolidin-1-yl)ethyl]pyrazol-4-yl]quinoxalin-6-yl]oxy-2-methylbenzimidazol-1-yl]methoxy]ethyl-trimethyl-silane (41.0 mg, 64.0 μmol) in trifluoroacetic acid (1.6 mL) was stirred at 25° C. for 1 h. The reaction mixture was concentrated in vacuo and the residue was purified by prep-HPLC (column: Phenomenex Synergi C18 150*25 mm*10 μm; mobile phase: [water (0.225% formic acid)-acetonitrile]; (B %: 5%-35%, 10 min) and re-purified by prep-TLC (silica gel, dichloromethane:methanol=10:1) to give 8-chloro-2-[1-[2-(3,3-difluoropyrrolidin-1-yl)ethyl]pyrazol-4-yl]-7-[(2-methyl-3H-benzimidazol-5-yl)oxy]quinoxaline (2.5 mg, 4.88 μmol, 7%) as a white solid. $^1$H NMR (400 MHz, $CD_3OD$) δ=9.15 (s, 1H), 8.61 (s, 1H), 8.36 (s, 1H), 7.90 (d, J=9.2 Hz, 1H), 7.53 (d, J=8.8 Hz, 1H), 7.34 (d, J=9.2 Hz, 1H), 7.18 (s, 1H), 7.01 (dd, J=2.0, 8.8 Hz, 1H), 4.40 (t, J=6.4 Hz, 2H), 3.04 (t, J=6.4 Hz, 2H), 2.97 (t, J=13.2 Hz, 2H), 2.83 (t, J=7.2 Hz, 2H), 2.57 (s, 3H), 2.32-2.18 (m, 2H); m/z ES+ $[M+H]^+$ 510.1.

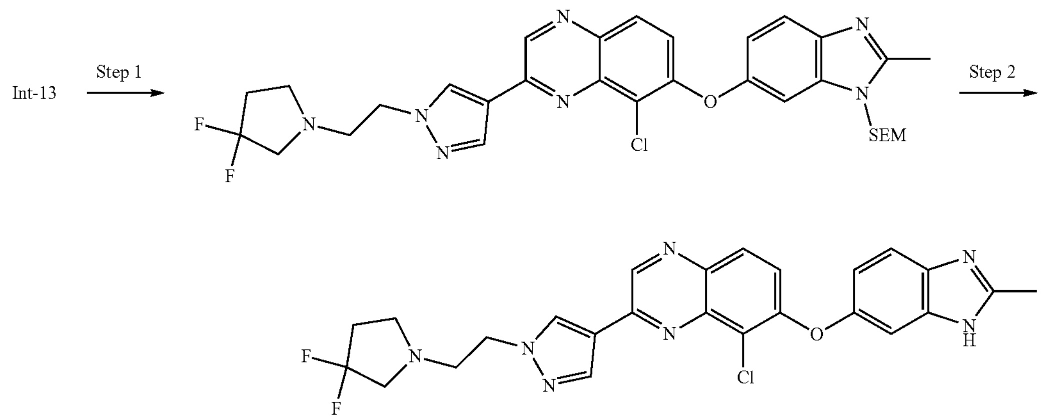

Example 62. Synthesis of 8-Chloro-2-[1-[2-(3,3-difluoroazetidin-1-yl)ethyl]pyrazol-4-yl]-7-[(2-methyl-3H-benzimidazol-5-yl)oxy]quinoxaline

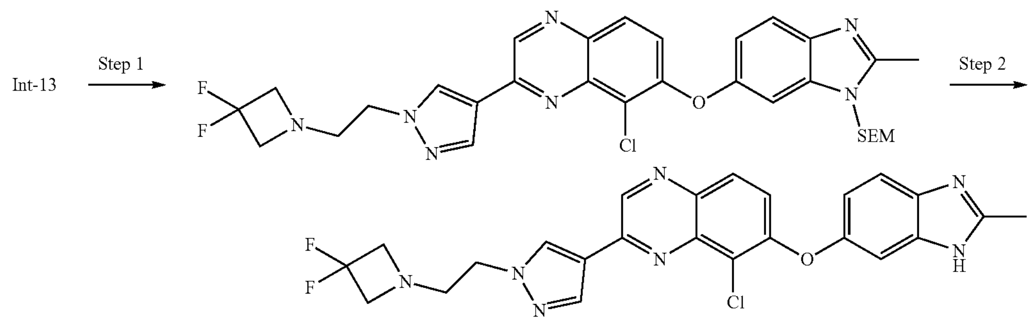

Step 1. 2-[[6-[5-Chloro-3-[1-[2-(3,3-difluoroazetidin-1-yl)ethyl]pyrazol-4-yl]quinoxalin-6-yl]oxy-2-methyl-benzimidazol-1-yl]methoxy]ethyl-trimethyl-silane To a solution of 2-[4-[8-chloro-7-[2-methyl-3-(2-trimethylsilylethoxymethyl)benzimidazol-5-yl]oxy-quinoxalin-2-yl]pyrazol-1-yl]ethyl methanesulfonate (200 mg, 318 μmol) and 3,3-difluoroazetidine hydrochloride (124 mg, 954 μmol) in acetonitrile (3 mL) was added sodium bicarbonate (134 mg, 1.59 mmol), the mixture was stirred at 80° C. for 12 h. The reaction mixture was filtered and concentrated in vacuo and the residue was purified by prep-TLC (silica gel, dichloromethane:methanol=10:1) to give 2-[[6-[5-chloro-3-[1-[2-(3,3-difluoroazetidin-1-yl)ethyl]pyrazol-4-yl]quinoxalin-6-yl]oxy-2-methyl-benzimidazol-1-yl]methoxy]ethyl-trimethyl-silane (37.0 mg, 59.1 μmol, 19%) as a yellow solid. m/z ES+ $[M+H]^+$ 626.2.

Step 2. 8-Chloro-2-[1-[2-(3,3-difluoroazetidin-1-yl)ethyl]pyrazol-4-yl]-7-[(2-methyl-3H-benzimidazol-5-yl)oxy]quinoxaline A solution of 2-[[6-[5-chloro-3-[1-[2-(3,3-difluoroazetidin-1-yl)ethyl]pyrazol-4-yl]quinoxalin-6-yl]oxy-2-methyl-benzimidazol-1-yl]methoxy]ethyl-trimethyl-silane (37.0 mg, 59.1 μmol) in trifluoroacetic acid (1.6 mL) was stirred at 25° C. for 1 h. The reaction mixture was concentrated in vacuo and the residue was purified by prep-HPLC (column: Phenomenex Synergi C18 150*25 mm*10 μm; mobile phase: [water (0.225% formic acid)-acetonitrile]; (B %: 5%-35%, 10 min) and re-purified by prep-TLC (silica gel, dichloromethane:methanol=10:1) to give 8-chloro-2-[1-[2-(3,3-difluoroazetidin-1-yl)ethyl]pyrazol-4-yl]-7-[(2-methyl-3H-benzimidazol-5-yl)oxy]quinoxaline (7.4 mg, 14.9 μmol, 25%) as a white solid. $^1H$ NMR (400 MHz, $CD_3OD$) δ=9.13 (s, 1H), 8.57 (s, 1H), 8.35 (s, 1H), 7.88 (d, J=9.2 Hz, 1H), 7.52 (d, J=8.8 Hz, 1H), 7.33 (d, J=9.2 Hz, 1H), 7.18 (d, J=1.6 Hz, 1H), 7 (dd, J=2.4, 8.8 Hz, 1H), 4.32 (t, J=6.0 Hz, 2H), 3.61 (t, J=12.0 Hz, 4H), 3.13 (t, J=6.0 Hz, 2H), 2.57 (s, 3H); m/z ES+ $[M+H]^+$ 496.0.

Example 63. Synthesis of 3-[4-[8-Chloro-7-[(2-methyl-3H-benzimidazol-5-yl)oxy]quinoxalin-2-yl]pyrazol-1-yl]cyclobutanol

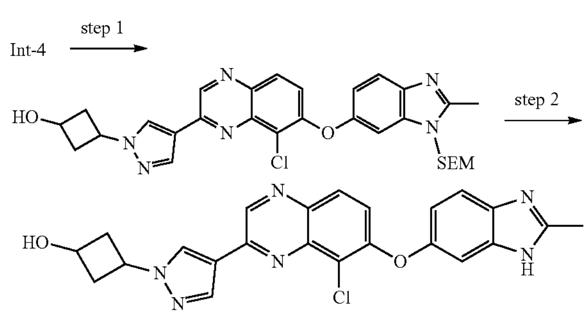

Step 1. 3-[[4-[8-Chloro-7-[2-methyl-3-(2-trimethylsilylethoxymethyl)benzimidazol-5-yloxy-quinoxalin-2-yl]pyrazol-1-yl]cyclobutanol To a solution of 3-[4-[8-chloro-7-[2-methyl-3-(2-trimethylsilylethoxymethyl)benzimidazol-5-yl]oxy-quinoxalin-2-yl]pyrazol-1-yl]cyclobutanone (170 mg, 300 μmol) in ethanol (2 mL) was added sodium borohydride (11.0 mg, 300 μmol) at 0° C., the mixture was stirred at 0° C. for 0.5 h. The reaction mixture was quenched with saturated ammonium chloride solution (30 mL) at 0° C., then diluted with water (20 mL) and extracted with ethyl acetate (4×50 mL). The combined organic layers were washed with water (2×10 mL), dried over sodium sulfate, filtered and concentrated under reduced pressure to give 3-[4-[8-chloro-7-[2-methyl-3-(2-trimethylsilylethoxymethyl)benzimidazol-5-yl]oxy-quinoxalin-2-yl]pyrazol-1-yl]cyclobutanol (180 mg, crude) as a yellow oil. m/z ES+ $[M+H]^+$ 577.1!

Step 2. 3-[4-[8-Chloro-7-[(2-methyl-3H-benzimidazol-5-yl)oxy]quinoxalin-2-yl]pyrazol-1-yl]cyclobutanol A solution of 3-[4-[8-chloro-7-[2-methyl-3-(2-trimethylsilylethoxymethyl)benzimidazol-5-yl]oxy-quinoxalin-2-yl]pyrazol-1-yl]cyclobutanol (170 mg, 300 μmol) in trifluoroacetic acid (1.5 mL) was stirred at 25° C. for 0.5 h. The reaction mixture was concentrated under reduced pressure.

The residue was purified by prep-HPLC (Neutral condition, column: Waters Xbridge 150×25 mm× 5 μm; mobile phase: [water (10 mM ammonium bicarbonate)-acetonitrile]; (B %: 22%-52%, 10 min) to give 3-[4-[8-chloro-7-[(2-methyl-3H-benzimidazol-5-yl)oxy]quinoxalin-2-yl]pyrazol-1-yl]cyclobutanol (5.9 mg, 13.3 μmol, 4.3%) as a white solid. $^1H$ NMR (400 MHz, DMSO-$d_6$) δ=12.38-12.19 (m, 1H), 9.32 (d, J=3.2 Hz, 1H), 8.80-8.76 (m, 1H), 8.38 (s, 1H), 7.96 (dd, J=4.8, 9.2 Hz, 1H), 7.57-7.46 (m, 1H), 7.37-7.27 (m, 1H), 7.26-7.15 (m, 1H), 7.01-6.89 (m, 1H), 5.37-5.26 (m, 1H), 4.57-4.47 (m, 1H), 4.06-3.95 (m, 1H), 2.86-2.75 (m, 2H), 2.49-2.47 (m, 3H), 2.46-2.38 (m, 2H); m/z ES+ $[M+H]^+$ 447.0.

Example 64. Synthesis of 3-[4-[8-Chloro-7-[(2-methyl-3H-benzimidazol-5-yl)oxy]quinoxalin-2-yl]pyrazol-1-yl]-1-methyl-cyclobutanol

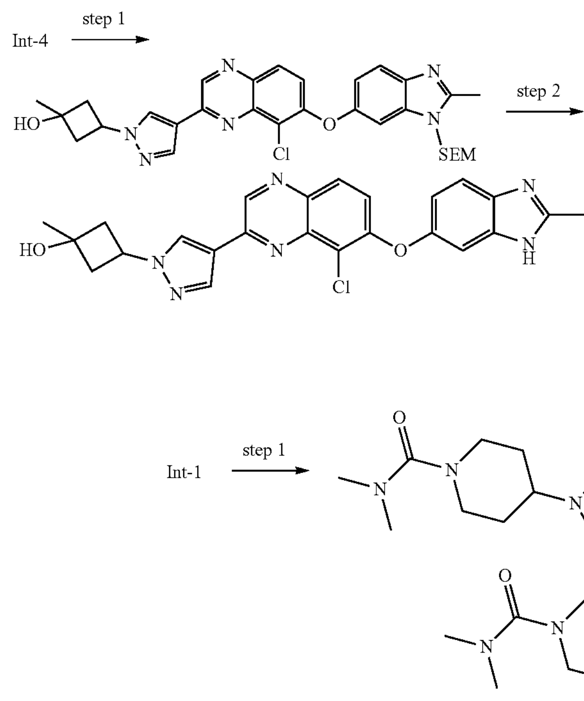

Step 1. 3-[4-[8-Chloro-7-[2-methyl-3-(2-trimethylsilylethoxymethyl)benzimidazol-5-yl]oxy-quinoxalin-2-yl]pyrazol-1-yl]-1-methyl-cyclobutanol To a solution of 3-[4-[8-chloro-7-[2-methyl-3-(2-trimethylsilylethoxymethyl)benzimidazol-5-yl]oxy-quinoxalin-2-yl]pyrazol-1-yl]cyclobutanone (100 mg, 170 μmol) in tetrahydrofuran (3 mL) was added methyl magnesium bromide (3 M in THF, 170 μL) at 0° C. The mixture was stirred at 0° C. for 1 h. The reaction mixture was quenched with saturated ammonium chloride solution (50 mL) at 0° C., then diluted with water (50 mL) and extracted with ethyl acetate (3×50 mL). The combined organic layers were washed with brine (2×25 mL), dried over sodium sulfate, filtered and concentrated under reduced pressure. The residue was purified by prep-TLC (silica gel, dichloromethane:methanol=10:1) to give 3-[4-[8-chloro-7-[2-methyl-3-(2-trimethylsilylethoxymethyl)benzimidazol-5-yl]oxy-quinoxalin-2-yl]pyrazol-1-yl]-1-methyl-cyclobutanol (40.0 mg, 67.7 μmol, 32%) as a white solid. m/z ES+ $[M+H]^+$ 591.1.

Step 2. 3-[4-[8-Chloro-7-[(2-methyl-3H-benzimidazol-5-yl)oxy]quinoxalin-2-yl]pyrazol-1-yl]-1-methyl-cyclobutanol A solution of 3-[4-[8-chloro-7-[2-methyl-3-(2-trimethylsilylethoxymethyl)benzimidazol-5-yl]oxy-quinoxalin-2-yl]pyrazol-1-yl]-1-methyl-cyclobutanol (30.0 mg, 51.0 μmol) in trifluoroacetic acid (0.3 mL) was stirred at 25° C. for 0.5 h. The reaction mixture was concentrated under reduced pressure. The residue was purified by prep-HPLC (neutral condition; column: Waters Xbridge 150×25 mm× 5 μm; mobile phase: [water (10 mM ammonium bicarbonate)-acetonitrile]; (B %: 27%-57%, 10 min) to give 3-[4-[8-chloro-7-[(2-methyl-3H-benzimidazol-5-yl)oxy]quinoxalin-2-yl]pyrazol-1-yl]-1-methyl-cyclobutanol (15.0 mg, 32.5 μmol, 64%) as a white solid. $^1H$ NMR (400 MHz, DMSO-$d_6$) δ=9.33 (s, 1H), 8.77 (s, 1H), 8.38 (s, 1H), 7.96 (d, J=9.2 Hz, 1H), 7.54 (d, J=8.8 Hz, 1H), 7.33 (d, J=9.2 Hz, 1H), 7.24 (s, 1H), 6.97 (d, J=8.4 Hz, 1H), 5.32 (s, 1H), 4.66 (s, 1H), 2.69-2.53 (m, 5H), 2.49-2.49 (m, 3H), 1.35 (s, 3H); m/z ES+ $[M+H]^+$ 461.0.

Example 65. Synthesis of 4-(4-(8-Chloro-7-((2-methyl-1H-benzo[d]imidazol-6-yl)oxy)quinoxalin-2-yl)-1H-pyrazol-1-yl)-N,N-dimethylpiperidine-1-carboxamide

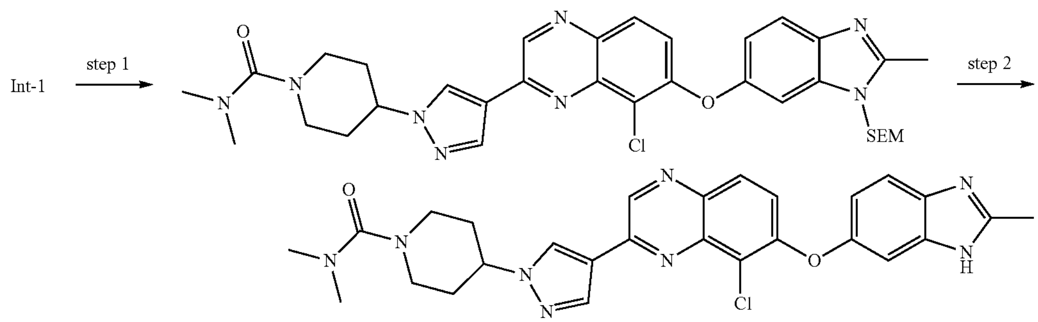

Step 1. 4-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-N,N-dimethylpiperidine-1-carboxamide To a solution of 8-chloro-7-((2-methyl-1-((2-(trimethylsilyl)ethoxy)methyl)-1H-benzo[d]imidazol-6-yl)oxy)-2-(1-(piperidin-4-yl)-1H-pyrazol-4-yl)quinoxaline (50.0 mg, 84.7 μmol) in dichloromethane (1 mL) was added triethylamine (25.7 mg, 254 μmol) and dimethylcarbamic chloride (18.2 mg, 169 μmol) at 0° C. The mixture was stirred at 25° C. for 1 h. The mixture was poured into water (10 mL) and extracted with ethyl acetate (3×30 mL). The combined organic layers were dried by sodium sulfate, filtered and concentrated under reduced pressure to give 4-(4-(8-chloro-7-((2-methyl-1-((2-(trimethylsilyl)ethoxy)methyl)-1H- benzo[d]imidazol-6-yl)oxy)quinoxalin-2-yl)-1H-pyrazol-1-yl)-N,N-dimethylpiperidine-1-carboxamide (50.0 mg, 75.6 μmol, 89%) as a yellow oil.

Step 2. 4-(4-(8-Chloro-7-((2-methyl-1H-benzo[d]imidazol-6-yl)oxy)quinoxalin-2-yl)-1H-pyrazol-1-yl)-N,N-dimethylpiperidine-1-carboxamide A solution of 4-[4-[8-chloro-7-[2-methyl-3-(2-trimethylsilylethoxymethyl)benzimidazol-5-yl]oxy-quinoxalin-2-yl]pyrazol-1-yl]-N,N-dimethyl-piperidine-1-carboxamide (50.0 mg, 75.6 μmol) in trifluoroacetic acid (1 mL) was stirred at 25° C. for 0.5 h. The mixture was concentrated under reduced pressure. The residue was purified by prep-HPLC (column: Phenomenex Luna C18 150*25 mm*10 μm; mobile phase: [water (0.2% formic acid)-acetonitrile]; (B %: 14%-44%, 10 min) to give 4-(4-(8-chloro-7-((2-methyl-1H-benzo[d]imidazol-6-yl)oxy)quinoxalin-2-yl)-1H-pyrazol-1-yl)-N,N-dimethylpiperidine-1-carboxamide (13.4 mg, 25.2 μmol, 32%) as a yellow solid. $^1$H NMR (400 MHz, $CD_3OD$) δ 9.26-9.10 (m, 1H), 8.71-8.58 (m, 1H), 8.44-8.30 (m, 1H), 8.13 (s, 1H), 8.03-7.85 (m, 1H), 7.62 (d, J=8.8 Hz, 1H), 7.46-7.35 (m, 1H), 7.24 (d, J=2.0 Hz, 1H), 7.13 (dd, J=2.4, 8.8 Hz, 1H), 4.61-4.43 (m, 1H), 3.86 (d, J=12.8 Hz, 2H), 3.04 (t, J=11.6 Hz, 2H), 2.92 (s, 6H), 2.68 (s, 3H), 2.29-2.09 (m, 4H); m/z ES+ $[M+H]^+$ 531.1.

Example 66. Synthesis of 3-[4-[8-Chloro-7-[(2-methyl-3H-benzimidazol-5-yl)oxy]quinoxalin-2-yl]pyrazol-1-yl]-2,2-dimethyl-propanenitrile and 3-[4-[8-Chloro-7-[(2-methyl-3H-benzimidazol-5-yl)oxy]quinoxalin-2-yl]pyrazol-1-yl]-2,2-dimethyl-propanamide

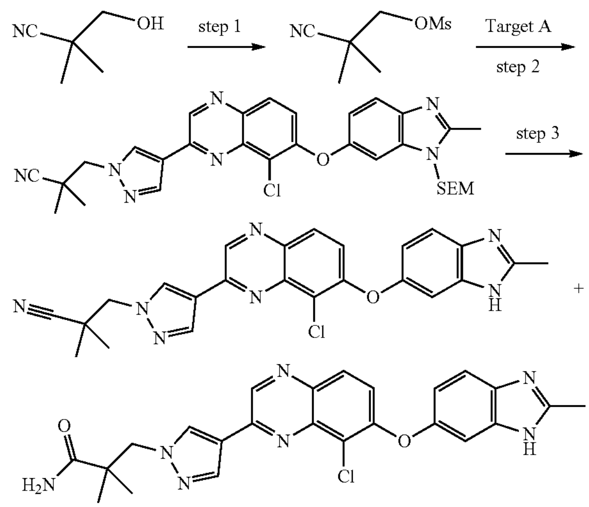

Step 1. (2-Cyano-2-methyl-propyl) methanesulfonate

To a solution of 3-hydroxy-2,2-dimethyl-propanenitrile (200 mg, 2.02 mmol) in ethyl acetate (3 mL) was added methanesulfonyl chloride (347 mg, 3.03 mmol) and triethylamine (612 mg, 6.05 mmol) at 0° C., the mixture was stirred at 25° C. for 2 h. The reaction mixture was diluted with water (3 mL) and extracted with ethyl acetate (3×3 mL). The combined organic layers were washed with brine (3×3 mL), dried over sodium sulfate, filtered and concentrated in vacuo to give (2-cyano-2-methyl-propyl) methanesulfonate (310 mg, 1.75 mmol, 86%) as a yellow oil. $^1$H NMR (400 MHz, $CDCl_3$) δ 4.12 (s, 2H), 3.12 (s, 3H), 1.44 (s, 6H).

Step 2. 3-[4-[8-Chloro-7-[2-methyl-3-(2-trimethylsilylethoxymethyl)benzimidazol-5-yl]oxy-quinoxalin-2-yl]pyrazol-1-yl]-2,2-dimethyl-propanenitrile To a solution of (2-cyano-2-methyl-propyl) methanesulfonate (76.9 mg, 434 μmol) and 2-[[6-[5-chloro-3-(1H-pyrazol-4-yl)quinoxalin-6-yl]oxy-2-methyl-benzimidazol-1-yl]methoxy]ethyl-trimethyl-silane (100 mg, 197 μmol) in N,N-dimethylformamide (1 mL) was added potassium carbonate (54.5 mg, 394 μmol) and potassium iodide (32.7 mg, 197 μmol). The mixture was stirred at 100° C. for 48 h. The reaction mixture was diluted with water (3 mL) and extracted with ethyl acetate (3×3 mL). The combined organic layers were washed with brine (3× 3 mL), dried over sodium sulfate, filtered and concentrated in vacuo to give 3-[4-[8-chloro-7-[2-methyl-3-(2-trimethylsilylethoxymethyl)benzimidazol-5-yl]oxy-quinoxalin-2-yl]pyrazol-1-yl]-2,2-dimethyl-propanenitrile (100 mg, crude) as a yellow oil. m/z ES+ $[M+H]^+$ 588.2.

Step 3. 3-[4-[8-Chloro-7-[(2-methyl-3H-benzimidazol-5-yl)oxy]quinoxalin-2-yl]pyrazol-1-yl]-2,2-dimethyl-propanenitrile and 3-[4-[8-Chloro-7-[(2-methyl-3H-benzimidazol-5-yl)oxy]quinoxalin-2-yl]pyrazol-1-yl]-2,2-dimethyl-propanamide A solution of 3-[4-[8-chloro-7-[2-methyl-3-(2-trimethylsilylethoxymethyl)benzimidazol-5-yl]oxy-quinoxalin-2-yl]pyrazol-1-yl]-2,2-dimethyl-propanenitrile (90.0 mg, 153 μmol) in trifluoroacetic acid (1 mL) was stirred at 25° C. for 1 h. The reaction mixture was filtered and concentrated in vacuo to give a residue and the residue was purified by prep-HPLC (column: Phenomenex Gemini-NX C18 75*30 mm*3 μm; mobile phase: [water (0.225% formic acid)-acetonitrile]; (B %: 12%-42%, 7 min) to give 3-[4-[8-chloro-7-[(2-methyl-3H-benzimidazol-5-yl)oxy]quinoxalin-2-yl]pyrazol-1-yl]-2,2-dimethyl-propanenitrile (11.6 mg, 25.1 μmol, 16%) as a white solid and 3-[4-[8-chloro-7-[(2-methyl-3H-benzimidazol-5-yl)oxy]quinoxalin-2-yl]pyrazol-1-yl]-2,2-dimethyl-propanamide (9.9 mg, 20.7 μmol, 13%) as an off-white solid. $^1$H NMR (400 MHz, $CD_3OD$) δ 9.20 (s, 1H), 8.68 (s, 1H), 8.41 (s, 1H), 8.23-8.17 (m, 1H), 7.93 (d, J=9.2 Hz, 1H), 7.57 (d, J=8.8 Hz, 1H), 7.39 (d, J=9.2 Hz, 1H), 7.21 (d, J=2.4 Hz, 1H), 7.07 (dd, J=2.4, 8.8 Hz, 1H), 4.47 (s, 2H), 2.62 (s, 3H), 1.47 (s, 6H); m/z ES+ $[M+H]^+$ 458.0. $^1$H NMR (400 MHz, DMSO-$d_6$) δ 12.49-12.02 (m, 1H), 9.31 (s, 1H), 8.55 (s, 1H), 8.36 (s, 1H), 8.16 (s, 1H), 7.95 (d, J=9.2 Hz, 1H), 7.59-7.43 (m, 1H), 7.31 (d, J=9.2 Hz, 1H), 7.28-7.14 (m, 2H), 7.07 (s, 1H), 6.94 (d, J=8.8 Hz, 1H), 4.35 (s, 2H), 2.49 (s, 3H), 1.14 (s, 6H); m/z ES+ $[M+H]^+$ 476.1.

Example 67. Synthesis of 2-[[4-[8-Chloro-7-[(2-methyl-3H-benzimidazol-5-yl)oxy]quinoxalin-2-yl]pyrazol-1-yl]methyl]morpholine and 2-[[4-[8-Chloro-7-[(2-methyl-3H-benzimidazol-5-yl)oxy]quinoxalin-2-yl]pyrazol-1-yl]methyl]-4-methyl-morpholine

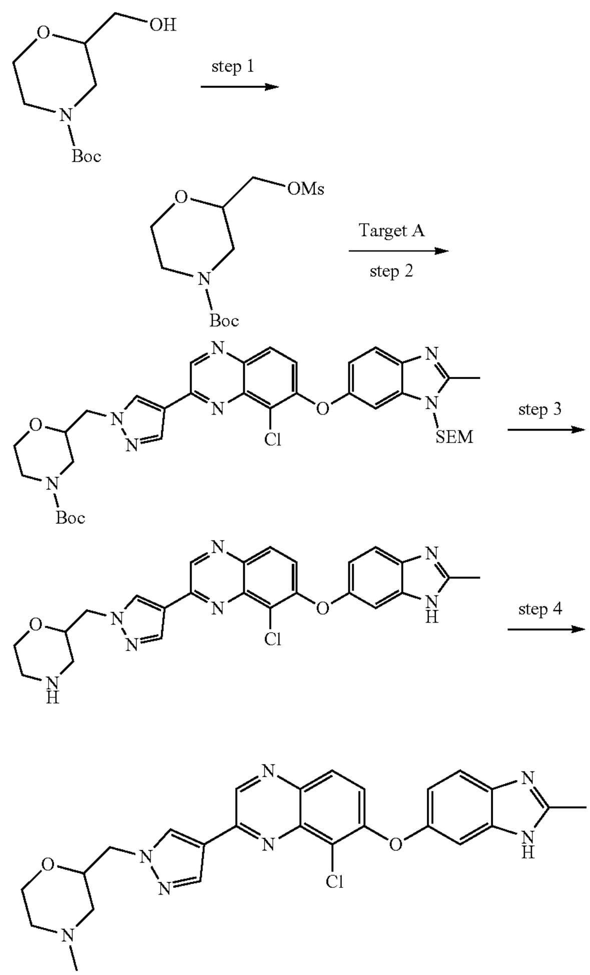

Step 1. tert-Butyl 2-(methylsulfonyloxymethyl) morpholine-4-carboxylate

To a solution of tert-butyl 2-(hydroxymethyl) morpholine-4-carboxylate (1 g, 4.60 mmol) in dichloromethane (10 mL) was added triethylamine (1.40 g, 13.8 mmol), then methanesulfonyl chloride (1.05 g, 9.21 mmol) was added at 0° C. The mixture was stirred at 25° C. for 1 h. The reaction mixture was quenched with water (50 mL) at 20° C. and extracted with ethyl acetate (2×50 mL). The combined organic layers were washed with brine (2×100 mL), dried over sodium sulfate, filtered and concentrated in vacuo to give tert-butyl 2-(methylsulfonyloxymethyl) morpholine-4-carboxylate (1.55 g, crude) as a yellow solid. $^1$H NMR (400 MHz, $CDCl_3$) δ=4.24 (d, J=4.8 Hz, 2H), 4.04-3.80 (m, 3H), 3.74-3.66 (m, 1H), 3.59-3.51 (m, 1H), 3.07 (s, 3H), 3.03-2.71 (m, 2H), 1.47 (s, 9H).

Step 2. tert-Butyl 2-[[4-[8-chloro-7-[2-methyl-3-(2-trimethylsilylethoxymethyl)benzimidazol-5-yl]oxy-quinoxalin-2-yl]pyrazol-1-yl]methyl]morpholine-4-carboxylate To a solution of 2-[[6-[5-chloro-3-(1H-pyrazol-4-yl)quinoxalin-6-yl]oxy-2-methyl-benzimidazol-1-yl]methoxy]ethyl-trimethylsilane (200 mg, 394 μmol) and tert-butyl 2-(methylsulfonyloxymethyl) morpholine-4-carboxylate (175 mg, 592 μmol) in N,N-dimethylformamide (4 mL) was added potassium carbonate (164 mg, 1.18 mmol). The mixture was stirred at 80° C. for 12 h. The reaction mixture was diluted with water (50 mL) and extracted with ethyl acetate (2×50 mL). The combined organic layers were washed with brine (2×100 mL), dried over sodium sulfate, filtered and concentrated in vacuo to give tert-butyl 2-[[4-[8-chloro-7-[2-methyl-3-(2-trimethylsilylethoxymethyl)benzimidazol-5-yl]oxy-quinoxalin-2-yl]pyrazol-1-yl]methyl]morpholine-4-carboxylate (315 mg, crude) as a yellow solid. m/z ES+ $[M+H]^+$ 706.4.

Step 3. 2-[[4-[8-Chloro-7-[(2-methyl-3H-benzimidazol-5-yl)oxy]quinoxalin-2-yl]pyrazol-1-yl]methyl]morpholine A solution of tert-butyl 2-[[4-[8-chloro-7-[2-methyl-3-(2-trimethylsilylethoxymethyl)benzimidazol-5-yl]oxy-quinoxalin-2-yl]pyrazol-1-yl]methyl]morpholine-4-carboxylate (500 mg, 708 μmol) in trifluoroacetic acid (5 mL) was stirred at 25° C. for 1 h. The reaction mixture was concentrated in vacuo and the residue was purified by prep-HPLC (column: Phenomenex Synergi C18 150*25 mm*10 μm; mobile phase: [water (0.225% formic acid)-acetonitrile]; (B %: 1%-30%, 10 min) to give 2-[[4-[8-chloro-7-[(2-methyl-3H-benzimidazol-5-yl)oxy]quinoxalin-2-yl]pyrazol-1-yl]methyl]morpholine (227 mg, 477 μmol, 68%) as a yellow solid. $^1$H NMR (400 MHz, DMSO-$d_6$) δ=9.32 (s, 1H), 8.65 (s, 1H), 8.39 (s, 1H), 8.22 (s, 1H), 7.95 (d, J=9.2 Hz, 1H), 7.51 (d, J=8.8 Hz, 1H), 7.32 (d, J=9.2 Hz, 1H), 7.21 (d, J=2.4 Hz, 1H), 6.94 (dd, J=2.4, 8.8 Hz, 1H), 4.43-4.28 (m, 2H), 4.01 (dd, J=4.4, 6.0 Hz, 1H), 3.90 (dd, J=2.4, 12.0 Hz, 1H), 3.65-3.51 (m, 1H), 3.14 (d, J=12.0 Hz, 1H), 2.98 (d, J=12.4 Hz, 1H), 2.89-2.77 (m, 1H), 2.69 (t, J=11.6 Hz, 1H), 2.49 (s, 3H); m/z ES+ $[M+H]^+$ 476.1

Step 4. 2-[[4-[8-Chloro-7-[(2-methyl-3H-benzimidazol-5-yl)oxy]quinoxalin-2-yl]pyrazol-1-yl]methyl]-4-methyl-morpholine To a solution of 2-[[4-[8-chloro-7-[(2-methyl-3H-benzimidazol-5-yl)oxy]quinoxalin-2-yl] pyrazol-1-yl]methyl]morpholine (150 mg, 315 μmol) in N,N-dimethylformamide (2 mL) was added paraformaldehyde (189 mg, 6.30 mmol) and formic acid (15.1 mg, 315 μmol). The mixture was stirred at 60° C. for 1.5 h. The reaction mixture was filtered and concentrated in vacuo and the residue was purified by prep-HPLC (column: Waters Xbridge 150*25 mm*5 μm; mobile phase: [water (10 mM ammonium bicarbonate)-acetonitrile]; (B %: 25%-55%, 10 min) to give 2-[[4-[8-chloro-7-[(2-methyl-3H-benzimidazol-5-yl)oxy]quinoxalin-2-yl]pyrazol-1-yl]methyl]-4-methyl-morpholine (15.2 mg, 31.0 μmol, 9%) as a white solid. $^1$H NMR (400 MHz, DMSO-$d_6$) δ=9.32 (s, 1H), 8.66 (s, 1H), 8.39 (s, 1H), 7.96 (d, J=9.2 Hz, 1H), 7.51 (d, J=8.8 Hz, 1H), 7.32 (d, J=9.2 Hz, 1H), 7.21 (d, J=2.0 Hz, 1H), 6.94 (dd, J=2.4, 8.8 Hz, 1H), 4.34 (d, J=5.6 Hz, 2H), 4.38-4.31 (m, 1H), 3.99-3.84 (m, 2H), 3.53 (t, J=10.8 Hz, 1H), 3-2.69 (m, 2H), 2.49 (s, 3H), 2.33 (s, 3H), 2.27-1.94 (m, 2H); m/z ES+ $[M+H]^+$ 490.1.

Example 68. Synthesis of 8-Chloro-2-(1-((3S,4S)-3-fluoro-1-(2,2,2-trifluoroethyl) piperidin-4-yl)-1H-pyrazol-4-yl)-7-((2-methyl-1H-benzo[d]imidazol-6-yl)oxy)quinoxaline

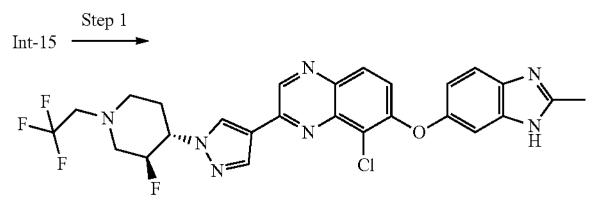

Step 1. 8-Chloro-2-(1-((3S,4S)-3-fluoro-1-(2,2,2-trifluoroethyl) piperidin-4-yl)-1H-pyrazol-4-yl)-7-((2-methyl-1H-benzo[d]imidazol-6-yl)oxy)quinoxaline To a solution of 8-chloro-2-(1-((3S,4S)-3-fluoropiperidin-4-yl)-1H-pyrazol-4-yl)-7-((2-methyl-1H-benzo[d]imidazol-6-yl)oxy)quinoxaline (50.0 mg, 105 μmol) in N,N-dimethylformamide (1 mL) was added diisopropylethylamine (27.0 mg, 209 μmol) and 2,2,2-trifluoroethyl trifluoromethanesulfonate (29.1 mg, 126 μmol), the mixture was stirred at 25° C. for 2 h. The reaction mixture was quenched with water (0.5 mL) and concentrated under reduced pressure. The residue was purified by prep-HPLC (neutral condition; column: Waters Xbridge 150*25 mm*5 μm; mobile phase: [water (10 mM ammonium bicarbonate)-acetonitrile]; (B %: 45%-75%, 8 min) to give 8-chloro-2-(1-((3S,4S)-3-fluoro-1-(2,2,2-trifluoroethyl) piperidin-4-yl)-1H-pyrazol-4-yl)-7-((2-methyl-1H-benzo[d]imidazol-6-yl)oxy)quinoxaline (10.4 mg, 18.0 μmol, 17%) as a yellow solid. $^1H$ NMR (400 MHz, DMSO-$d_6$) δ 9.33 (s, 1H), 8.85 (s, 1H), 8.43 (s, 1H), 7.98 (d, J=9.2 Hz, 1H), 7.58 (d, J=8.8 Hz, 1H), 7.36 (d, J=9.2 Hz, 1H), 7.28 (d, J=1.6 Hz, 1H), 7.03 (dd, J=2.4, 8.8 Hz, 1H), 5.07-4.88 (m, 1H), 4.61-4.51 (m, 1H), 3.41 (q, J=10.0 Hz, 3H), 3.01 (d, J=11.6 Hz, 1H), 2.70-2.61 (m, 1H), 2.56 (s, 3H), 2.18-2.05 (m, 2H); m/z ES+ $[M+H]^+$ 560.1.

Example 69. Synthesis of (E)-4-((3S,4S)-4-(4-(8-Chloro-7-((2-methyl-1H-benzo[d]imidazol-6-yl)oxy) quinoxalin-2-yl)-1H-pyrazol-1-yl)-3-fluoropiperidin-1-yl) but-3-en-2-one

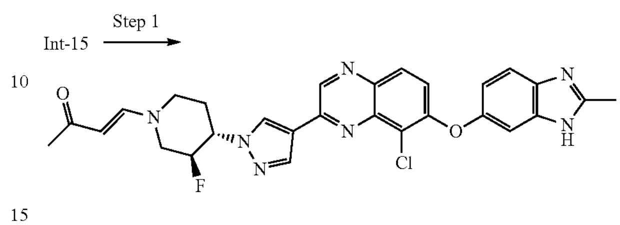

Step 1. (E)-4-((3S,4S)-4-(4-(8-Chloro-7-((2-methyl-1H-benzo[d]imidazol-6-yl)oxy)quinoxalin-2-yl)-1H-pyrazol-1-yl)-3-fluoropiperidin-1-yl) but-3-en-2-one To a solution of 8-chloro-2-(1-((3S,4S)-3-fluoropiperidin-4-yl)-1H-pyrazol-4-yl)-7-((2-methyl-1H-benzo[d]imidazol-6-yl)oxy)quinoxaline (50.0 mg, 105 μmol), 3-hydroxycyclobutanone (13.5 mg, 157 μmol) in dichloromethane (1 mL) was added triethylamine (12.7 mg, 126 μmol) and sodium triacetoxyborohydride (24.4 mg, 115 μmol), the mixture was stirred at 25° C. for 13 h. The reaction mixture was quenched with methanol (0.2 mL) at 25° C. and concentrated under reduced pressure. The residue was purified by prep-HPLC (neutral condition; column: Waters Xbridge 150*25 mm*5 μm; mobile phase: [water (10 mM ammonium bicarbonate)-acetonitrile]; (B %: 27%-57%, 10 min) to give (E)-4-((3S,4S)-4-(4-(8-chloro-7-((2-methyl-1H-benzo[d]imidazol-6-yl)oxy)quinoxalin-2-yl)-1H-pyrazol-1-yl)-3-fluoropiperidin-1-yl) but-3-en-2-one (16.4 mg, 28.5 μmol, 27%) as a yellow solid. $^1H$ NMR (400 MHz, $CD_3OD$) δ 9.16 (s, 1H), 8.67 (s, 1H), 8.41 (s, 1H), 7.90 (d, J=10.0 Hz, 1H), 7.66 (d, J=12.8 Hz, 1H), 7.53 (d, J=8.0 Hz, 1H), 7.35 (d, J=8.8 Hz, 1H), 7.18 (s, 1H), 7.01 (d, J=8.0 Hz, 1H), 5.42 (d, J=12.4 Hz, 1H), 5.09-4.96 (m, 1H), 4.77-4.54 (m, 2H), 4.22-4.11 (m, 1H), 3.89-3.78 (m, 1H), 3.45-3.34 (m, 1H), 2.57 (s, 3H), 2.39-2.24 (m, 2H), 2.15 (s, 3H); m/z ES+ $[M+H]^+$ 546.1.

Example 70. Synthesis of Azetidin-1-yl(4-(4-(8-chloro-7-((2-methyl-1H-benzo[d]imidazol-6-yl)oxy) quinoxalin-2-yl)-1H-pyrazol-1-yl) piperidin-1-yl) methanone

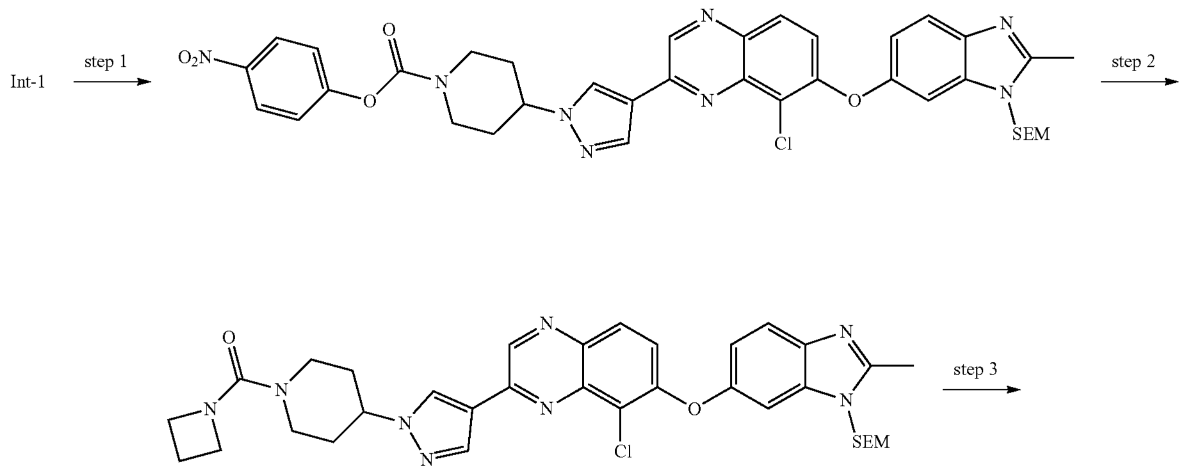

-continued

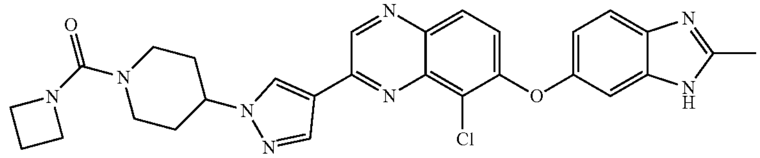

Step 1. 4-Nitrophenyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate To a solution of 8-chloro-7-((2-methyl-1-((2-(trimethylsilyl)ethoxy)methyl)-1H-benzo[d]imidazol-6-yl)oxy)-2-(1-(piperidin-4-yl)-1H-pyrazol-4-yl)quinoxaline (100 mg, 169 μmol), triethylamine (51.4 mg, 508 μmol) in dichloromethane (1 mL) was added 4-nitrophenyl carbonochloridate (68.3 mg, 338 μmol), the mixture was stirred at 25° C. for 1 h. The mixture was concentrated in vacuo and the residue was purified by column chromatography (silica gel, petroleum ether/ethyl acetate=1:1 to 0/1) to give 4-nitrophenyl 4-(4-(8-chloro-7-((2-methyl-1-((2-(trimethylsilyl)ethoxy) methyl)-1H-benzo[d]imidazol-6-yl)oxy)quinoxalin-2-yl)-1H-pyrazol-1-yl) piperidine-1-carboxylate (80.0 mg, 105 μmol, 62%) as a colorless oil. m/z ES+ $[M+H]^+$ 755.4.

Step 2. Azetidin-1-yl(4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidin-1-yl) methanone A solution of 4-nitrophenyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (80.0 mg, 105 μmol), azetidine (19.8 mg, 211 μmol), triethylamine (32.1 mg, 317 μmol) in tetrahydrofuran (1 mL) was stirred at 60° C. for 16 h. The mixture was poured into water (20 mL) and extracted with ethyl acetate (3×30 mL). The combined organic layers were dried by sodium sulfate, filtered and concentrated in vacuo to give azetidin-1-yl(4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidin-1-yl) methanone (70.0 mg, 103 μmol, 98%) as a yellow oil. m/z ES+ $[M+H]^+$ 673.4.

Step 3. Azetidin-1-yl(4-(4-(8-chloro-7-((2-methyl-1H-benzo[d]imidazol-6-yl)oxy)quinoxalin-2-yl)-1H-pyrazol-1-yl) piperidin-1-yl) methanone A solution of azetidin-1-yl(4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidin-1-yl) methanone (70.0 mg, 103 μmol) in trifluoroacetic acid (1 mL) was stirred at 25° C. for 10 min. The mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 15%-45%, 7 min) to give azetidin-1-yl(4-(4-(8-chloro-7-((2-methyl-1H-benzo[d]imidazol-6-yl)oxy)quinoxalin-2-yl)-1H-pyrazol-1-yl) piperidin-1-yl) methanone (20.5 mg, 37.7 μmol, 36%) as an off-white solid. $^1$H NMR (400 MHz, DMSO-$d_6$) δ 9.31 (s, 1H), 8.78 (s, 1H), 8.35 (s, 1H), 8.23 (s, 1H), 7.95 (d, J=9.2 Hz, 1H), 7.51 (d, J=7.6 Hz, 1H), 7.30 (d, J=8.4 Hz, 1H), 7.21 (s, 1H), 6.94 (d, J=8.4 Hz, 1H), 4.52 (s, 1H), 3.98-3.81 (m, 6H), 2.91 (t, J=12.8 Hz, 2H), 2.49-2.46 (m, 3H), 2.23-2.01 (m, 4H), 1.95-1.76 (m, 2H); m/z ES+ $[M+H]^+$ 543.1.

Example 71. Synthesis of 3-[4-[8-Chloro-7-[(2-methyl-3H-benzimidazol-5-yl)oxy]quinoxalin-2-yl]pyrazol-1-yl]cyclobutanone

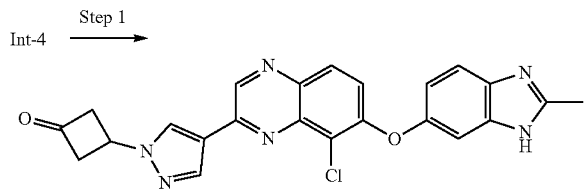

Step 1. 3-[4-[8-Chloro-7-[(2-methyl-3H-benzimidazol-5-yl)oxy]quinoxalin-2-yl]pyrazol-1-yl]cyclobutanone A solution of 3-[4-[8-chloro-7-[2-methyl-3-(2-trimethylsilylethoxymethyl)benzimidazol-5-yl]oxy-quinoxalin-2-yl]pyrazol-1-yl]cyclobutanone (30.0 mg, 52.2 μmol) in trifluoroacetic acid (0.3 mL) was stirred at 25° C. for 0.5 h. The reaction mixture was concentrated under reduced pressure. The residue was purified by prep-HPLC (formic acid condition; column: Phenomenex Luna C18 150×25 mm×10 μm; mobile phase: [water (0.225% formic acid)-acetonitrile]; (B %: 9%-39%, 10 min) to give 3-[4-[8-chloro-7-[(2-methyl-3H-benzimidazol-5-yl)oxy]quinoxalin-2-yl]pyrazol-1-yl] cyclobutanone (12.5 mg, 27.5 μmol, 52%) as a yellow gum. $^1$HNMR (400 MHz, DMSO-$d_6$) δ=9.33 (s, 1H), 8.95 (s, 1H), 8.45 (s, 1H), 7.96 (d, J=9.2 Hz, 1H), 7.52 (d, J=8.8 Hz, 1H), 7.33 (d, J=9.2 Hz, 1H), 7.23 (d, J=2.0 Hz, 1H), 6.96 (dd, J-2.4, 8.8 Hz, 1H), 5.41-5.31 (m, 1H), 3.70-3.64 (m, 4H), 2.50 (s, 3H); m/z ES+ $[M+H]^+$ 445.0.

Example 72. Synthesis of 8-Bromo-2-(1-((3,3-difluorocyclobutyl)methyl)-1H-pyrazol-4-yl)-7-((2-methyl-1H-benzo[d]imidazol-6-yl)oxy)quinoxaline

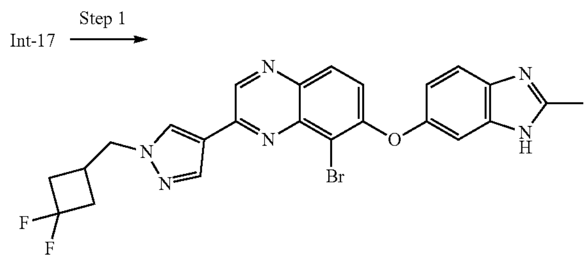

Step 1. 8-Bromo-2-(1-((3,3-difluorocyclobutyl) methyl)-1H-pyrazol-4-yl)-7-((2-methyl-1H-benzo[d] imidazol-6-yl)oxy)quinoxaline A solution of 8-bromo-2-(1-((3,3-difluorocyclobutyl) methyl)-1H-pyrazol-4-yl)-7-((2-methyl-1-((2-(trimethylsilyl)ethoxy)methyl)-1H-benzo[d]imidazol-6-yl)oxy)quinoxaline (55.0 mg, 83.9 μmol) in trifluoroacetic acid (1 mL) was stirred at 25° C. for 1 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 16%-46%, 10 min) to give 8-bromo-2-(1-((3,3-difluorocyclobutyl) methyl)-1H-pyrazol-4-yl)-7-((2-methyl-1H-benzo[d]imidazol-6-yl)oxy)quinoxaline (22.2 mg, 42.3 μmol, 50%) as a white solid. $^1$H NMR (400 MHz, $CD_3OD$) δ ppm=9.13 (s, 1H), 8.60 (s, 1H), 8.35 (s, 1H), 7.94 (d, J=9.2 Hz, 1H), 7.59 (d, J=8.7 Hz, 1H), 7.35 (d, J=9.2 Hz, 1H), 7.22 (d, J=1.6 Hz, 1H), 7.10 (dd, J=1.6, 8.8 Hz, 1H), 4.40 (d, J=6.8 Hz, 2H), 2.83-2.66 (m, 3H), 2.65 (s, 3H), 2.56-2.42 (m, 2H); m/z ES+ [M+H]$^+$ 525.0.

Example 73. Synthesis of 3-((4-(8-chloro-7-((2-methyl-1H-benzo[d]imidazol-6-yl)oxy)quinoxalin-2-yl)-1H-pyrazol-1-yl)methyl) morpholine and 3-((4-(8-chloro-7-((2-methyl-1H-benzo[d]imidazol-6-yl) oxy)quinoxalin-2-yl)-1H-pyrazol-1-yl)methyl)-4-methylmorpholine

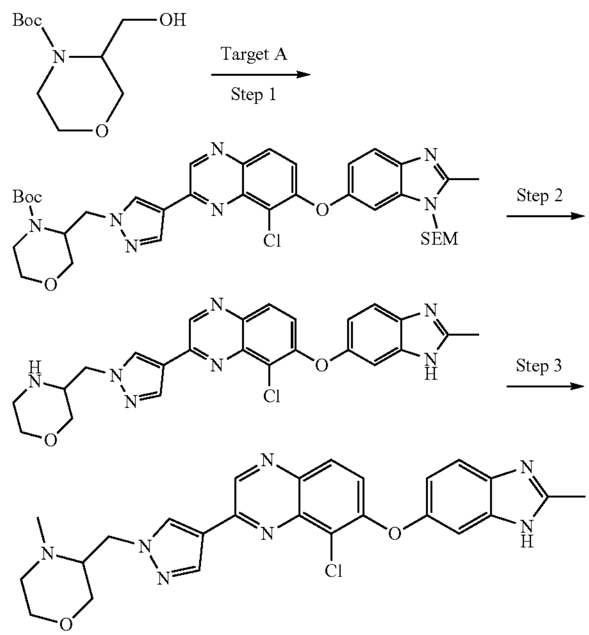

Step 1. tert-Butyl 3-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) methyl) morpholine-4-carboxylate To a solution of 2-[[6-[5-chloro-3-(1H-pyrazol-4-yl)quinoxalin-6-yl]oxy-2-methyl-benzimidazol-1-yl]methoxy] ethyl-trimethyl-silane (300 mg, 591 μmol), tert-butyl 3-(hydroxymethyl) morpholine-4-carboxylate (154 mg, 709 μmol) in toluene (5 mL) was added diisopropyl azodicarboxylate (179 mg, 887 μmol) and triphenylphosphine (232 mg, 887 μmol), the mixture was stirred at 60° C. for 12 h under nitrogen atmosphere. The reaction mixture was quenched with water (20 mL) at 25° C. and extracted with ethyl acetate (3×10$^0$ mL). The combined organic layers were washed with brine (3×10 mL), dried by sodium sulfate, filtered and concentrated under reduced pressure. The residue was purified by reversed-phase HPLC (0.1% formic acid condition) to give tert-butyl 3-((4-(8-chloro-7-((2-methyl-1-((2-(trimethylsilyl)ethoxy)methyl)-1H-benzo[d] imidazol-6-yl)oxy)quinoxalin-2-yl)-1H-pyrazol-1-yl) methyl) morpholine-4-carboxylate (150 mg, 212 μmol, 35%) as a yellow solid. m/z ES+ [M+H]$^+$ 706.3.

Step 2. 3-((4-(8-Chloro-7-((2-methyl-1H-benzo[d] imidazol-6-yl)oxy)quinoxalin-2-yl)-1H-pyrazol-1-yl) methyl) morpholine A solution of tert-butyl 3-[[4-[8-chloro-7-[2-methyl-3-(2-trimethylsilylethoxymethyl)benzimidazol-5-yl]oxy-quinoxalin-2-yl]pyrazol-1-yl]methyl]morpholine-4-carboxylate (150 mg, 42.4 μmol) in trifluoroacetic acid (7.70 g, 67.5 mmol) was stirred at 25° C. for 3 h. The mixture was concentrated in vacuo and the residue was purified by prep-HPLC (column: Waters Xbridge 150*25 mm*5 μm; mobile phase: [water (10 mM ammonium bicarbonate)-acetonitrile]; (B %: 19%-49%, 8 min) to give 3-((4-(8-chloro-7-((2-methyl-1H-benzo[d]imidazol-6-yl)oxy)quinoxalin-2-yl)-1H-pyrazol-1-yl)methyl) morpholine (120 mg, 252 μmol, 80%) as a white solid. $^1$H NMR (400 MHz, $CD_3OD$) δ 9.13 (s, 1H), 8.56 (s, 1H), 8.37 (s, 1H), 7.88 (d, J=9.2 Hz, 1H), 7.53 (d, J=8.8 Hz, 1H), 7.33 (d, J=9.2 Hz, 1H), 7.18 (s, 1H), 7.07-6.94 (m, 1H), 4.31-4.18 (m, 2H), 3.85-3.74 (m, 2H), 3.60-3.50 (m, 1H), 3.33 (d, J=6.8 Hz, 2H), 2.99-2.82 (m, 2H), 2.57 (s, 3H); m/z ES+ [M+H]$^+$ 476.1.

Step 3. 3-((4-(8-Chloro-7-((2-methyl-1H-benzo[d] imidazol-6-yl)oxy)quinoxalin-2-yl)-1H-pyrazol-1-yl) methyl)-4-methylmorpholine A solution of 3-[[4-[8-chloro-7-[(2-methyl-3H-benzimidazol-5-yl)oxy]quinoxalin-2-yl] pyrazol-1-yl]methyl]morpholine (70.0 mg, 118 μmol), formic acid (114 mg, 2.37 mmol), paraformaldehyde (71.2 mg, 2.37 mmol) in N,N-dimethylformamide (2 mL) was stirred at 60° C. for 16 h. The mixture was filtered and concentrated in vacuo. The residue was purified by prep-HPLC (column: Waters Xbridge 150*25 mm*5 μm; mobile phase: [water (10 mM ammonium bicarbonate)-acetonitrile]; (B %: 23%-53%, 9 min) to give 3-((4-(8-chloro-7-((2-methyl-1H-benzo[d]imidazol-6-yl)oxy)quinoxalin-2-yl)-1H-pyrazol-1-yl)methyl)-4-methylmorpholine (16.0 mg, 32.7 μmol, 27%) as a white solid. $^1$H NMR (400 MHz, DMSO-$d_6$) δ 12.42-12.18 (m, 1H), 9.31 (s, 1H), 8.72 (s, 1H), 8.37 (s, 1H), 7.96 (d, J=9.2 Hz, 1H), 7.66-7.42 (m, 1H), 7.39-7.11 (m, 2H), 6.94 (t, J=9.6 Hz, 1H), 4.53-4.44 (m, 1H), 4.31-4.22 (m, 1H), 3.66 (d, J=11.2 Hz, 1H), 3.59-3.53 (m, 1H), 3.46 (t, J=9.2 Hz, 1H), 3.30-3.22 (m, 1H), 2.70 (d, J=12.0 Hz, 1H), 2.59-2.56 (m, 1H), 2.49-2.49 (m, 3H), 2.37 (s, 3H), 2.28-2.19 (m, 1H); m/z ES+ [M+H]$^+$ 490.1.

Example 74. Synthesis of 8-Chloro-2-[1-[(1-fluorocyclopropyl)methyl]pyrazol-4-yl]-7-[(2-methyl-3H-benzimidazol-5-yl)oxy]quinoxaline

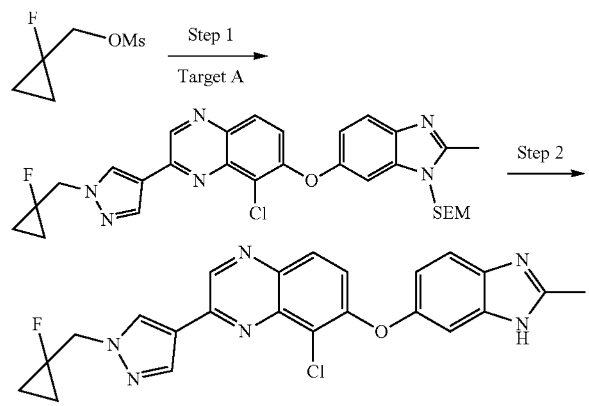

Step 1. 2-[[6-[5-Chloro-3-[1-[(1-fluorocyclopropyl)methyl]pyrazol-4-yl]quinoxalin-6-yl]oxy-2-methyl-benzimidazol-1-yl]methoxy]ethyl-trimethyl-silane A mixture of 2-[[6-[5-chloro-3-(1H-pyrazol-4-yl)quinoxalin-6-yl]oxy-2-methyl-benzimidazol-1-yl]methoxy]ethyl-trimethyl-silane (70.0 mg, 138 μmol), (1-fluorocyclopropyl)methyl methanesulfonate (23.2 mg, 138 μmol), potassium carbonate (57.2 mg, 414 μmol) in N,N-dimethylformamide (1 mL) was stirred at 80° C. for 12 h under nitrogen atmosphere. The reaction mixture was diluted with water (30 mL) and extracted with ethyl acetate (3×30 mL). The combined organic layer were dried over sodium sulphate, concentrated under reduced pressure. The residue was purified by column chromatography (petroleum ether/ethyl acetate=0:1) to give 2-[[6-[5-chloro-3-[1-[(1-fluorocyclopropyl)methyl]pyrazol-4-yl]quinoxalin-6-yl]oxy-2-methyl-benzimidazol-1-yl]methoxy]ethyl-trimethyl-silane (70.0 mg, 120 μmol, 87%) as a yellow solid. m/z ES+ $[M+1]^+$ 579.2.

Step 2. 8-Chloro-2-[1-[(1-fluorocyclopropyl)methyl]pyrazol-4-yl]-7-[(2-methyl-3H-benzimidazol-5-yl)oxy]quinoxaline A mixture of 2-[[6-[5-chloro-3-[1-[(1-fluorocyclopropyl)methyl]pyrazol-4-yl]quinoxalin-6-yl]oxy-2-methyl-benzimidazol-1-yl]methoxy]ethyl-trimethyl-silane (65.0 mg, 112 μmol) in trifluoroacetic acid (1 mL) was stirred at 25° C. for 1 h. The reaction mixture was diluted with water (10 mL) and extracted with ethyl acetate (3×30 mL). The combined organic layer were dried over sodium sulphate, concentrated under reduced pressure. The residue was purified by prep-HPLC (column: Phenomenex Gemini-NX C18 75*30 mm*3 μm; mobile phase: [water (0.225% formic acid)-acetonitrile]; (B %: 15%-45%, 7 min) to give 8-chloro-2-[1-[(1-fluorocyclopropyl)methyl]pyrazol-4-yl]-7-[(2-methyl-3H-benzimidazol-5-yl)oxy]quinoxaline (44.0 mg, 98.0 μmol, 85%) as a white solid. $^1H$ NMR (400 MHz, DMSO-$d_6$) δ=12.35-12.17 (m, 1H), 9.35 (s, 1H), 8.76 (s, 1H), 8.41 (s, 1H), 7.96 (d, J=9.2 Hz, 1H), 7.50 (s, 1H), 7.32 (d, J=9.2 Hz, 1H), 7.21 (s, 1H), 6.96-6.92 (m, 1H), 4.68 (d, J=22.4 Hz, 2H), 2.50 (s, 3H), 1.17-1 (m, 4H); m/z ES+ $[M+H]^+$ 449.0.

Example 75. Synthesis of (1R,4R)-5-[2-[4-[8-Chloro-7-[(2-methyl-3H-benzimidazol-5-yl)oxy]quinoxalin-2-yl]pyrazol-1-yl]ethyl]-2-oxa-5-azabicyclo[2.2.1]heptane

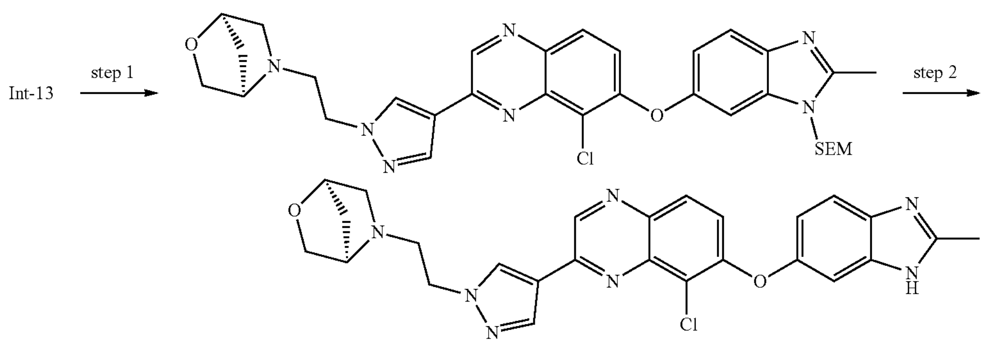

Step 1. 2-[[6-[5-Chloro-3-[1-[2-[(1R,4R)-2-oxa-5-azabicyclo[2.2.1]heptan-5-yl]ethyl]pyrazol-4-yl]quinoxalin-6-yl]oxy-2-methyl-benzimidazol-1-yl]methoxy]ethyl-trimethyl-silane To a mixture of 2-[4-[8-chloro-7-[2-methyl-3-(2-trimethylsilylethoxymethyl)benzimidazol-5-yl]oxy-quinoxalin-2-yl]pyrazol-1-yl]ethyl methanesulfonate (300 mg, 476 μmol) and (1R,4R)-2-oxa-5-azabicyclo[2.2.1]heptane;hydrochloride (193 mg, 1.43 mmol) in acetonitrile (5 mL) was added sodium bicarbonate (200 mg, 2.38 mmol), the reaction mixture was stirred at 80° C. for 12 h. The reaction mixture was quenched with water (40 mL) and extracted with ethyl acetate (2×50 mL). The combined organic layers were washed with brine (2×50 mL), dried over anhydrous sodium sulfate, filtered and concentrated under reduced pressure. The residue was purified by prep-TLC (silica gel, petroleum ether:ethyl acetate=0:1) to give 2-[[6-[5-chloro-3-[1-[2-[(1R,4R)-2-oxa-5-azabicyclo[2.2.1]heptan-5-yl]ethyl]pyrazol-4-yl]quinoxalin-6-yl]oxy-2-methyl-benzimidazol-1-yl]methoxy]ethyl-trimethyl-silane (60.0 mg, 94.9 μmol, 19%) as a yellow solid. m/z ES+ $[M+H]^+$ 632.5.

Step 2. (1R,4R)-5-[2-[4-[8-Chloro-7-[(2-methyl-3H-benzimidazol-5-yl)oxy]quinoxalin-2-yl]pyrazol-1-yl]ethyl]-2-oxa-5-azabicyclo[2.2.1]heptane A solution of 2-[[6-[5-chloro-3-[1-[2-[(1R,4R)-2-oxa-5-azabicyclo[2.2.1]heptan-5-yl]ethyl]pyrazol-4-yl]quinoxalin-6-yl]oxy-2-methyl-benzimidazol-1-yl]methoxy]ethyl-trimethyl-silane (50.0 mg, 79.0 μmol) in trifluoroacetic acid (1 mL) was stirred at 25° C. for 30 min. The reaction mixture was concentrated in vacuo and the residue was purified by prep-HPLC (column: Waters Xbridge 150*25 mm*5 μm; mobile phase: [water (10 mM ammonium bicarbonate)-acetonitrile]; (B %: 24%-54%, 10 min) to give (1R,4R)-5-[2-[4-[8-chloro-7-[(2-methyl-3H-benzimidazol-5-yl)oxy] quinoxalin-2-yl]pyrazol-1-yl]ethyl]-2-oxa-5-azabicyclo [2.2.1]heptane (1.5 mg, 2.93 μmol, 3%) as a yellow solid. $^1$H NMR (400 MHz, DMSO-$d_6$) δ=12.44-12.09 (m, 1H), 9.31 (s, 1H), 8.71 (br s, 1H), 8.36 (br s, 1H), 8.04-7.85 (m, 1H), 7.57-7.44 (m, 1H), 7.38-7.27 (m, 1H), 7.27-7.13 (m, 1H), 7-6.86 (m, 1H), 4.35-4.23 (m, 2H), 3.84-3.80 (m, 1H), 3.51-3.46 (m, 2H), 3.12-2.89 (m, 2H), 2.85-2.76 (m, 1H), 2.49-2.47 (m, 3H), 2.45-2.32 (m, 1H), 1.76-1.68 (m, 1H), 1.60-1.53 (m, 1H), 1.24 (s, 1H); m/z ES+ $[M+H]^+$ 502.1.

Example 76. Synthesis of 8-Chloro-7-[(2-methyl-3/I-benzimidazol-5-yl)oxy]-2-[1-(1-tetrahydropyran-4-ylazetidin-3-yl)pyrazol-4-yl]quinoxaline

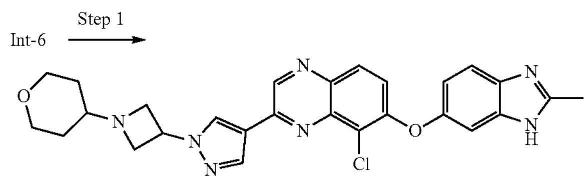

Step 1. 8-Chloro-7-[(2-methyl-3H-benzimidazol-5-yl)oxy]-2-[1-(1-tetrahydropyran-4-ylazetidin-3-yl) pyrazol-4-yl]quinoxaline To a solution of 2-[1-(azetidin-3-yl)pyrazol-4-yl]-8-chloro-7-[(2-methyl-3H-benzimidazol-5-yl)oxy]quinoxaline (80.0 mg, 185 μmol) and tetrahydropyran-4-one (24.1 mg, 241 μmol) in tetrahydrofuran (2 mL) was added diisopropylethylamine (120 mg, 926 μmol, 161) and sodium triacetoxyborohydride (78.5 mg, 371 μmol), the mixture was stirred at 25° C. for 3 h. The reaction mixture was diluted with water (50 mL) and extracted with ethyl acetate (2×50 mL). The combined organic layers were washed with brine (2×100 mL), dried over sodium sulfate, filtered and concentrated in vacuo and the residue was purified by prep-HPLC (column: Phenomenex Synergi C18 150*25 mm*10 μm; mobile phase: [water (0.225% formic acid)-acetonitrile]; (B %: 1%-30%, 10 min) to give 8-chloro-7-[(2-methyl-3H-benzimidazol-5-yl)oxy]-2-[1-(1-tetrahydropyran-4-ylazetidin-3-yl)pyrazol-4-yl]quinoxaline (28.7 mg, 55.7 μmol, 30%) as a yellow solid. $^1$H NMR (400 MHz, DMSO-$d_6$) δ=9.33 (s, 1H), 8.86 (s, 1H), 8.41 (s, 1H), 8.17 (s, 1H), 7.96 (d, J=9.2 Hz, 1H), 7.51 (d, J=8.4 Hz, 1H), 7.32 (d, J=8.8 Hz, 1H), 7.22 (s, 1H), 6.95 (d, J=8.0 Hz, 1H), 5.14 (s, 1H), 3.86-3.81 (m, 2H), 3.76 (s, 2H), 3.49 (s, 2H), 3.37-3.27 (m, 2H), 2.50 (s, 3H), 2.48-2.43 (m, 1H), 1.69-1.64 (m, 2H), 1.26-1.14 (m, 2H); m/z ES+ $[M+H]^+$ 516.0.

Example 77. Synthesis of 2-[3-[4-[8-chloro-7-[(2-methyl-3H-benzimidazol-5-yl)oxy]quinoxalin-2-yl] pyrazol-1-yl]azetidin-1-yl]acetonitrile

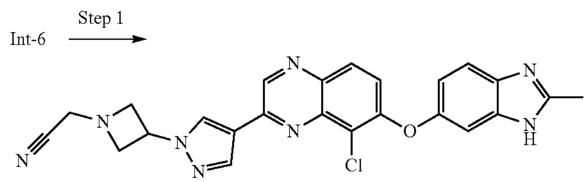

Step 1. 2-[3-[4-[8-Chloro-7-[(2-methyl-3H-benzimidazol-5-yl)oxy]quinoxalin-2-yl]pyrazol-1-yl]azetidin-1-yl]acetonitrile A mixture of 2-[1-(azetidin-3-yl)pyrazol-4-yl]-8-chloro-7-[(2-methyl-3H-benzimidazol-5-yl)oxy]quinoxaline (30 mg, 69.4 μmol), 2-bromoacetonitrile (6.67 mg, 55.5 μmol), potassium carbonate (20.5 mg, 148 μmol) in acetonitrile (2 mL) was stirred at 25° C. for 12 h. The reaction mixture was diluted with water (10 mL) and extracted with ethyl acetate (3× 30 mL). The combined organic layers were dried over sodium sulphate, concentrated under reduced pressure. The residue was purified by prep-HPLC (column: Phenomenex Gemini-NX C18 75*30 mm*3 um; mobile phase: [water (0.225% formic acid)-acetonitrile]; (B %: 12%-42%, 5 min) and then repurified by prep-HPLC (column: Waters Xbridge 150*25 mm*5 μm; mobile phase: [water (10 mM ammonium bicarbonate)-acetonitrile]; (B %: 25%-55%, 7 min) to give 2-[3-[4-[8-chloro-7-[(2-methyl-3H-benzimidazol-5-yl) oxy]quinoxalin-2-yl]pyrazol-1-yl]azetidin-1-yl]acetonitrile (2.7 mg, 5.69 μmol, 8%) as a white solid. $^1$H NMR (400 MHz, $CD_3OD$) δ=9.17 (s, 1H), 8.72 (s, 1H), 8.41 (s, 1H), 7.90 (d, J=9.2 Hz, 1H), 7.54 (d, J=8.8 Hz, 1H), 7.35 (d, J=9.2 Hz, 1H), 7.19 (d, J=2.0 Hz, 1H), 7.04-7.01 (m, 1H), 5.19 (t, J=6.4 Hz, 1H), 4.66-4.58 (m, 1H), 4.01-3.94 (m, 2H), 3.91-3.83 (m, 2H), 3.75 (s, 2H), 2.59 (s, 3H); m/z ES+ $[M+H]^+$ 471.0.

Example 78. Synthesis of 8-Chloro-7-[(2-methyl-3H-benzimidazol-5-yl)oxy]-2-[1-[1-(oxetan-3-yl) azetidin-3-yl]pyrazol-4-yl]quinoxaline

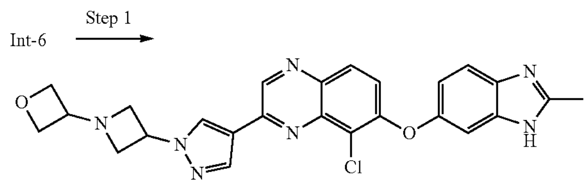

Step 1. 8-Chloro-7-[(2-methyl-3H-benzimidazol-5-yl)oxy]-2-[1-[1-(oxetan-3-yl)azetidin-3-yl]pyrazol-4-yl]quinoxaline To a solution of 2-[1-(azetidin-3-yl)pyrazol-4-yl]-8-chloro-7-[(2-methyl-3H-benzimidazol-5-yl)oxy]quinoxaline (50.0 mg, 115 μmol) in tetrahydrofuran (3 mL) was added oxetan-3-one (16.7 mg, 231 μmol), the mixture was stirred at 25° C. for 0.5 h. Then sodium triacetoxyborohydride (73.6 mg, 347 μmol) was added at 0° C. The mixture was stirred at 25° C. for 6 h. The reaction mixture was diluted with water (10 mL) and extracted with ethyl acetate (3×30 mL). The combined organic layers were dried over sodium sulphate, concentrated under reduced pressure. The residue was purified by prep-HPLC (column: Waters Xbridge 150*25 mm*5 μm; mobile phase: [water (10 mM ammonium bicarbonate)-acetonitrile]; (B %: 22%-52%, 9 min) to give 8-chloro-7-[(2-methyl-3H-benzimidazol-5-yl)oxy]-2-[1-[1-(oxetan-3-yl)azetidin-3-yl]pyrazol-4-yl]quinoxaline (26.9 mg, 55.2 μmol, 47%) as a white solid. $^1$H NMR (400 MHz, DMSO-$d_6$) δ=12.41-12.13 (m, 1H), 9.34 (s, 1H), 8.87 (s, 1H), 8.43 (s, 1H), 7.96 (d, J=9.2 Hz, 1H), 7.60-7.42 (m, 1H), 7.39-7.11 (m, 2H), 6.94 (d, J=8.0 Hz, 1H), 5.22 (t, J=6.8 Hz, 1H), 4.63 (t, J=6.8 Hz, 2H), 4.47 (t, J=5.6 Hz, 2H), 3.90-3.77 (m, 1H), 3.79 (t, J=7.2 Hz, 2H), 3.64 (t, J=6.8 Hz, 2H), 2.54-2.51 (m, 3H); m/z ES+ $[M+H]^+$ 488.1.

Example 79. Synthesis of 1-(Azetidin-1-yl)-2-[3-[4-[8-chloro-7-[(2-methyl-3H-benzimidazol-5-yl)oxy]quinoxalin-2-yl]pyrazol-1-yl]azetidin-1-yl]ethanone

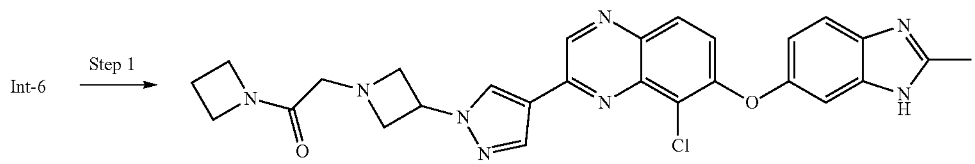 [SMILES: Cc1nc2ccc(Oc3ccc4ncc(-c5cnn(C6CN(CC(=O)N7CCC7)C6)c5)nc4c3Cl)cc2[nH]1]

Step 1. 1-(Azetidin-1-yl)-2-[3-[4-[8-chloro-7-[(2-methyl-3H-benzimidazol-5-yl)oxy]quinoxalin-2-yl]pyrazol-1-yl]azetidin-1-yl]ethanone To a solution of 2-[1-(azetidin-3-yl)pyrazol-4-yl]-8-chloro-7-[(2-methyl-3H-benzimidazol-5-yl)oxy]quinoxaline (50.0 mg, 115 μmol) in 1-methylpyrrolidin-2-one (2 mL) was added potassium carbonate (48.0 mg, 347 μmol) and 1-(azetidin-1-yl)-2-chloro-ethanone (15.1 mg, 113 μmol). The mixture was stirred at 25° C. for 6 h. The reaction mixture was diluted with water (10 mL) and extracted with ethyl acetate (3×30 mL). The combined organic layers were dried over sodium sulphate anhydrous, concentrated under reduced pressure. The residue was purified by prep-HPLC (column: Phenomenex Gemini-NX C18 75*30 mm*3 μm; mobile phase: [water (0.225% formic acid)-acetonitrile]; (B %: 5%-35%, 7 min) to give 1-(azetidin-1-yl)-2-[3-[4-[8-chloro-7-[(2-methyl-3H-benzimidazol-5-yl)oxy]quinoxalin-2-yl]pyrazol-1-yl]azetidin-1-yl]ethanone (10.2 mg, 19.3 μmol, 16%) as a white solid. $^1$H NMR (400 MHz, DMSO-$d_6$) δ=12.41-12.13 (m, 1H), 9.33 (s, 1H), 8.87 (s, 1H), 8.41 (s, 1H), 7.96 (d, J=9.2 Hz, 1H), 7.60-7.42 (m, 1H), 7.39-7.11 (m, 2H), 6.94 (d, J=8.0 Hz, 1H), 5.16 (t, J=6.8 Hz, 1H), 4.15 (t, J=7.6 Hz, 2H), 3.89-3.79 (m, 4H), 3.58 (t, J=7.2 Hz, 2H), 3.20 (s, 2H), 2.53-2.51 (m, 3H), 2.23-2.16 (m, 2H); m/z ES+ $[M+H]^+$ 529.1.

Example 80. Synthesis of 2-[3-[4-[8-Chloro-7-[(2-methyl-3H-benzimidazol-5-yl)oxy]quinoxalin-2-yl]pyrazol-1-yl]azetidin-1-yl]-1-(3-hydroxyazetidin-1-yl)ethanone

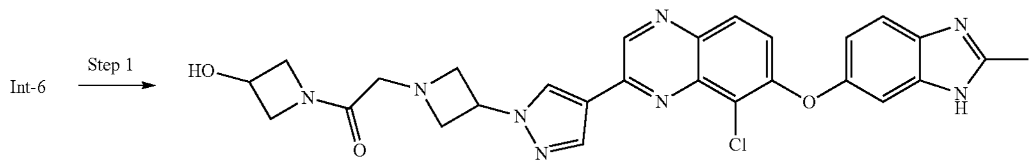 [SMILES: Cc1nc2ccc(Oc3ccc4ncc(-c5cnn(C6CN(CC(=O)N7CC(O)C7)C6)c5)nc4c3Cl)cc2[nH]1]

Step 1. 2-[3-[4-[8-Chloro-7-[(2-methyl-3H-benzimidazol-5-yl)oxy]quinoxalin-2-yl]pyrazol-1-yl]azetidin-1-yl]-1-(3-hydroxyazetidin-1-yl)ethanone To a solution of 2-[1-(azetidin-3-yl)pyrazol-4-yl]-8-chloro-7-[(2-methyl-3H-benzimidazol-5-yl)oxy]quinoxaline (50.0 mg, 115 μmol) in 1-methylpyrrolidin-2-one (2 mL) was added potassium carbonate (48.0 mg, 347 μmol) and 2-chloro-1-(3-hydroxyazetidin-1-yl)ethanone (15.5 mg, 104 μmol). The mixture was stirred at 25° C. for 3 h. The reaction mixture was diluted with water (10 mL) and extracted with ethyl acetate (3×30 mL). The combined organic layers were dried over sodium sulphate, concentrated under reduced pressure. The residue was purified by prep-HPLC (column: Waters Xbridge 150*25 mm*5 μm; mobile phase: [water (10 mM ammonium bicarbonate)-acetonitrile]; (B %: 16%-46%, 9 min) to give 2-[3-[4-[8-chloro-7-[(2-methyl-3H-benzimidazol-5-yl)oxy]quinoxalin-2-yl]pyrazol-1-yl]azetidin-1-yl]-1-(3-hydroxyazetidin-1-yl)

ethanone (16.6 mg, 30.5 μmol, 26%) as a white solid. $^1H$ NMR (400 MHz, DMSO-$d_6$) δ=12.43-12.15 (m, 1H), 9.34 (s, 1H), 8.87 (s, 1H), 8.42 (s, 1H), 7.96 (d, J=9.2 Hz, 1H), 7.51 (d, J=7.7 Hz, 1H), 7.37-7.14 (m, 2H), 6.95-6.93 (m, 1H), 5.73 (d, J=1.8 Hz, 1H), 5.16 (t, J=6.8 Hz, 1H), 4.45 (s, 1H), 4.32 (t, J=7.6 Hz, 1H), 4.05-4.01 (m, 1H), 3.89-3.80 (m, 1H), 3.83 (t, J=7.6 Hz, 2H), 3.57 (t, J=6.8 Hz, 3H), 3.22 (s, 2H), 2.52-2.51 (m, 3H); m/z ES+ $[M+H]^+$ 545.1.

Example 81. Synthesis of (1r,3r)-3-((4-(8-Chloro-7-((2-methyl-1H-benzo[d]imidazol-6-yl)oxy)quinoxalin-2-yl)-1H-pyrazol-1-yl)methyl)-1-methylcyclobutanol and (1s,3s)-3-((4-(8-Chloro-7-((2-methyl-1H-benzo[d]imidazol-6-yl)oxy)quinoxalin-2-yl)-1H-pyrazol-1-yl)methyl)-1-methylcyclobutanol

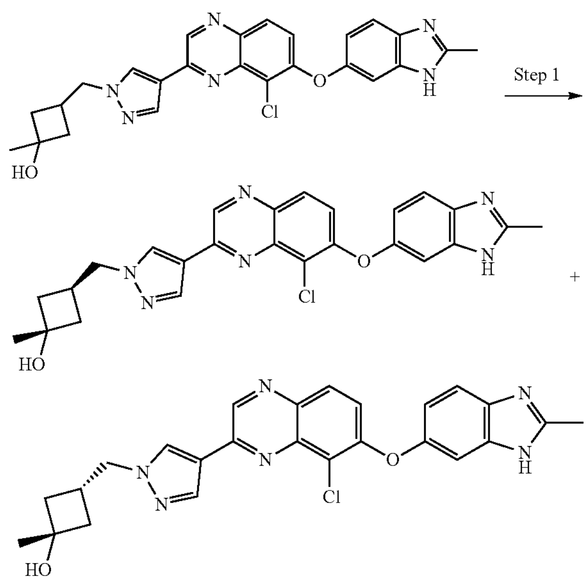

Step 1. (1r,3r)-3-((4-(8-Chloro-7-((2-methyl-1H-benzo[d]imidazol-6-yl)oxy)quinoxalin-2-yl)-1H-pyrazol-1-yl)methyl)-1-methylcyclobutanol and (1s,3s)-3-((4-(8-Chloro-7-((2-methyl-1H-benzo[d]imidazol-6-yl)oxy)quinoxalin-2-yl)-1H-pyrazol-1-yl)methyl)-1-methylcyclobutanol 3-((4-(8-chloro-7-((2-methyl-1H-benzo[d]imidazol-6-yl)oxy)quinoxalin-2-yl)-1H-pyrazol-1-yl)methyl)-1-methylcyclobutanol (650 mg, 1.37 mmol) was separated by SFC (column: Daicel Chiralpak IG (250 mm*30 mm, 10 μm); mobile phase: [0.1% ammonium hydroxide, methanol]; (B %: 60%-60%, 4.6 min) to give (1r,3r)-3-((4-(8-chloro-7-((2-methyl-1H-benzo[d]imidazol-6-yl)oxy)quinoxalin-2-yl)-1H-pyrazol-1-yl)methyl)-1-methylcyclobutanol (60.9 mg, 127 μmol, 9.3%) and (1s,3s)-3-((4-(8-chloro-7-((2-methyl-1H-benzo[d]imidazol-6-yl)oxy)quinoxalin-2-yl)-1H-pyrazol-1-yl)methyl)-1-methylcyclobutanol (386 mg, 773 μmol, 56%) both as green solids.

$^1H$ NMR (400 MHz, $CD_3OD$) δ=9.15 (s, 1H), 8.55 (s, 1H), 8.33 (s, 1H), 7.89 (d, J=9.2 Hz, 1H), 7.54 (d, J=8.8 Hz, 1H), 7.34 (d, J=9.2 Hz, 1H), 7.18 (d, J=2.0 Hz, 1H), 7.02 (dd, J=2.4, 8.8 Hz, 1H), 4.30 (d, J=7.6 Hz, 2H), 3.04-2.91 (m, 1H), 2.58 (s, 3H), 2.24-2.14 (m, 2H), 2.01-1.94 (m, 2H), 1.33 (s, 3H); m/z ES+ $[M+H]^+$ 475.0.

$^1H$ NMR (400 MHz, $CD_3OD$) δ=9.16 (s, 1H), 8.54 (s, 1H), 8.33 (s, 1H), 7.92 (d, J=9.2 Hz, 1H), 7.60 (d, J=8.8 Hz, 1H), 7.39 (d, J=9.2 Hz, 1H), 7.22 (d, J=2.0 Hz, 1H), 7.11 (dd, J=2.4, 8.8 Hz, 1H), 4.30 (d, J=7.2 Hz, 2H), 2.66 (s, 3H), 2.51-2.40 (m, 1H), 2.20-2.14 (m, 2H), 2.01-1.89 (m, 2H), 1.35 (s, 3H); m/z ES+ $[M+H]^+$ 475.0.

Example 82. Synthesis of 2-(1-(4-Azaspiro[2.5]octan-7-yl)-1H-pyrazol-4-yl)-8-chloro-7-((2-methyl-1H-benzo[d]imidazol-6-yl)oxy)quinoxaline

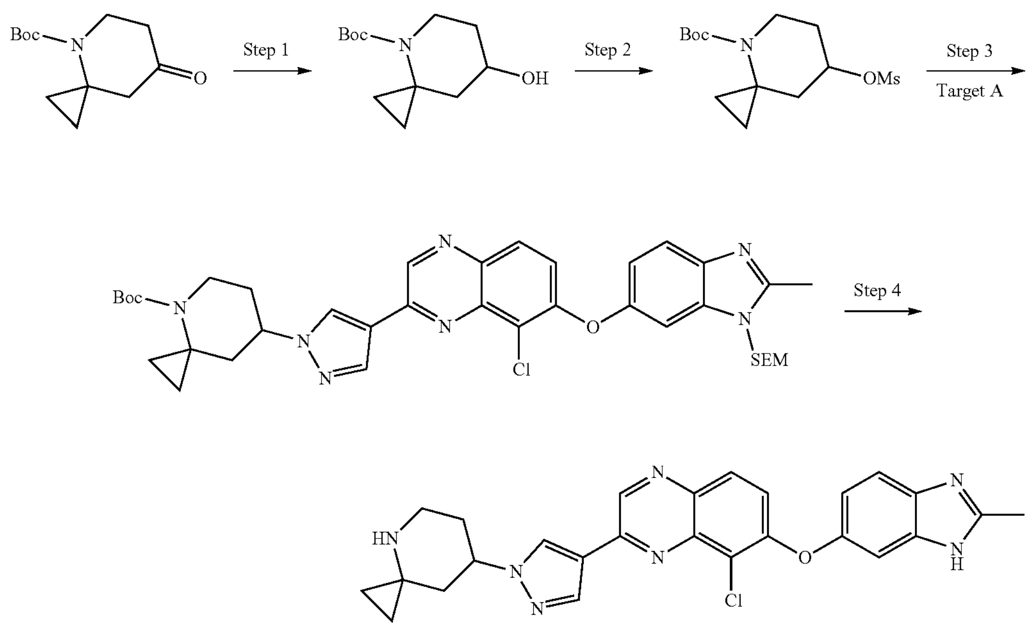

Step 1. tert-Butyl 7-hydroxy-4-azaspiro[2.5]octane-4-carboxylate

To a solution of tert-butyl 7-oxo-4-azaspiro[2.5]octane-4-carboxylate (100 mg, 444 μmol) in methanol (1 mL) was added sodium borohydride (25.2 mg, 666 μmol) portion-wise at 0° C. The mixture was stirred at 20° C. for 1 h. On completion, the mixture was quenched with saturated aqueous ammonium chloride (10 mL), diluted with water (40 mL) and extracted with ethyl acetate (30 mL×3). The combined organic layers were washed with brine (30 mL), dried over anhydrous sodium sulfate, filtered and concentrated in vacuum and the residue was purified by column chromatography (petroleum ether:ethyl acetate=2:1) to afford tert-butyl 7-hydroxy-4-azaspiro[2.5]octane-4-carboxylate (90.0 mg, 396 μmol, 89%) as a colorless oil. $^1$H NMR (400 MHz, $CDCl_3$) δ 4.05-3.89 (m, 2H), 3.05-2.90 (m, 1H), 2-1.87 (m, 1H), 1.82-1.71 (m, 1H), 1.47 (s, 9H), 1.46-1.38 (m, 2H), 1.22-1.12 (m, 1H), 0.88-0.79 (m, 1H), 0.66-0.53 (m, 1H), 0.50-0.41 (m, 1H).

Step 2. tert-Butyl 7-((methylsulfonyl)oxy)-4-azaspiro[2.5]octane-4-carboxylate

To a solution of tert-butyl 7-hydroxy-4-azaspiro[2.5]octane-4-carboxylate (90.0 mg, 396 μmol) and triethylamine (120 mg, 1.19 mmol) in dichloromethane (2 mL) was added methanesulfonyl chloride (68.0 mg, 594 μmol) at 0° C., then the mixture was stirred at 20° C. for 0.5 h. On completion, the mixture was diluted with dichloromethane (20 mL) and washed with water (15 mL×3). The organic layer was dried over sodium sulfate, and concentrated in vacuo to give tert-butyl 7-methylsulfonyloxy-4-azaspiro[2.5]octane-4-carboxylate (120 mg, 393 μmol, 99%) as a colorless oil. $^1$H NMR (400 MHz, $CDCl_3$) δ 5.03-4.92 (m, 1H), 3.99-3.80 (m, 1H), 3.15-3.07 (m, 1H), 3.03 (s, 3H), 2.12-1.91 (m, 2H), 1.81-1.62 (m, 2H), 1.47 (s, 9H), 1.46-1.38 (m, 1H), 1.20-1.09 (m, 1H), 0.91-0.81 (m, 1H), 0.77-0.65 (m, 1H), 0.61-0.52 (m, 1H).

Step 3. tert-Butyl 7-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-4-azaspiro[2.5]octane-4-carboxylate To a mixture of 2-[[6-[5-chloro-3-(1H-pyrazol-4-yl)quinoxalin-6-yl]oxy-2-methyl-benzimidazol-1-yl]methoxy]ethyl-trimethyl-silane (120 mg, 237 μmol) and tert-butyl 7-methylsulfonyloxy-4-azaspiro[2.5]octane-4-carboxylate (108 mg, 355 μmol) in dimethylsulfoxide (3 mL) was added potassium carbonate (65.4 mg, 473 μmol), the mixture was stirred at 80° C. for 2 h. On completion, the mixture was washed with water (40 mL) and extracted with ethyl acetate (20 mL×3). The combined organic layers were washed with brine (40 mL), dried over anhydrous sodium sulfate, filtered and concentrated in vacuum and the residue was purified by column chromatography (petroleum ether:ethyl acetate=2:1) to afford tert-butyl 7-[4-[8-chloro-7-[2-methyl-3-(2-trimethylsilylethoxymethyl)benzimidazol-5-yl]oxy-quinoxalin-2-yl]pyrazol-1-yl]-4-azaspiro[2.5]octane-4-carboxylate (120 mg, 168 μmol, 70%) as a yellow solid. m/z ES+ $[M+H]^+$ 716.3.

Step 4. 2-(1-(4-Azaspiro[2.5]octan-7-yl)-1H-pyrazol-4-yl)-8-chloro-7-((2-methyl-1H-benzo[d]imidazol-6-yl)oxy)quinoxaline A solution of tert-butyl 7-[4-[8-chloro-7-[2-methyl-3-(2-trimethylsilylethoxymethyl)benzimidazol-5-yl]oxy-quinoxalin-2-yl]pyrazol-1-yl]-4-azaspiro[2.5]octane-4-carboxylate (120 mg, 167 μmol) in trifluoroacetic acid (3 mL) was stirred at 20° C. for 1 h. On completion, the mixture was concentrated in vacuo and the residue was purified by prep-HPLC [column: Waters Xbridge 150*25 mm*5 μm; mobile phase: [water (ammonium bicarbonate)-acetonitrile]; (B %: 29%-59%, 9 min] to give 2-[1-(4-azaspiro[2.5]octan-7-yl)pyrazol-4-yl]-8-chloro-7-[(2-methyl-3H-benzimidazol-5-yl)oxy]quinoxaline (43.8 mg, 88.0 μmol, 52%) as a yellow solid. $^1$H NMR (400 MHz, DMSO-$d_6$) δ 12.59-12.10 (m, 1H), 9.32 (s, 1H), 8.75 (s, 1H), 8.36 (s, 1H), 7.96 (d, J=9.2 Hz, 1H), 7.62-7.42 (m, 1H), 7.38-7.14 (m, 2H), 6.95 (d, J=7.6 Hz, 1H), 4.59-4.46 (m, 1H), 3.10-3.01 (m, 1H), 2.80-2.69 (m, 1H), 2.49 (s, 3H), 2.36-2.28 (m, 1H), 2.16-2.06 (m, 1H), 1.98-1.87 (m, 1H), 1.57-1.48 (m, 1H), 0.68-0.59 (m, 1H), 0.55-0.42 (m, 3H); m/z ES+ $[M+H]^+$ 486.1.

Example 83. Synthesis of (1r,3r)-3-(4-(8-Chloro-7-((2-methyl-1H-benzo[d]imidazol-6-yl)oxy)quinoxalin-2-yl)-1H-pyrazol-1-yl)cyclobutanol and (1s,3s)-3-(4-(8-Chloro-7-((2-methyl-1H-benzo[d]imidazol-6-yl)oxy)quinoxalin-2-yl)-1H-pyrazol-1-yl)cyclobutanol

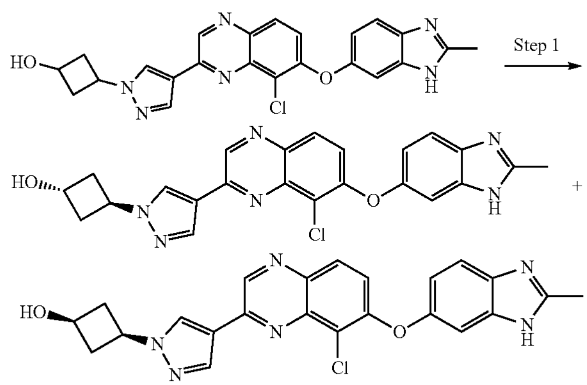

Step 1. (1r,3r)-3-(4-(8-Chloro-7-((2-methyl-1H-benzo[d]imidazol-6-yl)oxy)quinoxalin-2-yl)-1H-pyrazol-1-yl)cyclobutanol and (1s,3s)-3-(4-(8-Chloro-7-((2-methyl-1H-benzo[d]imidazol-6-yl)oxy)quinoxalin-2-yl)-1H-pyrazol-1-yl)cyclobutanol 3-(4-(8-chloro-7-((2-methyl-1H-benzo[d]imidazol-6-yl)oxy)quinoxalin-2-yl)-1H-pyrazol-1-yl)cyclobutanol (250 mg, 559 μmol) was separated by SFC (column: Daicel Chiralpak IF (250 mm*30 mm, 10 μm); mobile phase: [hexane-EtOH (0.1% ammonium hydroxide)]; (B %: 35%-35%, 17 min) to give (1r,3r)-3-[4-[8-chloro-7-[(2-methyl-3H-benzimidazol-5-yl)oxy]quinoxalin-2-yl]pyrazol-1-yl]cyclobutanol (102 mg, 207 μmol, 37%) as an off-white solid and (1s,3s)-3-(4-(8-chloro-7-((2-methyl-1H-benzo[d]imidazol-6-yl)oxy)quinoxalin-2-yl)-1H-pyrazol-1-yl)cyclobutanol (5.8 mg, 12.5 μmol, 2.2%) as an off-white solid.

$^1$H NMR (400 MHz, DMSO-$d_6$) δ 12.45-12.15 (m, 1H), 9.33 (d, J=4.0 Hz, 1H), 8.78 (s, 1H), 8.38 (s, 1H), 7.96 (dd, J=5.2, 9.2 Hz, 1H), 7.60-7.42 (m, 1H), 7.40-7.12 (m, 2H), 6.95 (dd, J=8.8, 11.2 Hz, 1H), 5.36 (d, J=6.8 Hz, 1H), 4.62-4.44 (m, 1H), 4.09-3.91 (m, 1H), 2.89-2.75 (m, 2H), 2.49 (s, 3H), 2.46-2.39 (m, 2H); m/z ES+ $[M+H]^+$ 447.0.

$^1H$ NMR (400 MHz, DMSO-$d_6$) δ 9.33 (s, 1H), 8.80 (s, 1H), 8.39 (s, 1H), 8.35 (s, 2H), 7.97 (d, J=9.2 Hz, 1H), 7.52 (d, J=8.8 Hz, 1H), 7.33 (d, J=9.2 Hz, 1H), 7.22 (s, 1H), 6.95 (dd, J=2.4, 8.6 Hz, 1H), 5.15-5 (m, 1H), 4.53 (s, 1H), 2.78-2.69 (m, 2H), 2.48-2.46 (m, 3H), 2.45-2.41 (m, 2H); m/z ES+ $[M+H]^+$ 447.0.

Example 84. Synthesis of 3-(4-(8-Chloro-7-((2-methyl-1H-benzo[d]imidazol-6-yl)oxy)quinoxalin-2-yl)-1H-pyrazol-1-yl)-1-methylcyclobutanol

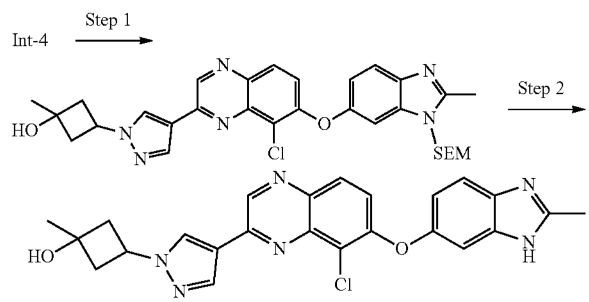

Step 1. 3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-1-methylcyclobutanol To a solution of 3-[4-[8-chloro-7-[2-methyl-3-(2-trimethylsilylethoxymethyl)benzimidazol-5-yl]oxy-quinoxalin-2-yl]pyrazol-1-yl]cyclobutanone (100 mg, 170 μmol) in tetrahydrofuran (3 mL) was added methylmagnesium bromide (3 M in THF, 170 μL) at 0° C. The mixture was stirred at 0° C. for 1 h. On completion, the reaction mixture was quenched with saturated aqueous ammonium chloride (50 mL) at 0° C., then diluted with water (50 mL) and extracted with ethyl acetate (50 mL×3). The combined organic layers were washed with brine (25 mL×2), dried over sodium sulfate, filtered and concentrated under reduced pressure. The residue was purified by prep-TLC (silica gel, dichloromethane: methanol=10:1) to give 3-[4-[8-chloro-7-[2-methyl-3-(2-trimethylsilylethoxymethyl)benzimidazol-5-yl]oxy-quinoxalin-2-yl]pyrazol-1-yl]-1-methyl-cyclobutanol (40 mg, 67.8 μmol, 32%) as a white solid. m/z ES+ $[M+H]^+$ 591.1.

Step 2. 3-(4-(8-Chloro-7-((2-methyl-1H-benzo[d]imidazol-6-yl)oxy)quinoxalin-2-yl)-1H-pyrazol-1-yl)-1-methylcyclobutanol A mixture of 3-[4-[8-chloro-7-[2-methyl-3-(2-trimethylsilylethoxymethyl)benzimidazol-5-yl]oxy-quinoxalin-2-yl]pyrazol-1-yl]-1-methyl-cyclobutanol (30.0 mg, 51.0 μmol) in trifluoroacetic acid (0.3 mL) was stirred at 25° C. for 0.5 h. On completion, the reaction mixture was concentrated under reduced pressure. The residue was purified by prep-HPLC (neutral condition; column: Waters Xbridge 150×25 mm× 5 μm; mobile phase: [water (10 mM ammonium bicarbonate)-acetonitrile]; (B %: 27%-57%, 10 min) to give 3-[4-[8-chloro-7-[(2-methyl-3H-benzimidazol-5-yl)oxy]quinoxalin-2-yl]pyrazol-1-yl]-1-methyl-cyclobutanol (15 mg, 33 μmol, 64%) as a white solid. $^1H$ NMR (400 MHz, DMSO-$d_6$) δ=9.33 (s, 1H), 8.77 (s, 1H), 8.38 (s, 1H), 7.96

(d, J=9.2 Hz, 1H), 7.54 (d, J=8.8 Hz, 1H), 7.33 (d, J=9.2 Hz, 1H), 7.24 (s, 1H), 6.97 (d, J=8.4 Hz, 1H), 5.32 (s, 1H), 4.66 (s, 1H), 2.69-2.53 (m, 5H), 2.49-2.49 (m, 3H), 1.35 (s, 3H); m/z ES+ $[M+H]^+$ 461.0.

Example 85. Synthesis of 3-(1-((3,3-Difluorocyclobutyl)methyl)-1H-pyrazol-4-yl)-6-((2-methyl-1H-benzo[d]imidazol-6-yl)oxy)quinoxalin-5-amine

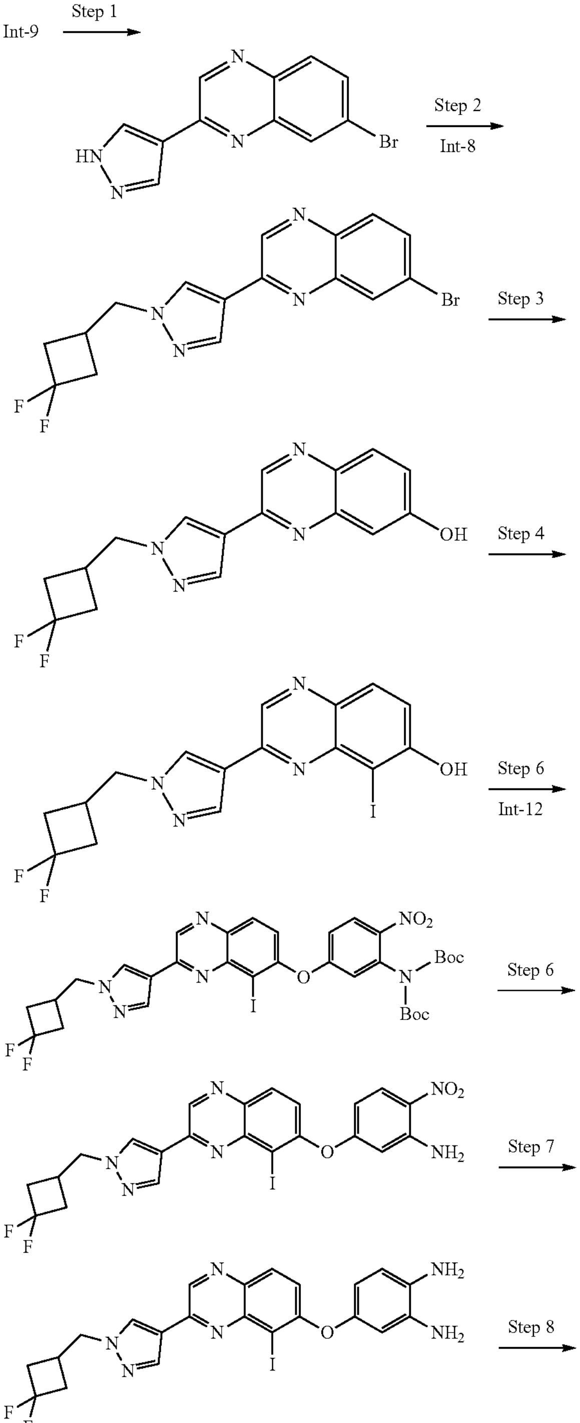

-continued

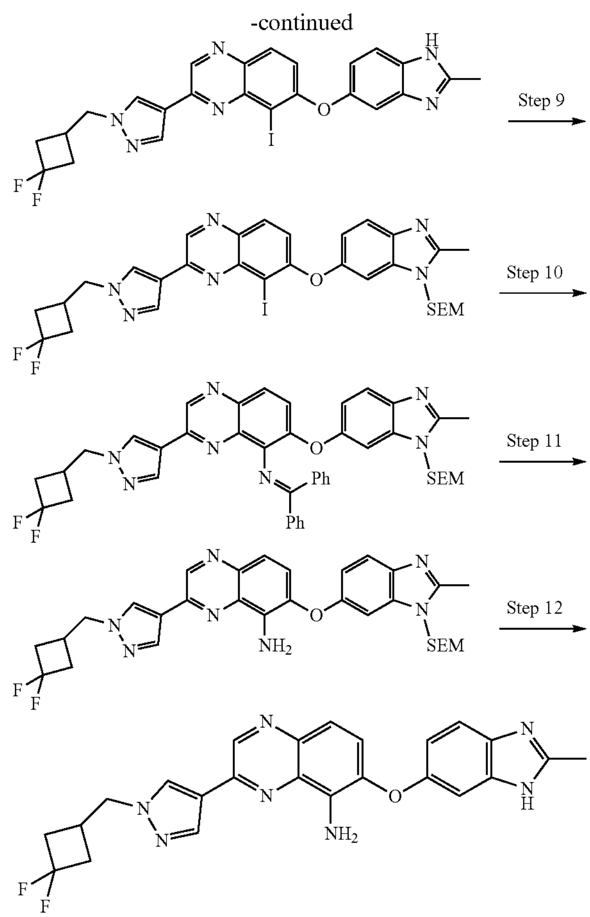

Step 1. 7-Bromo-2-(1H-pyrazol-4-yl)quinoxaline

To a solution of 7-bromo-2-(1-tetrahydropyran-2-ylpyrazol-4-yl)quinoxaline (5.2 g, 14.5 mmol) in dichloromethane (60 mL) was added trifluoroacetic acid (20 mL). The mixture was stirred at 20° C. for 1 h. The reaction mixture was concentrated under reduced pressure. The residue was diluted with sat. sodium bicarbonate (100 mL) and extracted with ethyl acetate (60 mL×3). The combined organic layers were dried over anhydrous sodium sulfate, filtered and concentrated under reduced pressure to give 7-bromo-2-(1H-pyrazol-4-yl)quinoxaline (5 g, crude) as a black solid. m/z ES+ $[M+H]^+$ 274.7.

Step 2. 7-Bromo-2-(1-((3,3-difluorocyclobutyl) methyl)-1H-pyrazol-4-yl)quinoxaline To a solution of 7-bromo-2-(1H-pyrazol-4-yl)quinoxaline (2.3 g, 8.36 mmol) in N,N-dimethyl formamide (40 mL) was added potassium carbonate (2.31 g, 16.7 mmol) and (3,3-difluorocyclobutyl)methyl methanesulfonate (1.67 g, 8.36 mmol). The mixture was stirred at 80° C. for 12 h. The reaction mixture was diluted with water (200 mL) and extracted with ethyl acetate (200 mL×3). The combined organic layers were dried over anhydrous sodium sulfate, filtered and concentrated under reduced pressure. The residue was purified by column chromatography (petroleum ether/ethyl acetate=5/1 to 1/1) to give a residue. The residue was triturated with petroleum ether:ethyl acetate (20:1, 60 mL) at 20° C. for 30 min to give 7-bromo-2-(1-((3,3-difluorocyclobutyl)methyl)-1H-pyrazol-4-yl)quinoxaline (800 mg, 2.12 mmol, 12%) as a yellow solid. $^1H$ NMR (400 MHz, DMSO-$d_6$) δ 9.43-9.31 (m, 1H), 8.73 (s, 1H), 8.34 (s, 1H), 8.20 (d, J=2.0 Hz, 1H), 7.99 (d, J=8.8 Hz, 1H), 7.88 (dd, J=2.0, 8.8 Hz, 1H), 4.37 (d, J=6.0 Hz, 2H), 3.30 (s, 1H), 2.77-2.57 (m, 4H); m/z ES+ $[M+H]^+$ 378.8.

Step 3. 3-(1-((3,3-Difluorocyclobutyl)methyl)-1H-pyrazol-4-yl)quinoxalin-6-ol

A mixture of 7-bromo-2-[1-[(3,3-difluorocyclobutyl) methyl]pyrazol-4-yl]quinoxaline (600 mg, 1.58 mmol), tris (dibenzylideneacetone) dipalladium (145 mg, 158 μmol), 2-di-t-butylphosphino-2',4',6'-tri-i-propyl-1,1'-biphenyl (67.2 mg, 158 μmol) and potassium hydroxide (888 mg, 15.8 mmol) in dioxane (10 mL) and water (2 mL) was degassed and purged with nitrogen for 3 times, and then the mixture was stirred at 100° C. for 1 h under nitrogen atmosphere. The mixture was concentrated under reduced pressure. The residue was purified by column chromatography (petroleum ether/ethyl acetate=5/1 to 1/1) to give 3-(1-((3,3-difluoro-cyclobutyl)methyl)-1H-pyrazol-4-yl)quinoxalin-6-ol (400 mg, 1.27 mmol, 68%) as a yellow solid. m/z ES+ $[M+H]^+$ 317.1.

Step 4. 3-[1-[(3,3-Difluorocyclobutyl)methyl]pyrazol-4-yl]-5-iodo-quinoxalin-6-ol To a solution of 3-[1-[(3,3-difluorocyclobutyl)methyl] pyrazol-4-yl]quinoxalin-6-ol (900 mg, 2.85 mmol) in chloroform (10 mL) was added nickel chloride (368 mg, 2.85 mmol), triethylamine (287 mg, 2.85 mmol) and N-iodosuccinimide (1.28 g, 5.69 mmol). The mixture was stirred at 60° C. for 2 hs. The reaction mixture was diluted with water (25 mL) and extracted with ethyl acetate (25 mL×3). The combined organic layers were dried over anhydrous sodium sulfate, filtered and concentrated under reduced pressure and the residue was purified by reversed-phase HPLC (0.1% formic acid condition) to give 3-[1-[(3,3-difluorocyclobutyl) methyl]pyrazol-4-yl]-5-iodo-quinoxalin-6-ol (1.10 g, 2.43 mmol, 85%) as a red solid. m/z ES+ $[M+H]^+$ 442.9.

Step 5. tert-Butyl N-tert-butoxycarbonyl-N-[5-[3-[1-[(3,3-difluorocyclobutyl)methyl]pyrazol-4-yl]-5-iodo-quinoxalin-6-yl]oxy-2-nitro-phenyl]carbamate To a solution of 3-[1-[(3,3-difluorocyclobutyl)methyl] pyrazol-4-yl]-5-iodo-quinoxalin-6-ol (1 g, 2.26 mmol) in N,N-dimethylformamide (10 mL) was added potassium carbonate (937 mg, 6.78 mmol) and tert-butyl N-tert-butoxycarbonyl-N-(5-fluoro-2-nitro-phenyl) carbamate (1.05 g, 2.94 mmol). The mixture was stirred at 80° C. for 12 hs. The reaction mixture was diluted with water (25 mL) and extracted with ethyl acetate (25 mL×3). The combined organic layers were dried over anhydrous sodium sulfate, filtered and concentrated under reduced pressure and the residue was purified by reversed-phase HPLC (water (0.1% formic acid)-acetonitrile]; (B %: 40%-60%, 7 min) to give tert-butyl N-tert-butoxycarbonyl-N-[5-[3-[1-[(3,3-difluoro-cyclobutyl)methyl]pyrazol-4-yl]-5-iodo-quinoxalin-6-yl] oxy-2-nitro-phenyl]carbamate (1.20 g, 1.32 mmol, 58%) as a yellow solid. $^1H$ NMR (400 MHz, $CDCl_3$) δ 9.03 (s, 1H), 8.28 (d, J=8.0 Hz, 2H), 8.19-8.06 (m, 2H), 7.41 (d, J=9.2 Hz, 1H), 7.02 (d, J=8.8 Hz, 1H), 6.90 (s, 1H), 4.37 (d, J=6.8 Hz, 2H), 2.87-2.69 (m, 3H), 2.56-2.39 (m, 2H), 1.50-1.36 (m, 18H).

Step 6. 5-[3-[1-[(3,3-Difluorocyclobutyl)methyl]pyrazol-4-yl]-5-iodo-quinoxalin-6-yl]oxy-2-nitro-aniline To a solution of tert-butyl N-tert-butoxycarbonyl-N-[5-[3-[1-[(3,3-difluorocyclobutyl)methyl]pyrazol-4-yl]-5-iodo-quinoxalin-6-yl]oxy-2-nitro-phenyl]carbamate (1 g, 1.28 mmol) in dioxane (5 mL) was added hydrochloric acid/dioxane (4 M, 10 mL). The mixture was stirred at 40° C. for 12 hs. The reaction mixture was concentrated under reduced pressure to give 5-[3-[1-[(3,3-difluorocyclobutyl)methyl]pyrazol-4-yl]-5-iodo-quinoxalin-6-yl]oxy-2-nitro-aniline (1 g, crude) as a yellow solid. m/z ES+ $[M+H]^+$ 579.1.

Step 7. 4-[3-[1-[(3,3-Difluorocyclobutyl)methyl]pyrazol-4-yl]-5-iodo-quinoxalin-6-yl]oxybenzene-1,2-diamine To a solution of 5-[3-[1-[(3,3-difluorocyclobutyl)methyl]pyrazol-4-yl]-5-iodo-quinoxalin-6-yl]oxy-2-nitro-aniline (900 mg, 1.56 mmol) in ethanol (10 mL) and water (1 mL) was added iron powder (695 mg, 12.4 mmol) and ammonium chloride (665 mg, 12.4 mmol). The mixture was stirred at 60° C. for 2 hs. The reaction mixture was concentrated under reduced pressure to give 4-[3-[1-[(3,3-difluorocyclobutyl)methyl]pyrazol-4-yl]-5-iodo-quinoxalin-6-yl]oxybenzene-1,2-diamine (1 g, crude) as a yellow solid. m/z ES+ $[M+H]^+$ 549.1.

Step 8. 2-[1-[(3,3-Difluorocyclobutyl)methyl]pyrazol-4-yl]-8-iodo-7-[(2-methyl-1H-benzimidazol-5-yl)oxy]quinoxaline To a solution of 4-[3-[1-[(3,3-difluorocyclobutyl)methyl]pyrazol-4-yl]-5-iodo-quinoxalin-6-yl]oxybenzene-1,2-diamine (900 mg, 1.64 mmol) and 1,1,1-trimethoxyethane (986 mg, 8.21 mmol) in methanol (10 mL) was added sulfamic acid (318 mg, 3.28 mmol), the mixture was stirred at 20° C. for 1 h. The mixture was concentrated in vacuo and the residue was purified by column chromatography (ethyl acetate:methanol=10:1) to give 2-[1-[(3,3-difluorocyclobutyl)methyl]pyrazol-4-yl]-8-iodo-7-[(2-methyl-1H-benzimidazol-5-yl)oxy]quinoxaline (600 mg, 1.05 mmol, 63%) as a yellow solid. $^1H$ NMR (400 MHz, DMSO-$d_6$) δ 9.23 (s, 1H), 8.74 (s, 1H), 8.3 (s, 1H), 8.02 (d, J=8.8 Hz, 1H), 7.59 (d, J=8.8 Hz, 1H), 7.28 (d, J=8.8 Hz, 1H), 7.24 (d, J=2.0 Hz, 1H), 7.03-6.97 (m, 1H), 4.41 (d, J=6.0 Hz, 2H), 2.75-2.65 (m, 4H), 2.57 (s, 3H), 2.56-2.54 (m, 1H).

Step 9. 2-[[5-[3-[1-[(3,3-Difluorocyclobutyl)methyl]pyrazol-4-yl]-5-iodo-quinoxalin-6-yl]oxy-2-methyl-benzimidazol-1-yl]methoxy]ethyl-trimethyl-silane To a solution of 2-[1-[(3,3-difluorocyclobutyl)methyl]pyrazol-4-yl]-8-iodo-7-[(2-methyl-1H-benzimidazol-5-yl)oxy]quinoxaline (500 mg, 873 μmol) in tetrahydrofuran (10 mL) was added sodium hydride (52.4 mg, 1.31 mmol, 60% in mineral oil) at 0° C., the mixture was stirred at 0° C. for 0.5 h. Then a solution of 2-(chloromethoxy)ethyl-trimethylsilane (189 mg, 1.14 mmol) in tetrahydrofuran (2 mL) was added dropwise, and the mixture was stirred at 0° C. for 1 h. The mixture was quenched with saturated ammonium chloride solution (10 mL), washed with water (60 mL) and extracted with ethyl acetate (40 mL×2). The combined organic layers were washed with brine (50 mL), dried over sodium sulfate and concentrated in vacuo and the residue was purified by column chromatography (100% ethyl acetate) to give 2-[[5-[3-[1-[(3,3-difluorocyclobutyl)methyl]pyrazol-4-yl]-5-iodo-quinoxalin-6-yl]oxy-2-methyl-benzimidazol-1-yl]methoxy]ethyl-trimethyl-silane (550 mg, 782 μmol, 89%) as a yellow solid. m/z ES+ $[M+H]^+$ 703.0.

Step 10. 3-(1-((3,3-Difluorocyclobutyl)methyl)-1H-pyrazol-4-yl)-N-(diphenylmethylene)-6-((2-methyl-1-((2-(trimethylsilyl)ethoxy)methyl)-1H-benzo[d]imidazol-6-yl)oxy)quinoxalin-5-amine To a solution of 2-[[5-[3-[1-[(3,3-difluorocyclobutyl)methyl]pyrazol-4-yl]-5-iodo-quinoxalin-6-yl]oxy-2-methyl-benzimidazol-1-yl]methoxy]ethyl-trimethyl-silane (50.0 mg, 71.2 μmol), diphenylmethanimine (25.8 mg, 142 μmol) and cesium carbonate (69.6 mg, 213 μmol) in tert-amyl alcohol (0.5 mL) was added XantPhos Pd G4 (6.85 mg, 7.12 μmol) under nitrogen, the mixture was then stirred at 90° C. for 16 h. On completion, the mixture was filtered and the filtrate was concentrated in vacuo and the residue was purified by prep-TLC (100% ethyl acetate) to give N-[3-[1-[(3,3-difluorocyclobutyl)methyl]pyrazol-4-yl]-6-[2-methyl-3-(2-trimethylsilylethoxymethyl)benzimidazol-5-yl]oxy-quinoxalin-5-yl]-1,1-diphenyl-methanimine (50 mg, 42.0 μmol, 59%) as a yellow solid. m/z ES+ $[M+H]^+$ 756.3.

Step 11. 3-(1-((3,3-Difluorocyclobutyl)methyl)-1H-pyrazol-4-yl)-6-((2-methyl-1-((2-(trimethylsilyl)ethoxy)methyl)-1H-benzo[d]imidazol-6-yl)oxy)quinoxalin-5-amine A mixture of N-[3-[1-[(3,3-difluorocyclobutyl)methyl]pyrazol-4-yl]-6-[2-methyl-3-(2-trimethylsilylethoxymethyl)benzimidazol-5-yl]oxy-quinoxalin-5-yl]-1,1-diphenyl-methanimine (50.0 mg, 66.1 μmol) in hydrogen chloride/dioxane (4 M, 0.1 mL) was stirred at 20° C. for 30 min. On completion, the mixture was concentrated in vacuo to give 3-[1-[(3,3-difluorocyclobutyl)methyl]pyrazol-4-yl]-6-[2-methyl-3-(2-trimethylsilylethoxymethyl)benzimidazol-5-yl]oxy-quinoxalin-5-amine (40 mg, crude) as a yellow solid, which was used for next step directly.

Step 12. 3-(1-((3,3-Difluorocyclobutyl)methyl)-1H-pyrazol-4-yl)-6-((2-methyl-1H-benzo[d]imidazol-6-yl)oxy)quinoxalin-5-amine A solution of 3-[1-[(3,3-difluorocyclobutyl)methyl]pyrazol-4-yl]-6-[2-methyl-3-(2-trimethylsilylethoxymethyl)benzimidazol-5-yl]oxy-quinoxalin-5-amine (40.0 mg, 67.6 μmol) in trifluoroacetic acid (0.2 mL) was stirred at 20° C. for 10 min. On completion, the mixture was concentrated in vacuo and the residue was purified by prep-HPLC [column: Phenomenex C18 75*30 mm*3 μm; mobile phase: [water (formic acid)-acetonitrile]; (B %: 15%-45%, 7 min] and then repurified by prep-TLC (dichloromethane:methanol=10:1) to give 3-[1-[(3,3-difluorocyclobutyl)methyl]pyrazol-4-yl]-6-[(2-methyl-3H-benzimidazol-5-yl)oxy]quinoxalin-5-amine (2 mg, 4.11 μmol, 6%) as a yellow solid. $^1H$ NMR (400 MHz, $CD_3OD$) δ 9.09 (s, 1H), 8.61 (s, 1H), 8.38 (s, 1H), 7.48 (d, J=8.8 Hz, 1H), 7.30 (d, J=0.8 Hz, 2H), 7.10 (s, 1H), 7.02 (dd, J=2.4, 8.8 Hz, 1H), 4.40 (d, J=6.8 Hz, 2H), 2.81-2.65 (m, 3H), 2.56 (s, 3H), 2.54-2.44 (m, 2H); m/z ES+ $[M+H]^+$ 462.0.

Example 86. Synthesis of 8-Chloro-7-((2-methyl-1H-benzo[d]imidazol-6-yl)oxy)-2-(1-((1r,3r)-3-(trifluoromethyl)cyclobutyl)-1H-pyrazol-4-yl)quinoxaline

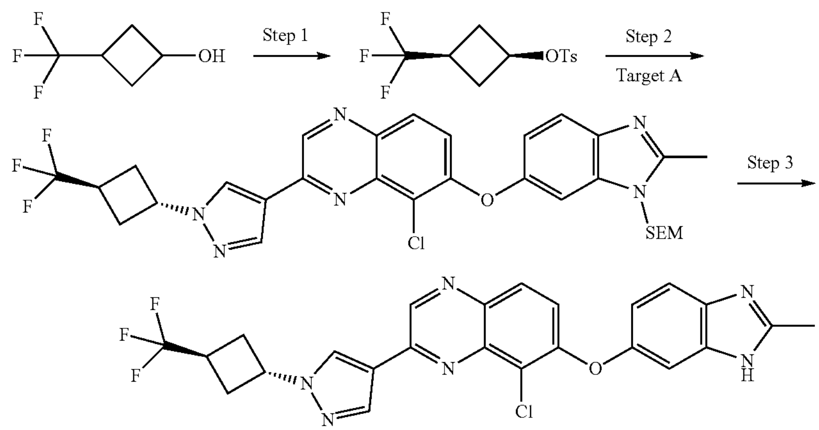

Step 1. (1s,3s)-3-(Trifluoromethyl)cyclobutyl 4-methylbenzenesulfonate

To a solution of 3-(trifluoromethyl)cyclobutanol (50.0 mg, 357 μmol) in dichloromethane (3 mL) was added triethylamine (72.7 mg, 718 μmol), 4-dimethylaminopyridine (5.0 mg, 40.9 μmol) and 4-methylbenzenesulfonyl chloride (170 mg, 892 μmol). The mixture was stirred at 25° C. for 12 h. On completion, the mixture was concentrated under reduced pressure. The residue was purified by prep-TLC (silica gel, petroleum ether:ethyl acetate=5:1) to give (1s,3s)-3-(trifluoromethyl)cyclobutyl 4-methylbenzenesulfonate (50 mg, 170 μmol, 48%) as a colorless oil. $^1$H NMR (400 MHz, $CDCl_3$) δ 7.89-7.74 (m, 2H), 7.36 (d, J=8.0 Hz, 2H), 4.82-4.67 (m, 1H), 2.53-2.42 (m, 6H), 2.37-2.24 (m, 2H).

Step 2. 8-Chloro-7-((2-methyl-1-((2-(trimethylsilyl)ethoxy)methyl)-1H-benzo[d]imidazol-6-yl)oxy)-2-(1-((1r,3r)-3-(trifluoromethyl)cyclobutyl)-1H-pyrazol-4-yl)quinoxaline To a solution of (1s,3s)-3-(trifluoromethyl)cyclobutyl 4-methylbenzenesulfonate (20 mg, 68 μmol) in N,N-dimethylformamide (1.2 mL) was added cesium carbonate (50 mg, 153 μmol) and 2-[[6-[5-chloro-3-(1H-pyrazol-4-yl)quinoxalin-6-yl]oxy-2-methyl-benzimidazol-1-yl]methoxy]ethyl-trimethyl-silane (35 mg, 69 μmol). The mixture was stirred at 80° C. for 6 h. On completion, the mixture was quenched with water (2 mL) and extracted with ethyl acetate (3 mL× 3). The combined organic phases were dried over anhydrous sodium sulfate, filtered and concentrated to give 8-chloro-7-((2-methyl-1-((2-(trimethylsilyl)ethoxy)methyl)-1H-benzo[d]imidazol-6-yl)oxy)-2-(1-((1r,3r)-3-(trifluoromethyl)cyclobutyl)-1H-pyrazol-4-yl)quinoxaline (62 mg, crude) as a yellow oil. m/z ES+ $[M+H]^+$ 629.0.

Step 3. 8-Chloro-7-((2-methyl-1H-benzo[d]imidazol-6-yl)oxy)-2-(1-((1r,3r)-3-(trifluoromethyl)cyclobutyl)-1H-pyrazol-4-yl)quinoxaline A solution of 8-chloro-7-((2-methyl-1-((2-(trimethylsilyl)ethoxy)methyl)-1H-benzo[d]imidazol-6-yl)oxy)-2-(1-((1r,3r)-3-(trifluoromethyl)cyclobutyl)-1H-pyrazol-4-yl)quinoxaline (60 mg, 95.4 μmol) in trifluoroacetic acid (1.2 mL) was stirred at 25° C. for 2 h. On completion, the mixture was filtered and concentrated under reduced pressure. The residue was purified by prep-HPLC (column: Phenomenex Luna C18 150*25 mm*10 μm; mobile phase: [water (formic acid)-acetonitrile]; (B %: 19%-49%, 10 min) to give 8-chloro-7-[(2-methyl-3H-benzimidazol-5-yl)oxy]-2-[1-[3-(trifluoromethyl)cyclobutyl]pyrazol-4-yl]quinoxaline (23.9 mg, 48 μmol, 50%) as a yellow solid. $^1$H NMR (400 MHz, DMSO-$d_6$) δ 9.36 (s, 1H), 8.82 (s, 1H), 8.43 (s, 1H), 8.02 (d, J=9.2 Hz, 1H), 7.71 (d, J=8.8 Hz, 1H), 7.46-7.37 (m, 2H), 7.22-7.15 (m, 1H), 5.04 (t, J=8.4 Hz, 1H), 3.54-3.40 (m, 1H), 3.25-3.07 (m, 2H), 2.71 (d, J=8.4 Hz, 2H), 2.68 (s, 3H); m/z ES+ $[M+H]^+$ 499.0.

Example 87. Synthesis of 8-Chloro-2-(1-(4,4-difluoro-1-methylcyclohexyl)-1H-pyrazol-4-yl)-7-((2-methyl-1H-benzo[d]imidazol-6-yl)oxy)quinoxaline and 8-chloro-2-(1-(4-fluoro-1-methylcyclohex-3-en-1-yl)-1H-pyrazol-4-yl)-7-((2-methyl-1H-benzo[d]imidazol-6-yl)oxy)quinoxaline

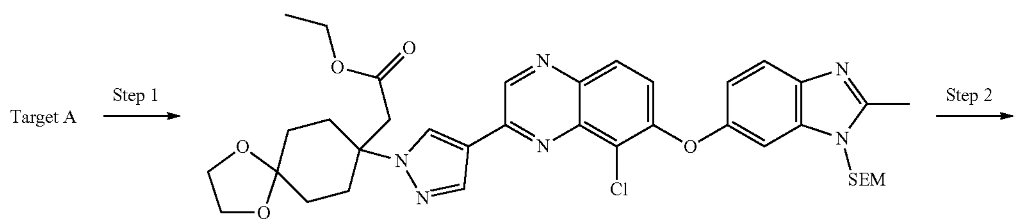

-continued

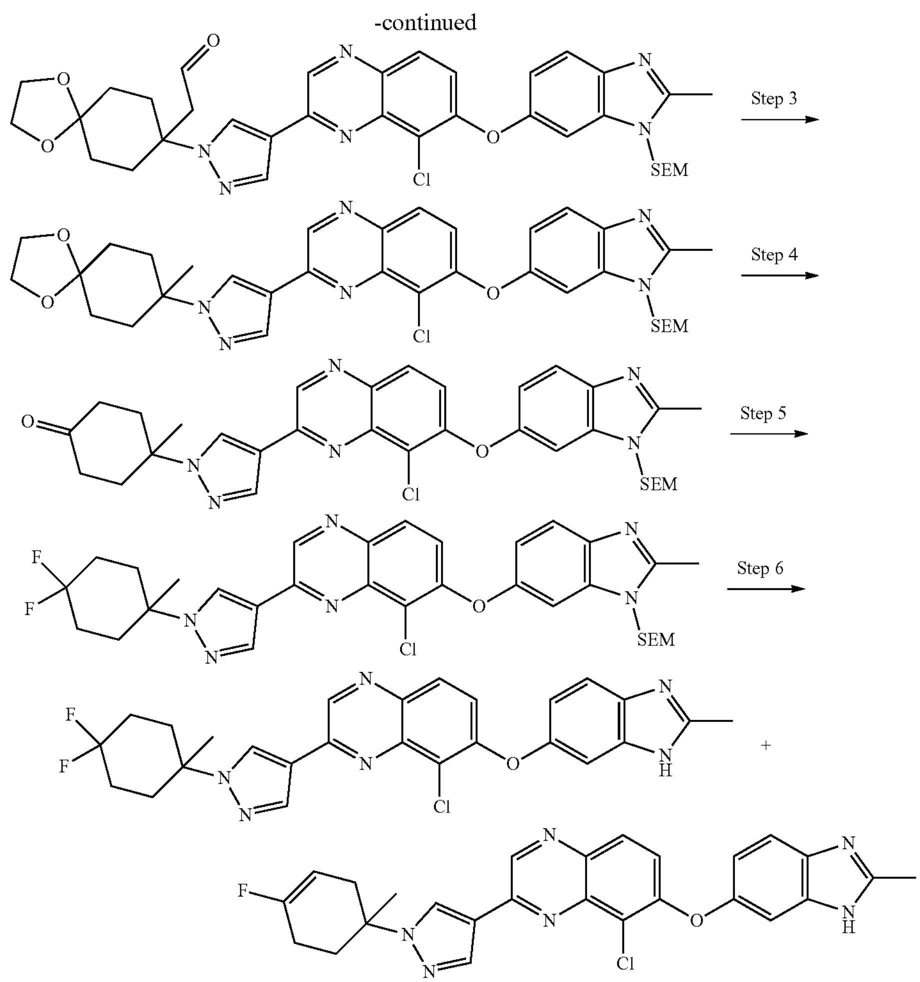

Step 1. Ethyl 2-(8-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-1,4-dioxaspiro[4.5]decan-8-yl)acetate To a solution of 2-[[6-[5-chloro-3-(1H-pyrazol-4-yl)quinoxalin-6-yl]oxy-2-methyl-benzimidazol-1-yl]methoxy]ethyl-trimethyl-silane (4 g, 7.89 mmol) in acetonitrile (40 mL) was added ethyl 2-(1,4-dioxaspiro[4.5]decan-8-ylidene)acetate (2.14 g, 9.47 mmol) and 1,8-diazabicyclo[5.4.0]undec-7-ene (1.44 g, 9.47 mmol), the mixture was stirred at 60° C. for 30 h. On completion, the mixture was diluted with ethyl acetate (100 mL) and washed with water (50 mL×2). The organic layers were dried over sodium sulfate and concentrated in vacuo and the residue was purified by column chromatography (100% ethyl acetate) to give ethyl 2-[8-[4-[8-chloro-7-[2-methyl-3-(2-trimethylsilylethoxymethyl)benzimidazol-5-yl]oxy-quinoxalin-2-yl]pyrazol-1-yl]-1,4-dioxaspiro[4.5]decan-8-yl]acetate (4.20 g, 5.73 mmol, 72%) as a yellow solid. m/z ES+ $[M+H]^+$ 733.3.

Step 2. 2-(8-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-1,4-dioxaspiro[4.5]decan-8-yl)acetaldehyde To a solution of ethyl 2-[8-[4-[8-chloro-7-[2-methyl-3-(2-trimethylsilylethoxymethyl)benzimidazol-5-yl]oxy-quinoxalin-2-yl]pyrazol-1-yl]-1,4-dioxaspiro[4.5]decan-8-yl]acetate (1.5 g, 2.05 mmol) in dichloromethane (100 mL) was added diisobutyl aluminium hydride (1 M, 10.2 mL) dropwise at −70° C., the mixture was stirred at −70° C. for 2 h. On completion, the mixture was slowly quenched with methanol (50 mL) at −70° C., then slowly warmed to 20° C. and stirred at 20° C. for 1 h. Then the mixture was filtered. The filtrate was dried and concentrated in vacuo to give 2-[8-[4-[8-chloro-7-[2-methyl-3-(2-trimethylsilylethoxymethyl)benzimidazol-5-yl]oxy-quinoxalin-2-yl]pyrazol-1-yl]-1,4-dioxaspiro[4.5]decan-8-yl]acetaldehyde (1.40 g, crude) as a yellow solid which was used for next step directly. m/z ES+ $[M+H]^+$ 689.1.

Step 3. 8-Chloro-2-(1-(8-methyl-1,4-dioxaspiro[4.5]decan-8-yl)-1H-pyrazol-4-yl)-7-((2-methyl-1-((2-(trimethylsilyl)ethoxy)methyl)-1H-benzo[d]imidazol-6-yl)oxy)quinoxaline To a solution of 2-[8-[4-[8-chloro-7-[2-methyl-3-(2-trimethylsilylethoxymethyl)benzimidazol-5-yl]oxy-quinoxalin-2-yl]pyrazol-1-yl]-1,4-dioxaspiro[4.5]decan-8-yl]acetaldehyde (1.4 g, 2.03 mmol) in toluene (30 mL) was added $Rh(PPh_3)_3Cl$ (1.69 g, 1.83 mmol) under nitrogen, the mixture was stirred at 120° C. for 16 h. On completion, the mixture was concentrated in vacuo and the residue was purified by column chromatography (100% ethyl acetate)

and then triturated with methanol (30 mL). The mixture was filtered and the filtrate was concentrated in vacuo and the residue was purified by prep-HPLC [column: Phenomenex Synergi Max-RP 250*50 mm*10 μm; mobile phase: [water (formic acid)-acetonitrile]; (B %: 37%-67%, 21 min] to give 2-[[6-[5-chloro-3-[1-(8-methyl-1,4-dioxaspiro[4.5]decan-8-yl)pyrazol-4-yl]quinoxalin-6-yl]oxy-2-methyl-benzimidazol-1-yl]methoxy]ethyl-trimethyl-silane (610 mg, 813 μmol, 40%) as a yellow solid. m/z ES+ $[M+H]^+$ 661.3.

Step 4. 4-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-4-methylcyclohexanone A solution of 2-[[6-[5-chloro-3-[1-(8-methyl-1,4-dioxaspiro[4.5]decan-8-yl)pyrazol-4-yl]quinoxalin-6-yl]oxy-2-methyl-benzimidazol-1-yl]methoxy]ethyl-trimethyl-silane (560 mg, 847 μmol) in formic acid (5 mL) and dichloromethane (5 mL) was stirred at 20° C. for 16 h. On completion, the mixture was washed with saturated aqueous sodium bicarbonate (40 mL) and extracted with ethyl acetate (30 mL×3). The combined organic layers were washed with brine (30 mL), dried over anhydrous sodium sulfate, filtered and concentrated in vacuum and the residue was purified by column chromatography (100% ethyl acetate) to afford 4-[4-[8-chloro-7-[2-methyl-3-(2-trimethylsilylethoxymethyl)benzimidazol-5-yl]oxy-quinoxalin-2-yl]pyrazol-1-yl]-4-methyl-cyclohexanone (310 mg, 490 μmol, 57%) as a yellow solid. m/z ES+ $[M+H]^+$ 617.3.

Step 5. 8-Chloro-2-(1-(4,4-difluoro-1-methylcyclohexyl)-1H-pyrazol-4-yl)-7-((2-methyl-1-((2-(trimethylsilyl)ethoxy)methyl)-1H-benzo[d]imidazol-6-yl)oxy)quinoxaline To a solution of 4-[4-[8-chloro-7-[2-methyl-3-(2-trimethylsilylethoxymethyl)benzimidazol-5-yl]oxy-quinoxalin-2-yl]pyrazol-1-yl]-4-methyl-cyclohexanone (150 mg, 243 μmol) in dichloromethane (3 mL) was added diethylaminosulphur trifluoride (78.4 mg, 486 μmol) dropwise at 0° C., the mixture was stirred at 35° C. for 2 h. On completion, the mixture was poured into saturated aqueous sodium bicarbonate (40 mL) and extracted with ethyl acetate (30 mL×3). The combined organic layers were washed with brine (30 mL), dried and concentrated in vacuo and the residue was purified by prep-TLC (100% ethyl acetate) to give 2-[[6-[5-chloro-3-[1-(4,4-difluoro-1-methyl-cyclohexyl)pyrazol-4-yl]quinoxalin-6-yl]oxy-2-methyl-benzimidazol-1-yl]methoxy]ethyl-trimethyl-silane (70 mg, 98.4 μmol, 40%) as a yellow solid. m/z ES+ $[M+H]^+$ 639.2.

Step 6. 8-Chloro-2-(1-(4,4-difluoro-1-methylcyclohexyl)-1H-pyrazol-4-yl)-7-((2-methyl-1H-benzo[d]imidazol-6-yl)oxy)quinoxaline and 8-Chloro-2-(1-(4-fluoro-1-methylcyclohex-3-en-1-yl)-1H-pyrazol-4-yl)-7-((2-methyl-1H-benzo[d]imidazol-6-yl)oxy)quinoxaline A solution of 2-[[6-[5-chloro-3-[1-(4,4-difluoro-1-methyl-cyclohexyl)pyrazol-4-yl]quinoxalin-6-yl]oxy-2-methyl-benzimidazol-1-yl]methoxy]ethyl-trimethyl-silane (160 mg, 250 μmol) in trifluoroacetic acid (3 mL) was stirred at 20° C. for 1 h. On completion, the mixture was concentrated in vacuo and the residue was purified by prep-HPLC [column: Phenomenex C18 75*30 mm*3 μm; mobile phase: [water (formic acid)-acetonitrile]; (B %: 32%-42%, 7 min] to give 8-chloro-2-[1-(4,4-difluoro-1-methyl-cyclohexyl)pyrazol-4-yl]-7-[(2-methyl-3H-benzimidazol-5-yl)oxy]quinoxaline (51.4 mg, 98.6 μmol, 39%) as a yellow solid and 8-chloro-2-[1-(4-fluoro-1-methyl-cyclohex-3-en-1-yl)pyrazol-4-yl]-7-[(2-methyl-3H-benzimidazol-5-yl)oxy]quinoxaline (23.4 mg, 47.8 μmol, 19%) as an off-white solid.

$^1H$ NMR (400 MHz, DMSO-$d_6$) δ 9.42 (s, 1H), 8.98 (s, 1H), 8.39 (s, 1H), 8.06 (d, J=9.2 Hz, 1H), 7.78 (d, J=8.8 Hz, 1H), 7.50-7.43 (m, 2H), 7.25 (dd, J=2.4, 8.8 Hz, 1H), 2.74 (s, 3H), 2.70-2.62 (m, 2H), 2.15-2 (m, 4H), 1.95-1.78 (m, 2H), 1.55 (s, 3H); m/z ES+ $[M+H]^+$ 509.0.

$^1H$ NMR (400 MHz, DMSO-$d_6$) δ 12.51-12.12 (m, 1H), 9.36 (s, 1H), 8.83 (s, 1H), 8.38 (s, 1H), 7.97 (d, J=9.1 Hz, 1H), 7.52 (d, J=6.8 Hz, 1H), 7.32 (d, J=9.2 Hz, 1H), 7.22 (s, 1H), 6.95 (dd, J=2.0, 8.8 Hz, 1H), 5.34-5.24 (m, 1H), 3.07-2.96 (m, 1H), 2.61-2.52 (m, 2H), 2.50 (s, 3H), 2.32-2.25 (m, 1H), 2.20-2.07 (m, 2H), 1.58 (s, 3H); m/z ES+ $[M+H]^+$ 489.0.

Example 88. Synthesis of (1s,3s)-3-(4-(8-Chloro-7-((7-fluoro-2-methyl-1H-benzo[d]imidazol-6-yl)oxy)quinoxalin-2-yl)-1H-pyrazol-1-yl)-1-methylcyclobutanol and (1r,3r)-3-(4-(8-Chloro-7-((7-fluoro-2-methyl-1H-benzo[d]imidazol-6-yl)oxy)quinoxalin-2-yl)-1H-pyrazol-1-yl)-1-methylcyclobutanol

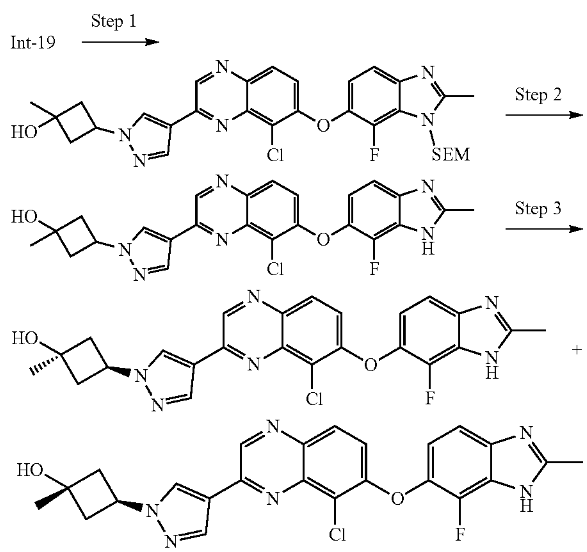

Step 1. 3-(4-(8-Chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)-1-methylcyclobutanol To a solution of 3-[4-[8-chloro-7-[4-fluoro-2-methyl-3-(2-trimethylsilylethoxymethyl)benzimidazol-5-yl]oxy-quinoxalin-2-yl]pyrazol-1-yl]cyclobutanone (110 mg, 185 μmol) in anhydrous tetrahydrofuran (3 mL) was added methyl magnesium bromide (3 M in THF, 185 μL) at 0° C. The mixture was stirred at 0° C. for 2 h. On completion, the mixture was quenched with sat. ammonium chloride (20 mL) at 0° C., and then diluted with water (20 mL) and extracted with ethyl acetate (20 mL×3). The combined organic layers were dried over anhydrous sodium sulfate, filtered and concentrated under reduced pressure. The residue was purified by column chromatography (silica gel, petroleum ether/ethyl acetate=3/1 to 1/4) to give 3-(4-(8-chloro-7-((7-fluoro-2-methyl-1-((2-(trimethylsilyl)ethoxy)methyl)-1H-benzo[d]imidazol-6-yl)oxy)quinoxalin-2-yl)-

1H-pyrazol-1-yl)-1-methylcyclobutanol (170 mg, 240 μmol, 65%) as a yellow oil. m/z ES+ $[M+H]^+$ 609.3.

Step 2. 3-(4-(8-chloro-7-((7-fluoro-2-methyl-1H-benzo[d]imidazol-6-yl)oxy)quinoxalin-2-yl)-1H-pyrazol-1-yl)-1-methylcyclobutanol A solution of 3-[4-[8-chloro-7-[4-fluoro-2-methyl-3-(2-trimethylsilylethoxymethyl)benzimidazol-5-yl]oxy-quinoxalin-2-yl]pyrazol-1-yl]-1-methyl-cyclobutanol (140 mg, 198 μmol) in trifluoroacetic acid (2 mL) was stirred at 25° C. for 0.5 h. On completion, the mixture was concentrated under reduced pressure. The residue was purified by prep-HPLC (formic acid condition; column: Phenomenex Luna C18 150*25 mm*10 μm; mobile phase: [water (formic acid)-acetonitrile]; (B %: 19%-49%, 10 min) to give 3-(4-(8-chloro-7-((7-fluoro-2-methyl-1H-benzo[d]imidazol-6-yl)oxy)quinoxalin-2-yl)-1H-pyrazol-1-yl)-1-methylcyclobutanol (70.0 mg, 146 μmol, 74%) as a white solid. m/z ES+ $[M+H]^+$ 479.1.

Step 3. (1s,3s)-3-(4-(8-Chloro-7-((7-fluoro-2-methyl-1H-benzo[d]imidazol-6-yl)oxy)quinoxalin-2-yl)-1H-pyrazol-1-yl)-1-methylcyclobutanol and (1r,3r)-3-(4-(8-Chloro-7-((7-fluoro-2-methyl-1H-benzo[d]imidazol-6-yl)oxy)quinoxalin-2-yl)-1H-pyrazol-1-yl)-1-methylcyclobutanol 3-(4-(8-Chloro-7-((7-fluoro-2-methyl-1H-benzo[d]imidazol-6-yl)oxy)quinoxalin-2-yl)-1H-pyrazol-1-yl)-1-methylcyclobutanol (70.0 mg, 146 μmol) was separated by SFC (basic condition;column: Daicel Chiralpak AD (250 mm*30 mm, 10 μm); mobile phase: [0.1% ammonium hydroxide/methanol]; (B %: 45%-45%, 3.6 min, total run 50 min) to give (1s,3s)-3-(4-(8-chloro-7-((7-fluoro-2-methyl-1H-benzo[d]imidazol-6-yl)oxy)quinoxalin-2-yl)-1H-pyrazol-1-yl)-1-methylcyclobutanol (44.5 mg, 92.9 μmol, 64%) as a white solid and (1r,3r)-3-(4-(8-chloro-7-((7-fluoro-2-methyl-1H-benzo[d]imidazol-6-yl)oxy)quinoxalin-2-yl)-1H-pyrazol-1-yl)-1-methylcyclobutanol (3.8 mg, 7.89 μmol, 5.4%) as a white solid.

$^1$H NMR (400 MHz, DMSO-$d_6$) δ ppm=9.31 (s, 1H), 8.76 (s, 1H), 8.38 (s, 1H), 7.93 (d, J=9.3 Hz, 1H), 7.33 (d, J=7.9 Hz, 1H), 7.22 (d, J=8.9 Hz, 1H), 7.09 (t, J=7.7 Hz, 1H), 5.32 (s, 1H), 4.65 (t, J=8.2 Hz, 1H), 2.65-2.54 (m, 4H), 2.53 (s, 3H), 1.35 (s, 3H). m/z ES+ $[M+H]^+$ 478.9. 1H NMR (400 MHz, DMSO-$d_6$) δ ppm=9.30 (s, 1H), 8.80 (s, 1H), 8.37 (s, 1H), 7.94 (d, J=9.2 Hz, 1H), 7.32 (d, J=8.6 Hz, 1H), 7.21 (d, J=9.0 Hz, 1H), 7.10 (t, J=7.4 Hz, 1H), 5.13 (s, 1H), 5.11-5.04 (m, 1H), 2.53 (s, 7H), 1.36 (s, 3H). m/z ES+ $[M+H]^+$ 478.9.

Example 89. Synthesis of (1s,3s)-3-((4-(8-chloro-7-((7-fluoro-2-methyl-1H-benzo[d]imidazol-6-yl)oxy)quinoxalin-2-yl)-1H-pyrazol-1-yl)methyl)-1-methylcyclobutanol and (1r,3r)-3-((4-(8-chloro-7-((7-fluoro-2-methyl-1H-benzo[d]imidazol-6-yl)oxy)quinoxalin-2-yl)-1H-pyrazol-1-yl)methyl)-1-methylcyclobutanol

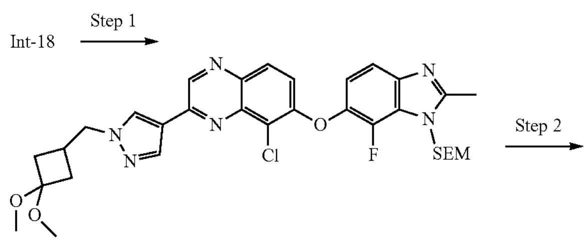

-continued

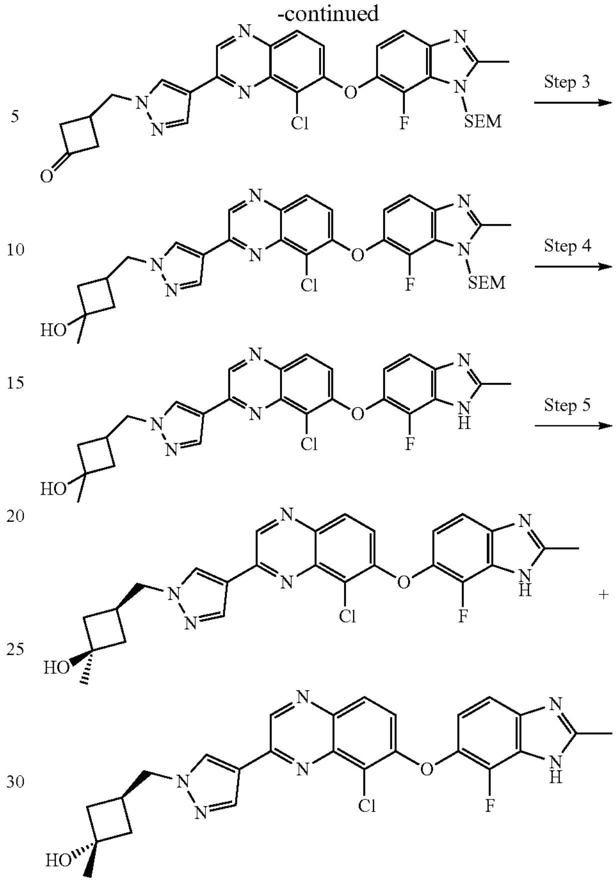

Step 1. 8-Chloro-2-(1-((3,3-dimethoxycyclobutyl)methyl)-1H-pyrazol-4-yl)-7-((7-fluoro-2-methyl-1-((2-(trimethylsilyl)ethoxy)methyl)-1H-benzo[d]imidazol-6-yl)oxy)quinoxaline To a solution of 2-[[6-[5-chloro-3-(1H-pyrazol-4-yl)quinoxalin-6-yl]oxy-7-fluoro-2-methyl-benzimidazol-1-yl]methoxy]ethyl-trimethyl-silane (270 mg, 514 μmol) and (3,3-dimethoxycyclobutyl)methyl methanesulfonate (138 mg, 617 μmol) in N,N-dimethylformamide (5 mL) was added potassium carbonate (142 mg, 1.03 mmol) and potassium iodide (85.4 mg, 514 μmol). The mixture was stirred at 100° C. for 12 h. The reaction mixture was poured into water (20 mL) and extracted with ethyl acetate (15 mL×3). The combined organic layers were washed with brine (20 mL), dried over anhydrous sodium sulfate, filtered and concentrated under reduced pressure. The residue was purified by column chromatography (silica gel, petroleum ether/ethyl acetate=3/1 to 0/1) to give 8-chloro-2-(1-((3,3-dimethoxycyclobutyl)methyl)-1H-pyrazol-4-yl)-7-((7-fluoro-2-methyl-1-((2-(trimethylsilyl)ethoxy)methyl)-1H-benzo[d]imidazol-6-yl)oxy)quinoxaline (280 mg, 416 μmol, 81%) as a yellow oil. m/z ES+ $[M+H]^+$ 653.3.

Step 2. 3-((4-(8-Chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)methyl)cyclobutanone A solution of 2-[[6-[5-chloro-3-[1-[(3,3-dimethoxycyclobutyl)methyl]pyrazol-4-yl]quinoxalin-6-yl]oxy-7-fluoro- 2-methyl-benzimidazol-1-yl]methoxy]ethyl-trimethyl-silane (260 mg, 398 μmol) in dichloromethane (2.5 mL) and formic acid (2.5 mL) was stirred at 25° C. for 1 h. On completion, the reaction mixture was concentrated under reduced pressure. The residue was diluted with sat. sodium bicarbonate (20 mL), and then extracted with ethyl acetate (15 mL×3). The combined organic layers were washed with brine (20 mL), dried over anhydrous sodium sulfate, filtered and concentrated under reduced pressure. The residue was purified by column chromatography (silica gel, petroleum ether/ethyl acetate=1/1 to 0/1) to give 3-((4-(8-chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)methyl)cyclobutanone (230 mg, 364 μmol, 91%) as a white solid. m/z ES+ $[M+H]^+$ 607.3.

Step 3. 3-((4-(8-Chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)methyl)-1-methylcyclobutanol To a solution of 3-[[4-[8-chloro-7-[4-fluoro-2-methyl-3-(2-trimethylsilylethoxymethyl)benzimidazol-5-yl]oxy-quinoxalin-2-yl]pyrazol-1-yl]methyl]cyclobutanone (210 mg, 346 μmol) in anhydrous tetrahydrofuran (5 mL) was added magnesium methyl bromide (3 M in THF, 346 μL) at 0° C. The mixture was stirred at 0° C. for 2 h. The reaction mixture was quenched with saturated aqueous ammonium chloride (10 mL) at 0° C., and then diluted with water (20 mL) and extracted with ethyl acetate (20 mL×3). The combined organic layers were washed with brine (25 mL), dried over anhydrous sodium sulfate, filtered and concentrated under reduced pressure. The residue was purified by prep-TLC (silica gel, dichloromethane:methanol=20:1) to give 3-((4-(8-chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)methyl)-1-methylcyclobutanol (65.0 mg, 83.4 μmol, 24%) as a yellow oil. m/z ES+ $[M+H]^+$ 623.3.

Step 4. 3-((4-(8-Chloro-7-((7-fluoro-2-methyl-1H-benzo[d]imidazol-6-yl)oxy)quinoxalin-2-yl)-1H-pyrazol-1-yl)methyl)-1-methylcyclobutanol A solution of 3-[[4-[8-chloro-7-[4-fluoro-2-methyl-3-(2-trimethylsilylethoxymethyl)benzimidazol-5-yl]oxy-quinoxalin-2-yl]pyrazol-1-yl]methyl]-1-methyl-cyclobutanol (65.0 mg, 83.4 μmol) in trifluoroacetic acid (1 mL) was stirred at 25° C. for 0.5 h. On completion, the mixture was concentrated under reduced pressure. The residue was purified by prep-HPLC (formic acid condition; column: Phenomenex Luna C18 150*25 mm*10 um; mobile phase: [water (formic acid)-acetonitrile]; (B %: 21%-51%, 10 min) to give 3-((4-(8-chloro-7-((7-fluoro-2-methyl-1H-benzo[d]imidazol-6-yl)oxy)quinoxalin-2-yl)-1H-pyrazol-1-yl)methyl)-1-methylcyclobutanol (30.0 mg, 59.0 μmol, 71%) as a white solid. m/z ES+ $[M+H]^+$ 493.2.

Step 5. (1s,3s)-3-((4-(8-Chloro-7-((7-fluoro-2-methyl-1H-benzo[d]imidazol-6-yl)oxy)quinoxalin-2-yl)-1H-pyrazol-1-yl)methyl)-1-methylcyclobutanol and (1r,3r)-3-((4-(8-Chloro-7-((7-fluoro-2-methyl-1H-benzo[d]imidazol-6-yl)oxy)quinoxalin-2-yl)-1H-pyrazol-1-yl)methyl)-1-methylcyclobutanol 3-((4-(8-Chloro-7-((7-fluoro-2-methyl-1H-benzo[d]imidazol-6-yl)oxy)quinoxalin-2-yl)-1H-pyrazol-1-yl)methyl)-1-methylcyclobutanol (30.0 mg, 59.0 μmol) was separated by SFC (column: Daicel Chiralpak IE (250 mm*30 mm, 10 μm); mobile phase: [hexane-EtOH (0.1% ammonium hydroxide)]; (B %: 55%-55%, 15 min) to give (1s,3s)-3-((4-(8-chloro-7-((7-fluoro-2-methyl-1H-benzo[d]imidazol-6-yl)oxy)quinoxalin-2-yl)-1H-pyrazol-1-yl)methyl)-1-methylcyclobutanol (5.4 mg, 11.0 μmol, 18%) as a brown solid and (1r,3r)-3-((4-(8-chloro-7-((7-fluoro-2-methyl-1H-benzo[d]imidazol-6-yl)oxy)quinoxalin-2-yl)-1H-pyrazol-1-yl)methyl)-1-methylcyclobutanol (25.6 mg, 51.3 μmol, 84%) as an off-white solid.

$^1$H NMR (400 MHz, $CD_3OD$) δ ppm=9.13 (s, 1H), 8.55 (s, 1H), 8.33 (s, 1H), 7.86 (d, J=9.2 Hz, 1H), 7.33 (d, J=8.4 Hz, 1H), 7.23 (d, J=9.2 Hz, 1H), 7.09 (dd, J=7.2, 8.6 Hz, 1H), 4.31 (d, J=7.2 Hz, 2H), 3.02-2.93 (m, 1H), 2.60 (s, 3H), 2.23-2.16 (m, 2H), 2.03-1.96 (m, 2H), 1.34 (s, 3H). m/z ES+ $[M+H]^+$ 492.9.

$^1$H NMR (400 MHz, $CD_3OD$) δ ppm=9.13 (s, 1H), 8.55 (s, 1H), 8.33 (s, 1H), 7.86 (d, J=9.3 Hz, 1H), 7.33 (d, J=8.6 Hz, 1H), 7.23 (d, J=9.3 Hz, 1H), 7.09 (dd, J=7.3, 8.5 Hz, 1H), 4.31 (d, J=7.6 Hz, 2H), 3.02-2.93 (m, 1H), 2.60 (s, 3H), 2.23-2.16 (m, 2H), 2.03-1.96 (m, 2H), 1.34 (s, 3H). m/z ES+ $[M+H]^+$ 492.9.

Example 90. Synthesis of 2-(4-(8-Chloro-7-((7-fluoro-2-methyl-1H-benzo[d]imidazol-6-yl)oxy)quinoxalin-2-yl)-1H-pyrazol-1-yl)-1-(3,3-difluoropyrrolidin-1-yl)ethanone

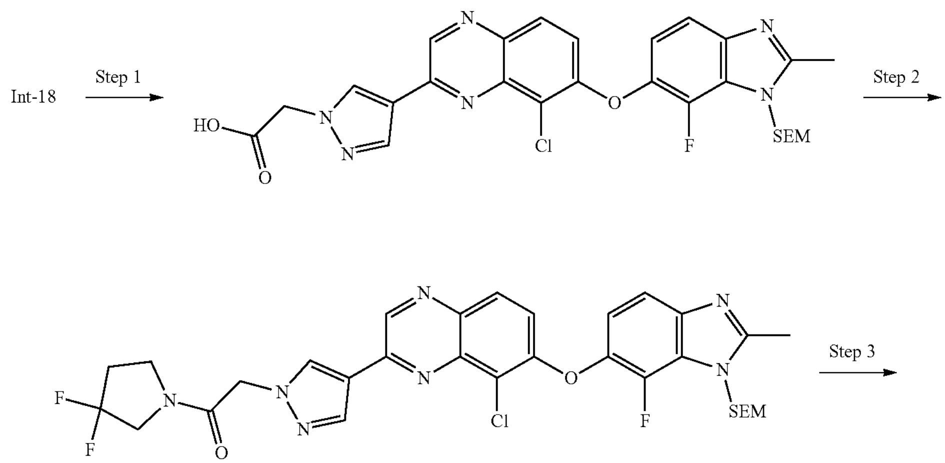

-continued

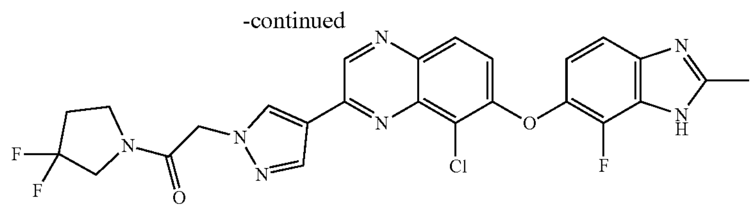

Step 1. 2-(4-(8-Chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl) acetic acid To a solution of 2-[[6-[5-chloro-3-(1H-pyrazol-4-yl)quinoxalin-6-yl]oxy-7-fluoro-2-methyl-benzimidazol-1-yl] methoxy]ethyl-trimethyl-silane (130 mg, 248 μmol) in anhydrous tetrahydrofuran (6 mL) was added sodium hydride (29.7 mg, 743 μmol, 60% in mineral oil). The mixture was stirred at 25° C. for 0.5 h. Then 2-bromoacetic acid (51.6 mg, 371 μmol, 26.7 μL) was added. The mixture was stirred at 60° C. for 1 h. On completion, the mixture was quenched with water (2 mL) at 25° C. and concentrated under reduced pressure. The residue was dissolved in water (1 mL) and then acidified by saturated aqueous citric acid until PH ~ 6. Then the mixture was filtered and the filtered cake was collected to give 2-(4-(8-chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl) acetic acid (140 mg, crude) as a yellow solid. $^1$H NMR (400 MHz, DMSO-$d_6$) δ 9.34 (s, 1H), 8.70 (s, 1H), 8.38 (s, 1H), 7.95 (d, J=8.8 Hz, 1H), 7.57-7.43 (m, 1H), 7.31-7.12 (m, 2H), 5.63 (d, J=10.4 Hz, 2H), 5.05 (s, 2H), 3.60-3.56 (m, 2H), 2.61 (d, J=7.2 Hz, 3H), 0.91-0.82 (m, 2H), 0.07 (s, 9H); m/z ES+ [M+H]$^+$ 583.2.

Step 2. 2-(4-(8-Chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)-1-(3,3-difluoropyrrolidin-1-yl)ethanone To a solution of 2-[4-[8-chloro-7-[4-fluoro-2-methyl-3-(2-trimethylsilylethoxymethyl)benzimidazol-5-yl]oxy-quinoxalin-2-yl]pyrazol-1-yl]acetic acid (130 mg, 223 μmol) and 3,3-difluoropyrrolidine hydrochloride (48.0 mg, 334 μmol) in dichloromethane (5 mL) was added diisopropylethylamine (86.5 mg, 669 μmol, 117 μL). Then EDCI (64.1 mg, 334 μmol) and HOBt (45.2 mg, 334 μmol) was added. The mixture was stirred at 25° C. for 12 h. On completion, the mixture was poured into water (20 mL) and extracted with dichloromethane (15 mL×3). The combined organic layers were washed with brine (20 mL), dried over sodium sulfate, filtered and concentrated under reduced pressure to give 2-(4-(8-chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)-1-(3,3-difluoropyrrolidin-1-yl)ethanone (160 mg, crude) as a yellow oil. m/z ES+ [M+H]$^+$ 672.4.

Step 3. 2-(4-(8-Chloro-7-((7-fluoro-2-methyl-1H-benzo[d]imidazol-6-yl)oxy)quinoxalin-2-yl)-1H-pyrazol-1-yl)-1-(3,3-difluoropyrrolidin-1-yl)ethanone A solution of 2-[4-[8-chloro-7-[4-fluoro-2-methyl-3-(2-trimethylsilylethoxymethyl)benzimidazol-5-yl]oxy-quinoxalin-2-yl]pyrazol-1-yl]-1-(3,3-difluoropyrrolidin-1-yl) ethanone (150 mg, 223 μmol) in trifluoroacetic acid (3 mL) was stirred at 25° C. for 0.5 h. On completion, the mixture was concentrated under reduced pressure. The residue was purified by prep-HPLC (formic acid condition; column: Phenomenex Luna C18 150*25 mm*10 μm; mobile phase: [water (formic acid)-acetonitrile]; (B %: 20%-50%, 10 min) to give 2-(4-(8-chloro-7-((7-fluoro-2-methyl-1H-benzo[d]imidazol-6-yl)oxy)quinoxalin-2-yl)-1H-pyrazol-1-yl)-1-(3,3-difluoropyrrolidin-1-yl)ethanone (33.8 mg, 62.3 μmol, 28%) as a white solid. $^1$H NMR (400 MHz, DMSO-$d_6$): δ ppm=9.33 (s, 1H), 8.65 (d, J=4.4 Hz, 1H), 8.39 (s, 1H), 7.95 (d, J=9.2 Hz, 1H), 7.34 (d, J=8.8 Hz, 1H), 7.23 (d, J=9.2 Hz, 1H), 7.10 (t, J=8.0 Hz, 1H), 5.31-5.21 (m, 2H), 4.10 (t, J=13.2 Hz, 1H), 3.89-3.77 (m, 2H), 3.63-3.59 (m, 1H), 2.63-2.55 (m, 1H), 2.53 (s, 3H), 2.45 (d, J=7.6 Hz, 1H); m/z ES+ [M+H]$^+$ 542.0.

Example 91. Synthesis of 1-((4-(8-(Cyclopent-1-en-1-yl)-7-((2-methyl-1H-benzo[d]imidazol-6-yl)oxy)quinoxalin-2-yl)-1H-pyrazol-1-yl)methyl)cyclopropanol

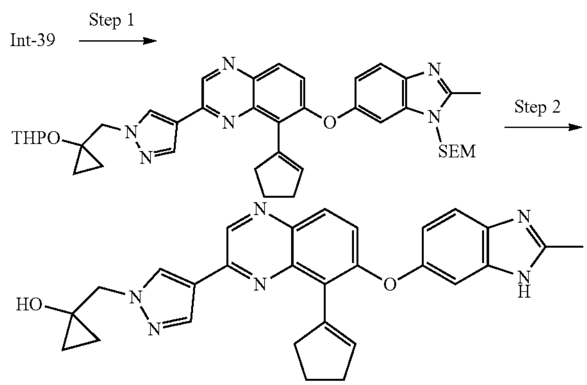

Step 1. 8-(Cyclopent-1-en-1-yl)-7-((2-methyl-1-((2-(trimethylsilyl)ethoxy)methyl)-1H-benzo[d]imidazol-6-yl)oxy)-2-(1-((1-((tetrahydro-2H-pyran-2-yl)oxy)cyclopropyl)methyl)-1H-pyrazol-4-yl)quinoxaline A mixture of 8-chloro-7-((2-methyl-1-((2-(trimethylsilyl)ethoxy)methyl)-1H-benzo[d]imidazol-6-yl)oxy)-2-(1-((1-((tetrahydro-2H-pyran-2-yl)oxy)cyclopropyl)methyl)-1H-pyrazol-4-yl)quinoxaline (150 mg, 227 μmol), 2-(cyclopent-1-en-1-yl)-4,4,5,5-tetramethyl-1,3,2-dioxaborolane (88.1 mg, 454 μmol), [2-(2-aminophenyl)phenyl] palladium (1+); bis(1-adamantyl)-butyl-phosphane;methanesulfonate (16.5 mg, 22.7 μmol), cesium carbonate (222 mg, 681 μmol) in water (0.4 mL) and cyclopentyl methyl ether (2 mL) was degassed and purged with nitrogen for 3 times, and then the mixture was stirred at 80° C. for 3 h under nitrogen atmosphere. On completion, the reaction mixture was concentrated under reduced pressure. The residue was purified by prep-TLC (silica gel, petroleum ether:ethyl acetate=1:3) to give 8-(cyclopent-1-en-1-yl)-7-((2-methyl-1-((2-(trimethylsilyl)ethoxy)methyl)-1H-benzo[d]imidazol-6-yl)oxy)-2-(1-((1-((tetrahydro-2H-pyran-2-yl)oxy)cyclopropyl)methyl)-1H-pyrazol-4-yl)quinoxaline (120 mg, 173 μmol, 76%) as a yellow solid. m/z ES+ $[M+H]^+$ 693.4.

Step 2. 1-((4-(8-(Cyclopent-1-en-1-yl)-7-((2-methyl-1H-benzo[d]imidazol-6-yl)oxy)quinoxalin-2-yl)-1H-pyrazol-1-yl)methyl)cyclopropanol A solution of 8-(cyclopent-1-en-1-yl)-7-((2-methyl-1-((2-(trimethylsilyl)ethoxy)methyl)-1H-benzo[d]imidazol-6-yl)oxy)-2-(1-((1-((tetrahydro-2H-pyran-2-yl)oxy)cyclopropyl)methyl)-1H-pyrazol-4-yl)quinoxaline (120 mg, 173 μmol) in trifluoroacetic acid (0.5 mL) was stirred at 25° C. for 1 h. On completion, the reaction mixture was concentrated under reduced pressure. The residue was purified by prep-HPLC (formic acid condition; column: Phenomenex Luna C18 150*25 mm*10 μm; mobile phase: [water (formic acid)-acetonitrile]; (B %: 14%-44%, 10 min) to give 1-((4-(8-(cyclopent-1-en-1-yl)-7-((2-methyl-1H-benzo[d]imidazol-6-yl)oxy)quinoxalin-2-yl)-1H-pyrazol-1-yl)methyl)cyclopropanol (44.3 mg, 90.8 μmol, 52%) as a yellow solid. $^1H$ NMR (400 MHz, DMSO-$d_6$) δ 9.26 (s, 1H), 8.57 (s, 1H), 8.23 (s, 1H), 7.92 (d, J=9.2 Hz, 1H), 7.55 (d, J=8.8 Hz, 1H), 7.33 (d, J=9.2 Hz, 1H), 7.13 (d, J=2.0 Hz, 1H), 6.96 (dd, J=2.4, 8.8 Hz, 1H), 6.04 (t, J=2.0 Hz, 1H), 5.72-5.50 (m, 1H), 4.28 (s, 2H), 2.86 (dt, J=2.0, 7.4 Hz, 2H), 2.57 (s, 3H), 2.55-2.51 (m, 2H), 1.96 (q, J=7.6 Hz, 2H), 0.78-0.74 (m, 2H), 0.72-0.68 (m, 2H); m/z ES+ $[M+H]^+$ 479.0.

Example 92. Synthesis of 8-Chloro-2-(1-((4,4-difluorocyclohexyl)methyl)-1H-pyrazol-4-yl)-7-((7-fluoro-2-methyl-1H-benzo[d]imidazol-6-yl)oxy)quinoxaline

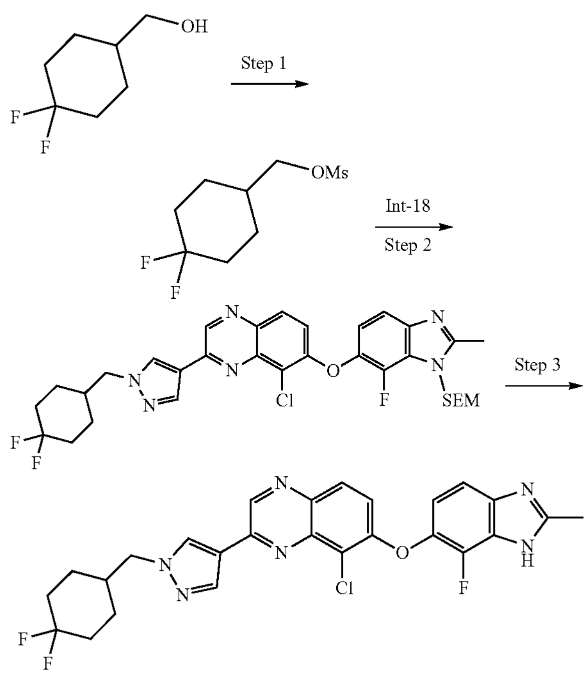

Step 1. (4,4-Difluorocyclohexyl)methyl methanesulfonate

To a solution of (4,4-difluorocyclohexyl) methanol (300 mg, 2 mmol) and triethylamine (436 mg, 4.31 mmol) in dichloromethane (5 mL) was added methanesulfonyl chloride (296 mg, 2.58 mmol) at 0° C., then the mixture was stirred at 0° C. for 1 h. The mixture was quenched with water (5 mL) and extracted with dichloromethane (8 mL×3), the combined organic phases were dried over anhydrous sodium sulfate, filtered and concentrated to give (4,4-difluorocyclohexyl)methyl methanesulfonate (490 mg, crude) as a light red solid. $^1H$ NMR (400 MHz, $CDCl_3$) δ=4.09 (d, J=6.0 Hz, 2H), 3.05-3.01 (m, 3H), 2.22-2.08 (m, 2H), 1.93-1.84 (m, 3H), 1.80-1.65 (m, 2H), 1.45-1.36 (m, 2H).

Step 2. 8-Chloro-2-(1-((4,4-difluorocyclohexyl)methyl)-1H-pyrazol-4-yl)-7-((7-fluoro-2-methyl-1-((2-(trimethylsilyl)ethoxy)methyl)-1H-benzo[d]imidazol-6-yl)oxy)quinoxaline To a solution of (4,4-difluorocyclohexyl)methyl methanesulfonate (100 mg, 438 μmol) and 2-[[6-[5-chloro-3-(1H-pyrazol-4-yl)quinoxalin-6-yl]oxy-7-fluoro-2-methyl-benzimidazol-1-yl]methoxy]ethyl-trimethyl-silane (230 mg, 438 μmol) in N,N-dimethylformamide (6 mL) was added potassium carbonate (180 mg, 1.30 mmol). The mixture was stirred at 80° C. for 3 h. On completion, the mixture was quenched with water (10 mL) and extracted with ethyl acetate (25 mL×3). The combined organic phases were dried over anhydrous sodium sulfate, filtered and concentrated to give 2-[[6-[5-chloro-3-[1-[(4,4-difluorocyclohexyl)methyl]pyrazol-4-yl]quinoxalin-6-yl]oxy-7-fluoro-2-methyl-benzimidazol-1-yl]methoxy]ethyl-trimethyl-silane (310 mg, crude) as a yellow oil. m/z ES+ $[M+H]^+$ 657.3.

Step 3. 8-Chloro-2-(1-((4,4-difluorocyclohexyl)methyl)-1H-pyrazol-4-yl)-7-((7-fluoro-2-methyl-1H-benzo[d]imidazol-6-yl)oxy)quinoxaline A solution of 2-[[6-[5-chloro-3-[1-[(4,4-difluorocyclohexyl)methyl]pyrazol-4-yl]quinoxalin-6-yl]oxy-7-fluoro-2-methyl-benzimidazol-1-yl]methoxy]ethyl-trimethyl-silane (300 mg, 456 μmol) in trifluoroacetic acid (3 mL) was stirred at 25° C. for 1 h. On completion, the mixture was concentrated under reduced pressure. The residue was purified by prep-HPLC (column: Phenomenex Luna C18 150*25 mm*10 μm; mobile phase: [water (formic acid)-acetonitrile]; (B %: 35%-65%, 10 min) to give 8-chloro-2-[1-[(4,4-difluorocyclohexyl)methyl]pyrazol-4-yl]-7-[(4-fluoro-2-methyl-3H-benzimidazol-5-yl)oxy]quinoxaline (206 mg, 390 μmol, 85%) as a yellow solid. $^1H$ NMR (400 MHz, $CD_3OD$) δ 9.20 (s, 1H), 8.59 (s, 1H), 8.37 (s, 1H), 7.95 (d, J=9.2 Hz, 1H), 7.55-7.51 (m, 1H), 7.38 (d, J=9.2 Hz, 1H), 7.35-7.28 (m, 1H), 4.20 (d, J=7.2 Hz, 2H), 2.83 (s, 3H), 2.87-2.80 (m, 1H), 2.14-2.03 (m, 3H), 1.92-1.79 (m, 2H), 1.77-1.73 (m, 2H), 1.46-1.36 (m, 2H); m/z ES+ $[M+H]^+$ 526.9.

Example 93. Synthesis of (1r,3r)-3-(4-(8-Chloro-7-((2-methyl-1H-benzo[d]imidazol-6-yl)oxy)quinoxalin-2-yl)-1H-pyrazol-1-yl)-1-methylcyclobutanol and (1s,3s)-3-(4-(8-Chloro-7-((2-methyl-1H-benzo[d]imidazol-6-yl)oxy)quinoxalin-2-yl)-1H-pyrazol-1-yl)-1-methylcyclobutanol

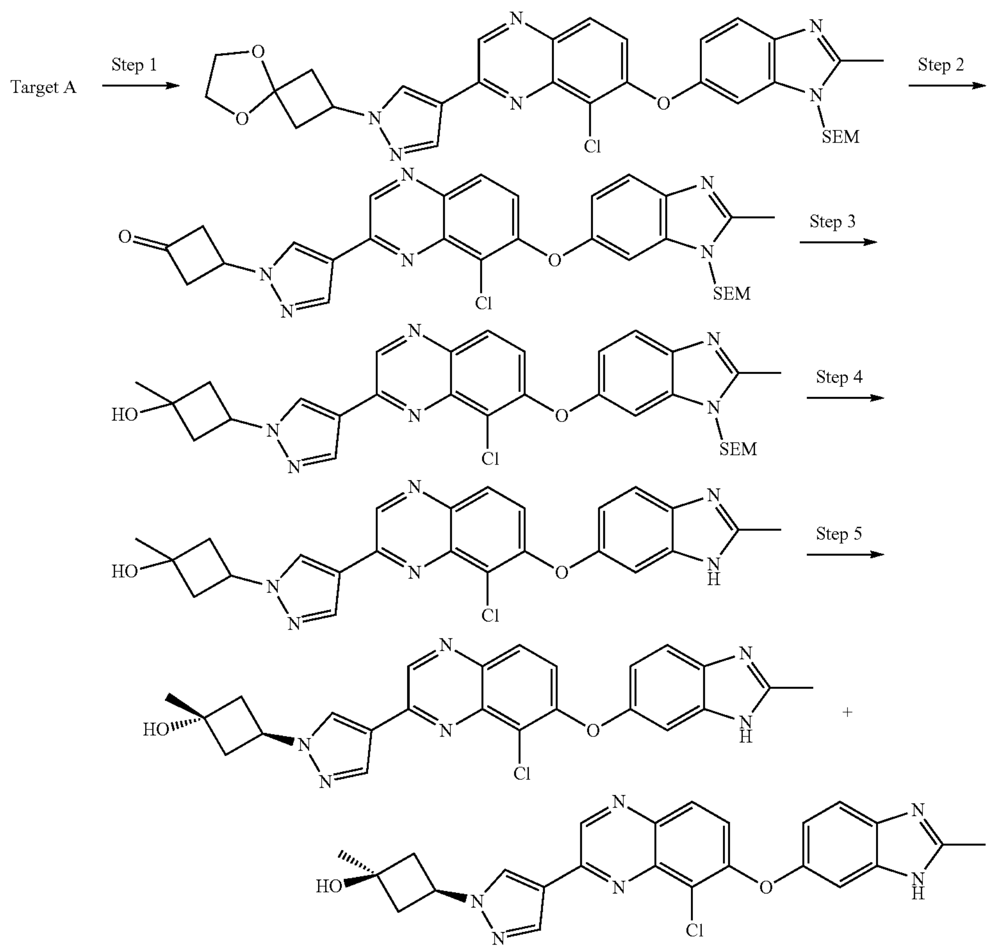

Step 1. 2-(1-(5,8-Dioxaspiro[3.4]octan-2-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline To a solution of 2-[[6-[5-chloro-3-(1H-pyrazol-4-yl)quinoxalin-6-yl]oxy-2-methyl-benzimidazol-1-yl]methoxy]ethyl-trimethyl-silane (3.50 g, 6.90 mmol) and 2-bromo-5,8-dioxaspiro[3.4]octane (2.13 g, 11.0 mmol) in N,N-dimethylformamide (50 mL) was added potassium carbonate (2.86 g, 20.7 mmol) and potassium iodide (115 mg, 690 μmol). The mixture was stirred at 100° C. for 12 h. On completion, the reaction mixture was diluted with water (30 mL) and extracted with ethyl acetate (100 mL×3). The combined organic layers were washed with brine (25 mL×2), dried over anhydrous sodium sulfate, filtered and concentrated under reduced pressure. The residue was purified by column chromatography (silica gel, dichloromethane:methanol=100:1 to 10:1) to give 2-(1-(5,8-dioxaspiro[3.4]octan-2-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline (3.5 g, 5.43 mmol, 79%) as a yellow solid. m/z ES+ $[M+H]^+$ 619.1.

Step 2. 3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)cyclobutanone To a solution of 2-[[6-[5-chloro-3-[1-(5,8-dioxaspiro[3.4]octan-2-yl)pyrazol-4-yl]quinoxalin-6-yl]oxy-2-methyl-benzimidazol-1-yl]methoxy]ethyl-trimethyl-silane (3.5 g, 5.65 mmol) in dichloromethane (18 mL) and water (1 mL) was added formic acid (42.7 g, 928 mmol, 35 mL). The mixture was stirred at 40° C. for 12 h. On completion, the reaction mixture was concentrated under reduced pressure. The residue was diluted with water (20 ml) and then basified by saturated aqueous sodium bicarbonate until pH=8~9. The mixture was then extracted with ethyl acetate (100 mL×2). The combined organic layers were washed with brine (50 mL×2), dried over anhydrous sodium sulfate, filtered and concentrated under reduced pressure. The crude product was purified by column chromatography (silica gel, dichloromethane:methanol=100:1 to 50:1) to give 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)cyclobutanone (2.5 g, 4.26 mmol, 75%) as a white solid. m/z ES+ $[M+H]^+$ 575.3.

Step 3. 3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-1-methylcyclobutanol To a solution of 3-[4-[8-chloro-7-[2-methyl-3-(2-trimethylsilylethoxymethyl)benzimidazol-5-yl]oxy-quinoxalin-2-yl]pyrazol-1-yl]cyclobutanone (300 mg, 522 μmol) in anhydrous tetrahydrofuran (3 mL) was added magnesium methyl bromide (3 M in THF, 522 μL) at 0° C. Then the mixture was stirred at 0° C. for 2 h. On completion, the reaction mixture was quenched with saturated aqueous ammonium chloride (50 mL) at 0° C., diluted with water (50 mL) and extracted with ethyl acetate (100 mL×3). The combined organic layers were washed with brine (25 mL×2), dried over anhydrous sodium sulfate, filtered and concentrated under reduced pressure. The residue was purified by column chromatography (silica gel, dichloromethane:methanol=80:1 to 50:1) to give 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-1-methylcyclobutanol (750 mg, 1.27 mmol, 49%) as a white solid. m/z ES+ $[M+H]^+$ 591.2.

Step 4. 3-(4-(8-Chloro-7-((2-methyl-1H-benzo[d]imidazol-6-yl)oxy)quinoxalin-2-yl)-1H-pyrazol-1-yl)-1-methylcyclobutanol A mixture of 3-[4-[8-chloro-7-[2-methyl-3-(2-trimethylsilylethoxymethyl)benzimidazol-5-yl]oxy-quinoxalin-2-yl]pyrazol-1-yl]-1-methyl-cyclobutanol (750 mg, 1.27 mmol) in trifluoroacetic acid (7.5 mL) was stirred at 25° C. for 0.5 h. On completion, the reaction mixture was concentrated under reduced pressure. Then the crude product was purified by prep-HPLC (formic acid condition; column: Phenomenex Luna C18 150×25 mm× 10 μm; mobile phase: [water (formic acid)-acetonitrile]; (B %: 10%-40%, 10 min) to give 3-[4-[8-chloro-7-[(2-methyl-3H-benzimidazol-5-yl)oxy]quinoxalin-2-yl]pyrazol-1-yl]-1-methyl-cyclobutanol (470 mg, 1.02 mmol, 80%) as a white solid. m/z ES+ $[M+H]^+$ 461.1.

Step 5. (1r,3r)-3-(4-(8-Chloro-7-((2-methyl-1H-benzo[d]imidazol-6-yl)oxy)quinoxalin-2-yl)-1H-pyrazol-1-yl)-1-methylcyclobutanol and (1s,3s)-3-(4-(8-Chloro-7-((2-methyl-1H-benzo[d]imidazol-6-yl)oxy)quinoxalin-2-yl)-1H-pyrazol-1-yl)-1-methylcyclobutanol 3-[4-[8-Chloro-7-[(2-methyl-3H-benzimidazol-5-yl)oxy]quinoxalin-2-yl]pyrazol-1-yl]-1-methyl-cyclobutanol (470 mg, 1.02 mmol) was separated by SFC (basic condition, column: Daicel Chiralpak IG (250 mm×30 mm, 10 μm); mobile phase: [heptane-ethyl alcohol (0.1% ammonium hydroxide)]; (B %: 40%-40%, 15 min) to give (1r,3r)-3-(4-(8-chloro-7-((2-methyl-1H-benzo[d]imidazol-6-yl)oxy)quinoxalin-2-yl)-1H-pyrazol-1-yl)-1-methylcyclobutanol (330 mg, 715 μmol, 70%) as a white solid and (1s,3s)-3-[4-[8-chloro-7-[(2-methyl-3H-benzimidazol-5-yl)oxy]quinoxalin-2-yl]pyrazol-1-yl]-1-methyl-cyclobutanol (28.0 mg, 54.7 μmol, 5.4%) as a white solid.

$^1H$ NMR (400 MHz, DMSO-$d_6$): δ ppm 12.57-12.07 (m, 1H), 9.31 (s, 1H), 8.76 (s, 1H), 8.38 (s, 1H), 7.95 (d, J=9.2 Hz, 1H), 7.51 (d, J=8.4 Hz, 1H), 7.31 (d, J=9.2 Hz, 1H), 7.21 (d, J=2.4 Hz, 1H), 6.94 (dd, J=2.0, 8.4 Hz, 1H), 5.32 (s, 1H), 4.65 (t, J=8.4 Hz, 1H), 2.64-2.54 (m, 4H), 2.49 (s, 3H), 1.35 (s, 3H); m/z ES+ $[M+H]^+$ 461.0.

$^1H$ NMR (400 MHz, DMSO-$d_6$): δ ppm δ=12.71-12.10 (m, 1H), 9.31 (s, 1H), 8.80 (s, 1H), 8.37 (s, 1H), 7.95 (d, J=9.6 Hz, 1H), 7.51 (d, J=8.8 Hz, 1H), 7.31 (d, J=9.2 Hz, 1H), 7.21 (s, 1H), 6.94 (dd, J=2.4, 8.8 Hz, 1H), 5.12 (s, 1H), 5.11-5.03 (m, 1H), 2.58-2.52 (m, 4H), 2.49-2.48 (m, 3H), 1.36 (s, 3H). m/z ES+ $[M+H]^+$ 461.0.

Example 94. Synthesis of 2-(1-((3,3-Difluorocyclobutyl)methyl)-1H-pyrazol-4-yl)-8-(2,5-dihydrofuran-3-yl)-7-((2-methyl-1H-benzo[d]imidazol-6-yl)oxy)quinoxaline

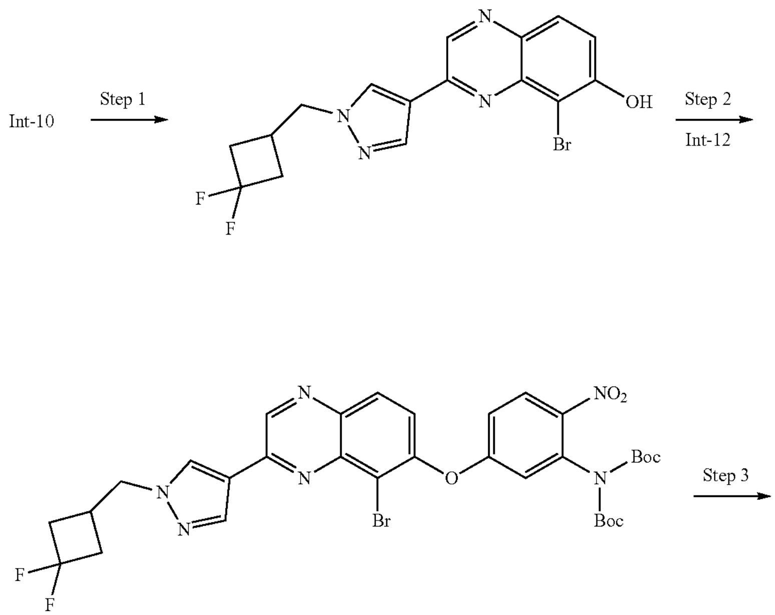

-continued
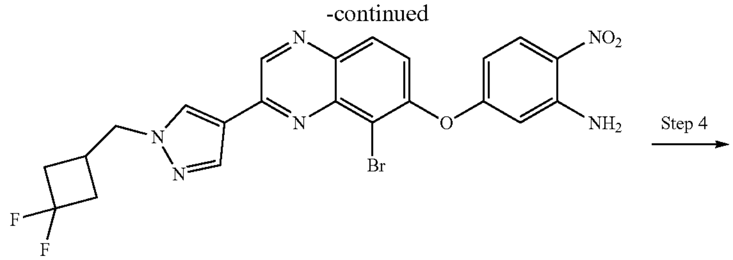
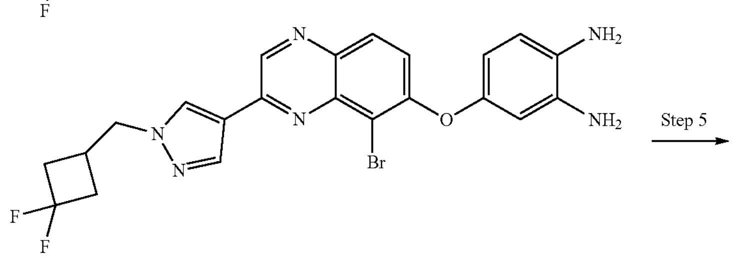
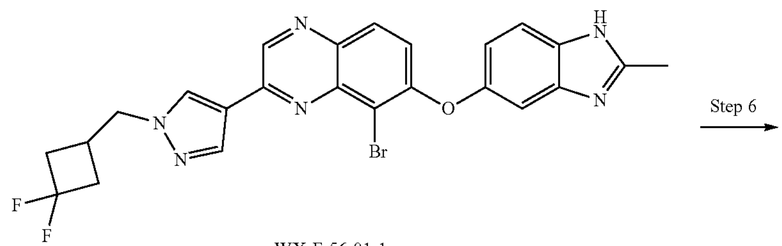
WX-F-56-01-1
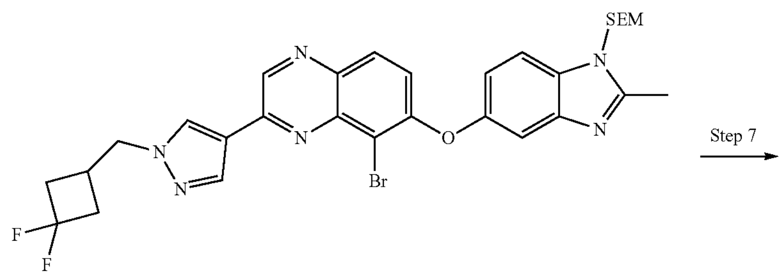
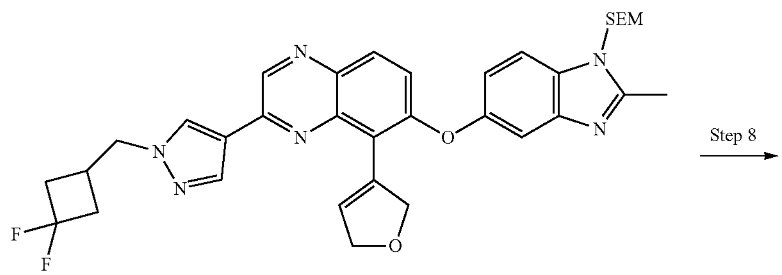
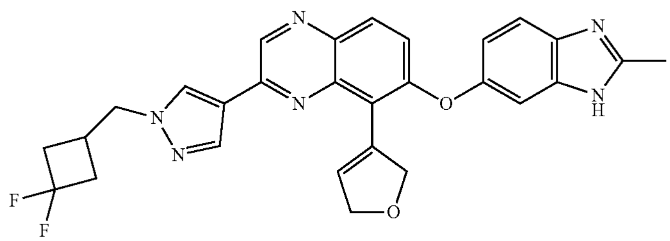

Step 1. 5-Bromo-3-(1-((3,3-difluorocyclobutyl) methyl)-1H-pyrazol-4-yl)quinoxalin-6-ol To a solution of 3-[1-[(3,3-difluorocyclobutyl)methyl] pyrazol-4-yl]quinoxalin-6-ol (900 mg, 2.85 mmol) in chloroform (15 mL) was added N-bromosuccinimide (1.01 g, 5.69 mmol), triethylamine (288 mg, 2.85 mmol) and nickel (II) chloride (369 mg, 2.85 mmol). The mixture was stirred at 60° C. for 2 h. On completion, the reaction mixture was filtered and concentrated under reduced pressure. The residue was purified by column chromatography (petroleum ether/ethyl acetate=10/1 to 3/1) to give 5-bromo-3-(1-((3,3-difluorocyclobutyl)methyl)-1H-pyrazol-4-yl) quinoxalin-6-ol (1.6 g, crude) as a yellow solid. m/z ES+ $[M+H]^+$ 397.1.

Step 2. tert-Butyl N-[5-[5-bromo-3-[1-[(3,3-difluorocyclobutyl)methyl]pyrazol-4-yl]quinoxalin-6-yl] oxy-2-nitro-phenyl]-N-tert-butoxycarbonyl-carbamate To a solution of 5-bromo-3-[1-[(3,3-difluorocyclobutyl) methyl]pyrazol-4-yl]quinoxalin-6-ol (1.25 g, 3.16 mmol) in N,N-dimethylformamide (20 mL) was added potassium carbonate (874 mg, 6.33 mmol) and tert-butyl N-tert-butoxycarbonyl-N-(5-fluoro-2-nitro-phenyl) carbamate (1.69 g, 4.74 mmol). The mixture was stirred at 80° C. for 12 h. On completion, the reaction mixture was diluted with water (100 mL), and then extracted with ethyl acetate (100 mL×3). The combined organic layers were dried over anhydrous sodium sulfate, filtered and concentrated under reduced pressure. The residue was purified by column chromatography (petroleum ether/ethyl acetate=10/1 to 5/1) to give tert-butyl N-[5-[5-bromo-3-[1-[(3,3-difluorocyclobutyl) methyl]pyrazol-4-yl] quinoxalin-6-yl]oxy-2-nitro-phenyl]-N-tert-butoxycarbonyl-carbamate (2.4 g, 2.62 mmol, 83%) as a brown oil. m/z ES+ $[M+H]^+$ 732.9.

Step 3. 5-((5-Bromo-3-(1-((3,3-difluorocyclobutyl) methyl)-1H-pyrazol-4-yl)quinoxalin-6-yl)oxy)-2-nitroaniline To a solution of tert-butyl N-[5-[5-bromo-3-[1-[(3,3-difluorocyclobutyl)methyl]pyrazol-4-yl]quinoxalin-6-yl]oxy-2-nitro-phenyl]-N-tert-butoxycarbonyl-carbamate (2.2 g, 3.01 mmol) in dichloromethane (15 mL) was added trifluoroacetic acid (5 mL). The mixture was stirred at 20° C. for 0.5 h. On completion, the reaction mixture was concentrated under reduced pressure. The residue was purified by column chromatography (petroleum ether/ethyl acetate=10/1 to 3/1) to give 5-((5-bromo-3-(1-((3,3-difluorocyclobutyl)methyl)-1H-pyrazol-4-yl)quinoxalin-6-yl)oxy)-2-nitroaniline (1.1 g, 1.86 mmol, 62%) as a yellow solid. m/z ES+ $[M+H]^+$ 533.0.

Step 4. 4-((5-Bromo-3-(1-((3,3-difluorocyclobutyl) methyl)-1H-pyrazol-4-yl)quinoxalin-6-yl)oxy)benzene-1,2-diamine To a solution of 5-[5-bromo-3-[1-[(3,3-difluorocyclobutyl)methyl]pyrazol-4-yl]quinoxalin-6-yl]oxy-2-nitroaniline (1 g, 1.88 mmol) in ethanol (20 mL) and water (2 mL) was added iron powder (526 mg, 9.41 mmol) and ammonium chloride (1.01 g, 18.8 mmol). The mixture was stirred at 60° C. for 2 h. On completion, the reaction mixture was filtered and concentrated under reduced pressure. The residue was diluted with water (50 mL) and extracted with ethyl acetate (50 mL×3). The combined organic layers were dried over anhydrous sodium sulfate, filtered and concentrated under reduced pressure to give 4-((5-bromo-3-(1-((3,3-difluorocyclobutyl)methyl)-1H-pyrazol-4-yl)quinoxalin-6-yl)oxy)benzene-1,2-diamine (1 g, crude) as a yellow solid. m/z ES+ $[M+18]^+$ 502.8.

Step 5. 8-Bromo-2-(1-((3,3-difluorocyclobutyl) methyl)-1H-pyrazol-4-yl)-7-((2-methyl-1H-benzo[d] imidazol-5-yl)oxy)quinoxaline To a solution of 4-[5-bromo-3-[1-[(3,3-difluorocyclobutyl)methyl]pyrazol-4-yl]quinoxalin-6-yl]oxybenzene-1,2-diamine (1 g, 1.99 mmol) in methanol (20 mL) was added sulfamic acid (387 mg, 3.99 mmol) and 1,1,1-trimethoxyethane (1.20 g, 9.97 mmol). The mixture was stirred at 20° C. for 2 h. On completion, the reaction mixture was concentrated under reduced pressure. The residue was purified by column chromatography (ethyl acetate/methanol=1/0 to 4/1) to give 8-bromo-2-(1-((3,3-difluorocyclobutyl)methyl)-1H-pyrazol-4-yl)-7-((2-methyl-1H-benzo [d]imidazol-5-yl)oxy)quinoxaline (800 mg, 1.43 mmol, 72%) as a red solid. $^1H$ NMR (400 MHz, DMSO-$d_6$) δ=9.31 (s, 1H), 8.76 (s, 1H), 8.37 (s, 1H), 8.06 (d, J=9.2 Hz, 1H), 7.73 (d, J=8.8 Hz, 1H), 7.45-7.36 (m, 2H), 7.25 (s, 1H), 7.12 (s, 1H), 7 (s, 1H), 4.39 (d, J=6.0 Hz, 2H), 2.70 (s, 2H), 2.69 (s, 3H), 2.66 (s, 1H), 2.55 (s, 1H); m/z ES+ $[M+18]^+$ 524.9.

Step 6. 8-Bromo-2-(1-((3,3-difluorocyclobutyl) methyl)-1H-pyrazol-4-yl)-7-((2-methyl-1-((2-(trimethylsilyl)ethoxy)methyl)-1H-benzo[d]imidazol-5-yl)oxy)quinoxaline To a solution of 8-bromo-2-[1-[(3,3-difluorocyclobutyl) methyl]pyrazol-4-yl]-7-[(2-methyl-1H-benzimidazol-5-yl) oxy]quinoxaline (560 mg, 1.07 mmol) in anhydrous tetrahydrofuran (10 mL) was added sodium hydride (85.3 mg, 2.13 mmol, 60% in mineral oil). The mixture was stirred at 0° C. for 0.5 h. Then (2-(chloromethoxy)ethyl)trimethylsilane (355 mg, 2.13 mmol) was added dropwise, and the resulting mixture was stirred at 20° C. for 2 h. On completion, the reaction mixture was quenched with water (20 mL) and extracted with ethyl acetate (15 mL×3). The combined organic layers were dried over anhydrous sodium sulfate, filtered and concentrated under reduced pressure. The residue was purified by column chromatography (ethyl acetate/ methanol=1/0 to 5/1) to give 8-bromo-2-(1-((3,3-difluorocyclobutyl)methyl)-1H-pyrazol-4-yl)-7-((2-methyl-1-((2-(trimethylsilyl)ethoxy)methyl)-1H-benzo[d]imidazol-5-yl) oxy)quinoxaline (170 mg, 246 μmol, 23%) as a yellow solid. $^1H$ NMR (400 MHz, $CD_3OD$) δ 9.14 (d, J=3.2 Hz, 1H), 8.60 (s, 1H), 8.37 (s, 1H), 7.95 (dd, J=4.4, 9.2 Hz, 1H), 7.63 (dd, J=6.8, 8.8 Hz, 1H), 7.40-7.23 (m, 2H), 7.13-7.04 (m, 1H), 5.69-5.44 (m, 2H), 4.40 (d, J=7.2 Hz, 2H), 3.70-3.51 (m, 2H), 2.73 (dd, J=8.0, 12.4 Hz, 3H), 2.65 (d, J=6.0 Hz, 3H), 2.55-2.44 (m, 2H), 0.97-0.74 (m, 2H), −0.04-−0.14 (m, 9H); m/z ES+ $[M+H]^+$ 657.0.

Step 7. 2-[[5-[3-[1-[(3,3-Difluorocyclobutyl)methyl] pyrazol-4-yl]-5-(2,5-dihydrofuran-3-yl)quinoxalin-6-yl]oxy-2-methyl-benzimidazol-1-yl]methoxy]ethyl-trimethyl-silane To a solution of 2-[[5-[5-bromo-3-[1-[(3,3-difluorocyclobutyl)methyl]pyrazol-4-yl]quinoxalin-6-yl]oxy-2-methyl-benzimidazol-1-yl]methoxy]ethyl-trimethyl-silane (50.0 mg, 76.3 μmol) in dioxane (1 mL) and water (0.2 mL) was added 2-(2,5-dihydrofuran-3-yl)-4,4,5,5-tetramethyl-1,3,2-dioxaborolane (44.9 mg, 229 μmol), methanesulfonato (2-dicyclohexylphosphino-2,4,6-tri-i-propyl-1,1'-biphenyl) (2-amino-1,1'-biphenyl-2-yl) palladium(II) (6.5 mg, 7.63 μmol) and potassium carbonate (31.6 mg, 229 μmol). The mixture was stirred at 100° C. for 1 h under nitrogen. On completion, the reaction mixture was concentrated under reduced pressure. The residue was purified by prep-TLC (ethyl acetate:methanol=20:1) to give 2-[[5-[3-[1-[(3,3-difluorocyclobutyl)methyl]pyrazol-4-yl]-5-(2,5-dihydrofuran-3-yl)quinoxalin-6-yl]oxy-2-methylbenzimidazol-1-yl] methoxy]ethyl-trimethyl-silane (50.0 mg, 69.8 μmol, 92%) as a yellow solid. m/z ES+ $[M+H]^+$ 645.1.

Step 8. 2-(1-((3,3-Difluorocyclobutyl)methyl)-1H-pyrazol-4-yl)-8-(2,5-dihydrofuran-3-yl)-7-((2-methyl-1H-benzo[d]imidazol-6-yl)oxy)quinoxaline A solution of 2-[[5-[3-[1-[(3,3-difluorocyclobutyl) methyl]pyrazol-4-yl]-5-(2,5-dihydrofuran-3-yl)quinoxalin-6-yl]oxy-2-methyl-benzimidazol-1-yl]methoxy]ethyl-trimethyl-silane (30 mg, 46.5 μmol) in trifluoroacetic acid (0.5 mL) was stirred at 20° C. for 0.5 h. On completion, the reaction mixture was filtered and concentrated under reduced pressure. The residue was purified by prep-HPLC (column: Phenomenex Luna C18 150*25 mm*10 μm; mobile phase: [water (formic acid)-acetonitrile]; (B %: 16%-46%, 10 min) to give 2-(1-((3,3-difluorocyclobutyl) methyl)-1H-pyrazol-4-yl)-8-(2,5-dihydrofuran-3-yl)-7-((2-methyl-1H-benzo[d]imidazol-6-yl)oxy)quinoxaline (8.8 mg, 17.1 μmol, 36.7%) as a yellow solid. $^1H$ NMR (400 MHz, $CDCl_3$) δ 9.07-8.97 (m, 1H), 8.23-8.10 (m, 2H), 7.95-7.85 (m, 1H), 7.59 (d, J=8.8 Hz, 1H), 7.29 (d, J=9.2 Hz, 1H), 7.19 (d, J=2.0 Hz, 1H), 7.07-6.98 (m, 1H), 6.65 (t, J=2.0 Hz, 1H), 5.43-5.24 (m, 2H), 4.97-4.82 (m, 2H), 4.35 (d, J=6.8 Hz, 2H), 2.86-2.76 (m, 3H), 2.73 (s, 3H), 2.54-2.39 (m, 2H); m/z ES+ $[M+H]^+$ 515.0.

Example 95. Synthesis of 3-(2-(4-(8-Chloro-7-((2-methyl-1H-benzo[d]imidazol-6-yl)oxy)quinoxalin-2-yl)-1H-pyrazol-1-yl) propan-2-yl)cyclobutanol and 3-(2-(4-(8-chloro-7-((2-methyl-1H-benzo[d]imidazol-6-yl)oxy)quinoxalin-2-yl)-1H-pyrazol-1-yl) propan-2-yl)cyclobutan-1-one and 8-chloro-2-(1-(2-(3,3-difluorocyclobutyl) propan-2-yl)-1H-pyrazol-4-yl)-7-((2-methyl-1H-benzo[d]imidazol-6-yl)oxy) quinoxaline

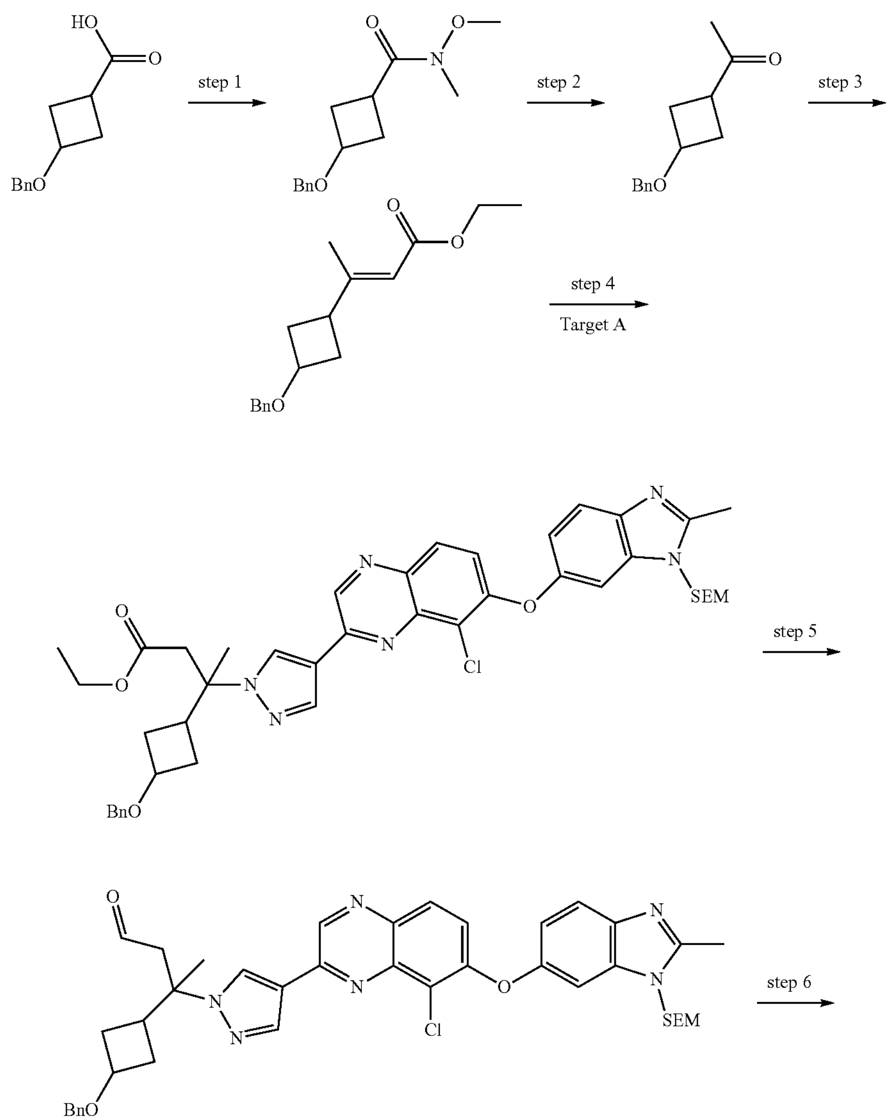

-continued

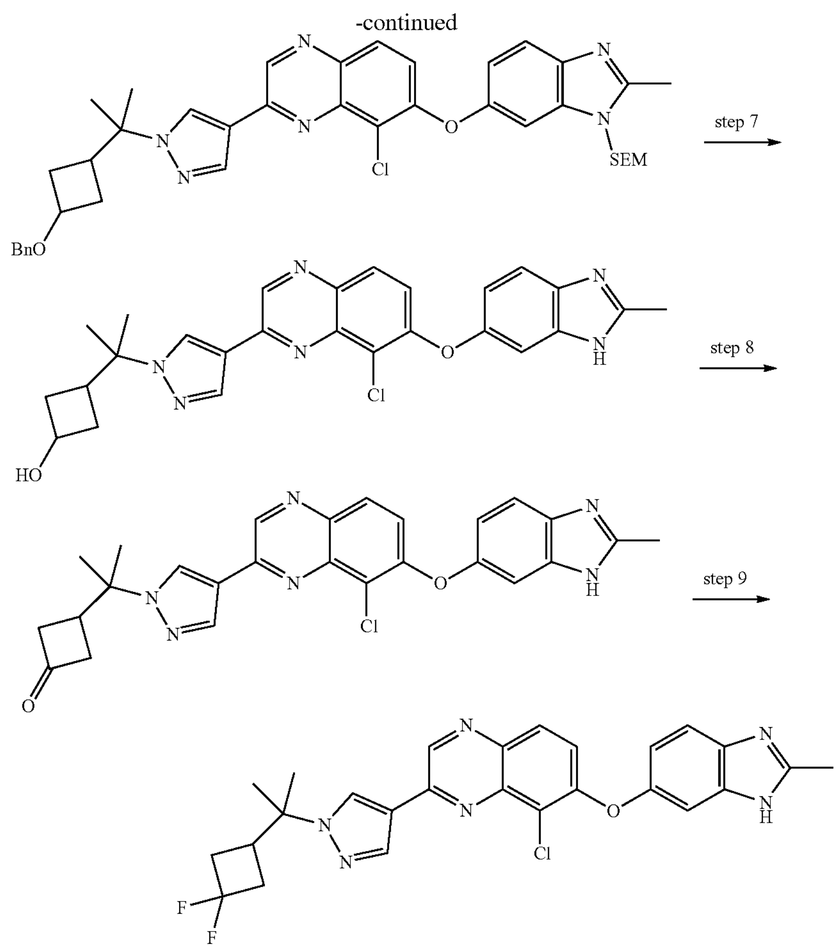

Step 1. 3-(Benzyloxy)-N-methoxy-N-methylcyclobutanecarboxamide

To a solution of 3-benzyloxycyclobutanecarboxylic acid (5 g, 24.2 mmol) and N-methoxymethanamine (3.55 g, 36.3 mmol, HCl salt) in N,N-dimethylformamide (50 mL) was added N,N-diisopropylethylamine (12.5 g, 96.9 mmol) and HATU (13.8 g, 36.3 mmol). The mixture was stirred at 25° C. for 12 hours. On completion, the reaction mixture was diluted with water (250 mL) and ethyl acetate (250 mL). The organic phase was separated, then washed with brine (100 mL), dried over sodium sulfate, filtered and concentrated under reduced pressure. The residue was purified by column chromatography (silica gel, petroleum ether/ethyl acetate=100/1 to 1/1) to give 3-benzyloxy-N-methoxy-N-methyl-cyclobutanecarboxamide (5 g, 19.0 mmol, 78%) as a colorless oil. $^1$H NMR (400 MHz, $CDCl_3$) δ 7.27 (s, 5H), 4.48-4.40 (m, 2H), 4.06-3.95 (m, 1H), 3.70-3.60 (m, 3H), 3.23-3.14 (m, 3H), 3.05-2.85 (m, 1H), 2.49-2.38 (m, 2H), 2.35-2.24 (m, 2H); m/z ES+ $[M+H]^+$ 250.1.

Step 2. 1-(3-(Benzyloxy)cyclobutyl)ethanone

To a solution of 3-benzyloxy-N-methoxy-N-methyl-cyclobutanecarboxamide (5 g, 20.0 mmol) in tetrahydrofuran (25 mL) was added methylmagnesium bromide (1 M, 26 mL, 26 mmol). The mixture was stirred at 0° C. for 2 hours under nitrogen atmosphere. On completion, the reaction mixture was quenched with saturated aqueous ammonium chloride (50 mL) at 0° C. and diluted with water (50 mL). The mixture was extracted with ethyl acetate (3× 50 mL). The combined organic layers were washed with brine (50 mL), dried over sodium sulfate, filtered and concentrated under reduced pressure to give 1-(3-benzyloxycyclobutyl) ethanone (4 g, 17.6 mmol, 88%) as a brown oil. $^1$H NMR (400 MHz, $CDCl_3$) δ 7.38-7.27 (m, 5H), 4.49-4.39 (m, 2H), 4.04-3.94 (m, 1H), 2.73 (dd, J=8.0, 9.6 Hz, 1H), 2.53-2.40 (m, 2H), 2.30-2.14 (m, 2H), 2.11 (s, 3H).

Step 3. (E)-Ethyl 3-(3-(benzyloxy)cyclobutyl) but-2-enoate

To a solution of ethyl 2-diethoxyphosphorylacetate (4.74 g, 21.1 mmol) in tetrahydrofuran (36 mL) was added sodium hydride (845 mg, 21.1 mmol, 60% in mineral oil), the mixture was stirred at 0° C. for 0.5 h. Then 1-(3-benzyloxycyclobutyl)ethanone (3.60 g, 17.6 mmol) was added. The mixture was stirred at 25° C. for 11.5 hours under nitrogen atmosphere. On completion, the reaction mixture was quenched with water (50 mL) at 0° C. and extracted with ethyl acetate (3×50 mL). The combined organic layers were washed with brine (50 mL), dried over sodium sulfate, filtered and concentrated under reduced pressure. The residue was purified by column chromatography (silica gel, petroleum ether/ethyl acetate=100/1 to 3/1) to give ethyl (E)-3-(3-benzyloxycyclobutyl) but-2-enoate (4.30 g, 15.3 mmol, 87%) as a brown oil. $^1$H NMR (400 MHz, $CDCl_3$) δ 7.42-7.28 (m, 5H), 5.74-5.56 (m, 1H), 4.43 (s, 2H), 4.23-

4.08 (m, 2H), 4.02-3.87 (m, 1H), 2.58-2.40 (m, 2H), 2.36-2.19 (m, 1H), 2.15-2.07 (m, 3H), 1.99-1.83 (m, 2H), 1.35-1.23 (m, 3H); m/z ES+ $[M+H]^+$ 275.1.

Step 4. Ethyl 3-(3-(benzyloxy)cyclobutyl)-3-(4-(8-chloro-7-((2-methyl-1-((2-(trimethylsilyl)ethoxy) methyl)-1H-benzo[d]imidazol-6-yl)oxy)quinoxalin-2-yl)-1H-pyrazol-1-yl) butanoate To a solution of 2-[[6-[5-chloro-3-(1H-pyrazol-4-yl)quinoxalin-6-yl]oxy-2-methyl-benzimidazol-1-yl]methoxy] ethyl-trimethyl-silane (2 g, 3.94 mmol) in acetonitrile (20 mL) was added 1,8-diazabicyclo[5.4.0]undec-7-ene (720 mg, 4.73 mmol) and ethyl (E)-3-(3-benzyloxycyclobutyl) but-2-enoate (1.30 g, 4.73 mmol). The mixture was stirred at 60° C. for 12 hours. On completion, the reaction mixture was diluted with water (50 mL) and ethyl acetate (100 mL). The organic phase was separated, washed with brine (50 mL), dried over sodium sulfate, filtered and concentrated under reduced pressure. The residue was purified by column chromatography (silica gel, petroleum ether/ethyl acetate=100/1 to 0/1) to give ethyl 3-(3-benzyloxycyclobutyl)-3-[4-[8-chloro-7-[2-methyl-3-(2-trimethylsilylethoxymethyl)benzimidazol-5-yl]oxy-quinoxalin-2-yl] pyrazol-1-yl]butanoate (1.70 g, 2.15 mmol, 54%) as a yellow solid. m/z ES+ $[M+H]^+$ 781.5.

Step 5. 3-(3-(Benzyloxy)cyclobutyl)-3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) butanal To a solution of ethyl 3-(3-benzyloxycyclobutyl)-3-[4-[8-chloro-7-[2-methyl-3-(2-trimethylsilylethoxymethyl)benzimidazol-5-yl]oxy-quinoxalin-2-yl]pyrazol-1-yl]butanoate (1.50 g, 1.92 mmol) in dichloromethane (75 mL) was added diisobutylaluminum hydride (1 M, 9.6 mL, 9.6 mmol) dropwise at −70° C. The mixture was stirred at −70° C. for 1 h under nitrogen atmosphere. On completion, the reaction mixture was slowly quenched with methanol (5 mL) at −70° C. and then warmed to 25° C. The mixture was filtered and the filtrate was concentrated under reduced pressure to give 3-(3-benzyloxycyclobutyl)-3-[4-[8-chloro-7-[2-methyl-3-(2-trimethylsilylethoxymethyl)benzimidazol-5-yl]oxy-quinoxalin-2-yl]pyrazol-1-yl]butanal (1.40 g, 1.54 mmol, 80%) as a yellow solid. m/z ES+ $[M+H]^+$ 739.3.

Step 6. 2-(1-(2-(3-(Benzyloxy)cyclobutyl) propan-2-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline To a solution of 3-(3-benzyloxycyclobutyl)-3-[4-[8-chloro-7-[2-methyl-3-(2-trimethylsilylethoxymethyl)benzimidazol-5-yl]oxy-quinoxalin-2-yl]pyrazol-1-yl]butanal (1.40 g, 1.90 mmol) in toluene (14 mL) was added $Rh(PPh_3)_3$ Cl (1.76 g, 1.90 mmol). The mixture was stirred at 120° C. for 12 hours under nitrogen atmosphere. On completion, the reaction mixture was filtered and concentrated under reduced pressure. The residue was purified by column chromatography (silica gel, petroleum ether/ethyl acetate=100/1 to 0/1) and reversed-phase HPLC (0.1% formic acid condition) to give 2-[[6-[3-[1-[1-(3-benzyloxy-cyclobutyl)-1-methyl-ethyl]pyrazol-4-yl]-5-chloro-quinoxalin-6-yl]oxy-2-methyl-benzimidazol-1-yl]methoxy] ethyl-trimethyl-silane (320 mg, 365 μmol, 19%) as a white solid. m/z ES+ $[M+H]^+$ 709.3.

Step 7. 3-(2-(4-(8-Chloro-7-((2-methyl-1H-benzo[d] imidazol-6-yl)oxy)quinoxalin-2-yl)-1H-pyrazol-1-yl) propan-2-yl)cyclobutanol To a solution of 2-[6-[3-[1-[1-(3-benzyloxycyclobutyl)-1-methyl-ethyl]pyrazol-4-yl]-5-chloro-quinoxalin-6-yl]oxy-2-methyl-benzimidazol-1-yl]methoxy]ethyl-trimethyl-silane (300 mg, 422 μmol) in dichloromethane (3 mL) was added tribromoborane (317 mg, 1.27 mmol) at 0° C. The mixture was stirred at 0° C. for 0.5 h under nitrogen atmosphere. On completion, the reaction mixture was quenched with water (5 mL) at 0° C., and extracted with dichloromethane (3× 20 mL). The combined organic layers were washed with brine (10 mL), dried over sodium sulfate, filtered and concentrated under reduced pressure and the residue was purified by prep-HPLC (column: Phenomenex Synergi C18 150*25 mm*10 μm; mobile phase: [water (formic acid)-acetonitrile]; (B %: 9%-39%, 10 min) to give 3-[1-[4-[8-chloro-7-[(2-methyl-3H-benzimidazol-5-yl)oxy] quinoxalin-2-yl]pyrazol-1-yl]-1-methyl-ethyl]cyclobutanol (130 mg, 263 μmol, 62%) as a white solid. $^1H$ NMR (400 MHz, DMSO-$d_6$) δ 12.91-11.57 (m, 1H), 9.38 (s, 1H), 8.88-8.71 (m, 1H), 8.34 (s, 1H), 7.96 (d, J=9.2 Hz, 1H), 7.52 (d, J=8.8 Hz, 1H), 7.32 (d, J=9.2 Hz, 1H), 7.22 (s, 1H), 6.96 (dd, J=2.4, 8.8 Hz, 1H), 5.32-4.58 (m, 1H), 3.84 (q, J=7.2 Hz, 1H), 2.50 (s, 3H), 2.29-2.05 (m, 3H), 1.68-1.47 (m, 8H); m/z ES+ $[M+H]^+$ 489.0.

Step 8. 3-(2-(4-(8-Chloro-7-((2-methyl-1H-benzo[d] imidazol-6-yl)oxy)quinoxalin-2-yl)-1H-pyrazol-1-yl) propan-2-yl)cyclobutanone To a solution of 3-[1-[4-[8-chloro-7-[(2-methyl-3H-benzimidazol-5-yl)oxy]quinoxalin-2-yl]pyrazol-1-yl]-1-methyl-ethyl]cyclobutanol (95.0 mg, 194 μmol) in dichloromethane (1 mL) and N,N-dimethylformamide (0.1 mL) was added Dess-Martin periodinane (123 mg, 291 μmol) at 0° C. The mixture was stirred at 25° C. for 12 hours under nitrogen atmosphere. On completion, the reaction mixture was quenched with saturated aqueous sodium thiosulfate (10 mL) and saturated aqueous sodium bicarbonate (10 mL) at 0° C., then diluted with water (10 mL) and extracted with dichloromethane (3×30 mL). The combined organic layers were washed with brine (10 mL), dried over sodium sulfate, filtered and concentrated under reduced pressure and the residue was purified by prep-HPLC (column: Phenomenex Synergi C18 150*25 mm*10 μm; mobile phase: [water (formic acid)-acetonitrile]; (B %: 11%-41%, 10 min) to give 3-[1-[4-[8-chloro-7-[(2-methyl-3H-benzimidazol-5-yl)oxy] quinoxalin-2-yl]pyrazol-1-yl]-1-methyl-ethyl]cyclobutanone (70.0 mg, 143 μmol, 73%) as a white solid. $^1H$ NMR (400 MHz, DMSO-$d_6$) δ 12.97-11.54 (m, 1H), 9.35 (s, 1H), 8.86 (s, 1H), 8.36 (s, 1H), 7.95 (d, J=9.2 Hz, 1H), 7.51 (d, J=8.8 Hz, 1H), 7.31 (d, J=9.2 Hz, 1H), 7.21 (s, 1H), 6.94 (dd, J=2.4, 8.8 Hz, 1H), 3.03 (s, 5H), 2.48 (s, 3H), 1.69 (s, 6H); m/z ES+ $[M+H]^+$ 487.0.

Step 9. 8-Chloro-2-(1-(2-(3,3-difluorocyclobutyl) propan-2-yl)-1H-pyrazol-4-yl)-7-((2-methyl-1H-benzo[d]imidazol-6-yl)oxy)quinoxaline To a solution of 3-[1-[4-[8-chloro-7-[(2-methyl-3H-benzimidazol-5-yl)oxy]quinoxalin-2-yl]pyrazol-1-yl]-1-methyl-ethyl]cyclobutanone (40.0 mg, 82.1 μmol) in dichloromethane (1 mL) was added bis(2-methoxyethyl) aminosulfur trifluoride (181 mg, 821 μmol) at 0° C. The mixture was stirred at 0° C. for 0.1 h under nitrogen atmosphere. On completion, the reaction mixture was quenched with saturated aqueous sodium bicarbonate (10 mL) at 0° C., and then diluted with water (10 mL) and extracted with dichloromethane (3×30 mL). The combined organic layers were washed with brine (10 mL), dried over sodium sulfate, filtered and concentrated under reduced pressure and the residue was purified by prep-HPLC (column: Phenomenex Synergi C18 150*25 mm*10 μm; mobile phase: [water (formic acid)-acetonitrile]; (B %: 25%-45%, 10 min) to give 8-chloro-2-[1-[1-(3,3-difluorocyclobutyl)-

1-methyl-ethyl]pyrazol-4-yl]-7-[(2-methyl-3H-benzimidazol-5-yl)oxy]quinoxaline (26.5 mg, 51.6 μmol, 62%) as a white solid. $^1$H NMR (400 MHz, DMSO-$d_6$) δ 12.72-11.88 (m, 1H), 9.38 (s, 1H), 8.85 (s, 1H), 8.38 (s, 1H), 7.97 (d, J=9.2 Hz, 1H), 7.52 (d, J=7.6 Hz, 1H), 7.32 (d, J=9.2 Hz, 1H), 7.22 (s, 1H), 6.95 (dd, J=2.0, 8.4 Hz, 1H), 2.83-2.66 (m, 1H), 2.61-2.54 (m, 4H), 2.50 (s, 3H), 1.65 (s, 6H); m/z ES+ $[M+H]^+$ 508.9.

Example 96. Synthesis of 3-(4-(8-Chloro-7-((7-fluoro-2-methyl-1H-benzo[d]imidazol-6-yl)oxy)quinoxalin-2-yl)-1H-pyrazol-1-yl)cyclobutanone

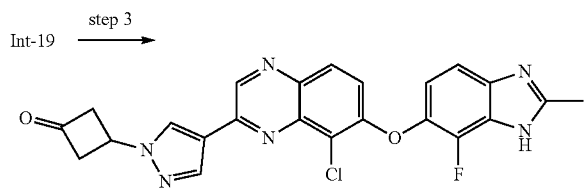

Step 1. 3-(4-(8-Chloro-7-((7-fluoro-2-methyl-1H-benzo[d]imidazol-6-yl)oxy)quinoxalin-2-yl)-1H-pyrazol-1-yl)cyclobutanone A mixture of 3-[4-[8-chloro-7-[4-fluoro-2-methyl-3-(2-trimethylsilylethoxymethyl)benzimidazol-5-yl]oxy-quinoxalin-2-yl]pyrazol-1-yl]cyclobutanone (30.0 mg, 51.0 μmol) in trifluoroacetic acid (0.5 mL) was stirred at 25° C. for 0.5 h. On completion, the reaction mixture was concentrated under reduced pressure. The residue was purified by prep-HPLC (formic acid condition; column: Phenomenex Luna C18 150×25 mm× 10 μm; mobile phase: [water (formic acid)-acetonitrile]; (B %: 19%-49%, 10 min) to give 3-[4-[8-chloro-7-[(4-fluoro-2-methyl-3H-benzimidazol-5-yl)oxy]quinoxalin-2-yl]pyrazol-1-yl]cyclobutanone (15.3 mg, 32.7 μmol, 65%) as a white solid. $^1$H NMR (400 MHz, DMSO-$d_6$) δ=9.33 (s, 1H), 8.96 (s, 1H), 8.46 (s, 1H), 7.95 (d, J=9.2 Hz, 1H), 7.34 (d, J=8.8 Hz, 1H), 7.24 (d, J=9.2 Hz, 1H), 7.09 (t, J=8.0 Hz, 1H), 5.44-5.29 (m, 1H), 3.70-3.64 (m, 4H), 2.53 (s, 3H); m/z ES+ $[M+H]^+$ 462.9.

Example 97. Synthesis of (1s,3s)-3-(4-(8-Chloro-7-((7-fluoro-2-methyl-1H-benzo[d]imidazol-6-yl)oxy)quinoxalin-2-yl)-1H-pyrazol-1-yl)cyclobutanol

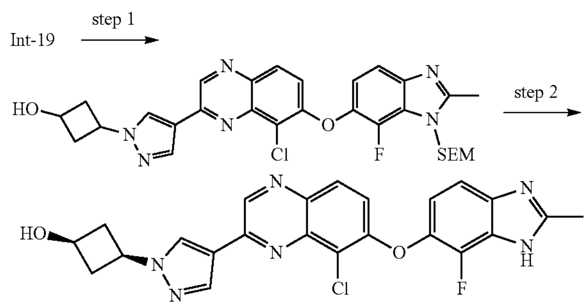

Step 1. 3-(4-(8-Chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)cyclobutanol To a solution of 3-[4-[8-chloro-7-[4-fluoro-2-methyl-3-(2-trimethylsilylethoxymethyl)benzimidazol-5-yl]oxy-quinoxalin-2-yl]pyrazol-1-yl]cyclobutanone (300 mg, 506 μmol) in ethanol (3 mL) was added sodium borohydride (19 mg, 506 μmol) at 0° C., The mixture was stirred at 0° C. for 0.5 h. On completion, the reaction mixture was quenched with saturated aqueous ammonium chloride (20 mL) at 0° C. and extracted with ethyl acetate (100 mL× 2). The combined organic layers were washed with brine (25 mL×2), dried over sodium sulfate, filtered and concentrated under reduced pressure. The residue was purified by prep-TLC (silica gel, dichloromethane:methanol=20:1) to give 3-[4-[8-chloro-7-[4-fluoro-2-methyl-3-(2-trimethylsilylethoxymethyl)benzimidazol-5-yl]oxy-quinoxalin-2-yl]pyrazol-1-yl]cyclobutanol (200 mg, 333 μmol, 66%) as a white solid. $^1$HNMR (400 MHz, DMSO-$d_6$) δ=9.34-9.32 (m, 1H), 8.78 (s, 1H), 8.38 (s, 1H), 7.97-7.92 (m, 1H), 7.54 (d, J=8.8 Hz, 1H), 7.25-7.19 (m, 2H), 5.65 (s, 2H), 5.35 (d, J=6.8 Hz, 1H), 4.56-4.45 (m, 1H), 3.70-3.64 (m, 1H), 3.56 (t, J=8.0 Hz, 2H), 2.84-2.76 (m, 2H), 2.62 (s, 3H), 2.47-2.39 (m, 2H), 0.86 (t, J=7.6 Hz, 2H), −0.07 (s, 9H); m/z ES+ $[M+H]^+$ 595.2.

Step 2. (1s,3s)-3-(4-(8-Chloro-7-((7-fluoro-2-methyl-1H-benzo[d]imidazol-6-yl)oxy)quinoxalin-2-yl)-1H-pyrazol-1-yl)cyclobutanol A solution of 3-(4-(8-chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)cyclobutanol (200 mg, 340 μmol) in trifluoroacetic acid (2 mL) was stirred at 25° C. for 0.5 h. On completion, the reaction mixture was concentrated under reduced pressure. The residue was purified by prep-HPLC (formic acid condition; column: Phenomenex Luna C18 150×25 mm×10 μm; mobile phase: [water (formic acid)-acetonitrile]; (B %: 16%-46%, 10 min) to give (1s,3s)-3-[4-[8-chloro-7-[(4-fluoro-2-methyl-3H-benzimidazol-5-yl)oxy]quinoxalin-2-yl]pyrazol-1-yl]cyclobutanol (84.5 mg, 0.18 mmol, 54%) as a white solid. $^1$H NMR (400 MHz, DMSO-$d_6$) δ 12.98-12.05 (m, 1H), 9.32 (s, 1H), 8.77 (s, 1H), 8.38 (s, 1H), 7.94 (d, J=9.2 Hz, 1H), 7.31 (s, 1H), 7.21 (d, J=9.2 Hz, 1H), 7.10 (s, 1H), 5.36 (d, J=6.8 Hz, 1H), 4.57-4.45 (m, 1H), 4.08-3.95 (m, 1H), 2.86-2.74 (m, 2H), 2.53 (s, 3H), 2.46-2.39 (m, 2H); m/z ES+ $[M+H]^+$ 464.9.

Example 98. Synthesis of 8-Chloro-2-(1-(1-(3,3-difluorocyclobutyl)ethyl)-1H-pyrazol-4-yl)-7-((2-methyl-1H-benzo[d]imidazol-6-yl)oxy)quinoxaline

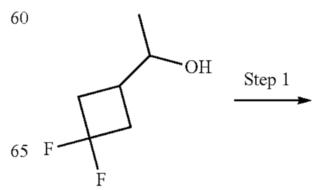

-continued

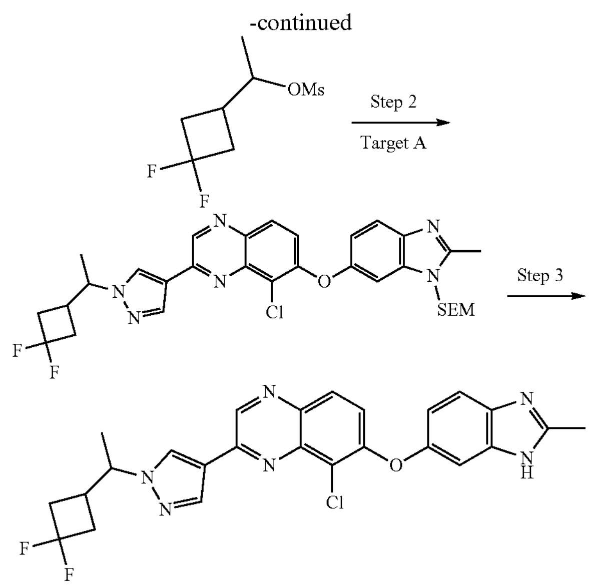

Step 1. 1-(3,3-Difluorocyclobutyl)ethyl methanesulfonate

To a solution of 1-(3,3-difluorocyclobutyl)ethanol (100 mg, 734 μmol) in dichloromethane (1 mL) was added N,N-diisopropylethylamine (111 mg, 1.10 mmol) and methanesulfonyl chloride (100 mg, 881 μmol) at 0° C. The mixture was stirred at 25° C. for 0.5 h. On completion, the reaction mixture was quenched with water (10 mL) at 0° C. and extracted with ethyl acetate (3× 20 mL). The combined organic layers were washed with brine (10 mL), dried over sodium sulfate, filtered and concentrated under reduced pressure to give 1-(3,3-difluorocyclobutyl)ethyl methanesulfonate (157 mg, crude) as a brown oil, which was used to the next step directly.

Step 2. 8-Chloro-2-(1-(1-(3,3-difluorocyclobutyl) ethyl)-1H-pyrazol-4-yl)-7-((2-methyl-1-((2-(trimethylsilyl)ethoxy)methyl)-1H-benzo[d]imidazol-6-yl) oxy)quinoxaline To a solution of 2-[[6-[5-chloro-3-(1H-pyrazol-4-yl)quinoxalin-6-yl]oxy-2-methyl-benz imidazol-1-yl]methoxy]ethyl-trimethyl-silane (200 mg, 394 μmol) and 1-(3,3-difluorocyclo butyl)ethyl methanesulfonate (118 mg, 552 μmol) in N,N-dimethylformamide (2 mL) was added potassium carbonate (109 mg, 788 μmol) and potassium iodide (6.55 mg, 39.4 μmol). The mixture was stirred at 100° C. for 12 hours. On completion, the reaction mixture was diluted with water (50 mL) and ethyl acetate (100 mL). The organic phase was separated, washed with brine (50 mL), dried over sodium sulfate, filtered and concentrated under reduced pressure. The residue was purified by column chromatography (silica gel, petroleum ether/ethyl acetate=100/1 to 0/1) to give 8-chloro-2-(1-(1-(3,3-difluorocyclobutyl)ethyl)-1H-pyrazol-4-yl)-7-((2-methyl-1-((2-(trimethylsilyl)ethoxy) methyl)-1H-benzo[d]imidazol-6-yl)oxy)quinoxaline (130 mg, 204 μmol, 51%) as a brown solid. m/z ES+ $[M+H]^+$ 625.3.

Step 3. 8-Chloro-2-(1-(1-(3,3-difluorocyclobutyl) ethyl)-1H-pyrazol-4-yl)-7-((2-methyl-1H-benzo[d] imidazol-6-yl)oxy)quinoxaline A solution of 2-[[6-[5-chloro-3-[1-[1-(3,3-difluorocyclobutyl)ethyl]pyrazol-4-yl]quinoxalin-6-yl]oxy-2-methyl-benzimidazol-1-yl]methoxy]ethyl-trimethyl-silane (130 mg, 207 μmol) in trifluoroacetic acid (1 mL) was stirred at 25° C. for 1 h. On completion, the reaction mixture was concentrated under reduced pressure and the residue was purified by prep-HPLC (column: Phenomenex Synergi C18 150*25 mm*10 μm; mobile phase: [water (formic acid)-acetonitrile]; (B %: 16%-46%, 10 min) to give 8-chloro-2-[1-[1-(3,3-difluorocyclobutyl)ethyl] pyrazol-4-yl]-7-[(2-methyl-3H-benzimidazol-5-yl)oxy]quinoxaline (41.9 mg, 84.7 μmol, 40%) as a white solid. $^1$H NMR (400 MHz, DMSO-$d_6$) δ 12.92-11.84 (m, 1H), 9.31 (s, 1H), 8.79 (s, 1H), 8.37 (s, 1H), 7.95 (d, J=9.2 Hz, 1H), 7.51 (d, J=8.8 Hz, 1H), 7.31 (d, J=9.2 Hz, 1H), 7.21 (d, J=1.6 Hz, 1H), 6.94 (dd, J=2.4, 8.8 Hz, 1H), 4.65-4.46 (m, 1H), 2.83-2.59 (m, 2H), 2.55-2.51 (m, 1H), 2.49 (s, 3H), 2.47-2.39 (m, 2H), 1.48 (d, J=6.8 Hz, 3H); m/z ES+ $[M+H]^+$ 495.0.

Example 99. Synthesis of (3-(4-(8-Chloro-7-((2-methyl-1H-benzo[d]imidazol-6-yl)oxy)quinoxalin-2-yl)-1H-pyrazol-1-yl)azetidin-1-yl) (3-hydroxyazetidin-1-yl) methanone

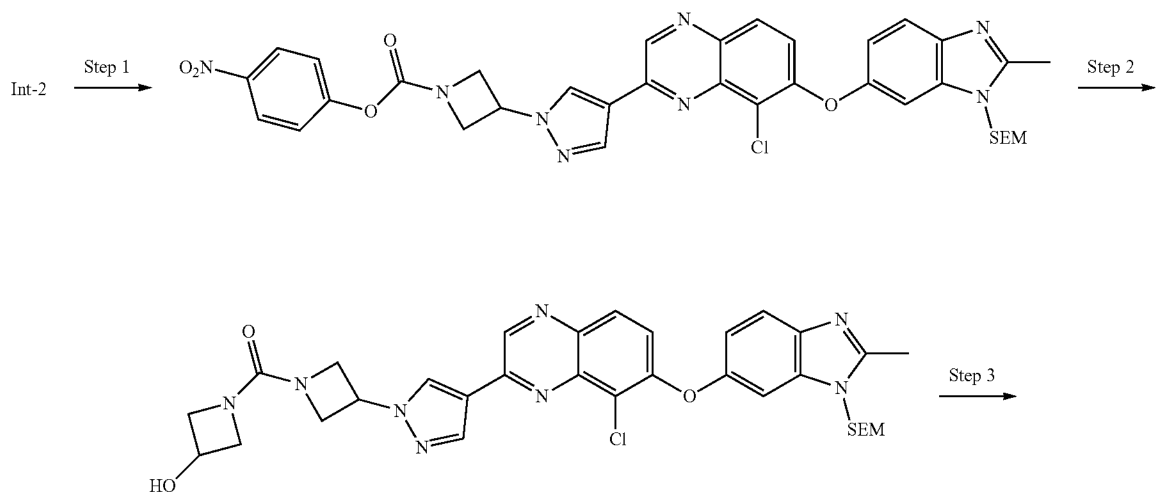

-continued

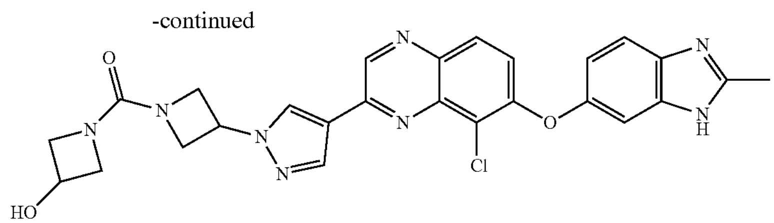

Step 1. 4-Nitrophenyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)azetidine-1-carboxylate To a mixture of 2-[[6-[3-[1-(azetidin-3-yl)pyrazol-4-yl]-5-chloro-quinoxalin-6-yl]oxy-2-methyl-benzimidazol-1-yl]methoxy]ethyl-trimethyl-silane (500 mg, 889 μmol) and (4-nitrophenyl) carbonochloridate (179 mg, 889 μmol) in dichloromethane (10 mL) was added triethylamine (180 mg, 1.78 mmol) in one portion under nitrogen. The mixture was stirred at 20° C. stirred for 2 hours. The reaction mixture was concentrated under reduced pressure to give 4-nitrophenyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)azetidine-1-carboxylate (0.6 g, 578 μmol, 65%) as a yellow solid. m/z ES+ $[M+H]^+$ 727.4

Step 2. (3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)azetidin-1-yl) (3-hydroxyazetidin-1-yl) methanone To a mixture of (4-nitrophenyl) 3-[4-[8-chloro-7-[2-methyl-3-(2-trimethylsilylethoxymethyl)benzimidazol-5-yl]oxy-quinoxalin-2-yl]pyrazol-1-yl]azetidine-1-carboxylate (300 mg, 413 μmol) and azetidin-3-ol hydrochloride (135.58 mg, 1.24 mmol) in dichloromethane (5 mL) was added N,N-diisopropylethylamine (41.7 mg, 413 μmol, 57.4 μL) in one portion at 25° C. The mixture was stirred at 25° C. for 16 hours. On completion, the reaction mixture was concentrated under reduced pressure. The residue was purified by reversed-phase HPLC (0.1% formic acid condition) to give (3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)azetidin-1-yl) (3-hydroxyazetidin-1-yl) methanone (80 mg, 96.8 μmol, 24%) as a yellow solid. m/z ES+ $[M+H]^+$ 661.4.

Step 3. (3-(4-(8-Chloro-7-((2-methyl-1H-benzo[d]imidazol-6-yl)oxy)quinoxalin-2-yl)-1H-pyrazol-1-yl)azetidin-1-yl) (3-hydroxyazetidin-1-yl) methanone A solution of (3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)azetidin-1-yl) (3-hydroxyazetidin-1-yl) methanone (80 mg, 121 μmol) in trifluoroacetic acid (3 mL) was stirred at 25° C. for 1 h. On completion, the reaction mixture was concentrated under reduced pressure. The residue was purified by prep-HPLC (column: Phenomenex Luna C18 150*25 mm*10 μm; mobile phase: [water (formic acid)-acetonitrile]; (B %: 7%-37%, 10 min) to give (3-(4-(8-chloro-7-((2-methyl-1H-benzo[d]imidazol-6-yl)oxy)quinoxalin-2-yl)-1H-pyrazol-1-yl)azetidin-1-yl) (3-hydroxyazetidin-1-yl) methanone (26.4 mg, 49.8 μmol, 41%) as a yellow solid. $^1$H NMR (400 MHz, $CD_3OD$) δ 9.20 (s, 1H), 8.66 (s, 1H), 8.42 (s, 1H), 7.99 (d, J=9.2 Hz, 1H), 7.76 (d, J=9.6 Hz, 1H), 7.49 (d, J=9.2 Hz, 1H), 7.36-7.28 (m, 2H), 5.41-5.29 (m, 1H), 4.61-4.53 (m, 1H), 4.52-4.45 (m, 2H), 4.44-4.37 (m, 2H), 4.26-4.19 (m, 2H), 3.83 (dd, J=4.4, 9.2 Hz, 2H), 2.83 (s, 3H); m/z ES+ $[M+H]^+$ 531.0.

Example 100. Synthesis of 3-(4-(8-Chloro-7-((2-methyl-1H-benzo[d]imidazol-6-yl)oxy)quinoxalin-2-yl)-1H-pyrazol-1-yl)-N,N-dimethylazetidine-1-carboxamide

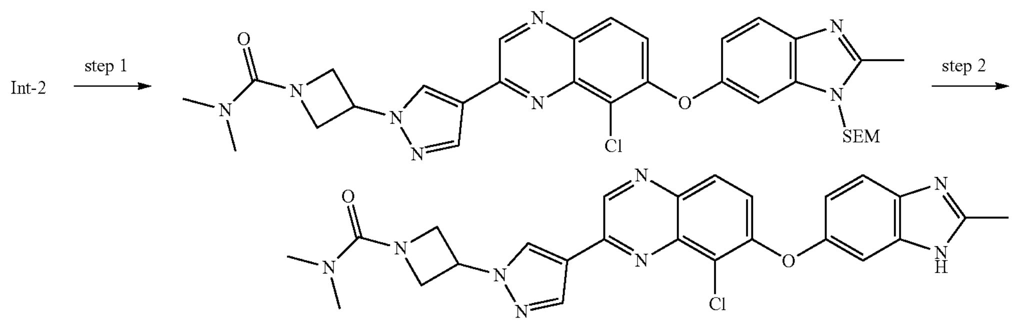

Step 1. 3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-N,N-dimethylazetidine-1-carboxamide To a mixture of 2-(1-(azetidin-3-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline (150 mg, 267 μmol) and N,N-dimethylcarbamoyl chloride (28.7 mg, 267 μmol, 24.5 μL) in dichloromethane (4 mL) was added N,N-diisopropylethylamine (81.0 mg, 801 μmol, 111 μL) at 0° C. The mixture was stirred at 0° C. for 30 min. On completion, the reaction mixture was quenched with water (5 mL) at 20° C., and then extracted with dichloromethane (5 mL×3). The combined organic layers were washed with brine (5 mL×3), dried over sodium sulfate, filtered and concentrated under reduced pressure. The residue was purified by reversed-phase HPLC (0.1% formic acid condition) to give 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-N,N-dimethylazetidine-1-carboxamide (80 mg, 125 μmol, 47%) as a yellow solid. m/z ES+ $[M+H]^+$ 633.4.

Step 2. 3-(4-(8-Chloro-7-((2-methyl-1H-benzo[d]imidazol-6-yl)oxy)quinoxalin-2-yl)-1H-pyrazol-1-yl)-N,N-dimethylazetidine-1-carboxamide A solution of 3-[4-[8-chloro-7-[2-methyl-3-(2-trimethylsilylethoxymethyl)benzimidazol-5-yl]oxy-quinoxalin-2-yl]pyrazol-1-yl]-N,N-dimethyl-azetidine-1-carboxamide (70 mg, 111 μmol) in trifluoroacetic acid (3 mL) was stirred at 25° C. for 1 h. On completion, the reaction mixture was concentrated under reduced pressure. The residue was purified by prep-HPLC (column: Phenomenex Luna C18 150*25 mm*10 μm; mobile phase: [water (formic acid)-acetonitrile]; (B %: 11%-41%, 10 min) to give 3-[4-[8-chloro-7-[(2-methyl-3H-benzimidazol-5-yl)oxy]quinoxalin-2-yl]pyrazol-1-yl]-N,N-dimethyl-azetidine-1-carboxamide (25.3 mg, 50.1 μmol, 45%) as an off-white solid. $^1H$ NMR (400 MHz, $CD_3OD$) δ 9.21-9.07 (m, 1H), 8.68 (s, 1H), 8.42 (s, 1H), 8.02-7.96 (m, 1H), 7.75 (d, J=9.6 Hz, 1H), 7.51-7.46 (m, 1H), 7.35-7.28 (m, 2H), 5.38-5.28 (m, 1H), 4.55-4.49 (m, 2H), 4.48-4.39 (m, 2H), 2.93 (s, 6H), 2.83 (s, 3H); m/z ES+ $[M+H]^+$ 503.0.

Example 101. Synthesis of 1-((4-(7-((5,7-Difluoro-2-methyl-1H-benzo[d]imidazol-6-yl)oxy)quinoxalin-2-yl)-1H-pyrazol-1-yl)methyl)cyclopropanol

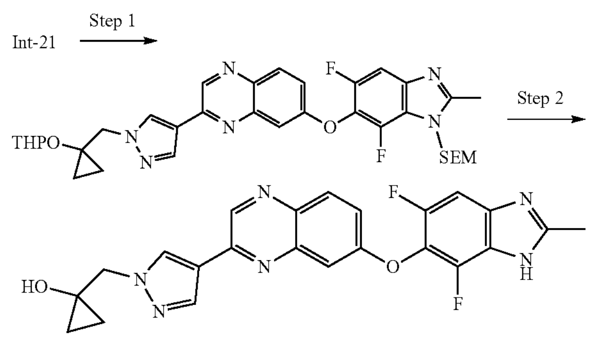

Step 1. 7-((5,7-Difluoro-2-methyl-1-((2-(trimethylsilyl)ethoxy)methyl)-1H-benzo[d]imidazol-6-yl)oxy)-2-(1-((1-((tetrahydro-2H-pyran-2-yl)oxy)cyclopropyl)methyl)-1H-pyrazol-4-yl)quinoxaline A mixture of 7-((5,7-difluoro-2-methyl-1-((2-(trimethylsilyl)ethoxy)methyl)-1H-benzo[d]imidazol-6-yl)oxy)-2-(1H-pyrazol-4-yl)quinoxaline (80.0 mg, 157 μmol), (1-tetrahydropyran-2-yloxycyclopropyl) methanol (32.5 mg, 189 μmol), diisopropyl azodicarboxylate (47.7 mg, 236 μmol), triphenylphosphine (61.9 mg, 236 μmol) in toluene (2 mL) was degassed and purged with nitrogen atmosphere for 3 times, then the mixture was stirred at 60° C. for 2 h under nitrogen atmosphere. On completion, the reaction mixture was concentrated under reduced pressure and the residue was purified by reversed-phase HPLC (0.1% formic acid condition) to give 7-((5,7-difluoro-2-methyl-1-((2-(trimethylsilyl)ethoxy)methyl)-1H-benzo[d]imidazol-6-yl)oxy)-2-(1-((1-((tetrahydro-2H-pyran-2-yl)oxy)cyclopropyl)methyl)-1H-pyrazol-4-yl)quinoxaline (50 mg, 37.7 μmol, 24%) as a yellow solid. m/z ES+ $[M+H]^+$ 663.1.

Step 2. 1-((4-(7-((5,7-Difluoro-2-methyl-1H-benzo[d]imidazol-6-yl)oxy)quinoxalin-2-yl)-1H-pyrazol-1-yl)methyl)cyclopropanol A solution of 7-((5,7-difluoro-2-methyl-1-((2-(trimethylsilyl)ethoxy)methyl)-1H-benzo[d]imidazol-6-yl)oxy)-2-(1-((1-((tetrahydro-2H-pyran-2-yl)oxy)cyclopropyl)methyl)-1H-pyrazol-4-yl)quinoxaline (50 mg, 75.4 μmol) in trifluoroacetic acid (1 mL) was stirred at 20° C. for 1 h. On completion, the reaction mixture was concentrated under reduced pressure. The residue was purified by prep-HPLC (column: Phenomenex Synergi C18 150*25 mm*10 μm; mobile phase: [water (formic acid)-acetonitrile]; (B %: 17%-44%, 9 min) to give 1-((4-(7-((5,7-difluoro-2-methyl-1H-benzo[d]imidazol-6-yl)oxy)quinoxalin-2-yl)-1H-pyrazol-1-yl)methyl)cyclopropanol (10.4 mg, 23.3 μmol, 31%) as a white solid. $^1H$ NMR (400 MHz, $CD_3OD$) δ 9.11 (s, 1H), 8.53 (s, 1H), 8.24 (s, 1H), 8.05 (d, J=9.2 Hz, 1H), 7.61 (dd, J=2.8, 9.2 Hz, 1H), 7.31 (d, J=9.2 Hz, 1H), 7.16 (d, J=2.4 Hz, 1H), 4.30 (s, 2H), 2.61 (s, 3H), 0.83 (d, J=5.6 Hz, 4H); m/z ES+ $[M+H]^+$ 449.0.

Example 102. Synthesis of 2-(4-(7-((5,7-Difluoro-2-methyl-1H-benzo[d]imidazol-6-yl)oxy)quinoxalin-2-yl)-1H-pyrazol-1-yl)ethanol

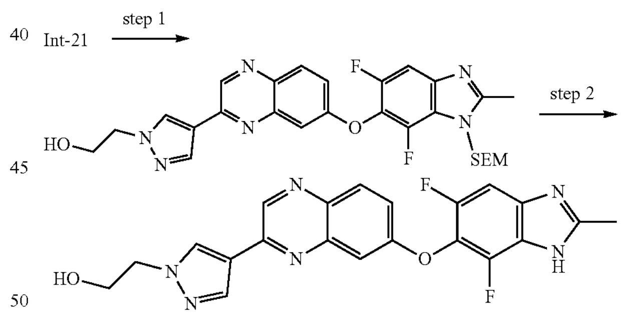

Step 1. 2-(4-(7-((5,7-Difluoro-2-methyl-1-((2-(trimethylsilyl)ethoxy)methyl)-1H-benzo[d]imidazol-6-yl)oxy)quinoxalin-2-yl)-1H-pyrazol-1-yl)ethanol To a solution of 2-[[5,7-difluoro-2-methyl-6-[3-(1H-pyrazol-4-yl)quinoxalin-6-yl oxy-benzimidazol-1-yl]methoxy]ethyl-trimethyl-silane (70 mg, 138 μmol) in N,N-dimethylformamide (1.5 mL) was added 1,3-dioxolan-2-one (36.4 mg, 413 μmol). The mixture was stirred at 140° C. for 2 h. On completion, the reaction mixture was concentrated under reduced pressure to give 2-(4-(7-((5,7-difluoro-2-methyl-1-((2-(trimethylsilyl)ethoxy)methyl)-1H-benzo[d]imidazol-6-yl)oxy)quinoxalin-2-yl)-1H-pyrazol-1-yl)ethanol (70 mg, crude) as a brown oil. m/z ES+ $[M+H]^+$ 553.3.

Step 2. 2-(4-(7-((5,7-Difluoro-2-methyl-1H-benzo[d]imidazol-6-yl)oxy)quinoxalin-2-yl)-1H-pyrazol-1-yl)ethanol A solution of 2-(4-(7-((5,7-difluoro-2-methyl-1-((2-(trimethylsilyl)ethoxy)methyl)-1H-benzo[d]imidazol-6-yl)oxy)quinoxalin-2-yl)-1H-pyrazol-1-yl)ethanol (70 mg, 127 μmol) in trifluoroacetic acid (1 mL) was stirred at 20° C. for 0.5 h. On completion, the reaction mixture was concentrated under reduced pressure. The residue was purified by prep-HPLC (column: Phenomenex Luna C18 150*25 mm*10 μm; mobile phase: [water (formic acid)-acetonitrile]; (B %: 17%-47%, 10 min) to give 2-(4-(7-((5,7-difluoro-2-methyl-1H-benzo[d]imidazol-6-yl)oxy)quinoxalin-2-yl)-1H-pyrazol-1-yl)ethanol (30.1 mg, 70.6 μmol, 56%) as a white solid. $^1$H NMR (400 MHz, $CD_3OD$) δ 9.10 (s, 1H), 8.47 (s, 1H), 8.26 (s, 1H), 8.06 (d, J=9.2 Hz, 1H), 7.62 (dd, J=2.8, 9.2 Hz, 1H), 7.37 (dd, J=1.2, 9.2 Hz, 1H), 7.18 (d, J=2.4 Hz, 1H), 4.31 (t, J=5.2 Hz, 2H), 3.94 (t, J=5.2 Hz, 2H), 2.65 (s, 3H); m/z ES+ $[M+H]^+$ 423.0.

Example 103. Synthesis of 1-(4-(7-((5,7-Difluoro-2-methyl-1H-benzo[d]imidazol-6-yl)oxy)quinoxalin-2-yl)-1H-pyrazol-1-yl)-2-methylpropan-2-ol

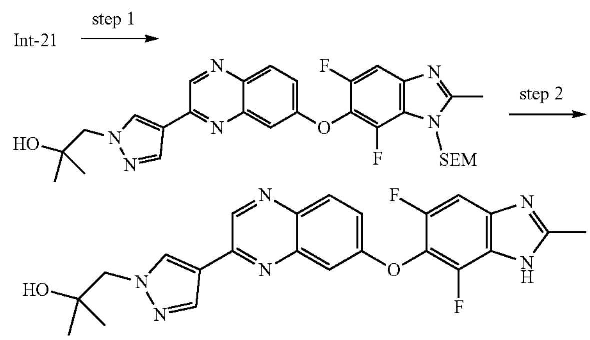

Step 1. 1-(4-(7-((5,7-Difluoro-2-methyl-1-((2-(trimethylsilyl)ethoxy)methyl)-1H-benzo[d]imidazol-6-yl)oxy)quinoxalin-2-yl)-1H-pyrazol-1-yl)-2-methylpropan-2-ol To a solution of 7-((5,7-difluoro-2-methyl-1-((2-(trimethylsilyl)ethoxy)methyl)-1H-benzo[d]imidazol-6-yl)oxy)-2-(1H-pyrazol-4-yl)quinoxaline (60 mg, 118 μmol) in N,N-dimethylformamide (1 mL) was added cesium carbonate (76.9 mg, 236 μmol) and 2,2-dimethyloxirane (25.5 mg, 354 μmol). The mixture was stirred at 100° C. for 1 h. On completion, the reaction mixture was diluted with water (20 mL) and extracted with ethyl acetate (20 mL×3). The combined organic layers were dried over anhydrous sodium sulfate, filtered and concentrated under reduced pressure to give 1-(4-(7-((5,7-difluoro-2-methyl-1-((2-(trimethylsilyl)ethoxy)methyl)-1H-benzo[d]imidazol-6-yl)oxy)quinoxalin-2-yl)-1H-pyrazol-1-yl)-2-methylpropan-2-ol (60 mg, crude) as a brown solid. m/z ES+ $[M+H]^+$ 581.1.

Step 2. 1-(4-(7-((5,7-Difluoro-2-methyl-1H-benzo[d]imidazol-6-yl)oxy)quinoxalin-2-yl)-1H-pyrazol-1-yl)-2-methylpropan-2-ol A solution of 1-(4-(7-((5,7-difluoro-2-methyl-1-((2-(trimethylsilyl)ethoxy)methyl)-1H-benzo[d]imidazol-6-yl)oxy)quinoxalin-2-yl)-1H-pyrazol-1-yl)-2-methylpropan-2-ol (60 mg, 103 μmol) in trifluoroacetic acid (0.5 mL) was stirred at 20° C. for 0.5 h. On completion, the reaction mixture was concentrated under reduced pressure. The residue was purified by prep-HPLC (column: Phenomenex C18 75*30 mm*3 μm; mobile phase: [water (formic acid)-acetonitrile]; (B %: 22%-52%, 7 min) to give 1-(4-(7-((5,7-difluoro-2-methyl-1H-benzo[d]imidazol-6-yl)oxy)quinoxalin-2-yl)-1H-pyrazol-1-yl)-2-methylpropan-2-ol (22.1 mg, 48.0 μmol, 47%) as a white solid. $^1$H NMR (400 MHz, $CD_3OD$) δ 9.09 (s, 1H), 8.44 (s, 1H), 8.23 (s, 1H), 8.05 (d, J=9.2 Hz, 1H), 7.61 (dd, J=2.8, 9.2 Hz, 1H), 7.33 (d, J=9.6 Hz, 1H), 7.17 (d, J=2.6 Hz, 1H), 4.17 (s, 2H), 2.63 (s, 3H), 1.21 (s, 6H); m/z ES+ $[M+H]^+$ 451.0.

Example 104. Synthesis of 1-((4-(8-Chloro-7-((2-methyl-1H-benzo[d]imidazol-6-yl)oxy)quinoxalin-2-yl)-1H-pyrazol-1-yl)methyl)cyclobutanol

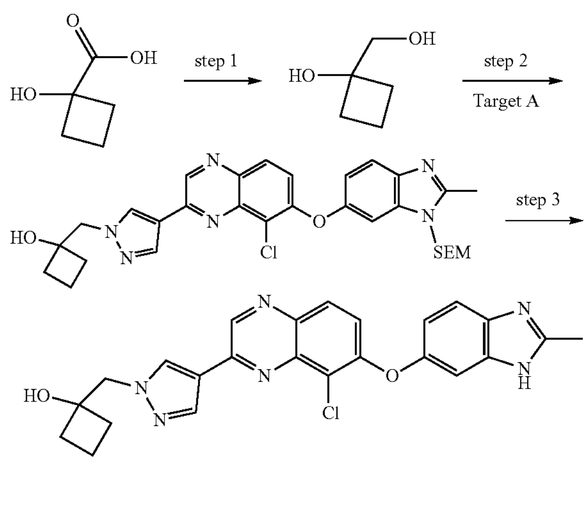

Step 1. 1-(Hydroxymethyl)cyclobutanol

A solution of lithium aluminum hydride (653 mg, 17.2 mmol) in tetrahydrofuran (5 mL) was degassed and purged with nitrogen for 3 times. Then 1-hydroxycyclobutanecarboxylic acid (500 mg, 4.31 mmol) in tetrahydrofuran (5 mL) was added dropwise at 25° C. Then the mixture was stirred at 70° C. for 1 h. On completion, the mixture was quenched with sodium sulfate tetrahydrate (20 g). The organic layer was dried over sodium sulfate, filtered and concentrated under reduced pressure. The residue was purified by column chromatography (silica gel, petroleum ether/ethyl acetate=1:1 to 0/1) to give 1-(hydroxymethyl)cyclobutanol (350 mg, 3.43 mmol, 79%) as a colourless oil. $^1$H NMR (400 MHz, $CDCl_3$) δ 3.73-3.58 (m, 2H), 2.86 (s, 1H), 2.35-1.97 (m, 5H), 1.87-1.70 (m, 1H), 1.62-1.39 (m, 1H).

Step 2. 1-((4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)cyclobutanol A mixture of 8-chloro-7-((2-methyl-1-((2-(trimethylsilyl)ethoxy)methyl)-1H-benzo[d]imidazol-6-yl)oxy)-2-(1H-pyrazol-4-yl)quinoxaline (100 mg, 197 μmol), 1-(hydroxymethyl)cyclobutanol (40 mg, 391 μmol), triphenylphosphine (77.6 mg, 295 μmol) and diisopropyl azodicarboxylate (59.8 mg, 295 μmol) in toluene (1 mL) was degassed and purged with nitrogen for 3 times. Then the mixture was stirred at 60° C. for 16 h under nitrogen atmosphere. On completion, the mixture was concentrated under reduced pressure. The residue was purified by prep-TLC (silica gel, petroleum ether/ethyl acetate=1/2) to give 1-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)cyclobutanol (100 mg, 169 μmol, 85%) as a yellow solid. m/z ES+ $[M+H]^+$ 591.2.

Step 3. 1-((4-(8-Chloro-7-((2-methyl-1H-benzo[d]imidazol-6-yl)oxy)quinoxalin-2-yl)-1H-pyrazol-1-yl)methyl)cyclobutanol A solution of 1-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)cyclobutanol (100 mg, 169 μmol) in trifluoroacetic acid (1 mL) was stirred at 25° C. for 10 min. On completion, the mixture was concentrated under reduced pressure. The residue was purified by prep-HPLC (column: Phenomenex Luna C18 150*25 mm*10 μm; mobile phase: [water (formic acid)-acetonitrile]; (B %: 25%-35%, 7 min) to give 1-((4-(8-chloro-7-((2-methyl-1H-benzo[d]imidazol-6-yl)oxy)quinoxalin-2-yl)-1H-pyrazol-1-yl)methyl)cyclobutanol (36.2 mg, 77.2 μmol, 45%) as an off-white solid. $^1$H NMR (400 MHz, DMSO-$d_6$) δ 9.22 (s, 1H), 8.61 (s, 1H), 8.36 (s, 1H), 7.98 (d, J=9.2 Hz, 1H), 7.68 (d, J=8.8 Hz, 1H), 7.45 (d, J=9.2 Hz, 1H), 7.27 (d, J=2.4 Hz, 1H), 7.21 (dd, J=2.4, 8.8 Hz, 1H), 4.40 (s, 2H), 2.74 (s, 3H), 2.36-2.19 (m, 2H), 2.17-2.01 (m, 2H), 1.90-1.78 (m, 1H), 1.76-1.58 (m, 1H); m/z ES+ $[M+H]^+$ 461.0.

Example 105. Synthesis of 2-(4-(8-Chloro-7-((7-fluoro-2-methyl-1H-benzo[d]imidazol-6-yl)oxy)quinoxalin-2-yl)-1H-pyrazol-1-yl)-1-morpholinoethanone

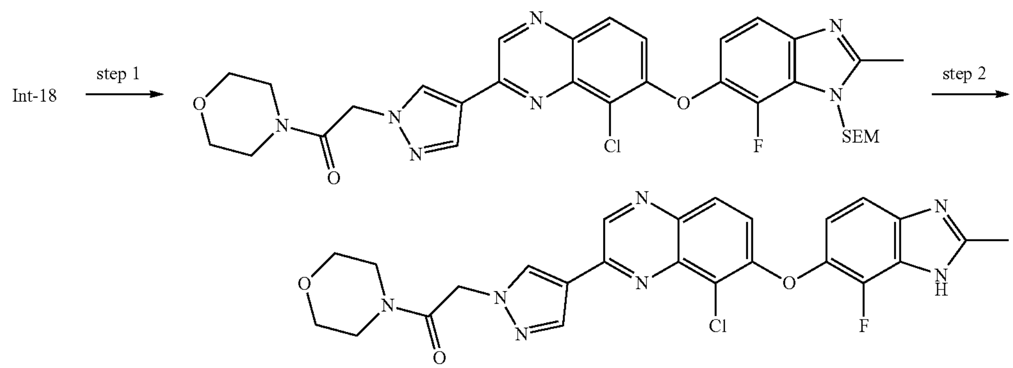

Step 1. 2-(4-(8-Chloro-7-((7-fluoro-2-methyl-1-((2-(trimethylsilyl)ethoxy)methyl)-1H-benzo[d]imidazol-6-yl)oxy)quinoxalin-2-yl)-1H-pyrazol-1-yl)-1-morpholinoethanone To a solution of 2-[[6-[5-chloro-3-(1H-pyrazol-4-yl)quinoxalin-6-yl]oxy-7-fluoro-2-methyl-benzimidazol-1-yl]methoxy]ethyl-trimethyl-silane (100 mg, 190 μmol) in N,N-dimethylformamide (2 mL) was added potassium carbonate (53 mg, 381 μmol) and 2-chloro-1-morpholino-ethanone (34 mg, 210 μmol). The mixture was stirred at 80° C. for 12 h. On completion, the reaction mixture was diluted with water (20 mL) and extracted with ethyl acetate (40 mL×3). The combined organic layers were washed with brine (20 mL×2), dried over sodium sulfate, filtered and concentrated under reduced pressure to give 2-[4-[8-chloro-7-[4-fluoro-2-methyl-3-(2-trimethylsilylethoxymethyl)benzimidazol-5-yl]oxy-quinoxalin-2-yl]pyrazol-1-yl]-1-morpholino-ethanone (150 mg, crude) as a yellow solid. m/z ES+ $[M+H]^+$ 652.3.

Step 2. 2-(4-(8-Chloro-7-((7-fluoro-2-methyl-1H-benzo[d]imidazol-6-yl)oxy)quinoxalin-2-yl)-1H-pyrazol-1-yl)-1-morpholinoethanone A solution of 2-[4-[8-chloro-7-[4-fluoro-2-methyl-3-(2-trimethylsilylethoxymethyl)benzimidazol-5-yl]oxy-quinoxalin-2-yl]pyrazol-1-yl]-1-morpholino-ethanone (150 mg, 230 μmol) in trifluoroacetic acid (1.8 mL) was stirred at 25° C. for 0.5 h. On completion, the reaction mixture was concentrated under reduced pressure. The residue was purified by prep-HPLC (formic acid condition; column: Shim-pack C18 150*25*10 μm; mobile phase: [water (formic acid)-acetonitrile]; (B %: 12%-42%, 10 min) to give 2-(4-(8-chloro-7-((7-fluoro-2-methyl-1H-benzo[d]imidazol-6-yl)oxy)quinoxalin-2-yl)-1H-pyrazol-1-yl)-1-morpholinoethanone (30.9 mg, 0.059 mmol, 26%) as a white solid. $^1$HNMR (400 MHz, DMSO-$d_6$) δ 9.38 (s, 1H), 8.65 (s, 1H), 8.38 (s, 1H), 8.02 (d, J=9.2 Hz, 1H), 7.64 (d, J=8.8 Hz, 1H), 7.44-7.36 (m, 2H), 5.32 (s, 2H), 3.69-3.44 (m, 8H), 2.81 (s, 3H); m/z ES+ $[M+H]^+$ 521.9.

Example 106. Synthesis of 8-Chloro-2-(1-(4,4-difluorocyclohexyl)-1H-pyrazol-4-yl)-7-((7-fluoro-2-methyl-1H-benzo[d]imidazol-6-yl)oxy)quinoxaline

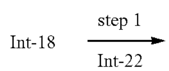

-continued

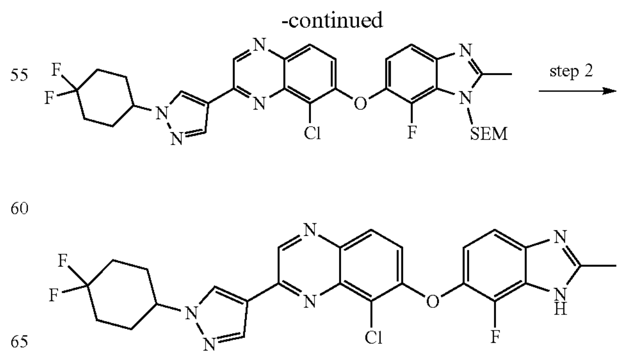

Step 1. 8-Chloro-2-(1-(4,4-difluorocyclohexyl)-1H-pyrazol-4-yl)-7-((7-fluoro-2-methyl-1-((2-(trimethylsilyl)ethoxy)methyl)-1H-benzo[d]imidazol-6-yl)oxy)quinoxaline To a solution of 8-chloro-7-((7-fluoro-2-methyl-1H-benzo[d]imidazol-6-yl)oxy)-2-(1H-pyrazol-4-yl)quinoxaline (150 mg, 285 μmol) and 4,4-difluorocyclohexyl methanesulfonate (122 mg, 571 μmol) in dimethylsulfoxide (1 mL) was added cesium carbonate (186 mg, 571 μmol) and potassium iodide (47.4 mg, 285 μmol). Then the mixture was stirred at 80° C. for 16 h. On completion, the mixture was poured into the water (10 mL) and extracted with ethyl acetate (30 mL×3). The combined organic layers were washed by brine (50 mL), dried over sodium sulfate, filtered and concentrated under reduced pressure to give 8-chloro-2-(1-(4,4-difluorocyclohexyl)-1H-pyrazol-4-yl)-7-((7-fluoro-2-methyl-1-((2-(trimethylsilyl)ethoxy)methyl)-1H-benzo[d]imidazol-6-yl)oxy)quinoxaline (180 mg, 279 μmol, 97%) as a yellow oil. m/z ES+ $[M+H]^+$ 643.2.

Step 2. 8-Chloro-2-(1-(4,4-difluorocyclohexyl)-1H-pyrazol-4-yl)-7-((7-fluoro-2-methyl-1H-benzo[d]imidazol-6-yl)oxy)quinoxaline A solution of 2-[[6-[5-chloro-3-[1-(4,4-difluorocyclohexyl)pyrazol-4-yl]quinoxalin-6-yl]oxy-7-fluoro-2-methyl-benzimidazol-1-yl]methoxy]ethyl-trimethyl-silane (180 mg, 279 μmol) in trifluoroacetic acid (1 mL) was stirred at 25° C. for 10 min. On completion, the mixture was concentrated under reduced pressure. The residue was purified by prep-HPLC (column: Phenomenex Luna C18 150*25 mm*10 μm; mobile phase: [water (formic acid)-acetonitrile]; (B %: 33%-63%, 10 min) to give 8-chloro-2-(1-(4,4-difluorocyclohexyl)-1H-pyrazol-4-yl)-7-((7-fluoro-2-methyl-1H-benzo[d]imidazol-6-yl)oxy)quinoxaline (100 mg, 190 μmol, 68%) as a white solid. $^1H$ NMR (400 MHz, $CD_3OD$) δ 9.22 (s, 1H), 8.67 (s, 1H), 8.39 (s, 1H), 7.96 (d, J=9.2 Hz, 1H), 7.52 (dd, J=1.2, 8.8 Hz, 1H), 7.38 (d, J=8.8 Hz, 1H), 7.30 (dd, J=7.2, 8.8 Hz, 1H), 4.60-4.43 (m, 1H), 2.82 (s, 3H), 2.31-2.22 (m, 6H), 2.09-2.01 (m, 2H); m/z ES+ $[M+H]^+$ 512.9.

Example 107. Synthesis of 8-Chloro-7-((2-methyl-1H-benzo[d]imidazol-6-yl)oxy)-2-(1-(1-(oxetan-3-yl) piperidin-4-yl)-1H-pyrazol-4-yl)quinoxaline

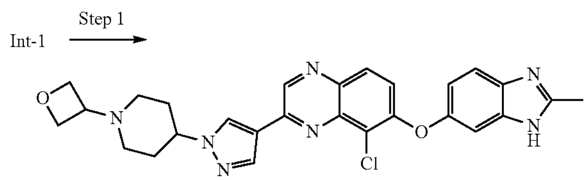

Step 1. 8-Chloro-7-((2-methyl-1H-benzo[d]imidazol-6-yl)oxy)-2-(1-(1-(oxetan-3-yl) piperidin-4-yl)-1H-pyrazol-4-yl)quinoxaline To a solution of 8-chloro-7-((2-methyl-1H-benzo[d]imidazol-6-yl)oxy)-2-(1-(piperidin-4-yl)-1H-pyrazol-4-yl)quinoxaline (50 mg, 108 μmol) and oxetan-3-one (23.5 mg, 326 μmol) in methanol (1 mL) was added sodium acetate (11.6 mg, 141 μmol) and sodium cyanoborohydride (20.5 mg, 326 μmol). The mixture was stirred at 25° C. for 6 h. On completion, the mixture was concentrated under reduced pressure. The residue was purified by prep-HPLC (column: Waters Xbridge 150*25 mm*5 μm; mobile phase: [water (0.05% ammonium hydroxide v/v)-acetonitrile]; (B %: 18%-48%, 9 min) to give 8-chloro-7-((2-methyl-1H-benzo[d]imidazol-6-yl)oxy)-2-(1-(1-(oxetan-3-yl) piperidin-4-yl)-1H-pyrazol-4-yl)quinoxaline (47.6 mg, 92.4 μmol, 77%) as an off-white solid. $^1H$ NMR (400 MHz, $CD_3OD$) δ 9.12 (s, 1H), 8.60 (s, 1H), 8.33 (s, 1H), 7.86 (d, J=9.2 Hz, 1H), 7.52 (d, J=8.8 Hz, 1H), 7.32 (d, J=9.2 Hz, 1H), 7.18 (d, J=2.0 Hz, 1H), 7 (dd, J=2.4, 8.8 Hz, 1H), 4.77-4.68 (m, 2H), 4.67-4.60 (m, 2H), 4.38-4.26 (m, 1H), 3.57 (q, J=6.4 Hz, 1H), 2.95 (d, J=10.8 Hz, 2H), 2.57 (s, 3H), 2.20 (dd, J=3.6, 9.2 Hz, 3H), 2.18-2.04 (m, 3H); m/z ES+ $[M+H]^+$ 516.1.

Example 108. Synthesis of 2-(1-(2-Azabicyclo[2.2.1]heptan-5-yl)-1H-pyrazol-4-yl)-8-chloro-7-((2-methyl-1H-benzo[d]imidazol-6-yl)oxy)quinoxaline and 8-Chloro-2-(1-(2-isopropyl-2-azabicyclo[2.2.1]heptan-5-yl)-1H-pyrazol-4-yl)-7-((2-methyl-1H-benzo[d]imidazol-6-yl)oxy)quinoxaline

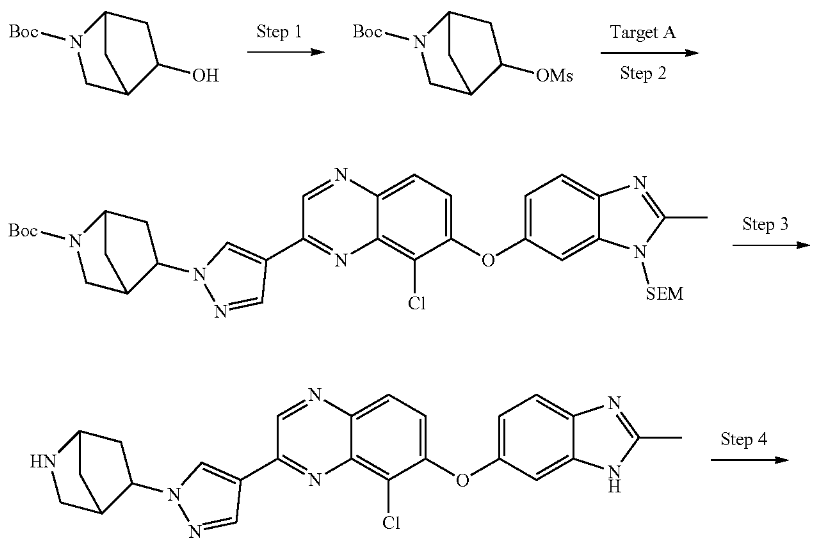

-continued

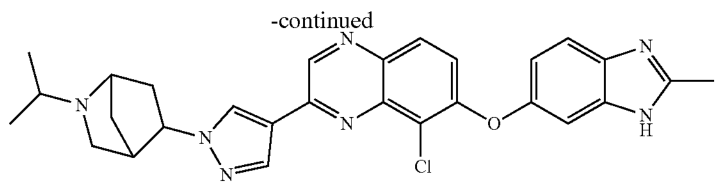

Step 1. tert-Butyl 5-methylsulfonyloxy-2-azabicyclo[2.2.1]heptane-2-carboxylate

To a solution of tert-butyl 5-hydroxy-2-azabicyclo[2.2.1]heptane-2-carboxylate (500 mg, 2.34 mmol) in dichloromethane (5 mL) was added methanesulfonyl chloride (403 mg, 3.52 mmol) and triethylamine (712 mg, 7.03 mmol). The mixture was stirred at 0° C. for 1 h. On completion, the reaction mixture was quenched with water (40 mL) and extracted with dichloromethane (40 mL×3). The combined organic layers were washed with brine (30 mL×3), dried over anhydrous sodium sulfate, filtered and concentrated under reduced pressure to give tert-butyl 5-methylsulfonyloxy-2-azabicyclo[2.2.1]heptane-2-carboxylate (550 mg, crude) as an orange oil.

Step 2. tert-Butyl 5-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-2-azabicyclo[2.2.1]heptane-2-carboxylate To a solution of 8-chloro-7-((2-methyl-1-((2-(trimethylsilyl)ethoxy)methyl)-1H-benzo[d] imidazol-6-yl)oxy)-2-(1H-pyrazol-4-yl)quinoxaline (400 mg, 789 μmol) in N,N-dimethylformamide (5 mL) was added potassium carbonate (327 mg, 2.37 mmol) and tert-butyl 5-((methylsulfonyl)oxy)-2-azabicyclo[2.2.1]heptane-2-carboxylate (460 mg, 1.58 mmol). The mixture was stirred at 80° C. for 14 h. On completion, the reaction mixture was filtered and concentrated under reduced pressure and the residue was purified by reversed-phase HPLC (0.1% formic acid condition, 90%-95%, 5 min) to give tert-butyl 5-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-2-azabicyclo[2.2.1]heptane-2-carboxylate (200 mg, 0.29 mmol, 36%) as an orange oil. m/z ES+ $[M+H]^+$ 702.6.

Step 3. 2-(1-(2-Azabicyclo[2.2.1]heptan-5-yl)-1H-pyrazol-4-yl)-8-chloro-7-((2-methyl-1H-benzo[d]imidazol-6-yl)oxy)quinoxaline A solution of tert-butyl 5-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-2-azabicyclo[2.2.1]heptane-2-carboxylate (200 mg, 283 μmol) in trifluoroacetic acid (1 mL) was stirred at 30° C. for 1 h. On completion, the reaction mixture was concentrated under reduced pressure. The residue was purified by prep-HPLC (formic acid condition; column: Phenomenex Luna C18 150*25 mm*10 um; mobile phase: [water (0.225% formic acid)-acetonitrile]; (B %: 3%-33%, 10 min) to give 2-(1-(2-azabicyclo[2.2.1]heptan-5-yl)-1H-pyrazol-4-yl)-8-chloro-7-((2-methyl-1H-benzo[d]imidazol-6-yl)oxy)quinoxaline (39.3 mg, 83.4 μmol, 29%) as an off-white solid. $^1H$ NMR (400 MHz, DMSO-$d_6$) δ 13.20-11.54 (m, 1H), 9.35 (s, 1H), 8.83 (s, 1H), 8.42 (s, 1H), 7.97 (d, J=9.2 Hz, 1H), 7.52 (d, J=8.8 Hz, 1H), 7.33 (d, J=9.2 Hz, 1H), 7.22 (d, J=2.0 Hz, 1H), 6.95 (dd, J=2.4, 8.8 Hz, 1H), 4.93 (dd, J=4.8, 7.6 Hz, 1H), 4.30 (s, 1H), 3.14-3.07 (m, 1H), 3.05-2.99 (m, 1H), 2.85 (s, 1H), 2.50 (s, 3H), 2.42-2.33 (m, 1H), 2.28-2.16 (m, 2H), 1.71 (d, J=11.6 Hz, 1H); m/z ES+ $[M+H]^+$ 472.1.

Step 4. 8-Chloro-2-(1-(2-isopropyl-2-azabicyclo[2.2.1]heptan-5-yl)-1H-pyrazol-4-yl)-7-((2-methyl-1H-benzo[d]imidazol-6-yl)oxy)quinoxaline To a solution of 2-(1-(2-azabicyclo[2.2.1]heptan-5-yl)-1H-pyrazol-4-yl)-8-chloro-7-((2-methyl-1H-benzo[d]imidazol-6-yl)oxy)quinoxaline (60.0 mg, 127 μmol), acetone (22.2 mg, 381 μmol) in methanol (1 mL) was added a solution of zinc chloride (22.5 mg, 165 μmol) and sodium triacetoxyborohydride (35.0 mg, 165 μmol) in methanol (0.5 mL). The mixture was stirred at 20° C. for 12 h. Then sodium cyanoborohydride (10.4 mg, 165 μmol) and sodium acetate (13.4 mg, 165 μmol) was added and the mixture was stirred at 20° C. for 2 h. On completion, the reaction mixture was quenched with water (0.2 mL) and then concentrated under reduced pressure. The residue was purified by prep-HPLC (formic acid condition;column: Phenomenex Luna C18 150*25 mm*10 um; mobile phase: [water (0.225% formic acid)-acetonitrile]; (B %: 5%-35%, 10 min) to give 8-chloro-2-(1-(2-isopropyl-2-azabicyclo[2.2.1]heptan-5-yl)-1H-pyrazol-4-yl)-7-((2-methyl-1H-benzo[d]imidazol-6-yl)oxy)quinoxaline (9.0 mg, 17.5 μmol, 14%) as a white solid. $^1H$ NMR (400 MHz, DMSO-$d_6$) δ=12.95-11.51 (m, 1H), 9.33 (s, 1H), 8.83 (s, 1H), 8.35 (s, 1H), 8.16 (s, 1H), 7.95 (d, J=9.2 Hz, 1H), 7.51 (d, J=8.4 Hz, 1H), 7.31 (d, J=9.2 Hz, 1H), 7.21 (s, 1H), 6.94 (dd, J=2.4, 8.4 Hz, 1H), 4.79 (dd, J=3.6, 7.6 Hz, 1H), 3.62 (s, 2H), 3.01-2.96 (m, 1H), 2.84 (td, J=6.0, 12.0 Hz, 1H), 2.49 (s, 3H), 2.28-2.21 (m, 2H), 2.04-1.97 (m, 1H), 1.90 (d, J=10.0 Hz, 1H), 1.57 (d, J=10.0 Hz, 1H), 1.13 (d, J=6.4 Hz, 3H), 1.07 (d, J=6.0 Hz, 3H); m/z ES+ $[M+H]^+$ 514.1.

Example 109. Synthesis of 2-(1-(2-Oxabicyclo[2.1.1]hexan-4-ylmethyl)-1H-pyrazol-4-yl)-8-chloro-7-((2-methyl-1H-benzo[d]imidazol-6-yl)oxy)quinoxaline

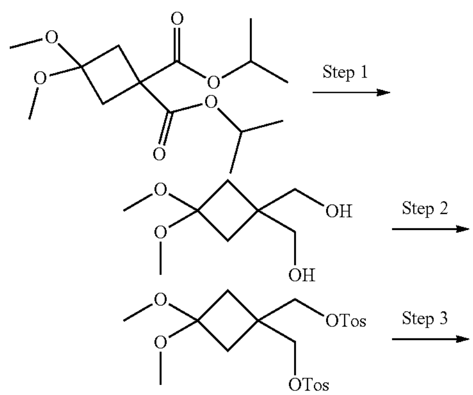

-continued

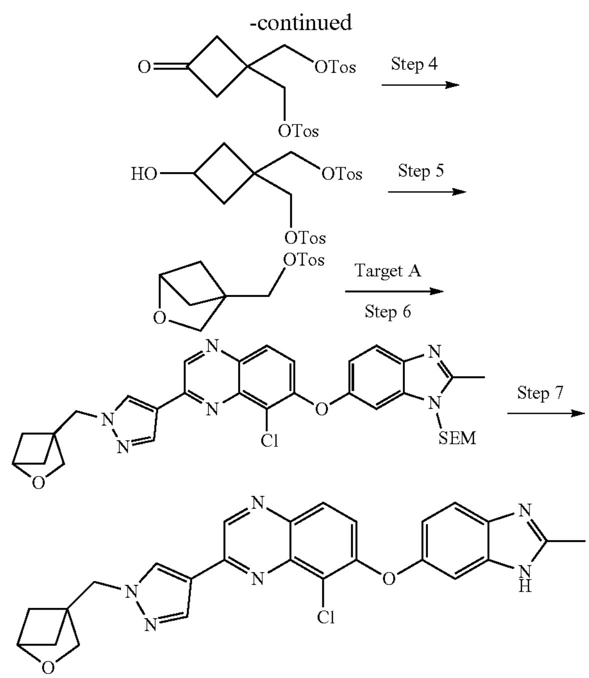

Step 1. (3,3-Dimethoxycyclobutane-1,1-diyl)dimethanol

To a solution of diisopropyl 3,3-dimethoxycyclobutane-1,1-dicarboxylate (10 g, 34.68 mmol) in tetrahydrofuran (100 mL) was added lithium aluminum hydride (3.95 g, 104 mmol) portion-wise at 0° C. The mixture was stirred at 25° C. for 12 h. The mixture was diluted with tetrahydrofuran (100 mL) and then carefully quenched by dropwise addition of water (4 mL), 15% sodium hydroxide (4 mL) and water (12 mL). The suspension was filtered and the filtrate was concentrated under reduced pressure. The residue was purified by column chromatography (silica gel, petroleum ether/ethyl acetate=5/1 to 0/1) to give (3,3-dimethoxycyclobutane-1,1-diyl)dimethanol (3.89 g, 22.08 mmol, 64%) as a white solid. $^1$H NMR (400 MHz, DMSO-$d_6$) δ=4.47 (t, J=5.4 Hz, 2H), 3.35 (d, J=5.5 Hz, 4H), 3 (s, 6H), 1.77 (s, 4H).

Step 2. (3,3-Dimethoxycyclobutane-1,1-diyl)bis (methylene)bis(4-methylbenzenesulfonate)

To a solution of [1-(hydroxymethyl)-3,3-dimethoxy-cyclobutyl]methanol (3.89 g, 22.08 mmol) in pyridine (40 mL) was added 4-methylbenzenesulfonyl chloride (12.6 g, 66.23 mmol) at 0° C. The mixture was stirred at 0° C. for 12 h. The reaction mixture was concentrated under reduced pressure. The residue was purified by column chromatography (silica gel, petroleum ether/ethyl acetate=10/1 to 1/1) to give (3,3-dimethoxycyclobutane-1,1-diyl)bis(methylene) bis(4-methylbenzenesulfonate) (4.5 g, 12.13 mmol, 55%) as a white solid. $^1$H NMR (400 MHz, DMSO-$d_6$) δ=7.74 (d, J=8.2 Hz, 4H), 7.49 (d, J=8.1 Hz, 4H), 3.93 (s, 4H), 2.89 (s, 6H), 2.43 (s, 6H), 1.85 (s, 4H).

Step 3. (3-Oxocyclobutane-1,1-diyl)bis(methylene) bis(4-methylbenzenesulfonate)

To a solution of (3,3-dimethoxycyclobutane-1,1-diyl)bis (methylene)bis(4-methylbenzenesulfonate) (1.06 g, 2.19 mmol) in acetonitrile (7 mL) was added hydrogen chloride/dioxane (4 M, 2.73 mL). The mixture was stirred at 25° C. for 12 h. The reaction mixture was diluted with water (30 mL) and extracted with ethyl acetate (20 mL×3). The combined organic layers were washed with brine (20 mL), dried over anhydrous sodium sulfate, filtered and concentrated under reduced pressure to give (3-oxocyclobutane-1,1-diyl)bis(methylene)bis(4-methylbenzenesulfonate) (860 mg, crude) as a white solid. $^1$H NMR (400 MHz, DMSO-$d_6$) δ=7.82 (d, J=8.2 Hz, 4H), 7.55 (d, J=8.1 Hz, 4H), 4.23 (s, 4H), 2.92 (s, 4H), 2.49 (s, 6H).

Step 4. (3-Hydroxycyclobutane-1,1-diyl)bis(methylene)bis(4-methylbenzenesulfonate)

To a solution of (3-oxocyclobutane-1,1-diyl)bis(methylene)bis(4-methylbenzenesulfonate) (860 mg, 1.96 mmol) in tetrahydrofuran (10 mL) was added sodium borohydride (148 mg, 3.92 mmol) at 0° C. The mixture was stirred at 25° C. for 2 h. The reaction mixture was poured into sat. ammonium chloride (30 mL) and extracted with ethyl acetate (20 mL×3). The combined organic layers were washed with brine (20 mL), dried over anhydrous sodium sulfate, filtered and concentrated under reduced pressure. The residue was purified by column chromatography (silica gel, petroleum ether/ethyl acetate=3/1 to 1/1) to give (3-hydroxycyclobutane-1,1-diyl)bis(methylene)bis(4-methylbenzenesulfonate) (790 mg, 1.79 mmol, 91%) as a white solid. $^1$H NMR (400 MHz, DMSO-$d_6$) δ=7.74 (t, J=7.6 Hz, 4H), 7.48 (d, J=8.0 Hz, 4H), 5.09 (d, J=6.4 Hz, 1H), 4.01-3.95 (m, 1H), 3.90 (d, J=17.6 Hz, 4H), 2.43 (s, 6H), 1.99-1.93 (m, 2H), 1.64-1.57 (m, 2H).

Step 5. 2-Oxabicyclo[2.1.1]hexan-4-ylmethyl 4-methylbenzenesulfonate

To a solution of (3-hydroxycyclobutane-1,1-diyl)bis (methylene)bis(4-methylbenzenesulfonate) (790 mg, 1.79 mmol) in tetrahydrofuran (10 mL) was added sodium hydride (215 mg, 5.38 mmol, 60% in mineral oil) at 0° C. The mixture was stirred at 25° C. for 12 h. The reaction mixture was poured into sat. ammonium chloride (30 mL) and extracted with ethyl acetate (20 mL×3). The combined organic layers were washed with brine (20 mL), dried over anhydrous sodium sulfate, filtered and concentrated under reduced pressure. The residue was purified by column chromatography (silica gel, petroleum ether/ethyl acetate=5/1 to 1/1) to give 2-oxabicyclo[2.1.1]hexan-4-ylmethyl 4-methylbenzenesulfonate (140 mg, 490 μmol, 27%) as a white solid. $^1$H NMR (400 MHz, $CDCl_3$) δ=7.80 (d, J=8.4 Hz, 2H), 7.37 (d, J=8.1 Hz, 2H), 4.54 (s, 1H), 4.30 (s, 2H), 3.57 (s, 2H), 2.47 (s, 3H), 1.75 (d, J=5.0 Hz, 2H), 1.56-1.52 (m, 2H).

Step 6. 2-(1-(2-Oxabicyclo[2.1.1]hexan-4-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline To a solution of 2-[[6-[5-chloro-3-(1H-pyrazol-4-yl)quinoxalin-6-yl]oxy-2-methyl-benzimidazol-1-yl]methoxy] ethyl-trimethyl-silane (100 mg, 98.6 μmol) and 2-oxabicyclo[2.1.1]hexan-4-ylmethyl 4-methylbenzenesulfonate (63.5 mg, 118 μmol) in N,N-dimethylformamide (2 mL) was added potassium carbonate (81.8 mg, 296 μmol). The mixture was stirred at 80° C. for 3 h. The reaction mixture was quenched with water (30 mL) and extracted with ethyl acetate (20 mL×3). The combined organic layers were dried over anhydrous sodium sulfate, filtered and concentrated under reduced pressure to give 2-(1-(2-oxabicyclo[2.1.1]hexan-4-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (150 mg, crude) as a yellow oil. m/z ES+ $[M+H]^+$ 603.3.

Step 7. 2-(1-(2-Oxabicyclo[2.1.1]hexan-4-ylmethyl)-1H-pyrazol-4-yl)-8-chloro-7-((2-methyl-1H-benzo[d]imidazol-6-yl)oxy)quinoxaline A solution of 2-[[6-[5-chloro-3-[1-(2-oxabicyclo[2.1.1]hexan-4-ylmethyl)pyrazol-4-yl]quinoxalin-6-yl]oxy-2-methyl-benzimidazol-1-yl]methoxy]ethyl-trimethyl-silane (140 mg, 232 μmol) in trifluoroacetic acid (3 mL) was stirred at 25° C. for 1 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 13%-43%, 10 min) to give 2-(1-(2-oxabicyclo[2.1.1]hexan-4-ylmethyl)-1H-pyrazol-4-yl)-8-chloro-7-((2-methyl-1H-benzo[d]imidazol-6-yl)oxy)quinoxaline (22.7 mg, 47.9 μmol, 21%) as a yellow solid. $^1H$ NMR (400 MHz, DMSO-$d_6$) δ=9.31 (s, 1H), 8.69 (s, 1H), 8.38 (s, 1H), 8.17 (s, 1H), 7.95 (d, J=9.3 Hz, 1H), 7.51 (d, J=8.6 Hz, 1H), 7.31 (d, J=9.2 Hz, 1H), 7.21 (d, J=1.3 Hz, 1H), 6.94 (dd, J=2.2, 8.6 Hz, 1H), 4.65 (s, 2H), 4.46 (s, 1H), 3.51 (s, 2H), 2.49 (s, 3H), 1.72 (d, J=4.5 Hz, 2H), 1.49-1.42 (m, 2H); m/z ES+ $[M+H]^+$ 473.1.

Example 110. Synthesis of 2-(1-(aziridin-2-ylmethyl)-1H-pyrazol-4-yl)-8-chloro-7-((2-methyl-1H-benzo[d]imidazol-6-yl)oxy)quinoxaline

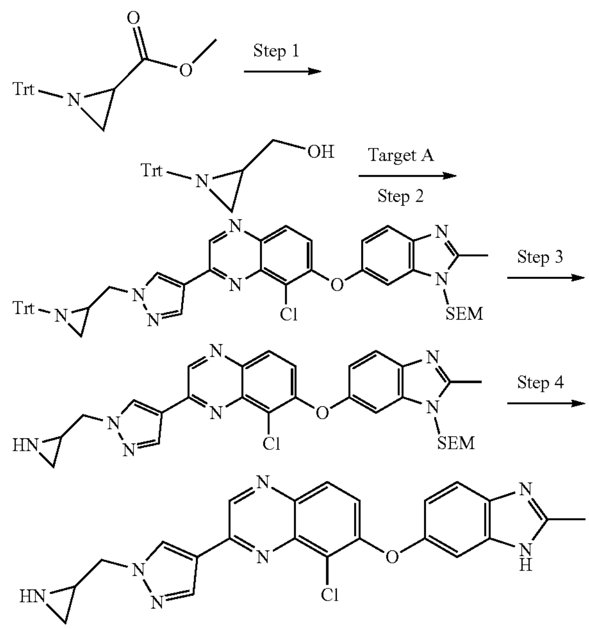

Step 1. (1-Tritylaziridin-2-yl) methanol

To a solution of methyl 1-tritylaziridine-2-carboxylate (700 mg, 2.04 mmol) in tetrahydrofuran (15 mL) was added lithium borohydride (164 mg, 7.54 mmol) at 0° C. The mixture was stirred at 20° C. for 2 h. On completion, the reaction mixture was quenched with sat. ammonium chloride (10 mL) at 0° C., and then diluted with water (30 mL) and extracted with ethyl acetate (30 mL×3). The combined organic layers were dried over anhydrous sodium sulfate, filtered and concentrated under reduced pressure to give (1-tritylaziridin-2-yl) methanol (900 mg, crude) as a white solid. $^1H$ NMR (400 MHz, $CDCl_3$) δ=7.45 (d, J=7.6 Hz, 6H), 7.26 (d, J=8.0 Hz, 9H), 3.87 (dd, J=3.2, 11.2 Hz, 1H), 3.69 (dd, J=2.8, 11.2 Hz, 1H), 2.18 (d, J=4.8 Hz, 1H), 1.86 (d, J=3.2 Hz, 1H), 1.56 (qd, J=3.2, 6.4 Hz, 1H), 1.12 (d, J=6.4 Hz, 1H).

Step 2. 8-Chloro-7-((2-methyl-1-((2-(trimethylsilyl)ethoxy)methyl)-1H-benzo[d]imidazol-6-yl)oxy)-2-(1-((1-tritylaziridin-2-yl)methyl)-1H-pyrazol-4-yl)quinoxaline To a solution of (1-tritylaziridin-2-yl) methanol (280 mg, 887 μmol) and 2-[[6-[5-chloro-3-(1H-pyrazol-4-yl)quinoxalin-6-yl]oxy-2-methyl-benzimidazol-1-yl]methoxy]ethyl-trimethyl-silane (300 mg, 592 μmol) in dichloromethane (6 mL) was added triphenylphosphine (233 mg, 887 μmol). Then diisopropyl azodicarboxylate (179 mg, 887 μmol) was added at 0° C. and the mixture was stirred at 25° C. for 1 h. On completion, the reaction mixture was filtered and concentrated under reduced pressure. The crude product was purified by reversed-phase HPLC (0.1% formic acid condition) to give 8-chloro-7-((2-methyl-1-((2-(trimethylsilyl)ethoxy)methyl)-1H-benzo[d]imidazol-6-yl)oxy)-2-(1-((1-tritylaziridin-2-yl)methyl)-1H-pyrazol-4-yl)quinoxaline (350 mg, 0.44 mmol, 66%) as a yellow solid. $^1H$ NMR (400 MHz, DMSO-$d_6$) δ 9.28 (d, J=4.4 Hz, 1H), 8.77 (s, 1H), 8.29 (s, 1H), 7.96 (dd, J=1.6, 9.2 Hz, 1H), 7.69-7.55 (m, 1H), 7.41 (d, J=7.6 Hz, 6H), 7.33-7.25 (m, 8H), 7.23-7.16 (m, 3H), 7.09-6.99 (m, 1H), 5.64-5.51 (m, 2H), 4.61 (dd, J=5.6, 14.0 Hz, 1H), 4.36 (dd, J=5.6, 14.0 Hz, 1H), 3.58-3.44 (m, 2H), 2.57 (d, J=7.2 Hz, 3H), 1.93 (d, J=2.8 Hz, 1H), 1.73 (dd, J=2.8, 5.6 Hz, 1H), 1.08 (d, J=6.0 Hz, 1H), 0.88-0.75 (m, 2H), −0.07 (s, 4H), −0.14-−0.17 (m, 5H); m/z ES+ $[M+H]^+$ 804.1.

Step 3. 2-(1-(Aziridin-2-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline To a solution of 8-chloro-7-((2-methyl-1-((2-(trimethylsilyl)ethoxy)methyl)-1H-benzo[d]imidazol-6-yl)oxy)-2-(1-((1-tritylaziridin-2-yl)methyl)-1H-pyrazol-4-yl)quinoxaline (100 mg, 124 μmol) in dichloromethane (1 mL) was added trifluoroacetic acid (0.1 mL). The mixture was stirred at 20° C. for 1 h. On completion, the reaction mixture was diluted with sat. sodium bicarbonate (10 mL) and extracted with ethyl acetate (10 mL×3). The combined organic layers were dried over anhydrous sodium sulfate, filtered and concentrated under reduced pressure to give 2-(1-(aziridin-2-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (100 mg, crude) as a yellow solid. m/z ES+ $[M+H]^+$ 562.2.

Step 4. 2-(1-(Aziridin-2-ylmethyl)-1H-pyrazol-4-yl)-8-chloro-7-((2-methyl-1H-benzo[d]imidazol-6-yl)oxy)quinoxaline A solution of 2-(1-(aziridin-2-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (60 mg, 107 μmol) in trifluoroacetic acid (1 mL) was stirred at 20° C. for 0.5 h. On completion, the reaction mixture was concentrated under reduced pressure. The residue was purified by prep-HPLC (column: Phenomenex Synergi C18 150*25 mm*10 μm; mobile phase: [water (0.225% formic acid)-acetonitrile]; (B %: 5%-25%, 10 min) and repurified by prep-HPLC (column: Waters Xbridge 150*25 mm*5 μm; mobile phase: [water (10 mM ammonium bicarbonate)-acetonitrile]; (B %: 17%-47%, 9 min) to give 2-(1-(aziridin-2-ylmethyl)-1H-pyrazol-4-yl)-8-chloro-7-((2-methyl-1H-benzo[d]imidazol-6-yl)oxy)quinoxaline (14.6 mg, 33.9 μmol, 32%) as a white solid. $^1$H NMR (400 MHz, DMSO-$d_6$) δ 12.23 (s, 1H), 9.33 (s, 1H), 8.71 (s, 1H), 8.38 (s, 1H), 7.96 (d, J=9.2 Hz, 1H), 7.59-7.41 (m, 1H), 7.37-7.22 (m, 2H), 7.17 (s, 1H), 7-6.86 (m, 1H), 4.34-4.18 (m, 1H), 4.12-4 (m, 1H), 2.48-2.45 (m, 3H), 2.37 (d, J=7.6 Hz, 1H), 1.74 (d, J=2.8 Hz, 1H), 1.45-1.29 (m, 1H); m/z ES+ $[M+H]^+$ 432.1.

Example 111. Synthesis of 2-(1-(5,8-dioxaspiro[3.4]octan-2-yl)-1H-pyrazol-4-yl)-8-chloro-7-((2-methyl-1H-benzo[d]imidazol-6-yl)oxy)quinoxaline

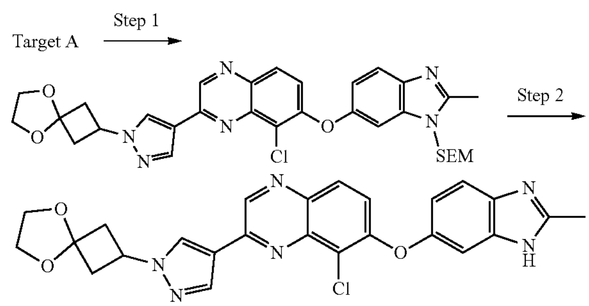

Step 1. 2-(1-(5,8-Dioxaspiro[3.4]octan-2-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline To a solution of 8-chloro-7-((2-methyl-1-((2-(trimethylsilyl)ethoxy)methyl)-1H-benzo[d]imidazol-6-yl)oxy)-2-(1H-pyrazol-4-yl)quinoxaline (500 mg, 980 μmol) and 2-bromo-5,8-dioxaspiro[3.4]octane (210 mg, 1.1 mmol) in N,N-dimethylformamide (5 mL) was added potassium carbonate (408 mg, 3.0 mmol) and potassium iodide (16 mg, 99 μmol). The mixture was stirred at 100° C. for 12 h. The reaction mixture was diluted with water (30 mL) and extracted with ethyl acetate (50 mL×2). The combined organic layers were washed with brine (15 mL×2), dried over anhydrous sodium sulfate, filtered and concentrated under reduced pressure. The residue was purified by column chromatography (silica gel, dichloromethane:methanol=100:1 to 10:1) to give 2-(1-(5,8-dioxaspiro[3.4]octan-2-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline (360 mg, 0.58 mmol, 52%) as a yellow solid. m/z ES+ $[M+H]^+$ 619.3.

Step 2. 2-(1-(5,8-Dioxaspiro[3.4]octan-2-yl)-1H-pyrazol-4-yl)-8-chloro-7-((2-methyl-1H-benzo[d]imidazol-6-yl)oxy)quinoxaline A solution of 2-(1-(5,8-dioxaspiro[3.4]octan-2-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline (50 mg, 81 μmol) in trifluoroacetic acid (0.5 mL) was stirred at 25° C. for 0.5 h. The reaction mixture was concentrated under reduced pressure. The residue was purified by prep-HPLC (neutral condition; column: Waters Xbridge 150*25 mm*5 μm; mobile phase: [water (10 mM ammonium bicarbonate)-acetonitrile]; (B %:: 35%-65%, 9 min) to give 2-(1-(5,8-dioxaspiro[3.4]octan-2-yl)-1H-pyrazol-4-yl)-8-chloro-7-((2-methyl-1H-benzo[d]imidazol-6-yl)oxy)quinoxaline (8.7 mg, 17.7 μmol, 22%) as a white solid. $^1$H NMR (400 MHz, DMSO-$d_6$) δ=12.39-12.18 (m, 1H), 9.31 (d, J=3.2 Hz, 1H), 8.81 (s, 1H), 8.41 (s, 1H), 7.95 (dd, J=5.2, 9.2 Hz, 1H), 7.57-7.44 (m, 1H), 7.37-7.27 (m, 1H), 7.27-7.15 (m, 1H), 6.98-6.89 (m, 1H), 4.89 (t, J=8.0 Hz, 1H), 3.96-3.90 (m, 2H), 3.89-3.83 (m, 2H), 2.96-2.87 (m, 2H), 2.86-2.77 (m, 2H), 2.49-2.46 (m, 3H); m/z ES+ $[M+H]^+$ 489.1.

Example 112. Synthesis of 2-(1-allylpyrazol-4-yl)-8-chloro-7-[(2-methyl-3H-benzimidazol-5-yl)oxy]quinoxaline

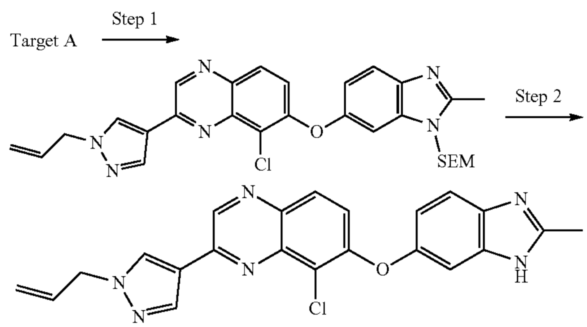

Step 1. 2-[[6-[3-(1-Allylpyrazol-4-yl)-5-chloro-quinoxalin-6-yl]oxy-2-methyl-benzimidazol-1-yl]methoxy]ethyl-trimethylsilane To a mixture of 2-[[6-[5-chloro-3-(1H-pyrazol-4-yl)quinoxalin-6-yl]oxy-2-methyl-benzimidazol-1-yl]methoxy]ethyl-trimethylsilane (100 mg, 197 μmol) in N,N-dimethyl formamide (2 mL) was added sodium hydride (15.8 mg, 394 μmol, 60% in mineral oil) at 0° C. The mixture was stirred at 0° C. for 0.5 h. Then 3-bromoprop-1-ene (40.0 mg, 330.65 μmol) was added and the mixture was stirred at 20° C. for 1.5 h. The mixture was quenched with water (10 mL) and extracted with ethyl acetate (15 mL×3). The combined organic phases were dried over anhydrous sodium sulfate, filtered and concentrated to give 2-[[6-[3-(1-allylpyrazol-4-yl)-5-chloro-quinoxalin-6-yl]oxy-2-methyl-benzimidazol-1-yl]methoxy]ethyl-trimethylsilane (120 mg, crude) as a yellow solid. m/z ES+ $[M+H]^+$ 547.1.

Step 2. 2-(1-Allylpyrazol-4-yl)-8-chloro-7-[(2-methyl-3H-benzimidazol-5-yl)oxy]quinoxaline A solution of 2-[[6-[3-(1-allylpyrazol-4-yl)-5-chloro-quinoxalin-6-yl]oxy-2-methyl-benzimidazol-1-yl]methoxy]ethyl-trimethyl-silane (100 mg, 183 μmol) in trifluoroacetic acid (1 mL) was stirred at 25° C. for 1 h. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 15%-45%, 7 min) to give 2-(1-allylpyrazol-4-yl)-8-chloro-7-[(2-methyl-3H-benzimidazol-5-yl)oxy]quinoxaline (50.4 mg, 0.12 mmol, 66%) as a yellow solid. $^1$H NMR (400 MHz, DMSO-$d_6$) δ 9.35 (s, 1H), 8.70 (s, 1H), 8.39 (s, 1H), 7.99 (d, J=9.2 Hz, 1H), 7.65 (d, J=8.8 Hz, 1H), 7.44-7.29 (m, 2H), 7.17-7.06 (m, 1H), 6.17-6.02 (m, 1H), 5.33-5.17 (m, 2H), 4.91 (br.d, J=5.6 Hz, 2H), 2.62 (s, 3H); m/z ES+ $[M+H]^+$ 417.1.

Example 113. Synthesis of 2-[4-[8-Chloro-7-[(2-methyl-3H-benzimidazol-5-yl)oxy]quinoxalin-2-yl]pyrazol-1-yl]-N-(2-hydroxyethyl) acetamide

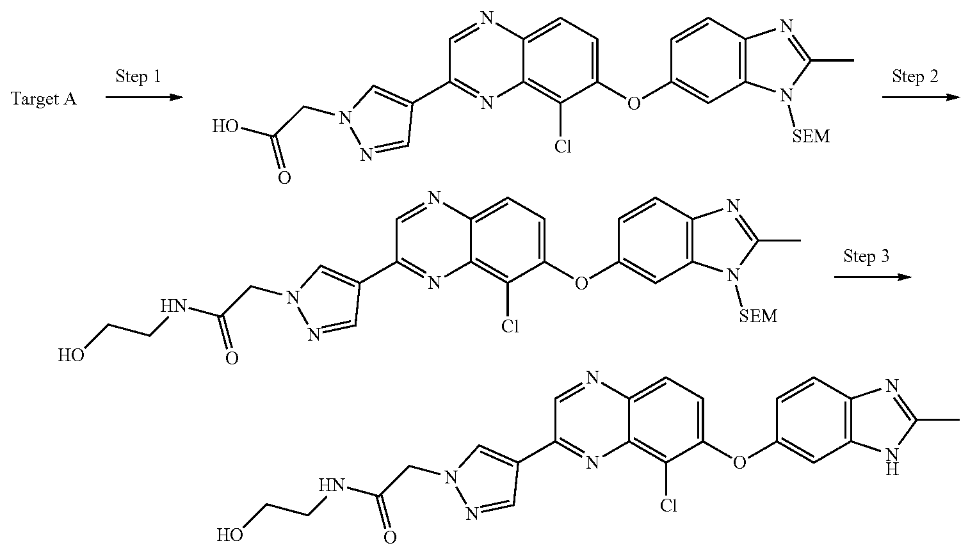

Step 1. 2-[4-[8-Chloro-7-[2-methyl-3-(2-trimethylsilylethoxymethyl)benzimidazol-5-yl]oxy-quinoxalin-2-yl]pyrazol-1-yl]acetic acid To a solution of 2-[[6-[5-chloro-3-(1H-pyrazol-4-yl)quinoxalin-6-yl]oxy-2-methyl-benzimidazol-1-yl]methoxy]ethyl-trimethyl-silane (200 mg, 394 μmol) in tetrahydrofuran (8 mL) was added sodium hydride (50.0 mg, 1.25 mmol, 60% in mineral oil). The mixture was stirred at 25° C. for 0.5 h. Then 2-bromoacetic acid (80.0 mg, 576 μmol) was added and the mixture was stirred at 60° C. for 1.5 h. On completion, the reaction mixture was quenched with water (2 mL) at 25° C. and then adjusted to pH=6 with sat. citric acid. The mixture was filtered and the filtered cake was collected to give 2-[4-[8-chloro-7-[2-methyl-3-(2-trimethylsilylethoxymethyl)benzimidazol-5-yl]oxy-quinoxalin-2-yl]pyrazol-1-yl]acetic acid (200 mg, 0.35 mmol, 86%) as a yellow solid. m/z ES+ $[M+H]^+$ 565.2.

Step 2. 2-[4-[8-Chloro-7-[2-methyl-3-(2-trimethylsilylethoxymethyl)benzimidazol-5-yl]oxy-quinoxalin-2-yl]pyrazol-1-yl]-N-(2-hydroxyethyl) acetamide To a solution of 2-[4-[8-chloro-7-[2-methyl-3-(2-trimethylsilylethoxymethyl)benzimidazol-5-yl]oxy-quinoxalin-2-yl]pyrazol-1-yl]acetic acid (100 mg, 177 μmol) in acetonitrile (3 mL) was added tris(2,2,2-trifluoroethyl)borate (120 mg, 390 μmol) and 2-aminoethanol (17 mg, 278 μmol). The mixture was stirred at 100° C. for 16 h. On completion, the mixture was concentrated under reduced pressure and the residue was purified by reversed-phase HPLC (mobile phase: [water (0.1% ammonium hydroxide)-acetonitrile]; (B %: 45%-80%, 6 min) to give 2-[4-[8-chloro-7-[2-methyl-3-(2-trimethylsilylethoxymethyl)benzimidazol-5-yl]oxy-quinoxalin-2-yl]pyrazol-1-yl]-N-(2-hydroxyethyl) acetamide (60 mg, 98.8 μmol, 55%) as a yellow solid. m/z ES+ $[M+H]^+$ 608.2.

Step 3. 2-[4-[8-Chloro-7-[(2-methyl-3H-benzimidazol-5-yl)oxy]quinoxalin-2-yl]pyrazol-1-yl]-N-(2-hydroxyethyl) acetamide A solution of 2-[4-[8-chloro-7-[2-methyl-3-(2-trimethylsilylethoxymethyl)benzimidazol-5-yl]oxy-quinoxalin-2-yl]pyrazol-1-yl]-N-(2-hydroxyethyl) acetamide (35 mg, 58 μmol) in trifluoroacetic acid (1 mL) was stirred at 25° C. for 1 h. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 8%-38%, 7 min) to give 2-[4-[8-chloro-7-[(2-methyl-3H-benzimidazol-5-yl)oxy]quinoxalin-2-yl]pyrazol-1-yl]-N-(2-hydroxyethyl) acetamide (23.6 mg, 49.5 μmol, 86%) as a white solid. $^1H$ NMR (400 MHz, DMSO-$d_6$) δ 9.35 (s, 1H), 8.69 (s, 1H), 8.37 (s, 1H), 8.29 (br.t, J=5.6 Hz, 1H), 7.99 (d, J=9.2 Hz, 1H), 7.61 (d, J=8.8 Hz, 1H), 7.37 (d, J=9.2 Hz, 1H), 7.31 (d, J=2.4 Hz, 1H), 7.10-7.02 (m, 1H), 5.01-4.88 (m, 2H), 4.85-4.65 (m, 1H), 3.45 (br.t, J=6.0 Hz, 2H), 3.22-3.17 (m, 2H), 2.58 (s, 3H); m/z ES+ $[M+H]^+$ 478.1.

Example 114. Synthesis of 2-[2-[4-[8-Chloro-7-[(2-methyl-3H-benzimidazol-5-yl)oxy]quinoxalin-2-yl]pyrazol-1-yl]ethylamino]ethanol

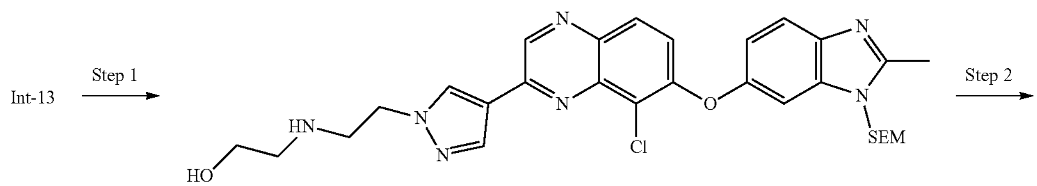

-continued

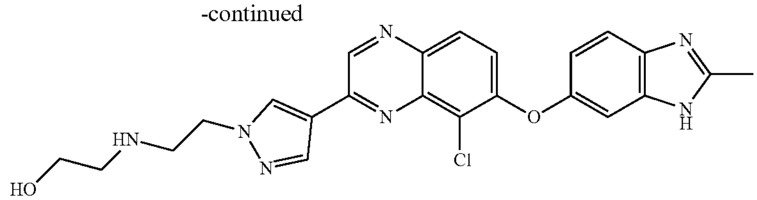

Step 1. 2-[2-[4-[8-Chloro-7-[2-methyl-3-(2-trimethylsilylethoxymethyl)benzimidazol-5-yl]oxy-quinoxalin-2-yl]pyrazol-1-yl]ethylamino]ethanol A mixture of 2-[4-[8-chloro-7-[2-methyl-3-(2-trimethylsilylethoxymethyl)benzimidazol-5-yl]oxy-quinoxalin-2-yl]pyrazol-1-yl]ethyl methanesulfonate (500 mg, 795 μmol) and 2-aminoethanol (971 mg, 15.9 mmol) was stirred at 80° C. for 4 h. On completion, the reaction mixture was concentrated under reduced pressure. The residue was purified by reversed-phase HPLC (0.1% formic acid condition) to give 2-[2-[4-[8-chloro-7-[2-methyl-3-(2-trimethylsilylethoxymethyl)benzimidazol-5-yl]oxy-quinoxalin-2-yl]pyrazol-1-yl]ethylamino]ethanol (0.22 g, 296 μmol, 37%) as a yellow solid. m/z ES+ $[M+H]^+$ 594.5.

Step 2. 2-[2-[4-[8-Chloro-7-[(2-methyl-3H-benzimidazol-5-yl)oxy]quinoxalin-2-yl]pyrazol-1-yl]ethylamino]ethanol A mixture of 2-[2-[4-[8-chloro-7-[2-methyl-3-(2-trimethylsilylethoxymethyl)benzimidazol-5-yl]oxy-quinoxalin-2-yl]pyrazol-1-ylethylamino]ethanol (0.22 g, 370 μmol) in trifluoroacetic acid (3 mL) was stirred at 20° C. for 2 h. On completion, the reaction mixture was filtered and concentrated under reduced pressure to give a residue. The residue was purified by prep-HPLC (column: Phenomenex Luna C18 150*25 mm*10 μm; mobile phase: [water (0.225% formic acid)-acetonitrile]; (B %: 1%-30%, 10 min) to give 2-[2-[4-[8-chloro-7-[(2-methyl-3H-benzimidazol-5-yl)oxy]quinoxalin-2-yl]pyrazol-1-yl]ethylamino]ethanol (63.6 mg, 137 μmol, 37%) as a yellow solid. $^1$H NMR (400 MHz, DMSO-$d_6$) δ 9.40 (s, 1H), 8.92-8.69 (m, 2H), 8.48 (s, 1H), 8.05 (d, J=9.2 Hz, 1H), 7.78 (d, J=8.8 Hz, 1H), 7.50-7.41 (m, 2H), 7.24 (dd, J=2.3, 8.8 Hz, 1H), 4.61 (t, J=6.4 Hz, 2H), 3.72-3.61 (m, 2H), 3.58-3.45 (m, 2H), 3.08 (br.s, 2H), 2.74 (s, 3H); m/z ES+ $[M+H]^+$ 464.1.

Example 115. Synthesis of 8-Chloro-7-((2-methyl-1H-benzo[d]imidazol-6-yl)oxy)-2-(1-(2-methyl-2-azabicyclo[2.2.1]heptan-5-yl)-1H-pyrazol-4-yl)quinoxaline

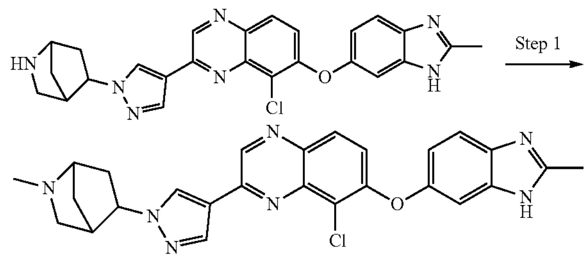

Step 1. 8-Chloro-7-((2-methyl-1H-benzo[d]imidazol-6-yl)oxy)-2-(1-(2-methyl-2-azabicyclo[2.2.1]heptan-5-yl)-1H-pyrazol-4-yl)quinoxaline To a solution of 2-(1-(2-azabicyclo[2.2.1]heptan-5-yl)-1H-pyrazol-4-yl)-8-chloro-7-((2-methyl-1H-benzo[d]imidazol-6-yl)oxy)quinoxaline (60.0 mg, 127 μmol) in N,N-dimethylformamide (1 mL) was added formic acid (122 mg, 2.54 mmol) and paraformaldehyde (76.4 mg, 2.54 mmol). The mixture was stirred at 60° C. for 13 h. On completion, the reaction mixture was filtered and concentrated under reduced pressure. The residue was purified by prep-HPLC (formic acid condition; column: Phenomenex Luna C18 150*25 mm*10 μm; mobile phase: [water (0.2% formic acid)-acetonitrile]; (B %: 3%-33%, 10 min) to give 8-chloro-7-((2-methyl-1H-benzo[d]imidazol-6-yl)oxy)-2-(1-(2-methyl-2-azabicyclo[2.2.1]heptan-5-yl)-1H-pyrazol-4-yl)quinoxaline (55.5 mg, 114 μmol, 89%) as a yellow solid. $^1$H NMR (400 MHz, DMSO-$d_6$) δ 13.05-10.51 (m, 1H), 9.34 (s, 1H), 8.83 (s, 1H), 8.42 (s, 1H), 7.96 (d, J=9.2 Hz, 1H), 7.51 (d, J=8.8 Hz, 1H), 7.33 (d, J=9.2 Hz, 1H), 7.22 (d, J=2.0 Hz, 1H), 6.94 (dd, J=2.0, 8.8 Hz, 1H), 5.03-4.96 (m, 1H), 4.05 (s, 1H), 3.11-3.04 (m, 1H), 3.04-2.98 (m, 1H), 2.81 (s, 4H), 2.49 (s, 3H), 2.37 (d, J=12.4 Hz, 1H), 2.22-2.11 (m, 2H), 1.97 (d, J=11.2 Hz, 1H); m/z ES+ $[M+H]^+$ 486.1.

Example 116. Synthesis of 2-[4-[8-Chloro-7-[(2-methyl-3H-benzimidazol-5-yl)oxy]quinoxalin-2-yl]pyrazol-1-yl]-N-(2-hydroxyethyl) acetamide

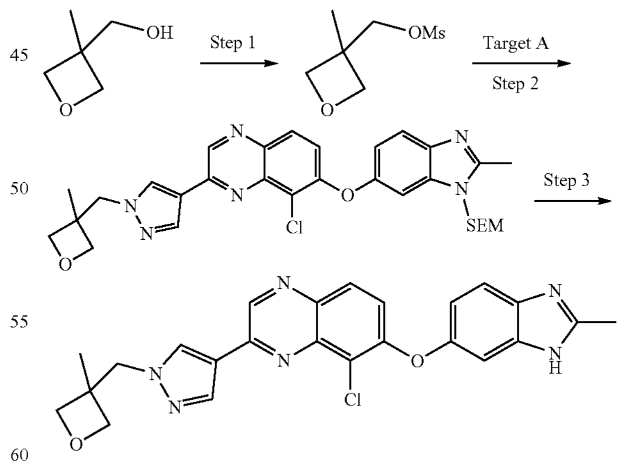

Step 1. (3-Methyloxetan-3-yl)methyl methanesulfonate

To a solution of (3-methyloxetan-3-yl) methanol (300 mg, 2.94 mmol) in dichloromethane (5 mL) was added triethylamine (891 mg, 1.23 mL) and methanesulfonyl chloride (504 mg, 4.41 mmol). The mixture was stirred at 0° C. for 1 h. On completion, the reaction mixture was quenched with sat. sodium bicarbonate solution (10 mL) at 25° C. and then extracted with ethyl acetate (25 mL×3). The combined organic layers were dried over anhydrous sodium sulfate, filtered and concentrated under reduced pressure to give (3-methyloxetan-3-yl)methyl methanesulfonate (500 mg, crude) as a yellow oil. $^1$H NMR (400 MHz, $CDCl_3$) δ 4.51 (d, J=6.4 Hz, 2H), 4.43 (d, J=6.4 Hz, 2H), 4.32 (s, 2H), 3.07 (s, 3H), 1.39 (s, 3H) . . .

Step 2. 2-[[6-[5-Chloro-3-[1-[(3-methyloxetan-3-yl)methyl]pyrazol-4-yl]quinoxalin-6-yl]oxy-2-methyl-benzimidazol-1-yl]methoxy]ethyl-trimethyl-silane To a solution of 2-[[6-[5-chloro-3-(1H-pyrazol-4-yl)quinoxalin-6-yl]oxy-2-methyl-benzimidazol-1-yl]methoxy]ethyl-trimethyl-silane (150 mg, 295 μmol) in N,N-dimethylformamide (3 mL) was added potassium carbonate (122 mg, 887 μmol), potassium iodide (49.1 mg, 295 μmol) and (3-methyloxetan-3-yl)methyl methanesulfonate (90.0 mg, 499 μmol). The mixture was stirred at 80° C. for 12 h. On completion, the reaction mixture was diluted with water (25 mL) and extracted with ethyl acetate (25 mL×3). The combined organic layers were dried over anhydrous sodium sulfate, filtered and concentrated under reduced pressure to give 2-[[6-[5-chloro-3-[1-[(3-methyloxetan-3-yl)methyl]pyrazol-4-yl]quinoxalin-6-yl]oxy-2-methyl-benzimidazol-1-yl]methoxy]ethyl-trimethyl-silane (220 mg, crude) as a yellow solid. m/z ES+ $[M+H]^+$ 591.3.

Step 3. 8-Chloro-7-[(2-methyl-3H-benzimidazol-5-yl)oxy]-2-[1-[(3-methyloxetan-3-yl)methyl]pyrazol-4-yl]quinoxaline To a solution of 2-[[6-[5-chloro-3-[1-[(3-methyloxetan-3-yl)methyl]pyrazol-4-yl]quinoxalin-6-yl]oxy-2-methyl-benzimidazol-1-yl]methoxy]ethyl-trimethyl-silane (150 mg, 253 μmol) in trifluoroacetic acid (1 mL) was added trifluoroacetic acid (770 mg, 6.75 mmol). The mixture was stirred at 25° C. for 0.5 h. On completion, the reaction mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 1%-30%, 7 min) to give 8-chloro-7-[(2-methyl-3H-benzimidazol-5-yl)oxy]-2-[1-[(3-methyloxetan-3-yl)methyl]pyrazol-4-yl]quinoxaline (65.6 mg, 142 μmol, 56%) as a yellow solid. $^1$H NMR (400 MHz, DMSO-$d_6$) δ 9.44 (s, 1H), 9.37 (s, 2H), 8.05 (d, J=9.2 Hz, 1H), 7.53 (d, J=8.4 Hz, 1H), 7.45 (d, J=9.2 Hz, 1H), 7.25 (d, J=2.4 Hz, 1H), 6.99-6.93 (m, 1H), 4.66 (d, J=12.0 Hz, 2H), 4.45 (d, J=12.0 Hz, 2H), 3.54 (s, 2H), 2.49 (s, 3H), 1.33 (s, 3H); m/z ES+ $[M+H]^+$ 461.1.

Example 117. Synthesis of 4-[[4-[8-Chloro-7-[(2-methyl-3H-benzimidazol-5-yl)oxy]quinoxalin-2-yl]pyrazol-1-yl]methyl]piperidine-1-carboxamide

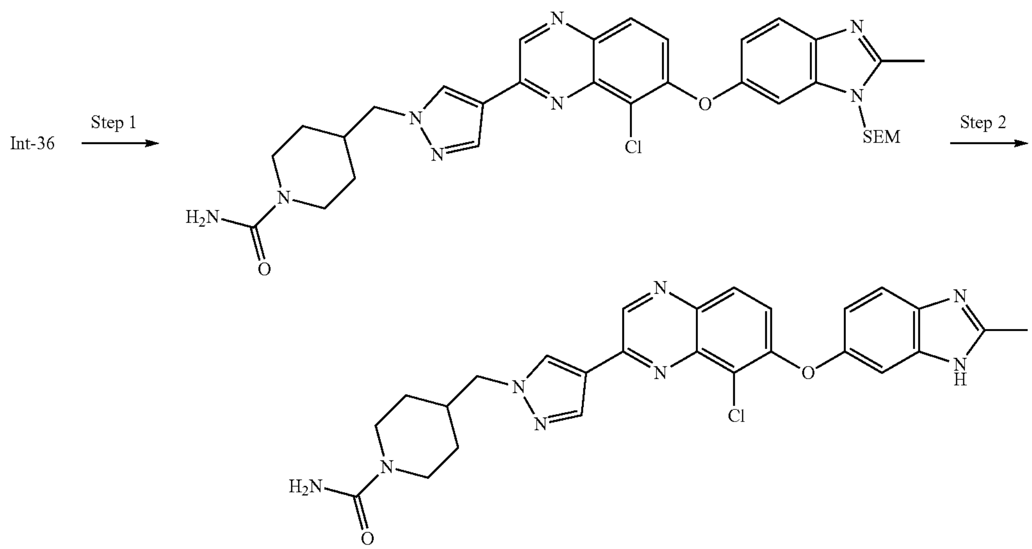

Step 1. 4-((4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl) piperidine-1-carboxamide To a solution of 2-[[6-[5-chloro-3-[1-(4-piperidylmethyl)pyrazol-4-yl]quinoxalin-6-yl]oxy-2-methyl-benzimidazol-1-yl]methoxy]ethyl-trimethyl-silane (200 mg, 330 μmol) and diisopropylethylamine (130 mg, 990 μmol) in dichloromethane (2 mL) was added isocyanato (trimethyl) silane (46 mg, 400 μmol, 53 μL) at 0° C. The mixture was stirred at 25° C. for 2 h. The reaction mixture was diluted with $H_2O$ (10 mL) and extracted with dichloromethane (25 mL×2). The combined organic layers were dried over anhydrous sodium sulfate, filtered and concentrated under reduced pressure. The residue was purified by prep-TLC (silica gel, to dichloromethane:methanol=10:1) give 4-[[4-[8-chloro-7-[2-methyl-3-(2-trimethylsilylethoxymethyl)benzimidazol-5-yl]oxy-quinoxalin-2-yl]pyrazol-1-yl]methyl]piperidine-1-carboxamide (100 mg, 155 μmol, 46%) as a white solid. m/z ES+ $[M+H]^+$ 647.2.

Step 2. 4-[[4-[8-Chloro-7-[(2-methyl-3H-benzimidazol-5-yl)oxy]quinoxalin-2-yl]pyrazol-1-yl]methyl] piperidine-1-carboxamide A solution of 4-[[4-[8-chloro-7-[2-methyl-3-(2-trimethylsilylethoxymethyl)benzimidazol-5-yl]oxy-quinoxalin-2-yl] pyrazol-1-yl]methyl]piperidine-1-carboxamide (70 mg, 108 μmol) in trifluoroacetic acid (0.7 mL) was stirred at 25° C. for 0.5 h. The reaction mixture was concentrated under reduced pressure. The residue was purified by prep-HPLC (basic condition: column: Waters Xbridge 150×25 mm× 5 μm; mobile phase: [water (0.05% ammonium hydroxide v/v)-acetonitrile]; (B %: 15%-45%, 9 min) to give 4-[[4-[8-chloro-7-[(2-methyl-3H-benzimidazol-5-yl)oxy]quinoxalin-2-yl]pyrazol-1-yl]methyl]piperidine-1-carboxamide (27.6 mg, 53.5 μmol, 48%) as a white solid. $^1$HNMR (400 MHz, DMSO-$d_6$) δ=12.16-11.91 (m, 1H), 9.26 (s, 1H), 8.63 (s, 1H), 8.33 (s, 1H), 7.95 (d, J=8.8 Hz, 1H), 7.57-7.42 (m, 1H), 7.39-7.32 (m, 1H), 7.27-7.07 (m, 1H), 6.98-6.88 (m, 1H), 5.61 (s, 2H), 4.17 (d, J=7.2 Hz, 2H), 3.93 (d, J=13.2 Hz, 2H), 2.74-2.64 (m, 2H), 2.49-2.49 (m, 3H), 2.19-2.03 (m, 1H), 1.55 (d, J=11.2 Hz, 2H), 1.17 (m, 2H); m/z ES+ $[M+H]^+$ 517.1.

Example 118. Synthesis of 2-(1-((1s,4s)-4-(azetidin-1-yl)cyclohexyl)-1H-pyrazol-4-yl)-8-chloro-7-((2-methyl-1H-benzo[d]imidazol-6-yl)oxy)quinoxaline and 2-(1-((1r,4r)-4-(azetidin-1-yl)cyclohexyl)-1H-pyrazol-4-yl)-8-chloro-7-((2-methyl-1H-benzo[d]imidazol-6-yl)oxy)quinoxaline

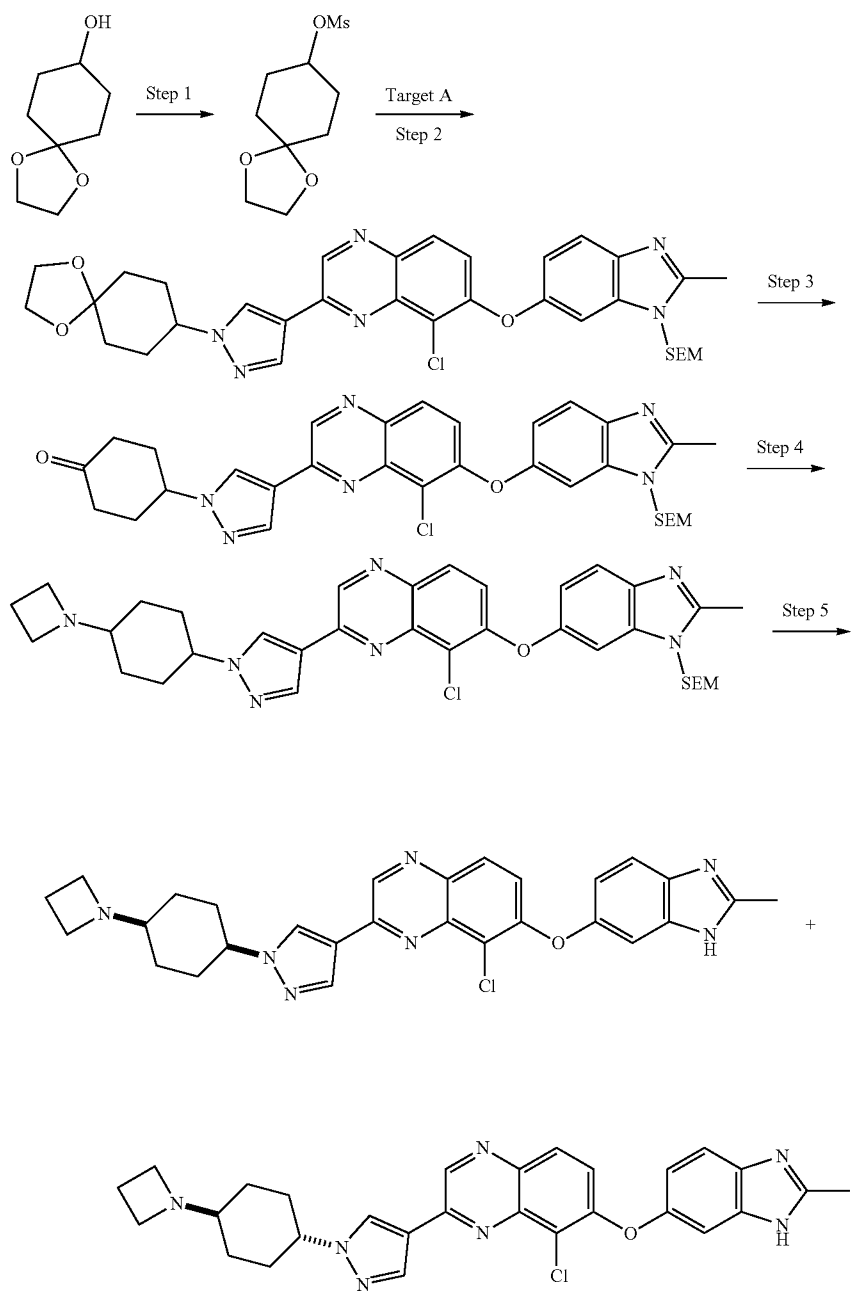

+

Step 1. 1,4-Dioxaspiro[4.5]decan-8-yl methanesulfonate

To a solution of 1,4-dioxaspiro[4.5]decan-8-ol (500 mg, 3.16 mmol) in dichloromethane (6 mL) was added methanesulfonyl chloride (543 mg, 4.74 mmol, 367 μL) and triethylamine (640 mg, 6.32 mmol, 880 μL). The mixture was stirred at 0° C. for 1 h. On completion, the reaction mixture was diluted with water (10 mL) and extracted with dichloromethane (10 mL×3). The combined organic layers were dried over anhydrous sodium sulfate, filtered and concentrated under reduced pressure to give 1,4-dioxaspiro[4.5]decan-8-yl methanesulfonate (800 mg, crude) as a yellow solid. $^1$H NMR (400 MHz, DMSO-$d_6$) δ 4.76 (td, J=3.6, 7.6 Hz, 1H), 3.89-3.84 (m, 4H), 3.17 (s, 3H), 1.93-1.75 (m, 4H), 1.73-1.50 (m, 4H).

Step 2. 2-(1-(1,4-Dioxaspiro[4.5]decan-8-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline To a solution of 1,4-dioxaspiro[4.5]decan-8-yl methanesulfonate (373 mg, 1.58 mmol) in N,N-dimethylformamide (6 mL) was added 2-[[6-[5-chloro-3-(1H-pyrazol-4-yl)quinoxalin-6-yl]oxy-2-methyl-benzimidazol-1-yl]methoxy]ethyl-trimethyl-silane (400 mg, 789 μmol), potassium iodide (131 mg, 789 μmol) and cesium carbonate (771 mg, 2.37 mmol). The mixture was stirred at 80° C. for 12 h. On completion, the reaction mixture was diluted with water (50 mL) and extracted with dichloromethane (50 mL×3). The combined organic layers were dried over anhydrous sodium sulfate, filtered and concentrated under reduced pressure. The residue was purified by column chromatography (dichloromethane/methanol=20/1 to 10/1) to give 2-(1-(1,4-dioxaspiro[4.5]decan-8-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline (600 mg, crude) as a yellow oil. m/z ES+ $[M+H]^+$ 647.2.

Step 3. 4-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)cyclohexanone To a solution of 2-(1-(1,4-dioxaspiro[4.5]decan-8-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline (600 mg, 927 μmol) in dichloromethane (6 mL) was added formic acid (3 mL). The mixture was stirred at 40° C. for 16 h. On completion, the reaction mixture was concentrated under reduced pressure to give 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)cyclohexanone (600 mg, crude) as a yellow oil. m/z ES+ $[M+H]^+$ 603.1.

Step 4. 2-(1-(4-(Azetidin-1-yl)cyclohexyl)-1H-pyrazol-4-yl)-8-chloro-7-((2-methyl-1-((2-(trimethylsilyl)ethoxy)methyl)-1H-benzo[d]imidazol-6-yl)oxy)quinoxaline To a solution of 4-[4-[8-chloro-7-[2-methyl-3-(2-trimethylsilylethoxymethyl)benzimidazol-5-yl]oxy-quinoxalin-2-yl]pyrazol-1-yl]cyclohexanone (250 mg, 414 μmol) and azetidine (116 mg, 1.24 mmol, HCl salt) in methanol (5 mL) was added triethylamine (126 mg, 1.24 mmol) and acetic acid (373 mg, 6.22 mmol). Then sodium triacetoxyborohydride (176 mg, 829 μmol) was added at 0° C. in two portions (slightly exothermic). The reaction mixture was stirred at 40° C. for 16 h. On completion, the reaction mixture was filtered and the filtrate was purified by reversed-phase HPLC (0.1% formic acid condition) to give 2-(1-(4-(azetidin-1-yl)cyclohexyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (100 mg, 156 μmol, 36%) as a yellow oil. m/z ES+ $[M+H]^+$ 644.2.

Step 5. 2-(1-((1s,4s)-4-(Azetidin-1-yl)cyclohexyl)-1H-pyrazol-4-yl)-8-chloro-7-((2-methyl-1H-benzo[d]imidazol-6-yl)oxy)quinoxaline and 2-(1-((1r,4r)-4-(azetidin-1-yl)cyclohexyl)-1H-pyrazol-4-yl)-8-chloro-7-((2-methyl-1H-benzo[d]imidazol-6-yl)oxy)quinoxaline A solution of 2-(1-(4-(azetidin-1-yl)cyclohexyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (65 mg, 101 μmol) in trifluoroacetic acid (1 mL) was stirred at 20° C. for 30 min. On completion, the reaction mixture was concentrated under reduced pressure. The residue was purified by prep-HPLC (column: Phenomenex Luna C18 150*25 mm*10 μm; mobile phase: [water (0.2% formic acid)-acetonitrile]; (B %: 10%-20%, 12 min) and further separated by SFC (column: Daicel ChiralPak IG (250*30 mm, 10 μm); mobile phase: [0.1% $NH_3H_2O$ MEOH]; (B %: 55%-55%, 6.1 min; 60 min) to give 2-(1-((1s,4s)-4-(azetidin-1-yl)cyclohexyl)-1H-pyrazol-4-yl)-8-chloro-7-((2-methyl-1H-benzo[d]imidazol-6-yl)oxy)quinoxaline (9.1 mg, 17.7 μmol, 18%) as a yellow solid and 2-(1-((1r,4r)-4-(azetidin-1-yl)cyclohexyl)-1H-pyrazol-4-yl)-8-chloro-7-((2-methyl-1H-benzo[d]imidazol-6-yl)oxy)quinoxaline (16.8 mg, 32.7 μmol, 31%) as a yellow gum.

$^1$H NMR (400 MHz, DMSO-$d_6$) δ 12.44-12.16 (m, 1H), 9.34 (s, 1H), 8.73 (s, 1H), 8.32 (s, 1H), 7.95 (d, J=9.2 Hz, 1H), 7.73-7.42 (m, 2H), 7.35-7.11 (m, 2H), 6.94 (d, J-7.6 Hz, 1H), 4.33-4.19 (m, 1H), 3.09 (t, J=6.8 Hz, 4H), 2.50 (s, 3H), 2.27 (s, 1H), 2.20-2.08 (m, 2H), 1.93 (td, J=6.4, 13.2 Hz, 2H), 1.83-1.74 (m, 2H), 1.67 (d, J=12.0 Hz, 2H), 1.50 (d, J=13.2 Hz, 2H); m/z ES+ $[M+H]^+$ 514.1.

$^1$H NMR (400 MHz, DMSO-$d_6$) δ 10.65-10.51 (m, 1H), 9.34 (s, 1H), 8.73 (s, 1H), 8.38 (s, 1H), 8 (d, J=9.2 Hz, 1H), 7.67 (d, J=8.8 Hz, 1H), 7.40 (d, J=9.2 Hz, 1H), 7.35 (s, 1H), 7.22-7.03 (m, 2H), 4.41-4.33 (m, 1H), 4.16-4.04 (m, 4H), 3.27 (s, 1H), 2.64 (s, 3H), 2.48-2.36 (m, 2H), 2.21 (d, J=10.8 Hz, 2H), 2.13-2.04 (m, 2H), 1.92-1.81 (m, 2H), 1.45-1.36 (m, 2H); m/z ES+ $[M+H]^+$ 514.1.

Example 119. Synthesis of 8-Chloro-7-[(2-methyl-3H-benzimidazol-5-yl)oxy]-2-[1-[(3-methyltetrahydrofuran-3-yl)methyl]pyrazol-4-yl]quinoxaline

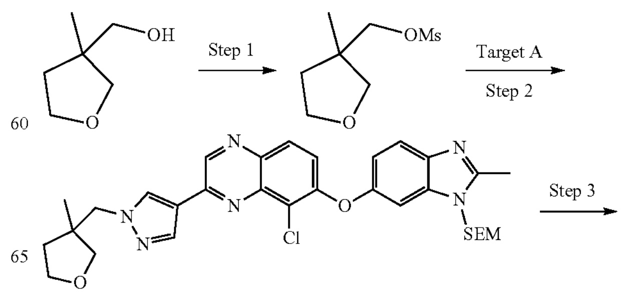

-continued

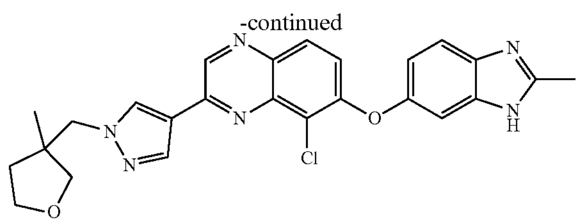

Step 1. (3-Methyltetrahydrofuran-3-yl)methyl methanesulfonate

To a solution of (3-methyltetrahydrofuran-3-yl) methanol (500 mg, 4.30 mmol) in dichloromethane (5 mL) was added triethylamine (1.31 g, 12.9 mmol) and methanesulfonyl chloride (739 mg, 6.46 mmol) at 0° C. The mixture was stirred at 0° C. for 2 h. The reaction mixture was quenched with water (15 mL) at 0° C., and then extracted with dichloromethane (10 mL×3). The combined organic layers were washed with brine (10 mL×3), dried over anhydrous sodium sulfate, filtered and concentrated in vacuo to give (3-methyltetrahydrofuran-3-yl)methyl methanesulfonate (600 mg, 3.09 mmol, 72%) as a yellow oil. $^1$H NMR (400 MHz, $CDCl_3$-d) δ 4.06 (s, 2H), 3.88 (dt, J=6.4, 8.0 Hz, 2H), 3.74-3.68 (m, 1H), 3.40 (d, J=8.8 Hz, 1H), 3.02 (s, 3H), 1.90-1.82 (m, 1H), 1.70 (ddd, J=6.0, 8.0, 12.8 Hz, 1H), 1.20 (s, 3H).

Step 2. 2-[[6-[5-Chloro-3-[1-[(3-methyltetrahydrofuran-3-yl)methyl]pyrazol-4-yl]quinoxalin-6-yl]oxy-2-methyl-benzimidazol-1-yl]methoxy]ethyl-trimethyl-silane To a solution of 2-[[6-[5-chloro-3-(1H-pyrazol-4-yl)quinoxalin-6-yl]oxy-2-methyl-benzimidazol-1-yl]methoxy]ethyl-trimethyl-silane (150 mg, 296 μmol) and (3-methyltetrahydrofuran-3-yl)methyl methanesulfonate (74.7 mg, 385 μmol) in N,N-dimethylformamide (1.5 mL) was added cesium carbonate (289 mg, 887 μmol) and potassium iodide (49.1 mg, 296 μmol). The mixture was stirred at 80° C. for 12 h. The reaction mixture was diluted with water (3 mL) and extracted with ethyl acetate (3 mL×3). The combined organic layers were washed with brine (3 mL×3), dried over anhydrous sodium sulfate, filtered and concentrated in vacuo to give 2-[[6-[5-chloro-3-[1-[(3-methyltetrahydrofuran-3-yl)methyl]pyrazol-4-yl]quinoxalin-6-yl]oxy-2-methyl-benzimidazol-1-yl]methoxy]ethyl-trimethyl-silane (150 mg, crude) as a yellow oil. m/z ES+ $[M+H]^+$ 605.3.

Step 3. 8-Chloro-7-[(2-methyl-3H-benzimidazol-5-yl)oxy]-2-[1-[(3-methyltetrahydrofuran-3-yl)methyl]pyrazol-4-yl]quinoxaline A solution of 2-[[6-[5-chloro-3-[1-[(3-methyltetrahydrofuran-3-yl)methyl]pyrazol-4-yl]quinoxalin-6-yl]oxy-2-methyl-benzimidazol-1-yl]methoxy]ethyl-trimethyl-silane (130 mg, 215 μmol) in trifluoroacetic acid (1 mL) was stirred at 25° C. for 1 h. The reaction mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 22%-32%, 7 min) to give 8-chloro-7-[(2-methyl-3H-benzimidazol-5-yl)oxy]-2-[1-[(3-methyltetrahydrofuran-3-yl)methyl]pyrazol-4-yl]quinoxaline (43.5 mg, 91.2 μmol, 43%) as an off-white solid. $^1$H NMR (400 MHz, DMSO-$d_6$) δ 9.34 (s, 1H), 8.73 (s, 1H), 8.38 (s, 1H), 8.13 (s, 1H), 7.99 (d, J=9.2 Hz, 1H), 7.62 (d, J=8.8 Hz, 1H), 7.37 (d, J=9.2 Hz, 1H), 7.31 (d, J=2.4 Hz, 1H), 7.07 (dd, J=2.4, 8.8 Hz, 1H), 4.26 (d, J=1.6 Hz, 2H), 3.81-3.77 (m, 2H), 3.34 (d, J=8.4 Hz, 2H), 2.59 (s, 3H), 1.98 (br d, J=12.0 Hz, 1H), 1.71-1.57 (m, 1H), 1.02 (s, 3H); m/z ES+ $[M+H]^+$ 475.1.

Example 120. Synthesis of 8-Chloro-2-(1-(4,4-difluorocyclohexyl)-1H-pyrazol-4-yl)-7-((2-methyl-1H-benzo[d]imidazol-6-yl)oxy)quinoxaline Int-22

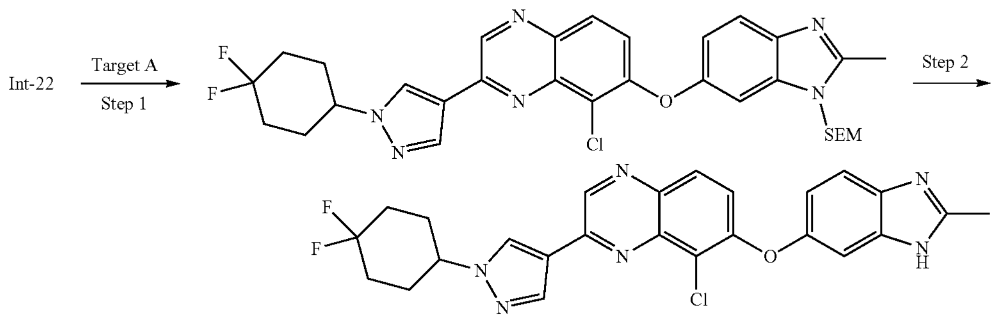

Step 1. 8-Chloro-2-(1-(4,4-difluorocyclohexyl)-1H-pyrazol-4-yl)-7-((2-methyl-1-((2-(trimethylsilyl)ethoxy)methyl)-1H-benzo[d]imidazol-6-yl)oxy)quinoxaline To a solution of 8-chloro-7-((2-methyl-1-((2-(trimethylsilyl)ethoxy)methyl)-1H-benzo[d]imidazol-6-yl)oxy)-2-(1H-pyrazol-4-yl)quinoxaline (100 mg, 197 μmol), 4,4-difluorocyclohexyl methanesulfonate (84.5 mg, 394 μmol) in dimethylsulfoxide (1 mL) was added cesium carbonate (192 mg, 591 μmol) and potassium iodide (32.7 mg, 197 μmol). The mixture was stirred at 80° C. for 12 h. On completion, the mixture was poured into water (50 mL) and extracted with ethyl acetate (30 mL×3). The organic layers were washed with brine (30 mL×3), dried over sodium sulfate, filtered and concentrated under reduced pressure. The residue was purified by prep-TLC (silica gel, dichloromethane: methanol=20:1) to give 8-chloro-2-(1-(4,4-difluorocyclohexyl)-1H-pyrazol-4-yl)-7-((2-methyl-1-((2-(trimethylsilyl)ethoxy)methyl)-1H-benzo[d]imidazol-6-yl)oxy)quinoxaline (90 mg, 144 μmol, 73%) as a yellow solid. m/z ES+ $[M+H]^+$ 625.3.

Step 2. 8-Chloro-2-(1-(4,4-difluorocyclohexyl)-1H-pyrazol-4-yl)-7-((2-methyl-1H-benzo[d]imidazol-6-yl)oxy)quinoxaline A solution of 8-chloro-2-(1-(4,4-difluorocyclohexyl)-1H-pyrazol-4-yl)-7-((2-methyl-1-((2-(trimethylsilyl)ethoxy)methyl)-1H-benzo[d]imidazol-6-yl)oxy)quinoxaline (85 mg, 135 μmol) in trifluoroacetic acid (1 mL) was stirred at 25° C. for 10 min. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 20%-50%, 7 min) to give 8-chloro-2-(1-(4,4-difluorocyclohexyl)-1H-pyrazol-4-yl)-7-((2-methyl-1H-benzo[d]imidazol-6-yl)oxy)quinoxaline (33.5 mg, 67.9 μmol, 49%) as a yellow solid. $^1$H NMR (400 MHz, $CD_3OD$) δ 9.27-9.02 (m, 1H), 8.72-8.54 (m, 1H), 8.46-8.25 (m, 1H), 8.15 (s, 1H), 8.01-7.77 (m, 1H), 7.66-7.54 (m, 1H), 7.46-7.29 (m, 1H), 7.23 (d, J=2.0 Hz, 1H), 7.18-7.01 (m, 1H), 4.50 (s, 1H), 2.67 (s, 3H), 2.30-1.98 (m, 8H); m/z ES+ $[M+H]^+$ 495.1.

Example 121. Synthesis of 2-(4-(8-Chloro-7-((2-methyl-1H-benzo[d]imidazol-6-yl)oxy)quinoxalin-2-yl)-1H-pyrazol-1-yl)-2-methylpropan-1-ol

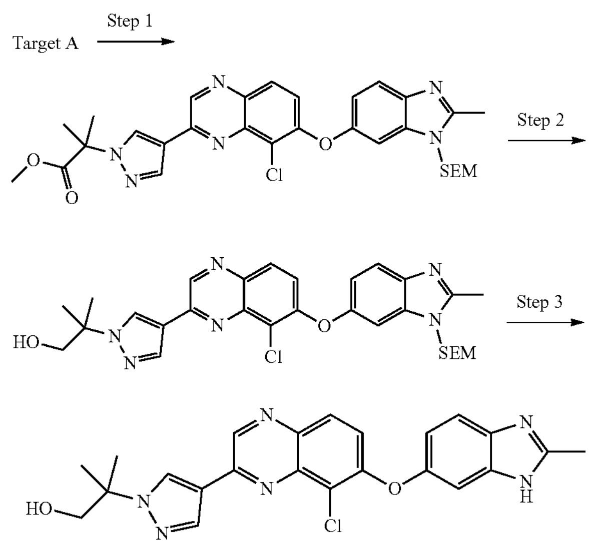

Step 1. Methyl 2-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-2-methylpropanoate To a solution of 2-[[6-[5-chloro-3-(1H-pyrazol-4-yl)quinoxalin-6-yl]oxy-2-methyl-benzimidazol-1-yl]methoxy]ethyl-trimethyl-silane (400 mg, 789 μmol) and methyl 2-bromo-2-methyl-propanoate (171 mg, 947 μmol) in N,N-dimethylformamide (6 mL) was added cesium carbonate (514 mg, 1.58 mmol). The mixture was stirred at 80° C. for 12 h. The reaction mixture was diluted with water (30 mL) and extracted with ethyl acetate (20 mL×3). The combined organic layers were dried over anhydrous sodium sulfate, filtered and concentrated under reduced pressure. The residue was purified by column chromatography (silica gel, dichloromethane/methanol=100/1 to 80/1) to give methyl 2-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-2-methylpropanoate (410 mg, 628 μmol, 79%) as a yellow oil. m/z ES+ $[M+H]^+$ 607.3.

Step 2. 2-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-2-methylpropan-1-ol To a solution of methyl 2-[4-[8-chloro-7-[2-methyl-3-(2-trimethylsilylethoxymethyl)benzimidazol-5-yl]oxy-quinoxalin-2-yl]pyrazol-1-yl]-2-methyl-propanoate (410 mg, 675 μmol) in ethanol (6 mL) was added sodium borohydride (76.6 mg, 2.03 mmol) at 0° C. The mixture was stirred at 25° C. for 4 h. The reaction mixture was diluted with water (30 mL) and extracted with ethyl acetate (20 mL×3). The combined organic layers were dried over anhydrous sodium sulfate, filtered and concentrated under reduced pressure. The residue was purified by column chromatography (silica gel, dichloromethane/methanol=1/0 to 80/1) to give 2-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-2-methylpropan-1-ol (280 mg, 377 μmol, 56%) as a yellow oil. m/z ES+ $[M+H]^+$ 579.3.

Step 3. 2-(4-(8-Chloro-7-((2-methyl-1H-benzo[d]imidazol-6-yl)oxy)quinoxalin-2-yl)-1H-pyrazol-1-yl)-2-methylpropan-1-ol A solution of 2-[4-[8-chloro-7-[2-methyl-3-(2-trimethylsilylethoxymethyl)benzimidazol-5-yl]oxy-quinoxalin-2-yl]pyrazol-1-yl]-2-methyl-propan-1-ol (80 mg, 108 μmol) in trifluoroacetic acid (1 mL) was stirred at 25° C. for 0.5 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 12%-42%, 10 min) to give 2-(4-(8-chloro-7-((2-methyl-1H-benzo[d]imidazol-6-yl)oxy)quinoxalin-2-yl)-1H-pyrazol-1-yl)-2-methylpropan-1-ol (33.5 mg, 74.7 μmol, 69%) as a yellow solid. $^1$H NMR (400 MHz, DMSO-$d_6$) δ=9.37 (s, 1H), 8.73 (s, 1H), 8.35 (s, 1H), 8.13 (s, 1H), 7.96 (d, J=9.3 Hz, 1H), 7.55 (d, J=8.6 Hz, 1H), 7.32 (d, J=9.3 Hz, 1H), 7.25 (d, J=2.3 Hz, 1H), 6.99 (dd, J=2.3, 8.7 Hz, 1H), 5.20-5.01 (m, 1H), 3.66 (s, 2H), 2.53 (s, 3H), 1.57 (s, 6H); m/z ES+ $[M+H]^+$ 449.1.

Example 122. Synthesis of 8-Chloro-2-(1-((3S,4S)-3-fluoro-1-(oxetan-3-yl) piperidin-4-yl)-1H-pyrazol-4-yl)-7-((2-methyl-1H-benzo[d]imidazol-6-yl)oxy)quinoxaline

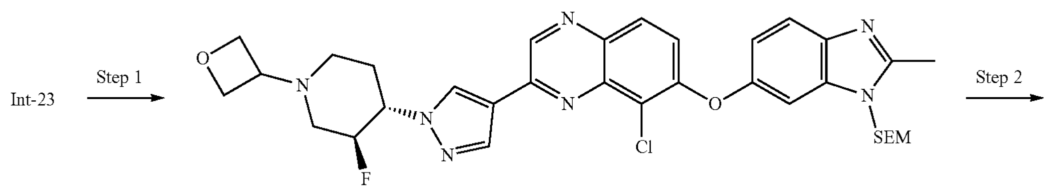

-continued

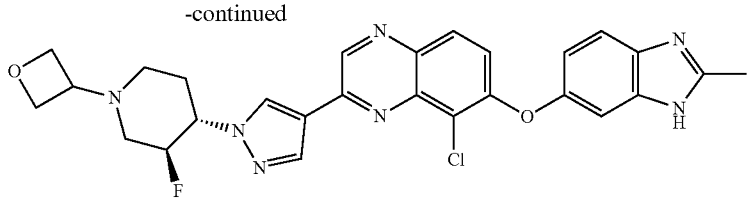

Step 1. 8-Chloro-2-(1-((3S,4S)-3-fluoro-1-(oxetan-3-yl) piperidin-4-yl)-1H-pyrazol-4-yl)-7-((2-methyl-1-((2-(trimethylsilyl)ethoxy)methyl)-1H-benzo[d]imidazol-6-yl)oxy)quinoxaline To a solution of 2-[[6-[5-chloro-3-[1-[(3S,4S)-3-fluoro-4-piperidyl]pyrazol-4-yl]quinoxalin-6-yl]oxy-2-methyl-benzimidazol-1-yl]methoxy]ethyl-trimethyl-silane (200 mg, 329 μmol) in tetrahydrofuran (5 mL) was added oxetan-3-one (47.4 mg, 658 μmol). The mixture was stirred at 25° C. for 0.5 h. Then sodium triacetoxyborohydride (209 mg, 987 μmol) was added at 0° C. The mixture was stirred at 25° C. for 1 h. The reaction mixture was diluted with water (30 mL) and extracted with dichloromethane (20 mL×3). The combined organic layers were dried over anhydrous sodium sulfate, filtered and concentrated under reduced pressure to give 8-chloro-2-(1-((3S,4S)-3-fluoro-1-(oxetan-3-yl) piperidin-4-yl)-1H-pyrazol-4-yl)-7-((2-methyl-1-((2-(trimethylsilyl)ethoxy)methyl)-1H-benzo[d]imidazol-6-yl)oxy)quinoxaline (230 mg, crude) as a yellow solid. m/z ES+ $[M+H]^+$ 664.3.

Step 2. 8-Chloro-2-(1-((3S,4S)-3-fluoro-1-(oxetan-3-yl) piperidin-4-yl)-1H-pyrazol-4-yl)-7-((2-methyl-1H-benzo[d]imidazol-6-yl)oxy)quinoxaline To a solution of 2-[[6-[5-chloro-3-[1-[(3S,4S)-3-fluoro-1-(oxetan-3-yl)-4-piperidyl]pyrazol-4-yl]quinoxalin-6-yl]oxy-2-methyl-benzimidazol-1-yl]methoxy]ethyl-trimethyl-silane (210 mg, 316 μmol) in tetrahydrofuran (5 mL) was added tetrabutylammonium fluoride (1 M in THF, 632 μL). The mixture was stirred at 80° C. for 12 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 11%-41%, 10 min) and repurified by prep-HPLC (neutral condition; column: Waters Xbridge 150*25 mm*5 μm; mobile phase: [water (10 mM ammonium bicarbonate)-acetonitrile]; (B %: 27%-57%, 10 min), which was further purified by prep-HPLC (formic acid condition; column: Shim-pack C18 150*25*10 μm; mobile phase: [water (0.225% formic acid)-acetonitrile]; (B %: 5%-35%, 10 min) to give 8-chloro-2-(1-((3S,4S)-3-fluoro-1-(oxetan-3-yl) piperidin-4-yl)-1H-pyrazol-4-yl)-7-((2-methyl-1H-benzo[d]imidazol-6-yl)oxy)quinoxaline (6.12 mg, 11.5 μmol, 3.7%) as a yellow solid. $^1H$ NMR (400 MHz, DMSO-$d_6$) δ=9.32 (s, 1H), 8.84 (s, 1H), 8.44 (s, 1H), 7.96 (d, J=9.2 Hz, 1H), 7.51 (d, J=8.4 Hz, 1H), 7.32 (d, J=9.2 Hz, 1H), 7.22 (s, 1H), 6.94 (dd, J=2.3, 8.6 Hz, 1H), 5.11-4.90 (m, 1H), 4.59-4.56 (m, 2H), 4.48 (td, J=6.2, 12.6 Hz, 2H), 3.65-3.59 (m, 1H), 3.25-3.20 (m, 1H), 2.82 (d, J=10.4 Hz, 1H), 2.53-2.51 (m, 1H), 2.49 (s, 3H), 2.20-2.02 (m, 4H); m/z ES+ $[M+H]^+$ 534.1.

Example 123. Synthesis of 2-(1-((1R,3r,5S)-8-azabicyclo[3.2.1]octan-3-yl)-1H-pyrazol-4-yl)-8-chloro-7-((2-methyl-1H-benzo[d]imidazol-6-yl)oxy)quinoxaline and 2-(1-((1R,3s,5S)-8-azabicyclo[3.2.1]octan-3-yl)-1H-pyrazol-4-yl)-8-chloro-7-((2-methyl-1H-benzo[d]imidazol-6-yl)oxy)quinoxaline

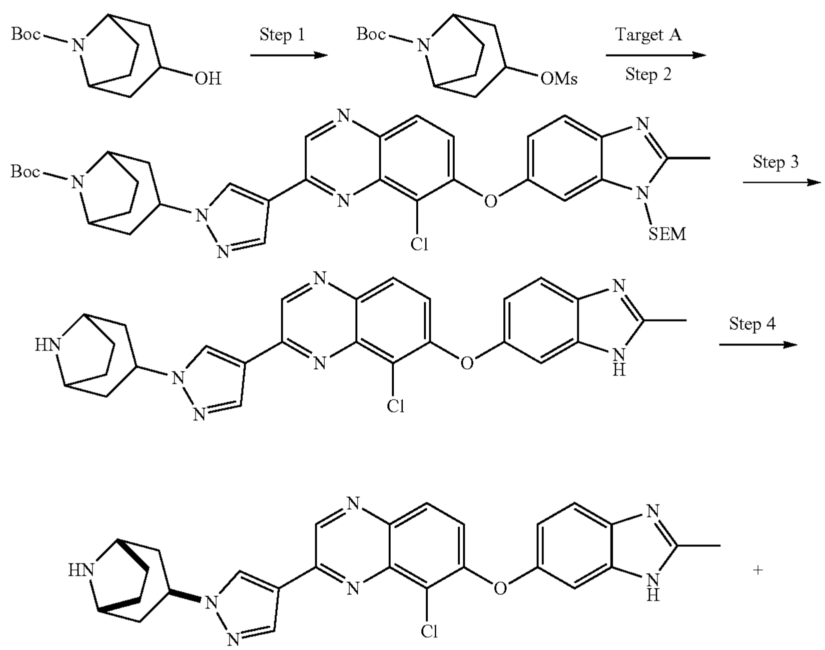

-continued

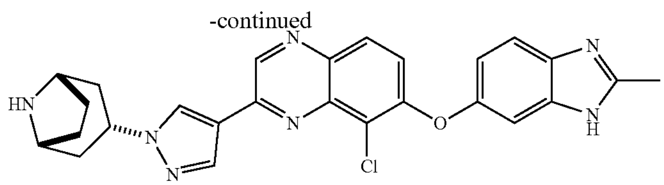

Step 1. tert-Butyl 5-methylsulfonyloxy-2-azabicyclo[2.2.1]heptane-2-carboxylate

To a solution of tert-butyl 5-hydroxy-2-azabicyclo[2.2.1]heptane-2-carboxylate (500 mg, 2.20 mmol) and triethylamine (569 mg, 4.40 mmol) in dichloromethane (5 mL) was added methanesulfonyl chloride (302 mg, 2.64 mmol). The mixture was stirred at 25° C. for 1 h. On completion, the reaction mixture was quenched with water (10 mL) and extracted with dichloromethane (10 mL×3). The combined organic layers were dried over anhydrous sodium sulfate, filtered and concentrated. The residue was purified by column chromatography (petroleum ether/ethyl acetate from 6/1 to 3/1) to give tert-butyl 5-methylsulfonyloxy-2-azabicyclo[2.2.1]heptane-2-carboxylate (500 mg, 1.64 mmol, 74%) as a colorless oil. $^1$H NMR (400 MHz, $CDCl_3$) δ 5.06-4.93 (m, 1H), 4.30-4.09 (m, 2H), 2.94 (s, 3H), 2.11-1.57 (m, 8H), 1.44-1.37 (m, 9H).

Step 2. tert-Butyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-8-azabicyclo[3.2.1]octane-8-carboxylate To a solution of 8-chloro-7-((2-methyl-1-((2-(trimethylsilyl)ethoxy)methyl)-1H-benzo[d] imidazol-6-yl)oxy)-2-(1H-pyrazol-4-yl)quinoxaline (300 mg, 592 μmol) in N-methylpyrrolidone (10 mL) was added cesium carbonate (245 mg, 0.79 mmol) and tert-butyl 3-methylsulfonyloxy-8-azabicyclo[3.2.1]octane-8-carboxylate (217 mg, 0.71 mmol). The mixture was stirred at 80° C. for 1 h. On completion, the reaction was quenched with water (30 mL) and extracted with ethyl acetate (30 mL×3). The combined organic layers were dried over anhydrous sodium sulfate, filtered and concentrated. The residue was purified by column chromatography (dichloromethane/methanol from 80/1 to 20/1) to give tert-butyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-8-azabicyclo[3.2.1]octane-8-carboxylate (450 mg, crude) as a yellow oil. m/z ES+ [M+H]$^+$ 716.3.

Step 3. 2-(1-(8-Azabicyclo[3.2.1]octan-3-yl)-1H-pyrazol-4-yl)-8-chloro-7-((2-methyl-1H-benzo[d]imidazol-6-yl)oxy)quinoxaline A solution of tert-butyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-8-azabicyclo[3.2.1]octane-8-carboxylate (400 mg, 558 μmol) in trifluoroacetic acid (1 mL) was stirred at 30° C. for 1 h. On completion, the reaction mixture was concentrated under reduced pressure to give 2-(1-(8-azabicyclo[3.2.1]octan-3-yl)-1H-pyrazol-4-yl)-8-chloro-7-((2-methyl-1H-benzo[d]imidazol-6-yl)oxy)quinoxaline (270 mg, crude) as a yellow oil. m/z ES+ [M+H]$^+$ 486.2.

Step 4. 2-(1-((1R,3r,5S)-8-azabicyclo[3.2.1]octan-3-yl)-1H-pyrazol-4-yl)-8-chloro-7-((2-methyl-1H-benzo[d]imidazol-6-yl)oxy)quinoxaline and 2-(1-((1R,3s,5S)-8-azabicyclo[3.2.1]octan-3-yl)-1H-pyrazol-4-yl)-8-chloro-7-((2-methyl-1H-benzo[d]imidazol-6-yl)oxy)quinoxaline 2-(1-(8-Azabicyclo[3.2.1]octan-3-yl)-1H-pyrazol-4-yl)-8-chloro-7-((2-methyl-1H-benzo[d]imidazol-6-yl)oxy)quinoxaline (80 mg, crude) was purified by prep-HPLC (formic acid condition; column: Phenomenex Luna C18 150*25 mm*10 μm; mobile phase: [water (0.225% formic acid)-acetonitrile]; (B %: 4%-34%, 10 min) to give 2-(1-((1R,3r,5S)-8-azabicyclo[3.2.1]octan-3-yl)-1H-pyrazol-4-yl)-8-chloro-7-((2-methyl-1-benzo[d]imidazol-6-yl)oxy)quinoxaline (24.9 mg, 51.3 μmol, 31%) as a yellow solid and 2-(1-((1R,3s,5S)-8-azabicyclo[3.2.1]octan-3-yl)-1H-pyrazol-4-yl)-8-chloro-7-((2-methyl-1H-benzo[d]imidazol-6-yl)oxy)quinoxaline (23.4 mg, 48.2 μmol, 29%) as an off-white solid.

$^1$H NMR (400 MHz, DMSO-$d_6$) δ 9.31 (s, 1H), 8.73 (s, 1H), 8.40 (s, 1H), 8.36 (s, 1H), 7.95 (d, J=9.2 Hz, 1H), 7.51 (d, J=8.4 Hz, 1H), 7.31 (d, J=9.2 Hz, 1H), 7.21 (d, J=2.4 Hz, 1H), 6.94 (dd, J=2.4, 8.8 Hz, 1H), 4.85 (td, J=6.0, 11.5 Hz, 1H), 3.96 (s, 2H), 2.49 (s, 3H), 2.37-2.23 (m, 2H), 2.11 (dd, J=4.8, 10.8 Hz, 2H), 1.97 (s, 4H); m/z ES+ [M+H]$^+$ 486.1.

$^1$H NMR (400 MHz, DMSO-$d_6$) δ 9.40 (s, 1H), 9.09 (s, 1H), 8.91 (s, 2H), 8.41 (s, 1H), 8.04 (d, J=9.2 Hz, 1H), 7.77 (d, J=8.8 Hz, 1H), 7.49-7.44 (m, 2H), 7.23 (dd, J=2.4, 8.8 Hz, 1H), 4.67 (t, J=6.4 Hz, 1H), 4.09 (s, 2H), 2.98 (d, J=16.0 Hz, 2H), 2.73 (s, 3H), 2.53 (dd, J=2.4, 7.6 Hz, 2H), 1.90-1.79 (m, 2H), 1.69 (d, J=8.0 Hz, 2H); m/z ES+ [M+H]$^+$ 486.1.

Example 124. Synthesis of 8-Chloro-7-((2-methyl-1H-benzo[d]imidazol-6-yl)oxy)-2-(1-((1R,3r,5S)-8-methyl-8-azabicyclo[3.2.1]octan-3-yl)-1H-pyrazol-4-yl)quinoxaline and 8-chloro-7-((2-methyl-1H-benzo[d]imidazol-6-yl)oxy)-2-(1-((1R,3s,5S)-8-methyl-8-azabicyclo[3.2.1]octan-3-yl)-1H-pyrazol-4-yl)quinoxaline

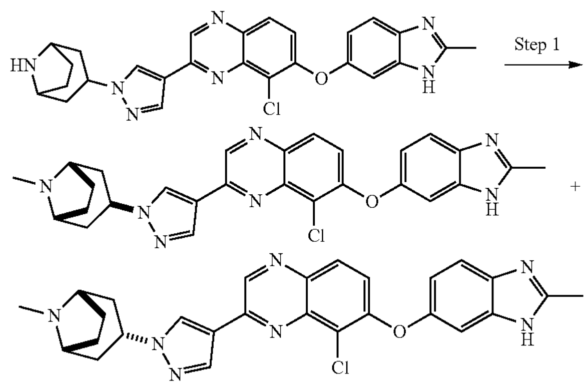

Step 1. 8-Chloro-7-((2-methyl-1H-benzo[d]imidazol-6-yl)oxy)-2-(1-((1R,3r,5S)-8-methyl-8-azabicyclo[3.2.1]octan-3-yl)-1H-pyrazol-4-yl)quinoxaline and 8-chloro-7-((2-methyl-1H-benzo[d]imidazol-6-yl)oxy)-2-(1-((1R,3s,5S)-8-methyl-8-azabicyclo[3.2.1]octan-3-yl)-1H-pyrazol-4-yl)quinoxaline To a solution of 2-(1-(8-azabicyclo[3.2.1]octan-3-yl)-1H-pyrazol-4-yl)-8-chloro-7-((2-methyl-1H-benzo[d]imidazol-6-yl)oxy)quinoxaline (100 mg, 206 μmol) in N,N-dimethylformamide (1 mL) was added formic acid (198 mg, 4.12 mmol) and paraformaldehyde (124 mg, 4.12 mmol). The mixture was stirred at 60° C. for 13 h. On completion, the reaction mixture was filtered and concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 4%-34%, 10 min) to give 8-chloro-7-((2-methyl-1H-benzo[d]imidazol-6-yl)oxy)-2-(1-((1R,3r,5S)-8-methyl-8-azabicyclo[3.2.1]octan-3-yl)-1H-pyrazol-4-yl)quinoxaline (9.3 mg, 18.6 μmol, 9%) as an off-white solid and 8-chloro-7-((2-methyl-1H-benzo[d]imidazol-6-yl)oxy)-2-(1-((1R,3s,5S)-8-methyl-8-azabicyclo[3.2.1]octan-3-yl)-1H-pyrazol-4-yl)quinoxaline (11.1 mg, 22.2 μmol, 11%) as an off-white solid. $^1$H NMR (400 MHz, DMSO-$d_6$) δ 9.30 (s, 1H), 8.75 (s, 1H), 8.36 (s, 1H), 8.30 (s, 2H), 7.94 (d, J=9.2 Hz, 1H), 7.51 (d, J=8.4 Hz, 1H), 7.31 (d, J=9.2 Hz, 1H), 7.21 (d, J=2.4 Hz, 1H), 6.94 (dd, J=2.4, 8.8 Hz, 1H), 4.73 (td, J=5.6, 11.6 Hz, 1H), 3.43 (s, 2H), 2.48 (s, 3H), 2.39 (s, 3H), 2.26 (t, J=11.6 Hz, 2H), 2.13-2.04 (m, 2H), 1.95 (dd, J=5.2, 10.0 Hz, 2H), 1.82 (d, J=8.0 Hz, 2H); m/z ES+ $[M+H]^+$ 500.1.

$^1$H NMR (400 MHz, DMSO-$d_6$) δ 9.34 (s, 1H), 9 (s, 1H), 8.36 (s, 1H), 8.32 (s, 2H), 7.95 (d, J=9.2 Hz, 1H), 7.51 (d, J=8.8 Hz, 1H), 7.31 (d, J=9.2 Hz, 1H), 7.21 (d, J=2.0 Hz, 1H), 6.94 (dd, J=2.0, 8.8 Hz, 1H), 4.54 (s, 1H), 3.50-3.41 (m, 2H), 2.77-2.64 (m, 2H), 2.61-2.51 (m, 2H), 2.49 (s, 3H), 2.43-2.36 (m, 3H), 2.03-1.89 (m, 2H), 1.55 (d, J=8.4 Hz, 2H); m/z ES+ $[M+H]^+$ 500.1.

Example 125. Synthesis of 8-Chloro-7-[(2-methyl-3H-benzimidazol-5-yl)oxy]-2-[1-(3-oxabicyclo[3.1.0]hexan-6-ylmethyl)pyrazol-4-yl]quinoxaline

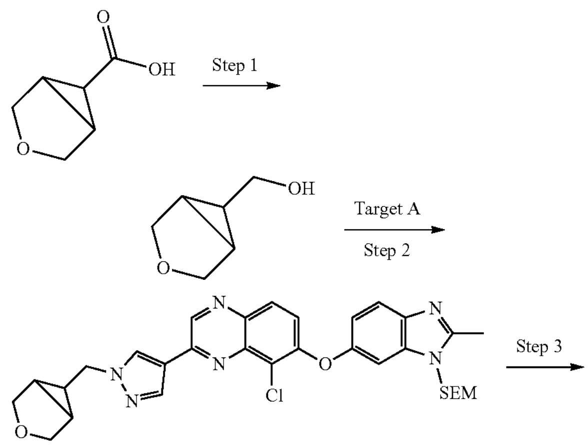

-continued

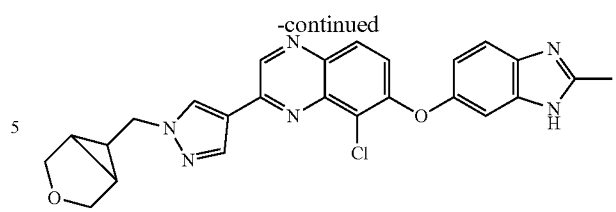

Step 1. 3-Oxabicyclo[3.1.0]hexan-6-ylmethanol

To a solution of 3-oxabicyclo[3.1.0]hexane-6-carboxylic acid (750 mg, 5.85 mmol) in tetrahydrofuran (10 mL) was added lithium aluminum hydride (333 mg, 8.78 mmol) portion-wise at 0° C. The mixture was stirred at 25° C. for 1 h. On completion, the mixture was carefully quenched with sodium sulfate decahydrate (10 g) and then dried by magnesium sulfate. The mixture was filtered and the filtrate was concentrated under reduced pressure. The residue was purified by column chromatography (silica gel, petroleum ether/ethyl acetate=1/0 to 1/1) to give 3-oxabicyclo[3.1.0]hexan-6-ylmethanol (250 mg, 2.19 mmol, 37%) as a colorless oil. $^1$H NMR (400 MHz, $CDCl_3$) δ 3.88 (d, J=8.2 Hz, 2H), 3.70 (d, J=8.2 Hz, 2H), 3.53 (d, J=7.2 Hz, 2H), 1.62-1.62 (m, 1H), 1.56-1.54 (m, 2H), 1.10 (d, J=3.6, 7.2 Hz, 1H).

Step 2. 2-[[6-[5-Chloro-3-[1-(3-oxabicyclo[3.1.0]hexan-6-ylmethyl)pyrazol-4-yl]quinoxalin-6-yl]oxy-2-methyl-benzimidazol-1-yl]methoxy]ethyl-trimethyl-silane To a solution of 2-[[6-[5-chloro-3-(1H-pyrazol-4-yl)quinoxalin-6-yl]oxy-2-methyl-benzimidazol-1-yl]methoxy]ethyl-trimethyl-silane (100 mg, 197 μmol) in dichloromethane (1 mL) was added 3-oxabicyclo[3.1.0]hexan-6-ylmethanol (27.0 mg, 236 μmol) and triphenylphosphine (77.6 mg, 295 μmol). Then diisopropyl azodicarboxylate (59.8 mg, 295 μmol) was added at 0° C. and the mixture was stirred at 25° C. for 12 h. On completion, the mixture was concentrated under reduced pressure. The residue was purified by prep-TLC (silica gel, dichloromethane:methanol=20:1) to give 2-[[6-[5-chloro-3-[1-(3-oxabicyclo[3.1.0]hexan-6-ylmethyl)pyrazol-4-yl]quinoxalin-6-yl]oxy-2-methyl-benzimidazol-1-yl]methoxy]ethyl-trimethyl-silane (25 mg, 41.5 μmol, 21%) as a white solid. m/z ES+ $[M+H]^+$ 603.1.

Step 3. 8-Chloro-7-[(2-methyl-3H-benzimidazol-5-yl)oxy]-2-[1-(3-oxabicyclo[3.1.0]hexan-6-ylmethyl)pyrazol-4-yl]quinoxaline A solution of 2-[[6-[5-chloro-3-[1-(3-oxabicyclo[3.1.0]hexan-6-ylmethyl)pyrazol-4-yl]quinoxalin-6-yl]oxy-2-methyl-benzimidazol-1-yl]methoxy]ethyl-trimethyl-silane (25 mg, 41.5 μmol) in trifluoroacetic acid (0.6 mL) was stirred at 25° C. for 0.5 h. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 15%-45%, 8 min) to give 8-chloro-7-[(2-methyl-3H-benzimidazol-5-yl)oxy]-2-[1-(3-oxabicyclo[3.1.0]hexan-6-ylmethyl)pyrazol-4-yl]quinoxaline (6.4 mg, 13.6 μmol, 32%) as an off-white solid. $^1$H NMR (400 MHz, $CD_3OD$) δ 9.19 (d, J=4.4 Hz, 1H), 8.63 (d, J=3.2 Hz, 1H), 8.38 (d, J=2.8 Hz, 1H), 7.93 (dd, J=4.4, 9.2 Hz, 1H), 7.56 (d, J=8.8 Hz, 1H), 7.37 (dd, J=2.6, 9.2 Hz, 1H), 7.20 (d, J=2.2 Hz, 1H), 7.04 (dd, J=2.4, 8.8 Hz, 1H), 4.23 (d, J=7.2 Hz, 2H), 3.88 (d, J=8.4 Hz, 2H), 3.72 (d, J=8.0 Hz, 2H), 2.60 (s, 3H), 1.87 (s, 2H), 1.34 (td, J=3.8, 7.2 Hz, 1H); m/z ES+ $[M+H]^+$ 473.1.

Example 126. Synthesis of 8-chloro-7-[(2-methyl-3H-benzimidazol-5-yl)oxy]-2-[1-[(4-methylsulfonyl-cyclohexyl)methyl]pyrazol-4-yl]quinoxaline

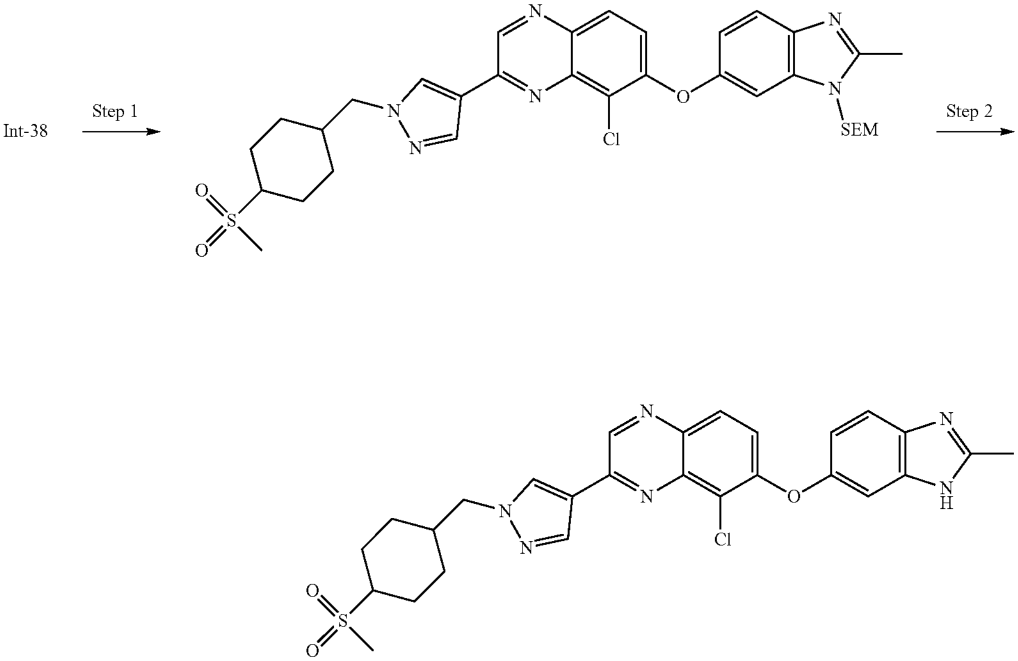

Step 1. 2-[[6-[5-chloro-3-[1-[(4-methylsulfonylcyclohexyl)methyl]pyrazol-4-yl]quinoxalin-6-yl]oxy-2-methyl-benzimidazol-1-yl]methoxy]ethyl-trimethyl-silane To a solution of 2-[[6-[5-chloro-3-[1-[(4-methylsulfanylcyclohexyl)methyl]pyrazol-4-yl]quinoxalin-6-yl]oxy-2-methyl-benzimidazol-1-yl]methoxy]ethyl-trimethyl-silane (20.0 mg, 30.8 μmol) in acetonitrile (1 mL) and water (1 mL) was added oxone (56.8 mg, 92.4 μmol) at 0° C. The mixture was stirred at 0° C. for 1 h. On completion, the mixture was poured into sat. sodium sulfite (10 mL) and extracted with ethyl acetate (30 mL×3). The organic layers were dried over sodium sulfate, filtered and concentrated under reduced pressure to give 2-[[6-[5-chloro-3-[1-[(4-methylsulfonylcyclohexyl)methyl]pyrazol-4-yl]quinoxalin-6-yl]oxy-2-methyl-benzimidazol-1-yl]methoxy]ethyl-trimethyl-silane (20 mg, crude) as a yellow oil. m/z ES+ $[M+H]^+$ 681.1.

Step 2. 8-Chloro-7-[(2-methyl-3H-benzimidazol-5-yl)oxy]-2-[1-[(4-methylsulfonylcyclohexyl)methyl]pyrazol-4-yl]quinoxaline A solution of 2-[[6-[5-chloro-3-[1-[(4-methylsulfonylcyclohexyl)methyl]pyrazol-4-yl]quinoxalin-6-yl]oxy-2-methyl-benzimidazol-1-yl]methoxy]ethyl-trimethyl-silane (20.0 mg, 29.4 μmol) in trifluoroacetic acid (1 mL) was stirred at 25° C. for 1 h. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 15%-45%, 7 min) to give 8-chloro-7-[(2-methyl-3H-benzimidazol-5-yl)oxy]-2-[1-[(4-methylsulfonylcyclohexyl)methyl]pyrazol-4-yl]quinoxaline (6.0 mg, 10.9 μmol, 37%) as an off-white solid. $^1$H NMR (400 MHz, $CD_3OD$) δ=9.18 (s, 1H), 8.68-8.50 (m, 1H), 8.35 (s, 1H), 8.11 (s, 1H), 7.94 (d, J=9.2 Hz, 1H), 7.64 (d, J=8.8 Hz, 1H), 7.41 (d, J=9.2 Hz, 1H), 7.25 (d, J=1.8 Hz, 1H), 4.30 (d, J=8.0 Hz, 2H), 4.16 (d, J=7.2 Hz, 1H), 2.98-2.86 (m, 3H), 2.70 (s, 3H), 2.49-2.48. (m, 1H), 2.45-2.28 (m, 1H), 2.24 (d, J=10.2 Hz, 1H), 2.10-1.94 (m, 3H), 1.88 (d, J=14.2 Hz, 1H), 1.78-1.60 (m, 3H), 1.58-1.46 (m, 1H), 1.34-1.12 (m, 1H); m/z ES+ $[M+H]^+$ 551.1.

Example 127. Synthesis of 8-Chloro-2-(1-(((3S,4R)-3-fluoro-1-methylpiperidin-4-yl)methyl)-1H-pyrazol-4-yl)-7-((2-methyl-1H-benzo[d]imidazol-6-yl)oxy)quinoxaline, 8-chloro-2-(1-(((3S,4S)-3-fluoro-1-methylpiperidin-4-yl)methyl)-1H-pyrazol-4-yl)-7-((2-methyl-1H-benzo[d]imidazol-6-yl)oxy)quinoxaline and 8-chloro-2-(1-((3-fluoropiperidin-4-yl)methyl)-1H-pyrazol-4-yl)-7-((2-methyl-1H-benzo[d]imidazol-6-yl)oxy)quinoxaline

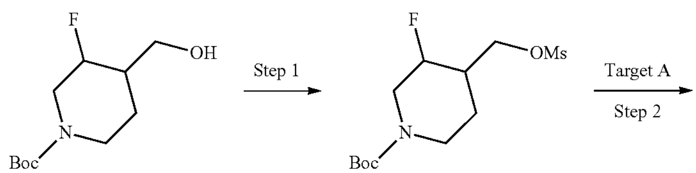

-continued

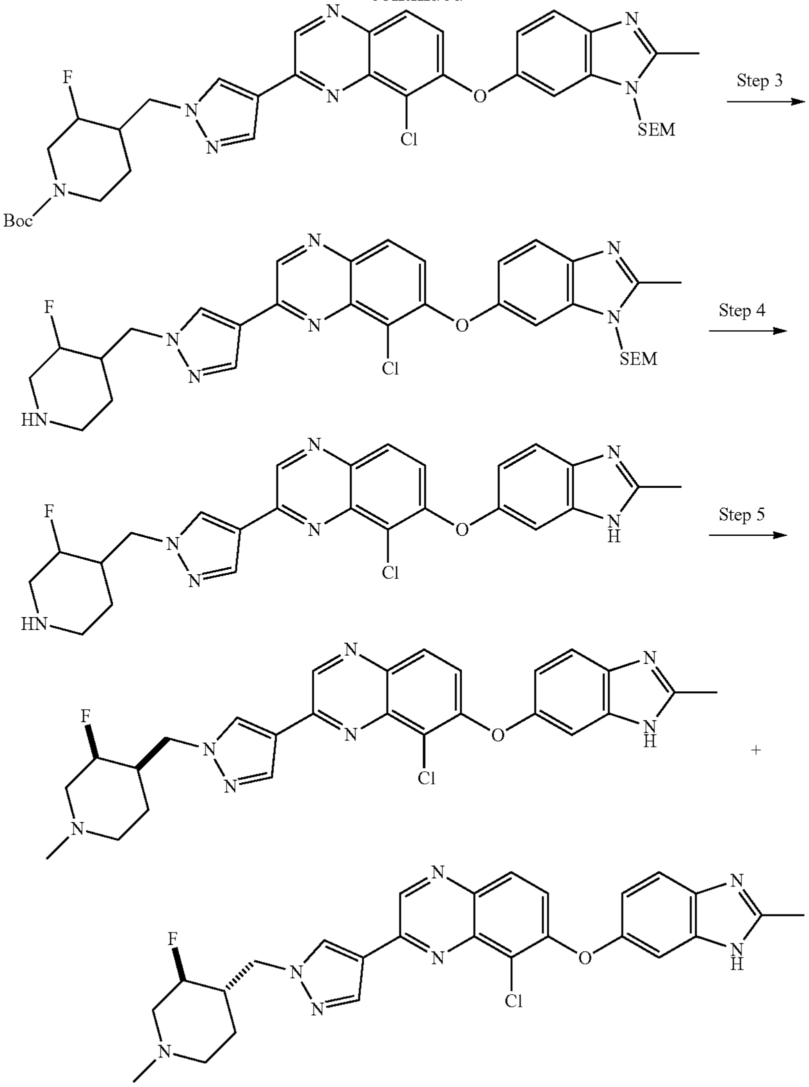

Step 1. tert-Butyl 3-fluoro-4-(methylsulfonyloxymethyl) piperidine-1-carboxylate To a solution of tert-butyl 3-fluoro-4-(hydroxymethyl) piperidine-1-carboxylate (500 mg, 2.14 mmol) in dichloromethane (5 mL) was added triethylamine (651 mg, 6.43 mmol) and methanesulfonyl chloride (368 mg, 3.22 mmol). The mixture was stirred at 0° C. for 1 h. The reaction mixture was quenched with water (4 mL) at 0° C. and extracted with dichloromethane (3 mL×3). The combined organic layers were washed with brine (5 mL×3), dried over anhydrous sodium sulfate, filtered and concentrated in vacuo to give tert-butyl 3-fluoro-4-(methylsulfonyloxymethyl) piperidine-1-carboxylate (600 mg, crude) as a yellow oil. $^1$H NMR (400 MHz, $CDCl_3$) δ 4.62-3.94 (m, 5H), 3.03 (d, J=0.4 Hz, 3H), 2.84 (br.d, J=12.4 Hz, 2H), 2.10-1.94 (m, 1H), 1.64-1.52 (m, 1H), 1.45 (s, 9H).

Step 2. tert-Butyl 4-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) methyl)-3-fluoropiperidine-1-carboxylate To a solution of 2-[[6-[5-chloro-3-(1H-pyrazol-4-yl)quinoxalin-6-yl]oxy-2-methyl-benzimidazol-1-yl]methoxy] ethyl-trimethyl-silane (200 mg, 394 μmol) in N,N-dimethylformamide (2 mL) was added potassium carbonate (164 mg, 1.18 mmol) and tert-butyl 3-fluoro-4-(methylsulfonyloxymethyl) piperidine-1-carboxylate (184 mg, 591 μmol). The mixture was stirred at 100° C. for 12 h. The reaction mixture was diluted with water (3 mL) and extracted with ethyl acetate (3 mL×3). The combined organic layers were washed with brine (3 mL×3), dried over anhydrous sodium sulfate, filtered and concentrated in vacuo. The residue was purified by column chromatography (silica gel, dichloromethane:methanol=50:1 to 20:1) to give tert-butyl 4-[[4-[8-chloro-7-[2-methyl-3-(2-trimethylsilylethoxymethyl) benzimidazol-5-yl]oxy-quinoxalin-2-yl]pyrazol-1-yl] methyl]-3-fluoro-piperidine-1-carboxylate (190 mg, 263 μmol, 67%) as a yellow oil. m/z ES+ $[M+H]^+$ 722.1.

Step 3. 2-[[6-[5-Chloro-3-[1-[(3-fluoro-4-piperidyl) methyl]pyrazol-4-yl]quinoxalin-6-yl]oxy-2-methyl-benzimidazol-1-yl]methoxy]ethyl-trimethyl-silane To a solution of tert-butyl 4-[[4-[8-chloro-7-[2-methyl-3-(2-trimethylsilylethoxymethyl)benzimidazol-5-yl]oxy-quinoxalin-2-yl]pyrazol-1-yl]methyl]-3-fluoro-piperidine-1-carboxylate (50 mg, 69.2 μmol) in dichloromethane (1 mL) was added trifluoroacetic acid (0.1 mL). The mixture was stirred at 25° C. for 1 h. The reaction mixture was quenched with sat. sodium bicarbonate (2 mL) at 25° C., then diluted with water (3 mL) and extracted with ethyl acetate (3 mL×3). The combined organic layers were washed with brine (3 mL×3). dried over anhydrous sodium sulfate, filtered and concentrated in vacuo to give 2-[[6-[5-chloro-3-[1-[(3-fluoro-4-piperidyl)methyl]pyrazol-4-yl]quinoxalin-6-yl]oxy-2-methyl-benzimidazol-1-yl]methoxy]ethyl-trimethyl-silane (40 mg, crude) as a yellow solid. m/z ES+$[M+H]^+$ 622.1.

Step 4. 8-Chloro-2-[1-[(3-fluoro-4-piperidyl)methyl] pyrazol-4-yl]-7-[(2-methyl-3H-benzimidazol-5-yl) oxy]quinoxaline To a solution of 2-[[6-[5-chloro-3-[1-[(3-fluoro-4-piperidyl)methyl]pyrazol-4-yl]quinoxalin-6-yl]oxy-2-methyl-benzimidazol-1-yl]methoxy]ethyl-trimethyl-silane (40 mg, 64.3 μmol) in tetrahydrofuran (0.5 mL) was added tetrabutylammonium fluoride (1 M in THF, 129 μL). The mixture was stirred at 80° C. for 16 h. The reaction mixture was filtered and concentrated in vacuo. The residue was purified by prep-HPLC (column: Phenomenex Gemini-NX C18 75*30 mm*3 μm; mobile phase: [water (0.225% formic acid)-acetonitrile]; (B %: 2%-32%, 7 min) to give 8-chloro-2-[1-[(3-fluoro-4-piperidyl)methyl]pyrazol-4-yl]-7-[(2-methyl-3H-benzimidazol-5-yl)oxy]quinoxaline (2.6 mg, 5.27 μmol, 8.2%) as a yellow solid. $^1$H NMR (400 MHz, $CD_3OD$) δ 9.14 (s, 1H), 8.62-8.59 (m, 1H), 8.40-8.37 (m, 1H), 8.32 (s, 2H), 7.89 (d, J=9.2 Hz, 1H), 7.53 (d, J=8.8 Hz, 1H), 7.35 (d, J=9.2 Hz, 1H), 7.19 (d, J=2.4 Hz, 1H), 7.01 (dd, J=2.4, 8.8 Hz, 1H), 4.85-4.55 (m, 2H), 4.54-4.28 (m, 2H), 3.71-3.58 (m, 1H), 3.49-3.34 (m, 1H), 3.25-3.14 (m, 1H), 3.11-2.99 (m, 1H), 2.58 (s, 3H), 2.08-1.87 (m, 1H), 1.83-1.83 (m, 1H), 1.83-1.60 (m, 1H); m/z ES+ $[M+H]^+$ 492.2.

Step 5. 8-Chloro-2-(1-(((3S,4R)-3-fluoro-1-methylpiperidin-4-yl)methyl)-1H-pyrazol-4-yl)-7-((2-methyl-1H-benzo[d]imidazol-6-yl)oxy)quinoxaline and 8-Chloro-2-(1-(((3R,4S)-3-fluoro-1-methylpiperidin-4-yl)methyl)-1H-pyrazol-4-yl)-7-((2-methyl-1H-benzo[d]imidazol-6-yl)oxy)quinoxaline To a solution of 8-chloro-2-[1-[(3-fluoro-4-piperidyl) methyl]pyrazol-4-yl]-7-[(2-methyl-3H-benzimidazol-5-yl) oxy]quinoxaline (60 mg, 122 μmol) in N,N-dimethylformamide (1 mL) was added formic acid (117 mg, 2.44 mmol) and paraformaldehyde (73.2 mg, 2.44 mmol). The mixture was stirred at 60° C. for 12 h. The reaction mixture was filtered and concentrated in vacuo. The residue was purified by prep-HPLC (column: Waters Xbridge 150*25 mm*5 μm; mobile phase: [water (10 mM ammonium bicarbonate)-acetonitrile]; (B %: 20%-50%, 10 min) and repurified by prep-HPLC (column: Phenomenex Luna C18 150*25 mm*10 μm; mobile phase: [water (0.225% formic acid)-acetonitrile]; (B %: 2%-32%, 10 min) to give 8-chloro-2-(1-(((3S,4R)-3-fluoro-1-methylpiperidin-4-yl)methyl)-1H-pyrazol-4-yl)-7-((2-methyl-1H-benzo[d]imidazol-6-yl)oxy) quinoxaline (4.1 mg, 7.84 μmol, 6.4%) as an off-white solid and 8-chloro-2-(1-(((3R,4S)-3-fluoro-1-methylpiperidin-4-yl)methyl)-1H-pyrazol-4-yl)-7-((2-methyl-1H-benzo[d]imidazol-6-yl)oxy)quinoxaline (19.9 mg, 39.1 μmol, 32%) as an off-white solid.

$^1$H NMR (400 MHz, DMSO-$d_6$) δ 9.31 (s, 1H), 8.73 (s, 1H), 8.40 (s, 1H), 8.25 (s, 2H), 7.96 (d, J=9.2 Hz, 1H), 7.51 (d, J=8.4 Hz, 1H), 7.32 (d, J=9.2 Hz, 1H), 7.21 (s, 1H), 6.94 (dd, J=2.4, 8.8 Hz, 1H), 4.73-4.44 (m, 2H), 4.34 (br dd, J=7.6, 13.6 Hz, 1H), 4.22-4.17 (m, 1H), 3.03 (br.d, J=11.2 Hz, 1H), 2.79 (br.d, J=11.2 Hz, 1H), 2.49-2.48 (m, 3H), 2.15 (s, 3H), 2.08-1.95 (m, 1H), 1.90 (br.t, J=10.8 Hz, 1H), 1.70-1.51 (m, 1H), 1.46-1:28 (m, 1H); m/z ES+ $[M+H]^+$ 506.1.

$^1$H NMR (400 MHz, DMSO-$d_6$) δ 9.33 (s, 1H), 8.73 (s, 1H), 8.40 (s, 1H), 8.20 (s, 2H), 7.97 (d, J=9.2 Hz, 1H), 7.52 (d, J=8.8 Hz, 1H), 7.33 (d, J=9.2 Hz, 1H), 7.22 (d, J=2.0 Hz, 1H), 6.95 (dd, J=2.4, 8.8 Hz, 1H), 4.59-4.25 (m, 4H), 3.13-3.06 (m, 1H), 2.66 (br.d, J=11.6 Hz, 1H), 2.50 (br.s, 3H), 2.22-2.19 (m, 3H), 2-1.93 (m, 1H), 1.89-1.79 (m, 1H), 1.59-1.49 (m, 1H), 1.39-1.24 (m, 1H); m/z ES+ $[M+H]^+$ 506.1.

Example 128. Synthesis of 4-((4-(8-Chloro-7-((2-methyl-1H-benzo[d]imidazol-6-yl)oxy)quinoxalin-2-yl)-1H-pyrazol-1-yl)methyl)cyclohexan-1-ol

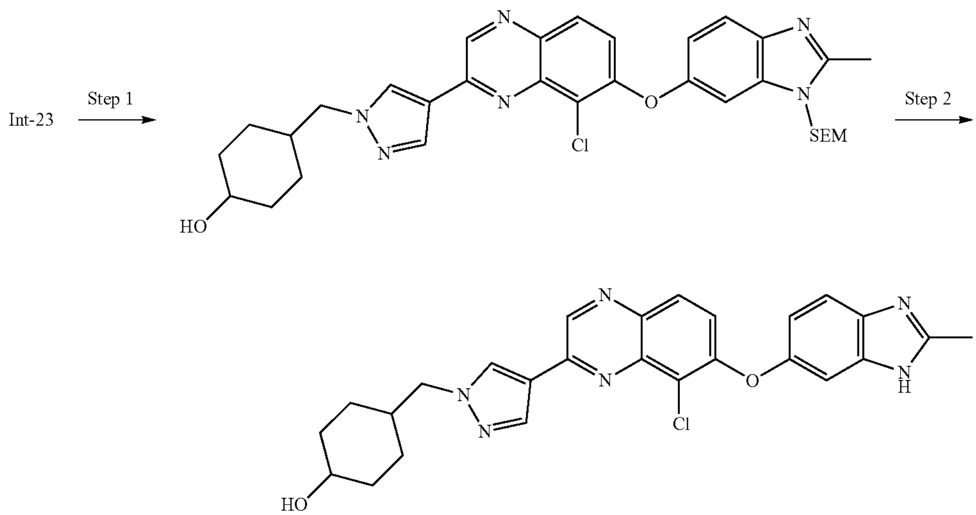

Step 1. 4-[[4-[8-Chloro-7-[2-methyl-3-(2-trimethylsilylethoxymethyl)benzimidazol-5-yl]oxy-quinoxalin-2-yl]pyrazol-1-yl]methyl]cyclohexanol To a solution of 4-[[4-[8-chloro-7-[2-methyl-3-(2-trimethylsilylethoxymethyl)benzimidazol-5-yl]oxy-quinoxalin-2-yl]pyrazol-1-yl]methyl]cyclohexanone (150 mg, 243 μmol) in methanol (2 mL) was added sodium cyanoborohydride (37.0 mg, 589 μmol) and acetic acid (42.0 mg, 699 μmol). The mixture was stirred at 25° C. for 1 h. On completion, the mixture was quenched with sat. sodium bicarbonate (1 mL) and extracted with ethyl acetate (3 mL×3). The combined organic phase was dried over anhydrous sodium sulfate, filtered and concentrated to give 4-[[4-[8-chloro-7-[2-methyl-3-(2-trimethylsilylethoxymethyl)benzimidazol-5-yl]oxy-quinoxalin-2-yl]pyrazol-1-yl]methyl]cyclohexanol (150 mg, crude) as a yellow solid. $^{1}$H NMR (400 MHz, DMSO-$d_6$) δ 9.31 (d, J=4.0 Hz, 1H), 8.69-8.62 (m, 1H), 8.36 (s, 1H), 7.99-7.92 (m, 1H), 7.59 (d, J=8.8 Hz, 1H), 7.45-7.39 (m, 1H), 7.31-7.27 (m, 1H), 7.03-6.96 (m, 1H), 5.54 (s, 2H), 3.55 (br.t, J=8.0 Hz, 1H), 3.51-3.44 (m, 2H), 3.40-3.37 (m, 2H), 2.57-2.55 (m, 3H), 1.74-1.64 (m, 3H), 1.64-1.51 (m, 4H), 1.46-1.38 (m, 2H), 0.82-0.74 (m, 2H); m/z ES+ $[M+H]^+$ 619.2.

Step 2. 4-((4-(8-Chloro-7-((2-methyl-1H-benzo[d]imidazol-6-yl)oxy)quinoxalin-2-yl)-1H-pyrazol-1-yl)methyl)cyclohexan-1-ol A solution of 4-[[4-[8-chloro-7-[2-methyl-3-(2-trimethylsilylethoxymethyl)benzimidazol-5-yl]oxy-quinoxalin-2-yl]pyrazol-1-yl]methyl]cyclohexanol (90.0 mg, 145 μmol) in trifluoroacetic acid (1 mL) was stirred at 25° C. for 1.5 h. On completion, the mixture was concentrated under reduced pressure. The residue was purified by prep-HPLC (column: Phenomenex Gemini-NX C18 75*30 mm*3 μm; mobile phase: [water (10 mM ammonium bicarbonate)-acetonitrile]; (B %: 16%-46%, 8 min) to give 4-((4-(8-chloro-7-((2-methyl-1H-benzo[d]imidazol-6-yl)oxy)quinoxalin-2-yl)-1H-pyrazol-1-yl)methyl)cyclohexan-1-ol (18.5 mg, 37.9 μmol, 26%) as a white solid. $^{1}$H NMR (400 MHz, DMSO-$d_6$) δ 9.31 (s, 1H), 8.67 (s, 1H), 8.36 (s, 1H), 7.97 (d, J=9.2 Hz, 1H), 7.55 (d, J=8.8 Hz, 1H), 7.34 (d, J=9.2 Hz, 1H), 7.25 (d, J=2.0 Hz, 1H), 7.01-6.97 (m, 1H), 4.51 (br.s, 1H), 4.08 (d, J=7.2 Hz, 2H), 3.54-3.45 (m, 1H), 2.53 (s, 3H), 1.83 (br.d, J=10.0 Hz, 3H), 1.63-1.48 (m, 2H), 1.16-0.99 (m, 4H); m/z ES+ $[M+H]^+$ 489.1.

Example 129. Synthesis of 4-((4-(8-chloro-7-((2-methyl-1H-benzo[d]imidazol-6-yl)oxy)quinoxalin-2-yl)-1H-pyrazol-1-yl)methyl)cyclohexanone

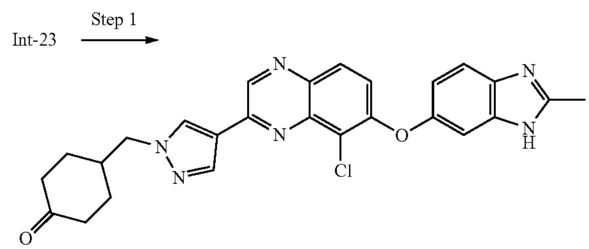

Step 1. 4-((4-(8-Chloro-7-((2-methyl-1H-benzo[d]imidazol-6-yl)oxy)quinoxalin-2-yl)-1H-pyrazol-1-yl)methyl)cyclohexanone A solution of 4-[[4-[8-chloro-7-[2-methyl-3-(2-trimethylsilylethoxymethyl)benzimidazol-5-yl]oxy-quinoxalin-2-yl]pyrazol-1-yl]methyl]cyclohexanone (60 mg, 97.2 μmol) in trifluoroacetic acid (2 mL) was stirred at 25° C. for 2 h. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 15%-45%, 7 min) to give 4-((4-(8-chloro-7-((2-methyl-1H-benzo[d]imidazol-6-yl)oxy)quinoxalin-2-yl)-1H-pyrazol-1-yl)methyl)cyclohexanone (22.6 mg, 46.4 μmol, 48%) as an off-white solid. $^{1}$H NMR (400 MHz, DMSO-$d_6$): δ=9.31 (s, 1H), 8.71 (s, 1H), 8.39 (s, 1H), 7.96 (d, J=9.2 Hz, 1H), 7.55 (d, J=8.8 Hz, 1H), 7.34 (d, J=9.2 Hz, 1H), 7.25 (d, J=2.4 Hz, 1H), 7.04-6.95 (m, 1H), 4.28-4.20 (m, 2H), 2.55-2.52 (m, 3H), 2.45-2.34 (m, 3H), 2.23 (br d, J=14.8 Hz, 2H), 1.93-1.82 (m, 2H), 1.55-1.41 (m, 2H); m/z ES+ $[M+H]^+$ 487.1.

Example 130. Synthesis of 3-((4-(8-chloro-7-((2-methyl-1H-benzo[d]imidazol-6-yl)oxy)quinoxalin-2-yl)-1H-pyrazol-1-yl)methyl)cyclobutanol

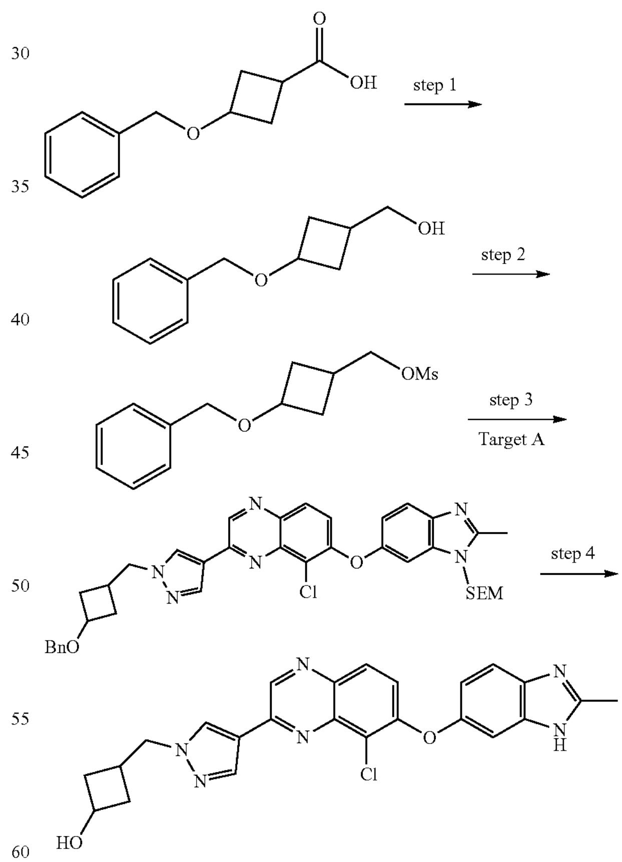

Step 1. (3-(Benzyloxy)cyclobutyl)methanol

A solution of lithium aluminum hydride (736 mg, 19.4 mmol) in anhydrous tetrahydrofuran (10 mL) was degassed and purged with nitrogen for 3 times, and then 3-benzyloxycyclobutanecarboxylic acid (1 g, 4.85 mmol) in anhydrous tetrahydrofuran (5 mL) was added at 0° C. The mixture was stirred at 25° C. for 16 h under nitrogen atmosphere. On completion, the reaction mixture was quenched by addition water (1 mL), 15% sodium hydroxide (1 mL) and water (3 mL) at 0° C. The mixture was filtered. The filtrate was dried over anhydrous sodium sulfate, filtrated and concentrated in vacuo to give (3-(benzyloxy)cyclobutyl) methanol (900 mg, 4.68 mmol, 96%) as a yellow oil. $^1$H NMR (400 MHz, $CDCl_3$): δ=7.31-7.18 (m, 5H), 4.38-4.32 (m, 2H), 3.90-3.80 (m, 1H), 3.54-3.52 (m, 2H), 2.30-2.27 (m, 2H), 2.12-2.08 (m, 1H), 1.71-1.62 (m, 2H).

Step 2. (3-(Benzyloxy)cyclobutyl)methyl methanesulfonate

To a solution of (3-benzyloxycyclobutyl)methanol (500 mg, 2.60 mmol) in dichloromethane (5 mL) was added triethylamine (790 mg, 7.80 mmol) and methanesulfonyl chloride (447 mg, 3.90 mmol) at 0° C. The mixture was stirred at 0° C. for 1 h. On completion, the reaction mixture was quenched by addition water (3 mL) and extracted with dichloromethane (3 mL×3). The combined organic layers were washed with brine (3 mL×3), dried over anhydrous sodium sulfate, filtered and concentrated in vacuo to give (3-benzyloxycyclobutyl)methyl methanesulfonate (600 mg, 2.22 mmol, 85%) as a yellow oil. $^1$H NMR (400 MHz, $CDCl_3$): δ=7.26-7.19 (m, 5H), 4.34 (s, 2H), 4.13-4.09 (m, 2H), 3.89 (t, J=7.2 Hz, 1H), 2.92 (s, 3H), 2.41-2.29 (m, 2H), 2.20-2.13 (m, 1H), 1.78-1.68 (m, 2H).

Step 3. 2-(1-((3-(Benzyloxy)cyclobutyl)methyl)-1H-pyrazol-4-yl)-8-chloro-7-((2-methyl-1-((2-(trimethylsilyl)ethoxy)methyl)-1H-benzo[d]imidazol-6-yl)oxy)quinoxaline To a solution of (3-benzyloxycyclobutyl)methyl methanesulfonate (320 mg, 1.18 mmol) in N,N-dimethylformamide (5 mL) was added cesium carbonate (643 mg, 1.97 mmol), potassium iodide (164 mg, 986 μmol) and 2-[[6-[5-chloro-3-(1H-pyrazol-4-yl)quinoxalin-6-yl]oxy-2-methyl-benzimidazol-1-yl]methoxy]ethyl-trimethyl-silane (500 mg, 986 μmol). The mixture was stirred at 80° C. for 16 h. On completion, the reaction mixture was diluted with water (3 mL) and extracted with ethyl acetate (3 mL×3). The combined organic layers were washed with brine (3 mL×3), dried over anhydrous sodium sulfate, filtered and concentrated in vacuo to give 2-(1-((3-(benzyloxy)cyclobutyl)methyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (780 mg, crude) as a yellow oil. m/z ES+ [M+H]$^+$ 681.2.

Step 4. 3-((4-(8-Chloro-7-((2-methyl-1H-benzo[d]imidazol-6-yl)oxy)quinoxalin-2-yl)-1H-pyrazol-1-yl)methyl)cyclobutanol To a mixture of 2-(1-((3-(benzyloxy)cyclobutyl)methyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (50 mg, 73.4 μmol) was added boron trichloride (1 M in toluene, 734 μL) at 0° C. The mixture was stirred at 0° C. for 2 h. On completion, the reaction was poured into water (3 mL) and adjusted to PH ~ 7 with saturated sodium bicarbonate. The mixture was extracted with ethyl acetate (3 mL×3). The combined organic layers were washed with brine (3 mL×3), dried over anhydrous sodium sulfate, filtered and concentrated in vacuo and the residue was purified by prep-HPLC (column: Phenomenex Gemini-NX C18 75*30 mm*3 μm; mobile phase: [water (0.225% formic acid)-acetonitrile]; (B %: 10%-40%, 7 min) twice to give 3-((4-(8-chloro-7-((2-methyl-1H-benzo[d]imidazol-6-yl)oxy)quinoxalin-2-yl)-1H-pyrazol-1-yl)methyl)cyclobutanol (12.8 mg, 27.5 μmol, 37%) as an off-white solid. $^1$H NMR (400 MHz, DMSO-$d_6$): δ=9.30 (s, 1H), 8.66 (s, 1H), 8.34 (s, 1H), 8.25 (s, 1H), 7.95 (d, J=9.2 Hz, 1H), 7.50 (d, J=8.8 Hz, 1H), 7.31 (d, J=9.2 Hz, 1H), 7.20 (br d, J=1.6 Hz, 1H), 6.94 (dd, J=2.4, 8.8 Hz, 1H), 4.35-4.13 (m, 3H), 3.98-3.91 (m, 1H), 2.49 (s, 3H), 2.32-2.06 (m, 3H), 2-1.60 (m, 2H); m/z ES+ [M+H]$^+$ 461.1.

Example 131. Synthesis of 3-((4-(8-chloro-7-((2-methyl-1H-benzo[d]imidazol-6-yl)oxy)quinoxalin-2-yl)-1H-pyrazol-1-yl)methyl)cyclobutanone

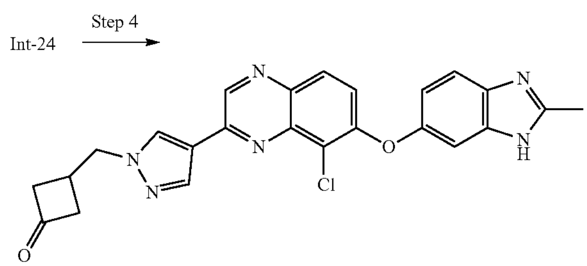

Step 1. 3-((4-(8-Chloro-7-((2-methyl-1H-benzo[d]imidazol-6-yl)oxy)quinoxalin-2-yl)-1H-pyrazol-1-yl)methyl)cyclobutanone A mixture of 3-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)cyclobutanone (45.0 mg, 76.4 μmol) in trifluoroacetic acid (0.5 mL) was stirred at 25° C. for 2 h. On completion, the reaction mixture was concentrated in vacuo and the residue was purified by prep-HPLC (column: Phenomenex Gemini-NX C18 75*30 mm*3 μm; mobile phase: [water (0.225% formic acid)-acetonitrile]; (B %: 12%-42%, 7 min) to give 3-((4-(8-chloro-7-((2-methyl-1H-benzo[d]imidazol-6-yl)oxy)quinoxalin-2-yl)-1H-pyrazol-1-yl)methyl)cyclobutanone (3.2 mg, 6.71 μmol, 8.8%) as a yellow gum. $^1$H NMR (400 MHz, DMSO-$d_6$): δ=9.31 (s, 1H), 8.78 (s, 1H), 8.39 (s, 1H), 8.32 (s, 1H), 7.96 (d, J-9.2 Hz, 1H), 7.51 (d, J=8.8 Hz, 1H), 7.32 (d, J=9.2 Hz, 1H), 7.21 (s, 1H), 6.99-6.88 (m, 1H), 4.49 (d, J=6.4 Hz, 2H), 3.17-3.12 (m, 2H), 3.03-2.97 (m, 3H), 2.50 (m, 3H); m/z ES+ [M+H]] 459.1.

Example 132. Synthesis of 8-chloro-6-methyl-7-((2-methyl-1H-benzo[d]imidazol-6-yl)oxy)-2-(1-((1-methylpiperidin-4-yl)methyl)-1H-pyrazol-4-yl)quinoxaline
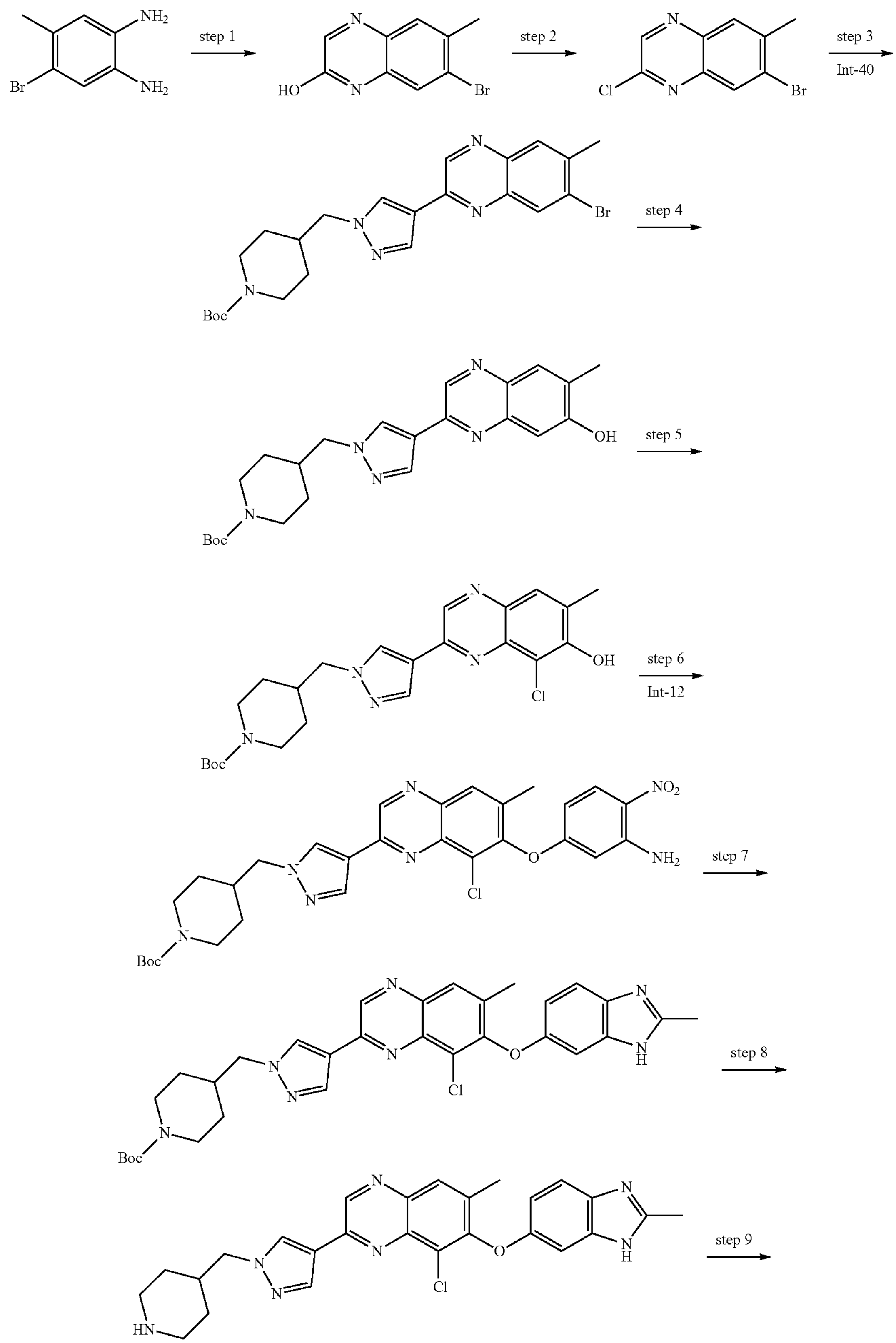

-continued

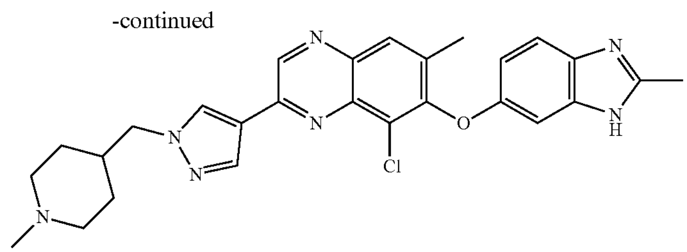

Step 1. 7-Bromo-6-methyl-quinoxalin-2-ol and 6-bromo-7-methylquinoxalin-2-ol

To a solution of 4-bromo-5-methyl-benzene-1,2-diamine (7 g, 34.8 mmol) in ethanol (100 mL) was added ethyl 2-oxoacetate (8.53 g, 41.7 mmol). The mixture was stirred at 60° C. for 16 h. The mixture was diluted with petroleum ether (200 mL) and stirred at 25° C. for 0.5 h. The solid formed was separated by filtration and dried in vacuo to give a mixture of 7-bromo-6-methyl-quinoxalin-2-ol and 6-bromo-7-methylquinoxalin-2-ol (7.0 g, crude) as a brown solid. m/z ES+ $[M+1]^+$ 239.0.

Step 2. 7-Bromo-2-chloro-6-methyl-quinoxaline

To a solution of 7-bromo-6-methyl-quinoxalin-2-ol (2 g, 8.37 mmol, mixture of regio-isomers) in toluene (15 mL) was added phosphorus oxychloride (12.8 g, 83.6 mmol) and the mixture was stirred at 100° C. for 3 h. The mixture was concentrated in vacuo. The residue was purified by column chromatography (petroleum ether/ethyl acetate-20/1 to 0/1) to give 7-bromo-2-chloro-6-methyl-quinoxaline (1 g, 3.84 mmol, 45%) as a white solid. m/z ES+ $[M+1]^+$ 258.9

Step 3. tert-Butyl 4-[[4-(7-bromo-6-methyl-quinoxalin-2-yl)pyrazol-1-yl]methyl]piperidine-1-carboxylate A solution of 7-bromo-2-chloro-6-methyl-quinoxaline (1 g, 3.88 mmol), tert-butyl 4-[[4-(4,4,5,5-tetramethyl-1,3,2-dioxaborolan-2-yl)pyrazol-1-yl]methyl]piperidine-1-carboxylate (1.52 g, 3.88 mmol), cyclopenta-2,4-dien-1-yl(diphenyl)phosphane;dichloropalladium;iron (284 mg, 388 μmol) and potassium acetate (762 mg, 7.77 mmol) in dioxane (10 mL) and water (2.5 mL) was stirred at 60° C. for 12 h under nitrogen. The reaction mixture was quenched with water (20 mL) at 25° C. and extracted with ethyl acetate (100 mL×3). The combined organic layers were washed with brine (10 mL×3), dried over anhydrous sodium sulfate, filtered and concentrated in vacuo and the residue was purified by column chromatography (petroleum ether/ethyl acetate=20/1 to 0/1) to give tert-butyl 4-[[4-(7-bromo-6-methyl-quinoxalin-2-yl)pyrazol-1-yl]methyl]piperidine-1-carboxylate (0.90 g, 1.85 mmol, 40%) as a brown solid. m/z ES+ $[M+1]^+$ 488.1.

Step 4. tert-Butyl 4-((4-(7-hydroxy-6-methylquinoxalin-2-yl)-1H-pyrazol-1-yl)methyl)piperidine-1-carboxylate A solution of tert-butyl 4-((4-(7-bromo-6-methylquinoxalin-2-yl)-1H-pyrazol-1-yl)methyl) piperidine-1-carboxylate (1.5 g, 3.08 mmol), tris(dibenzylideneacetone) dipalladium (282 mg, 308 μmol), t-Bu XPhos (130 mg, 308 μmol), potassium hydroxide (1.73 g, 30.8 mmol) in dioxane (16 mL) and water (8 mL) was stirred at 100° C. for 3 h under nitrogen atmosphere. On completion, the reaction mixture was quenched by addition water (20 mL) at 25° C. and extracted with ethyl acetate (100 mL×3). The combined organic layers were washed with brine (10 mL×3), dried over anhydrous sodium sulphate, filtered and concentrated under reduced pressure. The residue was purified by column chromatography (silica gel, petroleum ether/ethyl acetate=20/1 to 0/1) to give tert-butyl 4-((4-(7-hydroxy-6-methylquinoxalin-2-yl)-1H-pyrazol-1-yl)methyl) piperidine-1-carboxylate (1.3 g, 3.08 mmol, 99%) as a brown solid. $^1$H NMR (400 MHz, DMSO-$d_6$): δ=10.48 (d, J=30 Hz, 2H), 9.03 (d, J=29.6 Hz, 2H), 8.52 (d, J=21.6 Hz, 2H), 8.22 (d, J=15.2 Hz, 1H), 7.72 (d, J=5.6 Hz, 1H), 7.23 (d, J=16.8 Hz, 1H), 4.09 (d, J=7.2 Hz, 2H), 3.92 (d, J=10.4 Hz, 2H), 3.17 (d, J=5.2 Hz, 1H), 2.67 (s, 2H), 2.35 (d, J=5.2 Hz, 3H), 2.05 (s, 1H), 1.49 (d, J=11.6 Hz, 2H), 1.37 (s, 9H), 1.16-1.04 (m, 2H).

Step 5. tert-Butyl 4-((4-(8-chloro-7-hydroxy-6-methylquinoxalin-2-yl)-1H-pyrazol-1-yl)methyl) piperidine-1-carboxylate To a solution of tert-butyl 4-((4-(7-hydroxy-6-methylquinoxalin-2-yl)-1H-pyrazol-1-yl)methyl) piperidine-1-carboxylate (1.1 g, 2.60 mmol) in acetonitrile (10 mL) was added N-chlorosuccinimide (312 mg, 2.34 mmol). The mixture was stirred at 80° C. for 12 h. On completion, the reaction mixture was quenched by addition water (20 mL) at 25° C. and extracted with ethyl acetate (100 mL×3). The combined organic layers were washed with brine (10 mL×3), dried over anhydrous sodium sulphate, filtered and concentrated in vacuo and the residue was purified by reversed-phase HPLC (0.1% formic acid condition) and SFC (column; Daicel Chiralcel OJ (250 mm*30 mm, 10 μm); mobile phase: [0.1% ammonium hydroxide/methanol]; (B %: 70%-70%, 5.5 min; total run 50 min) to give tert-butyl 4-((4-(8-chloro-7-hydroxy-6-methylquinoxalin-2-yl)-1H-pyrazol-1-yl)methyl) piperidine-1-carboxylate (0.3 g, 0.66 mmol, 25%) as a yellow solid. $^1$H NMR (400 MHz, DMSO-$d_6$): δ=10.55-9.92 (m, 1H), 9.11 (s, 1H), 8.58 (s, 1H), 8.29 (s, 1H), 7.76 (s, 1H), 4.13 (d, J=7.2 Hz, 2H), 3.93 (d, J=11.6 Hz, 2H), 2.75-2.61 (m, 2H), 2.42 (s, 3H), 2.12-1.99 (m, 1H), 1.50 (d, J=12.0 Hz, 2H), 1.38 (s, 9H), 1.17-1.04 (m, 2H); m/z ES+ $[M+H]^+$ 458.2.

Step 6. tert-Butyl 4-((4-(7-(3-amino-4-nitrophenoxy)-8-chloro-6-methylquinoxalin-2-yl)-1H-pyrazol-1-yl)methyl) piperidine-1-carboxylate A solution of tert-butyl 4-((4-(8-chloro-7-hydroxy-6-methylquinoxalin-2-yl)-1H-pyrazol-1-yl)methyl) piperidine-1-carboxylate (300 mg, 655 μmol), tert-butyl N-tert-butoxycarbonyl-N-(5-fluoro-2-nitro-phenyl) carbamate (350 mg, 982 μmol), potassium carbonate (181 mg, 1.31 mmol)

and potassium iodide (10.8 mg, 65.5 μmol) in N,N-dimethylformamide (5 mL) was stirred at 100° C. for 16 h. On completion, the reaction mixture was quenched by addition water (20 mL) at 25° C. and extracted with ethyl acetate (100 mL×3). The combined organic layers were washed with brine (10 mL×3), dried over anhydrous sodium sulphate, filtrated and concentrated and the residue was purified by reversed-phase HPLC (0.1% formic acid condition) to give tert-butyl4-((4-(7-(3-amino-4-nitrophenoxy)-8-chloro-6-methylquinoxalin-2-yl)-1H-pyrazol-1-yl)methyl) piperidine-1-carboxylate (0.2 g, 0.34 mmol, 51%) as a yellow solid. m/z ES+ $[M+H]^+$ 594.3.

Step 7. tert-Butyl 4-((4-(8-chloro-6-methyl-7-((2-methyl-1H-benzo[d]imidazol-6-yl)oxy)quinoxalin-2-yl)-1H-pyrazol-1-yl)methyl) piperidine-1-carboxylate To a solution of tert-butyl 4-((4-(7-(3-amino-4-nitrophenoxy)-8-chloro-6-methylquinoxalin-2-yl)-1H-pyrazol-1-yl) methyl) piperidine-1-carboxylate (0.17 g, 286 μmol) in ethanol (10 mL) and water (3 mL) was added ammonium chloride (153 mg, 2.86 mmol) and iron power (79.9 mg, 1.43 mmol). The mixture was stirred at 60° C. for 12 h. On completion, the mixture was filtered and the filtrate was concentrated in vacuo and the residue was purified by reversed-phase HPLC (0.1% formic acid condition) to give tert-butyl 4-((4-(8-chloro-6-methyl-7-((2-methyl-1H-benzo[d]imidazol-6-yl)oxy)quinoxalin-2-yl)-1H-pyrazol-1-y]) methyl) piperidine-1-carboxylate (0.13 g, 0.22 mmol, 77%) as a green solid. m/z ES+ $[M+H]^+$ 588.2.

zol-6-yl)oxy)-2-(1-(piperidin-4-ylmethyl)-1H-pyrazol-4-yl) quinoxaline (0.1 g, TFA salt, crude) as a yellow solid. m/z ES+ $[M+H]^+$ 488.1.

Step 9. 8-Chloro-6-methyl-7-((2-methyl-1H-benzo[d]imidazol-6-yl)oxy)-2-(1-((1-methylpiperidin-4-yl)methyl)-1H-pyrazol-4-yl)quinoxaline A solution of 8-chloro-6-methyl-7-[(2-methyl-3H-benzimidazol-5-yl)oxy]-2-[1-(4-piperidylmethyl)pyrazol-4-yl] quinoxaline (0.09 g, 149 μmol, TFA salt), paraformaldehyde (89.7 mg, 2.99 mmol) and formic acid (143 mg, 2.99 mmol) in N,N-dimethylformamide (3 mL) was stirred at 60° C. for 16 h. On completion, the mixture was filtered and the filtrate was concentrated in vacuo and the residue was purified by prep-HPLC (column: Phenomenex Gemini-NX C18 75*30 mm*3 μm; mobile phase: [water (0.225% formic acid)-acetonitrile]; (B %: 5%-35%, 7 min) to give 8-chloro-6-methyl-7-((2-methyl-1H-benzo[d]imidazol-6-yl)oxy)-2-(1-((1-methylpiperidin-4-yl)methyl)-1H-pyrazol-4-yl) quinoxaline (16 mg, 31.8 μmol, 21%) as a white solid. $^1H$ NMR (400 MHz, DMSO-$d_6$): δ=9.35 (s, 1H), 8.67 (s, 1H), 8.35 (s, 1H), 8.23 (s, 1H), 8.03 (s, 1H), 7.51-7.36 (m, 1H), 6.85-6.71 (m, 2H), 4.14 (d, J=7.2 Hz, 2H), 2.90 (d, J=10.8 Hz, 2H), 2.43 (s, 3H), 2.33 (s, 3H), 2.27 (s, 3H), 2.08 (t, J=10.8 Hz, 2H), 1.93-1.86 (m, 1H), 1.54 (d, J=11.6 Hz, 2H), 1.36-1.26 (m, 2H); m/z ES+ $[M+H]^+$ 502.1.

Example 133. Synthesis of 4-((1r,3r)-3-(4-(8-chloro-7-((2-methyl-1H-benzo[d]imidazol-6-yl)oxy) quinoxalin-2-yl)-1H-pyrazol-1-yl)cyclobutyl) morpholine and 4-((1s,3s)-3-(4-(8-chloro-7-((2-methyl-1H-benzo[d]imidazol-6-yl)oxy)quinoxalin-2-yl)-1H-pyrazol-1-yl)cyclobutyl)morpholine Int-4

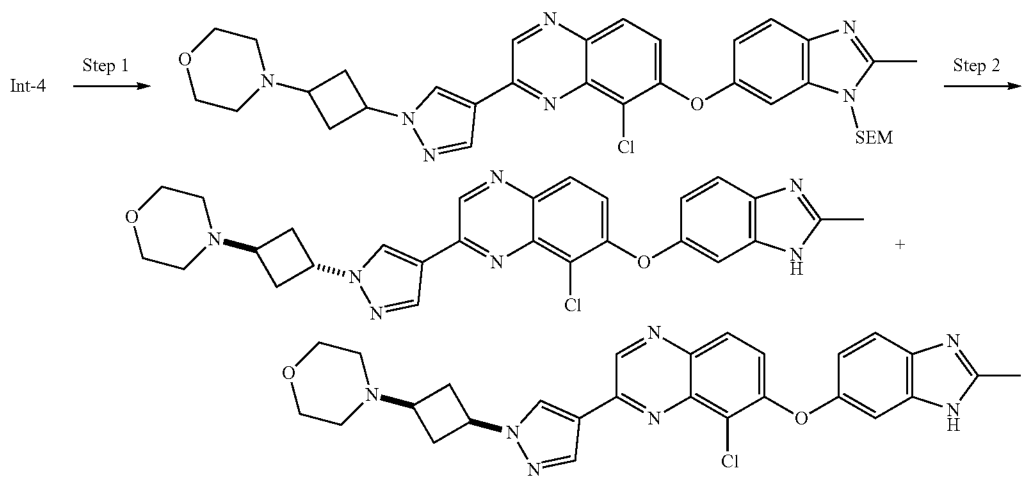

Step 8. 8-Chloro-6-methyl-7-((2-methyl-1H-benzo[d]imidazol-6-yl)oxy)-2-(1-(piperidin-4-ylmethyl)-1H-pyrazol-4-yl)quinoxaline To a solution of tert-butyl 4-[[4-[8-chloro-6-methyl-7-[(2-methyl-3H-benzimidazol-5-yl)oxy]quinoxalin-2-yl]pyrazol-1-yl]methyl]piperidine-1-carboxylate (0.1 g, 170 μmol) in dichloromethane (10 mL) was added trifluoroacetic acid (3.08 g, 27.0 mmol). The mixture was stirred at 25° C. for 1 h. On completion, the mixture was concentrated in vacuo to give 8-chloro-6-methyl-7-((2-methyl-1H-benzo[d]imida-

Step 1. 4-(3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)cyclobutyl) morpholine To a solution of 3-[4-[8-chloro-7-[2-methyl-3-(2-trimethylsilylethoxymethyl)benzimidazol-5-yl]oxy-quinoxalin-2-yl]pyrazol-1-yl]cyclobutanone (65 mg, 110 μmol) and morpholine (30 mg, 340 μmol, 30 L) in dichloromethane (1 mL) was added acetic acid (9.5 mg, 160 μmol, 9 μL) and 4 Å molecular sieve (100 mg). Then the reaction was cooled to 0° C. and sodium cyanoborohydride (14 mg, 230 μmol) was added. The mixture was stirred at 25° C. for 2 h. On completion, the reaction mixture was filtered. The filtrate was diluted with water (10 mL) and extracted with dichloromethane (50 mL×2). The combined organic layers were washed with saturated sodium bicarbonate (10 mL×2), dried over anhydrous sodium sulfate, filtered and concentrated under reduced pressure. The residue was purified by prep-TLC (silica gel, DCM:MeOH=20:1) to give 2-[[6-[5-chloro-3-[1-(3-morpholinocyclobutyl)pyrazol-4-yl]quinoxalin-6-yl]oxy-2-methyl-benzimidazol-1-yl]methoxy]ethyl-trimethyl-silane (30 mg, 46.4 μmol, 41%) as a white solid. m/z ES+ $[M+H]^+$ 646.3.

Step 2. 4-((1r,3r)-3-(4-(8-Chloro-7-((2-methyl-1H-benzo[d]imidazol-6-yl)oxy)quinoxalin-2-yl)-1H-pyrazol-1-yl)cyclobutyl) morpholine and 4-((1s,3s)-3-(4-(8-Chloro-7-((2-methyl-1H-benzo[d]imidazol-6-yl)oxy)quinoxalin-2-yl)-1H-pyrazol-1-yl) cyclobutyl)morpholine A solution of 2-[[6-[5-chloro-3-[1-(3-morpholinocyclobutyl)pyrazol-4-yl]quinoxalin-6-yl]oxy-2-methyl-benzimidazol-1-yl]methoxy]ethyl-trimethyl-silane (30 mg, 46 μmol) in trifluoroacetic acid (0.3 mL) was stirred at 25° C. for 0.5 h. On completion, the reaction mixture was concentrated under reduced pressure. The residue was purified by prep-HPLC (formic acid condition; column: Phenomenex Luna C18 150×25 mm× 10 μm; mobile phase: [water (0.225% formic acid)-acetonitrile]; (B %: 30%-33%, 10 min) to give 4-((1r,3r)-3-(4-(8-chloro-7-((2-methyl-1H-benzo[d]imidazol-6-yl)oxy)quinoxalin-2-yl)-1H-pyrazol-1-yl)cyclobutyl) morpholine (7.6 mg, 14.7 μmol, 32%) as a white solid and 4-((1s,3s)-3-(4-(8-chloro-7-((2-methyl-1H-benzo[d]imidazol-6-yl)oxy)quinoxalin-2-yl)-1H-pyrazol-1-yl)cyclobutyl) morpholine (1.9 mg, 3.7 μmol, 8.0%) as a white solid.

$^1$HNMR (400 MHz, DMSO-$d_6$): δ=12.78-11.72 (m, 1H), 9.33 (s, 1H), 8.80 (s, 1H), 8.38 (s, 1H), 7.94 (s, 1H), 7.51 (d, J=8.4 Hz, 1H), 7.32 (d, J=9.2 Hz, 1H), 7.21 (d, J=2.0 Hz, 1H), 6.94 (dd, J=2.0, 8.4 Hz, 1H), 4.83-4.70 (m, 1H), 3.63 (s, 4H), 2.80-2.55 (m, 4H), 2.49-2.49 (m, 3H), 2.41 (s, 5H); m/z ES+ $[M+H]^+$ 516.1.

$^1$HNMR (400 MHz, DMSO-$d_6$) δ=12.76-11.80 (m, 1H), 9.33 (s, 1H), 8.80 (s, 1H), 8.39 (s, 1H), 7.96 (d, J=9.6 Hz, 1H), 7.51 (d, J=8.8 Hz, 1H), 7.32 (d, J=9.2 Hz, 1H), 7.21 (d, J=2.0 Hz, 1H), 6.94 (dd, J=2.4, 8.4 Hz, 1H), 4.84-4.71 (m, 1H), 3.64 (s, 4H), 2.72-2.60 (m, 4H), 2.49-2.48 (m, 3H), 2.46-2.36 (m, 4H), 2.33 (s, 1H); m/z ES+ $[M+H]^+$ 516.1.

Example 134. Synthesis of 8-chloro-2-(1-(((1s,4s)-4-methoxycyclohexyl)methyl)-1H-pyrazol-4-yl)-7-((2-methyl-1H-benzo[d]imidazol-6-yl)oxy)quinoxaline and 8-chloro-2-(1-(((1r,4r)-4-methoxycyclohexyl)methyl)-1H-pyrazol-4-yl)-7-((2-methyl-1H-benzo[d]imidazol-6-yl)oxy)quinoxaline

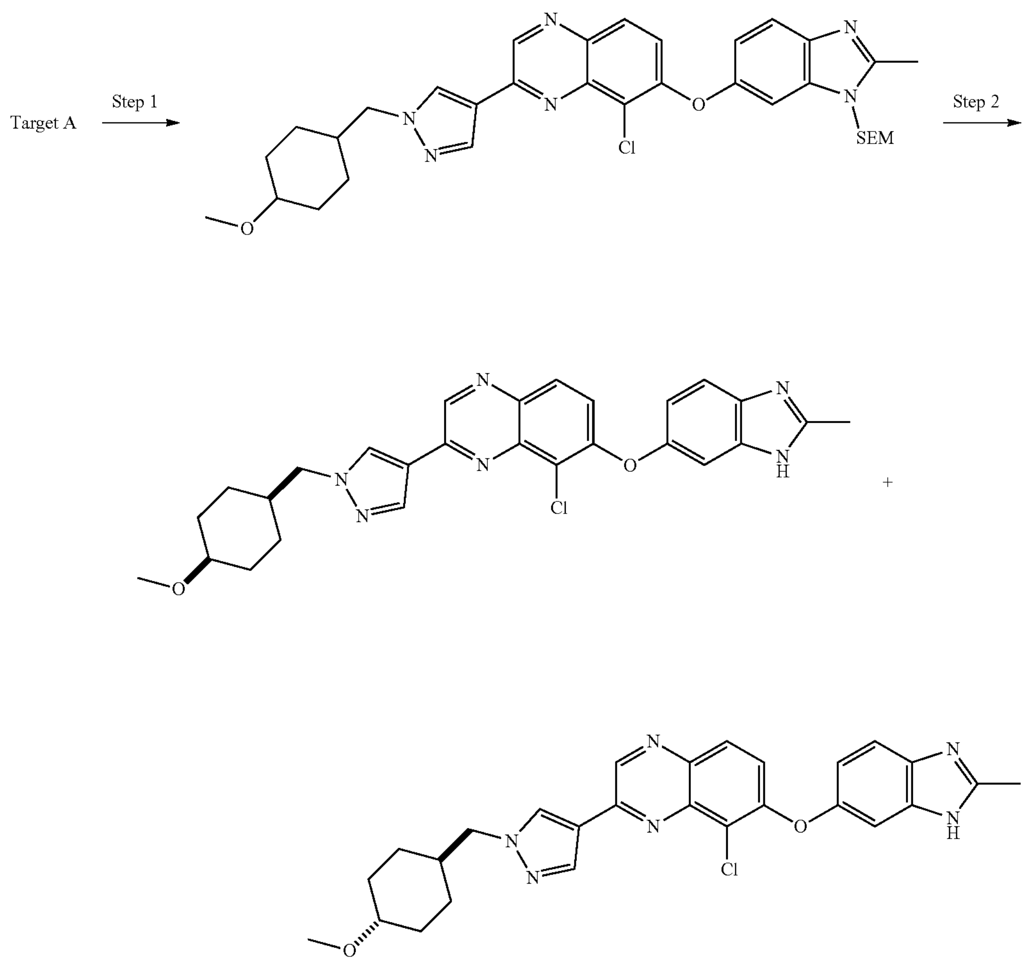

Step 1. 8-Chloro-2-(1-((4-methoxycyclohexyl)methyl)-1H-pyrazol-4-yl)-7-((2-methyl-1-((2-(trimethylsilyl)ethoxy)methyl)-1H-benzo[d]imidazol-6-yl)oxy)quinoxaline To a mixture of 1-(bromomethyl)-4-methoxy-cyclohexane (45 mg, 217 μmol) and 2-[[6-[5-chloro-3-(1H-pyrazol-4-yl)quinoxalin-6-yl]oxy-2-methyl-benzimidazol-1-yl]methoxy]ethyl-trimethyl-silane (100 mg, 197 μmol) in N,N-dimethylformamide (2 mL) was added potassium carbonate (54.5 mg, 394 μmol), then the mixture was stirred at 80° C. for 12 h. On completion, the mixture was quenched with water (10 mL) and extracted with ethyl acetate (15 mL×3). The combined organic layers were dried over anhydrous sodium sulfate, filtered and concentrated to give 2-[[6-[5-chloro-3-[1-[(4-methoxycyclohexyl)methyl]pyrazol-4-yl]quinoxalin-6-yl]oxy-2-methyl-benzimidazol-1-yl]methoxy]ethyl-trimethyl-silane (150 mg, crude) as a yellow solid. m/z ES+ $[M+H]^+$ 633.2.

Step 2. 8-Chloro-2-(1-(((1s,4s)-4-methoxycyclohexyl)methyl)-1H-pyrazol-4-yl)-7-((2-methyl-1H-benzo[d]imidazol-6-yl)oxy)quinoxaline and 8-Chloro-2-(1-(((1r,4r)-4-methoxycyclohexyl)methyl)-1H-pyrazol-4-yl)-7-((2-methyl-1H-benzo[d]imidazol-6-yl)oxy)quinoxaline A solution of 2-[[6-[5-chloro-3-[1-[(4-methoxycyclohexyl)methyl]pyrazol-4-yl]quinoxalin-6-yl]oxy-2-methyl-benzimidazol-1-yl]methoxy]ethyl-trimethyl-silane (140 mg, 221 μmol) in trifluoroacetic acid (2 mL) was stirred at 20° C. for 1 h. On completion, the mixture was concentrated under reduced pressure. The residue was purified by prep-HPLC (column: Unisil 3-100 C18 Ultra 150*50 mm*3 μm; mobile phase: [water (0.225% formic acid)-acetonitrile]; (B %: 20%-50%, 10 min) to give 8-chloro-2-(1-(((1s,4s)-4-methoxycyclohexyl)methyl)-1H-pyrazol-4-yl)-7-((2-methyl-1H-benzo[d]imidazol-6-yl)oxy)quinoxaline (29.5 mg, 58.6 μmol, 27%) as a yellow solid and 8-chloro-2-(1-(((1r,4r)-4-methoxycyclohexyl)methyl)-1H-pyrazol-4-yl)-7-((2-methyl-1H-benzo[d]imidazol-6-yl)oxy)quinoxaline (57 mg, 113 μmol, 51%) as an off-white solid.

$^1$H NMR (400 MHz, DMSO-$d_6$): δ=9.35 (s, 1H), 8.69 (s, 1H), 8.36 (s, 1H), 8.02 (d, J=9.2 Hz, 1H), 7.72 (d, J=8.8 Hz, 1H), 7.45-7.38 (m, 2H), 7.19 (br d, J=9.2 Hz, 1H), 4.10 (d, J=7.2 Hz, 2H), 3.45 (d, J=2.8 Hz, 1H), 3.22 (s, 3H), 2.68 (s, 3H), 2.04-1.96 (m, 2H), 1.88-1.81 (m, 1H), 1.65-1.58 (m, 2H), 1.11-1.02 (m, 4H); m/z ES+ $[M+H]^+$ 503.1.

$^1$H NMR (400 MHz, DMSO-$d_6$): δ=9.34 (s, 1H), 8.70 (s, 1H), 8.36 (s, 1H), 8.01 (d, J=9.2 Hz, 1H), 7.70 (d, J=8.8 Hz, 1H), 7.45-7.36 (m, 2H), 7.21-7.14 (m, 1H), 4.11 (d, J=7.2 Hz, 2H), 3.50-3.44 (m, 1H), 3.20 (s, 3H), 2.67 (s, 3H), 2.04-1.90 (m, 1H), 1.86-1.74 (m, 2H), 1.47-1.20 (m, 6H); m/z ES+ $[M+H]^+$ 503.1.

Example 135. Synthesis of 4-((4-(8-chloro-7-((2-methyl-1H-benzo[d]imidazol-6-yl)oxy)quinoxalin-2-yl)-1H-pyrazol-1-yl)methyl)-N,N-dimethylcyclohexanamine

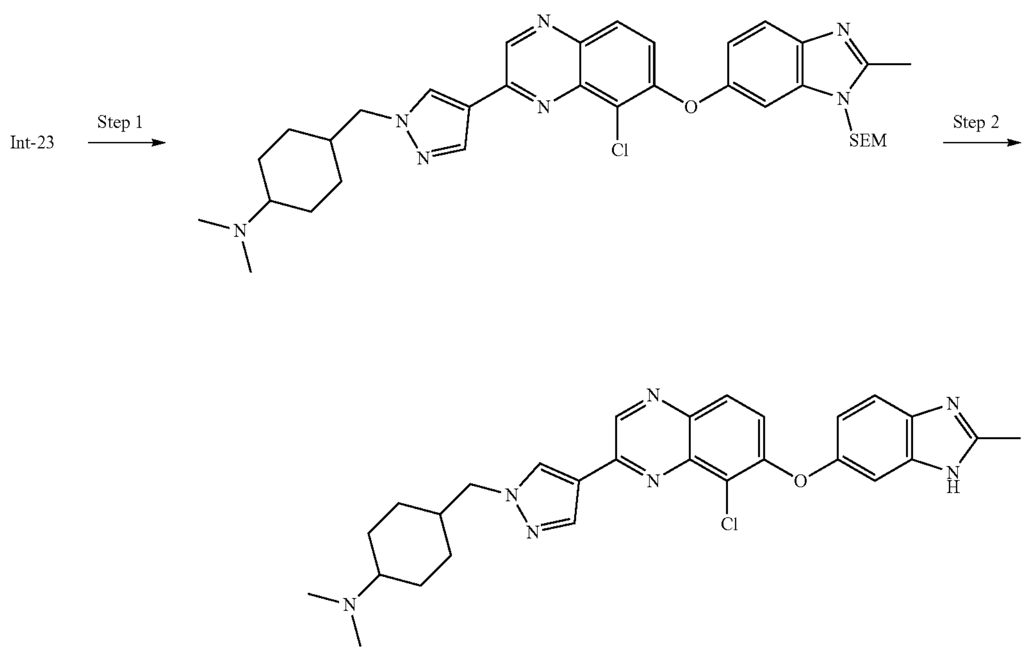

Step 1. 4-((4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-N,N-dimethylcyclohexanamine To a solution of 4-[[4-[8-chloro-7-[2-methyl-3-(2-trimethylsilylethoxymethyl)benzimidazol-5-yl]oxy-quinoxalin-2-yl]pyrazol-1-yl]methyl]cyclohexanone (100 mg, 162 μmol) in methanol (2 mL) was added N-methylmethanamine hydrochloride (75.0 mg, 920 μmol). The mixture was stirred at 25° C. for 0.2 h. Then sodium cyanoborohydride (25.0 mg, 398 μmol) was added and the mixture solution was stirred at 40° C. for 11.8 h. On completion, the mixture was quenched with 1 N hydrochloric acid solution to adjust pH ~ 7 and extracted with ethyl acetate (5 mL×3). The combined organic layers were dried over anhydrous sodium sulfate, filtered and concentrated and the residue was purified by prep-TLC (silica gel, dichloromethane:methanol=10:1) to give 4-[[4-[8-chloro-7-[2-methyl-3-(2-trimethylsilylethoxymethyl)benzimidazol-5-yl]oxy-quinoxalin-2-yl]pyrazol-1-yl]methyl]-N,N-dimethyl-cyclohexanamine (60 mg, 92.9 μmol, 57%) as a yellow solid. m/z ES+ $[M+H]^+$ 646.2.

Step 2. 4-((4-(8-Chloro-7-((2-methyl-1H-benzo[d]imidazol-6-yl)oxy)quinoxalin-2-yl)-1H-pyrazol-1-yl)methyl)-N,N-dimethylcyclohexanamine A solution of 4-[[4-[8-chloro-7-[2-methyl-3-(2-trimethylsilylethoxymethyl)benzimidazol-5-yl]oxy-quinoxalin-2-yl]pyrazol-1-yl]methyl]-N,N-dimethyl-cyclohexanamine (30 mg, 46.4 μmol) in trifluoroacetic acid (0.8 mL) was stirred at 25° C. for 1.5 h. On completion, the mixture was concentrated under reduced pressure. The residue was purified by prep-HPLC (column: Unisil 3-100 C18 Ultra 150*50 mm*3 μm; mobile phase: [water (0.225% formic acid)-acetonitrile]; (B %: 5%-35%, 10 min) to give 4-[[4-[8-chloro-7-[(2-methyl-3H-benzimidazol-5-yl)oxy]quinoxalin-2-yl]pyrazol-1-yl]methyl]-N,N-dimethyl-cyclohexanamine (9.1 mg, 17.6 μmol, 38%) as a yellow solid. $^1H$ NMR (400 MHz, DMSO-$d_6$): δ=9.31 (s, 1H), 8.70 (d, J=17.2 Hz, 1H), 8.38 (d, J=4.8 Hz, 1H), 8.18 (s, 1H), 7.95 (d, J=9.2 Hz, 1H), 7.51 (br d, J=8.8 Hz, 1H), 7.32 (d, J=9.2 Hz, 1H), 7.20 (s, 1H), 6.97-6.91 (m, 1H), 4.30-4.10 (m, 2H), 2.94-2.82 (m, 1H), 2.61 (s, 6H), 2.49 (s, 3H), 2.04-1.82 (m, 2H), 1.81-1.61 (m, 3H), 1.57-1.42 (m, 2H), 1.40-1.21 (m, 1H), 1.18-1.02 (m, 1H); m/z ES+ $[M+H]^+$ 516.1.

Example 136. Synthesis of 2-(4-(4-(8-chloro-7-((2-methyl-1H-benzo[d]imidazol-6-yl)oxy)quinoxalin-2-yl)-1H-pyrazol-1-yl) piperidin-4-yl)ethanol

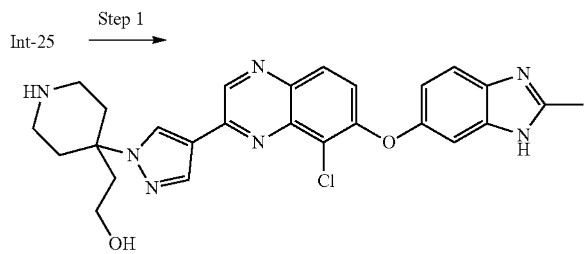

Step 1. 2-(4-(4-(8-Chloro-7-((2-methyl-1H-benzo[d]imidazol-6-yl)oxy)quinoxalin-2-yl)-1H-pyrazol-1-yl)piperidin-4-yl)ethanol To a solution of tert-butyl 4-[4-[8-chloro-7-[2-methyl-3-(2-trimethylsilylethoxymethyl)benzimidazol-5-yl]oxy-quinoxalin-2-yl]pyrazol-1-yl]-4-(2-hydroxyethyl) piperidine-1-carboxylate (90.0 mg, 123 μmol) in acetonitrile (1 mL) was added hydrochloric acid (6 M, 1 mL). The mixture was stirred at 60° C. for 3 h. On completion, the reaction mixture was concentrated in vacuo and the residue was purified by prep-HPLC (formic acid condition; column: Phenomenex Luna C18 150*25 mm*10 μm; mobile phase: [water (0.225% formic acid)-acetonitrile]; (B %: 1%-30%, 10 min) to give 2-(4-(4-(8-chloro-7-((2-methyl-1H-benzo[d]imidazol-6-yl)oxy)quinoxalin-2-yl)-1H-pyrazol-1-yl) piperidin-4-yl)ethanol (31.7 mg, 55.3 μmol, 45%, formic acid salt) as an off-white solid. $^1H$ NMR (400 MHz, DMSO-$d_6$): δ=9.38 (s, 1H), 8.99 (s, 1H), 8.43 (s, 1H), 8.20 (s, 1H), 7.97 (d, J=9.2 Hz, 1H), 7.51 (d, J=8.4 Hz, 1H), 7.32 (d, J=9.2 Hz, 1H), 7.21 (d, J=1.6 Hz, 1H), 6.94 (dd, J=2.0, 8.4 Hz, 1H), 3.31-3.15 (m, 4H), 2.88-2.72 (m, 4H), 2.49 (s, 3H), 2.27 (t, J=11.6 Hz, 2H), 2 (t, J=6.4 Hz, 2H); m/z ES+ $[M+H]^+$ 504.1.

Example 137. Synthesis of 2-(1-((1s,4s)-2-oxabicyclo[2.1.1]hexan-1-ylmethyl)-1H-pyrazol-4-yl)-8-chloro-7-((2-methyl-1H-benzo[d]imidazol-6-yl)oxy)quinoxaline

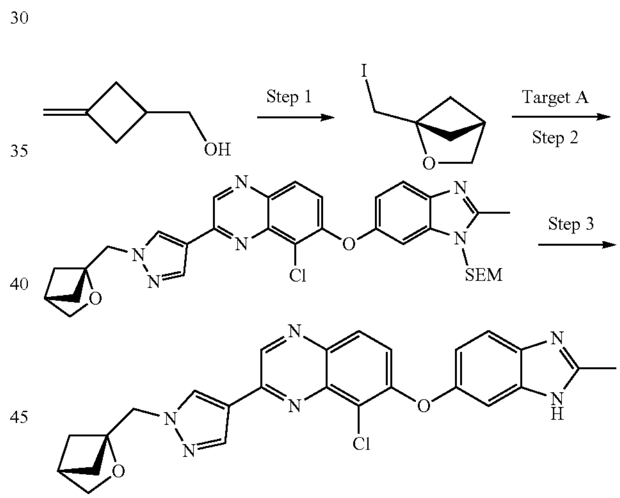

Step 1. (1s,4s)-1-(Iodomethyl)-2-oxabicyclo[2.1.1]hexane

To a solution of (3-methylenecyclobutyl) methanol (200 mg, 2.04 mmol) in methyl tert-butyl ether (2 mL) and water (1 mL) was added sodium bicarbonate (342 mg, 4.08 mmol) and iodine (1.03 g, 4.08 mmol). The mixture was stirred at 25° C. for 16 h. On completion, the mixture was quenched with sodium thiosulfate (100 mg) and extracted with ethyl acetate (30 mL×3). The organic layers were dried over sodium sulfate, filtered and concentrated under reduced pressure. The residue was purified by column chromatography (silica gel, petroleum ether/ethyl acetate=1/0 to 10/1) to give (1s,4s)-1-(iodomethyl)-2-oxabicyclo[2.1.1]hexane (70 mg, 0.31 mmol, 15%) as a yellow oil. $^1H$ NMR (400 MHz, $CDCl_3$): δ=3.85 (s, 2H), 3.49 (s, 2H), 2.87 (t, J=3.2 Hz, 1H), 1.8-1.78 (m, 2H), 1.57-1.55 (m, 2H).

Step 2. 2-(1-((1s,4s)-2-Oxabicyclo[2.1.1]hexan-1-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline To a solution of (1s,4s)-1-(iodomethyl)-2-oxabicyclo[2.1.1]hexane (53.0 mg, 236 μmol) and 8-chloro-7-((2-methyl-1-((2-(trimethylsilyl)ethoxy)methyl)-1H-benzo[d]imidazol-6-yl)oxy)-2-(1H-pyrazol-4-yl)quinoxaline (100 mg, 197 μmol) in N,N-dimethylformamide (1 mL) was added cesium carbonate (192 mg, 591 μmol). The mixture was stirred at 80° C. for 16 h. On completion, the mixture was poured into water (50 mL) and extracted with ethyl acetate (30 mL×3). The organic layers were washed by brine (30 mL×3), dried over sodium sulfate, filtered and concentrated under reduced pressure. The residue was purified by prep-TLC (silica gel, dichloromethane:methanol=10:1) to give 2-(1-((1s,4s)-2-oxabicyclo[2.1.1]hexan-1-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (110 mg, 182 μmol, 92%) as a yellow oil. m/z ES+ $[M+H]^+$ 603.2.

Step 3. 2-(1-((1s,4s)-2-Oxabicyclo[2.1.1]hexan-1-ylmethyl)-1H-pyrazol-4-yl)-8-chloro-7-((2-methyl-1H-benzo[d]imidazol-6-yl)oxy)quinoxaline A solution of 2-(1-((1s,4s)-2-oxabicyclo[2.1.1]hexan-1-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (110 mg, 182 μmol) in trifluoroacetic acid (1 mL) was stirred at 25° C. for 1 h. On completion, the mixture was concentrated under reduced pressure. The residue was purified by prep-HPLC (column: Phenomenex Luna C18 150*25 mm*10 μm; mobile phase: [water (0.225% formic acid)-acetonitrile]; (B %: 15%-45%, 10 min) to give 2-(1-((1s,4s)-2-oxabicyclo[2.1.1]hexan-1-ylmethyl)-1H-pyrazol-4-yl)-8-chloro-7-((2-methyl-1H-benzo[d]imidazol-6-yl)oxy)quinoxaline (50.1 mg, 106 μmol, 58%) as a white solid. $^1$H NMR (400 MHz, $CD_3OD$): δ=9.26-9.08 (m, 1H), 8.55 (s, 1H), 8.31 (s, 1H), 7.97 (d, J=9.2 Hz, 1H), 7.73 (d, J=9.2 Hz, 1H), 7.46 (d, J=9.2 Hz, 1H), 7.33-7.26 (m, 2H), 4.60 (s, 2H), 3.78 (s, 2H), 2.94 (t, J=3.2 Hz, 1H), 2.81 (s, 3H), 1.94-1.83 (m, 2H), 1.47 (dd, J=1.6, 4.4 Hz, 2H); m/z ES+ $[M+H]^+$ 473.1.

Example 138. Synthesis of (R)-3-((4-(8-chloro-7-((2-methyl-1H-benzo[d]imidazol-6-yl)oxy)quinoxalin-2-yl)-1H-pyrazol-1-yl)methyl)tetrahydrothiophene 1,1-dioxide and(S)-3-((4-(8-chloro-7-((2-methyl-1H-benzo[d]imidazol-6-yl)oxy)quinoxalin-2-yl)-1H-pyrazol-1-yl)methyl)tetrahydrothiophene 1,1-dioxide

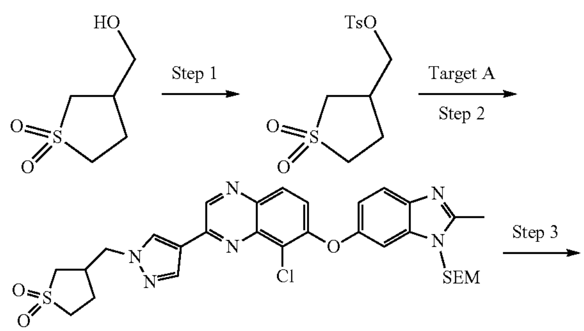

-continued

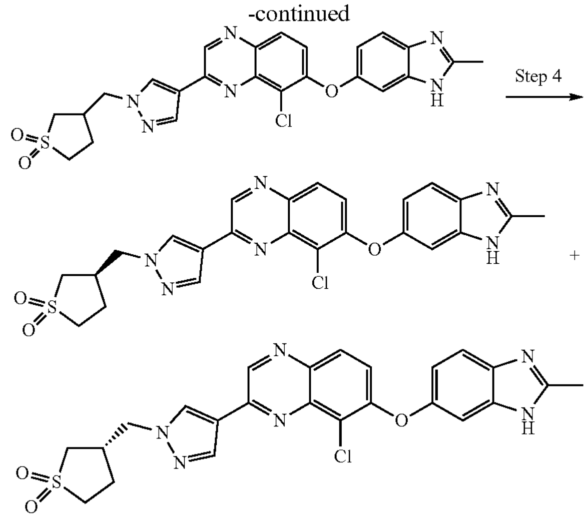

Step 1. (1,1-Dioxidotetrahydrothiophen-3-yl)methyl 4-methylbenzenesulfonate

To a solution of (1,1-dioxothiolan-3-yl) methanol (100 mg, 666 μmol) in dichloromethane (5 mL) was added 4-dimethylaminopyridine (80 mg, 655 μmol) and 4-methylbenzenesulfonyl chloride (126 mg, 661 μmol) at 0° C. Then triethylamine (138 mg, 1.37 mmol, 190 μL) was added and the mixture was stirred at 25° C. for 1 h. On completion, the mixture was quenched with water (6 mL) and then extracted with dichloromethane (8 mL×3). The combined organic layers were dried over anhydrous sodium sulfate, filtered and concentrated and the residue was purified by column chromatography (silica gel, petroleum ether/ethyl acetate=3/1 to 1/2) to give (1,1-dioxothiolan-3-yl)methyl 4-methylbenzenesulfonate (120 mg, 395 μmol, 58%) as a white solid. $^1$H NMR (400 MHz, $CDCl_3$): δ=7.79 (d, J=8.4 Hz, 2H), 7.38 (d, J=8.0 Hz, 2H), 4.15-4.02 (m, 2H), 3.22-3.12 (m, 2H), 3.09-2.98 (m, 1H), 2.87-2.72 (m, 2H), 2.47 (s, 3H), 2.38-2.27 (m, 1H), 2.02-1.89 (m, 1H).

Step 2. 3-((4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)tetrahydrothiophene 1,1-dioxide To a solution of (1,1-dioxothiolan-3-yl)methyl 4-methylbenzenesulfonate (80 mg, 263 μmol) in N,N-dimethylformamide (3 mL) was added cesium carbonate (170 mg, 522 μmol) and 2-[[6-[5-chloro-3-(1H-pyrazol-4-yl)quinoxalin-6-yl]oxy-2-methyl-benzimidazol-1-yl]methoxy]ethyl-trimethyl-silane (135 mg, 266 μmol). The mixture was stirred at 80° C. for 4 h. On completion, the mixture was quenched with water (3 mL) and extracted with ethyl acetate (5 mL×3). The combined organic layers were dried over anhydrous sodium sulfate, filtered and concentrated to give 2-[[6-[5-chloro-3-[1-[(1,1-dioxothiolan-3-yl)methyl]pyrazol-4-yl]quinoxalin-6-yl]oxy-2-methyl-benzimidazol-1-yl]methoxy]ethyl-trimethyl-silane (220 mg, crude) as a yellow oil. m/z ES+ $[M+H]^+$ 639.2.

Step 3. 3-((4-(8-Chloro-7-((2-methyl-1H-benzo[d]imidazol-6-yl)oxy)quinoxalin-2-yl)-1H-pyrazol-1-yl)methyl)tetrahydrothiophene 1,1-dioxide A solution of 2-[[6-[5-chloro-3-[1-[(1,1-dioxothiolan-3-yl)methyl]pyrazol-4-yl]quinoxalin-6-yl]oxy-2-methyl-benzimidazol-1-yl]methoxy]ethyl-trimethyl-silane (220 mg, 344 μmol) in trifluoroacetic acid (3 mL) was stirred at 25° C. for 2 h. On completion, the mixture was filtered and concentrated under reduced pressure. The residue was purified by reversed-phase HPLC (mobile phase: [water (0.1% formic acid)-acetonitrile]; (B %: 30%-62%, 8 min) to give 3-[[4-[8-chloro-7-[(2-methyl-3H-benzimidazol-5-yl)oxy]quinoxalin-2-yl]pyrazol-1-yl]methyl]thiolane 1,1-dioxide (120 mg, 236 μmol, 67%) as a yellow solid. m/z ES+ $[M+H]^+$ 509.3.

Step 4. (R)-3-((4-(8-chloro-7-((2-methyl-1H-benzo[d]imidazol-6-yl)oxy)quinoxalin-2-yl)-1H-pyrazol-1-yl)methyl)tetrahydrothiophene 1,1-dioxide and (S)-3-((4-(8-chloro-7-((2-methyl-1H-benzo[d]imidazol-6-yl)oxy)quinoxalin-2-yl)-1H-pyrazol-1-yl)methyl)tetrahydrothiophene 1,1-dioxide 3-[[4-[8-chloro-7-[(2-methyl-3H-benzimidazol-5-yl)oxy]quinoxalin-2-yl]pyrazol-1-yl]methyl]thiolane 1,1-dioxide (120 mg, 236 μmol) was separated by SFC (column: Daicel Chiralcel OJ (250 mm*30 mm*10 μm); mobile phase: [0.1% ammonium hydroxide/ethanol]; (B %: 60%-60%, 3.5 min, total run 40 min) and further purified by prep-HPLC (column: Phenomenex Gemini-NX C18 75*30 mm*3 μm; mobile phase: [water (0.225% formic acid)-acetonitrile]; (B %: 12%-42%, 7 min) to give (3R)-3-[[4-[8-chloro-7-[(2-methyl-3H-benzimidazol-5-yl)oxy]quinoxalin-2-yl]pyrazol-1-yl]methyl]thiolane 1,1-dioxide (58.9 mg, 116 μmol, 49%) as a yellow solid and (3S)-3-[[4-[8-chloro-7-[(2-methyl-3H-benzimidazol-5-yl)oxy]quinoxalin-2-yl]pyrazol-1-yl]methyl]thiolane 1,1-dioxide (28 mg, 55 μmol, 23%) as an off-white solid.

$^1$H NMR (400 MHz, DMSO-$d_6$): δ=9.33 (s, 1H), 8.76 (s, 1H), 8.41 (s, 1H), 7.98 (d, J=8.8 Hz, 1H), 7.57 (d, J=8.8 Hz, 1H), 7.36 (d, J=9.2 Hz, 1H), 7.27 (s, 1H), 7.02 (d, J=8.8 Hz, 1H), 4.40 (d, J=4.4 Hz, 2H), 3.21 (d, J=5.6 Hz, 2H), 3.13 (d, J=9.2 Hz, 1H), 3 (d, J=6.8 Hz, 2H), 2.55 (s, 3H), 2.27-2.13 (m, 1H), 1.99-1.82 (m, 1H); m/z ES+ $[M+H]^+$ 509.0. 1H NMR (400 MHz, DMSO-$d_6$): δ=9.31 (s, 1H), 8.75 (s, 1H), 8.41 (s, 1H), 8.19 (s, 1H), 7.95 (d, J=9.2 Hz, 1H), 7.51 (d, J=8.8 Hz, 1H), 7.32 (d, J=9.2 Hz, 1H), 7.21 (s, 1H), 6.98-6.90 (m, 1H), 4.40 (d, J=4.8 Hz, 2H), 3.29-3.20 (m, 2H), 3.18-3.07 (m, 1H), 3.04-2.96 (m, 2H), 2.49 (s, 3H), 2.25-2.13 (m, 1H), 1.97-1.81 (m, 1H); m/z ES+ $[M+H]^+$ 509.0.

Example 139. Synthesis of 2-(4-(4-(8-chloro-7-((2-methyl-1H-benzo[d]imidazol-6-yl)oxy)quinoxalin-2-yl)-1H-pyrazol-1-yl) piperidin-1-yl) acetamide Step 1. 2-(4-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidin-1-yl) acetamide To a solution of 8-chloro-7-((2-methyl-1-((2-(trimethylsilyl)ethoxy)methyl)-1H-benzo[d]imidazol-6-yl)oxy)-2-(1-(piperidin-4-yl)-1H-pyrazol-4-yl)quinoxaline (70.0 mg, 118 μmol) and 2-bromoacetamide (18.0 mg, 130 μmol) in acetonitrile (1 mL) was added sodium iodide (1.8 mg, 11.8 μmol) and potassium carbonate (32.8 mg, 237 μmol). The mixture was stirred at 60° C. for 3 h. On completion, the mixture was filtered and concentrated under reduced pressure to give 2-(4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidin-1-yl) acetamide (75 mg, 116 μmol, 97%) as a yellow oil. m/z ES+ $[M+H]^+$ 647.3.

Step 2. 2-(4-(4-(8-Chloro-7-((2-methyl-1H-benzo[d]imidazol-6-yl)oxy)quinoxalin-2-yl)-1H-pyrazol-1-yl) piperidin-1-yl) acetamide A solution of 2-[4-[4-[8-chloro-7-[2-methyl-3-(2-trimethylsilylethoxymethyl)benzimidazol-5-yl]oxy-quinoxalin-2-yl]pyrazol-1-yl]-1-piperidyl]acetamide (75 mg, 115 μmol) in trifluoroacetic acid (1 mL) was stirred at 25° C. for 0.5 h. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 2%-32%, 5 min) to give 2-(4-(4-(8-chloro-7-((2-methyl-1H-benzo[d]imidazol-6-yl)oxy)quinoxalin-2-yl)-1H-pyrazol-1-yl) piperidin-1-yl) acetamide (25.5 mg, 49.3 μmol, 42%) as a yellow solid. $^1$H NMR (400 MHz, $CD_3OD$): δ=9.18 (s, 1H), 8.64 (s, 1H), 8.44-8.31 (m, 1H), 8.11 (s, 1H), 7.93 (d, J=9.2 Hz, 1H), 7.61 (d, J=8.8 Hz, 1H), 7.39 (d, J=9.2 Hz, 1H), 7.23 (d, J=2.4 Hz, 1H), 7.12 (dd, J=2.4, 8.8 Hz, 1H), 4.64-4.50 (m, 1H), 3.70 (s, 2H), 3.53 (d, J=12.4 Hz, 2H), 3.10-2.96 (m, 2H), 2.67 (s, 3H), 2.50-2.26 (m, 4H); m/z ES+ $[M+H]^+$ 517.1.

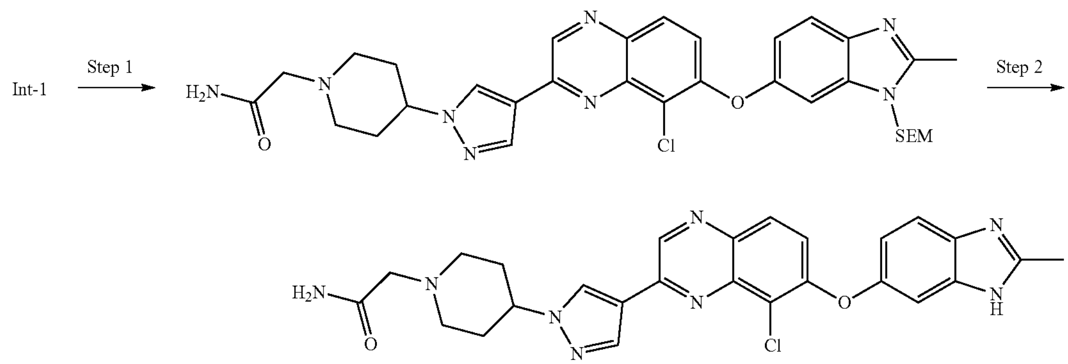

Example 140. Synthesis of 2-(4-(4-(8-chloro-7-((2-methyl-1H-benzo[d]imidazol-6-yl)oxy)quinoxalin-2-yl)-1H-pyrazol-1-yl) piperidin-1-yl)-N-methylacetamide

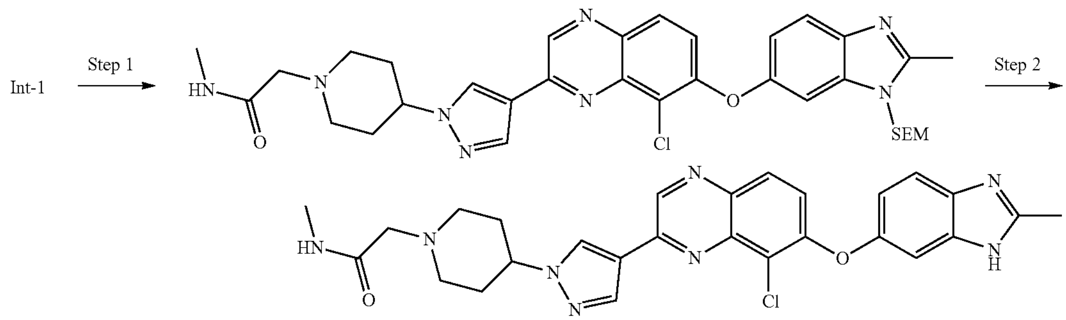

Step 1. 2-(4-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidin-1-yl)-N-methylacetamide A solution of 8-chloro-7-((2-methyl-1-((2-(trimethylsilyl) ethoxy)methyl)-1H-benzo[d]imidazol-6-yl)oxy)-2-(1-(piperidin-4-yl)-1H-pyrazol-4-yl)quinoxaline (70 mg, 118 μmol), 2-chloro-N-methylacetamide (14.0 mg, 130 μmol) and potassium phosphate (50.3 mg, 237 μmol) in acetonitrile (1 mL) was stirred at 40° C. for 16 h. On completion, the mixture was filtered and concentrated under reduced pressure to give 2-(4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidin-1-yl)-N-methylacetamide (75 mg, crude) as a yellow oil. m/z ES+ $[M+H]^+$ 661.3.

Step 2. 2-(4-(4-(8-Chloro-7-((2-methyl-1H-benzo[d]imidazol-6-yl)oxy)quinoxalin-2-yl)-1H-pyrazol-1-yl) piperidin-1-yl)-N-methylacetamide A solution of 2-(4-(4-(8-chloro-7-((2-methyl-1-((2-(trimethylsilyl)ethoxy)methyl)-1H-benzo[d]imidazol-6-yl)oxy) quinoxalin-2-yl)-1H-pyrazol-1-yl) piperidin-1-yl)-N-methylacetamide (75 mg, crude) in trifluoroacetic acid (1 mL) was stirred at 25° C. for 1 h. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 2%-32%, 7 min) to give 2-(4-(4-(8-chloro-7-((2-methyl-1H-benzo[d]imidazol-6-yl)oxy)quinoxalin-2-yl)-1H-pyrazol-1-yl) piperidin-1-yl)-N-methylacetamide (38.0 mg, 71.6 μmol, 62%) as an off-white solid. $^1H$ NMR (400 MHz, $CD_3OD$): δ=9.21 (s, 1H), 8.66 (s, 1H), 8.40 (s, 1H), 8.12 (s, 1H), 7.97 (d, J=9.2 Hz, 1H), 7.69 (d, J=9.2 Hz, 1H), 7.45 (d, J=9.2 Hz, 1H), 7.29 (d, J=2.4 Hz, 1H), 7.22 (dd, J=2.4, 8.8 Hz, 1H), 4.73-4.55 (m, 1H), 3.81 (s, 2H), 3.61 (d, J=12.4 Hz, 2H), 3.24-3.11 (m, 2H), 2.84 (s, 3H), 2.76 (s, 3H), 2.60-2.36 (m, 4H); m/z ES+ $[M+H]^+$ 531.1.

Example 141. Synthesis of 4-(4-(8-chloro-7-((2-methyl-1H-benzo[d]imidazol-6-yl)oxy)quinoxalin-2-yl)-1H-pyrazol-1-yl)-N-methylpiperidine-1-carboxamide

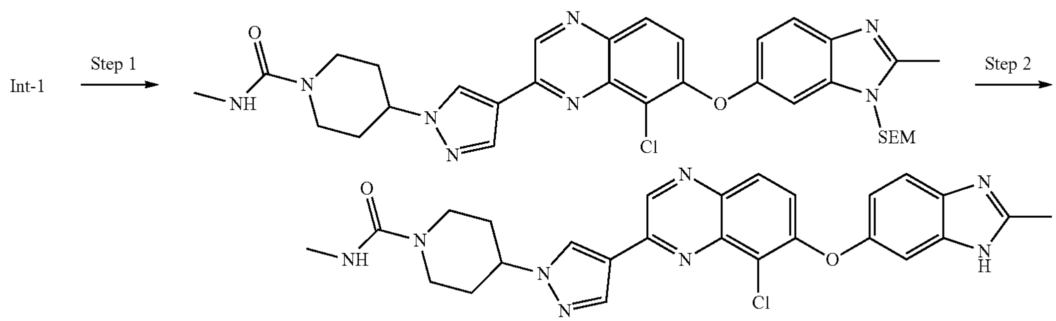

Step 1. 4-(4-(8-Chloro-7-((2-methyl-1-((2-(trimethylsilyl)ethoxy)methyl)-1H-benzo[d]imidazol-6-yl) oxy)quinoxalin-2-yl)-1H-pyrazol-1-yl)-N-methylpiperidine-1-carboxamide To a solution of 8-chloro-7-((2-methyl-1-((2-(trimethylsilyl)ethoxy)methyl)-1H-benzo[d]imidazol-6-yl)oxy)-2-(1-(piperidin-4-yl)-1H-pyrazol-4-yl)quinoxaline (70 mg, 118 μmol) and triethylamine (36.0 mg, 355. μmol) in dichloromethane (1 mL) was added methylcarbamic chloride (13.3 mg, 142 μmol). The mixture was stirred at 25° C. for 1 h. On completion, the mixture was poured into water (5 mL) and extracted with dichloromethane (10 mL×3). The organic layers were dried over sodium sulfate, filtered and concentrated under reduced pressure to give 4-(4-(8-chloro-7-((2-methyl-1-((2-(trimethylsilyl)ethoxy)methyl)-1H-benzo[d]

imidazol-6-yl)oxy)quinoxalin-2-yl)-1H-pyrazol-1-yl)-N-methylpiperidine-1-carboxamide (75 mg, crude) as a yellow oil. m/z ES+ $[M+H]^+$ 647.2.

Step 2. 4-(4-(8-Chloro-7-((2-methyl-1H-benzo[d]imidazol-6-yl)oxy)quinoxalin-2-yl)-1H-pyrazol-1-yl)-N-methylpiperidine-1-carboxamide A solution of 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-N-methylpiperidine-1-carboxamide (75 mg, 115 μmol) in trifluoroacetic acid (1 mL) was stirred at 25° C. for 1 h. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 12%-42%, 7 min) to give 4-(4-(8-chloro-7-((2-methyl-1H-benzo[d]imidazol-6-yl)oxy)quinoxalin-2-yl)-1H-pyrazol-1-yl)-N-methylpiperidine-1-carboxamide (34.4 mg, 66.5 μmol, 57%) as a white solid. $^1H$ NMR (400 MHz, $CD_3OD$): δ=9.16 (d, J=2.4 Hz, 1H), 8.61 (s, 1H), 8.33 (s, 1H), 8.10 (s, 1H), 7.92 (d, J=9.2 Hz, 1H), 7.64 (d, J=8.8 Hz, 1H), 7.40 (d, J=9.2 Hz, 1H), 7.25 (d, J=2.0 Hz, 1H), 7.17 (dd, J=2.4, 8.0 Hz, 1H), 4.59-4.43 (m, 1H), 4.18 (d, J=13.6 Hz, 2H), 3.09-2.95 (m, 2H), 2.75 (s, 3H), 2.71 (s, 3H), 2.17 (d, J=10.8 Hz, 2H), 2.07-1.96 (m, 2H); m/z ES+ $[M+H]^+$ 517.1.

Example 142. Synthesis of 8-chloro-7-((2-methyl-1H-benzo[d]imidazol-6-yl)oxy)-2-(1-(2-(oxetan-3-yl)-2-azabicyclo[2.2.1]heptan-5-yl)-1H-pyrazol-4-yl)quinoxaline

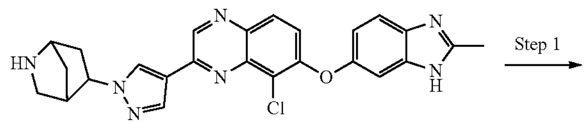

-continued

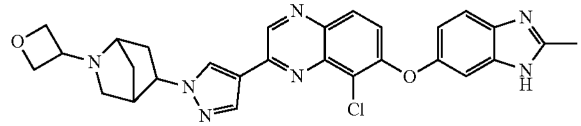

Step 1. 8-Chloro-7-((2-methyl-1H-benzo[d]imidazol-6-yl)oxy)-2-(1-(2-(oxetan-3-yl)-2-azabicyclo[2.2.1]heptan-5-yl)-1H-pyrazol-4-yl)quinoxaline To a solution of 2-(1-(2-azabicyclo[2.2.1]heptan-5-yl)-1H-pyrazol-4-yl)-8-chloro-7-((2-methyl-1H-benzo[d]imidazol-6-yl)oxy)quinoxaline (40.0 mg, 84.8 μmol) in methanol (1 mL) was added sodium cyanoborohydride (6.92 mg, 110 μmol), oxetan-3-one (18.3 mg, 254 μmol) and sodium acetate (9.04 mg, 110 μmol). The mixture was stirred at 25° C. for 12 h. On completion, the reaction mixture was quenched with water (0.2 mL) and concentrated under reduced pressure. The residue was purified by prep-HPLC (neutral condition; column: Waters Xbridge 150*25 mm*5 μm; mobile phase: [water (10 mM ammonium bicarbonate)-acetonitrile]; (B %: 28%-58%, 10 min) and repurified by prep-HPLC (basic condition; column: Waters Xbridge 150*25 mm*5 um; mobile phase: [water (0.05% ammonium hydroxide v/v)-acetonitrile]; (B %: 20%-50%, 8 min) to give 8-chloro-7-((2-methyl-1H-benzo[d]imidazol-6-yl)oxy)-2-(1-(2-(oxetan-3-yl)-2-azabicyclo[2.2.1]heptan-5-yl)-1H-pyrazol-4-yl)quinoxaline (33.7 mg, 63.9 μmol, 75%) as a white solid. $^1H$ NMR (400 MHz, DMSO-$d_6$): δ=12.40-12.19 (m, 1H), 9.32 (s, 1H), 8.82 (s, 1H), 8.34 (s, 1H), 7.96 (d, J=8.8 Hz, 1H), 7.60-7.44 (m, 1H), 7.38-7.14 (m, 2H), 6.95 (t, J=8.0 Hz, 1H), 4.67-4.54 (m, 3H), 4.47 (td, J=5.6, 20.0 Hz, 2H), 3.99 (t, J=6.0 Hz, 1H), 3.36 (s, 1H), 2.62 (td, J=2.8, 5.6 Hz, 1H), 2.58 (s, 1H), 2.50-2.48 (m, 3H), 2.46 (s, 1H), 2.26 (dd, J=2.8, 13.2 Hz, 1H), 2.05-1.96 (m, 1H), 1.83 (d, J=10.0 Hz, 1H), 1.54 (d, J=10.0 Hz, 1H); m/z ES+ $[M+H]^+$ 528.1.

Example 143. Synthesis of 2-(5-((4-(8-chloro-7-((2-methyl-1H-benzo[d]imidazol-6-yl)oxy)quinoxalin-2-yl)-1H-pyrazol-1-yl)methyl)-2-azabicyclo[2.2.1]heptan-2-yl) acetamide

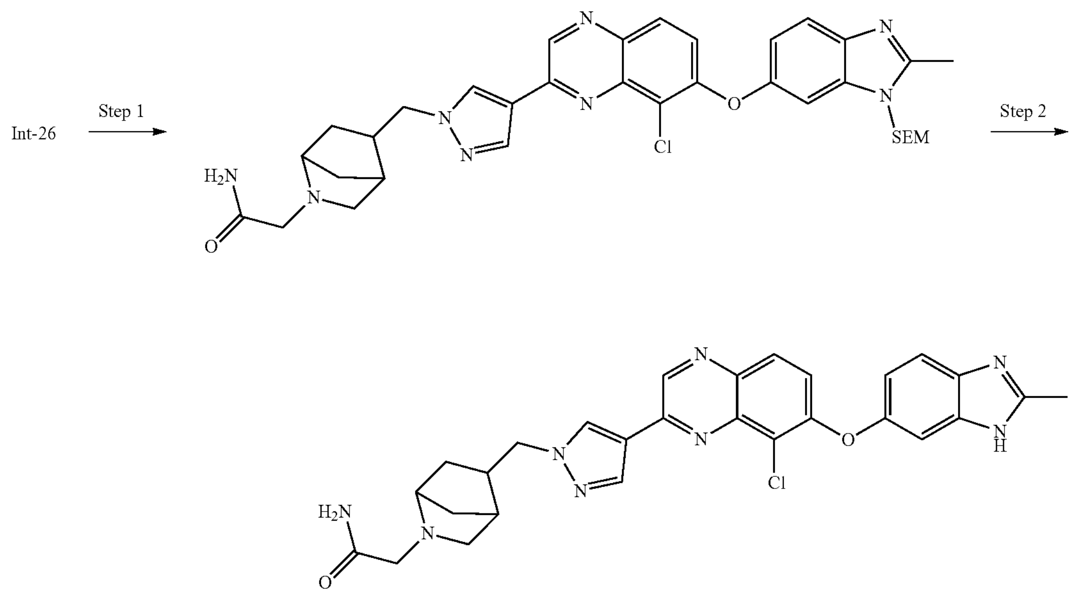 [SMILES: Cc1nc2ccc(Oc3ccc4ncc(-c5cnn(CC6CC7CC6CN7CC(N)=O)c5)nc4c3Cl)cc2n1COCC[Si](C)(C)C ; Cc1nc2ccc(Oc3ccc4ncc(-c5cnn(CC6CC7CC6CN7CC(N)=O)c5)nc4c3Cl)cc2[nH]1]

Step 1. 2-(5-((4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-2-azabicyclo[2.2.1]heptan-2-yl)acetamide To a solution of 2-(1-(2-azabicyclo[2.2.1]heptan-5-ylmethyl)-1H-pyrazol-4-yl)-8-chloro-7-((2-methyl-1-((2-(trimethylsilyl)ethoxy)methyl)-1H-benzo[d]imidazol-6-yl)oxy) quinoxaline (100 mg, 162 μmol) in N,N-dimethylformamide (1 mL) was added cesium carbonate (159 mg, 487 μmol) and 2-bromoacetamide (22.4 mg, 162 μmol). The mixture was stirred at 25° C. for 13 h. On completion, the reaction mixture was quenched with water (0.2 mL) and concentrated under reduced pressure and the residue was purified by reversed-phase HPLC (column: Phenomenex Luna C18 150*25 mm*10 μm; mobile phase: [water (formic acid)-acetonitrile]; (B %: 1%-30%, 10 min) to give 2-(5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-2-azabicyclo[2.2.1]heptan-2-yl) acetamide (40 mg, 59.4 μmol, 32%) as a yellow oil. m/z ES+ $[M+H]^+$ 673.5.

Step 2. 2-(5-((4-(8-Chloro-7-((2-methyl-1H-benzo[d]imidazol-6-yl)oxy)quinoxalin-2-yl)-1H-pyrazol-1-yl)methyl)-2-azabicyclo[2.2.1]heptan-2-yl) acetamide A solution of 2-(5-((4-(8-chloro-7-((2-methyl-1-((2-(trimethylsilyl)ethoxy)methyl)-1H-benzo[d]imidazol-6-yl)oxy) quinoxalin-2-yl)-1H-pyrazol-1-yl)methyl)-2-azabicyclo [2.2.1]heptan-2-yl) acetamide (40.0 mg, 59.4 μmol) in trifluoroacetic acid (1 mL) was stirred at 25° C. for 1 h. On completion, the reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 1%-30%, 10 min) to give 2-(5-((4-(8-chloro-7-((2-methyl-1H-benzo[d]imidazol-6-yl)oxy) quinoxalin-2-yl)-1H-pyrazol-1-yl)methyl)-2-azabicyclo [2.2.1]heptan-2-yl) acetamide (20.2 mg, 37.3 μmol, 63%) as an off-white solid. $^1H$ NMR (400 MHz, DMSO-$d_6$) δ 12.72-11.72 (m, 1H), 9.31 (s, 1H), 8.74 (s, 1H), 8.37 (s, 1H), 8.16 (s, 1H), 7.95 (d, J-9.2 Hz, 1H), 7.54-7.41 (m, 2H), 7.31 (d, J=9.2 Hz, 2H), 7.20 (s, 1H), 6.94 (dd, J=2.4, 8.8 Hz, 1H), 4.37 (dd, J=4.8, 7.6 Hz, 2H), 4.22-4.06 (m, 1H), 3.43 (s, 1H), 3.19 (d, J=14.4 Hz, 3H), 2.89-2.65 (m, 1H), 2.49 (s, 3H), 2.25 (s, 1H), 1.96-1.21 (m, 5H); m/z ES+ $[M+H]^+$ 543.1.

Example 144. Synthesis of 5-((4-(8-chloro-7-((2-methyl-1H-benzo[d]imidazol-6-yl)oxy)quinoxalin-2-yl)-1H-pyrazol-1-yl)methyl)-2-azabicyclo[2.2.1] heptane-2-carboxamide

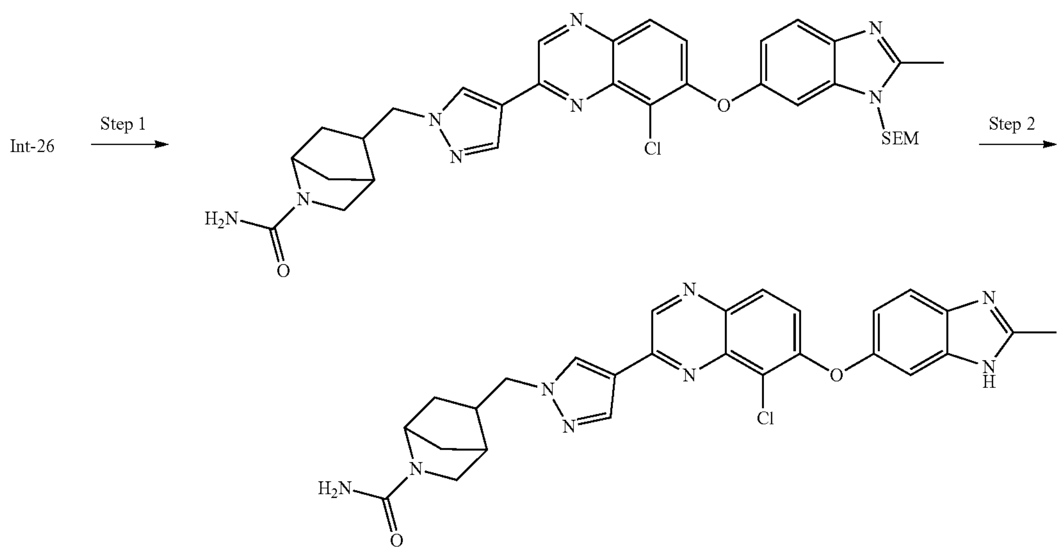

Step 1. 5-((4-(8-Chloro-7-((2-methyl-1-((2-(trimethylsilyl)ethoxy)methyl)-1H-benzo[d]imidazol-6-yl) oxy)quinoxalin-2-yl)-1H-pyrazol-1-yl)methyl)-2-azabicyclo[2.2.1]heptane-2-carboxamide To a solution of 2-(1-(2-azabicyclo[2.2.1]heptan-5-ylmethyl)-1H-pyrazol-4-yl)-8-chloro-7-((2-methyl-1-((2-(trimethylsilyl)ethoxy)methyl)-1H-benzo[d]imidazol-6-yl)oxy) quinoxaline (130 mg, 211 μmol) in dichloromethane (1 mL) was added diisopropylethylamine (81.8 mg, 633 μmol), then isocyanato (trimethyl) silane (29.2 mg, 253 μmol) was added at 0° C. The mixture was stirred at 25° C. for 12 h. On completion, the reaction mixture was concentrated under reduced pressure. The residue was purified by prep-TLC (silica gel, ethyl acetate: ethanol=5:1) to give 5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-2-azabicyclo[2.2.1]heptane-2-carboxamide (100 mg, 152 μmol, 54%) as a yellow oil. m/z ES+ $[M+H]^+$ 659.3.

Step 2. 5-((4-(8-Chloro-7-((2-methyl-1H-benzo[d]imidazol-6-yl)oxy)quinoxalin-2-yl)-1H-pyrazol-1-yl) methyl)-2-azabicyclo[2.2.1]heptane-2-carboxamide A solution of 5-((4-(8-chloro-7-((2-methyl-1-((2-(trimethylsilyl)ethoxy)methyl)-1H-benzo[d]imidazol-6-yl)oxy) quinoxalin-2-yl)-1H-pyrazol-1-yl)methyl)-2-azabicyclo [2.2.1]heptane-2-carboxamide (100 mg, 152 μmol) in trifluoroacetic acid (1 mL) was stirred at 25° C. for 1 h. On completion, the reaction mixture was concentrated under reduced pressure to give a residue. Then the residue was adjusted to pH ~ 8 with sat. ammonium hydroxide and then concentrated under reduced pressure. The residue was purified by prep-HPLC (neutral condition; column: Waters Xbridge 150*25 mm*5 μm; mobile phase: [water (10 mM ammonium bicarbonate)-acetonitrile]; (B %: 21%-51%, 10 min) to give 5-((4-(8-chloro-7-((2-methyl-1H-benzo[d]imidazol-6-yl)oxy)quinoxalin-2-yl)-1H-pyrazol-1-yl)methyl)-2-azabicyclo[2.2.1]heptane-2-carboxamide (11.1 mg, 21.0 μmol, 14%) as a white solid. $^1$H NMR (400 MHz, DMSO-$d_6$): δ=12.47-12.14 (m, 1H), 9.31 (s, 1H), 8.76 (s, 1H), 8.36 (s, 1H), 7.95 (d, J=9.2 Hz, 1H), 7.50 (d, J=8.8 Hz, 1H), 7.31 (d, J=9.2 Hz, 1H), 7.21 (s, 1H), 6.94 (dd, J=2.0, 8.8 Hz, 1H), 5.73 (s, 2H), 4.32-4.17 (m, 2H), 4.12 (s, 1H), 3.48 (d, J=10.0 Hz, 1H), 3.08 (d, J=8.0 Hz, 1H), 2.69-2.60 (m, 1H), 2.49 (s, 3H), 2.36-2.32 (m, 1H), 1.84-1.74 (m, 1H), 1.64 (d, J=8.0 Hz, 1H), 1.58-1.47 (m, 1H), 1.30-1.20 (m, 1H); m/z ES+ $[M+H]^+$ 529.1.

Example 145. Synthesis of 5-((4-(8-chloro-7-((2-methyl-1H-benzo[d]imidazol-6-yl)oxy)quinoxalin-2-yl)-1H-pyrazol-1-yl)methyl)-N-methyl-2-azabicyclo[2.2.1]heptane-2-carboxamide

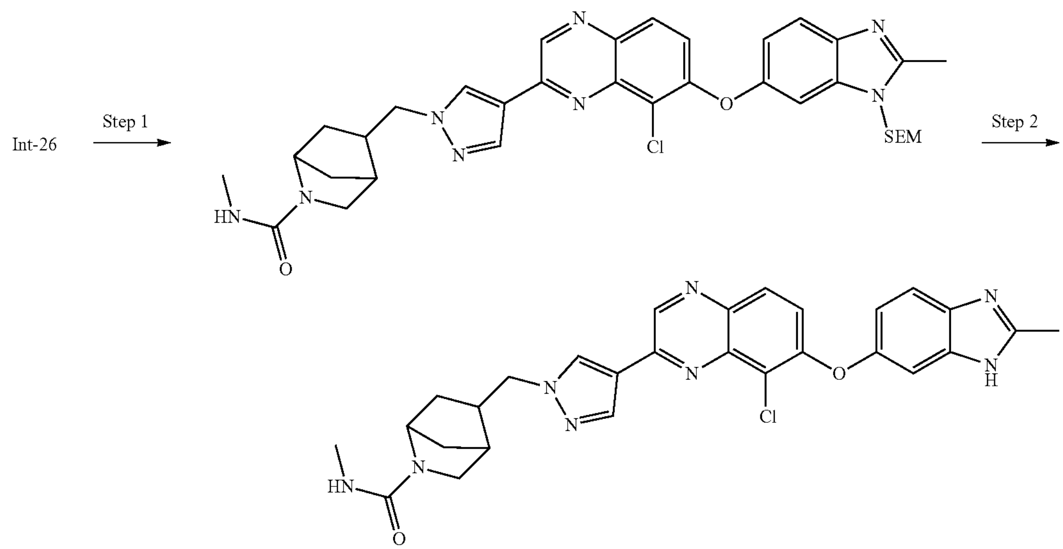

Step 1. 5-((4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-N-methyl-2-azabicyclo[2.2.1]heptane-2-carboxamide To a solution of 2-(1-(2-azabicyclo[2.2.1]heptan-5-ylmethyl)-1H-pyrazol-4-yl)-8-chloro-7-((2-methyl-1-((2-(trimethylsilyl)ethoxy)methyl)-1H-benzo[d]imidazol-6-yl)oxy)quinoxaline (80.0 mg, 130 μmol) in dichloromethane (1 mL) was added triethylamine (39.4 mg, 389 μmol) and methylcarbamic chloride (14.6 mg, 156 μmol). The mixture was stirred at 25° C. for 13 h. On completion, the reaction mixture was concentrated under reduced pressure. The residue was purified by prep-TLC (silica gel, ethyl acetate: ethanol=10:1) to give 5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-N-methyl-2-azabicyclo[2.2.1]heptane-2-carboxamide (80.0 mg, 119 μmol, 76%) as a yellow oil. m/z ES+ $[M+H]^+$ 673.2.

Step 2. 5-((4-(8-Chloro-7-((2-methyl-1H-benzo[d]imidazol-6-yl)oxy)quinoxalin-2-yl)-1H-pyrazol-1-yl)methyl)-N-methyl-2-azabicyclo[2.2.1]heptane-2-carboxamide A solution of 5-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)-N-methyl-2-azabicyclo[2.2.1]heptane-2-carboxamide (80.0 mg, 119 μmol) in trifluoroacetic acid (1 mL) was stirred at 25° C. for 1 h. On completion, the reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 10%-40%, 10 min) to give 5-((4-(8-chloro-7-((2-methyl-1H-benzo[d]imidazol-6-yl)oxy)quinoxalin-2-yl)-1H-pyrazol-1-yl)methyl)-N-methyl-2-azabicyclo[2.2.1]heptane-2-carboxamide (23.0 mg, 42.3 μmol, 36%) as an off-white solid. $^1$H NMR (400 MHz, DMSO-$d_6$): δ=9.32 (s, 1H), 8.76 (s, 1H), 8.36 (s, 1H), 7.98 (d, J=9.2 Hz, 1H), 7.59 (d, J=8.8 Hz, 1H), 7.36 (d, J=9.2 Hz, 1H), 7.29 (d, J=2.0 Hz, 1H), 7.04 (dd, J=2.4, 8.8 Hz, 1H), 6.13-5.96 (m, 1H), 4.35-4.18 (m, 2H), 4.13 (s, 1H), 3.46 (d, J=9.6 Hz, 1H), 3.09 (dd, J=2.4, 9.6 Hz, 1H), 2.67 (d, J=4.4 Hz, 1H), 2.62-2.58 (m, 3H), 2.57 (s, 3H), 2.35 (s, 1H), 1.89-1.71 (m, 1H), 1.68-1.48 (m, 2H), 1.36-1.13 (m, 1H); m/z ES+ $[M+H]^+$ 543.2.

Example 146. Synthesis of 2-(3-((4-(8-chloro-7-((2-methyl-1H-benzo[d]imidazol-6-yl)oxy)quinoxalin-2-yl)-1H-pyrazol-1-yl)methyl)azetidin-1-yl)-N-methylacetamide

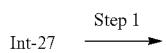

-continued

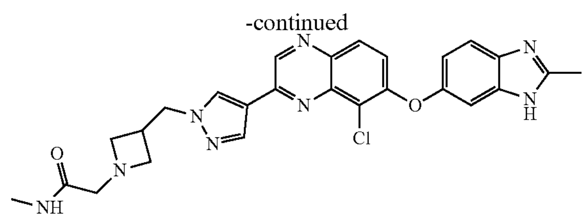

Step 1. 2-(3-((4-(8-Chloro-7-((2-methyl-1H-benzo[d]imidazol-6-yl)oxy)quinoxalin-2-yl)-1H-pyrazol-1-yl)methyl)azetidin-1-yl)-N-methylacetamide To a solution of 2-[1-(azetidin-3-ylmethyl)pyrazol-4-yl]-8-chloro-7-[(2-methyl-3H-benzimidazol-5-yl)oxy]quinoxaline (50 mg, 102 μmol, formic acid) in tetrahydrofuran (3 mL) was added triethylamine (31.7 mg, 314 μmol), potassium iodide (33.8 mg, 203 μmol) and 2-chloro-N-methyl-acetamide (10 mg, 93 μmol). The mixture was stirred at 25° C. for 20 h. On completion, the mixture was filtered and concentrated under reduced pressure. The residue was purified by prep-HPLC (column: Waters Xbridge 150*25 mm*5 μm; mobile phase: [water (0.05% ammonium hydroxide v/v)-acetonitrile]; (B %: 15%-42%, 8 min) to give 2-[[3-[4-[8-chloro-7-[(2-methyl-3H-benzimidazol-5-yl)oxy]quinoxalin-2-yl]pyrazol-1-yl]methyl]azetidin-1-yl]-N-methyl-acetamide (17.9 mg, 34.6 μmol, 34%) as a white solid. $^1$H NMR (400 MHz, DMSO-$d_6$): δ=9.31 (s, 1H), 8.71 (s, 1H), 8.36 (s, 1H), 7.95 (d, J=9.2 Hz, 1H), 7.61 (br d, J=3.6 Hz, 1H), 7.50 (d, J=8.4 Hz, 1H), 7.31 (d, J=9.2 Hz, 1H), 7.20 (d, J=2.0 Hz, 1H), 6.95-6.89 (m, 1H), 4.48 (d, J=7.2 Hz, 2H), 3.36 (t, J=7.2 Hz, 2H), 3.11 (t, J=6.4 Hz, 2H), 2.99 (s, 2H), 2.93-2.85 (m, 1H), 2.58 (d, J=4.4 Hz, 3H), 2.48 (s, 3H); m/z ES+ $[M+H]^+$ 517.1.

Example 147. Synthesis of 1-(azetidin-1-yl)-2-(3-((4-(8-chloro-7-((2-methyl-1H-benzo[d]imidazol-6-yl)oxy)quinoxalin-2-yl)-1H-pyrazol-1-yl)methyl)azetidin-1-yl)ethanone

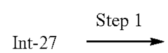

-continued

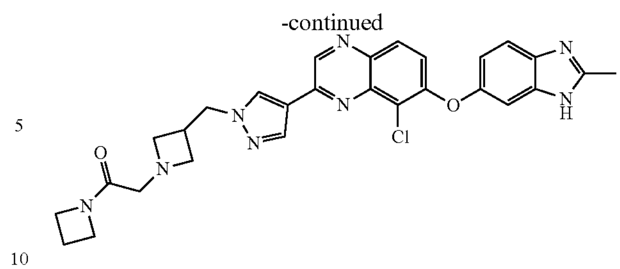

Step 1. 1-(Azetidin-1-yl)-2-(3-((4-(8-chloro-7-((2-methyl-1H-benzo[d]imidazol-6-yl)oxy)quinoxalin-2-yl)-1H-pyrazol-1-yl)methyl)azetidin-1-yl)ethanone To a solution of 2-[1-(azetidin-3-ylmethyl)pyrazol-4-yl]-8-chloro-7-[(2-methyl-3H-benzimidazol-5-yl)oxy]quinoxaline (55 mg, 123 μmol) in N,N-dimethylformamide (1.5 mL) was added potassium carbonate (55.0 mg, 398 μmol), 1-(azetidin-1-yl)-2-chloro-ethanone (16 mg, 120 μmol) and potassium iodide (55.0 mg, 331 μmol). The mixture was stirred at 25° C. for 2 h. On completion, the mixture was concentrated under reduced pressure. The residue was purified by prep-HPLC (column: Waters Xbridge 150*25 mm*5 μm; mobile phase: [water (0.05% ammonium hydroxide v/v)-acetonitrile]; (B %: 15%-45%, 8 min) and re-purified by prep-HPLC (column: Phenomenex Gemini-NX C18 75*30 mm*3 μm; mobile phase: [water (0.225% formic acid)-acetonitrile]; (B %: 2%-32%, 8 min) to give 1-(azetidin-1-yl)-2-[3-[[4-[8-chloro-7-[(2-methyl-3H-benzimidazol-5-yl)oxy]quinoxalin-2-yl]pyrazol-1-yl]methyl]azetidin-1-yl]ethanone (10.0 mg, 18.4 μmol, 14%, formic acid salt) as an off-white solid. $^1$H NMR (400 MHz, DMSO-$d_6$): δ=9.30 (s, 1H), 8.71 (s, 1H), 8.35 (s, 1H), 8.22 (s, 1H), 7.94 (d, J=9.2 Hz, 1H), 7.51 (d, J=8.4 Hz, 1H), 7.30 (d, J=9.2 Hz, 1H), 7.21 (s, 1H), 6.94 (d, J=8.8 Hz, 1H), 4.44 (d, J=7.2 Hz, 2H), 4.10 (t, J=7.6 Hz, 2H), 3.81 (t, J=7.6 Hz, 2H), 3.40 (t, J=7.6 Hz, 2H), 3.18 (t, J=6.4 Hz, 2H), 3.10 (s, 2H), 2.99-2.87 (m, 1H), 2.49 (br s, 3H), 2.23-2.10 (m, 2H); m/z ES+ $[M+H]^+$ 543.1.

Example 148. Synthesis of 2-(3-((4-(8-chloro-7-((2-methyl-1H-benzo[d]imidazol-6-yl)oxy)quinoxalin-2-yl)-1H-pyrazol-1-yl)methyl)azetidin-1-yl)-1-(3-hydroxyazetidin-1-yl)ethanone

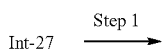

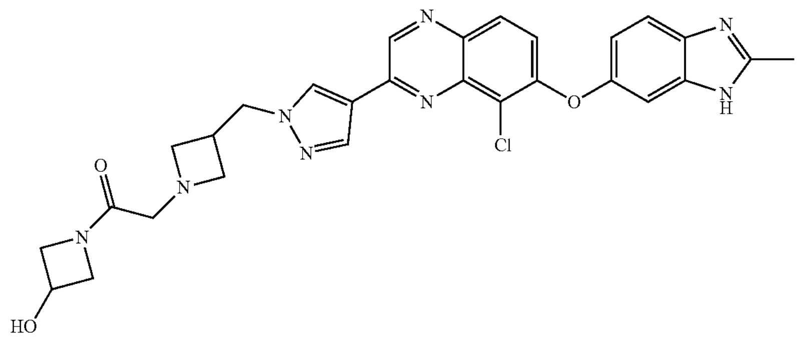

Step 1. 2-(3-((4-(8-Chloro-7-((2-methyl-1H-benzo[d]imidazol-6-yl)oxy)quinoxalin-2-yl)-1H-pyrazol-1-yl)methyl)azetidin-1-yl)-1-(3-hydroxyazetidin-1-yl)ethanone To a solution of 2-[1-(azetidin-3-ylmethyl)pyrazol-4-yl]-8-chloro-7-[(2-methyl-3H-benzimidazol-5-yl)oxy]quinoxaline (60 mg, 122 μmol, formic acid) in 1-methyl-2-pyrrolidinone (1 mL) was added sodium phosphate (58 mg, 354 μmol) and 2-chloro-1-(3-hydroxyazetidin-1-yl)ethanone (18.0 mg, 120 μmol). The mixture was stirred at 40° C. for 2.5 h. On completion, the mixture was filtered and concentrated under reduced pressure. The residue was purified by prep-HPLC (column: Waters Xbridge 150*25 mm*5 μm; mobile phase: [water (0.05% ammonium hydroxide v/v)-acetonitrile]; (B %: 15%-42%, 8 min) to give 2-[[3-[4-[8-chloro-7-[(2-methyl-3H-benzimidazol-5-yl)oxy]quinoxalin-2-yl]pyrazol-1-yl]methyl]azetidin-1-yl]-1-(3-hydroxyazetidin-1-yl)ethanone (29.8 mg, 53.3 μmol, 44%) as a white solid. $^1$H NMR (400 MHz, DMSO-$d_6$): δ=9.30 (s, 1H), 8.71 (s, 1H), 8.35 (s, 1H), 7.95 (d, J=9.2 Hz, 1H), 7.50 (d, J=8.8 Hz, 1H), 7.31 (d, J=9.2 Hz, 1H), 7.20 (d, J=2.0 Hz, 1H), 6.96-6.90 (m, 1H), 4.46-4.38 (m, 3H), 4.28 (t, J=8.0 Hz, 1H), 4.03-3.95 (m, 1H), 3.88-3.80 (m, 1H), 3.55 (d, J=4.4 Hz, 1H), 3.32 (t, J=7.2 Hz, 2H), 3.07 (t, J=6.4 Hz, 2H), 3.02 (s, 2H), 2.94-2.85 (m, 1H), 2.48 (s, 3H); m/z ES+ [M+H]$^+$ 559.1.

Example 149. Synthesis of 2-(3-((4-(8-chloro-7-((2-methyl-1H-benzo[d]imidazol-6-yl)oxy)quinoxalin-2-yl)-1H-pyrazol-1-yl)methyl)azetidin-1-yl) acetonitrile

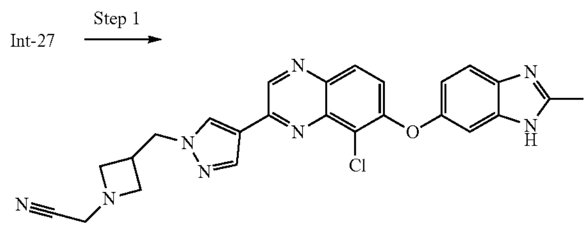

Step 1. 2-(3-((4-(8-Chloro-7-((2-methyl-1H-benzo[d]imidazol-6-yl)oxy)quinoxalin-2-yl)-1H-pyrazol-1-yl)methyl)azetidin-1-yl) acetonitrile To a solution of 2-[1-(azetidin-3-ylmethyl)pyrazol-4-yl]-8-chloro-7-[(2-methyl-3H-benzimidazol-5-yl)oxy]quinoxaline (55 mg, 112 μmol, formic acid salt) in acetonitrile (2 mL) was added potassium carbonate (33 mg, 239 μmol) and 2-bromoacetonitrile (11 mg, 91.7 μmol, 6.1 uL). The mixture was stirred at 25° C. for 4 h. On completion, the mixture was quenched with water (2 mL) and extracted with ethyl acetate (4 mL×3). The organic layers were dried over anhydrous sodium sulfate, filtered and concentrated and the residue was purified by prep-TLC (silica gel, dichloromethane:methanol=12:1) to give 2-[[3-[4-[8-chloro-7-[(2-methyl-3H-benzimidazol-5-yl)oxy]quinoxalin-2-yl]pyrazol-1-yl]methyl]azetidin-1-yl]acetonitrile (34.9 mg, 72 μmol, 63%) as an off-white solid. $^1$H NMR (400 MHz, DMSO-$d_6$): δ=12.51-12.16 (m, 1H), 9.28 (s, 1H), 8.72 (s, 1H), 8.34 (s, 1H), 7.93 (d, J=9.2 Hz, 1H), 7.51 (d, J=2.0 Hz, 1H), 7.36-7.13 (m, 2H), 6.94 (d, J=6.4 Hz, 1H), 4.43 (d, J=7.2 Hz, 2H), 3.61 (s, 2H), 3.39-3.35 (m, 2H), 3.16 (t, J=6.0 Hz, 2H), 3-2.87 (m, 1H), 2.49 (s, 3H); m/z ES+ [M+H]$^+$ 485.1.

Example 150. Synthesis of 1-(azetidin-1-yl)-2-(4-(8-chloro-7-((2-methyl-1H-benzo[d]imidazol-6-yl)oxy)quinoxalin-2-yl)-1H-pyrazol-1-yl)ethanone

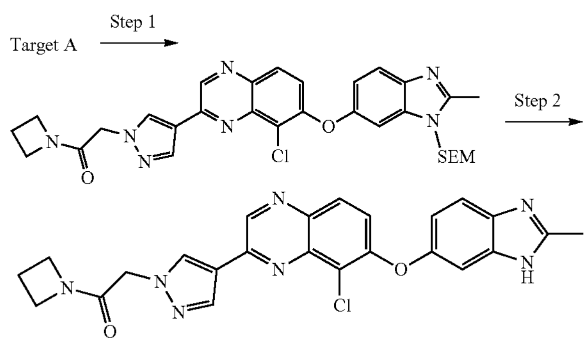

Step 1. 1-(Azetidin-1-yl)-2-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)ethanone To a solution of 2-[[6-[5-chloro-3-(1H-pyrazol-4-yl)quinoxalin-6-yl]oxy-2-methyl-benzimidazol-1-yl]methoxy]ethyl-trimethyl-silane (100 mg, 200 μmol) in tetrahydrofuran (2 mL) was added sodium hydride (25 mg, 630 μmol, 60% in mineral oil) at 25° C. The mixture was stirred at 25° C. for 0.5 h. Then 1-(azetidin-1-yl)-2-chloro-ethanone (38 mg, 290 μmol) was added. The reaction mixture was stirred at 60° C. for 1.5 h. On completion, the reaction mixture was quenched with water (100 mL) and extracted with ethyl acetate (100 mL×2). The combined organic layers were washed with brine (25 mL×2), dried over anhydrous sodium sulfate, filtered and concentrated under reduced pressure to give 1-(azetidin-1-yl)-2-[4-[8-chloro-7-[2-methyl-3-(2-trimethylsilylethoxymethyl)benzimidazol-5-yl]oxy-quinoxalin-2-yl]pyrazol-1-yl]ethanone (220 mg, crude) as a yellow oil. m/z ES+ [M+H]$^+$ 604.3.

Step 2. 1-(Azetidin-1-yl)-2-(4-(8-chloro-7-((2-methyl-1H-benzo[d]imidazol-6-yl)oxy)quinoxalin-2-yl)-1H-pyrazol-1-yl)ethanone A solution of 1-(azetidin-1-yl)-2-[4-[8-chloro-7-[2-methyl-3-(2-trimethylsilylethoxymethyl)benzimidazol-5-yl]oxy-quinoxalin-2-yl]pyrazol-1-yl]ethanone (200 mg, 330 μmol) in trifluoroacetic acid (2 mL) was stirred at 25° C. for 0.5 h. On completion, the reaction mixture was concentrated under reduced pressure. The residue was purified by prep-TLC (dichloromethane:methanol=10:1) to give 1-(azetidin-1-yl)-2-[4-[8-chloro-7-[(2-methyl-3H-benzimidazol-5-yl)oxy]quinoxalin-2-yl]pyrazol-1-yl]ethanone (17.8 mg, 37.6 μmol, 11.3%) as a white solid. $^1$HNMR (400 MHz, DMSO-$d_6$): δ=12.40-12.18 (m, 1H), 9.33 (s, 1H), 8.66 (s, 1H), 8.38 (s, 1H), 7.96 (d, J=8.8 Hz, 1H), 7.58-7.43 (m, 1H), 7.32 (d, J=10.4 Hz, 1H), 7.27-7.14 (m, 1H), 6.95 (t, J=8.8 Hz, 1H), 4.99 (s, 2H), 4.21 (t, J=8.0 Hz, 2H), 3.93 (t, J=7.6 Hz, 2H), 2.49-2.47 (m, 3H), 2.35-2.20 (m, 2H); m/z ES+ [M+H]$^+$ 474.1.

Example 151. Synthesis of 2-(4-(8-chloro-7-((2-methyl-1H-benzo[d]imidazol-6-yl)oxy)quinoxalin-2-yl)-1H-pyrazol-1-yl)-1-(3-hydroxyazetidin-1-yl) ethanone

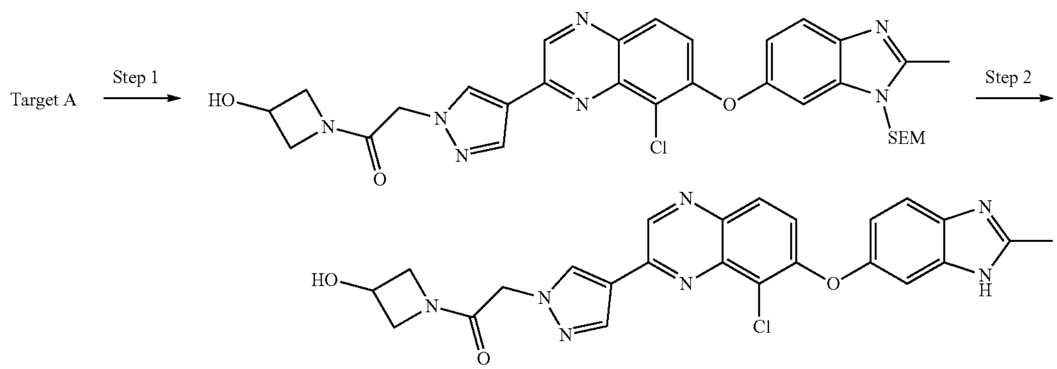

Step 1. 2-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-1-(3-hydroxyazetidin-1-yl)ethanone To a solution of 2-[[6-[5-chloro-3-(1H-pyrazol-4-yl)quinoxalin-6-yl]oxy-2-methyl-benzimidazol-1-yl]methoxy]ethyl-trimethyl-silane (150 mg, 295 μmol) in tetrahydrofuran (3 mL) was added sodium hydride (17.7 mg, 443 μmol, 60% in mineral oil) at 25° C. The mixture was stirred at 25° C. for 0.5 h. Then 2-chloro-1-(3-hydroxyazetidin-1-yl)ethanone (66.4 mg, 443 μmol) was added. The resulting mixture was stirred at 60° C. for 1.5 h. On completion, the reaction mixture was quenched with water (20 mL) at 25° C. Then the mixture was concentrated under reduced pressure. The residue was purified by reversed-phase HPLC (0.1% ammonium hydroxide conditions) to give 2-[4-[8-chloro-7-[2-methyl-3-(2-trimethylsilylethoxymethyl)benzimidazol-5-yl]oxy-quinoxalin-2-yl] pyrazol-1-yl]-1-(3-hydroxyazetidin-1-yl)ethanone (80.0 mg, 129 μmol, 40%) as a yellow solid. $^1$H NMR (400 MHz, $CDCl_3$): δ=9 (d, J=4.0 Hz, 1H), 8.41 (d, J=2.8 Hz, 1H), 8.29 (d, J=2.0 Hz, 1H), 7.90-7.83 (m, 1H), 7.68 (d, J=8.8 Hz, 1H), 7.45-7.38 (m, 1H), 7.15 (d, J=2.4 Hz, 1H), 7.10-7.01 (m, 1H), 5.50 (s, 1H), 5.41 (s, 1H), 4.88 (s, 2H), 4.75-4.65 (m, 1H), 4.42-4.29 (m, 2H), 4.10-3.93 (m, 2H), 3.58-3.49 (m, 2H), 2.67 (d, J=2.4 Hz, 3H), 0.94-0.85 (m, 2H), −0.04 (d, J=16.0 Hz, 9H).

Step 2. 2-(4-(8-Chloro-7-((2-methyl-1H-benzo[d]imidazol-6-yl)oxy)quinoxalin-2-yl)-1H-pyrazol-1-yl)-1-(3-hydroxyazetidin-1-yl)ethanone A solution of 2-[4-[8-chloro-7-[2-methyl-3-(2-trimethylsilylethoxymethyl)benzimidazol-5-yl]oxy-quinoxalin-2-yl] pyrazol-1-yl]-1-(3-hydroxyazetidin-1-yl)ethanone (75.0 mg, 120 μmol) in trifluoroacetic acid (0.5 mL) was stirred at 25° C. for 1 h. On completion, the reaction mixture was concentrated under reduced pressure. The residue was purified by prep-HPLC (column: Waters Xbridge 150*25 mm*5 μm; mobile phase: [water (0.05% ammonium hydroxide v/v)-acetonitrile]; (B %: 14%-44%, 8 min) to give 2-[4-[8-chloro-7-[(2-methyl-3H-benzimidazol-5-yl)oxy]quinoxalin-2-yl] pyrazol-1-yl]-1-(3-hydroxyazetidin-1-yl)ethanone (22.1 mg, 45 μmol, 36%) as an off-white solid. $^1$H NMR (400 MHz, DMSO-$d_6$): δ=12.44-12.15 (m, 1H), 9.33 (s, 1H), 8.66 (s, 1H), 8.38 (s, 1H), 8.06-7.89 (m, 1H), 7.58-7.43 (m, 1H), 7.38-7.14 (m, 2H), 7-6.89 (m, 1H), 5.80 (d, J=6.0 Hz, 1H), 5.02 (s, 2H), 4.58-4.46 (m, 1H), 4.41-4.33 (m, 1H), 4.18-4.07 (m, 1H), 3.98-3.89 (m, 1H), 3.70-3.62 (m, 1H), 2.49 (s, 3H); m/z ES+ $[M+H]^+$ 490.1.

Example 152. Synthesis of 2-(4-(8-chloro-7-((2-methyl-1H-benzo[d]imidazol-6-yl)oxy)quinoxalin-2-yl)-1H-pyrazol-1-yl) acetamide

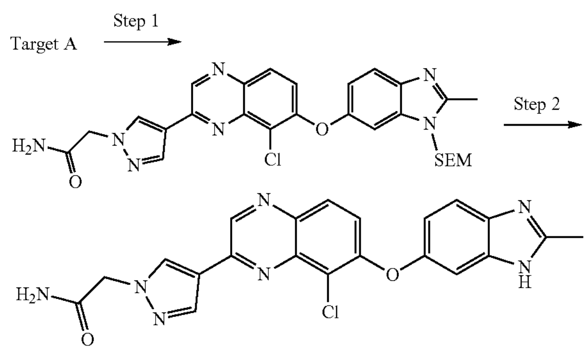

Step 1. 2-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl) acetamide To a solution of 2-[[6-[5-chloro-3-(1H-pyrazol-4-yl)quinoxalin-6-yl]oxy-2-methyl-benzimida-zol-1-yl]methoxy]ethyl-trimethyl-silane (100 mg, 197 μmol) in acetonitrile (3 mL) was added cesium carbonate (200 mg, 614 μmol), potassium iodide (70 mg, 422 μmol) and 2-bromoacetamide (30.0 mg, 218 μmol). The mixture was stirred at 80° C. for 2 h. On completion, the mixture was quenched with water (3 mL) and extracted with ethyl acetate (5 mL×3). The combined organic layers were dried over anhydrous sodium sulfate, filtered and concentrated to give 2-[4-[8-chloro-7-[2-methyl-3-(2-trimethylsilylethoxymethyl)benzimidazol-5-yl]oxy-quinoxalin-2-yl]pyrazol-1-yl]acetamide (110 mg, crude) as a yellow solid. m/z ES+ $[M+H]^+$ 564.2.

Step 2. 2-(4-(8-Chloro-7-((2-methyl-1H-benzo[d]imidazol-6-yl)oxy)quinoxalin-2-yl)-1H-pyrazol-1-yl)acetamide A solution of 2-[4-[8-chloro-7-[2-methyl-3-(2-trimethylsilylethoxymethyl)benzimidazol-5-yl]oxy-quinoxalin-2-yl]pyrazol-1-yl]acetamide (110 mg, 195 μmol) in trifluoroacetic acid (3 mL) was stirred at 25° C. for 2 h. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 8%-38%, 7 min) to give 2-[4-[8-chloro-7-[(2-methyl-3H-benzimidazol-5-yl)oxy]quinoxalin-2-yl]pyrazol-1-yl]acetamide (45.5 mg, 105 μmol, 54%) as a white solid. $^1$H NMR (400 MHz, DMSO-$d_6$): δ=9.34 (s, 1H), 8.67 (s, 1H), 8.37 (s, 1H), 7.98 (d, J=9.2 Hz, 1H), 7.64 (s, 1H), 7.57 (d, J=8.8 Hz, 1H), 7.35 (d, J=9.2 Hz, 2H), 7.27 (d, J=2.4 Hz, 1H), 7.05-6.98 (m, 1H), 4.92 (s, 2H), 2.54 (s, 3H); m/z ES+ $[M+H]^+$ 434.0.

Example 153. Synthesis of 2-(4-(8-chloro-7-((2-methyl-1H-benzo[d]imidazol-6-yl)oxy)quinoxalin-2-yl)-1H-pyrazol-1-yl)-1-(3-hydroxypyrrolidin-1-yl)ethanone

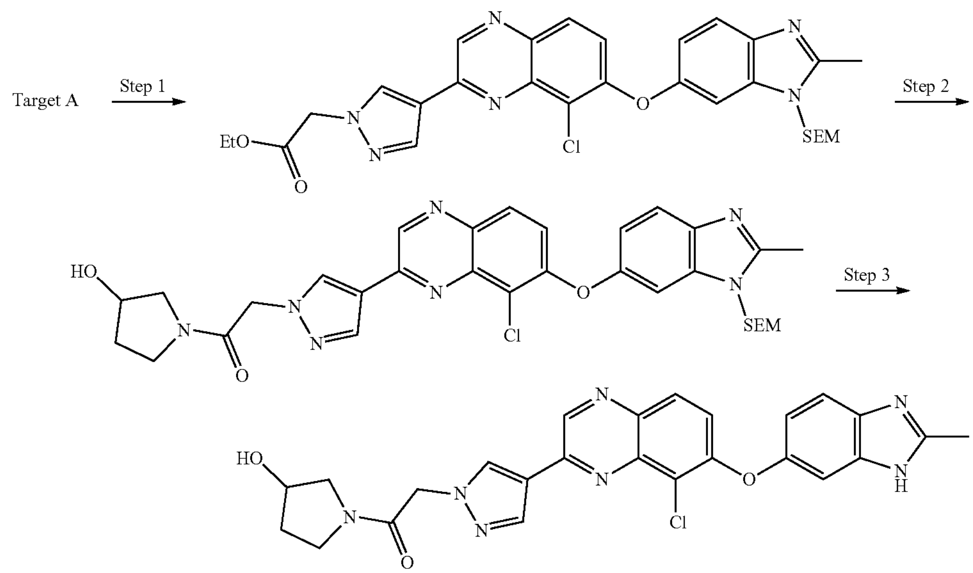

Step 1. Ethyl 2-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)acetate To a solution of 2-[[6-[5-chloro-3-(1H-pyrazol-4-yl)quinoxalin-6-yl]oxy-2-methyl-benzimidazol-1-yl]methoxy]ethyl-trimethylsilane (500 mg, 986 μmol) in tetrahydrofuran (20 mL) was added sodium hydride (118 mg, 2.96 mmol, 60% in mineral oil), the mixture was stirred at 25° C. for 0.5 h. Then ethyl 2-bromoacetate (247 mg, 1.48 mmol, 164 μL) was added and the mixture was stirred at 60° C. for 1.5 h. On completion, the reaction mixture was quenched with saturated ammonium chloride solution (30 mL) at 20° C. and then diluted with water (70 mL). The mixture was extracted with ethyl acetate (100 mL×2). The combined organic layers were washed with brine (150 mL×2), dried over anhydrous sodium sulfate, filtered and concentrated in vacuo and the residue was purified by column chromatography (silica gel, dichloromethane: ethyl alcohol=90:1 to 80:1) to give ethyl 2-(4-(8-chloro-7-((2-methyl-1-((2-(trimethylsilyl)ethoxy)methyl)-$^1$H-benzo[d]imidazol-6-yl)oxy)quinoxalin-2-yl)-1H-pyrazol-1-yl)acetate (280 mg, 0.47 mmol, 48%) as a yellow solid. $^1$H NMR (400 MHz, DMSO-$d_6$): δ=9.36-9.34 (m, 1H), 8.73 (s, 1H), 8.42 (s, 1H), 7.97 (d, J=9.2 Hz, 1H), 7.60 (d, J=8.8 Hz, 1H), 7.44 (d, J=2.4 Hz, 1H), 7.34 (d, J=9.2 Hz, 1H), 7.01 (dd, J=2.4, 8.8 Hz, 1H), 5.54 (s, 2H), 5.24 (s, 2H), 4.20 (q, J=7.2 Hz, 2H), 3.48 (t, J=8.0 Hz, 2H), 2.56 (s, 3H), 1.24 (t, J=7.2 Hz, 3H), 0.79 (t, J=8.0 Hz, 2H), −0.14 (s, 9H); m/z ES+ $[M+H]^+$ 593.1.

Step 2. 2-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-1-(3-hydroxypyrrolidin-1-yl)ethanone To a solution of pyrrolidin-3-ol (29.4 mg, 337 μmol) in ethanol (2 mL) was added 3,4,6,7,8,9-hexahydro-2Hpyrimido[1,2-a]pyrimidine (46.9 mg, 337 μmol) and ethyl 2-[4-[8-chloro-7-[2-methyl-3-(2-trimethylsilylethoxymethyl)benzimidazol-5-yl]oxy-quinoxalin-2-yl]pyrazol-1-yl]acetate (100 mg, 169 μmol). The mixture was stirred at 25° C. for 2 h. On completion, the reaction mixture was concentrated in vacuo and the residue was purified by prep-TLC (silica gel, dichloromethane: ethanol=10:1) to give 2-[4-[8-chloro-7-[2-methyl-3-(2-trimethylsilylethoxymethyl)benzimidazol-5-yl]oxy-quinoxalin-2-yl]pyrazol-1-yl]-1-(3-hydroxypyrrolidin-1-yl)ethanone (38 mg, 60 μmol, 36%) as a yellow solid. m/z ES+ $[M+H]^+$ 634.2.

Step 3. 2-(4-(8-Chloro-7-((2-methyl-1H-benzo[d]imidazol-6-yl)oxy)quinoxalin-2-yl)-1H-pyrazol-1-yl)-1-(3-hydroxypyrrolidin-1-yl)ethanone A solution of 2-[4-[8-chloro-7-[2-methyl-3-(2-trimethylsilylethoxymethyl)benzimidazol-5-yl]oxy-quinoxalin-2-yl]pyrazol-1-yl]-1-(3-hydroxypyrrolidin-1-yl)ethanone (35.0 mg, 55.2 μmol) in trifluoroacetic acid (0.8 mL) was stirred at 25° C. for 2 h. On completion, the reaction mixture was concentrated in vacuo to give a residue. The crude product was purified by prep-HPLC (column: Phenomenex Synergi C18 150*25 mm*10 μm; mobile phase: [water (0.225% formic acid)-acetonitrile]; (B %: 3%-33%, 10 min) to give 2-[4-[8-chloro-7-[(2-methyl-3H-benzimidazol-5-yl)oxy] quinoxalin-2-yl]pyrazol-1-yl]-1-(3-hydroxypyrrolidin-1-yl) ethanone (7.7 mg, 15.3 μmol, 28%) as a yellow gum. $^1$H NMR (400 MHz, DMSO-$d_6$): δ=9.33 (s, 1H), 8.64 (s, 1H), 8.36 (s, 1H), 7.96 (d, J=9.2 Hz, 1H), 7.51 (d, J=8.4 Hz, 1H), 7.31 (d, J=9.2 Hz, 1H), 7.22 (d, J=2.0 Hz, 1H), 6.95 (dd, J=2.4, 8.8 Hz, 1H), 5.22 (d, J=2.0 Hz, 1H), 5.17 (d, J=6.8 Hz, 1H), 4.41-4.28 (m, 1H), 3.67-3.60 (m, 2H), 3.42-3.32 (m, 3H), 2.49 (s, 3H), 2.05-1.74 (m, 2H); m/z ES+ $[M+H]^+$ 504.1.

Example 154. Synthesis of 1-(3-(4-(8-chloro-7-((2-methyl-1H-benzo[d]imidazol-6-yl)oxy)quinoxalin-2-yl)-1H-pyrazol-1-yl)cyclobutyl)azetidin-3-ol

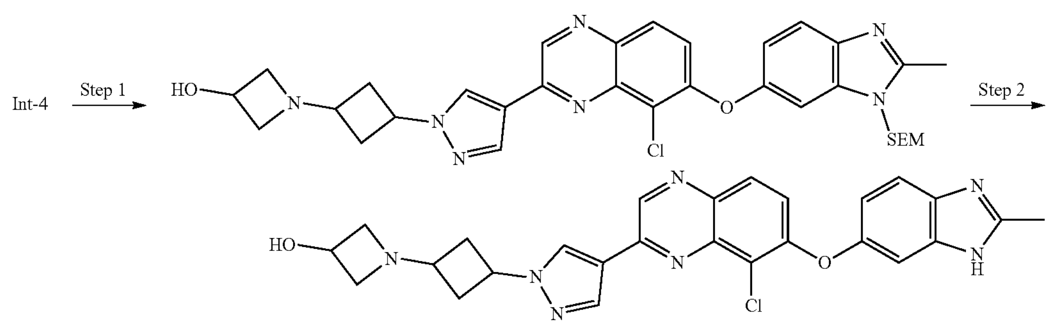

Step 1. 1-(3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)cyclobutyl) azetidin-3-ol A solution of 3-[4-[8-chloro-7-[2-methyl-3-(2-trimethylsilylethoxymethyl)benzimidazol-5-yl]oxy-quinoxalin-2-yl] pyrazol-1-yl]cyclobutanone (130 mg, 230 μmol), azetidin-3-ol hydrochloride (74 mg, 680 μmol), titanium tetraisopropanolate (130 mg, 450 μmol, 130 L) and diisopropylethylamine (88 mg, 680 μmol, 120 μL) in methanol (2 mL) was stirred at 60° C. for 2 h. Then sodium cyanoborohydride (14 mg, 230 μmol) was added and the reaction mixture was stirred at 25° C. for 2 h. On completion, the reaction mixture was filtered and concentrated under reduced pressure. The residue was purified by prep-TLC (silica gel, dichloromethane:methanol=10:1) to give 1-(3-(4-(8-chloro-7-((2-methyl-1-((2-(trimethylsilyl)ethoxy) methyl)-1H-benzo[d]imidazol-6-yl)oxy)quinoxalin-2-yl)-1H-pyrazol-1-yl)cyclobutyl)azetidin-3-ol (25 mg, 40 μmol, 17%) as a white solid. m/z ES+ $[M+H]^+$ 632.5.

Step 2. 1-(3-(4-(8-Chloro-7-((2-methyl-1H-benzo[d] imidazol-6-yl)oxy)quinoxalin-2-yl)-1H-pyrazol-1-yl) cyclobutyl)azetidin-3-ol A solution of 1-[3-[4-[8-chloro-7-[2-methyl-3-(2-trimethylsilylethoxymethyl)benzimidazol-5-yl]oxy-quinoxalin-2-yl]pyrazol-1-yl]cyclobutyl]azetidin-3-ol (20 mg, 31 μmol) in trifluoroacetic acid (0.3 mL) was stirred at 25° C. for 0.5 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 2%-32%, 10 min) to give 1-[3-[4-[8-chloro-7-[(2-methyl-3H-benzimidazol-5-yl)oxy]quinoxalin-2-yl]pyrazol-1-yl]cyclobutyl]azetidin-3-ol (8.4 mg, 16 μmol, 44%, formic acid salt) as a yellow solid. $^1$HNMR (400 MHz, DMSO-$d_6$): 8-9.35-9.29 (m, 1H), 8.80 (d, J=8.0 Hz, 1H), 8.40 (d, J=1.6 Hz, 1H), 8.15 (s, 1H), 7.96 (d, J=9.2 Hz, 1H), 7.51 (d, J=8.4 Hz, 1H), 7.32 (d, J=9.2 Hz, 1H), 7.21 (s, 1H), 6.94 (dd, J=2.0, 8.8 Hz, 1H), 5.16-4.70 (m, 1H), 4.34-4.26 (m, 1H), 3.75-3.69 (m, 2H), 3.45 (s, 1H), 3.35-3.30 (m, 1H), 3.22 (s, 1H), 3.02 (s, 1H), 2.69-2.57 (m, 2H), 2.49 (s, 3H), 2.43-2.31 (m, 2H); m/z ES+ $[M+H]^+$ 502.1.

Example 155. Synthesis of 8-chloro-2-(1-((3,3-difluorocyclobutyl)methyl)-3-methyl-1H-pyrazol-4-yl)-7-((2-methyl-1H-benzo[d]imidazol-6-yl)oxy)quinoxaline and 8-chloro-2-(1-((3,3-difluorocyclobutyl) methyl)-5-methyl-1H-pyrazol-4-yl)-7-((2-methyl-1H-benzo[d]imidazol-6-yl)oxy)quinoxaline

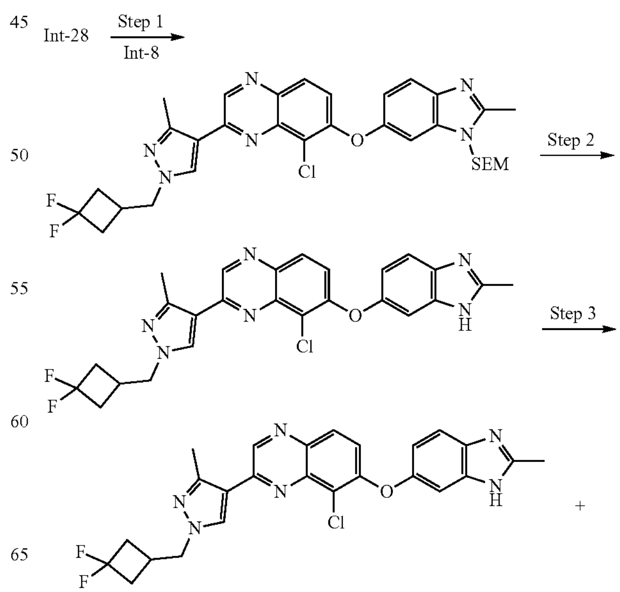

-continued

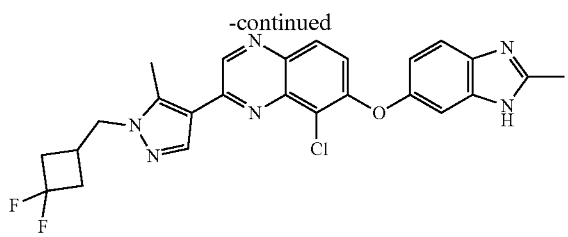

Step 1. 2-[[6-[5-Chloro-3-[1-[(3,3-difluorocyclobutyl)methyl]-5-methyl-pyrazol-4-yl]quinoxalin-6-yl]oxy-2-methyl-benzimidazol-1-yl]methoxy]ethyl-trimethyl-silane To a solution of 2-[[6-[5-chloro-3-(5-methyl-1H-pyrazol-4-yl)quinoxalin-6-yl]oxy-2-methyl-benzimidazol-1-yl]methoxy]ethyl-trimethyl-silane (200 mg, 383 μmol) in N,N-dimethyl formamide (2 mL) was added potassium carbonate (159 mg, 1.15 mmol) and (3,3-difluorocyclobutyl)methyl methanesulfonate (99.8 mg, 498 μmol). The mixture was stirred at 80° C. for 3 h. On completion, the reaction mixture was concentrated under reduced pressure and the residue was purified by reversed-phase HPLC (0.1% ammonium hydroxide) to give 2-[[6-[5-chloro-3-[1-[(3,3-difluorocyclobutyl)methyl]-5-methyl-pyrazol-4-yl]quinoxalin-6-yl]oxy-2-methyl-benzimidazol-1-yl]methoxy]ethyl-trimethyl-silane (mixture of regio-isomers, 70.0 mg, 111 μmol, 28%) as a yellow solid. m/z ES+ $[M+H]^+$ 625.2.

Step 2. 8-Chloro-2-[1-[(3,3-difluorocyclobutyl)methyl]-5-methyl-pyrazol-4-yl]-7-[(2-methyl-3H-benzimidazol-5-yl)oxy]quinoxaline To a solution of 2-[[6-[5-chloro-3-[1-[(3,3-difluorocyclobutyl)methyl]-5-methyl-pyrazol-4-yl]quinoxalin-6-yl]oxy-2-methyl-benzimidazol-1-yl]methoxy]ethyl-trimethyl-silane (60.0 mg, 95.9 μmol) in trifluoroacetic acid (0.5 mL) was added trifluoroacetic acid (923 mg, 8.10 mmol). The mixture was stirred at 25° C. for 0.5 h. On completion, the reaction mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 20%-50%, 7 min) to give 8-chloro-2-[1-[(3,3-difluorocyclobutyl)methyl]-5-methyl-pyrazol-4-yl]-7-[(2-methyl-3H-benzimidazol-5-yl)oxy]quinoxaline (mixture of regio-isomers, 45.0 mg, 90.9 μmol, 94%) as a white solid. m/z ES+ $[M+H]^+$ 495.0.

Step 3. 8-Chloro-2-[1-[(3,3-difluorocyclobutyl)methyl]-3-methyl-pyrazol-4-yl]-7-[(2-methyl-3H-benzimidazol-5-yl)oxy]quinoxaline and 8-chloro-2-[1-[(3,3-difluorocyclobutyl)methyl]-5-methyl-pyrazol-4-yl]-7-[(2-methyl-3H-benzimidazol-5-yl)oxy]quinoxaline 8-Chloro-2-[1-[(3,3-difluorocyclobutyl)methyl]-5-methyl-pyrazol-4-yl]-7-[(2-methyl-3H-benzimidazol-5-yl)oxy]quinoxaline (45.0 mg, 90.9 μmol) was separated by SFC (column: Daicel Chiralpak AD (250 mm*30 mm, 10 μm); mobile phase: [methanol-acetonitrile]; (B %: 60%-60%, 6 min, total run 60 min) to give 8-chloro-2-[1-[(3,3-difluorocyclobutyl)methyl]-3-methyl-pyrazol-4-yl]-7-[(2-methyl-3H-benzimidazol-5-yl)oxy]quinoxaline (21.3 mg, 43.0 μmol, 47%) as a white solid and 8-chloro-2-[1-[(3,3-difluorocyclobutyl)methyl]-5-methyl-pyrazol-4-yl]-7-[(2-methyl-3H-benzimidazol-5-yl)oxy]quinoxaline (15.9 mg, 32.1 μmol, 34%) as a white solid.

$^1$H NMR (400 MHz, DMSO-$d_6$) δ 9.24 (s, 1H), 8.80 (s, 1H), 7.96 (d, J=9.2 Hz, 1H), 7.55 (d, J=8.8 Hz, 1H), 7.32 (d, J=9.2 Hz, 1H), 7.25 (d, J=2.4 Hz, 1H), 6.01-6.96 (m, 1H), 4.28 (d, J=6.0 Hz, 2H), 2.77-2.70 (m, 2H), 2.70 (s, 3H), 2.68-2.66 (m, 1H), 2.57-2.53 (m, 2H), 2.52 (s, 3H); m/z ES+ $[M+H]^+$ 495.0.

$^1$H NMR (400 MHz, DMSO-$d_6$) § 12.54-12.11 (m, 1H), 9.32 (s, 1H), 8.44 (s, 1H), 7.95 (d, J-9.2 Hz, 1H), 7.51 (d, J=8.8 Hz, 1H), 7.30 (d, J=9.2 Hz, 1H), 7.22 (d, J=2.0 Hz, 1H), 6.97-6.92 (m, 1H), 4.33 (d, J=5.6 Hz, 2H), 2.90 (s, 3H), 2.73-2.63 (m, 3H), 2.58-2.52 (m, 2H), 2.49 (s, 3H); m/z ES+ $[M+H]^+$ 495.0.

Example 156. Synthesis of 2-(4-(8-chloro-7-((2-methyl-1H-benzo[d]imidazol-6-yl)oxy)quinoxalin-2-yl)-1H-pyrazol-1-yl)-1-(3-methoxypyrrolidin-1-yl)ethan-1-one

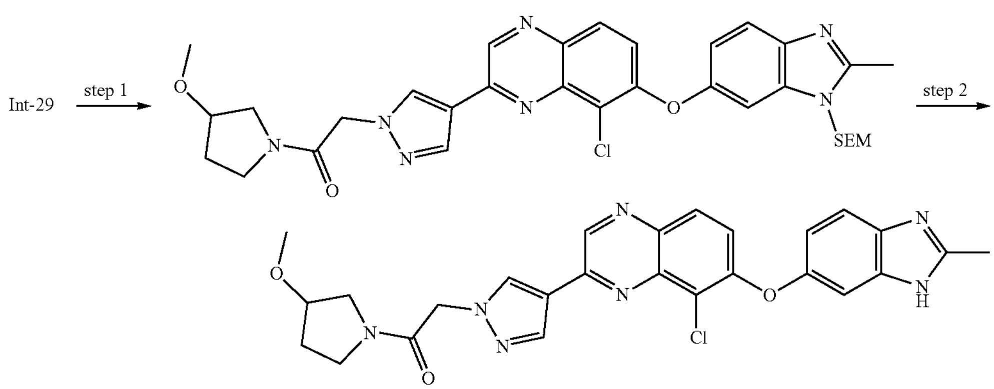

Step 1. 2-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-1-(3-methoxypyrrolidin-1-yl)ethan-1-one To a mixture of 2-[4-[8-chloro-7-[2-methyl-3-(2-trimethylsilylethoxymethyl)benzimidaz ol-5-yl]oxy-quinoxalin-2-yl]pyrazol-1-yl]acetic acid (100 mg, 176 μmol), 3-methoxypyrrolidine (36.0 mg, 265 μmol) and 3-(ethyliminomethylideneamino) propyl-dimethylazanium;chloride (50.8 mg, 265 μmol) in dichloromethane (1.5 mL) was added hydroxybenzotriazole (35.8 mg, 265 μmol) and diisopropylethylamine (68.6 mg, 530 μmol). The reaction mixture was stirred at 25° C. for 2 h. On completion, the reaction mixture was extracted with ethyl acetate (2×20 mL). The combined organic layers were washed with brine (2×20 mL), dried over anhydrous sodium sulfate, filtered and concentrated under reduced pressure to give 2-[4-[8-chloro-7-[2-methyl-3-(2-trimethylsilylethoxymethyl)benzimidazol-5-yl]oxy-quinoxalin-2-yl]pyrazol-1-yl]-1-(3-methoxypyrrolidin-1-yl)ethanone (110 mg, 169 μmol, 96%) as a yellow solid. m/z ES+ $[M+H]^+$ 648.1.

Step 2. 2-(4-(8-Chloro-7-((2-methyl-1H-benzo[d]imidazol-6-yl)oxy)quinoxalin-2-yl)-1H-pyrazol-1-yl)-1-(3-methoxypyrrolidin-1-yl)ethan-1-one A mixture of 2-[4-[8-chloro-7-[2-methyl-3-(2-trimethylsilylethoxymethyl)benzimidazol-5-yl]oxy-quinoxalin-2-yl]pyrazol-1-yl]-1-(3-methoxypyrrolidin-1-yl)ethanone (90.0 mg, 138 μmol) in trifluoroacetic acid (1 mL) was stirred at 25° C. for 0.5 h. On completion, the reaction mixture was concentrated in vacuo and the residue was purified by prep-HPLC (column: Waters Xbridge 150*25 mm*5 μm; mobile phase: [water (10 mM ammonium bicarbonate)-acetonitrile]; (B %: 25%-55%, 8 min) to give 2-[4-[8-chloro-7-[(2-methyl-3H-benzimidazol-5-yl)oxy]quinoxalin-2-yl]pyrazol-1-yl]-1-(3-methoxypyrrolidin-1-yl)ethanone (23.5 mg, 45.5 μmol, 33%) as a white solid. $^1H$ NMR (400 MHz, DMSO-$d_6$) δ 12.78-11.97 (m, 1H), 9.34 (s, 1H), 8.64 (s, 1H), 8.37 (s, 1H), 7.96 (d, J=9.2 Hz, 1H), 7.51 (d, J=8.8 Hz, 1H), 7.32 (d, J=9.0 Hz, 1H), 7.22 (d, J=2.0 Hz, 1H), 6.95 (m, 1H), 5.29-5.13 (m, 2H), 4.11-3.94 (m, 1H), 3.72-3.46 (m, 4H), 3.27 (d, J=16.0 Hz, 3H), 2.49 (s, 3H), 2.13-1.90 (m, 2H); m/z ES+ $[M+H]^+$ 518.1.

Example 157. Synthesis of 4-((4-(8-bromo-7-((2-methyl-1H-benzo[d]imidazol-6-yl)oxy)quinoxalin-2-yl)-1H-pyrazol-1-yl)methyl)tetrahydro-2H-thiopyran 1,1-dioxide and 3-(2-(4-(8-bromo-7-((2-methyl-1H-benzo[d]imidazol-6-yl)oxy)quinoxalin-2-yl)-1H-pyrazol-1-yl)ethyl)tetrahydrothiophene 1,1-dioxide

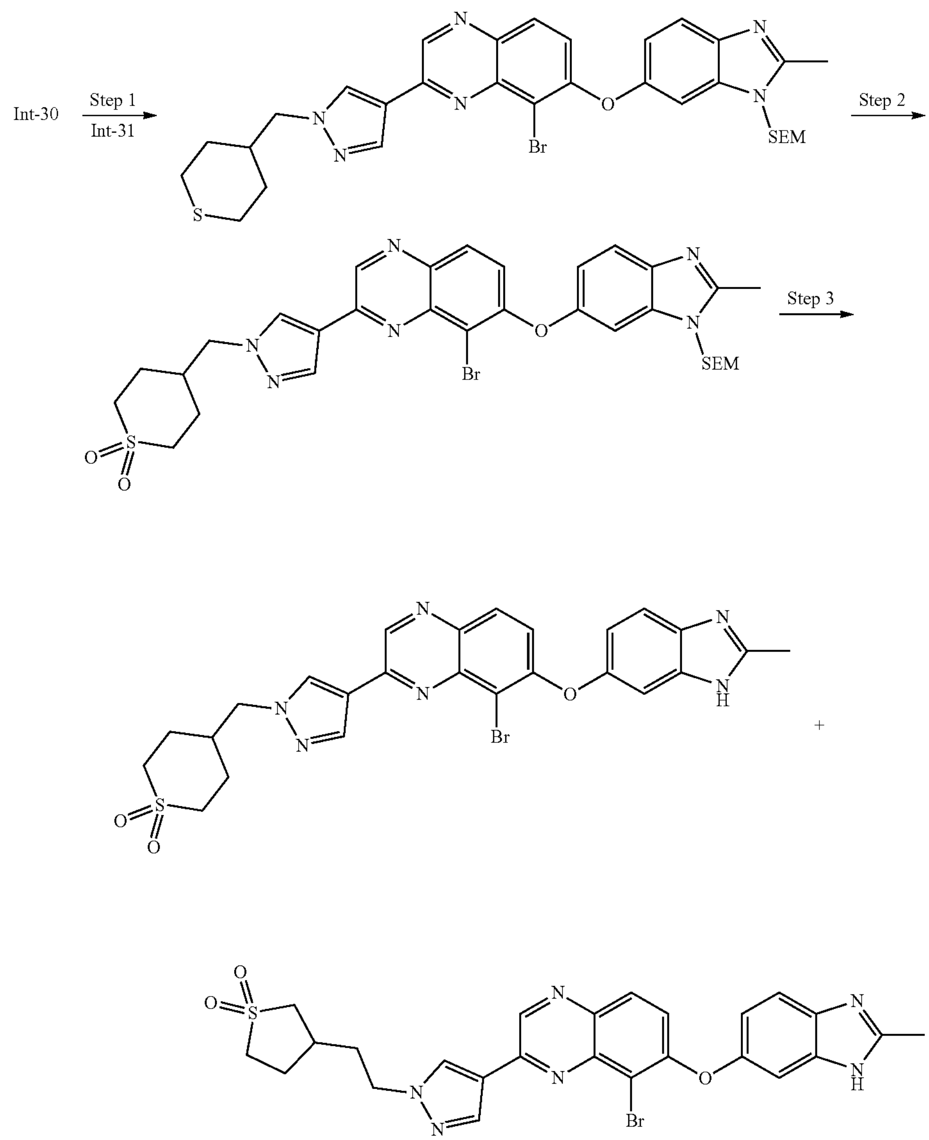

Step 1. 8-Bromo-7-((2-methyl-1-((2-(trimethylsilyl)ethoxy)methyl)-1H-benzo[d]imidazol-6-yl)oxy)-2-(1-((tetrahydro-2H-thiopyran-4-yl)methyl)-1H-pyrazol-4-yl)quinoxaline To a solution of 2-[[6-[5-bromo-3-(1H-pyrazol-4-yl)quinoxalin-6-yl]oxy-2-methyl-benzimidazol-1-yl]methoxy]ethyl-trimethyl-silane (30.0 mg, 54.4 μmol) and tetrahydrothiopyran-4-ylmethyl methanesulfonate (14.9 mg, 70.7 μmol) in N,N-dimethyl formamide (1 mL) was added potassium carbonate (22.6 mg, 163 μmol). The mixture was stirred at 80° C. for 12 h. The reaction mixture was diluted with water (20 mL) and extracted with ethyl acetate (15 mL×3). The combined organic layers were dried over sodium sulfate, filtered and concentrated under reduced pressure to give 8-bromo-7-((2-methyl-1-((2-(trimethylsilyl)ethoxy)methyl)-1H-benzo[d]imidazol-6-yl)oxy)-2-(1-((tetrahydro-2H-thiopyran-4-yl)methyl)-1H-pyrazol-4-yl)quinoxaline (35.0 mg, crude) as a yellow oil. m/z ES+ $[M+H]^+$ 667.2.

Step 2. 4-((4-(8-Bromo-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)tetrahydro-2H-thiopyran 1,1-dioxide To a solution of 2-[[6-[5-bromo-3-[1-(tetrahydrothiopyran-4-ylmethyl)pyrazol-4-yl]quinoxalin-6-yl]oxy-2-methyl-benzimidazol-1-yl]methoxy]ethyl-trimethyl-silane (35.0 mg, 52.6 μmol) in dichloromethane (1 mL) was added m-chloroperbenzoic acid (23.5 mg, 116 μmol, 85% purity) at 0° C. The mixture was stirred at 25° C. for 2 h. The mixture was poured into sodium sulfite aqueous solution (20 mL) and extracted with ethyl acetate (15 mL×3). The combined organic layers were dried with anhydrous sodium sulfate, filtered and concentrated to give 4-((4-(8-bromo-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)tetrahydro-2H-thiopyran 1,1-dioxide (36.0 mg, crude) as a yellow oil. m/z ES+ $[M+H]^+$ 697.2.

Step 3. 4-((4-(8-Bromo-7-((2-methyl-1H-benzo[d]imidazol-6-yl)oxy)quinoxalin-2-yl)-1H-pyrazol-1-yl)methyl)tetrahydro-2H-thiopyran 1,1-dioxide and 3-(2-(4-(8-bromo-7-((2-methyl-1H-benzo[d]imidazol-6-yl)oxy)quinoxalin-2-yl)-1H-pyrazol-1-yl)ethyl)tetrahydrothiophene 1,1-dioxide A solution of 2-[[6-[5-bromo-3-[1-[(1,1-dioxothian-4-yl)methyl]pyrazol-4-yl]quinoxalin-6-yl]oxy-2-methyl-benzimidazol-1-yl]methoxy]ethyl-trimethyl-silane (36.0 mg, 51.6 μmol) in trifluoroacetic acid (1 mL) was stirred at 25° C. for 0.5 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 11%-41%, 10 min) to give 4-((4-(8-bromo-7-((2-methyl-1H-benzo[d]imidazol-6-yl)oxy)quinoxalin-2-yl)-1H-pyrazol-1-yl)methyl)tetrahydro-2H-thiopyran 1,1-dioxide (3.8 mg, 6.6 μmol, 13%) as a white solid and 3-(2-(4-(8-bromo-7-((2-methyl-1H-benzo[d]imidazol-6-yl)oxy)quinoxalin-2-yl)-1H-pyrazol-1-yl)ethyl)tetrahydrothiophene 1,1-dioxide (8.2 mg, 14.3 μmol, 28%) as a white solid.

$^1$H NMR (400 MHz, DMSO-$d_6$) δ=9.28 (s, 1H), 8.70 (s, 1H), 8.40 (s, 1H), 8.18 (s, 1H), 7.99 (d, J=9.2 Hz, 1H), 7.59-7.43 (m, 1H), 7.36-7.11 (m, 2H), 6.93 (d, J=6.4 Hz, 1H), 4.25 (d, J=7.2 Hz, 2H), 3.14 (d, J=12.0 Hz, 2H), 3.09-3.02 (m, 2H), 2.49-2.48 (m, 3H), 2.31-2.22 (m, 1H), 1.93 (d, J=13.2 Hz, 2H), 1.72 (d, J=12.4 Hz, 2H); m/z ES+ $[M+H]^+$ 569.0.

$^1$H NMR (400 MHz, DMSO-$d_6$) δ=9.28 (s, 1H), 8.74 (s, 1H), 8.38 (s, 1H), 8.16 (s, 1H), 7.99 (d, J=9.2 Hz, 1H), 7.57-7.46 (m, 1H), 7.33-7.14 (m, 2H), 6.97-6.90 (m, 1H), 4.31 (t, J=6.8 Hz, 2H), 3.27-3.15 (m, 2H), 3.08-2.98 (m, 1H), 2.85-2.77 (m, 1H), 2.49-2.48 (m, 3H), 2.34-2.24 (m, 2H), 2.11-2.02 (m, 2H), 1.80 (t, J=10.4 Hz, 1H); m/z ES+ [M+H]] 569.0.

Example 158. Synthesis of 1-[4-[8-chloro-7-[(2-methyl-3H-benzimidazol-5-yl)oxy]quinoxalin-2-yl]pyrazol-1-yl]-2-methyl-propan-2-ol

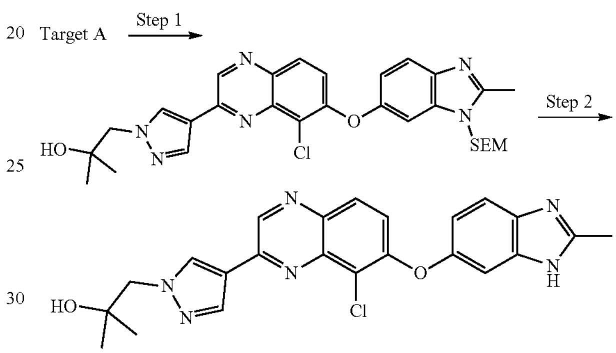

Step 1. 1-[4-[8-Chloro-7-[2-methyl-3-(2-trimethylsilylethoxymethyl)benzimidazol-5-yl]oxy-quinoxalin-2-yl]pyrazol-1-yl]-2-methyl-propan-2-ol To a solution of 2-[[6-[5-chloro-3-(1H-pyrazol-4-yl)quinoxalin-6-yl]oxy-2-methyl-benzimidazol-1-yl]methoxy]ethyl-trimethyl-silane (100 mg, 197 μmol) in N,N-dimethyl formamide (1.5 mL) was added cesium carbonate (193 mg, 592 μmol) and 2,2-dimethyloxirane (15.6 mg, 217 μmol). The mixture was stirred at 100° C. for 2 h. The reaction mixture was diluted with water (3 mL) and extracted with ethyl acetate (3 mL×3). The combined organic layers were washed with brine (3 mL×3), dried over sodium sulfate, filtered and concentrated in vacuo to give 1-[4-[8-chloro-7-[2-methyl-3-(2-trimethylsilylethoxymethyl)benzimidazol-5-yl]oxy-quinoxalin-2-yl]pyrazol-1-yl]-2-methyl-propan-2-ol (200 mg, crude) as a yellow oil. $^1$H NMR (400 MHz, DMSO-$d_6$) δ 9.34 (d, J=4.0 Hz, 1H), 8.61 (s, 1H), 8.36 (s, 1H), 7.95 (s, 1H), 7.70-7.55 (m, 1H), 7.47-7.23 (m, 2H), 7.01 (br dd, J=2.0, 8.8 Hz, 1H), 5.67-5.45 (m, 2H), 4.84 (s, 1H), 4.15 (s, 2H), 3.61-3.43 (m, 2H), 2.57 (br d, J=7.2 Hz, 3H), 1.13 (s, 6H), 0.79 (s, 2H), −0.01-−0.11 (m, 4H), −0.12-−0.19 (m, 5H).

Step 2. 1-[4-[8-Chloro-7-[(2-methyl-3H-benzimidazol-5-yl)oxy]quinoxalin-2-yl]pyrazol-1-yl]-2-methyl-propan-2-ol A solution of 1-[4-[8-chloro-7-[2-methyl-3-(2-trimethylsilylethoxymethyl)benzimidazol-5-yl]oxy-quinoxalin-2-yl]pyrazol-1-yl]-2-methyl-propan-2-ol (200 mg, 345 μmol) in trifluoroacetic acid (0.2 mL) was stirred at 25° C. for 1 h. The reaction mixture was concentrated in vacuo. The residue was purified by prep-HPLC (column: Phenomenex Luna C18 150*25 mm*10 μm; mobile phase: [water (0.225% formic acid)-acetonitrile]; (B %: 12%-42%, 10 min) and then repurified by prep-HPLC (column: Shim-pack C18 150*25*10 μm; mobile phase: [water (0.225% formic acid)-acetonitrile]; (B %: 1%-30%, 10 min) to give 1-[4-[8-chloro-7-[(2-methyl-3H-benzimidazol-5-yl)oxy]quinoxalin-2-yl] pyrazol-1-yl]-2-methyl-propan-2-ol (42.4 mg, 94.4 μmol, 27%) as a white solid. $^1$H NMR (400 MHz, DMSO-$d_6$) δ 12.66-11.98 (m, 1H), 9.33 (s, 1H), 8.61 (s, 1H), 8.36 (s, 1H), 8.19 (s, 1H), 7.96 (d, J=9.2 Hz, 1H), 7.51 (br d, J=7.6 Hz, 1H), 7.32 (br d, J=9.2 Hz, 1H), 7.21 (br s, 1H), 6.94 (br d, J=8.8 Hz, 1H), 4.83 (br s, 1H), 4.16 (s, 2H), 2.49-2.49 (m, 3H), 1.14 (s, 6H); m/z ES+ $[M+H]^+$ 449.1.

Example 159. Synthesis of 8-Chloro-2-[1-[(3-methoxycyclobutyl)methyl]pyrazol-4-yl]-7-[(2-methyl-3H-benzimidazol-5-yl)oxy]quinoxaline

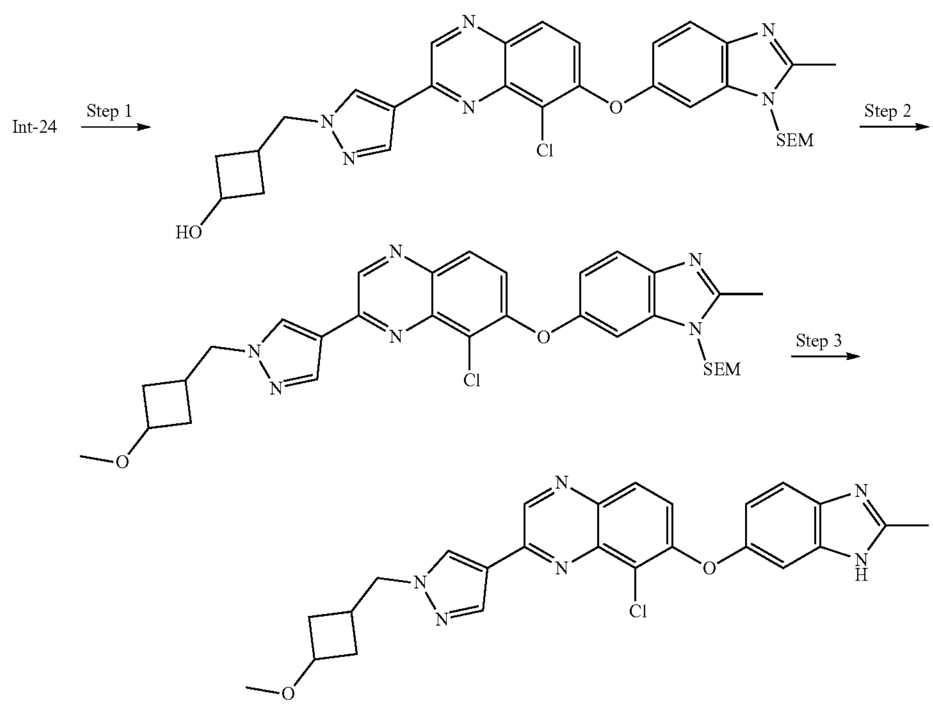

Step 1. 3-[[4-[8-Chloro-7-[2-methyl-3-(2-trimethylsilylethoxymethyl)benzimidazol-5-yl]oxy-quinoxalin-2-yl]pyrazol-1-yl]methyl]cyclobutanol To a solution of 3-[[4-[8-chloro-7-[2-methyl-3-(2-trimethylsilylethoxymethyl)benzimidazol-5-yl]oxy-quinoxalin-2-yl]pyrazol-1-yl]methyl]cyclobutanone (140 mg, 238 μmol) in ethanol (1.5 mL) was added sodium borohydride (18.0 mg, 475 μmol). The mixture was stirred at 0° C. for 1 h. The reaction mixture was quenched with water (3 mL) at 0° C., and then extracted with ethyl acetate (3 mL×3). The combined organic layers were washed with brine (3 mL×3), dried over sodium sulfate, filtered and concentrated in vacuo to give 3-[[4-[8-chloro-7-[2-methyl-3-2trimethylsilylethoxymethyl)benzimidazol-5-yl]oxy-quinoxalin-2-yl] pyrazol-1yl]methyl]cyclobutanol (110 mg, 186 μmol, 78%) as a yellow oil. m/z ES+ $[M+H]^+$ 591.1.

Step 2. 2-[[6-[5-Chloro-3-[1-[(3-methoxycyclobutyl)methyl]pyrazol-4-yl]quinoxalin-6-yl]oxy-2-methyl-benzimidazol-1-yl]methoxy]ethyl-trimethyl-silane To a solution of 3-[[4-[8-chloro-7-[2-methyl-3-(2-trimethylsilylethoxymethyl)benzimidazol-5-yl]oxy-quinoxalin-2-yl]pyrazol-1-yl]methyl]cyclobutanol (100 mg, 169 μmol) in tetrahydrofuran (1 mL) was added aqueous sodium hydroxide (10.2 mg, 254 μmol, 60 wt %) at 0° C. The mixture was stirred at 0° C. for 0.5 h. Then methyl iodide (24.0 mg, 169 μmol) was added. The mixture was stirred at 25° C. for 1.5 h. The reaction mixture was quenched with water (6 mL) at 0° C., and then extracted with ethyl acetate (5 mL×3). The combined organic layers were washed with brine (5 mL×3), dried over sodium sulfate, filtered and concentrated in vacuo to give 2-[[6-[5-chloro-3-[1-[(3-methoxycyclobutyl)methyl]pyrazol-4-yl]quinoxalin-6-yl] oxy-2-methyl-benzimidazol-1-yl]methoxy]ethyl-trimethyl-silane (140 mg, crude) as a brown solid. m/z ES+ $[M+H]^+$ 605.2.

Step 3. 8-Chloro-2-[1-[(3-methoxycyclobutyl) methyl]pyrazol-4-yl]-7-[(2-methyl-3H-benzimidazol-5-yl)oxy]quinoxaline A mixture of 2-[[6-[5-chloro-3-[1-[(3-methoxycyclobutyl)methyl]pyrazol-4-yl]quinoxalin-6-yl]oxy-2-methyl-benzimidazol-1-yl]methoxy]ethyl-trimethyl-silane (140 mg, 231 μmol) in trifluoroacetic acid (1.5 mL) was stirred at 25° C. for 1 h. The reaction mixture filtered and concentrated under reduced pressure. The residue was purified by prep-HPLC (column: Phenomenex Luna C18 150*25 mm*10 μm; mobile phase: [water (0.225% formic acid)-acetonitrile]; (B %: 12%-42%, 10 min) to give 8-chloro-2-[1-[(3-methoxycyclobutyl)methyl]pyrazol-4-yl]-

7-[(2-methyl-3H-benzimidazol-5-yl)oxy]quinoxaline (26.3 mg, 55.4 μmol, 24%) as a yellow solid. $^1$H NMR (400 MHz, DMSO-$d_6$) δ 9.33 (d, J=1.6 Hz, 1H), 8.77-8.66 (m, 1H), 8.35 (s, 1H), 8.14 (d, J=2.0 Hz, 1H), 7.99 (br d, J=9.2 Hz, 1H), 7.65 (br d, J=8.8 Hz, 1H), 7.38 (br d, J=9.2 Hz, 1H), 7.33 (s, 1H), 7.10 (br d, J=8.8 Hz, 1H), 4.37-4.21 (m, 2H), 4-3.70 (m, 1H), 3.17-3.03 (m, 3H), 2.79-2.68 (m, 1H), 2.67 (br s, 1H), 2.62 (s, 3H), 2.33-2.10 (m, 2H), 1.66 (br d, J=8.0 Hz, 2H); m/z ES+ [M+H]$^+$ 475.1.

Example 160. Synthesis of3-(4-(8-chloro-7-((2-methyl-1H-benzo[d]imidazol-6-yl)oxy)quinoxalin-2-yl)-1H-pyrazol-1-yl)-3-methylbutanamide

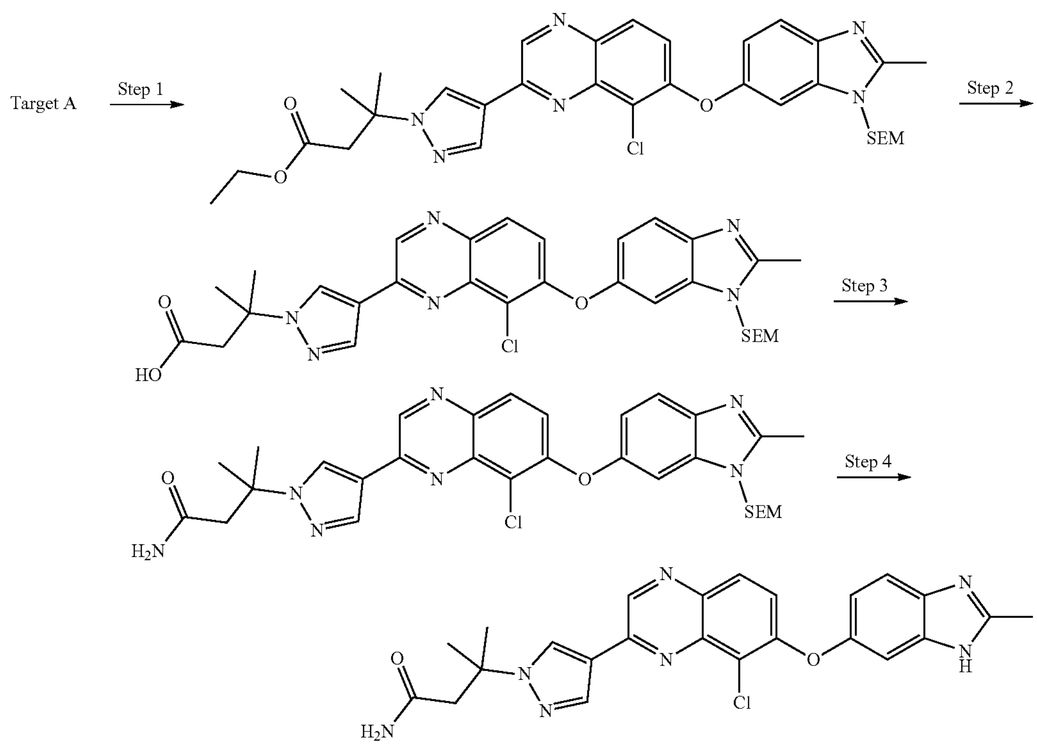

Step 1. Ethyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanoate To a solution of 2-[[6-[5-chloro-3-(1H-pyrazol-4-yl)quinoxalin-6-yl]oxy-2-methyl-benzimidazol-1-yl]methoxy]ethyl-trimethyl-silane (700 mg, 1.38 mmol) and ethyl 3-methylbut-2-enoate (265 mg, 2.07 mmol, 288 μL) in N,N-dimethyl formamide (14 mL) was added cesium carbonate (900 mg, 2.76 mmol). The mixture was stirred at 25° C. for 48 h. The reaction mixture was diluted with water (50 mL) and extracted with ethyl acetate (20 mL×3). The combined organic layers were dried over sodium sulfate, filtered and concentrated under reduced pressure. The residue was purified by column chromatography (silica gel, petroleum ether/ethyl acetate=1/0 to 1/9) to give ethyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanoate (340 mg, 455 μmol, 33%) as a yellow solid. $^1$H NMR (400 MHz, DMSO-$d_6$) δ=9.38-9.36 (m, 1H), 8.79 (s, 1H), 8.34 (s, 1H), 7.96 (d, J=9.2 Hz, 1H), 7.60 (d, J=8.8 Hz, 1H), 7.44 (d, J=2.3 Hz, 1H), 7.34-7.30 (m, 1H), 7.01 (dd, J=2.4, 8.8 Hz, 1H), 5.56-5.52 (m, 2H), 3.96 (q, J=7.2 Hz, 2H), 3.51-3.46 (m, 2H), 3 (s, 2H), 2.57-2.54 (m, 3H), 1.73 (s, 6H), 1.07 (t, J=7.2 Hz, 3H), 0.81-0.75 (m, 2H), −0.12-−0.16 (m, 9H).

Step 2. 3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanoic acid To a solution of ethyl 3-[4-[8-chloro-7-[2-methyl-3-(2-trimethylsilylethoxymethyl)benzimidazol-5-yl]oxy-quinoxalin-2-yl]pyrazol-1-yl]-3-methyl-butanoate (270 mg, 361 μmol, 85% purity) in methanol (2.5 mL), tetrahydrofuran (2.5 mL) and water (2.5 mL) was added lithium hydroxide monohydrate (45.5 mg, 1.08 mmol). The mixture was stirred at 25° C. for 1 h. The reaction mixture was concentrated in vacuo and then adjusted to pH ~ 5 with citric acid aqueous solution. The mixture was filtered and the filtered cake was collected to give 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanoic acid (150 mg, crude) as a yellow solid. m/z ES+ [M+H]$^+$ 607.3.

Step 3. 3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanamide To a solution of 3-[4-[8-chloro-7-[2-methyl-3-(2-trimethylsilylethoxymethyl)benzimidazol-5-yl]oxy-quinoxalin-2-yl]pyrazol-1-yl]-3-methyl-butanoic acid (150 mg, 247

μmol) and ammonium chloride (132 mg, 2.47 mmol) in N,N-dimethyl formamide (5 mL) was added diisopropylethylamine (95.8 mg, 741 μmol, 129 μL) and 2-(7-aza-1H-benzotriazole-1-yl)-1,1,3,3-tetramethyluronium hexafluorophosphate (141 mg, 371 μmol). The mixture was stirred at 25° C. for 12 h. The reaction mixture was diluted with water (20 mL) and extracted with ethyl acetate (15 mL×3). The combined organic layers were dried over sodium sulfate, filtered and concentrated under reduced pressure to give 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-3-methylbutanamide (180 mg, crude) as a yellow oil. m/z ES+ $[M+H]^+$ 606.3.

Step 4. 3-(4-(8-Chloro-7-((2-methyl-1H-benzo[d]imidazol-6-yl)oxy)quinoxalin-2-yl)-1H-pyrazol-1-yl)-3-methylbutanamide A solution of 3-[4-[8-chloro-7-[2-methyl-3-(2-trimethylsilylethoxymethyl)benzimidazol-5-yl]oxy-quinoxalin-2-yl]pyrazol-1-yl]-3-methyl-butanamide (50.0 mg, 82.5 μmol) in trifluoroacetic acid (1 mL) was stirred at 25° C. for 0.5 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 10%-40%, 10 min) to give 3-(4-(8-chloro-7-((2-methyl-1H-benzo[d]imidazol-6-yl)oxy)quinoxalin-2-yl)-1H-pyrazol-1-yl)-3-methylbutanamide (17.8 mg, 37.4 μmol, 45%) as an off-white solid. $^1H$ NMR (400 MHz, DMSO-$d_6$) δ=9.36 (s, 1H), 8.75 (s, 1H), 8.35 (s, 1H), 7.96 (d, J=9.2 Hz, 1H), 7.53 (d, J=8.6 Hz, 1H), 7.33-7.27 (m, 2H), 7.23 (s, 1H), 6.97 (d, J=8.6 Hz, 1H), 6.82 (s, 1H), 2.74 (s, 2H), 2.49-2.48 (m, 3H), 1.73 (s, 6H); m/z ES+ $[M+H]^+$ 476.1.

Example 161. Synthesis of 8-chloro-2-[1-[(3,3-difluorocyclopentyl)methyl]pyrazol-4-yl]-7-[(2-methyl-3H-benzimidazol-5-yl)oxy]quinoxaline Step 1. (3,3-Difluorocyclopentyl)methyl methanesulfonate To a solution of (3,3-difluorocyclopentyl) methanol (100 mg, 735 μmol) in dichloromethane (3 mL) was added triethylamine (145 mg, 1.44 mmol, 200 μL) and methylmethanedisulfonyl chloride (104 mg, 904 μmol, 70 μL). The mixture was stirred at 0° C. for 1 h. On completion, the mixture was quenched with water (3 mL) and extracted with ethyl acetate (10 mL×3). The combined organic layers were dried over anhydrous sodium sulfate, filtered and concentrated to give (3,3-difluorocyclopentyl)methyl methanesulfonate (200 mg, crude) as a yellow oil.

Step 2. 2-[[6-[5-Chloro-3-[1-[(3,3-difluorocyclopentyl)methyl]pyrazol-4-yl]quin-oxalin-6-yl]oxy-2-methyl-benzimidazol-1-yl]methoxy]ethyl-trimethyl-silane To a solution of (3,3-difluorocyclopentyl)methyl methanesulfonate (66.4 mg, 310 μmol) and 2-[[6-[5-chloro-3-(1H-pyrazol-4-yl)quinoxalin-6-yl]oxy-2-methyl-benzimidazol-1-yl]methoxy]ethyl-trimethyl-silane (100 mg, 197 μmol) in N,N-dimethylformamide (2 mL) was added potassium carbonate (75.0 mg, 543 μmol). The mixture was stirred at 80° C. for 12 h. On completion, the mixture was quenched with water (3 mL) and extracted with ethyl acetate (5 mL× 3). The combined organic layers were dried over anhydrous sodium sulfate, filtered and concentrated and the residue was purified by column chromatography (silica gel, petroleum ether/ethyl acetate=1/1 to 0/1) to give 2-[[6-[5-chloro-3-[1-[(3,3-difluorocyclopentyl)methyl]pyrazol-4-yl]quinoxalin-6-yl]oxy-2-methyl-benzimidazol-1-yl]methoxy]ethyl-trimethyl-silane (100 mg, 160 μmol, 80%) as a yellow oil. m/z ES+ $[M+H]^+$ 625.2.

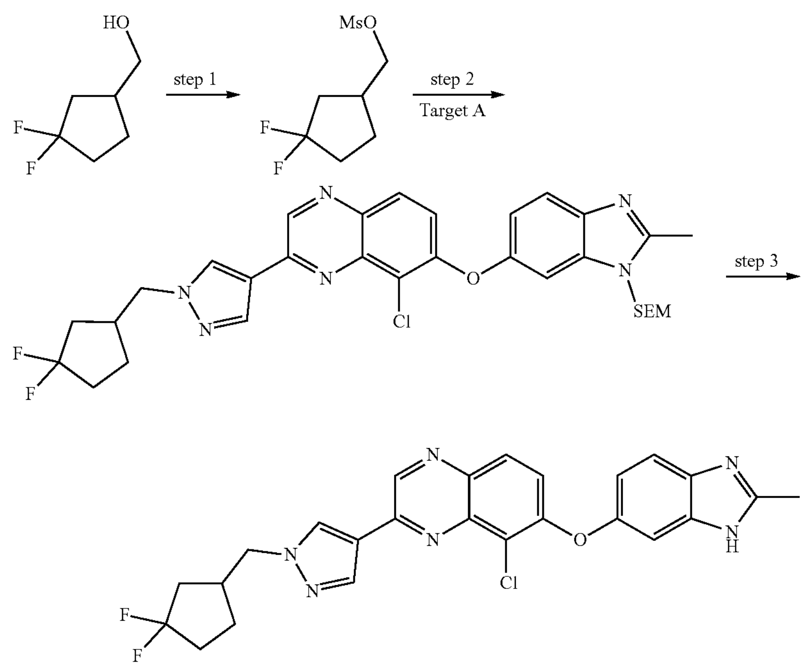

Step 3. 8-Chloro-2-[1-[(3,3-difluorocyclopentyl)methyl]pyrazol-4-yl]-7-[(2-methyl-3H-benzimidazol-5-yl)oxy]quinoxaline A solution of 2-[[6-[5-chloro-3-[1-[(3,3-difluorocyclopentyl)methyl]pyrazol-4-yl]quinoxalin-6-yl]oxy-2-methyl-benzimidazol-1-yl]methoxy]ethyl-trimethyl-silane (100 mg, 160 μmol) in trifluoroacetic acid (2 mL) was stirred at 20° C. for 2 h. On completion, the mixture was filtered and concentrated under reduced pressure. The residue was purified by prep-HPLC (column: Phenomenex Gemini-NX C18 75*30 mm*3 μm; mobile phase: [water (0.225% formic acid)-acetonitrile]; (B %: 20%-50%, 7 min) and re-purified by prep-HPLC (column: Waters Xbridge 150*25 mm*5 μm; mobile phase: [water (0.05% ammonium hydroxide v/v)-acetonitrile]; (B %: 33%-63%, 9 min) to give 8-chloro-2-[1-[(3,3-difluorocyclopentyl)methyl]pyrazol-4-yl]-7-[(2-methyl-3H-benzimidazol-5-yl)oxy]quinoxaline (27 mg, 54 μmol, 34%) as a white solid. $^1$H NMR (400 MHz, DMSO-$d_6$) δ 12.60-12 (m, 1H), 9.31 (s, 1H), 8.74 (s, 1H), 8.38 (s, 1H), 7.95 (d, J=9.2 Hz, 1H), 7.51 (br d, J=8.8 Hz, 1H), 7.31 (d, J=9.2 Hz, 1H), 7.21 (br s, 1H), 7.01-6.86 (m, 1H), 4.28 (d, J=7.2 Hz, 2H), 2.79-2.64 (m, 1H), 2.49 (br s, 3H), 2.28-1.80 (m, 5H), 1.65-1.53 (m, 1H); m/z ES+ $[M+H]^+$ 495.1.

Example 162. Synthesis of 2-[4-[8-chloro-7-[(2-methyl-3H-benzimidazol-5-yl)oxy]quinoxalin-2-yl]pyrazol-1-yl]-1-(3,3-difluoropyrrolidin-1-yl)ethanone

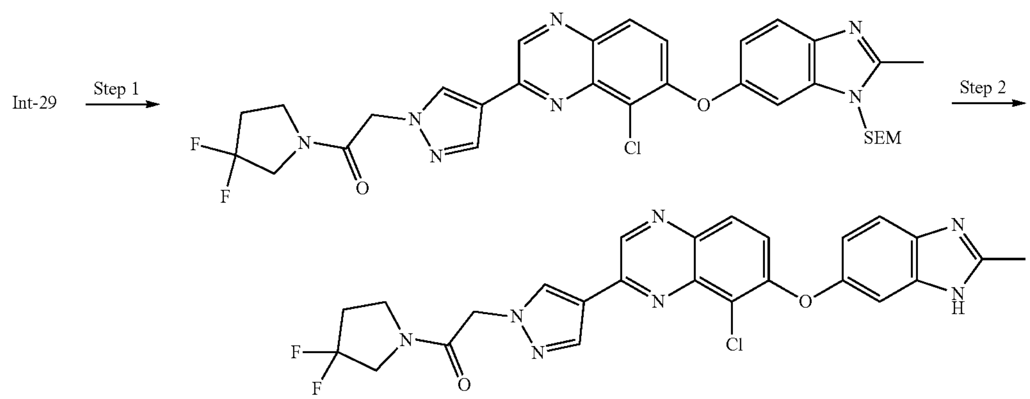

Step 1. 2-[4-[8-Chloro-7-[2-methyl-3-(2-trimethylsilylethoxymethyl)benzimidazol-5-yl]oxy-quinoxalin-2-yl]pyrazol-1-yl]-1-(3,3-difluoropyrrolidin-1-yl)ethanone To a solution of 2-[4-[8-chloro-7-[2-methyl-3-(2-trimethylsilylethoxymethyl)benzimidazol-5-yl]oxy-quinoxalin-2-yl]pyrazol-1-yl]acetic acid (100 mg, 177 μmol), 3,3-difluoropyrrolidine hydrochloride (38.1 mg, 265 μmol) and diisopropylethylamine (68.6 mg, 531 μmol, 92.5 μL) in dichloromethane (2 mL) was added 3-(ethyliminomethylideneamino) propyl-dimethylazanium;chloride (50.9| mg, 265 μmol) and hydroxybenzotriazole (35.9 mg, 265 μmol). The mixture was stirred at 25° C. for 2 h. On completion, the reaction mixture was diluted with water (30 mL) and extracted with ethyl acetate (30 mL×2). The combined organic layers were washed with brine (60 mL×2), dried over sodium sulfate, filtered and concentrated in vacuo to give 2-[4-[8-chloro-7-[2-methyl-3-(2-trimethylsilylethoxymethyl)benzimidazol-5-yl]oxy-quinoxalin-2-yl]pyrazol-1-yl]-1-(3,3-difluoropyrrolidin-1-yl)ethanone (121 mg, crude) as a yellow solid. m/z ES+ $[M+H]^+$ 654.2.

Step 2. 2-[4-[8-Chloro-7-[(2-methyl-3H-benzimidazol-5-yl)oxy]quinoxalin-2-yl]pyrazol-1-yl]-1-(3,3-difluoropyrrolidin-1-yl)ethanone A solution of 2-[4-[8-chloro-7-[2-methyl-3-(2-trimethylsilylethoxymethyl)benzimidazol-5-yl]oxy-quinoxalin-2-yl]pyrazol-1-yl]-1-(3,3-difluoropyrrolidin-1-yl)ethanone (112 mg, 171 μmol) in trifluoroacetic acid (1.8 mL) was stirred at 25° C. for 2 h. On completion, the reaction mixture was concentrated in vacuo to give a residue. The crude product was purified by prep-HPLC (column: Phenomenex Synergi C18 150*25 mm*10 μm; mobile phase: [water (0.225% formic acid)-acetonitrile]; (B %: 9%-39%, 10 min) to give 2-[4-[8-chloro-7-[(2-methyl-3H-benzimidazol-5-yl)oxy]quinoxalin-2-yl]pyrazol-1-yl]-1-(3,3-difluoropyrrolidin-1-yl)ethanone (41.6 mg, 79 μmol, 46%) as a white solid. $^1$H NMR (400 MHz, DMSO-$d_6$) δ=12.61-12.06 (m, 1H), 9.34 (s, 1H), 8.64 (d, J=4.4 Hz, 1H), 8.38 (d, J=1.2 Hz, 1H), 7.96 (d, J=9.2 Hz, 1H), 7.51 (d, J=8.0 Hz, 1H), 7.32 (d, J=9.2 Hz, 1H), 7.22 (s, 1H), 6.95 (dd, J=2.4, 8.8 Hz, 1H), 5.31-5.20 (m, 2H), 4.10 (t, J=13.2 Hz, 1H), 3.88-3.73 (m, 2H), 3.59 (t, J=7.6 Hz, 1H), 2.63-2.53 (m, 1H), 2.49 (s, 3H), 2.46-2.37 (m, 1H); m/z ES+ $[M+H]^+$ 524.0.

Example 163. Synthesis of 2-(1-((3S,4S)-3-fluoropiperidin-4-yl)-1H-pyrazol-4-yl)-8-methyl-7-((2-methyl-1H-benzo[d]imidazol-6-yl)oxy)quinoxaline Int-33 Step 1

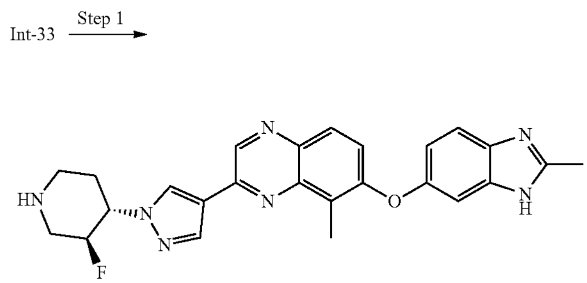

Step 1. 2-(1-((3S,4S)-3-Fluoropiperidin-4-yl)-1H-pyrazol-4-yl)-8-methyl-7-((2-methyl-1H-benzo[d]imidazol-6-yl)oxy)quinoxaline To a solution of 2-(1-((3S,4S)-3-fluoropiperidin-4-yl)-1H-pyrazol-4-yl)-8-methyl-7-((2-methyl-1-((2-(trimethylsilyl)ethoxy)methyl)-1H-benzo[d]imidazol-6-yl)oxy)quinoxaline (145 mg, 247 μmol) in tetrahydrofuran (2 mL) was added pyridine hydrofluoride (244 mg, 2.47 mmol, 0.22 mL). The mixture was stirred at 80° C. for 0.5 h. On completion, the reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 4%-34%, 10 min) to give 2-(1-((3S,4S)-3-fluoropiperidin-4-yl)-1H-pyrazol-4-yl)-8-methyl-7-((2-methyl-1H-benzo[d]imidazol-6-yl)oxy)quinoxaline (26.4 mg, 57.6 μmol, 23%) as an off-white solid. $^1$H NMR (400 MHz, DMSO-$d_6$) δ 9.25 (s, 1H), 8.78 (s, 1H), 8.43 (s, 1H), 7.84 (d, J=9.2 Hz, 1H), 7.47 (d, J=8.8 Hz, 1H), 7.25 (d, J=9.2 Hz, 1H), 7.07 (s, 1H), 6.88 (dd, J=2.0, 8.8 Hz, 1H), 5.09-4.91 (m, 1H), 4.69-4.60 (m, 1H), 3.49 (d, J=11.2 Hz, 1H), 3.14 (d, J=11.2 Hz, 1H), 2.87-2.73 (m, 2H), 2.69 (s, 3H), 2.47 (s, 3H), 2.15 (s, 2H); m/z ES+ $[M+H]^+$ 458.1.

Example 164. Synthesis of 8-cyclopropyl-7-((2-methyl-1H-benzo[d]imidazol-6-yl)oxy)-2-(1-(piperidin-4-yl)-1H-pyrazol-4-yl)quinoxaline

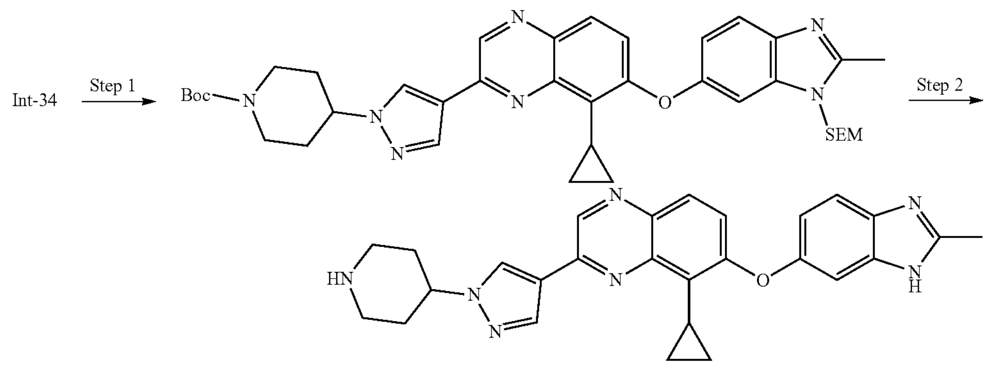

Step 1. 4-(4-(8-Cyclopropyl-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate To a solution of tert-butyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (70 mg, 101 μmol), cyclopropylboronic acid (87.1 mg, 1.01 mmol) in dioxane (1 mL) and water (0.1 mL) was added XPhos Pd G2 (8.0 mg, 10.1 μmol) and sodium carbonate (21.5 mg, 202 μmol). The mixture was stirred at 100° C. for 5 h under nitrogen. On completion, the mixture was concentrated under reduced pressure. The residue was purified by column chromatography (silica gel, petroleum ether/ethyl acetate=1/1 to 0/1) to give tert-butyl 4-(4-(8-cyclopropyl-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (70 mg, 10.1 μmol, 99%) as a yellow oil. m/z ES+ $[M+H]^+$ 696.4.

Step 2. 8-Cyclopropyl-7-((2-methyl-1H-benzo[d]imidazol-6-yl)oxy)-2-(1-(piperidin-4-yl)-1H-pyrazol-4-yl)quinoxaline A solution of tert-butyl 4-(4-(8-cyclopropyl-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (70 mg, 100 μmol) in trifluoroacetic acid (1 mL) was stirred at 25° C. for 0.5 h. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 5%-35%, 7 min) to give 8-cyclopropyl-7-((2-methyl-1H-benzo[d]imidazol-6-yl)oxy)-2-(1-(piperidin-4-yl)-1H-pyrazol-4-yl)quinoxaline (12.5 mg, 26.8 μmol, 26%) as a yellow solid. $^1$H NMR (400 MHz, $CD_3OD$) δ 9.09 (s, 1H), 8.56 (s, 1H), 8.39-8.22 (m, 2H), 7.77 (d, J=9.2 Hz, 1H), 7.53 (d, J=8.8 Hz, 1H), 7.28 (d, J=9.0 Hz, 1H), 7.07 (s, 1H), 6.99 (d, J=8.8 Hz, 1H), 4.71 (td, J=4.8, 9.6 Hz, 1H), 3.64 (d, J=13.2 Hz, 2H), 3.32-3.18 (m, 2H), 2.86 (d, J=5.6 Hz, 1H), 2.61 (s, 3H), 2.49-2.32 (m, 4H), 1.63 (d, J=3.2 Hz, 2H), 1.06 (d, J=8.8 Hz, 2H); m/z ES+ $[M+H]^+$ 466.1.

Example 165. Synthesis of 2-[4-[8-chloro-7-[(2-methyl-3H-benzimidazol-5-yl)oxy]quinoxalin-2-yl]pyrazol-1-yl]-1-(3-fluoropyrrolidin-1-yl)ethanone

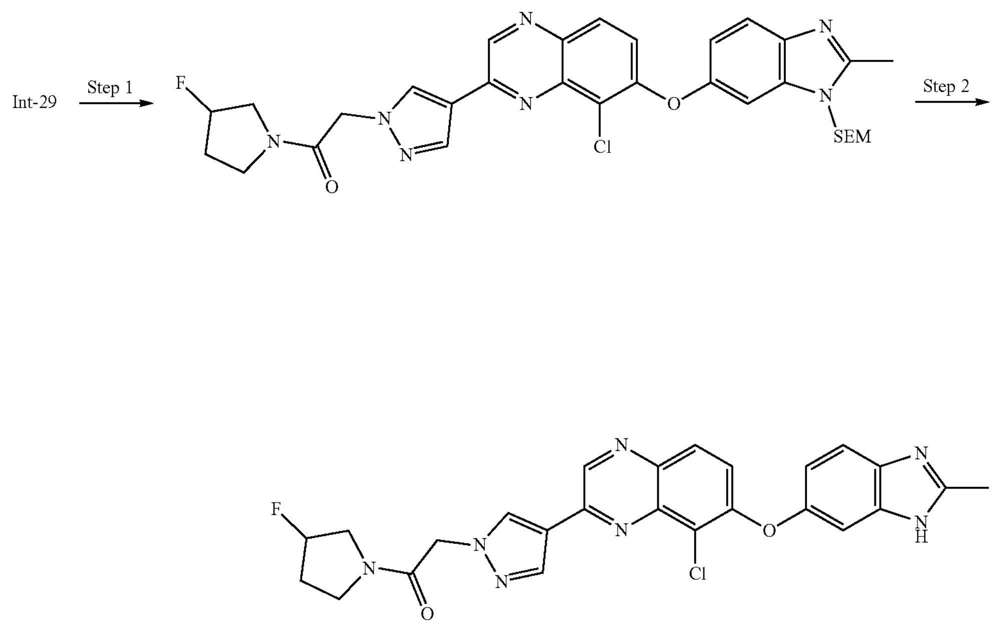

Step 1. 2-[4-[8-Chloro-7-[2-methyl-3-(2-trimethylsilylethoxymethyl)benzimidazol-5-yl]oxy-quinoxalin-2-yl]pyrazol-1-yl]-1-(3-fluoropyrrolidin-1-yl)ethanone To a solution of 2-[4-[8-chloro-7-[2-methyl-3-(2-trimethylsilylethoxymethyl)benzimidazol-5-yl]oxy-quinoxalin-2-yl]pyrazol-1-yl]acetic acid (100 mg, 177 μmol), 3-fluoropyrrolidine hydrochloride (33.3 mg, 265 μmol) and diisopropylethylamine (68.6 mg, 531 μmol, 92.5 μL) in dichloromethane (2 mL) was added 3-(ethyliminomethylideneamino) propyl-dimethylazanium;chloride (50.9 mg, 265 μmol) and hydroxybenzotriazole (35.9 mg, 265 μmol). The mixture was stirred at 25° C. for 12 h. On completion, the reaction mixture was diluted with water (30 mL) and extracted with ethyl acetate (30 mL×2). The combined organic layers were washed with brine (60 mL×2), dried over sodium sulfate, filtered and concentrated in vacuo to give 2-[4-[8-chloro-7-[2-methyl-3-(2-trimethylsilylethoxymethyl)benzimidazol-5-yl]oxy-quinoxalin-2-yl]pyrazol-1-yl]-1-(3-fluoropyrrolidin-1-yl)ethanone (113 mg, crude) as a yellow solid. m/z ES+ $[M+H]^+$ 636.2.

Step 2. 2-[4-[8-Chloro-7-[(2-methyl-3H-benzimidazol-5-yl)oxy]quinoxalin-2-yl]pyrazol-1-yl]-1-(3-fluoropyrrolidin-1-yl)ethanone A solution of 2-[4-[8-chloro-7-[2-methyl-3-(2-trimethylsilylethoxymethyl)benzimidazol-5-yl]oxy-quinoxalin-2-yl]pyrazol-1-yl]-1-(3-fluoropyrrolidin-1-yl)ethanone (100 mg, 157 μmol) in trifluoroacetic acid (1.8 mL) was stirred at 25° C. for 1 h. On completion, the reaction mixture was concentrated in vacuo to give a residue. The crude product was purified by prep-HPLC (column: Phenomenex Synergi C18 150*25 mm*10 μm; mobile phase: [water (0.225% formic acid)-acetonitrile]; (B %: 11%-31%, 10 min) to give 2-[4-[8-chloro-7-[(2-methyl-3H-benzimidazol-5-yl)oxy]quinoxalin-2-yl]pyrazol-1-yl]-1-(3-fluoropyrrolidin-1-yl)ethanone (35.9 mg, 70.9 μmol, 45%) as a white solid. $^1H$ NMR (400 MHz, DMSO-$d_6$) δ=12.66-12.12 (m, 1H), 9.34 (s, 1H), 8.65 (d, J=2.0 Hz, 1H), 8.38 (s, 1H), 7.96 (d, J=9.2 Hz, 1H), 7.51 (d, J=8.8 Hz, 1H), 7.32 (d, J=9.2 Hz, 1H), 7.22 (s, 1H), 6.95 (dd, J=2.0, 8.8 Hz, 1H), 5.55-5.14 (m, 3H), 3.94-3.81 (m, 1H), 3.75-3.44 (m, 3H), 2.50 (s, 3H), 2.31-2.02 (m, 2H); m/z ES+ $[M+H]^+$ 506.0.

Example 166. Synthesis of 2-[1-[[3-(azetidin-1-yl)cyclobutyl]methyl]pyrazol-4-yl]-8-chloro-7-[(2-methyl-3H-benzimidazol-5-yl)oxy]quinoxaline

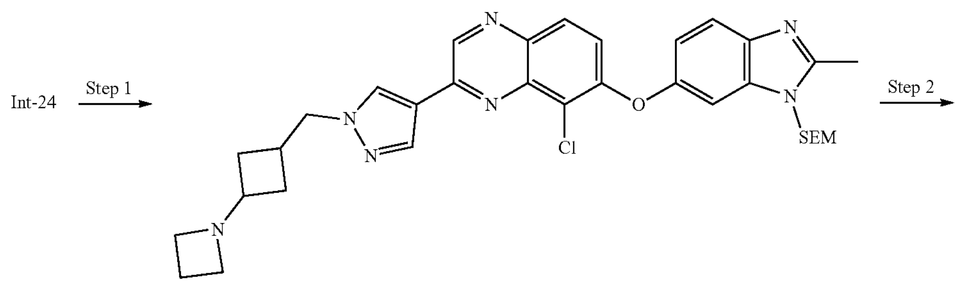

-continued

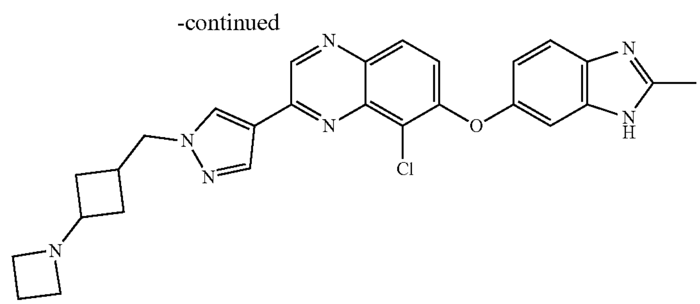

Step 1. 2-[[6-[3-[1-[3-(Azetidin-1-yl)cyclobutyl] methyl]pyrazol-4-yl]-5-chloro-quinoxalin-6-yl]oxy-2-methyl-benzimidazol-1-yl]methoxy]ethyl-trimethyl-silane A solution of 3-[[4-[8-chloro-7-[2-methyl-3-(2-trimethylsilylethoxymethyl)benzimidazol-5-yl]oxy-quinoxalin-2-yl] pyrazol-1-yl]methyl]cyclobutanone (160 mg, 272 μmol), azetidine hydrochloride (140 mg, 1.49 mmol) and acetic acid (1.6 mg, 27.2 μmol) in methanol (1.5 mL) was stirred at 25° C. for 0.2 h. Then sodium cyanoborohydride (34.1 mg, 543 μmol) was added and the mixture was stirred at 40° C. for 2.8 h. The reaction mixture was diluted with sat. sodium bicarbonate (3 mL) and extracted with ethyl acetate (3 mL×3). The combined organic layers were washed with brine (3 mL×3), dried over sodium sulfate, filtered and concentrated in vacuo to give 2-[[6-[3-[1-[[3-(azetidin-1-yl) cyclobutyl]methyl]pyrazol-4-yl]-5-chloro-quinoxalin-6-yl] oxy-2-methyl-benzimidazol-1-yl]methoxy]ethyl-trimethyl-silane (130 mg, 206 μmol, 76%) as a yellow oil. m/z ES+ $[M+H]^+$ 630.4.

Step 2. 2-[[1-[3-(Azetidin-1-yl)cyclobutyl]methyl] pyrazol-4-yl]-8-chloro-7-[(2-methyl-3H-benzimidazol-5-yl)oxy]quinoxaline A mixture of 2-[[6-[3-[1-[3-(azetidin-1-yl)cyclobutyl] methyl]pyrazol-4-yl]-5-chloro-quinoxalin-6-yl]oxy-2-methyl-benzimidazol-1-yl]methoxy]ethyl-trimethyl-silane (120 mg, 190 μmol) in trifluoroacetic acid (1 mL) was stirred at 25° C. for 1 h. The reaction mixture was concentrated in vacuo. The residue was purified by prep-HPLC (column: Phenomenex Gemini-NX C18 75*30 mm*3 μm; mobile phase: [water (0.225% formic acid)-acetonitrile]; (B %: 5%-35%, 7 min) to give 2-[1-[[3-(azetidin-1-yl)cyclobutyl] methyl]pyrazol-4-yl]-8-chloro-7-[(2-methyl-3H-benzimidazol-5-yl)oxy]quinoxaline (32.7 mg, 64.8 μmol, 34%) as a brown solid. $^1H$ NMR (400 MHz, DMSO-$d_6$) δ 10.61-10.30 (m, 1H), 9.36 (d, J=2.0 Hz, 1H), 8.71 (d, J=18.0 Hz, 1H), 8.39 (s, 1H), 8.03 (d, J=9.2 Hz, 1H), 7.73 (d, J=8.8 Hz, 1H), 7.52-7.35 (m, 2H), 7.19 (dd, J=2.0, 8.8 Hz, 1H), 4.34 (br dd, J=7.2, 17.6 Hz, 2H), 4.06 (br dd, J=4.0, 18.0 Hz, 2H), 3.88 (br d, J=3.6 Hz, 2H), 2.93-2.83 (m, 1H), 2.69 (s, 3H), 2.39-2.23 (m, 4H), 2.18 (br t, J=7.2 Hz, 2H), 2-1.91 (m, 1H); m/z ES+ $[M+H]^+$ 500.1.

Example 167. Synthesis of 8-Methyl-7-((2-methyl-1H-benzo[d]imidazol-6-yl)oxy)-2-(1-(piperidin-4-ylmethyl)-1H-pyrazol-4-yl)quinoxaline

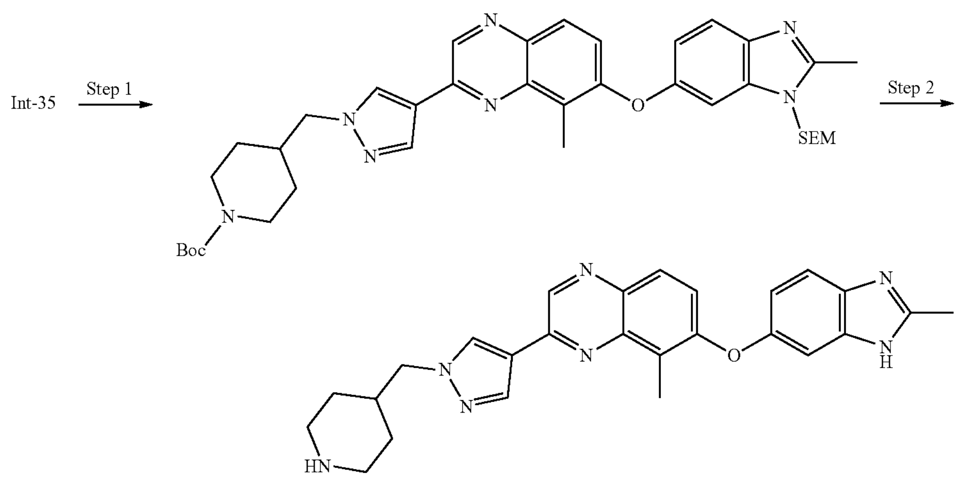

Step 1. tert-Butyl 4-((4-(8-methyl-7-((2-methyl-1-((2-(trimethylsilyl)ethoxy)methyl)-1H-benzo[d]imidazol-6-yl)oxy)quinoxalin-2-yl)-1H-pyrazol-1-yl) methyl) piperidine-1-carboxylate To a solution of tert-butyl 4-[[4-[8-chloro-7-[2-methyl-3-(2-trimethylsilylethoxymethyl)benzimidazol-5-yl]oxy-quinoxalin-2-yl]pyrazol-1-yl]methyl]piperidine-1-carboxylate (1 g, 1.40 mmol) and methylboronic acid (850 mg, 14.0 mmol) in dioxane (10 mL) and water (1 mL) was added sodium carbonate (450 mg, 4.30 mmol) and [2-(2-aminophenyl)phenyl]-chloro-palladium;dicyclohexyl-[3-(2,4,6-triisopropylphenyl)phenyl] phosphane (170 mg, 210 μmol).

The mixture was stirred at 110° C. for 8 h under nitrogen. On completion, the reaction mixture was filtered. The filtrate was diluted with water (10 mL) and extracted with ethyl acetate (50 mL×3). The combined organic layers were washed with brine (15 mL×2), dried over sodium sulfate, filtered and concentrated under reduced pressure to give a residue The residue was purified by column chromatography (silica gel, dichloromethane:methanol=100:1 to 20:1) to give tert-butyl 4-[[4-[8-methyl-7-[2-methyl-3-(2-trimethylsilylethoxymethyl)benzimidazol-5-yl]oxy-quinoxalin-2-yl]pyrazol-1-yl]methyl]piperidine-1-carboxylate (620 mg, 907 μmol, 65%) as a white solid. m/z ES+ $[M+H]^+$ 684.2.

Step 2. 8-Methyl-7-((2-methyl-1H-benzo[d]imidazol-6-yl)oxy)-2-(1-(piperidin-4-ylmethyl)-1H-pyrazol-4-yl)quinoxaline A solution of tert-butyl 4-[[4-[8-methyl-7-[2-methyl-3-(2-trimethylsilylethoxymethyl)benzimidazol-5-yl]oxy-quinoxalin-2-yl]pyrazol-1-yl]methyl]piperidine-1-carboxylate (620 mg, 906 μmol) in trifluoroacetic acid (6 mL) was stirred at 25° C. for 0.5 h. The reaction mixture was concentrated under reduced pressure to give 1.4 g crude product as a yellow oil. 100 mg crude product was purified by prep-HPLC (neutral condition; column: Waters Xbridge 150×25 mm×5 μm; mobile phase: [water (10 mM ammonium bicarbonate)-acetonitrile]; (B %: 23%-53%, 10 min) to give 8-methyl-7-[(2-methyl-3H-benzimidazol-5-yl)oxy]-2-[1-(4-piperidylmethyl)pyrazol-4-yl]quinoxaline (17.7 mg, 39.1 μmol, 18%) as a white solid. $^1$HNMR (400 MHz, DMSO-$d_6$) δ=12.46-11.82 (m, 1H), 9.22 (s, 1H), 8.66 (s, 1H), 8.33 (s, 1H), 7.84 (d, J=9.2 Hz, 1H), 7.46 (d, J=7.2 Hz, 1H), 7.24 (d, J=8.8 Hz, 1H), 7.06 (s, 1H), 6.87 (dd, J=2.0, 8.4 Hz, 1H), 4.08 (d, J=7.2 Hz, 2H), 2.90 (s, 2H), 2.69 (s, 3H), 2.47 (s, 3H), 2.45-2.36 (m, 3H), 2.03-1.89 (m, 1H), 1.45 (d, J=10.8 Hz, 2H), 1.18-1.03 (m, 2H); m/z ES+ $[M+H]^+$ 454.1.

Example 168. Synthesis of 8-Methyl-7-((2-methyl-1H-benzo[d]imidazol-6-yl)oxy)-2-(1-(piperidin-4-yl)-1H-pyrazol-4-yl)quinoxaline

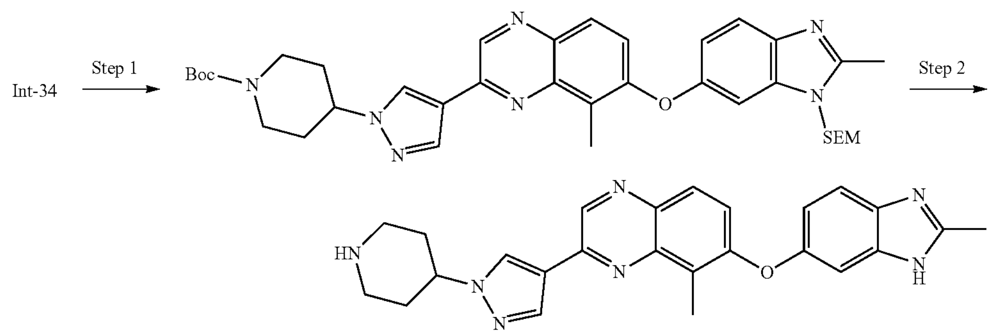

Step 1. 4-(4-(8-Methyl-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate To a solution of tert-butyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (100 mg, 144 μmol), methylboronic acid (26.0 mg, 434 μmol) in dioxane (1 mL) and water (0.1 mL) was added XPhos Pd G2 (11.4 mg, 14.4 μmol) and sodium carbonate (46.0 mg, 434 μmol). The mixture was stirred at 110° C. for 5 h under nitrogen. On completion, the mixture was concentrated under reduced pressure. The residue was purified by column chromatography (silica gel, petroleum ether/ethyl acetate=1/1 to 0/1) to give tert-butyl 4-(4-(8-methyl-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (90 mg, 134 μmol, 93%) as a yellow oil. m/z ES+ $[M+H]^+$ 670.4.

Step 2. 8-Methyl-7-((2-methyl-1H-benzo[d]imidazol-6-yl)oxy)-2-(1-(piperidin-4-yl)-1H-pyrazol-4-yl)quinoxaline A solution of tert-butyl 4-(4-(8-methyl-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (90 mg, 134 μmol) in trifluoroacetic acid (1 mL) was stirred at 25° C. for 0.5 h. On completion, the mixture was concentrated under reduced pressure. The residue was purified by prep-HPLC (column: Phenomenex Luna C18 150*25 mm*10 μm; mobile phase: [water (0.225% formic acid)-acetonitrile]; (B %: 7%-37%, 10 min) to give 8-methyl-7-((2-methyl-1H-benzo[d]imidazol-6-yl)oxy)-2-(1-(piperidin-4-yl)-1H-pyrazol-4-yl)quinoxaline (35.0 mg, 79.6 μmol, 59%) as an off-white solid. $^1$H NMR (400 MHz, $CD_3OD$) δ 9.18 (s, 1H), 8.64 (s, 1H), 8.40 (s, 1H), 7.93 (d, J=9.2 Hz, 1H), 7.75 (d, J=8.8 Hz, 1H), 7.42 (d, J=9.2 Hz, 1H), 7.30 (dd, J=2.2, 8.8 Hz, 1H), 7.23 (d, J=2.0 Hz, 1H), 4.72 (dd, J=5.2, 10.0 Hz, 1H), 3.64 (d, J=13.2 Hz, 2H), 3.32-3.24 (m, 2H), 2.84 (s, 3H), 2.74 (s, 3H), 2.51-2.31 (m, 4H); m/z ES+ $[M+H]^+$ 440.1.

Example 169. Synthesis of 8-chloro-7-[(2-methyl-3H-benzimidazol-5-yl)oxy]-2-[1-[2-[1-(oxetan-3-yl)-4-piperidyl]ethyl]pyrazol-4-yl]quinoxaline

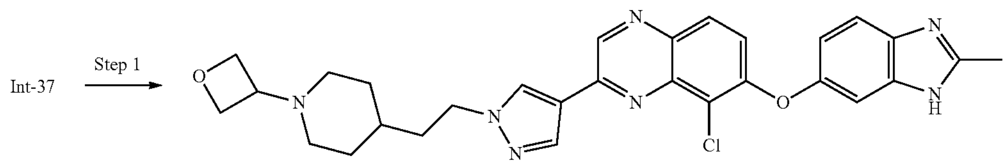 [SMILES: Cc1nc2ccc(Oc3ccc4ncc(-c5cnn(CCC6CCN(C7COC7)CC6)c5)nc4c3Cl)cc2[nH]1]

Step 1. 8-Chloro-7-[(2-methyl-3H-benzimidazol-5-yl)oxy]-2-[1-[2-[1-(oxetan-3-yl)-4-piperidyl]ethyl]pyrazol-4-yl]quinoxaline To a solution of 8-chloro-7-[(2-methyl-3H-benzimidazol-5-yl)oxy]-2-[1-[2-(4-piperidyl)ethyl]pyrazol-4-yl]quinoxaline (200 mg, 409 μmol) in methanol (5 mL) was added sodium cyanoborohydride (33.4 mg, 532 μmol), sodium acetate (43.7 mg, 532 μmol) and oxetan-3-one (295 mg, 4.10 mmol). The mixture was stirred at 20° C. for 2 h. On completion, the reaction mixture was concentrated under reduced pressure. The residue was purified by prep-HPLC (column: Waters Xbridge 150*25 mm*5 μm; mobile phase: [water (10 mM ammonium bicarbonate)-acetonitrile]; (B %: 31%-61%, 8 min) to give 8-chloro-7-[(2-methyl-3H-benzimidazol-5-yl)oxy]-2-[1-[2-[1-(oxetan-3-yl)-4-piperidyl]ethyl]pyrazol-4-yl]quinoxaline (38.7 mg, 71.1 μmol, 17%) as an off-white solid. $^1$H NMR (400 MHz, DMSO-$d_6$) δ 9.30 (s, 1H), 8.73 (s, 1H), 8.35 (s, 1H), 7.95 (d, J=9.2 Hz, 1H), 7.51 (d, J=8.8 Hz, 1H), 7.31 (d, J=9.2 Hz, 1H), 7.21 (d, J=1.6 Hz, 1H), 6.96-6.91 (m, 1H), 4.53-4.46 (m, 2H), 4.42-4.36 (m, 2H), 4.31-4.24 (m, 2H), 3.30-3.27 (m, 1H), 2.65 (d, J=10.8 Hz, 2H), 2.48 (s, 3H), 1.88-1.76 (m, 2H), 1.74-1.63 (m, 4H), 1.28-1.14 (m, 3H); m/z ES+ $[M+H]^+$ 544.1.

Example 170. Synthesis of 4-(4-(8-chloro-7-((2-methyl-1H-benzo[d]imidazol-6-yl)oxy)quinoxalin-2-yl)-1H-pyrazol-1-yl)quinuclidine

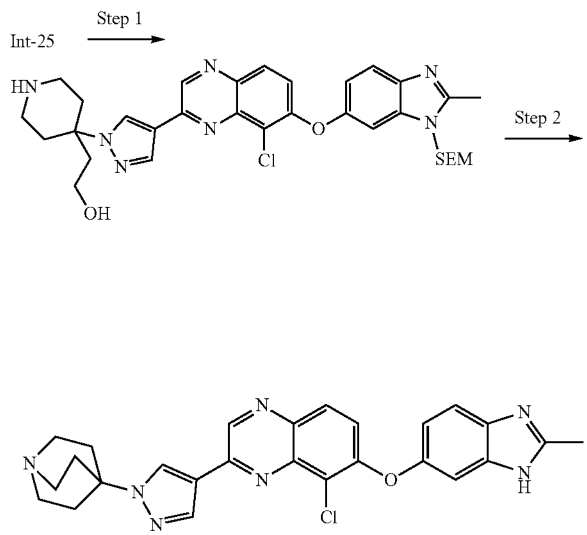

Step. 1. 2-(4-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidin-4-yl)ethanol To a solution of tert-butyl 4-[4-[8-chloro-7-[2-methyl-3-(2-trimethylsilylethoxymethyl)benzimidazol-5-yl]oxy-quinoxalin-2-yl]pyrazol-1-yl]-4-(2-hydroxyethyl) piperidine-1-carboxylate (100 mg, 136 μmol) in acetonitrile (3 mL) was added hydrochloric acid (6 M, 1 mL). The mixture was stirred at 25° C. for 1 h. The reaction mixture was diluted with sat. sodium bicarbonate (20 mL) and extracted with dichloromethane (15 mL×3). The combined organic layers were dried over sodium sulfate, filtered and concentrated under reduced pressure to give 2-(4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidin-4-yl)ethanol (90 mg, crude) as a yellow oil. m/z ES+ $[M+H]^+$ 634.3.

Step 2. 4-(4-(8-Chloro-7-((2-methyl-1H-benzo[d]imidazol-6-yl)oxy)quinoxalin-2-yl)-1H-pyrazol-1-yl)quinuclidine A solution of 2-[4-[4-[8-chloro-7-[2-methyl-3-(2-trimethylsilylethoxymethyl)benzimidazol-5-yl]oxy-quinoxalin-2-yl]pyrazol-1-yl]-4-piperidyl]ethanol (80.0 mg, 126 μmol) in hydrobromic acid (4.47 g, 26.5 mmol, 3 mL, 48%) was stirred at 100° C. for 12 h. The reaction mixture was concentrated under reduced pressure. The residue was purified by prep-HPLC (neutral condition; column: Waters Xbridge 150*25 mm*5 um; mobile phase: [water (10 mM ammonium bicarbonate)-acetonitrile]; (B %: 21%-51%, 10 min) and repurified by prep-HPLC (formic acid condition; column: Shim-pack C18 150*25*10 μm; mobile phase: [water (0.225% formic acid)-acetonitrile]; (B %: 1%-10%, 10 min) to give 4-(4-(8-chloro-7-((2-methyl-1H-benzo[d]imidazol-6-yl)oxy)quinoxalin-2-yl)-1H-pyrazol-1-yl)quinuclidine (13.0 mg, 22.7 μmol, 18%) as an orange gum. $^1$H NMR (400 MHz, DMSO-$d_6$) δ=9.67 (s, 1H), 9.48-9.36 (m, 2H), 8.37 (s, 2H), 8.06 (d, J=9.2 Hz, 1H), 7.53 (d, J=8.8 Hz, 1H), 7.45 (d, J=9.2 Hz, 1H), 7.25 (d, J=2.0 Hz, 1H), 6.96 (dd, J=2.0, 8.8 Hz, 1H), 4.80 (s, 2H), 3.16 (d, J=10.4 Hz, 2H), 2.97 (t, J=6.0 Hz, 2H), 2.83-2.70 (m, 2H), 2.49 (s, 3H), 2.23 (s, 2H), 2.06 (d, J=9.2 Hz, 2H); m/z ES+ $[M+H]^+$ 486.2.

Example 171. Synthesis of 8-Chloro-7-[(2-methyl-3H-benzimidazol-5-yl)oxy]-2-[1-[2-[1-(2,2,2-trifluoroethyl)-4-piperidyl]ethyl]pyrazol-4-yl]quinoxaline

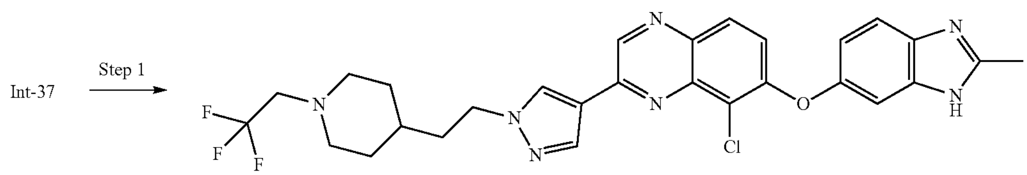 [SMILES: Cc1nc2ccc(Oc3ccc4ncc(-c5cnn(CCC6CCN(CC(F)(F)F)CC6)c5)nc4c3Cl)cc2[nH]1]

Step 1. 8-Chloro-7-[(2-methyl-3H-benzimidazol-5-yl)oxy]-2-[1-[2-[1-(2,2,2-trifluoroethyl)-4-piperidyl]ethyl]pyrazol-4-yl]quinoxaline To a solution of 8-chloro-7-[(2-methyl-3H-benzimidazol-5-yl)oxy]-2-[1-[2-(4-piperidyl)ethyl]pyrazol-4-yl]quinoxaline (200 mg, 409 μmol) in N,N-dimethyl formamide (2 mL) was added diisopropylethylamine (158 mg, 1.23 mmol) and 2,2,2-trifluoroethyl trifluoromethanesulfonate (142 mg, 614 μmol). The mixture was stirred at 25° C. for 2 h. On completion, the reaction mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 10%-40%, 7 min) to give 8-chloro-7-[(2-methyl-3H-benzimidazol-5-yl)oxy]-2-[1-[2-[1-(2,2,2-trifluoroethyl)-4-piperidyl]ethyl]pyrazol-4-yl]quinoxaline (31.8 mg, 55.8 μmol, 13%) as an off-white solid. $^1$H NMR (400 MHz, DMSO-$d_6$) δ 9.31 (s, 1H), 8.73 (s, 1H), 8.35 (s, 1H), 7.97 (d, J=9.2 Hz, 1H), 7.56 (d, J=8.8 Hz, 1H), 7.34 (d, J=9.2 Hz, 1H), 7.26 (d, J=2.4 Hz, 1H), 7.03-6.97 (m, 1H), 4.32-4.24 (m, 2H), 3.11-3.05 (m, 2H), 2.89 (d, J=10.8 Hz, 2H), 2.54 (s, 3H), 2.31-2.20 (m, 2H), 1.80 (d, J=5.2 Hz, 2H), 1.68 (d, J=8.8 Hz, 2H), 1.22 (s, 3H); m/z ES+ $[M+H]^+$ 570.1.

Example 172. Synthesis of 3-[[4-[8-chloro-7-[(2-methyl-3H-benzimidazol-5-yl)oxy]quinoxalin-2-yl]pyrazol-1-yl]methyl]-N,N-dimethyl-cyclobutanamine

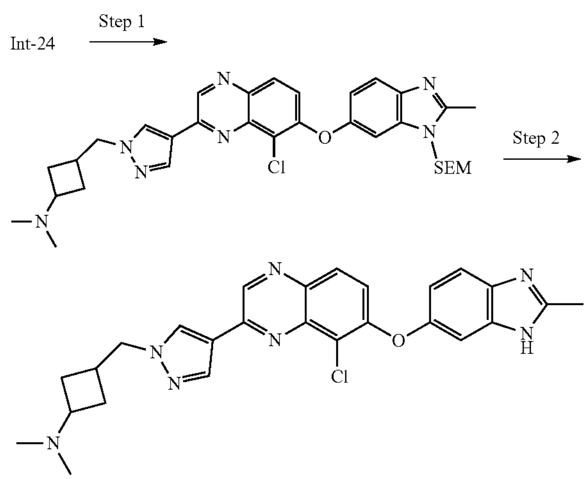

Step 1. 3-[[4-[8-Chloro-7-[2-methyl-3-(2-trimethylsilylethoxymethyl)benzimidazol-5-yl]oxy-quinoxalin-2-yl]pyrazol-1-yl]methyl]-N,N-dimethyl-cyclobutanamine To a solution of 3-[[4-[8-chloro-7-[2-methyl-3-(2-trimethylsilylethoxymethyl)benzimidazol-5-yl]oxy-quinoxalin-2-yl]pyrazol-1-yl]methyl]cyclobutanone (120 mg, 204 μmol) in methanol (1.5 mL) was added N-methylmethanamine hydrochloride (94.7 mg, 1.16 mmol) and sodium acetate (167 mg, 2.04 mmol). The mixture was stirred at 25° C. for 0.2 h. Then sodium cyanoborohydride (32.0 mg, 509 μmol) was added, and the mixture was stirred at 40° C. for 1.8 h. The reaction mixture was quenched with sat. sodium bicarbonate (2 mL) at 25° C., and then diluted with water (3 mL) and extracted with ethyl acetate (3 mL×3). The combined organic layers were washed with brine (3 mL×3), dried over sodium sulfate, filtered and concentrated in vacuo to give 3-[[4-[8-chloro-7-[2-methyl-3-(2-trimethylsilylethoxymethyl)benzimidazol-5-yl]oxy-quinoxalin-2-yl]pyrazol-1-yl]methyl]-N,N-dimethyl-cyclobutanamine (80 mg, 129 μmol, 63%) as a yellow solid. m/z ES+ $[M+H]^+$ 618.3.

Step 2. 3-[[4-[8-Chloro-7-[(2-methyl-3H-benzimidazol-5-yl)oxy]quinoxalin-2-yl]pyrazol-1-yl]methyl]-N,N-dimethyl-cyclobutanamine A mixture of 3-[[4-[8-chloro-7-[2-methyl-3-(2-trimethylsilylethoxymethyl)benzimidazol-5-yl]oxy-quinoxalin-2-yl]pyrazol-1-yl]methyl]-N,N-dimethyl-cyclobutanamine (70 mg, 113 μmol) in trifluoroacetic acid (1 mL) was stirred at 25° C. for 2 h. The reaction mixture was concentrated in vacuo. The residue was purified by prep-HPLC (column: Phenomenex Synergi C18 150*25 mm*10 μm; mobile phase: [water (0.225% formic acid)-acetonitrile]; (B %: 0%-30%, 10 min) to give 3-[[4-[8-chloro-7-[(2-methyl-3H-benzimidazol-5-yl)oxy]quinoxalin-2-yl]pyrazol-1-yl]methyl]-N,N-dimethyl-cyclobutanamine (26.7 mg, 54.7 μmol, 48%) as a yellow solid. $^1$H NMR (400 MHz, $CD_3OD$) δ 9.21 (s, 1H), 8.57 (s, 1H), 8.36 (s, 1H), 8 (d, J=9.2 Hz, 1H), 7.75 (d, J=9.2 Hz, 1H), 7.48 (d, J=9.2 Hz, 1H), 7.35-7.27 (m, 2H), 4.46-4.32 (m, 2H), 3.84-3.56 (m, 1H), 2.82 (s, 3H), 2.80-2.77 (m, 6H), 2.74-2.60 (m, 1H), 2.57-2.44 (m, 2H), 2.16-2.03 (m, 2H); m/z ES+ $[M+H]^+$ 488.1.

Example 173. Synthesis of 2-(1-((2,6,8-trioxaspiro[3.5]nonan-7-yl)methyl)-1H-pyrazol-4-yl)-8-chloro-7-((2-methyl-1H-benzo[d]imidazol-6-yl)oxy)quinoxaline and 8-chloro-7-((2-methyl-1H-benzo[d]imidazol-6-yl)oxy)-2-(1-((5-methylene-1,3-dioxan-2-yl)methyl)-1H-pyrazol-4-yl)quinoxaline

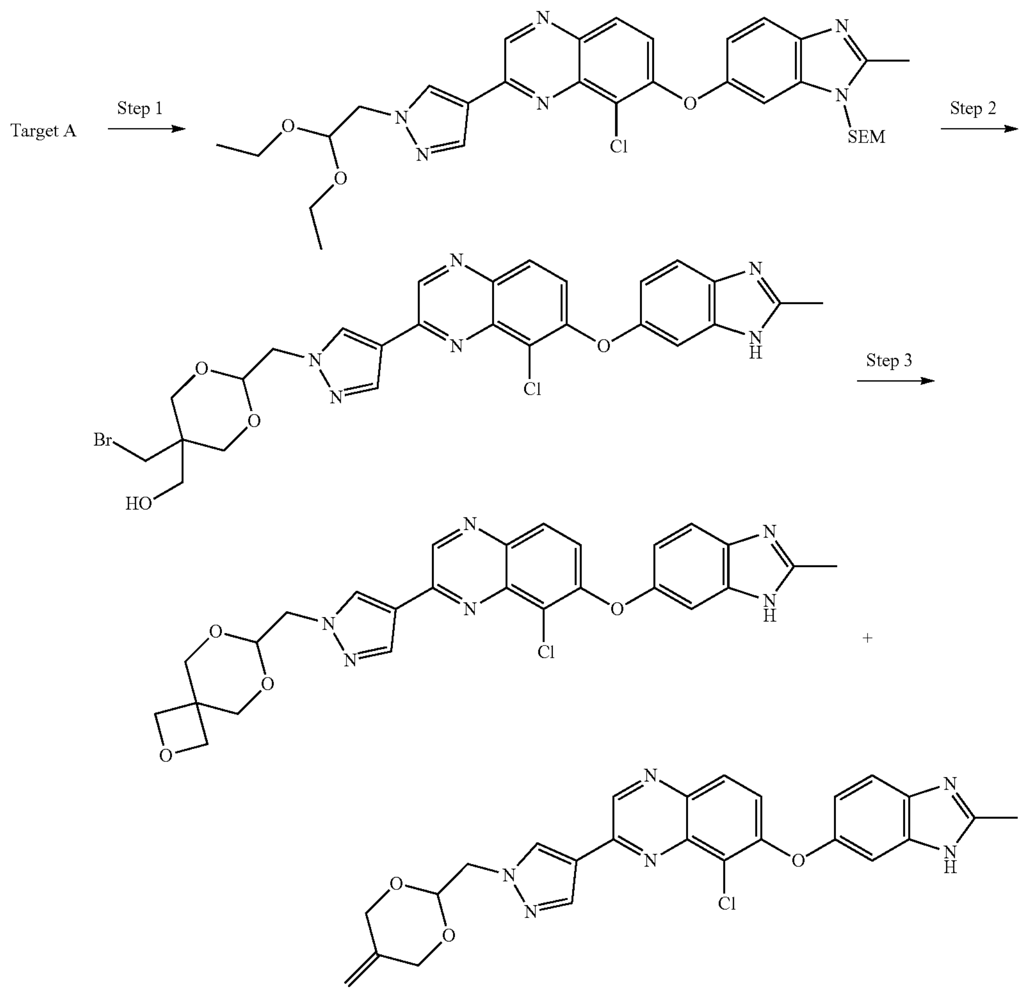

Step 1. 8-Chloro-2-(1-(2,2-diethoxyethyl)-1H-pyrazol-4-yl)-7-((2-methyl-1-((2-(trimethylsilyl)ethoxy)methyl)-1H-benzo[d]imidazol-6-yl)oxy)quinoxaline To a mixture of 2-[[6-[5-chloro-3-(1H-pyrazol-4-yl)quinoxalin-6-yl]oxy-2-methyl-benzimidazol-1-yl]methoxy]ethyl-trimethyl-silane (500 mg, 986 μmol) and 2-bromo-1,1-diethoxy-ethane (389 mg, 1.97 mmol) in N,N-dimethyl formamide (8 mL) was added cesium carbonate (964 mg, 2.96 mmol). The mixture was then heated to 100° C. and stirred for 4 h. On completion, the reaction mixture was quenched with water (50 mL) at 20° C., and then extracted with ethyl acetate (50 mL×3). The combined organic layers were washed with water (5 mL×2), dried over sodium sulfate, filtered and concentrated under reduced pressure to give 8-chloro-2-(1-(2,2-diethoxyethyl)-1H-pyrazol-4-yl)-7-((2-methyl-1-((2-(trimethylsilyl)ethoxy)methyl)-1H-benzo[d]imidazol-6-yl)oxy)quinoxaline (600 mg, 866 μmol, 88%) as a yellow oil. m/z ES+ $[M+H]^+$ 623.2.

Step 2. (5-(Bromomethyl)-2-((4-(8-chloro-7-((2-methyl-1H-benzo[d]imidazol-6-yl)oxy)quinoxalin-2-yl)-1H-pyrazol-1-yl)methyl)-1,3-dioxan-5-yl)methanol To a mixture of 8-chloro-2-(1-(2,2-diethoxyethyl)-1H-pyrazol-4-yl)-7-((2-methyl-1-((2-(trimethylsilyl)ethoxy)methyl)-1H-benzo[d]imidazol-6-yl)oxy)quinoxaline (200 mg, 321 μmol) and 2-(bromomethyl)-2-(hydroxymethyl)propane-1,3-diol (128 mg, 642 μmol) in toluene (5 mL) was added p-toluenesulfonic acid (11.1 mg, 64.2 μmol). The mixture was then heated to 100° C. and stirred for 16 h. On completion, the reaction mixture was concentrated under reduced pressure. The residue was purified by reversed-phase HPLC (0.1% formic acid conditions) to give [5-(bromomethyl)-2-[[4-[8-chloro-7-[(2-methyl-3H-benzimidazol-5-yl)oxy]quinoxalin-2-yl]pyrazol-1-yl]methyl]-1,3-dioxan-5-yl]methanol (90 mg, 144 μmol, 45%) as a yellow solid. m/z ES+ $[M+H]^+$ 601.3.

Step 3. 2-(1-((2,6,8-Trioxaspiro[3.5]nonan-7-yl)methyl)-1H-pyrazol-4-yl)-8-chloro-7-((2-methyl-1H-benzo[d]imidazol-6-yl)oxy)quinoxaline and 8-chloro-7-((2-methyl-1H-benzo[d]imidazol-6-yl)oxy)-2-(1-((5-methylene-1,3-dioxan-2-yl)methyl)-1H-pyrazol-4-yl)quinoxaline To a mixture of [5-(bromomethyl)-2-[[4-[8-chloro-7-[(2-methyl-3H-benzimidazol-5-yl)oxy]quinoxalin-2-yl]pyrazol-1-yl]methyl]-1,3-dioxan-5-yl]methanol (70 mg, 117 μmol) in tetrahydrofuran (4 mL) was added aqueous sodium hydroxide (18.7 mg, 468 μmol, 60 wt %). The mixture was then heated to 60° C. and stirred for 2 h. On completion, the reaction mixture was quenched by addition water (5 mL) at 0° C., and then extracted with ethyl acetate (10 mL×3). The combined organic layers were washed with water (2 mL×2), dried over sodium sulfate, filtered and concentrated under reduced pressure. The residue was purified by prep-HPLC (column: Phenomenex Luna C18 150*25 mm*10 μm; mobile phase: [water (0.225% formic acid)-acetonitrile]; (B %: 11%-41%, 10 min) and then repurified by prep-HPLC (column: Waters Xbridge 150*25 mm*5 μm; mobile phase: [water (10 mM ammonium bicarbonate)-acetonitrile]; (B %: 27%-57%, 10 min) to give 2-(1-((2,6,8-trioxaspiro[3.5]nonan-7-yl)methyl)-1H-pyrazol-4-yl)-8-chloro-7-((2-methyl-1H-benzo[d]imidazol-6-yl)oxy)quinoxaline (8.5 mg, 16.4 μmol, 14%) as a white solid and compound 8-chloro-7-((2-methyl-1H-benzo[d]imidazol-6-yl)oxy)-2-(1-((5-methylene-1,3-dioxan-2-yl)methyl)-1H-pyrazol-4-yl)quinoxaline (19.8 mg, 40.6 μmol, 35%) as a yellow solid. $^{1}$H NMR (400 MHz, DMSO-$d_6$) δ 9.32 (s, 1H), 8.66 (s, 1H), 8.38 (s, 1H), 7.97 (d, J=9.2 Hz, 1H), 7.53 (br d, J=8.4 Hz, 1H), 7.33 (d, J=9.2 Hz, 1H), 7.23 (br s, 1H), 6.97 (br d, J=8.4 Hz, 1H), 4.95 (t, J=5.2 Hz, 1H), 4.54 (s, 2H), 4.40-4.27 (m, 4H), 4.11 (s, 2H), 3.75 (br d, J=11.2 Hz, 2H), 2.51 (s, 3H); m/z ES+ $[M+H]^+$ 519.0.

$^{1}$H NMR (400 MHz, DMSO-$d_6$) δ 9.32 (s, 1H), 8.70-8.63 (m, 1H), 8.39 (s, 1H), 8.31 (s, 1H), 7.96 (d, J=9.2 Hz, 1H), 7.51 (br d, J=8.8 Hz, 1H), 7.32 (d, J=9.2 Hz, 1H), 7.21 (br s, 1H), 6.94 (dd, J=2.4, 8.8 Hz, 1H), 5.14 (t, J=5.2 Hz, 1H), 4.97 (s, 2H), 4.41-4.33 (m, 4H), 3.93-3.78 (m, 2H), 2.49 (br s, 3H); m/z ES+ $[M+H]^+$ 489.1.

Example 174. Synthesis of 1-[4-[2-[4-[8-chloro-7-[(2-methyl-3H-benzimidazol-5-yl)oxy]quinoxalin-2-yl]pyrazol-1-yl]ethyl]-1-piperidyl]propan-1-one

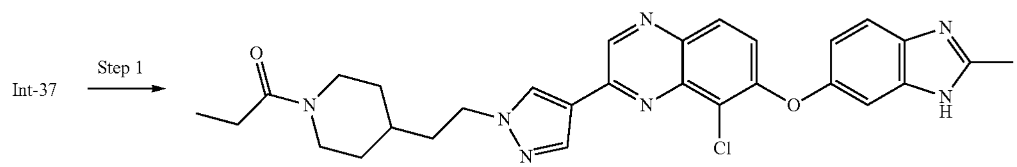 [SMILES: CCC(=O)N1CCC(CCn2cc(-c3cnc4ccc(Oc5ccc6nc(C)[nH]c6c5)c(Cl)c4n3)cn2)CC1]

Step 1. 1-[4-[2-[4-[8-Chloro-7-[(2-methyl-3H-benzimidazol-5-yl)oxy]quinoxalin-2-yl]pyrazol-1-yl]ethyl]-1-piperidyl]propan-1-one To a solution of 8-chloro-7-[(2-methyl-3H-benzimidazol-5-yl)oxy]-2-[1-[2-(4-piperidyl)ethyl]pyrazol-4-yl]quinoxaline (120 mg, 245 μmol) in tetrahydrofuran (2 mL) and water (1 mL) was added sodium bicarbonate (61.9 mg, 737 μmol) and propanoyl chloride (45.5 mg, 491 μmol). The mixture was stirred at 25° C. for 0.5 h. On completion, the reaction mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 15%-45%, 7 min) to give 1-[4-[2-[4-[8-chloro-7-[(2-methyl-3H-benzimidazol-5-yl)oxy]quinoxalin-2-yl]pyrazol-1-yl]ethyl]-1-piperidyl]propan-1-one (44.6 mg, 82.0 μmol, 33%) as a yellow solid. $^{1}$H NMR (400 MHz, DMSO-$d_6$) δ 12.46-12.05 (m, 1H), 9.30 (s, 1H), 8.74 (s, 1H), 8.35 (s, 1H), 7.95 (d, J=9.2 Hz, 1H), 7.58-7.42 (m, 1H), 7.31 (d, J=8.0 Hz, 1H), 7.25-7.11 (m, 1H), 6.94 (d, J=8.0 Hz, 1H), 4.36 (d, J=13.2 Hz, 1H), 4.32-4.24 (m, 2H), 3.82 (d, J=12.0 Hz, 1H), 2.98-2.87 (m, 1H), 2.54-2.51 (m, 1H), 2.49-2.49 (m, 3H), 2.31-2.24 (m, 2H), 1.89-1.69 (m, 4H), 1.56-1.41 (m, 1H), 1.24-1 (m, 2H), 0.99-0.94 (m, 3H); m/z ES+$[M+H]^+$ 544.1.

Example 175. Synthesis of 2-[1-[(3,3-difluorocyclobutyl)methyl]pyrazol-4-yl]-8-methyl-7-[(2-methyl-3H-benzimidazol-5-yl)oxy]quinoxaline

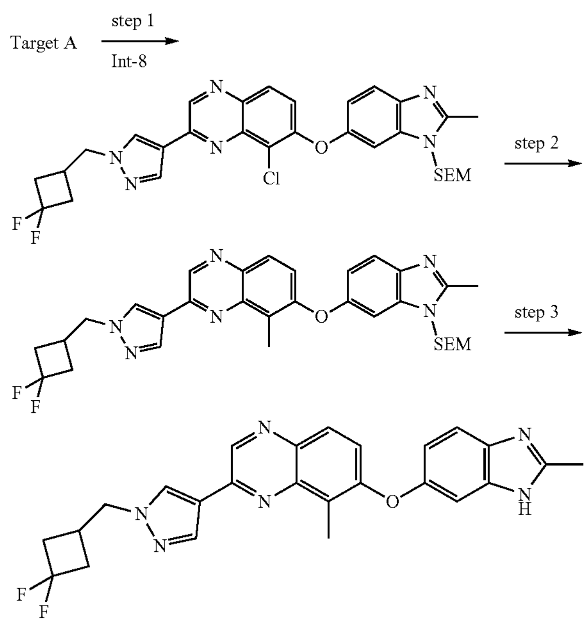

Step 1. 2-[[5-[5-Chloro-3-[1-[(3,3-difluorocyclobutyl)methyl]pyrazol-4-yl]quinoxalin-6-yl]oxy-2-methyl-benzimidazol-1-yl]methoxy]ethyl-trimethyl-silane To a solution of 2-[[5-[5-chloro-3-(1H-pyrazol-4-yl)quinoxalin-6-yl]oxy-2-methyl-benzimidazol-1-yl]methoxy]ethyl-trimethyl-silane (200 mg, 394 μmol), (3,3-difluorocyclobutyl)methyl methanesulfonate (94.8 mg, 473 μmol) in N,N-dimethyl formamide (2 mL) was added potassium carbonate (164 mg, 1.18 mmol). The mixture was stirred at 80° C. for 16 h. The reaction mixture was diluted with water (10 mL) and extracted with ethyl acetate (10 mL×3). The combined organic layers were washed with brine (10 ml×3), dried over sodium sulfate, filtered and concentrated in vacuo to give 2-[[5-[5-chloro-3-[1-[(3,3-difluorocyclobutyl) methyl]pyrazol-4-yl]quinoxalin-6-yl]oxy-2-methyl-benzimidazol-1-yl]methoxy]ethyl-trimethyl-silane (250 mg, crude) as a yellow oil. m/z ES+ $[M+H]^+$ 611.1.

Step 2. 2-[[5-[3-[1-[(3,3-Difluorocyclobutyl)methyl] pyrazol-4-yl]-5-methyl-quinoxalin-6-yl]oxy-2-methyl-benzimidazol-1-yl]methoxy]ethyl-trimethyl-silane A mixture of methylboronic acid (245 mg, 4.09 mmol), 2-[[5-[5-chloro-3-[1-[(3,3-difluorocyclobutyl)methyl]pyrazol-4-yl]quinoxalin-6-yl]oxy-2-methyl-benzimidazol-1-yl] methoxy]ethyl-trimethyl-silane (250 mg, 409 μmol), XPhos Pd G2 (32.2 mg, 40.9 μmol), sodium carbonate (130 mg, 1.23 mmol) in dioxane (3 mL) and water (0.6 mL) was degassed and purged with nitrogen for 3 times, and then the mixture was stirred at 100° C. for 2 h under nitrogen atmosphere. The reaction mixture was filtered and concentrated in vacuo. The residue was purified by column chromatography (silica gel, petroleum ether/ethyl acetate=2/1 to 0/1) to give 2-[[5-[3-[1-[(3,3-difluorocyclobutyl)methyl] pyrazol-4-yl]-5-methyl-quinoxalin-6-yl]oxy-2-methyl-benzimidazol-1-yl]methoxy]ethyl-trimethyl-silane (160 mg, 261 μmol, 64%) as a yellow oil. m/z ES+ $[M+H]^+$ 591.1.

Step 3. 2-[1-[(3,3-Difluorocyclobutyl)methyl]pyrazol-4-yl]-8-methyl-7-[(2-methyl-3H-benzimidazol-5-yl)oxy]quinoxaline A solution of 2-[[5-[3-[1-[(3,3-difluorocyclobutyl) methyl]pyrazol-4-yl]-5-methyl-quinoxalin-6-yl]oxy-2-methyl-benzimidazol-1-yl]methoxy]ethyl-trimethyl-silane (160 mg, 271 μmol) in trifluoroacetic acid (2 mL) was stirred at 25° C. for 2 h. The reaction mixture was concentrated in vacuo. The residue was purified by prep-HPLC (column: Phenomenex Gemini-NX C18 75*30 mm*3 μm; mobile phase: [water (0.225% formic acid)-acetonitrile]; (B %: 20%-50%, 7 min) to give 2-[1-[(3,3-difluorocyclobutyl) methyl]pyrazol-4-yl]-8-methyl-7-[(2-methyl-3H-benzimidazol-5-yl)oxy]quinoxaline (59.3 mg, 128 μmol, 47%) as a yellow solid. $^1H$ NMR (400 MHz, DMSO-$d_6$) δ 9.27-9.22 (m, 1H), 8.74 (s, 1H), 8.36 (s, 1H), 8.14 (s, 1H), 7.86 (d, J=9.2 Hz, 1H), 7.55 (d, J=8.8 Hz, 1H), 7.28 (d, J=9.2 Hz, 1H), 7.14 (d, J=1.6 Hz, 1H), 6.98 (dd, J=2.0, 8.8 Hz, 1H), 4.37 (br d, J=5.2 Hz, 2H), 2.68 (s, 6H), 2.55 (s, 3H), 2.53-2.51 (m, 2H); m/z ES+ $[M+H]^+$ 461.1.

Example 176. Synthesis of 2-(1-((3,3-difluorocyclobutyl)methyl)-1H-pyrazol-4-yl)-8-methyl-7-((2-methyl-1H-benzo[d]imidazol-6-yl)oxy)quinoxaline

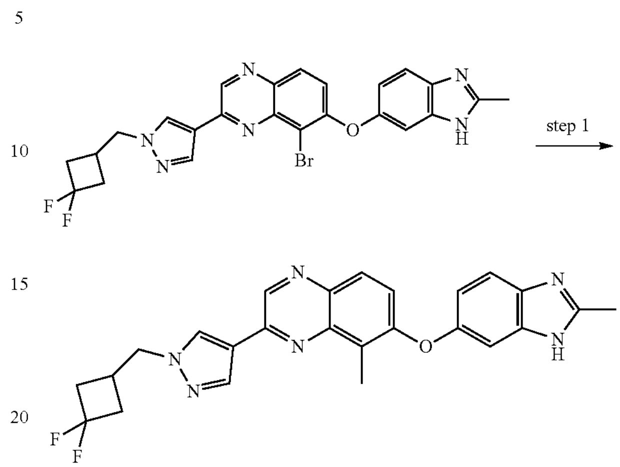

Step 1. 2-(1-((3,3-Difluorocyclobutyl)methyl)-1H-pyrazol-4-yl)-8-methyl-7-((2-methyl-1H-benzo[d] imidazol-6-yl)oxy)quinoxaline To a solution of 8-bromo-2-[1-[(3,3-difluorocyclobutyl) methyl]pyrazol-4-yl]-7-[(2-methyl-3H-benzimidazol-5-yl) oxy]quinoxaline (50.0 mg, 95.2 μmol) and methylboronic acid (57.0 mg, 952 μmol) in dioxane (1 mL) and water (0.1 mL) was added sodium carbonate (30.3 mg, 286 μmol) and XPhos Pd G2 (11.2 mg, 14.3 μmol). The mixture was stirred at 110° C. for 12 h under nitrogen. The reaction mixture was poured into water (20 mL) and extracted with ethyl acetate (15 mL×3). The combined organic layers were dried over sodium sulfate, filtered and concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 17%-47%, 10 min) to give 2-(1-((3,3-difluorocyclobutyl)methyl)-1H-pyrazol-4-yl)-8-methyl-7-((2-methyl-1H-benzo[d]imidazol-6-yl)oxy)quinoxaline (11.0 mg, 23.9 μmol, 25%) as an off-white solid. $^1H$ NMR (400 MHz, $CD_3OD$) δ=9.08 (s, 1H), 8.56 (s, 1H), 8.32 (s, 1H), 7.81 (d, J=9.2 Hz, 1H), 7.50 (d, J=8.8 Hz, 1H), 7.29 (d, J=9.2 Hz, 1H), 7.07 (d, J=2.0 Hz, 1H), 6.97 (dd, J=2.4, 8.8 Hz, 1H), 4.39 (d, J=6.8 Hz, 2H), 2.76-2.64 (m, 6H), 2.57 (s, 3H), 2.49 (dd, J=6.8, 14.0 Hz, 2H); m/z ES+ $[M+H]^+$ 461.1.

Example 177. Synthesis of 8-chloro-7-((2-methyl-1H-benzo[d]imidazol-6-yl)oxy)-2-(1-(1-(2,2,2-trifluoroethyl) piperidin-4-yl)-1H-pyrazol-4-yl)quinoxaline

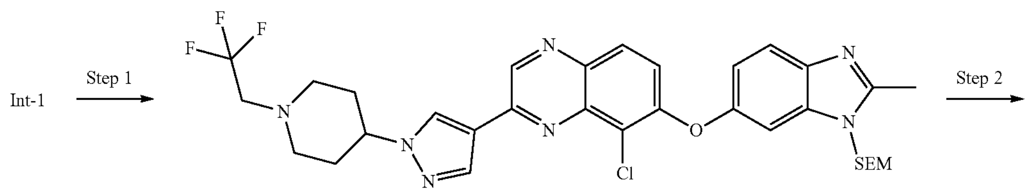

-continued

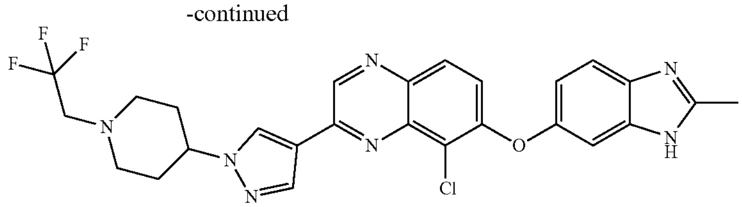

Step 1. 8-Chloro-7-((2-methyl-1-((2-(trimethylsilyl) ethoxy)methyl)-1H-benzo[d]imidazol-6-yl)oxy)-2-(1-(1-(2,2,2-trifluoroethyl) piperidin-4-yl)-1H-pyrazol-4-yl)quinoxaline To a solution of 8-chloro-7-((2-methyl-1-((2-(trimethylsilyl)ethoxy)methyl)-1H-benzo[d]imidazol-6-yl)oxy)-2-(1-(piperidin-4-yl)-1H-pyrazol-4-yl)quinoxaline (50 mg, 84.7 µmol) in N,N-dimethyl formamide (1 mL) was added diisopropylethylamine (21.9 mg, 169 µmol), 2,2,2-trifluoroethyl trifluoromethanesulfonate (23.6 mg, 102 µmol). The mixture was stirred at 25° C. for 16 h. On completion, the mixture was filtered and the filtrate was purified by reversed-phase HPLC (0.1% formic acid condition) to give 8-chloro-7-((2-methyl-1-((2-(trimethylsilyl)ethoxy)methyl)-1H-benzo[d]imidazol-6-yl)oxy)-2-(1-(1-(2,2,2-trifluoroethyl) piperidin-4-yl)-1H-pyrazol-4-yl)quinoxaline (50 mg, 74.4 µmol, 88%) as a yellow oil. m/z ES+ $[M+H]^+$ 672.5.

Step 2. 8-Chloro-7-((2-methyl-1H-benzo[d]imidazol-6-yl)oxy)-2-(1-(1-(2,2,2-trifluoroethyl) piperidin-4-yl)-1H-pyrazol-4-yl)quinoxaline A solution of 8-chloro-7-((2-methyl-1-((2-(trimethylsilyl) ethoxy)methyl)-1H-benzo[d]imidazol-6-yl)oxy)-2-(1-(1-(2,2,2-trifluoroethyl) piperidin-4-yl)-1H-pyrazol-4-yl)quinoxaline (50.0 mg, 74.4 µmol) in trifluoroacetic acid (1 mL) was stirred at 25° C. for 0.5 h. On completion, the mixture was concentrated under reduced pressure. The residue was purified by prep-HPLC (column: Phenomenex Gemini-NX C18 75*30 mm*3 µm; mobile phase: [water (0.225% formic acid)-acetonitrile]; (B %: 18%-48%, 7 min) to give 8-chloro-7-((2-methyl-1H-benzo[d]imidazol-6-yl)oxy)-2-(1-(1-(2,2,2-trifluoroethyl) piperidin-4-yl)-1H-pyrazol-4-yl)quinoxaline (20.3 mg, 37.4 µmol, 49% yield) as an off-white solid. $^1$H NMR (400 MHz, $CD_3OD$) δ 9.16 (d, J=3.6 Hz, 1H), 8.63 (d, J=2.4 Hz, 1H), 8.35 (d, J=2.4 Hz, 1H), 7.92 (dd, J=2.4, 9.2 Hz, 1H), 7.61 (d, J=8.8 Hz, 1H), 7.38 (dd, J=1.6, 9.2 Hz, 1H), 7.23 (d, J=2.2 Hz, 1H), 7.11 (dd, J=2.2, 8.8 Hz, 1H), 4.40-4.10 (m, 1H), 3.25-3.06 (m, 4H), 2.71-2.61 (m, 5H), 2.30-2.07 (m, 4H); m/z ES+ $[M+H]^+$ 542.1.

Example 178. Synthesis of 8-chloro-7-[(2-methyl-3H-benzimidazol-5-yl)oxy]-2-[1-[2-(4-piperidyl) ethyl]pyrazol-4-yl]quinoxaline

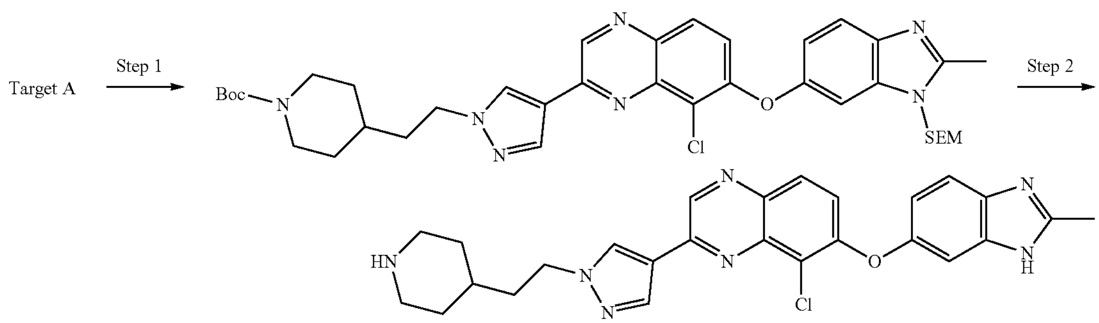

Int-37

Step 1. tert-Butyl 4-[2-[4-[8-chloro-7-[2-methyl-3-(2-trimethylsilylethoxymethyl)benzimidazol-5-yl] oxy-quinoxalin-2-yl]pyrazol-1-yl]ethyl]piperidine-1-carboxylate To a solution of 2-[[6-[5-chloro-3-(1H-pyrazol-4-yl)quinoxalin-6-yl]oxy-2-methyl-benzimidazol-1-yl]methoxy] ethyl-trimethyl-silane (832 mg, 1.64 mmol) in N,N-dimethyl formamide (10 mL) was added potassium carbonate (681 mg, 4.93 mmol) and tert-butyl 4-(2-bromoethyl) piperidine-1-carboxylate (480 mg, 1.64 mmol). The mixture was stirred at 80° C. for 2 h. On completion, the reaction mixture was diluted with water (25 mL) and extracted with ethyl acetate (25 mL×3). The combined organic layers were dried over anhydrous sodium sulfate, filtered and concentrated under reduced pressure to give tert-butyl 4-[2-[4-[8-chloro-7-[2-methyl-3-(2-trimethylsilylethoxymethyl)benzimidazol-5-yl] oxy-quinoxalin-2-yl]pyrazol-1-yl]ethyl]piperidine-1-carboxylate (1.20 g, crude) as a yellow oil. m/z ES+ $[M+H]^+$ 718.2.

Step 2. 8-Chloro-7-[(2-methyl-3H-benzimidazol-5-yl)oxy]-2-[1-[2-(4-piperidyl)ethyl]pyrazol-4-yl]quinoxaline A solution of tert-butyl 4-[2-[4-[8-chloro-7-[2-methyl-3-(2-trimethylsilylethoxymethyl)benzimidazol-5-yl]oxy-quinoxalin-2-yl]pyrazol-1-yl]ethyl]piperidine-1-carboxylate (100 mg, 139 µmol) in trifluoroacetic acid (1 mL) was stirred at 25° C. for 0.5 h. The reaction mixture was concentrated under reduced pressure. The residue was purified by prep- HPLC (column: Phenomenex Gemini-NX C18 75*30 mm*3 μm; mobile phase: [water (0.225% formic acid)-acetonitrile]; (B %: 5%-35%, 7 min) to give 8-chloro-7-[(2-methyl-3H-benzimidazol-5-yl)oxy]-2-[1-[2-(4-piperidyl) ethyl]pyrazol-4-yl]quinoxaline (26.1 mg, 53.6 μmol, 38%) as a yellow solid. $^1$H NMR (400 MHz, $CD_3OD$) δ 9.12 (s, 1H), 8.58 (s, 1H), 8.33 (s, 1H), 7.87 (d, J=9.2 Hz, 1H), 7.54 (d, J=8.8 Hz, 1H), 7.33 (d, J=9.2 Hz, 1H), 7.19 (d, J=1.6 Hz, 1H), 7.03 (dd, J=2.0, 8.4 Hz, 1H), 4.36 (t, J=6.8 Hz, 2H), 3.35-3.42 (m, 2H), 3.02-2.92 (m, 2H), 2.60 (s, 3H), 2.03-1.93 (m, 4H), 1.70-1.62 (m, 1H), 1.52-1.41 (m, 2H); m/z ES+ $[M+H]^+$ 488.1.

Example 179. Synthesis of 8-chloro-7-[(2-methyl-3H-benzimidazol-5-yl)oxy]-2-[1-[2-(1-methyl-4-piperidyl)ethyl]pyrazol-4-yl]quinoxaline

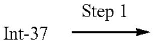

-continued

Step 1. 8-Chloro-7-[(2-methyl-3H-benzimidazol-5-yl)oxy]-2-[1-[2-(1-methyl-4-piperidyl)ethyl]pyrazol-4-yl]quinoxaline To a solution of 8-chloro-7-[(2-methyl-3H-benzimidazol-5-yl)oxy]-2-[1-[2-(4-piperidyl)ethyl]pyrazol-4-yl]quinoxaline (200 mg, 409 μmol) in N,N-dimethyl formamide (3 mL) was added paraformaldehyde (123 mg, 4.10 mmol) and formic acid (196 mg, 4.10 mmol). The mixture was stirred at 60° C. for 12 h. On completion, the reaction mixture was concentrated under reduced pressure. The residue was purified by prep-HPLC (column: Phenomenex Synergi C18 150*25 mm*10 μm; mobile phase: [water (0.225% formic acid)-acetonitrile]; (B %: 0%-30%, 10 min) to give 8-chloro-7-[(2-methyl-3H-benzimidazol-5-yl)oxy]-2-[1-[2-(1-methyl-4-piperidyl)ethyl]pyrazol-4-yl]quinoxaline (26.6 mg, 53.0 μmol, 12%) as a yellow gum. $^1$H NMR (400 MHz, DMSO-$d_6$) δ 9.30 (s, 1H), 8.74 (s, 1H), 8.36 (s, 1H), 8.20 (s, 1H), 7.95 (d, J=9.2 Hz, 1H), 7.51 (d, J=8.8 Hz, 1H), 7.31 (d, J=9.2 Hz, 1H), 7.21 (d, J=2.0 Hz, 1H), 6.97-6.91 (m, 1H), 4.31-4.26 (m, 2H), 3.54-3.29 (m, 2H), 3.13 (d, J=11.6 Hz, 2H), 2.50 (s, 3H), 2.49 (s, 3H), 1.83 (d, J=6.0 Hz, 4H), 1.42-1.27 (m, 3H), 4.17-4.14 (m, 3H), 3 (s, BH), 2.75-2.61 (m, 2H), 1.70-1.64 (m, 4H), 1.53-1.46 (m, 1H), 1.43 (s, 9H), 1.41-1.34 (m, 1H), 1.18-1.08 (m, 2H); m/z ES+ $[M+H]^+$ 502.1.

Example 180. Synthesis of 8-chloro-7-((2-methyl-1H-benzo[d]imidazol-6-yl)oxy)-2-(1-(1-methylpiperidin-4-yl)-1H-pyrazol-4-yl)quinoxaline

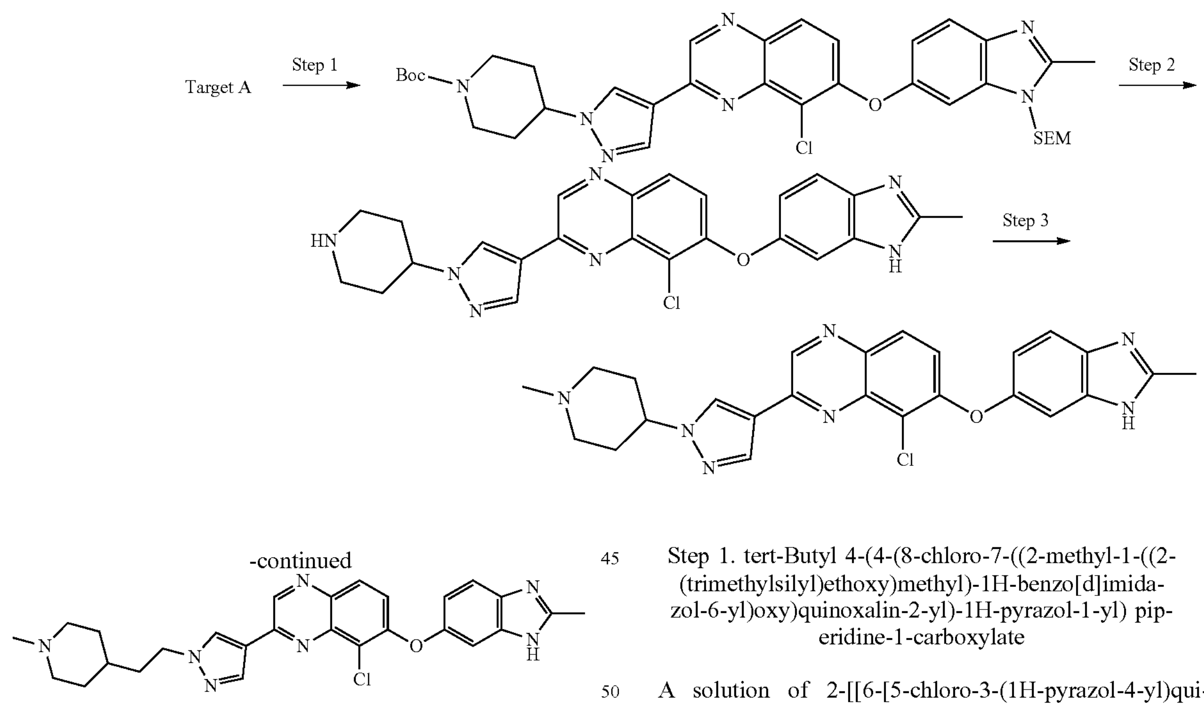

Step 1. tert-Butyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate A solution of 2-[[6-[5-chloro-3-(1H-pyrazol-4-yl)quinoxalin-6-yl]oxy-2-methyl-benzimidazol-1-yl]methoxy] ethyl-trimethyl-silane (500 mg, 986 μmol), tert-butyl 4-iodopiperidine-1-carboxylate (1.53 g, 4.93 mmol), cesium carbonate (642 mg, 1.97 mmol) in N,N-dimethyl formamide (5 mL) was stirred at 100° C. for 1 h. Then tert-butyl 4-iodopiperidine-1-carboxylate (920 mg, 2.96 mmol) was added and the mixture was stirred at 100° C. for 1 h. Further, tert-butyl 4-iodopiperidine-1-carboxylate (920 mg, 2.96 mmol) was added and the mixture was stirred at 100° C. for 1 h. On completion, the mixture was filtered and the filtrate was concentrated under reduced pressure. The residue was purified by reversed-phase HPLC (0.1% formic acid conditions) to give tert-butyl 4-(4-(8-chloro-7-((2-methyl-1-((2-(trimethylsilyl)ethoxy)methyl)-1H-benzo[d]imidazol-6-yl) oxy)quinoxalin-2-yl)-1H-pyrazol-1-yl) piperidine-1-carboxylate (320 mg, 463 μmol, 47%) as a yellow solid. m/z ES+ $[M+H]^+$ 690.2.

Step 2. 8-Chloro-7-((2-methyl-1H-benzo[d]imidazol-6-yl)oxy)-2-(1-(piperidin-4-yl)-1H-pyrazol-4-yl) quinoxaline A solution of tert-butyl 4-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (320 mg, 463 μmol) in trifluoroacetic acid (5 mL) was stirred at 25° C. for 10 min. On completion, the mixture was concentrated under reduced pressure. The residue was purified by prep-HPLC (column: Phenomenex Luna C18 150*25 mm*10 μm; mobile phase: [water (0.225% formic acid)-acetonitrile]; (B %: 2%-32%, 10 min) to give 8-chloro-7-((2-methyl-1H-benzo[d]imidazol-6-yl)oxy)-2-(1-(piperidin-4-yl)-1H-pyrazol-4-yl)quinoxaline (150 mg, 0,324 mmol, 70%) as a yellow solid. $^1$H NMR (400 MHz, $CD_3OD$) δ 9.24 (s, 1H), 8.67 (s, 1H), 8.42 (s, 1H), 8.01 (d, J=9.2 Hz, 1H), 7.74 (d, J=8.8 Hz, 1H), 7.49 (d, J=9.2 Hz, 1H), 7.36-7.24 (m, 2H), 4.73 (tt, J=4.8, 10.0 Hz, 1H), 3.64 (d, J=13.2 Hz, 2H), 3.32-3.22 (m, 2H), 2.81 (s, 3H), 2.53-2.29 (m, 4H); m/z ES+ $[M+H]^+$ 460.1.

Step 3. 8-Chloro-7-((2-methyl-1H-benzo[d]imidazol-6-yl)oxy)-2-(1-(1-methylpiperidin-4-yl)-1H-pyrazol-4-yl)quinoxaline To a solution of 8-chloro-7-((2-methyl-1H-benzo[d]imidazol-6-yl)oxy)-2-(1-(piperidin-4-yl)-1H-pyrazol-4-yl)quinoxaline (50 mg, 109 μmol) in N,N-dimethyl formamide (1 mL) was added paraformaldehyde (32.6 mg, 1.09 mmol) and formic acid (52.2 mg, 1.09 mmol). The mixture was stirred at 60° C. for 16 h. On completion, the mixture was filtered and concentrated under reduced pressure. The residue was purified by prep-HPLC (column: Phenomenex Synergi C18 150*25 mm*10 μm; mobile phase: [water (0.225% formic acid)-acetonitrile]; (B %: 0%-29%, 10 min) to give 8-chloro-7-((2-methyl-1H-benzo[d]imidazol-6-yl) oxy)-2-(1-(1-methylpiperidin-4-yl)-1H-pyrazol-4-yl)quinoxaline (36.2 mg, 0.076 mmol, 70%) as a yellow solid. $^1$H NMR (400 MHz, $CD_3OD$) δ 9.15 (s, 1H), 8.64 (s, 1H), 8.38 (s, 1H), 7.89 (d, J=9.2 Hz, 1H), 7.53 (d, J=8.8 Hz, 1H), 7.34 (d, J=9.2 Hz, 1H), 7.18 (s, 1H), 7.01 (d, J=8.8 Hz, 1H), 4.70-4.54 (m, 1H), 3.60 (d, J=12.4 Hz, 2H), 3.25-3.10 (m, 2H), 2.88 (s, 3H), 2.58 (s, 3H), 2.45-2.35 (m, 4H); m/z ES+ $[M+H]^+$ 474.1.

Example 181. Synthesis of 8-Chloro-2-(1-(1-(ethylsulfonyl)azetidin-3-yl)-1H-pyrazol-4-yl)-7-((2-methyl-1H-benzo[d]imidazol-6-yl)oxy)quinoxaline

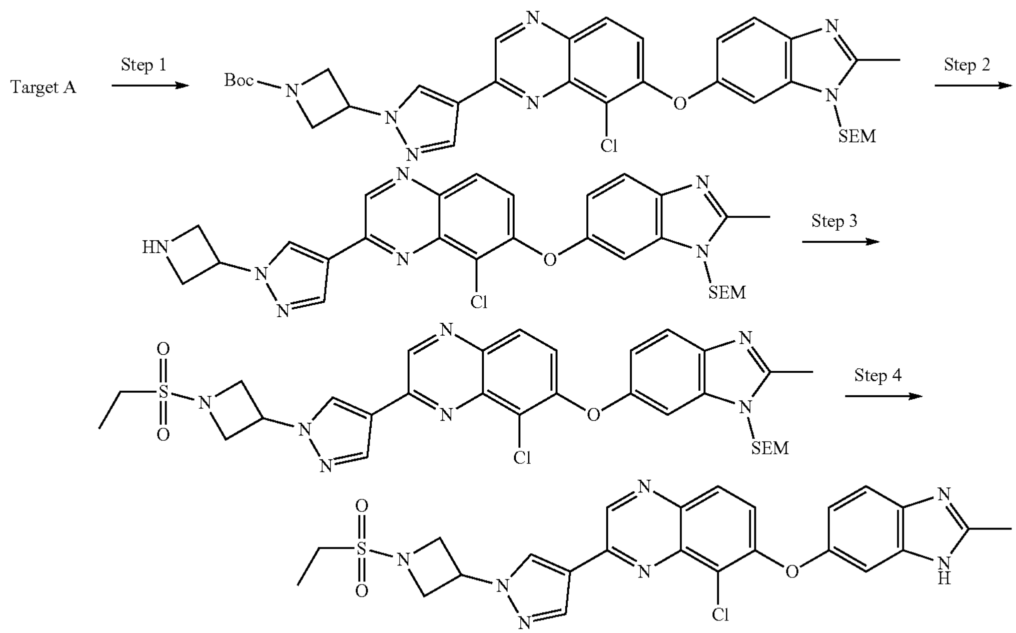

Step 1. tert-Butyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) azetidine-1-carboxylate To a solution of 2-[[6-[5-chloro-3-(1H-pyrazol-4-yl)quinoxalin-6-yl]oxy-2-methyl-benzimidazol-1-yl]methoxy] ethyl-trimethyl-silane (200 mg, 394 μmol) and tert-butyl 3-iodoazetidine-1-carboxylate (123 mg, 433 μmol) in N,N-dimethylformamide (4 mL) was added cesium carbonate (257 mg, 789 μmol). The mixture was stirred at 50° C. for 12 hours. The reaction mixture was diluted with water (20 mL) and extracted with ethyl acetate (15 mL×3). The combined organic layers were dried over sodium sulfate, filtered and concentrated under reduced pressure. The residue was purified by column chromatography (silica gel, dichloromethane/methanol=100/1 to 50/1) to give tert-butyl 3-(4-(8-chloro-7-((2-methyl-1-((2-(trimethylsilyl)ethoxy) methyl)-1H-benzo[d]imidazol-6-yl)oxy)quinoxalin-2-yl)-1H-pyrazol-1-yl) azetidine-1-carboxylate (210 mg, 314 μmol, 80%) as a yellow solid. m/z ES+ $[M+H]^+$ 662.3.

Step 2. 2-(1-(Azetidin-3-yl)-1H-pyrazol-4-yl)-8-chloro-7-((2-methyl-1-((2-(trimethylsilyl)ethoxy) methyl)-1H-benzo[d]imidazol-6-yl)oxy)quinoxaline To a solution of tert-butyl 3-[4-[8-chloro-7-[2-methyl-3-(2-trimethylsilylethoxymethyl)benzimidazol-5-yl]oxy-quinoxalin-2-yl]pyrazol-1-yl]azetidine-1-carboxylate (190 mg, 287 μmol) in dichloromethane (5 mL) was added trifluoroacetic acid (770 mg, 6.75 mmol, 0.5 mL). The mixture was stirred at 25° C. for 2 hours. The reaction mixture was diluted with sodium bicarbonate (30 mL) and extracted with dichloromethane (20 mL×3). The combined organic layers were dried over sodium sulfate, filtered and concentrated under reduced pressure to give 2-(1-(azetidin-3-yl)-1H-pyrazol-4-yl)-8-chloro-7-((2-methyl-1-((2-(trimethylsilyl)ethoxy)methyl)-1H-benzo[d]imidazol-6-yl)oxy)quinoxaline (300 mg, crude) as a yellow solid. m/z ES+ $[M+H]^+$ 562.2.

Step 3. 8-Chloro-2-(1-(1-(ethylsulfonyl) azetidin-3-yl)-1H-pyrazol-4-yl)-7-((2-methyl-1-((2-(trimethylsilyl)ethoxy)methyl)-1H-benzo[d]imidazol-6-yl)oxy) quinoxaline To a solution of 2-[[6-[3-[1-(azetidin-3-yl)pyrazol-4-yl]-5-chloro-quinoxalin-6-yl]oxy-2-methyl-benzimidazol-1-yl]methoxy]ethyl-trimethyl-silane (300 mg, 534 μmol) in dichloromethane (5 mL) was added diisopropylethylamine (207 mg, 1.60 mmol, 279 μL). Then ethanesulfonyl chloride (103 mg, 800 μmol, 75.7 μL) was added at 0° C. The mixture was stirred at 25° C. for 1 h. The reaction mixture was concentrated under reduced pressure to give 8-chloro-2-(1-(1-(ethylsulfonyl) azetidin-3-yl)-1H-pyrazol-4-yl)-7-((2-methyl-1-((2-(trimethylsilyl)ethoxy)methyl)-1H-benzo[d]imidazol-6-yl)oxy)quinoxaline (350 mg, crude) as a yellow oil. m/z ES+ $[M+H]^+$ 654.3.

Step 4. 8-Chloro-2-(1-(1-(ethylsulfonyl) azetidin-3-yl)-1H-pyrazol-4-yl)-7-((2-methyl-1H-benzo[d]imidazol-6-yl)oxy)quinoxaline A solution of 2-[[6-[5-chloro-3-[1-(1-ethylsulfonylazetidin-3-yl)pyrazol-4-yl]quinoxalin-6-yl]oxy-2-methyl-benzimidazol-1-yl]methoxy]ethyl-trimethyl-silane (350 mg, 535 μmol) in trifluoroacetic acid (5 mL) was stirred at 25° C. for 1 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 12%-42%, 10 min) to give 8-chloro-2-(1-(1-(ethylsulfonyl) azetidin-3-yl)-1H-pyrazol-4-yl)-7-((2-methyl-1H-benzo[d]imidazol-6-yl)oxy)quinoxaline (48.0 mg, 91.2 μmol, 17%) as an off-white solid. $^1H$ NMR (400 MHz, DMSO-$d_6$) δ=9.35 (s, 1H), 8.84 (s, 1H), 8.51 (s, 1H), 7.97 (d, J=9.2 Hz, 1H), 7.51 (d, J=8.8 Hz, 1H), 7.33 (d, J=9.2 Hz, 1H), 7.22 (s, 1H), 6.94 (dd, J=2.4, 8.8 Hz, 1H), 5.55-5.45 (m, 1H), 4.42-4.29 (m, 4H), 3.26 (dd, J=14.8, 7.2 Hz, 2H), 2.49 (s, 3H), 1.29 (t, J=7.2 Hz, 3H); m/z ES+ $[M+H]^+$ 524.0.

Example 182. Synthesis of 1-(3-(4-(8-chloro-7-((2-methyl-1H-benzo[d]imidazol-6-yl)oxy)quinoxalin-2-yl)-1H-pyrazol-1-yl) piperidin-1-yl)ethan-1-one

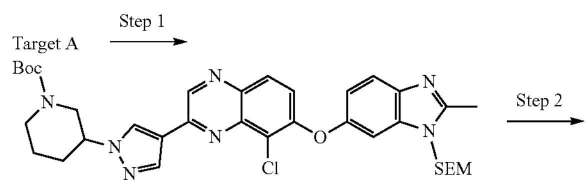

-continued

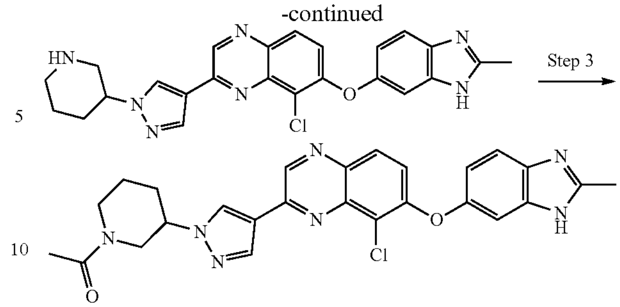

Step 1. tert-Butyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate To a solution of 8-chloro-7-((2-methyl-1-((2-(trimethylsilyl)ethoxy)methyl)-1H-benzo[d] imidazol-6-yl)oxy)-2-(1H-pyrazol-4-yl)quinoxaline (500 mg, 986 μmol) and tert-butyl 3-((methylsulfonyl)oxy) piperidine-1-carboxylate (551 mg, 1.97 mmol) in dimethyl sulfoxide (10 mL) was added cesium carbonate (964 mg, 2.96 mmol) and potassium iodide (164 mg, 986 μmol). The mixture was stirred at 80° C. for 12 h. On completion, the reaction mixture was quenched by addition water (0.2 mL) and concentrated under reduced pressure and the residue was purified by reversed-phase HPLC (0.1% formic acid condition, 80-90% acetonitrile, 8 min) to give tert-butyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (430 mg, 0.62 mmol, 57%) as an orange solid. m/z ES+ $[M+H]^+$ 690.3.

Step 2. 8-Chloro-7-((2-methyl-1H-benzo[d]imidazol-6-yl)oxy)-2-(1-(piperidin-3-yl)-1H-pyrazol-4-yl) quinoxaline A solution of tert-butyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (165 mg, 239 μmol) in trifluoroacetic acid (1 mL) was stirred at 30° C. for 1 h. On completion, the reaction mixture was concentrated under reduced pressure to give 8-chloro-7-((2-methyl-1H-benzo[d]imidazol-6-yl)oxy)-2-(1-(piperidin-3-yl)-1H-pyrazol-4-yl)quinoxaline (110 mg, crude) as an orange oil. m/z ES+ $[M+H]^+$ 460.1.

Step 3. 1-(3-(4-(8-Chloro-7-((2-methyl-1H-benzo[d]imidazol-6-yl)oxy)quinoxalin-2-yl)-1H-pyrazol-1-yl) piperidin-1-yl)ethan-1-one To a solution of 8-chloro-7-((2-methyl-1H-benzo[d]imidazol-6-yl)oxy)-2-(1-(piperidin-3-yl)-1H-pyrazol-4-yl)quinoxaline (100 mg, 217 μmol) in dichloromethane (1 mL) was added triethylamine (66.0 mg, 652 μmol, 90.8 μL) and acetyl chloride (15.4 mg, 196 μmol, 14.0 μL). The mixture was stirred at 0° C. for 20 min. Then acetyl chloride (17.0 mg, 217 μmol, 15.5 μL) was added and the mixture was stirred at 0° C. for 10 min. Further, acetyl chloride (17.0 mg, 217 μmol, 15.5 μL) was added and the mixture was stirred at 0° C. for 10 min. On completion, the reaction mixture was quenched with methanol (0.2 mL) and then concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 13%-43%, 10 min) to give 1-(3-(4-(8-chloro-7-((2-methyl-1H-benzo[d]imidazol-6-yl)oxy)quinoxalin-2-yl)-1H-pyrazol-1-yl) piperidin-1-yl)ethanone (45.6 mg, 0.091 mmol, 42%) as an off-white solid. $^1$H NMR (400 MHz, DMSO-$d_6$) δ 12.32 (br s, 1H), 9.33 (d, J=6.8 Hz, 1H), 8.80 (d, J=7.2 Hz, 1H), 8.41 (d, J=11.6 Hz, 1H), 7.96 (d, J=9.2 Hz, 1H), 7.51 (br d, J=8.4 Hz, 1H), 7.32 (d, J=9.2 Hz, 1H), 7.21 (s, 1H), 6.94 (dd, J=2.0, 8.8 Hz, [H), 4.68-4.43 (m, 1H), 4.36-4.16 (m, 1H), 4.08 (dd, J=3.6, 12.8 Hz, 0.5H), 3.82 (d, J=13.6 Hz, 0.5H), 3.54 (dd, J=13.2, 10.0 Hz, 0.5H), 3.16-3 (m, 1H), 2.85-2.77 (m, 0.5H), 2.49 (s, 3H), 2.26-2.12 (m, 2H), 2.06 (d, J=4.4 Hz, 3H), 1.88-1.77 (m, 1H), 1.68-1.46 (m, 1H); m/z ES+ $[M+H]^+$ 502.1.

Example 183. Synthesis of 2-(3-(4-(8-chloro-7-((2-methyl-1H-benzo[d]imidazol-6-yl)oxy)quinoxalin-2-yl)-1H-pyrazol-1-yl)-1-(ethylsulfonyl) azetidin-3-yl) acetonitrile

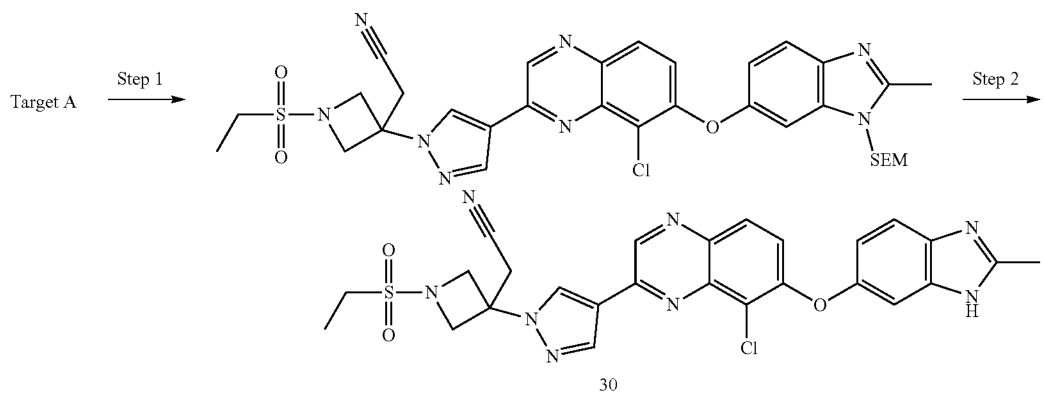

Step 1. 2-(3-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-1-(ethylsulfonyl) azetidin-3-yl) acetonitrile To a solution of 2-[[6-[5-chloro-3-(1H-pyrazol-4-yl)quinoxalin-6-yl]oxy-2-methyl-benzimidazol-1-yl]methoxy] ethyl-trimethyl-silane (100 mg, 197 μmol) in acetonitrile (2 mL) was added 2,3,4,6,7,8,9,10-octahydropyrimido[1,2-a] azepine (30.0 mg, 197 μmol) and 2-(1-ethylsulfonylazetidin-3-ylidene) acetonitrile (40.0 mg, 214 μmol). The mixture was stirred at 30° C. for 12 hs. On completion, the reaction mixture was diluted with water (5 mL) and extracted with ethyl acetate (15 mL×3). The combined organic layers were dried over anhydrous sodium sulfate, filtered and concentrated under reduced pressure to give 2-[3-[4-[8-chloro-7-[2-methyl-3-(2-trimethylsilylethoxymethyl)benzimidazol-5-yl]oxy-quinoxalin-2-yl]pyrazol-1-yl]-1-ethylsulfonyl-azetidin-3-yl]acetonitrile (120 mg, crude) as a yellow solid. m/z ES+ $[M+H]^+$ 693.1.

Step 2. 2-(3-(4-(8-Chloro-7-((2-methyl-1H-benzo[d] imidazol-6-yl)oxy)quinoxalin-2-yl)-1H-pyrazol-1-yl)-1-(ethylsulfonyl) azetidin-3-yl) acetonitrile A solution of 2-[3-[4-[8-chloro-7-[2-methyl-3-(2-trimethylsilylethoxymethyl)benzimidazol-5-yl]oxy-quinoxalin-2-yl]pyrazol-1-yl]-1-ethylsulfonyl-azetidin-3-yl]acetonitrile (70.0 mg, 100 μmol) in trifluoroacetic acid (1 mL) was stirred at 25° C. for 0.5 h. On completion, the reaction mixture was concentrated under reduced pressure. The residue was purified by prep-HPLC (column: Phenomenex Gemini-NX C18 75*30 mm*3 μm; mobile phase: [water (10 mM ammonium bicarbonate)-acetonitrile]; (B %: 22%-52%, 8 min) to give 2-[3-[4-[8-chloro-7-[(2-methyl-3H-benzimidazol-5-yl)oxy]quinoxalin-2-yl]pyrazol-1-yl]-1-ethylsulfonyl-azetidin-3-yl]acetonitrile (18.7 mg, 0.033 mmol, 32%) as an off-white solid. $^1$H NMR (400 MHz, DMSO-$d_6$) δ 12.31 (br s, 1H), 9.38 (s, 1H), 9.11 (s, 1H), 8.56 (s, 1H), 7.99 (d, J=9.2 Hz, 1H), 7.51 (d, J=8.0 Hz, 1H), 7.35 (d, J=9.2 Hz, 1H), 7.23 (s, 1H), 6.92 (dd, J=8.4, 2.0 Hz, 1H), 4.57 (d, J=9.2 Hz, 2H), 4.28 (d, J=9.2 Hz, 2H), 3.71 (s, 2H), 3.40-3.20 (m, 2H), 2.51 (s, 3H), 1.25 (t, J=7.2 Hz, 3H); m/z ES+ $[M+H]^+$ 563.0.

Example 184. Synthesis of 8-chloro-2-(1-(2-(2,5-dihydrofuran-2-yl)ethyl)-1H-pyrazol-4-yl)-7-((2-methyl-1H-benzo[d]imidazol-6-yl)oxy)quinoxaline

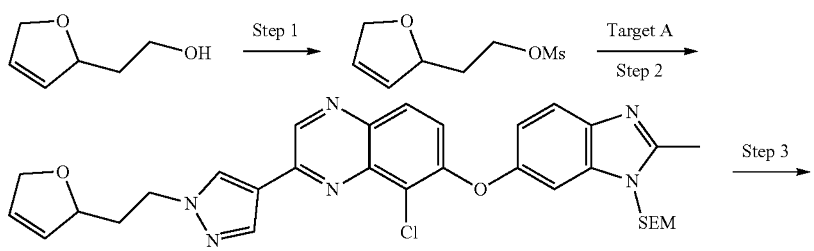

-continued

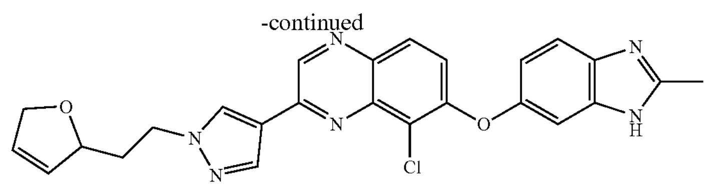

Step 1. 2-(2,5-Dihydrofuran-2-yl)ethyl methanesulfonate

To a solution of 2-(2,5-dihydrofuran-2-yl)ethan-1-ol (260 mg, 2.28 mmol) in dichloromethane (1 mL) was added triethylamine (921 mg, 9.11 mmol) and methanesulfonyl chloride (782 mg, 6.83 mmol). The mixture was stirred at 25° C. for 1 h. The mixture was poured into water (10 mL) and extracted with ethyl acetate (30 mL×3). The combined organic layer was dried by sodium sulfate, filtered and concentrated under reduced pressure. The residue was purified by column chromatography (silica gel, petroleum ether/ethyl acetate=10/1 to 1/1) to give 2-(2,5-dihydrofuran-2-yl)ethyl methanesulfonate (100 mg, 520 μmol, 22%) as a colourless oil. $^1$H NMR (400 MHz, $CDCl_3$) § 6.04-5.92 (m, 1H), 5.84-5.81 (m, 1H), 5.10-4.91 (m, 1H), 4.75-4.61 (m, 2H), 4.39 (dd, J=5.6, 7.2 Hz, 2H), 3.04 (s, 3H), 2.21-2.09 (m, 1H), 2-1.83 (m, 1H).

Step 2. 8-Chloro-2-(1-(2-(2,5-dihydrofuran-2-yl)ethyl)-1H-pyrazol-4-yl)-7-((2-methyl-1-((2-(trimethylsilyl)ethoxy)methyl)-1H-benzo[d]imidazol-6-yl)oxy)quinoxaline To a solution of 8-chloro-7-((2-methyl-1-((2-(trimethylsilyl)ethoxy)methyl)-1H-benzo[d]imidazol-6-yl)oxy)-2-(1H-pyrazol-4-yl)quinoxaline (100 mg, 197 μmol) in N,N-dimethylformamide (1 mL) was added 2-(2,5-dihydrofuran-2-yl)ethyl methanesulfonate (53.0 mg, 276 μmol) and potassium carbonate (81.7 mg, 591 μmol). The mixture was stirred at 80° C. for 12 h. On completion, the mixture was poured into water (20 mL) and extracted with ethyl acetate (30 mL×3). The organic layers were washed by brine (30 mL×3), filtered and concentrated under reduced pressure. The residue was purified by prep-TLC (silica gel, dichloromethane/methanol=20/1) to give 8-chloro-2-(1-(2-(2,5-dihydrofuran-2-yl)ethyl)-1H-pyrazol-4-yl)-7-((2-methyl-1-((2-(trimethylsilyl)ethoxy)methyl)-1H-benzo[d]imidazol-6-yl)oxy)quinoxaline (80 mg, 132 μmol, 67%) as a white solid. m/z ES+ [M+H]$^+$ 603.2.

Step 3. 8-Chloro-2-(1-(2-(2,5-dihydrofuran-2-yl)ethyl)-1H-pyrazol-4-yl)-7-((2-methyl-1H-benzo[d]imidazol-6-yl)oxy)quinoxaline A solution of 8-chloro-2-(1-(2-(2,5-dihydrofuran-2-yl)ethyl)-1H-pyrazol-4-yl)-7-((2-methyl-1-((2-(trimethylsilyl)ethoxy)methyl)-1H-benzo[d]imidazol-6-yl)oxy)quinoxaline (80 mg, 132 μmol) in trifluoroacetic acid (2 mL) was stirred at 25° C. for 0.5 h. On completion, the mixture was poured into water (50 mL) and extracted with ethyl acetate (30 mL×3). The organic layers were dried by sodium sulfate, filtered and concentrated under reduced pressure. The residue was purified by prep-HPLC (column: Phenomenex Synergi C18 150*25 mm*10 μm; mobile phase: [water (0.225% formic acid)-acetonitrile]; (B %: 14%-44%, 10 min) to give 8-chloro-2-(1-(2-(2,5-dihydrofuran-2-yl)ethyl)-1H-pyrazol-4-yl)-7-((2-methyl-1H-benzo[d]imidazol-6-yl)oxy)quinoxaline (38.9 mg, 82.1 μmol, 61%) as an off-white solid. $^1$H NMR (400 MHz, DMSO-$d_6$) δ 9.33 (s, 1H), 8.74 (s, 1H), 8.36 (s, 1H), 8 (d, J=9.2 Hz, 1H), 7.68 (d, J=8.8 Hz, 1H), 7.50-7.33 (m, 2H), 7.14 (dd, J=2.0, 8.8 Hz, 1H), 6.02 (dd, J=1.6, 6.2 Hz, 1H), 5.95-5.82 (m, 1H), 4.85-4.75 (m, 1H), 4.67-4.45 (m, 2H), 4.32 (t, J=7.2 Hz, 2H), 2.65 (s, 3H), 2.25-2.10 (m, 1H), 2.07-1.89 (m, 1H); m/z ES+ [M+H]$^+$ 473.1.

Example 185. Synthesis of 4-((4-(8-chloro-7-((2-methyl-1H-benzo[d]imidazol-6-yl)oxy)quinoxalin-2-yl)-1H-pyrazol-1-yl)methyl)tetrahydro-2H-thiopyran 1,1-dioxide

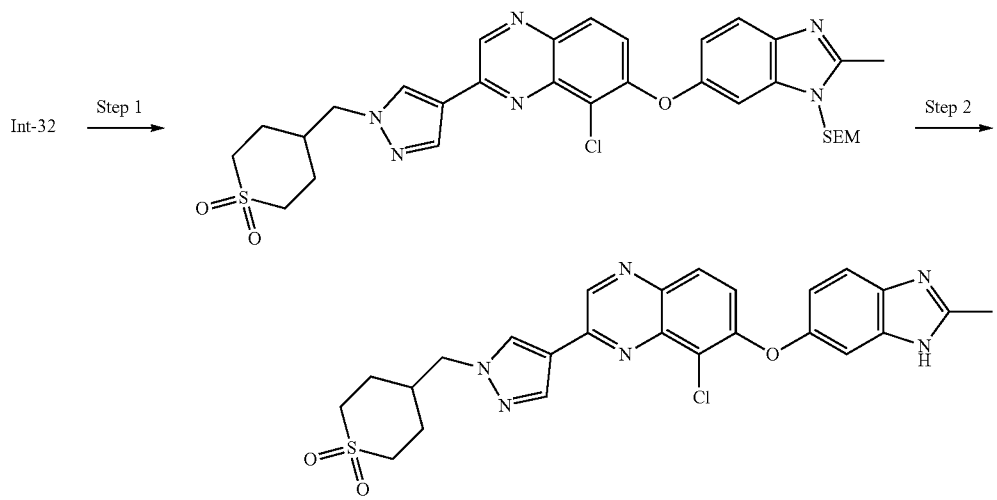

Step 1. 4-((4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)tetrahydro-2H-thiopyran 1,1-dioxide To a mixture of 8-chloro-7-((2-methyl-1-((2-(trimethylsilyl)ethoxy)methyl)-1H-benzo[d]imidazol-6-yl)oxy)-2-(1-((tetrahydro-2H-thiopyran-4-yl)methyl)-1H-pyrazol-4-yl)quinoxaline (0.20 g, 322 μmol) in dichloromethane (4 mL) was added 3-chloroperoxybenzoic acid (144 mg, 708 μmol, 85% purity) at 0° C. Then the mixture was stirred at 25° C. for 2 h. On completion, the mixture was poured into sodium sulfite aqueous solution (20 mL) and extracted with dichloromethane (15 mL×3). The combined organic layers were dried with anhydrous sodium sulfate, filtered and concentrated in vacuo. The residue was purified by column chromatography (silica gel, dichloromethane/methanol=60/1 to 20/1) to give 4-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)tetrahydro-2H-thiopyran 1,1-dioxide (170 mg, 0.26 mmol, 64%) as a white solid. m/z ES+ $[M+H]^+$ 653.3.

Step 2. 4-((4-(8-Chloro-7-((2-methyl-1H-benzo[d]imidazol-6-yl)oxy)quinoxalin-2-yl)-1H-pyrazol-1-yl)methyl)tetrahydro-2H-thiopyran 1,1-dioxide A solution of 4-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl)methyl)tetrahydro-2H-thiopyran 1,1-dioxide (0.17 g, 260 μmol) in trifluoroacetic acid (2 mL) was stirred at 15° C. for 1 h. On completion, the mixture was concentrated under reduced pressure. The residue was purified by prep-HPLC (column: Phenomenex Luna C18 150×25 mm×10 μm; mobile phase: [water (0.225% formic acid)-acetonitrile]; (B %: 11%-41%, 10 min) to afford 4-((4-(8-chloro-7-((2-methyl-1H-benzo[d]imidazol-6-yl)oxy)quinoxalin-2-yl)-1H-pyrazol-1-yl)methyl)tetrahydro-2H-thiopyran 1,1-dioxide (40.0 mg, 76.5 μmol, 29%) as a white solid. $^1H$ NMR (400 MHz, $CD_3OD$) ppm 9.21 (s, 1H), 8.64 (s, 1H), 8.39 (s, 1H), 7.97 (d, J=9.2 Hz, 1H), 7.67 (d, J=8.8 Hz, 1H), 7.44 (d, J=9.2 Hz, 1H), 7.27 (d, J=2.4 Hz, 1H), 7.17 (dd, J=8.4, 2.4 Hz, 1H), 4.36 (t, J=6.8 Hz, 2H), 3.30-3.20 (m, 2H), 3.12-3.03 (m, 1H), 2.82-2.76 (m, 1H), 2.73 (s, 3H), 2.51-2.40 (m, 2H), 2.26-2.13 (m, 2H), 1.98-1.87 (m, 1H); m/z ES+ $[M+H]^+$ 523.0.

Example 186. Synthesis of 8-chloro-7-((2-methyl-1H-benzo[d]imidazol-6-yl)oxy)-2-(1-((tetrahydro-2H-thiopyran-4-yl)methyl)-1H-pyrazol-4-yl)quinoxaline

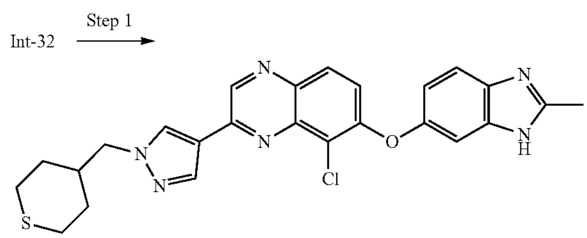

Step 1. 8-Chloro-7-((2-methyl-1H-benzo[d]imidazol-6-yl)oxy)-2-(1-((tetrahydro-2H-thiopyran-4-yl)methyl)-1H-pyrazol-4-yl)quinoxaline A solution of 2-[[6-[5-chloro-3-[1-(tetrahydrothiopyran-4-ylmethyl)pyrazol-4-yl]quinoxalin-6-yl]oxy-2-methyl-benzimidazol-1-yl]methoxy]ethyl-trimethyl-silane (60 mg, 96.5 μmol) in trifluoroacetic acid (1 mL) was stirred at 25° C. for 1 h. On completion, the mixture was concentrated under reduced pressure. The residue was purified by prep-HPLC (column: Phenomenex Luna C18 150*25 mm*10 μm; mobile phase: [water (0.225% formic acid)-acetonitrile]; (B %: 20%-50%, 10 min) to give 8-chloro-7-[(2-methyl-3H-benzimidazol-5-yl)oxy]-2-[1-(tetrahydrothiopyran-4-ylmethyl)pyrazol-4-yl]quinoxaline (18.04 mg, 0.037 mmol, 37%) as a white solid. $^1H$ NMR (400 MHz, DMSO-$d_6$) δ 9.34 (s, 1H), 8.76 (s, 1H), 8.37 (s, 1H), 8 (d, J=9.2 Hz, 1H), 7.66 (d, J=8.8 Hz, 1H), 7.39 (d, J=9.2 Hz, 1H), 7.35 (d, J=2.4 Hz, 1H), 7.11 (dd, J=8.8, 2.4 Hz, 1H), 4.31-4.12 (m, 2H), 2.88-2.75 (m, 3H), 2.63 (s, 3H), 2.60-2.58 (m, 1H), 2.16-1.92 (m, 3H), 1.96-1.86 (m, 1H), 1.65-1.26 (m, 1H); m/z ES+ $[M+H]^+$ 491.0.

Example 187. Synthesis of 8-chloro-2-(1-((3S,4S)-3-fluoropiperidin-4-yl)-1H-pyrazol-4-yl)-7-((2-methyl-1H-benzo[d]imidazol-6-yl)oxy)quinoxaline

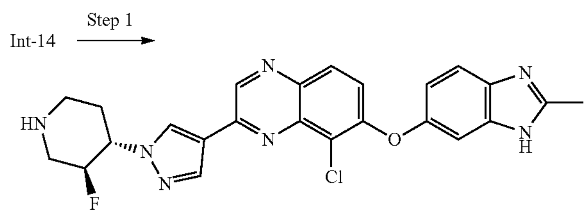

Step 1. 8-Chloro-2-(1-((3S,4S)-3-fluoropiperidin-4-yl)-1H-pyrazol-4-yl)-7-((2-methyl-1H-benzo[d]imidazol-6-yl)oxy)quinoxaline To a solution of tert-butyl (3S,4S)-4-[4-[8-chloro-7-[2-methyl-3-(2-trimethylsilylethoxymethyl)benzimidazol-5-yl]oxy-quinoxalin-2-yl]pyrazol-1-yl]-3-fluoro-piperidine-1-carboxylate (200 mg, 282 μmol) in tetrahydrofuran (5 mL) was added pyridine hydrofluoride (1.10 g, 11.1 mmol, 1 mL). The mixture was stirred at 80° C. for 1 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 1%-30%, 10 min) to give 8-chloro-2-(1-((3S,4S)-3-fluoropiperidin-4-yl)-1H-pyrazol-4-yl)-7-((2-methyl-1H-benzo[d]imidazol-6-yl)oxy)quinoxaline (67.1 mg, 127 μmol, 45%, formic acid salt) as an off-white solid. $^1H$ NMR (400 MHz, DMSO-$d_6$) δ=9.33 (s, 1H), 8.79 (s, 1H), 8.45 (s, 1H), 8.14 (s, 1H), 7.96 (d, J=9.2 Hz, 1H), 7.51 (d, J=8.8 Hz, 1H), 7.32 (d, J=9.2 Hz, 1H), 7.22 (d, J=2.0 Hz, 1H), 6.94 (dd, J=2.4, 8.8 Hz, 1H), 5.12-4.89 (m, 1H), 4.75-4.64 (m, 1H), 3.56-3.47 (m, 1H), 3.17 (d, J=10.4 Hz, 1H), 2.91-2.74 (m, 2H), 2.48 (s, 3H), 2.20-2.12 (m, 2H); m/z ES+ $[M+H]^+$ 478.1.

Example 188. Synthesis of 8-chloro-7-((2-methyl-1H-benzo[d]imidazol-6-yl)oxy)-2-(1-((4-(methylthio)cyclohexyl)methyl)-1H-pyrazol-4-yl)quinoxaline

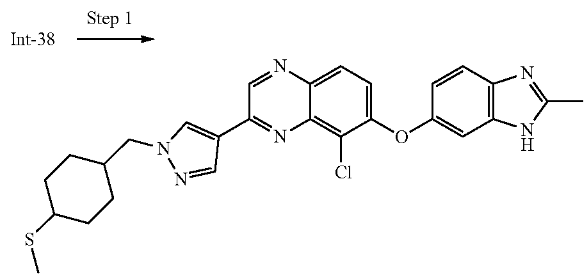

Step 1. 8-Chloro-7-((2-methyl-1H-benzo[d]imidazol-6-yl)oxy)-2-(1-((4-(methylthio)cyclohexyl)methyl)-1H-pyrazol-4-yl)quinoxaline A solution of 2-[[6-[5-chloro-3-[1-[(4-methylsulfanylcyclohexyl)methyl]pyrazol-4-yl]quinoxalin-6-yl]oxy-2-methyl-benzimidazol-1-yl]methoxy]ethyl-trimethyl-silane (20 mg, 30.8 μmol) in trifluoroacetic acid (2 mL) was stirred at 25° C. for 10 min. On completion, the mixture was concentrated under reduced pressure. The residue was purified by prep-HPLC (column: Phenomenex Synergi C18 150*25 mm*10 μm; mobile phase: [water (0.225% formic acid)-acetonitrile]; (B %: 22%-52%, 10 min) to give 8-chloro-7-[(2-methyl-3H-benzimidazol-5-yl)oxy]-2-[1-[(4-methylsulfanylcyclohexyl)methyl]pyrazol-4-yl]quinoxaline (9.6 mg, 18.5 μmol, 60%) as a white solid. $^1H$ NMR (400 MHz, $CD_3OD$) δ 9.15 (s, 1H), 8.61-8.48 (m, 1H), 8.41-8.28 (m, 1H), 7.89 (d, J=9.2 Hz, 1H), 7.53 (d, J=8.8 Hz, 1H), 7.34 (d, J=9.2 Hz, 1H), 7.18 (d, J=2.4 Hz, 1H), 7.01 (dd, J=2.4, 8.8 Hz, 1H), 4.23-4.04 (m, 2H), 2.58 (s, 3H), 2.13-2.08 (m, 1H), 2.06 (s, 3H), 2.04-1.97 (m, 1H), 1.95-1.66 (m, 4H), 1.61-1.42 (m, 3H), 1.28-1.11 (m, 1H); m/z ES+ $[M+H]^+$ 519.1.

Example 189. Synthesis of 8-chloro-7-((2-methyl-1H-benzo[d]imidazol-6-yl)oxy)-2-(1-(1-methylpiperidin-3-yl)-1H-pyrazol-4-yl)quinoxaline

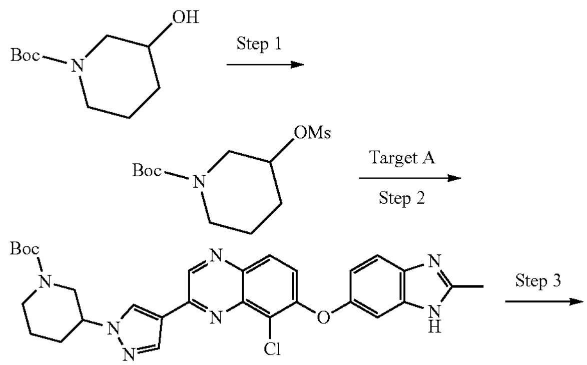

-continued

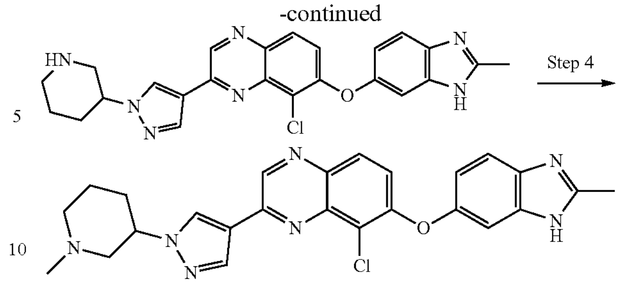

Step 1. tert-Butyl 3-((methylsulfonyl)oxy)piperidine-1-carboxylate

To a mixture of tert-butyl 3-hydroxypiperidine-1-carboxylate (5 g, 24.84 mmol) and triethylamine (5.03 g, 49.7 mmol, 6.92 mL) in dichloromethane (30 mL) was added methanesulfonyl chloride (3.13 g, 27.3 mmol, 2.12 mL) at 0° C. Then the mixture was stirred at 25° C. for 2 h. On completion, the reaction mixture was quenched by addition water (50 mL) at 0° C., then diluted with water (50 mL) and extracted with dichloromethane (100 mL×3). The combined organic layers were washed with brine (300 mL×3), dried over anhydrous sodium sulfate, filtered and concentrated under reduced pressure to give tert-butyl 3-((methylsulfonyl)oxy) piperidine-1-carboxylate (6.9 g, crude) as a yellow solid.

Step 2. tert-Butyl 3-(4-(8-chloro-7-((2-methyl-1H-benzo[d]imidazol-6-yl)oxy)quinoxalin-2-yl)-1H-pyrazol-1-yl)piperidine-1-carboxylate 1

To a solution of 8-chloro-2-(1H-pyrazol-4-yl)-7-((1-((2-(trimethylsilyl)ethoxy)methyl)-1H-benzo[d]imidazol-6-yl)oxy)quinoxaline (500 mg, 0.99 mmol) and tert-butyl 3-((methylsulfonyl)oxy) piperidine-1-carboxylate (551 mg, 1.97 mmol) in dimethylsulfoxide (10 mL) was added cesium carbonate (964 mg, 2.96 mmol) and potassium iodide (164 mg, 0.99 mmol). The mixture was stirred at 80° C. for 12 h. On completion, the reaction mixture was quenched by addition water (0.2 mL) and concentrated under reduced pressure and the residue was purified by reversed-phase HPLC (0.1% formic acid condition, 80-90% acetonitrile, 8 min) to give tert-butyl 3-(4-(8-chloro-7-((2-methyl-1H-benzo[d]imidazol-6-yl)oxy)quinoxalin-2-yl)-1H-pyrazol-1-yl) piperidine-1-carboxylate (430 mg, 0.56 mmol, 57%) as an yellow solid. m/z ES+ $[M+H]^+$ 690.4.

Step 3. 8-Chloro-7-((2-methyl-1H-benzo[d]imidazol-6-yl)oxy)-2-(1-(piperidin-3-yl)-1H-pyrazol-4-yl)quinoxaline A solution of tert-butyl 3-(4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) piperidine-1-carboxylate (100 mg, 145 μmol) in trifluoroacetic acid (1 mL) was stirred at 30° C. for 1 h. On completion, the reaction mixture was concentrated under reduced pressure to give 8-chloro-7-((2-methyl-1H-benzo[d]imidazol-6-yl)oxy)-2-(1-(piperidin-3-yl)-1H-pyrazol-4-yl)quinoxaline (67 mg, crude) as an orange oil.

Step 4. 8-Chloro-7-((2-methyl-1H-benzo[d]imidazol-6-yl)oxy)-2-(1-(1-methylpiperidin-3-yl)-1H-pyrazol-4-yl)quinoxaline To a solution of 8-chloro-7-((2-methyl-1H-benzo[d]imidazol-6-yl)oxy)-2-(1-(piperidin-3-yl)-1H-pyrazol-4-yl)quinoxaline (67.0 mg, 146 μmol) in N,N-dimethylformamide (1 mL) was added formic acid (140 mg, 2.91 mmol) and paraformaldehyde (87.5 mg, 2.91 mmol). The mixture was stirred at 60° C. for 12 h. On completion, the reaction mixture was filtered and concentrated under reduced pressure. The residue was purified by prep-HPLC (formic acid condition;column: Phenomenex Luna C18 150*25 mm*10 μm; mobile phase: [water (0.225% formic acid)-acetonitrile]; (B %: 2%-32%, 10 min) to give 8-chloro-7-((2-methyl-1H-benzo[d]imidazol-6-yl)oxy)-2-(1-(1-methylpiperidin-3-yl)-1H-pyrazol-4-yl)quinoxaline (46.4 mg, 0.098 mmol, 67%) as a yellow solid. $^1$H NMR (400 MHz, $CD_3OD$) δ 9.18 (s, 1H), 8.71 (s, 1H), 8.44 (s, 1H), 8.20 (s, 1H), 7.93 (d, J=9.2 Hz, 1H), 7.58 (d, J=8.8 Hz, 1H), 7.39 (d, J=9.2 Hz, 1H), 7.23 (d, J=2.4 Hz, 1H), 7.07 (dd, J=2.4, 8.8 Hz, 1H), 4.94-4.91 (m, 1H), 3.80-3.65 (m, 2H), 3.45-3.35 (m, 1H), 3.32-3.20 (m, 1H), 2.97 (s, 3H), 2.63 (s, 3H), 2.35-2.19 (m, 2H), 2.20-2.10 (m, 1H), 2.05-1.91 (m, 1H); m/z ES+ $[M+H]^+$ 474.1.

Example 190. Synthesis of 8-chloro-7-((2-methyl-1H-benzo[d]imidazol-6-yl)oxy)-2-(1-((2-methyl-2-azabicyclo[2.2.1]heptan-5-yl)methyl)-1H-pyrazol-4-yl)quinoxaline

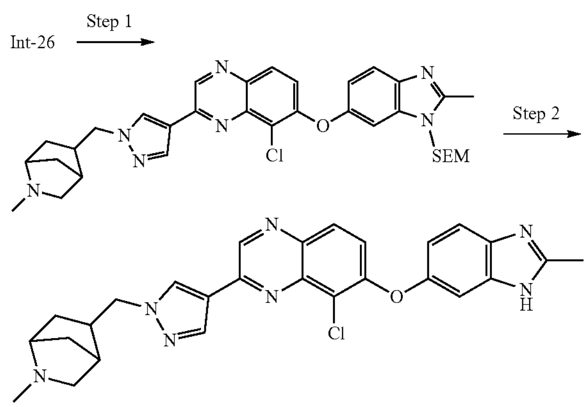

Step 1. 8-Chloro-7-((2-methyl-1-((2-(trimethylsilyl)ethoxy)methyl)-1H-benzo[d]imidazol-6-yl)oxy)-2-(1-((2-methyl-2-azabicyclo[2.2.1]heptan-5-yl)methyl)-1H-pyrazol-4-yl)quinoxaline To a solution of 2-(1-(2-azabicyclo[2.2.1]heptan-5-ylmethyl)-1H-pyrazol-4-yl)-8-chloro-7-((2-methyl-1-((2-(trimethylsilyl)ethoxy)methyl)-1H-benzo[d]imidazol-6-yl)oxy) quinoxaline (70.0 mg, 114 μmol) in N,N-dimethylformamide (1 mL) was added formic acid (109 mg, 2.27 mmol) and paraformaldehyde (68.2 mg, 2.27 mmol). The mixture was stirred at 60° C. for 2 h. On completion, the reaction mixture was filtered and concentrated under reduced pressure to give 8-chloro-7-((2-methyl-1-((2-(trimethylsilyl)ethoxy)methyl)-1H-benzo[d]imidazol-6-yl)oxy)-2-(1-((2-methyl-2-azabicyclo[2.2.1]heptan-5-yl)methyl)-1H-pyrazol-4-yl)quinoxaline (70.0 mg, crude) as a yellow oil. m/z ES+ $[M+H]^+$ 630.2.

Step 2. 8-Chloro-7-((2-methyl-1H-benzo[d]imidazol-6-yl)oxy)-2-(1-((2-methyl-2-azabicyclo[2.2.1]heptan-5-yl)methyl)-1H-pyrazol-4-yl)quinoxaline A solution of 8-chloro-7-((2-methyl-1-((2-(trimethylsilyl)ethoxy)methyl)-1H-benzo[d] imidazol-6-yl)oxy)-2-(1-((2-methyl-2-azabicyclo[2.2.1]heptan-5-yl)methyl)-1H-pyrazol-4-yl)quinoxaline (70.0 mg, 111 μmol) in trifluoroacetic acid (1 mL) was stirred at 20° C. for 2 h. On completion, the reaction mixture was concentrated under reduced pressure. The residue was purified by prep-HPLC (formic acid condition;column: Phenomenex Luna C18 150*25 mm*10 um; mobile phase: [water (0.225% formic acid)-acetonitrile]; (B %: 3%-33%, 10 min) to give 8-chloro-7-((2-methyl-1H-benzo[d]imidazol-6-yl)oxy)-2-(1-((2-methyl-2-azabicyclo [2.2.1]heptan-5-yl)methyl)-1H-pyrazol-4-yl)quinoxaline (44.1 mg, 0.088 mmol, 79%) as a yellow solid. $^1$H NMR (400 MHz, $CD_3OD$) δ 9.17 (s, 1H), 8.62 (s, 1H), 8.37 (s, 1H), 7.93 (d, J=9.2 Hz, 1H), 7.60 (d, J=8.8 Hz, 1H), 7.39 (d, J=9.2 Hz, 1H), 7.23 (s, 1H), 7.09 (dd, J=2.0, 8.8 Hz, 1H), 4.53-4.43 (m, 1H), 4.42-4.25 (m, 1H), 4.20-3.95 (m, 2H), 3.19-2.98 (m, 1H), 2.94 (s, 3H), 2.87-2.78 (m, 1H), 2.65 (s, 3H), 2.64-2.62 (m, 1H), 2.26-2.10 (m, 2H), 2-1.85 (m, 1H), 1.75-1.48 (m, 1H); m/z ES+ $[M+H]^+$ 500.1.

Example 191. Synthesis of 8-chloro-2-(1-((3,3-difluoropiperidin-4-yl)methyl)-1H-pyrazol-4-yl)-7-((2-methyl-1H-benzo[d]imidazol-6-yl)oxy)quinoxaline and 8-chloro-2-(1-((3,3-difluoro-1-methylpiperidin-4-yl)methyl)-1H-pyrazol-4-yl)-7-((2-methyl-1H-benzo[d]imidazol-6-yl)oxy) quinoxaline

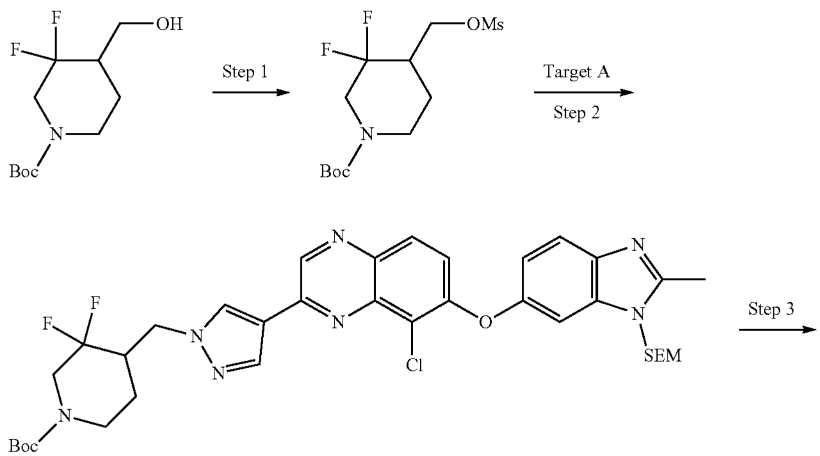

-continued

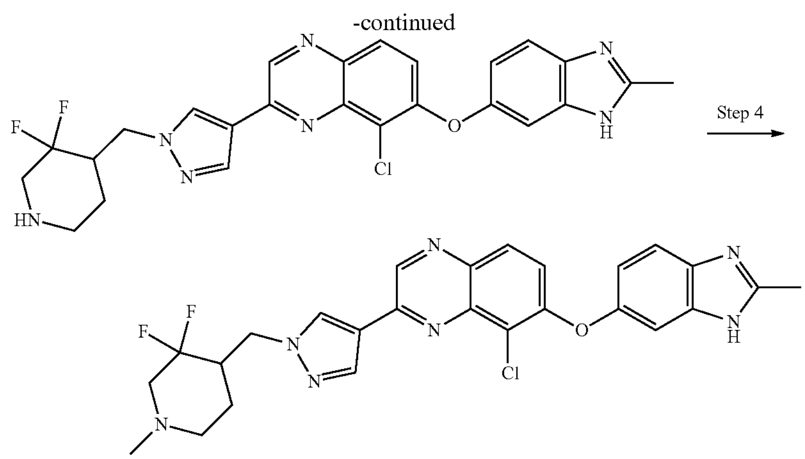

Step 1. tert-Butyl 3,3-difluoro-4-(((methylsulfonyl) oxy)methyl) piperidine-1-carboxylate To a solution of tert-butyl 3,3-difluoro-4-(hydroxymethyl) piperidine-1-carboxylate (500 mg, 1.99 mmol) in dichloromethane (10 mL) was added triethylamine (604 mg, 5.97 mmol) and methanesulfonyl chloride (341 mg, 2.98 mmol). The mixture was stirred at 0° C. for 1 h. On completion, the reaction mixture was diluted with sodium bicarbonate solution (10 mL) and extracted with ethyl acetate (25 mL×3). The combined organic layers were dried over anhydrous sodium sulfate, filtered and concentrated under reduced pressure to give tert-butyl 3,3-difluoro-4-(methylsulfonyloxymethyl) piperidine-1-carboxylate (1 g, crude) as a yellow oil. $^1$H NMR (400 MHz, $CDCl_3$) δ 4.58-4.52 (m, 1H), 4.35-4.15 (m, 3H), 3.04 (s, 3H), 2.85-2.75 (m, 1H), 2.44-2.24 (m, 1H), 2.01-1.91 (m, 1H), 1.68-1.54 (m, 1H), 1.46 (s, 9H), 1.43-1.38 (m, 1H).

Step 2. tert-Butyl 4-((4-(8-chloro-7-((2-methyl-1-((2-(trimethylsilyl)ethoxy)methyl)-1H-benzo[d]imidazol-6-yl)oxy)quinoxalin-2-yl)-1H-pyrazol-1-yl) methyl)-3,3-difluoropiperidine-1-carboxylate To a solution of 2-[[6-[5-chloro-3-(1H-pyrazol-4-yl)quinoxalin-6-yl]oxy-2-methyl-benzimidazol-1-yl]methoxy] ethyl-trimethyl-silane (200 mg, 394 μmol) in N,N-dimethylformamide (3 mL) was added potassium carbonate (163 mg, 1.18 mmol) and tert-butyl 3,3-difluoro-4-(methylsulfonyloxymethyl) piperidine-1-carboxylate (155 mg, 473 μmol). The mixture was stirred at 80° C. for 12 hs. On completion, the reaction mixture was diluted with water (5 mL) and extracted with ethyl acetate (5 mL×3). The combined organic layers were dried over anhydrous sodium sulfate, filtered and concentrated under reduced pressure. The residue was purified by prep-TLC (silica gel, dichloromethane:methanol=10:1) to give tert-butyl 4-[[4-[8-chloro-7-[2-methyl-3-(2-trimethylsilylethoxymethyl)benzimidazol-5-yl]oxy-quinoxalin-2-yl]pyrazol-1-yl]methyl]-3,3-difluoro-piperidine-1-carboxylate (80.0 mg, 0.11 mmol, 20%) as a yellow solid. m/z ES+ $[M+H]^+$ 740.3.

Step 3. 8-Chloro-2-(1-((3,3-difluoropiperidin-4-yl) methyl)-1H-pyrazol-4-yl)-7-((2-methyl-1H-benzo[d] imidazol-6-yl)oxy)quinoxaline A solution of tert-butyl 4-[[4-[8-chloro-7-[2-methyl-3-(2-trimethylsilylethoxymethyl)benzimidazol-5-yl]oxy-quinoxalin-2-yl]pyrazol-1-yl]methyl]-3,3-difluoro-piperidine-1-carboxylate (70.0 mg, 94.5 μmol) in trifluoroacetic acid (4 mL) was stirred at 25° C. for 0.5 h. On completion, the reaction mixture was concentrated under reduced pressure. The residue was purified by prep-HPLC (column: Phenomenex Gemini-NX C18 75*30 mm*3 um; mobile phase: [water (0.225% formic acid)-acetonitrile]; (B %: 12%-42%, 7 min) to give 8-chloro-2-[1-[(3,3-difluoro-4-piperidyl) methyl]pyrazol-4-yl]-7-[(2-methyl-3H-benzimidazol-5-yl) oxy]quinoxaline (22.2 mg, 0.044 mmol, 42%, formic acid salt) as an off-white solid. $^1$H NMR (400 MHz, DMSO-$d_6$) δ 9.31 (s, 1H), 8.79 (s, 1H), 8.43 (s, 1H), 8.13 (s, 1H), 7.96 (d, J=9.2 Hz, 1H), 7.51 (d, J=8.8 Hz, 1H), 7.33 (d, J=9.2 Hz, 1H), 7.21 (s, 1H), 6.98-6.89 (m, 1H), 4.65-4.55 (m, 1H), 4.36-4.24 (m, 1H), 3.50-3.41 (m, 1H), 3.19-3.03 (m, 2H), 2.87-2.64 (m, 2H), 2.49 (s, 3H), 1.72-1.44 (m, 2H); m/z ES+ $[M+H]^+$ 510.0.

Step 4. 8-Chloro-2-(1-((3,3-difluoro-1-methylpiperidin-4-yl)methyl)-1H-pyrazol-4-yl)-7-((2-methyl-1H-benzo[d]imidazol-6-yl)oxy)quinoxaline To a solution of 8-chloro-2-[1-[(3,3-difluoro-4-piperidyl) methyl]pyrazol-4-yl]-7-[(2-methyl-3H-benzimidazol-5-yl) oxy]quinoxaline (80.0 mg, 156 μmol) in N,N-dimethylformamide (1 mL) was added formic acid (75.3 mg, 1.57 mmol) and paraformaldehyde (47.11 mg, 1.57 mmol). The mixture was stirred at 60° C. for 12 h. On completion, the reaction mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 2%-32%, 7 min) to give 8-chloro-2-[1-[(3,3-difluoro-1-methyl-4-piperidyl)methyl]pyrazol-4-yl]-7-[(2-methyl-3H-benzimidazol-5-yl)oxy]quinoxaline (28.5 mg, 0.054 mmol, 34%) as an off-white solid. $^1$H NMR (400 MHz, DMSO-$d_6$) δ 9.30 (s, 1H), 8.77 (s, 1H), 8.40 (s, 1H), 7.95 (d, J=9.2 Hz, 1H), 7.51 (d, J=8.8 Hz, 1H), 7.32 (d, J=9.2 Hz, 1H), 7.21 (s, 1H), 6.98-6.89 (m, 1H), 4.64-4.53 (m, 1H), 4.29-4.18 (m, 1H), 3.32-3.28 (m, 1H), 3.07-2.97 (m, 1H), 2.74 (d, J=11.2 Hz, 1H), 2.49 (s, 3H), 2.37-2.24 (m, 1H), 2.22 (s, 3H), 2.04-1.87 (m, 1H), 1.60-1.38 (m, 2H); m/z ES+ $[M+H]^+$ 524.1.

Example 192. Synthesis of 8-chloro-7-((2-methyl-1H-benzo[d]imidazol-6-yl)oxy)-2-(1-(2-(pyrrolidin-1-yl)ethyl)-1H-pyrazol-4-yl)quinoxaline

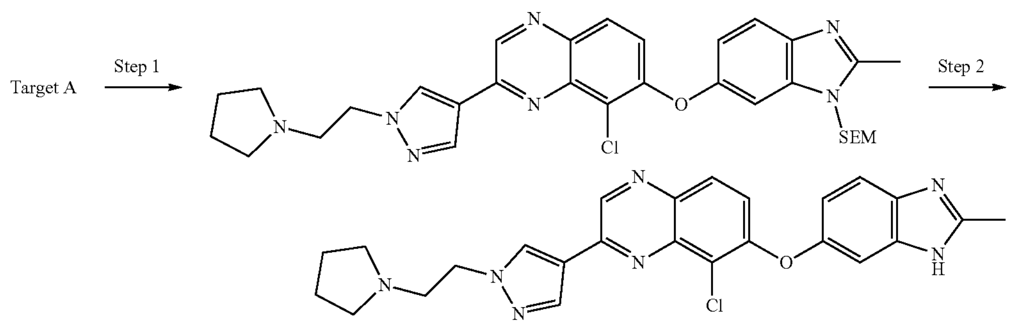

Step 1. 8-Chloro-7-((2-methyl-1-((2-(trimethylsilyl)ethoxy)methyl)-1H-benzo[d]imidazol-6-yl)oxy)-2-(1-(2-(pyrrolidin-1-yl)ethyl)-1H-pyrazol-4-yl)quinoxaline To a solution of 2-[[6-[5-chloro-3-(1H-pyrazol-4-yl)quinoxalin-6-yl]oxy-2-methyl-benzimidazol-1-yl]methoxy]ethyl-trimethyl-silane (170 mg, 335 μmol) in N,N-dimethylformamide (2 mL) was added potassium carbonate (139 mg, 1.01 mmol) and 1-(2-chloroethyl)pyrrolidine hydrochloride salt (57 mg, 335 μmol). The mixture was stirred at 80° C. for 12 h. On completion, the mixture was quenched with water (8 mL) and extracted with ethyl acetate (10 mL×3). The combined organic phase was dried over anhydrous sodium sulfate, filtered and concentrated to give 2-[[6-[5-chloro-3-[1-(2-pyrrolidin-1-ylethyl)pyrazol-4-yl]quinoxalin-6-yl]oxy-2-methyl-benzimidazol-1-yl]methoxy]ethyl-trimethyl-silane (300 mg, crude) as a yellow oil. m/z ES+ $[M+H]^+$ 604.1.

Step 2. 8-Chloro-7-((2-methyl-1H-benzo[d]imidazol-6-yl)oxy)-2-(1-(2-(pyrrolidin-1-yl)ethyl)-1H-pyrazol-4-yl)quinoxaline A solution of 2-[[6-[5-chloro-3-[1-(2-pyrrolidin-1-ylethyl)pyrazol-4-yl]quinoxalin-6-yl]oxy-2-methyl-benzimidazol-1-yl]methoxy]ethyl-trimethyl-silane (100 mg, 165 μmol) in trifluoroacetic acid (2 mL) was stirred at 25° C. for 1 h. On completion, the mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 2%-32%, 7 min) to give 8-chloro-7-((2-methyl+1H-benzo[d]imidazol-6-yl)oxy)-2-(1-(2-(pyrrolidin-1-yl)ethyl)-1H-pyrazol-4-yl)quinoxaline (30 mg, 0.063 mmol, 38%) as a yellow solid. $^1H$ NMR (400 MHz, $CDCl_3$) δ 8.97 (s, 1H), 8.42 (s, 1H), 8.31 (s, 1H), 7.84 (d, J=9.2 Hz, 1H), 7.53 (d, J=8.8 Hz, 1H), 7.29 (s, 1H), 7.22 (d, J=2.4 Hz, 1H), 7.05-7 (m, 1H), 4.70 (t, J=6.0 Hz, 2H), 3.65 (t, J=6.0 Hz, 2H), 3.15-3 (m, 4H), 2.66 (s, 3H), 2 (br t, J=6.4 Hz, 4H); m/z ES+ $[M+H]^+$ 474.1.

Example 193. Synthesis of 6-((2-methyl-1H-benzo[d]imidazol-6-yl)oxy)-3-(1-((1-methylpiperidin-4-yl)methyl)-1H-pyrazol-4-yl)quinoxaline-5-carbonitrile

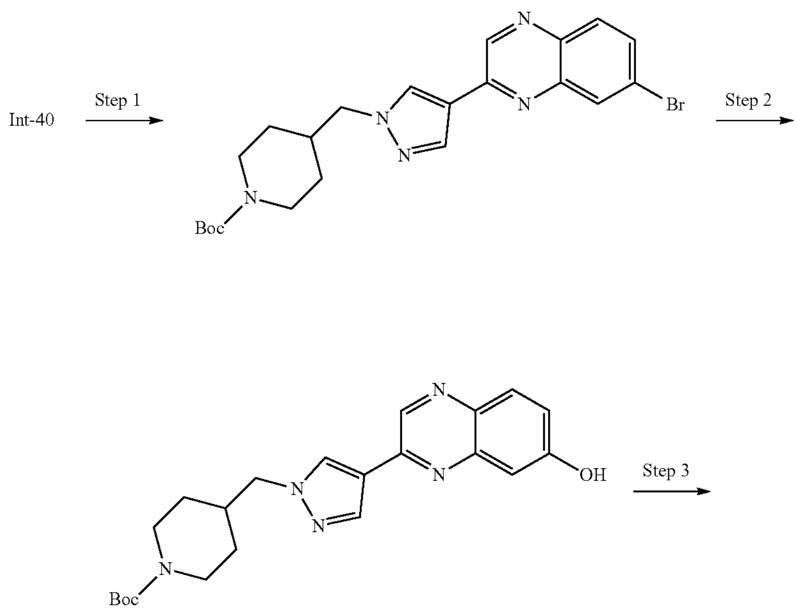

-continued

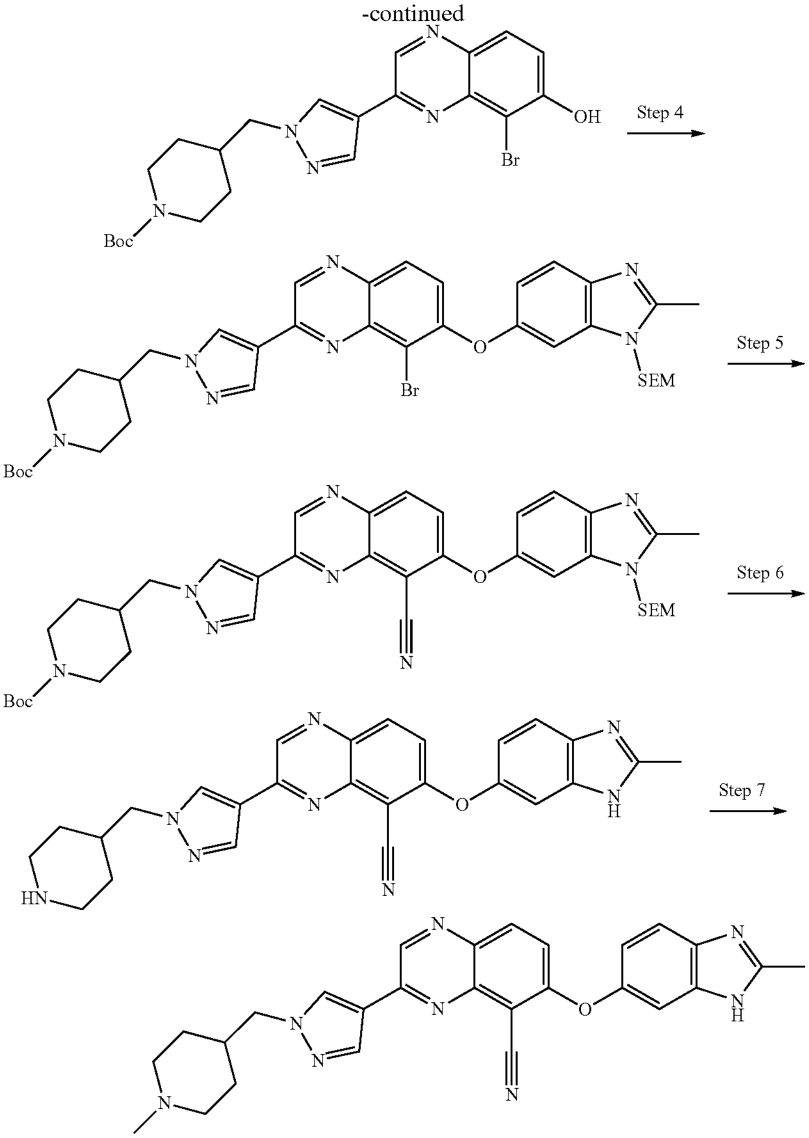

Step 1. tert-Butyl 4-[[4-(7-bromoquinoxalin-2-yl) pyrazol-1-yl]methyl]piperidine-1-carboxylate To a mixture of 7-bromo-2-chloro-quinoxaline (0.250 g, 1.03 mmol) and tert-butyl 4-[[4-(4,4,5,5-tetramethyl-1,3,2-dioxaborolan-2-yl)pyrazol-1-yl]methyl]piperidine-1-carboxylate (430 mg, 1.10 mmol) in dioxane (10 mL) and water (2 mL) was added potassium acetate (302 mg, 3.08 mmol) and cyclopenta-2,4-dien-1-yl(diphenyl)phosphane;dichloropalladium;iron (II) (75.1 mg, 103 μmol). The mixture was stirred at 60° C. for 12 hours under nitrogen. The mixture was quenched with water (20 mL) and extracted with ethyl acetate (25 mL×3). The combined organic phases were dried over anhydrous sodium sulfate, filtered and concentrated and the residue was purified by column chromatography (petroleum ether:ethyl acetate=10:1 to 1:2) to give tert-butyl 4-[[4-(7-bromoquinoxalin-2-yl)pyrazol-1-yl]methyl]piperidine-1-carboxylate (220 mg, 470 μmol, 43%) as a yellow solid. $^1$H NMR (400 MHz, $CDCl_3$) δ 9.09 (s, 1H), 8.41-8.04 (m, 3H), 7.94 (d, J=8.8 Hz, 1H), 7.78 (d, J=8.8 Hz, 1H), 4.21-4.08 (m, 4H), 2.79-2.64 (m, 2H), 2.26-2.14 (m, 1H), 1.68-1.59 (m, 2H), 1.46 (s, 9H), 1.31-1.26 (m, 2H); m/z ES+ $[M+H]^+$ 472.1.

Step 2. tert-Butyl 4-((4-(7-hydroxyquinoxalin-2-yl)-1H-pyrazol-1-yl)methyl) piperidine-1-carboxylate To a solution of tert-butyl 4-[[4-(7-bromoquinoxalin-2-yl)pyrazol-1-yl]methyl]piperidine-1-carboxylate (27.0 g, 58.0 mmol) in dioxane (280 mL) and water (140 mL) was added tris(dibenzylideneacetone) dipalladium (5.30 g, 5.8 mmol), 2-di-t-butylphosphino-2',4',6'-tri-i-propyl-1,1'-biphenyl (2.50 g, 5.80 mmol) and potassium hydroxide (32.0 g, 0.58 mol). The mixture was degassed and purged with nitrogen for 3 times, and then stirred at 100° C. for 3 h under nitrogen. The reaction mixture was diluted with water (500 mL) and extracted with dichloromethane (300 mL×3). The combined organic layers were dried over anhydrous sodium sulfate, filtered and concentrated under reduced pressure. The residue was purified by column chromatography (petroleum ether/ethyl acetate=3/1 to dichloromethane/methanol=20/1) to give tert-butyl 4-((4-(7-hydroxyquinoxalin-2-yl)-1H-pyrazol-1-yl)methyl) piperidine-1-carboxylate (20.0 g, 48.9 mmol, 84%) as a yellow solid. m/z ES+ $[M+H]^+$ 410.0.

Step 3. tert-Butyl 4-((4-(8-bromo-7-hydroxyquinoxalin-2-yl)-1H-pyrazol-1-yl)methyl) piperidine-1-carboxylate To a solution of tert-butyl 4-[[4-(7-hydroxyquinoxalin-2-yl)pyrazol-1-yl]methyl]piperidine-1-carboxylate (500 mg, 1.22 mmol) in acetonitrile (10 mL) was added N-bromosuccinimide (196 mg, 1.10 mmol) portion-wise at 0° C. The mixture was stirred at 80° C. for 12 hours. The reaction mixture was filtered and carefully concentrated under reduced pressure. The residue was purified by column chromatography (silica gel, petroleum ether/ethyl acetate=20/1 to 1/1) to give tert-butyl 4-((4-(8-bromo-7-hydroxyquinoxalin-2-yl)-1H-pyrazol-1-yl)methyl) piperidine-1-carboxylate (490 mg, 0.97 mmol, 79%) as a yellow solid. m/z ES+ $[M+H]^+$ 488.0.

Step 4. tert-Butyl 4-((4-(8-bromo-7-((2-methyl-1-((2-(trimethylsilyl)ethoxy)methyl)-1H-benzo[d]imidazol-6-yl)oxy)quinoxalin-2-yl)-1H-pyrazol-1-yl) methyl) piperidine-1-carboxylate To a solution of tert-butyl 4-[[4-(8-bromo-7-hydroxyquinoxalin-2-yl)pyrazol-1-yl]methyl]piperidine-1-carboxylate (245 mg, 502 μmol) and [2-methyl-3-(2-trimethylsilylethoxymethyl)benzimidazol-5-yl]boronic acid (307 mg, 1 mmol) in 1,2-dichloroethane (6 mL) was added copper acetate (109 mg, 602 μmol), 4 Å molecular sieves (500 mg) and cesium carbonate (409 mg, 1.25 mmol). The mixture was stirred at 60° C. for 3 hours under oxygen at 15 psi. The reaction mixture was filtered and concentrated under reduced pressure. The residue was purified by column chromatography (silica gel, dichloromethane/methanol=1/0 to 40/1) to give tert-butyl 4-((4-(8-bromo-7-((2-methyl-1-((2-(trimethylsilyl)ethoxy)methyl)-1H-benzo[d]imidazol-6-yl)oxy)quinoxalin-2-yl)-1H-pyrazol-1-yl)methyl) piperidine-1-carboxylate (230 mg, 285 μmol, 28%) as a yellow solid. m/z ES+ $[M+H]^+$ 750.1.

Step 5. tert-Butyl 4-((4-(8-cyano-7-((2-methyl-1-((2-(trimethylsilyl)ethoxy)methyl)-1H-benzo[d]imidazol-6-yl)oxy)quinoxalin-2-yl)-1H-pyrazol-1-yl) methyl) piperidine-1-carboxylate To a solution of tert-butyl 4-[[4-[8-bromo-7-[2-methyl-3-(2-trimethylsilylethoxymethyl)benzimidazol-5-yl]oxy-quinoxalin-2-yl]pyrazol-1-yl]methyl]piperidine-1-carboxylate (100 mg, 134 μmol) and propanedinitrile (17.64 mg, 267 μmol, 16.8 μL) in N,N-dimethylformamide (5 mL) was added copper iodide (12.7 mg, 66.8 μmol), 4-ditert-butylphosphanyl-N,N-dimethyl-aniline;dichloropalladium (1.89 mg, 2.67 μmol), 1,10-phenantholine (6.02 mg, 33.39 μmol), sodium tert-butoxide (25.7 mg, 267 μmol) and potassium fluoride (15.5 mg, 267 μmol). The mixture was stirred at 130° C. for 12 hours under nitrogen. The reaction mixture was diluted with $H_2O$ (30 mL) and extracted with ethyl acetate (20 mL×3). The combined organic layers were dried over sodium sulfate, filtered and concentrated under reduced pressure. The residue was purified by column chromatography (silica gel, dichloromethane:methanol=100/1 to 20/1) to give 8-chloro-7-((2-methoxypyridin-4-yl)oxy)-2-(1-((1-methylpiperidin-4-yl)methyl)-1H-pyrazol-4-yl)quinoxaline (50 mg, 60.3 μmol, 45%) as a yellow oil. m/z ES+ $[M+H]^+$ 695.1.

Step 6. 6-((2-Methyl-1H-benzo[d]imidazol-6-yl) oxy)-3-(1-(piperidin-4-ylmethyl)-1H-pyrazol-4-yl) quinoxaline-5-carbonitrile A solution of tert-butyl 4-[[4-[8-cyano-7-[2-methyl-3-(2-trimethylsilylethoxymethyl)benzimidazol-5-yl]oxy-quinoxalin-2-yl]pyrazol-1-yl]methyl]piperidine-1-carboxylate (50 mg, 60.3 μmol) in trifluoroacetic acid (1 mL) was stirred at 25° C. for 0.5 h. The reaction mixture was concentrated under reduced pressure to give 6-((2-methyl-1H-benzo[d]imidazol-6-yl)oxy)-3-(1-(piperidin-4-ylmethyl)-1H-pyrazol-4-yl)quinoxaline-5-carbonitrile (40 mg, crude, trifluoroacetic acid) as a yellow oil. m/z ES+ $[M+H]^+$ 465.0.

Step 7. 6-((2-Methyl-1H-benzo[d]imidazol-6-yl) oxy)-3-(1-((1-methylpiperidin-4-yl)methyl)-1H-pyrazol-4-yl)quinoxaline-5-carbonitrile To a solution of 6-[(2-methyl-3H-benzimidazol-5-yl) oxy]-3-[1-(4-piperidylmethyl)pyrazol-4-yl]quinoxaline-5-carbonitrile (40 mg, 69.14 μmol, trifluoroacetic acid) in N,N-dimethylformamide (1 mL) was added aqueous formaldehyde (56.1 mg, 691 μmol, 51 μL, 37%). The mixture was stirred at 25° C. for 0.5 h. Then sodium triacetoxyborohydride (73.3 mg, 346 μmol) was added. The mixture was stirred at 25° C. for 1 h. The reaction mixture was diluted with water (30 mL) and extracted with ethyl acetate (20 mL×3). The combined organic layers were dried over sodium sulfate, filtered and concentrated under reduced pressure. The residue was purified by prep-HPLC (formic acid condition; column: Phenomenex Luna C18 150*25 mm*10 um; mobile phase: [water (0.225% formic acid)-acetonitrile]; (B %: 1%-30%, 10 min) to give 6-((2-methyl-1H-benzo[d]imidazol-6-yl)oxy)-3-(1-((1-methylpiperidin-4-yl)methyl)-1H-pyrazol-4-yl)quinoxaline-5-carbonitrile (9.0 mg, 18.8 μmol, 27%) as a yellow solid. $^1H$ NMR (400 MHz, DMSO-$d_6$) δ=9.34 (s, 1H), 8.71 (s, 1H), 8.38 (s, 1H), 8.19 (d, J=9.6 Hz, 1H), 7.58 (d, J=8.4 Hz, 1H), 7.43 (s, 1H), 7.17 (d, J=9.2 Hz, 1H), 7.06 (d, J=7.2 Hz, 1H), 4.17 (d, J=7.2 Hz, 2H), 2.89 (d, J=11.2 Hz, 2H), 2.49 (s, 3H), 2.26 (s, 3H), 2.06 (t, J=10.4 Hz, 2H), 1.97-1.87 (m, 1H), 1.54 (d, J=11.6 Hz, 2H), 1.39-1.26 (m, 2H); m/z ES+ $[M+H]^+$ 479.2.

Example 194. Synthesis of 2-(4-(8-chloro-7-((2-methyl-1H-benzo[d]imidazol-6-yl)oxy)quinoxalin-2-yl)-1H-pyrazol-1-yl)-1-(pyrrolidin-1-yl)ethan-1-one

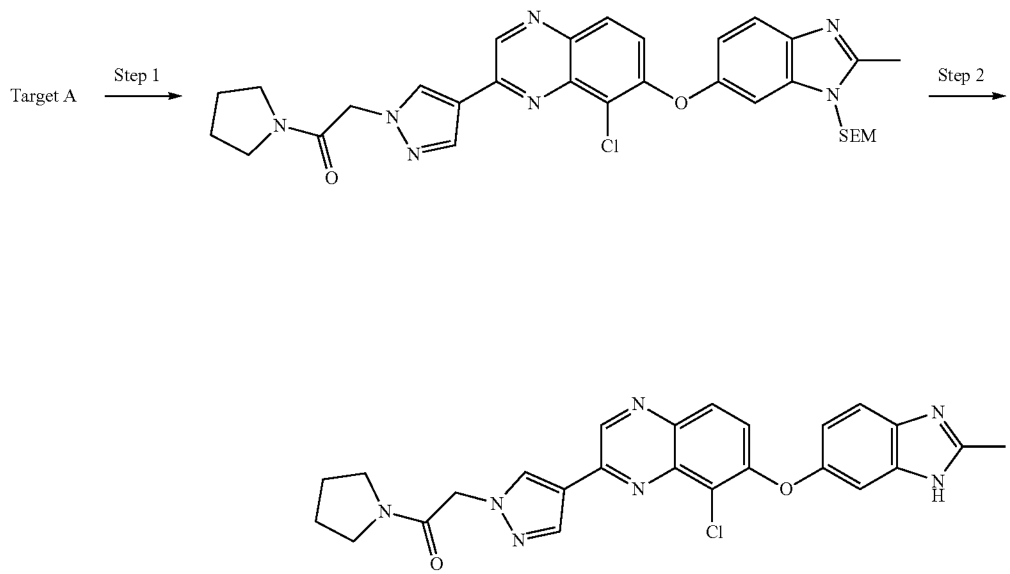

Step 1. 2-(4-(8-Chloro-7-((2-methyl-1-((2-(trimethylsilyl)ethoxy)methyl)-1H-benzo[d]imidazol-6-yl)oxy)quinoxalin-2-yl)-1H-pyrazol-1-yl)-1-(pyrrolidin-1-yl)ethan-1-one To a solution of 2-[[6-[5-chloro-3-(1H-pyrazol-4-yl)quinoxalin-6-yl]oxy-2-methyl-benzimidazol-1-yl]methoxy]ethyl-trimethyl-silane (150 mg, 295 μmol) in N,N-dimethylformamide (2 mL) was added potassium carbonate (122 mg, 887 μmol) and 2-chloro-1-pyrrolidin-1-yl-ethanone (50.0 mg, 338 μmol). The mixture was stirred at 80° C. for 12 hs. On completion, the reaction mixture was diluted with water (25 mL) and extracted with ethyl acetate (25 mL×3). The combined organic layers were dried over anhydrous sodium sulfate, filtered and concentrated under reduced pressure to give 2-[4-[8-chloro-7-[2-methyl-3-(2-trimethylsilylethoxymethyl)benzimidazol-5-yl]oxy-quinoxalin-2-yl]pyrazol-1-yl]-1-pyrrolidin-1-yl-ethanone (200 mg, crude) as a yellow oil. m/z ES+ $[M+H]^+$ 618.2.

Step 2. 2-(4-(8-chloro-7-((2-methyl-1H-benzo[d]imidazol-6-yl)oxy)quinoxalin-2-yl)-1H-pyrazol-1-yl)-1-(pyrrolidin-1-yl)ethan-1-one A solution of 2-[4-[8-chloro-7-[2-methyl-3-(2-trimethylsilylethoxymethyl)benzimidazol-5-yl]oxy-quinoxalin-2-yl]pyrazol-1-yl]-1-pyrrolidin-1-yl-ethanone (200 mg, 323 μmol) in trifluoroacetic acid (5.5 mL) was stirred at 25° C. for 0.5 h. On completion, the reaction mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 12%-42%, 7 min) to give 2-[4-[8-chloro-7-[(2-methyl-3H-benzimidazol-5-yl)oxy]quinoxalin-2-yl]pyrazol-1-yl]-1-pyrrolidin-1-yl-ethanone (39.3 mg, 0.081 mmol, 24%) as an off-white solid. $^1H$ NMR (400 MHz, DMSO-$d_6$) δ 9.34 (s, 1H), 8.63 (s, 1H), 8.36 (s, 1H), 7.98 (d, J=9.2 Hz, 1H), 7.58 (d, J=8.8 Hz, 1H), 7.35 (d, J=9:2 Hz, 1H), 7.28 (d, J=2.0 Hz, 1H), 7.06-7 (m, 1H), 5.19 (s, 2H), 3.54 (t, J=6.8 Hz, 2H), 3.35 (t, J=6.8 Hz, 2H), 2.55 (s, 3H), 2.01-1.88 (m, 2H), 1.85-1.76 (m, 2H); m/z ES+ $[M+H]^+$ 488.1.

Example 195. Synthesis of 8-chloro-7-((2-methyl-1H-benzo[d]imidazol-6-yl)oxy)-2-(1-((1-(vinylsulfonyl)piperidin-4-yl)methyl)-1H-pyrazol-4-yl)quinoxaline

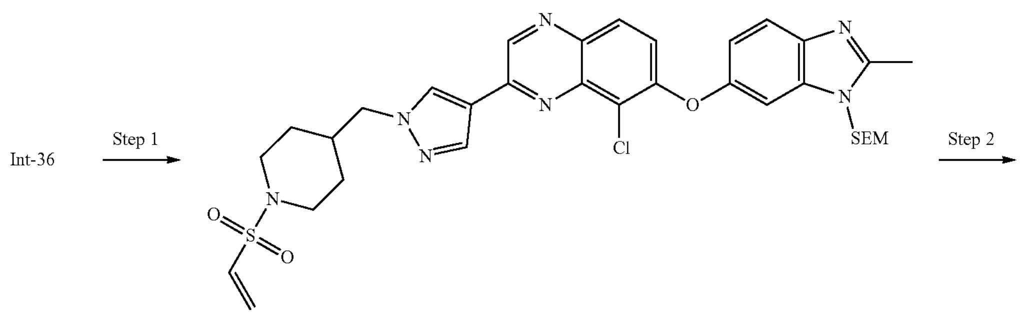

-continued

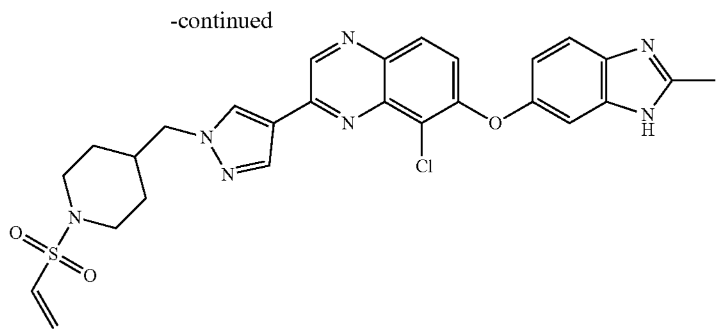

Step 1. 8-Chloro-7-((2-methyl-1-((2-(trimethylsilyl) ethoxy)methyl)-1H-benzo[d]imidazol-6-yl)oxy)-2-(1-((1-(vinylsulfonyl) piperidin-4-yl)methyl)-1H-pyrazol-4-yl)quinoxaline To a solution of 2-[[6-[5-chloro-3-[1-(4-piperidylmethyl) pyrazol-4-yl]quinoxalin-6-yl]oxy-2-methyl-benzimidazol-1-yl]methoxy]ethyl-trimethyl-silane (50 mg, 82.8 μmol) in dichloromethane (1 mL) was added diisopropylethylamine (53.48 mg, 414 μmol, 72 μL). Then 2-chloroethanesulfonyl chloride (13.49 mg, 82.8 μmol, 9 μL) was added at 0° C. The mixture was stirred at 25° C. for 1 h. The reaction mixture was concentrated under reduced pressure to give 8-chloro-7-((2-methyl-1-((2-(trimethylsilyl)ethoxy)methyl)-1H-benzo[d]imidazol-6-yl)oxy)-2-(1-((1-(vinylsulfonyl) piperidin-4-yl)methyl)-1H-pyrazol-4-yl)quinoxaline (60 mg, crude) as a yellow solid. m/z ES+ $[M+H]^+$ 694.2.

Step 2. 8-chloro-7-((2-methyl-1H-benzo[d]imidazol-6-yl)oxy)-2-(1-((1-(vinylsulfonyl) piperidin-4-yl) methyl)-1H-pyrazol-4-yl)quinoxaline A solution of 2-[[6-[5-chloro-3-[1-[(1-vinylsulfonyl-4-piperidyl)methyl]pyrazol-4-yl]quinoxalin-6-yl]oxy-2-methyl-benzimidazol-1-yl]methoxy]ethyl-trimethyl-silane (60 mg, 86.42 μmol) in trifluoroacetic acid (1 mL) was stirred at 25° C. for 1 h. The reaction mixture was concentrated under reduced pressure. The residue was purified by prep-HPLC (formic acid condition; column: Phenomenex Luna C18 150*25 mm*10 μm; mobile phase: [water (0.225% formic acid)-acetonitrile]; (B %: 17%-47%, 10 min) to give 8-chloro-7-((2-methyl-1H-benzo[d]imidazol-6-yl)oxy)-2-(1-((1-(vinylsulfonyl) piperidin-4-yl)methyl)-1H-pyrazol-4-yl)quinoxaline (6.4 mg, 11.3 μmol, 13%) as an off-white solid. $^1$H NMR (400 MHz, DMSO-$d_6$) δ=9.31 (s, 1H), 8.69 (s, 1H), 8.38 (s, 1H), 7.95 (d, J=9.2 Hz, 1H), 7.51 (d, J=8.4 Hz, 1H), 7.31 (d, J=9.2 Hz, 1H), 7.21 (s, 1H), 6.94 (dd, J=2.4, 8.8 Hz, 1H), 6.78 (dd, J=10.0, 16.4 Hz, 1H), 6.16-6.05 (m, 2H), 4.19 (d, J=7.2 Hz, 2H), 3.54 (d, J=12.0 Hz, 2H), 2.64-2.55 (m, 2H), 2.49 (s, 3H), 2.10-1.96 (m, 1H), 1.64 (d, J=11.2 Hz, 2H), 1.38-1.24 (m, 2H); m/z ES+ $[M+H]^+$ 564.1.

Example 196. Synthesis of 8-chloro-2-(1-((3,3-difluorocyclobutyl)methyl)-1H-pyrazol-4-yl)-7-((2-methyl-1H-benzo[d]imidazol-6-yl)oxy)quinoxaline Step 1

Target A

-continued

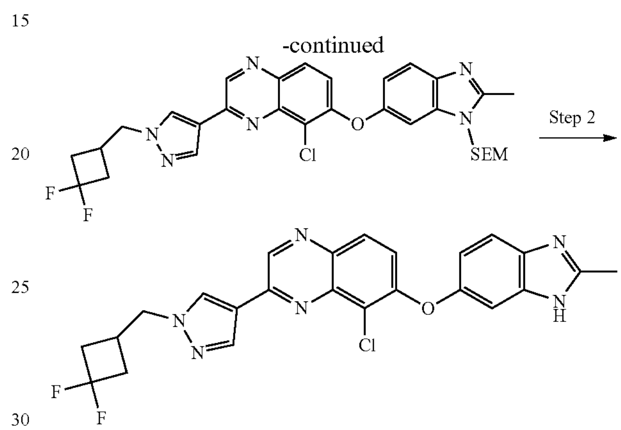

Step 1. 8-Chloro-2-(1-((3,3-difluorocyclobutyl) methyl)-1H-pyrazol-4-yl)-7-((2-methyl-1-((2-(trimethylsilyl)ethoxy)methyl)-1H-benzo[d]imidazol-6-yl)oxy)quinoxaline To a solution of 2-[[6-[5-chloro-3-(1H-pyrazol-4-yl)quinoxalin-6-yl]oxy-2-methyl-benzimidazol-1-yl]methoxy] ethyl-trimethyl-silane (150 mg, 295 μmol) in N,N-dimethylformamide (2 mL) was added potassium carbonate (122 mg, 887 μmol) and 3-(bromomethyl)-1,1-difluoro-cyclobutane (60.0 mg, 324 μmol). The mixture was stirred at 80° C. for 12 hs. On completion, the reaction mixture was diluted with water (5 mL) and extracted with ethyl acetate (15 mL×3). The combined organic layers were dried over anhydrous sodium sulfate, filtered and concentrated under reduced pressure to give 2-[[6-[5-chloro-3-[1-[(3,3-difluorocyclobutyl)methyl]pyrazol-4-yl]quinoxalin-6-yl]oxy-2-methyl-benzimidazol-1-yl]methoxy]ethyl-trimethyl-silane (180 mg, crude) as a yellow solid. m/z ES+ $[M+H]^+$ 611.2.

Step 2. 8-Chloro-2-(1-((3,3-difluorocyclobutyl) methyl)-1H-pyrazol-4-yl)-7-((2-methyl-1H-benzo[d] imidazol-6-yl)oxy)quinoxaline A solution of 2-[[6-[5-chloro-3-[1-[(3,3-difluorocyclobutyl)methyl]pyrazol-4-yl]quinoxalin-6-yl]oxy-2-methyl-benzimidazol-1-yl]methoxy]ethyl-trimethyl-silane (140 mg, 229 μmol) in trifluoroacetic acid (2 mL) was stirred at 25° C. for 0.5 h. On completion, the reaction mixture was concentrated under reduced pressure. The residue was purified by prep-HPLC (column: Phenomenex Gemini-NX C18 75*30 mm*3 μm; mobile phase: [water (0.225% formic acid)-acetonitrile]; (B %: 20%-50%, 7 min) to give 8-chloro-2-[1-[(3,3-difluorocyclobutyl)methyl]pyrazol-4-yl]-7-[(2- methyl-3H-benzimidazol-5-yl)oxy]quinoxaline (71.3 mg, 0.15 mmol, 64%) as an off-white solid. $^1$H NMR (400 MHz, DMSO-$d_6$) δ 9.33 (s, 1H), 8.77 (s, 1H), 8.38 (s, 1H), 7.99 (d, J=9.2 Hz, 1H), 7.63 (d, J=8.8 Hz, 1H), 7.38 (d, J=9.2 Hz, 1H), 7.33 (s, 1H), 7.09 (d, J-8.4 Hz, 1H), 4.39 (d, J=4.8 Hz, 2H), 2.76-2.58 (m, 3H), 2.60 (s, 3H), 2.57-2.53 (m, 1H), 2.48-2.41 (m, 1H); m/z ES+ $[M+H]^+$ 481.1.

Example 197. Synthesis of 8-chloro-2-(1-(2,2-diethoxyethyl)-1H-pyrazol-4-yl)-7-((2-methyl-1H-benzo[d]imidazol-6-yl)oxy)quinoxaline and 2-(1-((1,3-dioxan-2-yl)methyl)-1H-pyrazol-4-yl)-8-chloro-7-((2-methyl-1H-benzo[d]imidazol-6-yl)oxy)quinoxaline

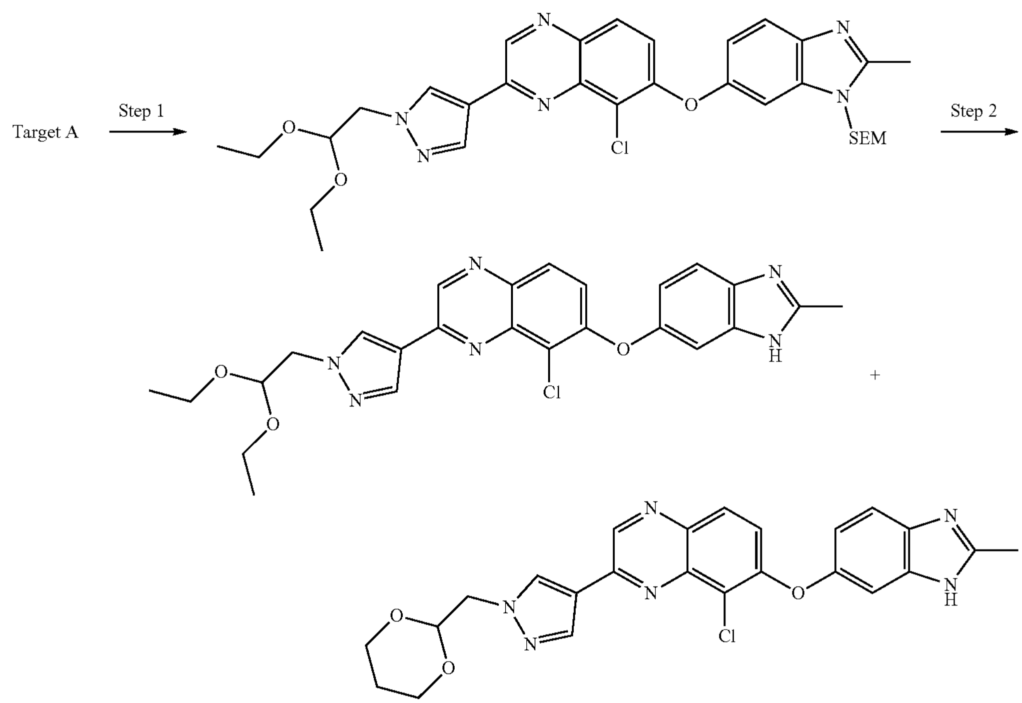

Step 1. 8-Chloro-2-(1-(2,2-diethoxyethyl)-1H-pyrazol-4-yl)-7-((2-methyl-1-((2-(trimethylsilyl)ethoxy)methyl)-1H-benzo[d]imidazol-6-yl)oxy)quinoxaline To a mixture of 2-[[6-[5-chloro-3-(1H-pyrazol-4-yl)quinoxalin-6-yl]oxy-2-methyl-benzimidazol-1-yl]methoxy]ethyl-trimethyl-silane (200 mg, 394 μmol) and 2-bromo-1,1-diethoxy-ethane (155 mg, 789 μmol, 119 μL) in N,N-dimethylformamide (3 mL) was added cesium carbonate (3864 mg, 1.18 mmol) in one portion at 20° C. The mixture was then heated to 100° C. and stirred for 4 hours. On completion, the reaction mixture was quenched by addition water (20 mL) at 20° C., and then extracted with ethyl acetate (10 mL×3). The combined organic layers were washed with water (20 mL×3), dried over sodium sulfate, filtered and concentrated under reduced pressure to give 2-[[6-[5-chloro-3-[1-(2,2-diethoxyethyl)pyrazol-4-yl]quinoxalin-6-yl]oxy-2-methyl-benzimidazol-1-yl]methoxy]ethyl-trimethyl-silane (0.25 g, 0.40 mmol, 97%) as a yellow oil. m/z ES+ $[M+H]^+$ 623.4.

Step. 2. 8-Chloro-2-(1-(2,2-diethoxyethyl)-1H-pyrazol-4-yl)-7-((2-methyl-1H-benzo[d]imidazol-6-yl)oxy)quinoxaline and 2-(1-((1,3-dioxan-2-yl)methyl)-1H-pyrazol-4-yl)-8-chloro-7-((2-methyl-1H-benzo[d]imidazol-6-yl)oxy)quinoxaline To a mixture of 2-[[6-[5-chloro-3-[1-(2,2-diethoxyethyl)pyrazol-4-yl]quinoxalin-6-yl]oxy-2-methyl-benzimidazol-1-yl]methoxy]ethyl-trimethyl-silane (250 mg, 401 μmol) and propane-1,3-diol (61.0 mg, 802 μmol, 58 μL) in toluene (5 mL) was added p-toluenesulfonic acid monohydrate (7.6 mg, 40.1 μmol) in one portion at 20° C. The mixture was then heated to 120° C. and stirred for 16 hours. On completion, the reaction mixture was concentrated under reduced pressure. The residue was purified by prep-HPLC (column: Phenomenex Luna C18 150*25 mm*10 μm; mobile phase: [water (0.225% formic acid)-acetonitrile]; (B %: 15%-45%, 10 min) and repurified by prep-HPLC (column: Phenomenex Gemini-NX C18 75*30 mm*3 μm; mobile phase: [water (10 mM ammonium bicarbonate)-acetonitrile]; (B %: 20%-50%, 8 min). The impure product was further purified by prep-HPLC (column: Phenomenex Gemini-NX C18 75*30 mm*3 um; mobile phase: [water (10 mM ammonium bicarbonate)-acetonitrile]; (B %: 28%-58%, 8 min) to give 8-chloro-2-[1-(2,2-diethoxyethyl)pyrazol-4-yl]-7-[(2-methyl-3H-benzimidazol-5-yl)oxy] (quinoxaline (8.2 mg, 0.017 mmol, 4.1%) as a yellow gum and 2-(1-((1,3-dioxan-2-yl)methyl)-1H-pyrazol-4-yl)-8-chloro-7-((2-methyl-1H-benzo[d]imidazol-6-yl)oxy)quinoxaline (10.0 mg, 0.021 mmol, 5.0%) as a yellow gum.

$^1$H NMR (400 MHz, DMSO-$d_6$) δ 12.28 (br s, 1H), 9.32 (s, 1H), 8.69 (s, 1H), 8.38 (s, 1H), 7.96 (d, J=9.2 Hz, 1H), 7.50 (d, J=8.8 Hz, 1H), 7.32 (d, J=8.8 Hz, 1H), 7.21 (s, 1H), 6.94 (d, J=9.2 Hz, 1H), 4.91 (t, J=5.6 Hz, 1H), 4.33 (d, J=5.6 Hz, 2H), 3.75-3.56 (m, 2H), 3.51-3.40 (m, 2H), 2.49 (s, 3H), 1.08 (t, J=7.2 Hz, 6H); m/z ES+ $[M+H]^+$ 493.1.

$^1$H NMR (400 MHz, DMSO-$d_6$) 9.31 (s, 1H), 8.64 (s, 1H), 8.37 (s, 1H), 7.95 (d, J=9.2 Hz, 1H), 7.51 (d, J=8.4 Hz, 1H), 7.32 (d, J=9.2 Hz, 1H), 7.21 (d, J=2.0 Hz, 1H), 6.94 (dd, J=2.4, 8.4 Hz, 1H), 4.98 (t, J=4.8 Hz, 1H), 4.32 (d, J=4.8

Hz, 2H), 4.05 (dd, J=4.8, 11.2 Hz, 2H), 3.86-3.68 (m, 2H), 2.49 (s, 3H), 2.02-1.77 (m, 1H), 1.38 (d, J=13.6 Hz, 1H); m/z ES+ $[M+H]^+$ 477.0.

Example 198. 1-[(4-{7-[(7-fluoro-2-methyl-1H-1,3-benzodiazol-6-yl)oxy]-8-(oxolan-3-yl)quinoxalin-2-yl}-1H-pyrazol-1-yl)methyl] cyclopropan-1-ol

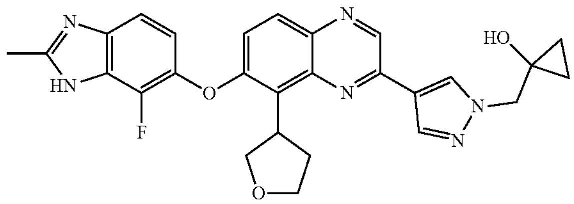 [SMILES: Cc1nc2ccc(Oc3ccc4ncc(-c5cnn(CC6(O)CC6)c5)nc4c3C3CCOC3)c(F)c2[nH]1]

m/z ES+ $[M+H]^+$ 501.0; $^1$H NMR (400 MHz, $CD_3OD$) δ 9.13 (s, 1H), 8.64 (s, 1H), 8.47 (br, 1H), 8.36 (s, 1H), 7.84 (d, J=9.6 Hz, 1H), 7.35 (d, J=8.8 Hz, 1H), 7.20 (d, J=9.2 Hz, 1H), 7.08 (m, 2H), 5.06 (quint, J=9.2 Hz, 1H), 4.41 (dd, J=7.6, 8.8 Hz, 1H), 4.37 (s, 2H), 4.31 (m, 1H), 4.22 (t, J=8.4 Hz, 1H), 4.11 (q, J=8.0 Hz, 1H), 2.82 (m, 1H), 2.62 (s, 3H), 2.40 (m, 1H), 0.90 (m, 4H).

Example 199. 2-{1-[(3,3-difluorocyclobutyl) methyl]-1H-pyrazol-4-yl}-8-(2,2-dimethyl-2,5-dihydrofuran-3-yl)-7-[(2-methyl-1H-1,3-benzodiazol-6-yl)oxy]quinoxaline

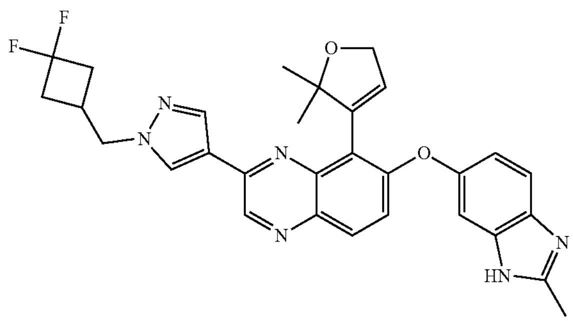 [SMILES: Cc1nc2ccc(Oc3ccc4ncc(-c5cnn(CC6CC(F)(F)C6)c5)nc4c3C3=CCOC3(C)C)cc2[nH]1]

m/z ES+ $[M+H]^+$ 543.0; $^1$H NMR (400 MHz, DMSO) δ 12.10 (br, 1H), 9.20 (s, 1H), 8.62 (s, 1H), 8.25 (s, 1H), 7.93 (d, J=9.2 Hz, 1H), 7.47 (d, J=8.0 Hz, 1H), 7.24 (d, J=9.2 Hz, 1H), 7.11 (s, 1H), 6.87 (d, J=8.8 Hz, 1H), 5.86 (s, 1H), 4.74 (s, 2H), 4.38 (d, J=5.2 Hz, 1H), 2.67 (m, 4H), 2.50 (m, 1H), 2.53 (m, 1H), 2.47 (s, 3H), 1.35 (s, 6H).

Example 200. 2-{1-[(3,3-difluorocyclobutyl) methyl]-1H-pyrazol-4-yl}-7-[(7-fluoro-2-methyl-1H-1,3-benzodiazol-6-yl)oxy]-8-(oxolan-3-yl)quinoxaline

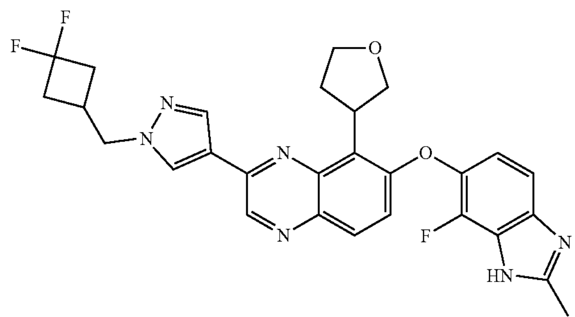 [SMILES: Cc1nc2ccc(Oc3ccc4ncc(-c5cnn(CC6CC(F)(F)C6)c5)nc4c3C3CCOC3)c(F)c2[nH]1]

m/z ES+ $[M+H]^+$ 535.0; $^1$H NMR (400 MHz, $CD_3OD$) δ 9.12 (s, 1H), 8.58 (s, 1H), 8.34 (s, 1H), 7.86 (d, J=9.2 Hz, 1H), 7.51 (d, J=8.8 Hz, 1H), 7.27 (m, 2H), 5.00 (quint, J=9.2 Hz, 1H), 2.80 (s, 3H), 2.79-2.60 (m, 4H), 2.58-2.43 (m, 2H), 2.43-2.35 (m, 1H).

Example 201. 1-({4-[8-(5,5-dimethyl-2,5-dihydrofuran-3-yl)-7-[(7-fluoro-2-methyl-1H-1,3-benzodiazol-6-yl)oxy]quinoxalin-2-yl]-1H-pyrazol-1-yl}methyl)cyclopropan-1-ol

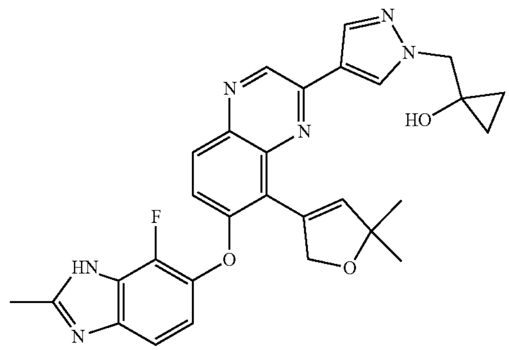 [SMILES: Cc1nc2ccc(Oc3ccc4ncc(-c5cnn(CC6(O)CC6)c5)nc4c3C3=CC(C)(C)OC3)c(F)c2[nH]1]

m/z ES+ $[M+H]^+$ 527.0; $^1$H NMR (400 MHz, $CD_3OD$) δ 9.12 (s, 1H), 8.56 (s, 1H), 8.27 (s, 1H), 7.88 (d, J=9.2 Hz, 1H), 7.28 (m, 2H), 7.00 (t, J=8.0 Hz, 1H), 6.49 (s, 1H), 5.27 (d, J=2.0 Hz, 2H), 4.34 (s, 2H), 2.60 (s, 3H), 1.46 (s, 6H), 0.86 (d, J=6.4 Hz, 4H).

Example 202. 3-{6-[(7-fluoro-2-methyl-1H-1,3-benzodiazol-6-yl)oxy]-3-{1-[(1-hydroxycyclopropyl)methyl]-1H-pyrazol-4-yl} quinoxalin-5-yl}-1,3-oxazolidin-2-one

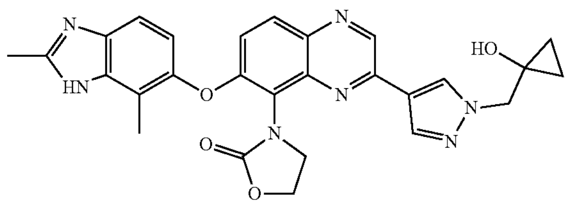 [SMILES: Cc1nc2ccc(Oc3ccc4ncc(-c5cnn(CC6(O)CC6)c5)nc4c3N3CCOC3=O)c(C)c2[nH]1]

m/z ES+ $[M+H]^+$ 516.0; $^1$H NMR (400 MHz, $CD_3OD$) δ 9.19 (s, 1H), 8.62 (s, 1H), 8.34 (s, 1H), 8.02 (d, J=9.6 Hz, 1H), 7.35 (m, 2H), 7.17 (dd, J=8.8, 9.2 Hz, 1H), 4.81 (m, 1H), 4.64 (q, J=8.4 Hz, 1H), 4.45-4.32 (m, 3H), 4.16 (m, 1H), 2.62 (s, 3H), 0.86 (m, 4H).

Example 203. 1-[(4-{7-[(2-methyl-1H-1,3-benzodiazol-6-yl)oxy]-8-(morpholin-4-yl)quinoxalin-2-yl}-1H-pyrazol-1-yl)methyl] cyclopropan-1-ol

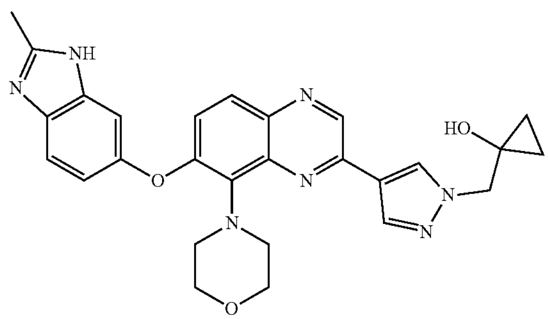 [SMILES: Cc1nc2ccc(Oc3ccc4ncc(-c5cnn(CC6(O)CC6)c5)nc4c3N3CCOCC3)cc2[nH]1]

m/z ES+ $[M+H]^+$ 498.0; $^1$H NMR (400 MHz, $CD_3OD$) δ 8.98 (s, 1H), 8.46 (s, 1H), 8.18 (s, 1H), 7.61 (d, J=9.2 Hz, 1H), 7.36 (d, J=8.8 Hz, 1H), 7.26 (d, J=9.2 Hz, 1H), 6.89 (d, J=2.0 Hz, 1H), 6.83 (dd, J=2.0, 8.4 Hz, 1H), 4.20 (s, 2H), 3.63 (m, 4H), 3.39 (m, 4H), 2.44 (s, 3H), 0.76 (m, 4H).

Example 204. 2-{1-[(3,3-difluorocyclobutyl) methyl]-1H-pyrazol-4-yl}-8-(5,5-dimethyl-2,5-dihydrofuran-3-yl)-7-[(2-methyl-1H-1,3-benzodiazol-6-yl)oxy]quinoxaline

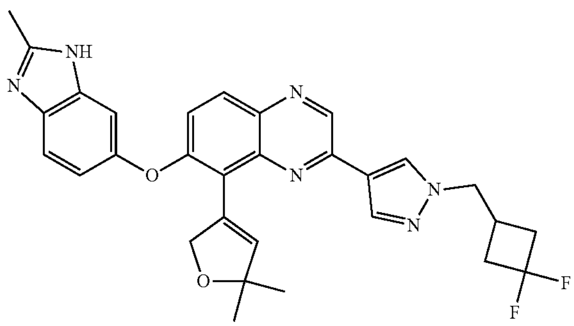 [SMILES: Cc1nc2ccc(Oc3ccc4ncc(-c5cnn(CC6CC(F)(F)C6)c5)nc4c3C3=CC(C)(C)OC3)cc2[nH]1]

m/z ES+ $[M+H]^+$ 543.0; $^1$H NMR (400 MHz, DMSO) δ 9.24 (s, 1H), 8.64 (s, 1H), 8.25 (s, 1H), 7.93 (d, J=9.2 Hz, 1H), 7.50 (d, J=8.4 Hz, 1H), 7.31 (d, J=9.2 Hz, 1H), 7.11 (d, J=2.4 Hz, 1H), 6.90 (dd, J=2.4, 8.8 Hz, 1H), 6.52 (t, J=2.0 Hz, 1H), 5.12 (d, J=2.0 Hz, 2H), 4.39 (d, J=5.2 Hz, 2H), 2.68 (m, 4H), 2.55 (m, 1H), 2.50 (s, 3H), 1.33 (s, 6H).

Example 205. 1-({4-[8-(2,5-dihydrofuran-3-yl)-7-[(7-fluoro-2-methyl-1H-1,3-benzodiazol-6-yl)oxy] quinoxalin-2-yl]-1H-pyrazol-1-yl}methyl)cyclopropan-1-ol

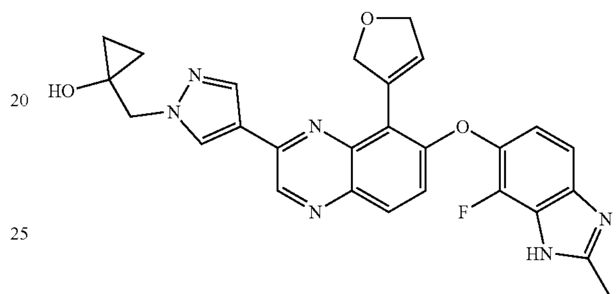

m/z ES+ $[M+H]^+$ 499.0; $^1$H NMR (400 MHz, $CD_3OD$) δ 9.14 (s, 1H), 8.58 (s, 1H), 8.26 (s, 1H), 7.83 (d, J=8.8 Hz, 1H), 7.30 (br, 1H), 7.27 (d, J=9.2 Hz, 1H), 7.05 (t, J=7.2 Hz, 1H), 6.72 (t, J=2.0 Hz, 1H), 5.34 (m, 2H), 5.00-4.95 (m, 2H), 2.60 (s, 3H), 0.89 (m, 4H).

Example 206. 1-[3-(3-{1-[(3,3-difluorocyclobutyl) methyl]-1H-pyrazol-4-yl}-6-[(2-methyl-1H-1,3-benzodiazol-6-yl)oxy]quinoxalin-5-yl)-2,5-dihydro-1H-pyrrol-1-yl]ethan-1-one

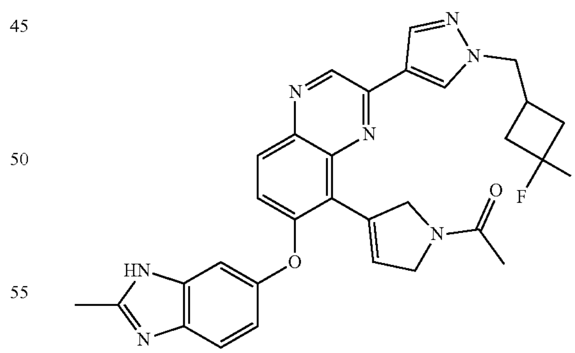

m/z ES+ $[M+H]^+$ 556.1; $^1$H NMR (400 MHz, DMSO) δ 9.24 (d, J=6.8 Hz, 1H), 8.67 (d, J=8.4 Hz, 1H), 8.30 (d, J=24.8 Hz, 1H), 7.93 (dd, J=3.2, 9.2 Hz, 1H), 7.48 (d, J=8.4 Hz, 1H), 7.27 (dd, J=6.8, 9.2 Hz, 1H), 7.15 (m, 1H), 6.90 (td, J=2.8, 8.8 Hz, 1H), 6.45 (td, J=1.6, 10.8 Hz, 1H), 4.93 (s, 1H), 4.73 (s, 1H), 4.54 (s, 1H), 4.37 (s, 2H), 4.32 (s, 1H), 2.68 (m, 3H), 2.54 (m, 2H), 2.47 (s, 3H), 2.01 (d, J=8.4 Hz, 3H).

Example 207. 2-{1-[(3,3-difluorocyclobutyl) methyl]-1H-pyrazol-4-yl}-8-(5,5-dimethyl-2,5-dihydrofuran-3-yl)-7-[(7-fluoro-2-methyl-1H-1,3-benzodiazol-6-yl)oxy]quinoxaline

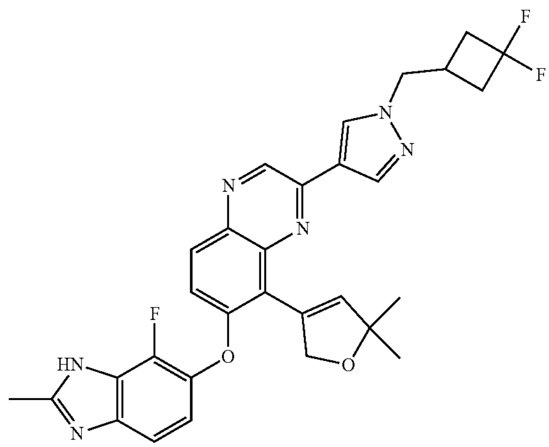 [SMILES: Cc1nc2ccc(Oc3ccc4ncc(-c5cnn(CC6CC(F)(F)C6)c5)nc4c3C3=CC(C)(C)OC3)c(F)c2[nH]1]

m/z ES+ $[M+H]^+$ 561.0; $^1H$ NMR (400 MHz, DMSO) δ 12.70 (br, 1H), 9.22 (s, 1H), 8.64 (s, 1H), 8.25 (s, 1H), 7.90 (d, J=9.6 Hz, 1H), 7.27 (m, 1H), 7.21 (d, J=9.2 Hz, 1H), 6.97 (m, 1H), 6.55 (s, 1H), 5.17 (d, J=2.0 Hz, 2H), 4.39 (d, J=5.2 Hz, 2H), 2.69 (m, 4H), 2.51 (m, 1H), 2.50 (s, 3H), 1.38 (s, 6H).

Example 208. 4-(4-{8-chloro-7-[(2-methyl-1H-1,3-benzodiazol-6-yl)oxy]quinoxalin-2-yl}-1H-pyrazol-1-yl)-1-(methylimino)-1λ$^6$-thian-1-one

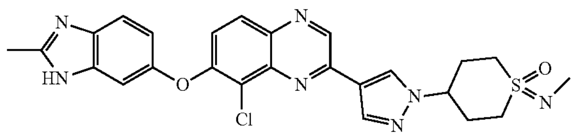

m/z ES+ $[M+H]^+$ 521.9; $^1H$ NMR (400 MHz, DMSO) § 12.32 (br, 1H), 9.33 (s, 1H), 8.78 (s, 1H), 8.37 (s, 1H), 7.95 (d, J=9.6 Hz, 1H), 7.51 (m, 1H), 7.32 (d, J=8.8 Hz, 1H), 7.21 (m, 1H), 6.94 (d, J=8.0 Hz, 1H), 4.6 (m, 1H), 2.67 (s, 3H), 2.55 (m, 2H), 2.50 (s, 3H), 2.45-2.20 (m, 6H).

Example 209. 2-{1-[(3,3-difluorocyclobutyl) methyl]-1H-pyrazol-4-yl}-7-[(7-fluoro-2-methyl-1H-1,3-benzodiazol-6-yl)oxy]-8-(furan-3-yl)quinoxaline

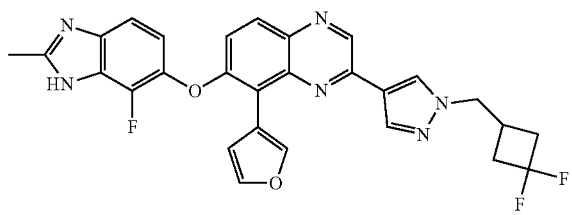 [SMILES: Cc1nc2ccc(Oc3ccc4ncc(-c5cnn(CC6CC(F)(F)C6)c5)nc4c3-c3ccoc3)c(F)c2[nH]1]

m/z ES+ $[M+H]^+$ 531.1; $^1H$ NMR (400 MHz, DMSO) δ 12.72 (br, 1H), 9.25 (s, 1H), 8.64 (s, 1H), 8.44 (s, 1H), 8.31 (s, 1H), 7.90 (d, J=9.6 Hz, 1H), 7.82 (t, J=1.6 Hz, 1H), 7.31 (d, J=8.4 Hz, 1H), 7.26 (s, 1H), 7.23 (d, J=9.2 Hz, 1H), 7.03 (t, J=7.6 Hz, 1H), 4.39 (d, J=5.6 Hz, 2H), 2.70 (m, 4H), 2.52 (s, 3H).

Example 210. [4-(4-{8-chloro-7-[(2-methyl-1H-1,3-benzodiazol-6-yl)oxy]quinoxalin-2-yl}-1H-pyrazol-1-yl) piperidin-1-yl] (imino)methyl-λ$^6$-sulfanone

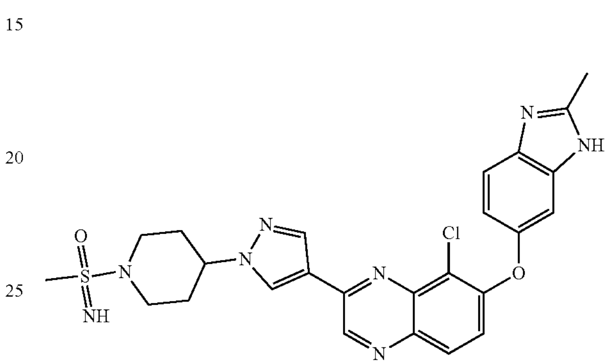

m/z ES+ $[M+H]^+$ 537.0; $^1H$ NMR (400 MHz, $CD_3OD$) δ 9.13 (s, 1H), 8.62 (s, 1H), 8.35 (s, 1H), 7.86 (d, J=9.2 Hz, 1H), 7.52 (d, J=8.8 Hz, 1H), 7.32 (d, J=9.2 Hz, 1H), 7.18 (s, 1H), 7.00 (dd, J=2.0, 8.8 Hz, 1H), 4.45 (m, 1H), 3.99 (m, 2H), 2.98 (m, 2H), 2.91 (s, 3H), 2.57 (s, 3H), 2.35-2.19 (m, 4H).

Example 211. 2-{1-[(3,3-difluorocyclobutyl) methyl]-1H-pyrazol-4-yl}-8-(2,5-dihydro-1H-pyrrol-3-yl)-7-[(2-methyl-1H-1,3-benzodiazol-6-yl)oxy] quinoxaline

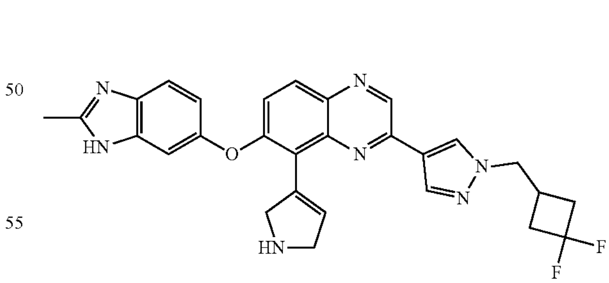

m/z ES+ $[M+H]^+$ 514.0; $^1H$ NMR (400 MHz, DMSO) δ 9.25 (s, 1H), 8.80 (s, 1H), 8.42 (s, 1H), 8.32 (s, 1H), 7.95 (d, J=9.6 Hz, 1H), 7.50 (d, J=8.4 Hz, 1H), 7.25 (d, J=9.2 Hz, 1H), 7.18 (d, J=2.0 Hz, 1H), 6.91 (dd, J=2.0, 8.4 Hz, 1H), 6.50 (s, 1H), 4.69 (s, 2H), 4.38 (d, J=5.2 Hz, 2H), 4.19 (s, 2h), 3.43 (m, 1H), 2.69 (m, 4H), 2.48 (s, 3H).

Example 212. tert-butyl 3-(3-{1-[(3,3-difluorocyclobutyl)methyl]-1H-pyrazol-4-yl}-6-[(2-methyl-1H-1,3-benzodiazol-6-yl)oxy]quinoxalin-5-yl)-2,5-dihydro-1H-pyrrole-1-carboxylate

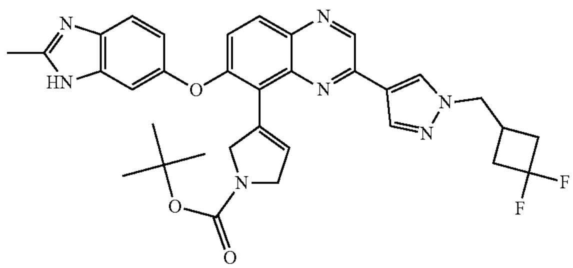 [SMILES: Cc1nc2ccc(Oc3ccc4ncc(-c5cnn(CC6CC(F)(F)C6)c5)nc4c3C3=CCN(C(=O)OC(C)(C)C)C3)cc2[nH]1]

m/z ES+ $[M+H]^+$ 614.1; $^1$H NMR (400 MHz, $CD_3OD$) δ 9.10 (s, 1H), 8.50 (d, J=6.4 Hz, 1H), 8.25 (d, J=3.6 Hz, 1H), 7.92 (d, J=9.2 Hz, 1H), 7.54 (d, J=8.8 Hz, 1H), 7.36 (dd, J=6.0, 8.8 Hz, 1H), 7.13 (s, 1H), 7.01 (d, J=8.8 Hz, 1H), 6.33 (d, J=16 Hz, 1H), 4.74 (s, 2H), 4.38 (d, J=6.8 Hz, 2H), 4.31 (br, 2H), 2.80-2.65 (m, 3H), 2.62 (s, 3H), 2.49 (m, 2H), 1.48 (s, 9H).

Example 213. 4-(4-{8-chloro-7-[(2-methyl-1H-1,3-benzodiazol-6-yl)oxy]quinoxalin-2-yl}-1H-pyrazol-1-yl)-1-imino-1λ$^6$-thian-1-one

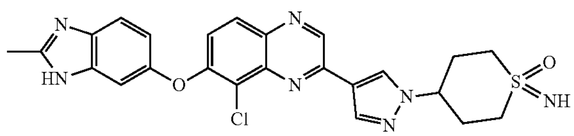 [SMILES: Cc1nc2ccc(Oc3ccc4ncc(-c5cnn(C6CCS(=N)(=O)CC6)c5)nc4c3Cl)cc2[nH]1]

m/z ES+ $[M+H]^+$ 507.9; $^1$H NMR (400 MHz, DMSO) δ 9.33 (s, 1H), 8.78 (s, 1H), 8.37 (s, 1H), 7.95 (d, J=9.2 Hz, 1H), 7.50 (d, J=8.8 Hz, 1H), 7.31 (d, J=9.2 Hz, 1H), 7.21 (d, J=2.0 Hz, 1H), 6.94 (dd, J=2.4, 8.4 Hz, 2H), 4.74 (m, 1H), 3.34 (m, 3H), 3.16 (d, J=12.4 Hz, 2H), 2.53 (m, 2H), 2.48 (s, 3H), 2.33 (d, J=11.2 Hz, 2H).

Example 214. {[4-(4-{8-chloro-7-[(2-methyl-1H-1,3-benzodiazol-6-yl)oxy]quinoxalin-2-yl}-1H-pyrazol-1-yl) piperidin-1-yl](methyl)oxo-λ$^6$-sulfanylidene} (methyl)amine

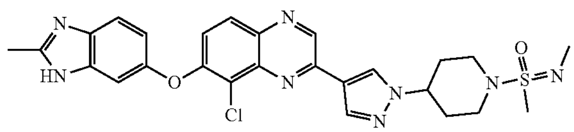

m/z ES+ $[M+H]^+$ 551.0; $^1$H NMR (400 MHz, $CD_3OD$) δ 9.15 (s, 1H), 8.66 (s, 1H), 8.37 (s, 1H), 7.89 (d, J=9.2 Hz, 1H), 7.52 (d, J=8.8 Hz, 1H), 7.34 (d, J=9.2 Hz, 1H), 7.18 (d, J=2.0 Hz, 1H), 7.00 (dd, J=2.4, 8.8 Hz, 1H), 4.46 (m, 1H), 3.83-3.75 (m, 2H), 3.01 (m, 2H), 2.91 (s, 3H), 2.66 (s, 3H), 2.66 (s, 3H), 2.30-2.15 (m, 4H).

Example 215. 2-{1-[(3,3-difluorocyclobutyl) methyl]-1H-pyrazol-4-yl}-7-[(2-methyl-1H-1,3-benzodiazol-6-yl)oxy]-8-(oxan-3-yl)quinoxaline

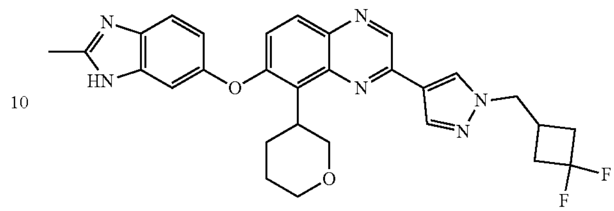

m/z ES+ $[M+H]^+$ 531.0; $^1$H NMR (400 MHz, $CD_3OD$) § 8.20 ($, 1H), 8.51 (s, 1H), 8.00 (d, J=9.2 Hz, 1H), 7.97 (s, 1H), 7.60-7.53 (m, 2H), 7.28 (s, 1H), 7.18 (d, J=2.4 Hz, 1H), 7.05 (d, J=8.8 Hz, 1H), 4.36 (d, J=6.8 Hz, 1H), 4.05 (ddd, J=2.8, 10.8, 28 Hz, 2H), 3.80 (t, J=10.4 Hz, 2H), 3.68-3.50 (m, 2H), 2.80-2.65 (m, 3H), 2.59 (s, 3H), 2.50-2.35 (m, 2H), 2.15 (br, 2H), 1.8 (br, 2H).

Example 216. 2-{1-[(3,3-difluorocyclobutyl) methyl]-1H-pyrazol-4-yl}-7-[(7-fluoro-2-methyl-1H-1,3-benzodiazol-6-yl)oxy]-8-(2,2,5,5-tetramethyl-2,5-dihydrofuran-3-yl)quinoxaline

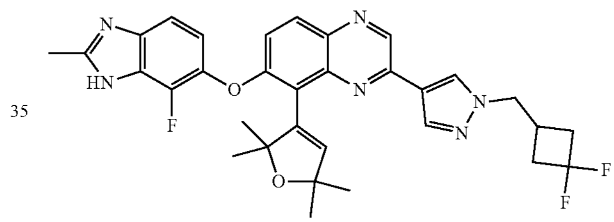

m/z ES+ $[M+H]^+$ 589.0; $^1$H NMR (400 MHz, DMSO) δ 9.19 (s, 1H), 8.60 (s, 1H), 8.21 (s, 1H), 7.93 (d, J=9.2 Hz, 1H), 7.28 (d, J=8.4 Hz, 1H), 7.19 (d, J=9.2 Hz, 1H), 6.94 (t, J=7.6 Hz, 1H), 5.74 (s, 1H), 4.37 (d, J=5.6 Hz, 2H), 2.68 (m, 4H), 2.52 (s, 3H), 1.40 (s, 6H), 1.36 (s, 6H).

Example 217. 2-{1-[(3,3-difluorocyclobutyl) methyl]-1H-pyrazol-4-yl}-8-(2,5-dihydrofuran-3-yl)-7-[(7-fluoro-2-methyl-1H-1,3-benzodiazol-6-yl)oxy] quinoxaline

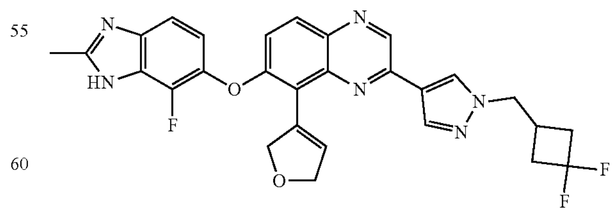

m/z ES+ $[M+H]^+$ 533.2; $^1$H NMR (400 MHz, DMSO) δ 12.57 (br, 1H), 9.20 (d, J=5.6 Hz, 1H), 8.65 (s, 1H), 8.28 (s, 1H), 7.87 (d, J=9.2 Hz, 1H), 7.27 (d, J-8.8 Hz, 1H), 7.15 (d, J=8.8 Hz, 1H), 7.00 (t, J=7.6 Hz, 1H), 6.73 (t, J=1.6 Hz, 1H), 5.20 (m, 2H), 4.80 (m, 2H), 4.37 (d, J=5.0 Hz, 2H), 2.75-2.65 (m, 4H), 2.55-2.51 (m, 1H), 2.50 (s, 3H).

Example 218. 2-{1-[(3,3-difluorocyclobutyl) methyl]-1H-pyrazol-4-yl}-7-[(2-methyl-1H-1,3-benzodiazol-6-yl)oxy]-8-(2,2,5,5-tetramethyl-2,5-dihydrofuran-3-yl)quinoxaline

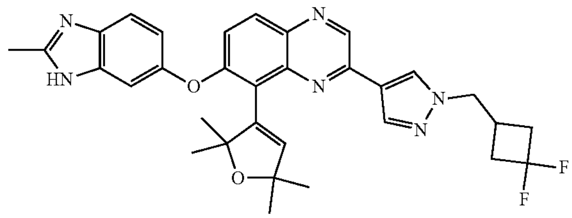 [SMILES: Cc1nc2ccc(Oc3ccc4ncc(-c5cnn(CC6CC(F)(F)C6)c5)nc4c3C3=CC(C)(C)OC3(C)C)cc2[nH]1]

m/z ES+ $[M+H]^+$ 571.1; $^1$H NMR (400 MHz, DMSO) δ 9.20 (s, 1H), 8.60 (s, 1H), 8.21 (s, 1H), 7.95 (d, J=9.2 Hz, 1H), 7.45 (d, J=8.4 Hz, 1H), 7.30 (d, J=9.2 Hz, 1H), 7.06 (s, 1H), 6.86 (dd, J=2.4, 8.4 Hz, 1H), 5.68 (s, 1H), 4.37 (t, J=5.6 Hz, 2H), 2.68 (m, 3H), 2.46 (s, 3H), 1.36 (s, 6H), 1.34 (s, 6H).

Example 219. 2-{1-[(3,3-difluorocyclobutyl) methyl]-1H-pyrazol-4-yl}-8-(5,6-dihydro-2H-pyran-3-yl)-7-[(2-methyl-1H-1,3-benzodiazol-6-yl)oxy] quinoxaline

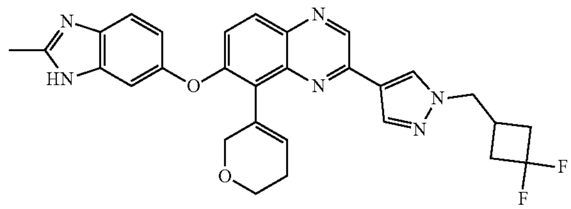 [SMILES: Cc1nc2ccc(Oc3ccc4ncc(-c5cnn(CC6CC(F)(F)C6)c5)nc4c3C3=CCCOC3)cc2[nH]1]

m/z ES+ $[M+H]^+$ 529.0; $^1$H NMR (400 MHz, $CD_3OD$) δ 9.08 (s, 1H), 8.51 (s, 1H), 8.27 (s, 1H), 7.91 (d, J=9.2 Hz, 1H), 7.52 (d, J=8.8 Hz, 1H), 7.37 (d, J=9.2 Hz, 1H), 7.09 (d, J=2.0 Hz, 1H), 6.99 (dd, J=2.0, 8.4 Hz, 1H), 5.96 (br, 1H), 4.44 (d, J=2.0 Hz, 2H), 4.37 (d, J=7.2 Hz, 2H), 3.86 (t, J=5.6 Hz, 2H), 2.80-2.60 (m, 3H), 2.65 (s, 3H), 2.55-2.40 (m, 2H), 2.34 (br, 2H), 2.53-2.35 (m, 2H) 2.14 (m, 2H), 1.81 (d, J=13.6 Hz, 2H).

Example 220. 8-chloro-2-[1-(3,3-difluoropropyl)-1H-pyrazol-4-yl]-7-[(2-methyl-1H-1,3-benzodiazol-6-yl)oxy]quinoxaline

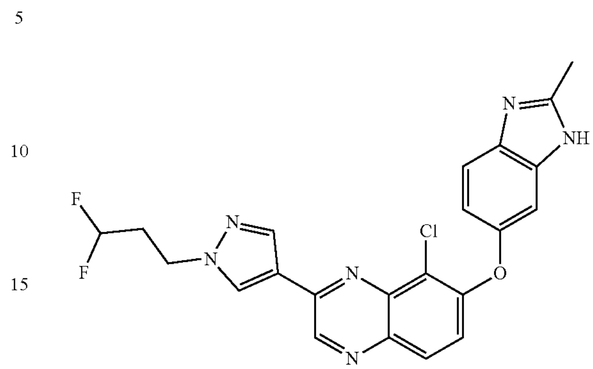

m/z ES+ $[M+H]^+$ 454.9; $^1$H NMR (400 MHz, DMSO) δ 9.36 (s, 1H), 8.77 (s, 1H), 8.40 (s, 1H), 8.04 (d, J=9.2 Hz, 1H), 7.78 (d, J=8.8 Hz, 1H), 7.47-7.45 (m, 2H), 7.26 (dd, J=2.0, 8.8 Hz, 1H), 6.20 (tt, J=4.4, 56.4 Hz, 1H), 4.43 (t, J=6.8 Hz, 2H), 2.74 (s, 3H), 2.52 (m, 2H).

Example 221. 1-[(4-{8-chloro-7-[(2-methyl-1H-1,3-benzodiazol-6-yl)oxy]quinoxalin-2-yl}-1H-pyrazol-1-yl)methyl]cyclopropan-1-amine

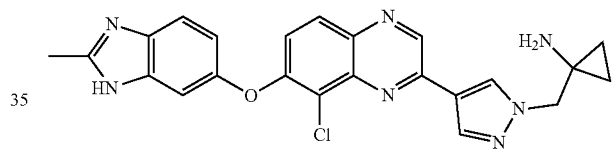

m/z ES+ $[M+H]^+$ 445.9; $^1$H NMR (400 MHz, DMSO) δ 9.33 (s, 1H), 8.81 (s, 1H), 8.41 (s, 1H), 7.95 (d, J=8.8 Hz, 1H), 7.28 (d, J=8.8 Hz, 1H), 7.51 (d, J=8.8 Hz, 1H), 7.31 (d, J=9.6 Hz, 1H), 7.21 (d, J=1.6 Hz, 1H), 6.94 (dd, J=2.0, 8.8 Hz, 1H), 4.44 (s, 2H), 3.36 (t, J=6.4 Hz, 1H), 3.32 (t, J=6.4 Hz, 1H), 2.50 (s, 3H), 1.97-1.87 (m, 4H).

Example 222. 2-{1-[(3,3-difluorocyclobutyl) methyl]-1H-pyrazol-4-yl}-7-[(2-methyl-1H-1,3-benzodiazol-6-yl)oxy]-8-(oxan-4-yl)quinoxaline

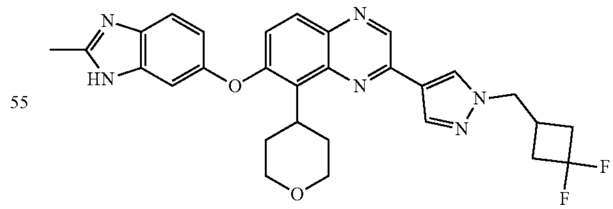

m/z. ES+ $[M+H]^+$ 531.0; $^1$H NMR (400 MHz, $CD_3OD$) δ 8.19 (s, 1H), 8.02 (d, J=9.2 Hz, 1H), 7.96 (s, 1H), 7.57-7.53 (m, 2H), 7.28 (d, J=1.6 Hz, 1H), 7.19 (d, J=2.4 Hz, 1H), 7.05 (dd, J=2.0, 8.8 Hz, 1H), 4.35 (d, J=6.4 Hz, 2H), 4.07 (dd, J=2.4, 10.8 Hz, 2H), 3.60 (m, 2H), 3.31 (s, 3H), 2.75-2.58 (m, 3H), 2.59 (s, 3H), 2.53-2.35 (m, 2H) 2.14 (m, 2H), 1.81 (d, J=13.6 Hz, 2H).

Example 3-(3-{1-[(3,3-difluorocyclobutyl)methyl]-1H-pyrazol-4-yl}-6-[(7-fluoro-2-methyl-1H-1,3-benzodiazol-6-yl)oxy]quinoxalin-5-yl)-1,3-oxazolidin-2-one

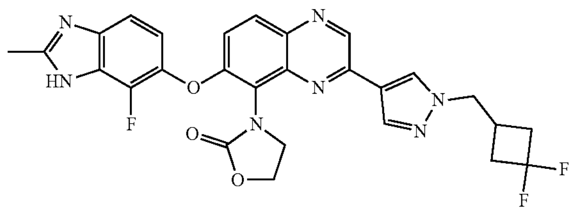 [SMILES: Cc1nc2ccc(Oc3ccc4ncc(-c5cnn(CC6CC(F)(F)C6)c5)nc4c3N3CCOC3=O)c(F)c2[nH]1]

m/z ES+ $[M+H]^+$ 550.3; $^1$H NMR (400 MHz, DMSO) δ 12.60 (s, 1H), 9.25 (s, 1H), 8.73 (s, 1H), 8.33 (s, 1H), 7.98 (d, J=9.6 Hz, 1H), 7.28 (d, J=8.8 Hz, 1H), 7.20 (d, J=9.2 Hz, 1H), 7.05 (m, 1H), 4.72 (dd, J=2.4, 6.4 Hz, 1H), 4.51 (m, 1H), 4.36 (d, J=5.6 Hz, 2H), 4.30 (m, 1H), 3.93 (m, 1H), 2.73-2.57 (m, 4H), 5.58-2.50 (m, 1H), 2.50 (s, 3H).

Example 224. 2-{1-[(3,3-difluorocyclobutyl) methyl]-1H-pyrazol-4-yl}-7-[(7-fluoro-2-methyl-1H-1,3-benzodiazol-6-yl)oxy]-8-(1H-imidazol-1-yl) quinoxaline

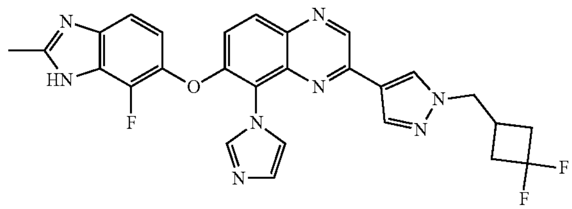 [SMILES: Cc1nc2ccc(Oc3ccc4ncc(-c5cnn(CC6CC(F)(F)C6)c5)nc4c3-n3ccnc3)c(F)c2[nH]1]

m/z ES+ $[M+H]^+$ 531.1; $^1$H NMR (400 MHz, DMSO) δ 12.66 (br, 1H), 9.30 (m, 1H), 8.54 (s, 1H), 8.20-8.10 (m, 1H), 8.16 (s, 1H), 8.06 (d, J=9.2 Hz, 1H), 7.62 (d, J=6.4 Hz, 1H), 7.35-7.05 (m, 4H), 4.36 (d, J=4.8 Hz, 2H), 2.70-2.60 (m, 2H), 2.52 (s, 3H).

Example 225. 2-{1-[(3,3-difluorocyclobutyl) methyl]-1H-pyrazol-4-yl}-7-[(2-methyl-1H-1,3-benzodiazol-6-yl)oxy]-8-(oxetan-3-yl)quinoxaline

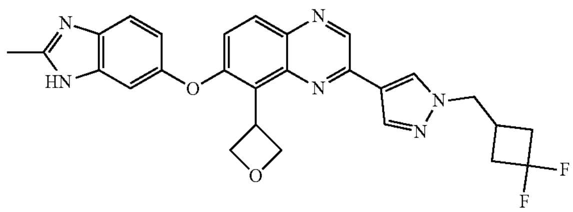 [SMILES: Cc1nc2ccc(Oc3ccc4ncc(-c5cnn(CC6CC(F)(F)C6)c5)nc4c3C3COC3)cc2[nH]1]

m/z ES+ $[M+H]^+$ 503.0; $^1$H NMR (400 MHz, DMSO) δ 9.81 (m, 1H), 9.22 (s, 1H), 8.71 (s, 1H), 8.35 (s, 1H), 7.86 (d, J=9.2 Hz, 1H), 7.48 (d, J=8.4 Hz, 1H), 7.20 (d, J=9.2 Hz, 1H), 6.89 (dd, J=2.4, 8.8 Hz, 1H), 6.53 (s, 1H), 4.37 (d, J=5.6 Hz, 2H), 3.57 (m, 2H), 2.83 (m, 2H), 2.75-2.65 (m, 4H), 2.55-2.51 (m, 2H), 2.48 (s, 3H).

Example 226. N-{1-[(4-{8-chloro-7-[(2-methyl-1H-1,3-benzodiazol-6-yl)oxy]quinoxalin-2-yl}-1H-pyrazol-1-yl)methyl] cyclopropyl}acetamide

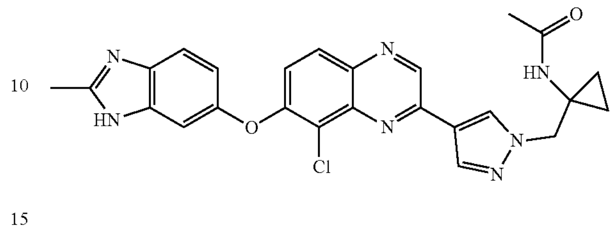

m/z ES+ $[M+H]^+$ 488.0; $^1$H NMR (400 MHz, DMSO) δ 9.34 (s, 1H), 8.65 (s, 2H), 8.34 (s, 1H), 8.12 (s, 1H), 7.96 (d, J=9.6 Hz, 1H), 7.51 (d, J=8.8 Hz, 1H), 7.31 (d, J=9.2 Hz, 1H), 7.21 (d, J=2.0 Hz, 1H), 6.94 (dd, J=2.4, 8.4 Hz, 1H), 4.35 (s, 2H), 2.50 (s, 3H), 1.75 (s, 3H), 0.98 (m, 2H), 0.71 (m, 2H).

Example 227. N-{1-[(4-{8-chloro-7-[(2-methyl-1H-1,3-benzodiazol-6-yl)oxy]quinoxalin-2-yl}-1H-pyrazol-1-yl)methyl] cyclopropyl} methanesulfonamide

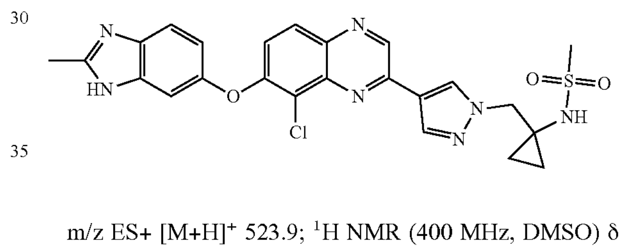

m/z ES+ $[M+H]^+$ 523.9; $^1$H NMR (400 MHz, DMSO) δ 9.41 (s, 1H), 8.68 (s, 2H), 8.40 (s, 1H), 8.06 (d, J=9.2 Hz, 1H), 7.82 (d, J=8.8 Hz, 1H), 7.64 (s, 1H), 7.49 (d, J=9.2 Hz, 1H), 7.45 (d, J=2.4 Hz, 1H), 7.31 (dd, J=2.4, 9.2 Hz, 1H), 4.37 (s, 2H), 2.96 (s, 3H), 2.79 (s, 3H), 1.01 (s, 4H).

Example 228. 2-{1-[(3,3-difluorocyclobutyl) methyl]-1H-pyrazol-4-yl}-8-(3,6-dihydro-2H-pyran-4-yl)-7-[(2-methyl-1H-1,3-benzodiazol-6-yl)oxy] quinoxaline

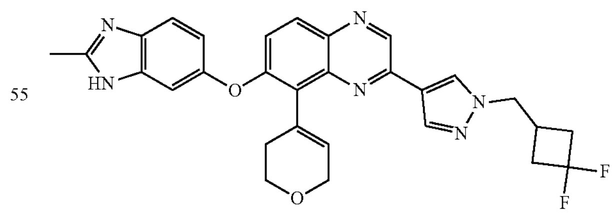

m/z ES+ $[M+H]^+$ 529.0; $^1$H NMR (400 MHz, $CD_3OD$) δ 9.11 (s, 1H), 8.50 (s, 1H), 8.25 (s, 1H), 7.95 (d, J=9.2 Hz, 1H), 7.62 (d, J=8.8 Hz, 1H), 7.43 (d, J=9.2 Hz, 1H), 7.15 (d, J=1.6 Hz, 1H), 7.12 (dd, J=2.0, 8.8 Hz, 1H), 5.83 (s, 1H), 4.38 (d, J=6.8 Hz, 2H), 4.27 (d, J=2.4 Hz, 2H), 3.84 (t, J=5.2 Hz, 2H), 2.72 (s, 3H), 2.80-2.60 (m, 3H), 2.55-2.40 (m, 4H).

Example 229. 8-chloro-2-(1-{6,6-difluorospiro[3.3]heptan-2-yl}-1H-pyrazol-4-yl)-7-[(2-methyl-1H-1,3-benzodiazol-6-yl)oxy]quinoxaline

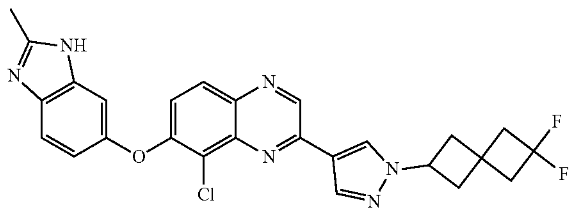 [SMILES: Cc1nc2ccc(Oc3ccc4ncc(-c5cnn(C6CC7(C6)CC(F)(F)C7)c5)nc4c3Cl)cc2[nH]1]

m/z ES+ $[M+H]^+$ 506.9; $^1H$ NMR (400 MHz, DMSO) δ 9.31 (s, 1H), 8.78 (s, 2H), 8.38 (s, 1H), 7.96 (d, J=9.2 Hz, 1H), 7.53 (d, J=8.4 Hz, 1H), 7.32 (d, J=9.2 Hz, 1H), 7.23 (d, J=2.0 Hz, 1H), 6.97 (dd, J=2.4, 8.8 Hz, 1H), 4.98 (quint, J=8.4 Hz, 1H), 2.64 (m, 8H), 2.51 (s, 3H).

Example 230. 1-[(4-{8-chloro-7-[(7-fluoro-2-methyl-1H-1,3-benzodiazol-6-yl)oxy]quinoxalin-2-yl}-1H-pyrazol-1-yl)methyl] cyclobutane-1,3-diol

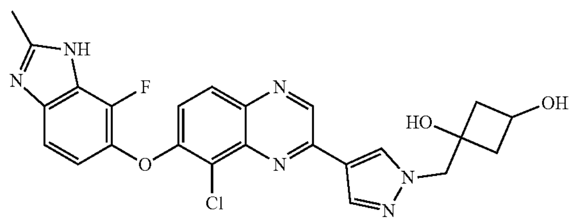 [SMILES: Cc1nc2ccc(Oc3ccc4ncc(-c5cnn(CC6(O)CC(O)C6)c5)nc4c3Cl)c(F)c2[nH]1]

m/z ES+ $[M+H]^+$ 494.9; $^1H$ NMR (400 MHz, DMSO) δ 9.31 (s, 1H), 8.56 (s, 2H), 8.44 (s, 1H), 8.35 (s, 1H), 7.93 (d, J=9.6 Hz, 1H), 7.34 (d, J=8.8 Hz, 1H), 7.09 (t, J=8.0 Hz, 1H), 4.31 (s, 2H), 4.28 (m, 1H), 2.52 (s, 3H), 2.16 (m, 2H), 2.04 (m, 2H).

Example 231. 1-[(4-{7-[(7-fluoro-2-methyl-1H-1,3-benzodiazol-6-yl)oxy]-8-(1H-imidazol-1-yl)quinoxalin-2-yl}-1H-pyrazol-1-yl)methyl]cyclopropan-1,3-diol

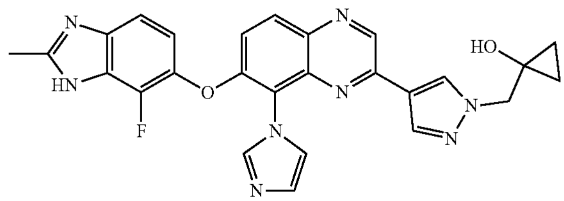 [SMILES: Cc1nc2ccc(Oc3ccc4ncc(-c5cnn(CC6(O)CC6)c5)nc4c3-n3ccnc3)c(F)c2[nH]1]

m/z ES+ $[M+H]^+$ 497.2; $^1H$ NMR (400 MHz, DMSO) δ 9.36 (s, 1H), 8.50 (s, 2H), 8.15 (s, 1H), 8.11 (d, J=9.6 Hz, 1H), 7.76 (br, 1H), 7.42 (m, 1H), 7.34 (d, J=8.4 Hz, 1H), 7.30 (d, J=9.6 Hz, 1H), 7.17 (t, J=8.0 Hz, 1H), 5.61 (s, 1H), 4.26 (s, 2H), 2.52 (s, 3H), 0.71 (m, 4H).

Example 232. 8-chloro-2-{1-[(1S)-1-(4,4-difluorocyclohexyl)ethyl]-1H-pyrazol-4-yl}-7-[(2-methyl-1H-1,3-benzodiazol-6-yl)oxy]quinoxaline

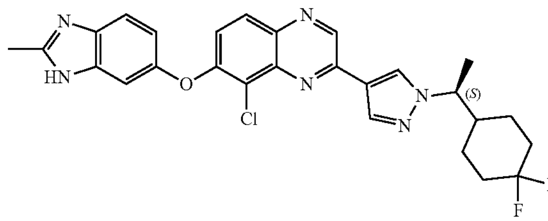

m/z ES+ $[M+H]^+$ 523.0; $^1H$ NMR (400 MHz, $CD_3OD$) δ 9.12 (s, 1H), 8.57 (s, 1H), 8.35 (s, 1H), 7.86 (d, J=9.2 Hz, 1H), 7.52 (d, J=8.8 Hz, 1H), 7.31 (d, J=9.2 Hz, 1H), 7.18 (d, J=2.4 Hz, 1H), 7.00 (dd, J=2.4, 8.8 Hz, 1H), 4.28 (m, 1H), 2.56 (s, 3H), 2.10-1.76 (m, 5H), 1.60 (d, J=6.8 Hz, 3H), 1.45-1.20 (m, 4H).

Example 233. 8-chloro-2-{1-[(1R)-1-(4,4-difluorocyclohexyl)ethyl]-1H-pyrazol-4-yl}-7-[(2-methyl-1H-1,3-benzodiazol-6-yl)oxy]quinoxaline

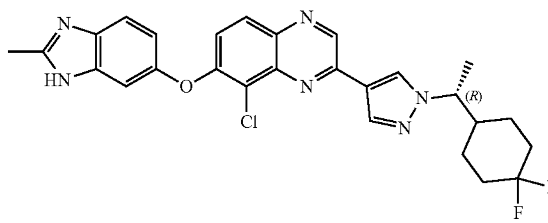

m/z ES+ $[M+H]^+$ 523.0; $^1H$ NMR (400 MHz, $CD_3OD$) δ 9.13 (s, 1H), 8.57 (s, 1H), 8.36 (s, 1H), 7.86 (d, J=9.2 Hz, 1H), 7.52 (d, J=8.8 Hz, 1H), 7.31 (d, J=9.2 Hz, 1H), 7.18 (d, J=2.4 Hz, 1H), 7.00 (dd, J=2.4, 8.8 Hz, 1H), 4.28 (m, 1H), 2.56 (s, 3H), 2.10-1.76 (m, 5H), 1.60 (d, J=63.8 Hz, 3H), 1.42-1.24 (m, 3H), 2.15 (s, 4H).

Example 234. (2S)-2-(4-{8-chloro-7-[(7-fluoro-2-methyl-1H-1,3-benzodiazol-6-yl)oxy]quinoxalin-2-yl}-1H-pyrazol-1-yl) propan-1-ol

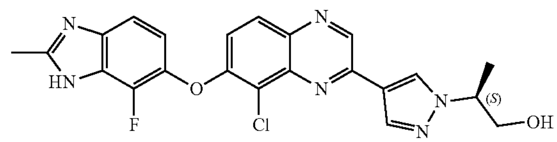

m/z ES+ $[M+H]^+$ 452.9; $^1H$ NMR (400 MHz, DMSO) δ 9.31 (s, 1H), 8.69 (s, 1H), 8.36 (s, 1H), 7.93 (d, J=9.2 Hz, 1H), 7.34 (d, J=8.4 Hz, 1H), 7.21 (d, J=9.2 Hz, 1H), 7.09 (t, J=8.4 Hz, 1H), 5.04 (m, 1H), 4.50 (m, 1H), 3.71 (m, 2H), 2.52 (s, 3H), 1.46 (d, J=6.8 Hz, 3H).

Example 235. (2R)-2-(4-{8-chloro-7-[(7-fluoro-2-methyl-1H-1,3-benzodiazol-6-yl)oxy]quinoxalin-2-yl}-1H-pyrazol-1-yl) propan-1-ol

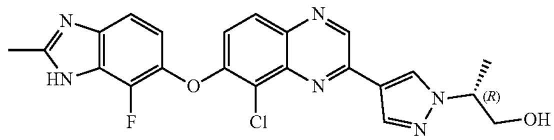

m/z ES+ $[M+H]^+$ 452.9; $^1$H NMR (400 MHz, DMSO) δ 12.70 (br, 1H), 9.31 (s, 1H), 8.69 (s, 1H), 8.36 (s, 1H), 7.93 (d, J=9.2 Hz, 1H), 7.34 (d, J=8.4 Hz, 1H), 7.21 (d, J=8.8 Hz, 1H), 7.09 (t, J=8.4 Hz, 1H), 5.04 (m, 1H), 4.50 (m, 1H), 3.72 (m, 2H), 2.53 (s, 3H), 1.47 (d, J=6.8 Hz, 3H).

Example 236. 8-chloro-2-{1-[(1S)-1-(3,3-difluorocyclobutyl)ethyl]-1H-pyrazol-4-yl}-7-[(7-fluoro-2-methyl-1H-1,3-benzodiazol-6-yl)oxy]quinoxaline

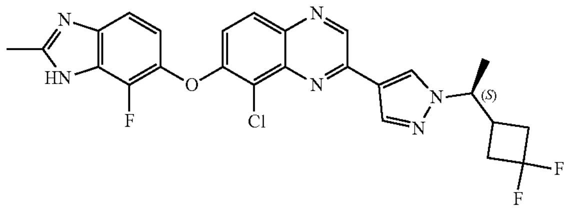

m/z ES+ $[M+H]^+$ 512.9; $^1$H NMR (400 MHz, DMSO) δ 12.68 (br, 1H), 9.31 (s, 1H), 8.80 (s, 1H), 8.38 (s, 1H), 7.94 (d, J=9.2 Hz, 1H), 7.34 (d, J=8.0 Hz, 1H), 7.22 (d, J=9.2 Hz, 1H), 7.09 (t, J=8.0 Hz, 1H), 4.56 (quint, J=6.0 Hz, 1H), 2.8-2.61 (m, 4H), 2.53 (s, 3H), 2.43 (m, 1H), 1.48 (d, J=6.4 Hz, 3H).

Example 237. 8-chloro-2-{1-[(1R)-1-(3,3-difluorocyclobutyl)ethyl]-1H-pyrazol-4-yl}-7-[(7-fluoro-2-methyl-1H-1,3-benzodiazol-6-yl)oxy]quinoxaline

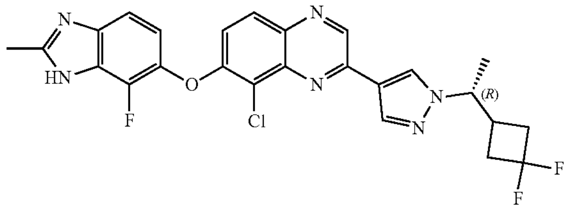

-m/z ES+ $[M+H]^+$ 512.9; $^1$H NMR (400 MHz, DMSO) δ 12.70 (br, 1H), 9.31 (s, 1H), 8.80 (s, 1H), 8.38 (s, 1H), 7.94 (d, J=9.2 Hz, 1H), 7.34 (d, J=4.0 Hz, 1H), 7.22 (d, J=9.2 Hz, 1H), 7.09 (dd, J=2.8, 8.0 Hz, 1H), 4.56 (m, 1H), 2.8-2.61 (m, 4H), 2.59 (s, 3H), 2.43 (m, 1H), 1.48 (d, J=6.4 Hz, 3H).

Example 238. 8-chloro-2-{1-[(1-methoxycyclopropyl)methyl]-1H-pyrazol-4-yl}-7-[(2-methyl-1H-1,3-benzodiazol-6-yl)oxy]quinoxaline

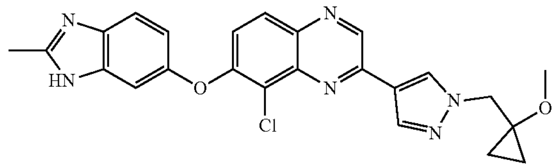

m/z ES+ $[M+H]^+$ 460.9; $^1$H NMR (400 MHz, DMSO) δ 9.34 (s, 1H), 8.71 (s, 1H), 8.36 (s, 1H), 7.96 (d, J=9.2 Hz, 1H), 7.51 (d, J=8.4 Hz, 1H), 7.32 (d, J=9.2 Hz, 1H), 7.22 (d, J=2.0 Hz, 1H), 6.96 (dd, J=2.0, 8.4 Hz, 1H), 4.43 (s, 2H), 3.27 (s, 3H), 0.84 (s, 4H).

Example 239. 8-chloro-2-{1-[(5-methyl-1,3,4-oxadiazol-2-yl)methyl]-1H-pyrazol-4-yl}-7-[(2-methyl-1H-1,3-benzodiazol-6-yl)oxy]quinoxaline

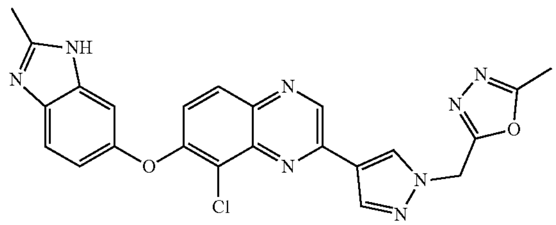

m/z ES+ $[M+H]^+$ 473.3; $^1$H NMR (400 MHz, DMSO) δ 12.28 (d, J=39.9 Hz, 1H), 9.35 (d, J=4.2 Hz, 1H), 8.89 (s, 1H), 8.45 (s, 1H), 7.97 (dd, J=5.4, 9.2 Hz, 1H), 7.51 (dd, J=8.6, 31.8 Hz, 1H), 7.34 (dd, J=9.2, 20.5 Hz, 1H), 7.22 (dd, J=2.0, 36.3 Hz, 1H), 6.94 (ddd, J=2.2, 8.6, 13.4 Hz, 1H), 5.84 (s, 2H), 2.51 (s, 3H), 2.48 (s, 3H).

Example 240. methyl 2-(4-{8-chloro-7-[(7-fluoro-2-methyl-1H-1,3-benzodiazol-6-yl)oxy]quinoxalin-2-yl}-1H-pyrazol-1-yl)-2-methylpropanoate

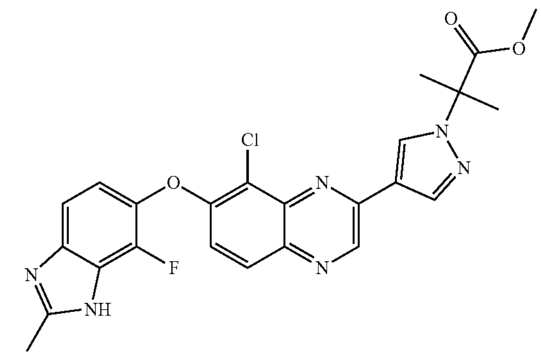

m/z ES+ $[M+H]^+$ 495.2; $^1$H NMR (400 MHz, DMSO) δ 12.66 (s, 1H), 9.38 (s, 1H), 8.92 (s, 1H), 8.39 (s, 1H), 7.95 (d, J=9.3 Hz, 1H), 7.33 (d, J=7.3 Hz, 1H), 7.23 (d, J=8.7 Hz, 1H), 7.11 (t, J=7.7 Hz, 1H), 3.67 (s, 3H), 2.53 (s, 3H), 1.89 (s, 6H).

Example 241. 2-(4-{8-chloro-7-[(2-methyl-1H-1,3-benzodiazol-6-yl)oxy]quinoxalin-2-yl}-1H-pyrazol-1-yl)-1-(4-methoxypiperidin-1-yl)ethan-1-one

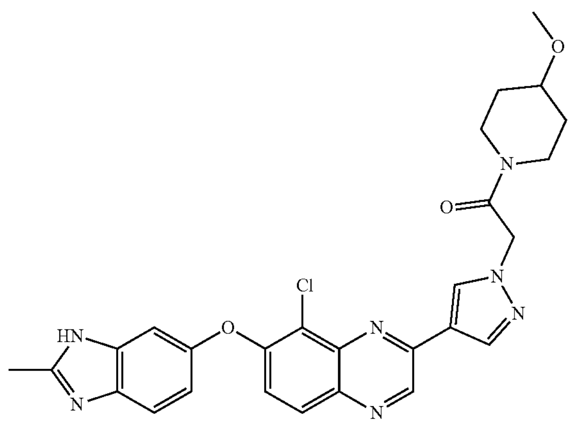 [SMILES: COC1CCN(C(=O)Cn2cc(-c3cnc4ccc(Oc5ccc6nc(C)[nH]c6c5)c(Cl)c4n3)cn2)CC1]

m/z ES+ $[M+H]^+$ 532.3; $^1$H NMR (400 MHz, DMSO) δ 12.33 (s, 1H), 9.33 (s, 1H), 8.63 (s, 1H), 8.36 (s, 1H), 7.96 (d, J=9.2 Hz, 1H), 7.51 (d, J=8.6 Hz, 1H), 7.32 (d, J=9.2 Hz, 1H), 7.22 (s, 1H), 6.95 (dd, J=2.3, 8.6 Hz, 1H), 5.31 (s, 2H), 4.04 (s, 3H), 3.89-3.77 (m, 1H), 3.77-3.66 (m, 1H), 3.53-3.39 (m, 1H), 3.28 (s, 3H), 3.24-3.01 (m, 2H), 1.99-1.86 (m, 1H), 1.86-1.73 (m, 1H), 1.63-1.44 (m, 1H), 1.44-1.27 (m, 1H).

Example 242. 1-(4-acetylpiperazin-1-yl)-2-(4-{8-chloro-7-[(2-methyl-1H-1,3-benzodiazol-6-yl)oxy]quinoxalin-2-yl}-1H-pyrazol-1-yl)ethan-1-one

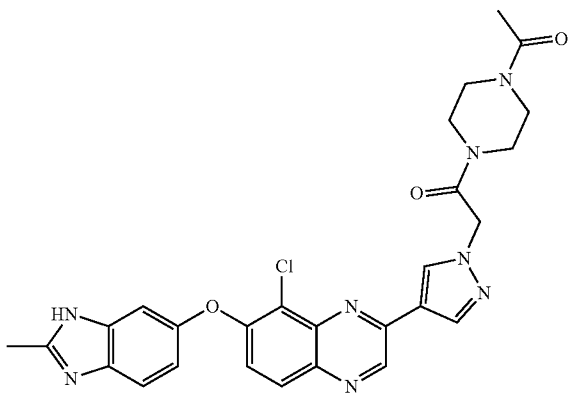 [SMILES: CC(=O)N1CCN(C(=O)Cn2cc(-c3cnc4ccc(Oc5ccc6nc(C)[nH]c6c5)c(Cl)c4n3)cn2)CC1]

m/z ES+ $[M+H]^+$ 545.5; $^1$H NMR (400 MHz, $CD_3OD$) δ 9.10 (s, 1H), 8.53 (s, 1H), 8.34 (s, 1H), 7.52 (d, J=9.2 Hz, 1H), 7.19 (s, 1H), 7.02 (dd, J=1.8, 8.6 Hz, 1H), 5.32 (s, 2H), 3.65 (dd, J=10.3, 22.5 Hz, 8H), 2.58 (s, 3H), 2.15 (s, 3H).

Example 243. 2-(4-{8-chloro-7-[(7-fluoro-2-methyl-1H-1,3-benzodiazol-6-yl)oxy]quinoxalin-2-yl}-1H-pyrazol-1-yl)-2-methylpropanoic acid

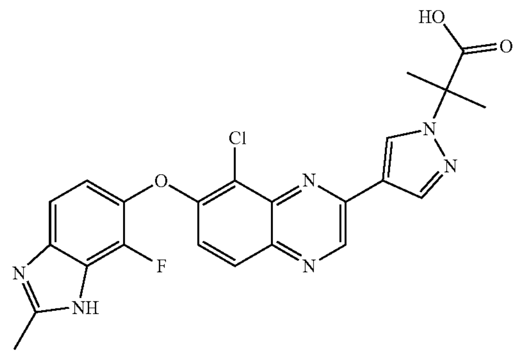 [SMILES: Cc1nc2ccc(Oc3ccc4ncc(-c5cnn(C(C)(C)C(=O)O)c5)nc4c3Cl)c(F)c2[nH]1]

m/z ES+ $[M+H]^+$ 481.3; $^1$H NMR (400 MHz, DMSO) δ 9.37 (s, 1H), 8.88 (s, 1H), 8.36 (s, 1H), 7.94 (d, J=9.3 Hz, 1H), 7.34 (d, J=8.3 Hz, 1H), 7.22 (d, J=9.2 Hz, 1H), 7.09 (d, J=8.0 Hz, 1H), 2.53 (s, 3H), 1.85 (s, 6H).

Example 244. 4-[(4-{8-methanesulfonyl-7-[(2-methyl-1H-1,3-benzodiazol-6-yl)oxy]quinoxalin-2-yl}-1H-pyrazol-1-yl)methyl]-1λ$^6$-thiane-1,1-dione

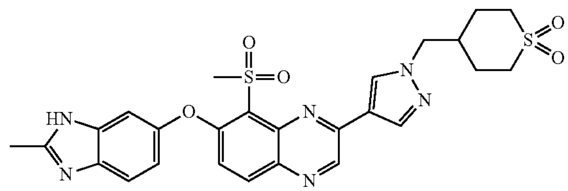 [SMILES: Cc1nc2ccc(Oc3ccc4ncc(-c5cnn(CC6CCS(=O)(=O)CC6)c5)nc4c3S(C)(=O)=O)cc2[nH]1]

m/z ES+ $[M+H]^+$ 567.1; $^1$H NMR (500 MHz, DMSO) δ 9.35 (s, 1H), 8.71 (s, 1H), 8.40 (d, J=0.5 Hz, 1H), 8.20 (d, J=9.3 Hz, 1H), 7.59-7.50 (m, 1H), 7.30 (d, J=9.3 Hz, 1H), 7.28-7.24 (m, 1H), 6.99-6.95 (m, 1H), 4.28 (d, J=7.1 Hz, 2H), 3.73 (s, 3H), 3.31 (s, 3H), 3.17 (td, J=13.6, 3.4 Hz, 2H), 3.12-3.04 (m, 2H), 2.34-2.26 (m, 1H), 1.97-1.91 (m, 2H), 1.80-1.69 (m, 2H).

Example 245. 1-(3-{1-[(3,3-difluorocyclobutyl)methyl]-1H-pyrazol-4-yl}-6-[(2-methyl-1H-1,3-benzodiazol-6-yl)oxy]quinoxalin-5-yl)pyrrolidin-2-one

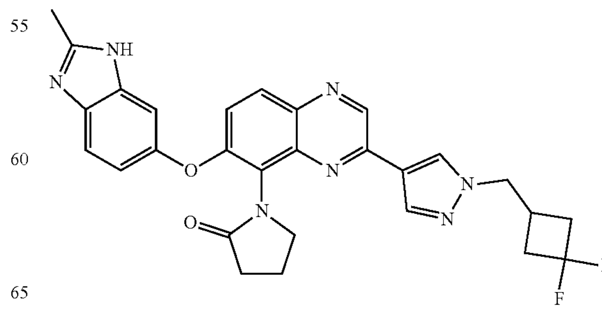

m/z ES+ $[M+H]^+$ 530.0; $^1$H NMR (400 MHz, $CD_3OD$) δ 9.13 (s, 1H), 8.52 (s, 1H), 8.27 (s, 1H), 7.99 (d, J=9.2 Hz, 1H), 7.52 (d, J=8.4 Hz, 1H), 7.37 (d, J=9.2 Hz, 1H), 7.25 (d, J=2.0 Hz, 1H), 7.04 (dd, J=2.4, 8.8 Hz, 1H), 4.38 (d, J=6.8 Hz, 2H), 4.14 (q, J=7.2 Hz, 1H), 3.82 (m, 1H), 2.73-2.68 (m, 4H), 2.58 (s, 3H), 2.52-2.51 (m, 4H), 2.17-2.14 (m, 1H).

Example 246. (2S)-1-(4-{8-chloro-7-[(7-fluoro-2-methyl-1H-1,3-benzodiazol-6-yl)oxy]quinoxalin-2-yl}-1H-pyrazol-1-yl) propan-2-ol

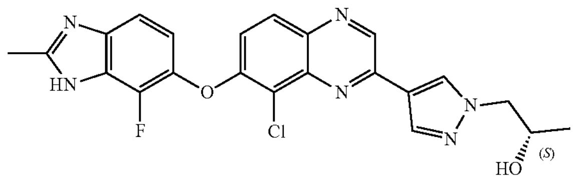

m/z ES+ $[M+H]^+$ 452.9; $^1$H NMR (400 MHz, DMSO-$d_6$) δ 9.32 (s, 1H), 8.65 (s, 1H), 8.37 (s, 1H), 7.94 (d, J=9.2 Hz, 1H), 7.35 (d, J=8.8 Hz, 1H), 7.23 (d, J=9.2 Hz, 1H), 7.11 (m, 1H), 5.20-4-98 (br, 1H), 4.19-4.05 (m, 3H), 2.54 (s, 3H), 1.11 (d, J=6.0 Hz, 1H).

Example 247. (2S)-1-(4-{8-chloro-7-[(2-methyl-1H-1,3-benzodiazol-6-yl)oxy]quinoxalin-2-yl}-1H-pyrazol-1-yl) propan-2-ol

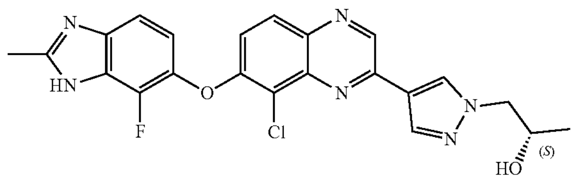

m/z ES+ $[M+H]^+$ 434.9; $^1$H NMR (400 MHz, DMSO-$d_6$) δ 12.34-12.22 (br, 1H), 9.32 (s, 1H), 8.64 (s, 1H), 8.36 (s, 1H), 7.95 (d, J=9.2 Hz, 1H), 7.50 (d, J=8.4 Hz, 1H), 7.31 (d, J=9.2 Hz, 1H), 7.21 (br, 1H), 6.95 (dd, J=2.4, 8.4 Hz, 1H), 5.01 (br, 1H), 4.19-4.05 (m, 3H), 2.48 (s, 3H), 1.10 (d, J=5.2 Hz, 1H).

Example 248. 4-chloro-N-(3-{1-[(3,3-difluorocyclobutyl)methyl]-1H-pyrazol-4-yl}-6-[(2-methyl-1H-1,3-benzodiazol-6-yl)oxy]quinoxalin-5-yl) butanamide

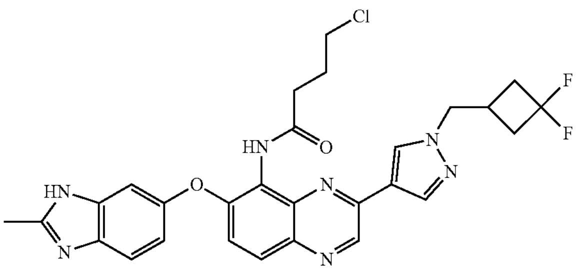 [SMILES: Cc1nc2ccc(Oc3ccc4ncc(-c5cnn(CC6CC(F)(F)C6)c5)nc4c3NC(=O)CCCCl)cc2[nH]1]

m/z ES+ $[M+H]^+$ 566.0; $^1$H NMR (400 MHz, $CD_3OD$) δ 9.11 (s, 1H), 8.53 (s, 1H), 8.32 (s, 1H), 7.91 (d, J=9.2 Hz, 1H), 7.49 (d, J=8.4 Hz, 1H), 7.36 (d, J=9.2 Hz, 1H), 7.20 (br, 1H), 7.01 (dd, J=2.0, 8.4 Hz, 1H), 4.38 (d, J=7.2 Hz, 2H), 3.68 (t, J=7.2 Hz, 2H), 2.74-2.66 (m, 4H), 2.56 (s, 3H), 2.46 (m, 2H), 2.17 (m, 2H).

Example 249. 8-chloro-7-[(7-fluoro-2-methyl-1H-1,3-benzodiazol-6-yl)oxy]-2-{1-[4-(2,2,2-trifluoroethyl)-4-azaspiro[2.5]octan-7-yl]-1H-pyrazol-4-yl} quinoxaline

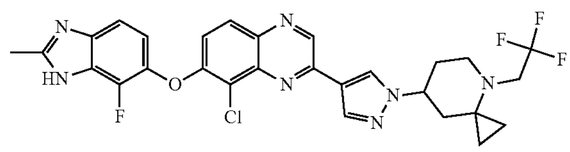 [SMILES: Cc1nc2ccc(Oc3ccc4ncc(-c5cnn(C6CCN(CC(F)(F)F)C7(CC7)C6)c5)nc4c3Cl)c(F)c2[nH]1]

m/z ES+ $[M+H]^+$ 586.3; $^1$H NMR (400 MHz, DMSO-$d_6$) δ 13.08-12.26 (br, 1H), 9.32 (s, 1H), 8.80 (s, 1H), 8.39 (s, 1H), 7.94 (d, J=9.6 Hz, 1H), 7.34 (d, J=8.0 Hz, 1H), 7.23 (d, J=9.6 Hz, 1H), 7.10 (m, 1H), 7.10 (t, J=8.4 Hz, 1H), 4.57 (m, 1H), 3.59 (m, 1H), 3.40 (m, 1H), 3.01 (m, 2H), 2.53 (s, 3H), 2.35 (m, 1H), 2.25 (m, 1H), 1.88 (m, 1H), 1.36 (m, 1H), 0.67 (m, 3H), 0.51 (m, 1H).

Example 250. 3-(4-{8-chloro-7-[(7-fluoro-2-methyl-1H-1,3-benzodiazol-6-yl)oxy]quinoxalin-2-yl}-1H-pyrazol-1-yl)-1,1,1-trifluoro-2-methylpropan-2-ol

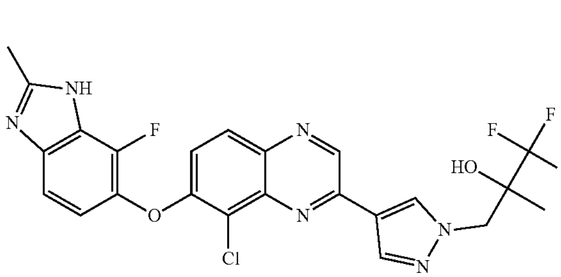

m/z ES+ $[M+H]^+$ 521.0; $^1$H NMR (400 MHz, DMSO-$d_6$) δ 9.35 (s, 1H), 8.70 (s, 1H), 8.43 (s, 1H), 7.95 (d, J=9.2 Hz, 1H), 7.35 (d, J=8.8 Hz, 1H), 7.24 (d, J=9.2 Hz, 1H), 7.30 (d, J=2.0 Hz, 1H), 7.10 (t, J=8.4 Hz, 1H), 6.55 (s, 1H), 4.86 (q, J=14.0 Hz, 1H), 2.53 (s, 3H), 1.26 (s, 3H).

Example 251. (4r)-6-(4-{8-chloro-7-[(2-methyl-1H-1,3-benzodiazo]-6-yl)oxy]quinoxalin-2-yl}-1H-pyrazol-1-yl)spiro[3.3]heptan-2-ol

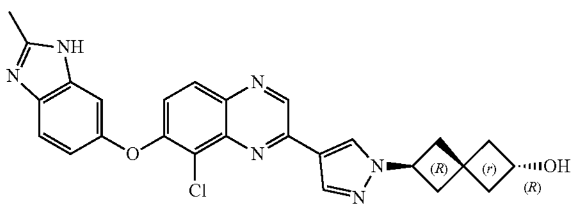

m/z ES+ $[M+H]^+$ 486.9; $^1$H NMR (400 MHz, DMSO-$d_6$) δ 9.32 (s, 1H), 8.75 (s, 1H), 8.35 (s, 1H), 7.98 (d, J=9.2 Hz, 1H), 7.61 (d, J=8.8 Hz, 1H), 7.37 (d, J=9.2 Hz, 1H), 7.30 (d, J=2.0 Hz, 1H), 7.06 (dd, J=2.0, 8.4 Hz, 1H), 5.01 (br, 1H), 4.88 (quint, J=8.4 Hz, 1H), 4.02 (m, 1H), 2.58-2.54 (m, 5H), 2.46-2.41 (m, 3H), 2.29 (m, 1H), 1.92 (m, 2H).

Example 252. (4s)-6-(4-{8-chloro-7-[(2-methyl-1H-1,3-benzodiazol-6-yl)oxy]quinoxalin-2-yl}-1H-pyrazol-1-yl)spiro[3.3]heptan-2-ol

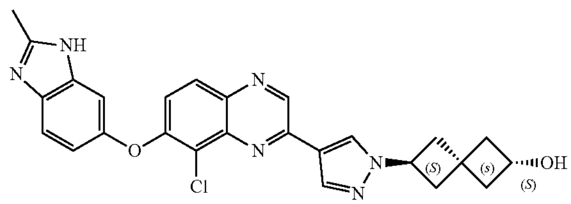

m/z ES+ $[M+H]^+$ 486.9; $^1$H NMR (400 MHz, DMSO-$d_6$) δ 9.31 (s, 1H), 8.74 (s, 1H), 8.35 (s, 1H), 7.97 (d, J=9.2 Hz, 1H), 7.58 (d, J=8.4 Hz, 1H), 7.35 (d, J=9.2 Hz, 1H), 7.27 (d, J=1.6 Hz, 1H), 7.03 (dd, J=2.0, 8.4 Hz, 1H), 5.0 (br, 1H), 4.88 (quint, J=8.4 Hz, 1H), 2.55-2.47 (m, 5H), 2.43 (m, 3H), 1.92 (m, 2H).

Example 253. (2S)-2-(4-{8-chloro-7-[(2-methyl-1H-1,3-benzodiazo]-6-yl)oxy]quinoxalin-2-yl}-1H-pyrazol-1-yl) propan-1-ol

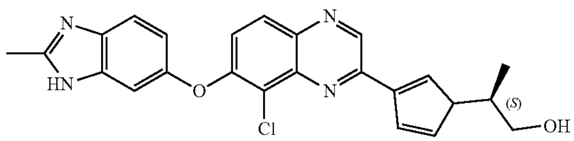

m/z ES+ $[M+H]^+$ 434.9; $^1$H NMR (400 MHz, DMSO-$d_6$) δ 9.35 (s, 1H), 8.70 (s, 1H), 8.36 (s, 1H), 8.0 (d, J=9.2 Hz, 1H), 7.69 (d, J=8.4 Hz, 1H), 7.40 (d, J=9.2 Hz, 1H), 7.38 (m, 1H), 7.16 (dd, J=2.0, 8.8 Hz, 1H), 4.50 (m, 1H), 3.71 (m, 2H), 3.09 (m, 1H), 2.66 (s, 3H), 1.46 (d, J=6.8 Hz, 1H).

Example 254. (2R)-2-(4-{8-chloro-7-[(2-methyl-1H-1,3-benzodiazol-6-yl)oxy]quinoxalin-2-yl}-1H-pyrazol-1-yl) propan-1-ol

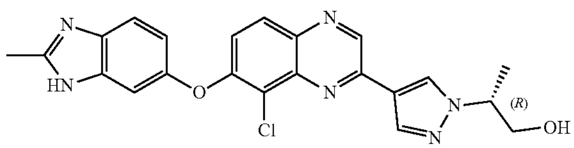

m/z ES+ $[M+H]^+$ 434.9; $^1$H NMR (400 MHz, DMSO-$d_6$) δ 9.32 (s, 1H), 8.69 (s, 1H), 8.35 (s, 1H), 7.95 (d, J=9.2 Hz, 1H), 7.52 (d, J=8.4 Hz, 1H), 7.31 (d, J=9.2 Hz, 1H), 7.23 (d, J=2.4 Hz, 1H), 6.96 (dd, J=2.4, 8.4 Hz, 1H), 5.04 (br, 1H), 4.50 (m, 1H), 3.70 (m, 2H), 2.51 (s, 3H), 1.46 (d, J=7.2 Hz, 1H),

Example 255. (4r)-6-(4-{8-chloro-7-[(7-fluoro-2-methyl-1H-1,3-benzodiazol-6-yl)oxy]quinoxalin-2-yl}-1H-pyrazol-1-yl)spiro[3.3]heptan-2-ol

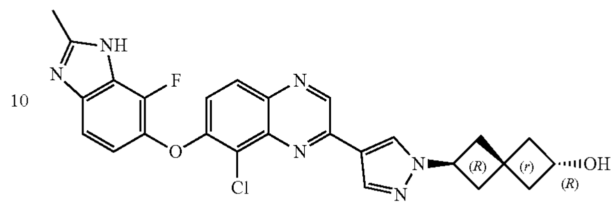

m/z ES+ $[M+H]^+$ 504.9; $^1$H NMR (400 MHz, DMSO-$d_6$) δ 9.29 (s, 1H), 8.74 (s, 1H), 8.34 (s, 1H), 7.93 (d, J=9.2 Hz, 1H), 7.36 (d, J=8.4 Hz, 1H), 7.23 (d, J=9.2 Hz, 1H), 7.11 (t, J=7.6 Hz, 1H), 4.88 (quint, J=8.4 Hz, 1H), 4.03 (quint, J=7.2 Hz, 1H), 2.54 (m, 5H), 2.44 (m, 3H), 2.28 (m, 1H), 1.91 (m, 2H).

Example 256. (4s)-6-(4-{8-chloro-7-[(7-fluoro-2-methyl-1H-1,3-benzodiazol-6-yl)oxy]quinoxalin-2-yl}-1H-pyrazol-1-yl)spiro[3.3]heptan-2-ol

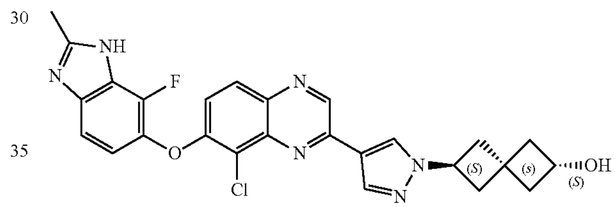

m/z ES+ $[M+H]^+$ 504.9; $^1$H NMR (400 MHz, DMSO-$d_6$) δ 9.29 (s, 1H), 8.74 (s, 1H), 8.35 (s, 1H), 7.93 (d, J=8.8 Hz, 1H), 7.33 (d, J=8.8 Hz, 1H), 7.21 (d, J=9.2 Hz, 1H), 7.08 (m, 1H), 5.01 (d, J=5.2 Hz, 1H), 4.90 (quint, J=8.0 Hz, 1H), 4.03 (m, 1H), 2.17 (m, 2H), 2.52 (s, 3H), 2.45 (m, 3H), 2.28 (m, 1H), 1.92 (m, 2H).

Example 257. 1-[(4-{8-iodo-7-[(2-methyl-1H-1,3-benzodiazol-6-yl)oxy]quinoxalin-2-yl}-1H-pyrazol-1-yl)methyl] cyclopropan-1-ol

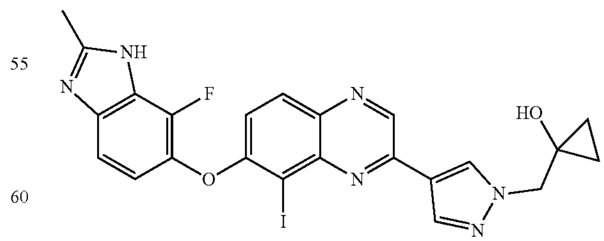

m/z ES+ $[M+H]^+$ 538.8; $^1$H NMR (400 MHz, $CD_3OD$) δ 9.14 (s, 1H), 8.66 (s, 1H), 8.39 (s, 1H), 7.99 (d, J=8.8 Hz, 1H), 7.68 (d, J=8.8 Hz, 1H), 7.34 (d, J=9.2 Hz, 1H), 7.26 (s, 1H), 7.21 (m, 1H), 4.38 (s, 2H), 2.27 (s, 3H), 0.29 (m, 4H).

Example 258. (2R)-1-(4-{8-chloro-7-[(7-fluoro-2-methyl-1H-1,3-benzodiazol-6-yl)oxy]quinoxalin-2-yl}-1H-pyrazol-1-yl) propan-2-ol

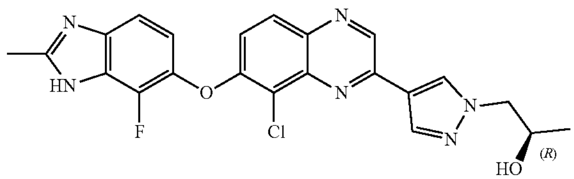

m/z ES+ $[M+H]^+$ 452.9; $^1$H NMR (400 MHz, $CD_3OD$) δ 9.13 (s, 1H), 8.56 (s, 1H), 8.36 (s, 1H), 7.86 (d, J=9.2 Hz, 1H), 7.33 (d, J-7.6 Hz, 1H), 7.23 (d, J=9.3 Hz, 1H), 7.09 (t, J=7.6 Hz, 1H), 4.22 (m, 3H), 2.60 (s, 3H), 1.24 (d, J=6.0 Hz, 3H).

Example 259. 1-(4-{8-chloro-7-[(7-fluoro-2-methyl-1H-1,3-benzodiazol-6-yl)oxy]quinoxalin-2-yl}-1H-pyrazol-1-yl)-2-methylpropan-2-ol

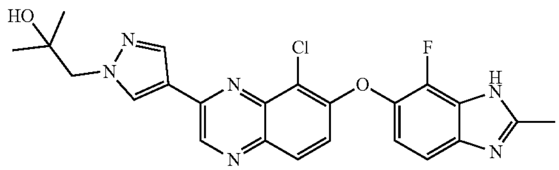 [SMILES: Cc1nc2ccc(Oc3ccc4ncc(-c5cnn(CC(C)(C)O)c5)nc4c3Cl)c(F)c2[nH]1]

m/z ES+ $[M+H]^+$ 467.3; $^1$H NMR (400 MHz, $CD_3OD$) δ 9.08 (s, 1H), 8.52 (s, 1H), 8.31 (s, 1H), 7.81 (d, J=9.3 Hz, 1H), 7.30 (d, J=8.6 Hz, 1H), 7.20 (d, J=9.3 Hz, 1H), 7.07 (app t, J=7.9 Hz, 1H), 4.21 (s, 2H), 2.59 (s, 3H), 1.24 (s, 6H).

Example 260. (2R)-1-(4-{8-chloro-7-[(2-methyl-1H-1,3-benzodiazol-6-yl)oxy]quinoxalin-2-yl}-1H-pyrazol-1-yl) propan-2-ol

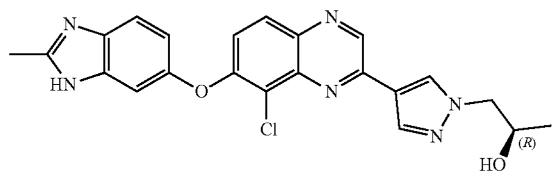

m/z ES+ $[M+H]^+$ 434.9; $^1$H NMR (400 MHz, $CD_3OD$) δ 9.19 (s, 1H), 8.56 (s, 1H), 8.35 (s, 1H), 7.95 (d, J=3.6 Hz, 1H), 7.66 (d, J=8.8 Hz, 1H), 7.43 (d, J=9.2 Hz, 1H), 7.25 (d, J=2.0 Hz, 1H), 7.20 (dd, J=2.4, 8.8 Hz, 1H), 4.21 (m, 1H), 2.73 (s, 3H), 4.39 (d, J=6.8 Hz, 1H), 4.32 (m, 1H), 4.24 (m, 1H), 2.73 (s, 3H), 1.24 (d, J=6.0 Hz, 3H).

Example 261. 2-{1-[(3,3-difluorocyclobutyl) methyl]-1H-pyrazol-4-yl}-8-(2,5-dimethyl-1H-pyrrol-1-yl)-7-[(2-methyl-1H-1,3-benzodiazol-6-yl)oxy] quinoxaline

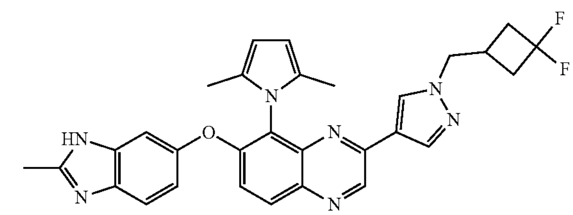 [SMILES: Cc1nc2ccc(Oc3ccc4ncc(-c5cnn(CC6CC(F)(F)C6)c5)nc4c3-n3c(C)ccc3C)cc2[nH]1]

m/z ES+ $[M+H]^+$ 540.0; $^1$H NMR (400 MHz, $CD_3OD$) δ 9.12 (s, 1H), 8.56 (s, 1H), 8.37 (s, 1H), 8.12 (s, 1H), 8.06 (d, J=9.6 Hz, 1H), 7.46 (d, J=9.2 Hz, 2H), 7.11 (br, 1H) 6.91 (dd, J=2.4, 8.8 Hz, 1H), 5.89 (s, 2H), 4.32 (d, J=6.8 Hz, 1H), 2.69 (m, 3H), 2.55 (s, 1H), 2.44 (m, 1H), 6.41 (s, 6H).

Example 262. 2-{1-[(3,3-difluorocyclobutyl) methyl]-1H-pyrazol-4-yl}-7-[(2-methyl-1H-1,3-benzodiazol-6-yl)oxy]-8-(oxolan-3-yl)quinoxaline

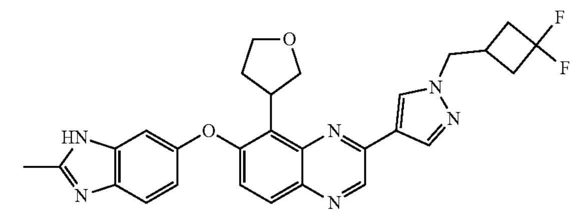 [SMILES: Cc1nc2ccc(Oc3ccc4ncc(-c5cnn(CC6CC(F)(F)C6)c5)nc4c3C3CCOC3)cc2[nH]1]

m/z ES+ $[M+H]^+$ 517.0; $^1$H NMR (400 MHz, $CD_3OD$) δ 9.09 (s, 1H), 8.56 (s, 1H), 8.32 (s, 1H), 7.85 (d, J=9.2 Hz, 1H), 7.51 (d, J=8.4 Hz, 1H), 7.29 (d, J=8.8 Hz, 1H), 7.11 (s, 1H) 6.97 (dd, J=2.4, 8.8 Hz, 1H), 4.93 (m, 1H), 4.39 (d, J=6.8 Hz, 1H), 4.32 (m, 1H), 4.24 (m, 1H), 4.15 (m, 1H), 4.04 (m, 1H), 2.2 (m, 4H), 2.51 (s, 3H), 2.47 (m, 2H), 2.31 (m, 1H).

Example 263. 8-chloro-7-[(7-fluoro-2-methyl-1H-1,3-benzodiazol-6-yl)oxy]-2-(1-{4-methyl-4-azaspiro[2.5]octan-7-yl}-1H-pyrazol-4-yl)quinoxaline

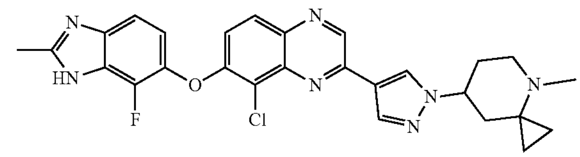

m/z ES+ $[M+H]^+$ 518.4; $^1$H NMR (400 MHz, DMSO-$d_6$) δ 12.7-12.58 (br, 1H), 9.31 (s, 1H), 8.81 (s, 1H), 8.37 (s, 1H), 8.15 (s, 1H), 7.94 (d, J=9.2 Hz, 1H), 7.34 (d, J=8.8 Hz, 1H), 7.23 (d, J=9.2 Hz, 1H), 7.10 (d, J=8.0 Hz, 1H), 4.53 (m, 1H), 2.95 (m, 2H), 2.56 (m, 1H), 2.53 (s, 3H), 2.43 (s, 3H), 2.30 (m, 1H), 1.86 (m, 1H), 1.29 (m, 1H), 0.66-0.54 (m, 3H), 0.46 (m, 1H).

Example 264. 8-chloro-7-[(7-chloro-2-methyl-1H-1,3-benzodiazol-6-yl)oxy]-2-{1-[(3,3-difluorocyclobutyl)methyl]-1H-pyrazol-4-yl} quinoxaline

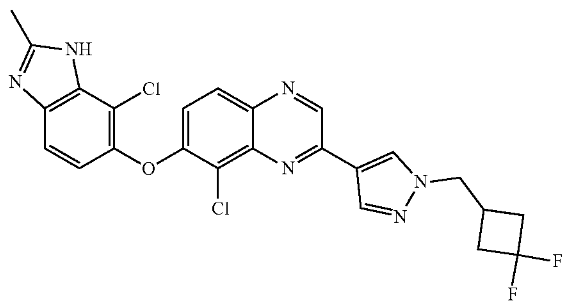 [SMILES: Cc1nc2ccc(Oc3ccc4ncc(-c5cnn(CC6CC(F)(F)C6)c5)nc4c3Cl)c(Cl)c2[nH]1]

m/z ES+ $[M+H]^+$ 514.8; $^1$H NMR (400 MHz, DMSO-$d_6$) δ 13.11-12.51 (br, 1H), 9.30 (s, 1H), 8.76 (s, 1H), 8.38 (s, 1H), 7.92 (d, J=8.8 Hz, 1H), 7.49 (d, J=8.4 Hz, 1H), 7.12-7.08 (m, 2H), 4.39 (d, J=5.6 Hz, 1H), 2.69 (m, 3H), 2.54 (s, 3H).

Example 265. 1-[(4-{7-[(7-chloro-2-methyl-1H-1,3-benzodiazol-6-yl)oxy]-8-fluoroquinoxalin-2-yl}-1H-pyrazol-1-yl)methyl] cyclopropan-1-ol

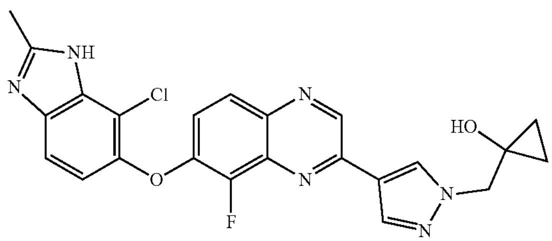 [SMILES: Cc1nc2ccc(Oc3ccc4ncc(-c5cnn(CC6(O)CC6)c5)nc4c3F)c(Cl)c2[nH]1]

m/z ES+ $[M+H]^+$ 464.9; $^1$H NMR (400 MHz, DMSO-$d_6$) δ 9.34 (s, 1H), 8.69 (s, 1H), 8.35 (s, 1H), 7.81 (d, J=9.2 Hz, 1H), 7.47 (d, J=8.8 Hz, 1H), 7.21 (t, J=8.8 Hz, 1H), 7.10 (t, J=8.4 Hz, 1H), 4.28 (s, 2H), 2.54 (s, 3H), 0.76 (m, 2H), 0.72 (m, 2H).

Example 266. 3-[(4-{8-chloro-7-[(7-fluoro-2-methyl-1H-1,3-benzodiazol-6-yl)oxy]quinoxalin-2-yl}-1H-pyrazol-1-yl)methylJoxetan-3-ol

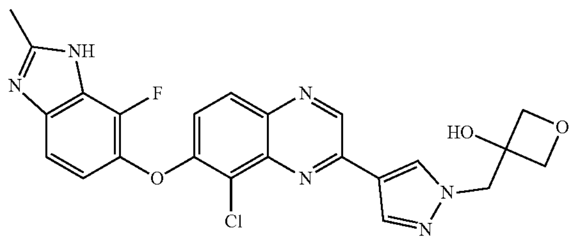 [SMILES: Cc1nc2ccc(Oc3ccc4ncc(-c5cnn(CC6(O)COC6)c5)nc4c3Cl)c(F)c2[nH]1]

m/z ES+ $[M+H]^+$ 480.9; $^1$H NMR (400 MHz, $CD_3OD$) δ 9.28 (s, 1H), 9.25 (s, 1H), 8.51 (br, 1H), 7.98 (d, J=9.6 Hz, 1H), 7.37 (m, 2H) 7.12 (m, 1H), 4.83 (s, 2H), 4.66 (d, J=12.4 Hz, 1H), 3.86 (s, 2H), 2.61 (s, 3H).

Example 267. 2-(1-{4-azaspiro[2.5]octan-7-yl}-1H-pyrazol-4-yl)-8-chloro-7-[(7-fluoro-2-methyl-1H-1,3-benzodiazol-6-yl)oxy]quinoxaline

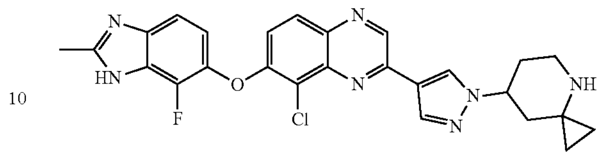

m/z ES+ $[M+H]^+$ 504.3; $^1$H NMR (400 MHz, $CD_3OD$) δ 9.17 (s, 1H), 8.66 (s, 1H), 8.41 (s, 1H), 7.90 (d, J=9.2 Hz, 1H), 7.36 (d, J=8.8 Hz, 1H), 7.27 (d, J=9.2 Hz, 1H), 7.11 (dd, J=8.8, 9.2 Hz, 1H), 4.76 (m, 1H), 3.50 (m, 1H), 3.25 (m, 1H), 2.68 (m, 1H), 2.62 (s, 3H), 2.43 (m, 1H), 2.32 (m, 1H), 1.83 (m, 1H), 1.03-0.98 (m, 2H), 0.92-0.87 (m, 2H).

Example 268. 1-[(4-{8-chloro-7-[(7-fluoro-2-methyl-1H-1,3-benzodiazol-6-yl)oxy]quinoxalin-2-yl}-1H-pyrazol-1-yl)methyl] cyclobutan-1-ol

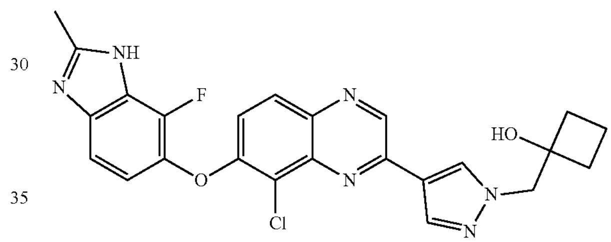

m/z ES+ $[M+H]^+$ 478.9; $^1$H NMR (400 MHz, DMSO-$d_6$) δ 9.33 (s, 1H), 8.61 (s, 1H), 8.36 (s, 1H), 7.93 (d, J=9.2 Hz, 1H), 7.34 (d, J=8.4 Hz, 1H), 7.22 (d, J=9.2 Hz, 1H), 7.09 (t, J=8.0 Hz, 1H), 5.50 (br, 1H), 4.31 (s, 2H), 2.53 (s, 3H), 2.17-2.13 (m, 2H), 2.02-1.94 (m, 2H), 1.67 (m, 1H), 1.55 (m, 1H).

Example 269. propan-2-yl 4-{8-chloro-7-[(7-fluoro-2-methyl-1H-1,3-benzodiazol-6-yl)oxy]quinoxalin-2-yl}-1H-pyrazole-1-carboxylate

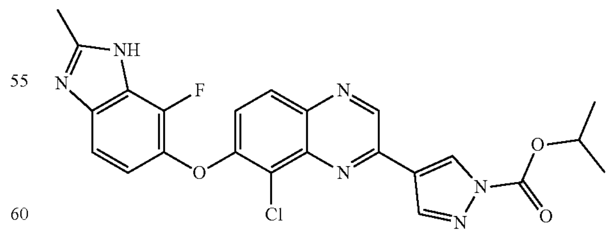

m/z ES+ $[M+H]^+$ 480.9; $^1$H NMR (400 MHz, DMSO-$d_6$) δ 12.7 (br, 1H), 9.52 (s, 1H), 9.35 (s, 1H), 8.63 (d, J=0.4 Hz, 1H), 7.99 (d, J=9.2 Hz, 1H), 7.37-7.30 (m, 2H), 7.11 (dd, J=7.6, 8.4 Hz, 1H), 5.24 (septet, J=6.4 Hz, 2H), 2.52 (s, 3H), 1.44 (d, J=6.4 Hz, 2H).

Example 270. 2-(4-{8-chloro-7-[(7-fluoro-2-methyl-1H-1,3-benzodiazol-6-yl)oxy]quinoxalin-2-yl}-1H-pyrazol-1-yl)-2-methylpropan-1-ol

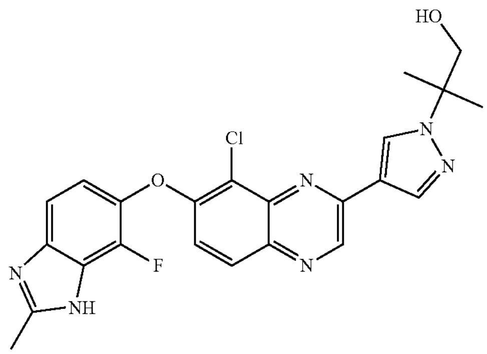 [SMILES: Cc1nc2ccc(Oc3ccc4ncc(-c5cnn(C(C)(C)CO)c5)nc4c3Cl)c(F)c2[nH]1]

m/z ES+ $[M+H]^+$ 467.3; $^1$H NMR (400 MHz, $CD_3OD$) δ 9.19 (s, 1H), 8.68 (s, 1H), 8.39 (s, 1H), 7.88 (d, J=9.2 Hz, 1H), 7.34 (d, J=8.7 Hz, 1H), 7.24 (d, J=9.2 Hz, 1H), 7.09 (dd, J=8.6, 7.3 Hz, 1H), 3.83 (s, 2H), 2.61 (s, 3H), 1.67 (s, 6H).

Example 271. (1r,3r)-3-(4-{8-chloro-7-[(7-fluoro-2-methyl-1H-1,3-benzodiazol-6-yl)oxy]quinoxalin-2-yl}-1H-pyrazol-1-yl)cyclobutan-1-ol

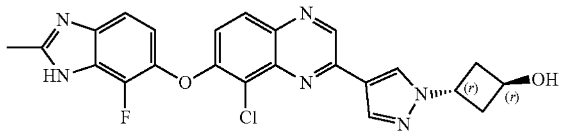

m/z ES+ $[M+H]^+$ 465.0; $^1$H NMR (400 MHz, DMSO-$d_6$) δ 9.31 (s, 1H), 8.79 (s, 1H), 8.38 (s, 1H), 7.93 (d, J=9.2 Hz, 1H), 7.34 (d, J=8.4 Hz, 1H), 7.22 (d, J=9.2 Hz, 1H), 7.09 (t, J=7.4 Hz, 1H), 5.12-5.07 (m, 1H), 4.55-4.49 (m, 1H), 2.75-2.72 (m, 2H), (Is, 3H), 3.06 (s, 3H), 2.44-2.40 (m, 2H).

Example 272. 3-(4-{8-chloro-7-[(7-fluoro-2-methyl-1H-1,3-benzodiazol-6-yl)oxy]quinoxalin-2-yl}-1H-pyrazol-1-yl)-1,1,1-trifluoropropan-2-ol

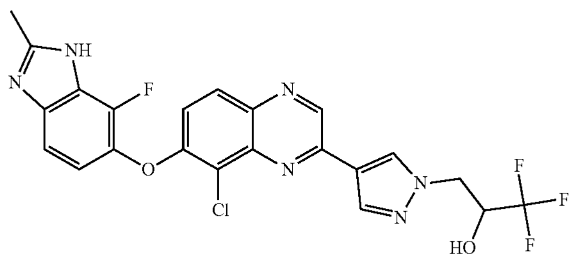 [SMILES: Cc1nc2ccc(Oc3ccc4ncc(-c5cnn(CC(O)C(F)(F)F)c5)nc4c3Cl)c(F)c2[nH]1]

m/z ES+ $[M+H]^+$ 506.9; $^1$H NMR (400 MHz, DMSO-$d_6$) δ 12.76 (br, 1H) 9.32 (s, 1H), 8.77 (s, 1H), 8.44 (s, 1H), 7.95 (d, J=9.6 Hz, 1H), 7.34 (d, J=8.8 Hz, 1H), 7.24 (d, J=9.6 Hz, 1H), 7.09 (t, J=8.4 Hz, 1H), 6.88-6.84 (m, 1H), 4.55 (m, 2H), 4.40 (m, 2H), 2.52 (s, 3H).

Example 273. 8-chloro-7-[(7-fluoro-2-methyl-1H-1,3-benzodiazol-6-yl)oxy]-2-[1-({5H,6H,8H-imidazo[4,3-c][1,4]oxazin-3-yl}methyl)-1H-pyrazol-4-yl]quinoxaline

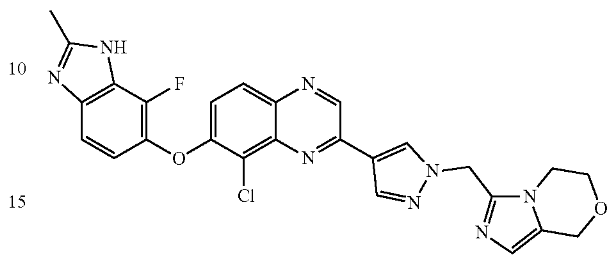

m/z ES+ $[M+H]^+$ 530.9; $^1$H NMR (400 MHz, DMSO-$d_6$) δ 9.33 (s, 1H), 8.76 (s, 1H), 8.39 (s, 1H), 7.94 (d, J=9.2 Hz, 1H), 7.74 (d, J=8.4 Hz, 1H), 7.23 (d, J=9.2 Hz, 1H), 7.09 (t, J=7.8 Hz, 1H), 6.77 (s, 1H), 5.58 (s, 2H), 4.77 (s, 2H), 4.09 (m, 2H), 3.97 (m, 2H).

Example 274. Biological Activity of Exemplary Compounds

The following is a non-limiting example that describes a cell proliferation assay used to determine the biological activity of the compounds of the present disclosure. More specifically, the assay as used to assess the ability of the compounds to inhibit cell proliferation.

Briefly, SNU-16 (FGFR2-amplification) cells, were resuspended at 18,520c/ml mL in RPMI containing 10% Heat Inactivated FBS, 1% L-glutamine and dispensed in duplicate (463c/well) into 384 well plates. UM-UC-14 (FGFR3-S249C) cells were resuspended at 40,000c/ml mL in RPMI containing 10% Heat Inactivated FBS, 1% L-glutamine and dispensed in duplicate (1000c/well) into 384 well plates. DMS-114 (FGFR1 overexpression) cells and were resuspended at 40,000c/ml mL in RPMI containing 10% Heat Inactivated FBS, 1% L-glutamine and dispensed in duplicate (1000c/well) into 384 well plates. RT-112 (FGFR3-Tacc3 fusion) cells were resuspended at 40,000c/ml mL in RPMI containing 10% Heat Inactivated FBS, 1% L-glutamine and dispensed in duplicate (1000c/well) into 384 well plates. To determine the effect of the compounds of the present disclosure on cell proliferation, SNU-16, UM-UC-14, DMS-114 and RT112 cells were incubated for 72 hours in the presence of vehicle control (DMSO) or a compound of the present disclosure at varying concentrations. Inhibition of cell growth was subsequently determined by luminescent quantification (Envision by Perkin Elmer) of intracellular ATP content using CellTiterGlo (Promega), according to the protocol provided by the manufacturer. To determine the IC50 values, the vehicle-treated cells were normalized as viable cells and analyzed using the CDD Vault software (Collaborative Drug Discovery, Burlingame, CA).

Tables A1 and A2 assign each compound a potency code: A, B, C, or D. According to the code, A represents an IC50 value <20 nM; B represents an IC50 value >20 nM and <100 nM; C represents an IC50 value >100 nM and <400 nM; and D represents an IC50 value ≥400 nM.

TABLE A1

| Compound No. | UM-UC-14, FGFR3 S249C, $IC_{50}$ (nM) | DMS-114, FGFR1, $IC_{50}$ (nM) | RT112, FGFR3-TACC3, $IC_{50}$ (nM) | SNU-16, FGFR2 Amplification, $IC_{50}$ (nM) |
|---|---|---|---|---|
| 1 | | B | | B |
| 2 | B | D | B | B |
| 3 | B | C | B | B |
| 4 | B | C | B | B |
| 5 | B | D | B | B |
| 6 | C | D | B | B |
| 7 | B | C | B | B |
| 8 | B | C | A | B |
| 9 | B | D | B | B |
| 10 | C | D | B | B |
| 11 | C | D | B | B |
| 12 | B | C | B | B |
| 13 | B | D | B | B |
| 14 | A | C | A | A |
| 15 | B | D | B | B |
| 16 | C | D | C | C |
| 17 | D | D | D | D |
| 18 | B | D | B | B |
| 19 | C | D | B | C |
| 20 | B | D | B | B |
| 21 | B | C | A | B |
| 22 | C | D | B | B |
| 23 | A | C | A | A |
| 24 | A | C | A | A |
| 25 | B | C | A | A |
| 26 | B | C | A | A |
| 27 | B | D | B | C |
| 28 | B | C | B | B |
| 29 | D | D | C | D |
| 30 | A | C | A | A |
| 31 | B | C | B | B |
| 32 | B | D | B | B |
| 33 | C | D | B | B |
| 34 | B | D | A | |
| 35 | B | D | A | A |
| 36 | C | D | C | C |
| 37 | B | C | B | B |
| 38 | B | C | A | B |
| 39 | B | C | B | B |
| 40 | B | D | B | B |
| 41 | C | D | C | C |
| 42 | B | D | B | B |
| 43 | B | D | B | B |
| 44 | C | D | C | C |
| 45 | B | C | B | B |
| 46 | D | D | C | C |
| 47 | | D | B | C |
| 48 | D | D | D | D |
| 49 | D | D | D | D |
| 50 | D | D | D | D |
| 51 | D | D | C | D |
| 52 | C | D | C | C |
| 53 | A | C | A | A |
| 54 | C | D | C | |
| 55 | C | D | C | C |
| 56 | D | D | C | |
| 57 | C | D | D | |
| 58 | B | C | B | |
| 59 | A | C | A | A |
| 60 | D | D | D | D |
| 61 | D | D | D | D |
| 62 | C | D | B | B |
| 63 | D | D | C | C |
| 64 | C | D | C | C |
| 65 | D | D | D | D |
| 66 | C | D | C | C |
| 67 | B | D | B | B |
| 68 | B | D | B | B |

TABLE A2

| Compound No. | UM-UC-14, FGFR3 S249C, $IC_{50}$ (nM) | DMS-114, FGFR1, $IC_{50}$ (nM) | RT112, FGFR3-TACC3, $IC_{50}$ (nM) | SNU-16, FGFR2 Amplification, $IC_{50}$ (nM) |
|---|---|---|---|---|
| 69 | C | D | C | C |
| 70 | B | B | B | |
| 71 | B | C | C | |
| 72 | B | B | A | |
| 73 | A | B | A | A |
| 74 | D | D | D | D |
| 75 | C | D | C | B |
| 76 | A | C | A | A |
| 77 | B | B | A | A |
| 78 | C | D | C | C |
| 79 | A | B | A | A |
| 80 | B | D | B | B |
| 81 | A | C | A | A |
| 82 | B | C | B | A |
| 83 | B | D | C | C |
| 84 | D | D | C | C |
| 85 | C | D | B | B |
| 86 | A | C | A | A |
| 87 | D | D | D | D |
| 88 | B | C | B | B |
| 89 | B | C | B | A |
| 90 | B | C | B | B |
| 91 | B | D | B | B |
| 92 | C | D | C | C |
| 93 | B | D | C | C |
| 94 | D | D | D | D |
| 95 | D | D | C | C |
| 96 | R | C | B | B |
| 97 | C | D | C | B |
| 98 | D | D | C | C |
| 99 | D | D | C | C |
| 100 | B | C | A | B |
| 101 | C | D | C | |
| 102 | A | B | A | |
| 103 | C | D | C | |
| 104 | B | D | B | |
| 105 | B | D | B | |
| 106 | A | C | A | A |
| 107 | A | C | A | A |
| 108 | B | C | B | A |
| 109 | A | C | A | A |
| 110 | B | D | B | B |
| 111 | B | D | B | B |
| 112 | A | C | B | A |
| 113 | B | D | B | |
| 114 | D | D | C | |
| 115 | D | D | D | D |
| 116 | C | D | D | |
| 117 | D | D | D | |
| 118 | A | C | A | |
| 119 | A | C | B | B |
| 120 | C | D | C | |
| 121 | B | D | B | B |
| 122 | B | D | B | B |
| 123 | A | C | B | B |
| 124 | B | D | B | B |
| 125 | B | D | B | |
| 126 | B | C | B | B |
| 127 | A | C | A | A |
| 128 | A | C | A | A |
| 129 | B | D | B | |
| 130 | A | C | A | A |
| 131 | A | C | A | A |
| 132 | | | B | B |
| 133 | | | C | D |
| 134 | | | B | B |
| 135 | | | A | A |
| 136 | | | C | C |
| 137 | | | C | C |
| 138 | | | D | D |
| 139 | B | B | A | A |
| 140 | B | D | B | B |
| 141 | C | D | C | B |
| 142 | A | C | A | |
| 143 | D | D | C | C |

TABLE A2-continued

| Compound No. | UM-UC-14, FGFR3 S249C, $IC_{50}$ (nM) | DMS-114, FGFR1, $IC_{50}$ (nM) | RT112, FGFR3-TACC3, $IC_{50}$ (nM) | SNU-16, FGFR2 Amplification, $IC_{50}$ (nM) |
|---|---|---|---|---|
| 144 | D | D | C | B |
| 145 | D | D | C | B |
| 146 | B | D | B | B |
| 147 | C | D | B | C |
| 148 | A | B | A | A |
| 149 | A | C | A | A |
| 150 | B | D | B | B |
| 151 | A | B | A | A |
| 152 | B | C | B | B |
| 153 | B | C | B | B |
| 154 | C | D | B | B |
| 155 | A | B | | |
| 156 | A | B | | |
| 157 | B | C | | |
| 158 | D | D | | |
| 159 | D | D | | |
| 160 | B | C | | |
| 161 | B | D | | |
| 162 | B | B | | |
| 163 | B | C | | |
| 164 | B | B | | |
| 165 | B | D | | |
| 166 | B | C | | |
| 167 | A | B | | |
| 168 | B | D | | |
| 169 | D | D | | |
| 170 | C | D | | |
| 171 | C | D | | |
| 172 | C | D | | |
| 173 | B | C | | |
| 174 | A | C | | A |
| 175 | B | C | | A |
| 176 | A | C | | C |
| 177 | D | D | | D |
| 178 | D | D | | B |
| 179 | A | C | A | A |
| 180 | B | D | | B |
| 181 | B | D | | A |
| 182 | B | D | | B |
| 183 | C | D | C | C |
| 184 | B | D | B | B |
| 185 | B | D | B | B |
| 186 | D | D | D | D |
| 187 | B | D | B | B |
| 188 | B | D | B | B |
| 189 | B | D | B | B |
| 190 | D | D | D | D |
| 191 | C | D | C | C |
| 192 | B | D | B | B |
| 193 | C | D | B | C |
| 194 | C | D | C | C |
| 195 | B | D | B | B |
| 196 | C | D | C | C |
| 197 | C | D | B | C |
| 198 | C | D | B | C |
| 199 | C | D | C | C |
| 200 | C | D | C | C |
| 201 | B | D | B | B |
| 202 | B | D | B | B |
| 203 | B | D | B | B |
| 204 | B | D | B | B |
| 205 | C | D | C | C |
| 206 | B | C | B | B |
| 207 | B | C | B | B |
| 208 | D | D | C | C |
| 209 | C | D | B | C |
| 210 | C | D | B | C |
| 211 | C | D | C | C |
| 212 | B | C | B | B |
| 213 | B | C | B | B |
| 214 | B | C | B | B |
| 215 | B | D | B | B |
| 216 | C | D | C | C |
| 217 | B | D | B | B |
| 218 | B | C | B | B |
| 219 | C | D | C | C |
| 220 | B | D | B | B |
| 221 | B | D | B | B |
| 222 | D | D | D | D |
| 223 | B | C | B | B |
| 224 | D | D | D | D |
| 225 | B | D | B | B |
| 226 | B | D | B | C |
| 227 | B | D | B | B |
| 228 | B | D | B | B |
| 229 | B | D | B | B |
| 230 | B | D | B | B |
| 231 | B | D | B | B |
| 232 | B | D | B | B |
| 233 | B | D | B | B |
| 234 | B | D | B | B |
| 235 | B | D | B | B |
| 236 | B | D | B | B |
| 237 | B | C | A | B |
| 238 | B | C | B | B |
| 239 | D | D | D | D |
| 240 | B | C | B | B |
| 241 | B | C | A | B |
| 242 | B | D | B | B |
| 243 | B | D | B | B |
| 244 | B | D | B | C |
| 245 | B | D | B | B |
| 246 | B | D | B | B |
| 247 | B | D | B | B |
| 248 | B | C | B | B |
| 249 | B | D | B | B |
| 250 | B | D | A | A |
| 251 | B | D | B | B |
| 252 | B | D | B | B |
| 253 | C | D | C | C |
| 254 | B | D | B | B |
| 255 | B | D | B | B |
| 256 | C | D | C | C |
| 257 | B | C | A | A |
| 258 | B | D | B | B |
| 259 | B | D | B | B |
| 260 | B | C | B | B |
| 261 | A | B | Å | A |
| 262 | C | D | B | B |
| 263 | C | D | C | C |
| 264 | B | C | B | B |
| 265 | B | C | B | B |
| 266 | C | D | C | C |
| 267 | B | D | B | B |
| 268 | B | D | B | B |
| 269 | D | D | D | D |
| 270 | D | D | B | C |
| 271 | B | D | A | B |
| 272 | B | D | B | B |
| 273 | B | D | B | B |
| 274 | B | D | B | B |
| 275 | C | D | D | D |
| 276 | C | D | B | C |
| 277 | C | D | B | B |
| 278 | A | D | A | A |
| 279 | A | D | A | A |
| 280 | B | D | B | B |
| 281 | B | D | B | B |
| 282 | C | D | B | B |
| 283 | B | D | B | B |
| 284 | B | D | B | B |
| 285 | B | D | B | B |
| 286 | B | D | B | C |
| 287 | B | D | B | B |
| 288 | B | D | B | B |
| 289 | B | C | B | B |
| 290 | B | D | B | B |
| 291 | B | D | B | B |
| 292 | B | D | C | C |
| 293 | B | C | B | B |

TABLE A2-continued

| Compound No. | UM-UC-14, FGFR3 S249C, $IC_{50}$ (nM) | DMS-114, FGFR1, $IC_{50}$ (nM) | RT112, FGFR3-TACC3, $IC_{50}$ (nM) | SNU-16, FGFR2 Amplification, $IC_{50}$ (nM) |
|---|---|---|---|---|
| 294 | A | C | B | B |
| 295 | D | D | D | D |
| 296 | B | D | B | B |
| 297 | B | D | B | B |
| 298 | B | D | B | C |
| 299 | B | D | B | B |
| 300 | A | D | B | B |
| 301 | B | D | A | A |
| 302 | C | D | C | C |
| 303 | B | D | B | B |
| 304 | B | D | B | C |
| 305 | A | C | A | A |
| 306 | C | D | B | C |
| 307 | B | C | A | A |
| 308 | B | D | B | B |
| 309 | B | C | B | B |
| 310 | B | D | B | B |
| 311 | B | C | A | A |
| 312 | D | D | D | D |
| 313 | B | D | B | B |
| 314 | C | C | B | B |
| 315 | B | D | B | B |
| 316 | B | D | B | B |
| 317 | D | D | C | B |
| 318 | D | D | D | D |
| 319 | B | D | B | B |
| 320 | C | D | B | B |
| 321 | B | D | B | B |
| 322 | B | D | A | B |
| 323 | B | D | B | A |
| 324 | B | D | B | B |
| 325 | B | D | A | A |
| 326 | C | D | C | B |
| 327 | A | D | A | A |
| 328 | B | D | B | B |
| 329 | A | C | A | A |
| 330 | B | D | A | A |
| 331 | B | D | A | A |
| 332 | B | D | B | B |
| 333 | B | D | B | B |
| 334 | D | D | D | D |
| 335 | B | D | B | B |
| 336 | B | D | B | B |
| 337 | B | D | B | B |
| 338 | B | C | B | B |
| 339 | A | C | A | A |
| 340 | B | C | A | A |
| 341 | D | D | D | D |
| 342 | B | D | B | B |
| 343 | B | D | A | A |
| 344 | C | D | C | C |
| 345 | D | D | D | D |
| 346 | B | D | B | B |
| 347 | C | D | B | B |
| 348 | D | D | C | D |
| 349 | D | D | D | D |
| 350 | C | D | B | C |
| 351 | B | C | B | B |
| 352 | D | D | D | D |
| 353 | B | D | B | B |
| 354 | B | C | A | B |
| 355 | B | C | B | B |
| 356 | B | C | B | B |
| 357 | B | D | B | B |
| 358 | C | D | C | B |
| 359 | B | D | B | B |
| 360 | B | D | B | B |
| 361 | B | C | B | C |
| 362 | B | C | B | B |
| 363 | B | D | B | B |
| 364 | A | C | A | B |
| 365 | B | D | B | B |
| 366 | B | D | B | B |
| 367 | B | C | A | B |
| 368 | B | C | B | B |
| 369 | B | D | B | B |
| 370 | B | C | B | A |
| 371 | C | D | B | B |
| 372 | B | D | B | B |
| 373 | B | D | B | B |
| 374 | B | D | A | B |
| 375 | B | C | A | B |
| 376 | B | D | B | B |
| 377 | B | D | B | B |
| 378 | B | D | B | B |
| 379 | B | C | B | B |
| 380 | B | D | A | B |
| 381 | B | D | B | B |
| 382 | B | C | B | B |
| 383 | B | D | B | B |
| 384 | D | D | D | D |
| 385 | B | C | A | B |
| 386 | B | D | B | B |
| 387 | B | D | B | B |
| 388 | C | D | C | C |
| 389 | C | D | B | B |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (I'):

(I')

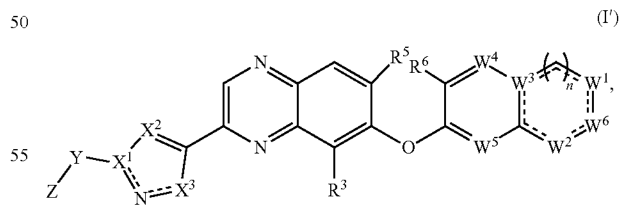

or a pharmaceutically acceptable salt or stereoisomer thereof, wherein:

each ⎓ independently represents a single bond or a double bond;

n is 0 or 1;

$W^1$ is $C(R^{W1})$ when connected to one double bond and one single bond, $N(R^{W1})$ when connected to two single bonds, or N when connected to one double bond and one single bond;

$R^{W1}$ is H, $C_1$-$C_6$ alkyl, or —S(═O)$_2$—($C_1$-$C_6$ alkyl);

$W^2$ is C($R^{W2}$) when connected to one double bond and one single bond, N($R^{W2}$) or O when connected to two single bonds, or N when connected to one double bond and one single bond;

$R^{W2}$ is H, $C_1$-$C_6$ alkyl, or —S(═O)$_2$—($C_1$-$C_6$ alkyl);

$W^3$ is C or N;

$W^4$ is C($R^{W4}$) or N;

$R^{W4}$ is H, halogen, cyano, $C_1$-$C_6$ alkyl, or —S(═O)$_2$—($C_1$-$C_6$ alkyl);

$W^5$ is C($R^{W5}$) or N;

$R^{W5}$ is H, halogen, cyano, $C_1$-$C_6$ alkyl, or —S(═O)$_2$—($C_1$-$C_6$ alkyl);

$W^6$ is C($R^{W6}$) when connected to one double bond and one single bond, N($R^{W6}$) when connected to two single bonds, or N when connected to one double bond and one single bond;

$R^{W6}$ is H, halogen, cyano, $C_1$-$C_6$ alkyl, $C_1$-$C_6$ alkoxyl, $C_1$-$C_6$ haloalkyl, or —S(═O)$_2$—($C_1$-$C_6$ alkyl);

$X^1$ is C or N;

$X^2$ is N, O, or C($R^{X2}$);

$R^{X2}$ is H or $C_1$-$C_6$ alkyl;

$X^3$ is N, O, or C($R^{X3}$);

$R^{X3}$ is H or $C_1$-$C_6$ alkyl;

$R^3$ is H, halogen, cyano, $NH_2$, —NH($C_1$-$C_6$ alkyl), —NHC(═O)($C_1$-$C_6$ haloalkyl), —NHC(•)O($C_1$-$C_6$ alkyl), —N($C_1$-$C_6$ alkyl)$_2$, —S(═O)$_2$—($C_1$-$C_6$ alkyl), —C(═O)H, —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$- $C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the —NH($C_1$-$C_6$ alkyl), —NHC(═O)($C_1$-$C_6$ haloalkyl), —NHC(═O)O($C_1$-$C_6$ alkyl), N($C_1$-$C_6$ alkyl)$_2$, —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl is optionally substituted with one or more $R^{3a}$;

each $R^{3a}$ independently is halogen, cyano, oxo, —OH, $NH_2$, —NH($C_1$-$C_6$ alkyl), —NHC(═O)O($C_1$-$C_6$ alkyl), —N($C_1$-$C_6$ alkyl)$_2$, —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, 3- to 12-membered heterocycloalkyl, $C_6$-$C_{10}$ aryl, or 5- to 10-membered heteroaryl, wherein the —NHC(═O)O($C_1$-$C_6$ alkyl) is optionally substituted with one or more halogen;

$R^5$ is H, halogen, cyano, or $C_1$-$C_6$ alkyl;

$R^6$ is H, halogen, cyano, or $C_1$-$C_6$ alkyl;

Y is absent, $C_1$-$C_6$ alkyl, $C_2$-$C_6$ alkenyl, or $C_1$-$C_6$ alkoxyl, wherein the $C_1$-$C_6$ alkyl, $C_2$-$C_6$ alkenyl, or $C_1$-$C_6$ alkoxyl is optionally substituted with one or more halogen, oxo, cyano, —OH, —$NH_2$, —NH($C_1$-$C_6$ alkyl)-OH, $C_1$-$C_6$ alkyl, $C_2$-$C_6$ alkenyl, $C_1$-$C_6$ alkoxyl optionally substituted with —($C_1$-$C_6$ alkyl) ($C_6$-$C_{10}$ aryl), or $C_3$-$C_{12}$ cycloalkyl;

Z is absent, H, $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl, wherein the $C_3$-$C_{12}$ cycloalkyl, $C_3$-$C_{12}$ cycloalkenyl, 3- to 12-membered heterocycloalkyl, 3- to 12-membered heterocycloalkenyl, $C_6$-$C_{10}$ aryl, or 5- to 10-membered heteroaryl is optionally substituted with one or more $R^Z$;

each $R^Z$ independently is oxo, halogen, cyano, —OH, =$NR^{Za}$, —$NH_2$, —NH$R^{Za}$, —NH($C_1$-$C_6$ alkyl), —N($C_1$-$C_6$ alkyl)$_2$, —S($C_1$-$C_6$ alkyl), —S(═O)(═$NR^{Za}$)—($C_1$-$C_6$ alkyl), —S(═O)$_2$—($C_1$-$C_6$ alkyl), —S(═O)$_2$—($C_2$-$C_6$ alkenyl), —C(═O) (3- to 12-membered heterocycloalkyl), —C(═O)NH($C_1$-$C_6$ alkyl), —C(═O)$NR^{Za}$, —C(═O)—($C_1$-$C_6$ alkyl), —C(═O)—($C_2$-$C_6$ alkenyl), —C(═O)—($C_1$-$C_6$ alkoxyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, 3- to 12-membered heterocycloalkyl, or 5- to 10-membered heteroaryl, wherein the —NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, 3- to 12-membered heterocycloalkyl, or 5- to 10-membered heteroaryl is optionally substituted with one or more $R^{Za}$, each $R^{Za}$ independently is H, oxo, halogen, cyano, —OH, —$NH_2$, —NH($C_1$-$C_6$ alkyl), —N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, or 3- to 12-membered heterocycloalkyl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_{12}$ cycloalkyl, or 3- to 12-membered heterocycloalkyl is optionally substituted with one or more $R^{Zb}$; and each $R^{Zb}$ independently is oxo, halogen, cyano, —OH, —$NH_2$, —NH($C_1$-$C_6$ alkyl), —N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, or $C_1$-$C_6$ alkoxyl.

2. The compound, pharmaceutically acceptable salt, or stereoisomer of claim 1, wherein:

n is 0;

RW1 is H;

$R^{W2}$ is H;

$W^3$ is N;

$W^4$ is C($R^{W4}$);

$R^{W4}$ is H or halogen;

$W^5$ is C($R^{W5}$);

$R^{W5}$ is H or halogen;

$R^{W6}$ is H or $C_1$-$C_6$ alkyl;

$X^1$ is N;

$X^2$ is C($R^{X2}$);

$X^3$ is C($R^{X3}$);

$R^3$ is H, halogen, cyano, —$NH_2$, —NHC(═O)O($C_1$-$C_6$ alkyl), —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, $C_2$-$C_6$ alkenyl, $C_3$-$C_{12}$ cycloalkyl, 3- to 12-membered heterocycloalkyl, 3- to 12-membered heterocycloalkenyl, or 5- to 10-membered heteroaryl, wherein the —NHC(═O)O($C_1$-$C_6$ alkyl), —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, 3- to 12-membered heterocycloalkyl, 3- to 12-membered heterocycloalkenyl, or 5- to 10-membered heteroaryl is optionally substituted with one or more $R^{3a}$, each $R^{3a}$ independently is halogen, oxo, —NHC(═O)O($C_1$-$C_6$ alkyl), —S(═O)$_2$—($C_1$-$C_6$ alkyl), —C(═O)($C_1$-$C_6$ alkyl), —C(═O)O($C_1$-$C_6$ alkyl), $C_1$-$C_6$ alkyl, or $C_2$-$C_6$ alkenyl, wherein —NHC(═O)O($C_1$-$C_6$ alkyl) is optionally substituted with one or more halogen;

$R^5$ is H or $C_1$-$C_6$ alkyl;

$R^6$ is H or halogen;

Y is absent, $C_1$-$C_6$ alkyl, $C_2$-$C_6$ alkenyl, or $C_1$-$C_6$ alkoxyl, wherein the $C_1$-$C_6$ alkyl, $C_2$-$C_6$ alkenyl, or $C_1$-$C_6$ alkoxyl is optionally substituted with one or more halogen, oxo, cyano, —OH, —$NH_2$, $C_1$-$C_6$ alkyl, $C_2$-$C_6$ alkenyl, $C_1$-$C_6$ alkoxyl optionally substituted with —($C_1$-$C_6$ alkyl) ($C_6$-$C_{10}$aryl), or $C_3$-$C_{12}$ cycloalkyl;

Z is absent, $C_3$-$C_{12}$ cycloalkyl, 3- to 12-membered heterocycloalkyl, 3- to 12-membered heterocycloalkenyl, $C_6$-$C_{10}$ aryl, or 5- to 10-membered heteroaryl, wherein the $C_3$-$C_{12}$ cycloalkyl, 3- to 12-membered heterocycloalkyl, 3- to 12-membered heterocycloalkenyl, $C_6$-$C_{10}$ aryl, or 5- to 10-membered heteroaryl is optionally substituted with one or more $R^Z$;

each $R^Z$ independently is oxo, halogen, —OH, =$NR^{Za}$, $NH_2$, $NHR^{Za}$, NH($C_1$-$C_6$ alkyl), N($C_1$-$C_6$ alkyl)$_2$, —S($C_1$-$C_6$ alkyl), —S(═O)(═$NR^{Za}$)—($C_1$-$C_6$ alkyl), —S(═O)$_2$—($C_1$-$C_6$ alkyl), —S(═O)$_2$—($C_2$-$C_6$ alkenyl), —C(═O)NH($C_1$-$C_6$ alkyl), —C(═O)$NR^{Za}$, —C(═O)—($C_1$-$C_6$ alkyl), —C(═O)—($C_2$-$C_6$ alkenyl), —C(═O)—($C_1$-$C_6$ alkoxyl), $C_1$-$C_6$ alkyl, $C_2$-$C_6$ alkenyl, $C_1$-$C_6$ alkoxyl, $C_3$-$C_{12}$ cycloalkyl, 3- to 12-membered heterocycloalkyl, or 5- to 10-membered heteroaryl, wherein the NH($C_1$-$C_6$ alkyl), N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_1$-$C_6$ alkoxyl, $C_3$-$C_{12}$ cycloalkyl, 3- to 12-membered heterocycloalkyl, or 5- to 10-membered heteroaryl is optionally substituted with one or more $R^{Za}$, each $R^{Za}$ independently is H, oxo, halogen, cyano, —OH, —$NH_2$, —NH($C_1$-$C_6$ alkyl), —N($C_1$-$C_6$ alkyl)$_2$, —S(═O)$_2$—($C_1$-$C_6$ alkyl), —C(═O)—($C_1$-$C_6$ alkyl), $C_1$-$C_6$ alkyl, $C_2$-$C_6$ alkenyl, $C_1$-$C_6$ alkoxyl, $C_3$-$C_{12}$ cycloalkyl, or 3- to 12-membered heterocycloalkyl, wherein the —NH($C_1$-$C_6$ alkyl), —N($C_1$-$C_6$ alkyl)$_2$, —S(═O)$_2$—($C_1$-$C_6$ alkyl), —C(═O)—($C_1$-$C_6$ alkyl), $C_1$-$C_6$ alkyl, $C_2$-$C_6$ alkenyl, $C_1$-$C_6$ alkoxyl, $C_3$-$C_{12}$ cycloalkyl, or 3- to 12-membered heterocycloalkyl is optionally substituted with one or more $R^{Zb}$, and each $R^{2b}$ independently is oxo, halogen, or —OH.

3. A compound of Formula (I):

(I)

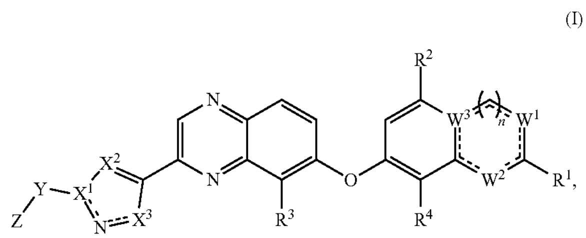

or a pharmaceutically acceptable salt or stereoisomer thereof, wherein:

each ⎓ independently represents a single bond or a double bond;

n is 0 or 1;

$W^1$ is C($R^{W1}$) when connected to one double bond and one single bond, N($R^{W1}$) when connected to two single bonds, or N when connected to one double bond and one single bond;

$R^{W1}$ is H, $C_1$-$C_6$ alkyl, or —S(═O)$_2$—($C_1$-$C_6$ alkyl);

$W^2$ is C($R^{W2}$) when connected to one double bond and one single bond, N($R^{W2}$) when connected to two single bonds, or N when connected to one double bond and one single bond;

$R^{W2}$ is H, $C_1$-$C_6$ alkyl, or —S(═O)$_2$—($C_1$-$C_6$ alkyl);

$W^3$ is C or N;

$X^1$ is C or N;

$X^2$ is N, O, or C($R^{X2}$);

$R^{X2}$ is H or $C_1$-$C_6$ alkyl;

$X^3$ is N, O, or C($R^{X3}$);

$R^{X3}$ is H or $C_1$-$C_6$ alkyl;

$R^1$ is H, halogen, cyano, or $C_1$-$C_6$ alkyl;

$R^2$ is H, halogen, cyano, or $C_1$-$C_6$ alkyl;

$R^3$ is H, halogen, cyano, or $C_1$-$C_6$ alkyl;

$R^4$ is H, halogen, cyano, or $C_1$-$C_6$ alkyl;

Y is absent or $C_1$-$C_6$ alkyl optionally substituted with one or more oxo or —OH;

Z is H, $C_3$-$C_8$ cycloalkyl, or 3- to 8-membered heterocycloalkyl, wherein the $C_3$-$C_8$ cycloalkyl or 3- to 8-membered heterocycloalkyl is optionally substituted with one or more $R^2$;

each $R^Z$ independently is oxo, halogen, cyano, —OH, —$NH_2$, —NH($C_1$-$C_6$ alkyl), —N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the —NH($C_1$-$C_6$ alkyl), —N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Za}$, each $R^{Za}$ independently is oxo, halogen, cyano, —OH, —$NH_2$, —NH($C_1$-$C_6$ alkyl), —N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl, wherein the —NH($C_1$-$C_6$ alkyl), —N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, $C_1$-$C_6$ alkoxyl, $C_3$-$C_8$ cycloalkyl, or 3- to 8-membered heterocycloalkyl is optionally substituted with one or more $R^{Zb}$; and each $R^{Zb}$ independently is oxo, halogen, cyano, —OH, —$NH_2$, —NH($C_1$-$C_6$ alkyl), —N($C_1$-$C_6$ alkyl)$_2$, —S(═O)$_2$—($C_1$-$C_6$ alkyl), —C(═O)—($C_1$-$C_6$ alkyl), —C(═O)—($C_2$-$C_6$ alkenyl), $C_1$-$C_6$ alkyl, $C_2$-$C_6$ alkenyl, $C_2$-$C_6$ alkynyl, or $C_1$-$C_6$ alkoxyl.

4. The compound, pharmaceutically acceptable salt, or stereoisomer of claim 3, wherein:

Z is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^Z$.

5. The compound, pharmaceutically acceptable salt, or stereoisomer of claim 3, wherein:

Y is $C_1$-$C_6$ alkyl optionally substituted with one or more oxo or —OH; and

Z is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^Z$.

6. The compound, pharmaceutically acceptable salt, or stereoisomer of claim 3, wherein

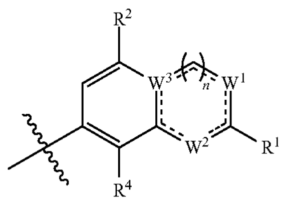

is

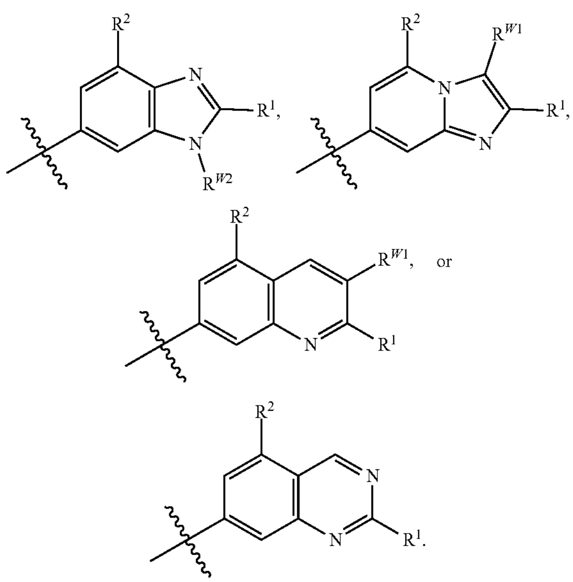

7. The compound, pharmaceutically acceptable salt, or stereoisomer of claim 3, wherein

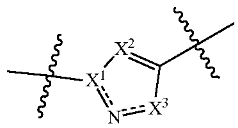

is

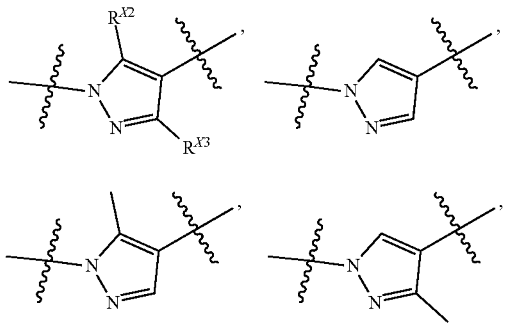

-continued

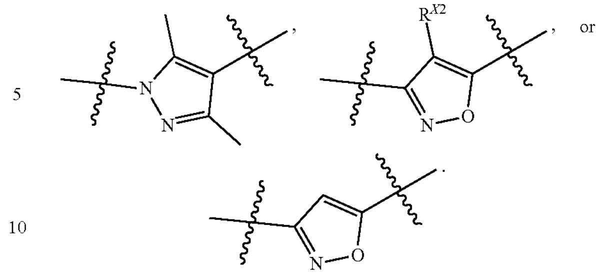

8. The compound, pharmaceutically acceptable salt, or stereoisomer of claim 3, wherein $R^1$ is H.

9. The compound, pharmaceutically acceptable salt, or stereoisomer of claim 3, wherein $R^1$ is halogen, cyano, or $C_1$-$C_6$ alkyl.

10. The compound, pharmaceutically acceptable salt, or stereoisomer of claim 3, wherein $R^2$ is H.

11. The compound, pharmaceutically acceptable salt, or stereoisomer of claim 3, wherein $R^2$ is halogen, cyano, or $C_1$-$C_6$ alkyl.

12. The compound, pharmaceutically acceptable salt, or stereoisomer of claim 3, wherein $R^3$ is halogen, cyano, or $C_1$-$C_6$ alkyl.

13. The compound, pharmaceutically acceptable salt, or stereoisomer of claim 3, wherein $R^4$ is H.

14. The compound, pharmaceutically acceptable salt, or stereoisomer of claim 3, wherein $R^4$ is halogen, cyano, or $C_1$-$C_6$ alkyl.

15. The compound, pharmaceutically acceptable salt, or stereoisomer of claim 3, wherein Y is $C_1$-$C_6$ alkyl optionally substituted with one or more oxo or —OH.

16. The compound, pharmaceutically acceptable salt, or stereoisomer of claim 3, wherein Z is $C_3$-$C_8$ cycloalkyl or 3- to 8-membered heterocycloalkyl, wherein the $C_3$-$C_8$ cycloalkyl or 3- to 8-membered heterocycloalkyl is optionally substituted with one or more $R^Z$.

17. The compound, pharmaceutically acceptable salt, or stereoisomer of claim 3, wherein the compound is of Formula (I-a), (I-b), (I-c), (I-d), (II), (II-a), (II-b), (II-c), or (II-d):

(I-a)

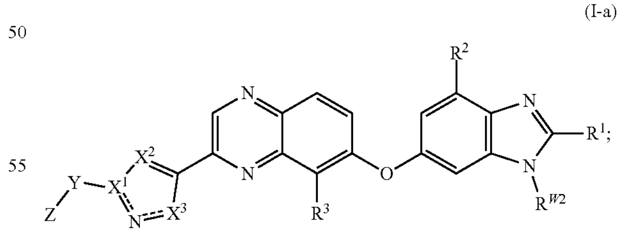

(I-b)

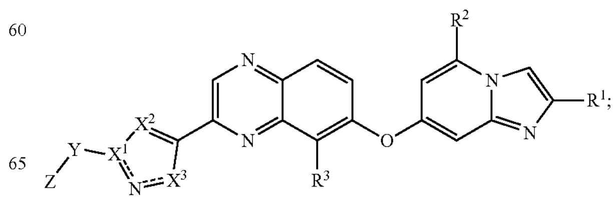

-continued
(I-c)
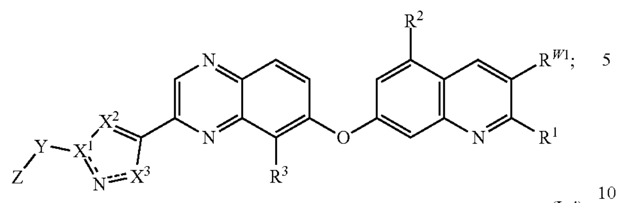
(I-d)
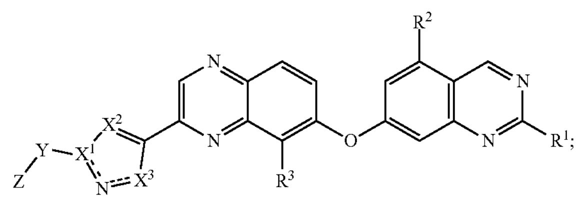
(II)
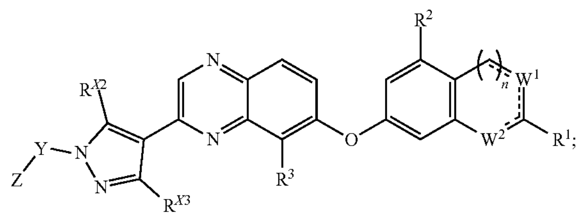
(II-a)
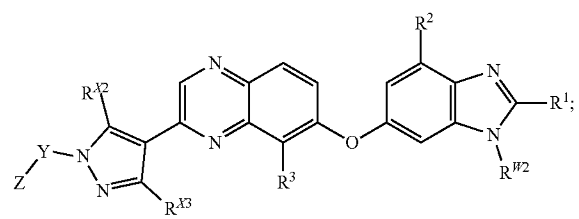
(II-b)
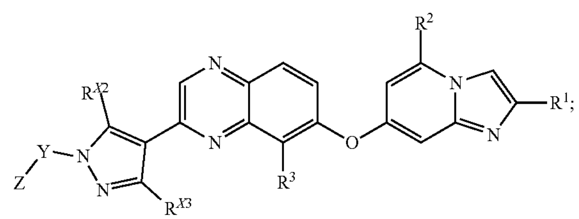
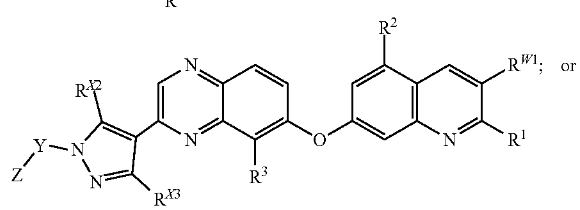
or
(II-d)
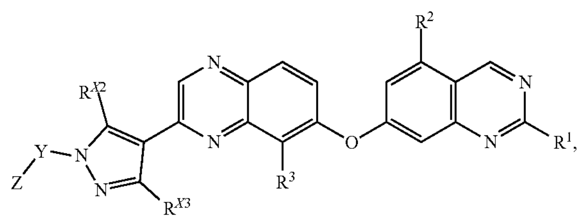
or a pharmaceutically acceptable salt or stereoisomer thereof.
18. A compound selected from;
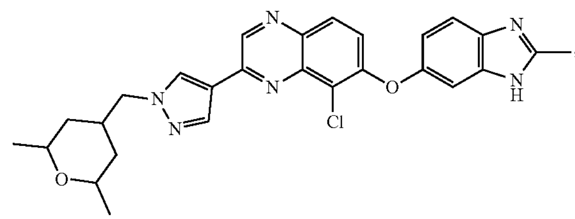
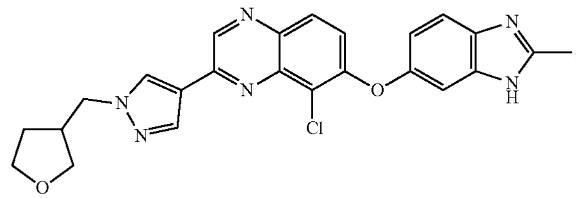
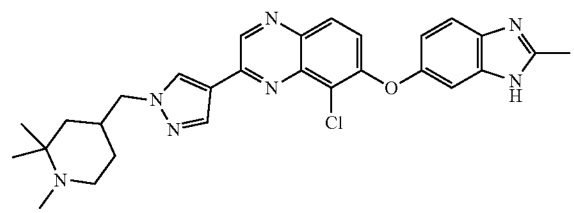
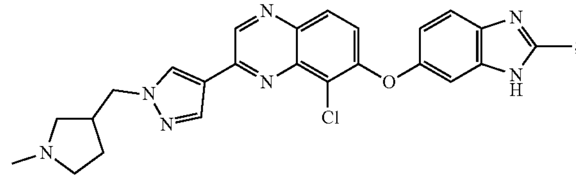
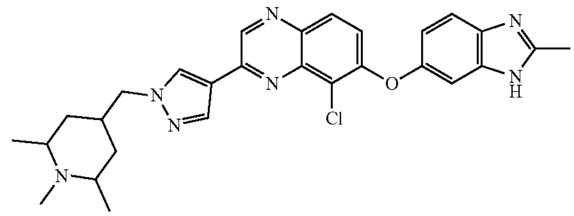
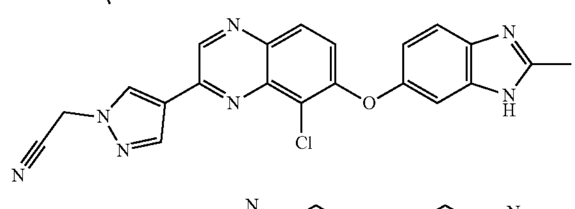
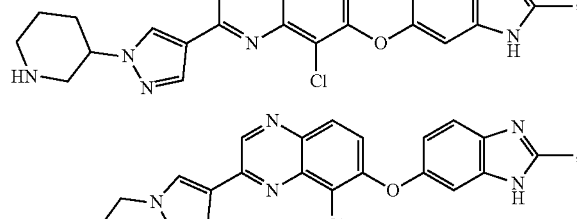

-continued
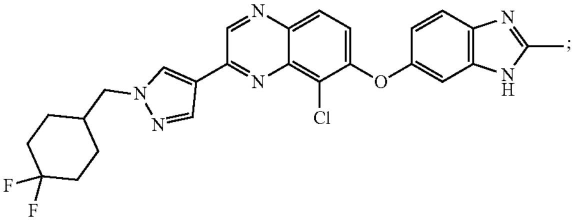
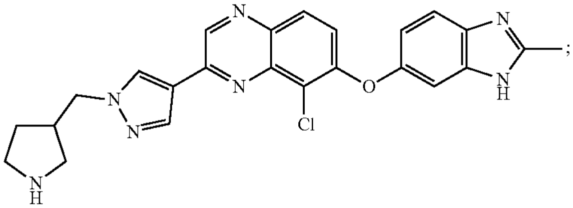
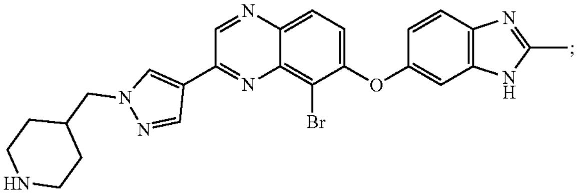
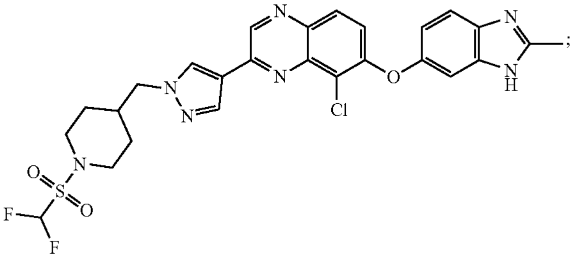
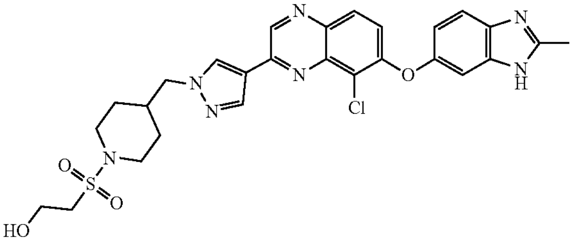
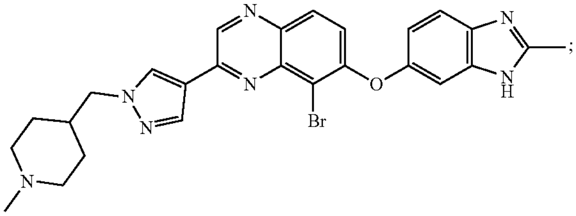
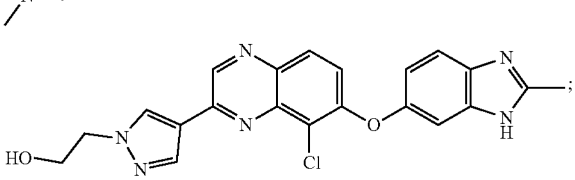
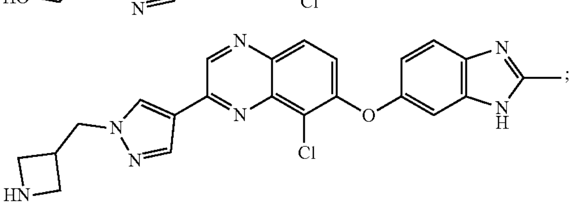
-continued
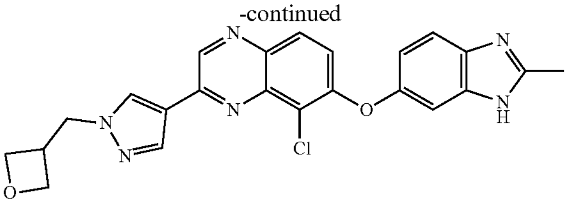
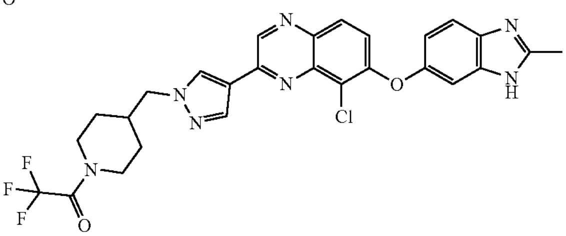
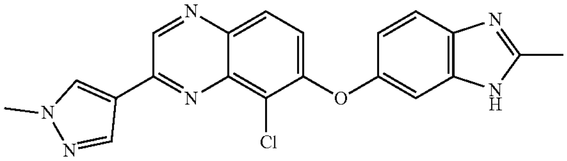
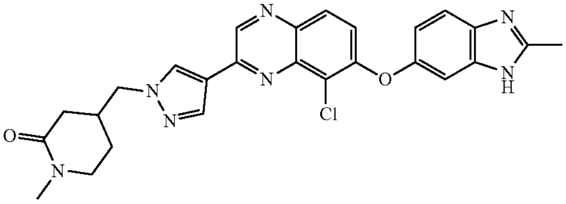
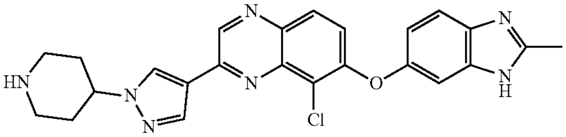
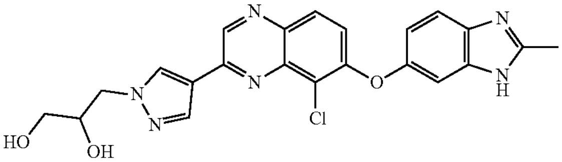
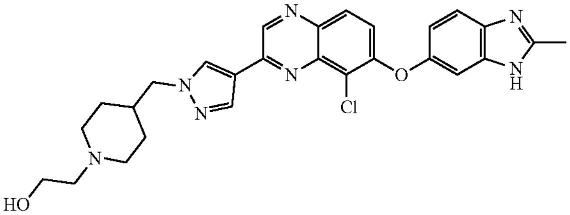
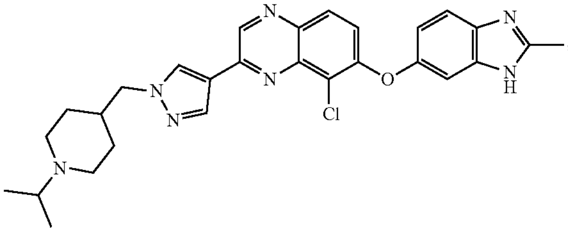

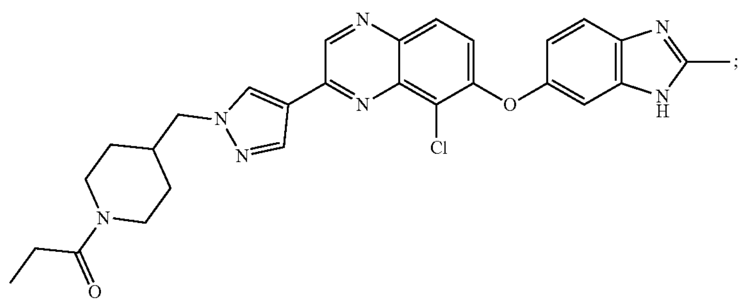
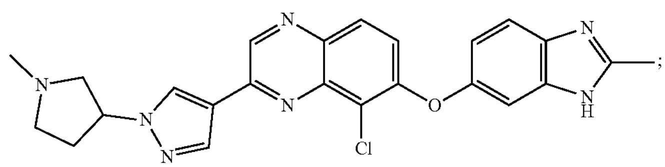
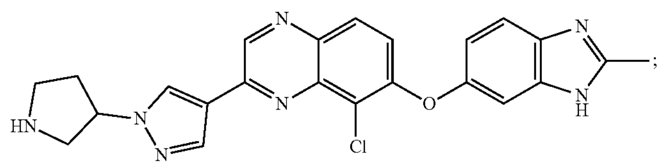
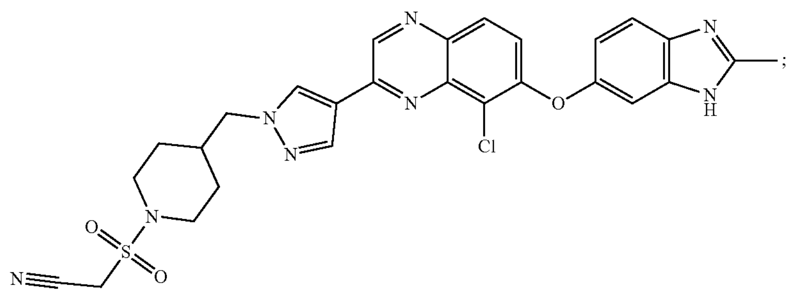
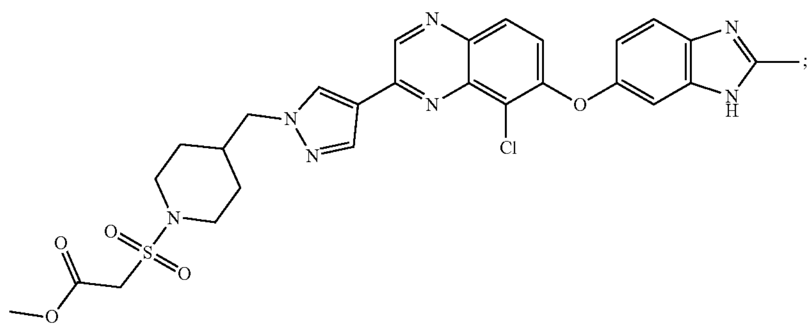
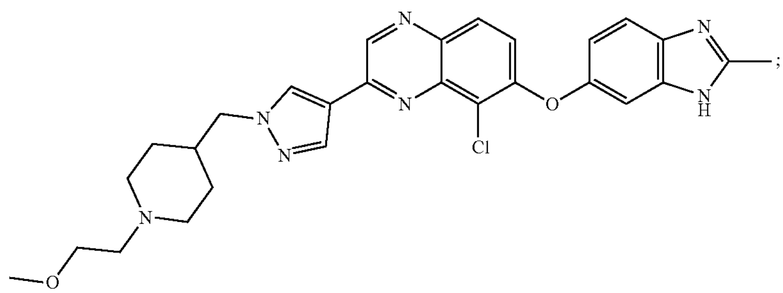

-continued
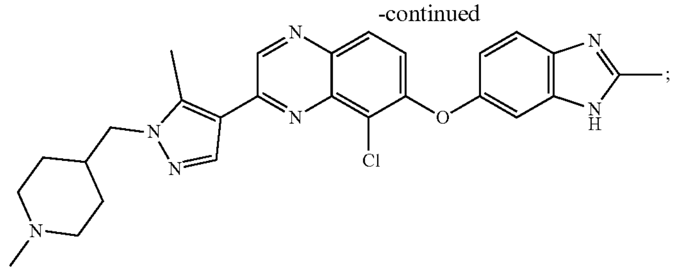
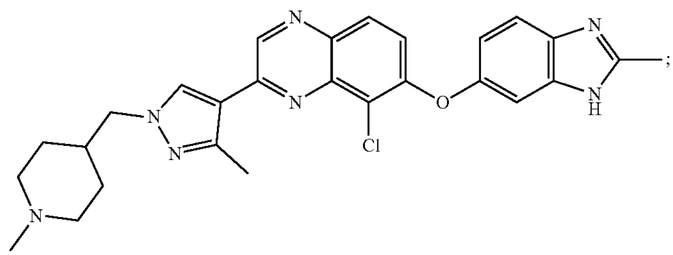
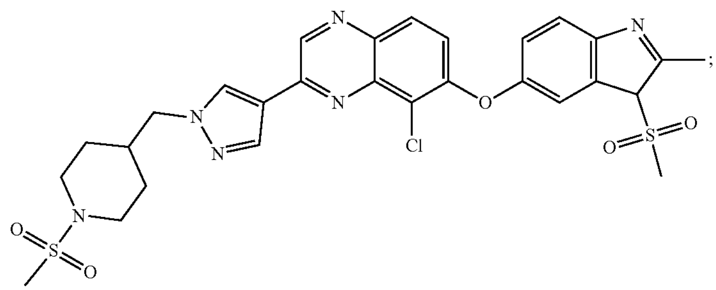
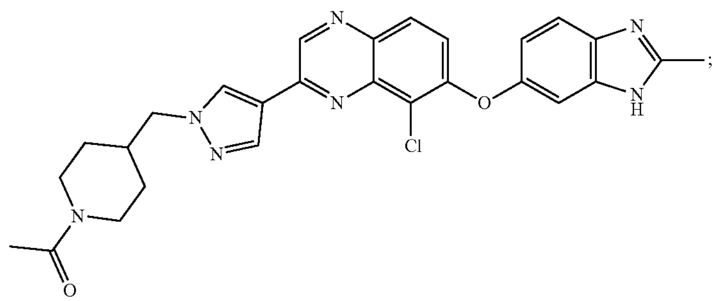
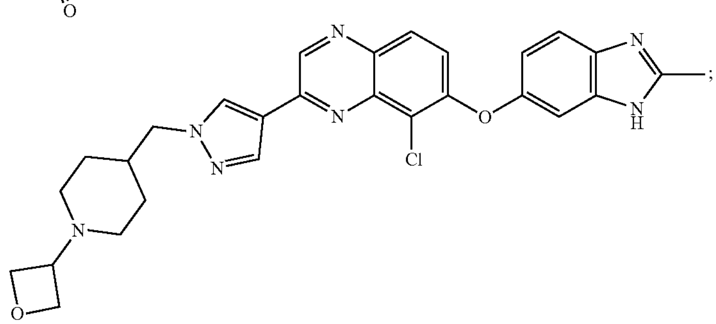
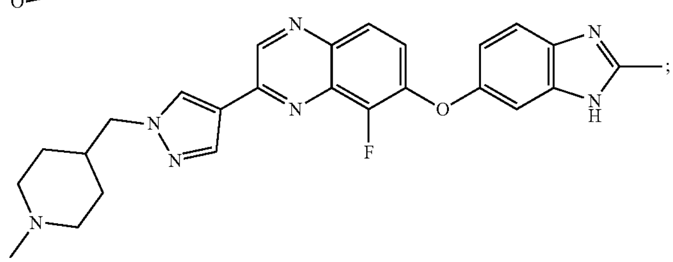

-continued
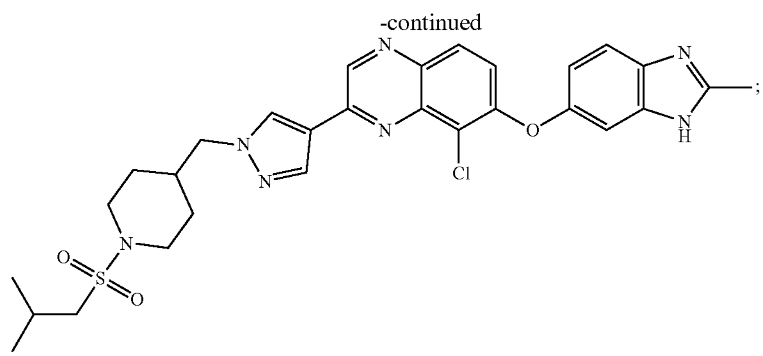
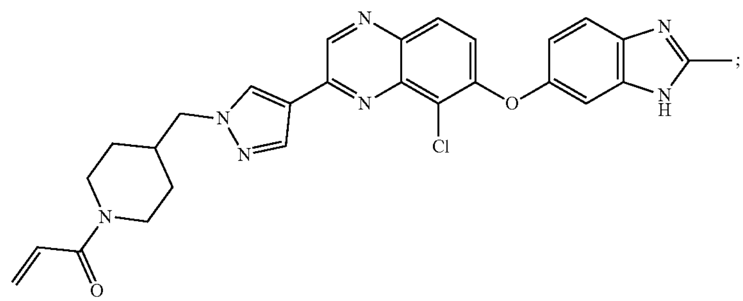
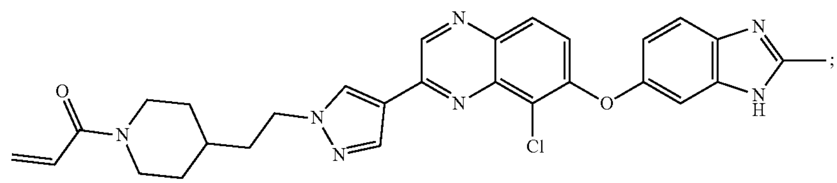
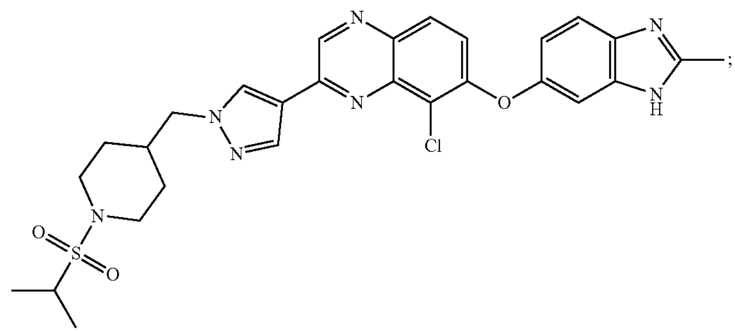
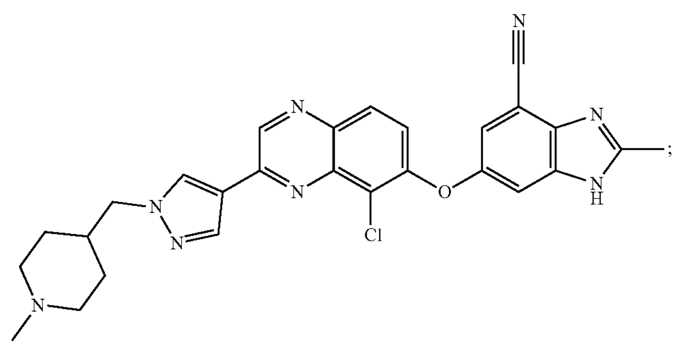

-continued
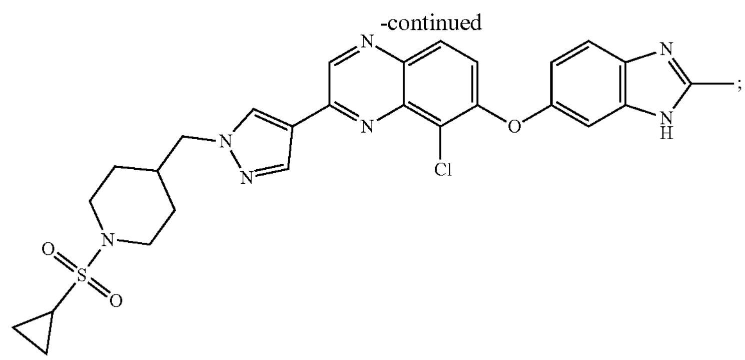
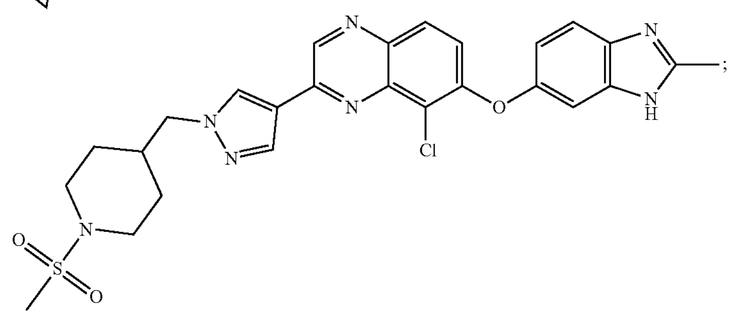
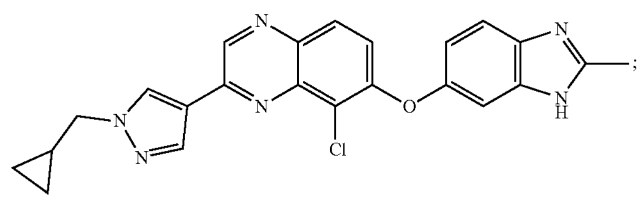
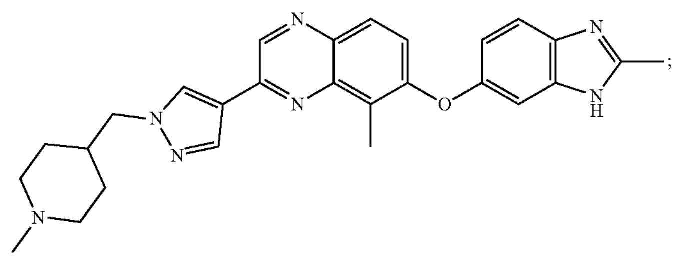
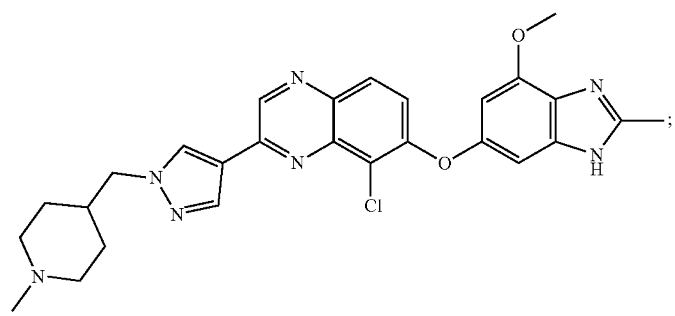
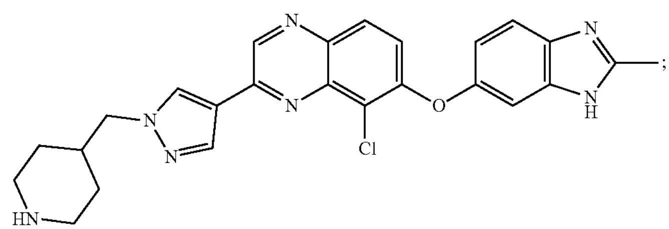

-continued
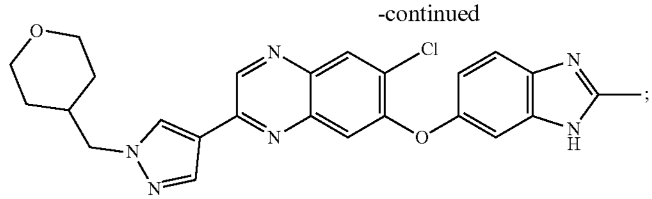
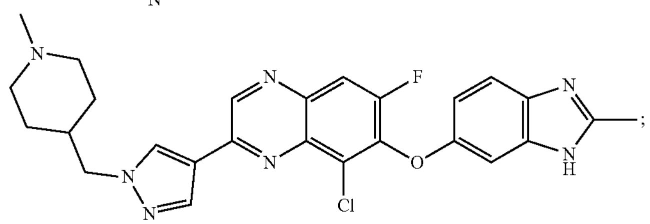
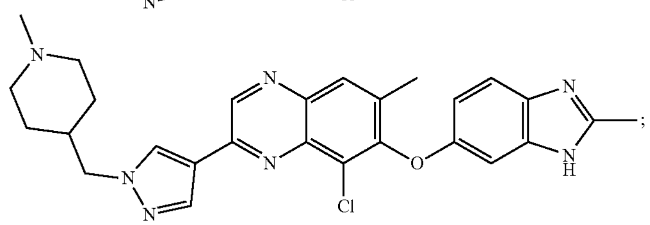
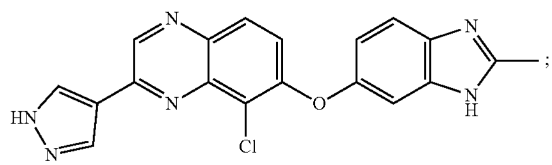
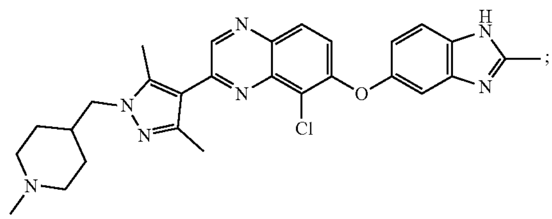
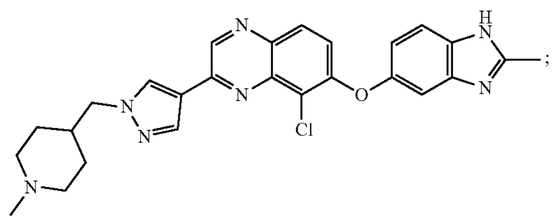
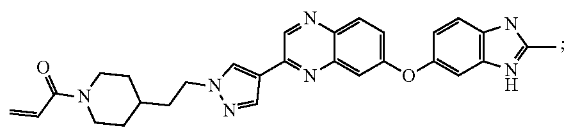
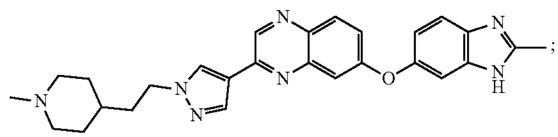
-continued
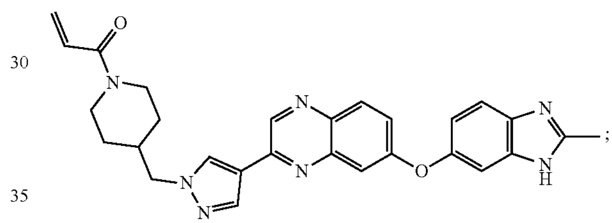
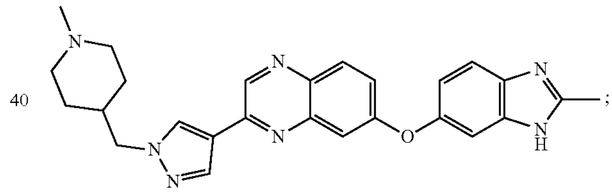
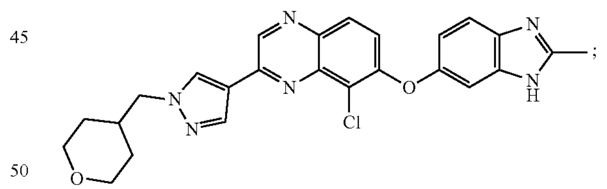
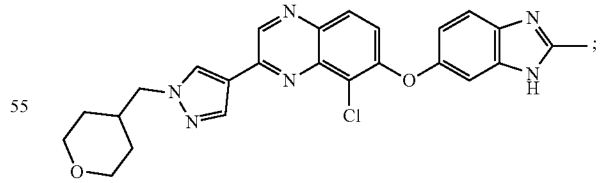
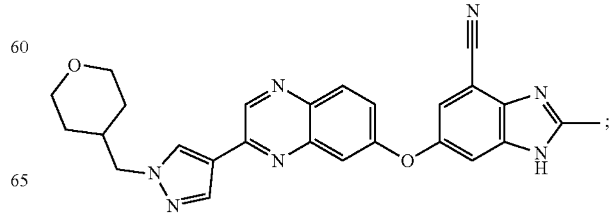

-continued
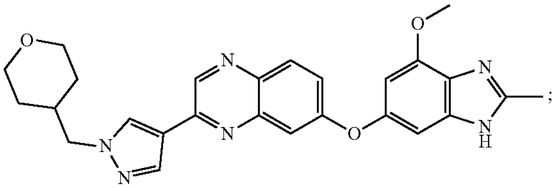
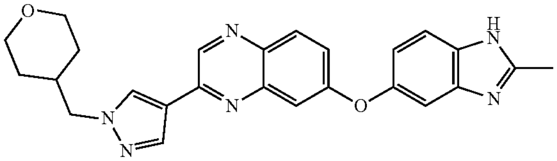
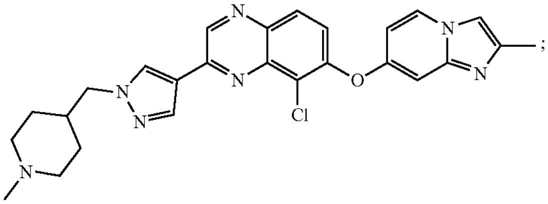
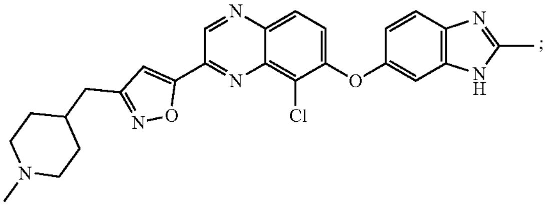
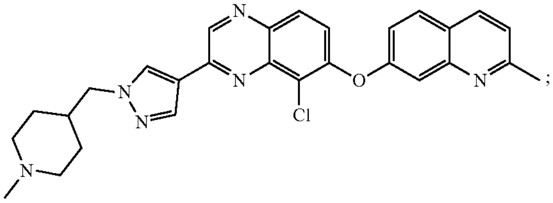
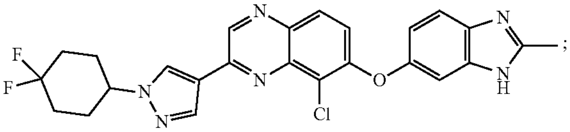
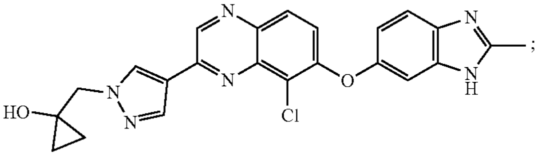
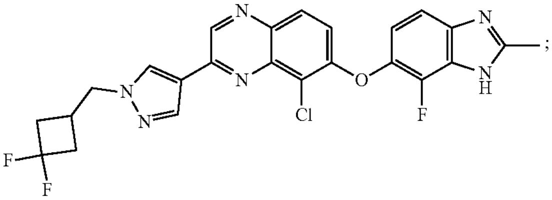
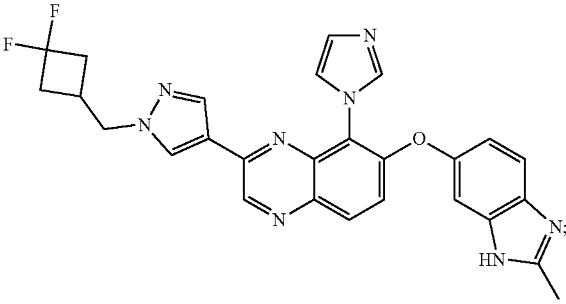
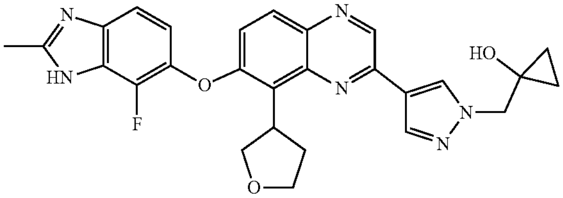
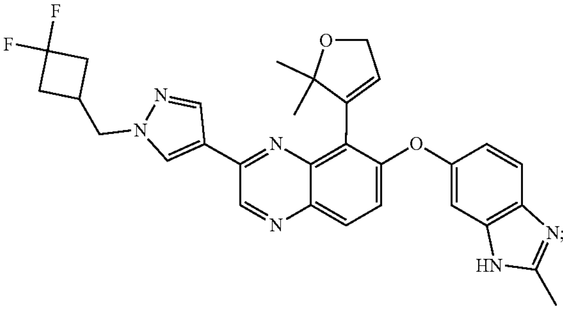
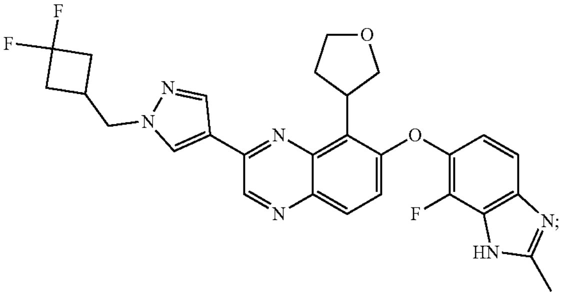
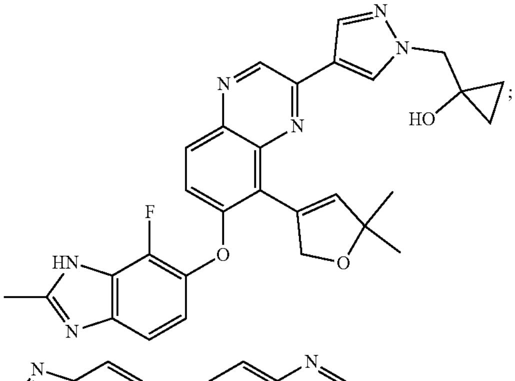
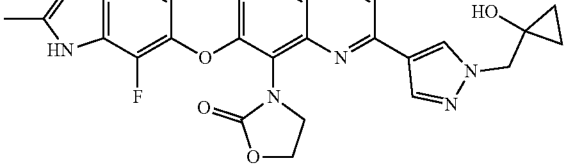

-continued
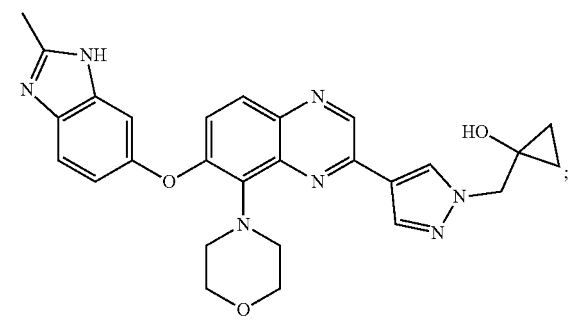
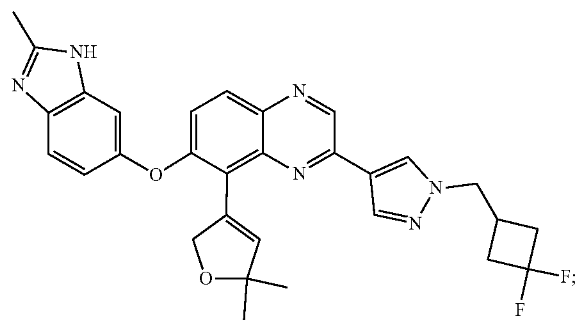
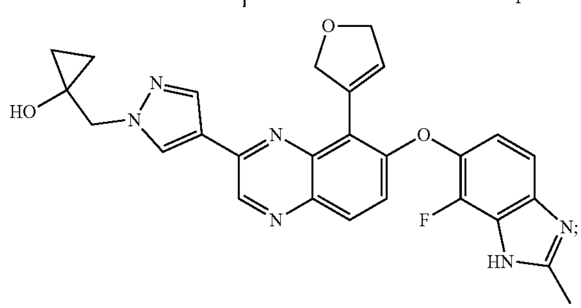
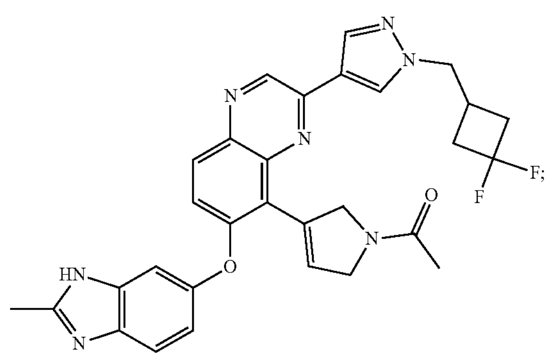
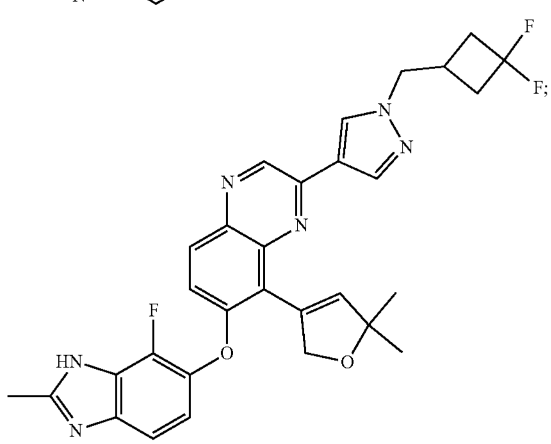
-continued
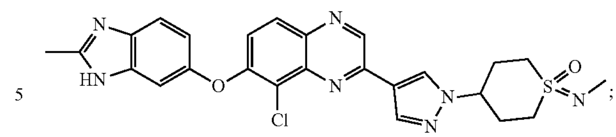
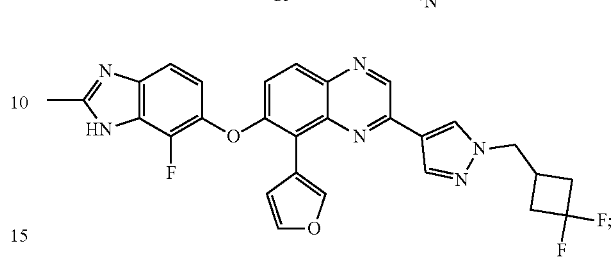
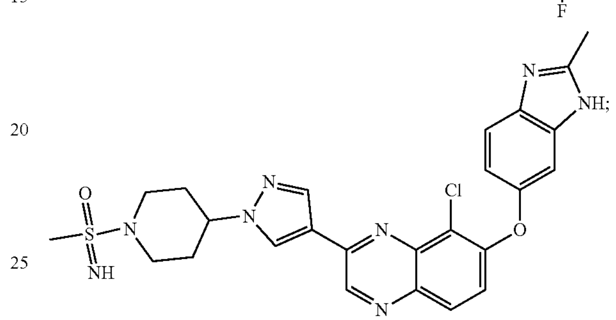
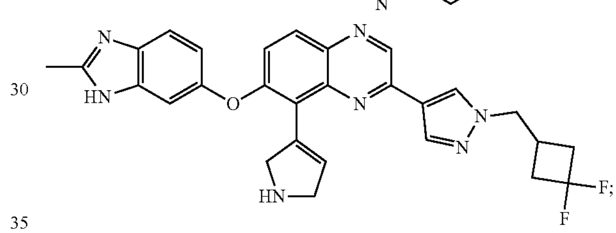
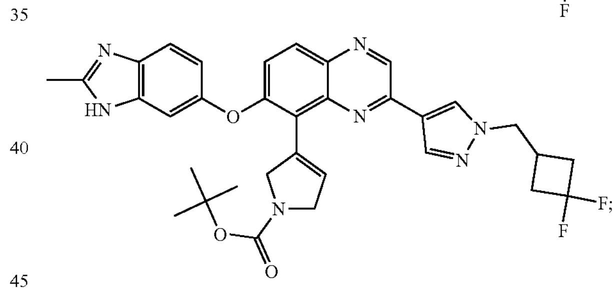
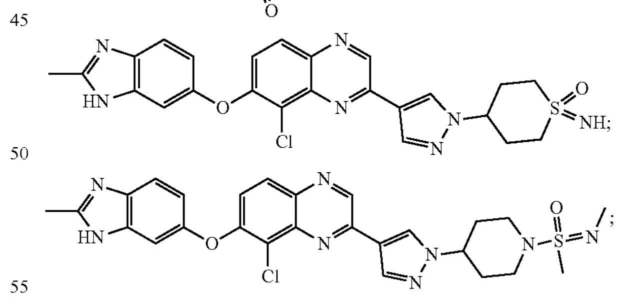
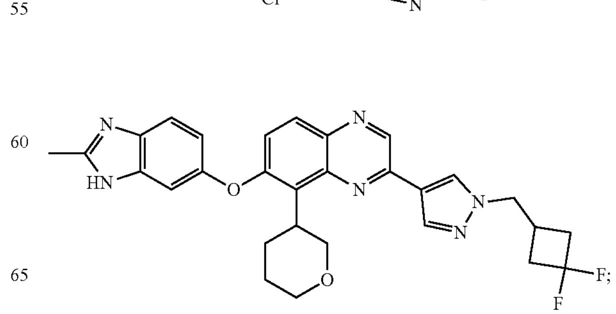

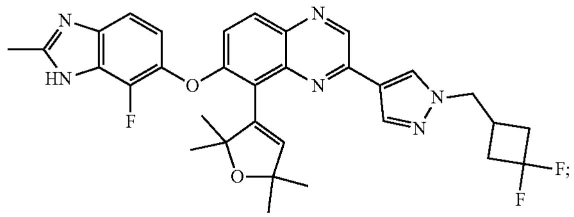
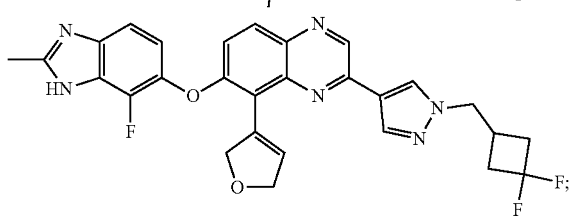
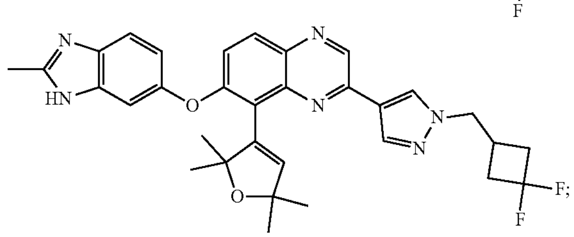
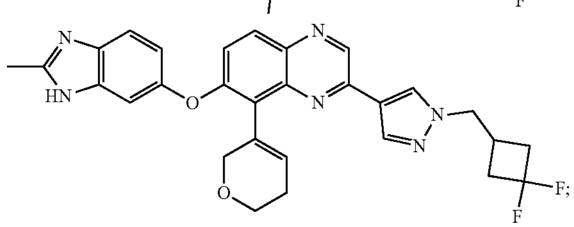
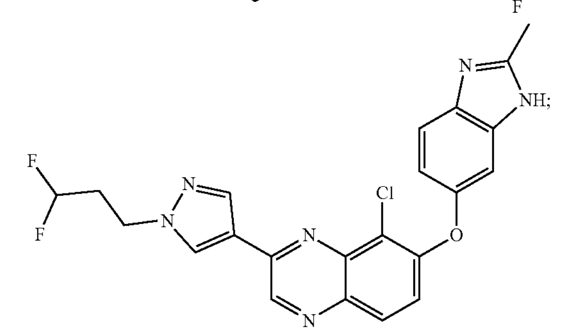
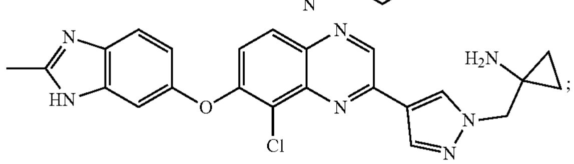
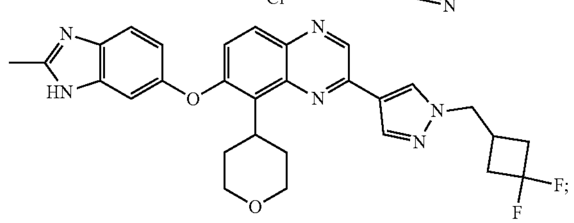
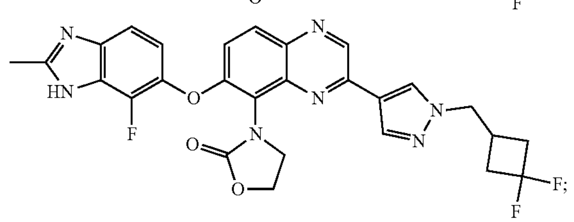
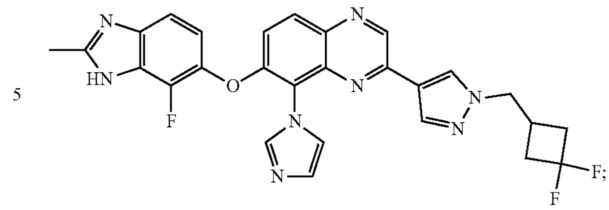
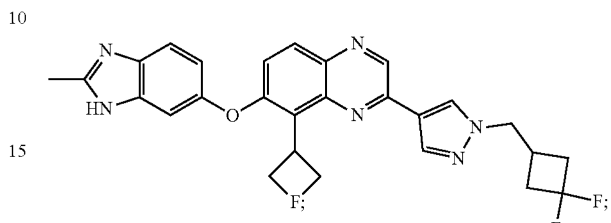
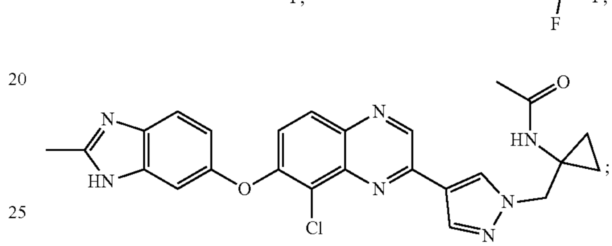
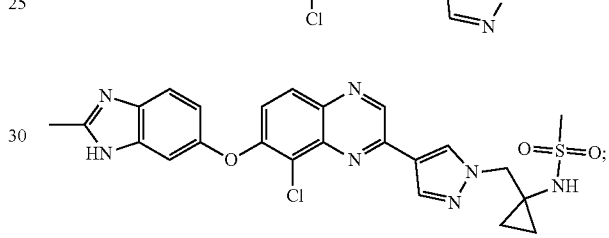
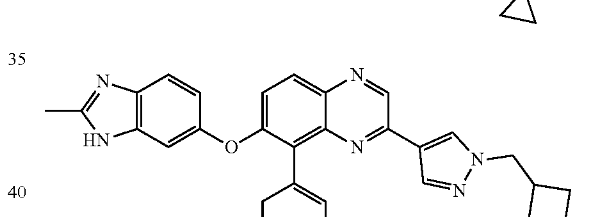
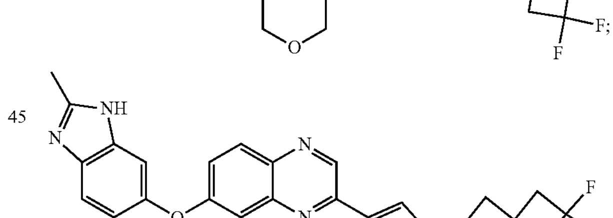
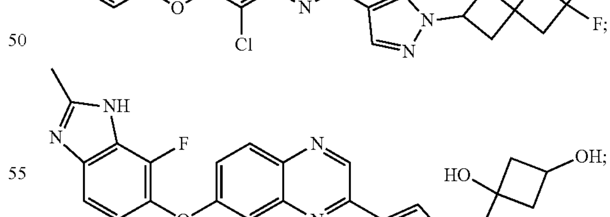
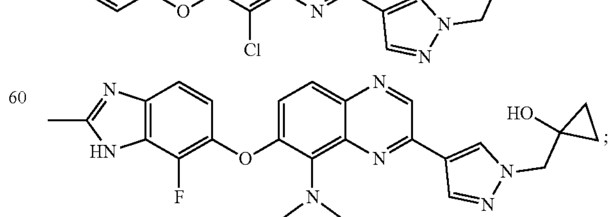
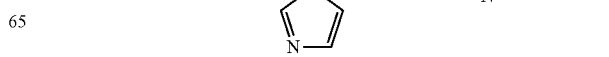

-continued
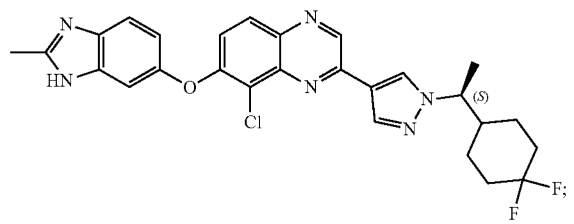
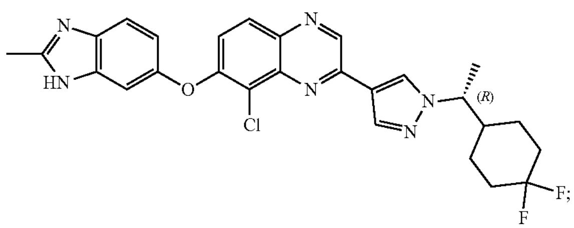
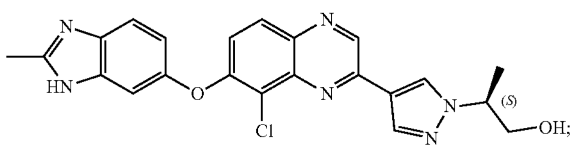
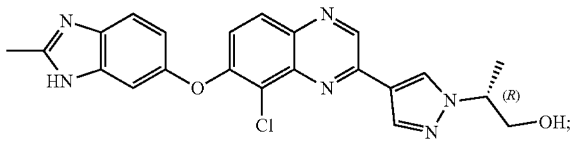
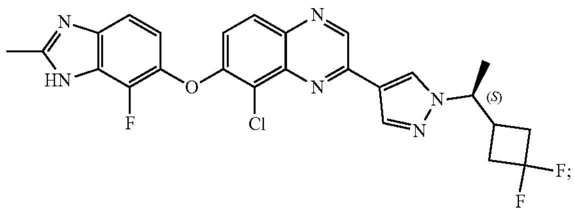
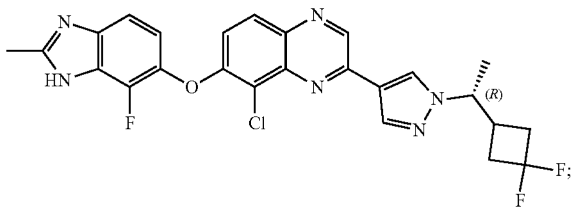
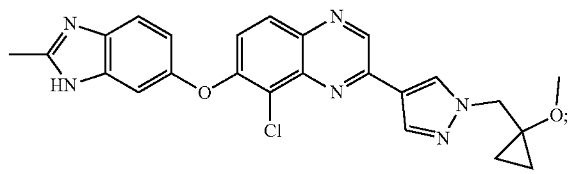
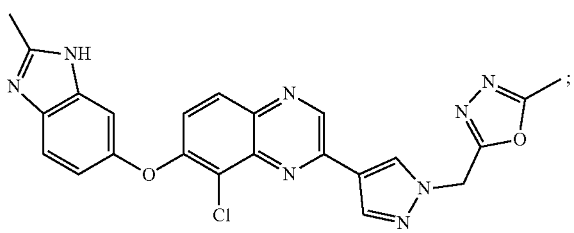
-continued
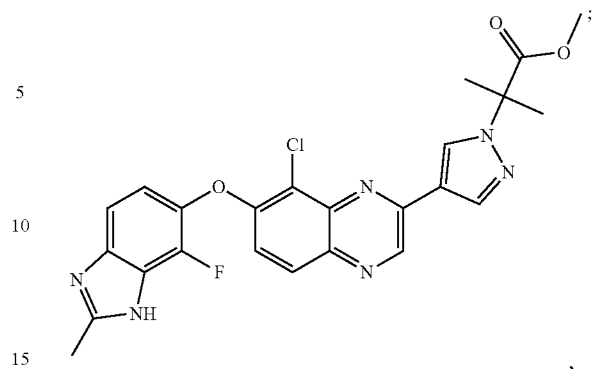
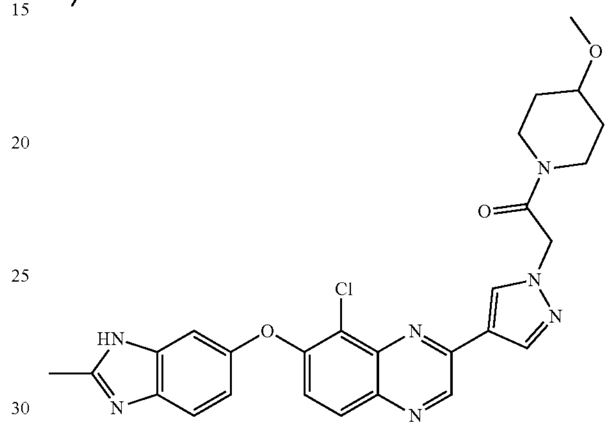
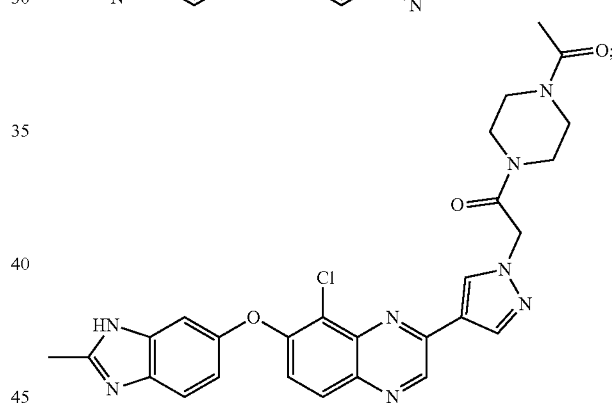
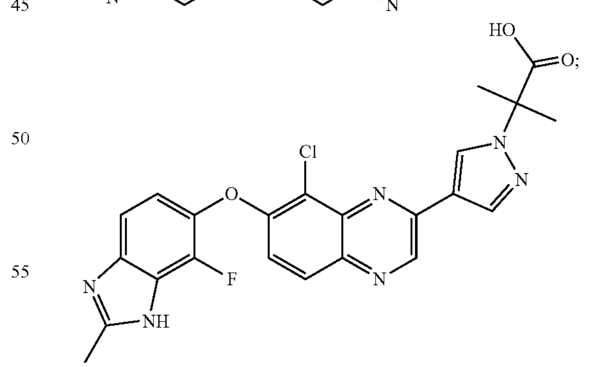
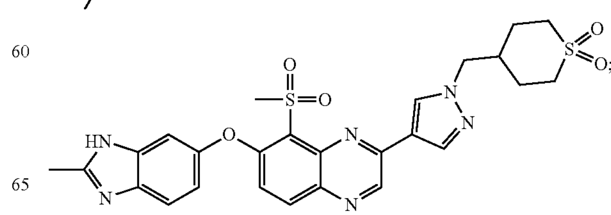

-continued
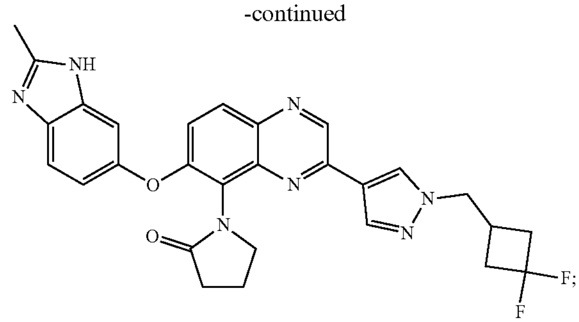
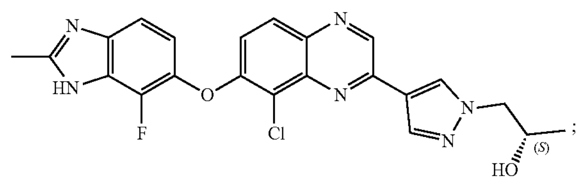
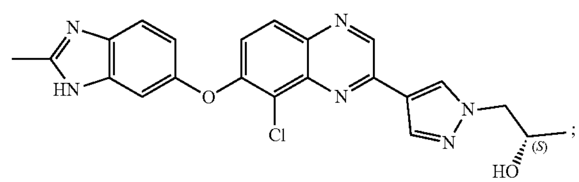
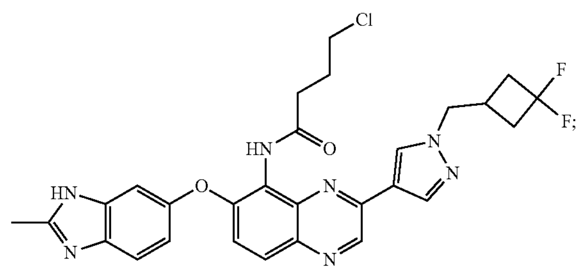
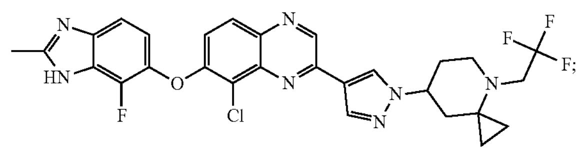
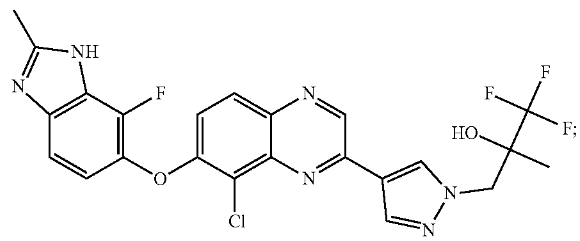
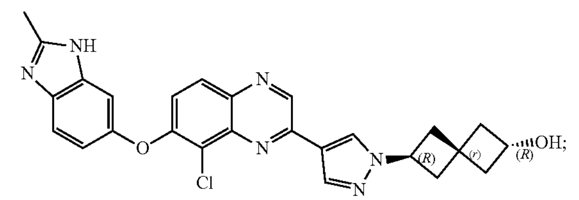
-continued
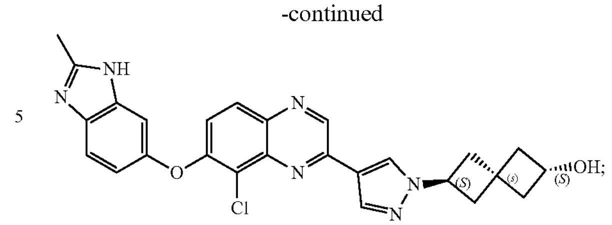
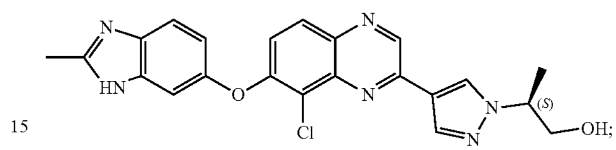
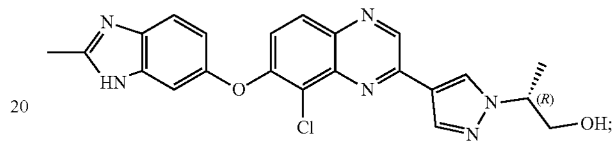
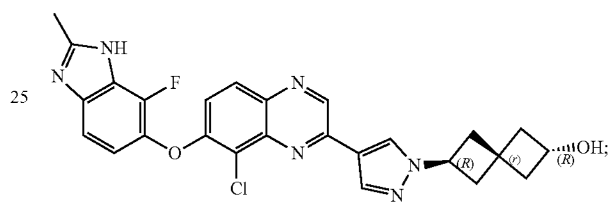
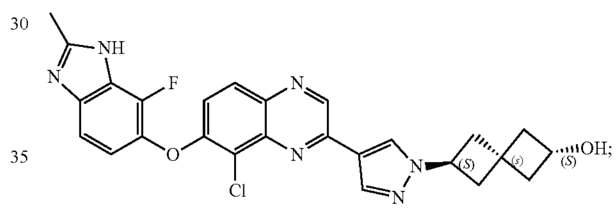
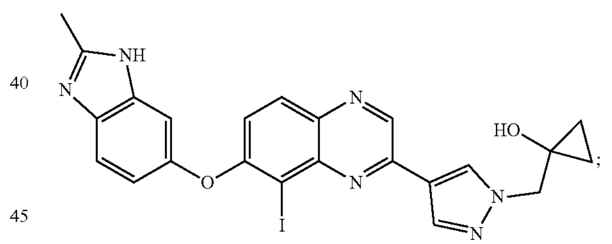
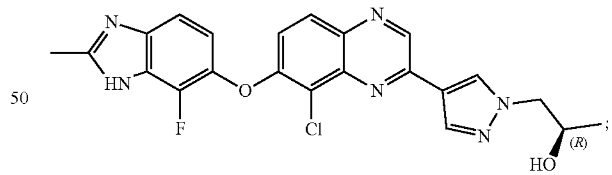
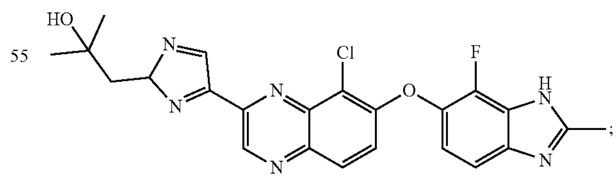
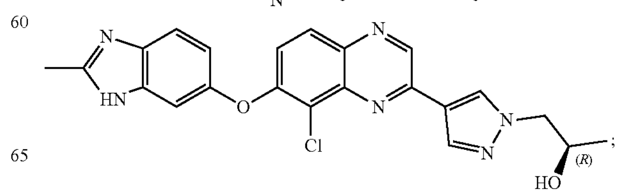

-continued
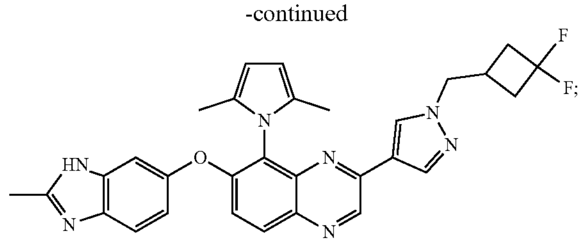
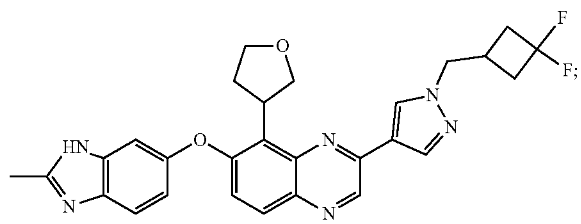
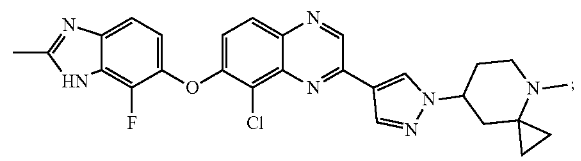
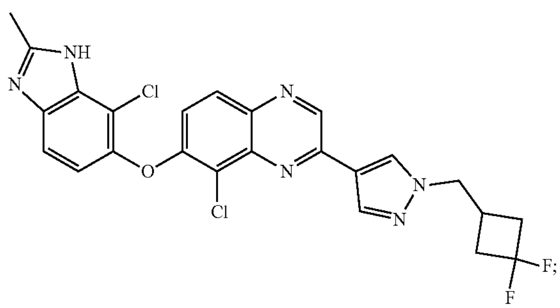
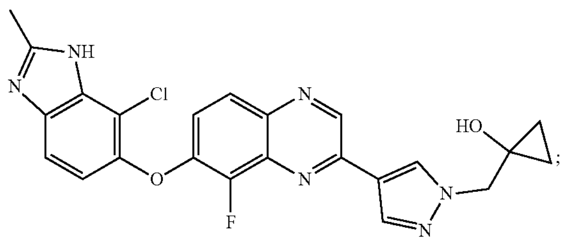
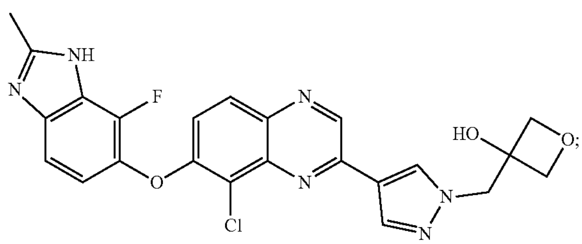
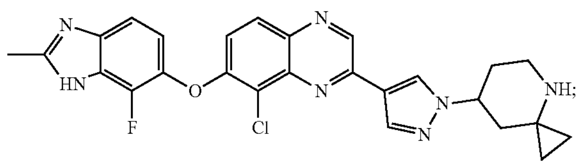
-continued
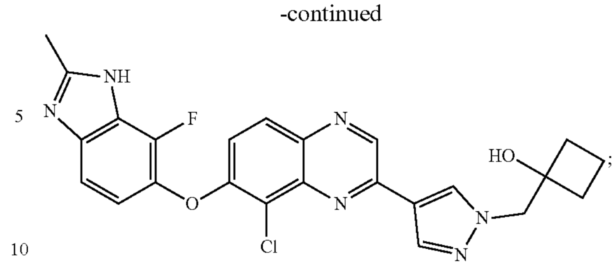
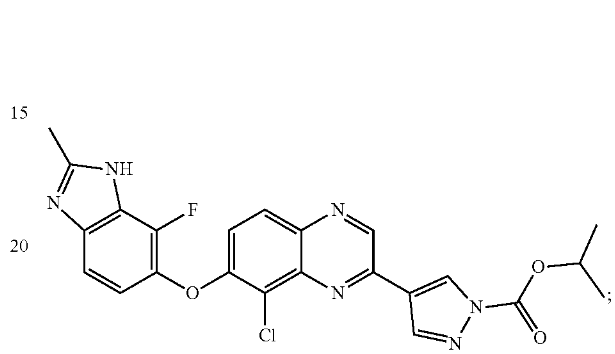
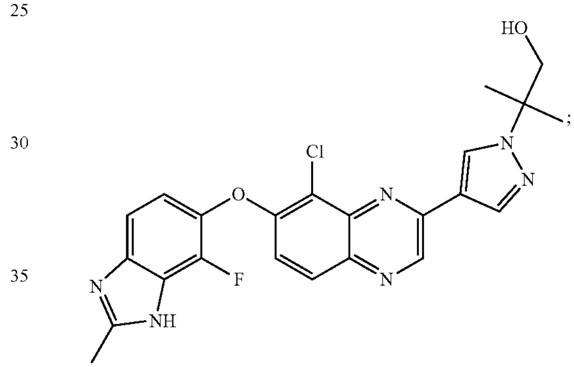
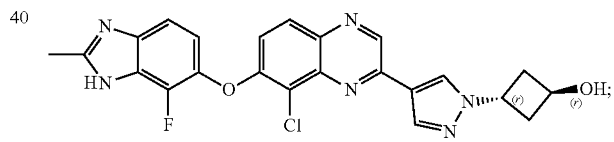
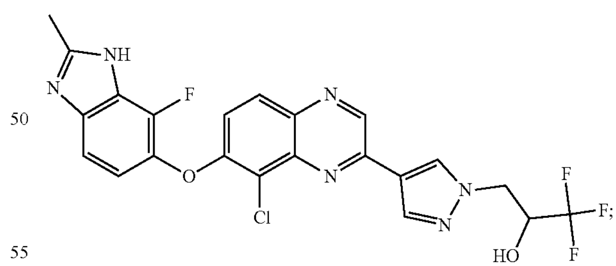
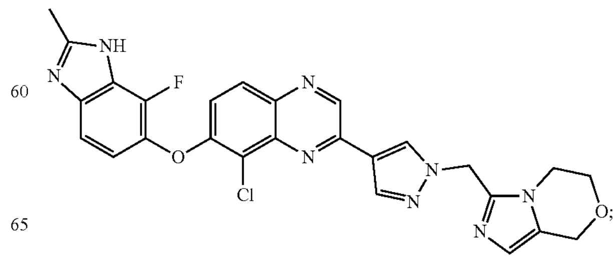

-continued
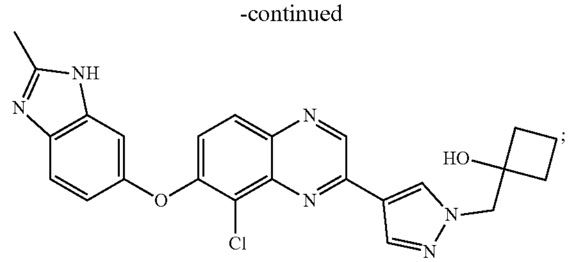
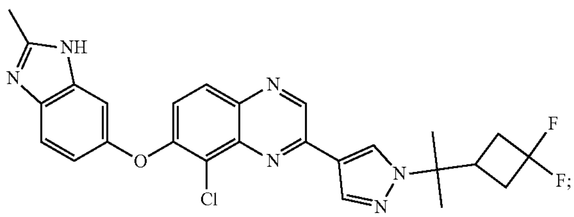
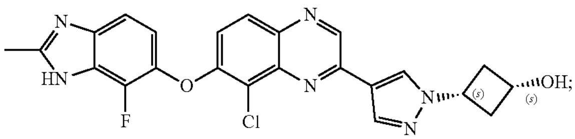
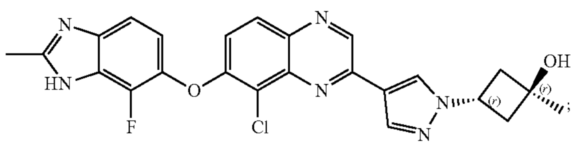
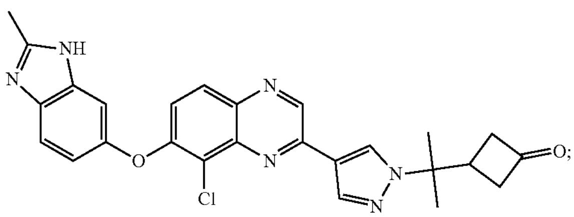
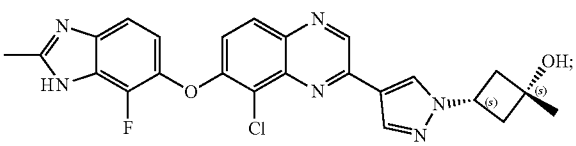
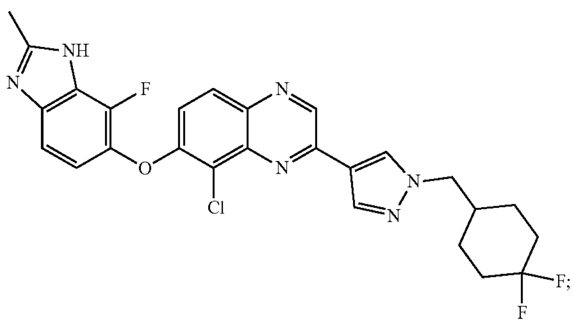
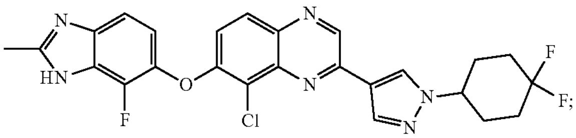
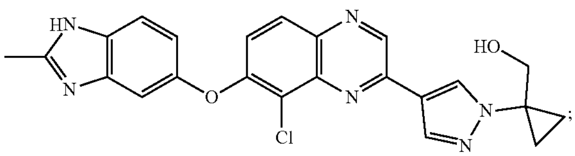
-continued
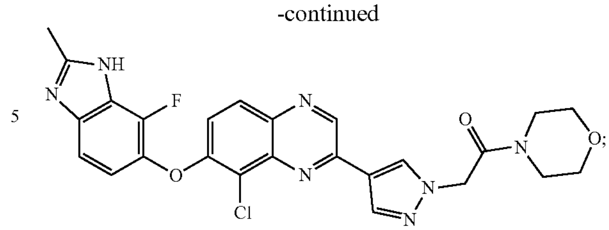
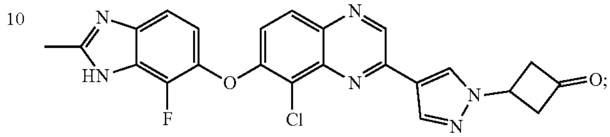
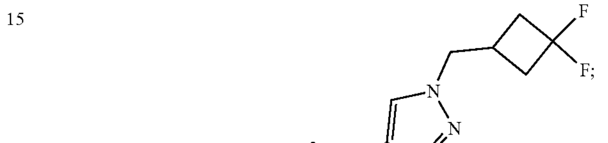
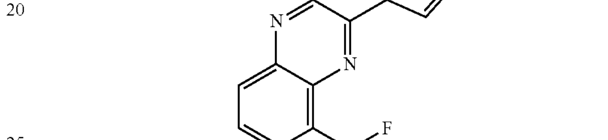
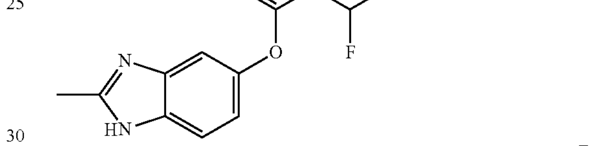
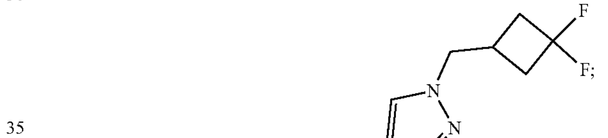
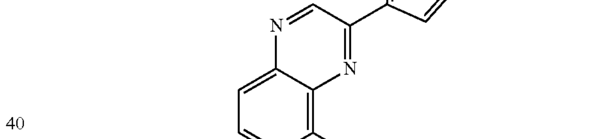
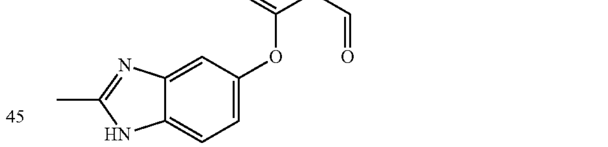
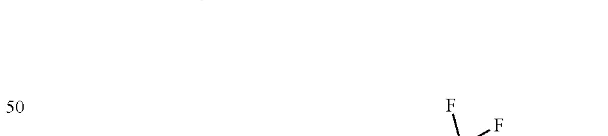
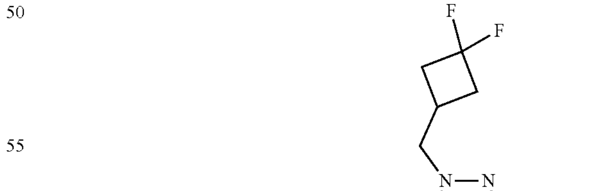
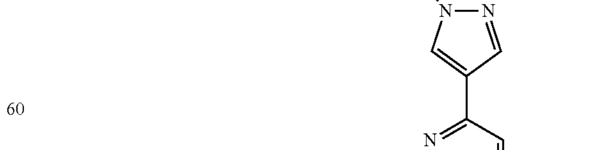
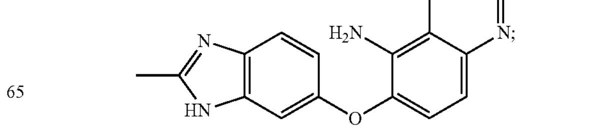

-continued
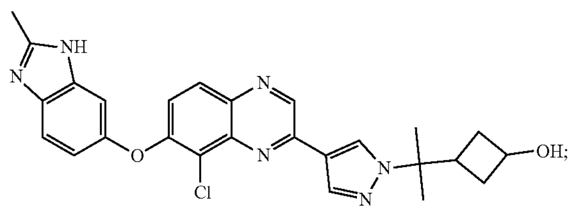
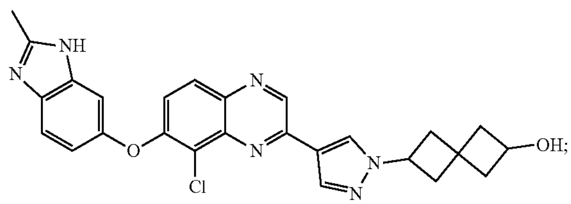
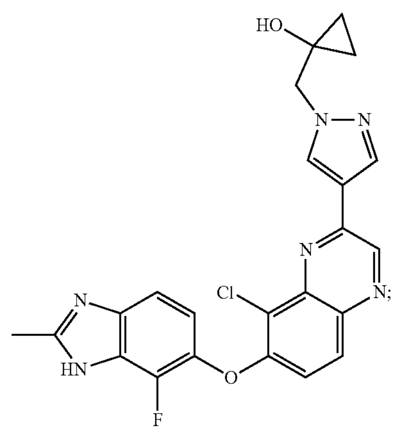
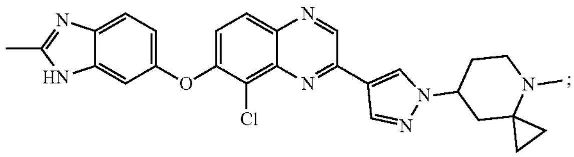
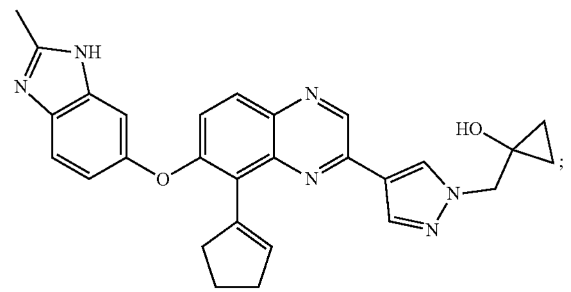
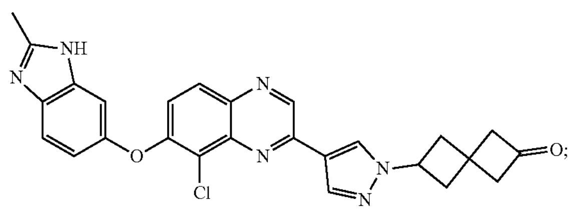
-continued
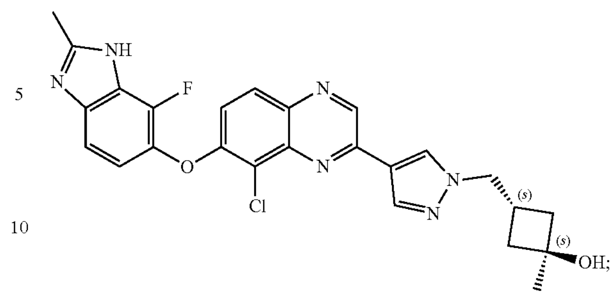
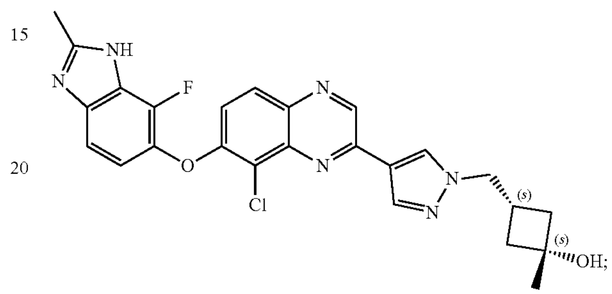
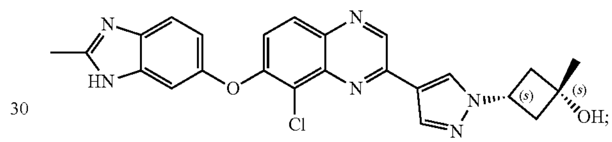
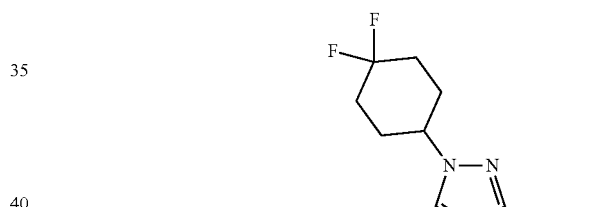
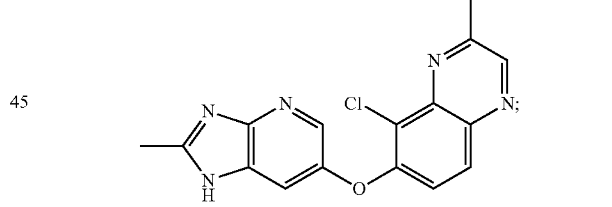
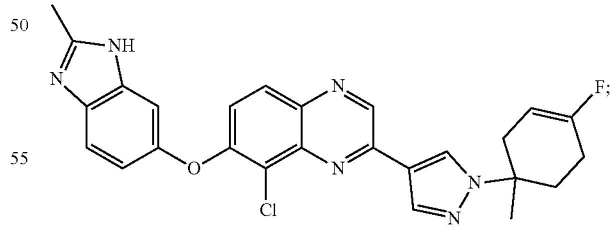
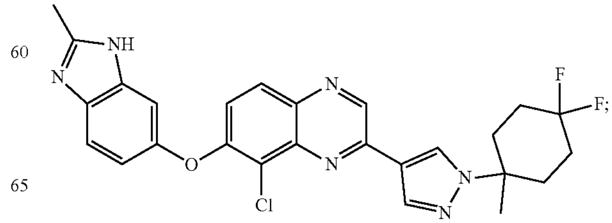

-continued
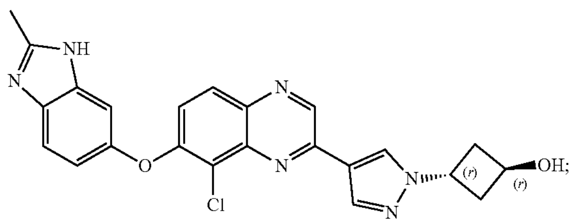
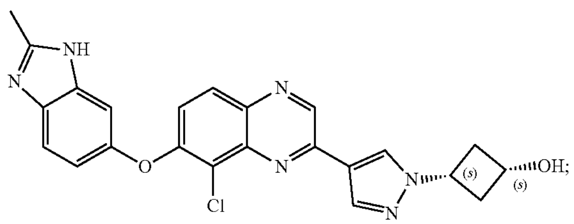
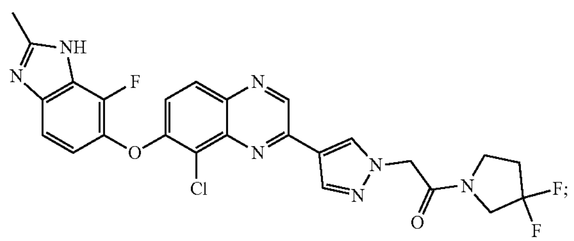
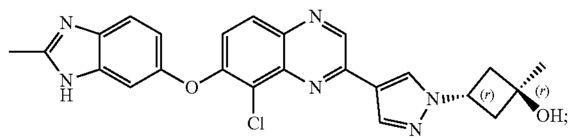
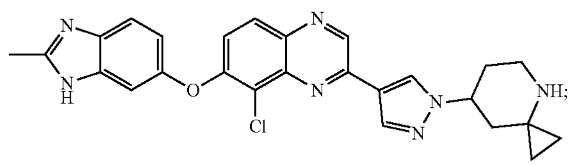
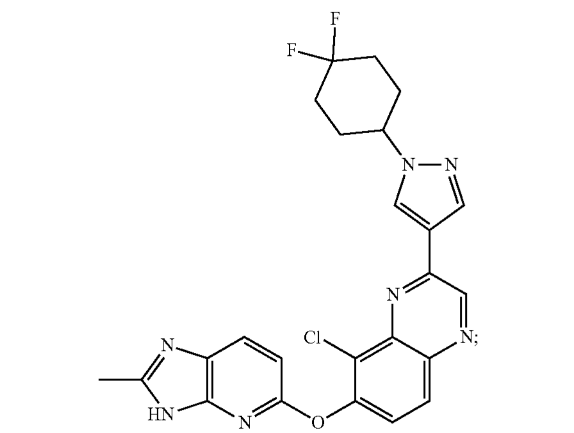
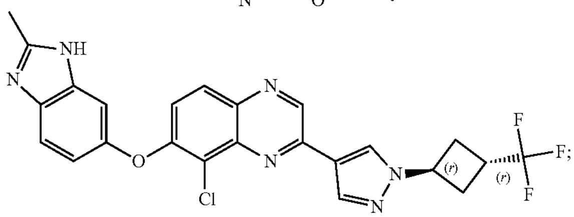
-continued
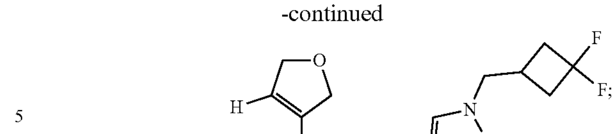
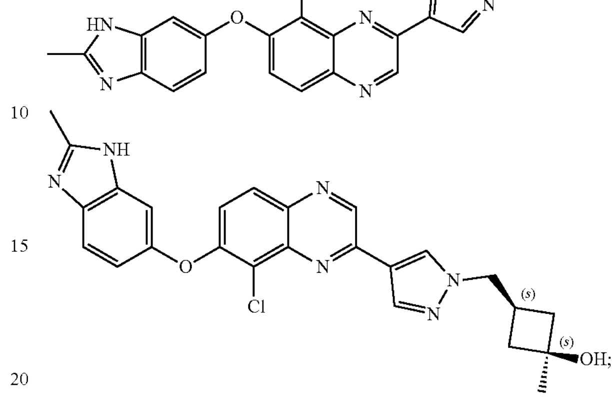
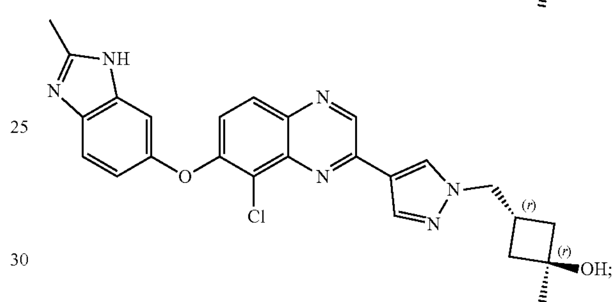
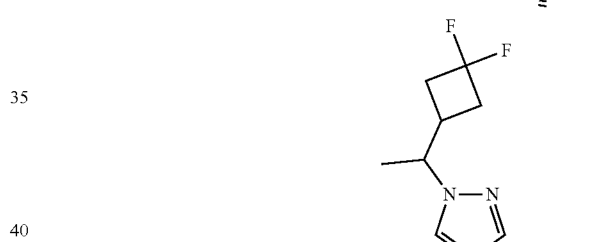
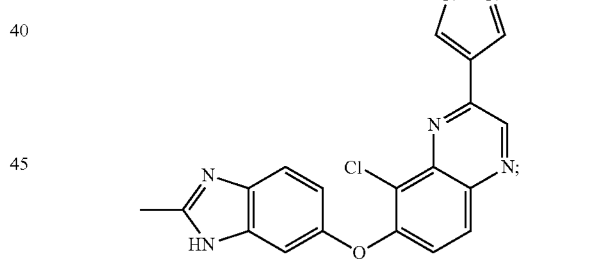
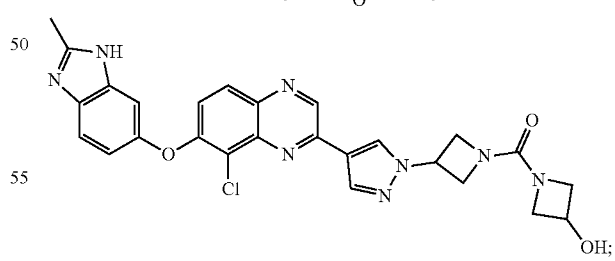
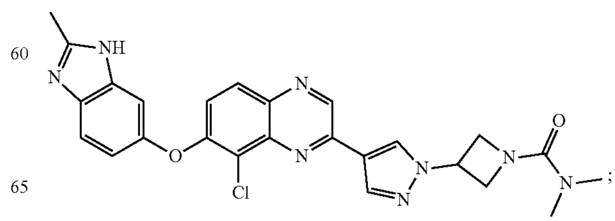

-continued
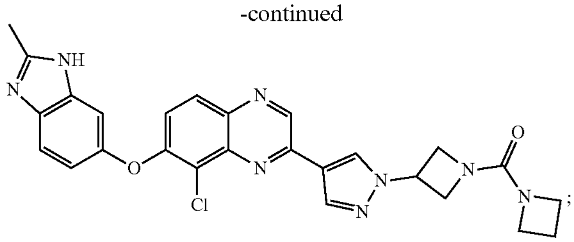
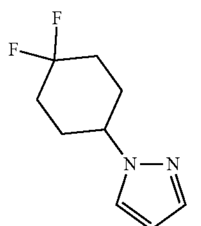
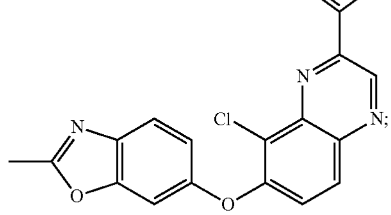
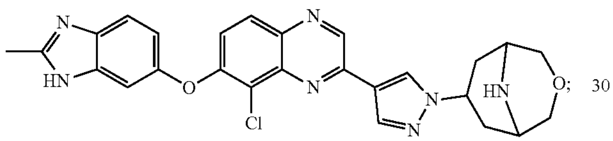
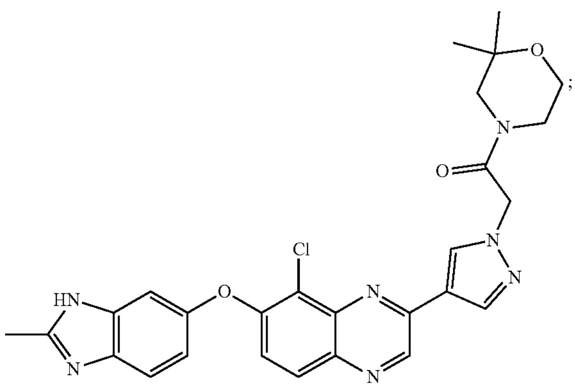
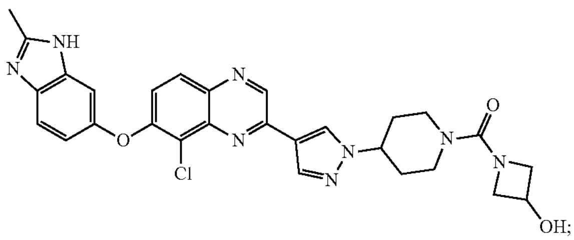
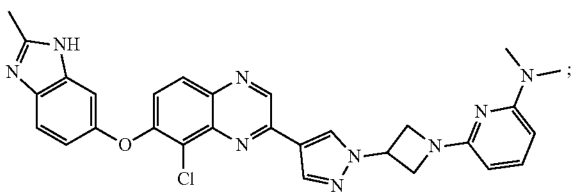
-continued
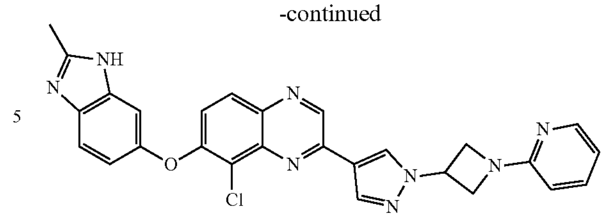
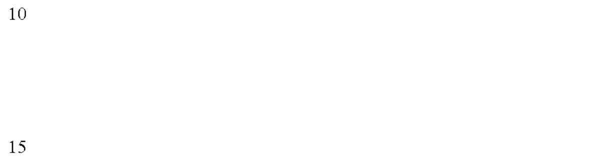
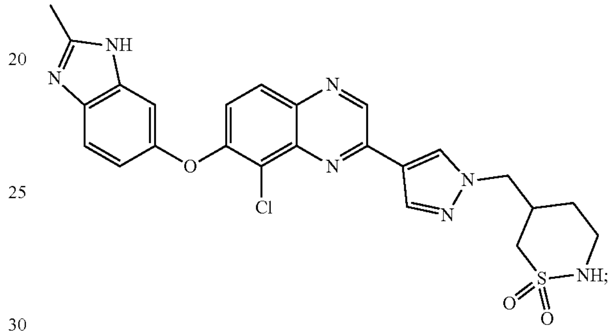
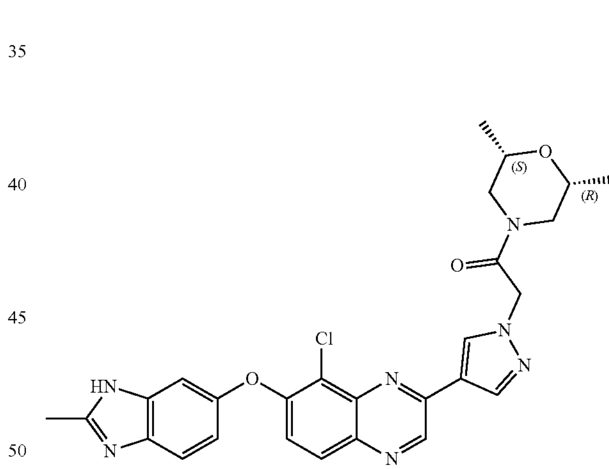
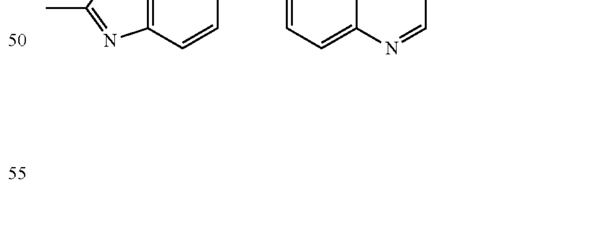
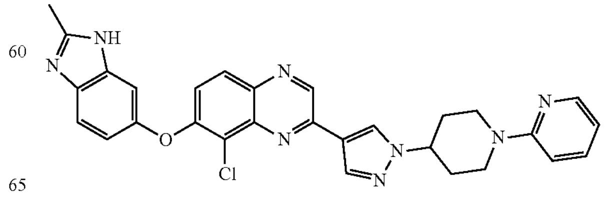

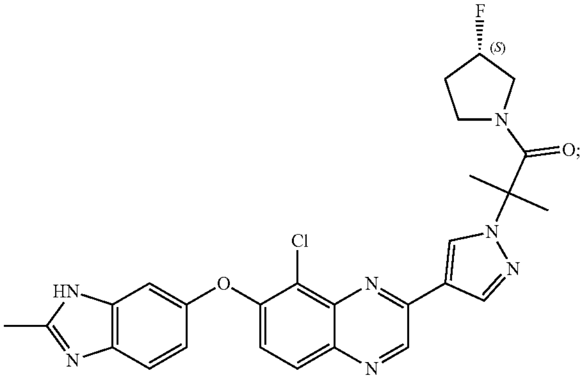
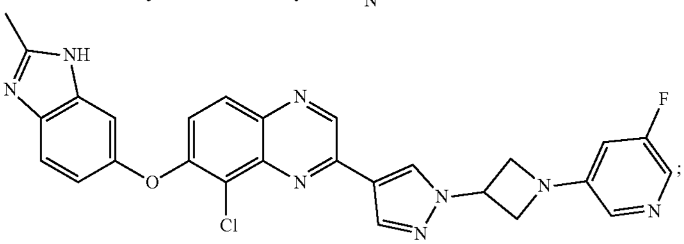
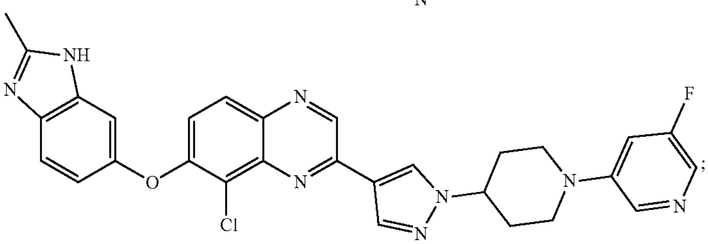
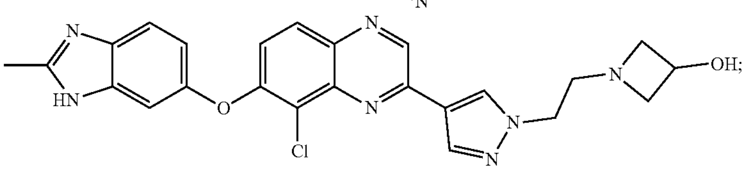
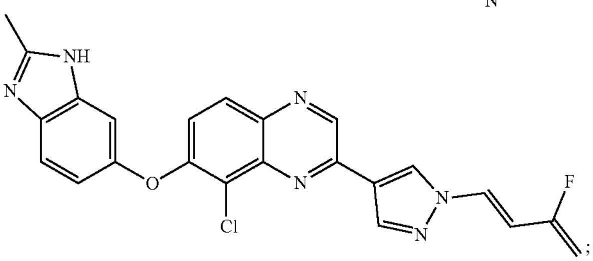
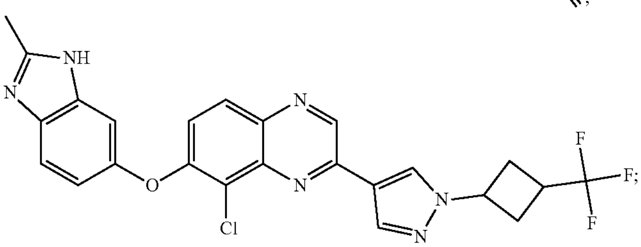
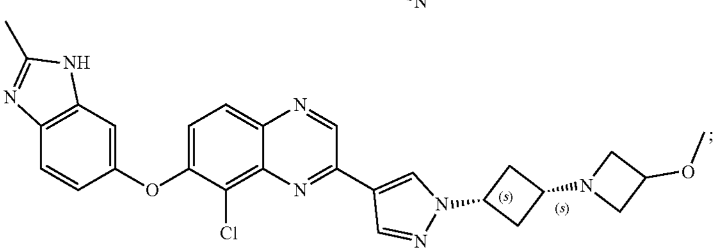

-continued
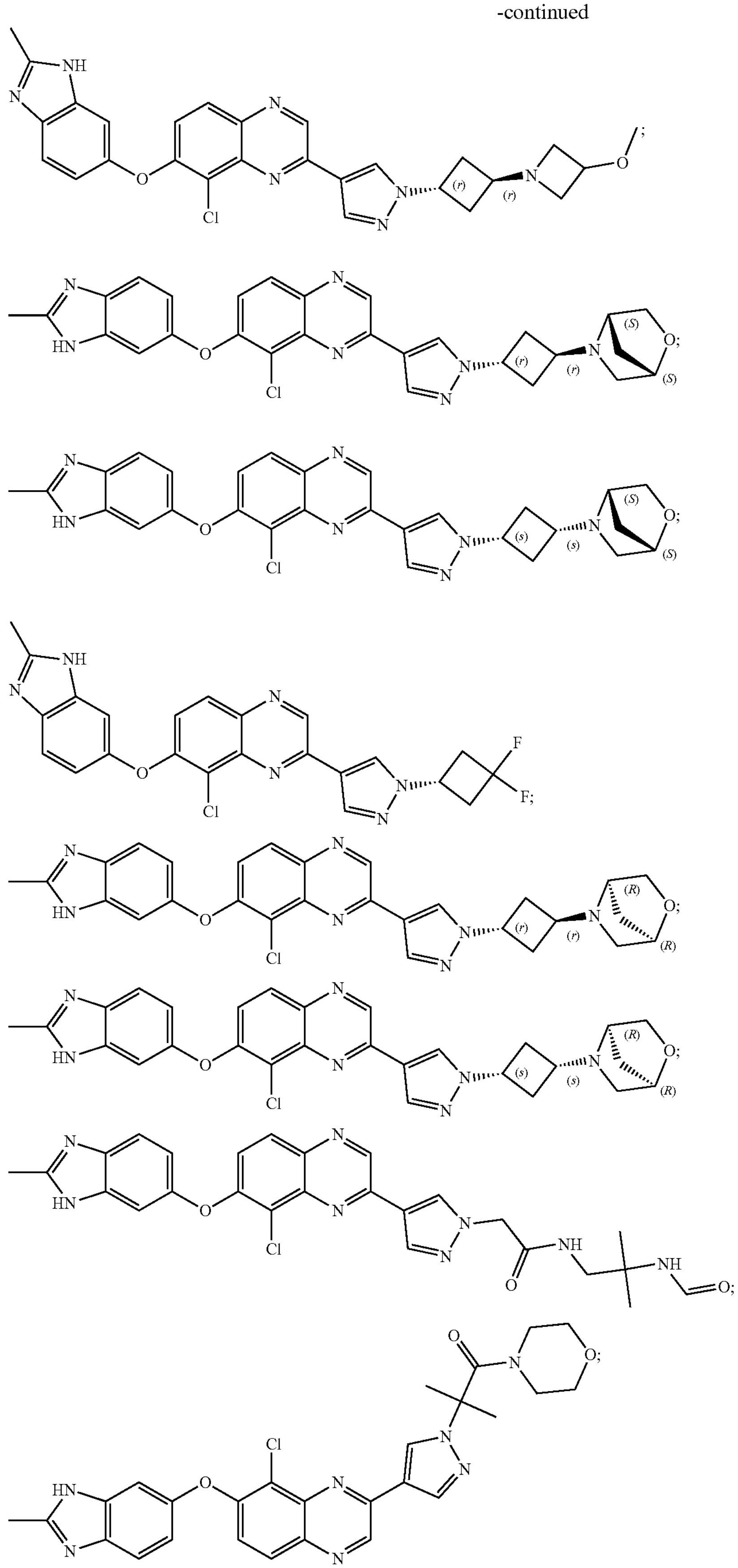

-continued
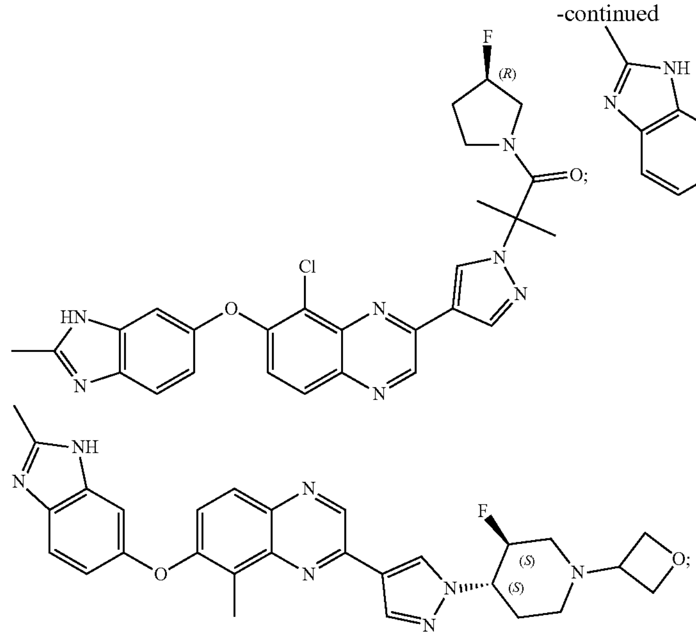
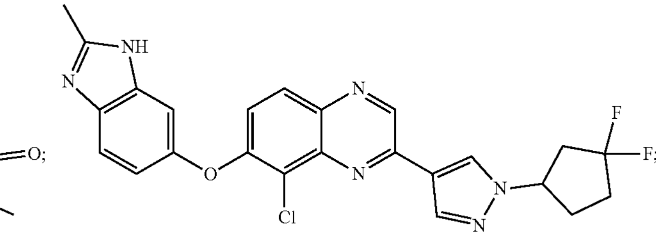
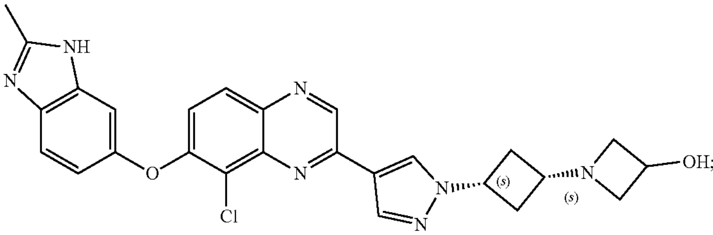
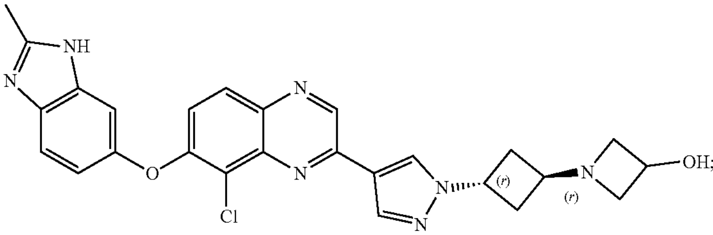
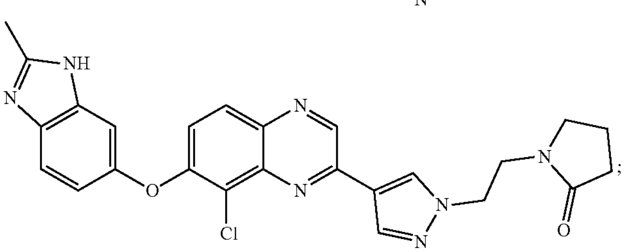
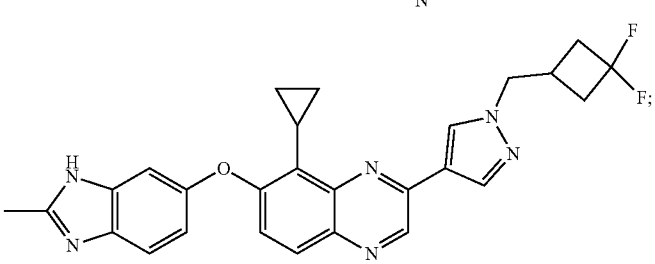

-continued
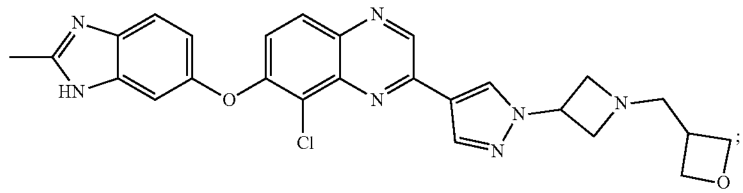
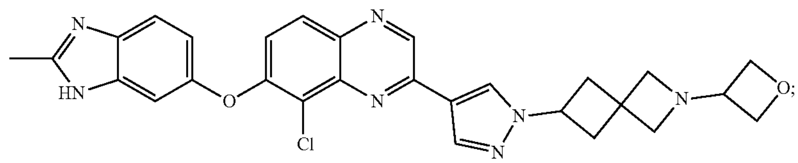
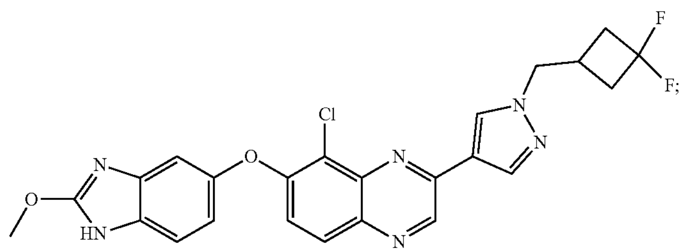
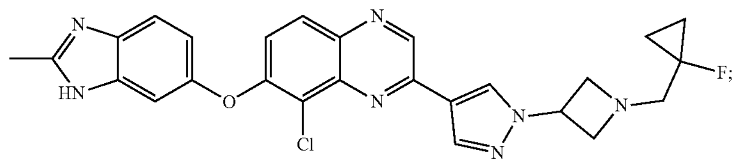
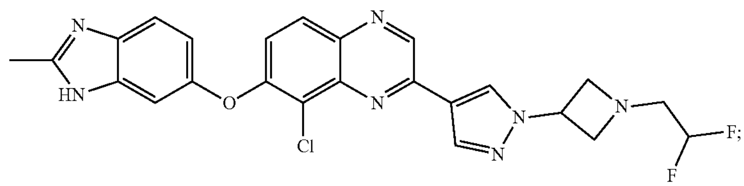
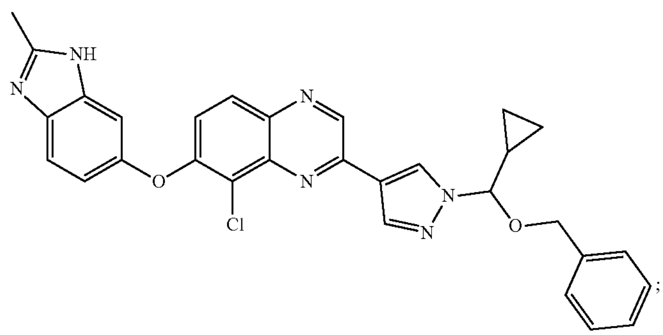
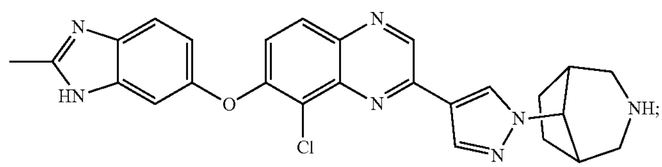
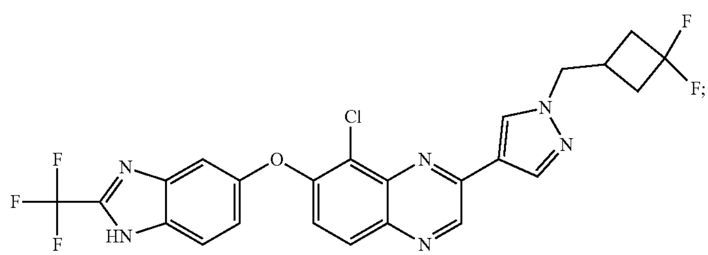

-continued
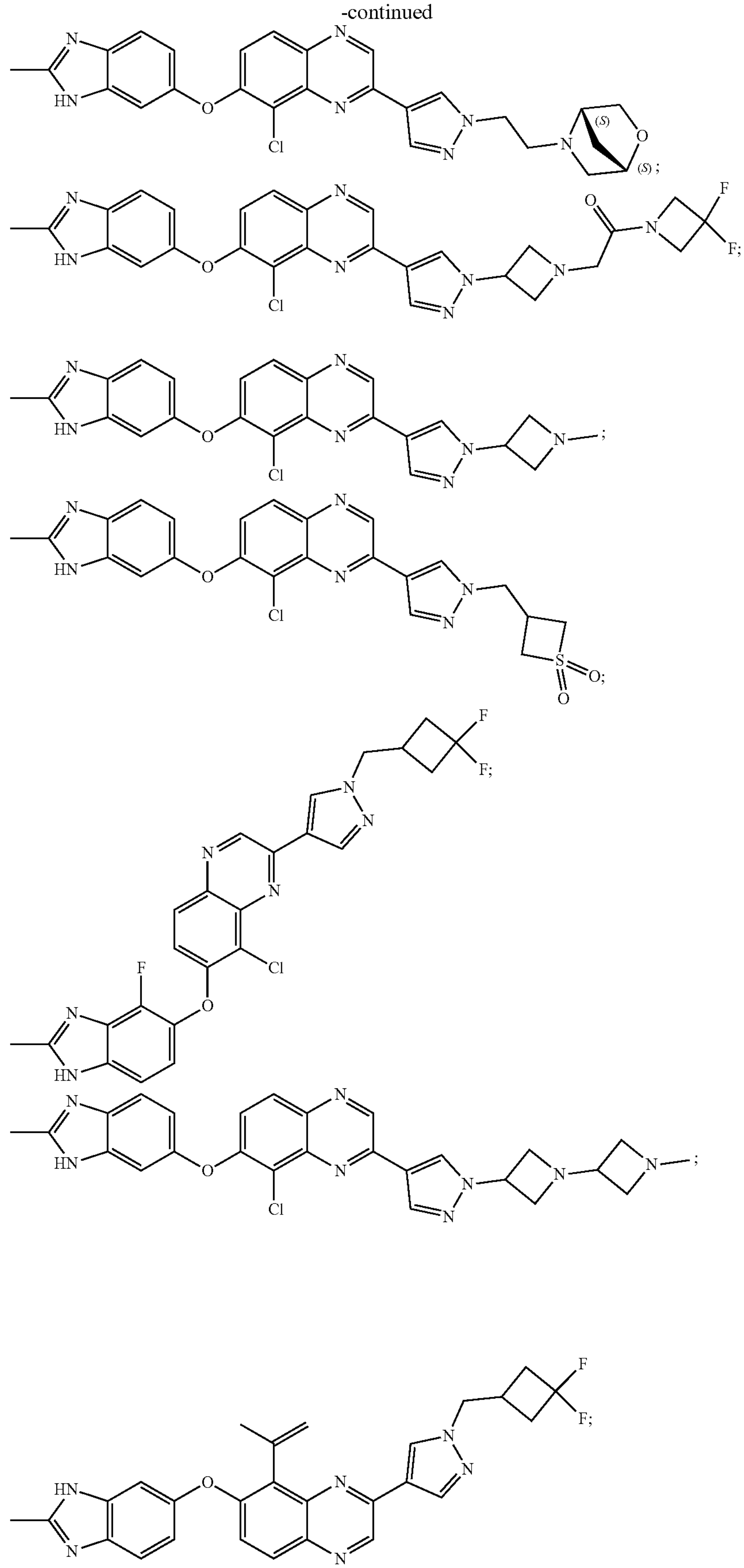

-continued
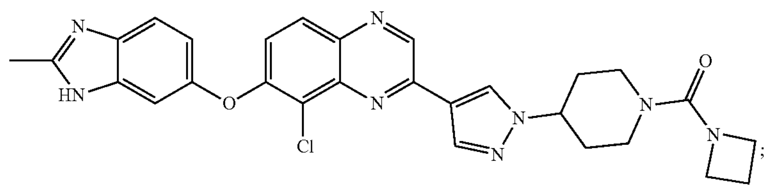
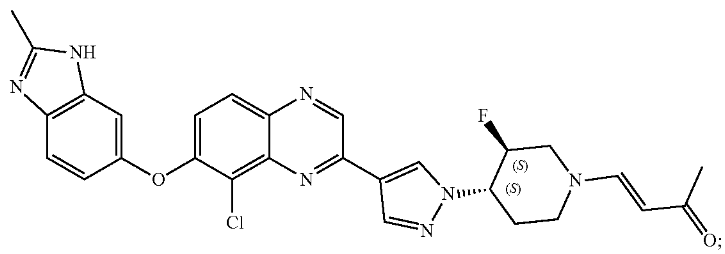
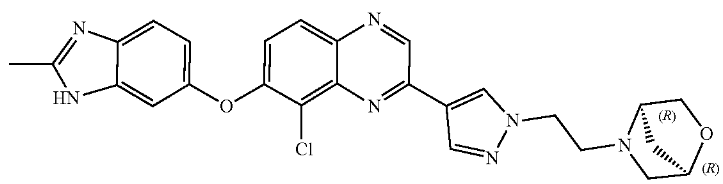
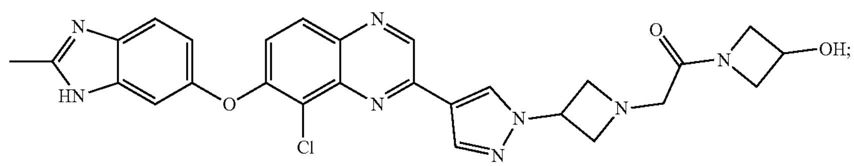
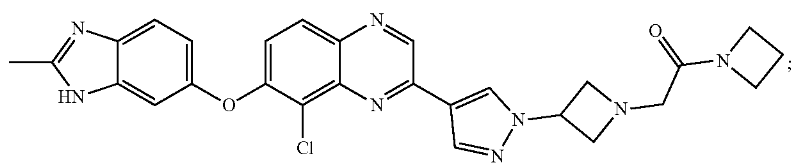
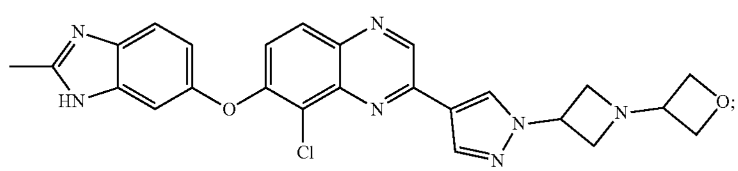
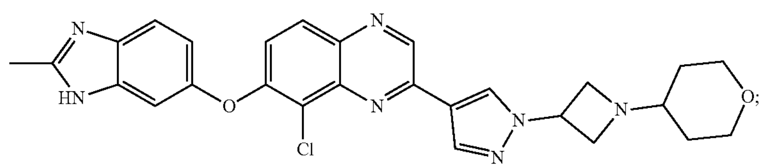
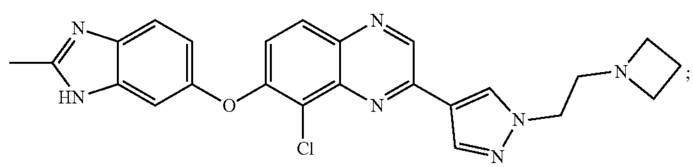

-continued
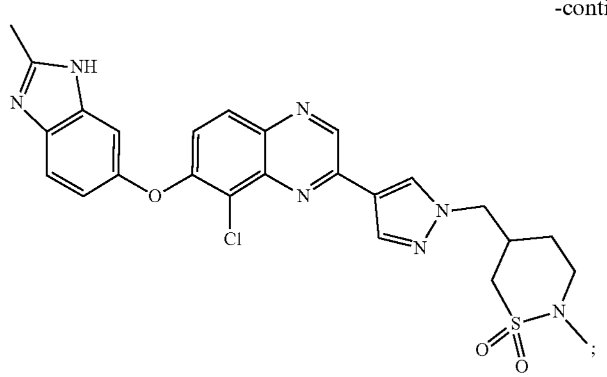
;
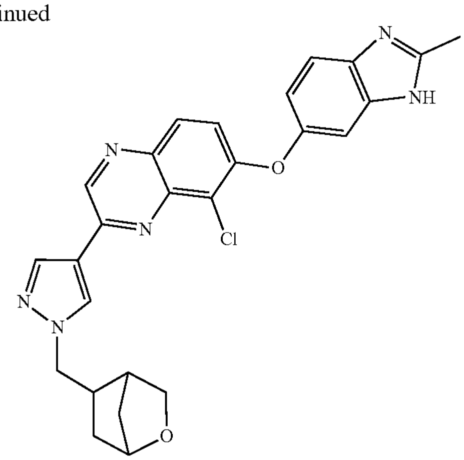
;
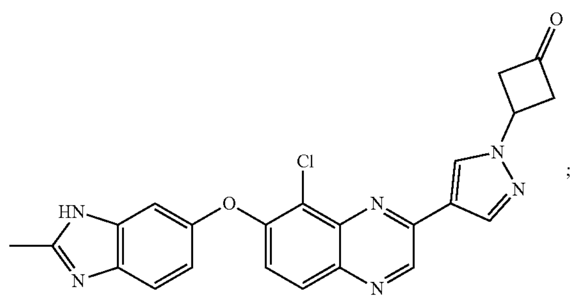
;
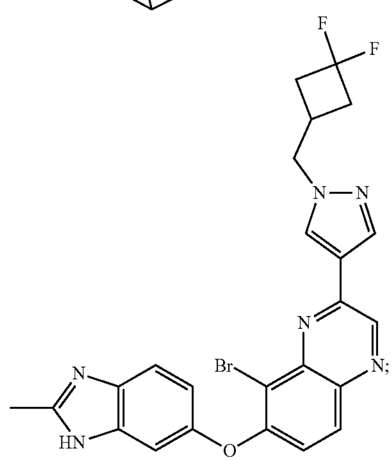
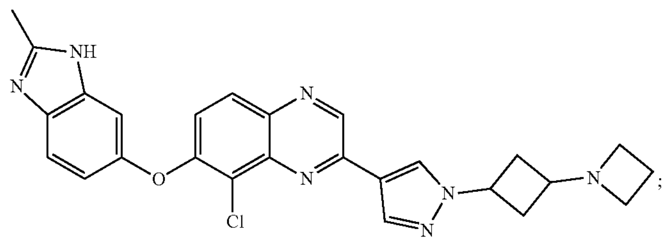
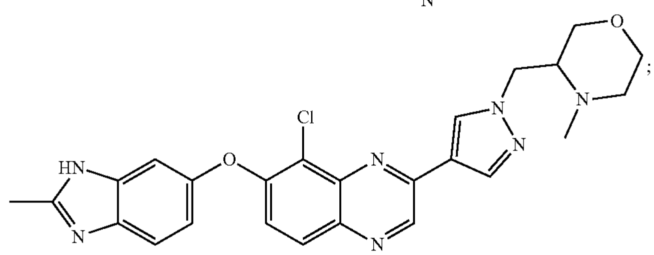
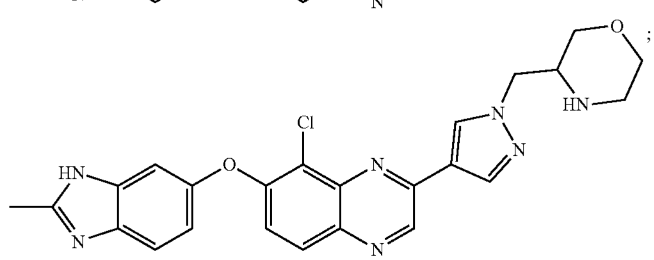
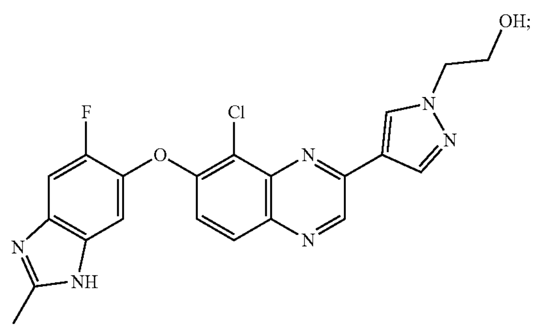

-continued
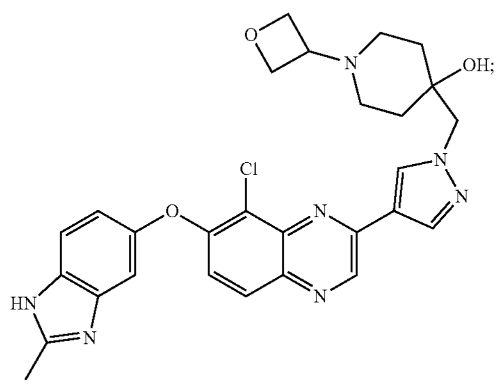
-continued
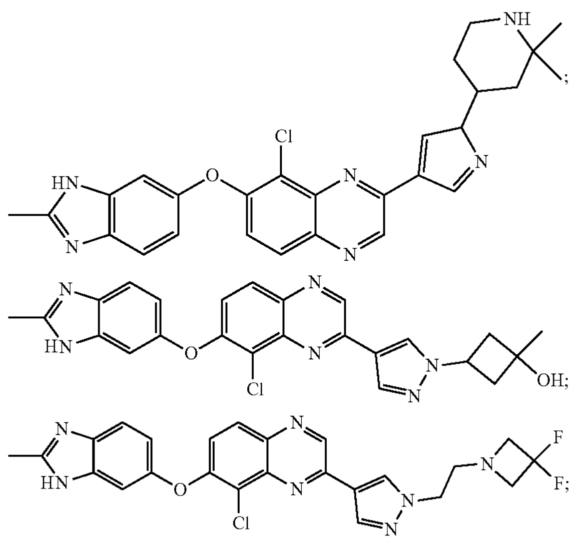
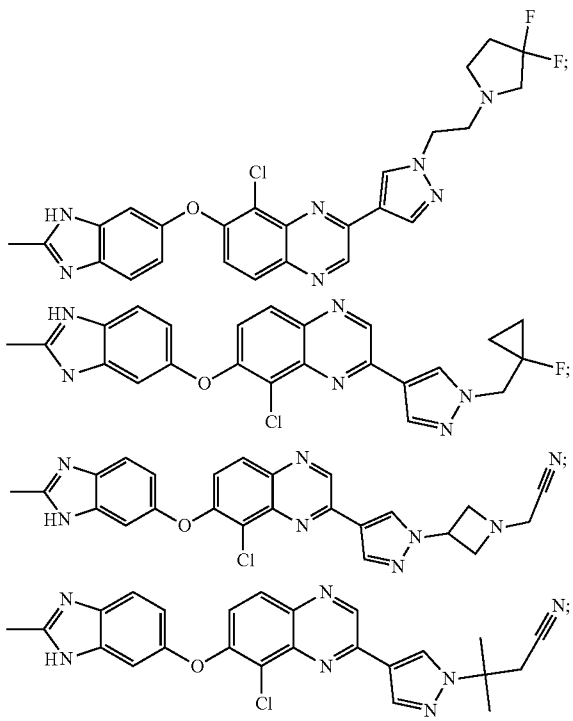
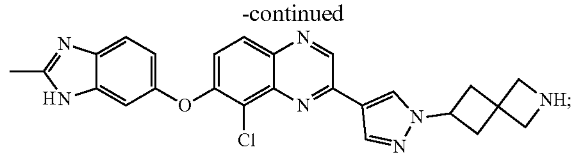
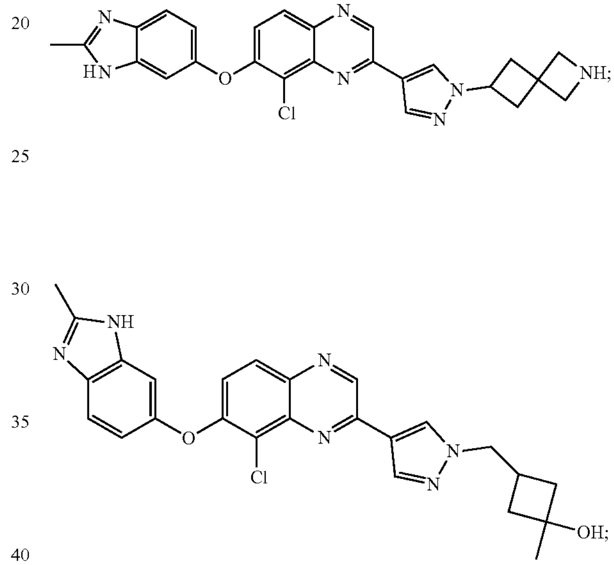
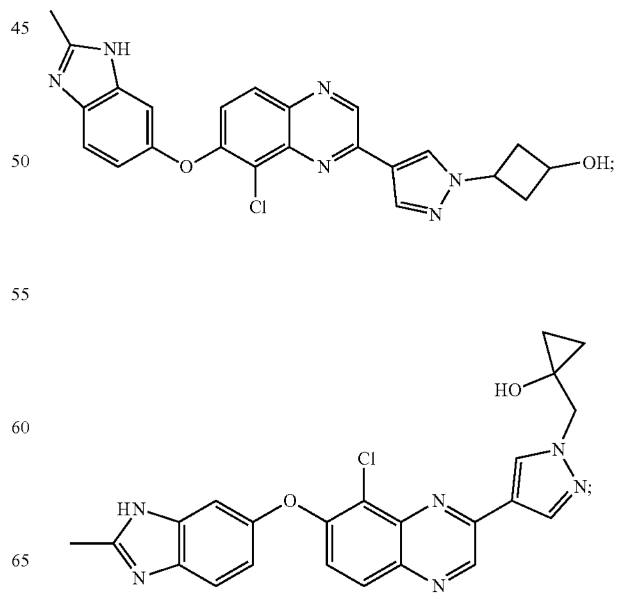

-continued
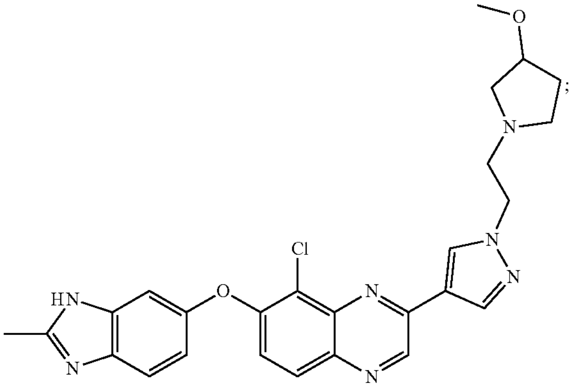
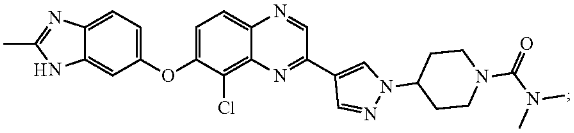
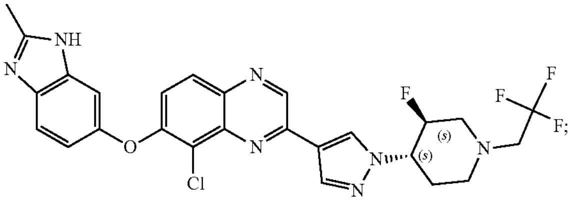
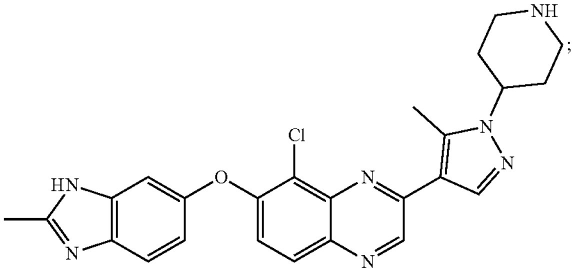
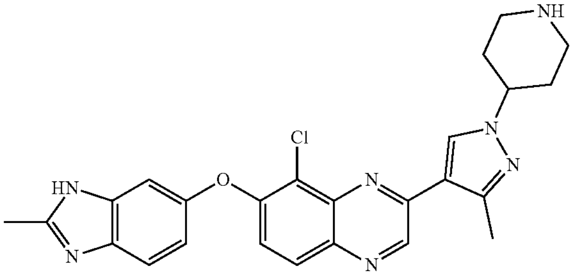
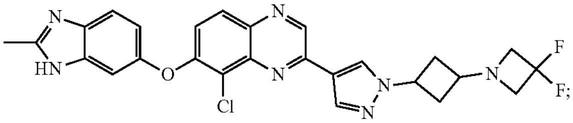
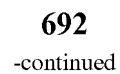
-continued
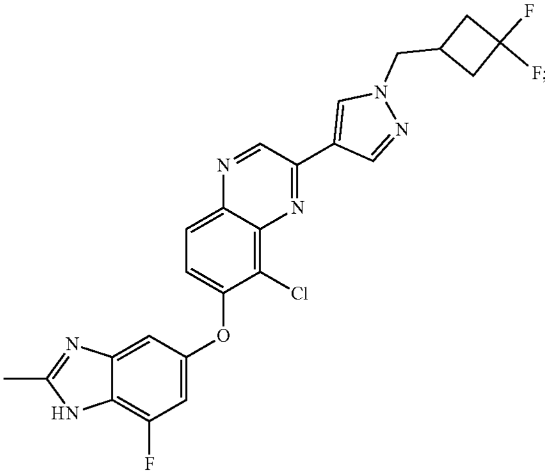
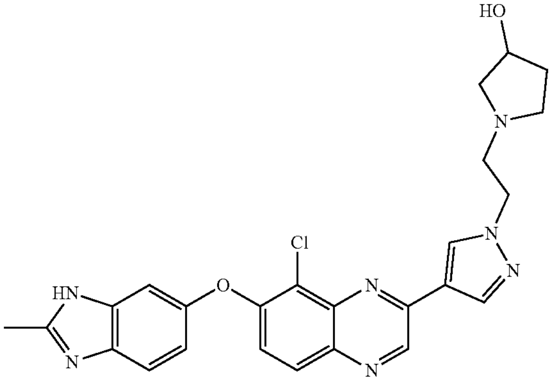
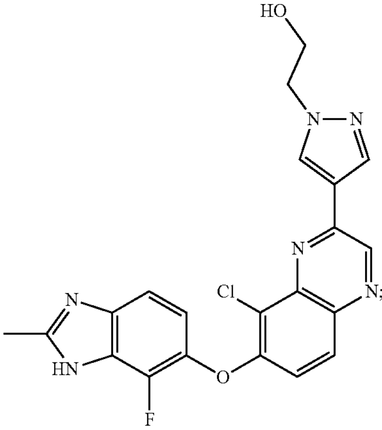
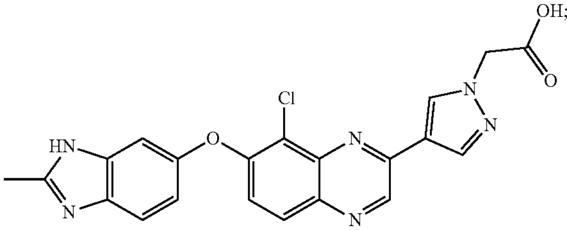

-continued
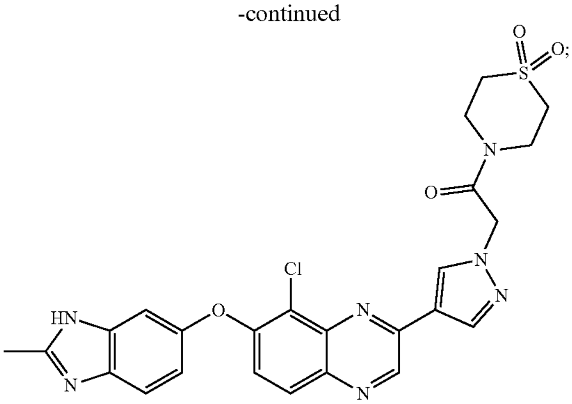
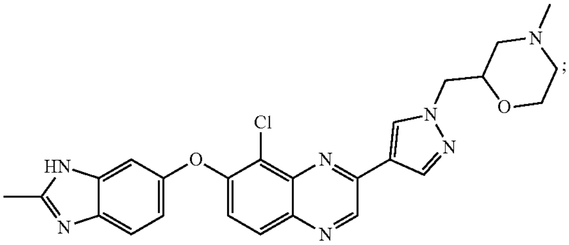
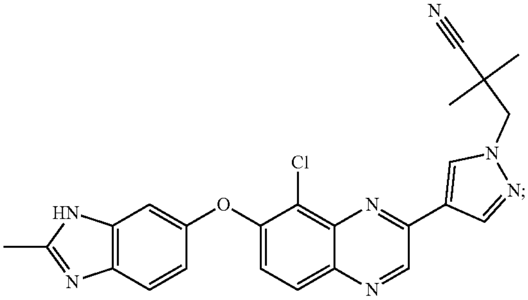
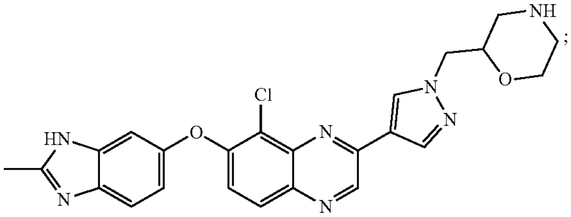
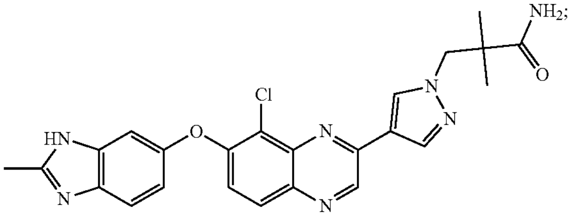
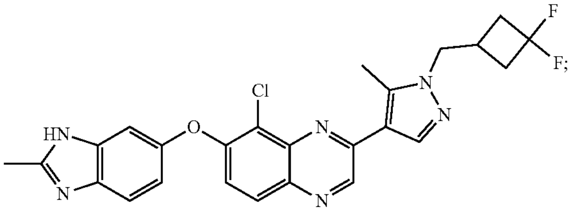
-continued
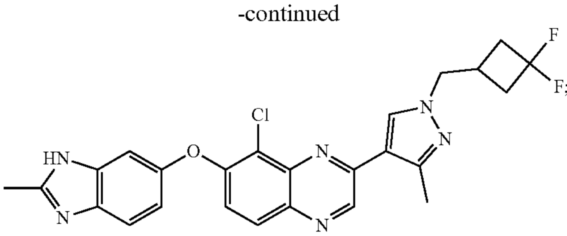
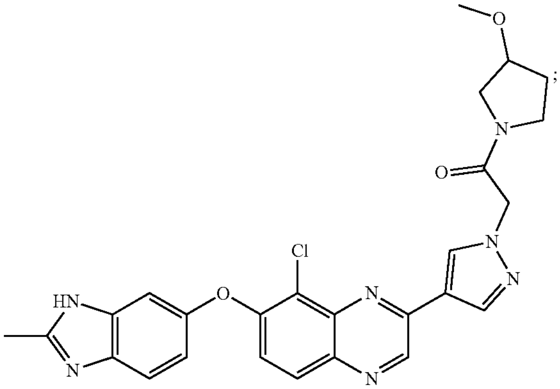
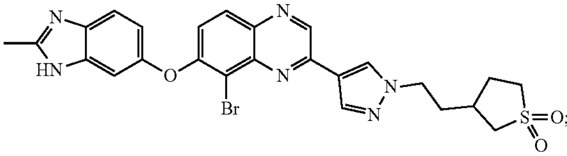
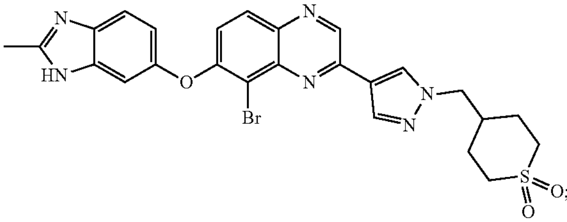
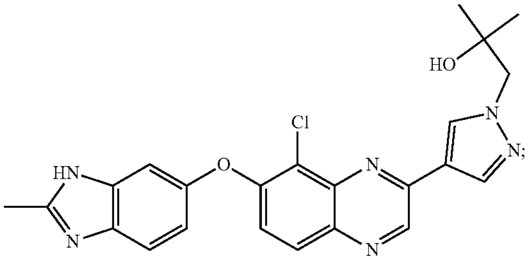
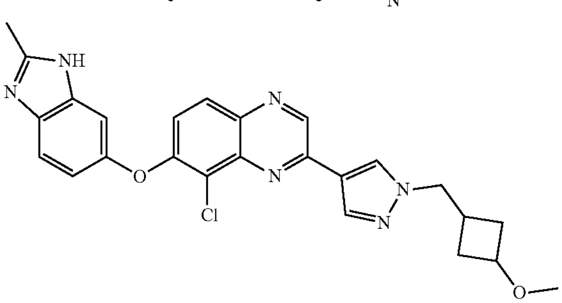
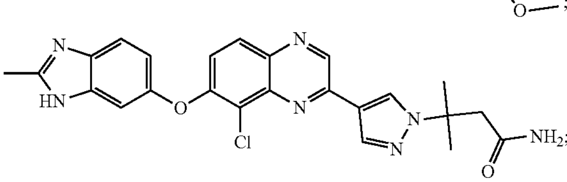

-continued
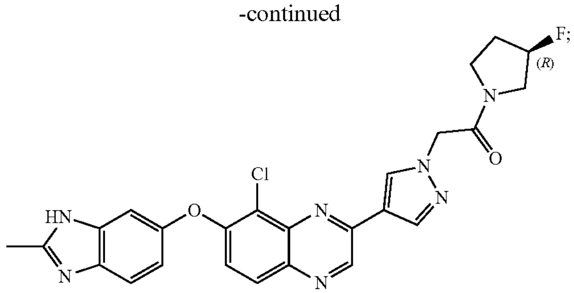
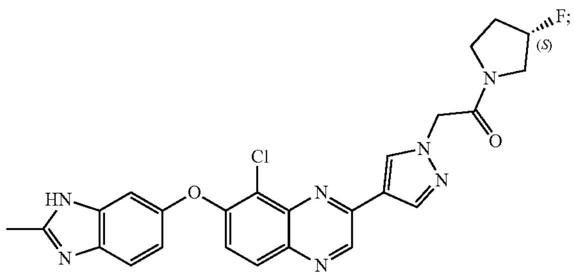
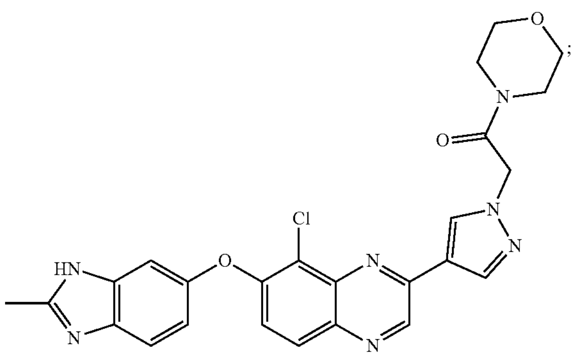
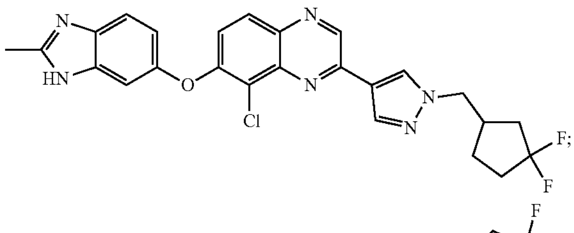
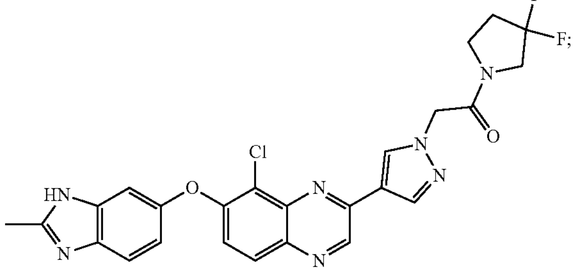
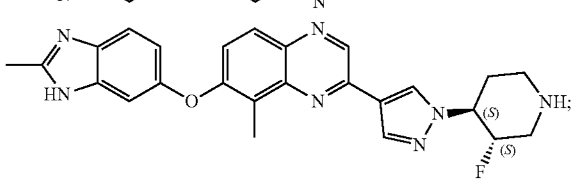
-continued
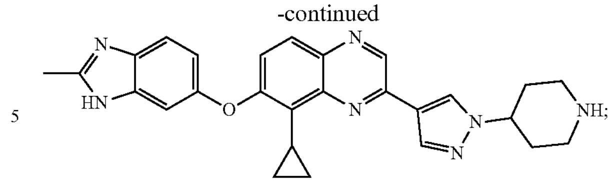
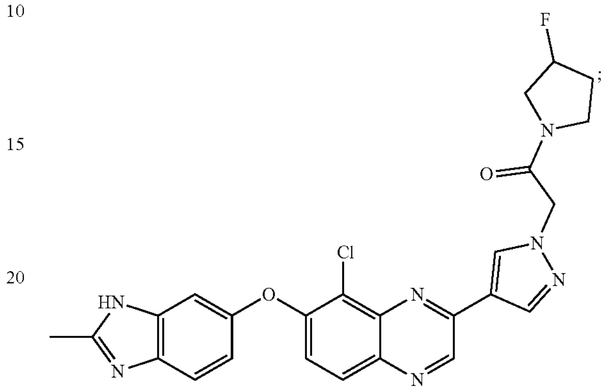
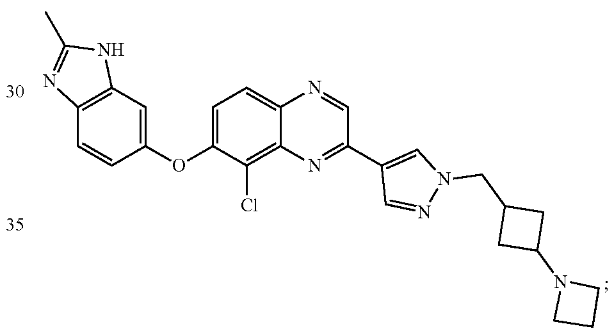
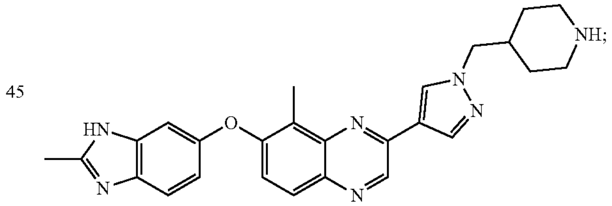
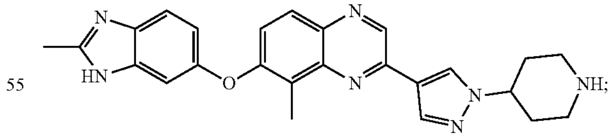
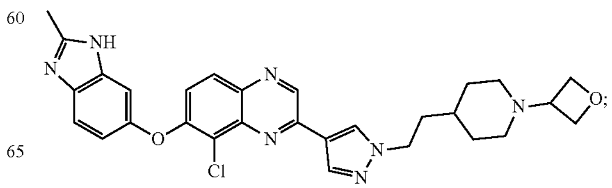

-continued
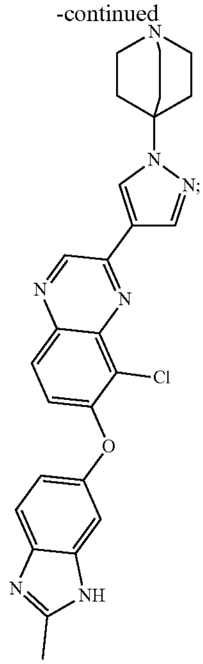
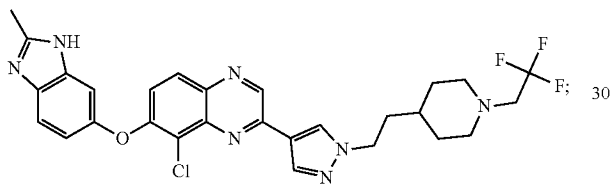
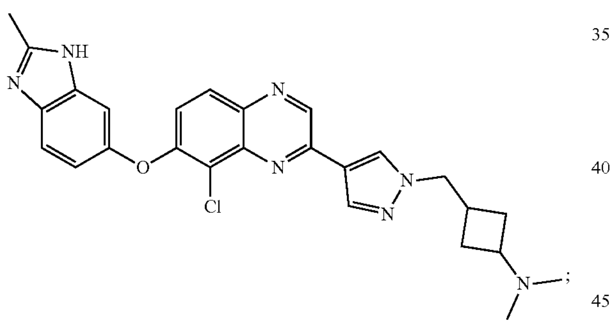
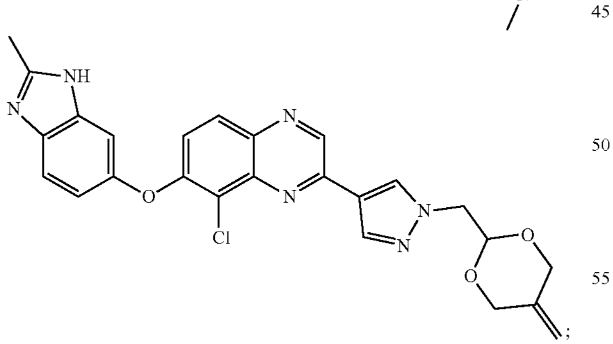
-continued
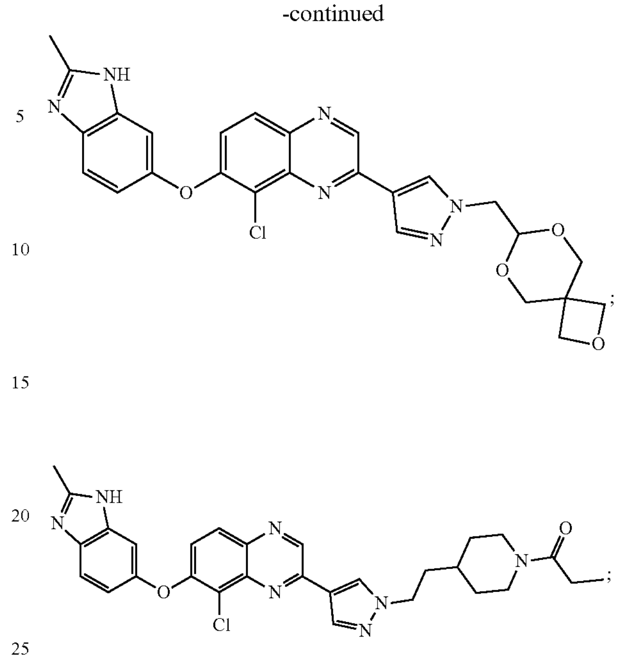
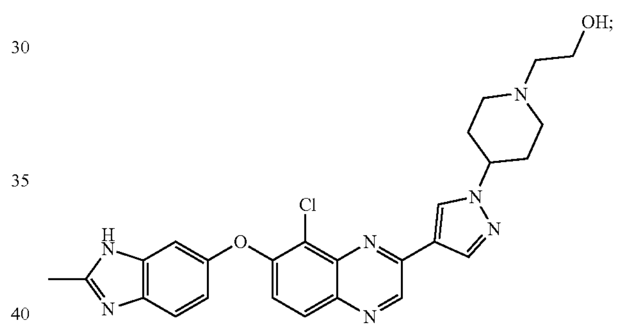
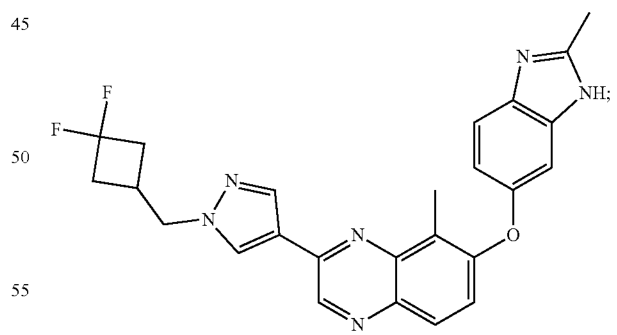
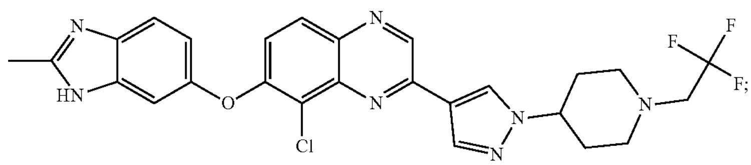

-continued
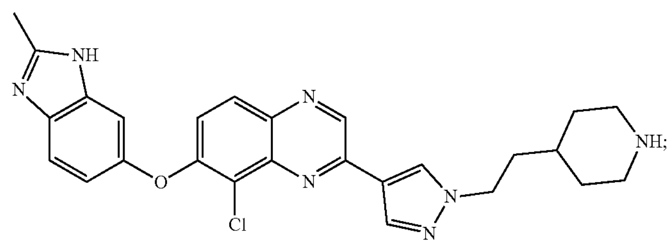
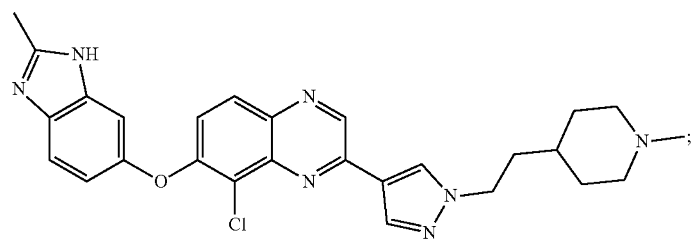
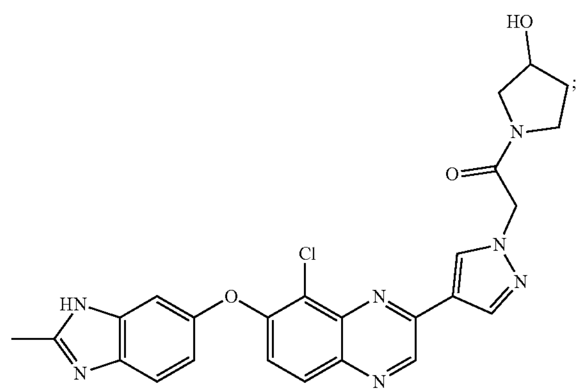
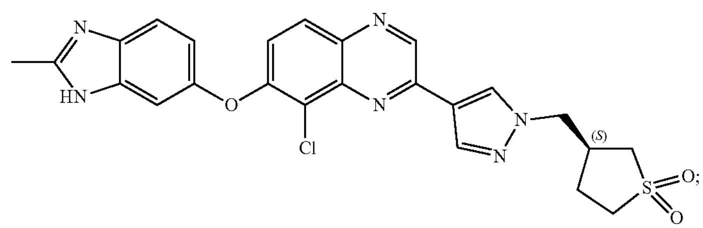
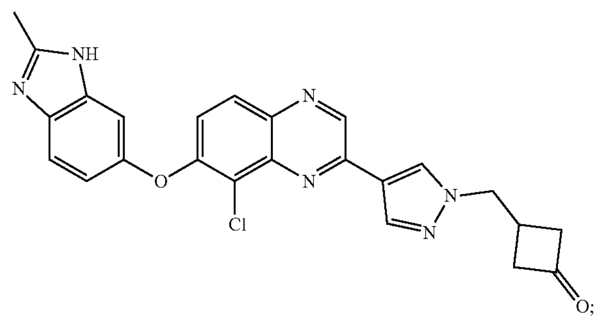
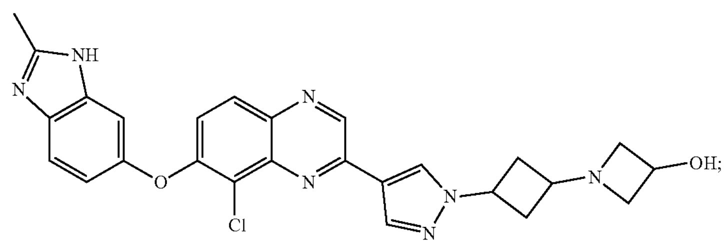

-continued
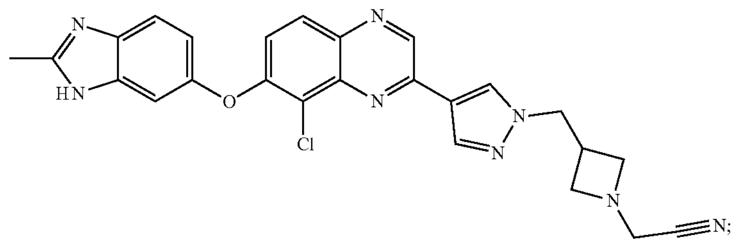
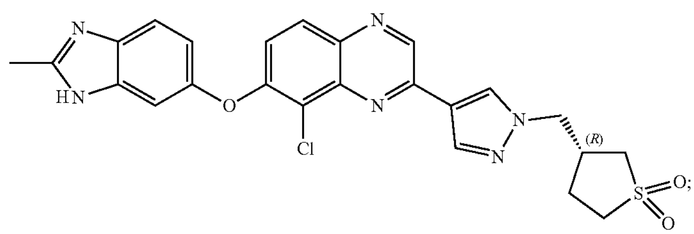
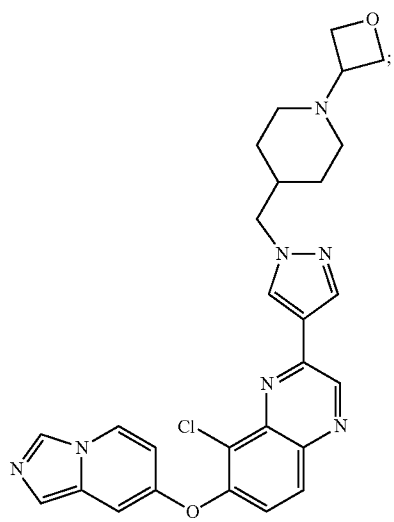
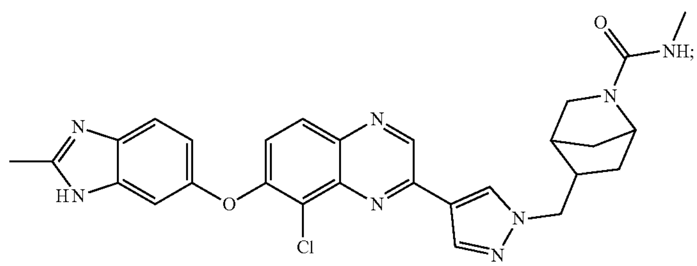
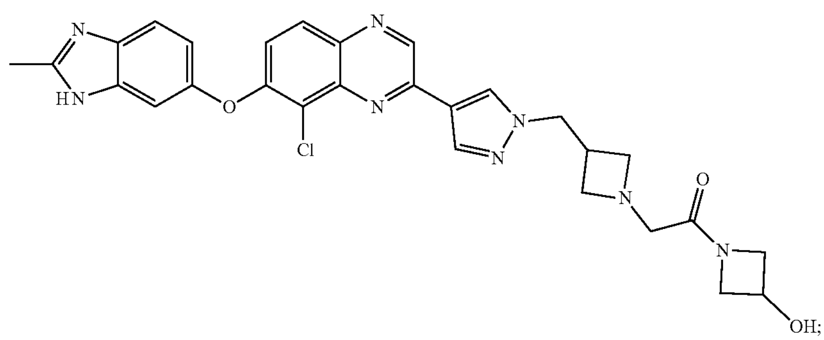

-continued
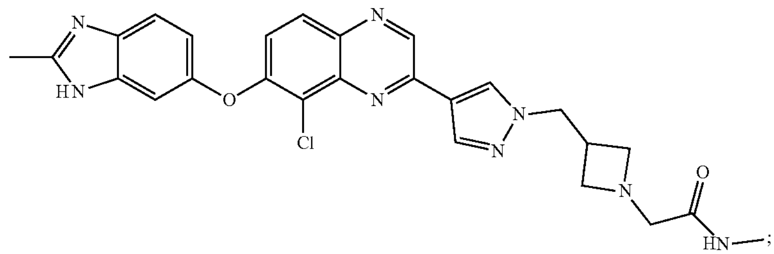
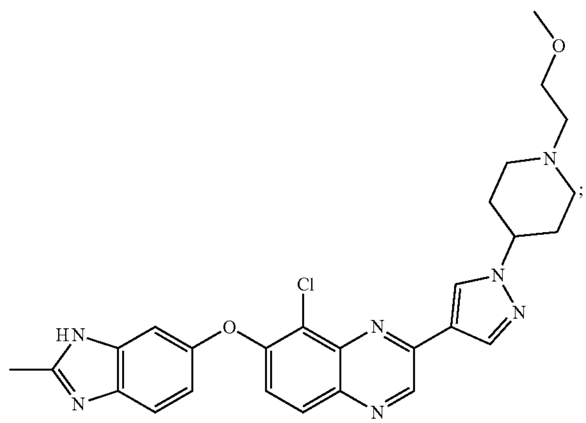
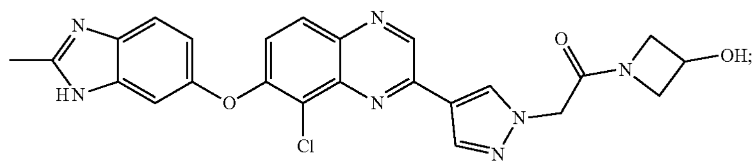
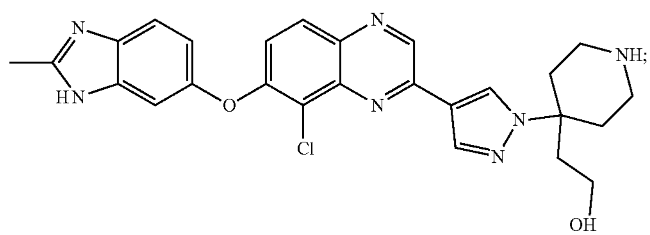
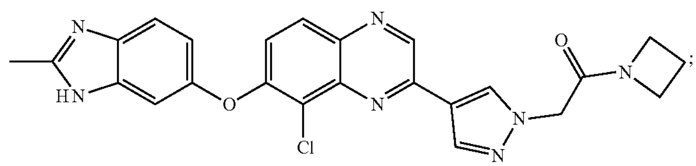
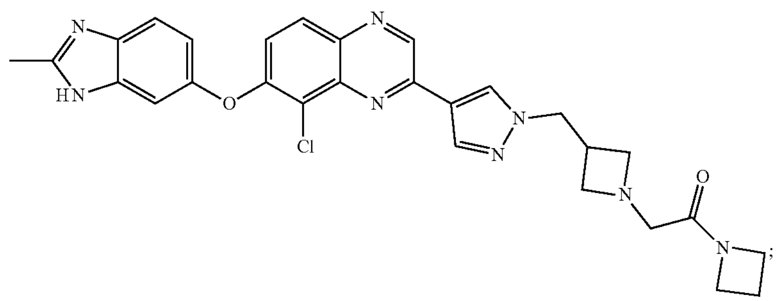

-continued
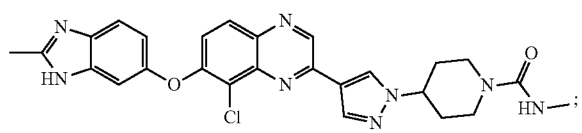
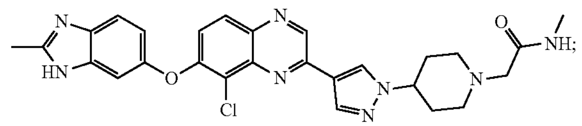
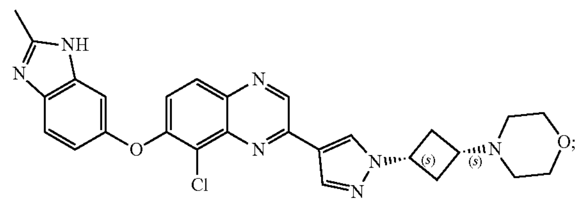
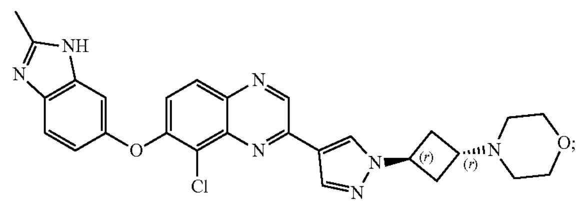
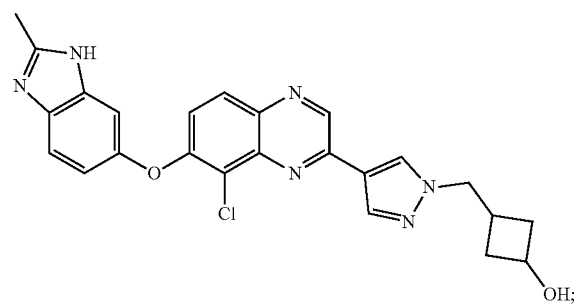
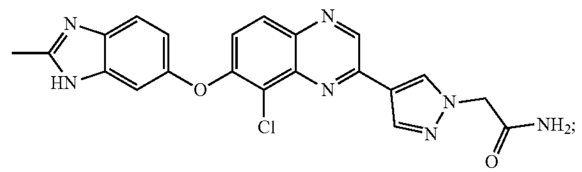
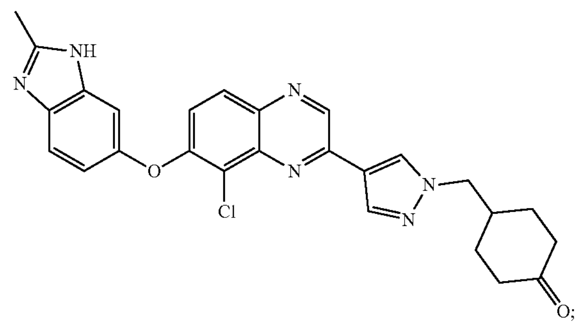
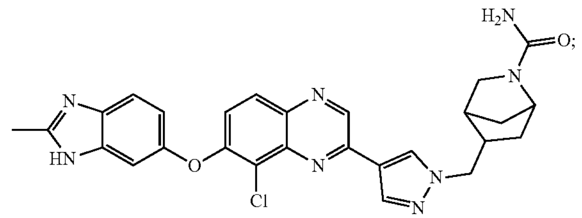
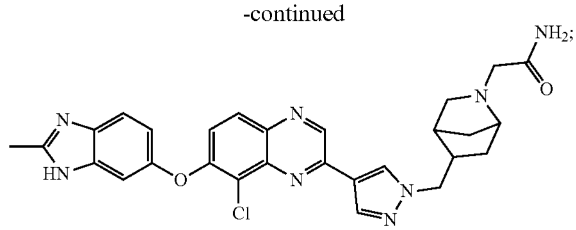
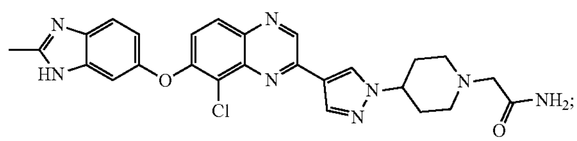
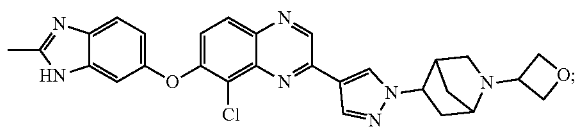
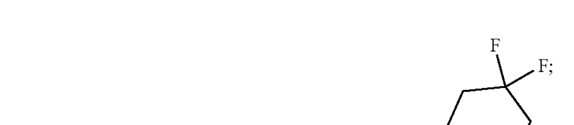
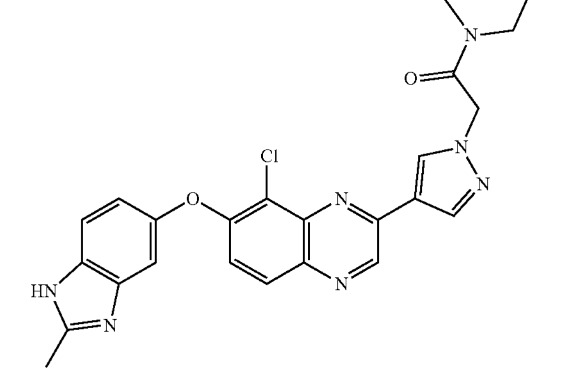
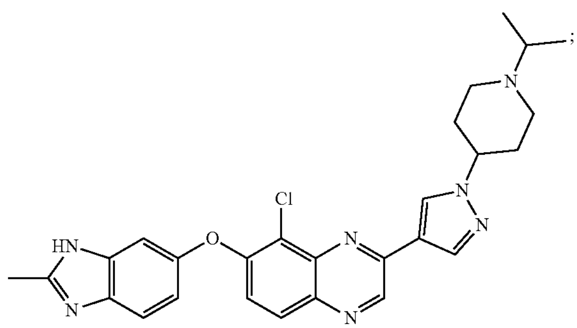
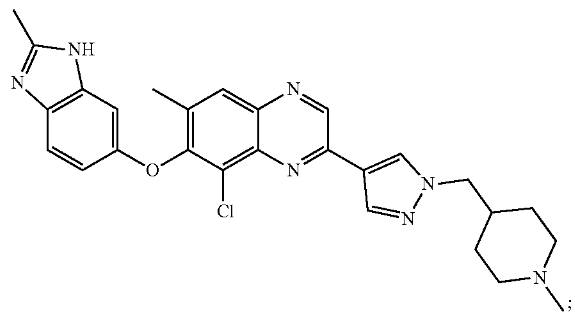
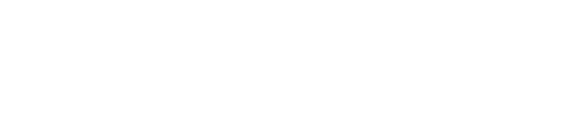

-continued
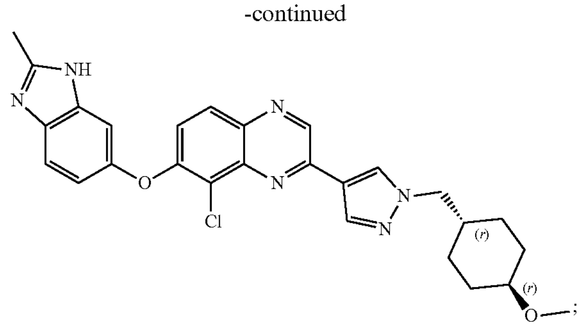
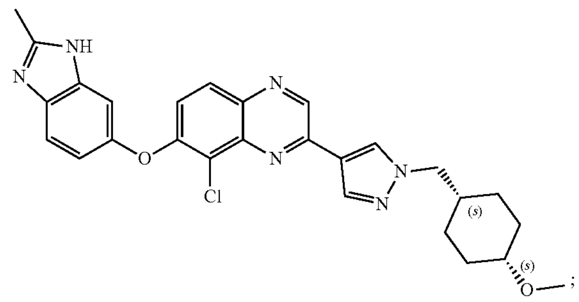
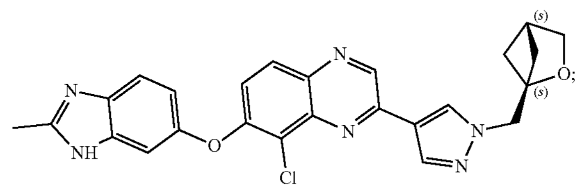
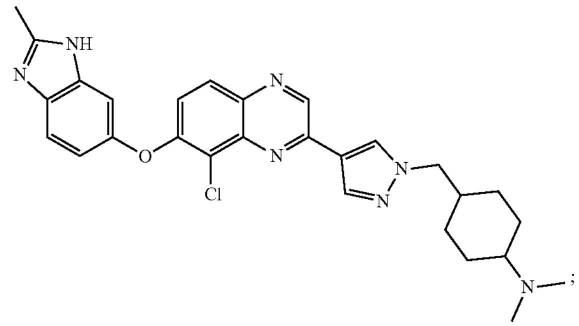
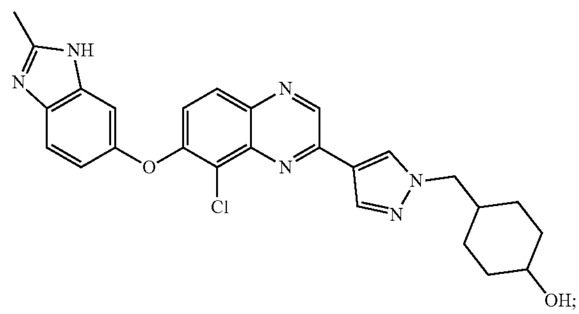
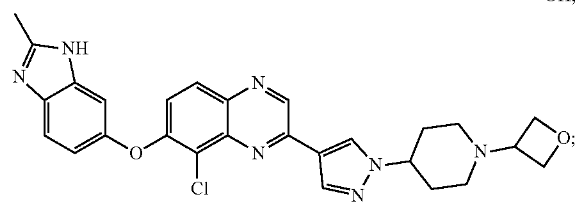
-continued
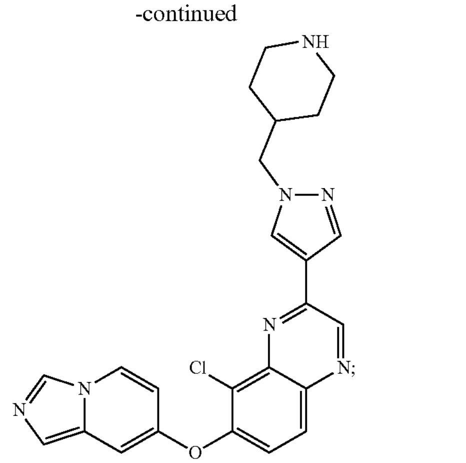
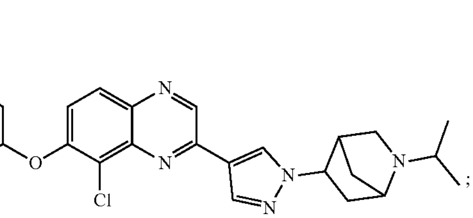
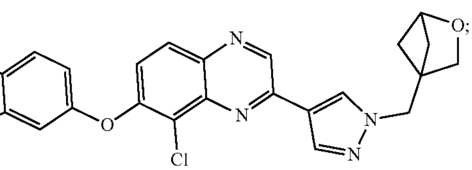
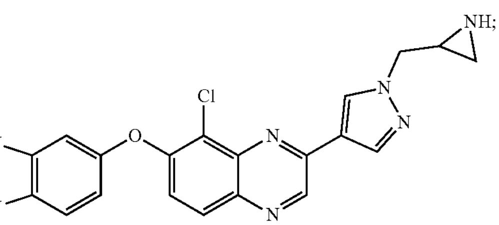
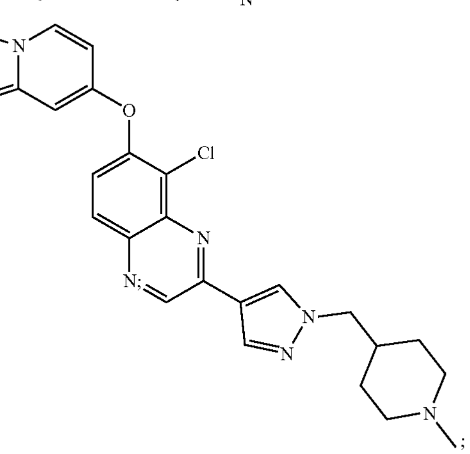
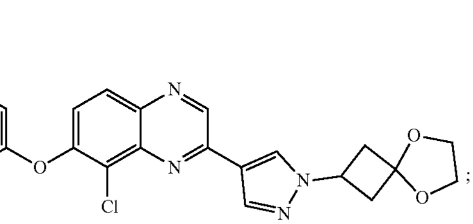

-continued
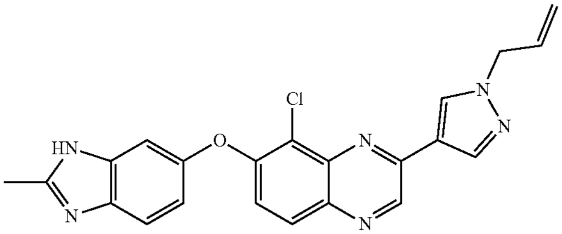
;
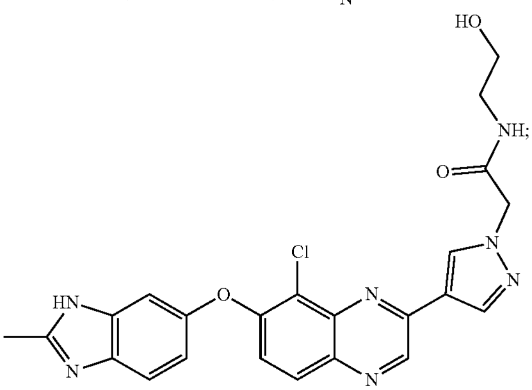
;
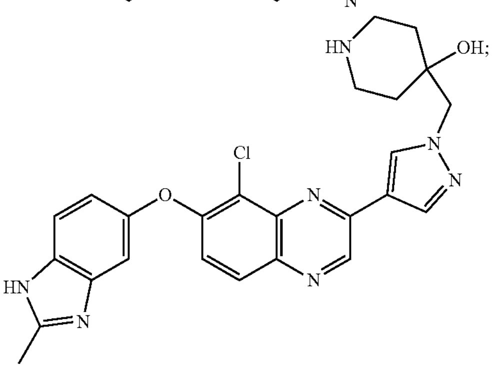
;
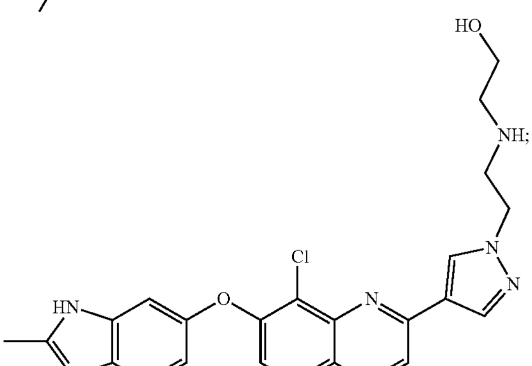
;
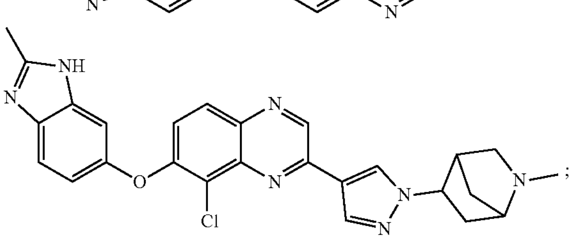
;
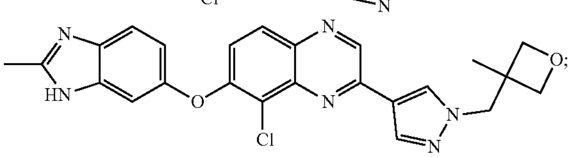
;
-continued
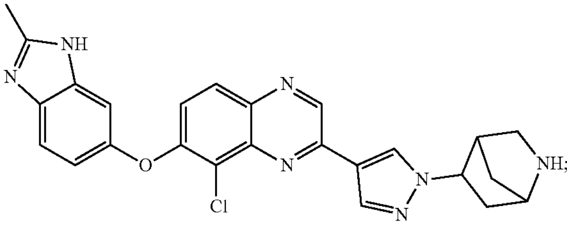
;
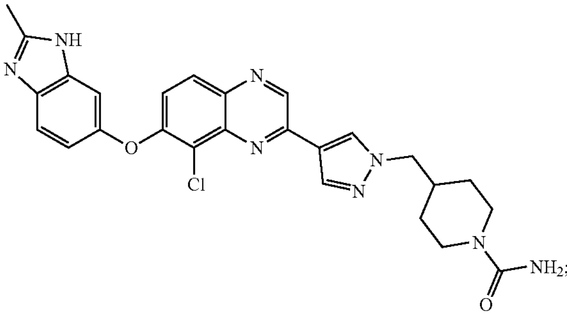
;
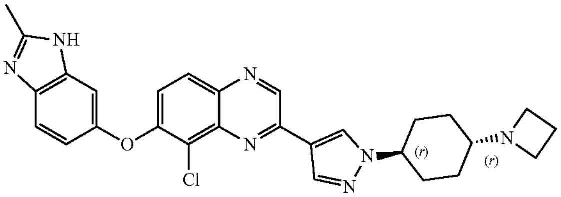
;
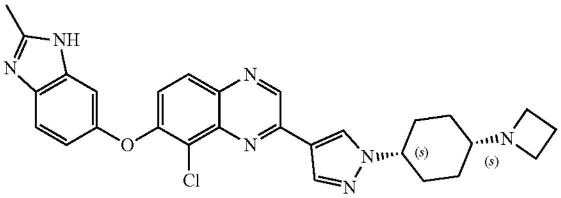
;
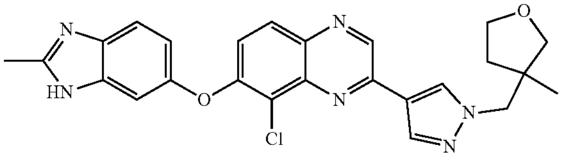
;
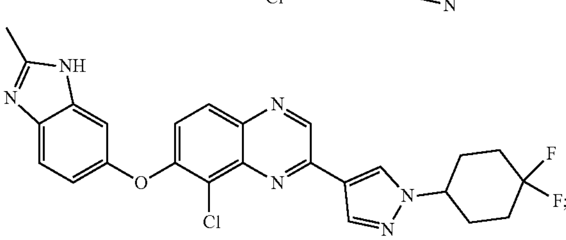
;
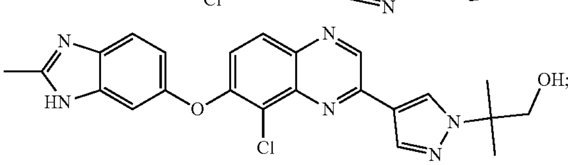
;

-continued
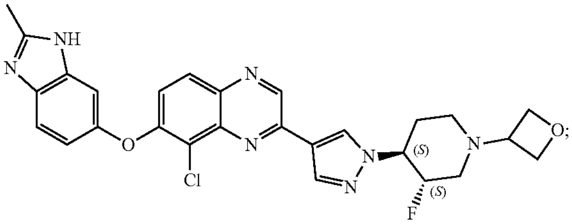
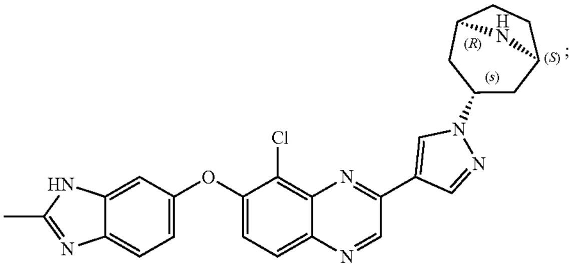
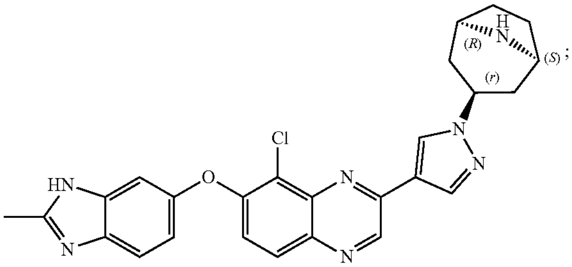
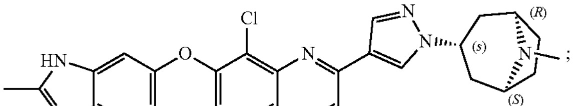
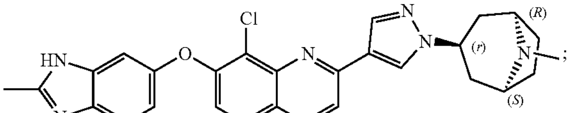
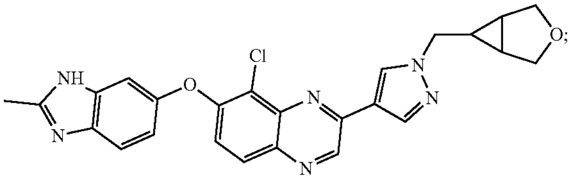
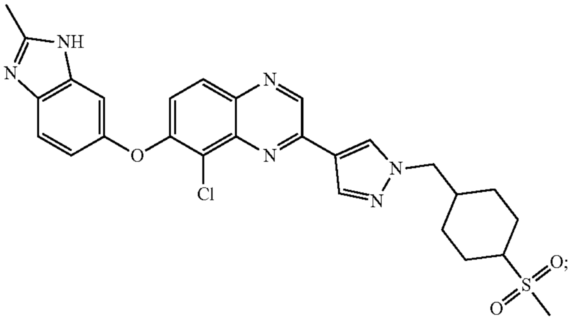
-continued
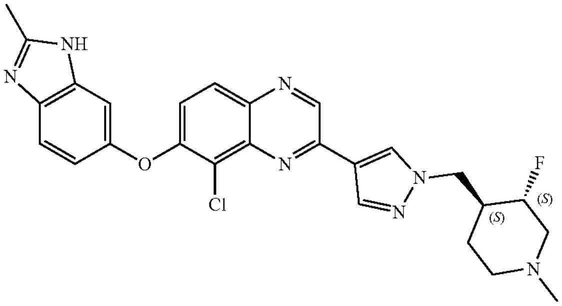
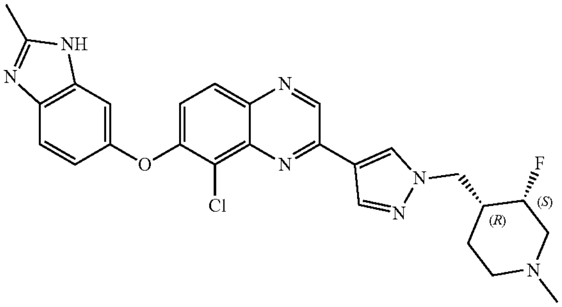
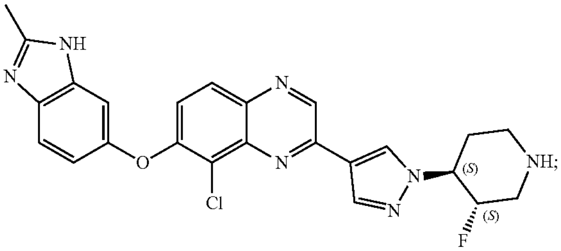
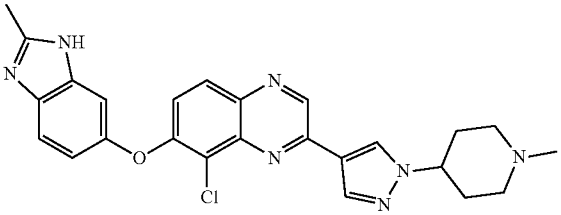
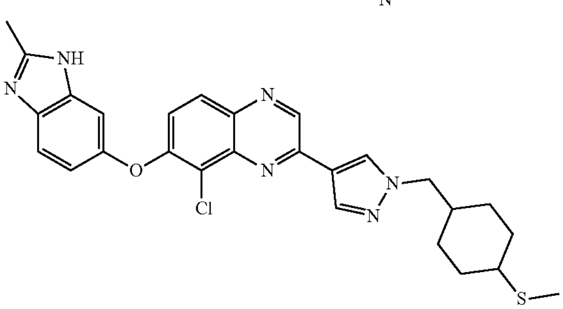
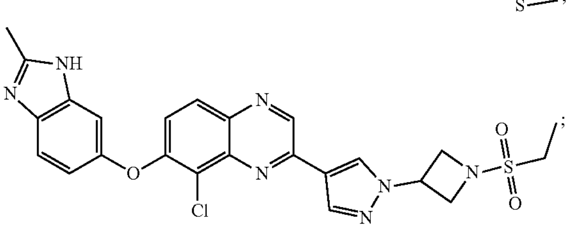

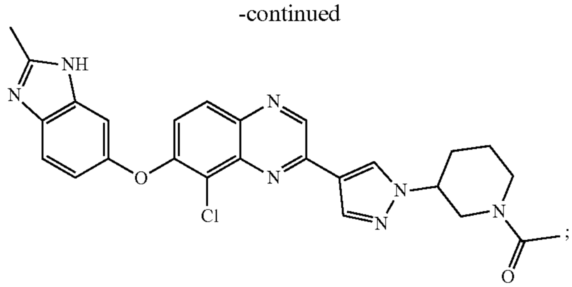
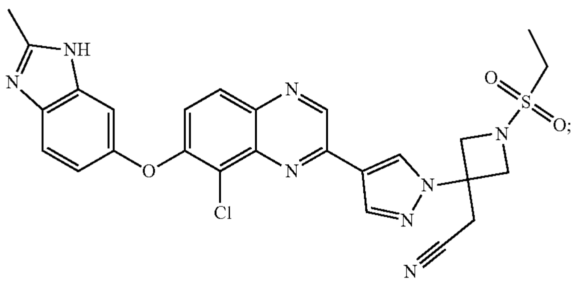
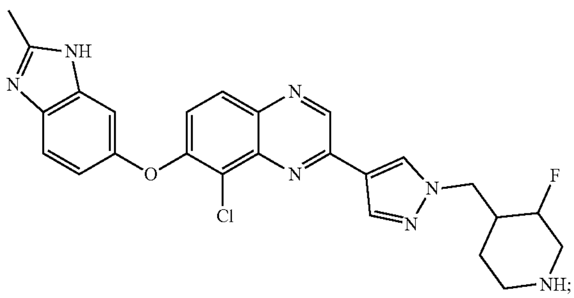
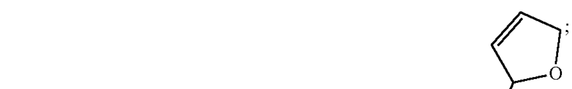
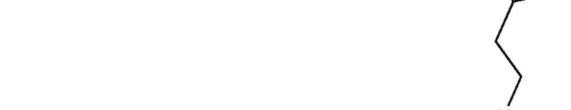
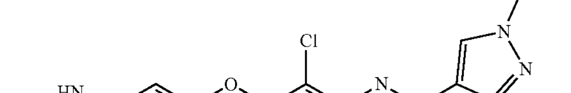
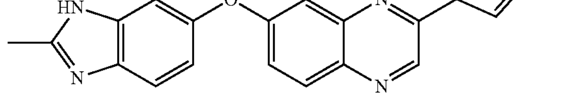
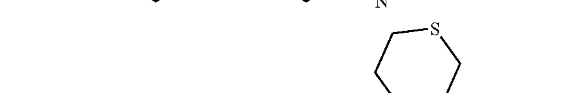
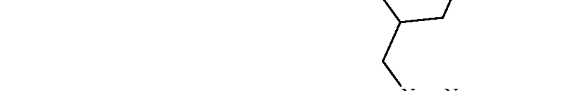
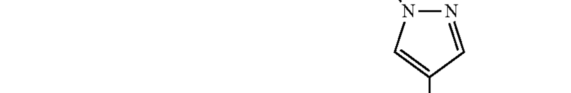
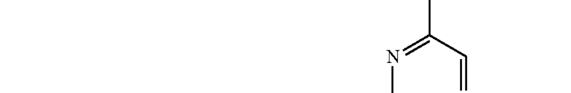
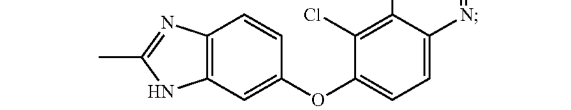
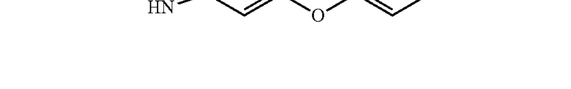
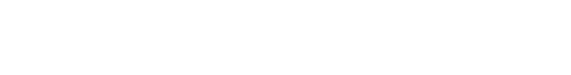
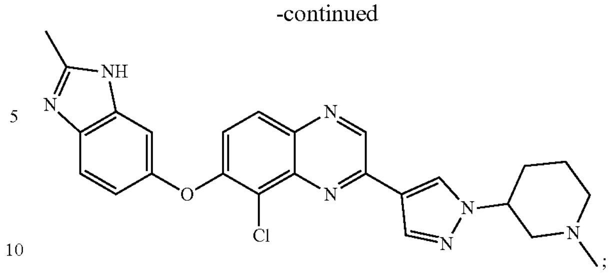
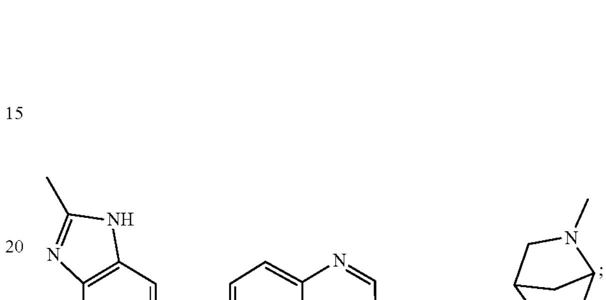
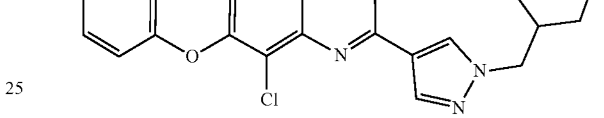
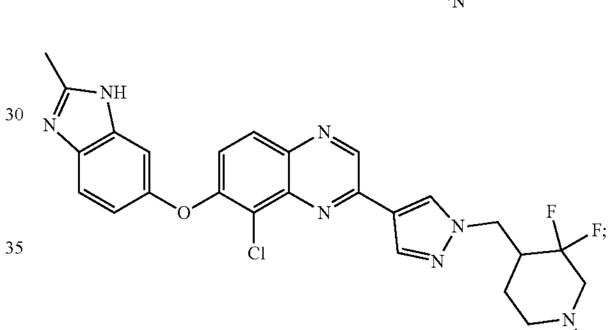
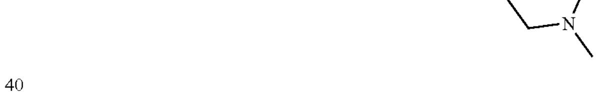
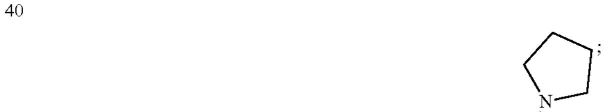
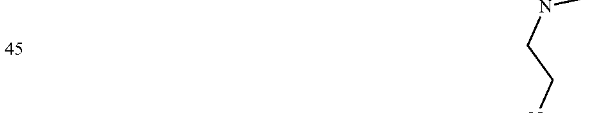
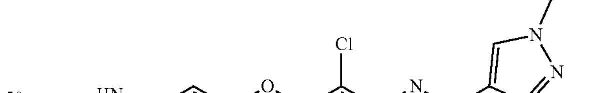
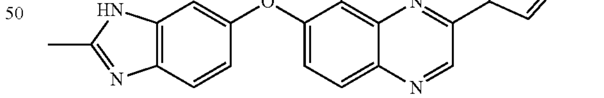
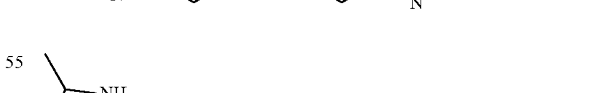
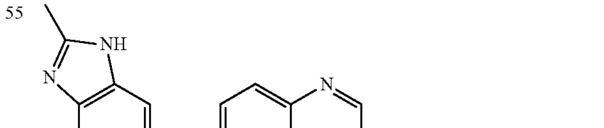
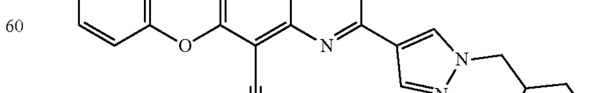
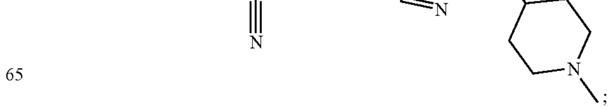
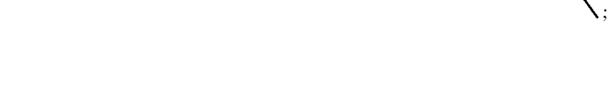
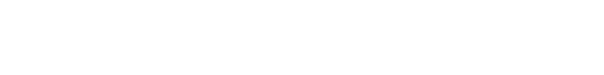

-continued

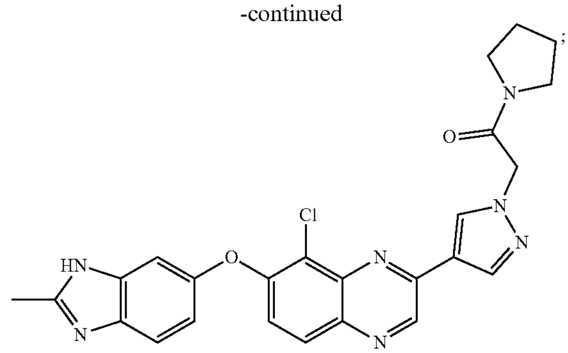

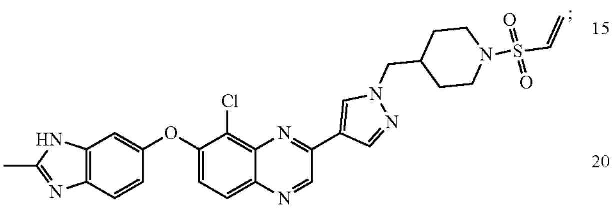

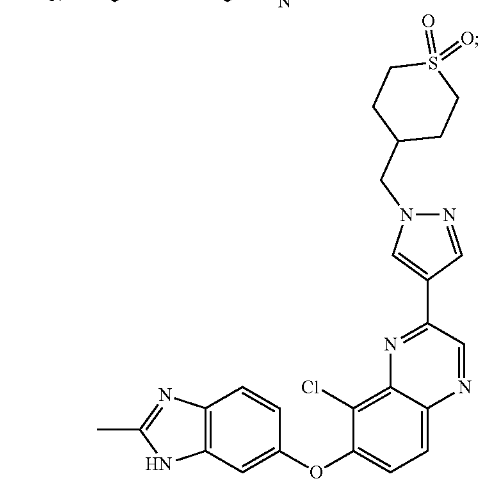

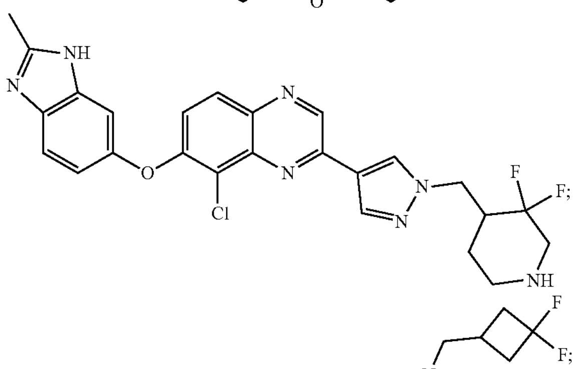

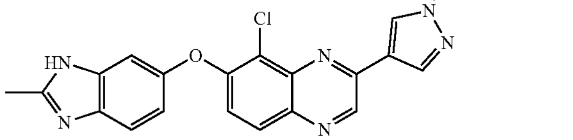

-continued

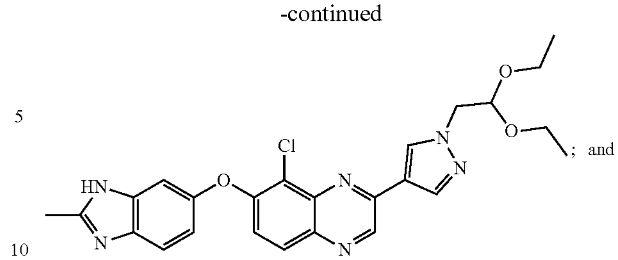

and

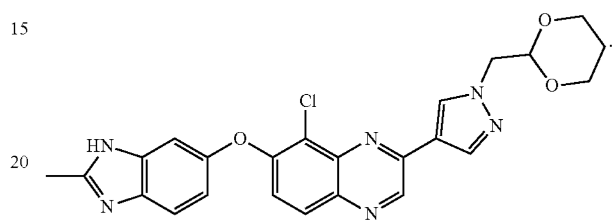

or a pharmecutically acceptable salt or stereoisomer thereof.

19. The compound, pharmaceutically acceptable salt, or stereoisomer of claim 18, wherein the compound is:

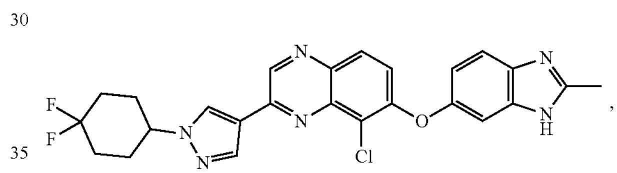

or a pharmaceutically acceptable salt or stereoisomer thereof.

20. A pharmaceutical composition comprising the compound, pharmaceutically acceptable salt, or stereoisomer of claim 19, and one or more pharmaceutically acceptable carriers, adjuvants, diluents, or excipients.

21. A method of treating lung cancer, bladder cancer, kidney cancer, or gastric cancer in a subject, the method comprising administering to the subject a compound, pharmaceutically acceptable salt, or stereoisomer of claim 19.

22. A pharmaceutical composition comprising the compound, pharmaceutically acceptable salt, or stereoisomer of claim 3, and one or more pharmaceutically acceptable carriers, adjuvants, diluents, or excipients.

23. A method of treating lung cancer, bladder cancer, kidney cancer, or gastric cancer in a subject, the method comprising administering to the subject a compound, pharmaceutically acceptable salt, or stereoisomer of claim 3.

* * * * *